(12) United States Patent
Hunter et al.

(10) Patent No.: US 7,166,570 B2
(45) Date of Patent: Jan. 23, 2007

(54) MEDICAL IMPLANTS AND FIBROSIS-INDUCING AGENTS

(75) Inventors: William L. Hunter, Vancouver (CA); David M. Gravett, Vancouver (CA); Philip M. Toleikis, Vancouver (CA); Arpita Maiti, Vancouver (CA); Pierre E. Signore, Vancouver (CA); Richard T. Liggins, Coquitlam (CA); Dechi Guan, Vancouver (CA)

(73) Assignee: Angiotech International AG, Zug (CH)

( * ) Notice: Subject to any disclaimer, the term of this patent is extended or adjusted under 35 U.S.C. 154(b) by 0 days.

(21) Appl. No.: 11/006,893

(22) Filed: Dec. 7, 2004

(65) Prior Publication Data

US 2005/0147643 A1 Jul. 7, 2005

Related U.S. Application Data

(63) Continuation of application No. 10/986,230, filed on Nov. 10, 2004.

(60) Provisional application No. 60/586,861, filed on Jul. 9, 2004, provisional application No. 60/578,471, filed on Jun. 9, 2004, provisional application No. 60/523,908, filed on Nov. 23, 2003, provisional application No. 60/524,023, filed on Nov. 20, 2003, provisional application No. 60/518,785, filed on Nov. 10, 2003.

(51) Int. Cl.
*A61K 38/00* (2006.01)
*A61K 38/17* (2006.01)

(52) U.S. Cl. .......................................... 514/2; 530/353

(58) Field of Classification Search ................ 128/898; 424/489; 601/2; 514/2; 530/353
See application file for complete search history.

(56) References Cited

U.S. PATENT DOCUMENTS 5,162,430 A 11/1992 Rhee et al. ................ 525/54.1

(Continued)

FOREIGN PATENT DOCUMENTS

WO WO 90/13260 A1 11/1990

(Continued)

OTHER PUBLICATIONS

Ludwick, J. 2002 Grand Rounds Archive, Baylor College of Medicine.*

(Continued)

*Primary Examiner*—Jon Weber
*Assistant Examiner*—Marsha Tsay
(74) *Attorney, Agent, or Firm*—Seed IP Law Group PLLC

(57) ABSTRACT

Implants are used in combination with a fibrosis-inducing agent in order to induce fibrosis that may otherwise not occur when the implant is placed within an animal or increase fibrosis between the implant and the host tissue.

9 Claims, 15 Drawing Sheets

Cyclosporin A activates proliferation of human smooth muscle cells.

U.S. PATENT DOCUMENTS

| | | | |
|---|---|---|---|
| 5,204,382 A | 4/1993 | Wallace et al. | 523/115 |
| 5,213,580 A | 5/1993 | Slepian et al. | 623/1 |
| 5,290,552 A | 3/1994 | Sierra et al. | 424/94.64 |
| 5,310,562 A | 5/1994 | Margolin | 424/489 |
| 5,456,693 A | 10/1995 | Conston et al. | 606/192 |
| 5,611,358 A | 3/1997 | Suval | 128/898 |
| 5,612,052 A | 3/1997 | Shalaby | 424/426 |
| 5,614,587 A | 3/1997 | Rhee et al. | 525/54.1 |
| 5,752,974 A | 5/1998 | Rhee et al. | 606/214 |
| 5,843,072 A | 12/1998 | Furumoto et al. | 606/9 |
| 5,874,500 A | 2/1999 | Rhee et al. | 525/54.1 |
| 5,888,546 A | 3/1999 | Ji et al. | 424/484 |
| 6,096,309 A | 8/2000 | Prior et al. | 424/94.63 |
| 6,110,484 A | 8/2000 | Sierra | 424/426 |
| 6,248,763 B1 | 6/2001 | Scivoletto | 514/356 |
| 6,436,061 B1 | 8/2002 | Costantino | 601/2 |
| 6,475,500 B1 | 11/2002 | Vatter et al. | 424/401 |
| 6,524,598 B1 | 2/2003 | Sunkel et al. | 424/401 |
| 6,726,674 B1 | 4/2004 | Leu | 604/508 |
| 2002/0010418 A1 | 1/2002 | Lary et al. | 504/101.04 |
| 2002/0077589 A1 | 6/2002 | Tessari | 604/82 |
| 2003/0120201 A1 | 6/2003 | Abergel | 604/28 |
| 2003/0190336 A1 | 10/2003 | Adams et al. | 424/401 |
| 2004/0043052 A1 | 3/2004 | Hunter et al. | 424/426 |
| 2004/0086474 A1 | 5/2004 | Rabe et al. | 424/63 |
| 2004/0091543 A1 | 5/2004 | Bell et al. | 424/489 |
| 2004/0161435 A1 | 8/2004 | Gupta | 424/401 |
| 2004/0219214 A1 | 11/2004 | Gravett et al. | 424/484 |
| 2004/0225077 A1 | 11/2004 | Gravett et al. | 525/418 |
| 2004/0228821 A1 | 11/2004 | Sunkel et al. | 424/70.12 |
| 2004/0231070 A1 | 11/2004 | Morrissey et al. | 8/405 |
| 2005/0107738 A1 | 5/2005 | Slater et al. | 604/96.01 |
| 2005/0113768 A1 | 5/2005 | Slater et al. | 604/508 |

FOREIGN PATENT DOCUMENTS

| | | |
|---|---|---|
| WO | WO 2004/045549 | 6/2004 |
| WO | WO 2006/023203 | 3/2006 |

OTHER PUBLICATIONS

Klasson, D.H., et al. 1966 Angiology 17(6): 369-376.*
Pharmaceutical Dosage Forms: Disperse Systems vol. 1, pp. 18-26, 32-42. 46-47. 1996.*
Pharmaceutical Dosage Forms: Disperse Systems vol. 3, pp. 163-166. 265-297: 1998.*

* cited by examiner

Cyclosporin A activates proliferation of human smooth muscle cells.

MEDICAL IMPLANTS AND FIBROSIS-INDUCING AGENTS

CROSS REFERENCE TO RELATED APPLICATIONS

This application is a Continuation of co-pending U.S. Utility Application Ser. No. 10/986,230, filed Nov. 10, 2004 now pending, which application claims the benefit under 35 USC 119(e) of U.S. Provisional Application Ser. No. 60/518, 785, filed Nov. 10, 2003; U.S. Provisional Application Ser. No. 60/523,908, filed Nov. 20, 2003; U.S. Provisional Application Ser. No. 60/524,023, filed Nov. 20, 2003; U.S. Provisional Application Ser. No. 60/586,861, filed Jul. 9, 2004; and U.S. Provisional Application Ser. No. 60/578,471, filed Jun. 9, 2004, which applications are incorporated herein by reference in their entireties.

BACKGROUND OF THE INVENTION

1. Field of the Invention

The present invention relates generally to pharmaceutical compositions, methods and devices, and more specifically, to compositions and methods for preparing medical implants to make them more adherent to, or, more readily incorporated within a living tissue. The pharmaceutical agents and compositions are utilized to create novel drug-coated implants and medical devices which induce a fibrotic response in the surrounding tissue such that the device is effectively anchored in situ and its performance is enhanced.

2. Description of the Related Art

The clinical performance of numerous medical devices depends upon the device being effectively anchored into the surrounding tissue to provide either structural support or to facilitate scarring and healing. Effective attachment of the device into the surrounding tissue, however, is not always readily achieved. One reason for ineffective attachment is that implantable medical devices generally are composed of materials that are highly biocompatible and designed to reduce the host tissue response. These materials (e.g., stainless steel, titanium based alloys, fluoropolymers, and ceramics) typically do not provide a good substrate for host tissue attachment and ingrowth during the scarring process. As a result of poor attachment between the device and the host tissue, devices can have a tendency to migrate within the vessel or tissue in which they are implanted. The extent to which a particular type of medical device can move or migrate after implantation depends on a variety of factors including the type and design of the device, the material(s) from which the device is formed, the mechanical attributes (e.g., flexibility and ability to conform to the surrounding geometry at the implantation site), the surface properties, and the porosity of the device or device surface. The tendency of a device to loosen after implantation also depends on the type of tissue and the geometry at the treatment site, where the ability of the tissue to conform around the device generally can help to secure the device in the implantation site. Device migration can result in device failure and, depending on the type and location of the device, can lead to leakage, vessel occlusion, and/or damage to the surrounding tissue.

Numerous methods and device modifications have been proposed to secure implantable medical devices in place in the body. In one approach, the medical device is anchored mechanically to biological tissue. For example, artificial implants can be anchored to the surrounding tissues by physical and mechanical means (e.g., screws, cements and porous surfaces) or by friction. For example, mechanical attachment of a device to the site can be effected by using a fastener, such as a suture or staple. In another approach, the device includes in its design mechanical means for fastening it into the surrounding tissue. For example, the device may include metallic spikes, anchors, hooks, barbs, pins, clamps, or a flange or lip to affix the device in place (see, e.g., U.S. Pat. Nos. 4,523,592; 6,309,416; 6,302,905; and 6,152,937). A disadvantage of mechanical fasteners, however, is that they can damage the tissue or vessel wall when the device is deployed.

Other methods for preventing device migration have focused on mechanically altering the surface characteristics of the device. One such approach involves scoring or abrading the surface of the implant. The roughened surfaces promote cell, bone or tissue adhesion for better affixing of the implants in the body (see, e.g., WO 96/29030A1). Medical devices, such as implantable orthopedic devices, may be fixed to host tissue (e.g., bone) with an adhesive, such as a polymethyl methacrylate (PMMA) bone cement or a bone cement made from calcium phosphates and calcium aluminate (see, e.g., U.S. Pat. No. 6,723,334). A drawback of bone cements, however, is that over time the cemented bone-prosthesis interface can degenerate, and/or the cement itself may weaken and fail, resulting in loosening of the implant.

Chemical or biological modifications of the device surface have been used to enhance adhesion between an implantable medical device and the surrounding host tissue. For example, devices have been coated with a substance to enhance the healing process and/or adhesion of the device to the host tissue. In one approach, implantable medical devices have been developed which permit infiltration by specific desirable tissue cells. One type of tissue infiltration involves the process known as "endothelialization", i.e., migration of endothelial cells from adjacent tissue onto or into the device surface. Methods for promoting endothelialization have included applying a porous coating to the device which allows tissue growth into the interstices of the implant surface (see, e.g., WO 96/37165A1). Other efforts at improving host tissue ingrowth capability and adhesion of the implant to host tissue include an electrically charged or ionic material (e.g., fluoropolymer) in the tissue-contacting surface of the device (see, e.g., WO 95/19796A1; J. E. Davies, in Surface Characterization of Biomaterials, B. D. Ratner, ed., pp. 219–234 (1988); and U.S. Pat. No. 5,876, 743); biocompatible organic polymers (e.g., polymers substituted with carbon, sulfur or phosphorous oxyacid groups) to promote osteogenesis at the host-implant interface (see, e.g., U.S. Pat. No. 4,795,475); and coatings made from biological materials (e.g., collagen) to enhance tissue repair, growth and adaptation at the implant-tissue interface (e.g., U.S. Pat. No. 5,002,583).

The above-described approaches, however, have failed to provide a satisfactory long-term solution to the problem of device migration. Thus, there is still a need for an effective, long-lasting and biocompatible approach for anchoring implantable medical devices into or onto biological tissue.

BRIEF SUMMARY OF THE INVENTION

Briefly stated, the present invention provides compositions for delivery of selected therapeutic agents via medical implants or implantable medical devices, as well as methods for making and using these implants and devices. Within one aspect of the invention, drug-coated or drug-impregnated implants and medical devices are provided which induce adhesion or fibrosis in the surrounding tissue, or facilitate "anchoring" of the device/implant in situ, thus enhancing the efficacy. Within various embodiments, fibrosis is induced by local or systemic release of specific pharmacological agents that become localized to the adjacent tissue.

The repair of tissues following a mechanical or surgical intervention involves two distinct processes: (1) regeneration (the replacement of injured cells by cells of the same type) and (2) fibrosis (the replacement of injured cells by connective tissue). There are four general components to the process of fibrosis (or scarring) including: formation of new blood vessels (angiogenesis), migration and proliferation of fibroblasts, deposition of extracellular matrix (ECM), and remodeling (maturation and organization of the fibrous tissue). As utilized herein, "induces (promotes) fibrosis" should be understood to refer to agents or compositions which increase or accelerate the formation of fibrous tissue (i.e., by inducing or promoting one or more of the processes of angiogenesis, fibroblast migration or proliferation, ECM production, and/or remodeling). In addition, numerous therapeutic agents described in this invention can have the additional benefit of also promoting tissue regeneration.

Within one embodiment of the invention, an implant or device is adapted to include or to release an agent that induces fibrosis or regeneration through one or more of the mechanisms sited above. Thus, the present invention provides devices that comprise a medical implant and at least one of (i) a fibrosis-inducing agent and (ii) a composition that comprises a fibrosis-inducing agent. The agent is present so as to induce fibrosis formation that may otherwise not occur or increase fibrosis in a statistically significant manner when the implant is placed within an animal. In another aspect the present invention is directed to methods wherein both an implant and at least one of (i) a fibrosis-inducing agent and (ii) a composition that comprises a fibrosis-inducing agent, are placed into an animal, and the agent causes the formation of fibrosis that may otherwise not occur or increase fibrosis in a statistically significant manner. These and other aspects of the invention are summarized below.

Thus, in various independent aspects, the present invention provides the following: a device, comprising an orthopedic implant and a fibrosis-inducing agent or a composition comprising a fibrosis-inducing agent, wherein the agent induces fibrosis; a device, comprising a male or female sterilization implant and a fibrosis-inducing agent or a composition comprising a fibrosis-inducing agent, wherein the agent induces fibrosis; a device, comprising an implant for treating or preventing urinary incontinence device and a fibrosis-inducing agent or a composition comprising a fibrosis-inducing agent, wherein the agent induces fibrosis; a device, comprising an implant for treating or preventing gastroesophageal reflux disease (GERD) and a fibrosis-inducing agent or a composition comprising a fibrosis-inducing agent, wherein the agent induces fibrosis; a device, comprising an implant for treating or preventing obesity and a fibrosis-inducing agent or a composition comprising a fibrosis-inducing agent, wherein the agent induces fibrosis; a device, comprising an implant for treating or preventing fecal incontinence device and a fibrosis-inducing agent or a composition comprising a fibrosis-inducing agent, wherein the agent induces fibrosis; a device, comprising an embolization implant and a fibrosis-inducing agent or a composition comprising a fibrosis-inducing agent, wherein the agent induces fibrosis; a device, comprising a soft palate implant and a fibrosis-inducing agent or a composition comprising a fibrosis-inducing agent, wherein the agent induces fibrosis; a device, comprising a hernia repair mesh implant and a fibrosis-inducing agent or a composition comprising a fibrosis-inducing agent, wherein the agent induces fibrosis; and a device, comprising a stent graft and a fibrosis-inducing agent or a composition comprising a fibrosis-inducing agent, wherein the agent induces fibrosis. These and other devices are described in more detail herein.

In each of the aforementioned devices, in separate aspects the present invention provides that the agent is: an arterial vessel wall irritan; selected from the group consisting of talcum powder, metallic beryllium and oxides thereof, copper, silk, silica, crystalline silicates, talc, quartz dust, and ethanol; a component of extracellular matrix selected from fibronectin, collagen, fibrin, or fibrinogen; a polymer is selected from the group consisting of polylysine, poly(ethylene-co-vinylacetate), chitosan, N-carboxybutylchitosan, and RGD proteins; vinyl chloride or a polymer of vinyl chloride; an adhesive selected from the group consisting of cyanoacrylates and crosslinked poly(ethylene glycol)-methylated collagen; an inflammatory cytokine (e.g., TGFβ, PDGF, VEGF, bFGF, TNFα, NGF, GM-CSF, IGF-a, IL-1, IL-1-β, IL-8, IL-6, and growth hormone); connective tissue growth factor (CTGF); a bone morphogenic protein (BMP) (e.g., BMP-2, BMP-3, BMP-4, BMP-5, BMP-6, or BMP-7); leptin, and bleomycin or an analogues or derivative thereof. Optionally, the device may additionally comprise a proliferative agent that stimulates cellular proliferation. Examples of proliferative agents include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

In additional aspects, for each of the aforementioned devices combined with each of the aforementioned agents, it is, for each combination, independently disclosed that the agent may be present in a composition along with a polymer. In one embodiment of this aspect, the polymer is biodegradable. In another embodiment of this aspect, the polymer is non-biodegradable. Other features and characteristics of the polymer, which may serve to describe the present invention for every combination of device and agents described above, are set forth in greater detail herein.

In another aspect, the invention provides a composition, comprising a fibrosis-inducing agent and a bulking agent, wherein the fibrosis-inducing agent induces fibrosis. In another aspect, the invention provides a composition, comprising a fibrosis-inducing agent and a sealant, wherein the agent induces fibrosis. Exemplary fibrosis-inducing agents include, without limitation: an arterial vessel wall irritant selected from the group consisting of talcum powder, metallic beryllium and oxides thereof, copper, silk, silica, crystalline silicates, talc, quartz dust, and ethanol; a component of extracellular matrix selected from fibronectin, collagen, fibrin, or fibrinogen; a polymer selected from polylysine, poly(ethylene-co-vinylacetate), chitosan, N-carboxybutylchitosan, and RGD proteins; vinyl chloride or a polymer of vinyl chloride; an adhesive selected from the group consisting of cyanoacrylates and crosslinked poly(ethylene glycol)-methylated collagen; an inflammatory cytokine (e.g., TGFβ, PDGF, VEGF, bFGF, TNFα, NGF, GM-CSF, IGF-a, IL-1, IL-8, IL-6, and growth hormone); CTGF; BMP (e.g., BMP-2, BMP-3, BMP-4, BMP-5, BMP-6, or BMP-7); and bleomycin or an analogue or derivative thereof. Optionally, the device may additionally comprise an agent that stimulates cellular proliferation. Examples of proliferative agents include: dexamethasone, isotretinoin, 17-β-estradiol, estradiol, diethylstibesterol, cyclosporine A, all-trans retinoic acid (ATRA), and analogues and derivatives thereof. Bulking agents and sealants are described herein.

In addition to devices, the present invention also provides methods. For example, in additional aspects of the present invention, for each of the aforementioned devices, and for each of the aforementioned combinations of the devices with the fibrosis-inducing agents, the present invention provides methods whereby a specified device is implanted into an animal, and a specified agent associated with the device induces fibrosis that may otherwise not occur or increases fibrosis in a statistically significant manner. Each of the devices identified herein may be a "specified device", and each of the fibrosis-inducing agents identified herein may be a "fibrosis-inducing agent", where the present invention provides, in independent embodiments, for each possible combination of the device and the agent.

The agent may be associated with the device prior to the device being placed within the animal. For example, the agent (or composition comprising the agent) may be coated onto an implant, and the resulting device then placed within the animal. In addition, or alternatively, the agent may be independently placed within the animal in the vicinity of where the device is to be, or is being, placed within the animal. For example, the agent may be sprayed or otherwise placed onto the tissue that can be contacting the medical implant or may otherwise undergo scarring. To this end, the present invention provides, in independent aspects: a method for treating or preventing spider veins or varicose veins, comprising injecting into the vein a composition comprising a fibrosis-inducing agent; a method for sterilizing a female patient, comprising injecting into a Fallopian tube a composition comprising a fibrosis-inducing agent; a method for treating or preventing urinary incontinence, comprising injecting into an urethra a composition comprising a fibrosis-inducing agent; a method for treating or preventing GERD, comprising injecting into a lower esophageal sphincter a composition comprising a fibrosis-inducing agent; a method for treating or preventing fecal incontinence, comprising injecting into an anal sphincter a composition comprising a fibrosis-inducing agent; a method for treating or preventing snoring or sleep apnea, comprising injecting into a soft palate a composition comprising a fibrosis-inducing agent; a method for blocking an artery, comprising injecting into the artery a composition comprising a fibrosis-inducing agent; a method for sealing an air leak in a lung, comprising spraying onto the surface of the lung a composition comprising a fibrosis-inducing agent; a method for treating or preventing diverticulitis, comprising delivering into a diverticulum a composition comprising a fibrosis-inducing agent; a method for treating or preventing arthritis, comprising injecting into a damaged joint a composition comprising a fibrosis-inducing agent; a method for repairing a damaged shoulder capsule, comprising spraying onto an anterior capsule a composition comprising a fibrosis-inducing agent; a method for repairing a damaged tendon or ligament, comprising spraying onto the tendon or ligament a composition comprising a fibrosis-inducing agent; a method for treating a damaged spinal disc, comprising injecting into an intervertebral disc space a composition comprising a fibrosis-inducing agent.

In additional aspects, for each of the aforementioned methods used in combination with each of the aforementioned agents, it is, for each combination, independently disclosed that the agent may be present in a composition along with a polymer. In one embodiment of this aspect, the polymer is biodegradable. In another embodiment of this aspect, the polymer is non-biodegradable. Other features and characteristics of the polymer, which may serve to describe the present invention for every combination of device and agents described above, are set forth in greater detail herein. In addition to, or in lieu of the polymer, the composition may contain collagen.

These and other aspects of the present invention can become evident upon reference to the following detailed description. In addition, various references are set forth herein which describe in more detail certain procedures and/or compositions (e.g., polymers), and are therefore incorporated by reference in their entirety.

DETAILED DESCRIPTION OF THE INVENTION

Figure 1:
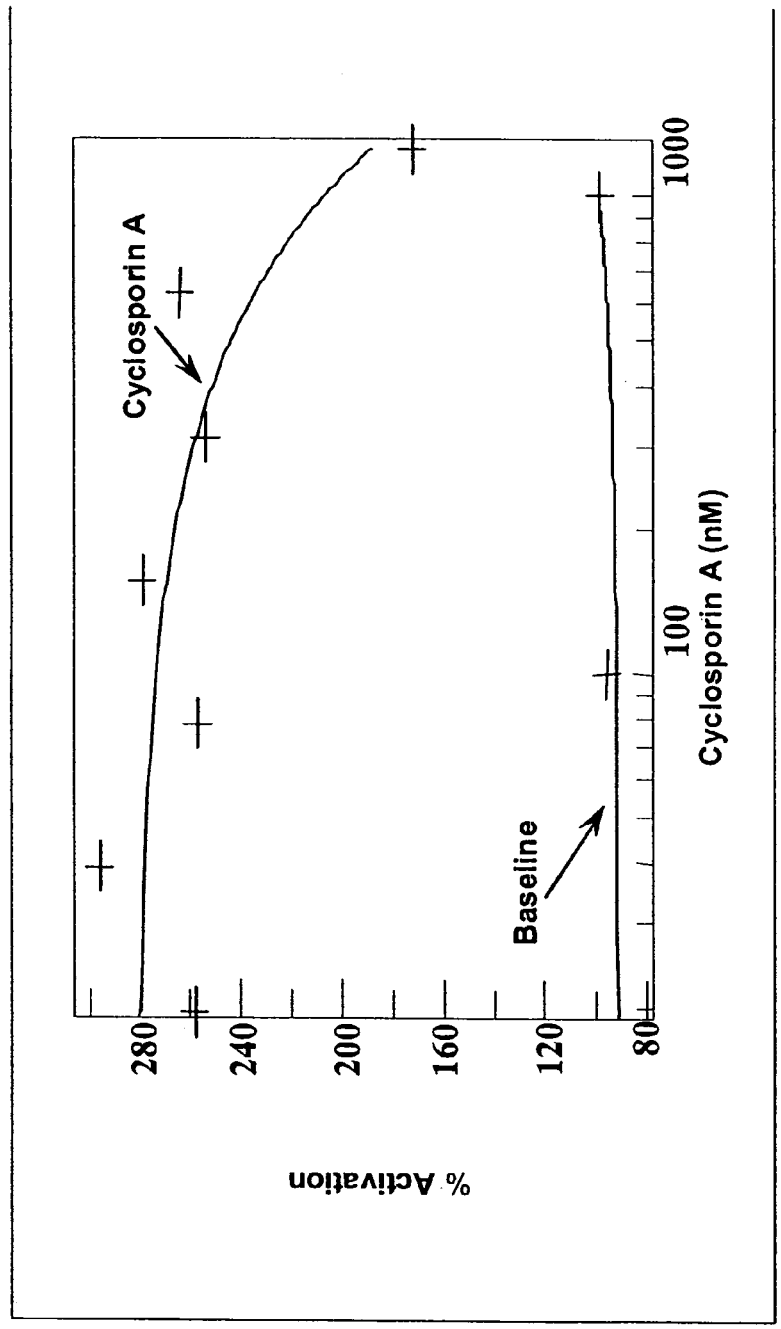
FIG. 1 is a graph showing the effect of cyclosporine A on proliferation of human smooth muscle cells.

The present invention discloses pharmaceutical agents which promote one or more aspects of the production of fibrous (scar) tissue or tissue regeneration. Furthermore, compositions and methods are described for coating medical devices and implants with drug-delivery compositions such that the pharmaceutical agent is delivered in therapeutic levels over a period sufficient for fibrosis and healing to occur. The present invention also describes various compositions and methods for enhancing the production of scar tissue adjacent to or on the surface of the implant are described. Numerous specific implants and devices are described that are capable of producing superior clinical results as a result of being coated with agents that promote scarring and healing, as well as other related advantages.

Definitions

Prior to setting forth the invention, it may be helpful to an understanding thereof to first set forth definitions of certain terms that is used hereinafter.

"Medical Device" (or "implant," or "medical implant," or implantable medical device") refers to any object placed in the body for the purpose of restoring physiological function, reducing/alleviating symptoms associated with disease, and/or repairing/replacing damaged or diseased organs and tissues. While normally composed of biologically compatible synthetic materials (e.g., medical-grade stainless steel, titanium and other metals, polymers such as polyurethane, silicon, polylactic acid (PLA), polyglycolic acid (PLGA) and other materials), other materials that are exogenous, some medical devices and implants include materials derived from animals (e.g., "xenografts" such as whole animal organs; animal tissues such as heart valves; naturally occurring or chemically-modified molecules such as collagen, hyaluronic acid, proteins, carbohydrates and others), human donors (e.g., "allografts" such as whole organs; tissues such as bone grafts, skin grafts and others), or from the patients themselves (e.g., "autografts" such as saphenous vein grafts, skin grafts, tendon/ligament/muscle transplants). Medical devices of particular utility in the present invention include, but are not restricted to, orthopaedic implants (artificial joints, ligaments and tendons, screws, plates, and other implantable hardware), dental implants, intravascular implants (particularly arterial and venous occlusion devices and implants; vascular destructive implants), male and female contraceptive or sterilization devices and implants, implantable tissue bulking agents for incontinence (esophageal, urethral, anal), soft palate implants, embolization agents, pulmonary sealants, surgical meshes (e.g., hernia repair meshes, tissue scaffolds), fistula treatments, and spinal implants (e.g., artificial intervertebral discs, spinal fusion devices, etc.).

"Fibrosis," "Scarring," or "Fibrotic Response" refers to the formation of fibrous tissue in response to injury or medical intervention. Therapeutic agents which promote (also referred to interchangeably herein as "induce," "stimulate," "cause," and the like) fibrosis or scarring are referred to interchangeably herein as "fibrosis-inducing agents," "scarring agents," "fibrosing agents," "adhesion-inducing agents," and the like, where these agents do so through one or more mechanisms including: inducing or promoting angiogenesis, stimulating migration or proliferation of connective tissue cells (such as fibroblasts, smooth muscle cells, vascular smooth muscle cells), inducing ECM production, and/or promoting tissue remodeling. In addition, numerous therapeutic agents described in this invention can have the additional benefit of also promoting tissue regeneration (the replacement of injured cells by cells of the same type).

"Sclerosing" refers to a tissue reaction in which an irritant is applied locally to a tissue which results in an inflammatory reaction and is followed by scar tissue formation at the site of irritation. A pharmaceutical agent that induces or promotes sclerosis is referred to as a "sclerosant," or a "sclerosing agent." Representative examples of sclerosants include ethanol, dimethyl sulfoxide, surfactants (e.g., Triton X, sorbitan monolaurate, sorbitan sesquioleate, glycerol monostearate and polyoxyethylene, polyoxyethylene cetyl ether, etc.), sucrose, sodium chloride, dextrose, glycerin, minocycline, tetracycline, doxycycline, polidocanol, sodium tetradecyl sulfate, sodium morrhuate, ethanolamine, phenol, sarapin and sotradecol.

"Release of an agent" refers to any statistically significant presence of the agent, or a subcomponent thereof, which has disassociated from the implant/device.

Any concentration ranges, percentage range, or ratio range recited herein are to be understood to include concentrations, percentages or ratios of any integer within that range and fractions thereof, such as one tenth and one hundredth of an integer, unless otherwise indicated. Also, any number range recited herein relating to any physical feature, such as polymer subunits, size or thickness, are to be understood to include any integer within the recited range, unless otherwise indicated. It should be understood that the terms "a" and "an" as used above and elsewhere herein refer to "one or more" of the enumerated components. As used herein, the term "about" means ±15%.

As discussed above, the present invention provides compositions, methods and devices relating to medical implants, which greatly increase their ability to scar in place and incorporate into the surrounding tissue. Described in more detail below are methods for constructing medical implants, compositions and methods for generating medical implants which promote fibrosis, and methods for utilizing such medical implants.

A. Medical Implants

Medical implants of the present invention contain and/or are adapted to release an agent which induces or promotes adhesion between the implant and tissue or a fibrotic reaction. In certain embodiments, the medical implant, when placed in to a tissue, releases an agent that induces or promotes adhesion between the implant and the tissue or a fibrotic reaction. In other embodiments, the medical implant contains or is made of a fibrosing agent, but does not release the fibrosing agent. In such embodiments, the fibrosing agent contained in the medical implant induces or promotes fibrosis by direct contact of the agent to the tissue where the implant is placed.

Representative examples of medical implants include: orthopaedic implants (artificial joints, ligaments and tendons, screws, plates, and other implantable hardware), dental implants, intravascular implants (particularly arterial and venous occlusion devices and implants; vascular destructive implants), male and female contraceptive or sterilization devices and implants, implantable tissue bulking agents for incontinence (esophageal, urethral, anal), soft palate implants, embolization agents, pulmonary sealants, surgical meshes (e.g., hernia repair meshes, tissue scaffolds), fistula treatments, and spinal implants (e.g., artificial intervertebral discs, spinal fusion devices, etc.).

B. Therapeutic Agents

Briefly, numerous therapeutic agents (also referred to herein as 'therapeutic agents' or 'drugs') have been identified that can be utilized within the context of the present invention. The agent may be formulated with one or more other materials, e.g., a polymeric carrier, where formulations are discussed below. Many suitable therapeutic agents are specifically identified herein, and others may be readily determined based upon in vitro and in vivo (animal) models such as those provided in Examples 13–20; 33–34; and 40. Therapeutic agents which promote fibrosis can be identified through in vivo models such as the rat carotid artery model (Examples 17–20).

In one aspect, the fibrosis or adhesion-inducing agent is silk. Silk refers to a fibrous protein, and may be obtained from a number of sources, typically spiders and silkworms. Typical silks contain about 75% of actual fiber, referred to as fibroin, and about 35% sericin, which is a gummy protein that holds the filaments together. Silk filaments are generally very fine and long—as much as 300–900 meters long. There are several species of domesticated silkworm that are used in commercial silk production, however, *Bombyx mori* is the most common, and most silk comes from this source. Other suitable silkworms include *Philosamia cynthia ricini, Antheraea yamamai, Antheraea pernyi,* and *Antheraea mylitta*. Spider silk is relatively more difficult to obtain, however, recombinant techniques hold promise as a means to obtain spider silk at economical prices (see, e.g., U.S. Pat. Nos. 6,268,169; 5,994,099; 5,989,894; and 5,728,810, which are exemplary only). Biotechnology has allowed researchers to develop other sources for silk production, including animals (e.g., goats) and vegetables (e.g., potatoes). Silk from any of these sources may be used in the present invention.

A commercially available silk protein is available from Croda, Inc., of Parsippany, N.J., and is sold under the trade names CROSILK LIQUID (silk amino acids), CROSILK 10,000 (hydrolyzed silk), CROSILK POWDER (powdered silk), and CROSILKQUAT (cocodiammonium hydroxypropyl silk amino acid). Another example of a commercially available silk protein is SERICIN, available from Pentapharm, LTD, a division of Kordia, BV, of the Netherlands. Further details of such silk protein mixtures can be found in U.S. Pat. No. 4,906,460, to Kim, et al., assigned to Sorenco. Silk useful in the present invention includes natural (raw) silk, hydrolyzed silk, and modified silk, i.e., silk that has undergone a chemical, mechanical, or vapor treatment, e.g., acid treatment or acylation (see, e.g., U.S. Pat. No. 5,747,015).

Raw silk is typically twisted into a strand sufficiently strong for weaving or knitting. Four different types of silk thread may be produced by this procedure: organzine, crepe, tram and thrown singles. Organzine is a thread made by giving the raw silk a preliminary twist in one direction and then twisting two of these threads together in the opposite direction. Crepe is similar to organzine but is twisted to a much greater extent. Twisting in only one direction two or more raw silk threads makes tram. Thrown singles are individual raw silk threads that are twisted in only one direction. Any of these types of silk threads may be used in the present invention.

The silk used in the present invention may be in any suitable form that allows the silk to be joined with the medical implant, e.g., the silk may be in thread or powder-based forms. The silk can be prepared in the powdered form by several different methods. For example the silk can be milled (e.g., cryomill) into a powdered form. Alternatively the silk can be dissolved in a suitable solvent (e.g., HFIP or 9M LiBr) and then sprayed (electrospray, spray dry) or added to a non-solvent to produce a powder. Furthermore, the silk may have any molecular weight, where various molecular weights are typically obtained by the hydrolysis of natural silk, where the extent and harshness of the hydrolysis conditions determines the product molecular weight. For example, the silk may have an average (number or weight) molecular weight of about 200 to 5,000. See, e.g., JP-B-59-29199 (examined Japanese patent publication) for a description of conditions that may be used to hydrolyze silk.

A discussion of silk may be found in the following documents, which are exemplary only: Hinman, M. B., et al. "Synthetic spider silk: a modular fibre" *Trends in Biotechnology,* 2000, 18(9) 374–379; Vollrath, F. and Knight, D. P. "Liquid crystalline spinning of spider silk" *Nature,* 2001, 410(6828) 541–548; and Hayashi, C. Y., et al. "Hypotheses that correlate the sequence, structure, and mechanical properties of spider silk proteins" *Int. J. Biol. Macromolecules,* 1999, 24(2–3), 265–270; and U.S. Pat. No. 6,427,933.

Other representative examples of fibrosis and adhesion-inducing agents include irritants (e.g., talc, talcum powder, copper, metallic beryllium (or its oxides), wool (e.g., animal wool, wood wolol, and synthetic wool), quartz dust, silica, crystalline silicates), polymers (e.g., polylysine, polyurethanes, poly(ethylene terephthalate), polytetrafluoroethylene (PTFE), poly(alkylcyanoacrylates), and poly(ethylene-co-vinylacetate)); vinyl chloride and polymers of vinyl chloride; peptides with high lysine content; growth factors and inflammatory cytokines involved in angiogenesis, fibroblast migration, fibroblast proliferation, ECM synthesis and tissue remodeling, such as epidermal growth factor (EGF) family, transforming growth factor-α (TGF-α), transforming growth factor-β (TGF-9-1, TGF-9-2, TGF-9-3, platelet-derived growth factor (PDGF), fibroblast growth factor (acidic—aFGF; and basic—bFGF), fibroblast stimulating factor-1, activins, vascular endothelial growth factor (including VEGF-2, VEGF-3, VEGF-A, VEGF-B, VEGF-C, placental growth factor—PIGF), angiopoietins, insulin-like growth factors (IGF), hepatocyte growth factor (HGF), connective tissue growth factor (CTGF), myeloid colony-stimulating factors (CSFs), monocyte chemotactic protein, granulocyte-macrophage colony-stimulating factors (GM-CSF), granulocyte colony-stimulating factor (G-CSF), macrophage colony-stimulating factor (M-CSF), erythropoietin, interleukins (particularly IL-1, IL-8, and IL-6), tumor necrosis factor-α (TNF9), nerve growth factor (NGF), interferon-α, interferon-β, histamine, endothelin-1, angiotensin II, growth hormone (GH), and synthetic peptides, analogues or derivatives of these factors are also suitable for release from specific implants and devices to be described later. Other examples include CTGF (connective tissue growth factor); inflammatory microcrystals (e.g., crystalline minerals such as crystalline silicates); bromocriptine, methylsergide, methotrexate, chitosan, N-carboxybutyl chitosan, carbon tetrachloride, thioacetamide, fibrosin, ethanol, bleomycin, naturally occurring or synthetic peptides containing the Arg-Gly-Asp (RGD) sequence, generally at one or both termini (see e.g., U.S. Pat. No. 5,997,895), and tissue adhesives, such as cyanoacrylate and crosslinked poly(ethylene glycol)-methylated collagen compositions, such as described below. Other examples of fibrosis-inducing agents include bone morphogenic proteins (e.g., BMP-2, BMP-3, BMP-4, BMP-5, BMP-6 (Vgr-1), BMP-7 (OP-1), BMP-8, BMP-9, BMP-10, BMP-11, BMP-12, BMP-13, BMP-14, BMP-15, and BMP-16. Of these, BMP-2, BMP-3, BMP-4, BMP-5, BMP-6, and BMP-7 are of particular utility. Bone morphogenic proteins are described, for example, in U.S. Pat. Nos. 4,877,864; 5,013,649; 5,661,007; 5,688,678; 6,177,406; 6,432,919; and 6,534,268 and Wozney, J. M., et al. (1988) *Science:* 242 (4885); 1528–1534.

Other representative examples of fibrosis-inducing agents include crosslinked compositions that comprise amino-functional groups. For example, amino-functionalized polyethylene glycol (e.g., 4-armed tetra-amino PEG [10k]) can be reacted with a 4-armed NHS functionalized PEG (e.g., pentaerythritol poly(ethylene glycol)ether tetra-succinimidyl glutarate) under basic buffer conditions. In another example a 4-armed thiol functionalized PEG (e.g., pentaerythritol poly(ethylene glycol)ether tetra-thiol) can be substituted for the 4-arm amino-functionalized PEG such that the amount of amino functional groups in the final composition can be varied. These reagents can be mixed at the time of application to provide an in situ forming crosslinked hydrogel. These reagents could be premixed to produce the crosslinked material. The material can be made in various forms such as rods, tubes, films, slabs or spheres. The crosslinked material could also be milled to produce a particulate material. These materials can be dried (e.g., air, vacuum, freeze-dried) and used as a dry powdered material. Alternatively the materials can be hydrated just prior to application. These materials can further comprise one of the fibrosis-inducing agents described herein.

Other representative examples of fibrosis-inducing agents include components of extracellular matrix (e.g., fibronectin, fibrin, fibrinogen, collagen (e.g., bovine collagen), fibrillar and non-fibrillar collagen, adhesive glycoproteins, proteoglycans (e.g., heparin sulfate, chondroitin sulfate, dermatan sulfate), hyaluronan, secreted protein acidic and rich in cysteine (SPARC), thrombospondins, tenacin, and cell adhesion molecules (including integrins, vitronectin, fibronectin, laminin, hyaluronic acid, elastin, bitronectin), proteins found in basement membranes, and fibrosin) and inhibitors of matrix metalloproteinases, such as TIMPs (tissue inhibitors of matrix metalloproteinases) and synthetic TIMPs, e.g., marimistat, batimistat, doxycycline, tetracycline, minocycline, TROCADE, Ro-1130830, CGS 27023A, and BMS-275291.

Within various embodiments of the invention, a device is coated with a first composition that promotes fibrosis (and/or restenosis) and a second composition or compound which acts to have an inhibitory effect on pathological processes in or around the treatment site. Representative examples of agents which can inhibit pathological processes in the treatment site include, but not limited to, the following classes of compounds: anti-inflammatory agents (e.g., dexamethasone, cortisone, fludrocortisone, prednisone, prednisolone, 6α-methylprednisolone, triamcinolone, and betamethasone); Matrix Metalloproteinase (MMP) inhibitors (e.g., marimistat, batimistat, TIMP's representative examples of which are included in U.S. Pat. Nos. 5,665,777; 5,985,911; 6,288,261; 5,952,320; 6,441,189; 6,235,786; 6,294,573; 6,294,539; 6,563,002; 6,071,903; 6,358,980; 5,852,213; 6,124,502; 6,160,132; 6,197,791; 6,172,057; 6,288,086; 6,342,508; 6,228,869; 5,977,408; 5,929,097; 6,498,167; 6,534,491; 6,548,524; 5,962,481; 6,197,795; 6,162,814; 6,441,023; 6,444,704; 6,462,073; 6,162,821; 6,444,639; 6,262,080; 6,486,193; 6,329,550; 6,544,980; 6,352,976; 5,968,795; 5,789,434; 5,932,763; 6,500,847; 5,925,637; 6,225,314; 5,804,581; 5,863,915; 5,859,047; 5,861,428; 5,886,043; 6,288,063; 5,939,583; 6,166,082; 5,874,473; 5,886,022; 5,932,577; 5,854,277; 5,886,024; 6,495,565; 6,642,255; 6,495,548; 6,479,502; 5,696,082; 5,700,838; 6,444,639; 6,262,080; 6,486,193; 6,329,550; 6,544,980; 6,352,976; 5,968,795; 5,789,434; 5,932,763; 6,500,847; 5,925,637; 6,225,314; 5,804,581; 5,863,915; 5,859,047; 5,861,428; 5,886,043; 6,288,063; 5,939,583; 6,166,082; 5,874,473; 5,886,022; 5,932,577; 5,854,277; 5,886,024; 6,495,565; 6,642,255; 6,495,548; 6,479,502; 5,696,082; 5,700,838; 5,861,436; 5,691,382; 5,763,621; 5,866,717; 5,902,791; 5,962,529; 6,017,889; 6,022,873; 6,022,898; 6,103,739; 6,127,427; 6,258,851; 6,310,084; 6,358,987; 5,872,152; 5,917,090; 6,124,329; 6,329,373; 6,344,457; 5,698,706; 5,872,146; 5,853,623; 6,624,144; 6,462,042; 5,981,491; 5,955,435; 6,090,840; 6,114,372; 6,566,384; 5,994,293; 6,063,786; 6,469,020; 6,118,001; 6,187,924; 6,310,088; 5,994,312; 6,180,611; 6,110,896; 6,380,253; 5,455,262; 5,470,834; 6,147,114; 6,333,324; 6,489,324; 6,362,183; 6,372,758; 6,448,250; 6,492,367; 6,380,258; 6,583,299; 5,239,078; 5,892,112; 5,773,438; 5,696,147; 6,066,662; 6,600,057; 5,990,158; 5,731,293; 6,277,876; 6,521,606; 6,168,807; 6,506,414; 6,620,813; 5,684,152; 6,451,791; 6,476,027; 6,013,649; 6,503,892; 6,420,427; 6,300,514; 6,403,644; 6,177,466; 6,569,899; 5,594,006; 6,417,229; 5,861,510; 6,156,798; 6,387,931; 6,350,907; 6,090,852; 6,458,822; 6,509,337; 6,147,061; 6,114,568; 6,118,016; 5,804,593; 5,847,153; 5,859,061; 6,194,451; 6,482,827; 6,638,952; 5,677,282; 6,365,630; 6,130,254; 6,455,569; 6,057,369; 6,576,628; 6,110,924; 6,472,396; 6,548,667; 5,618,844; 6,495,578; 6,627,411; 5,514,716; 5,256,657; 5,773,428; 6,037,472; 6,579,890; 5,932,595; 6,013,792; 6,420,415; 5,532,265; 5,639,746; 5,672,598; 5,830,915; 6,630,516; 5,324,634; 6,277,061; 6,140,099; 6,455,570; 5,595,885; 6,093,398; 6,379,667; 5,641,636; 5,698,404; 6,448,058; 6,008,220; 6,265,432; 6,169,103; 6,133,304; 6,541,521; 6,624,196; 6,307,089; 6,239,288; 5,756,545; 6,020,366; 6,117,869; 6,294,674; 6,037,361; 6,399,612; 6,495,568; 6,624,177; 5,948,780; 6,620,835; 6,284,513; 5,977,141; 6,153,612; 6,297,247; 6,559,142; 6,555,535; 6,350,885; 5,627,206; 5,665,764; 5,958,972; 6,420,408; 6,492,422; 6,340,709; 6,022,948; 6,274,703; 6,294,694; 6,531,499; 6,465,508; 6,437,177; 6,376,665; 5,268,384; 5,183,900; 5,189,178; 6,511,993; 6,617,354; 6,331,563; 5,962,466; 5,861,427; 5,830,869; and 6,087,359), cytokine inhibitors (chlorpromazine, mycophenolic acid, rapamycin, 1α-hydroxy vitamin $D_3$), IMPDH (inosine monophosplate dehydrogenase) inhibitors (e.g., mycophenolic acid, ribaviran, aminothiadiazole, thiophenfurin, tiazofurin, viramidine) (Representative examples are included in U.S. Pat. Nos. 5,536,747; 5,807,876; 5,932,600; 6,054,472; 6,128,582; 6,344,465; 6,395,763; 6,399,773; 6,420,403; 6,479,628; 6,498,178; 6,514,979; 6,518,291; 6,541,496; 6,596,747; 6,617,323; and 6,624,184, U.S. Patent Application Nos. 2002/0040022A1, 2002/0052513A1, 2002/0055483A1, 2002/0068346A1, 2002/0111378A1, 2002/0111495A1, 2002/0123520A1, 2002/0143176A1, 2002/0147160A1, 2002/0161038A1, 2002/0173491A1, 2002/0183315A1, 2002/0193612A1, 2003/0027845A1, 2003/0068302A1, 2003/0105073A1, 2003/0130254A1, 2003/0143197A1, 2003/0144300A1, 2003/0166201A1, 2003/0181497A1, 2003/0186974A1, 2003/0186989A1, and 2003/0195202A1, and PCT Publication Nos. WO 00/24725A1, WO 00/25780A1, WO 00/26197A1, WO 00/51615A1, WO 00/56331A1, WO 00/73288A1, WO 01/00622A1, WO 01/66706A1, WO 01/79246A2, WO 01/81340A2, WO 01/85952A2, WO 02/16382A1, WO 02/18369A2, WO 02/051814A1, WO 02/057287A2, WO 02/057425A2, WO 02/060875A1, WO 02/060896A1, WO 02/060898A1, WO 02/068058A2, WO 03/020298A1, WO 03/037349A1, WO 03/039548A1, WO 03/045901A2, WO 03/047512A2, WO 03/053958A1, WO 03/055447A2, WO 03/059269A2, WO 03/063573A2, WO 03/087071A1, WO 99/001545A1, WO 97/40028A1, WO 97/41211A1, WO 98/40381A1, and WO 99/55663A1), p38 MAP kinase inhibitors (MAPK) (e.g., GW-2286, CGP-52411, BIRB-798, SB220025, RO-320-1195, RWJ-67657, RWJ-68354, SCIO-469) (Representative examples are included in U.S. Pat. Nos. 6,300,347; 6,316,464; 6,316,466; 6,376,527; 6,444,696; 6,479,507; 6,509,361; 6,579,874, and 6,630,485, and U.S. Patent Application Publication Nos. 2001/0044538A1, 2002/0013354A1, 2002/0049220A1, 2002/0103245A1, 2002/0151491A1, 2002/0156114A1, 2003/0018051A1, 2003/0073832A1, 2003/0130257A1, 2003/0130273A1, 2003/0130319A1, 2003/0139388A1, 2003/0139462A1, 2003/0149031A1, 2003/0166647A1, and 2003/0181411A1, and PCT Publication Nos. WO 00/63204A2, WO 01/21591A1, WO 01/35959A1, WO 01/74811A2, WO 02/18379A2, WO 02/064594A2, WO 02/083622A2, WO 02/094842A2, WO 02/096426A1, WO 02/101015A2, WO 02/103000A2, WO 03/008413A1, WO 03/016248A2, WO 03/020715A1, WO 03/024899A2, WO 03/031431A1, WO 03/040103A1, WO 03/053940A1, WO 03/053941A2, WO 03/063799A2, WO 03/079986A2, WO 03/080024A2, WO 03/082287A1, WO 97/44467A1, WO 99/01449A1, and WO 99/58523A1), and immunomodulatory agents (rapamycin, everolimus, ABT-578, azathioprine azithromycin, analogues of rapamycin, tacrolimus and derivatives thereof (e.g., EP 0184162B1 and those described in U.S. Pat. No. 6,258,823) and everolimus and derivatives thereof (e.g., U.S. Pat. No. 5,665,772). Further representative examples of sirolimus analogues and derivatives include ABT-578 and those found in PCT Publication Nos. WO 97/10502, WO 96/41807, WO 96/35423, WO 96/03430, WO 96/00282, WO 95/16691, WO 95/15328, WO 95/07468, WO 95/04738, WO 95/04060, WO 94/25022, WO 94/21644, WO 94/18207, WO 94/10843, WO 94/09010, WO 94/04540, WO 94/02485, WO 94/02137, WO 94/02136, WO 93/25533, WO 93/18043, WO 93/13663, WO 93/11130, WO 93/10122, WO 93/04680, WO 92/14737, and WO 92/05179 and in U.S. Pat. Nos. 6,342,507; 5,985,890; 5,604,234; 5,597,715; 5,583,139; 5,563,172; 5,561,228; 5,561,137; 5,541,193; 5,541,189; 5,534,632; 5,527,907; 5,484,799; 5,457,194; 5,457,182; 5,362,735; 5,324,644; 5,318,895; 5,310,903; 5,310,901; 5,258,389; 5,252,732; 5,247,076; 5,225,403; 5,221,625; 5,210,030; 5,208,241; 5,200,411; 5,198,421; 5,147,877; 5,140,018; 5,116,756; 5,109,112; 5,093,338; and 5,091,389.

Other examples of drugs that may be included in the compositions and devices of the invention include tyrosine kinase inhibitors, such as imantinib, ZK-222584, CGP-52411, CGP-53716, NVP-K980-NX, CP-127374, CP-564959, PD-171026, PD-173956, PD-180970, SU-0879, and SKI-606. Other examples of drugs that may be included in the compositions and devices of the invention include MMP inhibitors such as nimesulide, PKF-241-466, PKF-242-484, CGS-27023A, SAR-943, primomastat, SC-77964, PNU-171829, AG-3433, PNU-142769, SU-5402, and dexlipotam. Other examples of drugs that may be included in the compositions and devices of the invention include p38 MAP kinase inhibitors such as CGH-2466 and PD-98-59. Other examples of of drugs that may be included in the compositions and devices of the invention include immunosuppressants such as argyrin B, macrocyclic lactone, ADZ-62-826, CCl-779, tilomisole, amcinonide, FK-778, AVE-1726, and MDL-28842. Other examples of cytokine inhibitors include TNF-484A, PD-172084, CP-293121, CP-353164, and PD-168787. Other examples of drugs that may be included in the compositions and devices of the invention include include NFKB inhibitors, such as, AVE-0547, AVE-0545, and IPL-576092. Other examples of drugs that may be included in the compositions and devices of the invention include include HMGCoA reductase inhibitors, such as, pravestatin, atorvastatin, fluvastatin, dalvastatin, glenvastatin, pitavastatin, CP-83101, U-20685, apoptosis antagonist (e.g., troloxamine, TCH-346 (N-methyl-N-propargyl-10-aminomethyl-dibenzo(b,f)oxepin), caspase inhibitors (e.g., PF-5901 (benzenemethanol, alpha-pentyl-3-(2-quinolinylmethoxy)-), and JNK inhibitor (e.g., AS-602801).

Within various embodiments of the invention, a device incorporates or is coated with a composition which promotes fibrosis (and/or restenosis), as well as a composition or compound which acts to stimulate cellular proliferation. Representative examples of agents that stimulate cellular proliferation include, pyruvic acid, naltrexone, leptin, D-glucose, insulin, amlodipine, alginate oligosaccharides, minoxidil, dexamethasone, isotretinoin (13-cis retinoic acid), 17-β-estradiol, estradiol, 1-a-25 dihydroxyvitamin $D_3$, diethylstibesterol, cyclosporine A, L-NAME (L-NG-nitroarginine methyl ester (hydrochloride)), all-trans retinoic acid (ATRA), and analogues and derivatives thereof. Other examples of agents that stimulate cellular proliferation include: sphingosine 1-phosphate receptor agonist (e.g., FTY-720 (1,3-propanediol, 2-amino-2-(2-(4-octylphenyl) ethyl)-, hydrochloride; immunostimulants, such as Imupedone (methanone, [5-amino-2-(4-methyl-1-piperidinyl)phenyl](4-chlorophenyl)-, DIAPEP227 synthetic peptide (Peptor Ltd., Israel)); and nerve growth factor agonist, e.g., NG-012 (5H,9H,13H,21H,25H,-dibenzo[k,u][1,5,9,15,19] pentaoxacyclotetracosin-5,9,13,21,25-pentone, 7,8,11,12, 15,16,23,24,27,28-decahydro-2,4,18,20-tetrahydroxy-11-(hydroxymethyl)-7,15,23,27-tetramethyl-,NG-121, SS-701 (2,2':6',2"-terpyridine, 4'-(4-methylphenyl)-, trihydrochloride, AMPAlex (piperidine, 1-(6-quinoxalinylcarbonyl)-, RG H-2716 (8-[4,4-bis(4-fluorophenyl)butyl]-3-(1,1-dimethylethyl)-4-methylene-1-oxa-3,8-diaza-spiro[4.5]decan-2-one, and TDN-345 (1-oxa-3,8-diazaspiro[4.5]decan-2-one, 8-[4,4-bis(4-fluorophenyl)butyl]-3-(1,1-dimethylethyl)-4-methylene-).

Within various embodiments of the invention, a device incorporates or is coated on one aspect with a composition which promotes fibrosis (and/or restenosis), as well as with a composition or compound which prevents restenosis on another aspect of the device. Representative examples of agents that inhibit restenosis include paclitaxel, sirolimus, everolimus, vincristine, biolimus, mycophenolic acid, ABT-578, cervistatin, simvastatin, methylprednisolone, dexamethasone, actinomycin-D, angiopeptin, L-arginine, estradiol, 17-β-estradiol, tranilast, methotrexate, batimistat, halofuginone, BCP-671, QP-2, lantrunculin D, cytochalasin A, nitric oxide, and analogues and derivatives thereof.

The medical implant may include a fibrosing agent and an anti-thrombotic agent and/or antiplatelet agent, which reduces the likelihood of thrombotic events upon implantation of a medical implant. Within various embodiments of the invention, a device is coated on one aspect with a composition which promotes fibrosis (and/or restenosis), as well as being coated with a composition or compound which prevents thrombosis on another aspect of the device. Representative examples of anti-thrombotic and/or antiplatelet agents include heparin, heparin fragments, organic salts of heparin, heparin complexes (e.g., benzalkonium heparinate, tridodecylammonium heparinate), dextran, sulfonated carbohydrates such as dextran sulphate, coumadin, coumarin, heparinoid, danaparoid, argatroban chitosan sulfate, chondroitin sulfate, danaparoid, lepirudin, hirudin, AMP, adenosine, 2-chloroadenosine, aspirin, phenylbutazone, indomethacin, meclofenamate, hydrochloroquine, dipyridamole, iloprost, streptokinase, and factor Xa inhibitors, such as DX9065a, magnesium, and tissue plasminogen activator. In one aspect, the anti-thrombotic agent is a modified heparin compound, such as a hydrophobically modified heparin or modified hirudin compound (e.g., stearylkonium heparin, benzalkonium heparin, cetylkonium heparin, or trdodecylmethyl ammonium heparin). Further examples of anti-thrombotic agents include plasminogen, lys-plasminogen, alpha-2-antiplasmin, urokinase, ticlopidine, clopidogrel, glycoprotein IIb/IIIa inhibitors such as abciximab, eptifibatide, and tirogiban. Other agents capable of affecting the rate of clotting include glycosaminoglycans, danaparoid, 4-hydroxycourmarin, warfarin sodium, dicumarol, phenprocoumon, indan-1,3-dione, acenocoumarol, anisindione, and rodenticides including bromadiolone, brodifacoum, diphenadione, chlorophacinone, and pidnone. The thrombogenicity of a medical implant may be reduced by coating the implant with a polymeric formulation that has anti-thrombogenic properties. For example, a medical device may be coated with a hydrophilic polymer gel. The polymer gel can comprise a hydrophilic, biodegradable polymer that is physically removed from the surface of the device over time, thus reducing adhesion of platelets to the device surface. The gel composition can include a polymer or a blend of polymers. Representative examples include alginates, chitosan and chitosan sulfate, hyaluronic acid, dextran sulfate, PLURONIC polymers (e.g., F-127 or F87) and chain extended PLURONIC polymers (BASF Corporation, Mt. Olive, N.J.), various polyester-polyether block copolymers of various configurations (e.g., AB, ABA, or BAB, where A is a polyester such as PLA, PGA, PLGA, PCL or the like), examples of which include MePEG-PLA, PLA-PEG-PLA, and the like). In one embodiment, the anti-thrombotic composition can include a crosslinked gel formed from a combination of molecules (e.g., PEG) having two or more terminal electrophilic groups and two or more nucleophilic groups.

In one aspect, the present invention also provides for the combination of a medical implant (as well as compositions and methods for making medical implants) that includes a fibrosing agent and an anti-infective agent, which reduces the likelihood of infections in medical implants. Infection is a common complication of the implantation of foreign bodies such as medical devices. Foreign materials provide an ideal site for micro-organisms to attach and colonize. It is also hypothesized that there is an impairment of host defenses to infection in the microenvironment surrounding a foreign material. These factors make medical implants particularly susceptible to infection and make eradication of such an infection difficult, if not impossible, in most cases.

The present invention provides agents (e.g., chemotherapeutic agents) that can be incorporated onto or into, or released from, an implantable device, and which have potent antimicrobial activity at extremely low doses. A wide variety of anti-infective agents can be utilized in combination with a fibrosing agent according to the invention. Discussed in more detail below are several representative examples of Chemotehrapeutic/anti-infective agents that can be used: (A) anthracyclines (e.g., doxorubicin and mitoxantrone), (B) fluoropyrimidines (e.g., 5-FU), (C) folic acid antagonists (e.g., methotrexate), (D) podophylotoxins (e.g., etoposide), (E) camptothecins, (F) hydroxyureas, and (G) platinum complexes (e.g., cisplatin).

(A) Anthracyclines

Anthracyclines have the following general structure, where the R groups may be a variety of organic groups:

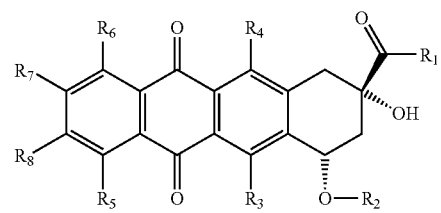

According to U.S. Pat. No. 5,594,158, suitable R groups are as follows: $R_1$ is $CH_3$ or $CH_2OH$; $R_2$ is daunosamine or H; $R_3$ and $R_4$ are independently one of OH, $NO_2$, $NH_2$, F, Cl, Br, I, CN, H or groups derived from these; $R_5$ is hydrogen, hydroxyl, or methoxy; and $R_{6-8}$ are all hydrogen. Alternatively, $R_5$ and $R_6$ are hydrogen and $R_7$ and $R_8$ are alkyl or halogen, or vice versa.

According to U.S. Pat. No. 5,843,903, $R_1$ may be a conjugated peptide. According to U.S. Pat. No. 4,296,105, $R_5$ may be an ether linked alkyl group. According to U.S. Pat. No. 4,215,062, $R_5$ may be OH or an ether linked alkyl group. $R_1$ may also be linked to the anthracycline ring by a group other than C(O), such as an alkyl or branched alkyl group having the C(O) linking moiety at its end, such as —$CH_2CH(CH_2$—X)C(O)—$R_1$, wherein X is H or an alkyl group (see, e.g., U.S. Pat. No. 4,215,062). $R_2$ may alternately be a group linked by the functional group =N—NHC(O)—Y, where Y is a group such as a phenyl or substituted phenyl ring. Alternately $R_3$ may have the following structure:

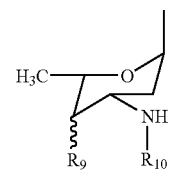

in which $R_9$ is OH either in or out of the plane of the ring, or is a second sugar moiety such as $R_3$. $R_{10}$ may be H or form a secondary amine with a group such as an aromatic group, saturated or partially saturated 5 or 6 membered heterocyclic having at least one ring nitrogen (see U.S. Pat. No. 5,843, 903). Alternately, $R_{10}$ may be derived from an amino acid, having the structure —C(O)CH(NHR$_{11}$)(R$_{12}$), in which $R_{11}$ is H, or forms a $C_{3-4}$ membered alkylene with $R_{12}$. $R_{12}$ may be H, alkyl, aminoalkyl, amino, hydroxyl, mercapto, phenyl, benzyl or methylthio (see U.S. Pat. No. 4,296,105).

Exemplary anthracyclines are doxorubicin, daunorubicin, idarubicin, epirubicin, pirarubicin, zorubicin, and carubicin. Suitable compounds have the structures:

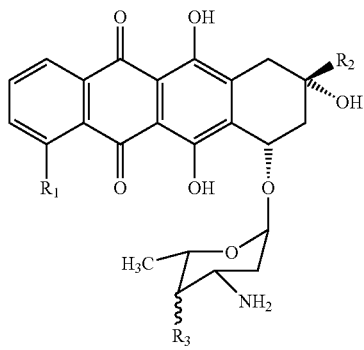

|  | $R_1$ | $R_2$ | $R_3$ |
|---|---|---|---|
| Doxorubicin: | $OCH_3$ | $C(O)CH_2OH$ | OH out of ring plane |
| Epirubicin: (4' epimer of doxorubicin) | $OCH_3$ | $C(O)CH_2OH$ | OH in ring plane |
| Daunorubicin: | $OCH_3$ | $C(O)CH_3$ | OH out of ring plane |
| Idarubicin: | H | $C(O)CH_3$ | OH out of ring plane |
| Pirarubicin: | $OCH_3$ | $C(O)CH_2OH$ | 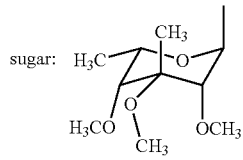 |
| Zorubicin: | $OCH_3$ | $C(CH_3)(=N)NHC(O)C_6H_5$ | OH |
| Carubicin: | OH | $C(O)CH_3$ | OH out of ring plane |

Other suitable anthracyclines are anthramycin, mitoxantrone, menogaril, nogalamycin, aclacinomycin A, olivomycin A, chromomycin $A_3$, and plicamycin having the structures:

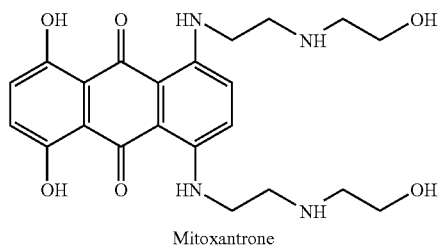
Mitoxantrone

|  | $R_1$ | $R_2$ | $R_3$ |
|---|---|---|---|
| Menogaril | H | $OCH_3$ | H |
| Nogalamycin | O-sugar | H | $COOCH_3$ |

-continued

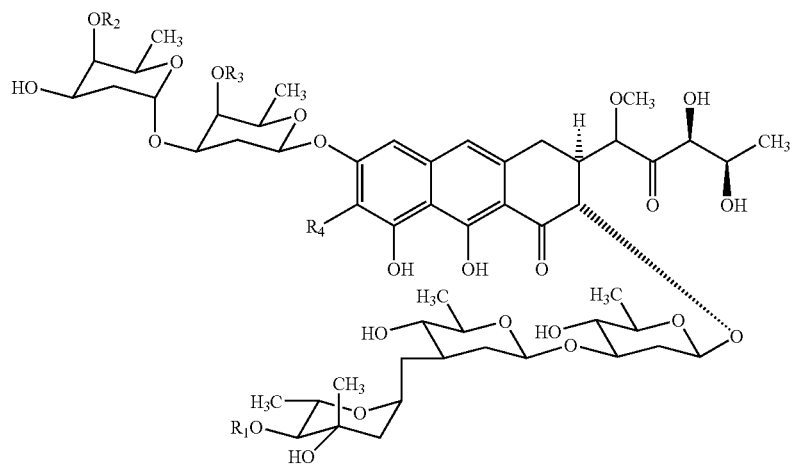

| | $R_1$ | $R_2$ | $R_3$ | $R_4$ |
|---|---|---|---|---|
| Olivomycin A | $COCH(CH_3)_2$ | $CH_3$ | $COCH_3$ | H |
| Chromomycin $A_3$ | $COCH_3$ | $CH_3$ | $COCH_3$ | $CH_3$ |
| Plicamycin | H | H | H | $CH_3$ |

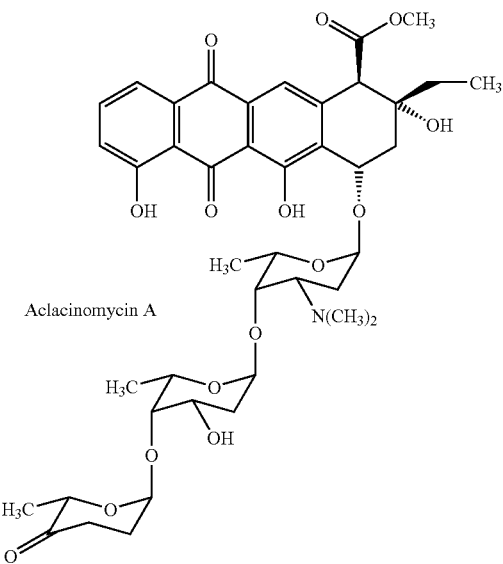

Aclacinomycin A

Other representative anthracyclines include, FCE 23762, a doxorubicin derivative (Quaglia et al., *J. Liq. Chromatogr.* 17(18):3911–3923, 1994), annamycin (Zou et al., *J. Pharm. Sci.* 82(11):1151–1154, 1993), ruboxyl (Rapoport et al., *J. Controlled Release* 58(2):153–162, 1999), anthracycline disaccharide doxorubicin analogue (Pratesi et al., *Clin. Cancer Res.* 4(11):2833–2839, 1998), N-(trifluoroacetyl)doxorubicin and 4'-O-acetyl-N-(trifluoroacetyl)doxorubicin (Berube & Lepage, Synth. Commun. 28(6):1109–1116, 1998), 2-pyrrolinodoxorubicin (Nagy et al., *Proc. Natl. Acad. Sci. U.S.A.* 95(4):1794–1799, 1998), disaccharide doxorubicin analogues (Arcamone et al., *J. Nat'l Cancer Inst* 89(16):1217–1223, 1997), 4-demethoxy-7-O-[2,6-dideoxy-4-O-(2,3,6-trideoxy-3-amino-α-L-lyxo-hexopyranosyl)-α-L-lyxo-hexopyranosyl]adriamicinone disaccharide analogue (Monteagudo et al., *Carbohydr. Res.* 300(1):11–16, 1997), 2-pyrrolinodoxorubicin (Nagy et al., *Proc. Nat'lAcad. Sci. U.S.A.* 94(2):652–656, 1997), mor-pholinyl doxorubicin analogues (Duran et al., *Cancer Chemother. Pharmacol.* 38(3):210–216, 1996), enaminomalonyl-β-alanine doxorubicin derivatives (Seitz et al., *Tetrahedron Lett.* 36(9):1413–16, 1995), cephalosporin doxorubicin derivatives (Vrudhula et al., *J. Med. Chem.* 38(8): 1380–5, 1995), hydroxyrubicin (Solary et al., *Int. J. Cancer* 58(1):85–94, 1994), methoxymorpholino doxorubicin derivative (Kuhl et al., *Cancer Chemother. Pharmacol.* 33(1):10–16, 1993), (6-maleimidocaproyl)hydrazone doxorubicin derivative (Willner et al., *Bioconjugate Chem.* 4(6): 521–7, 1993), N-(5,5-diacetoxypent-1-yl) doxorubicin (Cherif & Farquhar, *J. Med. Chem.* 35(17):3208–14, 1992), FCE 23762 methoxymorpholinyl doxorubicin derivative (Ripamonti et al., *Br. J. Cancer* 65(5):703–7, 1992), N-hydroxysuccinimide ester doxorubicin derivatives (Demant et al., *Biochim. Biophys. Acta* 1118(1):83–90, 1991), polydeoxynucleotide doxorubicin derivatives (Ruggiero et al., *Biochim. Biophys. Acta* 1129(3):294–302, 1991), morpholinyl doxorubicin derivatives (EPA 434960), mitoxantrone doxorubicin analogue (Krapcho et al., *J. Med. Chem.* 34(8):2373–80. 1991), AD198 doxorubicin analogue (Traganos et al., *Cancer Res.* 51(14):3682–9, 1991), 4-demethoxy-3'-N-trifluoroacetyidoxorubicin (Horton et al., *Drug Des. Delivery* 6(2):123–9, 1990), 4'-epidoxorubicin (Drzewoski et al., *Pol. J. Pharmacol. Pharm.* 40(2):159–65, 1988; Weenen et al., *Eur. J. Cancer Clin. Oncol.* 20(7): 919–26, 1984), alkylating cyanomorpholino doxorubicin derivative (Scudder et al., *J. Nat'l Cancer Inst* 80(16): 1294–8, 1988), deoxydihydroiodooxorubicin (EPA 275966), adriblastin (Kalishevskaya et al., *Vestn. Mosk. Univ.*, 16(Biol. 1):21–7, 1988), 4'-deoxydoxorubicin (Schoeizel et al., *Leuk. Res.* 10(12):1455–9, 1986), 4-demethyoxy-4'—O— methyldoxorubicin (Giuliani et al., *Proc. Int. Congr. Chemother.* 16:285–70–285–77, 1983), 3'-deamino-3'-hydroxydoxorubicin (Horton et al., *J. Antibiot* 37(8):853–8, 1984), 4-demethoxy doxorubicin analogues (Barbieri et al., *Drugs Exp. Clin. Res.* 10(2):85–90, 1984), N-L-leucyl doxorubicin derivatives (Trouet et al., Anthracyclines (*Proc. Int. Symp. Tumor Pharmacother.*), 179–81, 1983), 3'-deamino-3'-(4-methoxy-1-piperidinyl) doxorubicin derivatives (U.S. Pat. No. 4,314,054), 3'-deamino-3'-(4-mortholinyl) doxorubicin derivatives (U.S. Pat. No. 4,301,277), 4'-deoxydoxorubicin and 4'-o-methyldoxorubicin (Giuliani et al., *Int. J. Cancer* 27(1):5–13, 1981), aglycone doxorubicin derivatives (Chan & Watson, *J. Pharm. Sci.* 67(12):1748–52, 1978), SM 5887 (Pharma Japan 1468:20, 1995), MX-2 (Pharma Japan 1420:19, 1994), 4'-deoxy-13(S)-dihydro-4'-iododoxorubicin (EP 275966), morpholinyl doxorubicin derivatives (EPA 434960), 3'-deamino-3'-(4-methoxy-1-piperidinyl) doxorubicin derivatives (U.S. Pat. No. 4,314,054), doxorubicin-14-valerate, morpholinodoxorubicin (U.S. Pat. No. 5,004,606), 3'-deamino-3'-(3"-cyano-4"-morpholinyl doxorubicin; 3'-deamino-3'-(3"-cyano-4"-morpholinyl)-13-dihydoxorubicin); (3'-deamino-3'-(3"-cyano-4"-morpholinyl) daunorubicin; 3'-deamino-3'-(3"-cyano-4"-morpholinyl)-3-dihydrodaunorubicin; and 3'-deamino-3'-(4"-morpholinyl-5-iminodoxorubicin and derivatives (U.S. Pat. No. 4,585,859), 3'-deamino-3'-(4-methoxy-1-piperidinyl) doxorubicin derivatives (U.S. Pat. No. 4,314,054) and 3-deamino-3-(4-morpholinyl) doxorubicin derivatives (U.S. Pat. No. 4,301,277).

(B) Fluoropyrimidine Analogues

In another aspect, the therapeutic agent is a fluoropyrimidine analog, such as 5-fluorouracil, or an analogue or derivative thereof, including carmofur, doxifluridine, emitefur, tegafur, and floxuridine. Exemplary compounds have the structures:

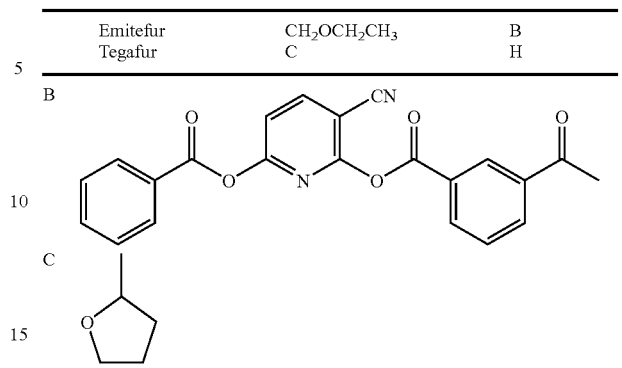

| A | | | |
|---|---|---|---|
| | $R_1$ | | $R_2$ |
| 5-Fluorouracil | H | | H |
| Carmofur | C(O)NH(CH$_2$)$_5$CH$_3$ | | H |
| Doxifluridine | A$_1$ | | H |
| Floxuridine | A$_2$ | | H |

| -continued | | |
|---|---|---|
| Emitefur | CH$_2$OCH$_2$CH$_3$ | B |
| Tegafur | C | H |

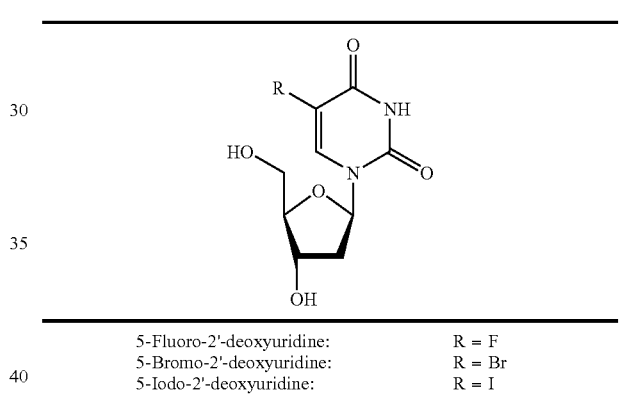

Other suitable fluoropyrimidine analogues include 5-FudR (5-fluoro-deoxyuridine), or an analogue or derivative thereof, including 5-iododeoxyuridine (5-ludR), 5-bromodeoxyuridine (5-BudR), fluorouridine triphosphate (5-FUTP), and fluorodeoxyuridine monophosphate (5-dFUMP). Exemplary compounds have the structures:

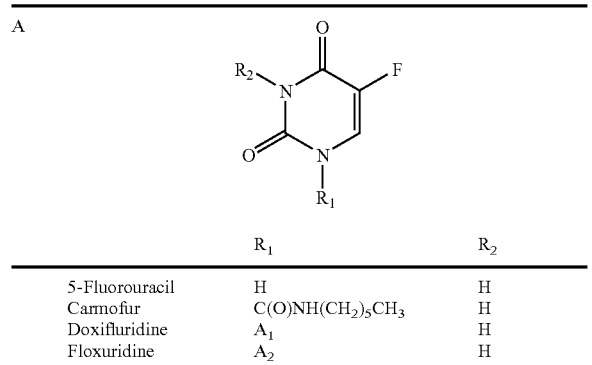

| | |
|---|---|
| 5-Fluoro-2'-deoxyuridine: | R = F |
| 5-Bromo-2'-deoxyuridine: | R = Br |
| 5-Iodo-2'-deoxyuridine: | R = I |

Other representative examples of fluoropyrimidine analogues include N3-alkylated analogues of 5-fluorouracil (Kozai et al., *J. Chem. Soc., Perkin Trans.* 1(19):3145–3146, 1998), 5-fluorouracil derivatives with 1,4-oxaheteroepane moieties (Gomez et al., *Tetrahedron* 54(43):13295–13312, 1998), 5-fluorouracil and nucleoside analogues (Li, *Anticancer Res.* 17(1A):21–27, 1997), cis- and trans-5-fluoro-5,6-dihydro-6-alkoxyuracil (Van der Wilt et al., *Br. J. Cancer* 68(4):702–7, 1993), cyclopentane 5-fluorouracil analogues (Hronowski & Szarek, *Can. J. Chem.* 70(4):1162–9, 1992), A-OT-fluorouracil (Zhang et al., *Zongguo Yiyao Gongye Zazhi* 20(11):513–15, 1989), N4-trimethoxybenzoyl-5'-deoxy-5-fluorocytidine and 5'-deoxy-5-fluorouridine (Miwa et al., *Chem. Pharm. Bull.* 38(4):998–1003, 1990), 1-hexylcarbamoyl-5-fluorouracil (Hoshi et al., *J. Pharmacobio-Dun.* 3(9):478–81, 1980; Maehara et al., *Chemotherapy (Basel)* 34(6):484–9, 1988), B-3839 (Prajda et al., *In Vivo* 2(2):151–4, 1988), uracil-1-(2-tetrahydrofuryl)-5-fluorouracil (Anai et al., *Oncology* 45(3):144–7, 1988), 1-(2'-deoxy-2'-fluoro-β-D-arabinofuranosyl)-5-fluorouracil (Suzuko et al., *Mol. Pharmacol.* 31(3):301–6, 1987), doxifluridine (Matuura et al., *Oyo Yakuri* 29(5):803–31, 1985), 5'-deoxy-5-fluorouridine (Bollag & Hartmann, *Eur. J.*

Cancer 16(4):427–32, 1980), 1-acetyl-3-O-toluyl-5-fluorouracil (Okada, *Hiroshima J. Med. Sci.* 28(1):49–66, 1979), 5-fluorouracil-m-formylbenzene-sulfonate (JP 55059173), N'-(2-furanidyl)-5-fluorouracil (JP 53149985) and 1-(2-tetrahydrofuryl)-5-fluorouracil (JP 52089680).

These compounds are believed to function as therapeutic agents by serving as antimetabolites of pyrimidine.

(C) Folic Acid Antagonists

In another aspect, the therapeutic agent is a folic acid antagonist, such as methotrexate or derivatives or analogues thereof, including edatrexate, trimetrexate, raltitrexed, piritrexim, denopterin, tomudex, and pteropterin. Methotrexate analogues have the following general structure:

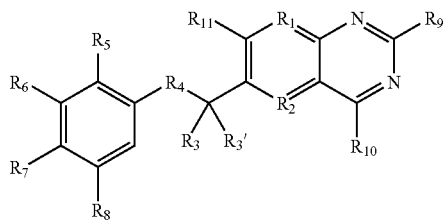

The identity of the R group may be selected from organic groups, particularly those groups set forth in U.S. Pat. Nos. 5,166,149 and 5,382,582. For example, $R_1$ may be N, $R_2$ may be N or $C(CH_3)$, $R_3$ and $R_3'$ may H or alkyl, e.g., $CH_3$, $R_4$ may be a single bond or NR, where R is H or alkyl group. $R_5$, $R_6$, and/or $R_8$ may be H, $OCH_3$, or alternately they can be halogens or hydro groups. $R_7$ is a side chain of the general structure:

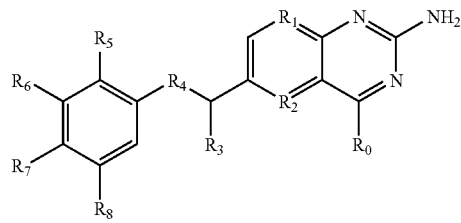

wherein n=1 for methotrexate, n=3 for pteropterin. The carboxyl groups in the side chain may be esterified or form a salt such as a $Zn^{2+}$ salt. $R_9$ and $R_{10}$ can be $NH_2$ or may be alkyl substituted.

Exemplary folic acid antagonist compounds have the structures:

| | $R_0$ | $R_1$ | $R_2$ | $R_3$ | $R_4$ | $R_5$ | $R_6$ | $R_7$ | $R_8$ |
|---|---|---|---|---|---|---|---|---|---|
| Methotrexate | $NH_2$ | N | N | H | $N(CH_3)$ | H | H | A (n = 1) | H |
| Edatrexate | $NH_2$ | N | N | H | $CH(CH_2CH_3)$ | H | H | A (n = 1) | H |
| Trimetrexate | $NH_2$ | CH | $C(CH_3)$ | H | NH | H | $OCH_3$ | $OCH_3$ | $OCH_3$ |
| Pteropterin | OH | N | N | H | NH | H | H | A (n = 3) | H |
| Denopterin | OH | N | N | $CH_3$ | $N(CH_3)$ | H | H | A (n = 1) | H |
| Peritrexim | $NH_2$ | N | $C(CH_3)$ | H | single bond | $OCH_3$ | H | H | $OCH_3$ |

A:

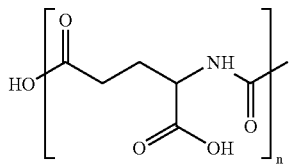

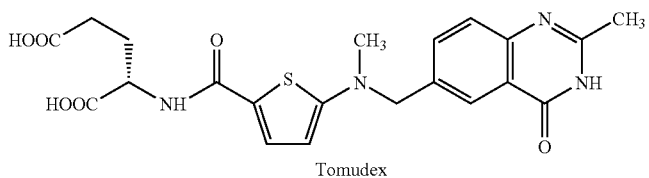

Tomudex

Other representative examples include 6-S-aminoacyloxymethyl mercaptopurine derivatives (Harada et al., *Chem. Pharm. Bull.* 43(10):793–6, 1995), 6-mercaptopurine (6-MP) (Kashida et al., *Biol. Pharm. Bull.* 18(11):1492–7, 1995), 7,8-polymethyleneimidazo-1,3,2-diazaphosphorines (Nilov et al., *Mendeleev Commun.* 2:67, 1995), azathioprine (Chifotides et al., *J. Inorg. Biochem.* 56(4):249–64, 1994), methyl-D-glucopyranoside mercaptopurine derivatives (Da Silva et al., *Eur. J. Med. Chem.* 29(2):149–52, 1994) and s-alkynyl mercaptopurine derivatives (Ratsino et al., *Khim.-Farm. Zh.* 15(8):65–7, 1981); indoline ring and a modified ornithine orglutamic acid-bearing methotrexate derivatives (Matsuoka et al., *Chem. Pharm. Bull.* 45(7):1146–1150, 1997), alkyl-substituted benzene ring C bearing methotrexate derivatives (Matsuoka et al., *Chem. Pharm. Bull.* 44(12): 2287–2293, 1996), benzoxazine or benzothiazine moiety-bearing methotrexate derivatives (Matsuoka et al., *J. Med. Chem.* 40(1):105–111, 1997), 10-deazaminopterin analogues (DeGraw et al., *J. Med. Chem.* 40(3):370–376, 1997), 5-deazaminopterin and 5,10-dideazaminopterin methotrexate analogues (Piper et al., *J. Med. Chem.* 40(3):377–384, 1997), indoline moiety-bearing methotrexate derivatives (Matsuoka et al., *Chem. Pharm. Bull.* 44(7):1332–1337, 1996), lipophilic amide methotrexate derivatives (Pignatello et al., *World Meet. Pharm. Biopharm. Pharm. Technol.*, 563–4, 1995), L-threo-(2S,4S)-4-fluoroglutamic acid and DL-3,3-difluoroglutamic acid-containing methotrexate analogues (Hart et al., *J. Med. Chem.* 39(1):56–65, 1996), methotrexate tetrahydroquinazoline analogue (Gangjee, et al, *J. Heterocycl. Chem.* 32(1):243–8, 1995), N-(α-aminoacyl)methotrexate derivatives (Cheung et al., *Pteridines* 3(1–2):101–2, 1992), biotin methotrexate derivatives (Fan et al., *Pteridines* 3(1–2):131–2, 1992), D-glutamic acid or D-erythrou, threo-4-fluoroglutamic acid methotrexate analogues (McGuire et al., *Biochem. Pharmacol.* 42(12):2400–3, 1991), β,γ-methano methotrexate analogues (Rosowsky et al., *Pteridines* 2(3):133–9, 1991), 10-deazaminopterin (10-EDAM) analogue (Braakhuis et al., *Chem. Biol. Pteridines, Proc. Int Symp. Pteridines Folic Acid Deriv.*, 1027–30, 1989), γ-tetrazole methotrexate analogue (Kalman et al., *Chem. Biol. Pteridines, Proc. Int Symp. Pteridines Folic Acid Deriv.*, 1154–7, 1989), N-(L-α-aminoacyl)methotrexate derivatives (Cheung et al., *Heterocycles* 28(2):751–8, 1989), meta and ortho isomers of aminopterin (Rosowsky et al., *J. Med. Chem.* 32(12):2582, 1989), hydroxymethylmethotrexate (DE 267495), γ-fluoromethotrexate (McGuire et al., *Cancer Res.* 49(16):4517–25, 1989), polyglutamyl methotrexate derivatives (Kumar et al., *Cancer Res.* 46(10):5020–3, 1986), gem-diphosphonate methotrexate analogues (WO 88/06158), α- and γ-substituted methotrexate analogues (Tsushima et al., *Tetrahedron* 44(17):5375–87, 1988), 5-methyl-5-deaza methotrexate analogues (U.S. Pat. No. 4,725, 687), Nδ-acyl-Nα-(4-amino-4-deoxypteroyl)-L-ornithine derivatives (Rosowsky et al., *J. Med. Chem.* 31(7):1332–7, 1988), 8-deaza methotrexate analogues (Kuehl et al., *Cancer Res.* 48(6):1481–8, 1988), acivicin methotrexate analogue (Rosowsky et al., *J. Med. Chem.* 30(8):1463–9, 1987), polymeric platinol methotrexate derivative (Carraher et al., *Polym. Sci. Technol. (Plenum)*, 35(Adv. Biomed. Polym.): 311–24, 1987), methotrexate-γ-dimyristoylphophatidylethanolamine (Kinsky et al., *Biochim. Biophys. Acta* 917(2): 211–18, 1987), methotrexate polyglutamate analogues (Rosowsky et al., Chem. Biol. Pteridines, Pteridines Folic Acid Deriv., Proc. Int. Symp. Pteridines Folic Acid Deriv.: Chem., Biol. Clin. Aspects:985–8, 1986), poly-γ-glutamyl methotrexate derivatives (Kisliuk et al., Chem. Biol. Pteridines, Pteridines Folic Acid Deriv., Proc. Int. Symp. Pteridines Folic Acid Deriv.: Chem., Biol. Clin. Aspects: 989–92, 1986), deoxyuridylate methotrexate derivatives (Webber et al., Chem. Biol. Pteridines, Pteridines Folic Acid Deriv., Proc. Int. Symp. Pteridines Folic Acid Deriv.: Chem., Biol. Clin. Aspects:659–62, 1986), iodoacetyl lysine methotrexate analogue (Delcamp et al., Chem. Biol. Pteridines, Pteridines Folic Acid Deriv., Proc. Int. Symp. Pteridines Folic Acid Deriv.: Chem., Biol. Clin. Aspects:807–9, 1986), 2, .omega.-diaminoalkanoid acid-containing methotrexate analogues (McGuire et al., *Biochem. Pharmacol.* 35(15): 2607–13, 1986), polyglutamate methotrexate derivatives (Kamen & Winick, *Methods Enzymol.* 122 (Vitam. Coenzymes, Pt. G):339–46, 1986), 5-methyl-5-deaza analogues (Piper et al., *J. Med. Chem.* 29(6):1080–7, 1986), quinazoline methotrexate analogue (Mastropaolo et al., *J. Med. Chem.* 29(1):155–8, 1986), pyrazine methotrexate analogue (Lever & Vestal, *J. Heterocycl. Chem.* 22(1):5–6, 1985), cysteic acid and homocysteic acid methotrexate analogues (U.S. Pat. No. 4,490,529), γ-tert-butyl methotrexate esters (Rosowsky et al., *J. Med. Chem.* 28(5):660–7, 1985), fluorinated methotrexate analogues (Tsushima et al., *Heterocycles* 23(1):45–9, 1985), folate methotrexate analogue (Trombe, *J. Bacteriol* 160(3):849–53, 1984), phosphonoglutamic acid analogues (Sturtz & Guillamot, *Eur. J. Med. Chem.—Chim. Ther.* 19(3):267–73, 1984), poly(L-lysine) methotrexate conjugates (Rosowsky et al., *J. Med. Chem.* 27(7):888–93, 1984), dilysine and trilysine methotrexate derivates (Forsch & Rosowsky, *J. Org. Chem.* 49(7):1305–9, 1984), 7-hydroxymethotrexate (Fabre et al., *Cancer Res.* 43(10):4648–52, 1983), poly-γ-glutamyl methotrexate analogues (Piper & Montgomery, *Adv. Exp. Med. Biol.*, 163 (Folyl Antifolyl Polyglutamates):95–100, 1983), 3',5'-dichloromethotrexate (Rosowsky & Yu, *J. Med. Chem.* 26(10):1448–52, 1983), diazoketone and chloromethylketone methotrexate analogues (Gangjee et al., *J. Pharm. Sci.* 71(6):717–19, 1982), 10-propargylaminopterin and alkyl methotrexate homologs (Piper et al., *J. Med. Chem.* 25(7): 877–80, 1982), lectin derivatives of methotrexate (Lin et al., *JNCI* 66(3):523–8, 1981), polyglutamate methotrexate derivatives (Galivan, Mol. Pharmacol. 17(1):105–10, 1980), halogentated methotrexate derivatives (Fox, *JNCI* 58(4): J955–8, 1977), 8-alkyl-7,8-dihydro analogues (Chaykovsky et al., *J. Med. Chem.* 20(10):J1323–7, 1977), 7-methyl methotrexate derivatives and dichloromethotrexate (Rosowsky & Chen, *J. Med. Chem.* 17(12):J1308–11, 1974), lipophilic methotrexate derivatives and 3',5'-dichloromethotrexate (Rosowsky, *J. Med. Chem.* 16(10):J1190–3, 1973), deaza amethopterin analogues (Montgomery et al., *Ann. N.Y. Acad. Sci.* 186:J227–34, 1971), MX068 (Pharma Japan, 1658:18, 1999) and cysteic acid and homocysteic acid methotrexate analogues (EPA 0142220);

These compounds are believed to act as antimetabolites of folic acid.

(D) Podophyllotoxins

In another aspect, the therapeutic agent is a Podophyllotoxin, or a derivative or an analogue thereof. Exemplary compounds of this type are etoposide or teniposide, which have the following structures:

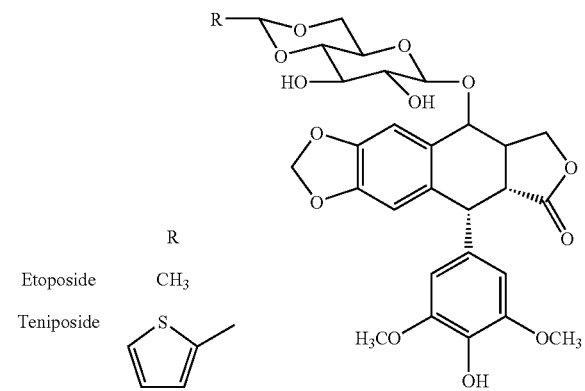

Etoposide    R  CH₃

Teniposide

Other representative examples of podophyllotoxins include Cu(II)-VP-16 (etoposide) complex (Tawa et al., *Bioorg. Med. Chem.* 6(7):1003–1008, 1998), pyrrolecarboxamidino-bearing etoposide analogues (Ji et al., *Bioorg. Med. Chem. Lett.* 7(5):607–612, 1997), 4β-amino etoposide analogues (Hu, University of North Carolina Dissertation, 1992), γ-lactone ring-modified arylamino etoposide analogues (Zhou et al., *J. Med. Chem.* 37(2):287–92, 1994), N-glucosyl etoposide analogue (Allevi et al., *Tetrahedron Lett.* 34(45):7313–16, 1993), etoposide A-ring analogues (Kadow et al., *Bioorg. Med. Chem. Leff.* 2(1):17–22, 1992), 4'-deshydroxy-4'-methyl etoposide (Saulnier et al., *Bioorg. Med. Chem. Lett.* 2(10):1213–18, 1992), pendulum ring etoposide analogues (Sinha et al., *Eur. J. Cancer* 26(5): 590–3, 1990) and E-ring desoxy etoposide analogues (Saulnier et al., *J. Med. Chem.* 32(7):1418–20, 1989).

These compounds are believed to act as topoisomerase 11 inhibitors and/or DNA cleaving agents.

(E) Camptothecins

In another aspect, the therapeutic agent is camptothecin, or an analogue or derivative thereof. Camptothecins have the following general structure.

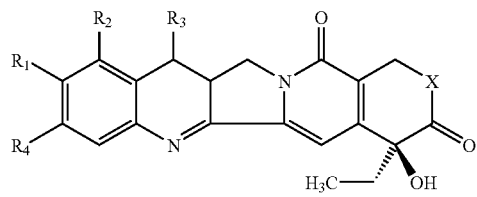

In this structure, X is typically 0, but can be other groups, e.g., NH in the case of 21-lactam derivatives. $R_1$ is typically H or OH, but may be other groups, e.g., a terminally hydroxylated $C_{1-3}$ alkane. $R_2$ is typically H or an amino containing group such as $(CH_3)_2NHCH_2$, but may be other groups e.g., $NO_2$, $NH_2$, halogen (as disclosed in, e.g., U.S. Pat. No. 5,552,156) or a short alkane containing these groups. $R_3$ is typically H or a short alkyl such as $C_2H_5$. $R_4$ is typically H but may be other groups, e.g., a methylenedioxy group with $R_1$.

Exemplary camptothecin compounds include topotecan, irinotecan (CPT-11), 9-aminocamptothecin, 21-lactam-20 (S)-camptothecin, 10,11-methylenedioxycamptothecin, SN-38, 9-nitrocamptothecin, 10-hydroxycamptothecin. Exemplary compounds have the structures:

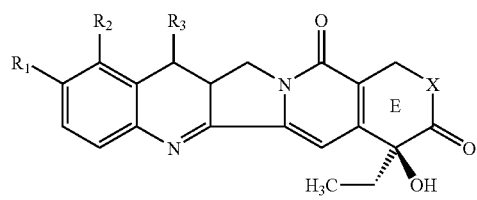

| | $R_1$ | $R_2$ | $R_3$ |
|---|---|---|---|
| Camptothecin: | H | H | H |
| Topotecan: | OH | $(CH_3)_2NHCH_2$ | H |
| SN-38: | OH | H | $C_2H_5$ |

X: O for most analogs, NH for 21-lactam analogs

Camptothecins have the five rings shown here. The ring labeled E must be intact (the lactone rather than carboxylate form) for maximum activity and minimum toxicity.

Camptothecins are believed to function as topoisomerase I inhibitors and/or DNA cleavage agents.

(F) Hydroxyureas

The therapeutic agent of the present invention may be a hydroxyurea. Hydroxyureas have the following general structure:

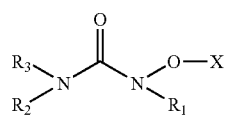

Suitable hydroxyureas are disclosed in, for example, U.S. Pat. No. 6,080,874, wherein $R_1$ is:

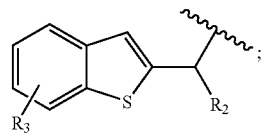

and $R_2$ is an alkyl group having 1–4 carbons and $R_3$ is one of H, acyl, methyl, ethyl, and mixtures thereof, such as a methylether.

Other suitable hydroxyureas are disclosed in, e.g., U.S. Pat. No. 5,665,768, wherein $R_1$ is a cycloalkenyl group, for example N-[3-[5-(4-fluorophenylthio)-furyl]-2-cyclopenten-1-yl]N-hydroxyurea; $R_2$ is H or an alkyl group having 1 to 4 carbons and $R_3$ is H; X is H or a cation.

Other suitable hydroxyureas are disclosed in, e.g., U.S. Pat. No. 4,299,778, wherein $R_1$ is a phenyl group substituted with one or more fluorine atoms; $R_2$ is a cyclopropyl group; and $R_3$ and X is H.

Other suitable hydroxyureas are disclosed in, e.g., U.S. Pat. No. 5,066,658, wherein $R_2$ and $R_3$ together with the adjacent nitrogen form:

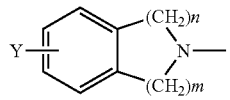

wherein m is 1 or 2, n is 0–2 and Y is an alkyl group.

In one aspect, the hydroxyurea has the structure:

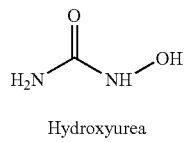

Hydroxyurea

These compounds are thought to function by inhibiting DNA synthesis.

(G) Platinum Complexes

In another aspect, the therapeutic agent is a platinum compound. In general, suitable platinum complexes may be of Pt(II) or Pt(IV) and have this basic structure:

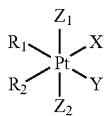

wherein X and Y are anionic leaving groups such as sulfate, phosphate, carboxylate, and halogen; $R_1$ and $R_2$ are alkyl, amine, amino alkyl may be further substituted, and are basically inert or bridging groups. For Pt(II) complexes $Z_1$ and $Z_2$ are non-existent. For Pt(IV) $Z_1$ and $Z_2$ may be anionic groups such as halogen, hydroxy, carboxylate, ester, sulfate or phosphate. See, e.g., U.S. Pat. Nos. 4,588,831 and 4,250,189.

Suitable platinum complexes may contain multiple Pt atoms. See, e.g., U.S. Pat. Nos. 5,409,915 and 5,380,897. For example bisplatinum and triplatinum complexes of the type:

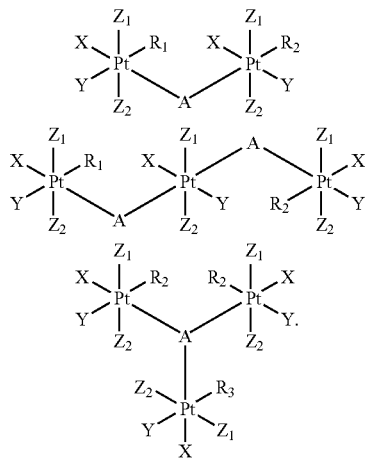

Exemplary platinum compounds are cisplatin, carboplatin, oxaliplatin, and miboplatin having the structures:

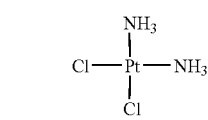
Cisplatin

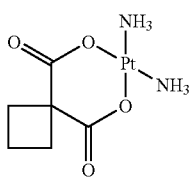
Carboplatin

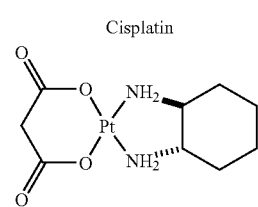
Oxaliplatin

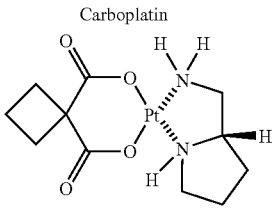
Miboplatin

Other representative platinum compounds include $(CPA)_2$ Pt[DOLYM] and (DACH)Pt[DOLYM] cisplatin (Choi et al., *Arch. Pharmacal Res.* 22(2):151–156, 1999), Cis-[PtCl$_2$(4, 7-H-5-methyl-7-oxo]1,2,4[triazolo[1,5-a]pyrimidine)$_2$] (Navarro et al., *J. Med. Chem.* 41(3):332–338, 1998), [Pt (cis-1,4-DACH)(trans-C[$_2$)(CBDCA)].½MeOH cisplatin (Shamsuddin et al., *Inorg. Chem.* 36(25):5969–5971, 1997), 4-pyridoxate diammine hydroxy platinum (Tokunaga et al., *Pharm. Sci.* 3(7):353–356, 1997), Pt(II) . . . Pt(II) (Pt$_2$ [NHCHN(C(CH$_2$)(CH$_3$))]$_4$) (Navarro et al., *Inorg. Chem.* 35(26): 7829–7835, 1996), 254-S cisplatin analogue (Koga et al., *Neurol. Res.* 18(3):244–247, 1996), o-phenylenediamine ligand bearing cisplatin analogues (Koeckerbauer & Bednarski, *J. Inorg. Biochem.* 62(4):281–298, 1996), trans, cis-[Pt(OAc)$_2$I$_2$(en)] (Kratochwil et al., *J. Med. Chem.* 39(13):2499–2507, 1996), estrogenic 1,2-diarylethylenediamine ligand (with sulfur-containing amino acids and glutathione) bearing cisplatin analogues (Bednarski, *J. Inorg. Biochem.* 62(1):75, 1996), cis-1,4-diaminocyclohexane cisplatin analogues (Shamsuddin et al., *J. Inorg. Biochem.* 61(4):291–301, 1996), 5' orientational isomer of cis-[Pt (NH$_3$)(4-aminoTEMP-O){d(GpG)}] (Dunham & Lippard, *J. Am. Chem. Soc.* 117(43):10702–12, 1995), chelating diamine-bearing cisplatin analogues (Koeckerbauer & Bednarski, *J. Pharm. Sci.* 84(7):819–23, 1995), 1,2-diarylethyleneamine ligand-bearing cisplatin analogues (Otto et al., *J. Cancer Res. Clin. Oncol.* 121(1):31–8, 1995), (ethylenediamine)platinum(II) complexes (Pasini et al., *J. Chem. Soc., Dalton Trans.* 4:579–85, 1995), $C_{1-973}$ cisplatin analogue (Yang et al., *Int. J. Oncol.* 5(3):597–602, 1994), cis-diaminedichloroplatinum(II) and its analogues cis-1,1-cyclobutanedicarbosylato(2R)-2-methyl-1,4-butanediamineplatinum(II) and cis-diammine(glycolato)platinum (Claycamp & Zimbrick, *J. Inorg. Biochem.* 26(4):257–67, 1986; Fan et al., *Cancer Res.* 48(11):3135–9, 1988; Heiger-Bernays et al., *Biochemistry* 29(36):8461–6, 1990; Kikkawa et al., *J. Exp. Clin. Cancer Res.* 12(4):233–40, 1993; Murray et al., *Biochemistry* 31(47):11812–17, 1992; Takahashi et al., *Cancer Chemother. Pharmacol.* 33(1):31–5, 1993), cis-amine-cyclohexylamine-dichloroplatinum(II) (Yoshida et al., *Biochem. Pharmacol.* 48(4):793–9, 1994), gem-diphosphonate cisplatin analogues (FR 2683529), (meso-1,2-bis(2, 6-dichloro-4-hydroxyplenyl)ethylenediamine) dichloroplatinum(II) (Bednarski et al., *J. Med. Chem.* 35(23):4479–85, 1992), cisplatin analogues containing a tethered dansyl group (Hartwig et al., *J. Am. Chem. Soc.* 114(21):8292–3, 1992), platinum(II) polyamines (Siegmann et al., *Inorg. Met.-Containing Polym. Mater.*, (*Proc. Am. Chem. Soc. Int. Symp.*), 335–61, 1990), cis-(3H)dichloro (ethylenediamine)platinum(II) (Eastman, *Anal. Biochem.* 197(2):311–15, 1991), trans-diamminedichloroplatinum(II) and cis-(Pt(NH$_3$)$_2$(N$_3$-cytosine)Cl) (Bellon & Lippard, *Biophys. Chem.* 35(2–3):179–88, 1990), 3H-cis-1,2-diaminocyclohexanedichloroplatinum(II) and 3H-cis-1,2-diaminocyclohexane-malonatoplatinum (II) (Oswald et al., *Res. Commun. Chem. Pathol. Pharmacol.* 64(1):41–58, 1989), diaminocarboxylatoplatinum (EPA 296321), trans-(D,1)-1, 2-diaminocyclohexane carrier ligand-bearing platinum analogues (Wyrick & Chaney, *J. Labelled Compd. Radiopharm.* 25(4):349–57, 1988), aminoalkylaminoanthraquinone-derived cisplatin analogues (Kitov et al., *Eur. J. Med. Chem.* 23(4):381–3, 1988), spiroplatin, carboplatin, iproplatin and JM40 platinum analogues (Schroyen et al., *Eur. J. Cancer Clin. Oncol.* 24(8):1309–12, 1988), bidentate tertiary diamine-containing cisplatinum derivatives (Orbell et al., *Inorg. Chim. Acta* 152(2):125–34, 1988), platinum(II), platinum(IV) (Liu & Wang, *Shandong Yike Daxue Xuebao* 24(1):35–41, 1986), cis-diammine(1,1-cyclobutanedicarboxylato-)platinum(II) (carboplatin, JM8) and ethylenediammine-malonatoplatinum(II) (JM40) (Begg et al., *Radiother. Oncol.* 9(2):157–65, 1987), JM8 and JM9 cisplatin analogues (Harstrick et al., *Int J. Androl.* 10(1); 139–45, 1987), (NPr4)2((PtCL4).cis-(PtCl2—(NH2Me)2)) (Brammer et al., *J. Chem. Soc., Chem. Commun.* 6:443–5, 1987), aliphatic tricarboxylic acid platinum complexes (EPA 185225), and cis-dichloro(amino acid)(tert-butylamine) platinum(II) complexes (Pasini & Bersanetti, *Inorg. Chim. Acta* 107(4):259–67, 1985). These compounds are thought to function by binding to DNA, i.e., acting as alkylating agents of DNA.

As medical implants are made in a variety of configurations and sizes, the exact dose administered will vary with device size, surface area, design and portions of the implant coated. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the medical implant, the preferred anticancer/anti-infective agents, used alone or in combination, should be administered under the following dosing guidelines:

(a) Anthracyclines. Utilizing the anthracycline doxorubicin as an example, whether applied as a polymer coating, incorporated into the polymers which make up the implant components, or applied without a carrier polymer, the total dose of doxorubicin applied to the implant should not exceed 25 mg (range of 0.1 µg to 25 mg). In a particularly preferred embodiment, the total amount of drug applied should be in the range of 1 µg to 5 mg. The dose per unit area (i.e., the amount of drug as a function of the surface area of the portion of the implant to which drug is applied and/or incorporated) should fall within the range of 0.01 µg–100 µg per $mm^2$ of surface area. In a particularly preferred embodiment, doxorubicin should be applied to the implant surface at a dose of 0.1 µg/$mm^2$–10 µg/$mm^2$. As different polymer and non-polymer coatings will release doxorubicin at differing rates, the above dosing parameters should be utilized in combination with the release rate of the drug from the implant surface such that a minimum concentration of $10^{-7}$–$10^{-4}$ M of doxorubicin is maintained on the surface. It is necessary to insure that surface drug concentrations exceed concentrations of doxorubicin known to be lethal to multiple species of bacteria and fungi (i.e., are in excess of $10^{-4}$ M; although for some embodiments lower concentrations are sufficient). In a preferred embodiment, doxorubicin is released from the surface of the implant such that anti-infective activity is maintained for a period ranging from several hours to several months. In a particularly preferred embodiment the drug is released in effective concentrations for a period ranging from 1 week-6 months. It should be readily evident based upon the discussions provided herein that analogues and derivatives of doxorubicin (as described previously) with similar functional activity can be utilized for the purposes of this invention; the above dosing parameters are then adjusted according to the relative potency of the analogue or derivative as compared to the parent compound (e.g., a compound twice as potent as doxorubicin is administered at half the above parameters, a compound half as potent as doxorubicin is administered at twice the above parameters, etc.).

Utilizing mitoxantrone as another example of an anthracycline, whether applied as a polymer coating, incorporated into the polymers which make up the implant, or applied without a carrier polymer, the total dose of mitoxantrone applied should not exceed 5 mg (range of 0.01 µg to 5 mg). In a particularly preferred embodiment, the total amount of drug applied should be in the range of 0.1 µg to 1 mg. The dose per unit area (i.e., the amount of drug as a function of the surface area of the portion of the implant to which drug is applied and/or incorporated) should fall within the range of 0.01 µg–20 µg per $mm^2$ of surface area. In a particularly preferred embodiment, mitoxantrone should be applied to the implant surface at a dose of 0.05 µg/$mm^2$–3 µg/$mm^2$. As different polymer and non-polymer coatings will release mitoxantrone at differing rates, the above dosing parameters should be utilized in combination with the release rate of the drug from the implant surface such that a minimum concentration of $10^{-5}$–$10^{-6}$ M of mitoxantrone is maintained. It is necessary to insure that drug concentrations on the implant surface exceed concentrations of mitoxantrone known to be lethal to multiple species of bacteria and fungi (i.e., are in excess of $10^{-5}$ M; although for some embodiments lower drug levels will be sufficient). In a preferred embodiment, mitoxantrone is released from the surface of the implant such that anti-infective activity is maintained for a period ranging from several hours to several months. In a particularly preferred embodiment the drug is released in effective concentrations for a period ranging from 1 week-6 months. It should be readily evident based upon the discussions provided herein that analogues and derivatives of mitoxantrone (as described previously) with similar functional activity can be utilized for the purposes of this invention; the above dosing parameters are then adjusted according to the relative potency of the analogue or derivative as compared to the parent compound (e.g., a compound twice as potent as mitoxantrone is administered at half the above parameters, a compound half as potent as mitoxantrone is administered at twice the above parameters, etc.).

(b) Fluoropyrimidines Utilizing the fluoropyrimidine 5-fluorouracil as an example, whether applied as a polymer coating, incorporated into the polymers which make up the implant, or applied without a carrier polymer, the total dose of 5-fluorouracil applied should not exceed 250 mg (range of 1.0 µg to 250 mg). In a particularly preferred embodiment, the total amount of drug applied should be in the range of 10 µg to 25 mg. The dose per unit area (i.e., the amount of drug as a function of the surface area of the portion of the implant to which drug is applied and/or incorporated) should fall within the range of 0.1 µg–1 mg per $mm^2$ of surface area. In a particularly preferred embodiment, 5-fluorouracil should be applied to the implant surface at a dose of 1.0 µg/$mm^2$–50 µg/$mm^2$. As different polymer and non-polymer coatings will release 5-fluorouracil at differing rates, the above dosing parameters should be utilized in combination with the release rate of the drug from the implant surface such that a minimum concentration of $10^{-4}$–$10^{-7}$ M of 5-fluorouracil is maintained. It is necessary to insure that surface drug concentrations exceed concentrations of 5-fluorouracil known to be lethal to numerous species of bacteria and fungi (i.e., are in excess of $10^{-4}$ M; although for some embodiments lower drug levels will be sufficient). In a preferred embodiment, 5-fluorouracil is released from the implant surface such that anti-infective activity is maintained for a period ranging from several hours to several months. In a particularly preferred embodiment the drug is released in effective concentrations for a period ranging from 1 week-6 months. It should be readily evident based upon the discussions provided herein that analogues and derivatives of 5-fluorouracil (as described previously) with similar functional activity can be utilized for the purposes of this invention; the above dosing parameters are then adjusted according to the relative potency of the analogue or derivative as compared to the parent compound (e.g., a compound twice as potent as 5-fluorouracil is administered at half the above parameters, a compound half as potent as 5-fluorouracil is administered at twice the above parameters, etc.).

(c) Podophylotoxins Utilizing the podophylotoxin etoposide as an example, whether applied as a polymer coating, incorporated into the polymers which make up the cardiac implant, or applied without a carrier polymer, the total dose of etoposide applied should not exceed 25 mg (range of 0.1 µg to 25 mg). In a particularly preferred embodiment, the total amount of drug applied should be in the range of 1 µg to 5 mg. The dose per unit area (i.e., the amount of drug as a function of the surface area of the portion of the implant to which drug is applied and/or incorporated) should fall within the range of 0.01 µg–100 µg per mm² of surface area. In a particularly preferred embodiment, etoposide should be applied to the implant surface at a dose of 0.1 µg/mm²–10 µg/mm². As different polymer and non-polymer coatings will release etoposide at differing rates, the above dosing parameters should be utilized in combination with the release rate of the drug from the implant surface such that a concentration of $10^{-5}$–$10^{-6}$ M of etoposide is maintained. It is necessary to insure that surface drug concentrations exceed concentrations of etoposide known to be lethal to a variety of bacteria and fungi (i.e., are in excess of $10^{-5}$ M; although for some embodiments lower drug levels will be sufficient). In a preferred embodiment, etoposide is released from the surface of the implant such that anti-infective activity is maintained for a period ranging from several hours to several months. In a particularly preferred embodiment the drug is released in effective concentrations for a period ranging from 1 week-6 months. It should be readily evident based upon the discussions provided herein that analogues and derivatives of etoposide (as described previously) with similar functional activity can be utilized for the purposes of this invention; the above dosing parameters are then adjusted according to the relative potency of the analogue or derivative as compared to the parent compound (e.g., a compound twice as potent as etoposide is administered at half the above parameters, a compound half as potent as etoposide is administered at twice the above parameters, etc.).

(d) Combination therapy. It should be readily evident based upon the discussions provided herein that combinations of anthracyclines (e.g., doxorubicin or mitoxantrone), fluoropyrimidines (e.g., 5-fluorouracil), folic acid antagonists (e.g., methotrexate and/or podophylotoxins (e.g., etoposide) can be utilized to enhance the antibacterial activity of the implant coating. Similarly anthracyclines (e.g., doxorubicin or mitoxantrone), fluoropyrimidines (e.g., 5-fluorouracil), folic acid antagonists (e.g., methotrexate and/or podophylotoxins (e.g., etoposide) can be combined with traditional antibiotic and/or antifungal agents to enhance efficacy. The anti-infective agent may be further combined with antithrombotic and/or antiplatelet agents (for example, heparin, dextran sulphate, danaparoid, lepirudin, hirudin, AMP, adenosine, 2-chloroadenosine, aspirin, phenylbutazone, indomethacin, meclofenamate, hydrochloroquine, dipyridamole, iloprost, ticlopidine, clopidogrel, abcixamab, eptifibatide, tirofiban, streptokinase, and/or tissue plasminogen activator) to enhance efficacy.

C. Methods for Generating Medical Devices which Contain or Release a Fibrosis-Inducing Agent In the practice of this invention, drug-coated, drug-impregnated, or drug containing implants and medical devices are provided which induce adhesion or fibrosis in the surrounding tissue, or facilitate "anchoring" of the device/implant in situ, thus enhancing the efficacy. Within various embodiments, fibrosis is induced by local or systemic release of specific pharmacological agents that become localized to the tissue adjacent to the device or implant. There are numerous methods available for optimizing delivery of the fibrosis-inducing agent to the site of the intervention and several of these are described below.

1) Devices and Implants that Contain or Release Fibrosis-Inducing Agents

Medical devices or implants of the present invention contain and/or are adapted to release an agent which induces fibrosis or adhesion to the surrounding tissue. Medical devices or implants may be adapted to have incorporated into their structure a fibrosis-inducing agent, adapted to have a surface coating of a fibrosis-inducing agent and/or adapted to release a fibrosis-inducing agent by (a) directly affixing to the implant or device a desired fibrosis-inducing agent or composition containing the fibrosis-inducing agent (e.g., by either spraying the medical implant with a drug and/or carrier (polymeric or non-polymeric)-drug composition to create a film or coating on all, or parts of the internal or external surface of the device; by dipping the implant or device into a drug and/or carrier (polymeric or non-polymeric)-drug solution to coat all or parts of the device or implant; or by other covalent or non-covalent (e.g., mechanically attached via knotting or the use of an adhesive or thermal treatment, electrostatic, ionic, hydrogen bonded or hydrophobic interactions) attachment of the therapeutic agent to the device or implant surface); (b) by coating the medical device or implant with a substance such as a hydrogel which can in turn absorb the desired fibrosis-inducing agent or composition; (c) by interweaving a "thread" composed of, or coated with, the fibrosis-inducing agent into the medical implant or device (e.g., a polymeric strand composed of materials that induce fibrosis (e.g., silk, collagen, EVA, PLA, polyurethanes, polymerized drug compositions) or polymers which comprise and/or release a fibrosis-inducing agent from the thread); (d) by covering all, or portions of the device or implant with a sleeve, cover or mesh containing a fibrosis-inducing agent (i.e., a covering comprised of a fibrosis-inducing agent—polymers such as silk, collagen, EVA, PLA, polyurethanes or polymerized compositions containing fibrosis-inducing agents); (e) constructing all, or parts of the device or implant itself with the desired agent or composition (e.g., constructing the device from polymers such as silk, collagen, EVA, PLA, polyurethanes or polymerized compositions of fibrosis-inducing agents); (f) otherwise impregnating the device or implant with the desired fibrosis-inducing agent or composition; (g) scoring (i.e., creating ridges or indentations) on all, or parts, of the device or implant surface to produce irritation of the tissue and ultimately fibrosis; (h) composing all, or parts, of the device or implant from metal alloys that induce fibrosis (e.g., copper); (i) constructing all, or parts of the device or implant itself from a degradable or non-degradable polymer that releases one or more fibrosis-inducing agents; (j) utilizing specialized multi-drug releasing medical device systems (described, e.g., in U.S. Pat. No. 6,562,065; U.S. Patent Application Publication Nos. 2003/0199970 and 2003/0167085; and in PCT Publication Nos. WO 03/015664 and WO 02/32347) to deliver fibrosis-inducing agents alone or in combination.

In one aspect, a medical device may be modified by attaching fibers (threads) to the surface of the device. The fibers may be polymeric and/or may be formed of or coated with a fibrosing material, such as silk. For example, the threads may be formed from a silk suture material. The presence of the threads can result in an enhanced cellular and/or extracellular matrix response to the exterior of the device. The threads can be attached to the device by using any one or a combination of the following methods, including use of an adhesive, thermal welding, stitching, wrapping, weaving, knotting, and the like. The threads can be coated with a material that delays the time it takes for the thread material to come into contact with the surrounding tissue and blood, thus allowing placement of the device without concern of thrombotic events due to the presence of the polymeric threads. Examples of materials that can be used to prepare coatings capable of degrading or dissolving upon implantation include gelatin, polyesters (e.g., PLGA, PLA, MePEG-PLGA, PLGA-PEG-PLGA, and blends thereof), lipids, fatty acids, sugar esters, nucleic acid esters, polyanhydrides, polyorthoesters, and PVA. The coating may further contain a fibrosing agent and/or a biologically active agent that may, for example, reduce the probability of an immediate thrombotic event (e.g., heparin, hydrophobic quaternary amine heparin complexes, and the like). In addition to the polymeric threads, all or a portion of the device may be coated with a polymeric carrier that contains a fibrosis-inducing agent.

The fibers (threads) may further comprise a coating or composition that is affected by an applied magnetic field. For example, a device such as a stent graft may be coated with polymeric threads that are coated, contain, or are formed from a fibrosing agent (e.g., silk suture). A magnetic field can be applied to the coated device to orient and align the polymeric fibers relative to each other and the surface of the device to increase the surface area of the fibers exposed to biological mediators which would stimulate a fibrotic reaction. The magnetically active component can be associated with the polymeric fiber using a variety of methods. The magnetically active component may be incorporated during manufacture of the fiber, for example, by incorporating a magnetically active material such as magnetite into a polymer feed prior to extrusion of the polymeric fiber. The magnetically active component can be coated onto the entire fiber or a portion of the fiber using, for example, an adhesive or a polymeric coating. The polymeric fiber (or a portion thereof) can be heated or plasticized with a solvent and then rolled in the magnetically active component, such that the magnetic material protrudes above the surface of the fiber or is embedded into the surface of the fiber.

The threads (either with or without a magnetic component) may be attached to the device in various configurations that can result in either partial or complete coverage of the exterior of the device. The polymeric threads may be affixed to the ends of a device or to the central portion of a device, and the attachment may be in a vertical, horizontal, or diagonal manner.

2) Systemic, Regional and Local Delivery of Fibrosis-inducing Agents

A variety of drug-delivery technologies are available for systemic, regional and local delivery of therapeutic agents. Several of these techniques may be suitable to achieve preferentially elevated levels of fibrosis-inducing agents in the vicinity of the medical device or implant, including: (a) using drug-delivery catheters for local, regional or systemic delivery of fibrosing agents to the tissue surrounding the device or implant (typically, drug delivery catheters are advanced through the circulation or inserted directly into tissues under radiological guidance until they reach the desired anatomical location; the fibrosing agent can then be released from the catheter lumen in high local concentrations in order to deliver therapeutic doses of the drug to the tissue surrounding the device or implant); (b) drug localization techniques such as magnetic, ultrasonic or MRI-guided drug delivery; (c) chemical modification of the fibrosis-inducing drug or formulation designed to increase uptake of the agent into damaged tissues (e.g., modification of the drug or formulation to include antibodies directed against damaged or healing tissue components such as macrophages, neutrophils, smooth muscle cells, fibroblasts, extracellular matrix components, neovascular tissue); (d) chemical modification of the fibrosis-inducing drug or formulation designed to localize the drug to areas of bleeding or disrupted vasculature such as encapsulation of the drug into site directed liposomes; and/or (e) direct injection of the fibrosis-inducing agent, for example under endoscopic vision.

3) Infiltration of Fibrosis-Inducing Agents into the Tissue Surrounding a Device or Implant Alternatively, the tissue cavity into which the device or implant is placed can be treated with a fibrosis-inducing agent prior to, during, or after the implantation procedure. This can be accomplished in several ways including: (a) topical application of the fibrosing agent into the anatomical space where the device can be placed (particularly useful for this embodiment is the use of polymeric carriers which release the fibrosing agent over a period ranging from several hours to several weeks—fluids, suspensions, emulsions, microemulsions, microspheres, pastes, gels, microparticulates, sprays, aerosols, solid implants and other formulations which release a fibrosing agent can be delivered into the region where the device or implant can be inserted via specialized delivery catheters or other applicators); (b) microparticulate silk and/or silk strands (e.g., linear, branched, and/or coiled) are also useful for directed delivery into the implantation site; (c) sprayable collagen-containing formulations such as COSTASIS (Angiotech Pharmaceuticals, Inc., Vancouver, BC) or materials made from 4-armed thiol PEG (10K), a 4-armed NHS PEG(10K) and methylated collagen (described below), or materials made from 4-armed thiol PEG (10K), a 4-armed NHS PEG(10K) and collagen or gelatin, either alone, or loaded with a fibrosis-inducing agent, applied to the implantation site (or the implant/device surface); (d) sprayable in situ forming PEG-containing formulations such as COSEAL (Angiotech Pharmaceuticals, Inc., Canada), FOCALSEAL (Genzyme Corporation, Cambridge, Mass.), SPRAYGEL or DURASEAL (both from Confluent Surgical, Inc., Waltham, Mass.), either alone, or loaded with a fibrosis-inducing agent, applied to the implantation site (or the implant/device surface);

(e) fibrinogen-containing formulations such as FLOSEAL or TISSEAL (both from Baxter Healthcare Corporation; Fremont, Calif.), either alone, or loaded with a fibrosis-inducing agent, applied to the implantation site (or the implant/device surface); (f) hyaluronic acid-containing formulations (either non-crosslinked, crosslinked or chemically modified) such as PERLANE or RESTYLANE (both from Q-Med AB, Sweden), HYLAFORM (Inamed Corporation; Santa Barbara, Calif.), SYNVISC (Biomatrix, Inc.; Ridgefied, N.J.), SEPRAFILM or SEPRACOAT (both from Genzyme Corporation; Cambridge, Mass.) loaded with a fibrosis with a fibrosis-inducing agent applied to the implantation site (or the implant/device surface); (g) polymeric gels for surgical implantation such as REPEL (Life Medical Sciences, Inc.; Princeton, N.J.) or FLOWGEL (Baxter Healthcare Corporation, Deerfield, Ill.) loaded with a fibrosis-inducing agent applied to the implantation site (or the implant/device surface); (h) orthopedic "cements" used to hold prostheses and tissues in place loaded with a fibrosis-inducing agent applied to the implantation site (or the implant/device surface), such as OSTEOBOND (Zimmer, Inc., Warsaw, Ind.), LVC (Wright Medical Technology, Inc., Arlington, Tenn.), SIMPLEX P (Stryker Corporation, Kalamazoo, Mich.), PALACOS (Smith & Nephew PLC Corporation, United Kingdom), and ENDURANCE (Johnson & Johnson, Inc., New Brunswick, N.J.); (i) surgical adhesives containing one or more cyanoacrylate monomers (e.g., methyl cyanoacrylate, ethyl cyanoacrylate, butyl cyanoacrylate, octyl cyanoacrylate, methoxypropyl cyanoacrylate) such as DERMABOND (Johnson & Johnson, Inc.), INDERMIL (United States Surgical; Norwalk, Conn.), GLUSTITCH (Blacklock Medical Products, Inc., Canada) or TISSUMEND II (Veterinary Products Laboratories; *Phoenix*, Ariz.), VETBOND (3M Company; St. Paul, Minn.), TISSUEMEND (TEI Biosciences, Inc.; Boston, Mass.), HISTOACRYL or HISTOACRYL BLUE (Davis & Geck; St. Louis, Mo.) and ORABASE SOOTHE-N-SEAL LIQUID PROTECTANT (Colgate-Palmolive Company; New York; N.Y.), either alone, or loaded with a fibrosis-inducing agent, applied to the implantation site (or the implant/device surface); (j) implants containing hydroxyapatite (or synthetic bone material such as calcium sulfate, VITOSS and CORTOSS (both from Orthovita, Inc., Malvern, Pa.)) loaded with a fibrosis-inducing agent applied to the implantation site (or the implant/device surface); (k) other biocompatible tissue fillers loaded with a fibrosis-inducing agent, such as those made by BioCure, Inc. (Norcross, Ga.), 3M Company and Neomend, Inc. (Sunnyvale, Calif.), loaded with a fibrosis-inducing agent applied to the implantation site (or the implant/device surface); (l) polysaccharide gels such as the ADCON series of gels (Gliatech, Inc.; Cleveland, Ohio); (m) films, sponges or meshes such as INTERCEED or VICRYL mesh (Ethicon, Inc., a Johnson & Johnson Company, Somerville, N.J.), and GELFOAM (Pharmacia & Upjohn Company; Kalamazoo, Mich.) loaded with a fibrosis-inducing agent applied to the implantation site (or the implant/device surface); (n) a hydrogel that is formed from an amino-functionalized polyethylene glycol (e.g., 4-armed tetra-amino PEG [10k]) and a 4-armed NHS functionalized PEG (e.g., pentaerythritol poly(ethylene glycol)ether tetra-succinimidyl glutarate [10K]). This hydrogel may further contain collagen, methylated collagen and/or gelatin. This hydrogel can further comprise the fibrosis-inducing agents described above (e.g., silk powder or silk threads), and (O) compositions that enhance osteointegration and/or osteogenesis, including materials composed of beta-tricalcium phosphate (e.g., VITOSS, PROOSTEON 500R made by E-Interpore-Cross International), hydroxyapatite or $Ca_{10}(PO_4)_6OH$ (e.g., OSTEOGRAF made by Ceramed Denta, Inc., Lakewood, Colo.), calcium carbonate or $CaCO_3$, calcium sulfate (e.g., OSTEOSET and ALLOMATRIX made by Wright Medical Technology, Inc.), calcium phosphate (e.g., CALCIBON made by Merck & Co., Inc., Whitehouse Station, N.J., NORIAN SRS made by Synthes-Strates, Switzerland), as well as synthetic bone fillers (e.g., CORTOSS and processed bone fillers, e.g., BIOOSS made by Geistlich Biomaterials, Inc., Switzerland). Representative examples of these materials are described in U.S. Pat. Nos. 3,929,971; 4,861,733; 6,527,810; 4,772,468; 4,882,149; 5,167,961; 6,576,015; 4,839,215; 5,614,206; 5,807,567; 6,030,636; 6,652,887; 6,206,957; 6,485,754; 4,347,234; 4,291,013; 5,129,905; 5,336,264; 5,569,442; 5,571,493; 5,683,667; 5,709,742; 5,820,632; 5,658,332; 5,681,872; 5,914,356; 5,939,039; 6,325,987; 6,383,519; 6,458,162; 6,736,799; 6,521,246; and 6,709,744.

In one aspect, the fibrosis-inducing agent may be delivered as a solution. The fibrosis-inducing agent can be incorporated directly into the solution to provide a homogeneous solution or dispersion. In certain embodiments, the solution is an aqueous solution. The aqueous solution may further include buffer salts, as well as viscosity modifying agents (e.g., hyaluronic acid, alginates, CMC, and the like). In another aspect of the invention, the solution can include a biocompatible solvent, such as ethanol, DMSO, glycerol, PEG-200, PEG-300 or NMP.

4) Coating and Sustained-Release Preparations of Fibrosis-Inducing Agents

For many of the aforementioned embodiments, the fibrosis-inducing agent can be incorporated or coated onto the device. For example, a desired fibrosis-inducing agent may be admixed with, blended with, conjugated to, or, otherwise modified to contain a polymeric composition (which may be either biodegradable or non-biodegradable) or non-polymeric composition. The polymeric or non-polymeric composition (i.e., carrier) can be used to coat the device or as a component of the materials used to manufacture the device. In other embodiments, the localized sustained delivery of the fibrosis inhibiting agent may be required. For example, a desired fibrosis-inducing agent may be admixed with, blended with, conjugated to, or otherwise modified to contain a polymeric composition (which may be either biodegradable or non-biodegradable) or non-polymeric composition in order to release the fibrosis-inducing agent over a period of time. For the above embodiments, biodegradable and non-biodegradable polymers, polymer conjugates as well as non-polymeric materials can be used to accomplish the incorporation of the fibrosis-inducing agent onto or into the device.

Representative examples of biodegradable polymers suitable for the delivery of fibrosis-inducing agents include albumin, collagen, gelatin, hyaluronic acid, starch, cellulose and cellulose derivatives (e.g., methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextrans, polysaccharides, fibrinogen, poly(ether ester) multiblock copolymers, based on poly(ethylene glycol) and poly(butylene terephthalate), tyrosine-derived polycarbonates (e.g., U.S. Pat. No. 6,120,491), poly(hydroxyl acids), poly(D,L-lactide), poly(D,L-lactide-co-glycolide), poly(glycolide), poly(hydroxybutyrate), polydioxanone, poly(alkyl-carbonate) and poly(orthoesters), polyesters, poly(hydroxyvaleric acid), polydioxanone, poly(ethylene terephthalate), poly(malic acid), poly(tartronic acid), poly(acrylamides), polyanhydrides, poly(ester-amides), poly(ester-imides), poly(ester-ureas), poly(ester-urethane-ureas), poly(anhydride-esters), poly(anhydride-imides), polyphosphazenes, poly(amino acids), poly(alkylene oxide)-poly(ester) block copolymers (e.g., X—Y, X—Y—X or Y—X—Y, where X is a polyalkylene oxide and Y is a polyester (e.g., PLGA, PLA, PCL, polydioxanone and copolymers thereof), and copolymers as well as blends thereof. (see generally, Ilium, L., Davids, S. S. (eds.) "Polymers in Controlled Drug Delivery" Wright, Bristol, 1987; Arshady, *J. Controlled Release* 17:1–22, 1991; Pitt, *Int. J. Phar.* 59:173–196, 1990; Holland et al., *J. Controlled Release* 4:155–0180, 1986).

Representative examples of non-degradable polymers suitable for the delivery of fibrosis-inducing agents include poly(ethylene-co-vinyl acetate) ("EVA") copolymers, silicone rubber, acrylic polymers (e.g., polyacrylic acid, polymethylacrylic acid, polymethylmethacrylate, poly(butyl methacrylate)), poly(alkylcyanoacrylate) (e.g., poly(ethylcyanoacrylate), poly(butylcyanoacrylate), poly(hexylcyanoacrylate), and poly(octylcyanoacrylate)), polyethylene, polypropylene, polyamides (nylon 6,6), polyurethanes (including hydrophilic polyurethanes), poly(ester-urethanes), poly(ether-urethanes), poly(ester-urea), poly(carbonate urethane)s, polyethers (poly(ethylene oxide), poly(propylene oxide), polyoxyalkylene ether block copolymers based on ethylene oxide and propylene oxide such as PLURONICs and PLURONICs R and poly(tetramethylene glycol)), styrene-based polymers (polystyrene, poly(styrene sulfonic acid), poly(styrene)-block-poly(isobutylene)-block-poly (styrene), poly(styrene)-poly(isoprene) block copolymers], and vinyl polymers (polyvinylpyrrolidone, poly(vinyl alcohol), poly(vinyl acetate phthalate) as well as copolymers and blends thereof. Polymers may also be developed which are either anionic (e.g., alginate, carrageenan, carboxymethyl cellulose, poly(acrylamido-2-methyl propane sulfonic acid) and copolymers thereof, poly(methacrylic acid) and copolymers thereof, and poly(acrylic acid) and copolymers thereof, as well as blends thereof) or cationic (e.g., chitosan, poly-L-lysine, polyethylenimine, and poly(allyl amine) and blends thereof (see generally, Dunn et al., *J. Applied Polymer Sci.* 50:353–365, 1993; Cascone et al., *J. Materials Sci.: Materials in Medicine* 5:770–774, 1994; Shiraishi et al., *Biol. Pharm. Bull.* 16(11):1164–1168, 1993; Thacharodi and Rao, *Int'l J. Pharm.* 120:115–118, 1995; Miyazaki et al., *Int'l J. Pharm.* 118:257–263, 1995).

Particularly preferred polymeric carriers include poly (ethylene-co-vinyl acetate), cellulose esters (nitrocellulose), poly(hydroxymethacrylate), poly(methylmethacrylate), poly (ethylene-co-acrylic acid), poly(vinylpyrrolidone) polyurethanes (e.g., CHRONOFLEX AL and CHRONOFLEX AR (both from CardioTech International, Inc., Woburn, Mass.) and BIONATE (Polymer Technology Group, Inc., Emeryville, Calif.), poly(D,L-lactic acid) oligomers and polymers, poly(L-lactic acid) oligomers and polymers, poly (glycolic acid), copolymers of lactic acid and glycolic acid, poly(caprolactone), poly(valerolactone), polyanhydrides, poly(anhydride esters), poly(ester-amides), poly(ester-ureas), copolymers of poly(caprolactone) or poly(lactic acid) with a polyethylene glycol (e.g., MePEG), silicone rubbers, poly(styrene)block-poly(isobutylene)-block-poly (styrene), poly(acrylate) polymers, and blends, admixtures, or co-polymers of any of the above. Other preferred polymers include collagen, poly(alkylene oxide)-based polymers, polysaccharides such as hyaluronic acid, chitosan and fucans, and copolymers of polysaccharides with degradable polymers, as well as crosslinked compositions of the above.

Other representative polymers capable of sustained localized delivery of fibrosis-inducing agents include carboxylic polymers, polyacetates, polyacrylamides, polycarbonates, polyethers, substituted polyethylenes, polyvinylbutyrals, polysilanes, polyureas, polyoxides, polystyrenes, polysulfides, polysulfones, polysulfonides, polyvinylhalides, pyrrolidones, isoprene rubbers, thermal-setting polymers, cross-linkable acrylic and methacrylic polymers, ethylene acrylic acid copolymers, styrene acrylic copolymers, vinyl acetate polymers and copolymers, vinyl acetal polymers and copolymers, epoxies, melamines, other amino resins, phenolic polymers, and copolymers thereof, water-insoluble cellulose ester polymers (including cellulose acetate propionate, cellulose acetate, nitrocellulose, cellulose acetate butyrate, cellulose nitrate, cellulose acetate phthalate, and mixtures thereof), polyvinylpyrrolidone (pvp), polyethylene glycols, polyethylene oxides, polyvinyl alcohol, polyethers, polyhydroxyacrylate, dextran, xanthan, hydroxypropyl cellulose, methyl cellulose, and homopolymers and copolymers of N-vinylpyrrolidone, N-vinyllactam, N-vinyl butyrolactam, N-vinyl caprolactam, other vinyl compounds having polar pendant groups, acrylate and methacrylate having hydrophilic esterifying groups, hydroxyacrylate, and acrylic acid, and combinations thereof; cellulose esters and ethers, ethyl cellulose, nitro-cellulose, hydroxyethyl cellulose, cellulose nitrate, cellulose acetate, cellulose acetate butyrate, cellulose acetate propionate, polyacrylate, natural and synthetic elastomers, acetal, styrene polybutadiene, acrylic resin, polyvinylidene chloride, polycarbonate, homopolymers and copolymers of vinyl compounds, polyvinylchloride, and polyvinylchloride acetate.

Representative examples of patents relating to drug-delivery polymers and their preparation include PCT Publication Nos. WO 98/19713, WO 01/17575, WO 01/41821, WO 01/41822, and WO 01/15526 (as well as their corresponding U.S. applications), and U.S. Pat. Nos. 4,500,676, 4,582,865, 4,629,623, 4,636,524, 4,713,448, 4,795,741, 4,913,743, 5,069,899, 5,099,013, 5,128,326, 5,143,724, 5,153,174, 5,246,698, 5,266,563, 5,399,351, 5,525,348, 5,800,412, 5,837,226, 5,942,555, 5,997,517, 6,007,833, 6,071,447, 6,090,995, 6,106,473, 6,110,483, 6,121,027, 6,156,345, 6,214,901, 6,368,611 6,630,155, 6,528,080, RE37,950, 6,461631, 6,143,314, 5,990,194, 5,792,469, 5,780,044, 5,759,563, 5,744,153, 5,739,176, 5,733,950, 5,681,873, 5,599,552, 5,340,849, 5,278,202, 5,278,201, 6,589,549, 6,287,588, 6,201,072, 6,117,949, 6,004,573, 5,702,717, 6,413,539, and 5,714,159, 5,612,052 and U.S. Patent Application Publication Nos. 2003/0068377, 2002/0192286, 2002/0076441, and 2002/0090398.

It should be obvious to one of skill in the art that the polymers as described herein can also be blended or copolymerized in various compositions as required to deliver therapeutic doses of fibrosis-inducing agents to blood vessels in the treatment site.

Polymeric carriers for fibrosis-inducing agents can be fashioned in a variety of forms, with desired release characteristics and/or with specific properties depending upon the device, composition or implant being utilized. For example, polymeric carriers may be fashioned to release a fibrosis-inducing agent upon exposure to a specific triggering event such as pH (see, e.g., Heller et al., "Chemically Self-Regulated Drug Delivery Systems," in *Polymers in Medicine III,* Elsevier Science Publishers B.V., Amsterdam, 1988, pp. 175–188; Kang et al., *J. Applied Polymer Sci.* 48:343–354, 1993; Dong et al., *J. Controlled Release* 19:171–178, 1992; Dong and Hoffman, *J. Controlled Release* 15:141–152, 1991; Kim et al., *J. Controlled Release* 28: 143–152, 1994; Cornejo-Bravo et al., *J. Controlled Release* 33:223–229, 1995; Wu and Lee, *Pharm. Res.* 10(10):1544–1547, 1993; Serres et al., *Pharm. Res.* 13(2): 196–201, 1996; Peppas, "Fundamentals of pH- and Temperature-Sensitive Delivery Systems," in Gurny et al. (eds.), *Pulsatile Drug Delivery*, Wissenschaftliche Verlagsgesellschaft mbH, Stuttgart, 1993, pp. 41–55; Doelker, "Cellulose Derivatives," 1993, in Peppas and Langer (eds.), *Biopolymers I*, Springer-Verlag, Berlin). Representative examples of pH-sensitive polymers include poly(acrylic acid) and its derivatives (including for example, homopolymers such as poly(aminocarboxylic acid); poly(acrylic acid); poly(methyl acrylic acid), copolymers of such homopolymers, and copolymers of poly(acrylic acid) and acrylmonomers such as those discussed above. Other pH sensitive polymers include polysaccharides such as cellulose acetate phthalate; hydroxypropylmethylcellulose phthalate; hydroxypropylmethylcellulose acetate succinate; cellulose acetate trimellilate; and chitosan. Yet other pH sensitive polymers include any mixture of a pH sensitive polymer and a water-soluble polymer.

Likewise, fibrosis-inducing agents can be delivered via polymeric carriers which are temperature sensitive (see, e.g., Chen et al., "Novel Hydrogels of a Temperature-Sensitive Pluronic Grafted to a Bioadhesive Polyacrylic Acid Backbone for Vaginal Drug Delivery," in *Proceed. Intern. Symp. Control. Rel. Bioact Mater.* 22:167–168, Controlled Release Society, Inc., 1995; Okano, "Molecular Design of Stimuli-Responsive Hydrogels for Temporal Controlled Drug Delivery," in *Proceed. Intern. Symp. Control. Rel. Bioact Mater.* 22:111–112, Controlled Release Society, Inc., 1995; Johnston et al., *Pharm. Res.* 9(3):425–433, 1992; Tung, *Int'l J. Pharm.* 107:85–90, 1994; Harsh and Gehrke, *J. Controlled Release* 17: 175–186, 1991; Bae et al., *Pharm. Res.* 8(4):531–537, 1991; Dinarvand and D'Emanuele, *J. Controlled Release* 36:221–227, 1995; Yu and Grainger, "Novel Thermo-sensitive Amphiphilic Gels: Poly N-isopropylacrylamide-co-sodium acrylate-co-n-N-alkylacrylamide Network Synthesis and Physicochemical Characterization," Dept. of Chemical & Biological Sci., Oregon Graduate Institute of Science & Technology, Beaverton, Oreg., pp. 820–821; Zhou and Smid, "Physical Hydrogels of Associative Star Polymers," Polymer Research Institute, Dept. of Chemistry, College of Environmental Science and Forestry, State Univ. of New York, Syracuse, N.Y., pp. 822–823; Hoffman et al., "Characterizing Pore Sizes and Water 'Structure' in Stimuli-Responsive Hydrogels," Center for Bioengineering, Univ. of Washington, Seattle, Wash., p. 828; Yu and Grainger, "Thermo-sensitive Swelling Behavior in Crosslinked N-isopropylacrylamide Networks: Cationic, Anionic and Ampholytic Hydrogels," Dept. of Chemical & Biological Sci., Oregon Graduate Institute of Science & Technology, Beaverton, Oreg., pp. 829–830; Kim et al., *Pharm. Res.* 9(3):283–290, 1992; Bae et al., *Pharm. Res.* 8(5):624–628, 1991; Kono et al., *J. Controlled Release* 30:69–75, 1994; Yoshida et al., *J. Controlled Release* 32:97–102, 1994; Okano et al., *J. Controlled Release* 36:125–133, 1995; Chun and Kim, *J. Controlled Release* 38:39–47, 1996; D'Emanuele and Dinarvand, *Int'l J. Pharm.* 118:237–242, 1995; Katono et al., *J. Controlled Release* 16: 215–228, 1991; Hoffman, "Thermally Reversible Hydrogels Containing Biologically Active Species," in Migliaresi et al. (eds.), *Polymers in Medicine III*, Elsevier Science Publishers B.V., Amsterdam, 1988, pp. 161–167; Hoffman, "Applications of Thermally Reversible Polymers and Hydrogels in Therapeutics and Diagnostics," in *Third International Symposium on Recent Advances in Drug Delivery Systems*, Salt Lake City, Utah, Feb. 24–27, 1987, pp. 297–305; Gutowska et al., *J. Controlled Release* 22:95–104, 1992; Palasis and Gehrke, *J. Controlled Release* 18:1–12, 1992; Paavola et al., *Pharm. Res.* 12(12):1997–2002, 1995).

Representative examples of thermogelling polymers, and their gelatin temperature [LCST (° C.)] include homopolymers such as poly(N-methyl-N-n-propylacrylamide), 19.8; poly(N-n-propylacrylamide), 21.5; poly(N-methyl-N-isopropylacrylamide), 22.3; poly(N-n-propylmethacrylamide), 28.0; poly(N-isopropylacrylamide), 30.9; poly(N, n-diethylacrylamide), 32.0; poly(N-isopropylmethacrylamide), 44.0; poly(N-cyclopropylacrylamide), 45.5; poly(N-ethylmethyacrylamide), 50.0; poly(N-methyl-N-ethylacrylamide), 56.0; poly(N-cyclopropylmethacrylamide), 59.0; and poly (N-ethylacrylamide), 72.0. Moreover, thermogelling polymers may be made by preparing copolymers between (among) monomers of the above, or by combining such homopolymers with other water-soluble polymers such as acrylmonomers (e.g., acrylic acid and derivatives thereof, such as methylacrylic acid, acrylate and derivatives thereof, such as butyl methacrylate, acrylamide, and N-n-butyl acrylamide).

Other representative examples of thermogelling polymers include cellulose ether derivatives such as hydroxypropyl cellulose, 41° C.; methyl cellulose, 55° C.; hydroxypropylmethyl cellulose, 66° C.; and ethylhydroxyethyl cellulose, polyalkylene oxide-polyester block copolymers of the structure X—Y, Y—X—Y and X—Y—X where X is a polyalkylene oxide and Y is a biodegradable polyester (e.g., PLG-PEG-PLG) and PLURONICS such as F-127, 10–15° C.; L-122, 19° C.; L-92, 26° C.; L-81, 20° C.; and L-61, 24° C.

Representative examples of patents relating to thermally gelling polymers and their preparation include U.S. Pat. Nos. 6,451,346; 6,201,072; 6,117,949; 6,004,573; 5,702,717; and 5,484,610 and PCT Publication Nos. WO 99/07343; WO 99/18142; WO 03/17972; WO 01/82970; WO 00/18821; WO 97/15287; WO 01/41735; WO 00/00222 and WO 00/38651.

Fibrosis-inducing agents may be linked by occlusion in the matrices of the polymer, bound by covalent linkages, or encapsulated in microcapsules. Within certain preferred embodiments of the invention, therapeutic compositions are provided in non-capsular formulations such as microspheres (ranging from nanometers to micrometers in size), pastes, and threads of various size, films and sprays.

Within certain aspects of the present invention, therapeutic compositions may be fashioned in any size ranging from 50 nm to 500 μm, depending upon the particular use. These compositions can be in the form of microspheres (porous or non-porous), microparticles, and/or nanoparticles. These compositions can be formed, for example, by spray-drying methods, milling methods, coacervation methods, W/O (water-oil) emulsion methods, W/O/W emulsion methods, and solvent evaporation methods. In some embodiments, these compositions can include microemulsions, emulsions, liposomes and micelles. Alternatively, such compositions may also be readily applied as a "spray", which solidifies into a film or coating for use as a device/implant surface coating or to line the tissues of the implantation site. Such sprays may be prepared from microspheres of a wide array of sizes, including for example, from 0.1 μm to 3 μm, from 10 μm to 30 μm, and from 30 μm to 100 μm.

Therapeutic compositions of the present invention may also be prepared in a variety of paste or gel forms. For example, within one embodiment of the invention, therapeutic compositions are provided which are liquid at one temperature (e.g., temperature greater than 37° C., such as 40° C., 45° C., 50° C., 55° C. or 60° C.), and solid or semi-solid at another temperature (e.g., ambient body temperature, or any temperature lower than 37° C.). Such "thermopastes" may be readily made utilizing a variety of techniques (see, e.g., PCT Publication WO 98/24427). Other pastes may be applied as a liquid, which solidify in vivo due to dissolution of a water-soluble component of the paste and precipitation of encapsulated drug into the aqueous body environment. These pastes and gels containing fibrosis-inducing agents are particularly useful for application to the surface of tissues which can be in contact with the implant or device.

In one aspect, the fibrosing agent or a composition comprising the fibrosing agent may be combined with a film or mesh or may be in the form or a film or mesh.

Films or meshes may take a variety of forms including, but not limited to, surgical meshes, membranes (e.g., barrier membranes), surgical sheets, surgical patches, surgical wraps, bandages, liquid bandages, surgical dressings, gauze, fabrics, tapes, surgical membranes, polymer matrices, shells, envelopes, tissue coverings, and other types of surgical matrices, and scaffolds.

In one aspect, the device comprises or may be in the form of a film. The film may be formed into one of many geometric shapes. Depending on the application, the film may be formed into the shape of a tube or may be a thin, elastic sheet of polymer. Generally, films are less than 5, 4, 3, 2, or 1 mm thick, more preferably less than 0.75 mm, 0.5 mm, 0.25 mm, or, 0.10 mm thick. Films can also be generated of thicknesses less than 50 µm, 25 µm or 10 µm. Films generally are flexible with a good tensile strength (e.g., greater than 50, preferably greater than 100, and more preferably greater than 150 or 200 N/cm$^2$), good adhesive properties (i.e., adheres to moist or wet surfaces), and have controlled permeability. Polymeric films (which may be porous or non-porous) are particularly useful for application to the surface of a device or implant as well as to the surface of tissue, cavity or an organ.

Films may be made by several processes, including for example, by casting, and by spraying, or may be formed at the treatment site in situ. For example, a sprayable formulation may be applied onto the treatment site which then forms into a solid film.

In another aspect, the device may comprise or be in the form of a mesh. A mesh, as used herein, is a material composed of a plurality of fibers or filaments (i.e., a fibrous material), where the fibers or filaments are arranged in such a manner (e.g., interwoven, knotted, braided, overlapping, looped, knitted, interlaced, intertwined, webbed, felted, and the like) so as to form a porous structure. Typically, a mesh is a pliable material, such that it has sufficient flexibility to be wrapped around a device. In certain aspects, the mesh may be sufficiently pliable so as to be capable of being wrapped around the external surface of a body passageway or cavity, or a portion thereof. The mesh may be capable of providing support to the structure (e.g., the vessel or cavity wall). In certain aspects, the mesh may be adapted to release an amount of the therapeutic agent.

Mesh materials may take a variety of forms. For example, the mesh may be in a woven, knit, or non-woven form and may include fibers or filaments that are randomly oriented relative to each other or that are arranged in an ordered array or pattern. In one embodiment, for example, a mesh may be in the form of a fabric, such as, for example, a knitted, braided, crocheted, woven, non-woven (e.g., a melt-blown or wet-laid) or webbed fabric. In one embodiment, a mesh may include a natural or synthetic biodegradable polymer that may be formed into a knit mesh, a weave mesh, a sprayed mesh, a web mesh, a braided mesh, a looped mesh, and the like. Preferably, a mesh or wrap has intertwined threads that form a porous structure, which may be, for example, knitted, woven, or webbed.

The structure and properties of the mesh used in a device depend on the application and the desired mechanical (i.e., flexibility, tensile strength, and elasticity), degradation properties, and the desired loading and release characteristics for the selected therapeutic agent(s). The mesh should have mechanical properties, such that the device can remain sufficiently strong until the surrounding tissue has healed. Factors that affect the flexibility and mechanical strength of the mesh include, for example, the porosity, fabric thickness, fiber diameter, polymer composition (e.g., type of monomers and initiators), process conditions, and the additives that are used to prepare the material.

Typically, the mesh possesses sufficient porosity to permit the flow of fluids through the pores of the fiber network and to facilitate tissue ingrowth. Generally, the interstices of the mesh should be wide enough apart to allow light visible by eye, or fluids, to pass through the pores. However, materials having a more compact structure also may be used. The flow of fluid through the interstices of the mesh may depend on a variety of factors, including, for example, the stitch count or thread density. The porosity of the mesh may be further tailored by, for example, filling the interstices of the mesh with another material (e.g., particles or polymer) or by processing the mesh (e.g., by heating) in order to reduce the pore size and to create non-fibrous areas. Fluid flow through the mesh of the invention can vary depending on the properties of the fluid, such as viscosity, hydrophilicity/hydrophobicity, ionic concentration, temperature, elasticity, pseudoplasticity, particulate content, and the like. The interstices of the mesh can be large enough so as to not prevent the release of impregnated or coated therapeutic agent(s) from the mesh, and the interstices preferably do not prevent the exchange of tissue fluid at the application site.

Mesh materials should be sufficiently flexible so as to be capable of conforming to the shape of a device surface or an anatomotical surface. In certain cases, the mesh material may be sufficiently flexible so as to be capable of being wrapped around all or a portion of the external surface of a body passageway or cavity. Flexible mesh materials are typically in the form of flexible woven or knitted sheets having a thickness ranging from about 25 microns to about 3000 microns; preferably from about 50 to about 1000 microns. Mesh materials for use in the practice of the invention typically range from about 100 to 400 microns in thickness.

The diameter and length of the fibers or filaments may range in size depending on the form of the material (e.g., knit, woven, or non-woven), and the desired elasticity, porosity, surface area, flexibility, and tensile strength. The fibers may be of any length, ranging from short filaments to long threads (i.e., several microns to hundreds of meters in length). Depending on the application, the fibers may have a monofilament or a multifilament construction.

The mesh may include fibers that are of same dimension or of different dimensions, and the fibers may be formed from the same or different types of biodegradable polymers. Woven materials, for example, may include a regular or irregular array of warp and weft strands and may include one type of polymer in the weft direction and another type (having the same or a different degradation profile from the first polymer) in the warp direction. The degradation profile of the weft polymer may be different than or the same as the degradation profile of the warp polymer. Similarly, knit materials may include one or more types (e.g., monofilament, multi-filament) and sizes of fibers and may include fibers made from the same or from different types of biodegradable polymers.

The structure of the mesh (e.g., fiber density and porosity) may impact the amount of therapeutic agent that may be loaded into or onto the device. For example, a fabric having a loose weave characterized by a low fiber density and high porosity can have a lower thread count, resulting in a reduced total fiber volume and surface area. As a result, the amount of agent that may be loaded into or onto, with a fixed carrier: therapeutic agent ratio, the fibers can be lower than for a fabric having a high fiber density and lower porosity. It is generally preferable that the mesh also should not invoke biologically detrimental inflammatory or toxic response, should be capable of being fully metabolized in the body, have an acceptable shelf life (of about at least one year or more), and be easily sterilized.

The device may include multiple mesh materials in any combination or arrangement. For example, a portion of the device may be a knitted material and another portion may be a woven material. In another embodiment, the device may more than one layer (e.g., a layer of woven material fused to a layer of knitted material or to another layer of the same type or a different type of woven material). In some embodiments, multi-layer constructions (e.g., device having two or more layers of material) may be used, for example, to enhance the performance properties of the device (e.g. for enhancing the rigidity or for altering the porosity, elasticity, or tensile strength of the device) or for increasing the amount of drug loading.

The mesh or film may be formed of or include a polymer. The polymer may be a biodegradable or a non-biodegradable polymer, or a combination thereof.

Biodegradable compositions that may be used to prepare the mesh of film include polymers that comprise albumin, collagen, hyaluronic acid and derivatives, sodium alginate and derivatives, chitosan and derivatives gelatin, starch, cellulose polymers (for example methylcellulose, hydroxypropylcellulose, hydroxypropylmethylcellulose, carboxymethylcellulose, cellulose acetate phthalate, cellulose acetate succinate, hydroxypropylmethylcellulose phthalate), casein, dextran and derivatives, polysaccharides, poly(caprolactone), fibrinogen, poly(hydroxyl acids), poly(L-lactide) poly(D, L lactide), poly(D, L-lactide-co-glycolide), poly(L-lactide-co-glycolide), copolymers of lactic acid and glycolic acid, copolymers of $\epsilon$-caprolactone and lactide, copolymers of glycolide and $\epsilon$-caprolactone, copolymers of lactide and 1,4-dioxane-2-one, polymers and copolymers that include one or more of the residue units of the monomers D-lactide, L-lactide, D,L-lactide, glycolide, $\epsilon$-caprolactone, trimethylene carbonate, 1,4-dioxane-2-one or 1,5-dioxepan-2-one, poly(glycolide), poly(hydroxybutyrate), poly(alkylcarbonate) and poly(orthoesters), polyesters, poly(hydroxyvaleric acid), polydioxanone, poly(ethylene terephthalate), poly(malic acid), poly(tartronic acid), polyanhydrides, polyphosphazenes, poly(amino acids). These compositions include copolymers of the above polymers as well as blends and combinations of the above polymers. (see, generally, Illum, L., Davids, S. S. (eds.) "Polymers in Controlled Drug Delivery" Wright, Bristol, 1987; Arshady, *J. Controlled Release* 17:1–22, 1991; Pitt, *Int. J. Phar.* 59:173–196, 1990; Holland et al., *J. Controlled Release* 4:155–0180, 1986).

In one aspect, the mesh or film includes a biodegradable or resorbable polymer that is formed from one or more monomers selected from the group consisting of lactide, glycolide, e-caprolactone, trimethylene carbonate, 1,4-dioxan-2-one, 1,5-dioxepan-2-one, 1,4-dioxepan-2-one, hydroxyvalerate, and hydroxybutyrate. In one aspect, the polymer may include, for example, a copolymer of a lactide and a glycolide. In another aspect, the polymer includes a poly(caprolactone). In yet another aspect, the polymer includes a poly(lactic acid), poly(L-lactide)/poly(D,L-Lactide) blends or copolymers of L-lactide and D,L-lactide. In yet another aspect, the polymer includes a copolymer of lactide and e-caprolactone. In yet another aspect, the polymer includes a polyester (e.g., a poly(lactide-co-glycolide). The poly(lactide-co-glycolide) may have a lactide:glycolide ratio ranges from about 20:80 to about 2:98, a lactide:glycolide ratio of about 10:90, or a lactide:glycolide ratio of about 5:95. In one aspect, the poly(lactide-co-glycolide) is poly(L-lactide-co-glycolide). Other examples of biodegradable materials include polyglactin, polyglycolic acid, autogenous, heterogenous, and xenogeneic tissue (e.g., pericardium or small intestine submucosa), and oxidized, regenerated cellulose. These meshes can be knitted, woven or non-woven meshes. Other examples of non-woven meshes include electrospun materials.

Representative examples of non-biodegradable compositions for use in forming films and meshes include ethylene-co-vinyl acetate copolymers, acrylic-based and methacrylic-based polymers (e.g., poly(acrylic acid), poly(methylacrylic acid), poly(methylmethacrylate), poly(hydroxyethylmethacrylate), poly(alkylcynoacrylate), poly(alkyl acrylates), poly(alkyl methacrylates)), polyolefins such as poly(ethylene) or poly(propylene), polyamides (e.g., nylon 6,6), poly(urethanes) (e.g. poly(ester urethanes), poly(ether urethanes), poly(carbonate urethanes), poly(ester-urea)), polyesters (e.g., PET, polybutyleneterephthalate, and polyhexyleneterephthalate), polyethers (poly(ethylene oxide), poly (propylene oxide), poly(ethylene oxide)-poly(propylene oxide) copolymers, diblock and triblock copolymers, poly (tetramethylene glycol)), silicone containing polymers and vinyl-based polymers (polyvinylpyrrolidone, poly(vinyl alcohol), poly(vinyl acetate phthalate), poly(styrene-co-isobutylene-co-styrene), fluorine containing polymers (fluoropolymers) such as fluorinated ethylene propylene (FEP) or polytetrafluoroethylene (e.g., expanded PTFE).

A variety of film mesh materials have been described which may be combined with a scarring agent. For example, the film or mesh may be a biodegradable polymeric matrix that conforms to the tissue and releases the agent in a controlled release manner. See e.g., U.S. Pat. No. 6,461,640. The film or mesh may be a self-adhering silicone sheet which is impregnated with an antioxidant and/or antimicrobial. See e.g., U.S. Pat. No. 6,572,878. The film or mesh may be a pliable shield with attachment ports and fenestrations that is adapted to cover a bony dissection in the spine. See e.g., U.S. Pat. No. 5,868,745 and U.S. Patent Application No. 2003/0078588. The film or mesh may be a resorbable micro-membrane having a single layer of non-porous polymer base material of poly-lactide. See e.g., U.S. Pat. No. 6,531,146 and U.S. Application No. 2004/0137033. The film or mesh may be a wound dressing garment composed of an outer pliable layer and a self-adhesive inner gel lining which serves as a dressing for contacting wounds. See e.g., U.S. Pat. No. 6,548,728. The film or mesh may be a bandage with a scar treatment pad with a layer of silicone elastomer or silicone gel. See e.g., U.S. Pat. Nos. 6,284,941 and 5,891,076. The film or mesh may be a crosslinkable system with at least three reactive compounds each having a polymeric molecular core with at least one functional group. See e.g., U.S. Pat. No. 6,458,889. The film or mesh may be composed of a prosthetic fabric having a 3-dimensional structure separating two surfaces in which one is open to post-surgical cell colonization and one is linked to a film of collagenous material. See e.g., U.S. Pat. No. 6,451,032. The film or mesh may be composed by crosslinking two synthetic polymers, one having nucleophilic groups and the other having electrophilic groups, such that they form a matrix that may be used to incorporate a biologically active compound. See e.g., U.S. Pat. Nos. 6,323,278; 6,166,130; 6,051,648 and 5,874,500. The film or mesh may be a conformable warp-knit fabric of oxidized regenerated cellulose or other bioresorbable material which acts like a physical barrier to prevent postoperative adhesions. See e.g., U.S. Pat. No. 5,007,916. Meshes for use in the practice of the invention also are described in U.S. Pat. No. 6,575,887, and co-pending application, entitled "Perivascular Wraps," filed Sep. 26, 2003 (U.S. Ser. No. (U.S. Ser. No. 10/673,046), which is hereby incorporated by reference in its entirety.

In one aspect, the fibrosing agent can be incorporated into a biodegradable or dissolvable film or mesh that is then applied to the treatment site prior or post implantation of the prosthesis/implant. Exemplary materials for the manufacture of these films or meshes are hyaluronic acid (crosslinked or non-crosslinked), cellulose derivatives (e.g., hydroxypropyl cellulose), PLGA, collagen and crosslinked poly(ethylene glycol).

Films and meshes, which may be combined with one or more scarring agents according to the present invention, include commercially available products. Examples of films and meshes into which a fibrosis-inducing agent can be incorporated include INTERCEED (Johnson & Johnson, Inc.), PRECLUDE (W.L. Gore), and POLYACTIVE (poly (ether ester) multiblock copolymers (Osteotech, Inc., Shrewsbury, N.J.), based on poly(ethylene glycol) and poly (butylene terephthalate), and SURGICAL absorbable hemostat gauze-like sheet from Johnson & Johnson. Another mesh is a prosthetic polypropylene mesh with a bioresorbable coating called SEPRAMESH Biosurgical Composite (Genzyme Corporation, Cambridge, Mass.). One side of the mesh is coated with a bioresorbable layer of sodium hyaluronate and carboxymethylcellulose, providing a temporary physical barrier that separates the underlying tissue and organ surfaces from the mesh. The other side of the mesh is uncoated, allowing for complete tissue ingrowth similar to bare polypropylene mesh. In one embodiment, the fibrosis-inducing agent may be applied only to the uncoated side of SEPRAMESH and not to the sodium hyaluronate/carboxymethylcellulose coated side. Other films and meshes include: (a) BARD MARLEX mesh (C.R. Bard, Inc.), which is a very dense knitted fabric structure with low porosity; (b) monofilament polypropylene mesh such as PROLENE available from Ethicon, Inc. Somerville, N.J. (see, e.g., U.S. Pat. Nos. 5,634,931 and 5,824,082)); (c) SURGISIS GOLD and SURGISIS IHM soft tissue graft (both from Cook Surgical, Inc.) which are devices specifically configured for use to reinforce soft tissue in repair of inguinal hernias in open and laparoscopic procedures; (d) thin walled polypropylene surgical meshes such as are available from Atrium Medical Corporation (Hudson, N.H.) under the trade names PROLITE, PROLITE ULTRA, and LITEMESH; (e) COMPOSIX hernia mesh (C.R. Bard, Murray Hill, N.J.), which incorporates a mesh patch (the patch includes two layers of an inert synthetic mesh, generally made of polypropylene, and is described in U.S. Pat. No. 6,280,453) that includes a filament to stiffen and maintain the device in a flat configuration; (f) VISILEX mesh (from C.R. Bard, Inc.), which is a polypropylene mesh that is constructed with monofilament polypropylene; (g) other meshes available from C.R. Bard, Inc. which include PERFIX Plug, KUGEL Hernia Patch, 3D MAX mesh, LHI mesh, DULEX mesh, and the VENTRALEX Hernia Patch; and (h) other types of polypropylene monofilament hernia mesh and plug products include HERTRA mesh 1, 2, and 2A, HERMESH 3, 4 & 5 and HERNIAMESH plugs T1, T2, and T3 from Herniamesh USA, Inc. (Great Neck, N.Y.).

Other examples of commercially available meshes which may be combined with fibrosing agents include the following. Boston Scientific Corporation sells the TRELEX NATURAL Mesh which is composed of a knitted polypropylene material. Ethicon, Inc. makes the absorbable VICRYL (polyglactin 910) meshes (knitted and woven) and MERSILENE Polyester Fiber Mesh. Dow Corning Corporation (Midland, Mich.) sells a mesh material formed from silicone elastomer known as SILASTIC Rx Medical Grade Sheeting (Platinum Cured). United States Surgical/Syneture (Norwalk, Conn.) sells a mesh made from absorbable polyglycolic acid under the trade name DEXON Mesh Products. Membrana Accurel Systems (Germany) sells the CELGARD microporous polypropylene fiber and membrane. Gynecare Worldwide, a division of Ethicon, Inc. sells a mesh material made from oxidized, regenerated cellulose known as INTERCEED TC7.

Numerous types of meshes and films and polymers for use with meshes and films have been described above. Methods for incorporating the fibrosing compositions onto or into the film or mesh include: (a) affixing (directly or indirectly) to the film or mesh a fibrosing composition (e.g., by either a spraying process or dipping process as described above, with or without a carrier), (b) incorporating or impregnating into the film or mesh a fibrosing composition (e.g., by either a spraying process or dipping process as described above, with or without a carrier (c) by coating the film or mesh with a substance such as a hydrogel which can in turn absorb the fibrosing composition, (d) constructing the film or mesh itself or a portion of the film or mesh with a fibrosing composition, or (e) by covalently binding the fibrosing agent directly to the film or mesh surface or to a linker (small molecule or polymer) that is coated or attached to the film or mesh surface. For devices that are coated, the coating process can be performed in such a manner as to (a) coat only one surface of the film or mesh or (b) coat all or parts of both sides of the film or mesh.

The therapeutic agent(s) may be an integral part of the film or mesh (i.e., may reside within the fibers of the mesh). The fibrosis inhibiting agent can be incorporated directly into the film or mesh or it can be incorporated into a secondary carrier (polymeric or non-polymeric), as described above, that is then incorporated into the film or mesh.

Alternatively, or in addition, the film or mesh may be coated with a fibrosing agent or a composition that includes the fibrosing agent. The coating may take the form of a surface-adherent coating, mask, film, gel, foam, or mold.

A variety of polymeric compositions have been described that may be used in conjunction with the films and meshes of the invention. Such compositions may be in the form of, for example, gels, sprays, liquids, and pastes, or may be polymerized from monomeric or prepolymeric constituents in situ. For example, the composition may be a polymeric tissue coating which is formed by applying a polymerization initiator to the tissue and then covering it with a water-soluble macromer that is polymerizable using free radical initiators under the influence of UV light. See e.g., U.S. Pat. Nos. 6,177,095 and 6,083,524. The composition may be an aqueous composition including a surfactant, pentoxifylline and a polyoxyalkylene polyether. See e.g., U.S. Pat. No. 6,399,624. The composition may be a hydrogel-forming, self-solvating, absorbable polyester copolymers capable of selective, segmental association into compliant hydrogels mass upon contact with an aqueous environment. See e.g., U.S. Pat. No. 5,612,052. The composition may be composed of fluent pre-polymeric material that is emitted to the tissue surface and then exposed to activating energy in situ to initiate conversion of the applied material to non-fluent polymeric form. See e.g., U.S. Pat. Nos. 6,004,547 and 5,612,050. The composition may be composed of a gas mixture of oxygen present in a volume ratio of 1 to 20%. See e.g., U.S. Pat. No. 6,428,500. The composition may be composed of an anionic polymer having an acid sulfate and sulfur content greater than 5% which acts to inhibit monocyte or macrophage invasion. See e.g., U.S. Pat. No. 6,417, 173. The composition may be composed of a non-gelling polyoxyalkylene composition with or without a therapeutic agent. See e.g., U.S. Pat. No. 6,436,425. The composition may be coated onto tissue surfaces and may be composed of an aqueous solution of a hydrophilic, polymeric material (e.g., polypeptides or polysaccharide) having greater than 50,000 molecular weight and a concentration range of 0.01% to 15% by weight. See e.g., U.S. Pat. No. 6,464,970.

Other representative examples of polymeric compositions which may be coated onto the film or mesh include poly (ethylene glycol)-based systems, hyaluronic acid and crosslinked hyaluronic acid compositions. These compositions can be applied as the final composition or they can be applied as materials that form crosslinked gel in situ.

Other compositions that can be combined with scarring agents in conjunction with films and meshes, include, but are not limited to: (a) sprayable PEG-containing formulations such as COSEAL, SPRAYGEL, FOCALSEAL or DURASEAL; (b) hyaluronic acid-containing formulations such as RESTYLANE, HYLAFORM, PERLANE, SYNVISC, SEPRAFILM, SEPRACOAT, INTERGEL, (c) polymeric gels such as REPEL or FLOWGEL, (d) dextran sulfate gels such as the ADCON range of products, and (e) lipid based compositions such as ADSURF (Brittania Pharmaceuticals).

Prior to implantation, the film or mesh may be trimmed or cut from a sheet of bulk material to match the configuration of the widened foramen, canal, or dissection region, or at a minimum, to overlay the exposed tissue area. The film or mesh may be bent or shaped to match the particular configuration of the placement region. The film or mesh may also be rolled in a cuff shape or cylindrical shape and placed around the exterior periphery of the desired tissue. The film or mesh may be provided in a relatively large bulk sheet and then cut into shapes to mold the particular structure and surface topography of the tissue or device to be wrapped. Alternatively, the film or mesh may be pre-shaped into one or more patterns for subsequent use. The films and meshes may be typically rectangular in shape and be placed at the desired location within the surgical site by direct surgical placement or by endoscopic techniques. The film or mesh may be secured into place by wrapping it onto itself (i.e., self-adhesive), or by securing it with sutures, staples, sealant, and the like. Alternatively, the film or mesh may adhere readily to tissue and therefore, additional securing mechanisms may not be required.

Within further aspects of the present invention, polymeric carriers are provided which are adapted to contain and release a hydrophobic fibrosis-inducing compound, and/or the carrier containing the hydrophobic compound, in combination with a carbohydrate, protein or polypeptide. Within certain embodiments, the polymeric carrier contains or comprises regions, pockets, or granules of one or more hydrophobic compounds. For example, within one embodiment of the invention, hydrophobic compounds may be incorporated within a matrix which contains the hydrophobic fibrosis-inducing compound, followed by incorporation of the matrix within the polymeric carrier. A variety of matrices can be utilized in this regard, including for example, carbohydrates and polysaccharides such as starch, cellulose, dextran, methylcellulose, sodium alginate, heparin, chitosan and hyaluronic acid and proteins or polypeptides such as albumin, collagen and gelatin. Within alternative embodiments, hydrophobic compounds may be contained within a hydrophobic core, and this core contained within a hydrophilic shell.

Within another aspect of the present invention, polymeric carriers can be materials that are formed in situ. In one embodiment, the precursors can be monomers or macromers that contain unsaturated groups which can be polymerized or crosslinked. The monomers or macromers can then, for example, be injected into the treatment area or onto the surface of the treatment area and polymerized or crosslinked in situ using a radiation source (e.g., visible or UV light) or a free radical system (e.g., potassium persulfate and ascorbic acid or iron and hydrogen peroxide). The polymerization or crosslinking step can be performed immediately prior to, simultaneously to, or post injection of the reagents into the treatment site. Representative examples of compositions that undergo free radical polymerization or crosslinking reactions are described in WO 01/44307, WO 01/68720, WO 02/072166, WO 03/043552, WO 93/17669, and WO 00/64977, U.S. Pat. Nos. 5,900,245; 6,051,248; 6,083,524; 6,177,095; 6,201,065; 6,217,894; 6,639,014; 6,352,710; 6,410,645; 6,531,147; 5,567,435; 5,986,043; and 6,602,975, and U.S. Patent Application Publication Nos. 2002/012796, 2002/0127266, 2002/0151650, 2003/0104032, 2002/0091229, and 2003/0059906.

In another embodiment, the reagents can undergo an electrophilic-nucleophilic reaction to produce a crosslinked matrix. Polymers terminated with nucleophilic groups such as amine, sulfhydryl, hydroxyl, $-PH_2$ or $CO-NH-NH_2$ can be used as the nucleophilic reagents and polymers terminated with electrophilic groups such as succinimidyl, carboxylic acid, aldehyde, epoxide, isocyanate, vinyl, vinyl sulfone, maleimide, $-S-S-(C_5H_4N)$ or activated esters, such as are used in peptide synthesis can be used as the electrophilic reagents. For example, a 4-armed thiol derivatized poly(ethylene glycol) (e.g., pentaerythritol poly(ethylene glycol)ether tetra-sulfhydryl) can be reacted with a 4 armed NHS-derivatized polyethylene glycol (e.g., pentaerythritol poly(ethylene glycol)ether tetra-succinimidyl glutarate) under basic conditions (pH>about 8). Representative examples of compositions that undergo such electrophilic-nucleophilic crosslinking reactions are described, for example, in U.S. Pat. Nos. 5,752,974; 5,807,581; 5,874,500; 5,936,035; 6,051,648; 6,165,489; 6,312,725; 6,458,889; 6,495,127; 6,534,591; 6,624,245; 6,566,406; 6,610,033; 6,632,457; U.S. Patent Application Publication No. 2003/0077272A1; and co-pending patent applications entitled "Tissue Reactive Compounds and Compositions and Uses Thereof" (U.S. Ser. No. 60/437,384, filed Dec. 30, 2002, and U.S. Ser. No. 60/44,924, filed Jan. 17, 2003) and "Drug Delivery from Rapid Gelling Polymer Composition" (U.S. Ser. No. 60/437,471, filed Dec. 30, 2002, and U.S. Ser. No. 60/440,875, filed Jan. 17, 2003).

In another embodiment, the electrophilic- or nucleophilic-terminated polymers can further comprise a polymer that can enhance the mechanical and/or adhesive properties of the in situ forming compositions. This polymer can be a degradable or non-degradable polymer. For example, the polymer may be collagen or a collagen derivative, for example methylated collagen. An example of an in situ forming composition uses pentaerythritol poly(ethylene glycol)ether tetra-sulfhydryl] (4-armed thiol PEG), pentaerythritol poly(ethylene glycol)ether tetra-succinimidyl glutarate] (4-armed NHS PEG) and methylated collagen as the reactive reagents. This composition, when mixed with the appropriate buffers can produce a crosslinked hydrogel. (See, e.g., U.S. Pat. Nos. 5,874,500; 6,051,648; 6,166,130; 5,565,519 and 6,312,725).

In another embodiment, the in situ forming material polymer can be a polyester. Polyesters that can be used in in situ forming compositions include poly(hydroxyesters). In another embodiment, the polyester can comprise the residues of one or more of the monomers selected from lactide, lactic acid, glycolide, glycolic acid, e-caprolactone, gamma-caprolactone, hydroxyvaleric acid, hydroxybutyric acid, beta-butyrolactone, gamma-butyrolactone, gamma-valerolactone, ?-decanolactone, d-decanolactone, trimethylene carbonate, 1,4-dioxane-2-one or 1,5-dioxepan-2-one. Representative examples of these types of compositions are described in U.S. Pat. Nos. 5,874,500; 5,936,035; 6,312,725; 6,495,127 and PCT Publication Nos. WO 2004/028547.

In another embodiment, the electrophilic-terminated polymer can be partially or completely replaced by a small molecule or oligomer that comprises an electrophilic group (e.g., disuccinimidyl glutarate).

In another embodiment, the nucleophilic-terminated polymer can be partially or completely replaced by a small molecule or oligomer that comprises a nucleophilic group (e.g., dicysteine, dilysine, trilysine, etc.).

Other examples of in situ forming materials that can be used include those based on the crosslinking of proteins (described in, for example, U.S. Pat. Nos. RE38158; 4,839,345; 5,514,379, 5,583,114; 6,310,036; 6,458,147; 6,371,975; U.S. Patent Application Publication Nos. 2004/0063613A1, 2002/0161399A1, and 2001/0018598A1, and PCT Publication Nos. WO 03/090683, WO 01/45761, WO 99/66964, and WO 96/03159) and those based on isocyanate or isothiocyanate capped polymers (see, e.g., PCT Publication No. WO 04/021983).

Other examples of in situ forming materials can include reagents that comprise one or more cyanoacrylate groups. These reagents can be used to prepare a poly(alkylcyanoacrylate) or poly(carboxyalkylcyanoacrylate) (e.g., poly(ethylcyanoacrylate), poly(butylcyanoacrylate), poly(isobutylcyanoacrylate), poly(hexylcyanoacrylate), poly(methoxypropylcyanoacrylate), and poly(octylcyanoacrylate)).

Examples of commercially available cyanoacrylates that can be used include DERMABOND, INDERMIL, GLUSTITCH, VETBOND, HISTOACRYL, TISSUEMEND, TISSUMEND II, HISTOACRYL BLUE and ORABASE SOOTHE-N-SEAL LIQUID PROTECTANT.

In another embodiment, the cyanoacrylate compositions can further comprise additives to stabilize the reagents or alter the rate of reaction of the cyanoacrylate. For example, a trimethylene carbonate based polymer or an oxalate polymer of poly(ethylene glycol) or a $\epsilon$-caprolactone based copolymer can be mixed with a 2-alkoxyalkylcyanoacrylate (e.g., 2-methoxypropylcyanoacrylate). Representative examples of these compositions are described in U.S. Pat. Nos. 5,350,798 and 6,299,631.

In another embodiment, the cyanoacrylate composition can be prepared by capping heterochain polymers with a cyanoacrylate group. The cyanoacrylate-capped heterochain polymer preferably has at least two cyanoacrylate ester groups per chain. The heterochain polymer can comprise an absorbable poly(ester), poly(ester-carbonate), poly(ether-carbonate) and poly(ether-ester). The poly(ether-ester)s described in U.S. Pat. Nos. 5,653,992 and 5,714,159 can also be used as the heterochain polymers. A triaxial poly($\epsilon$-caprolactone-co-trimethylene carbonate) is an example of a poly(ester-carbonate) that can be used. The heterochain polymer may be a polyether. Examples of polyethers that can be used include poly(ethylene glycol), poly(propylene glycol) and block copolymers of poly(ethylene glycol) and poly(propylene glycol) (e.g., PLURONICS group of polymers including but not limited to PLURONIC F127 or F68). Representative examples of these compositions are described in U.S. Pat. No. 6,699,940.

As described above, the fibrosing agent can be coated onto the entire device or a portion of the device using the polymeric coatings described above. This can be accomplished, for example, by dipping, spraying, electrospinning, painting or by vacuum deposition. In addition to the coating compositions and methods described above, there are various other coating compositions and methods that are known in the art. Representative examples of these coating compositions and methods are described in U.S. Pat. Nos. 6,610,016; 6,358,557; 6,306,176; 6,110,483; 6,106,473; 5,997,517; 5,800,412; 5,525,348; 5,331,027; 5,001,009; 6,562,136; 6,406,754; 6,344,035; 6,254,921; 6,214,901; 6,077,698; 6,603,040; 6,278,018; 6,238,799; 6,096,726; 5,766,158; 5,599,576; 4,119,094; 4,100,309; 6,599,558; 6,369,168; 6,521,283; 6,497,916; 6251964; 6,225,431; 6,087,462; 6,083,257; 5,739,237; 5,739,236; 5,705,583; 5648442; 5645883; 5,556,710; 5,496,581; 4,689,386; 6,214,115; 6,090,901; 6,599,448; 6,054,504; 4,987,182; 4,847,324; and 4,642,267, U.S. Patent Application Publication Nos. 2003/0129130; 2001/0026834; 2003/0190420; 2001/0000785; 2003/0059631; 2003/0190405; 2002/0146581; 2003/020399; 2003/0129130, 2001/0026834; 2003/0190420; 2001/0000785; 2003/0059631; 2003/0190405; 2002/0146581; and 2003/020399, and PCT Publication Nos. WO 02/055121; WO 01/57048; WO 01/52915; and WO 01/01957.

Within another aspect of the invention, the biologically active agent can be delivered with a non-polymeric agent. Examples of non-polymeric agents include sucrose derivatives (e.g., sucrose acetate isobutyrate, sucrose oleate), sterols such as cholesterol, stigmasterol, beta-sitosterol, and estradiol; cholesteryl esters such as cholesteryl stearate; $C_{12}$–$C_{24}$ fatty acids such as lauric acid, myristic acid, palmitic acid, stearic acid, arachidic acid, behenic acid, and lignoceric acid; $C_{18}$–$C_{36}$ mono-, di- and triacylglycerides such as glyceryl monooleate, glyceryl monolinoleate, glyceryl monolaurate, glyceryl monodocosanoate, glyceryl monomyristate, glyceryl monodicenoate, glyceryl dipalmitate, glyceryl didocosanoate, glyceryl dimyristate, glyceryl didecenoate, glyceryl tridocosanoate, glyceryl trimyristate, glyceryl tridecenoate, glycerol tristearate and mixtures thereof; sucrose fatty acid esters such as sucrose distearate and sucrose palmitate; sorbitan fatty acid esters such as sorbitan monostearate, sorbitan monopalmitate and sorbitan tristearate; $C_{16}$–$C_{18}$ fatty alcohols such as cetyl alcohol, myristyl alcohol, stearyl alcohol, and cetostearyl alcohol; esters of fatty alcohols and fatty acids such as cetyl palmitate and cetearyl palmitate; anhydrides of fatty acids such as stearic anhydride; phospholipids including phosphatidylcholine (lecithin), phosphatidylserine, phosphatidylethanolamine, phosphatidylinositol, and lysoderivatives thereof; sphingosine and derivatives thereof; spingomyelins such as stearyl, palmitoyl, and tricosanyl spingomyelins; ceramides such as stearyl and palmitoyl ceramides; glycosphingolipids; lanolin and lanolin alcohols, calcium phosphate, sintered and unscintered hydoxyapatite, zeolites; and combinations and mixtures thereof.

Representative examples of patents relating to non-polymeric delivery systems and their preparation include U.S. Pat. Nos. 5,736,152; 5,888,533; 6,120,789; 5,968,542; and 5,747,058.

Other carriers that may likewise be utilized to contain and deliver fibrosis-inducing agents described herein include: hydroxypropyl cyclodextrin (Cserhati and Hollo, *Int. J. Pharm.* 108:69–75, 1994), liposomes (see, e.g., Sharma et al., *Cancer Res.* 53:5877–5881, 1993; Sharma and Straubinger, *Pharm. Res.* 11(60):889–896, 1994; WO 93/18751; U.S. Pat. No. 5,242,073), liposome/gel (WO 94/26254), nanocapsules (Bartoli et al., *J. Microencapsulation* 7(2): 191–197, 1990), micelles (Alkan-Onyuksel et al., *Pharm. Res.* 11(2):206–212, 1994), nanoparticles (Violante and Lanzafame PMCR), nanoparticles—modified (U.S. Pat. No. 5,145,684), nanoparticles (surface modified) (U.S. Pat. No. 5,399,363), micelle (surfactant) (U.S. Pat. No. 5,403,858), synthetic phospholipid compounds (U.S. Pat. No. 4,534, 899), gas borne dispersion (U.S. Pat. No. 5,301,664), liquid emulsions, foam, spray, gel, lotion, cream, ointment, dispersed vesicles, particles or droplets solid- or liquid-aerosols, microemulsions (U.S. Pat. No. 5,330,756), polymeric shell (nano- and micro-capsule) (U.S. Pat. No. 5,439,686), emulsions (Tarr et al., *Pharm Res.* 4: 62–165, 1987), nanospheres (Hagan et al., *Proc. Intern. Symp. Control Rel. Bioact. Mater.* 22, 1995; Kwon et al., *Pharm Res.* 12(2): 192–195; Kwon et al., *Pharm Res.* 10(7):970–974; Yokoyama et al., *J. Contr. Rel.* 32:269–277, 1994; Gref et al., Science 263: 1600–1603, 1994; Bazile et al., *J. Pharm. Sci.* 84:493–498, 1994) and implants (U.S. Pat. No. 4,882, 168, Jampel et al., *Invest Ophthalm. Vis. Science* 34(11): 3076–3083, 1993; Walter et al., *Cancer Res.* 54:22017–2212, 1994).

In another embodiment, the fibrosis inducing agent can be incorporated into a composition that enhances osteointegration and/or osteogenesis. Examples of these compositions include materials composed of beta-tricalcium phosphate (e.g., VITOSS, PROOSTEON 500R), hydroxyapatite or $Ca_{10}(PO_4)_6OH$ (e.g., OSTEOGRAF, calcium carbonate or $CaCO_3$, calcium sulfate (e.g., OSTEOSET and ALLOMATRIX), calcium phosphate (e.g., CALCIBON or NORIAN SRS) as well as synthetic bone fillers (e.g., CORTOSS) and processed bone fillers (e.g., BIOOSS). Representative examples of these materials are described in U.S. Pat. Nos. 3,929,971; 4,861,733; 6,527,810; 4,772,468; 4,882,149; 5,167,961; 6,576,015; 4,839,215; 5,614,206; 5,807,567; 6,030,636; 6,652,887; 6,206,957; 6,485,754; 4,347,234; 4,291,013; 5,129,905; 5,336,264; 5,569,442; 5,571,493; 5,683,667; 5,709,742; 5,820,632; 5,658,332; 5,681,872; 5,914,356; 5,939,039; 6,325,987; 6,383,519; 6,458,162; 6,736,799; 6,521,246; and 6,709,744.

Within another aspect of the invention, the fibrosis-inducing agent can further comprise a secondary carrier. The secondary carrier can be in the form of microspheres (e.g., PLGA, PLLA, PDLLA, PCL, gelatin, polydioxanone, poly (alkylcyanoacrylate)), nanospheres (e.g., PLGA, PLLA, PDLLA, PCL, gelatin, polydioxanone, poly(alkylcyanoacrylate)), liposomes, emulsions, microemulsions, micelles (e.g., SDS, block copolymers of the form X—Y, X—Y—X or Y—X—Y, where X is a poly(alkylene oxide) or an alkyl ether thereof and Y is a polyester (e.g., PLGA, PLLA, PDLLA, PCL, polydioxanone)), zeolites or cyclodextrins.

Within another aspect of the invention, these fibrosis-inducing agent/secondary carrier compositions can be a) incorporated directly into or onto the device, b) incorporated into a solution, c) incorporated into a gel or viscous solution, d) incorporated into the composition used for coating the device, or e) incorporated into or onto the device following coating of the device with a coating composition.

For example, fibrosis-inducing agent loaded PLGA microspheres may be incorporated into a polyurethane coating solution which is then coated onto the device.

In yet another example, the device can be coated with a polyurethane and then allowed to partially dry such that the surface is still tacky. A particulate form of the fibrosis-inducing agent or fibrosis-inducing agent/secondary carrier can then be applied to all or a portion of the tacky coating after which the device is dried.

In yet another example, the device can be coated with one of the coatings described above. A thermal treatment process can then be used to soften the coating, after which the fibrosis-inducing agent or the fibrosis-inducing agent/secondary carrier is applied to the entire device or to a portion of the device (e.g., outer surface).

Within another aspect of the invention, a coated device which inhibits or reduces an in vivo fibrotic reaction is further coated with a compound or composition which delays the release of and/or activity of the fibrosis-inducing agent. Representative examples of such agents include biologically inert materials such as gelatin, PLGA/MePEG film, PLA, polyurethanes, silicone rubbers, surfactants, lipids, or polyethylene glycol, as well as biologically active materials such as heparin (e.g., to induce coagulation).

For example, in one embodiment of the invention, the active agent on the device is top-coated with a physical barrier. Such barriers can include non-degradable materials or biodegradable materials such as gelatin, PLGA/MePEG film, PLA, polyethylene glycol, or the like. In one embodiment, the rate of diffusion of the therapeutic agent in the barrier coat is slower that the rate of diffusion of the therapeutic agent in the coating layer. In the case of PLGA/MePEG, once the PLGA/MePEG becomes exposed to the bloodstream, the MePEG can dissolve out of the PLGA, leaving channels through the PLGA to an underlying layer containing the fibrosis-inducing agent (e.g., silk or cyclosporine A), which can then diffuse into the vessel wall and initiate its biological activity.

In another embodiment of the invention, for example, a particulate form of the active agent (e.g., silk or cyclosporine A) may be coated onto the device using a polymer (e.g., PLG, PLA, or polyurethane). A second polymer, that dissolves slowly or degrades (e.g., MePEG-PLGA or PLG) and that does not contain the active agent, may be coated over the first layer. Once the top layer dissolves or degrades, it exposes the under coating, which allows the active agent to be exposed to the treatment site or to be released from the coating.

Within another aspect of the invention, the outer layer of the coated device, which induces an in vivo fibrotic response, is further treated to crosslink the outer layer of the coating. This can be accomplished by subjecting the coated device to a plasma treatment process. The degree of crosslinking and nature of the surface modification can be altered by changing the RF power setting, the location with respect to the plasma, the duration of treatment as well as the gas composition introduced into the plasma chamber.

Protection of a biologically active surface can also be utilized by coating the device or implant surface with an inert molecule that prevents access to the active site through steric hindrance, or by coating the surface with an inactive form of the fibrosis-inducing agent, which is later activated. For example, the device can be coated with an enzyme, which causes either release of the fibrosis-inducing agent or activates the fibrosis-inducing agent.

Another example of a suitable device surface coating includes an anti-coagulant such as heparin, which can be coated on top of the fibrosis-inducing agent such that the presence of the heparin or other anti-coagulant delays coagulation at the treatment site. As the heparin or other anticoagulant dissolves away, the anticoagulant activity may slow or stop, and the newly exposed fibrosis-inducing agent (e.g., silk or cyclosporine A) is capable of inhibiting or reducing fibrosis from occurring in the adjacent tissue.

In another strategy, the device can be coated with an inactive form of the fibrosis-inducing agent, which is then activated once the device is deployed. Such activation may be achieved by injecting another material into the treatment area after the device (as described below) is deployed or after the fibrosis-inducing agent has been administered to the treatment area (via, e.g., injections, spray, wash, drug delivery catheters or balloons). For example, the device may be coated with an inactive form of the fibrosis-inducing agent. Once the device is deployed, the activating substance is injected or applied into or onto the treatment site where the inactive form of the fibrosis-inducing agent has been applied.

For example, a device may be coated with a biologically active fibrosis-inducing agent, in the usual manner. The coating containing the active fibrosis-inducing agent may then be covered (e.g., coated) with polyethylene glycol. The PEG and the fibrosing agent containing coating may be bonded through the formulation of a bond between reactive groups on the two layers. For example, an ester bond may be formed using a condensation reaction. Prior to the deployment of the device, an esterase is injected into the treatment site around the outside of the implanted device. The esterase can cleave the bond between the ester and the fibrosis-inducing agent, thereby allowing the agent to initiate fibrosis.

In another aspect, a medical device may include a plurality of reservoirs within its structure, each reservoir configured to house and protect a therapeutic drug. The reservoirs may be formed from divets in the device surface or micropores or channels in the device body. In one aspect, the reservoirs are formed from voids in the structure of the device. The reservoirs may house a single type of drug or more than one type of drug. The druG(s) may be formulated with a carrier (e.g., a polymeric or non-polymeric material) that is loaded into the reservoirs. The filled reservoir can function as a drug delivery depot which can release drug over a period of time dependent on the release kinetics of the drug from the carrier. In certain embodiments, the reservoir may be loaded with a plurality of layers. Each layer may include a different drug having a particular amount (dose) of drug, and each layer may have a different composition to further tailor the amount of drug that is released from the substrate. The multi-layered carrier may further include a barrier layer that prevents release of the druG(s). The barrier layer can be used, for example, to control the direction that the drug elutes from the void.

Within certain embodiments of the invention, the therapeutic compositions may also comprise additional ingredients such as surfactants (e.g., PLURONICS, such as F-127, L-122, L-101, L-92, L-81, and L-61), anti-inflammatory agents, anti-thrombotic agents, anti-infective agents, preservatives, anti-oxidants and/or anti-platelet agents.

Within certain embodiments of the invention, the therapeutic agent or carrier can also comprise radio-opaque, echogenic materials and magnetic resonance imaging (MRI) responsive materials (i.e., MRI contrast agents) to aid in visualization of the device under ultrasound, fluoroscopy and/or MRI. For example, a device may be made with or coated with a composition which is echogenic or radiopaque (e.g., made with echogenic or radiopaque with materials such as powdered tantalum, tungsten, barium carbonate, bismuth oxide, barium sulfate, metrazimide, iopamidol, iohexol, iopromide, iobitridol, iomeprol, iopentol, ioversol, ioxilan, iodixanol, iotrolan, acetrizoic acid derivatives, diatrizoic acid derivatives, iothalamic acid derivatives, ioxithalamic acid derivatives, metrizoic acid derivatives, iodamide, lypophylic agents, iodipamide and ioglycamic Acid or, by the addition of microspheres or bubbles which present an acoustic interface). Visualization of a device by ultrasonic imaging may be achieved using an echogenic coating. Echogenic coatings are described in, e.g., U.S. Pat. Nos. 6,106,473 and 6,610,016. For visualization under MRI, contrast agents (e.g., gadolinium (III) chelates or iron oxide compounds) may be incorporated into or onto the device, such as, as a component in a coating or within the void volume of the device (e.g., within a lumen, reservoir, or within the structural material used to form the device). In some embodiments, a medical device may include radio-opaque or MRI visible markers (e.g., bands) that may be used to orient and guide the device during the implantation procedure.

Medical implants may, alternatively, or in addition, be visualized under visible light, using fluorescence, or by other spectroscopic means. Visualization agents that can be included for this purpose include dyes, pigments, and other colored agents. In one aspect, the medical implant may further include a colorant to improve visualization of the implant in vivo and/or ex vivo. Frequently, implants can be difficult to visualize upon insertion, especially at the margins of implant. A coloring agent can be incorporated into a medical implant to reduce or eliminate the incidence or severity of this problem. The coloring agent provides a unique color, increased contrast, or unique fluorescence characteristics to the device. In one aspect, a solid implant is provided that includes a colorant such that it is readily visible (under visible light or using a fluorescence technique) and easily differentiated from its implant site. In another aspect, a colorant can be included in a liquid or semi-solid composition. For example, a single component of a two component mixture may be colored, such that when combined ex-vivo or in-vivo, the mixture is sufficiently colored.

The coloring agent may be, for example, an endogenous compound (e.g., an amino acid or vitamin) or a nutrient or food material and may be a hydrophobic or a hydrophilic compound. Preferably, the colorant has a very low or no toxicity at the concentration used. Also preferred are colorants that are safe and normally enter the body through absorption such as β-carotene. Representative examples of colored nutrients (under visible light) include fat soluble vitamins such as Vitamin A (yellow); water soluble vitamins such as Vitamin B12 (pink-red) and folic acid (yellow-orange); carotenoids such as β-carotene (yellow-purple) and lycopene (red). Other examples of coloring agents include natural product (berry and fruit) extracts such as anthrocyanin (purple) and saffron extract (dark red). The coloring agent may be a fluorescent or phosphorescent compound such as α-tocopherolquinol (a Vitamin E derivative) or L-tryptophan. Derivatives, analogues, and isomers of any of the above colored compounds also may be used. The method for incorporating a colorant into an implant or therapeutic composition may be varied depending on the properties of and the desired location for the colorant. For example, a hydrophobic colorant may be selected for hydrophobic matrices. The colorant may be incorporated into a carrier matrix, such as micelles. Further, the pH of the environment may be controlled to further control the color and intensity.

In one aspect, the composition of the present invention include one or more coloring agents, also referred to as dyestuffs, which will be present in an effective amount to impart observable coloration to the composition, e.g., the gel. Examples of coloring agents include dyes suitable for food such as those known as F. D. & C. dyes and natural coloring agents such as grape skin extract, beet red powder, beta carotene, annato, carmine, turmeric, paprika, and so forth. Derivatives, analogues, and isomers of any of the above colored compound also may be used. The method for incorporating a colorant into an implant or therapeutic composition may be varied depending on the properties of and the desired location for the colorant. For example, a hydrophobic colorant may be selected for hydrophobic matrices. The colorant may be incorporated into a carrier matrix, such as micelles. Further, the pH of the environment may be controlled to further control the color and intensity.

In one aspect, the compositions of the present invention include one or more preservatives or bacteriostatic agents, present in an effective amount to preserve the composition and/or inhibit bacterial growth in the composition, for example, bismuth tribromophenate, methyl hydroxybenzoate, bacitracin, ethyl hydroxybenzoate, propyl hydroxybenzoate, erythromycin, chlorocresol, benzalkonium chlorides, and the like. Additional examples of the preservative include paraoxybenzoic acid esters, chlorobutanol, benzyl alcohol, phenethyl alcohol, dehydroacetic acid, sorbic acid, and the like. In one aspect, the compositions of the present invention include one or more bactericidal (also known as bacteriacidal) agents.

In one aspect, the compositions of the present invention include one or more antioxidants, present in an effective amount. Examples of the antioxidant include sulfites, alpha-tocopherol and ascorbic acid.

Within related aspects of the present invention, devices and compositions are provided that may or may not be associated with a device, which release an agent which induces fibrosis in vivo upon deployment of the device or administration of the composition. In certain aspects, the fibrosis-inducing agent or composition that comprises the fibrosis-inducing agent is delivered locally or regionally to the treatment site from the device or composition.

Within certain aspects of the present invention, the therapeutic composition should be biocompatible, and release one or more fibrosing agents over a period of several hours, days, or months.

The devices of the present invention may be configured to release the scarring agent at one or more phases, the one or more phases having similar or different performance (e.g., release) profiles. The therapeutic agent may be made available to the tissue at amounts which may be sustainable, intermittent, or continuous; in one or more phases; and/or rates of delivery; effective to increase or promote any one or more components of fibrosis (or scarring), including: formation of new blood vessels (angiogenesis), migration and proliferation of connective tissue cells (such as fibroblasts or smooth muscle cells), deposition of extracellular matrix (ECM), and remodeling (maturation and organization of the fibrous tissue); or the agent can act as a vascular wall irritant.

Thus, the release rate may be programmed to impact fibrosis (or scarring) by releasing the scarring agent at a time such that at least one of the components of fibrosis is promoted or increased. Moreover, the predetermined release rate may reduce agent loading and/or concentration as well as potentially providing minimal drug washout and thus, increases efficiency of drug effect. Any one of at least one scarring agent(s) may perform one or more functions, including promoting the formation of new blood vessels (angiogenesis), promoting the migration and proliferation of connective tissue cells (such as fibroblasts or smooth muscle cells), promoting the deposition of extracellular matrix (ECM), promoting remodeling (maturation and organization of the fibrous tissue) and/or acting as a vascular wall irritant. In one embodiment, the rate of release may provide a sustainable level of the scarring agent to the treatment site. In another embodiment, the rate of release is substantially constant. The rate may decrease and/or increase over time, and it may optionally include a substantially non-release period. The release rate may comprise a plurality of rates. In an embodiment, the plurality of release rates may include rates selected from the group consisting of substantially constant, decreasing, increasing, and substantially non-releasing.

The total amount of scarring agent made available on, in or near the device may be in an amount ranging from about 0.01 µg (micrograms) to about 2500 mg (milligrams). Generally, the scarring agent may be in the amount ranging from 0.01 µg to about 10 µg; or from 10 µg to about 1 mg; or from 1 mg to about 10 mg; or from 10 mg to about 100 mg; or from 100 mg to about 500 mg; or from 500 mg to about 2500 mg.

The surface amount of scarring agent on, in or near the device may be in an amount ranging from less than 0.01 µg to about 250 µg per $mm^2$ of device surface area. Generally, the scarring agent may be in the amount ranging from less than 0.01 $µg/mm^2$; or from 0.01 µg to about 10 $µg/mm^2$; or from 10 µg to about 25 $µg/mm^2$; or from 25 µg to about 250 $µg/mm^2$.

The scarring agent that is on, in or near the device may be released from the composition and/or device in a time period that may be measured from the time of implantation, which ranges from about less than 1 day to about 180 days. Generally, the release time may also be from about less than 1 day to about 7 days; from 7 days to about 14 days; from 14 days to about 28 days; from 28 days to about 56 days; from 56 days to about 90 days; from 90 days to about 180 days.

In one aspect, "quick release" or "burst" therapeutic compositions are provided that release greater than 10%, 20%, or 25% (w/v) of a fibrosis-inducing agent over a period of 7 to 10 days. Such "quick release" compositions should, within certain embodiments, be capable of releasing therapeutic levels (where applicable) of a desired fibrosing agent. Within other embodiments, "slow release" therapeutic compositions are provided that release less than 1% (w/v) of a fibrosis-inducing agent over a period of 7 to 10 days. Within other embodiments therapeutic compositions are provided that release either less than 1% (w/v) of a fibrosing-inducing agent over a period longer than 10 days or do not release the therapeutic composition at all, but maintain the composition for a very long period of time such as for the entire duration of the device placement in the body.

The amount of scarring agent released from the composition and/or device as a function of time may be determined based on the in vitro release characteristics of the agent from the composition. The in vitro release rate may be determined by placing the scarring agent within the composition or device in an appropriate buffer such as 0.1M phosphate buffer (pH 7.4)) at 37° C. Samples of the buffer solution are then periodically removed for analysis by either HPLC or by gravimetric means, and the buffer is replaced to avoid any saturation effects.

Based on the in vitro release rates, the release of scarring agent per day may range from an amount ranging from about 0.0 μg (micrograms) to about 2500 mg (milligrams). Generally, the scarring agent that may be released in a day may be in the amount ranging from 0.0 to 0.01 μg; 0.01 μg to about 10 μg; or from 10 μg to about 1 mg; or from 1 mg to about 10 mg; or from 10 mg to about 100 mg; or from 100 mg to about 500 mg; or from 500 mg to about 2500 mg. In one embodiment, the scarring agent is made available to the susceptible tissue site in a constant but substantially unchanging manner so that the agent remains at the tissue essentially permanently. In another embodiment, the scarring agent is made available to the susceptible tissue in a sustained and/or controlled manner which results in increased efficiency and/or efficacy. Further, the release rates may vary during either or both of the initial and subsequent release phases. There may also be additional phase(s) for release of the same substance(s) and/or different substance(s).

Further, therapeutic compositions of the present invention should preferably be have a stable shelf-life for at least several months and capable of being produced and maintained under sterile conditions. The composition may be sterile either by preparing them under aseptic environment and/or they may be terminally sterilized using methods available in the art. Many pharmaceuticals are manufactured to be sterile and this criterion is defined by the USP XXII <1211>. The term "USP" refers to U.S. Pharmacopeia (see www.usp.org, Rockville, Md.). Sterilization may be accomplished by a number of means accepted in the industry and listed in the USP XXII <1211>, including gas sterilization, ionizing radiation or, when appropriate, filtration. Sterilization may be maintained by what is termed aseptic processing, defined also in USP XXII >1211>. Acceptable gases used for gas sterilization include ethylene oxide. Acceptable radiation types used for ionizing radiation methods include gamma, for instance from a cobalt 60 source and electron beam. A typical dose of gamma radiation is 2.5 MRad. Sterilization may also occur by terminally using gamma radiation or electron beam sterilization methods. Filtration may be accomplished using a filter with suitable pore size, for example 0.22 μm and of a suitable material, for instance polytetrafluoroethylene (e.g., TEFLON). A combination of these methods may also be used to prepare the composition in the sterile form.

In another aspect, the compositions and devices of the present invention are contained in a container that allows them to be used for their intended purpose. Properties of the container that are important are a volume of empty space to allow for the addition of a constitution medium, such as water or other aqueous medium, e.g., saline, acceptable light transmission characteristics in order to prevent light energy from damaging the composition in the container (refer to USP XXII <661>), an acceptable limit of extractables within the container material (refer to USP XXII), an acceptable barrier capacity for moisture (refer to USP XXII <671>) or oxygen. In the case of oxygen penetration, this may be controlled by including in the container, a positive pressure of an inert gas, such as high purity nitrogen, or a noble gas, such as argon.

Typical materials used to make containers for pharmaceuticals include USP Type I through III and Type NP glass (refer to USP XXII <661>), polyethylene, TEFLON, silicone, and gray-butyl rubber. For parenterals, USP Types I to III glass and polyethylene are preferred.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

For all the previously described embodiments, examples of suitable fibrosing agents include tissue irritants such tissue as silk, wool, asbestos, silica, bleomycin, neomycin, talcum powder, metallic beryllium, and copper are particularly suitable for the practice of this invention. Other agents which may be incorporated into or onto the implant or device or released from the implant or device include extracellular matrix components such as fibrous structural proteins (e.g., fibrillar collagens, nonfibrillar collagen and elastins), adhesive glycoproteins (e.g., laminin and fibronectin), proteoglycans (e.g., heparin sulphate, chondroitin sulphate, dermatan sulphate), hyaluronan (e.g., hyaluronic acid), secreted protein acidic and rich in cysteine (SPARC), thrombospondins, tenacin, inhibitors of matrix metalloproteinases (e.g., TIMPs and synthetic TIMPs such as marimistat, batimistat, doxycycline, tetracycline, minocycline, TROCADE, Ro-1130830, CGS 27023A, BMS-275291) and polylysine. Growth factors and inflammatory cytokines involved in angiogenesis, fibroblast migration, fibroblast proliferation, ECM synthesis and tissue remodeling such as epidermal growth factor (EGF) family, transforming growth factor-α (TGF-α), transforming growth factor-β (TGF-9-1, TGF-9-2, TGF-9-3), platelet-derived growth factor (PDGF), fibroblast growth factor (acidic—aFGF; and basic—bFGF), bone morphogenic proteins, activins, vascular endothelial growth factor (VEGF, VEGF-B, VEGF-C, placental growth factor—PIGF), angiopoietins, insulin-like growth factors (IGF), hepatocyte hrowth factor (HGF), connective tissue growth factor (CTGF), myeloid colony-stimulating factors (CSFs), granulocyte-macrophage colony-stimulating factors (GM-CSF), granulocyte colony-stimulating factor (G-CSF), macrophage colony-stimulating factor (M-CSF), erythropoietin, interleukins (particularly IL-1, IL-8, IL-6), tumor necrosis factor-α (TNF9), nerve growth factor (NGF), interferon-α, interferon-β, and growth hormone (GH) are also suitable for incorporation and release from specific intravascular devices. Other agents which may be coated onto or released by the implant or device include adhesives such as cyanoacrylate or materials made from 4-armed thiol PEG (10K), a 4-armed NHS PEG(10K) and methylated collagen.

5) Coating of Devices with Fibrosis-Inducing Agents

As described above, a range of polymeric and non-polymeric materials can be used to incorporate the fibrosis-inducing agent onto or into a device. Coating of the device with these fibrosis-inducing agent containing compositions or with the fibrosis-inducing agent only is one process that can be used to incorporate the fibrosis-inducing agent into or onto the device.

a) Dip Coating

Dip coating is an example of a coating process that can be used to associate the fibrosis-inducing agent with the device. In one embodiment, the fibrosis-inducing agent is dissolved in a solvent for the fibrosis agent and is then coated onto the device.

Fibrosis-Inducing Agent with an Inert Solvent

In one embodiment, the solvent is an inert solvent for the device such that the solvent does not dissolve the medical device to any great extent and is not absorbed by the device to any great extent. The device can be immersed, either partially or completely, in the fibrosis-inducing agent/solvent solution for a specific period of time. The rate of immersion into the fibrosis-inducing agent/solvent solution can be altered (e.g., 0.001 cm per sec to 50 cm per sec). The device can then be removed from the solution. The rate at which the device can be withdrawn from the solution can be altered (e.g., 0.001 cm per sec to 50 cm per sec). The coated device can be air-dried. The dipping process can be repeated one or more times depending on the specific application. The device can be dried under vacuum to reduce residual solvent levels. This process can result in the fibrosis-inducing agent being coated on the surface of the device.

Fibrosis-Inducing Agent with a Swelling Solvent

In one embodiment, the solvent is one that can not dissolve the device but can be absorbed by the device. These solvents can thus swell the device to some extent. The device can be immersed, either partially or completely, in the fibrosis-inducing agent/solvent solution for a specific period of time (seconds to days). The rate of immersion into the fibrosis-inducing agent/solvent solution can be altered (e.g., 0.001 cm per sec to 50 cm per sec). The device can then be removed from the solution. The rate at which the device can be withdrawn from the solution can be altered (e.g., 0.001 cm per sec to 50 cm per sec). The coated device can be air-dried. The dipping process can be repeated one or more times depending on the specific application. The device can be dried under vacuum to reduce residual solvent levels. This process can result in the fibrosis-inducing agent being adsorbed into the medical device. The fibrosis-inducing agent may also be present on the surface of the device. The amount of surface associated fibrosis-inducing agent may be reduced by dipping the coated device into a solvent for the fibrosis-inducing agent or by spraying the coated device with a solvent for the fibrosis-inducing agent.

Fibrosis-Inducing Agent with a Solvent

In one embodiment, the solvent is one that can be absorbed by the device and that can dissolve the device. The device can be immersed, either partially or completely, in the fibrosis-inducing agent/solvent solution for a specific period of time (seconds to hours). The rate of immersion into the fibrosis-inducing agent/solvent solution can be altered (e.g., 0.001 cm per sec to 50 cm per sec). The device can then be removed from the solution. The rate at which the device can be withdrawn from the solution can be altered (e.g., 0.001 cm per sec to 50 cm per sec). The coated device can be air-dried. The dipping process can be repeated one or more times depending on the specific application. The device can be dried under vacuum to reduce residual solvent levels. This process can result in the fibrosis-inducing agent being adsorbed into the medical device as well as being surface associated. Preferably, the exposure time of the device to the solvent may be such as to not incur significant permanent dimensional changes to the device. The fibrosis-inducing agent may also be present on the surface of the device. The amount of surface associated fibrosis-inducing agent may be reduced by dipping the coated device into a solvent for the fibrosis-inducing agent or by spraying the coated device with a solvent for the fibrosis-inducing agent.

In one embodiment, the fibrosis-inducing agent and a polymer are dissolved in a solvent, for both the polymer and the fibrosing agent, and are then coated onto the device.

In the above description, the device can be a device that has not been modified or device that has been further modified by coating with a polymer, surface treated by plasma treatment, flame treatment, corona treatment, surface oxidation or reduction, surface etching, mechanical smoothing or roughening, or grafting prior to the coating process.

In any one of the above dip coating methods, the surface of the device can be treated with a plasma polymerization method prior to coating of the scarring agent or scarring agent containing composition, such that a thin polymeric layer is deposited onto the device surface. Examples of such methods include parylene coating of devices and the use of various monomers such hydrocyclosiloxane monomers. Parylene coating may be especially advantageous if the device, or portions of the device, are composed of materials (e.g., stainless steel, nitinol) that do not allow incorporation of the therapeutic agent(s) into the surface layer using one of the above methods. A parylene primer layer may be deposited onto the device using a parylene coater (e.g., PDS 2010 LABCOTER2 from Cookson Electronics) and a suitable reagent (e.g., di-p-xylylene or dichloro-di-p-xylylene) as the coating feed material. Parylene compounds are commercially available, for example, from Specialty Coating Systems, Indianapolis, Ind.), including PARYLENE N (di-p-xylylene), PARYLENE C (a monchlorinated derivative of PARYLENE N, and PARYLENE D, a dichlorinated derivative of Parylene N.J.).

Fibrosis-Inducing Agent/Polymer with an Inert Solvent

In one embodiment, the solvent is an inert solvent for the device such that the solvent does not dissolve the medical device to any great extent and is not absorbed by the device to any great extent. The device can be immersed, either partially or completely, in the fibrosis-inducing agent/polymer/solvent solution for a specific period of time. The rate of immersion into the fibrosis-inducing agent/polymer/solvent solution can be altered (e.g., 0.001 cm per sec to 50 cm per sec). The device can then be removed from the solution. The rate at which the device can be withdrawn from the solution can be altered (e.g., 0.001 cm per sec to 50 cm per sec). The coated device can be air-dried. The dipping process can be repeated one or more times depending on the specific application. The device can be dried under vacuum to reduce residual solvent levels. This process can result in the fibrosis-inducing agent/polymer being coated on the surface of the device.

Fibrosis-Inducing Agent/Polymer with a Swelling Solvent

In one embodiment, the solvent is one that can not dissolve the device but can be absorbed by the device. These solvents can thus swell the device to some extent. The device can be immersed, either partially or completely, in the fibrosis-inducing agent/polymer/solvent solution for a specific period of time (seconds to days). The rate of immersion into the fibrosis-inducing agent/polymer/solvent solution can be altered (e.g., 0.001 cm per sec to 50 cm per sec). The device can then be removed from the solution. The rate at which the device can be withdrawn from the solution can be altered (e.g., 0.001 cm per sec to 50 cm per sec). The coated device can be air-dried. The dipping process can be repeated one or more times depending on the specific application. The device can be dried under vacuum to reduce residual solvent levels. This process can result in the fibrosis-inducing agent/polymer being coated onto the surface of the device as well as the potential for the fibrosis-inducing agent being adsorbed into the medical device. The fibrosis-inducing agent may also be present on the surface of the device. The amount of surface associated fibrosis-inducing agent may be reduced by dipping the coated device into a solvent for the fibrosis-inducing agent or by spraying the coated device with a solvent for the fibrosis-inducing agent.

Fibrosis-Inducing Agent/Polymer with a Solvent

In one embodiment, the solvent is one that can be absorbed by the device and that can dissolve the device. The device can be immersed, either partially or completely, in the fibrosis-inducing agent/solvent solution for a specific period of time (seconds to hours). The rate of immersion into the fibrosis-inducing agent/solvent solution can be altered (e.g., 0.001 cm per sec to 50 cm per sec). The device can then be removed from the solution. The rate at which the device can be withdrawn from the solution can be altered (e.g., 0.001 cm per sec to 50 cm per sec). The coated device can be air-dried. The dipping process can be repeated one or more times depending on the specific application. The device can be dried under vacuum to reduce residual solvent levels. In the preferred embodiment, the exposure time of the device to the solvent may be such that there is not significant permanent dimensional changes to the device (other than those associated with the coating itself). The fibrosis-inducing agent may also be present on the surface of the device. The amount of surface associated fibrosis-inducing agent may be reduced by dipping the coated device into a solvent for the fibrosis-inducing agent or by spraying the coated device with a solvent for the fibrosis-inducing agent.

In the above description the device can be a device that has not been modified as well as a device that has been further modified by coating with a polymer (e.g., parylene), surface treated by plasma treatment, flame treatment, corona treatment, surface oxidation or reduction, surface etching, mechanical smoothing or roughening, or grafting prior to the coating process.

In another embodiment, a suspension of the fibrosis-inducing agent in a polymer solution can be prepared. The suspension can be prepared by choosing a solvent that can dissolve the polymer but not the fibrosis-inducing agent or a solvent that can dissolve the polymer and in which the fibrosis-inducing agent is above its solubility limit. In similar processes described above, a device can be dipped into the suspension of the fibrosis-inducing agent and polymer solution such that the device is coated with a polymer that has a fibrosing agent suspended within it.

b) Spray Coating

Spray coating is another type of coating process that can be used. In the spray coating process, a solution or suspension of the fibrosis-inducing agent, with or without a polymeric or non-polymeric carrier, is nebulized and directed to the device to be coated by a stream of gas. One can use spray devices such as an air-brush (for example models 2020, 360, 175, 100, 200, 150, 350, 250, 400, 3000, 4000, 5000, 6000 from Badger Air-brush Company, Franklin Park, Ill.), spray painting equipment, TLC reagent sprayers (for example Part # 14545 and 14654, Alltech Associates, Inc. Deerfield, Ill., and ultrasonic spray devices (for example those available from Sono-Tek, Milton, N.Y.). One can also use powder sprayers and electrostatic sprayers.

In one embodiment, the fibrosis-inducing agent is dissolved in a solvent for the fibrosis agent and is then sprayed onto the device.

Fibrosis-Inducing Agent with an Inert Solvent

In one embodiment, the solvent is an inert solvent for the device such that the solvent does not dissolve the medical device to any great extent and is not absorbed by the device to any great extent. The device can be held in place or the device can be mounted onto a mandrel or rod that has the ability to move in an X, Y or Z plane or a combination of these planes. Using one of the above described spray devices, the device can be spray coated such that the device is either partially or completely coated with the fibrosis-inducing agent/solvent solution. The rate of spraying of the fibrosis-inducing agent/solvent solution can be altered (e.g., 0.001 ml per sec to 10 ml per sec) to ensure that a good coating of the fibrosis-inducing agent is obtained. The coated device can be air-dried. The spray coating process can be repeated one or more times depending on the specific application. The device can be dried under vacuum to reduce residual solvent levels. This process can result in the fibrosis-inducing agent being coated on the surface of the device.

Fibrosis-Inducing Agent with a Swelling Solvent

In one embodiment, the solvent is one that can not dissolve the device but can be absorbed by the device. These solvents can thus swell the device to some extent. The device can be spray coated, either partially or completely, in the fibrosis-inducing agent/solvent solution. The rate of spraying of the fibrosis-inducing agent/solvent solution can be altered (e.g., 0.001 ml per sec to 10 ml per sec) to ensure that a good coating of the fibrosis-inducing agent is obtained. The coated device can be air-dried. The spray coating process can be repeated one or more times depending on the specific application. The device can be dried under vacuum to reduce residual solvent levels. This process can result in the fibrosis-inducing agent being adsorbed into the medical device. The fibrosis-inducing agent may also be present on the surface of the device. The amount of surface associated fibrosis-inducing agent may be reduced by dipping the coated device into a solvent for the fibrosis-inducing agent or by spraying the coated device with a solvent for the fibrosis-inducing agent.

Fibrosis-Inducing Agent with a Solvent

In one embodiment, the solvent is one that can be absorbed by the device and that can dissolve the device. The device can be spray coated, either partially or completely, in the fibrosis-inducing agent/solvent solution. The rate of spraying of the fibrosis-inducing agent/solvent solution can be altered (e.g., 0.001 ml per sec to 10 ml per sec) to ensure that a good coating of the fibrosis-inducing agent is obtained. The coated device can be air-dried. The spray coating process can be repeated one or more times depending on the specific application. The device can be dried under vacuum to reduce residual solvent levels. This process can result in the fibrosis-inducing agent being adsorbed into the medical device as well as being surface associated. Preferably, the exposure time of the device to the solvent may be such as to not incur significant permanent dimensional changes to the device. The fibrosis-inducing agent may also be present on the surface of the device. The amount of surface associated fibrosis-inducing agent may be reduced by dipping the coated device into a solvent for the fibrosis-inducing agent or by spraying the coated device with a solvent for the fibrosis-inducing agent.

In one embodiment, the fibrosis-inducing agent and a polymer are dissolved in a solvent, for both the polymer and the fibrosing agent, and are then spray coated onto the device. In the above description, the device can be a device that has not been modified as well as a device that has been further modified by coating with a polymer (e.g., parylene), surface treated by plasma treatment, flame treatment, corona treatment, surface oxidation or reduction, surface etching, mechanical smoothing or roughening, or grafting prior to the coating process.

Fibrosis-Inducing Agent/Polymer with an Inert Solvent

In one embodiment, the solvent is an inert solvent for the device such that the solvent does not dissolve the medical device to any great extent and is not absorbed by the device to any great extent. The device can be spray coated, either partially or completely, in the fibrosis-inducing agent/polymer/solvent solution for a specific period of time. The rate of spraying of the fibrosis-inducing agent/solvent solution can be altered (e.g., 0.001 ml per sec to 10 ml per sec) to ensure that a good coating of the fibrosis-inducing agent is obtained. The coated device can be air-dried. The spray coating process can be repeated one or more times depending on the specific application. The device can be dried under vacuum to reduce residual solvent levels. This process can result in the fibrosis-inducing agent/polymer being coated on the surface of the device.

Fibrosis-Inducing Agent/Polymer with a Swelling Solvent

In one embodiment, the solvent is one that can not dissolve the device but can be absorbed by the device. These solvents can thus swell the device to some extent. The device can be spray coated, either partially or completely, in the fibrosis-inducing agent/polymer/solvent solution. The rate of spraying of the fibrosis-inducing agent/solvent solution can be altered (e.g., 0.001 ml per sec to 10 ml per sec) to ensure that a good coating of the fibrosis-inducing agent is obtained. The coated device can be air-dried. The spray coating process can be repeated one or more times depending on the specific application. The device can be dried under vacuum to reduce residual solvent levels. This process can result in the fibrosis-inducing agent/polymer being coated onto the surface of the device as well as the potential for the fibrosis-inducing agent being adsorbed into the medical device. The fibrosis-inducing agent may also be present on the surface of the device. The amount of surface associated fibrosis-inducing agent may be reduced by dipping the coated device into a solvent for the fibrosis-inducing agent or by spraying the coated device with a solvent for the fibrosis-inducing agent.

Fibrosis-Inducing Agent/Polymer with a Solvent

In one embodiment, the solvent is one that can be absorbed by the device and that can dissolve the device. The device can be spray coated, either partially or completely, in the fibrosis-inducing agent/solvent solution. The rate of spraying of the fibrosis-inducing agent/solvent solution can be altered (e.g., 0.001 ml per sec to 10 ml per sec) to ensure that a good coating of the fibrosis-inducing agent is obtained. The coated device can be air-dried. The spray coating process can be repeated one or more times depending on the specific application. The device can be dried under vacuum to reduce residual solvent levels. Preferably, the exposure time of the device to the solvent may be such as to not incur significant permanent dimensional changes to the device (other than those associated with the coating itself). The fibrosis-inducing agent may also be present on the surface of the device. The amount of surface associated fibrosis-inducing agent may be reduced by dipping the coated device into a solvent for the fibrosis-inducing agent or by spraying the coated device with a solvent for the fibrosis-inducing agent.

In the above description, the device can be a device that has not been modified as well as a device that has been further modified by coating with a polymer (e.g., parylene), surface treated by plasma treatment, flame treatment, corona treatment, surface oxidation or reduction, surface etching, mechanical smoothing or roughening, or grafting prior to the coating process.

c) Direct Attachment

In certain embodiments, the fibrosis inducing agent can be attached directly to the device. This can be accomplished by using an adhesive (e.g., cyanoacrylate, polymer/solvent solution), using a thermal process and or by sewing the fibrosis agent into or onto the device. In one embodiment, the fibrosis inducing agent can be in the form of particles (irregular, regular, porous, spherical), threads, fibers, knits, weaves or electrospun material. For example, silk can be prepared as a knitted, woven or electrospun material. This material can then be placed on the surface of the device. Sutures and/or an adhesive can then be used to secure the silk material to the device.

In another embodiment, the fibrosis inducing agent can be dissolved in a suitable solvent. This solution can then be applied to the device using an electrospraying or electrospinning process. Polymeric or non-polymeric additives can be added to this solution to assist in the electrospraying or electrospinning process and or to assist in the adhesion of the fibrosis inducing agent to the device. For example, silk can be dissolved in HFIP and this can then be electrosprayed or electrospun onto the device (e.g., stent).

In another embodiment, the fibrosis-inducing agent can be incorporated into the device during or post manufacture of the device. For example silk fibers could be woven into a hernia mesh to provide a product that contains the fibrosis-inducing agent that is incorporated into the device.

D. Methods for Utilizing Medical Implants

Medical devices and implants of the present invention may be utilized to induce a fibrotic reaction around the device/implant that results in an enhanced bond between the tissue and the prosthesis. Such medical devices and implants provide a solution to the following common problems associated with a variety of clinical interventions.

1. Treatments for Degenerative Disc Disease (DDD)

Back pain is the number one cause of healthcare expenditures in the United States and accounts for over $50 billion in costs annually ($100 billion worldwide). Over 12 million people in the U.S. have some form of degenerative disc disease (DDD) and 10% of them (1.2 million) can require surgery to correct their problem.

In healthy individuals, the vertebral column is composed of vertebral bone plates separated by intervertebral discs that form strong joints and absorb spinal compression during movement. The intervertebral disc is comprised of an inner gel-like substance called the nucleus pulposus which is surrounded by a tough fibrocartilagenous capsule called the annulus fibrosis. The nucleus pulposus is composed of a loose framework of collagen fibrils and connective tissue cells (resembling fibroblasts and chondrocytes) embedded in a gelatinous matrix of glycosaminoglycans and water. The annulus fibrosus is composed of numerous concentric rings of fibrocartilage that anchor into the vertebral bodies. The most common cause of DDD occurs when tears in the annulus fibrosis create an area of localized weakness that allow bulging, herniation or sequestration of the nucleus pulposis and annulus fibrosis into the spinal canal and/or spinal foramena. The bulging or herniated disc often compresses nerve tissue such as spinal cord fibers or spinal cord nerve root fibers. Pressure on the spinal cord or nerve roots from the damaged intervertebral disc results in neuronal dysfunction (numbness, weakness, tingling), crippling pain, bowel or bladder disturbances and can frequently cause long-term disability. Although many cases of DDD can spontaneously resolve, a significant number of patients can require surgical intervention in the form of minimally invasive procedures, microdiscectomy, major surgical resection of the disc, spinal fusion (fusion of adjacent vertebral bone plates using various techniques and devices), and/or implantation of an artificial disc. The present invention provides for the application of an adhesion or fibrosis-inducing agent in the surgical management of DDD.

(i) Minimally Invasive Treatments of DDD

The present invention provides injectable compositions that iriclude a bulking or filling agent and a fibrosing agent for direct injection into damaged intervertebral discs. An injectable material containing a fibrosis-inducing agent that can be injected into an intervertebral disc space (alone or in combination with polymeric carrier, which may be in the form, e.g., of a gel, paste, or spray) is used to enhance scarring and support the annular ring of the disc (e.g., by inducing the production of fibrous tissue and fibrocartilage), thus reducing the risk of disc rupture and restoring disc function without surgery (embodiments for application during disc surgery are described below). In another embodiment, the injectable composition containing a fibrosis-inducing agent can further contain an agent that promotes bone growth if permanent fixation (immobilization) of adjacent vertebra is desired.

In this procedure, a needle is inserted into the intervertebral disc, a guidewire is advanced into the tissue and a dual lumen catheter (for many of the hydrogels described below such as COSEAL, COSTASIS, FLOSEAL, TISSEAL, VITOSS, and materials made from 4-armed thiol PEG (10K), 4-armed NHS PEG(10K) and methylated collagen, such as described above or a single lumen catheter (for materials such as cyanoacrylate, CORTOSS, bone cement, apatitehydroxyapatite, calcium phosphate, calcium sulfate, hyaluronic acid, proteins, carbohydrates, sclerosing agents, and the like) is advanced into the disc. When performing direct injection of the intervertebral disc, techniques can be used to enhance visualization of needle (or catheter) placement within the disc including, but not limited to, the use of a needle coated with an ultrasound imaging coating formulation, such as ECHO—COAT (Angiotech Pharmaceuticals, Inc.) or the addition of contrast agents (e.g., barium, tantalum, technitium, gadolinium, etc.) for localization by x-ray. After correct positioning has been confirmed, the guidewire is removed, and a composition containing a fibrosis-inducing agent, with or without a bone morphogenic protein(s), and/or an osteogenic growth factor (such as transforming growth factor, platelet-derived growth factor, fibroblast growth factor) is injected via the catheter into the disc. Chemonucleolysis agents such as collagenase, chymopapain or other tissue-degrading enzymes may also be used to chemically degrade the remaining disc tissue prior to the injection of the fibrosing composition. Over time the fibrosis-inducing agent, with or without a bone morphogenic protein, and/or an osteogenic growth factor can encourage fibrous ankylosis, followed by bony ankylosis of the intervertebral space leading to increased stability and reduced pain.

The injectable material may contain a polymer system that can provide sustained release of the fibrosis-inducing agent, bone morphogenic protein, and/or osteogenic growth factor to enhance efficacy and reduce the need for repeat administrations of active agents. The polymeric injection material suitable for delivery of a fibrosis-inducing agent, bone morphogenic protein, and/or growth factor that promotes bone growth can be either a non-degradable or a degradable material. Suitable non-degradable materials include crosslinked compositions that comprise PVA, PVP, polyacrylamide, methyl methacrylate (MMA) and methyl methacrylate-styrene (MMA-styrene) which when mixed together form polymethyl methacrylate (PMMA) or bone cement (e.g., SIMPLEX P made by Stryker Howmedica, ZIMMER REGULAR and ZIMMER LOW VISCOSITY CEMENT, PALACOS, CMW-1 and CMW-2, ENDURANCE), synthetic cancellous bone void fillers (e.g., CORTOSS), pHEMA, poly(vinyl PEG), poly(styrene sulfonate), poly(acrylic acid), poly(methacrylic acid), as well as other polymers that are known to form hydrogels. Other compositions include blends and copolymers of the agents listed above. Suitable degradable materials include, but are not limited to, resorbable ceramics composed of β-tricalcium phosphate (e.g., VITOSS and PROOSTEON 500R), hydroxyapatite or $Ca_{10}(PO_4)_6OH$ (e.g., BIOOSS and OSTEOGRAF), calcium carbonate or $CaCO_3$, calcium sulfate (e.g., OSTEOSET and ALLOMATRIX made by Wright Medical Technology, Inc.), calcium phosphate (e.g., CAL-CIBON or NORIAN SRS), crosslinked materials of PEG, gelatin, collagen, bone allografts (e.g., ALLOGRO (Allosource Corporation, Centennial, Colo.), ORTHOBLAST (GenSci Regeneration Sciences, Inc., Canada), OPTE-FORM (Exactech, Inc., Gainesville, Fla.), GRAFTON (Osteotech, Inc., Eatontown, N.J.), mesenchymal stem cells, hyaluronic acid, hyaluronic acid derivatives, polysaccharides, carbohydrates, proteins (e.g., albumin, casein, whey proteins, plant proteins, and fish proteins), autologous bone, demineralized bone matrix, cellulose derivatives (e.g., HPC), chitosan, chitosan derivatives, polyester-polyalkylene oxide block copolymers (e.g., PLGA-PEG-PLGA and MePEG-PLGA, and the like) and other low molecular weight polymers that can be excreted. An injectable material of particular interest is prepared from a 4-armed thiol PEG (10K), a 4-armed NHS PEG(10K) and methylated collagen such as described above.

In a preferred embodiment, the injectable material also contains a biologically active agent capable of inducing fibrosis and ankylosis in the disc space. In one embodiment, the injectable material is loaded with a fibrosis-inducing agent and injected into the intervertebral disc to help repair the annulus and prevent herniation of the nucleus pulposis. In another embodiment, the injectable material contains biologically active agents capable of inducing bone growth such bone morphogenic proteins and growth factors (transforming growth factor, platelet-derived growth factor, fibroblast growth factor) to promote bony ankylosis and fusion of adjacent vertebra.

In addition to, or in lieu of, fibrosis-inducing agents, bone morphogenic proteins and growth factors, the injectable material can be utilized to deliver a sclerosant to the articular space. Sclerosants include compounds such as ethanol, DMSO, surfactants, sucrose, NaCl, dextrose, glycerin, minocycline, tetracycline, doxycycline, polidocanol, sodium tetradecyl sulfate, sodium morrhuate, sotradecol and others. The injectable material can further comprise agents such as glycerol, glycerin, PEG 200, triethyl citrate, and triacetin as plasticizers.

The injectable materials described above can be further modified to be comprised of, or contain, polymeric threads. Polymeric threads have the ability to induce a fibroproliferative response from the surrounding tissue. These polymer threads can be degradable or non-degradable. Degradable threads can be composed of degradable polyesters, polyanhydrides, poly(anhydride esters), poly(ester-amides), poly (ester-ureas), polyorthoesters, polyphosphoesters, polyphosphazines, cyanoacrylate polymers, collagen, chitosan, hyaluronic acid, chromic cat gut, alginates, starch, cellulose, cellulose esters, blends and copolymers thereof, as well as other known degradable polymers. Non-degradable polymers that can be used include, but are not limited to, polyesters (e.g., PET), polyurethanes, silicones, PE, PP, PS, PAA, PMA, silk, blends, copolymers thereof as well as other known polymers. The threads can be composed of a single composition or composed of a blend of differing compositions. The polymeric threads themselves can be further modified through the addition of a polymeric coating applied to the threads. The polymer used for coating the thread can be similar to that described above for the threads themselves. The polymer coating may further comprise a biologically active agent that has the ability to induce a fibroproliferative or osteogenic response. The agents that can be used are further described in the section (vi) below.

The injectable materials described above can be utilized to deliver a particulate material that has the ability to induce fibrosis in the intervertebral disc. These particles can be either degradable or non-degradable and are similar to those described above for threads. Additional particulate materials useful for the practice of this embodiment include silk, talc, starch, glass, silicates, silica, calcium phosphate, calcium sulfate, calcium carbonate, hydroxyapatite, synthetic mineral (e.g., VITOSS and CORTOSS, PMMA, silver nitrate, ceramic particles and other inorganic particles known in the art to induce a fibroprqliferative response followed by mineralization. The particles used in this embodiment can be all of the same composition or a blend of differing compositions. These particles can also be used as a coating applied to the polymeric strands as described above.

The injectable materials can also be constructed such that it is comprised of both polymeric threads and particles. The threads and particles used are similar to those described above and may be of uniform composition or blended composition. Virtually any combination of threads of differing compositions and particles of differing compositions can be utilized in this embodiment. The hydrogel, the polymeric threads, and the particles can all be utilized to deliver one or more biologically active agents, as described below.

One specific composition comprises rods prepared from a methylated collagen-crosslinked poly(ethylene glycol) composition such as described above, which has powdered silk particles and/or mineral particles added to the composition prior to curing. Once deployed, the rod can absorb water, fill the disc space and adhere to any fibrocartilage or exposed bone. This expansion can prevent the rod from moving, while the powdered silk and/or mineral particles can initiate an ankylosing response. As the material starts to degrade, the material can support the bone tissue ingrowth that is initiated and potentiated by the particles. Bone morphogenic proteins and/or growth factors (described previously and below) are also useful for inclusion in this composition. To further increase the rate of initiation of this fibroproliferative response, a sclerosant such as a surfactant (SDS), ethanolamine oleate or DMSO can be added. In addition, one can also add or replace all (or a portion) of the 4-armed thiol PEG with a 4-armed amino PEG. The amino PEG can provide a gel that can take a longer time to degrade and can provide some positive charge to further attract cellular material.

Another embodiment consists of an injectable implant composed of silk fibers or from a polymerized version of the fibrosing agent itself (i.e., repeating units of the fibrosing agent polymerized together). Bone morphogenic proteins and/or growth factors (described previously and below) also may be added to this composition.

In addition to the hydrogels, bone cements, and materials containing calcium phosphate described above, there are several other injectable compositions suitable for use in minimally invasive intervertebral disc procedures. All involve the deployment of a biomaterial into the nucleus pulposis with or without the addition of a fibrosis-inducing agent, bone morphogenic protein(s), and/or a suitable growth factor(s). The following compositions can be delivered into the intervertebral disc via specialized delivery catheters, an endoscope, a needle or other applicator, a surgically placed drain or access port, or other transdermal access device, including administration of: (a) fluids, suspensions, emulsions, microemulsions, microspheres, pastes, gels, microparticulates, sprays, aerosols, solid implants and other formulations which release a biologically active fibrosis-inducing agent(s); (b) microparticulate silk and/or silk strands (linear, branched, and/or coiled) either alone, or loaded with an additional fibrosis-inducing agent, bone morphogenic protein, and/or growth factor are also useful for directed injection into the intervertebral disc; (c) injectable collagen-containing formulations such as COSTASIS or materials made from 4-armed thiol PEG (10K), 4-armed NHS PEG(10K) and methylated collagen such as described above, either alone, or loaded with a fibrosis-inducing agent, bone morphogenic protein, and/or growth factor, injected into the intervertebral disc; (d) injectable PEG-containing formulations such as COSEAL, FOCALSEAL, SPRAYGEL or DURASEAL, either alone, or loaded with a fibrosis-inducing agent, bone morphogenic protein, and/or growth factor, injected into the intervertebral disc; (e) fibrinogen-containing formulations such as FLOSEAL or TISSEAL, either alone, or loaded with a fibrosis-inducing agent, bone morphogenic protein, and/or growth factor, injected into the intervertebral disc; (f) hyaluronic acid-containing formulations such as RESTYLANE, HYLAFORM, PERLANE, SYNVISC, SEPRAFILM, SEPRACOAT either alone, or loaded with a fibrosis-inducing agent, bone morphogenic protein, and/or growth factor injected into the intervertebral disc; (g) polymeric gels for surgical implantation such as REPEL or FLOWGEL either alone, or loaded with a fibrosis-inducing agent, bone morphogenic protein, and/or growth factor injected into the intervertebral disc; (h) orthopedic "cements" such as OSTEOBOND, low viscosity cement (LVC), SIMPLEX P, PALACOS, CORTOSS and ENDURANCE, either alone, or loaded with a fibrosis-inducing agent, bone morphogenic protein, and/or growth factor injected into the intervertebral disc; (i) surgical adhesives containing cyanoacrylates such as DERMABOND, INDERMIL, GLUSTITCH, VETBOND, HISTOACRYL, TISSUEMEND, TISSUMEND II, HISTOACRYL BLUE and ORABASE SOOTHE-N-SEAL LIQUID PROTECTANT or as described above, either alone, or loaded with a fibrosis-inducing agent, bone morphogenic protein, and/or growth factor, injected into the intervertebral disc; (j) surgical implants containing hydroxyapatite, calcium phosphate (such as VITOSS), or calcium sulfate, alone or loaded with a fibrosis-inducing agent, bone morphogenic protein, and/or growth factor, injected into the intervertebral disc; (k) other biocompatible tissue fillers, such as those made by BioCure, 3M Company and Neomend, either alone, or loaded with a fibrosis-inducing agent, bone morphogenic protein, and/or growth factor, injected into the intervertebral disc; (l) polysaccharide gels such as the ADCON series of gels, either alone, or loaded with a fibrosis-inducing agent, bone morphogenic protein, and/or growth factor, injected into the intervertebral disc; (m) films, sponges or meshes such as INTERCEED, VICRYL mesh, and GELFOAM either alone, or loaded with a fibrosis-inducing agent, bone morphogenic protein, and/or growth factor, injected into the intervertebral disc; and/or (n) a hydrogel that is formed from an amino-functionalized polyethylene glycol (e.g., 4-armed tetra-amino PEG [10k]) and a 4-armed NHS functionalized PEG (e.g., pentaerythritol poly(ethylene glycol)ether tetra-succinimidyl glutarate [10K]). This hydrogel may further contain collagen, methylated collagen and/or gelatin. This hydrogel can further comprise the fibrosis-inducing agents described above (e.g., silk powder or silk threads). In many of these embodiments, it may also be useful to add a radio-opaque material (e.g., tantalum, barium, other metal, or a contrast material) such that the injected material can be visualized radiographically or by MRI.

It should be apparent to one of skill in the art that potentially any fibrosis-inducing agents described above may be utilized alone, or in combination, in the practice of this embodiment. Exemplary fibrosing agents for use in spinal prostheses (e.g., devices and bulking agents) include talc, silk, wool, chitosan, polylysine, fibronectin, bleomycin, and CTGF, as well as analogues and derivatives of the aforementioned.

Optionally, the device may additionally comprise an inflammatory cytokine (e.g., TGFβ, PDGF, VEGF, bFGF, TNFα, NGF, GM-CSF, IGF-a, IL-1, IL-1-β, IL-8, IL-6, or growth hormone) and/or a bone morphogenic protein (BMP) (e.g., BMP-2, BMP-3, BMP-4, BMP-5, BMP-6, or BMP-7 or an analogue or derivative thereof).

Furthermore, the device may comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof. The administration and dosages of these agents for use in these embodiments are described in section (vi) below.

(ii) Open Surgical Disc Resection and Microdiscectomy

Spinal disc removal is mandatory and urgent in cauda equine syndrome when there is a significant neurological deficit; particularly bowel or bladder dysfunction. It is also performed electively to relieve pain and eliminate lesser neurological symptoms.

For open surgical resection of a ruptured lumbar disc (laminectomy) the patient is placed in a modified kneeling position under general anesthesia. An incision is made in the posterior midline and the tissue is dissected away to expose the appropriate interspace; the ligamentum flavum is dissected and in some cases portions of the bony lamina are removed to allow adequate visualization. The nerve root is carefully retracted away to expose the herniated fragment and the defect in the annulus. Typically, the cavity of the disc is entered from the tear in the annulus and the loose fragments of the nucleus pulposus are removed with pituitary forceps. Any additional fragments of disc sequestered inside or outside of the disc space are also carefully removed and the disc space is forcefully irrigated to remove to remove any residual fragments. If tears are present in the dura, the dura is closed with sutures that are often augmented with fibrin glue. The tissue is then closed with absorbable sutures.

Microlumbar disc excision (microdiscectomy) can be performed as an outpatient procedure and has largely replaced laminectomy as the intervention of choice for herniated discs. A one inch incision is made from the spinous process above the disc affected to the spinous process below. Using an operating microscope, the tissue is dissected down to the ligamentum flavum and bone is removed from the lamina until the nerve root can be clearly identified. The nerve root is carefully retracted and the tears in the annulus are visualized under magnification. Microdisc forceps are used to remove disc fragments through the annular tear and any sequestered disc fragments are also removed. As with laminectomy, the disc space is irrigated to remove any disc fragments, any dural tears are repaired and the tissue is closed with absorbable sutures. It should be noted that anterior (abdominal) approaches can also be used for both open and endoscopic lumbar disc excision. Cervical and thoracic disc excisions are similar to lumbar procedures and can also be performed from a posterior approach (with laminectomy) or as an anterior discectomy with fusion.

The present invention provides injectable compositions to promote scarring of the annulus, scarring of dural defects and stabilization of adjacent vertebra. The fibrosing agent or fibrosing agent containing composition is delivered under direct vision during open or endoscopic disc excision. Here the composition containing the fibrosis-inducing agent is applied to the annulus or the dural defect directly (in open surgical procedures) or through the side port of an endoscope. The fibrosis-inducing agent can assist in the production of strong fibrotic tissue in the annulus fibrosis at the previous site of herniation or rupture. This can reinforce the weak portion of the intervertebral disc and reduce the likelihood of subsequent re-rupture. In dural defects, the fibrosis-inducing agent can assist in the healing of the dura and prevent complications such as CSF leakage.

The material may also be composed of a polymer system to provide sustained release of the fibrosis-inducing agent. The material suitable for delivery of a fibrosis-inducing agent for the purposes of this invention can be composed of a non-degradable or a degradable material. Suitable non-degradable materials can include crosslinked compositions that comprise PVA, PVP, polyacrylamide, methyl methacrylate (MMA) and methyl methacrylate styrene (MMA-styrene) which when mixed together form polymethyl methacrylate (PMMA) or bone cement (e.g., SIMPLEX P ZIMMER REGULAR or ZIMMER LOW VISCOSITY CEMENT, PALACOS, CMW-1, CMW-2 or ENDURANCE), synthetic cancellous bone void fillers (e.g., CORTOSS), PHEMA, poly(vinyl PEG), poly(styrene sulfonate), poly(acrylic acid), poly(methacrylic acid), as well as other polymers that are known to form hydrogels. Additional compositions include blends and copolymers of the agents listed above. Suitable degradable materials include, but are not limited to, resorbable ceramics composed of β-tricalcium phosphate (e.g., VITOSS and PROOSTEON 500R), hydroxyapatite or $Ca_{10}(PO_4)_6OH$ (e.g., BIOOSS, OSTEOGRAF), calcium carbonate or $CaCO_3$, calcium sulfate (e.g., OSTEOSET and ALLOMATRIX), calcium phosphate (e.g., CALCIBON or NORIAN SRS), crosslinked materials of PEG, gelatin, collagen, bone allografts (e.g., ALLOGRO, ORTHOBLAST, OPTEFORM, GRAFTON), mesenchymal stem cells, hyaluronic acid, hyaluronic acid derivatives, polysaccharides, carbohydrates, proteins (e.g., albumin, casein, whey proteins, plant proteins, and fish proteins), autologous bone, demineralized bone matrix, cellulose derivatives (HPC etc), chitosan, chitosan derivatives, polyester-polyalkylene oxide block copolymers (e.g., PLGA-PEG-PLGA and MePEG-PLGA, and the like) and other low molecular weight polymers that can be excreted.

One material that is of particular interest for use in annulus and dural repairs during intervertebral disc surgery is an injectable material prepared from a 4-armed thiol PEG (10K), a 4-armed NHS PEG(10K) and methylated collagen such as described above. In a preferred embodiment, the injectable material also contains a biologically active agent capable of inducing fibrosis to reinforce the annulus fibrosis (to reduce the risk of repeat herniation or rupture) or assist in the repair of dural defects (to prevent CSF leaks). Preferred biologically active agents for use in combination with the injectable material include fibrosis-inducing agents and growth factors (e.g., transforming growth factor, platelet-derived growth factor, fibroblast growth factor), whose dosages and release kinetics are all described in detail in section (vi) below.

The materials described above can further modified to be comprised of, or contain, polymeric threads. Polymeric threads have the ability to induce a fibroproliferative response in the annulus fibrosis or the dura. These polymer threads can be degradable or non-degradable. Degradable threads can be composed of degradable polyesters, polyanhydrides, poly(anhydride esters), poly(ester-amides), poly(ester-ureas), polyorthoesters, polyphosphoesters, polyphosphazines, cyanoacrylate polymers, collagen, chitosan, hyaluronic acid, chromic cat gut, alginates, starch, cellulose, cellulose esters, blends and copolymers thereof, as well as other known degradable polymers. Non-degradable polymers that can be used include, but are not limited to, polyesters (e.g., PET), polyurethanes, silicones, PE, PP, PS, PM, PMA, silk, blends, copolymers thereof. The threads used can be composed of a single composition or composed of a blend of differing compositions. The polymeric threads themselves can be further modified through the addition of a polymeric coating applied to the threads. The polymer used for coating the thread can be similar to that described above for the threads themselves. The polymer coating may further comprise a biologically active agent that has the ability to induce a fibroproliferative response. The agents that can be used are further described in the section (vi) below.

The materials described above can also be utilized to deliver a particulate material that has the ability to induce fibrosis. These particles can be either degradable or non-degradable and are similar to those described above for threads. In addition to those, particulate materials useful for the practice of this embodiment include silk, talc, starch, glass, silicates, silica, calcium phosphate, calcium sulfate, calcium carbonate, hydroxyapatite, synthetic mineral (e.g., VITOSS and CORTOSS), PMMA, silver nitrate, ceramic particles and other inorganic particles known in the art to induce a fibroproliferative response followed by mineralization. The particles used in this embodiment can be all of the same composition or a blend of differing compositions. These particles can also be used as a coating applied to the polymeric strands as described above.

As is readily apparent, the materials used in the present invention can also be constructed such that they are comprised of both polymeric threads and particles. The threads and particles used are similar to those described above and may be of uniform composition or blended composition. Virtually any combination of threads of differing compositions and particles of differing compositions can be utilized in this embodiment. The hydrogels (e.g., injectable materials prepared from a 4-armed thiol PEG (10K), a 4-armed NHS PEG(10K) and methylated collagen), the polymeric threads, and the particles can all be utilized to deliver one or more biologically active agents, as described below.

Other compositions are suitable for use in open surgical disc resection and microdiscectomy. All involve the deployment of a biomaterial and a fibrosis-inducing agent to reinforce the annulus fibrosis or assist in dural repair. The following compositions can be delivered during surgical disc resection and microdiscectomy either directly, using specialized delivery catheters, via an endoscope, or through a needle or other applicator: (a) fluids, suspensions, emulsions, microemulsions, microspheres, pastes, gels, microparticulates, sprays, aerosols, solid implants and other formulations which release a fibrosis-inducing agent(s); (b) microparticulate silk and/or silk strands (linear, branched, and/or coiled) either alone, or loaded with an additional fibrosis-inducing agent and/or growth factor; (c) collagen-containing formulations such as COSTASIS or materials made from 4-armed thiol PEG (10K), 4-armed NHS PEG (10K) and methylated collagen such as described above, either alone, or loaded with a fibrosis-inducing agent and/or growth factor; (d) injectable PEG-containing formulations such as COSEAL, FOCALSEAL, SPRAYGEL or DURASEAL loaded with a fibrosis-inducing agent and/or growth factor; (e) fibrinogen-containing formulations such as FLOSEAL or TISSEAL loaded with a fibrosis-inducing agent and/or growth factor; (f) hyaluronic acid-containing formulations such as RESTYLANE, HYLAFORM, PERLANE, SYNVISC, SEPRAFILM, SEPRACOAT loaded with a fibrosis-inducing agent and/or growth factor; (g) polymeric gels for surgical implantation such as REPEL or FLOWGEL loaded with a fibrosis-inducing agent and/or growth factor injected into the joint space; (h) orthopedic "cements" such as OSTEOBOND, LVC, SIMPLEX P, PALACOS, CORTOSS, and ENDURANCE loaded with a fibrosis-inducing agent and/or growth factor; (i) surgical adhesives containing cyanoacrylates such as DERMABOND, INDERMIL, GLUSTITCH, VETBOND, HISTOACRYL, TISSUEMEND, TISSUMEND II, HISTOACRYL BLUE and ORABASE SOOTHE-N-SEAL LIQUID PROTECTANT or as described above, loaded with a fibrosis-inducing agent and/or growth factor; (j) surgical implants containing hydroxyapatite, calcium phosphate (such as VITOSS, Orthovita), or calcium sulfate loaded with a fibrosis-inducing agent and/or growth factor; (k) other biocompatible tissue fillers, such as those made by BioCure, 3M Company and Neomend loaded with a fibrosis-inducing agent and/or growth factor; (l) polysaccharide gels such as the ADCON series of gels loaded with a fibrosis-inducing agent and/or growth factor; (m) films, sponges or meshes such as INTERCEED, VICRYL mesh, and GELFOAM either alone, or loaded with a fibrosis-inducing agent, bone morphogenic protein, and/or growth factor, injected into the intervertebral disc; and/or (n) a hydrogel that is formed from an amino-functionalized polyethylene glycol (e.g., 4-armed tetra-amino PEG [10k]) and a 4-armed NHS functionalized PEG (e.g., pentaerythritol poly(ethylene glycol)ethertetra-succinimidyl glutarate [10K]). This hydrogel mayfurther contain collagen, methylated collagen and/or gelatin. This hydrogel can further comprise the fibrosis-inducing agents described above (e.g., silk powder or silk threads). and/or (m) films, sponges or meshes such as INTERCEED, VICRYL mesh, and GELFOAM either alone, or loaded with a fibrosis-inducing agent and/or growth factor.

It should be apparent to one of skill in the art that potentially any fibrosis-inducing agents described above may be utilized alone, or in combination, in the practice of this embodiment. Exemplary fibrosing agents for use in spinal prostheses (e.g., devices and bulking agents) include talc, silk, wool, chitosan, polylysine, fibronectin, bleomycin, and CTGF, as well as analogues and derivatives of the aforementioned.

Optionally, the device may additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) and/or a bone morphogenic protein (BMP) (e.g., BMP-2, BMP-3, BMP-4, BMP-5, BMP-6, or BMP-7 or an analogue or derivative thereof).

Furthermore, the device may alone or additionally comprise an agent that stimulates cellular proliferation.

Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof. The administration and dosages of these agents for use in these embodiments are described in section (vi) below.

(iii) Treatments of Vertebral Compression Fractures

Osteoporosis is a progressive degenerative bone disease characterized by decreased bone mineral density, degradation of bone microarchitecture and reduced bone strength. The weakened bone is often unable to withstand stress, or even normal weight-bearing activities, and is at an increased risk for sustaining fractures. Fractures are the most common clinical manifestation of osteoporosis and the condition is often asymptomatic until the breakage occurs. Osteoporosis is the cause of 1.3 million fractures each year in the U.S. and is estimated to cost the healthcare system over $10 billion annually. Fractures of the hip, wrist and other long bones are common in osteoporosis, but approximately 550,000 patients in the U.S. (700,000 worldwide) suffer vertebral compression fractures as a result of their disease. Here, the weakened cancellous bone of the vertebral column essentially collapses (compresses) under the weight placed on it during normal activities and the vertebra loses height (i.e., the center of the vertebra collapses and the two endplates of the vertebra move closer together). Compression of the vertebra leads to pain, a loss of height, curvature of the spine (kyphosis), and in some cases, breathing problems due to pressure placed on the chest cavity and lungs.

Traditionally, vertebral compression fractures have been treated conservatively with bed rest. In severe cases, spinal fusion and/or open fracture reduction (repairing the fracture with surgically placed orthopedic plates and screws) have also been used in the management of vertebral compression fractures. Recently, two minimally invasive procedures—vertebroplasty and kyphoplasty—have been developed to treat vertebral compression fractures due to osteoporosis or, less commonly, due to bone tumors. Vertebroplasty utilizes bone cement (polymethylmethacrylate —PMMA) injected under pressure into the fracture under x-ray guidance to stabilize the fracture, provide support and reduce pain. This procedure can often be performed as an outpatient and provides almost immediate symptomatic relief and early mobilization. Kyphoplasty involves the insertion of a balloon (KYPHX Inflatable Bone Tamp made by Kyphon Inc., Sunnyvale, Calif.) into the fracture which is then inflated inside the bone to create a void, stabilize the fracture and straighten the bone and spine (i.e., restore the vertebral height lost as a result of the compression fracture). The surgeon then injects bone filler (typically PMMA or a calcium phosphate-based material) via specialized access devices (Inflation Syringe and Bone Access System also made by Kyphon, Inc. (Sunnyvale, Calif.) into the space under C-arm image-guided fluoroscopy to support the fractured vertebra). Injecting the bone cement into the balloon-created cavity enables the injection to be performed under low pressure and reduces the incidence of neurological injury associated with cement leakage. In vertebroplasty, where the cement is injected under pressure, cement leakage occurs in 30–73% of patients versus only 8–9% of those treated with kyphoplasty.

In both vertebroplasty and kyphoplasty the fractured bone is reinforced and replaced by bone cement. Unfortunately, bone cement is significantly stronger than the adjacent bone and can exert an incompressible mass effect on the surrounding vertebra leading to compressions and fractures in the vertebra above and below the treated segment. The present invention provides injectable compositions that include a bulking or filling agent and a fibrosing agent for direct injection into vertebral compression fractures as part of vertebroplasty or kyphoplasty. A material containing a fibrosis-inducing agent (alone or in combination with polymeric carrier, which may be in the form of, e.g., a gel, paste, or spray) is injected into a vertebral compression fracture can be used to promote the growth of endogenous scar tissue to fill the vertebral body defect, thus more closely mimicking normal tissue dynamics and reducing the incidence of adjacent vertebral fractures. In another embodiment, the injectable composition containing a fibrosis-inducing agent can further contain an agent that promotes bone growth (e.g., bone morphogenic proteins, growth factors, etc.). When performing an injection into a vertebral compression fracture, it may also be necessary to add compositions to enhance visualization of needle (or catheter). Suitable agents and methods for use in combination with a fibrosis-inducing agent (with or without an agent that promotes bone growth) include, but are not limited to, the use of a needle coated with ECHO—COAT or the addition of contrast agents (e.g., barium, tantalum, technitium, gadolinium) for localization by x-ray or MRI.

The injectable material may also contain a polymer system that can provide sustained release of the fibrosis-inducing agent (with or without a concomitant bone morphogenic protein, and/or osteogenic growth factor) to enhance efficacy and reduce the need for repeat administrations of active agents. Preferred polymeric carriers for delivery of a injectable fibrosis-inducing agent (with or without a bone morphogenic protein, and/or growth factor that promotes bone growth) for the treatment of vertebral compression fractures are degradable materials which, after providing initial tissue support, are gradually replaced by the body's own scar tissue. Suitable degradable materials for use in this embodiment include, but are not limited to, resorbable ceramics composed of β-tricalcium phosphate (e.g., VITOSS and PROOSTEON 500R), hydroxyapatite or $Ca_{10}(PO_4)_6OH$ (e.g., BIOOSS and OSTEOGRAF), calcium carbonate or $CaCO_3$, calcium sulfate (e.g., OSTEOSET and ALLOMATRIX), calcium phosphate (e.g., CALCIBON or NORIAN SRS), crosslinked materials of PEG, gelatin, collagen, bone allografts (e.g., ALLOGRO, ORTHOBLAST, OPTEFORM, GRAFTON), mesenchymal stem cells, hyaluronic acid (such as RESTYLANE, HYLAFORM, PERLANE, SYNVISC, SEPRAFILM, SEPRACOAT), hyaluronic acid derivatives, polysaccharides, carbohydrates, fibrinogen-containing formulations (such as FLOSEAL or TISSEAL), proteins (e.g., albumin, casein, whey proteins, plant proteins, and fish proteins, and the like), autologous bone, demineralized bone matrix, cellulose derivatives (e.g., HPC etc), chitosan, chitosan derivatives, polyester-polyalkylene oxide block copolymers (e.g., PLGA-PEG-PLGA and MePEG-PLGA, and the like) and other low molecular weight polymers that can be excreted. Injectable PEG-containing formulations such as COSEAL, FOCALSEAL, SPRAYGEL or DURASEAL loaded with a fibrosis-inducing agent, bone morphogenic protein, and/or growth factor can also be used for injection into a vertebral compression fracture. Loading these materials with a fibrosis-inducing agent (with or without a bone morphogenic protein, and/or growth factor that promotes bone growth) can produce an injectable material that can provide initial support and symptomatic relief, but degrade with time as the body's own scar tissue grows in to repair the defect.

One injectable material that is of particular interest for injection into vertebral compression fractures is prepared from a 4-armed thiol PEG (10K), a 4-armed NHS PEG(10K) and methylated collagen such as described above. In a preferred embodiment, the injectable material also contains a biologically active fibrosis-inducing agent (with or without a bone morphogenic protein, and/or growth factor that promotes bone growth). In one embodiment, the injectable material is loaded with a fibrosis-inducing agent is injected into a vertebral compression fracture to provide stability and symptomatic relief, form a scaffold that supports fibrous and bony ingrowth, deliver active agents that can promote repair, and degrade once tissue repair is complete. In another embodiment, the injectable material contains biologically active agents capable of inducing bone growth such bone morphogenic proteins and growth factors (transforming growth factor, platelet-derived growth factor, fibroblast growth factor) to promote bony ankylosis and fusion of adjacent vertebra. In some circumstances, the injectable material may contain a fibrosis-inducing agent as well as a bone morphogenic protein and/or growth factors that promote bone growth.

In certain embodiments (for example, in the treatment of more unstable fractures) it may be desirable to use a bone cement to deliver the fibrosis-inducing agent to a vertebral compression fracture. Suitable non-degradable materials include crosslinked compositions that comprise PVA, PVP, polyacrylamide, methyl methacrylate (MMA) and methyl methacrylate styrene (MMA-styrene) which when mixed together form polymethyl methacrylate (PMMA) or bone cement (e.g., SIMPLEX P, ZIMMER REGULAR and ZIMMER LOW VISCOSITY CEMENT, PALACOS, CMW-1, CMW-2 or ENDURANCE). Also of utility in this embodiment are synthetic cancellous bone void fillers (e.g., CORTOSS), PHEMA, poly(vinyl PEG), poly(styrene sulfonate), poly(acrylic acid), poly(methacrylic acid), as well as other polymers that are known to form hydrogels. Surgical adhesives containing cyanoacrylates such as DERMABOND, INDERMIL, GLUSTITCH, TISSUEMEND, VETBOND, HISTOACRYL BLUE and ORABASE SOOTHE-N-SEAL LIQUID PROTECTANT loaded with a fibrosis-inducing agent, bone morphogenic protein, and/or growth factor are also suitable for injection into vertebral compression fracture. Additional compositions include blends and copolymers of the agents listed above. In each case the material is loaded with a fibrosis-inducing agent (with or without a bone morphogenic protein, and/or growth factor that promotes bone growth) and injected into a vertebral compression fracture (as part of vertebroplasty or kyphoplasty) to stabilize the fracture and encourage the ingrowth of tissue. The addition of fibrous tissue in and around the non-degradable implant can make the material behave more like native tissue and reduce the incidence of adjacent fractures.

All of the injectable materials described above can be further modified to be comprised of, or contain, polymeric threads. Polymeric threads have the ability to induce a fibroproliferative response from the surrounding tissue. These polymer threads can be degradable or non-degradable. Degradable threads can be composed of degradable polyesters, polyanhydrides, polyorthoesters, polyphosphoesters, polyphosphazines, cyanoacrylate polymers, collagen, chitosan, hyaluronic acid, chromic cat gut, alginates, starch, cellulose, cellulose esters, blends and copolymers thereof, as well as other known degradable polymers. Non-degradable polymers that can be used include, but are not limited to, polyesters (e.g., PET), polyurethanes, silicones, PE, PP, PS, PM, PMA, silk, blends, copolymers thereof as well as other known polymers. The threads used can be composed of a single composition or composed of a blend of differing compositions. The polymeric threads themselves can be further modified through the addition of a polymeric coating applied to the threads. The polymer used for coating the thread can be similar to that described above for the threads themselves. The polymer coating may further comprise a biologically active agent that has the ability to induce a fibroproliferative or osteogenic response. The fibrosis-inducing agents that can be used are further described in the section (vi) below.

The injectable materials described above can be utilized to deliver a particulate material that has the ability to induce fibrosis in an intervertebral fracture. These particles can be either degradable or non-degradable and are similar to those described above for threads. Microparticulate silk and/or silk strands (linear, branched, and/or coiled) either alone, or loaded with an additional fibrosis-inducing agent, bone morphogenic protein, and/or growth factor are also useful for directed injection into a vertebral compression fracture. Additional particulate materials useful for the practice of this embodiment include talc, starch, glass, silicates, silica, calcium phosphate, calcium sulfate, calcium carbonate, hydroxyapatite, synthetic mineral (e.g., VITOSS and CORTOSS), PMMA, silver nitrate, ceramic particles and other inorganic particles known in the art to induce a fibroproliferative response followed by mineralization. The particles used in this embodiment can be all of the same composition or a blend of differing compositions. These particles can also be used as a coating applied to the polymeric strands as described above.

The injectable materials can also be constructed such that it is comprised of both polymeric threads and particles. The threads and particles used are similar to those described above and may be of uniform composition or blended composition. Virtually any combination of threads of differing compositions and particles of differing compositions can be utilized in this embodiment. The hydrogels, the polymeric threads, and the particles can all be utilized to deliver one or more biologically active agents, as described below.

One specific composition comprising threads and/or particles is prepared from 4-armed thiol PEG (10K), 4-armed NHS PEG(10K) and methylated collagen such as described above and contains powdered silk particles (or silk threads) and/or mineral particles added to the composition prior to curing. Once deployed, the composition can absorb water, fill the fracture space and adhere to adjacent bone. This expansion can stabilize the fracture and restore vertebral height, while the powdered silk and/or mineral particles can initiate an ankylosing response. As the 4-armed thiol PEG (10K), 4-armed NHS PEG(10K) and methylated collagen composition starts to degrade, the material can support the bone tissue ingrowth that is initiated and potentiated by the particles. Bone morphogenic proteins and/or growth factors (described previously and below) are also useful for inclusion in this composition. In addition, one may also add or replace all (or a portion) of the 4-armed thiol PEG with a 4-armed amino PEG. The amino PEG can provide a gel that can take a longer time to degrade and can provide some positive charge to further attract cellular material.

A second specific embodiment consists of an injectable implant composed of silk fibers or a polymerized version of the fibrosing agent itself (i.e., repeating units of the fibrosing agent polymerized together). Bone morphogenic proteins and/or growth factors (described previously and below) may also be added to this composition.

It should be apparent to one of skill in the art that potentially any fibrosis-inducing agents described above may be utilized alone, or in combination, in the practice of this embodiment. Exemplary fibrosing agents for use in spinal prostheses (e.g., devices and bulking agents) include talc, silk, wool, chitosan, polylysine, fibronectin, bleomycin, and CTGF, as well as analogues and derivatives of the aforementioned.

Optionally, the device may additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) and/or a bone morphogenic protein (BMP) (e.g., BMP-2, BMP-3, BMP-4, BMP-5, BMP-6, or BMP-7 or an analogue or derivative thereof).

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

The administration and dosages of these agents for use in the above embodiments are described in section (vi) below.

(iv) Spinal Fusion Devices

In some cases, it may be necessary to promote bony fusion of adjacent vertebral segments (in effect biologically "welding" the segments together). Fusion of one or more vertebral segments alleviates pain by restricting vertebral motion across the damaged intervertebral disc(s). Surgical spinal fusion can be accomplished using a variety of procedures, implants and devices.

Typically, the vertebral canal is exposed through open surgery (either anteriorly and/or posteriorly) and all or parts of the damaged disc are removed sufficient to allow decompression of the affected cord or nerve roots. Bone grafts (autografts or allografts) or bone substitutes are used to promote vertebral fusion, while the fixation devices serve to immobilize the region until bony fixation takes place. As part of the spinal fusion surgery, it is often necessary to augment the procedure through the insertion of an implant or device that stabilizes the fusing spinal segments while the bone graft or bone substitute fuses the mobile segments. Examples of implants and devices designed to splint the segments during the healing process include: fusion devices (including fusion baskets, fusion cage apparatus, interbody cages, interbody implants, fusion cage anchoring devices, fusion stabilization chamber, fusion cage anchoring plates), bone fixation devices (including anchoring bone plates, bone screws, and other fixation hardware) and tissue fillers/implants (including bone cement, allograft material, autograft material, collagen, and other biocompatible tissue fillers). All of these implants are suitable for coating with, or delivery of, a fibrosis-inducing agent(s) to promote healing and accelerate fusion of the vertebral bodies.

Spinal fusion cages are interbody devices that fit within the intervertebral space and/or the anterior region of the vertebral column. Fusion cages have various shapes including rectangular or cylindrical and a plurality of openings and helical threading. Fusion cages are often composed of an outer body and a hollow cavity that may or may not be used to insert bone growth-promoting material for stimulating bone fusion. For example, the prosthesis may be an interbody fusion cage that has an externally threaded stem projecting from a domed outer end which is fixed using an assembly of a plate, a fastener and bone screws. See e.g., U.S. Pat. No. 6,156,037. The prosthesis may be a fusion cage with a threaded outer surface adapted for promoting fusion with bone structures when a bone-growth-inducing substance is packed into the cage body. See e.g., U.S. Pat. Nos. 4,961,740; 5,015,247; 4,878,915; and 4,501,269. The prosthesis may be a generally tubular shell with a helical thread projecting with a plurality of pillars with holes to facilitate bone ingrowth and mechanical anchoring (see e.g., U.S. Pat. Nos. 6,071,310 and 5,489,308) or it may be biologically active and serve to promote fusion with the adjacent vertebral bone plates (see e.g., U.S. Pat. Nos. 5,489,308 and 6,520,993). Other U.S. patents that describe threaded spinal implants include U.S. Pat. Nos. 5,263,953; 5,458,638; and 5,026,373.

In another aspect, the prosthesis may be a bone fixation device designed to promote vertebral fusion in order to limit movement between adjacent vertebrae. For example, bone dowels, rods, hooks, wires, wedges, plates, screws and other components may be used to fix the vertebral segments into place. The fixation device may fit within the intervertebral space or it may encompass both the intervertebral space and the anterior region of the vertebral column or it may only encompass the anterior region of the vertebral column. A bone fixation device may be used with a fusion cage to assist in stabilizing the device within the intervertebral area. For example, the prosthesis may be in the form of a solid annular body having a plurality of discrete bone-engaging teeth protruding on the superior and inferior surfaces and having a central opening that may be filled with a bone growth-promoting material. See e.g., U.S. Pat. No. 6,520,993. The prosthesis may have a disk-like body with weld-like raised parts disposed on opposite surfaces to enhance lateral stability in situ. See e.g., U.S. Pat. No. 4,917,704. The prosthesis may be composed of opposite end pieces that maintain the height of the intervertebral space with an integral central element that is smaller in diameter wherein osteogenic material is disposed within the annular pocket between the end pieces. See e.g., U.S. Pat. No. 6,146,420. The prosthesis may be composed of first and second side surfaces extending parallel to each other with upper and lower surfaces that engage the adjacent vertebrae. See e.g., U.S. Pat. No. 5,716,415. The prosthesis may be a fusion stabilization chamber composed of a hollow intervertebral spacer and an end portion with at least one hole for affixing into the surrounding bone. See e.g., U.S. Pat. No. 6,066,175. The prosthesis may be composed of a metallic body tapering conically from the ventral to the dorsal end and having a plurality of fishplates extending from opposite sides with openings for bone screws. See e.g., U.S. Pat. No. 4,955,908. The prosthesis may be composed of a pair of plates which may have protrusions for engaging the adjacent vertebrae and an alignment device disposed between the engaging plates for separating the plates to maintain them in lordotic alignment. See e.g., U.S. Pat. No. 6,576,016. The prosthesis may be a plurality of implants that are inserted side by side into the disc space to promote bone fusion across an intervertebral space. See e.g., U.S. Pat. No. 5,522,899. The prosthesis may be an anchoring device composed of an anchoring plate with a central portion configured for attachment to a vertebral implant (e.g., fusion cage) and the end portions adapted to fasten in a fixed manner to a bony segment of the vertebra. See e.g., U.S. Pat. No. 6,306,170. The prosthesis may be a bone fixation apparatus composed of a bone plate and a fastener apparatus (e.g., bone screws). See e.g., U.S. Pat. Nos. 6,342,055; 6,454,769; 6,602,257; and 6,620,163.

Spinal prostheses, which may be combined with one or more fibrosis-inducing agents according to the present invention, include commercially available products.

Examples include: the INTERFIX Threaded Fusion Device (by Medtronic Sofamor Danek, Memphis, Term.), the BAK/C Cervical Interbody Fusion System and the CERVI-LOK Cervical Fixation System (by Centerpulse SPINE-TECH, Minneapolis, Minn.), the SC-ACUFIX Anterior Cervical Plate System (by Spinal Concepts, Austin, Tex.), the ACROFLE TDR prostheses and the CHARITE Artificial Disc (by DePuy Spine, Inc., Raynham, Mass.), the PRO-DISC system and PRODISC Cervical-C IDE disc replacement (by Synthes-Stratec, Switzerland) and the PROSTHETIC DISC NUCLEUS (by Raymedica, Inc., Minneapolis, Minn.).

In all of the aforementioned spinal fusion devices, the addition of a fibrosis-inducing agent may assist in the spinal fusion process by promoting the production of fibrous tissue. In one aspect, the present invention provides spinal fusion devices (including fusion baskets, fusion cage apparatus, interbody cages, interbody implants, fusion cage anchoring devices, fusion stabilization chamber, fusion cage anchoring plates; bone fixation devices including anchoring bone plates, bone screws, and other fixation hardware; and tissue fillers/implants including bone cement, allograft material, autograft material, collagen, and other biocompatible tissue fillers) that include a fibrosis-inducing agent or a composition that includes a fibrosis-inducing agent to promote scarring and fixation of the device into the surrounding bone. In one aspect, a spinal fusion device is coated with a fibrosing agent or a composition that includes the fibrosing agent to enhance healing. In another aspect, the fibrosing agent may be incorporated into the glue/cement that holds the spinal fusion device in place. In another aspect, the spinal fusion device is covered (all or in part) with a silk mesh or lattice to encourage scarring and anchoring into the surrounding bone. For example, a silk mesh or lattice can be coated onto all or a portion of the surface of fusion cage or other bone fixation hardware to encourage scarring and anchoring into the surrounding bone.

Numerous polymeric and non-polymeric carrier systems described previously can be used to provide sustained release of the fibrosis-inducing agent from the spinal fusion device. Methods for incorporating fibrosing compositions onto or into the spinal fusion devices include: (a) directly affixing to the device a fibrosing composition (e.g., by either a spraying process or dipping process as described above, with or without a carrier); (b) directly incorporating into the device a fibrosing composition (e.g., by either a spraying process or dipping process as described above, with or without a carrier); (c) by coating the device with a substance such as a hydrogel which can in turn absorb the fibrosing composition; (d) by interweaving a fibrosing composition (for example a silk strand or another polymeric thread which releases a fibrosis-inducing agent) into the device structure; (e) by inserting the device into a sleeve or mesh which is comprised of, or coated with, a fibrosing composition; (f) constructing the device itself, or a portion of the device, with a fibrosing composition; or (g) by covalently binding the fibrosing agent directly to the device surface, or to a linker (small molecule or polymer) that is coated or attached to the device surface. For these devices, the coating process can be performed in such a manner as to (a) coat the surfaces of the device that is in contact with the bone, (b) coat the surfaces of the device that are not in contact with the bone or (c) coat all or parts of both the bone-contacting and non-bone contacting surfaces of the device.

In addition to coating the spinal fusion device with the fibrosing composition, the fibrosis-inducing agent can be mixed with the materials that are used in the construction of the device such that the fibrosing agent is incorporated into the final device.

It should be apparent to one of skill in the art that potentially any adhesion or fibrosis-inducing agents described above may be utilized alone, or in combination, in the practice of this embodiment. Exemplary fibrosing agents for use in spinal fusion devices (including fusion baskets, fusion cage apparatus, interbody cages, interbody implants, fusion cage anchoring devices, fusion stabilization chamber, fusion cage anchoring plates; bone fixation devices including anchoring bone plates, bone screws, and other fixation hardware; and tissue fillers/implants including bone cement, allograft material, autograft material, collagen, and other biocompatible tissue fillers) include talc, silk, wool, chitosan, polylysine, fibronectin, bleomycin, and CTGF, as well as analogues and derivatives of the aforementioned.

Optionally, the device may additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) and/or a bone morphogenic protein (BMP) (e.g., BMP-2, BMP-3, BMP-4, BMP-5, BMP-6, or BMP-7 or an analogue or derivative thereof).

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

The administration and dosages of these agents for use in these embodiments are described in section (vi) below.

(v) Intervertebral Disc Prostheses

In certain cases of DDD, the damaged vertebral segment may be treated using a intervertebral disc prosthesis that maintains vertebral anatomy and movement within the vertebral joint. This is often conducted when damage to more than one vertebral segment occurs. As used herein, the term "intervertebral disc prostheses" (or "artificial disc") refers to implants and/or devices that are located in, on, or near the spine and which enhance the ability of the spine to perform its function in the patient. Examples of intervertebral disc prostheses include, without limitation, artificial spinal discs and related devices including vertebral implants, vertebral disc prostheses, lumbar disc implants, cervical disc implants, implantable intervertebral prostheses, spinal prostheses, artificial discs, prosthetic implants, prosthetic spinal discs, spinal disc endoprostheses, spinal implants, artificial spinal discs, intervertebral implants, implantable spinal grafts, artificial lumbar discs, spinal nucleus implants, and intervertebral disc spacers.

An artificial disc suitable for combining with a fibrosis-inducing agent according to the present invention may be composed of a single material or several materials including, without limitation, allograft bone material (see e.g., U.S. Pat. No. 6,143,033), metals (see e.g., U.S. Pat. No. 4,955, 908), and/or synthetic materials (see e.g., U.S. Pat. Nos. 6,264,695; 6,419,706; 5,824,093; and 4,911,718). The prosthesis must be biocompatible and may consist of biodegradable or non-biodegradable components depending on the intended function of the device. See e.g., U.S. Pat. No. 4,772,287. The intervertebral disc prosthesis may be biologically inert and serve as a mechanical means of stabilizing the vertebral column (see e.g., U.S. Pat. Nos. 4,955,908 and 5,716,415) or as a means of preserving spinal function. In another aspect, the prosthesis may be an alternative to spinal fusion. The prosthesis may be a disc designed to provide normal movement between vertebral bone plates. The artificial disc may be intended to mimic the natural shock absorbent function of the natural disc. The artificial disc may be composed of a center core and end elements that support the disc against the adjacent vertebra or it may be intended to replace only a portion of the natural intervertebral disc (e.g., nucleus pulposus). For example, the artificial disc may be in the form of an elastomeric section sandwiched between two rigid plates. See e.g., U.S. Pat. Nos. 6,162,252; 5,534,030; 5,017,437; and 5,031,437. The intervertebral disc prosthesis may be an elongated prosthetic disc nucleus composed of a hydrogel core and a constraining flexible jacket that allows the core to deform and reform. See e.g., U.S. Pat. No. 5,824,093. The artificial disc may be composed of a rigid superior and inferior concaval-convex elements and a nuclear body which is located between the concave surfaces to permit movement. See e.g., U.S. Pat. No. 6,156,067. The artificial disc may be a partial spinal prosthesis composed of a core made of an elastic material such as silicone polymer or an elastomer which is covered by a casing made of a rigid material which is in contact with the adjacent vertebrae. See e.g., U.S. Pat. No. 6,419,706. The intervertebral disc prosthesis may replace only the nucleus pulposus tissue by using a spinal nucleus implant comprised of a swellable, biomimetic plastic with a hydrophobic and hydrophilic phase which can be expanded in situ to conform to the natural size and shape. See e.g., U.S. Pat. No. 6,264,695. The artificial disc may be composed of a central core formed from a biocompatible elastomer wrapped by multi-layered laminae made from elastomer and fibers. See e.g., U.S. Pat. No. 4,911,718. The intervertebral disc prosthesis may be composed of a fluid-filled inner bladder with an outer layer of strong, inert fibers intermingled with a bioresorbable material which promotes tissue ingrowth. See e.g., U.S. Pat. No. 4,772,287.

In one aspect, the present invention provides intervertebral disc prostheses that include a fibrosis-inducing agent or a composition that includes a fibrosis-inducing agent to promote scarring and fixation of the device into the surrounding bone and yet retain the flexibility of the natural disc. In one aspect, an artificial disc is coated with a fibrosis-inducing agent (or a composition that includes a fibrosis-inducing agent) to enhance healing and the formation of fibrous tissue similar to the annulus fibrosis. In another aspect, the fibrosing agent may be incorporated into the glue/cement that holds the artificial disc in place. In another aspect, the intervertebral disc prosthesis is covered (all or in part) with a silk mesh or lattice to encourage scarring and anchoring of the implant into the surrounding bone.

Numerous polymeric and non-polymeric carrier systems described previously can be used to provide sustained release of the fibrosis-inducing agent from the artificial disc. Methods for incorporating fibrosing compositions onto or into intervertebral disc prostheses include: (a) directly affixing to the device a fibrosing composition (e.g., by either a spraying process or dipping process as described above, with or without a carrier); (b) directly incorporating into the device a fibrosing composition (e.g., by either a spraying process or dipping process as described above, with or without a carrier); (c) by coating the device with a substance such as a hydrogel which can in turn absorb the fibrosing composition; (d) by interweaving a fibrosing composition (for example a silk strand or another polymeric thread which releases a fibrosis-inducing agent) into the device structure; (e) by inserting the device into a sleeve or mesh which is comprised of, or coated with, a fibrosing composition; (f) constructing the device itself, or a portion of the device, with a fibrosing composition; or (g) by covalently binding the fibrosing agent directly to the device surface, or to a linker (small molecule or polymer) that is coated or attached to the device surface. For these devices, the coating process can be performed in such a manner as to (a) coat the surfaces of the device that is in contact with the vertebral bone, (b) coat the surfaces of the device that are not in contact with the bone or (c) coat all or parts of both the bone-contacting and non-bone contacting surfaces of the device.

In addition to coating the artificial disc with the fibrosing composition, the fibrosing agent can be mixed with the materials that are used to make the device such that the fibrosing agent is incorporated into the final prosthetic intervertebral disc.

In one embodiment, the therapeutic agent can be incorporated directly into the formulation (for example, direct incorporation of the fibrosis-inducing agent into the swellable, biomimetic polymers used to create an artificial nucleus pulposus tissue that expands in situ to conform to the natural size and shape of the intervertebral disc core). In another embodiment, the fibrosis-inducing agent can be incorporated into a secondary carrier (e.g., micelles, liposomes, emulsions, microspheres, nanospheres etc, as described above) that are then used in the construction of, or as constituents of, an artificial disc.

It should be apparent to one of skill in the art that potentially any fibrosis-inducing agents described above may be utilized alone, or in combination, in the practice of this embodiment. Exemplary fibrosing agents for use in spinal prostheses (e.g., devices and bulking agents) include talc, silk, wool, chitosan, polylysine, fibronectin, bleomycin, and CTGF, as well as analogues and derivatives of the aforementioned.

Optionally, the device may additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) and/or a bone hormone) and/or a bone morphogenic protein (BMP) (e.g., BMP-2, BMP-3, BMP-4, BMP-5, BMP-6, or BMP-7 or an analogue or derivative thereof).

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

The administration and dosages of these agents for use in these embodiments are described in section (vi) below.

(vi) Fibrosis-inducing Agents for Use in Spinal Conditions

As spinal prostheses and injectables are made in a variety of configurations and sizes, the exact dose administered can vary with the amount injected or with the device size, surface area and design. However, certain principles can be applied in the application of this art. Drug dose can be calculated as a function of dose per unit area (of the portion of the device being coated), total drug dose administered can be measured, and appropriate surface concentrations of active drug can be determined. Regardless of the method of application of the drug to the spinal prostheses, the exemplary fibrosing agents, used alone or in combination, should be administered under the following dosing guidelines:

Utilizing talc as an exemplary fibrosis-inducing agent, whether it is applied using a polymer coating, incorporated into the polymers which make up the device or implant, or applied without a polymeric carrier, the total dose of talc delivered from a spinal prosthesis, or coated onto the surface of a spinal prosthesis, should not exceed 100 mg (range of 1 µg to 100 mg). In one embodiment, the total amount of talc released from the prosthesis should be in the range of 10 µg to 50 mg. The dose per unit area of the device (i.e., the dosage of talc as a function of the surface area of the portion of the device to which drug is applied and/or incorporated) should fall within the range of 0.05 µg–10 µg per mm$^2$ of surface area coated. In another embodiment, talc should be applied to a spinal prosthesis surface at a dose of 0.05 µg/mm$^2$–10 µg/mm$^2$ of surface area coated. In one embodiment, talc is released from the surface of a spinal prosthesis or from composition (e.g., a bulking agent) such that fibrosis in the tissue is promoted for a period ranging from several hours to several months. Drug concentrations in a bulking agent or other such material should be within the range described above except values are in mm$^3$. For example, talc may be released in effective concentrations for a period ranging from 1 hour–30 days. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymer coating, incorporated into the polymers which make up the device or implant, or applied without a polymeric carrier, the total dose of silk delivered from a spinal prosthesis, or coated onto the surface of a spinal prosthesis, should not exceed 100 mg (range of 1 µg to 100 mg). In one embodiment, the total amount of silk released from the prosthesis should be in the range of 10 µg to 50 mg. The dose per unit area of the device (i.e., the dosage of silk as a function of the surface area of the portion of the device to which drug is applied and/or incorporated) should fall within the range of 0.05 µg–10 µg per mm$^2$ of surface area coated. In another embodiment, silk should be applied to a spinal prosthesis surface at a dose of 0.05 µg/mm$^2$–10 µg/mm$^2$ of surface area coated. As specific (polymeric and non-polymeric) drug delivery vehicles and specific medical devices can release silk at differing rates, the above dosing parameters should be utilized in combination with the release rate of the drug from the spinal prosthesis such that a minimum concentration of 0.01 nM to 1000 µM of silk is delivered to the tissue. In one embodiment, silk is released from the surface of a spinal prosthesis or from an injectable composition (e.g., a bulking agent) such that fibrosis in the tissue is promoted for a period ranging from several hours to several months. For example, silk may be released in effective concentrations for a period ranging from 1 hour–30 days. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymer coating, incorporated into the polymers which make up the device or implant, or applied without a polymeric carrier, the total dose of chitosan delivered from a spinal prosthesis, or coated onto the surface of a spinal prosthesis, should not exceed 100 mg (range of 1 µg to 100 mg). In one embodiment, the total amount of chitosan released from the prosthesis should be in the range of 10 µg to 50 mg. The dose per unit area of the device (i.e., the dosage of chitosan as a function of the surface area of the portion of the device to which drug is applied and/or incorporated) should fall within the range of 0.05 µg–10 µg per mm$^2$ of surface area coated. In another embodiment, chitosan should be applied to a spinal prosthesis surface at a dose of 0.05 µg/mm$^2$–10 µg/mm$^2$ of surface area coated. As specific (polymeric and non-polymeric) drug delivery vehicles and specific medical devices can release chitosan at differing rates, the above dosing parameters should be utilized in combination with the release rate of the drug from the spinal prosthesis such that a minimum concentration of 0.01 nM to 1000 µM of chitosan is delivered to the tissue. In one embodiment, chitosan is released from the surface of a spinal prosthesis or from an injectable composition (e.g., a bulking agent) such that fibrosis in the tissue is promoted for a period ranging from several hours to several months. For example, chitosan may be released in effective concentrations for a period ranging from 1 hour–30 days. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as an exemplary fibrosis-inducing agent, whether it is applied using a polymer coating, incorporated into the polymers which make up the device or implant, or applied without a polymeric carrier, the total dose of polylysine delivered from a spinal prosthesis, or coated onto the surface of a spinal prosthesis, should not exceed 100 mg (range of 1 µg to 100 mg). In one embodiment, the total amount of polylysine released from the prosthesis should be in the range of 10 µg to 50 mg. The dose per unit area of the device (i.e., the dosage of polylysine as a function of the surface area of the portion of the device to which drug is applied and/or incorporated) should fall within the range of 0.05 µg–10 µg per mm$^2$ of surface area coated. In another embodiment, polylysine should be applied to a spinal prosthesis surface at a dose of 0.05 µg/mm$^2$–10 µg/mm$^2$ of surface area coated. As specific (polymeric and non-polymeric) drug delivery vehicles and specific medical devices can release polylysine at differing rates, the above dosing parameters should be utilized in combination with the release rate of the drug from the spinal prosthesis such that a minimum concentration of 0.01 nM to 1000 µM of polylysine is delivered to the tissue. In one embodiment, polylysine is released from the surface of a spinal prosthesis or from a composition (e.g., a bulking agent) such that fibrosis in the tissue is promoted for a period ranging from several hours to several months. For example, polylysine may be released in effective concentrations for a period ranging from 1 hour–30 days. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymer coating, incorporated into the polymers which make up the device or implant, or applied without a polymeric carrier, the total dose of fibronectin delivered from a spinal prosthesis, or coated onto the surface of a spinal prosthesis, should not exceed 100 mg (range of 1 μg to 100 mg). In one embodiment, the total amount of fibronectin released from the prosthesis should be in the range of 10 μg to 50 mg. The dose per unit area of the device (i.e., the dosage of fibronectin as a function of the surface area of the portion of the device to which drug is applied and/or incorporated) should fall within the range of 0.05 μg–10 μg per $mm^2$ of surface area coated. In another embodiment, talc should be applied to a spinal prosthesis surface at a dose of 0.05 $μg/mm^2$–10 $μg/mm^2$ of surface area coated. As specific (polymeric and non-polymeric) drug delivery vehicles and specific medical devices can release fibronectin at differing rates, the above dosing parameters should be utilized in combination with the release rate of the drug from the spinal prosthesis such that a minimum concentration of 0.01 nM to 1000 μM of fibronectin is delivered to the tissue. In one embodiment, fibronectin is released from the surface of a spinal prosthesis or from a composition (e.g., a bulking agent) such that fibrosis in the tissue is promoted for a period ranging from several hours to several months. For example, fibronectin may be released in effective concentrations for a period ranging from 1 hour–30 days. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, whether it is applied using a polymer coating, incorporated into the polymers which make up the device or implant, or applied without a polymeric carrier, the total dose of bleomycin delivered from a spinal prosthesis, or coated onto the surface of a spinal prosthesis, should not exceed 100 mg (range of 0.01 μg to 100 mg). In one embodiment, the total amount of bleomycin released from the prosthesis should be in the range of 0.10 μg to 50 mg. The dose per unit area of the device (i.e., the dosage of bleomycin as a function of the surface area of the portion of the device to which drug is applied and/or incorporated) should fall within the range of 0.005 μg–10 μg per $mm^2$ of surface area coated. In another embodiment, bleomycin should be applied to a spinal prosthesis surface at a dose of 0.005 $μg/mm^2$–10 $μg/mm^2$ of surface area coated. As specific (polymeric and non-polymeric) drug delivery vehicles and specific medical devices can release bleomycin at differing rates, the above dosing parameters should be utilized in combination with the release rate of the drug from the spinal prosthesis such that a minimum concentration of 0.001 nM to 1000 μM of bleomycin is delivered to the tissue. In one embodiment, bleomycin is released from the surface of a spinal prosthesis or from a composition (e.g., a bulking agent) such that fibrosis in the tissue is promoted for a period ranging from several hours to several months. For example, bleomycin may be released in effective concentrations for a period ranging from 1 hour–30 days. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as an exemplary fibrosis-inducing agent, whether it is applied using a polymer coating, incorporated into the polymers which make up the device or implant, or applied without a polymeric carrier, the total dose of CTGF delivered from a spinal prosthesis, or coated onto the surface of a spinal prosthesis, should not exceed 100 mg (range of 0.01 μg to 100 mg). In one embodiment, the total amount of CTGF released from the prosthesis should be in the range of 0.10 μg to 50 mg. The dose per unit area of the device (i.e., the dosage of CTGF as a function of the surface area of the portion of the device to which drug is applied and/or incorporated) should fall within the range of 0.005 μg–10 μg per $mm^2$ of surface area coated. In another embodiment, CTGF should be applied to a spinal prosthesis surface at a dose of 0.005 $μg/mm^2$–10 $μg/mm^2$ of surface area coated. As specific (polymeric and non-polymeric) drug delivery vehicles and specific medical devices can release CTGF at differing rates, the above dosing parameters should be utilized in combination with the release rate of the drug from the spinal prosthesis such that a minimum concentration of 0.001 nM to 1000 μM of CTGF is delivered to the tissue. In one embodiment, CTGF is released from the surface of a spinal prosthesis or from a composition (e.g., a bulking agent) such that fibrosis in the tissue is promoted for a period ranging from several hours to several months. For example, CTGF may be released in effective concentrations for a period ranging from 1 hour–30 days. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

As described above, the device may additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) and/or a bone morphogenic protein (BMP) (e.g., BMP-2, BMP-3, BMP-4, BMP-5, BMP-6, or BMP-7 or an analogue or derivative thereof.

Bone morphogenic protein(s) (e.g., BMP-2, BMP-3, BMP-4, BMP-5, BMP-6, or BMP-7 or an analogue or derivative thereof) are to be used in formulations at concentrations that range from 0.001 μg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the bone morphogenic protein is released in effective concentrations for a period ranging from 1–180 days. The total dose for a single application is typically not to exceed 500 mg (range of 0.001 μg to 500 mg); preferred 1 μg to 250 mg. When used as a device coating, the dose is per unit area of 0.001 μg–1000 μg per mm$^2$; with a preferred dose of 0.01 μg/mm$^2$–200 μg/mm$^2$. Minimum concentration of $10^{-9}$–$10^{-4}$ M of bone morphogenic protein is to be maintained on the device surface.

Inflammatory cytokines are to be used in formulations at concentrations that range from 0.0001 μg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 μg to 100 mg); preferred 0.001 μg to 50 mg. When used as a device coating, the dose is per unit area of 0.0001 μg–500 μg per mm$^2$; with a preferred dose of 0.001 μg/mm$^2$–200 μg/mm$^2$. Minimum concentration of $10^{-10}$–$10^{-4}$ g/ml of inflammatory cytokine is to be maintained on the device surface.

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin D$_3$, diethylstibesterol, cyclosporine A, L-NAME, all-trans retinoic acid (ATRA), and analogues and derivatives thereof. Doses used are those concentrations which are demonstrated to stimulate cell proliferation (see Example 16). The proliferative agents are to be used in formulations at concentrations that range from 0.1 ng/ml to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 μg to 200 mg); preferred 0.001 μg to 100 mg. When used as a device coating, the dose is per unit area of 0.00001 μg–500 μg per mm$^2$; with a preferred dose of 0.0001 μg/mm$^2$–200 μg/mm$^2$. Minimum concentration of $10^{-11}$–$10^{-6}$ M of proliferative agent is to be maintained on the device surface.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention. Briefly then, some aspects of the present invention are: a method comprising introducing into an intervertebral disc space of a patient in need thereof, a therapeutically effective amount of a fibrosing agent or a composition comprising a fibrosing agent, where the fibrosing agent induces a fibrotic response at the intervertebral disc space of the patient, thereby providing the patient with a beneficial result. Optionally, any one or more of the following criteria may be used to describe this aspect of the invention: the beneficial result is the repair of a spinal disc; the beneficial result is fibrous ankylosis; the beneficial result is bony ankylosis; the agent promotes regeneration; the agent promotes angiogenesis; the agent promotes fibroblast migration; the agent promotes fibroblast proliferation; the agent promotes deposition of extracellular matrix (ECM); the agent promotes remodeling, i.e., the maturation and organization of fibrous tissue; the agent is an arterial vessel wall irritant; the fibrosing agent is or comprises silk; the fibrosing agent is or comprises silkworm silk; the fibrosing agent is or comprises spider silk; the fibrosing agent is or comprises recombinant silk; the fibrosing agent is or comprises raw silk; the fibrosing agent is or comprises hydrolyzed silk; the fibrosing agent is or comprises acid-treated silk; the fibrosing agent is or comprises acylated silk; the fibrosing agent is in the form of strands; the fibrosing agent is in the form of tufts; the fibrosing agent is in the form of microparticulates; the fibrosing agent is or comprises mineral particles; the fibrosing agent is or comprises talc; the fibrosing agent is or comprises chitosan; the fibrosing agent is or comprises polylysine; the fibrosing agent is or comprises fibronectin; the fibrosing agent is or comprises bleomycin; the fibrosing agent is or comprises CTGF; the fibrosing agent is in the form of a thread, or is in contact with a thread where, optionally, the thread is biodegradable (e.g., it comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester) or the thread is non-biodegradable (e.g., it comprises a material selected from the group consisting of polyester, polyurethane, silicone, polyethylene, polypropylene, polystyrene, polyacrylate, polymethacrylate, and silk), the thread is coated with a polymer, the thread is coated with a pharmaceutical agent that induces a fibrotic response in the patient, the thread is coated with a pharmaceutical agent that induces an osteogenic response in the patient; the composition further comprises an agent that promotes bone growth; the agent that promotes bone growth is a bone morphogenic protein or the agent that promotes bone growth is an osteogenic growth factor (e.g., transforming growth factor, platelet-derived growth factor, and fibroblast growth factor); the composition further comprises a pharmaceutical agent that induces sclerosis (a sclerosant, e.g., a sclerosant is selected from the group consisting of ethanol, dimethyl sulfoxide, sucrose, sodium chloride, dextrose, glycerin, minocycline, tetracycline, doxycycline, polidocanol, sodium tetradecyl sulfate, sodium morrhuate, and sotradecol, or the sclerosant may be a surfactant); the composition further comprises an inflammatory cytokine (e.g., an inflammatory cytokine selected from the group consisting of TGFβ, PDGF, VEGF, bFGF, TNFα, NGF, GM-CSF, IGF-a, IL-1, IL-1-β, IL-8, IL-6, and growth hormone); the composition further comprises an agent that stimulates cell proliferation (e.g., a cell proliferation agent selected from the group consisting of dexamethasone, isotretinoin (13-cis retinoic acid), 17-β-estradiol, estradiol, 1-a-25 dihydroxyvitamin D$_3$, diethylstibesterol, cyclosporine A, L-NAME, all-trans retinoic acid (ATRA), and analogues and derivatives thereof); the composition further comprises a bulking agent; the composition further comprises a sealant; the composition further comprises a polymeric carrier; the composition further comprises a resorbable ceramic; the composition further comprises a contrast agent; the composition further comprises a thread; the composition is in the form of a gel; the composition is in the form of a paste; the composition is in the form of a spray; the composition is in the form of an aerosol; the composition is in the form of a suspension; the composition is in the form of an emulsion or microemulsion; the composition is in the form of a microsphere; the composition is in the form of a microparticulate; the composition is in the form of a solid implant.

2. Joint Implants

The present invention provides for the combination of a fibrosis-inducing agent and a prosthetic joint implant. As used herein, the term "joint implants" refer to implants that are designed to replace joints that have been physically impaired or damaged. Examples of joint implants include, without limitation, orthopedic implants, orthopedic prostheses, modular implants, prosthetic joints, modular prostheses, joint prostheses, partial prostheses, hip implants, knee implants, shoulder implants and digit implants. Other types of orthopedic implants that may be used in conjunction with joint implants include, e.g., hardware, such as internal and external fixation devices, pins, plates and screws.

In one aspect, the orthopedic implant is an internal fixation implant. Internal fixation implants are medical devices that can be implanted (usually permanently) into a patient in minimally invasive orthopedic reconstructions and are often indicated for immobilization and stabilization of extremity fractures and unstable fractures.

Representative examples of internal fixation implants include intramedullary fixation devices such as intermedullary nails and plate and screw combinations; intramedullary rods, vertical transarticular pins for stabilization of severe ankle fractures, plates (e.g., plates made from titanium, stainless steel, and the like), plates with prongs to support subchondral bone, dorsal plates for volar applications, elastic plates, screws, clips, pins, staples, pegs, wires, sublaminar wires, and metal prostheses for holding vertebrae in place.

Internal fixation implants may be used in a variety of open reduction internal fixation (ORIF) procedures. Open reduction internal fixation is a method of surgically repairing a fractured bone that typically involves either the use of plates and screws or an intramedullary (IM) rod to align and stabilize fractures. For example, IM rods can be inserted into the bone marrow canal in the center of the long bones of the extremities (e.g., femur or tibia).

In another aspect, the orthopedic implant is a component (e.g., a pin, wire, stopper, or dowel) of an external fixation device or an implanted portion (i.e., a portion that is situated within the body of the patient) of an external fixation device (also referred to herein as an "external fixation implant"). External fixation devices are medical devices that can be used to immobilize bones to allow a fracture to heal. External fixation devices are used in a variety of minimally invasive orthopedic surgeries as an alternative to other types of fixation devices, such as casts and internal fixation devices.

Briefly, external fixation may be accomplished by placing pins or screws into the bone on both sides of the fracture. The pins are then secured together outside the skin with clamps and rods which can form an external frame.

An external fixation device typically includes a scaffold or frame that has attached to it wires, pins, and the like which is placed outside of an extremity, such as a limb. The device remains in place until healing has occurred, at which point it is then removed, leaving no foreign material in the extremity.

External fixation devices may take a variety of forms and may have monolateral, multiplanar or hybrid constructions. A monolateral fixation device includes a bar or rail with attached pins that transfix a bone (e.g., a femur). A multiplanar external fixation device can include rings or sections of rings, with attached pins and/or wires, which are used to secure fixation of a bone. A hybrid system can include a frame consisting of both rings (multiplanar) and bars (monolateral).

External fixation devices also may be classified by their function, for example, the device may be stationary or moving. Stationary devices may be used for alignment of the bony fragments (e.g., for acute stabilization of fractures) and remain in place from the time of application to removal. Moving fixation devices, in contrast, may be used in gradual reduction of acute extremity fractures. The configuration of a moving fixation device can change over time for gradual correction.

External fixation devices may be used to treat a variety of conditions. For example, an external fixation device may be used for the fixation of injuries such as joint fractures. External fixation can provide for acute or gradual fracture reduction. In particular, external fixation devices may be used in the treatment of juxta-articular fractures, open fractures, and fractures with bone loss, including, for example, fractures near joints such as distal radius, proximal tibial plateau, and distal tibial pilon fractures. Other applications of external fixation devices include reconstructive orthopedic procedures such as treatment of deformities, bone loss, contractures, treatment of non-unions (hypertrophic or atrophic), and limb length discrepancy.

A modular prosthesis is a prosthesis that has multiple (two or more) components, which can be assembled to form a unitary biomechanical structure. Various features of the components can be adjusted by the surgeon prior to implantation of the prosthesis so as to accommodate the needs of each patient. For example, a modular prosthesis can have component that can be independently adjusted (rotationally and axially) by the surgeon, or the length of a component may be changed. Modular prostheses can be used in a variety of surgical procedures. The modular prosthesis may be an adjustable long bone prosthesis that can be adjusted within the patient to account for discrepancies in the measurement of a long bone to be replaced. Prosthetic joints having modular components exist for replacement of the hip, knee, and ankle joints. Other representative examples of modular orthopedic prostheses include a modular femoral stem, modular shoulder prosthesis, and modular elbow prostheses.

The long-term cause of failure for many artificial joints is loosening occurring over time between the implant and the surrounding bone that anchors the implant in place. Inadequate bone and tissue growth may lead to unsuccessful acute incorporation of the implant or late loosening may occur with time. In the case of the hip, for example, up to 5% of patients can suffer from joint loosening by 10 years post implant. Symptoms include pain that can become debilitating and ultimately lead to repeat surgery and possible revision of the implant.

(i) Hip Implants

In artificial hip joints, the hip implant replaces the head of femur (i.e., ball) and/or the acetabulum (i.e., socket) of the joint. Typically the hip joint is replaced due to irreparable damage caused by non-inflammatory degenerative joint disease (e.g., osteoarthritis, post traumatic arthritis), inflammatory degenerative joint disease (e.g., rheumatoid arthritis, infectious arthritis), trauma (e.g., fracture of the pelvis or hip), congenital hip dysplasia, or joint dislocation and other fracture-induced damage to the femur and/or acetabulum. Hip implants typically include two or three component systems, which include the femoral stem or shank, the femoral neck, and the spherical ball which adapts to the acetabulum or prosthetic acetabular cup. The femoral stem, neck and ball, as well as the acetabular cup may be composed of metal (e.g., titanium, titanium alloy, cobalt-chromium or chromium-molybdenum) or polymer composite. To fix the hip implant to the existing femur of the host, the hip implant may be cemented into the bone using bone cement (e.g., methylmethacrylate) or the hip implant may be fixed using a cementless surface treatment (e.g., porous coating, such as hydroxyapatite porous coating, or spongy coating) whereby the hip implant allows bony growth from the femur to anchor it into place.

In one aspect, hip implants may be used to provide a full hip replacement. For example, the hip implant may be a three-modular designed total prosthesis with primary fixation, which may include a partially threaded elongated pin for insertion into the femoral body, which provides rotational adjustment between the body and the pin for various alignments and size combinations. See e.g., U.S. Pat. No. 4,938,773. The hip implant may be composed of a ball, neck and fixation element with a bearing element that is adapted to restrain dislocations of the ball and provide a means for selecting the orientation of the fixation element. See e.g., U.S. Pat. No. 6,042,611. The hip implant may be designed of two mutually articulating components composed of a cobalt chromium alloy with one having a low carbon content and the other component having a high carbon content. See e.g., U.S. Pat. No. 5,904,720.

In another aspect, hip implants may be adapted for cementing into place to ensure the implant is stabilized in the accurate position. For example, hip implants may be composed of cement spacers along the shaft which, upon implantation within the medullary canal of the femur, allows for optimal thickness of the cement mantle. See e.g., U.S. Pat. No. 5,314,489.

In another aspect, hip implants may be modular in which components may be adjusted to adapt to the host's shape or dimensions. For example, the hip implant may be a modular hip prosthesis composed of a plurality of removable, different size tubular sleeves that may be used to extend the femoral stem component or neck size which allows the implant to be custom fitted to a particular host. See e.g., U.S. Pat. No. 5,507,830.

In another aspect, hip implants may be designed to provide shock absorbency within the joint. For example, the hip implant may be composed of an elongate element that extends coaxially from the ball section that slidably extends into a chamber that contains a spring for shock absorbency. See e.g., U.S. Pat. No. 5,389,107. The hip implant may be a modular shock absorbent prosthesis designed to have adjustable femoral stem, neck and ball, as well as adjustable tension due to its unique coupling modular spring mechanism. See e.g., U.S. Pat. No. 6,336,941.

In another aspect, hip implants may be composed of a composite material to provide greater stiffness or retention within the femur. For example, the hip implant may be composed of a plurality of layers of fibers (e.g., composed of carbon, ceramic, metal or fiberglass) in a matrix (e.g., a polymeric matrix) where the fibers may be substantially unidirectional in each respective layer. See e.g., U.S. Pat. Nos. 5,522,904, 5,163,962, 5,064,439 and 4,892,552. The hip implant may have a stem composed of an inner metal core and an outer composite shell having fibers bonded with a thermoplastic resin and which the distal end is adapted to be inserted into a cavity formed in a bone. See e.g., U.S. Pat. No. 5,314,492. The hip implant may be composed of an expandable material that absorbs body fluid and expands within an opening of the bone of the host's body such that a portion of the implant is retained within the bone and a portion of the implant is outside the bone. See e.g., U.S. Pat. No. 6,361,565.

In another aspect, hip implants may be only partial hip replacements. For example, the hip implant may be a prosthetic acetabular cup assembly being composed of a bearing component for receiving a ball attached to a femur and a shell component for attachment to an acetabulum. See e.g., U.S. Pat. No. 5,049,158. Still other hip implants may be revision hip prostheses which have design features to augment the fixation of the implant into an area with bone-deficiency. For example, the hip implant may be a long stem hip joint prosthetic device having a long distal section of the femoral component which extends beyond the isthmus of the femur when implanted in the medullary canal and is designed with a specially curved distal section. See e.g., U.S. Pat. No. 4,871,369. Additional descriptions of hip implants are provided in U.S. Pat. Nos. 5,755,810; 5,336,265; 5,286,260; 5,019,108; 4,986,834; 4,808,186; and 4,670,015.

Hip implants, which may be combined with one or more drugs according to the present invention, include numerous commercially available products, for example, the S—ROM Total Hip System and the AML Total Hip System from DePuy Orthopaedics, Inc. (Warsaw, Ind.).

In one aspect, the present invention provides hip prostheses that include a fibrosis-inducing agent or a composition that includes a fibrosis-inducing agent to promote scarring to provide fixation of the device into the surrounding bone. In one aspect, the hip prosthesis is coated with a fibrosing agent or a composition that includes the fibrosing agent. In another aspect, the fibrosing agent may be incorporated into a glue or cement that holds the prosthesis in place. In another aspect, the hip prosthesis is covered (all or in part) with a silk mesh or lattice to encourage scarring and anchoring into the surrounding bone. For example, a silk mesh or lattice can be coated onto all or a portion of the surface of the implant stem to encourage scarring and anchoring into the surrounding bone.

Numerous polymeric and non-polymeric carrier systems described previously can be used in the practice of this embodiment. These compositions can further include one or more fibrosis-inducing agents to promote the formation of granulation tissue. Methods for incorporating fibrosing compositions onto or into the orthopedic implants include: (a) directly affixing to the device a fibrosing composition (e.g., by either a spraying process or dipping process as described above, with or without a carrier); (b) directly incorporating into the device a fibrosing composition (e.g., by either a spraying process or dipping process as described above, with or without a carrier); (c) by coating the device with a substance such as a hydrogel which can in turn absorb the fibrosing composition; (d) by interweaving fibrosing composition coated thread (or the polymer itself formed into a thread) into the device structure; (e) by inserting the device into a sleeve or mesh which is comprised of or coated with a fibrosing composition; (f) constructing the device itself or a portion of the device with a fibrosing composition; and/or (g) by covalently binding the fibrosing agent directly to the device surface or to a linker (small molecule or polymer) that is coated or attached to the device surface. For these devices, the coating process can be performed in such a manner as to a) coat the surfaces of the device that is in contact with the bone, b) coat the surfaces of the device that are not in contact with the bone or c) coat all or parts of both the bone-contacting and non-bone contacting surface of the device.

In addition to coating the device with the fibrosing composition, the fibrosing agent can be mixed with the materials that are used to make the device such that the fibrosing agent is incorporated into the final device.

It should be apparent to one of skill in the art that potentially any adhesion or fibrosis-inducing agents described previously may be utilized alone, or in combination, in the practice of this embodiment. Exemplary fibrosing agents for use in hip prostheses implants include talc, silk, wool, chitosan, polylysine, fibronectin, bleomycin, and CTGF, as well as analogues and derivatives of the aforementioned.

As hip prostheses are made in a variety of configurations and sizes, the exact dose administered can vary with device size, surface area and design. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the hip prostheses, the exemplary fibrosing agents, used alone or in combination, should be administered under the following dosing guidelines:

Utilizing talc as an exemplary fibrosis-inducing agent, whether it is applied using a polymer coating, incorporated into the polymers which make up the device or implant, or applied without a polymeric carrier, the total dose of talc delivered from a hip prosthesis, or coated onto the surface of a hip prosthesis, should not exceed 100 mg (range of 1 µg to 100 mg). In one embodiment, the total amount of talc released from the prosthesis should be in the range of 10 µg to 50 mg. The dose per unit area of the device (i.e., the dosage of talc as a function of the surface area of the portion of the device to which drug is applied and/or incorporated) should fall within the range of 0.05 µg–10 µg per $mm^2$ of surface area coated. In another embodiment, talc should be applied to a hip prosthesis surface at a dose of 0.05 $µg/mm^2$–10 $µg/mm^2$ of surface area coated. In one embodiment, talc is released from the surface of a hip prosthesis such that fibrosis in the tissue is promoted for a period ranging from several hours to several months. For example, talc may be released in effective concentrations for a period ranging from 1 hour–30 days. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymer coating, incorporated into the polymers which make up the device or implant, or applied without a polymeric carrier, the total dose of silk delivered from a hip prosthesis, or coated onto the surface of a hip prosthesis, should not exceed 100 mg (range of 1 µg to 100 mg). In one embodiment, the total amount of silk released from the prosthesis should be in the range of 10 µg to 50 mg. The dose per unit area of the device (i.e., the dosage of silk as a function of the surface area of the portion of the device to which drug is applied and/or incorporated) should fall within the range of 0.05 µg–10 µg per $mm^2$ of surface area coated. In another embodiment, silk should be applied to a hip prosthesis surface at a dose of 0.05 $µg/mm^2$–10 $µg/mm^2$ of surface area coated. As specific (polymeric and non-polymeric) drug delivery vehicles and specific medical devices can release silk at differing rates, the above dosing parameters should be utilized in combination with the release rate of the drug from the hip prosthesis such that a minimum concentration of 0.01 nM to 1000 µM of silk is delivered to the tissue. In one embodiment, silk is released from the surface of a hip prosthesis such that fibrosis in the tissue is promoted for a period ranging from several hours to several months. For example, silk may be released in effective concentrations for a period ranging from 1 hour–30 days. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymer coating, incorporated into the polymers which make up the device or implant, or applied without a polymeric carrier, the total dose of chitosan delivered from a hip prosthesis, or coated onto the surface of a hip prosthesis, should not exceed 100 mg (range of 1 µg to 100 mg). In one embodiment, the total amount of chitosan released from the prosthesis should be in the range of 10 µg to 50 mg. The dose per unit area of the device (i.e., the dosage of chitosan as a function of the surface area of the portion of the device to which drug is applied and/or incorporated) should fall within the range of 0.05 µg–10 µg per $mm^2$ of surface area coated. In another embodiment, chitosan should be applied to a hip prosthesis surface at a dose of 0.05 $µg/mm^2$–10 $µg/mm^2$ of surface area coated. As specific (polymeric and non-polymeric) drug delivery vehicles and specific medical devices can release chitosan at differing rates, the above dosing parameters should be utilized in combination with the release rate of the drug from the hip prosthesis such that a minimum concentration of 0.01 nM to 1000 µM of chitosan is delivered to the tissue. In one embodiment, chitosan is released from the surface of a hip prosthesis such that fibrosis in the tissue is promoted for a period ranging from several hours to several months. For example, chitosan may be released in effective concentrations for a period ranging from 1 hour–30 days. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as an exemplary fibrosis-inducing agent, whether it is applied using a polymer coating, incorporated into the polymers which make up the device or implant, or applied without a polymeric carrier, the total dose of polylysine delivered from a hip prosthesis, or coated onto the surface of a hip prosthesis, should not exceed 100 mg (range of 1 µg to 100 mg). In one embodiment, the total amount of polylysine released from the prosthesis should be in the range of 10 µg to 50 mg. The dose per unit area of the device (i.e., the dosage of polylysine as a function of the surface area of the portion of the device to which drug is applied and/or incorporated) should fall within the range of 0.05 μg–10 μg per mm$^2$ of surface area coated. In another embodiment, polylysine should be applied to a hip prosthesis surface at a dose of 0.05 μg/mm$^2$–10 μg/mm$^2$ of surface area coated. As specific (polymeric and non-polymeric) drug delivery vehicles and specific medical devices can release polylysine at differing rates, the above dosing parameters should be utilized in combination with the release rate of the drug from the hip prosthesis such that a minimum concentration of 0.01 nM to 1000 μM of polylysine is delivered to the tissue. In one embodiment, polylysine is released from the surface of a hip prosthesis such that fibrosis in the tissue is promoted for a period ranging from several hours to several months. For example, polylysine may be released in effective concentrations for a period ranging from 1 hour–30 days. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymer coating, incorporated into the polymers which make up the device or implant, or applied without a polymeric carrier, the total dose of fibronectin delivered from a hip prosthesis, or coated onto the surface of a hip prosthesis, should not exceed 100 mg (range of 1 μg to 100 mg). In one embodiment, the total amount of fibronectin released from the prosthesis should be in the range of 10 μg to 50 mg. The dose per unit area of the device (i.e., the dosage of fibronectin as a function of the surface area of the portion of the device to which drug is applied and/or incorporated) should fall within the range of 0.05 μg–10 μg per mm$^2$ of surface area coated. In another embodiment, fibronectin should be applied to a hip prosthesis surface at a dose of 0.05 μg/mm$^2$–10 μg/mm$^2$ of surface area coated. As specific (polymeric and non-polymeric) drug delivery vehicles and specific medical devices can release fibronectin at differing rates, the above dosing parameters should be utilized in combination with the release rate of the drug from the hip prosthesis such that a minimum concentration of 0.01 nM to 1000 μM of fibronectin is delivered to the tissue. In one embodiment, fibronectin is released from the surface of a hip prosthesis such that fibrosis in the tissue is promoted for a period ranging from several hours to several months. For example, fibronectin may be released in effective concentrations for a period ranging from 1 hour–30 days. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, whether it is applied using a polymer coating, incorporated into the polymers which make up the device or implant, or applied without a polymeric carrier, the total dose of bleomycin delivered from a hip prosthesis, or coated onto the surface of a hip prosthesis, should not exceed 100 mg (range of 0.01 μg to 100 mg). In one embodiment, the total amount of bleomycin released from the prosthesis should be in the range of 0.10 μg to 50 mg. The dose per unit area of the device (i.e., the dosage of bleomycin as a function of the surface area of the portion of the device to which drug is applied and/or incorporated) should fall within the range of 0.005 μg–10 μg per mm$^2$ of surface area coated. In another embodiment, bleomycin should be applied to a hip prosthesis surface at a dose of 0.005 μg/mm$^2$–10 μg/mm$^2$ of surface area coated. As specific (polymeric and non-polymeric) drug delivery vehicles and specific medical devices can release bleomycin at differing rates, the above dosing parameters should be utilized in combination with the release rate of the drug from the hip prosthesis such that a minimum concentration of 0.001 nM to 1000 μM of bleomycin is delivered to the tissue. In one embodiment, bleomycin is released from the surface of a hip prosthesis such that fibrosis in the tissue is promoted for a period ranging from several hours to several months. For example, bleomycin may be released in effective concentrations for a period ranging from 1 hour–30 days. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as an exemplary fibrosis-inducing agent, whether it is applied using a polymer coating, incorporated into the polymers which make up the device or implant, or applied without a polymeric carrier, the total dose of CTGF delivered from a hip prosthesis, or coated onto the surface of a hip prosthesis, should not exceed 100 mg (range of 0.01 μg to 100 mg). In one embodiment, the total amount of CTGF released from the prosthesis should be in the range of 0.10 μg to 50 mg. The dose per unit area of the device (i.e., the dosage of CTGF as a function of the surface area of the portion of the device to which drug is applied and/or incorporated) should fall within the range of 0.005 μg–10 μg per mm$^2$ of surface area coated. In another embodiment, CTGF should be applied to a hip prosthesis surface at a dose of 0.005 μg/mm$^2$–10 μg/mm$^2$ of surface area coated. As specific (polymeric and non-polymeric) drug delivery vehicles and specific medical devices can release CTGF at differing rates, the above dosing parameters should be utilized in combination with the release rate of the drug from the hip prosthesis such that a minimum concentration of 0.001 nM to 1000 μM of CTGF is delivered to the tissue. In one embodiment, CTGF is released from the surface of a hip prosthesis such that fibrosis in the tissue is promoted for a period ranging from several hours to several months. For example, CTGF may be released in effective concentrations for a period ranging from 1 hour–30 days. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Optionally, the device may additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) and/or a bone morphogenic protein (BMP) (e.g., BMP-2, BMP-3, BMP-4, BMP-5, BMP-6, or BMP-7 or an analogue or derivative thereof).

Bone morphogenic protein(s) (e.g., BMP-2, BMP-3, BMP-4, BMP-5, BMP-6, or BMP-7 or an analogue or derivative thereof) are to be used in formulations at concentrations that range from 0.001 μg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the bone morphogenic protein is released in effective concentrations for a period ranging from 1–180 days. The total dose for a single application is typically not to exceed 500 mg (range of 0.001 μg to 500 mg); preferred 1 μg to 250 mg. When used as a device coating, the dose is per unit area of 0.001 μg–1000 μg per; with a preferred dose of 0.01 μg/mm$^2$–200 μg/mm$^2$. Minimum concentration of $10^{-9}$–$10^{-4}$ M of bone morphogenic protein is to be maintained on the device surface.

Inflammatory cytokines are to be used in formulations at concentrations that range from 0.0001 μg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 μg to 100 mg); preferred 0.001 μg to 50 mg. When used as a device coating, the dose is per unit area of 0.0001 μg–500 μg per mm$^2$; with a preferred dose of 0.001 μg/mm$^2$–200 μg/mm$^2$. Minimum concentration of $10^{-10}$–$10^{-4}$ g/ml of inflammatory cytokine is to be maintained on the device surface.

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin D$_3$, diethylstibesterol, cyclosporine A, L-NAME, all-trans retinoic acid (ATRA), and analogues and derivatives thereof. Doses used are those concentrations which are demonstrated to stimulate cell proliferation (see Example 16). The proliferative agents are to be used in formulations at concentrations that range from 0.1 ng/ml to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 μg to 200 mg); preferred 0.001 μg to 100 mg. When used as a device coating, the dose is per unit area of 0.00001 μg–500 μg per mm$^2$; with a preferred dose of 0.0001 μg/mm$^2$–200 μg/mm$^2$. Minimum concentration of $10^{-11}$–$10^{-6}$ M of proliferative agent is to be maintained on the device surface.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

(ii) Knee Implants

In one aspect, the present invention provides knee implants that induce fibrosis or adhesion of the implant into the surrounding tissue. Knee replacement surgery is generally indicated for patients with severe knee pain and disability caused by damage to their articular cartilage as a result of rheumatoid arthritis, osteoarthritis or trauma. It is highly successful procedure in relieving pain and restoring joint function. Knee arthroplasty procedures are broadly categorized as primary or revision and are either unicompartmental (partial) or total. Knee prostheses (referred to herein as knee implants) can be used to replace all or a portion of the knee joint. In a total knee arthroplasty (TKA), the diseased cartilage surfaces of the thighbone (femur), the shinbone (tibia) and the kneecap (patella) are replaced by prostheses made of metal alloys (e.g., titanium- or cobalt/chromium-based alloys) and high-grade plastics and polymeric materials (e.g., ultrahigh-density polyethylene). Most of the other structures of the knee, such as the connecting ligaments, remain intact. Up to three bone surfaces may be replaced during a TKA: the distal ends (condyles) of the femur, the proximal surface of the tibia and the posterior surface of the patella. Components are designed so that metal always articulates against plastic, which provides smooth movement and results in minimal wear.

Knee joint implants typically have three components (i.e., a femoral, a tibial, and a patellar component). The metal femoral component curves around the end of the thighbone and has an interior groove so the patella can move up and down smoothly against the bone as the knee bends and straightens. Usually, one large piece is used to resurface the end of the bone. If only one condyle of the femur is damaged, a smaller piece may be used (unicompartmental knee replacement) to resurface just that part of the bone. Some designs (e.g., posterior stabilized designs) have an internal post with a circular-shaped device (cam) that works with a corresponding tibial component to help prevent the femur from sliding forward too far on the tibia when the knee is bent. The tibial component is a flat metal platform with a polyethylene cushion. The cushion may be part of the platform (fixed) or separate (mobile) with either a flat surface (PCL-retaining) or a raised, sloping surface (PCL-substituting). The patellar component is a dome-shaped piece of polyethylene that duplicates the shape of the kneecap anchored to a flat metal plate. Once the knee prosthesis is implanted and aligned, the knee replacement is fixed in place by cement, using a cementless procedure, or via a hybrid fixation procedure.

A variety of knee prostheses have been described. For example, knee prostheses have been described in U.S. Pat. Nos. 6,443,991; 6,402,786; 6,068,658; 6,558,427; 6,554,866; 6,447,549; 6,419,707; 6,143,034; 6,120,546; and 6,074,424. Knee implants suitable for combining with one or more fibrosis-inducing agents according to the present invention, include numerous commercially available products. These include, for example, the NEXGEN LEGACY Knee Posterior Stabilized (LPS) and NEXGEN LEGACY LPS Femoral Component from Zimmer. Other examples of knee implants suitable for the delivery of fibrosis-inducing agents include Stryker Howmedica Osteonics DURACON Total Knee System, SCORPIO Knee System, and SCORPIO Cruciate Retaining Single Axis Knee; implants available from DePuy Orthopaedics such as the LCS Total Knee System, P.F.C. Sigma RP Platform Knee System, Keane Uni-Compartmental Knee System, P.F.C. Sigma Uni-Compartmental Knee System, AMK Total Knee System, P.F.C. Sigma Knee System (Cruciate-Retaining), the P.F.C. Sigma Knee System (Cruciate-Substituting), the Coordinate Revision Knee System, the P.F.C. Sigma Knee System TC3 Revision implant, and the S-ROM Noiles Rotating Hinge; knee implants from Smith & Nephew Orthopaedics such as the GENESID I and GENESIS II Total Knee Systems. Other manufacturers of primary and revision knee joint implants suitable for use in this invention include Biomet, Inc. (Warsaw, Ind.), Sulzer Orthopedics, Inc. (Austin, Tex.), Wright Medical Technologies, Exactech, Inc., Encore Orthopedics Corporation (Henderson, Nev.), Implex now known as Zimmer, Inc., StelKast Company (McMurray, Pa.), Hayes Medical, Inc. (El Dorado Hills, Calif.), and Link Orthopedics (PineBrook, N.J.).

In one aspect, the present invention provides knee prostheses that include a fibrosis-inducing agent or a composition that includes a fibrosis-inducing agent to promote scarring and fixation of the device into the surrounding bone. In one aspect, the knee prosthesis is coated with a fibrosing agent or a composition that includes the fibrosing agent. In another aspect, the fibrosing agent may be incorporated into the glue or cement that holds the prosthesis in place. In another aspect, the knee prosthesis is covered (all or in part) with a silk mesh or lattice to encourage scarring and anchoring into the surrounding bone. For example, a silk mesh or lattice can be coated onto all or a portion of the surface of the implant stem to encourage scarring and anchoring into the surrounding bone.

Numerous polymeric and non-polymeric carrier systems described above can be used in the practice of this embodiment. These compositions can further include one or more fibrosis-inducing agents to promote the formation of granulation tissue. Methods for incorporating fibrosing compositions onto or into the orthopedic implants include: (a) directly affixing to the device a fibrosing composition (e.g., by either a spraying process or dipping process as described above, with or without a carrier); (b) directly incorporating into the device a fibrosing composition (e.g., by either a spraying process or dipping process as described above, with or without a carrier); (c) by coating the device with a substance such as a hydrogel which can in turn absorb the fibrosing composition; (d) by interweaving fibrosing composition coated thread (or the polymer itself formed into a thread) into the device structure; (e) by inserting the device into a sleeve or mesh which is comprised of or coated with a fibrosing composition; (f) constructing the device itself or a portion of the device with a fibrosing composition, or (g) by covalently binding the fibrosing agent directly to the device surface or to a linker (small molecule or polymer) that is coated or attached to the device surface. For these devices, the coating process can be performed in such a manner as to a) coat the surfaces of the device that is in contact with the bone, b) coat the surfaces of the device that are not in contact with the bone or c) coat all or parts of both the bone-contacting and non-bone contacting surface of the device.

In addition to coating the device with the fibrosing composition, the fibrosing agent can be mixed with the materials that are used to make the device such that the fibrosing agent is incorporated into the final device.

It should be apparent to one of skill in the art that potentially any adhesion or fibrosis-inducing agents described above may be utilized alone, or in combination, in the practice of this embodiment. Exemplary fibrosing agents for use in knee prostheses include talc, silk, wool, chitosan, polylysine, fibronectin, bleomycin, and CTGF, as well as analogues and derivatives of the aforementioned.

As knee prostheses are made in a variety of configurations and sizes, the exact dose administered can vary with device size, surface area and design. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the knee prostheses, the exemplary fibrosing agents, used alone or in combination, should be administered under the following dosing guidelines:

Utilizing talc as an exemplary fibrosis-inducing agent, whether it is applied using a polymer coating, incorporated into the polymers which make up the device or implant, or applied without a polymeric carrier, the total dose of talc delivered from a knee prosthesis, or coated onto the surface of a knee prosthesis, should not exceed 100 mg (range of 1 µg to 100 mg). In one embodiment, the total amount of talc released from the prosthesis should be in the range of 10 µg to 50 mg. The dose per unit area of the device (i.e., the dosage of talc as a function of the surface area of the portion of the device to which drug is applied and/or incorporated) should fall within the range of 0.05 µg–10 µg per $mm^2$ of surface area coated. In another embodiment, talc should be applied to a knee prosthesis surface at a dose of 0.05 $\mu g/mm^2$–10 $\mu g/mm^2$ of surface area coated. In one embodiment, talc is released from the surface of a knee prosthesis such that fibrosis in the tissue is promoted for a period ranging from several hours to several months. For example, talc may be released in effective concentrations for a period ranging from 1 hour–30 days. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymer coating, incorporated into the polymers which make up the device or implant, or applied without a polymeric carrier, the total dose of silk delivered from a knee prosthesis, or coated onto the surface of a knee prosthesis, should not exceed 100 mg (range of 1 µg to 100 mg). In one embodiment, the total amount of silk released from the prosthesis should be in the range of 10 µg to 50 mg. The dose per unit area of the device (i.e., the dosage of silk as a function of the surface area of the portion of the device to which drug is applied and/or incorporated) should fall within the range of 0.05 µg–10 µg per $mm^2$ of surface area coated. In another embodiment, silk should be applied to a knee prosthesis surface at a dose of 0.05 $\mu g/mm^2$–10 $\mu g/mm^2$ of surface area coated. As specific (polymeric and non-polymeric) drug delivery vehicles and specific medical devices can release silk at differing rates, the above dosing parameters should be utilized in combination with the release rate of the drug from the knee prosthesis such that a minimum concentration of 0.01 nM to 1000 µM of silk is delivered to the tissue. In one embodiment, silk is released from the surface of a knee prosthesis such that fibrosis in the tissue is promoted for a period ranging from several hours to several months. For example, silk may be released in effective concentrations for a period ranging from 1 hour–30 days. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymer coating, incorporated into the polymers which make up the device or implant, or applied without a polymeric carrier, the total dose of chitosan delivered from a knee prosthesis, or coated onto the surface of a knee prosthesis, should not exceed 100 mg (range of 1 µg to 100 mg). In one embodiment, the total amount of chitosan released from the prosthesis should be in the range of 10 µg to 50 mg. The dose per unit area of the device (i.e., the dosage of chitosan as a function of the surface area of the portion of the device to which drug is applied and/or incorporated) should fall within the range of 0.05 µg–10 µg per mm$^2$ of surface area coated. In another embodiment, chitosan should be applied to a knee prosthesis surface at a dose of 0.05 µg/mm$^2$–10 µg/mm$^2$ of surface area coated. As specific (polymeric and non-polymeric) drug delivery vehicles and specific medical devices can release chitosan at differing rates, the above dosing parameters should be utilized in combination with the release rate of the drug from the knee prosthesis such that a minimum concentration of 0.01 nM to 1000 µM of chitosan is delivered to the tissue. In one embodiment, chitosan is released from the surface of a knee prosthesis (e.g., a bulking agent) such that fibrosis in the tissue is promoted for a period ranging from several hours to several months. For example, chitosan may be released in effective concentrations for a period ranging from 1 hour–30 days. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as a exemplary fibrosis-inducing agent, whether it is applied using a polymer coating, incorporated into the polymers which make up the device or implant, or applied without a polymeric carrier, the total dose of polylysine delivered from a knee prosthesis, or coated onto the surface of a knee prosthesis, should not exceed 100 mg (range of 1 µg to 100 mg). In one embodiment, the total amount of polylysine released from the prosthesis should be in the range of 10 µg to 50 mg. The dose per unit area of the device (i.e., the dosage of polylysine as a function of the surface area of the portion of the device to which drug is applied and/or incorporated) should fall within the range of 0.05 µg–10 µg per mm$^2$ of surface area coated. In another embodiment, polylysine should be applied to a knee prosthesis surface at a dose of 0.05 µg/mm$^2$–10 µg/mm$^2$ of surface area coated. As specific (polymeric and non-polymeric) drug delivery vehicles and specific medical devices can release polylysine at differing rates, the above dosing parameters should be utilized in combination with the release rate of the drug from the knee prosthesis such that a minimum concentration of 0.01 nM to 1000 µM of polylysine is delivered to the tissue. In one embodiment, polylysine is released from the surface of a knee prosthesis such that fibrosis in the tissue is promoted for a period ranging from several hours to several months. For example, polylysine may be released in effective concentrations for a period ranging from 1 hour–30 days. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymer coating, incorporated into the polymers which make up the device or implant, or applied without a polymeric carrier, the total dose of fibronectin delivered from a knee prosthesis, or coated onto the surface of a knee prosthesis, should not exceed 100 mg (range of 1 µg to 100 mg). In one embodiment, the total amount of fibronectin released from the prosthesis should be in the range of 10 µg to 50 mg. The dose per unit area of the device (i.e., the dosage of fibronectin as a function of the surface area of the portion of the device to which drug is applied and/or incorporated) should fall within the range of 0.05 µg–10 µg per mm$^2$ of surface area coated. In another embodiment, fibronectin should be applied to a knee prosthesis surface at a dose of 0.05 µg/mm$^2$–10 µg/mm$^2$ of surface area coated. As specific (polymeric and non-polymeric) drug delivery vehicles and specific medical devices can release fibronectin at differing rates, the above dosing parameters should be utilized in combination with the release rate of the drug from the knee prosthesis such that a minimum concentration of 0.01 nM to 1000 µM of fibronectin is delivered to the tissue. In one embodiment, fibronectin is released from the surface of a knee prosthesis such that fibrosis in the tissue is promoted for a period ranging from several hours to several months. For example, fibronectin may be released in effective concentrations for a period ranging from 1 hour–30 days. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, whether it is applied using a polymer coating, incorporated into the polymers which make up the device or implant, or applied without a polymeric carrier, the total dose of bleomycin delivered from a knee prosthesis, or coated onto the surface of a knee prosthesis, should not exceed 100 mg (range of 0.01 µg to 100 mg). In one embodiment, the total amount of bleomycin released from the prosthesis should be in the range of 0.10 µg to 50 mg. The dose per unit area of the device (i.e., the dosage of bleomycin as a function of the surface area of the portion of the device to which drug is applied and/or incorporated) should fall within the range of 0.005 µg–10 µg per mm$^2$ of surface area coated. In another embodiment, bleomycin should be applied to a knee prosthesis surface at a dose of 0.005 µg/mm$^2$–10 µg/mm$^2$ of surface area coated. As specific (polymeric and non-polymeric) drug delivery vehicles and specific medical devices can release bleomycin at differing rates, the above dosing parameters should be utilized in combination with the release rate of the drug from the knee prosthesis such that a minimum concentration of 0.001 nM to 1000 µM of bleomycin is delivered to the tissue. In one embodiment, bleomycin is released from the surface of a knee prosthesis such that fibrosis in the tissue is promoted for a period ranging from several hours to several months. For example, bleomycin may be released in effective concentrations for a period ranging from 1 hour–30 days. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as an exemplary fibrosis-inducing agent, whether it is applied using a polymer coating, incorporated into the polymers which make up the device or implant, or applied without a polymeric carrier, the total dose of CTGF delivered from a knee prosthesis, or coated onto the surface of a knee prosthesis, should not exceed 100 mg (range of 0.01 µg to 100 mg). In one embodiment, the total amount of CTGF released from the prosthesis should be in the range of 0.10 µg to 50 mg. The dose per unit area of the device (i.e., the dosage of CTGF as a function of the surface area of the portion of the device to which drug is applied and/or incorporated) should fall within the range of 0.005 µg–10 µg per mm$^2$ of surface area coated. In another embodiment, CTGF should be applied to a knee prosthesis surface at a dose of 0.005 µg/mm$^2$–10 µg/mm$^2$ of surface area coated. As specific (polymeric and non-polymeric) drug delivery vehicles and specific medical devices can release CTGF at differing rates, the above dosing parameters should be utilized in combination with the release rate of the drug from the knee prosthesis such that a minimum concentration of 0.001 nM to 1000 µM of CTGF is delivered to the tissue. In one embodiment, CTGF is released from the surface of a knee prosthesis such that fibrosis in the tissue is promoted for a period ranging from several hours to several months. For example, CTGF may be released in effective concentrations for a period ranging from 1 hour–30 days. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Optionally, the device may additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) and/or a bone morphogenic protein (BMP) (e.g., BMP-2, BMP-3, BMP-4, BMP-5, BMP-6, or BMP-7 or an analogue or derivative thereof).

Bone morphogenic protein(s) (e.g., BMP-2, BMP-3, BMP-4, BMP-5, BMP-6, or BMP-7 or an analogue or derivative thereof) are to be used in formulations at concentrations that range from 0.001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the bone morphogenic protein is released in effective concentrations for a period ranging from 1–180 days. The total dose for a single application is typically not to exceed 500 mg (range of 0.001 µg to 500 mg); preferred 1 µg to 250 mg. When used as a device coating, the dose is per unit area of 0.001 µg–1000 µg per mm$^2$; with a preferred dose of 0.01 µg/mm$^2$–200 µg/mm$^2$. Minimum concentration of $10^{-9}$–$10^{-4}$ M of bone morphogenic protein is to be maintained on the device surface.

Inflammatory cytokines are to be used in formulations at concentrations that range from 0.0001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 µg to 100 mg); preferred 0.001 µg to 50 mg. When used as a device coating, the dose is per unit area of 0.0001 µg–500 µg per mm$^2$; with a preferred dose of 0.001 µg/mm$^2$–200 µg/mm$^2$. Minimum concentration of $10^{-10}$–$10^{-4}$ g/ml of inflammatory cytokine is to be maintained on the device surface.

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin D$_3$, diethylstibesterol, cyclosporine A, L-NAME, all-trans retinoic acid (ATRA), and analogues and derivatives thereof. Doses used are those concentrations which are demonstrated to stimulate cell proliferation (see, e.g., Example 16). The proliferative agents are to be used in formulations at concentrations that range from 0.1 ng/ml to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 µg to 200 mg); preferred 0.001 µg to 100 mg. When used as a device coating, the dose is per unit area of 0.00001 µg–500 µg per mm$^2$; with a preferred dose of 0.0001 µg/mm$^2$–200 µg/mm$^2$. Minimum concentration of $10^{-11}$–$10^{-6}$ M of proliferative agent is to be maintained on the device surface.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

(iii) Shoulder Implants

Shoulder joint reconstruction is typically indicated to alleviate pain and restore lost function arising from medical conditions such as fractures, osteoarthritis, rheumatoid arthritis, avascular necrosis, and tumor growth (benign or malignant). Hemiarthroplasties (partial shoulder implants), which involve implanting only the humeral components, typically are performed on patients suffering from shoulder fractures and avascular necrosis. Total shoulder replacement (implanting of both the humeral and glenoid components) is more common in patients suffering from osteoarthritis and rheumatoid arthritis. Joint replacement in conjunction with excision of a tumor is fairly rare, occurring in less than one percent of patients who receive shoulder replacement surgeries. In a cancer patient, removal of bone may necessitate partial or total replacement of the joint.

Numerous shoulder prostheses have been described (see, e.g., U.S. Pat. Nos. 6,494,913; 6,193,758; 6,168,628; 6,102,953; 6,045,582; 5,961,555; 5,593,448; 5,549,682; and 5,108,440). Shoulder implants suitable for combining with one or more fibrosis-inducing agents according to the present invention, include numerous commercially available products. These include shoulder implants manufactured by DePuy Orthopaedics (e.g., GLOBAL TX Total Shoulder System, GLOBAL Shoulder Eccentric Head, GLOBAL Total Shoulder System), Biomet (e.g., Bio-Modular, Bi-Angular/Bi-Polar, Proximal Humeral Replacement, and Integrated Shoulder System), Stryker Howmedica Osteonics (e.g., SOLAR Shoulder Bipolar Heads, Humeral Heads, Humeral Components, and Glenoid Components), Sulzer (e.g., Anatomical Shoulder and Select Shoulder), Zimmer (Bigliani/Flatow Shoulder), and Smith & Nephew Orthopaedics (e.g., COFIELD 2 Total Shoulder System, NEER II Total Shoulder System, and Modular Shoulder System).

In one aspect, the present invention provides shoulder prostheses that include a fibrosis-inducing agent or a composition that includes a fibrosis-inducing agent to promote scarring and fixation of the device into the surrounding bone. In one aspect, the shoulder prosthesis is coated with a fibrosing agent or a composition that includes the fibrosing agent. In another aspect, the fibrosing agent may be incorporated into the glue or cement that holds the prosthesis in place. In another aspect, the shoulder prosthesis is covered (all or in part) with a silk mesh or lattice to encourage scarring and anchoring into the surrounding bone. For example, a silk mesh or lattice can be coated onto all or a portion of the surface of the implant stem to encourage scarring and anchoring into the surrounding bone.

Numerous polymeric and non-polymeric carrier systems described above can be used in the practice of this embodiment. These compositions can further include one or more fibrosis-inducing agents to promote the formation of granulation tissue. Methods for incorporating fibrosing compositions onto or into the orthopedic implants include: (a) directly affixing to the device a fibrosing composition (e.g., by either a spraying process or dipping process as described above, with or without a carrier); (b) directly incorporating into the device a fibrosing composition (e.g., by either a spraying process or dipping process as described above, with or without a carrier); (c) by coating the device with a substance such as a hydrogel which can in turn absorb the fibrosing composition; (d) by interweaving fibrosing composition coated thread (or the polymer itself formed into a thread) into the device structure; (e) by inserting the device into a sleeve or mesh which is comprised of or coated with a fibrosing composition; (f) constructing the device itself or a portion of the device with a fibrosing composition; or (g) by covalently binding the fibrosing agent directly to the device surface or to a linker (small molecule or polymer) that is coated or attached to the device surface. For these devices, the coating process can be performed in such a manner as to a) coat the surfaces of the device that is in contact with the bone, b) coat the surfaces of the device that are not in contact with the bone or c) coat all or parts of both the bone-contacting and non-bone contacting surface of the device.

In addition to coating the device with the fibrosing composition, the fibrosing agent can be mixed with the materials that are used to make the device such that the fibrosing agent is incorporated into the final device.

It should be apparent to one of skill in the art that potentially any adhesion or fibrosis-inducing agents described above may be utilized alone, or in combination, in the practice of this embodiment. Exemplary fibrosing agents for use in shoulder prostheses include talc, silk, wool, chitosan, polylysine, fibronectin, bleomycin, and CTGF, as well as analogues and derivatives of the aforementioned.

As shoulder prostheses are made in a variety of configurations and sizes, the exact dose administered can vary with device size, surface area and design. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the shoulder prostheses, the exemplary fibrosing agents, used alone or in combination, should be administered under the following dosing guidelines:

Utilizing talc as an exemplary fibrosis-inducing agent, whether it is applied using a polymer coating, incorporated into the polymers which make up the device or implant, or applied without a polymeric carrier, the total dose of talc delivered from a shoulder prosthesis, or coated onto the surface of a shoulder prosthesis, should not exceed 100 mg (range of 1 µg to 100 mg). In one embodiment, the total amount of talc released from the prosthesis should be in the range of 10 µg to 50 mg. The dose per unit area of the device (i.e., the dosage of talc as a function of the surface area of the portion of the device to which drug is applied and/or incorporated) should fall within the range of 0.05 µg–10 µg per $mm^2$ of surface area coated. In another embodiment, talc should be applied to a shoulder prosthesis surface at a dose of 0.05 µg/$mm^2$–10 µg/$mm^2$ of surface area coated. In one embodiment, talc is released from the surface of a shoulder prosthesis such that fibrosis in the tissue is promoted for a period ranging from several hours to several months. For example, talc may be released in effective concentrations for a period ranging from 1 hour–30 days. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymer coating, incorporated into the polymers which make up the device or implant, or applied without a polymeric carrier, the total dose of silk delivered from a shoulder prosthesis, or coated onto the surface of a shoulder prosthesis, should not exceed 100 mg (range of 1 µg to 100 mg). In one embodiment, the total amount of silk released from the prosthesis should be in the range of 10 µg to 50 mg. The dose per unit area of the device (i.e., the dosage of silk as a function of the surface area of the portion of the device to which drug is applied and/or incorporated) should fall within the range of 0.05 μg–10 μg per mm$^2$ of surface area coated. In another embodiment, silk should be applied to a shoulder prosthesis surface at a dose of 0.05 μg/mm$^2$–10 μg/mm$^2$ of surface area coated. As specific (polymeric and non-polymeric) drug delivery vehicles and specific medical devices can release silk at differing rates, the above dosing parameters should be utilized in combination with the release rate of the drug from the shoulder prosthesis such that a minimum concentration of 0.01 nM to 1000 μM of silk is delivered to the tissue. In one embodiment, silk is released from the surface of a shoulder prosthesis such that fibrosis in the tissue is promoted for a period ranging from several hours to several months. For example, silk may be released in effective concentrations for a period ranging from 1 hour–30 days. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymer coating, incorporated into the polymers which make up the device or implant, or applied without a polymeric carrier, the total dose of chitosan delivered from a shoulder prosthesis, or coated onto the surface of a shoulder prosthesis, should not exceed 100 mg (range of 1 μg to 100 mg). In one embodiment, the total amount of chitosan released from the prosthesis should be in the range of 10 μg to 50 mg. The dose per unit area of the device (i.e., the dosage of chitosan as a function of the surface area of the portion of the device to which drug is applied and/or incorporated) should fall within the range of 0.05 μg–10 μg per mm$^2$ of surface area coated. In another embodiment, chitosan should be applied to a shoulder prosthesis surface at a dose of 0.05 μg/mm$^2$–10 μg/mm$^2$ of surface area coated. As specific (polymeric and non-polymeric) drug delivery vehicles and specific medical devices can release chitosan at differing rates, the above dosing parameters should be utilized in combination with the release rate of the drug from the shoulder prosthesis such that a minimum concentration of 0.01 nM to 1000 μM of chitosan is delivered to the tissue. In one embodiment, chitosan is released from the surface of a shoulder prosthesis such that fibrosis in the tissue is promoted for a period ranging from several hours to several months. For example, chitosan may be released in effective concentrations for a period ranging from 1 hour–30 days. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as an exemplary fibrosis-inducing agent, whether it is applied using a polymer coating, incorporated into the polymers which make up the device or implant, or applied without a polymeric carrier, the total dose of polylysine delivered from a shoulder prosthesis, or coated onto the surface of a shoulder prosthesis, should not exceed 100 mg (range of 1 μg to 100 mg). In one embodiment, the total amount of polylysine released from the prosthesis should be in the range of 10 μg to 50 mg. The dose per unit area of the device (i.e., the dosage of polylysine as a function of the surface area of the portion of the device to which drug is applied and/or incorporated) should fall within the range of 0.05 μg–10 μg per mm$^2$ of surface area coated. In another embodiment, polylysine should be applied to a shoulder prosthesis surface at a dose of 0.05 μg/mm$^2$–10 μg/mm$^2$ of surface area coated. As specific (polymeric and non-polymeric) drug delivery vehicles and specific medical devices can release polylysine at differing rates, the above dosing parameters should be utilized in combination with the release rate of the drug from the shoulder prosthesis such that a minimum concentration of 0.01 nM to 1000 μM of polylysine is delivered to the tissue. In one embodiment, polylysine is released from the surface of a shoulder prosthesis such that fibrosis in the tissue is promoted for a period ranging from several hours to several months. For example, polylysine may be released in effective concentrations for a period ranging from 1 hour–30 days. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymer coating, incorporated into the polymers which make up the device or implant, or applied without a polymeric carrier, the total dose of fibronectin delivered from a shoulder prosthesis, or coated onto the surface of a shoulder prosthesis, should not exceed 100 mg (range of 1 μg to 100 mg). In one embodiment, the total amount of fibronectin released from the prosthesis should be in the range of 10 μg to 50 mg. The dose per unit area of the device (i.e., the dosage of fibronectin as a function of the surface area of the portion of the device to which drug is applied and/or incorporated) should fall within the range of 0.05 μg–10 μg per mm$^2$ of surface area coated. In another embodiment, fibronectin should be applied to a shoulder prosthesis surface at a dose of 0.05 μg/mm$^2$–10 μg/mm$^2$ of surface area coated. As specific (polymeric and non-polymeric) drug delivery vehicles and specific medical devices can release fibronectin at differing rates, the above dosing parameters should be utilized in combination with the release rate of the drug from the shoulder prosthesis such that a minimum concentration of 0.01 nM to 1000 μM of fibronectin is delivered to the tissue. In one embodiment, fibronectin is released from the surface of a shoulder prosthesis such that fibrosis in the tissue is promoted for a period ranging from several hours to several months. For example, fibronectin may be released in effective concentrations for a period ranging from 1 hour–30 days. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, whether it is applied using a polymer coating, incorporated into the polymers which make up the device or implant, or applied without a polymeric carrier, the total dose of bleomycin delivered from a shoulder prosthesis, or coated onto the surface of a shoulder prosthesis, should not exceed 100 mg (range of 0.01 µg to 100 mg). In one embodiment, the total amount of bleomycin released from the prosthesis should be in the range of 0.10 µg to 50 mg. The dose per unit area of the device (i.e., the dosage of bleomycin as a function of the surface area of the portion of the device to which drug is applied and/or incorporated) should fall within the range of 0.005 µg–10 µg per mm$^2$ of surface area coated. In another embodiment, bleomycin should be applied to a shoulder prosthesis surface at a dose of 0.005 µg/mm$^2$–10 µg/mm$^2$ of surface area coated. As specific (polymeric and non-polymeric) drug delivery vehicles and specific medical devices can release bleomycin at differing rates, the above dosing parameters should be utilized in combination with the release rate of the drug from the shoulder prosthesis such that a minimum concentration of 0.001 nM to 1000 µM of bleomycin is delivered to the tissue. In one embodiment, bleomycin is released from the surface of a shoulder prosthesis such that fibrosis in the tissue is promoted for a period ranging from several hours to several months. For example, bleomycin may be released in effective concentrations for a period ranging from 1 hour–30 days. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as an exemplary fibrosis-inducing agent, whether it is applied using a polymer coating, incorporated into the polymers which make up the device or implant, or applied without a polymeric carrier, the total dose of CTGF delivered from a shoulder prosthesis, or coated onto the surface of a shoulder prosthesis, should not exceed 100 mg (range of 0.01 µg to 100 mg). In one embodiment, the total amount of CTGF released from the prosthesis should be in the range of 0.10 µg to 50 mg. The dose per unit area of the device (i.e., the dosage of CTGF as a function of the surface area of the portion of the device to which drug is applied and/or incorporated) should fall within the range of 0.005 µg–10 µg per mm$^2$ of surface area coated. In another embodiment, CTGF should be applied to a shoulder prosthesis surface at a dose of 0.005 µg/mm$^2$–10 µg/mm$^2$ of surface area coated. As specific (polymeric and non-polymeric) drug delivery vehicles and specific medical devices can release CTGF at differing rates, the above dosing parameters should be utilized in combination with the release rate of the drug from the shoulder prosthesis such that a minimum concentration of 0.001 nM to 1000 µM of CTGF is delivered to the tissue. In one embodiment, CTGF is released from the surface of a shoulder prosthesis such that fibrosis in the tissue is promoted for a period ranging from several hours to several months. For example, CTGF may be released in effective concentrations for a period ranging from 1 hour–30 days. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Optionally, the device may additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) and/or a bone morphogenic protein (BMP) (e.g., BMP-2, BMP-3, BMP-4, BMP-5, BMP-6, or BMP-7 or an analogue or derivative thereof).

Bone morphogenic protein(s) (e.g., BMP-2, BMP-3, BMP-4, BMP-5, BMP-6, or BMP-7 or an analogue or derivative thereof) are to be used in formulations at concentrations that range from 0.001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the bone morphogenic protein is released in effective concentrations for a period ranging from 1–180 days. The total dose for a single application is typically not to exceed 500 mg (range of 0.001 µg to 500 mg); preferred 1 µg to 250 mg. When used as a device coating, the dose is per unit area of 0.001 µg–1000 µg per mm$^2$; with a preferred dose of 0.01 µg/mm$^2$–200 µg/mm$^2$. Minimum concentration of $10^{-9}$–$10^{-4}$ M of bone morphogenic protein is to be maintained on the device surface.

Inflammatory cytokines are to be used in formulations at concentrations that range from 0.0001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 µg to 100 mg); preferred 0.001 µg to 50 mg. When used as a device coating, the dose is per unit area of 0.0001 µg–500 µg per mm$^2$; with a preferred dose of 0.001 µg/mm$^2$–200 µg/mm$^2$. Minimum concentration of $10^{-10}$–$10^{-4}$ g/ml of inflammatory cytokine is to be maintained on the device surface.

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin D$_3$, diethylstibesterol, cyclosporine A, L-NAME, all-trans retinoic acid (ATRA), and analogues and derivatives thereof. Doses used are those concentrations which are demonstrated to stimulate cell proliferation (see, e.g., Example 16). The proliferative agents are to be used in formulations at concentrations that range from 0.1 ng/ml to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 µg to 200 mg); preferred 0.001 µg to 100 mg. When used as a device coating, the dose is per unit area of 0.00001 µg–500 µg per $mm^2$; with a preferred dose of 0.0001 $µg/mm^2$–200 $µg/mm^2$. Minimum concentration of $10^{-11}$–$10^{-6}$ M of proliferative agent is to be maintained on the device surface.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

(iv) Infiltration of Fibrosing-Inducing Agents into the Tissue Surrounding an Artificial Joint Alternatively, the tissue cavity into which the artificial joint is placed (usually the bony cavity where the stem of the artificial joint is inserted) can be treated with a fibrosis-inducing agent prior to, during, or after the implantation of the prosthetic joint. This can be accomplished in several ways including: (a) topical application of the fibrosing agent into the anatomical space where the artificial joint can be placed (particularly useful for this embodiment is the use of polymeric carriers which release the fibrosing agent over a period ranging from several hours to several weeks—fluids, suspensions, emulsions, microemulsions, microspheres, pastes, gels, microparticulates, sprays, aerosols, solid implants and other formulations which release a fibrosing agent can be delivered into the region where the prosthetic joint can be inserted); (b) microparticulate silk and/or silk strands (linear, branched, and/or coiled) for directed delivery into the implantation site; (c) sprayable collagen-containing formulations such as COSTASIS or materials made from 4-armed thiol PEG (10K), a 4-armed NHS PEG (10K) and methylated collagen such as described above, either alone, or loaded with a fibrosis-inducing agent, applied to the implantation site (or the implant/device surface); (d) sprayable PEG-containing formulations such as COSEAL, FOCALSEAL, SPRAYGEL or DURASEAL, either alone, or loaded with a fibrosis-inducing agent, applied to the implantation site (or the implant/device surface); (e) fibrinogen-containing formulations such as FLOSEAL or TISSEAL, either alone, or loaded with a fibrosis-inducing agent, applied to the implantation site (or the implant/device surface); (f) hyaluronic acid-containing formulations such as RESTYLANE, HYLAFORM, PERLANE, SYNVISC, SEPRAFILM, SEPRACOAT loaded with a fibrosis-inducing agent applied to the implantation site (or the implant/device surface); (g) polymeric gels for surgical implantation such as REPEL or FLOWGEL loaded with a fibrosis-inducing agent applied to the implantation site (or the implant/device surface); (h) orthopedic cements used to hold prostheses and tissues in place loaded with a fibrosis-inducing agent applied to the implantation site (or the implant/device surface), such as OSTEOBOND, LVC, SIMPLEX P, PALACOS, and ENDURANCE; (i) surgical adhesives containing cyanoacrylates such as DERMABOND, INDERMIL, GLUSTITCH, VETBOND, HISTOACRYL, TISSUEMEND, TISSUMEND II, HISTOACRYL BLUE and ORABASE SOOTHE-N-SEAL LIQUID PROTECTANT or as described above, either alone, or loaded with a fibrosis-inducing agent, applied to the implantation site (or the implant/device surface); (j) implants containing hydroxyapatite (or synthetic bone material such as calcium sulfate, VITOSS and CORTOSS) loaded with a fibrosis-inducing agent applied to the implantation site (or the implant/device surface); (k) other biocompatible tissue fillers loaded with a fibrosis-inducing agent, such as those made by BioCure, 3M Company and Neomend, loaded with a fibrosis-inducing agent applied to the implantation site (or the implant/device surface); (l) polysaccharide gels such as the ADCON series of gels; (m) films, sponges or meshes such as INTERCEED, VICRYL mesh, and GELFOAM either alone, or loaded with a fibrosis-inducing agent, bone morphogenic protein, and/or growth factor, injected into or around the joint; and/or (n) a hydrogel that is formed from an amino-functionalized polyethylene glycol (e.g., 4-armed tetra-amino PEG [10k]) and a 4-armed NHS functionalized PEG (e.g., pentaerythritol poly(ethylene glycol)ether tetra-succinimidyl glutarate [10K]). This hydrogel may further contain collagen, methylated collagen and/or gelatin. This hydrogel can further comprise the fibrosis-inducing agents described above (e.g., silk powder or silk threads).(m) films, sponges or meshes such as INTERCEED, VICRYL mesh, and GELFOAM loaded with a fibrosis-inducing agent applied to the implantation site (or the implant/device surface).

It should be apparent to one of skill in the art that potentially any fibrosis-inducing agents described above may be utilized alone, or in combination, in the practice of this embodiment. Exemplary fibrosing agents for infiltration into the tissues surrounding a joint prosthesis include talc, silk, wool, chitosan, polylysine, fibronectin, bleomycin, and CTGF, as well as analogues and derivatives of the aforementioned.

As joint prostheses are made in a variety of configurations and sizes, the exact dose administered into the tissue surrounding the implant can vary with device size, surface area and design. However, certain principles can be applied in the application of this art. Drug dose can be calculated as a function of dose per unit area (of the implanted portion of the device), total drug dose administered can be measured and appropriate surface concentrations of active drug can be determined. Regardless of the method of application of the drug, the exemplary fibrosing agents, used alone or in combination, should be administered under the following dosing guidelines:

Utilizing talc as an exemplary fibrosis-inducing agent, whether it is applied using a polymeric carrier or applied without a polymeric carrier, the total dose of talc delivered should not exceed 100 mg (range of 1 µg to 100 mg). In one embodiment, the total amount of talc released from around the prosthesis should be in the range of 10 µg to 50 mg. The dose per unit area of the device (i.e., the dosage of talc as a function of the surface area of the implanted portion of the device) should fall within the range of 0.05 µg–10 µg per $mm^2$. In one embodiment, talc is released such that fibrosis in the tissue is promoted for a period ranging from several hours to several months. For example, talc may be released in effective concentrations for a period ranging from 1 hour–30 days. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymeric carrier or applied without a polymeric carrier, the total dose of silk delivered into the tissue surrounding a prosthesis should not exceed 100 mg (range of 1 μg to 100 mg). In one embodiment, the total amount of silk released around the prosthesis should be in the range of 10 μg to 50 mg. The dose per unit area of the device (i.e., the dosage of silk as a function of the surface area of the portion of the device which is implanted) should fall within the range of 0.05 μg–10 μg per mm$^2$. As specific (polymeric and non-polymeric) drug delivery vehicles can release silk at differing rates, the above dosing parameters should be utilized in combination with the release rate of the drug such that a minimum concentration of 0.01 nM to 1000 μM of silk is delivered to the tissue. In one embodiment, silk is released into the tissue surrounding a prosthesis such that fibrosis in the tissue is promoted for a period ranging from several hours to several months. For example, silk may be released in effective concentrations for a period ranging from 1 hour–30 days. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymeric carrier or applied without a polymeric carrier, the total dose of chitosan delivered into the tissue surrounding a prosthesis should not exceed 100 mg (range of 1 μg to 100 mg). In one embodiment, the total amount of chitosan released around the prosthesis should be in the range of 10 μg to 50 mg. The dose per unit area of the device (i.e., the dosage of chitosan as a function of the surface area of the portion of the device which is implanted) should fall within the range of 0.05 μg–10 μg per mm$^2$. As specific (polymeric and non-polymeric) drug delivery vehicles can release chitosan at differing rates, the above dosing parameters should be utilized in combination with the release rate of the drug such that a minimum concentration of 0.01 nM to 1000 μM of chitosan is delivered to the tissue. In one embodiment, chitosan is released into the tissue surrounding a prosthesis such that fibrosis in the tissue is promoted for a period ranging from several hours to several months. For example, chitosan may be released in effective concentrations for a period ranging from 1 hour–30 days. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as an exemplary fibrosis-inducing agent, whether it is applied using a polymeric carrier or applied without a polymeric carrier, the total dose of polylysine delivered into the tissue surrounding a prosthesis should not exceed 100 mg (range of 1 μg to 100 mg). In one embodiment, the total amount of polylysine released should be in the range of 10 μg to 50 mg. The dose per unit area of the device (i.e., the dosage of polylysine as a function of the surface area of the implanted portion of the device) should fall within the range of 0.05 μg–10 μg per mm$^2$. As specific (polymeric and non-polymeric) drug delivery vehicles can release polylysine at differing rates, the above dosing parameters should be utilized in combination with the release rate of the drug such that a minimum concentration of 0.01 nM to 1000 μM of polylysine is delivered to the tissue. In one embodiment, polylysine is released into the region surrounding a prosthesis such that fibrosis in the tissue is promoted for a period ranging from several hours to several months. For example, polylysine may be released in effective concentrations for a period ranging from 1 hour–30 days. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymeric carrier or applied without a polymeric carrier, the total dose of fibronectin delivered into the tissue surrounding a prosthesis should not exceed 100 mg (range of 1 μg to 100 mg). In one embodiment, the total amount of fibronectin released should be in the range of 10 μg to 50 mg. The dose per unit area of the device (i.e., the dosage of fibronectin as a function of the surface area of the portion of the device which is implanted) should fall within the range of 0.05 μg–10 μg per mm$^2$. As specific (polymeric and non-polymeric) drug delivery vehicles can release fibronectin at differing rates, the above dosing parameters should be utilized in combination with the release rate of the drug such that a minimum concentration of 0.01 nM to 1000 μM of fibronectin is delivered to the tissue surrounding the prosthesis. In one embodiment, fibronectin is released adjacent to the artificial joint such that fibrosis in the tissue is promoted for a period ranging from several hours to several months. For example, fibronectin may be released in effective concentrations for a period ranging from 1 hour–30 days. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, whether it is applied using a polymeric carrier or applied without a polymeric carrier, the total dose of bleomycin delivered into the tissue surrounding a prosthesis should not exceed 100 mg (range of 0.01 μg to 100 mg). In one embodiment, the total amount of bleomycin released should be in the range of 0.10 μg to 50 mg. The dose per unit area of the device (i.e., the dosage of bleomycin as a function of the surface area of the portion of the device which is implanted) should fall within the range of 0.005 μg–10 μg per mm$^2$. As specific (polymeric and non-polymeric) drug delivery vehicles can release bleomycin at differing rates, the above dosing parameters should be utilized in combination with the release rate of the drug such that a minimum concentration of 0.001 nM to 1000 μM of bleomycin is delivered to the tissue surrounding the joint prosthesis. In one embodiment, bleomycin is released around the prosthesis such that fibrosis in the tissue is promoted for a period ranging from several hours to several months. For example, bleomycin may be released in effective concentrations for a period ranging from 1 hour–30 days. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as an exemplary fibrosis-inducing agent, whether it is applied using a polymeric carrier or applied without a polymeric carrier, the total dose of CTGF delivered into the tissue surrounding a prosthesis should not exceed 100 mg (range of 0.01 µg to 100 mg). In one embodiment, the total amount of CTGF released should be in the range of 0.10 µg to 50 mg. The dose per unit area of the device (i.e., the dosage of CTGF as a function of the surface area of the portion of the device which is implanted) should fall within the range of 0.005 µg–10 µg per mm$^2$. As specific (polymeric and non-polymeric) drug delivery vehicles can release CTGF at differing rates, the above dosing parameters should be utilized in combination with the release rate of the drug such that a minimum concentration of 0.001 nM to 1000 µM of CTGF is delivered to the tissue surrounding the artificial joint. In one embodiment, CTGF is released such that fibrosis in the tissue is promoted for a period ranging from several hours to several months. For example, CTGF may be released in effective concentrations for a period ranging from 1 hour–30 days. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Optionally, the device may additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) and/or a bone morphogenic protein (BMP) (e.g., BMP-2, BMP-3, BMP-4, BMP-5, BMP-6, or BMP-7 or an analogue or derivative thereof).

Bone morphogenic protein(s) (e.g., BMP-2, BMP-3, BMP-4, BMP-5, BMP-6, or BMP-7 or an analogue or derivative thereof) are to be used in formulations at concentrations that range from 0.001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the bone morphogenic protein is released in effective concentrations for a period ranging from 1–180 days. The total dose for a single application is typically not to exceed 500 mg (range of 0.001 µg to 500 mg); preferred 1 µg to 250 mg. When used as a device coating, the dose is per unit area of 0.001 µg–1000 µg per mm$^2$; with a preferred dose of 0.01 µg/mm$^2$–200 µg/mm$^2$. Minimum concentration of $10^{-9}$–$10^4$ M of bone morphogenic protein is to be maintained on the device surface.

Inflammatory cytokines are to be used in formulations at concentrations that range from 0.0001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 µg to 100 mg); preferred 0.001 µg to 50 mg. When used as a device coating, the dose is per unit area of 0.0001 µg–500 µg per mm$^2$; with a preferred dose of 0.001 µg/mm$^2$–200 µg/mm$^2$. Minimum concentration of $10^{-10}$–$10^{-4}$ g/ml of inflammatory cytokine is to be maintained on the device surface.

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin D$_3$, diethylstibesterol, cyclosporine A, L-NAME, all-trans retinoic acid (ATRA), and analogues and derivatives thereof. Doses used are those concentrations which are demonstrated to stimulate cell proliferation (see, e.g., Example 16). The proliferative agents are to be used in formulations at concentrations that range from 0.1 ng/ml to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 µg to 200 mg); preferred 0.001 µg to 100 mg. When used as a device coating, the dose is per unit area of 0.00001 µg–500 µg per mm$^2$; with a preferred dose of 0.0001 µg/mm$^2$–200 µg/mm$^2$. Minimum concentration of $10^{-11}$–$10^{-6}$ M of proliferative agent is to be maintained on the device surface.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

3. Dental Devices

In one aspect, the present invention provides dental devices and implants that include a fibrosis or adhesion-inducing agent to assist in the incorporation of the implant into the surrounding tissue. A variety of devices is used in dental applications. Representative examples include dental implants and guided bone regeneration devices.

In one aspect, a dental implant of specific importance is a small titanium fixture that serves as a replacement for the root portion of a missing natural tooth. The dental implant is placed in the bone of the upper or lower jaw and functions as an anchor for the replacement tooth. They may be used to support the replacement of a single missing tooth or a complete functional set for individuals who have lost many or all of their teeth. Dental implants can be implanted in the bone (endosteal) or on the bone (subperiosteal). Endosteal implants are the most commonly used type of implant. There are various types of endosteal implants, which may include screws, cylinders or blades surgically placed into the jawbone. Each implant holds one or more prosthetic teeth. This type of implant is generally used as an alternative for patients with bridges or removable dentures. Subperiosteal implants are placed on top of the jaw with the metal framework's posts protruding through the gum to hold the prosthesis. These types of implants are used for patients who are unable to wear conventional dentures and who have minimal bone height.

A variety of dental implants suitable for combination with a fibrosis-inducing agent have been described (see, e.g., U.S. Pat. Nos. 6,627,321; 6,582,228; 6,572,373; 6,527,553; and 6,506,051).

In one aspect, the fibrosing agent may be incorporated into the glue or cement that holds the device in place. In another aspect, the dental device is covered (all or in part) with a silk mesh or lattice to encourage scarring and anchoring into the surrounding bone. For example, a silk mesh or lattice can be coated onto all or a portion of the surface of the implant stem to encourage scarring and anchoring into the surrounding bone.

In another aspect, the device used to deliver a fibrosis-inducing agent may be a guided tissue regeneration (GTR) device, such as a GTR membrane. A GTR membrane is a resorbable or non-resorbable membrane made of biologically or non-biologically derived material. GTR membranes may be used in conjunction with a dental implant or to treat bone loss. GTR membranes may be made from a variety of materials, including, e.g., collagen (e.g., porcine collagen, types I and II), PTFE, polylactic acid, lactide and glycolide polymers, and ePTFE). GTR membranes are commercially available from W.L. Gore & Associates (Newark, Del.) (e.g., GORE-TEX and GORE-RESOLUT regenerative material), Guidor, Atrix Laboratories, Inc. (Fort Collins, Colo.), Geistlich Biomaterials, Inc. (e.g., BIO-GIDE), LifeCore Biomedical, Inc. (Chaska, Minn.), Ethicon Inc. (e.g., VICRYL), THM Biomedical now known as Kensey Nash Corporation (Exton, Pa.), and Suzler Calcitek, Inc. (Carlsbad, Calif.).

In another aspect, the dental device suitable for combining with a fibrosis-inducing agent is used for guided bone regeneration (GBR) to augment insufficient bone tissue and guide regrowth. GBR devices include, e.g., resorbable bone substitutes for filling bony defects. Such devices may consist of biomaterials (e.g., demineralized bone and bovine-derived materials) and synthetic materials, such as crystalline hydroxyapatite and calcium sulfate. A variety of dental bone substitutes are commercially available, including the following products: OSTEOGRAF/N, OSTEOGRAF/LD, OSTEOGRAF/D, AND PERMARIDGE (all from Ceramad), bioactive glass, such as PERIOGLAS (U.S. Biomaterials), OSTEOGEN (Impladent, Inc.), VITOSS and CORTOSS.

In another aspect, the present invention provides dental implants containing a fibrosis-inducing agent for use in the treatment of common periodontal conditions. Briefly, periodontal disease is an inflammatory disease of the supporting structures of the teeth, including the ligaments, cementum, periosteum, alveolar bone and adjacent gingiva which anchor the teeth in place. The condition begins with bleeding of the gums, but can progress to loosening of the teeth, receding gums, abscesses in pockets between the gums and the teeth, and necrotizing ulcerative gingivitis. In advanced stages, procedures such as gingivectomy, gingivoplasty, and correction of the bony architecture of the teeth may be required for treatment of the condition. Traditional treatment involves open-flap debridement of the periodontal pocket with removal of diseased cementum, periodontal ligament and alveolar bone that have been destroyed by periodontal infection. Unfortunately, epithelial tissue can occasionally migrate into the surgically created defect impairing proper healing of the cementum, ligament and bone.

Dental implants have been developed in an attempt to control the healing process and optimize tissue regeneration. Commonly used implants include permanent implants, such as e-PTFE membranes (e.g., GORE-TEX from W.L. Gore). Commonly used implants include, e.g., BIOMEND, available from Sulzer Medica, Inc. (Houston, Tex.), which is a collagen membrane composed of compressed Type I collagen matrix derived from bovine Achilles tendon. The collagen membrane (supplied as sheets, e.g., 15 mm×20 mm; 20 mm×30 mm; and 30 mm×40 mm) is cut to the appropriate size and shape, hydrated and placed as a barrier between the overlying gingival tissue and the debrided periodontal defect; the barrier can be sutured in place, but this is not always required. The membrane is placed snugly against the tooth root and draped over the surrounding alveolar bone (extending at least 3 mm beyond the defect margins) to effectively maintain the regenerative space. Primary closure with mucoperiosteal flaps over the collagen membrane is important as exposure of the membrane to the oral cavity can result in premature degradation. The barrier prevents faster growing epithelial tissue from entering the region and allows the slower growing periodontal ligament and bone cells to repopulate the area and effect appropriate healing. The collagen membrane is bioresorbable, is retained for 6 to 7 weeks, and is fully absorbed by host enzymes (e.g., collagenase) within 8 weeks.

However, limited durability of the collagen implant can become a clinical problem if it completely absorbs prior to the completion of healing—this is particularly relevant with large tissue defects. In an attempt to address this problem, manufacturers have attempted to produce a collagen implant with improved durability through increased collagen crosslinking (often through exposure of the collagen to aldehydes). Utilizing this process, products such as BIOMEND EXTEND (Sulzer Medica, Inc.) can function as a barrier for longer periods of time, such that the collagen is not absorbed into the surrounding tissue for approximately 18 weeks. Another collagen dental implant product, OSSIX (Colbar R&D Ltd., Israel), uses a metabolite to crosslink collagen and prolong the structural integrity of the matrix for periods of up to 6 months.

In addition to the commercially available collagen-based products for the management of periodontal disease described above, other types of collagen-based implants may be used in the practice of the invention. Representative examples of such implants include those that are used in variety of dental procedures including: COLLATAPE (Sulzer Medica, Inc.), which is a collagen-based implant used in the repair of minor oral wounds, closure of grafted sites and repair of Schneiderian Membranes; COLLACOTE (Sulzer Medica, Inc.), a collagen-based wound dressing used for palatal donor sites and in mucosal flaps; and COLLAPLUG (Sulzer Medica, Inc.), a solid collagen-based implant used in the repair of larger tissue defects such extraction sites or biopsy sites.

In one aspect, the present invention provides dental devices that include a fibrosis-inducing agent or a composition that includes a fibrosis-inducing agent to promote fibrosis in the periodontal pocket. In one aspect, the dental device or material used to fill or maintain the periodontal pocket is coated with, composed of, or contains a fibrosing agent or a composition that includes a fibrosing agent.

Numerous polymeric and non-polymeric carrier systems described above can be used in the practice of this embodiment. These compositions can further include one or more fibrosis-inducing agents to promote the formation of fibrous tissue around the dental implant. Methods for incorporating fibrosing compositions onto or into the dental implant (such as endosteal or perioosteal titanium implants) include: (a) directly affixing to the dental hardware a fibrosing composition (e.g., by either a spraying process or dipping process as described above, with or without a carrier); (b) directly incorporating into the dental hardware a fibrosing composition (e.g., by either a spraying process or dipping process as described above, with or without a carrier); (c) by coating the dental hardware with a substance such as a hydrogel which can in turn absorb the fibrosing composition; (d) by interweaving a thread coated with a fibrosis-inducing composition (or the a fibrosis-inducing polymer itself formed into a thread) into the device structure; (e) by inserting the device into a sleeve or mesh which is comprised of, or coated with, a fibrosing composition; (f) constructing the device itself, or a portion of the device, with a composition containing a fibrosing agent; or (g) by covalently binding the fibrosing agent directly to the device surface or to a linker (small molecule or polymer) that is coated or attached to the device surface. For dental hardware devices, the coating process can be performed in such a manner as to (a) coat the surfaces of the device that is in contact with the bone, (b) coat the surfaces of the device that are not in contact with the bone or (c) coat all or parts of both the bone-contacting and non-bone contacting surface of the device. In addition to coating the device with the fibrosing composition, the fibrosing agent can be mixed with the materials that are used to make the device such that the fibrosing agent is incorporated into the final device.

For the management of periodontal disease, polymeric gels, pastes, injectables, solutions, microparticles and solid implants placed into the periodontal pocket are a preferred form of locally delivering a fibrosis-inducing agent. All involve the deployment of a biomaterial containing a fibrosis-inducing agent into the surgically-created periodontal pocket (as described above). The practice of this embodiment can be performed in several ways including: (a) topical application of the fibrosing agent onto the periodontal pocket (particularly useful for this embodiment is the use of polymeric carriers which release the fibrosing agent over a period ranging from several hours to several weeks—fluids, suspensions, emulsions, microemulsions, microspheres, pastes, gels, microparticulates, sprays, aerosols, solid implants and other formulations which release a fibrosing agent and can be delivered into the region via specialized delivery catheters or other applicators); (b) placement of microparticulate silk and/or silk strands (linear, branched, and/or coiled) into the periodontal pocket; (c) sprayable collagen-containing formulations such as COSTASIS or materials made from 4-armed thiol PEG (10K), a 4-armed NHS PEG(10K) and methylated collagen such as described above, either alone, or loaded with a fibrosis-inducing agent, applied into periodontal pocket; (d) sprayable PEG-containing formulations such as COSEAL, FOCALSEAL, SPRAY-GEL or DURASEAL, either alone, or loaded with a fibrosis-inducing agent, applied to the periodontal pocket; (e) fibrinogen-containing formulations such as FLOSEAL or TISSEAL, either alone, or loaded with a fibrosis-inducing agent, applied to the periodontal pocket; (f) hyaluronic acid-containing formulations such as RESTYLANE, HYLAFORM, PERLANE, SYNVISC, SEPRAFILM, SEPRACOAT loaded with a fibrosis-inducing agent applied to the periodontal pocket; (g) polymeric gels for surgical implantation such as REPEL or FLOWGEL loaded with a fibrosis-inducing agent applied to the periodontal pocket; (h) orthopedic "cements" such as OSTEOBOND, LVC, SIMPLEX P, PALACOS, ENDURANCE, and CORTOSS loaded with a fibrosis-inducing agent applied to the periodontal pocket; (i) surgical adhesives containing cyanoacrylates such as DERMABOND, INDERMIL, GLUSTITCH, VETBOND, HISTOACRYL, TISSUEMEND, TISSUMEND II, HISTOACRYL BLUE and ORABASE SOOTHE-N-SEAL LIQUID PROTECTANT or as described above loaded with a fibrosis-inducing agent, applied to the periodontal pocket; (j) surgical implants containing hydroxyapatite, calcium sulfate, or VITOSS loaded with a fibrosis-inducing agent applied to the periodontal pocket; (k) other biocompatible tissue fillers, such as those made by BioCure, 3M Company and Neomend, loaded with a fibrosis-inducing agent, applied to the periodontal pocket; (l) polysaccharide gels such as the ADCON series of gels loaded with a fibrosis-inducing agent applied to the periodontal pocket; (m) films, sponges or meshes such as INTERCEED, VICRYL mesh, and GELFOAM loaded with a fibrosis-inducing agent applied to the periodontal pocket; and/or (n) a hydrogel that is formed from an amino-functionalized polyethylene glycol (e.g., 4-armed tetra-amino PEG [10k]) and a 4-armed NHS functionalized PEG (e.g., pentaerythritol poly(ethylene glycol)ether tetra-succinimidyl glutarate [10K]). This hydrogel may further contain collagen, methylated collagen and/or gelatin. This hydrogel can further comprise the fibrosis-inducing agents described above (e.g., silk powder or silk threads).

In many of the embodiments described above it may also be useful to add a radio-opaque material (such as tantalum, barium, other metal, or contrast material) such that the injected material can be visualized radiographically or by MRI. The contrast agent may be a water soluble or water insoluble radio-opaque material.

It should be apparent to one of skill in the art that potentially any adhesion or fibrosis-inducing agents described above may be utilized alone, or in combination, in the practice of this embodiment. Exemplary fibrosing agents for use in dental prostheses include talc, silk, wool, chitosan, polylysine, fibronectin, bleomycin, and CTGF, as well as analogues and derivatives of the aforementioned.

Optionally, the device may additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or a bone morphogenic protein (BMP) (e.g., BMP-2, BMP-3, BMP-4, BMP-5, BMP-6, or BMP-7 or an analogue or derivative thereof).

As dental prostheses are made in a variety of configurations and sizes, the exact dose administered can vary with device size, surface area and design. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the dental prostheses or periodontal implant, the exemplary fibrosing agents, used alone or in combination, should be administered under the following dosing guidelines:

Utilizing talc as an exemplary fibrosis-inducing agent, whether it is applied using a polymer coating, incorporated into the polymers which make up the device or implant, or applied without a polymeric carrier, the total dose of talc delivered from a dental prosthesis, or coated onto the surface of a dental prosthesis, should not exceed 100 mg (range of 1 µg to 100 mg). In one embodiment, the total amount of talc released from the prosthesis should be in the range of 10 µg to 50 mg. The dose per unit area of the device (i.e., the dosage of talc as a function of the surface area of the portion of the device to which drug is applied and/or incorporated) should fall within the range of 0.05 µg–10 µg per mm$^2$ of surface area coated. In another embodiment, talc should be applied to a dental prosthesis surface at a dose of 0.05 µg/mm$^2$–10 µg/mm$^2$ of surface area coated. In one embodiment, talc is released from the surface of a dental prosthesis such that fibrosis in the tissue is promoted for a period ranging from several hours to several months. For example, talc may be released in effective concentrations for a period ranging from 1 hour–30 days. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymer coating, incorporated into the polymers which make up the device or implant, or applied without a polymeric carrier, the total dose of silk delivered from a dental prosthesis, or coated onto the surface of a dental prosthesis, should not exceed 100 mg (range of 1 µg to 100 mg). In one embodiment, the total amount of silk released from the prosthesis should be in the range of 10 µg to 50 mg. The dose per unit area of the device (i.e., the dosage of silk as a function of the surface area of the portion of the device to which drug is applied and/or incorporated) should fall within the range of 0.05 µ-10 µg per mm$^2$ of surface area coated. In another embodiment, silk should be applied to a dental prosthesis surface at a dose of 0.05 µg/mm$^2$–10 µg/mm$^2$ of surface area coated. As specific (polymeric and non-polymeric) drug delivery vehicles and specific medical devices can release silk at differing rates, the above dosing parameters should be utilized in combination with the release rate of the drug from the dental prosthesis such that a minimum concentration of 0.01 nM to 1000 µM of silk is delivered to the tissue. In one embodiment, silk is released from the surface of a dental prosthesis such that fibrosis in the tissue is promoted for a period ranging from several hours to several months. For example, silk may be released in effective concentrations for a period ranging from 1 hour–30 days. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymer coating, incorporated into the polymers which make up the device or implant, or applied without a polymeric carrier, the total dose of chitosan delivered from a dental prosthesis, or coated onto the surface of a dental prosthesis, should not exceed 100 mg (range of 1 µg to 100 mg). In one embodiment, the total amount of chitosan released from the prosthesis should be in the range of 10 µg to 50 mg. The dose per unit area of the device (i.e., the dosage of chitosan as a function of the surface area of the portion of the device to which drug is applied and/or incorporated) should fall within the range of 0.05 µg–10 µg per mm$^2$ of surface area coated. In another embodiment, chitosan should be applied to a dental prosthesis surface at a dose of 0.05 µg/mm$^2$–10 µg/mm$^2$ of surface area coated. As specific (polymeric and non-polymeric) drug delivery vehicles and specific medical devices can release chitosan at differing rates, the above dosing parameters should be utilized in combination with the release rate of the drug from the dental prosthesis such that a minimum concentration of 0.01 nM to 1000 µM of chitosan is delivered to the tissue. In one embodiment, chitosan is released from the surface of a dental prosthesis such that fibrosis in the tissue is promoted for a period ranging from several hours to several months. For example, chitosan may be released in effective concentrations for a period ranging from 1 hour–30 days. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as a exemplary fibrosis-inducing agent, whether it is applied using a polymer coating, incorporated into the polymers which make up the device or implant, or applied without a polymeric carrier, the total dose of polylysine delivered from a dental prosthesis, or coated onto the surface of a dental prosthesis, should not exceed 100 mg (range of 1 µg to 100 mg). In one embodiment, the total amount of polylysine released from the prosthesis should be in the range of 10 µg to 50 mg. The dose per unit area of the device (i.e., the dosage of polylysine as a function of the surface area of the portion of the device to which drug is applied and/or incorporated) should fall within the range of 0.05 µg–10 µg per mm$^2$ of surface area coated. In another embodiment, polylysine should be applied to a dental prosthesis surface at a dose of 0.05 µg/mm$^2$–10 µg/mm$^2$ of surface area coated. As specific (polymeric and non-polymeric) drug delivery vehicles and specific medical devices can release polylysine at differing rates, the above dosing parameters should be utilized in combination with the release rate of the drug from the dental prosthesis such that a minimum concentration of 0.01 nM to 1000 µM of polylysine is delivered to the tissue. In one embodiment, polylysine is released from the surface of a dental prosthesis such that fibrosis in the tissue is promoted for a period ranging from several hours to several months. For example, polylysine may be released in effective concentrations for a period ranging from 1 hour–30 days. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymer coating, incorporated into the polymers which make up the device or implant, or applied without a polymeric carrier, the total dose of fibronectin delivered from a dental prosthesis, or coated onto the surface of a dental prosthesis, should not exceed 100 mg (range of 1 µg to 100 mg). In one embodiment, the total amount of fibronectin released from the prosthesis should be in the range of 10 µg to 50 mg. The dose per unit area of the device (i.e., the dosage of fibronectin as a function of the surface area of the portion of the device to which drug is applied and/or incorporated) should fall within the range of 0.05 µg–10 µg per mm² of surface area coated. In another embodiment, talc should be applied to a dental prosthesis surface at a dose of 0.05 µg/mm²–10 µg/mm² of surface area coated. As specific (polymeric and non-polymeric) drug delivery vehicles and specific medical devices can release fibronectin at differing rates, the above dosing parameters should be utilized in combination with the release rate of the drug from the dental prosthesis such that a minimum concentration of 0.01 nM to 1000 µM of fibronectin is delivered to the tissue. In one embodiment, fibronectin is released from the surface of a dental prosthesis such that fibrosis in the tissue is promoted for a period ranging from several hours to several months. For example, fibronectin may be released in effective concentrations for a period ranging from 1 hour–30 days. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as a exemplary fibrosis-inducing agent, whether it is applied using a polymer coating, incorporated into the polymers which make up the device or implant, or applied without a polymeric carrier, the total dose of bleomycin delivered from a dental prosthesis, or coated onto the surface of a dental prosthesis, should not exceed 100 mg (range of 0.01 µg to 100 mg). In one embodiment, the total amount of bleomycin released from the prosthesis should be in the range of 0.10 µg to 50 mg. The dose per unit area of the device (i.e., the dosage of bleomycin as a function of the surface area of the portion of the device to which drug is applied and/or incorporated) should fall within the range of 0.005 µg–10 µg per mm² of surface area coated. In another embodiment, bleomycin should be applied to a dental prosthesis surface at a dose of 0.005 µg/mm²–10 µg/mm² of surface area coated. As specific (polymeric and non-polymeric) drug delivery vehicles and specific medical devices can release bleomycin at differing rates, the above dosing parameters should be utilized in combination with the release rate of the drug from the dental prosthesis such that a minimum concentration of 0.001 nM to 1000 µM of bleomycin is delivered to the tissue. In one embodiment, bleomycin is released from the surface of a dental prosthesis such that fibrosis in the tissue is promoted for a period ranging from several hours to several months. For example, bleomycin may be released in effective concentrations for a period ranging from 1 hour–30 days. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as a exemplary fibrosis-inducing agent, whether it is applied using a polymer coating, incorporated into the polymers which make up the device or implant, or applied without a polymeric carrier, the total dose of CTGF delivered from a dental prosthesis, or coated onto the surface of a dental prosthesis, should not exceed 100 mg (range of 0.01 µg to 100 mg). In one embodiment, the total amount of CTGF released from the prosthesis should be in the range of 0.10 µg to 50 mg. The dose per unit area of the device (i.e., the dosage of CTGF as a function of the surface area of the portion of the device to which drug is applied and/or incorporated) should fall within the range of 0.005 µg–10 µg per mm² of surface area coated. In another embodiment, CTGF should be applied to a dental prosthesis surface at a dose of 0.005 µg/mm²–10 µg/mm² of surface area coated. As specific (polymeric and non-polymeric) drug delivery vehicles and specific medical devices can release CTGF at differing rates, the above dosing parameters should be utilized in combination with the release rate of the drug from the dental prosthesis such that a minimum concentration of 0.001 nM to 1000 µM of CTGF is delivered to the tissue. In one embodiment, CTGF is released from the surface of a dental prosthesis such that fibrosis in the tissue is promoted for a period ranging from several hours to several months. For example, CTGF may be released in effective concentrations for a period ranging from 1 hour–30 days. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Bone morphogenic protein(s) (e.g., BMP-2, BMP-3, BMP-4, BMP-5, BMP-6, or BMP-7 or an analogue or derivative thereof), if present, are to be used in formulations at concentrations that range from 0.001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the bone morphogenic protein is released in effective concentrations for a period ranging from 1–180 days. The total dose for a single application is typically not to exceed 500 mg (range of 0.001 µg to 500 mg); preferred 1 µg to 250 mg. When used as a device coating, the dose is per unit area of 0.001 µg–1000 µg per mm²; with a preferred dose of 0.01 µg/mm²–200 µg/mm². Minimum concentration of $10^{-9}$–$10^{-4}$ M of bone morphogenic protein is to be maintained on the device surface.

Inflammatory cytokines, if present, are to be used in formulations at concentrations that range from 0.0001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 μg to 100 mg); preferred 0.001 μg to 50 mg. When used as a device coating, the dose is per unit area of 0.0001 μg–500 μg per mm$^2$; with a preferred dose of 0.001 μg/mm$^2$–200 μg/mm$^2$. Minimum concentration of $10^{-10}$–$10^{-4}$ g/ml of inflammatory cytokine is to be maintained on the device surface.

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof. Doses used are those concentrations which are demonstrated to stimulate cell proliferation (see, e.g., Example 16). The proliferative agents are to be used in formulations at concentrations that range from 0.0.1 ng/ml to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 μg to 200 mg); preferred 0.001 μg to 100 mg. When used as a device coating, the dose is per unit area of 0.00001 μg–500 μg per mm$^2$; with a preferred dose of 0.0001 μg/mm$^2$–200 μg/mm$^2$. Minimum concentration of $10^{-11}$–$10^{-6}$ M of proliferative agent is to be maintained on the device surface.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

4. Orthopedic Implants

In one aspect, the present invention provides orthopedic implants that include a fibrosis-inducing agent or a composition that includes a fibrosis-inducing agent to promote scarring and fixation of the device into the surrounding bone or tissue.

(i) Orthopedic Hardware Coated with a Fibrosis-Inducing Agent

In one aspect, the orthopedic implant is an orthopedic "hardware" device that has been coated with a fibrosing agent or a fibrosing agent containing composition. Representative examples of orthopedic hardware devices include internal and external fixation devices, fixation screws (degradable or non-degradable), interferential screws (degradable and non-degradable), trochanteric screws, plates, wires (e.g., K-wires), pins, and nails used in fracture repairs, reconstructive procedures, and joint fusion procedures (e.g., ankle fusions, cervical and lumbar spinal fusions). Compositions also are provided for coating devices used in fusion procedures and superior repair of fractures. Orthopedic implants such as, for example, fixation screws, pins, plates, nails, wires and plates coated with a fibrosing agent, coated with a composition containing a fibrosing agent, or composed of a polymer that releases a fibrosing agent (particularly for polymeric, biodegradable orthopedic hardware) are used to encourage better anchorage of the implant into the surrounding bone. Alternatively, or in addition, the fibrosing agent may be incorporated into the glue or cement that holds the implant in place. In another aspect, the orthopedic hardware is covered (all or in part) with a silk mesh or lattice to encourage scarring and anchoring into the surrounding bone. For example, a silk mesh or lattice can be coated onto all or a portion of the surface of the implant stem to encourage scarring and anchoring into the surrounding bone.

In another aspect, the orthopedic implant is a collagen implant for use as a substitute for autogenous or allogenous bone grafts. A variety of collagen implants have been developed for use in orthopedic surgery as a substitute for autogenous or allogenous bone grafts. Collagen is the principle organic component of bone and can be combined with mineral formulations, autogenous bone marrow, bone graft, and/or growth factors (such as BMPs) for use as a bone substitute or a skeletal repair product. Typical applications include, but are not restricted to, total joint replacement surgery (e.g., artificial hips, knees, etc.), spinal fusion surgery, long bone fractures, repair of traumatic bone defects, voids, or gaps, to augment an autograft, and as a bone filler at bone graft harvesting sites. Examples of commercially available collagen-based bone grafts include COLLAGRAFT Paste and COLLAGRAFT Strips made by Angiotech Pharmaceuticals, Inc. COLLAGRAFT is a combination of highly purified Type I bovine dermal fibrillar collagen and a mixture of 65% hydroxyapatite and 35% tricalcium phosphate. This material closely resembles human bone and is resorbed and replaced with bone during the healing process. Representative examples of bone grafts are described in U.S. Pat. Nos. 6,083,522 and 6,280,474 and in PCT Publication No. WO 98/52498.

Numerous polymeric and non-polymeric carrier systems described above can be used in the practice of this embodiment. These compositions can further include one or more fibrosis-inducing agents to promote the formation of granulation tissue (described further in section (iii) below). Methods for incorporating fibrosing compositions onto or into the orthopedic implants include: (a) directly affixing to the device a fibrosing composition (e.g., by either a spraying process or dipping process as described above, with or without a carrier); (b) directly incorporating into the device a fibrosing composition (e.g., by either a spraying process or dipping process as described above, with or without a carrier); (c) by coating the device with a substance such as a hydrogel which can in turn absorb the fibrosing composition; (d) by interweaving into the device a thread coated with a fibrosing composition (or a polymeric version of the fibrosing agent is itself formed into a thread); (e) by inserting the device into a sleeve or mesh which is comprised of, or coated with, a fibrosing composition; (f) constructing the device itself or a portion of the device with a fibrosing composition (particularly effective for biodegradable orthopedic hardware and collagen implants); or (g) by covalently binding the fibrosing agent directly to the device surface or to a linker (small molecule or polymer) that is coated or attached to the device surface. For these devices, the coating process can be performed in such a manner as to (a) coat the surfaces of the device that is in contact with the bone; (b) coat the surfaces of the device that are not in contact with bone, or (c) coat all or parts of both the bone-contacting and non-bone contacting surface of the device.

It should be apparent to one of skill in the art that potentially any adhesion or fibrosis-inducing agent may be utilized alone, or in combination, in the practice of this embodiment as described above. Exemplary fibrosing agents for use in the coating of orthopedic hardware include talc, silk, wool, chitosan, polylysine, fibronectin, bleomycin, and/ or CTGF as well as analogues and derivatives of the aforementioned. The correct administration and dosage is the same as that described previously in section 2(i), 2(ii) and 2(iii) for artificial hips, knees and shoulder prostheses.

(ii) Minimally-Invasive Joint Fusion

In another aspect, the present invention provides injectable compositions to promote scarring and fixation (immobilization) of a joint without the need for open surgery. In some clinical situations it is desirable to immobilize a joint that has been severely damaged or is the cause of chronic pain. For example, a composition including an adhesion or fibrosis-inducing agent may be injected into an arthritic or damaged joint to promote scarring and fixation (i.e., immobilization) of the joint (particularly interphalageal joints, tarsal-metatarsal joints, metacarpal joints, ankle joints, knee joints, proximal tibia-fibular joint, hip joint, sacro-iliac joint, acromio-clavicular joint, sterno-clavicular joint and facet joints in the cervical, thoracic, and lumbar spine). In this procedure, a needle is inserted into the joint cavity, a guidewire is advanced into the joint space, a dual lumen catheter (for many of the hydrogels described below such as a material made from 4-armed thiol PEG (10K), a 4-armed NHS PEG(10K) and methylated collagen such as described above, COSEAL, COSTASIS, FLOSEAL, TISSEAL, VITOSS) or a single lumen catheter (for materials such as cyanoacrylate, CORTOSS, bone cement, hydroxyapatite, calcium phosphate, calcium sulfate, hyaluronic acid, proteins, carbohydrates, sclerosing agents, and the like) is advanced over the guidewire into the articular space, the guidewire is removed, and a composition containing a fibrosis-inducing agent, bone morphogenic protein(s), and/or osteogenic growth factor (such as transforming growth factor, platelet-derived growth factor, fibroblast growth factor) is injected via the catheter into joint until the joint space is filled. Agents such as collagenase, chymopapain, or other tissue-degrading enzymes may also be used to chemically degrade the remaining cartilage prior to, or during, the injection of the joint-fusing composition. Over time, the fibrosis-inducing agent, bone morphogenic protein, and/or osteogenic growth factor can encourage fibrous ankylosis, followed by bony ankylosis of the treated joint, leading to decreased (or complete loss of) range of motion, stability, and/or reduced pain.

When performing direct injection of the joint, techniques can be used to enhance visualization of needle (or catheter) placement within the joint space including, but not limited to, the use of a needle coated with ECHO—COAT, the injection of air to enable localization by ultrasound, or the addition of contrast agents (barium, tantalum, technitium, gadolinium, and the like) for localization by x-ray or MRI.

One method of administration, the fibrosing agent and/or osteogenic agent is delivered under direct vision during arthroscopic evaluation of the joint. Here the composition containing the fibrosis-inducing agent, bone morphogenic protein, and/or osteogenic growth factor is injected into the articular space through the side port of an arthroscope, preferably after the remaining articular cartilage has been mechanically or chemically debrided. In some cases, the fibrosis-inducing agent may also be delivered directly to the tissue during open joint fusion surgery to enhance the efficacy of this procedure.

The injectable material may be also composed of an injectable polymer system for use in minimally invasive joint fusion. Additionally, the polymer system can provide sustained release of the fibrosis-inducing agent, bone morphogenic protein, and/or osteogenic growth factor to enhance efficacy and reduce the need for repeated intra-articular administrations of active agents. The injection material suitable for delivery of a fibrosis-inducing agent, bone morphogenic protein, and/or growth factor that promotes bone growth for the purposes of this invention can be composed of a non-degradable or a degradable material. Suitable non-degradable materials can include crosslinked compositions that comprise PVA, PVP, polyacrylamide, methyl methacrylate (MMA) and methyl methacrylate styrene (MMA-styrene) which when mixed together form polymethyl methacrylate (PMMA) or bone cement (e.g., SIMPLEX P, ZIMMER REGULAR and ZIMMER LOW VISCOSITY CEMENT, PALACOS, CMW-1 and CMW-2, ENDURANCE, synthetic cancellous bone void fillers (e.g., CORTOSS), pHEMA, poly(vinyl PEG), poly(styrene sulfonate), poly(acrylic acid), poly(methacrylic acid), as well as other polymers that are known to form hydrogels. Additional compositions include blends and copolymers of the agents listed above. Suitable degradable materials include, but are not limited to, resorbable ceramics composed of β-tricalcium phosphate (e.g., VITOSS, PROOSTEON 500R), hydroxyapatite or $Ca_{10}(PO_4)_6OH$ (e.g., BIOOSS, OSTEOGRAF), calcium carbonate or $CaCO_3$, calcium sulfate (e.g., OSTEOSET and ALLOMATRIX), calcium phosphate (e.g., CALCIBON or NORIAN SRS), crosslinked materials of PEG, gelatin, collagen, bone allografts (e.g., ALLOGRO, ORTHOBLAST, OPTEFORM, GRAFTON), mesenchymal stem cells, hyaluronic acid, hyaluronic acid derivatives, polysaccharides, carbohydrates, proteins (e.g., albumin, casein, whey proteins, plant proteins, or fish proteins, and the like), autologous bone, demineralized bone matrix, cellulose derivatives (e.g., HPC), chitosan, chitosan derivatives, polyester-polyalkylene oxide block copolymers (e.g., PLGA-PEG-PLGA or MePEG-PLGA) and other low molecular weight polymers that can be excreted. One material that is of particular interest is prepared from a 4-armed thiol PEG (10K), a 4-armed NHS PEG(10K) and methylated collagen such as described above. In one embodiment, the injectable material also contains a biologically active agent capable of inducing fibrosis and ankylosis in the treated joint. Preferred biologically active agents include fibrosis-inducing agents, bone morphogenic proteins, and growth factors (transforming growth factor, platelet-derived growth factor, fibroblast growth factor), whose dosages and release kinetics are all described in detail in section (iii) below.

In addition to, or in lieu of, fibrosis-inducing agents, bone morphogenic proteins and growth factors, the injectable material can be utilized to deliver a sclerosant to the articular space. Sclerosants include compounds such as ethanol, DMSO, surfactants, sucrose, NaCl, dextrose, glycerin, minocycline, tetracycline, doxycycline, polidocanol, sodium tetradecyl sulfate, sodium morrhuate, sotradecol and others. The hydrogel can further comprise agents such as glycerol, glycerin, PEG 200, triethyl citrate, and triacetin as plasticizers.

The injectable materials described above can further modified to be comprised of, or contain, polymeric threads. Polymeric threads have the ability to induce a fibroproliferative response from the surrounding tissue. These polymer threads can be degradable or non-degradable. Degradable threads can be composed of degradable polyesters, polyanhydrides, poly(anhydride esters), poly(ester-amides), poly(ester-ureas), polyorthoesters, polyphosphoesters, polyphosphazines, cyanoacrylate polymers, collagen, chitosan, hyaluronic acid, chromic cat gut, alginates, starch, cellulose, cellulose esters, blends and copolymers thereof, as well as other known degradable polymers. Non-degradable polymers that can be used include, but are not limited to, polyesters (e.g., PET), polyurethanes, silicones, PE, PP, PS, PAA, PMA, silk, blends, copolymers thereof as well as others known polymers. The threads used can be composed of a single composition or composed of a blend of differing compositions. The polymeric threads themselves can be further modified through the addition of a polymeric coating applied to the threads. The polymer used for coating the thread can be similar to that described above for the threads themselves. The polymer coating may further comprise a biologically active agent that has the ability to induce a fibroproliferative or osteogenic response. The agents that can be used are further described in the section (iii) below.

The injectable materials described above can be utilized to deliver a particulate material that has the ability to induce ankylosis in the joint. These particles can be either degradable or non-degradable and are similar to those described above for threads. In addition, particulate materials useful for the practice of this embodiment include talc, starch, glass, silicates, silica, calcium phosphate, calcium sulfate, calcium carbonate, hydroxyapatite, synthetic mineral (VITOSS and CORTOSS), PMMA, silver nitrate, ceramic particles and other inorganic particles known in the art to induce a fibroproliferative response followed by mineralization. The particles used in this embodiment can be all of the same composition or a blend of differing compositions. These particles can also be used as a coating applied to the polymeric strands as described above.

The injectable material can also be constructed such that it is comprised of both polymeric threads and particles. The threads and particles used are similar to those described above and may be of uniform composition or blended composition. Virtually any combination of threads of differing compositions and particles of differing compositions can be utilized in this embodiment. The hydrogel, the polymeric threads, and the particles can all be utilized to deliver one or more biologically active agents, as described below.

One specific composition comprises rods prepared from a methylated collagen-crosslinked poly(ethylene glycol) composition such as described above which has powdered silk particles and/or mineral particles added to the composition prior to curing. Once deployed, the rod can absorb water, fill the joint space and adhere to any articular cartilage or exposed bone. This expansion can prevent the rod from moving, while the powdered and/or mineral silk can initiate an ankylosing response. As the material starts to degrade, the material can support the bone tissue ingrowth that is initiated and potentiated by the particles. Bone morphogenic proteins and/or growth factors (described previously and below) are also useful for the addition to this composition. To further increase the rate of initiation of this fibroproliferative response, a sclerosant such as a surfactant (SDS), ethanolamine oleate or DMSO can be added. In addition, one may also add or replace all (or a portion) of the 4-armed thiol PEG with a 4-armed amino PEG. The amino PEG can provide a gel that can take a longer time to degrade and can provide some positive charge to further attract cellular material.

A second specific embodiment consists of an injectable implant composed of silk fibers or a polymerized version of the fibrosing agent itself (i.e., repeating units of the fibrosing agent polymerized together). The addition of bone morphogenic proteins and/or growth factors (described previously and below) is also useful for the addition to this composition.

In addition to the hydrogels, bone cements, and materials containing calcium phosphate described above, there are several other injectable compositions suitable for use in minimally invasive joint fusion procedures. All involve the deployment of a biomaterial into the joint space, with or without, the addition of a fibrosis-inducing agent, bone morphogenic protein(s), and/or a suitable growth factor(s). The following compositions can be delivered into the joint via specialized delivery catheters, an endoscope (arthroscope; typically via a sideport), a needle or other applicator, a surgically placed drain or access port, or other transdermal access device, including administration of: (a) fluids, suspensions, emulsions, microemulsions, microspheres, pastes, gels, microparticulates, sprays, aerosols, solid implants and other formulations which release a biologically active agent(s); (b) microparticulate silk and/or silk strands (linear, branched, and/or coiled) either alone, or loaded with an additional fibrosis-inducing agent, bone morphogenic protein, and/or growth factor are also useful for directed injection into the joint; (c) injectable collagen-containing formulations such as COSTASIS or materials prepared from a 4-armed thiol PEG (10K), a 4-armed NHS PEG (10K) and methylated collagen such as described above, either alone, or loaded with a fibrosis-inducing agent, bone morphogenic protein, and/or growth factor, injected into the joint space; (d) injectable PEG-containing formulations such as COSEAL, FOCALSEAL, SPRAYGEL or DURASEAL, either alone, or loaded with a fibrosis-inducing agent, bone morphogenic protein, and/or growth factor, injected into the joint space; (e) fibrinogen-containing formulations such as FLOSEAL or TISSEAL, either alone, or loaded with a fibrosis-inducing agent, bone morphogenic protein, and/or growth factor, injected into the joint space; (f) hyaluronic acid-containing formulations such as RESTYLANE, HYLAFORM, PERLANE, SYNVISC, SEPRAFILM, SEPRACOAT, either alone, or loaded with a fibrosis-inducing agent, bone morphogenic protein, and/or growth factor injected into the joint space; (g) polymeric gels for surgical implantation such as REPEL or FLOWGEL either alone, or loaded with a fibrosis-inducing agent, bone morphogenic protein, and/or growth factor injected into the joint space; (h) orthopedic "cements" such as OSTEOBOND, LVC, SIMPLEX P, PALACOS, CORTOSS, and ENDURANCE, either alone, or loaded with a fibrosis-inducing agent, bone morphogenic protein, and/or growth factor injected into the joint space; (i) surgical adhesives containing cyanoacrylates such as DERMABOND, INDERMIL, GLUSTITCH, VETBOND, HISTOACRYL, TISSUEMEND, TISSUMEND II, HISTOACRYL BLUE and ORABASE SOOTHE-N-SEAL LIQUID PROTECTANT or as described above, either alone, or loaded with a fibrosis-inducing agent, bone morphogenic protein, and/or growth factor, injected into the joint space; (j) surgical implants containing hydroxyapatite, calcium phosphate (such as VITOSS), or calcium sulfate, alone or loaded with a fibrosis-inducing agent, bone morphogenic protein, and/or growth factor, injected into the joint space; (k) other biocompatible tissue fillers, such as those made by BioCure, 3M Company and Neomend, either alone, or loaded with a fibrosis-inducing agent, bone morphogenic protein, and/or growth factor, injected into the joint space; (l) polysaccharide gels such as the ADCON series of gels, either alone, or loaded with a fibrosis-inducing agent, bone morphogenic protein, and/or growth factor, injected into the joint space; (m) films, sponges or meshes such as INTERCEED, VICRYL mesh, and GELFOAM either alone, or loaded with a fibrosis-inducing agent, bone morphogenic protein, and/or growth factor, injected into the joint space; and/or (n) a hydrogel that is formed from an amino-functionalized polyethylene glycol (e.g., 4-armed tetra-amino PEG [10k]) and a 4-armed NHS functionalized PEG (e.g., pentaerythritol poly(ethylene glycol)ether tetra-succinimidyl glutarate [10K]). This hydrogel may further contain collagen, methylated collagen and/or gelatin. This hydrogel can further comprise the fibrosis-inducing agents described above (e.g., silk powder or silk threads). In many of these embodiments, it may also be useful to add a radio-opaque material (such as tantalum, barium, other metal, or contrast material) such that the injected material can be visualized radiographically or MRI.

It should be apparent to one of skill in the art that potentially any adhesion or fibrosis-inducing agent may be utilized alone, or in combination, in the practice of this embodiment as described above. Exemplary fibrosing agents for use in minimally invasive joint fusion procedures include talc, silk, wool, chitosan, polylysine, fibronectin, bleomycin, CTGF, bone morphogenic proteins, and/or osteogenic growth factors (such as transforming growth factor, platelet-derived growth factor, fibroblast growth factor) as well as analogues and derivatives of the aforementioned.

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or a bone morphogenic protein (BMP) (e.g., BMP-2, BMP-3, BMP-4, BMP-5, BMP-6, or BMP-7 or an analogue or derivative thereof).

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

The correct administration and dosage can be described further in section (c) below.

(iii) Fibrosing Agents for Minimally Invasive Joint Fusion

Exemplary fibrosing and osteogenic agents for use in minimally invasive joint fusion include talc, silk, wool, chitosan, polylysine, fibronectin, bleomycin, CTGF, bone morphogenic proteins, and/or osteogenic growth factors (such as transforming growth factor, platelet-derived growth factor, fibroblast growth factor) as well as analogues and derivatives of the aforementioned. In some clinical situations, repeated injections of the active agents described below may be required.

The exact dose administered can vary depending upon the particular joint being treated. However, certain principles can be applied in the application of this art. Drug dose can be calculated as a function of dose per unit volume (of the amount being injected), total drug dose administered can be measured and appropriate surface concentrations of active drug can be determined. Regardless of the method of application of the drug to the affected joint, the exemplary fibrosing agents, bone morphogenic proteins, and/or osteogenic growth factors (such as transforming growth factor, platelet-derived growth factor, fibroblast growth factor), used alone or in combination, should be administered under the following dosing guidelines:

Utilizing talc as an exemplary fibrosis-inducing agent, whether it is applied using a polymer coating, incorporated into the polymers which make up the injectable, or administered without a polymeric carrier, the total dose of talc administered into a joint in any single injection should not exceed 100 mg (range of 1 µg to 100 mg). In one embodiment, the total amount of talc administered should be in the range of 10 µg to 50 mg. The dose per unit volume injected should fall within the range of 0.05 µg–10 µg per $mm^3$. In one embodiment, talc is released from the injectable such that ankylosis in the joint is promoted for a period ranging from several hours to several months. For example, talc may be released in effective concentrations for a period ranging from 2–12 weeks. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymer coating, incorporated into the polymers which make up the injectable, or administered without a polymeric carrier, the total dose of silk delivered to the joint in any single injection should not exceed 100 mg (range of 1 µg to 100 mg). In one embodiment, the total amount of silk administered to the joint should be in the range of 10 µg to 50 mg. The dose per unit volume injected should fall within the range of 0.05 µg–10 µg per $mm^3$. As specific (polymeric and non-polymeric) drug delivery vehicles can release silk at differing rates, the above dosing parameters should be utilized in combination with the release rate of the drug from the carrier such that a minimum concentration of 0.01 nM to 1000 µM of silk is continuously delivered to the tissue over the desired therapeutic time period. In one embodiment, silk is released into the joint such that ankylosis is promoted for a period ranging from several hours to several months. For example, silk may be released in effective concentrations for a period ranging from 2–12 weeks. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymer coating, incorporated into the polymers which make up the injectable, or administered without a polymeric carrier, the total dose of chitosan delivered into the joint should not exceed 100 mg (range of 1 µg to 100 mg). In one embodiment, the total amount of chitosan administered into the joint in any single injection should be in the range of 10 µg to 50 mg. The dose per unit volume injected should fall within the range of 0.05 µg–10 µg per $mm^3$. As specific (polymeric and non-polymeric) drug delivery vehicles can release chitosan at differing rates, the above dosing parameters should be utilized in combination with the release rate of the drug from the carrier such that a minimum concentration of 0.01 nM to 1000 µM of chitosan is continuously delivered to the joint tissue. In one embodiment, chitosan is released into the joint such that ankylosis is promoted for a period ranging from several hours to several months. For example, chitosan may be released in effective concentrations for a period ranging from 2–12 weeks. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as a exemplary fibrosis-inducing agent, whether it is applied using a polymer coating, incorporated into the polymers which make up the injectable, or administered without a polymeric carrier, the total dose of polylysine delivered into the joint in a single injection should not exceed 100 mg (range of 1 µg to 100 mg). In one embodiment, the total amount of polylysine delivered to the joint should be in the range of 10 µg to 50 mg. The dose per unit volume injected should fall within the range of 0.05 µg–10 µg per $mm^3$. In another embodiment, polylysine should be injected into the joint at a dose of 0.05–10 µg/$mm^3$. As specific (polymeric and non-polymeric) drug delivery vehicles can release polylysine at differing rates, the above dosing parameters should be utilized in combination with the release rate of the drug from the carrier such that a minimum concentration of 0.01 nM to 1000 µM of polylysine is continuously delivered to the joint tissue. In one embodiment, polylysine is administered to the joint such that ankylosis is promoted for a period ranging from several hours to several months. For example, polylysine may be released in effective concentrations for a period ranging from 2–12 weeks. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymer coating, incorporated into the polymers which make up the injectable, or administered without a polymeric carrier, the total dose of fibronectin delivered into the joint in a single injection should not exceed 100 mg (range of 1 µg to 100 mg). In one embodiment, the total amount of fibronectin injected into the joint should be in the range of 10 µg to 50 mg. The dose per unit volume of the injection should fall within the range of 0.05 µg–10 µg per $mm^3$. In another embodiment, talc should be administered at a dose of 0.05–10 µg/$mm^3$ of injected material. As specific (polymeric and non-polymeric) drug delivery vehicles can release fibronectin at differing rates, the above dosing parameters should be utilized in combination with the release rate of the drug from the carrier such that a minimum concentration of 0.01 nM to 1000 µM of fibronectin is continuously delivered to the tissue. In one embodiment, fibronectin is released into the joint such that ankylosis is promoted for a period ranging from several hours to several months. For example, fibronectin may be released in effective concentrations for a period ranging from 2–12 weeks. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, whether it is applied using a polymer coating, incorporated into the polymers which make up the injectable, or administered without a polymeric carrier, the total dose of bleomycin administered to a joint in a single injection should not exceed 100 mg (range of 0.01 µg to 100 mg). In one embodiment, the total amount of bleomycin injected into the joint should be in the range of 0.10 µg to 50 mg. The dose per unit volume injected should fall within the range of 0.005 µg–10 µg per $mm^3$. As specific (polymeric and non-polymeric) drug delivery vehicles can release bleomycin at differing rates, the above dosing parameters should be utilized in combination with the release rate of the drug from the carrier such that a minimum concentration of 0.001 nM to 1000 µM of bleomycin is continuously delivered to the joint. In one embodiment, bleomycin is released from the injection such that ankylosis in the joint is promoted for a period ranging from several hours to several months. For example, bleomycin may be released in effective concentrations for a period ranging from 2–12 weeks. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as an exemplary fibrosis-inducing agent, whether it is applied using a polymer coating, incorporated into the polymers which make up the injectable, or administered without a polymeric carrier, the total dose of CTGF administered to the joint in a single injection should not exceed 100 mg (range of 0.01 µg to 100 mg). In one embodiment, the total amount of CTGF injected into the joint should be in the range of 0.10 µg to 50 mg. The dose per unit volume of the injection should fall within the range of 0.005 µg–10 µg per $mm^3$. In another embodiment, CTGF should be injected at a dose of 0.005–10 µg/$mm^3$. As specific (polymeric and non-polymeric) drug delivery vehicles can release CTGF at differing rates, the above dosing parameters should be utilized in combination with the release rate of the drug from the carrier such that a minimum concentration of 0.001 nM to 1000 µM of CTGF is continuously delivered to the joint. In one embodiment, CTGF is released from the injectable such that ankylosis in the joint is promoted for a period ranging from several hours to several months. For example, CTGF may be released in effective concentrations for a period ranging from 2–12 weeks. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or a bone morphogenic protein (BMP) (e.g., BMP-2, BMP-3, BMP-4, BMP-5, BMP-6, or BMP-7 or an analogue or derivative thereof).

Inflammatory cytokines are to be used in formulations at concentrations that range from 0.0001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 µg to 100 mg); preferred 0.001 µg to 50 mg. When used as a device coating, the dose is per unit area of 0.0001 µg–500 µg per mm$^2$; with a preferred dose of 0.001 µg/mm$^2$–200 µg/mm$^2$. Minimum concentration of $10^{-10}$–$10^{-4}$ g/ml of inflammatory cytokine is to be maintained on the device surface.

Bone morphogenic protein(s) (e.g., BMP-2, BMP-3, BMP-4, BMP-5, BMP-6, or BMP-7 or an analogue or derivative thereof) are to be used in formulations at concentrations that range from 0.001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the bone morphogenic protein is released in effective concentrations for a period ranging from 1–180 days. The total dose for a single application is typically not to exceed 500 mg (range of 0.001 µg to 500 mg); preferred 1 µg to 250 mg. When used as a device coating, the dose is per unit area of 0.001 µg–1000 µg per mm$^2$; with a preferred dose of 0.01 µg/mm$^2$–200 µg/mm$^2$. Minimum concentration of $10^{-9}$–$10^{-4}$ M of bone morphogenic protein is to be maintained on the device surface.

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof. Doses used are those concentrations which are demonstrated to stimulate cell proliferation (Example 16). The proliferative agents are to be used in formulations at concentrations that range from 0.01 ng/mL to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 µg to 200 mg); preferred 0.001 µg to 100 mg. When used as a device coating, the dose is per unit area of 0.00001 µg–500 µg per mm$^2$; with a preferred dose of 0.0001 µg/mm$^2$–200 µg/mm$^2$. Minimum concentration of $10^{-11}$–$10^{-6}$ M of proliferative agent is to be maintained on the device surface.

It should be readily evident to one of skill in the art that any of the previously described fibrosis-inducing agents, bone morphogenic proteins, or osteogenic growth factors, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

5. Female and Male Sterilization Devices

Permanent, highly reliable, minimally invasive methods of preventing conception are required in both men's and women's health. Although tubal ligation and vasectomy have a low failure rate (approximately 1%), recently there have been advancements in making the procedures less invasive. This is particularly true for tubal ligation where a surgical procedure, either open or endoscopic, is required to "clip" the fallopian tubes. Newer implants have been designed to obstruct the fallopian tubes (or vas deferens in the male) through the non-surgical placement of implants that block the interior lumen of the reproductive tract. Unfortunately, since the reproductive tract is not physically severed (and the two ends clipped shut as in the surgical procedure), there remains the possibility that the fallopian tube (or vas deferens) can re-cannulate over time and restore fertility. The present invention provides compositions, implants and devices that include a fibrosis-inducing agent to promote scarring of the walls of the reproductive tract in the vicinity of the implant or device. The result is the formation of permanent scar tissue between the walls of the fallopian tube (or vas deferens) that completely obstructs the lumen, prevents the movement of the gametes through the tract, and lowers the failure rate of the procedure (measured as the prevention of unwanted pregnancies).

(i) Permanent Female Contraceptive Devices (a) Fallopian Tube Implants

Numerous techniques and devices are known and available to ligate or obstruct the fallopian tube such that the ovum cannot reach the uterus and conception and implantation cannot occur. As described above, surgical ligation and/or clipping of the fallopian tubes has been considered the "gold standard" for permanent contraception in women for many years. Various clamps and clips for this purpose have been described, including for example: a duct clamp described in U.S. Pat. No. 4,489,725; valved sterilization devices described in U.S. Pat. Nos. 3,704,704 and 3,777,737; and temporary sterilization devices described in U.S. Pat. No. 3,918,431. These devices are suitable for coating with a fibrosis-inducing agent to further enhance their effectiveness and reduce their failure rate. Unfortunately, these procedures have the obvious disadvantage of requiring placement during open or endoscopic surgery.

However, a preferred embodiment of the present invention involves delivering a fibrosis-inducing agent in combination with a variety of devices and implants designed for placement in the fallopian tubes without the need for surgery. Although variable in design, all are intended to be placed transvaginally (i.e., the device or implant is inserted into the vagina, through the uterus, and placed into the interior lumen of the fallopian tube), thus eliminating the need for surgical access to the external (intra-abdominal/pelvic) surface of the fallopian tube via the abdomen. As a result, these implants obstruct the fallopian tube from the inside (luminal surface) and can be performed in a conscious patient in much the same manner as a gynecological exam. Examples of fallopian tube implants suitable for delivering a fibrosis-inducing agent that enhances tubal occlusion include: implantable, intrafallopian, female sterilization devices (such as those described in U.S. Pat. Nos. 6,245,090; 6,068,626; and 3,675,639); occlusive wire or coil fallopian tube implants (such as those described in U.S. Pat. No. 5,601,600); transcatheter occluding implants (such as those described in U.S. Pat. No. 6,245,090); and fallopian tube stents (for example those described in U.S. Pat. No. 5,474, 089). In addition, contraceptive uterine implants, such as intrauterine devices (IUDs), can also be suitable for use in this embodiment.

Specific female sterilization devices (fallopian tube implants) suitable for the delivery of one or more fibrosis-inducing agents according to the present invention include several commercially available products. For example, the ESSURE device is a catheter-delivered stent filled with fiber (a soft micro-insert) designed to occlude the fallopian tubes (Conceptus, Inc., San Carlos, Calif.) and is described in U.S. Pat. Nos. 6,176,240; 6,526,979; 5,601,600; and 5,746,769. The ECLIPSE from Ovion (Redwood City, Calif.) is a self-expanding nitinol stent filled with polyester fibers that is delivered transvaginally via a catheter into the fallopian tubes. Other contraceptive fallopian tube implants include porous plastic fibers (Adiana, Redwood, Calif.) and single rod implants such as IMPLANON from Organon Corporation (West Orange, N.J.).

Regardless of the specific design, the aforementioned contraceptive implants can be adapted to release an agent which induces fibrosis or adhesion within the fallopian tube. The result can be enhanced scarring around the implant, more complete (and permanent) filling and/or occlusion of the lumen of the fallopian tube, and a reduction in the likelihood that female or male reproductive cells can traverse the blockade and come in contact with each other— thereby reducing the incidence of unwanted intrauterine pregnancy or tubal pregnancy. Fallopian tube implants may be adapted to have a fibrosis-inducing agent incorporated into their structure, adapted to have a surface coating of a fibrosis-inducing agent and/or adapted to release a fibrosis-inducing agent. This can be accomplished in several manners including: (a) directly affixing to the fallopian tube implant/device a desired fibrosis-inducing agent, or affixing a composition containing the fibrosis-inducing agent (for example, by spraying the implant with a drug and/or drug-carrier (polymeric or non-polymeric) composition to create a film/coating on all (or parts) of the internal and/or external surface of the device; by dipping the implant or device into a drug and/or drug-carrier (polymeric or non-polymeric) solution to coat all (or parts) of the device/implant; or by covalent or non-covalent attachment (such as mechanical attachment via knotting, using an adhesive, thermal treatment, electrostatic attachment, ionic attachment, hydrophobic interactions, or hydrogen bonding) of the therapeutic agent to the device/implant surface); (b) by coating the fallopian tube device/implant with a substance such as a hydrogel which can in turn absorb the desired fibrosis-inducing agent or composition; (c) by interweaving a "thread" composed of, or coated with, the fibrosis-inducing agent into the fallopian tube implant/device (e.g., a polymeric strand composed of a fibrosis-inducing agent (e.g., silk, collagen, EVA, PLA, polyurethanes, polymerized drug compositions) or a thread coated with a polymer which is comprised of, or releases a fibrosis-inducing agent); (d) by covering all, or portions of the fallopian tube device/implant with a sleeve, cover or mesh containing a fibrosis-inducing agent (i.e., a covering comprised of a fibrosis-inducing agent—polymers such as silk, collagen, EVA, PLA, polyurethanes—or polymerized compositions that release fibrosis-inducing agents); (e) constructing all, or parts of the fallopian tube implant/device from a fibrosis-inducing agent (e.g., constructing it from polymers such as silk, collagen, EVA, PLA, polyurethanes or polymerized compositions of fibrosis-inducing agents)—which may be particularly effective for the IMPLANON rod or the Adiana porous fibers; (f) for fallopian tube stent devices (such as the ESSURE or ECLIPSE), the central "filling" material can be composed of, or coated with, the fibrosis-inducing agent (e.g., polymeric fibers composed of a fibrosis-inducing agent (e.g., silk, collagen, EVA, PLA, polyurethanes, polymerized drug compositions) or coating the fibers with a polymer which is comprised of, or releases a fibrosis-inducing agent); (g) otherwise impregnating the fallopian tube implant/device with the desired fibrosis-inducing agent or composition; (h) scoring (i.e., creating ridges or indentations) on all, or parts, of the device or implant surface to produce irritation and ultimately fibrosis; (i) composing all, or parts, of the device or implant from metal alloys that induce fibrosis (e.g., copper); (j) constructing all, or parts of the device or implant itself from a degradable or non-degradable polymer that releases one or more fibrosis-inducing agents—which may be particularly effective for the IMPLANON rod, the Adiana porous fibers or the central filling material in the ESSURE or ECLIPSE devices; and/or (k) utilizing specialized multi-drug releasing medical device systems (described, e.g., in U.S. Pat. No. 6,562,065; U.S. Patent Application Publication Nos. 2003/0199970 and 2003/0167085 and in WO 03/015664 and WO 02/32347) to deliver fibrosis-inducing agents alone, or in combination.

It should be apparent to one of skill in the art that potentially any adhesion or fibrosis-inducing agent may be utilized alone, or in combination, in the practice of this embodiment as described above. Exemplary fibrosing agents for use in fallopian tube implants and devices include talc, silk, wool, chitosan, polylysine, fibronectin, bleomycin, and CTGF, as well as analogues and derivatives of the aforementioned.

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or a bone morphogenic protein (BMP) (e.g., BMP-2, BMP-3, BMP-4, BMP-5, BMP-6, OR BMP-7 or an analogue or derivative thereof).

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

The correct administration and dosage can be described further in section (c) below.

(b) Injectable Fallopian Tube Implants

Another preferred embodiment of the present invention involves delivering a fibrosis-inducing agent in combination with a biomaterial designed for injection into the fallopian tubes to "plug" or obstruct the tube. Many different biomaterials are suitable for injection into the fallopian tube via a transvaginal route of administration (i.e., the delivery device is inserted into the vagina, through the uterus, placed into the interior lumen of the fallopian tube, and the biomaterial containing a fibrosis-inducing agent is injected into the lumen of the fallopian tube), thus eliminating the need for surgical access to the external (intra-abdominal/pelvic) surface of the fallopian tube via the abdomen. As a result, these implants obstruct the fallopian tube from the inside (luminal surface) and can be performed in a conscious patient in much the same manner as a gynecological exam. The biomaterial can obstruct the lumen of the tube, while the fibrosis-inducing agent encourages the formation of scar tissue between the walls of the fallopian tube to permanently obstruct the lumen, prevent the movement of the gametes through the tract, and lower the failure rate of the procedure (measured as the prevention of unwanted pregnancies).

The injectable material may be composed of a hydrogel for use in the sterilization of a mammalian female. The hydrogel can be composed of a non-degradable or a degradable material. Non-degradable materials can include crosslinked compositions that comprise PVA, PVP, polyacrylamide, pHEMA, poly(vinyl PEG), poly(styrene sulfonate), poly(acrylic acid), poly(methacrylic acid), as well as other polymers that are known to form hydrogels. Additional compositions include blends and copolymers of the agents listed above. Degradable materials include, but are not limited to, crosslinked materials of PEG, gelatin, collagen, hyaluronic acid, hyaluronic acid derivatives, polysaccharides, carbohydrates, proteins (e.g., albumin, casein, whey proteins, plant proteins, and fish proteins), cellulose derivatives (e.g., HPC), chitosan, chitosan derivatives, polyester-polyalkylene oxide block copolymers (e.g., PLGA-PEG-PLGA and MePEG-PLGA) and other low molecular weight polymers that can be excreted. One material that is of particular interest is prepared from a 4-armed thiol PEG (10K), a 4-armed NHS PEG(10K) and methylated collagen such as described above. In a preferred embodiment, the hydrogel also contains a biologically active agent capable of inducing fibrosis in the fallopian tube. Preferred, biologically active, fibrosis-inducing, agents, their dosages and their release kinetics, are all described in detail in section (c) below.

In addition to, or in lieu of, fibrosis-inducing agents, the hydrogel can be utilized to deliver a sclerosant to the fallopian tube. Sclerosants include compounds such as ethanol, DMSO, surfactants, sucrose, NaCl, dextrose, glycerin, minocycline, tetracycline, doxycycline, polidocanol, sodium tetradecyl sulfate, sodium morrhuate, sotradecol and others. The hydrogel can further comprise agents such as glycerol, glycerin, PEG 200, triethyl citrate, and triacetin as plasticizers.

The hydrogels described above can further modified to be comprised of, or contain, polymeric threads. Polymeric threads have the ability to induce a fibroproliferative response from the surrounding tissue in the fallopian tube. These polymer threads can be degradable or non-degradable. Degradable threads can be composed of degradable polyesters, polyanhydrides, poly(anhydride esters), poly(ester-amides), poly(ester-ureas), polyorthoesters, polyphosphoesters, polyphosphazines, cyanoacrylate polymers, collagen, chitosan, hyaluronic acid, chromic cat gut, alginates, starch, cellulose, cellulose esters, blends and copolymers thereof, as well as other known degradable polymers. Non-degradable polymers that can be used include, but are not limited to, polyesters (e.g., PET), polyurethanes, silicones, PE, PP, PS, PAA, PMA, silk, blends, copolymers thereof as well as other known polymers. The threads used can be composed of a single composition or composed of a blend of differing compositions. The polymeric threads themselves can be further modified through the addition of a polymeric coating applied to the threads. The polymer used for coating the thread can be similar to that described above for the threads themselves. The polymer coating may further comprise a biologically active agent that has the ability to induce a fibroproliferative response. The agents that can be used are further described in the section (c) below.

The hydrogels described above can be utilized to deliver a particulate material that has the ability to induce a fibroproliferative response in the fallopian tube. These particles can be either degradable or non-degradable and are similar to those described above for threads. In addition to those, particulate materials useful for the practice of this embodiment include talc, starch, glass, silicates, silica, silver nitrate, ceramic particles and other inorganic particles known in the art to induce a fibroproliferative response. The particles used in this embodiment can be all of the same composition or a blend of differing compositions. These particles can also be used as a coating applied to the polymeric strands as described above.

As is readily apparent, the hydrogel can also be constructed such that it is comprised of both polymeric threads and particles. The threads and particles used are similar to those described above and may be of uniform composition or blended composition. Virtually any combination of threads of differing compositions and particles of differing compositions can be utilized in this embodiment. The hydrogel, the polymeric threads, and the particles can all be utilized to deliver one or more biologically active agents, as described below.

In a further embodiment, the hydrogel can be formed into a variety of shapes and sizes for implantation into the fallopian tubes. For example, the hydrogel can be shaped into a rod of the desired length or subsequently cut to the appropriate length. The hydrogel can be made into another shape and then further processed to form a rod of the appropriate dimensions. The rods can be cylindrical in shape or they can have a tapered shape or an hourglass shape. The hydrogel can also be formed into a rectangular shape by adding the appropriate reagents to a mould and then curing the composition. A cork-borer type device of the appropriate dimensions can be used to produce rods. The thickness of the initial hydrogel can determine if these rods have to be further cut into the appropriate lengths. These rods can be then dehydrated by freeze drying or by air drying. The freeze-dried rods may have more of a foam structure while the air dried rods may be of a more solid nature. The particles and/or biologically active agents can be incorporated into the hydrogel prior to the curing stage. The particles can be applied to the surface by rolling the rods in the particles or by applying the particles to the surface by dipping, spraying or painting. The particles can be applied in combination with a coating polymer that may dissolve or degrade. This coating polymer may be gelatin, hydroxypropyl cellulose, MePEG-PLA, MePEG-polyester, polyester-PEG-polyester, or the like.

The polymer threads can be added prior to the curing stage or they can be added after the hydrogel has cured. The polymer threads can be added before or after the drying stage of the rods. The threads may be wrapped around the external surface of the rod. The needle may be used to pass the threads through the rod in a vertical, horizontal, diagonal manner or a combination thereof. The threads may be placed such that they form loops protruding from the surface of the rod.

One specific composition comprises rods prepared from a methylated collagen-crosslinked poly(ethylene glycol) composition such as described above which has powdered silk particles added to the composition prior to curing. Once deployed, the rod can absorb water and thereby occlude the fallopian tube. This expansion can prevent the rod from moving, while the powdered silk can initiate a fibroproliferative response. As the methylated collagen-crosslinked poly(ethylene glycol) composition starts to degrade, the material can support the fibrous tissue ingrowth that is initiated and potentiated by the silk particles. To further increase the rate of initiation of this fibroproliferative response, a sclerosant such as a surfactant (SDS), ethanolamine oleate or DMSO can be added. In addition, one may also add or replace all (or a portion) of the 4-armed thiol PEG with a 4-armed amino PEG. The amino PEG can provide a gel that can take a longer time to degrade and can provide some positive charge to further attract cellular material.

A second specific embodiment consists of an implant composed of silk fibers or from a polymerized version of the fibrosing agent itself (i.e., repeating units of the fibrosing agent polymerized together).

In addition to the hydrogels and related implants described above, there are several other ways to practice this embodiment. All involve the deployment of a biomaterial into the lumen of the fallopian tube with or without the addition of a fibrosis-inducing agent. The practice of this embodiment can be performed in several ways including: (a) topical application of the fibrosing agent onto the luminal surface of the fallopian tube (particularly useful for this embodiment is the use of polymeric carriers which release the fibrosing agent over a period ranging from several hours to several weeks—fluids, suspensions, emulsions, microemulsions, microspheres, pastes, gels, microparticulates, sprays, aerosols, solid implants and other formulations which release a fibrosing agent can be delivered into the fallopian tube via specialized delivery catheters or other applicators); (b) microparticulate silk and/or silk strands (linear, branched, and/or coiled), either alone, or loaded with an additional fibrosis-inducing agent are also useful for directed injection into the fallopian tube; (c) sprayable collagen-containing formulations such as COSTASIS or materials made from 4-armed thiol PEG (10K), a 4-armed NHS PEG(10K) and methylated collagen such as described above, either alone, or loaded with a fibrosis-inducing agent, applied to the lumen of the fallopian tube; (d) sprayable PEG-containing formulations such as COSEAL, FOCALSEAL, SPRAYGEL or DURASEAL, either alone, or loaded with a fibrosis-inducing agent, applied to the lumen of the fallopian tube; (e) fibrinogen-containing formulations such as FLOSEAL or TISSEAL, either alone, or loaded with a fibrosis-inducing agent, applied to the lumen of the fallopian tube; (f) hyaluronic acid-containing formulations such as RESTYLANE, HYLAFORM, PERLANE, SYNVISC, SEPRAFILM, SEPRACOAT loaded with a fibrosis-inducing agent applied to the lumen of the fallopian tube; (g) polymeric gels for surgical implantation such as REPEL or FLOWGEL, either alone, or loaded with a fibrosis-inducing agent applied to the lumen of the fallopian tube; (h) orthopedic "cements" such as OSTEOBOND, LVC, SIMPLEX P, PALACOS, CORTOSS, and ENDURANCE, either alone, or loaded with a fibrosis-inducing agent applied to the luminal surface of the fallopian tube; (i) surgical adhesives containing cyanoacrylates such as DERMABOND, INDERMIL, GLUSTITCH, VETBOND, HISTOACRYL, TISSUEMEND, TISSUMEND II, HISTOACRYL BLUE and ORABASE SOOTHE-N-SEAL LIQUID PROTECTANT or as described above, either alone, or loaded with a fibrosis-inducing agent, applied to the lumen of the fallopian tube; (j) surgical implants containing hydroxyapatite, calcium phosphate (e.g., VITOSS), or calcium sulfate, either alone, or loaded with a fibrosis-inducing agent applied to the lumen of the fallopian tube; (k) other biocompatible tissue fillers, such as those made by BioCure, 3M Company and Neomend, either alone, or loaded with a fibrosis-inducing agent, applied to the lumen of the fallopian tube; (l) polysaccharide gels such as the ADCON series of gels loaded with a fibrosis-inducing agent applied to the lumen of the fallopian tube; (m) films, sponges or meshes such as INTERCEED, VICRYL mesh, and GEL-FOAM, either alone, or loaded with a fibrosis-inducing agent applied to the lumen of the fallopian tube and/or (n) a hydrogel that is formed from an amino-functionalized polyethylene glycol (e.g., 4-armed tetra-amino PEG [10k]) and a 4-armed NHS functionalized PEG (e.g., pentaerythritol poly(ethylene glycol)ether tetra-succinimidyl glutarate [10K]). This hydrogel may further contain collagen, methylated collagen and/or gelatin. This hydrogel can further comprise the fibrosis-inducing agents described above (e.g., silk powder or silk threads).

In many of the embodiments described above it may also be useful to add a radio-opaque material (such as tantalum, technetium, gadolinium, barium, other metal, or contrast material) such that the injected material can be visualized radiographically or MRI. The contrast agent may be a water soluble or water insoluble radio-opaque material. Alternatively the gel or the coated implant can contain air bubbles (e.g., ECHO-COAT) or air can be injected into the tube such that visualization by ultrasound is enhanced.

It should be apparent to one of skill in the art that potentially any adhesion or fibrosis-inducing agent may be utilized alone, or in combination, in the practice of this embodiment as described above. Exemplary fibrosing agents for use in fallopian tube implants and devices include talc, silk, wool, chitosan, polylysine, fibronectin, bleomycin, and CTGF, as well as analogues and derivatives of the aforementioned.

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone).

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

The correct administration and dosage can be described further in section (c) below.

(c) Fibrosing Agents for Fallopian Tube Implants

As fallopian tube implants are made in a variety of configurations and sizes, the exact dose administered can vary with device size, surface area and design. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the sterilization device, the exemplary fibrosing agents, used alone or in combination, should be administered under the following dosing guidelines:

Utilizing talc as an exemplary fibrosis-inducing agent, whether it is applied using a polymer coating, incorporated into the polymers which make up the device or implant, incorporated into an injectable, or applied without a polymeric carrier, the total dose of talc delivered from a sterilization device, or coated onto the surface of a sterilization device, should not exceed 100 mg (range of 1 µg to 100 mg). In one embodiment, the total amount of talc released from the prosthesis should be in the range of 10 µg to 50 mg. The dose per unit area of the device (i.e., the dosage of talc as a function of the surface area of the portion of the device to which drug is applied and/or incorporated) should fall within the range of 0.05 µg–10 µg per $mm^2$ of surface area coated. In another embodiment, talc should be applied to a sterilization device surface at a dose of 0.05 µg/mm$^2$–10 µg/mm$^2$ of surface area coated. In one embodiment, talc is released from the surface of a sterilization device such that fibrosis in the tissue is promoted for a period ranging from several hours to several months. For example, talc may be released in effective concentrations for a period ranging from 1 hour–30 days. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymer coating, incorporated into the polymers which make up the device or implant, incorporated into an injectable, or applied without a polymeric carrier, the total dose of silk delivered from a sterilization device, or coated onto the surface of a sterilization device, should not exceed 100 mg (range of 1 µg to 100 mg). In one embodiment, the total amount of silk released from the prosthesis should be in the range of 10 µg to 50 mg. The dose per unit area of the device (i.e., the dosage of silk as a function of the surface area of the portion of the device to which drug is applied and/or incorporated) should fall within the range of 0.05 µg–10 µg per mm$^2$ of surface area coated. In another embodiment, silk should be applied to a sterilization device surface at a dose of 0.05 µg/mm$^2$–10 µg/mm$^2$ of surface area coated. As specific (polymeric and non-polymeric) drug delivery vehicles and specific medical devices can release silk at differing rates, the above dosing parameters should be utilized in combination with the release rate of the drug from the sterilization device such that a minimum concentration of 0.01 nM to 1000 µM of silk is delivered to the tissue. In one embodiment, silk is released from the surface of a sterilization device such that fibrosis in the tissue is promoted for a period ranging from several hours to several months. For example, silk may be released in effective concentrations for a period ranging from 1 hour–30 days. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymer coating, incorporated into the polymers which make up the device or implant, incorporated into an injectable, or applied without a polymeric carrier, the total dose of chitosan delivered from a sterilization device, or coated onto the surface of a sterilization device, should not exceed 100 mg (range of 1 µg to 100 mg). In one embodiment, the total amount of chitosan released from the prosthesis should be in the range of 10 µg to 50 mg. The dose per unit area of the device (i.e., the dosage of chitosan as a function of the surface area of the portion of the device to which drug is applied and/or incorporated) should fall within the range of 0.05 µg–10 µg per mm$^2$ of surface area coated. In another embodiment, chitosan should be applied to a sterilization device surface at a dose of 0.05 µg/mm$^2$–10 µg/mm$^2$ of surface area coated. As specific (polymeric and non-polymeric) drug delivery vehicles and specific medical devices can release chitosan at differing rates, the above dosing parameters should be utilized in combination with the release rate of the drug from the sterilization device such that a minimum concentration of 0.01 nM to 1000 µM of chitosan is delivered to the tissue. In one embodiment, chitosan is released from the surface of a sterilization device such that fibrosis in the tissue is promoted for a period ranging from several hours to several months. For example, chitosan may be released in effective concentrations for a period ranging from 1 hour–30 days. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as a exemplary fibrosis-inducing agent, whether it is applied using a polymer coating, incorporated into the polymers which make up the device or implant, incorporated into an injectable, or applied without a polymeric carrier, the total dose of polylysine delivered from a sterilization device, or coated onto the surface of a sterilization device, should not exceed 100 mg (range of 1 µg to 100 mg). In one embodiment, the total amount of polylysine released from the prosthesis should be in the range of 10 µg to 50 mg. The dose per unit area of the device (i.e., the dosage of polylysine as a function of the surface area of the portion of the device to which drug is applied and/or incorporated) should fall within the range of 0.05 µg–10 µg per mm$^2$ of surface area coated. In another embodiment, polylysine should be applied to a sterilization device surface at a dose of 0.05 µg/mm$^2$–10 µg/mm$^2$ of surface area coated. As specific (polymeric and non-polymeric) drug delivery vehicles and specific medical devices can release polylysine at differing rates, the above dosing parameters should be utilized in combination with the release rate of the drug from the sterilization device such that a minimum concentration of 0.01 nM to 1000 µM of polylysine is delivered to the tissue. In one embodiment, polylysine is released from the surface of a sterilization device such that fibrosis in the tissue is promoted for a period ranging from several hours to several months. For example, polylysine may be released in effective concentrations for a period ranging from 1 hour–30 days. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymer coating, incorporated into the polymers which make up the device or implant, incorporated into an injectable, or applied without a polymeric carrier, the total dose of fibronectin delivered from a sterilization device, or coated onto the surface of a sterilization device, should not exceed 100 mg (range of 1 µg to 100 mg). In one embodiment, the total amount of fibronectin released from the prosthesis should be in the range of 10 µg to 50 mg. The dose per unit area of the device (i.e., the dosage of fibronectin as a function of the surface area of the portion of the device to which drug is applied and/or incorporated) should fall within the range of 0.05 µg–10 µg per mm$^2$ of surface area coated. In another embodiment, fibronectin should be applied to a sterilization device surface at a dose of 0.05 µg/mm$^2$–10 µg/mm$^2$ of surface area coated. As specific (polymeric and non-polymeric) drug delivery vehicles and specific medical devices can release fibronectin at differing rates, the above dosing parameters should be utilized in combination with the release rate of the drug from the sterilization device such that a minimum concentration of 0.01 nM to 1000 µM of fibronectin is delivered to the tissue. In one embodiment, fibronectin is released from the surface of a sterilization device such that fibrosis in the tissue is promoted for a period ranging from several hours to several months. For example, fibronectin may be released in effective concentrations for a period ranging from 1 hour–30 days. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, whether it is applied using a polymer coating, incorporated into the polymers which make up the device or implant, incorporated into an injectable, or applied without a polymeric carrier, the total dose of bleomycin delivered from a sterilization device, or coated onto the surface of a sterilization device, should not exceed 100 mg (range of 0.01 µg to 100 mg). In one embodiment, the total amount of bleomycin released from the prosthesis should be in the range of 0.10 µg to 50 mg. The dose per unit area of the device (i.e., the dosage of bleomycin as a function of the surface area of the portion of the device to which drug is applied and/or incorporated) should fall within the range of 0.005 µg–10 µg per mm$^2$ of surface area coated. In another embodiment, bleomycin should be applied to a sterilization device surface at a dose of 0.005 µg/mm$^2$–10 µg/mm$^2$ of surface area coated. As specific (polymeric and non-polymeric) drug delivery vehicles and specific medical devices can release bleomycin at differing rates, the above dosing parameters should be utilized in combination with the release rate of the drug from the sterilization device such that a minimum concentration of 0.001 nM to 1000 µM of bleomycin is delivered to the tissue. In one embodiment, bleomycin is released from the surface of a sterilization device such that fibrosis in the tissue is promoted for a period ranging from several hours to several months. For example, bleomycin may be released in effective concentrations for a period ranging from 1 hour–30 days. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as an exemplary fibrosis-inducing agent, whether it is applied using a polymer coating, incorporated into the polymers which make up the device or implant, incorporated into an injectable, or applied without a polymeric carrier, the total dose of CTGF delivered from a sterilization device, or coated onto the surface of a sterilization device, should not exceed 100 mg (range of 0.01 µg to 100 mg). In one embodiment, the total amount of CTGF released from the prosthesis should be in the range of 0.10 µg to 50 mg. The dose per unit area of the device (i.e., the dosage of CTGF as a function of the surface area of the portion of the device to which drug is applied and/or incorporated) should fall within the range of 0.005 µg–10 µg per mm$^2$ of surface area coated. In another embodiment, CTGF should be applied to a sterilization device surface at a dose of 0.005 µg/mm$^2$–10 µg/mm$^2$ of surface area coated. As specific (polymeric and non-polymeric) drug delivery vehicles and specific medical devices can release CTGF at differing rates, the above dosing parameters should be utilized in combination with the release rate of the drug from the a sterilization device such that a minimum concentration of 0.001 nM to 1000 µM of CTGF is delivered to the tissue. In one embodiment, CTGF is released from the surface of a sterilization device such that fibrosis in the tissue is promoted for a period ranging from several hours to several months. For example, CTGF may be released in effective concentrations for a period ranging from 1 hour–30 days. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone). Inflammatory cytokines are to be used in formulations at concentrations that range from 0.0001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 µg to 100 mg); preferred 0.001 µg to 50 mg. When used as a device coating, the dose is per unit area of 0.0001 µg–500 µg per mm$^2$; with a preferred dose of 0.001 µg/mm$^2$–200 µg/mm$^2$. Minimum concentration of $10^{-10}$–$10^4$ g/ml of inflammatory cytokine is to be maintained on the device surface.

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin D$_3$, diethylstibesterol, cyclosporine A, L-NAME, all-trans retinoic acid (ATRA), and analogues and derivatives thereof. Doses used are those concentrations which are demonstrated to stimulate cell proliferation (Example 16).

The proliferative agents are to be used in formulations at concentrations that range from 0.01 ng/ml to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 μg to 200 mg); preferred 0.001 μg to 100 mg. When used as a device coating, the dose is per unit area of 0.00001 μg–500 μg per $mm^2$; with a preferred dose of 0.0001 $μg/mm^2$–200 $μg/mm^2$. Minimum concentration of $10^{-11}$–$10^{-6}$ M of proliferative agent is to be maintained on the device surface.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

(ii) Male Permanent Contraceptive Devices

For permanent contraception in men, vasectomy is a commonly used, highly effective method for the control of fertility. A common vasectomy procedure involves injecting local anesthetic alongside the vas deferens, opening the scrotum with pointed dissecting forceps, pulling the vas through the puncture, and occluding or cutting the vas deferens (e.g., using a ligation technique in which the vas is ligatured at one or both ends with a suture, application of an implantable clip, or by cutting and/or cauterizing the vas).

(a) Deferens Implants

Several devices for male contraception have been disclosed including valved sterilization devices for surgical insertion within the vas deferens described in U.S. Pat. Nos. 3,704,704 and 3,777,737, a reversible male sterilization device described in U.S. Pat. No. 4,682,592, and vasectomy and Intra-Vas devices described in U.S. Pat. Nos. 3,589,355 and 4,200,088, 3,648,683, and 3,589,355. Commercially available vasectomy clips include those produced by Advanced Meditech International, Inc. (Flushing, N.Y.) and the VASCLIP from VMBC, LLC (Roseville, Minn.) In the present invention, the incorporation of a fibrosis-inducing agent onto or into vasectomy sutures, clips, or implantable devices (such as those described above) can promote fibrosis of the vas deferens, produce a more complete occlusion, and increase the success rate of the procedure.

For clips, sutures, and other implanted devices, there are several methods available for incorporating fibrosing compositions onto or into the vas deferens implant, including: (a) directly affixing to the device a fibrosing composition (e.g., by either a spraying process or dipping process as described above, with or without a carrier); (b) directly incorporating into the device a fibrosing composition (e.g., by either a spraying process or dipping process as described above, with or without a carrier); (c) by coating the device with a substance such as a hydrogel which can in turn absorb the fibrosing composition; (d) by interweaving into the device structure a thread coated with a fibrosis-inducing agent (or the fibrosis agent-polymer composition itself is formed into a thread); (e) by inserting the device into a sleeve or mesh which is comprised of, or coated with, a fibrosing composition; (f) constructing the device itself (or a portion of the device) with a fibrosing composition; or (g) by covalently binding the fibrosing agent directly to the device surface or to a linker (small molecule or polymer) that is coated or attached to the device surface.

In addition to coating the device with the fibrosing composition, the fibrosing agent can be mixed with the materials that are used to make the device such that the fibrosing agent is incorporated into the final structure of device itself.

In another embodiment, a film or mesh that further comprises a fibrosis-inducing agent can be wrapped around the vas deferens or a cut portion of the vas deferens. This can promote fibrosis of the cut vas deferens and can increase the success rate of the procedure. In another embodiment, the fibrosis-inducing agent can be incorporated into an in situ forming gel composition. Following the application of a clip, ligation with a suture, or cutting of the vas deferens, the in situ forming composition can be applied to the treatment site (e.g., the cut end of the vas deferens) so as to promote fibrosis and increase the success rate of the procedure.

It should be apparent to one of skill in the art that potentially any adhesion or fibrosis-inducing agent may be utilized alone, or in combination, in the practice of this embodiment as described above. Exemplary fibrosing agents for use in vas deferens implants and devices include talc, silk, wool, chitosan, polylysine, fibronectin, bleomycin, and CTGF, as well as analogues and derivatives of the aforementioned.

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone).

Furthermore, the device may additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

The correct administration and dosage can be described further in section (c) below.

(b) Injectable Vas Deferens Implants

A particularly preferred embodiment of the present invention involves percutaneous delivery of a fibrosis-inducing agent in combination with a biomaterial designed for injection into the vas deferens to "plug" or obstruct the male reproductive tract. The vas deferens is located by palpation (on both sides), a needle is inserted into the lumen, a guidewire is advanced into the lumen of the vas deferens, a dual lumen catheter (for many of the hydrogels described below such as materials prepared from a 4-armed thiol PEG (10K), a 4-armed NHS PEG(10K) and methylated collagen such as described above, COSEAL, COSTASIS, FLOSEAL, TISSEAL) or a single lumen catheter (for materials such as cyanoacrylate, hyaluronic acid, proteins, carbohydrates, sclerosing agents etc.) is advanced over the guidewire into the lumen of the vas deferens, the guidewire is removed, and a composition containing a fibrosis-inducing agent is injected via the catheter into the vas deferens until the lumen is completely occluded. Techniques can be used to enhance visualization of needle (or catheter) placement within the vas deferens including, but not limited to, the use of a needle coated with ECHO—COAT or the injection of air to enable localization by ultrasound, or the addition of contrast agents (e.g., barium, tantalum, technitium, gadolinium) for localization by x-ray or MRI. The injectable implant can obstruct the vas deferens from the inside (luminal surface) and can be implanted in a conscious patient through a single (left and right) needle puncture-reducing the time required to perform the procedure, the invasiveness (a surgical incision is not required), and the risk of infection. The biomaterial physically obstructs the lumen of the tube, while the fibrosis-inducing agent encourages the formation of scar tissue between adjacent walls of the vas deferens, leading to permanent obstruction of the lumen. This prevents the movement of sperm cells through the male reproductive tract, and can lower the failure rate of the procedure (measured as the prevention of unwanted pregnancies).

The injectable material may be composed of a hydrogel for use in the sterilization of a mammalian male. The hydrogel can be composed of a non-degradable or a degradable material. Non-degradable materials can include crosslinked compositions that comprise PVA, PVP, polyacrylamide, pHEMA, poly(vinyl PEG), poly(styrene sulfonate), poly(acrylic acid), poly(methacrylic acid), as well as other polymers that are known to form hydrogels. Additional compositions include blends and copolymers of the agents listed above. Degradable materials include, but are not limited to, crosslinked materials of PEG, gelatin, collagen, hyaluronic acid, hyaluronic acid derivatives, polysaccharides, carbohydrates, proteins (e.g., albumin, casein, whey proteins, plant proteins, and fish proteins), cellulose derivatives (e.g., HPC), chitosan, chitosan derivatives, polyester-polyalkylene oxide block copolymers (e.g., PLGA-PEG-PLGA and MePEG-PLGA, etc) and other low molecular weight polymers that can be excreted. One material that is of particular interest is prepared from a 4-armed thiol PEG (10K), a 4-armed NHS PEG(10K) and methylated collagen such as described above. The hydrogel may also contain a biologically active agent capable of inducing fibrosis in the vas deferens. Preferred, biologically active, fibrosis-inducing, agents, their dosages and their release kinetics, are all described in detail in section (c) below.

In addition to, or in lieu of, fibrosis-inducing agents, the hydrogel can be utilized to deliver a sclerosant to the vas deferens. Sclerosants include compounds such as ethanol, DMSO, surfactants, sucrose, NaCl, dextrose, glycerin, minocycline, tetracycline, doxycycline, polidocanol, sodium tetradecyl sulfate, sodium morrhuate, sotradecol and others. The hydrogel can further comprise agents such as glycerol, glycerin, PEG 200, triethyl citrate, and triacetin as plasticizers.

The hydrogels described above can further modified to be comprised of, or contain, polymeric threads. Polymeric threads have the ability to induce a fibroproliferative response from the surrounding tissue in the vas deferens. These polymer threads can be degradable or non-degradable. Degradable threads can be composed of degradable polyesters, polyanhydrides, poly(anhydride esters), poly(ester-amides), poly(ester-ureas), polyorthoesters, polyphosphoesters, polyphosphazines, cyanoacrylate polymers, collagen, chitosan, hyaluronic acid, chromic cat gut, alginates, starch, cellulose, cellulose esters, blends and copolymers thereof, as well as other known degradable polymers. Non-degradable polymers that can be used include, but are not limited to, polyesters (e.g., PET), polyurethanes, silicones, PE, PP, PS, PAA, PMA, silk, blends, copolymers thereof as well as other known polymers. The threads used can be composed of a single composition or composed of a blend of differing compositions. The polymeric threads themselves can be further modified through the addition of a polymeric coating applied to the threads. The polymer used for coating the thread can be similar to that described above for the threads themselves. The polymer coating may further comprise a biologically active agent that has the ability to induce a fibroproliferative response. The agents that can be used are further described in the section (c) below.

The hydrogels described above can be utilized to deliver a particulate material that has the ability to induce a fibroproliferative response in the vas deferens. These particles can be either degradable or non-degradable and are similar to those described above for threads. In addition to those, particulate materials useful for the practice of this embodiment include talc, starch, glass, silicates, silica, silver nitrate, ceramic particles and other inorganic particles known in the art to induce a fibroproliferative response. The particles used in this embodiment can be all of the same composition or a blend of differing compositions. These particles can also be used as a coating applied to the polymeric strands as described above.

The hydrogel can also be constructed such that it is comprised of both polymeric threads and particles. The threads and particles used are similar to those described above and may be of uniform composition or blended composition. Virtually any combination of threads of differing compositions and particles of differing compositions can be utilized in this embodiment. The hydrogel, the polymeric threads, and the particles can all be utilized to deliver one or more biologically active agents, as described below.

One specific composition comprises rods prepared from a methylated collagen-crosslinked poly(ethylene glycol) composition such as described above which has powdered silk particles added to the composition prior to curing. Once deployed, the rod can absorb water and thereby occlude the vas deferens. This expansion can prevent the rod from moving, while the powdered silk can initiate a fibroproliferative response. As the methylated collagen-crosslinked poly(ethylene glycol) material starts to degrade, the material can support the fibrous tissue ingrowth that is initiated and potentiated by the silk particles. To further increase the rate of initiation of this fibroproliferative response, a sclerosant such as a surfactant (SDS), ethanolamine oleate or DMSO can be added. In addition, one may also add or replace all (or a portion) of the 4-armed thiol PEG with a 4-armed amino PEG. The amino PEG can provide a gel that can take a longer time to degrade and can provide some positive charge to further attract cellular material.

Another embodiment consists of an injectable implant composed of silk fibers or from a polymerized version of the fibrosing agent itself (i.e., repeating units of the fibrosing agent polymerized together).

In addition to the hydrogels and related implants described above, there are several other ways to practice this embodiment. All involve the deployment of a biomaterial into the lumen of the vas deferens, with or without, the addition of a fibrosis-inducing agent. The practice of this embodiment can be performed in several ways including: (a) injection of the fibrosing agent onto the luminal surface of the vas deferens (particularly useful for this embodiment is the use of polymeric carriers which release the fibrosing agent over a period ranging from several hours to several weeks-fluids, suspensions, emulsions, microemulsions, microspheres, pastes, gels, microparticulates, sprays, aerosols, solid implants and other formulations which release a fibrosing agent can be delivered into the vas deferens via specialized delivery catheters or other applicators); (b) microparticulate silk and/or silk strands (linear, branched, and/or coiled) either alone, or loaded with an additional fibrosis-inducing agent are also useful for directed injection into the vas deferens; (c) injectable collagen-containing formulations such as COSTASIS or materials prepared from a 4-armed thiol PEG (10K), a 4-armed NHS PEG(10K) and methylated collagen such as described above, either alone, or loaded with a fibrosis-inducing agent, injected into the lumen of the vas deferens; (d) injectable PEG-containing formulations such as COSEAL, FOCALSEAL, SPRAYGEL or DURASEAL, either alone, or loaded with a fibrosis-inducing agent, injected into the lumen of the vas deferens; (e) fibrinogen-containing formulations such as FLOSEAL or TISSEAL, either alone, or loaded with a fibrosis-inducing agent, injected into the lumen of the vas deferens; (f) hyaluronic acid-containing formulations such as RESTY-LANE, HYLAFORM, PERLANE, SYNVISC, SEPRA-FILM, SEPRACOAT, either alone, or loaded with a fibrosis-inducing agent injected into the lumen of the vas deferens; (g) polymeric gels for surgical implantation such as REPEL or FLOWGEL either alone, or loaded with a fibrosis-inducing agent injected into the lumen of the vas deferens; (h) orthopedic "cements" such as OSTEOBOND, LVC, SIMPLEX P, PALACOS, CORTOSS, and ENDURANCE, either alone, or loaded with a fibrosis-inducing agent injected into the luminal surface of the vas deferens; (i) surgical adhesives containing cyanoacrylates such as DERMABOND, INDERMIL, GLUSTITCH, VETBOND, HISTOACRYL, TISSUEMEND, TISSUMEND II, HISTOACRYL BLUE and ORABASE SOOTHE-N-SEAL LIQUID PROTECTANT or as described above, either alone, or loaded with a fibrosis-inducing agent, injected into the lumen of the vas deferens; (j) surgical implants containing hydroxyapatite such as VITOSS (Orthovita) or calcium sulfate, alone or loaded with a fibrosis-inducing agent injected into the lumen of the vas deferens; (k) other biocompatible tissue fillers, such as those made by BioCure, 3M Company and Neomend, either alone, or loaded with a fibrosis-inducing agent, injected into the lumen of the vas deferens; (l) polysaccharide gels such as the ADCON series of gels, either alone, or loaded with a fibrosis-inducing agent injected into the lumen of the vas deferens; (m) films, sponges or meshes such as INTERCEED, VICRYL mesh, and GELFOAM either alone, or loaded with a fibrosis-inducing agent injected into the lumen of the vas deferens; and/or (n) a hydrogel that is formed from an amino-functionalized polyethylene glycol (e.g., 4-armed tetra-amino PEG [10k]) and a 4-armed NHS functionalized PEG (e.g., pentaerythritol poly(ethylene glycol)ether tetra-succinimidyl glutarate [10K]). This hydrogel may further contain collagen, methylated collagen and/or gelatin. This hydrogel can further comprise the fibrosis-inducing agents described above (e.g., silk powder or silk threads).

In many of the embodiments described above it may also be useful to add a radio-opaque material (such as tantalum, barium, other metal, or contrast material) such that the injected material can be visualized radiographically or by MRI. The contrast agent may be a water soluble or water insoluble radio-opaque material.

It should be apparent to one of skill in the art that potentially any adhesion or fibrosis-inducing agent may be utilized alone, or in combination, in the practice of this embodiment as described above. Exemplary fibrosing agents for use in vas deferens implants and devices include talc, silk, wool, chitosan, polylysine, fibronectin, bleomycin, and CTGF, as well as analogues and derivatives of the aforementioned.

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone).

Furthermore, the device may additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

The correct administration and dosage can be described further in section (c) below.

(c) Fibrosing Agents for Vas Deferens Implants

As vas deferens implantables and injectables are made in a variety of configurations and sizes, the exact dose administered can vary with device size, surface area and design. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the sterilization device, the exemplary fibrosing agents, used alone or in combination, should be administered under the following dosing guidelines:

Utilizing talc as an exemplary fibrosis-inducing agent, whether it is applied using a polymer coating, incorporated into the polymers which make up the device or implant, incorporated into an injectable, or applied without a polymeric carrier, the total dose of talc delivered from a sterilization device, or coated onto the surface of a sterilization device, should not exceed 100 mg (range of 1 μg to 100 mg). In one embodiment, the total amount of talc released from the prosthesis should be in the range of 10 μg to 50 mg. The dose per unit area of the device (i.e., the dosage of talc as a function of the surface area of the portion of the device to which drug is applied and/or incorporated) should fall within the range of 0.05 μg–10 μg per $mm^2$ of surface area coated. In another embodiment, talc should be applied to a sterilization device surface at a dose of 0.05 μg/$mm^2$–10 μg/$mm^2$ of surface area coated. In one embodiment, talc is released from the surface of a sterilization device such that fibrosis in the tissue is promoted for a period ranging from several hours to several months. For example, talc may be released in effective concentrations for a period ranging from 1 hour–30 days. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymer coating, incorporated into the polymers which make up the device or implant, incorporated into an injectable, or applied without a polymeric carrier, the total dose of silk delivered from a sterilization device, or coated onto the surface of a sterilization device, should not exceed 100 mg (range of 1 μg to 100 mg). In one embodiment, the total amount of silk released from the prosthesis should be in the range of 10 μg to 50 mg. The dose per unit area of the device (i.e., the dosage of silk as a function of the surface area of the portion of the device to which drug is applied and/or incorporated) should fall within the range of 0.05 μg–10 μg per $mm^2$ of surface area coated. In another embodiment, silk should be applied to a sterilization device surface at a dose of 0.05 μg/$mm^2$–10 μg/$mm^2$ of surface area coated. As specific (polymeric and non-polymeric) drug delivery vehicles and specific medical devices can release silk at differing rates, the above dosing parameters should be utilized in combination with the release rate of the drug from the sterilization device such that a minimum concentration of 0.01 nM to 1000 μM of silk is delivered to the tissue. In one embodiment, silk is released from the surface of a sterilization device such that fibrosis in the tissue is promoted for a period ranging from several hours to several months. For example, silk may be released in effective concentrations for a period ranging from 1 hour–30 days. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymer coating, incorporated into the polymers which make up the device or implant, incorporated into an injectable, or applied without a polymeric carrier, the total dose of chitosan delivered from a sterilization device, or coated onto the surface of a sterilization device, should not exceed 100 mg (range of 1 μg to 100 mg). In one embodiment, the total amount of chitosan released from the prosthesis should be in the range of 10 μg to 50 mg. The dose per unit area of the device (i.e., the dosage of chitosan as a function of the surface area of the portion of the device to which drug is applied and/or incorporated) should fall within the range of 0.05 μg–10 μg per $mm^2$ of surface area coated. In another embodiment, chitosan should be applied to a sterilization device surface at a dose of 0.05 μg/$mm^2$–10 μg/$mm^2$ of surface area coated. As specific (polymeric and non-polymeric) drug delivery vehicles and specific medical devices can release chitosan at differing rates, the above dosing parameters should be utilized in combination with the release rate of the drug from the sterilization device such that a minimum concentration of 0.01 nM to 1000 μM of chitosan is delivered to the tissue. In one embodiment, chitosan is released from the surface of a sterilization device such that fibrosis in the tissue is promoted for a period ranging from several hours to several months. For example, chitosan may be released in effective concentrations for a period ranging from 1 hour–30 days. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as a exemplary fibrosis-inducing agent, whether it is applied using a polymer coating, incorporated into the polymers which make up the device or implant, incorporated into an injectable, or applied without a polymeric carrier, the total dose of polylysine delivered from a sterilization device, or coated onto the surface of a sterilization device, should not exceed 100 mg (range of 1 μg to 100 mg). In one embodiment, the total amount of polylysine released from the prosthesis should be in the range of 10 μg to 50 mg. The dose per unit area of the device (i.e., the dosage of polylysine as a function of the surface area of the portion of the device to which drug is applied and/or incorporated) should fall within the range of 0.05 μg–10 μg per $mm^2$ of surface area coated. In another embodiment, polylysine should be applied to a sterilization device surface at a dose of 0.05 μg/$mm^2$–10 μg/$mm^2$ of surface area coated. As specific (polymeric and non-polymeric) drug delivery vehicles and specific medical devices can release polylysine at differing rates, the above dosing parameters should be utilized in combination with the release rate of the drug from the sterilization device such that a minimum concentration of 0.01 nM to 1000 μM of polylysine is delivered to the tissue. In one embodiment, polylysine is released from the surface of a sterilization device such that fibrosis in the tissue is promoted for a period ranging from several hours to several months. For example, polylysine may be released in effective concentrations for a period ranging from 1 hour–30 days. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymer coating, incorporated into the polymers which make up the device or implant, incorporated into an injectable, or applied without a polymeric carrier, the total dose of fibronectin delivered from a sterilization device, or coated onto the surface of a sterilization device, should not exceed 100 mg (range of 1 μg to 100 mg). In one embodiment, the total amount of fibronectin released from the prosthesis should be in the range of 10 μg to 50 mg. The dose per unit area of the device (i.e., the dosage of fibronectin as a function of the surface area of the portion of the device to which drug is applied and/or incorporated) should fall within the range of 0.05 μg–10 μg per $mm^2$ of surface area coated. In another embodiment, fibronectin should be applied to a sterilization device surface at a dose of 0.05 μg/$mm^2$–10 μg/$mm^2$ of surface area coated. As specific (polymeric and non-polymeric) drug delivery vehicles and specific medical devices can release fibronectin at differing rates, the above dosing parameters should be utilized in combination with the release rate of the drug from the sterilization device such that a minimum concentration of 0.01 nM to 1000 μM of fibronectin is delivered to the tissue. In one embodiment, fibronectin is released from the surface of a sterilization device such that fibrosis in the tissue is promoted for a period ranging from several hours to several months. For example, fibronectin may be released in effective concentrations for a period ranging from 1 hour–30 days. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, whether it is applied using a polymer coating, incorporated into the polymers which make up the device or implant, incorporated into an injectable, or applied without a polymeric carrier, the total dose of bleomycin delivered from a sterilization device, or coated onto the surface of a sterilization device, should not exceed 100 mg (range of 0.01 µg to 100 mg). In one embodiment, the total amount of bleomycin released from the prosthesis should be in the range of 0.10 µg to 50 mg. The dose per unit area of the device (i.e., the dosage of bleomycin as a function of the surface area of the portion of the device to which drug is applied and/or incorporated) should fall within the range of 0.005 µg–10 µg per mm$^2$ of surface area coated. In another embodiment, bleomycin should be applied to a sterilization device surface at a dose of 0.005 µg/mm$^2$–10 µg/mm$^2$ of surface area coated. As specific (polymeric and non-polymeric) drug delivery vehicles and specific medical devices can release bleomycin at differing rates, the above dosing parameters should be utilized in combination with the release rate of the drug from the sterilization device such that a minimum concentration of 0.001 nM to 1000 µM of bleomycin is delivered to the tissue. In one embodiment, bleomycin is released from the surface of a sterilization device such that fibrosis in the tissue is promoted for a period ranging from several hours to several months. For example, bleomycin may be released in effective concentrations for a period ranging from 1 hour–30 days. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as an exemplary fibrosis-inducing agent, whether it is applied using a polymer coating, incorporated into the polymers which make up the device or implant, incorporated into an injectable, or applied without a polymeric carrier, the total dose of CTGF delivered from a sterilization device, or coated onto the surface of a sterilization device, should not exceed 100 mg (range of 0.01 µg to 100 mg). In one embodiment, the total amount of CTGF released from the prosthesis should be in the range of 0.10 µg to 50 mg. The dose per unit area of the device (i.e., the dosage of CTGF as a function of the surface area of the portion of the device to which drug is applied and/or incorporated) should fall within the range of 0.005 µg–10 µg per mm$^2$ of surface area coated. In another embodiment, CTGF should be applied to a sterilization device surface at a dose of 0.005 µg/mm$^2$–10 µg/mm$^2$ of surface area coated. As specific (polymeric and non-polymeric) drug delivery vehicles and specific medical devices can release CTGF at differing rates, the above dosing parameters should be utilized in combination with the release rate of the drug from the a sterilization device such that a minimum concentration of 0.001 nM to 1000 µM of CTGF is delivered to the tissue. In one embodiment, CTGF is released from the surface of a sterilization device such that fibrosis in the tissue is promoted for a period ranging from several hours to several months. For example, CTGF may be released in effective concentrations for a period ranging from 1 hour–30 days. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone). Inflammatory cytokines are to be used in formulations at concentrations that range from 0.0001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 µg to 100 mg); preferred 0.001 µg to 50 mg. When used as a device coating, the dose is per unit area of 0.0001 µg–500 µg per mm$^2$; with a preferred dose of 0.001 µg/mm$^2$–200 µg/mm$^2$. Minimum concentration of $10^{-10}$–$10^{-4}$ g/ml of inflammatory cytokine is to be maintained on the device surface.

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin D$_3$, diethylstibesterol, cyclosporine A, L-NAME, all-trans retinoic acid (ATRA), and analogues and derivatives thereof. Doses used are those concentrations which are demonstrated to stimulate cell proliferation (Example 16). The proliferative agents are to be used in formulations at concentrations that range from 0.01 ng/ml to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 µg to 200 mg); preferred 0.001 µg to 100 mg. When used as a device coating, the dose is per unit area of 0.00001 µg–500 µg per mm$^2$; with a preferred dose of 0.0001 µg/mm$^2$–200 µg/mm$^2$. Minimum concentration of $10^{-11}$–$10^{-6}$ M of proliferative agent is to be maintained on the device surface.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

6. Urinary Incontinence

The present invention provides compositions and devices for use in the management of urinary incontinence. Urinary incontinence, or the involuntary loss of urine, is a common medical condition which affects 20% of women and 1–2% of men at some point in their lifetime. The most common form of incontinence is stress incontinence, or the inadvertent leakage of urine in response to activities that cause an increase in intraabdominal pressure (such as sneezing, coughing, or straining). This occurs when intravesical pressure (pressure in the bladder) exceeds the pressure in the urethra, forcing urine from the bladder and into the urethra in the absence of detrusor (bladder muscle) contraction.

Several conditions are thought to result in stress incontinence, including: (1) descent of the bladder neck and internal urethral sphincter out of the abdomen; and (2) intrinsic urethral sphincter failure due to trauma, surgery, childbirth or malignancy. Corrective measures are aimed principally at supporting the proximal urethral and bladder neck within the abdominal cavity by surgical or non-surgical means. A second approach involves the use of urethral bulking agents designed to increase urethral pressure and reduce stress incontinence.

Regardless of their composition, urethral bulking agents are designed to provide physical support for the urethra and prevent the leakage of urine. Unfortunately, the symptomatic relief is often only temporary for most patients and the procedure must be repeated. Biodegradable injectable materials (such as collagen, hyaluronic acid and others described below) are absorbed by the body over time and lose their structural integrity—necessitating replacement of the material via repeat injection. Non degradable materials (such as acrylics, hydroxyapatite, polymeric beads, and others described below) do not regenerate the normal structural anatomy or biomechanics of the tissues surrounding the urethra. The addition of a fibrosis-inducing agent to a urethral bulking agent solves several of these problems. The fibrosis-inducing agent encourages the formation of the body's own fibrous tissue (including collagen) around the urethra. This results in the formation of continuously sustainable connective tissue which supports the urethra in a manner more closely approximating normal pelvic anatomy and biomechanics. The result is a treatment that lasts longer, provides better symptomatic relief and requires fewer re-interventions.

(i) Injectable Urinary Bulking Agents Containing a Fibrosing Agent

Bulking agents for use in treating urinary incontinence which may be combined with one or more fibrosis-inducing agents according to the present invention, include commercially available products for the management of stress incontinence. CONTIGEN (purified bovine dermal glutaraldehyde crosslinked collagen dispersed in phosphate buffered physiologic saline at 35 mg/ml available through C.R. Bard, Billerica, Mass.) is a widely used urethral bulking agent. Other collagen based injectable products, including those derived from non-bovine, human, or recombinant sources can also be utilized in this embodiment. Other representative examples of commercially available bulking agents that can be used to treat urinary incontinence include hydroxyapatite loaded gel (COAPATITE from BioForm Medical, Inc., San Mateo, Calif.), micronized alloderm acellular matrix (CYMETRA from LifeCell Corporation, Branchburg, N.J.), non-animal stabilized hyaluronic acid (NASHA and DEFLUX from Q-Med), pyrolytic carbon-coated microbeads in hydrogel containing beta-glucan (DURASPHERE from Carbon Medical Technologies, Inc. St. Paul, Minn. and Boston Scientific Corporation, Natick, Mass.), engineered collagen fibrils (Organogenesis, Inc., Canton, Mass.), hylan polymer (HYLAGEL URO from Genzyme), MACROPLASTIQUE (polydimethylsiloxane in hydrogel carrier) from Uroplasty, Inc. (Minneapolis, Minn.), microspheres (e.g., acrylic beads, such as those available from Biosphere Medical, Inc. Marlborough, Mass.), urethral bulking agents containing silk and elastin proteins (Protein Polymer Technologies, San Diego, Calif.), cross-linked silicon microballoon filled with biocompatible polymer (UROVIVE from American Medical Systems, Minnetonka, Minn.), and URYX bulking agent and Embolyx from Microtherapeutics, Inc., San Clemente, Calif. and Genyx Medical, Inc., Aliso Viejo, Calif. Other manufacturers of carriers suitable for use in bulking compositions include C.R. Bard, Inc. (Murray Hill, N.J.), Collagenesis, Inc. (Acton, Mass.), American Medical Systems, Mentor, Uromed Corporation (Norwood, Mass.), Boston Scientific Corporation, Johnson & Johnson (Ethicon, Inc.), Cook Group, Inc. (Bloomington, Ind.), W.L. Gore & Associates, and SURX, Inc. (Pleasonton, Calif.).

Administration of a fibrosis-agent loaded bulking agent may typically be performed by transurethral injection. If the carrier of the fibrosis-inducing agent contains collagen, the patient should have completed two skin tests (conducted 2 weeks apart) to test for an allergic response prior to administration. If these tests are negative, the collagen injection containing a fibrosis-inducing agent can be administered to the patient. A refrigerated, single use, pre-loaded syringe agent with a fine gauge needle (23 gauge transurethral injection needle with a stabilizing cannula) containing 2.5 ml of the implant material (the fibrosis-inducing agent and the urethral bulking agent) is used. The patient is placed in the lithotomy position and 10 ml of 2% lidocaine is inserted into the urethra for anesthesia. In women, the bladder neck is visualized cystoscopically. Via the injection port of the cystoscope, the needle is inserted at the 4 o'clock position, at a sharp angle, 1–1.5 cm distal to the bladder neck into the plane just beneath the bladder mucosa. The needle is then advanced with the cystoscope parallel to the long axis of the urethra until it lies just below the mucosa of the bladder neck. The fibrosis-inducing agent and the urethral bulking agent is injected slowly into this site. The procedure is then repeated at the 8 o'clock position. Methylene blue, or other nontoxic coloring agents, can be added to the implant to assist with visualization of the injection.

Alternatively, periurethral injection of a fibrosis-inducing agent loaded into a urethral bulking agent can also be used for the treatment of incontinence. A refrigerated, single use, pre-loaded syringe with a fine gauge needle (periurethral injection needle) containing 2.5 ml of the implant material (the fibrosis-inducing agent and the urethral bulking agent) is used. The patient is placed in the lithotomy position, 10 ml of 2% lidocaine is inserted into the urethra for anesthesia and the bladder neck is visualized cystoscopically (in men the urethra can also be visualized via suprapubic cystoscopic approach). The needle is inserted transvaginally or suprapubically into the area immediately adjacent and lateral to the urethra. When it reaches the appropriate position near the bladder neck (as seen cystoscopically and described above), the fibrosis-inducing agent loaded into a urethral bulking agent is injected slowly into this site. Methylene blue, or other nontoxic coloring agents, can be added to the implant to assist with visualization of the injection.

It should be apparent to one of skill in the art that potentially any adhesion or fibrosis-inducing agent may be utilized (alone or in combination) with any injectable urethral bulking agent in the practice of this invention. Exemplary fibrosing agents for use in combination with injectable urethral bulking agents include talc, silk, wool, chitosan, polylysine, fibronectin, bleomycin, and CTGF, as well as analogues and derivatives of the aforementioned.

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or an analogue or derivative thereof.

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

The correct administration and dosage can be described further in section (iii) below.

(ii) Urinary Slings Containing a Fibrosis-Inducing Agent

In another aspect, stress incontinence and weakening of the urethra muscle may be treated with a pubovaginal sling procedure. This operation can create enough compression on the urethra to help the patient regain bladder control. Slings for treating urinary incontinence are described in, e.g., U.S. Pat. Nos. 6,641,524; 6,592,610; 6,387,040; 6,328,686; 6,306,079; 6,221,005; 6,110,101; 6,056,687; 6,042,536; and 6,042,534 and U.S. Patent Application Publication Nos. 2003/0199732A1; 2003/0149440A1; 2002/0183588A1; 2002/0058959A1; and 2002/0022841 A1.

Slings for use in treating urinary incontinence which may be combined with one or more fibrosis-inducing agents according to the present invention, include numerous commercially available products. For example, the SUSPEND TUTOPLAST (Processed Fascia Lata sling from Mentor) and REPLIFORM Tissue Regeneration Matrix (human allograft dermal collagen fibers from Boston Scientific Corporation (Natick, Mass.)) can be used. Products such as FORTAGEN Surgical Mesh and GRAFTPATCH (both from Organogenesis Inc., Canton, Mass.), and SURGISIS (Cook Biotech, Inc., West Lafayette, Ind.) consist of a multilaminate sheet composed primarily of Type I collagen (usually porcine or bovine) that is used to reinforce soft tissues during operative repair. Indications include defects of the abdominal and thoracic wall, muscle flap reinforcement, rectal and vaginal prolapse, repair of tissue flap donor sites, ostomy reinforcement, reconstruction of the pelvic floor, hernia repair, suture line reinforcement and reconstructive purposes. Surgical slings, such as the FORTAFLEX Surgical Sling (Organogenesis, Inc.) and the SURGISIS Sling are also composed predominantly of Type I Collagen (usually porcine or bovine) and are utilized in open urological surgery procedures. Indications include pubourethral support, prolapse repair (urethral, vaginal, rectal and colonic), rectoceles, cystoceles, enteroceles, mastoplexy, reconstruction of the pelvic floor, bladder support, sacrocolposuspension and other reconstructive procedures. Other representative examples of slings for use in the present invention include Tension-Free Vaginal Tape (TVT) from Ethicon, Inc. (Somerville, N.J.), the SPARC Female Sling System (a "vaginal tape" product from American Medical Systems), the AMS Silicone-Coated Mesh Sling (American Medical Systems), BIOSLING (InjecTx/ProSurg), VERITAS Collagen Matrix Urological Sling (Synovis Life Technologies, Inc., St. Paul, Minn.), slings made from PTFE, such as Gore-Tex MYCROMESH from Gore, the STRATESIS Urethral Sling made from acellular porcine small intestine mucosa (Cook, Inc.), slings made from allograph fascia, such as the ALLOSLING (Alliant Medical), and slings made from human allograft fascia, such as FASLATA Allograft Tissue (C.R. Bard). Slings can also be prepared from, e.g., polypropylene mesh (C.R. Bard), and MERSILENE polyester fiber mesh (Ethicon, Inc.).

Numerous polymeric and non-polymeric drug delivery systems described above can be used to deliver fibrosis-inducing agents from urological slings and implants. The methods for incorporating fibrosing compositions onto or into the urinary incontinence devices include: (a) directly affixing to the urinary incontinence implant a fibrosing composition (e.g., by either a spraying process or dipping process as described above, with or without a carrier); (b) directly incorporating into the device a fibrosing composition (e.g., by either a spraying process or dipping process as described above, with or without a carrier); (c) by coating the device with a substance such as a hydrogel which can in turn absorb the fibrosing composition; (d) by interweaving fibrosing composition coated thread (or the polymer itself formed into a thread) into the device structure; (e) by inserting the device into a sleeve or mesh which is comprised of or coated with a fibrosing composition; (f) constructing the device itself or a portion of the device with a fibrosing composition, or (g) by covalently binding the fibrosing agent directly to the device surface or to a linker (small molecule or polymer) that is coated or attached to the device surface. For these devices, the coating process can be performed in such a manner as to a) coat the exterior surfaces of the device, b) coat the interior surfaces of the device or c) coat all or parts of both external and internal surface of the device.

In addition to coating the device with the fibrosing composition, the fibrosing agent can be mixed with the materials that are used to make the device such that the fibrosing agent is incorporated into the final device.

In one embodiment, fibrosis-inducing agents can be incorporated directly into the formulation to produce a suspension or a solution (e.g., silk powder, bleomycin) or it can be incorporated into a secondary carrier (e.g., micelles, liposomes, microspheres, microparticles, nanospheres, microparticulates, emulsions and/or micromulsions) that is then incorporated into the bulking composition. In another embodiment, the fibrosis-inducing agent can be electrostatically or covalently bound to one or more of the polymeric components of the in situ forming composition.

In another embodiment, the fibrosis-inducing agent can be incorporated into the bulking agent during the manufacture of the agent. For example, silk powder can be added as a reagent during the manufacture of microspheres that are used as bulking agents.

It should be apparent to one of skill in the art that potentially any adhesion or fibrosis-inducing agents described above may be utilized alone, or in combination, in the practice of this embodiment. Exemplary fibrosing agents for use in urinary incontinence devices and compositions include talc, silk, wool, chitosan, polylysine, fibronectin, bleomycin, and CTGF, as well as analogues and derivatives of the aforementioned.

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or an analogue or derivative thereof.

Furthermore, the device may additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

(iii) Fibrosing Agents for Use in Urinary Incontinence Implants

As urinary incontinence devices are made in a variety of configurations and sizes (including injectable bulking agents and slings), the exact dose administered can vary with implant or device size, surface area and design. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the urinary incontinence implant or device, the exemplary fibrosing agents, used alone or in combination, should be administered under the following dosing guidelines:

Utilizing talc as an exemplary fibrosis-inducing agent, whether it is applied using a polymer coating, incorporated into the polymers which make up the device or implant, or applied without a polymeric carrier, the total dose of talc delivered from a urinary incontinence device, or coated onto the surface of a urinary incontinence device, should not exceed 100 mg (range of 1 µg to 100 mg). In one embodiment, the total amount of talc released from the prosthesis should be in the range of 10 µg to 50 mg. The dose per unit volume of the injectable urinary bulking agent (i.e., the dosage of talc as a function of the volume of urinary bulking agent injected) should fall within the range of 0.05 µg–10 µg per mm$^3$. In another embodiment, talc should be applied to a urinary sling incontinence device surface at a dose of 0.05 µg/mm$^2$–10 µg/mm$^2$ of surface area coated. In one embodiment, talc is released from a urinary incontinence bulking agent, implant or device such that fibrosis in the tissue is promoted for a period ranging from several hours to several months. For example, talc may be released in effective concentrations for a period ranging from 1–9 months. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymer coating, incorporated into the polymers which make up the device or implant, or applied without a polymeric carrier, the total dose of silk delivered from a urinary incontinence device, or coated onto the surface of a urinary incontinence device, should not exceed 100 mg (range of 1 µg to 100 mg). In one embodiment, the total amount of silk released from the prosthesis should be in the range of 10 µg to 50 mg. The dose per unit volume of the injectable urinary bulking agent (i.e., the dosage of silk as a function of the volume of urinary bulking agent injected) should fall within the range of 0.05 µg–10 µg per mm$^3$. In another embodiment, silk should be applied to a urinary sling incontinence device surface at a dose of 0.05 µg/mm$^2$–10 µg/mm$^2$ of surface area coated. As specific (polymeric and non-polymeric) drug delivery vehicles and specific medical devices can release silk at differing rates, the above dosing parameters should be utilized in combination with the release rate of the drug from the urinary incontinence bulking agent, implant or device such that a minimum concentration of 0.01 nM to 1000 µM of silk is delivered to the tissue. In one embodiment, silk is released from a urinary incontinence bulking agent, implant or device such that fibrosis in the tissue is promoted for a period ranging from several hours to several months. For example, silk may be released in effective concentrations for a period ranging from 1–9 months. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymer coating, incorporated into the polymers which make up the device or implant, or applied without a polymeric carrier, the total dose of chitosan delivered from a urinary incontinence device, or coated onto the surface of a urinary incontinence device, should not exceed 100 mg (range of 1 µg to 100 mg). In one embodiment, the total amount of chitosan released from the prosthesis should be in the range of 10 µg to 50 mg. The dose per unit volume of the injectable urinary bulking agent (i.e., the dosage of chitosan as a function of the volume of urinary bulking agent injected) should fall within the range of 0.05 µg–10 µg per mm$^3$. In another embodiment, chitosan should be applied to a urinary sling incontinence device surface at a dose of 0.05 µg/mm$^2$–10 µg/mm$^2$ of surface area coated. As specific (polymeric and non-polymeric) drug delivery vehicles and specific medical devices can release chitosan at differing rates, the above dosing parameters should be utilized in combination with the release rate of the drug from the urinary incontinence bulking agent, implant or device such that a minimum concentration of 0.01 nM to 1000 µM of chitosan is delivered to the tissue. In one embodiment, chitosan is released from a urinary incontinence bulking agent, implant or device such that fibrosis in the tissue is promoted for a period ranging from several hours to several months. For example, chitosan may be released in effective concentrations for a period ranging from 1–9 months. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as an exemplary fibrosis-inducing agent, whether it is applied using a polymer coating, incorporated into the polymers which make up the device or implant, or applied without a polymeric carrier, the total dose of polylysine delivered from a urinary incontinence device, or coated onto the surface of a urinary incontinence device, should not exceed 100 mg (range of 1 µg to 100 mg). In one embodiment, the total amount of polylysine released from the prosthesis should be in the range of 10 µg to 50 mg. The dose per unit volume of the injectable urinary bulking agent (i.e., the dosage of polylysine as a function of the volume of urinary bulking agent injected) should fall within the range of 0.05 µg–10 µg per mm$^3$. In another embodiment, polylysine should be applied to a urinary sling incontinence device surface at a dose of 0.05 µg/mm$^2$–10 µg/mm$^2$ of surface area coated. As specific (polymeric and non-polymeric) drug delivery vehicles and specific medical devices can release polylysine at differing rates, the above dosing parameters should be utilized in combination with the release rate of the drug from the urinary incontinence bulking agent, implant or device such that a minimum concentration of 0.01 nM to 1000 µM of polylysine is delivered to the tissue. In one embodiment, polylysine is released from a urinary incontinence bulking agent, implant or device such that fibrosis in the tissue is promoted for a period ranging from several hours to several months. For example, polylysine may be released in effective concentrations for a period ranging from 1–9 months. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymer coating, incorporated into the polymers which make up the device or implant, or applied without a polymeric carrier, the total dose of fibronectin delivered from a urinary incontinence device, or coated onto the surface of a urinary incontinence device, should not exceed 100 mg (range of 1 µg to 100 mg). In one embodiment, the total amount of fibronectin released from the prosthesis should be in the range of 10 µg to 50 mg. The dose per unit volume of the injectable urinary bulking agent (i.e., the dosage of fibronectin as a function of the volume of urinary bulking agent injected) should fall within the range of 0.05 µg–10 µg per $mm^3$. In another embodiment, talc should be applied to a urinary sling incontinence device surface at a dose of 0.05 $µg/mm^2$–10 $µg/mm^2$ of surface area coated. As specific (polymeric and non-polymeric) drug delivery vehicles and specific medical devices can release fibronectin at differing rates, the above dosing parameters should be utilized in combination with the release rate of the drug from the urinary incontinence bulking agent, implant or device such that a minimum concentration of 0.01 nM to 1000 µM of fibronectin is delivered to the tissue. In one embodiment, fibronectin is released from a urinary incontinence bulking agent, implant or device such that fibrosis in the tissue is promoted for a period ranging from several hours to several months. For example, fibronectin may be released in effective concentrations for a period ranging from 1–9 months. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, whether it is applied using a polymer coating, incorporated into the polymers which make up the device or implant, or applied without a polymeric carrier, the total dose of bleomycin delivered from a urinary incontinence device, or coated onto the surface of a urinary incontinence device, should not exceed 100 mg (range of 0.01 µg to 100 mg). In one embodiment, the total amount of bleomycin released from the prosthesis should be in the range of 0.10 µg to 50 mg. The dose per unit volume of the injectable urinary bulking agent (i.e., the dosage of bleomycin as a function of the volume of urinary bulking agent injected) should fall within the range of 0.005 µg–10 µg per $mm^3$. In another embodiment, bleomycin should be applied to a urinary sling incontinence device surface at a dose of 0.005 $µg/mm^2$–10 $µg/mm^2$ of surface area coated. As specific (polymeric and non-polymeric) drug delivery vehicles and specific medical devices can release bleomycin at differing rates, the above dosing parameters should be utilized in combination with the release rate of the drug from the urinary incontinence bulking agent, implant or device such that a minimum concentration of 0.001 nM to 1000 µM of bleomycin is delivered to the tissue. In one embodiment, bleomycin is released from a urinary incontinence bulking agent, implant or device such that fibrosis in the tissue is promoted for a period ranging from several hours to several months. For example, bleomycin may be released in effective concentrations for a period ranging from 1–9 months. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as an exemplary fibrosis-inducing agent, whether it is applied using a polymer coating, incorporated into the polymers which make up the device or implant, or applied without a polymeric carrier, the total dose of CTGF delivered from a urinary incontinence device, or coated onto the surface of a urinary incontinence device, should not exceed 100 mg (range of 0.01 µg to 100 mg). In one embodiment, the total amount of CTGF released from the prosthesis should be in the range of 0.10 µg to 50 mg. The dose per unit volume of the injectable urinary bulking agent (i.e., the dosage of CTGF as a function of the volume of urinary bulking agent injected) should fall within the range of 0.005 µg–10 µg per $mm^3$. In another embodiment, CTGF should be applied to a urinary sling incontinence device surface at a dose of 0.005 $µg/mm^2$–10 $µg/mm^2$ of surface area coated. As specific (polymeric and non-polymeric) drug delivery vehicles and specific medical devices can release CTGF at differing rates, the above dosing parameters should be utilized in combination with the release rate of the drug from the urinary incontinence bulking agent, implant or device such that a minimum concentration of 0.001 nM to 1000 µM of CTGF is delivered to the tissue. In one embodiment, CTGF is released from a urinary incontinence bulking agent, implant or device such that fibrosis in the tissue is promoted for a period ranging from several hours to several months. For example, CTGF may be released in effective concentrations for a period ranging from 1–9 months. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone or an analogue or derivative thereof). Inflammatory cytokines are to be used in formulations at concentrations that range from 0.0001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 µg to 100 mg); preferred 0.001 µg to 50 mg. When used as a device coating, the dose is per unit area of 0.0001 µg–500 µg per mm$^2$; with a preferred dose of 0.001 µg/mm$^2$–200 µg/mm$^2$. Minimum concentration of $10^{-10}$–$10^{-4}$ g/ml of inflammatory cytokine is to be maintained on the device surface.

Furthermore, the device may additionally comprise an agent that stimulates cellular proliferation. Examples include: dexamethasone, isotretinoin (13-cis retinoic acid), 17-β-estradiol, estradiol, 1-a-25 dihydroxyvitamin D$_3$, diethylstibesterol, cyclosporine A, L-NAME, all-trans retinoic acid (ATRA), and analogues and derivatives thereof. Doses used are those concentrations which are demonstrated to stimulate cell proliferation (Example 16). The proliferative agents are to be used in formulations at concentrations that range from 0.1 ng/ml to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 µg to 200 mg); preferred 0.001 µg to 100 mg. When used as a device coating, the dose is per unit area of 0.00001 µg–500 µg per mm$^2$; with a preferred dose of 0.0001 µg/mm$^2$–200 µg/mm$^2$. Minimum concentration of $10^{-11}$–$10^{-6}$ M of proliferative agent is to be maintained on the device surface.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

7. Venous Occluding Materials Containing Fibrosing Agents

A variety of devices and injectable implants have been developed for injection into veins for cosmetic purposes. Typically, a needle or catheter is advanced into an unwanted vein (primarily "spider" veins or varicose veins) and a sclerosing agent is injected into the vessel to scar the vein shut. Unfortunately, currently available agents often do not produce permanent fibrosis (true luminal scarring where the walls of the vessel permanently adhere to each other and fibrous tissue occludes the vessel) leading to the possibility of recannulization, re-establishment of venous flow, and ultimately recurrence of the vein (i.e., failure of the procedure). The present invention describes the addition of fibrosis-inducing agents to the materials injected into the vein for the purpose of producing a permanent, obstructive scar in the vascular lumen that results in regression and absorption of the unwanted vein. If venous flow is permanently prevented in the vein due to obstructive fibrosis, the body resorbs the non-functioning vessel and eliminates the vein, leaving little or no chance for recurrence.

There are several commercially available sclerosing agents that are used to treat spider veins and varicose veins, which may be combined with one or more fibrosis-inducing drugs according to the present invention. For example, Wyeth Pharmaceuticals (Collegeville, Pa.), a division of Wyeth (Madison, N.J.), sells SOTRADECOL, which is a sodium tetradecyl sulfate injection. Other sclerosing agents available for treating spider veins and varicose veins (and may be suitable for delivery of a fibrosis-inducing agent) include sodium morrhuate, ethanolamine oleate, compositions containing ethanol, DMSO, surfactants, sucrose, NaCl, dextrose, glycerin, minocycline, tetracycline, doxycycline, polidocanol, sodium tetradecyl sulfate, sodium morrhuate, sotradecol and others. Other examples of compositions suitable for cosmetic vascular injection include silk (e.g., microparticulate silk), polymeric gels composed of fibrosis-inducing agents (such as those available from Polymerix Corporation) and fibrosis-inducing agents loaded into vascular fillers.

A variety of polymer based products have been developed for intra-vascular injection for the purposes of arterial embolization (described in greater detail in the section 12(ii) on arterial embolization below). Many of these intra-vascular polymer systems are suitable for the treatment of spider veins and varicose veins and can be made more efficacious through the addition of a fibrosis-inducing agent. Examples of products suitable for combining with a fibrosis-inducing agent include, for example, TRUFILL n-butyl cyanoacrylate (n-BCA) Liquid Embolic System (available from Cordis, a division of Johnson and Johnson, Miami, Fla.); ONYX Liquid Embolic System (Micro Therapeutics, Irvine, Calif.). Other examples of materials suitable for the delivery of a fibrosis-inducing agent into the venous system include polymer/solvent systems in which the solvent diffuses from the polymer matrix once it has been injected into the vein (e.g., degradable polymeric systems from Atrix, non-degradable polymeric compositions from ONYX and EMBOLYX, and in situ forming materials from Biocure, Angiotech Pharmaceuticals, Inc., 3M Company, and Neomend. Other types of commercially available embolic agents that can be loaded or made with a fibrosis-inducing agent for venous occlusion include PVA particles (from Cook, Inc. and Angiodynamics Inc.), and microsphere formulations (e.g., EMBOSPHERE and EMBOGOLD from Biosphere, Inc. (Rockland, Mass.) and BEAD BLOCK from Biocompatibles Ltd., United Kingdom).

In one embodiment, the injectable vascular material is composed of an injectable polymer system combined with a fibrosis-inducing agent. One injectable polymer system that is of particular interest is prepared from a 4-armed thiol PEG (10K), a 4-armed NHS PEG(10K) and methylated collagen such as described above. The injectable vascular material may be combined with a fibrosis-inducing agent (e.g., talc, silk, wool, chitosan, polylysine, fibronectin, bleomycin, CTGF, bone morphogenic proteins, transforming growth factor, platelet-derived growth factor, fibroblast growth factor, as well as analogues and derivatives of these compounds) and injected into a varicose vein or spider vein. In addition to, or in lieu of, fibrosis-inducing agents, bone morphogenic proteins and growth factors, the injectable material can also be utilized to deliver a sclerosant to the vein. Sclerosants include compounds such as ethanol, DMSO, surfactants, sucrose, sodium morrhuate, ethanolamine oleate NaCl, dextrose, glycerin, minocycline, tetracycline, doxycycline, polidocanol, sodium tetradecyl sulfate, sodium morrhuate, sotradecol and others. The injectable material can further comprise agents such as glycerol, glycerin, PEG 200, triethyl citrate, and triacetin as plasticizers.

In another embodiment, the injectable intra-vascular materials described above can be further modified to be extruded from the catheter (or needle) as a polymeric "thread" or contain polymeric threads. Polymeric threads have the ability to induce clotting as well as a fibroproliferative response from the vascular wall. The injectable "threads" can be loaded with, coated with, or comprised of a fibrosis-inducing agent (e.g., an injectable implant composed of silk fibers or a polymerized version of the fibrosing agent itself). These polymer threads can be degradable or non-degradable. Degradable threads can be composed of degradable polyesters, polyanhydrides, poly(anhydride esters), poly(ester-amides), poly(ester-ureas), polyorthoesters, polyphosphoesters, polyphosphazines, cyanoacrylate polymers, collagen, chitosan, hyaluronic acid, chromic cat gut, alginates, starch, cellulose, cellulose esters, blends and copolymers thereof, as well as other known degradable polymers. Non-degradable polymers that can be used include, but are not limited to, polyesters (e.g., PET), polyurethanes, silicones, PE, PP, PS, PAA, PMA, silk, blends, copolymers thereof as well as other known polymers. The threads used can be composed of a single composition or composed of a blend of differing compositions. The polymeric threads themselves can be further modified through the addition of a polymeric coating applied to the threads. The polymer used for coating the thread can be similar to that described above for the threads themselves. The polymer coating may further comprise a biologically active fibrosis-inducing agent.

In another embodiment, the intra-vascular injectable materials described above can be formulated to be delivered from the catheter (or needle) as a particulate material that has the ability to induce clotting and fibrosis. The injectable particles can be loaded with, coated with, or comprised of a fibrosis-inducing agent. These particles can be either degradable or non-degradable and are similar in composition to those described above for threads. In addition to the aforementioned polymers, particulate materials useful for the practice of this embodiment include talc, starch, glass, silicates, silica, calcium phosphate, calcium sulfate, calcium carbonate, hydroxyapatite, synthetic mineral (VITOSS and CORTOSS), PMMA, silver nitrate, ceramic particles and other inorganic particles known in the art to induce a fibroproliferative response. The particles used in this embodiment can be all of the same composition or a blend of differing compositions. These particles can also be used as a coating applied to the polymeric strands as described above.

As is readily apparent, the injectable intravascular material can also be constructed such that it is comprised of both polymeric threads and particles. The threads and particles used are similar to those described above and may be of uniform composition or blended composition. Virtually any combination of threads of differing compositions and particles of differing compositions can be utilized in this embodiment. The hydrogel, the polymeric threads, and the particles can all be utilized to deliver one or more fibrosis-inducing agents.

In addition to the injectable materials described above, there are several other injectable compositions suitable for intra-vascular administration in the treatment of spider veins and varicose veins. All involve the deployment of a biomaterial into the lumen of the vein, with or without, the addition of a fibrosis-inducing agent, bone morphogenic protein(s), and/or a suitable growth factor(s). The following compositions can be delivered into the vein via specialized delivery catheters, an endoscope (e.g., angioscope; typically the material is delivered via a sideport in the device), a needle or other applicator, a surgically placed access device, or other transdermal intra-vascular access device and include administration of: (a) fluids, suspensions, emulsions, microemulsions, microspheres, pastes, gels, microparticulates, sprays, aerosols, solid implants and other formulations which release a biologically active agent(s); (b) microparticulate silk and/or silk strands (linear, branched, and/or coiled) either alone, or loaded with an additional fibrosis-inducing agent, bone morphogenic protein, and/or growth factor injected into the vein; (c) injectable collagen-containing formulations such as COSTASIS or materials made from 4-armed thiol PEG (10K), a 4-armed NHS PEG (10K) and methylated collagen such as described above, either alone, or loaded with a fibrosis-inducing agent, bone morphogenic protein, and/or growth factor, injected into the vein; (d) injectable PEG-containing formulations such as COSEAL, FOCALSEAL, SPRAYGEL or DURASEAL, either alone, or loaded with a fibrosis-inducing agent, bone morphogenic protein, and/or growth factor, injected into the vein; (e) fibrinogen-containing formulations such as FLOSEAL or TISSEAL, either alone, or loaded with a fibrosis-inducing agent, bone morphogenic protein, and/or growth factor, injected into the vein; (f) hyaluronic acid-containing formulations such as RESTYLANE, HYLAFORM, PERLANE, SYNVISC, SEPRAFILM, SEPRACOAT, either alone, or loaded with a fibrosis-inducing agent, bone morphogenic protein, and/or growth factor injected into the vein; (g) polymeric gels for surgical implantation such as REPEL or FLOWGEL either alone, or loaded with a fibrosis-inducing agent, bone morphogenic protein, and/or growth factor injected into the vein; (h) orthopedic "cements" such as OSTEOBOND, LVC, SIMPLEX P, PALACOS, CORTOSS, and ENDURANCE, either alone, or loaded with a fibrosis-inducing agent, bone morphogenic protein, and/or growth factor injected into the vein; (i) surgical adhesives containing cyanoacrylates such as DERMABOND, INDERMIL, GLUSTITCH, VETBOND, HISTOACRYL, TISSUEMEND, TISSUMEND II, HISTOACRYL BLUE and ORABASE SOOTHE-N-SEAL LIQUID PROTECTANT or as described above, either alone, or loaded with a fibrosis-inducing agent, bone morphogenic protein, and/or growth factor, injected into the vein; (j) surgical implants containing hydroxyapatite, calcium phosphate (such as VITOSS), or calcium sulfate, alone or loaded with a fibrosis-inducing agent, bone morphogenic protein, and/or growth factor, injected into the vein; (k) other biocompatible tissue fillers, such as those made by BioCure, 3M Company and Neomend, either alone, or loaded with a fibrosis-inducing agent, bone morphogenic protein, and/or growth factor, injected into the vein; (l) polysaccharide gels such as the ADCON series of gels, either alone, or loaded with a fibrosis-inducing agent, bone morphogenic protein, and/or growth factor, injected into the vein; (m) films, sponges or meshes such as INTERCEED, VICRYL mesh, and GELFOAM either alone, or loaded with a fibrosis-inducing agent, bone morphogenic protein, and/or growth factor, injected into the vein; and/or (n) a hydrogel that is formed from an amino-functionalized polyethylene glycol (e.g., 4-armed tetra-amino PEG [10k]) and a 4-armed NHS functionalized PEG (e.g., pentaerythritol poly(ethylene glycol) ether tetra-succinimidyl glutarate [10K]). This hydrogel may further contain collagen, methylated collagen and/or gelatin. This hydrogel can further comprise the fibrosis-inducing agents described above (e.g., silk powder or silk threads).

In many of these embodiments, it may also be useful to add a radio-opaque material (such as tantalum, barium, other metal, or contrast material) such that the injected material can be visualized radiographically or MRI. Also, when performing direct injection into the vein, techniques can be used to enhance visualization of needle (or catheter) via ultrasound through the use of a needle coated with ECHO—COAT or the injection of air (microbubbles).

In one preferred method of administration for the treatment of large varicose veins, the fibrosing agent is delivered under direct vision during angioscopic evaluation of the vessel. Here the composition containing the fibrosis-inducing agent, bone morphogenic protein, and/or growth factor is injected into the lumen of the varicose vein through the side port of an angioscope. In some cases, the fibrosis-inducing agent may also be delivered directly to the lumen of the vein (or the tissue surrounding the vein) during open surgery.

It should be apparent to one of skill in the art that potentially any adhesion or fibrosis-inducing agent may be utilized alone, or in combination, in the practice of this embodiment as described above. Exemplary fibrosing agents for use in venous destruction procedures include talc, silk, wool, chitosan, polylysine, fibronectin, bleomycin, CTGF, bone morphogenic proteins, and/or osteogenic growth factors (such as transforming growth factor, platelet-derived growth factor, fibroblast growth factor) as well as analogues and derivatives of the aforementioned. In some clinical situations, repeated injections of the active agents described below may be required.

The exact dose administered can vary depending upon the particular vein being treated. However, certain principles can be applied in the application of this art. Drug dose can be calculated as a function of dose per unit volume (of the amount being injected), total drug dose administered can be measured and appropriate surface concentrations of active drug can be determined. Regardless of the method of application of the drug to the vein, the exemplary fibrosing agents, bone morphogenic proteins, and/or growth factors (such as transforming growth factor, platelet-derived growth factor, fibroblast growth factor), used alone or in combination, should be administered under the following dosing guidelines:

Utilizing talc as an exemplary fibrosis-inducing agent, whether it is applied using a polymer coating, incorporated into the polymers which make up the injectable, or administered without a polymeric carrier, the total dose of talc administered into the venous system in any single injection should not exceed 100 mg (range of 1 µg to 100 mg). In one embodiment, the total amount of talc administered should be in the range of 10 µg to 50 mg. The dose per unit volume injected should fall within the range of 0.05 µg–10 µg per $mm^3$. As specific (polymeric and non-polymeric) drug delivery vehicles and specific implants can release talc at differing rates, the above dosing parameters should be utilized in combination with the release rate of the drug from the carrier such that a minimum concentration of 0.01 nM to 1000 µM of talc is continuously delivered to the vein over the desired therapeutic period. In one embodiment, talc is released from the injectable such that fibrosis in the vein is promoted for a period ranging from several hours to several months. For example, talc may be released in effective concentrations for a period ranging from 2–12 weeks. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymer coating, incorporated into the polymers which make up the injectable, or administered without a polymeric carrier, the total dose of silk delivered to the venous system in any single injection should not exceed 100 mg (range of 1 µg to 100 mg). In one embodiment, the total amount of silk administered to the vein should be in the range of 10 µg to 50 mg. The dose per unit volume injected should fall within the range of 0.05 µg–10 µg per $mm^3$. As specific (polymeric and non-polymeric) drug delivery vehicles can release silk at differing rates, the above dosing parameters should be utilized in combination with the release rate of the drug from the carrier such that a minimum concentration of 0.01 nM to 1000 µM of silk is continuously delivered to the tissue over the desired therapeutic time period. In one embodiment, silk is released into the lumen of the vein such that fibrosis is promoted for a period ranging from several hours to several months. For example, silk may be released in effective concentrations for a period ranging from 2–12 weeks. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymer coating, incorporated into the polymers which make up the injectable, or administered without a polymeric carrier, the total dose of chitosan delivered into the vein should not exceed 100 mg (range of 1 µg to 100 mg). In one embodiment, the total amount of chitosan administered into the vein in any single injection should be in the range of 10 µg to 50 mg. The dose per unit volume injected should fall within the range of 0.05 µg–10 µg per $mm^3$. As specific (polymeric and non-polymeric) drug delivery vehicles can release chitosan at differing rates, the above dosing parameters should be utilized in combination with the release rate of the drug from the carrier such that a minimum concentration of 0.01 nM to 1000 µM of chitosan is continuously delivered into the vein. In one embodiment, chitosan is released into the lumen of the vein such that fibrosis is promoted for a period ranging from several hours to several months. For example, chitosan may be released in effective concentrations for a period ranging from 2–12 weeks. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as a exemplary fibrosis-inducing agent, whether it is applied using a polymer coating, incorporated into the polymers which make up the injectable, or administered without a polymeric carrier, the total dose of polylysine delivered into the vein in a single injection should not exceed 100 mg (range of 1 µg to 100 mg). In one embodiment, the total amount of polylysine delivered to the vein should be in the range of 10 µg to 50 mg. The dose per unit volume injected should fall within the range of 0.05

µg–10 µg per mm$^3$. In another embodiment, polylysine should be injected into the vein at a dose of 0.05–10 µg/mm$^3$. As specific (polymeric and non-polymeric) drug delivery vehicles can release polylysine at differing rates, the above dosing parameters should be utilized in combination with the release rate of the drug from the carrier such that a minimum concentration of 0.01 nM to 1000 µM of polylysine is continuously delivered to the vein. In one embodiment, polylysine is administered to the lumen of the vein such that fibrosis is promoted for a period ranging from several hours to several months. For example, polylysine may be released in effective concentrations for a period ranging from 2–12 weeks. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymer coating, incorporated into the polymers which make up the injectable, or administered without a polymeric carrier, the total dose of fibronectin delivered into the vein in a single injection should not exceed 100 mg (range of 1 µg to 100 mg). In one embodiment, the total amount of fibronectin injected into the vein should be in the range of 10 µg to 50 mg. The dose per unit volume of the injection should fall within the range of 0.05 µg–10 µg per mm$^3$. In another embodiment, talc should be administered at a dose of 0.05–10 µg/mm$^3$ of injected material. As specific (polymeric and non-polymeric) drug delivery vehicles can release fibronectin at differing rates, the above dosing parameters should be utilized in combination with the release rate of the drug from the carrier such that a minimum concentration of 0.01 nM to 1000 µM of fibronectin is continuously delivered to the vein. In one embodiment, fibronectin is released into the lumen of the vein such that fibrosis is promoted for a period ranging from several hours to several months. For example, fibronectin may be released in effective concentrations for a period ranging from 2–12 weeks. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, whether it is applied using a polymer coating, incorporated into the polymers which make up the injectable, or administered without a polymeric carrier, the total dose of bleomycin administered to a vein in a single injection should not exceed 100 mg (range of 0.01 µg to 100 mg). In one embodiment, the total amount of bleomycin injected into the vein should be in the range of 0.10 µg to 50 mg. The dose per unit volume injected should fall within the range of 0.005 µg–10 µg per mm$^3$. As specific (polymeric and non-polymeric) drug delivery vehicles can release bleomycin at differing rates, the above dosing parameters should be utilized in combination with the release rate of the drug from the carrier such that a minimum concentration of 0.001 nM to 1000 µM of bleomycin is continuously delivered to the vein. In one embodiment, bleomycin is released from the injection such that fibrosis in the vein is promoted for a period ranging from several hours to several months. For example, bleomycin may be released in effective concentrations for a period ranging from 2–12 weeks. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as an exemplary fibrosis-inducing agent, whether it is applied using a polymer coating, incorporated into the polymers which make up the injectable, or administered without a polymeric carrier, the total dose of CTGF administered to the vein in a single injection should not exceed 100 mg (range of 0.01 µg to 100 mg). In one embodiment, the total amount of CTGF injected into the vein should be in the range of 0.10 µg to 50 mg. The dose per unit volume of the injection should fall within the range of 0.005 µg–10 µg per mm$^3$. In another embodiment, CTGF should be injected at a dose of 0.005–10 µg/mm$^3$. As specific (polymeric and non-polymeric) drug delivery vehicles can release CTGF at differing rates, the above dosing parameters should be utilized in combination with the release rate of the drug from the carrier such that a minimum concentration of 0.001 nM to 1000 µM of CTGF is continuously delivered to the vein. In one embodiment, CTGF is released from the injectable such that fibrosis in the vein is promoted for a period ranging from several hours to several months. For example, CTGF may be released in effective concentrations for a period ranging from 2–12 weeks. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone). Inflammatory cytokines are to be used in formulations at concentrations that range from 0.0001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 µg to 100 mg); preferred 0.001 µg to 50 mg. When used as a device coating, the dose is per unit area of 0.0001 µg–500 µg per mm$^2$; with a preferred dose of 0.001 µg/mm$^2$–200 µg/mm$^2$. Minimum concentration of $10^{-10}$–$10^{-4}$ g/ml of inflammatory cytokine is to be maintained on the device surface.

Furthermore, the device may alone or additionally comprise an agent that stimulates cellular proliferation.

Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof. Doses used are those concentrations which are demonstrated to stimulate cell proliferation (see, e.g., Example 16). The proliferative agents are to be used in formulations at concentrations that range from 0.1 ng/ml to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 μg to 200 mg); preferred 0.001 μg to 100 mg. When used as a device coating, the dose is per unit area of 0.00001 μg–500 μg per $mm^2$; with a preferred dose of 0.0001 $μg/mm^2$–200 $μg/mm^2$. Minimum concentration of $10^{-11}$–$10^{-6}$ M of proliferative agent is to be maintained on the device surface.

It should be readily evident to one of skill in the art that any of the previously described fibrosis-inducing agents, bone morphogenic proteins, or osteogenic growth factors, or derivatives and analogues thereof, can be utilized to create variations of the above compositions without deviating from the spirit and scope of the invention.

It should also be apparent that the agent can be utilized in a composition with or without polymer carrier and that altering the carrier does not deviate from the scope of this invention.

8. Fecal Incontinence

The present invention provides compositions and devices for use in the management of fecal incontinence. Fecal incontinence is the inability to control bowel movements. Reasons for fecal incontinence include, e.g., damage to the nerves of the pelvic floor, trauma to the anal and/or rectal area, a birth defect, altered stool consistency, or abnormal rectal capacity, and diseases such as diabetes, multiple sclerosis and colorectal disease. In women, fecal incontinence can be the result of a difficult childbirth.

(i) Anal Sphincter Bulking Agents

Fecal incontinence may be treated by injecting a bulking agent close to the anal sphincter to reinforce closure of the anal sphincter. Bulking agents which may be combined with one or more fibrosis-inducing agents according to the present invention, include numerous commercially available products. For example, injectable microspheres from Artes Medical, Inc. (San Diego, Calif.), ENTERYX (ethylene vinyl alcohol polymer implant from Boston Scientific Corporation), and CONTIGEN (purified bovine dermal glutaraldehyde crosslinked collagen dispersed in phosphate buffered physiologic saline at 35 mg/ml available through C.R. Bard, Billerica, Mass.) are widely used bulking agents. Other collagen based injectable products, including those derived from non-bovine, human, or recombinant sources can also be utilized in this embodiment. Additional representative examples of commercially available bulking agents that can be used to treat fecal incontinence include hydroxyapatite loaded gel (COAPATITE), micronized alloderm acellular matrix (CYMETRA), non-animal stabilized hyaluronic acid (NASHA) (DEFLUX), pyrolytic carbon-coated micro-beads in hydrogel containing beta-glucan (DURASPHERE), engineered collagen fibrils (Organogenesis), hylan polymer (HYLAGEL URO), MACROPLASTIQUE (polydimethylsiloxane in hydrogel carrier), microspheres (e.g., acrylic beads, such as those available from Biosphere Medical), urethral bulking agents containing silk and elastin proteins (such as those available from Protein Polymer Technologies), cross-linked silicon microballoon filled with biocompatible polymer (UROVIVE), and URYX bulking agent and Embolyx from Microtherapeutics, Inc., San Clemente, Calif. and Genyx Medical, Inc., Aliso Viejo, Calif. Other manufacturers of carriers suitable for use in bulking compositions include C.R. Bard, Collagenesis, American Medical Systems, Mentor, Uromed, Boston Scientific Corporation, Johnson & Johnson (Ethicon, Inc.), Cook Urologic, W.L. Gore, and SURx.

Regardless of their composition, bulking agents are designed to provide physical support for the anal sphincter and prevent the leakage of feces. Unfortunately, the symptomatic relief is often only temporary for most patients and the procedure must be repeated. Biodegradable injectable materials (such as collagen, hyaluronic acid and others described above) are absorbed by the body over time and lose their structural integrity—necessitating replacement of the material via repeat injection. Non-degradable materials (such as acrylics, hydroxyapatite, polymeric beads, and others described above) do not regenerate the normal structural anatomy or biomechanics of the tissues surrounding the anal sphincter. The addition of a fibrosis-inducing agent to a bulking agent can solve several of these problems. The fibrosis-inducing agent can encourage the formation of the body's own fibrous tissue (including collagen) around the anal sphincter. This results in the formation of continuously sustainable connective tissue which supports the anal sphincter in a manner more closely approximating normal rectal anatomy and biomechanics. The result is a treatment that lasts longer, provides better symptomatic relief and requires fewer re-interventions.

In one aspect, the present invention provides injectable compositions (bulking agents) for use in treating fecal incontinence. Specifically, the fibrosis-inducing agent can be produced with or without a carrier (such as collagen, hyaluronic acid, and/or another biocompatible polymer) which is then injected in and around the anal sphincter to provide support and continence. In one embodiment, fibrosis-inducing agents can be incorporated directly into the formulation to produce a suspension or a solution (e.g., silk powder, bleomycin) or it can be incorporated into a secondary carrier (e.g., micelles, liposomes, microspheres, microparticies, nanospheres, microparticulates, emulsions, and/or microemulsions) that is then incorporated into the bulking composition. In another embodiment, the fibrosis-inducing agent can be electrostatically or covalently bound to one or more of the polymeric components of the in situ forming composition. Injection of the bulking agent (many commercial examples of which were described above) containing the fibrosing agent into the perimuscular space (alone or in combination with a polymeric carrier) can enhance scarring and support to the anal sphincter and may result in endogenous collagen production.

In another embodiment, the fibrosis-inducing agent can be incorporated into the bulking agent during the manufacture of the agent. For example, silk powder can be added as a reagent during the manufacture of microspheres that are used as bulking agents.

It should be apparent to one of skill in the art that potentially any adhesion or fibrosis-inducing agents described above may be utilized alone, or in combination, in the practice of this embodiment. Exemplary fibrosing agents for use in fecal incontinence devices and compositions include talc, silk, wool, chitosan, polylysine, fibronectin, bleomycin, and CTGF, as well as analogues and derivatives of the aforementioned.

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or an analogue or derivative thereof.

Furthermore, the device may additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

The appropriate agents and their dosages can be further described below in section (iii).

(ii) Prosthetic Anal Sphincters

Another approach to treating fecal incontinence involves implantation of prostheses or devices, such as ablation devices, nerve stimulators, pumps, and stapling devices. Devices for treating fecal incontinence are described in, e.g., U.S. Pat. Nos. 6,428,467; 6,013,023; 5,421,827; 4,428,365; and 4,351,322 and in U.S. Published Patent Application Publication No. 2002/0120219A1.

Devices for treating fecal incontinence which may be combined with one or more fibrosis-inducing drugs according to the present invention include a variety of commercially available products. For example, the SECCA system (Curon Medical) uses radio frequency ablation to tighten the muscles of the anal sphincter. The ACTICON Neosphincter (made by Acticon LLC and sold by American Medical Systems) is an implantable prosthesis that contains hand inflatable pump connected to an inflatable ring in an artificial sphincter. The sacral nerve stimulator (Medtronic, Inc., Minneapolis, Minn.), is a device that addresses the neuropathy that results in fecal incontinence. The PROXIMATE stapling device from Ethicon EndoSurgery lifts up or repositions the mucosa or anal canal tissue to its original position.

In the present invention, fibrosis-inducing agents are combined with prosthetic anal sphincters to enhance scarring around the device and to re-enforce rectal anatomy to restore fecal continence. Numerous polymeric and non-polymeric carrier systems described previously can be used to deliver one or more fibrosis-inducing agents to promote the formation of granulation tissue around the implanted device. The methods for incorporating fibrosis-inducing agents onto or into the fecal incontinence devices include: (a) directly affixing to the device a fibrosing composition (e.g., by either a spraying process or dipping process as described above, with or without a carrier); (b) directly incorporating into the device a fibrosing composition (e.g., by either a spraying process or dipping process as described above, with or without a carrier); (c) by coating the device with a substance such as a hydrogel which can in turn absorb the fibrosing composition; (d) by interweaving fibrosing composition coated thread (or the polymer itself formed into a thread) into the device structure; (e) by inserting the device into a sleeve or mesh which is comprised of or coated with a fibrosing composition; (f) constructing the device itself or a portion of the device with a fibrosing composition; or (g) by covalently binding the fibrosing agent directly to the device surface or to a linker (small molecule or polymer) that is coated or attached to the device surface. For these devices, the coating process can be performed in such a manner as to a) coat the exterior surfaces of the device, b) coat the interior surfaces of the device or c) coat all or parts of both external and internal surface of the device.

In addition to coating the device with the fibrosing composition, the fibrosing agent can be mixed with the materials that are used to make the device such that the fibrosing agent is incorporated into the final device.

It should be apparent to one of skill in the art that potentially any adhesion or fibrosis-inducing agents described above may be utilized alone, or in combination, in the practice of this embodiment. Exemplary fibrosing agents for use in fecal incontinence devices and compositions include talc, silk, wool, chitosan, polylysine, fibronectin, bleomycin, and CTGF, as well as analogues and derivatives of the aforementioned.

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or an analogue or derivative thereof.

Furthermore, the device may additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

Preferred specific agents and dosages of use for coating implantable, prosthetic devices used in the management of fecal incontinence are described in section (iii) immediately below.

(iii) Fibrosis-Inducing Agents for Fecal Incontinence

As fecal incontinence devices are made in a variety of configurations and sizes (including injectables and prosthetic implants), the exact dose administered can vary with device or implant size, surface area and design. However, certain principles can be applied in the application of this art. Drug dose can be calculated as a function of dose per unit volume/area (of the total volume of bulking agent injected or of the surface area of the portion of the prosthetic device being coated), total drug dose administered can be measured and appropriate surface concentrations of active drug can be determined. Regardless of the method of application of the fibrosis-inducing agent in the management of fecal incontinence, the exemplary fibrosing agents, used alone or in combination, should be administered under the following dosing guidelines:

Utilizing talc as an exemplary fibrosis-inducing agent, whether it is applied using a polymer coating, incorporated into the polymers which make up the device or implant, or applied without a polymeric carrier, the total dose of talc delivered in a bulking agent injection, or coated onto the surface of a fecal incontinence implant or device, should not exceed 100 mg (range of 1 μg to 100 mg). In one embodiment, the total amount of talc released should be in the range of 10 μg to 50 mg. The dose per unit volume of the injectable bulking agent (i.e., the dosage of talc as a function of the volume of bulking agent injected) should fall within the range of 0.05 μg–10 μg per $mm^3$. In another embodiment, talc should be applied to a fecal incontinence implant or device surface at a dose of 0.05 μg/$mm^2$–10 μg/$mm^2$ of surface area coated. In one embodiment, talc is released from a fecal incontinence bulking agent, implant or device such that fibrosis in the tissue is promoted for a period ranging from several hours to several months. For example, in a preferred embodiment talc may be released in effective concentrations for a period ranging from 3–12 months. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymer coating, incorporated into the polymers which make up the device or implant, or applied without a polymeric carrier, the total dose of silk delivered in a bulking agent injection, or coated onto the surface of a fecal incontinence implant or device, should not exceed 100 mg (range of 1 µg to 100 mg). In one embodiment, the total amount of silk released should be in the range of 10 µg to 50 mg. The dose per unit volume of the injectable bulking agent (i.e., the dosage of silk as a function of the volume of bulking agent injected) should fall within the range of 0.05 µg–10 µg per $mm^3$. In another embodiment, silk should be applied to a fecal incontinence device surface at a dose of 0.05 µg/$mm^2$–10 µg/$mm^2$ of surface area coated. As specific (polymeric and non-polymeric) drug delivery vehicles and specific bulking agents and prosthetic devices can release silk at differing rates, the above dosing parameters should be utilized in combination with the release rate of the drug from the fecal incontinence bulking agent, implant or device such that a minimum concentration of 0.01 nM to 1000 µM of silk is delivered to the tissue. In one embodiment, silk is released from a fecal incontinence bulking agent, implant or device such that fibrosis in the tissue is promoted for a period ranging from several hours to several months. For example, in a preferred embodiment silk may be released in effective concentrations for a period ranging from 3–12 months. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymer coating, incorporated into the polymers which make up the device or implant, or applied without a polymeric carrier, the total dose of chitosan delivered in a bulking agent injection, or coated onto the surface of a fecal incontinence implant or device, should not exceed 100 mg (range of 1 µg to 100 mg). In one embodiment, the total amount of chitosan released should be in the range of 10 µg to 50 mg. The dose per unit volume of the injectable bulking agent (i.e., the dosage of chitosan as a function of the volume of bulking agent injected) should fall within the range of 0.05 µg–10 µg per $mm^3$. In another embodiment, chitosan should be applied to a fecal incontinence device surface at a dose of 0.05 µg/$mm^2$–10 µg/$mm^2$ of surface area coated. As specific (polymeric and non-polymeric) drug delivery vehicles and specific bulking agents and prosthetic devices can release chitosan at differing rates, the above dosing parameters should be utilized in combination with the release rate of the drug from the fecal incontinence bulking agent, implant or device such that a minimum concentration of 0.01 nM to 1000 µM of chitosan is delivered to the tissue. In one embodiment, chitosan is released from a fecal incontinence bulking injection, implant or device such that fibrosis in the tissue is promoted for a period ranging from several hours to several months. For example, in a preferred embodiment chitosan may be released in effective concentrations for a period ranging from 3–12 months. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as a exemplary fibrosis-inducing agent, whether it is applied using a polymer coating, incorporated into the polymers which make up the device or implant, or applied without a polymeric carrier, the total dose of polylysine delivered in a bulking agent injection, or coated onto the surface of a fecal incontinence implant or device, should not exceed 100 mg (range of 1 µg to 100 mg). In one embodiment, the total amount of polylysine released should be in the range of 10 µg to 50 mg. The dose per unit volume of the injectable bulking agent (i.e., the dosage of polylysine as a function of the volume of bulking agent injected) should fall within the range of 0.05 µg–10 µg per $mm^3$. In another embodiment, polylysine should be applied to a fecal incontinence device surface at a dose of 0.05 µg/$mm^2$–10 µg/$mm^2$ of surface area coated. As specific (polymeric and non-polymeric) drug delivery vehicles and specific bulking agents and prosthetic devices can release polylysine at differing rates, the above dosing parameters should be utilized in combination with the release rate of the drug from the fecal incontinence bulking agent, device or implant such that a minimum concentration of 0.01 nM to 1000 µM of polylysine is delivered to the tissue. In one embodiment, polylysine is released from a fecal incontinence bulking injection, implant or device such that fibrosis in the tissue is promoted for a period ranging from several hours to several months. For example, in a preferred embodiment polylysine may be released in effective concentrations for a period ranging from 3–12 months. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymer coating, incorporated into the polymers which make up the device or implant, or applied without a polymeric carrier, the total dose of fibronectin delivered from in a bulking agent injection, or coated onto the surface of a fecal incontinence implant or device, should not exceed 100 mg (range of 1 µg to 100 mg). In one embodiment, the total amount of fibronectin released should be in the range of 10 µg to 50 mg. The dose per unit volume of the injectable bulking agent (i.e., the dosage of fibronectin as a function of the volume of bulking agent injected) should fall within the range of 0.05 µg–10 µg per $mm^3$. In another embodiment, fibronectin should be applied to a fecal incontinence device surface at a dose of 0.05 µg/$mm^2$–10 µg/$mm^2$ of surface area coated. As specific (polymeric and non-polymeric) drug delivery vehicles and specific bulking agents and prosthetic devices can release fibronectin at differing rates, the above dosing parameters should be utilized in combination with the release rate of the drug from the fecal incontinence bulking agent, implant or device such that a minimum concentration of 0.01 nM to 1000 μM of fibronectin is delivered to the tissue. In one embodiment, fibronectin is released from a fecal incontinence bulking injection, implant or device such that fibrosis in the tissue is promoted for a period ranging from several hours to several months. For example, in a preferred embodiment fibronectin may be released in effective concentrations for a period ranging from 3–12 months. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, whether it is applied using a polymer coating, incorporated into the polymers which make up the device or implant, or applied without a polymeric carrier, the total dose of bleomycin delivered in a bulking agent injection, or coated onto the surface of a fecal incontinence implant or device, should not exceed 100 mg (range of 0.01 μg to 100 mg). In one embodiment, the total amount of bleomycin released should be in the range of 0.10 μg to 50 mg. The dose per unit volume of the injectable bulking agent (i.e., the dosage of bleomycin as a function of the volume of bulking agent injected) should fall within the range of 0.005 μg–10 μg per mm$^3$. In another embodiment, bleomycin should be applied to a fecal incontinence device surface at a dose of 0.005 μg/mm$^2$–10 μg/mm$^2$ of surface area coated. As specific (polymeric and non-polymeric) drug delivery vehicles and specific bulking agents and prosthetic devices can release bleomycin at differing rates, the above dosing parameters should be utilized in combination with the release rate of the drug from the fecal incontinence bulking agent, implant or device such that a minimum concentration of 0.001 nM to 1000 μM of bleomycin is delivered to the tissue. In one embodiment, bleomycin is released from a fecal incontinence bulking injection, implant or device such that fibrosis in the tissue is promoted for a period ranging from several hours to several months. For example, in a preferred embodiment bleomycin may be released in effective concentrations for a period ranging from 3–12 months. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as an exemplary fibrosis-inducing agent, whether it is applied using a polymer coating, incorporated into the polymers which make up the device or implant, or applied without a polymeric carrier, the total dose of CTGF delivered in a bulking agent injection, or coated onto the surface of a fecal incontinence implant or device, should not exceed 100 mg (range of 0.01 μg to 100 mg). In one embodiment, the total amount of CTGF released should be in the range of 0.10 μg to 50 mg. The dose per unit volume of the injectable bulking agent (i.e., the dosage of CTGF as a function of the volume of bulking agent injected) should fall within the range of 0.005 μg–10 μg per mm$^3$. In another embodiment, CTGF should be applied to a fecal incontinence device surface at a dose of 0.005 μg/mm$^2$–10 μg/mm$^2$ of surface area coated. As specific (polymeric and non-polymeric) drug delivery vehicles and specific bulking agents and prosthetic devices can release CTGF at differing rates, the above dosing parameters should be utilized in combination with the release rate of the drug from the fecal incontinence bulking agent, implant or device such that a minimum concentration of 0.001 nM to 1000 μM of CTGF is delivered to the tissue. In one embodiment, CTGF is released from a fecal incontinence bulking injection, implant or device such that fibrosis in the tissue is promoted for a period ranging from several hours to several months. For example, in a preferred embodiment CTGF may be released in effective concentrations for a period ranging from 3–12 months. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or an analogue or derivative thereof. Inflammatory cytokines are to be used in formulations at concentrations that range from 0.0001 μg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 μg to 100 mg); preferred 0.001 μg to 50 mg. When used as a device coating, the dose is per unit area of 0.0001 μg–500 μg per mm$^2$; with a preferred dose of 0.001 μg/mm$^2$–200 μg/mm$^2$. Minimum concentration of $10^{-10}$–$10^{-4}$ g/ml of inflammatory cytokine is to be maintained on the device surface.

Furthermore, the device may additionally comprise an agent that stimulates cellular proliferation. Examples include: dexamethasone, isotretinoin (13-cis retinoic acid), 17-β-estradiol, estradiol, 1-a-25 dihydroxyvitamin D$_3$, diethylstibesterol, cyclosporine A, L-NAME, all-trans retinoic acid (ATRA), and analogues and derivatives thereof. Doses used are those concentrations which are demonstrated to stimulate cell proliferation (see, e.g., Example 16). The proliferative agents are to be used in formulations at concentrations that range from 0.1 ng/ml to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 μg to 200 mg); preferred 0.001 μg to 100 mg. When used as a device coating, the dose is per unit area of 0.00001 µg–500 µg per mm$^2$; with a preferred dose of 0.0001 µg/mm$^2$–200 µg/mm$^2$. Minimum concentration of $10^{-11}$–$10^{-6}$ M of proliferative agent is to be maintained on the device surface.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

9. Gastroesophageal Reflux Disease (GERD)

The present invention provides compositions and devices for use in the management of gastroesophageal reflux disease (GERD). GERD occurs when the lower esophageal sphincter (the muscle between the stomach and the esophagus) is unable to prevent the contents of the stomach from refluxing back into the esophagus. Gastric acid and enzymes are quite corrosive to the epithelial lining of the esophagus and can cause erosions, ulceration, scarring and narrowing of the esophagus. Repetitive reflux into the esophagus can result in irreversible injury and also predisposes the patient to the development of esophageal cancer.

(i) GERD Bulking Agents

One approach to treating GERD involves lower esophageal sphincter augmentation. One method for augmenting the lower esophageal sphincter involves delivery (e.g., injection) of a bulking agent (e.g., a collagen bulking agent) into the vicinity of the lower esophageal sphincter (LES) (e.g., into the perimuscular space of the LES) to restore the structure of the tissue and reduce backflow into the esophagus. Another approach involves implantation of bulking devices or devices that deliver expandable polymeric compositions (e.g., hydrogel prostheses).

As mentioned above, GERD may be treated by injecting a bulking agent close to the lower esophageal sphincter to reinforce closure of the LES. Bulking agents which may be combined with one or more fibrosis-inducing agents according to the present invention, include numerous commercially available products. For example, injectable microspheres from Artes Medical, ENTERYX and CONTIGEN (purified bovine dermal glutaraldehyde crosslinked collagen dispersed in phosphate buffered physiologic saline at 35 mg/ml available through C.R. Bard, Billerica, Mass.) are widely used bulking agents. Other collagen based injectable products, including those derived from non-bovine, human, or recombinant sources can also be utilized in this embodiment. Additional representative examples of commercially available bulking agents that can be loaded with a fibrosis-inducing agent and used to treat GERD include COAPATITE, CYMETRA, DEFLUX, DURASPHERE, engineered collagen fibrils from Organogenesis, HYLAGEL URO, MACROPLASTIQUE, microspheres (e.g., acrylic beads, such as those available from Biosphere Medical), LES bulking agents containing silk and elastin proteins (such as those available from Protein Polymer Technologies), UROVIVE, and URYX bulking agent. Another device suitable for use with a fibrosis-inducing agent in the management of GERD includes the GATEKEEPER Reflux Repair System made by Medtronic, Inc. (Minneapolis, Minn.). Other manufacturers of carriers suitable for delivering a fibrosis-inducing agent for use in GERD bulking compositions include C.R. Bard, Collagenesis, American Medical Systems, Mentor, Uromed, BSX, Johnson & Johnson (Ethicon, Inc.), Cook Inc., W.L. Gore & Associates, and SURx.

Examples of implantable lower esophageal bulking devices are also described in WO 00/12027A1 and U.S. Pat. No. 6,401,718.

Regardless of their composition, bulking agents are designed to provide physical support for the lower esophageal sphincter and prevent the reflux of gastric contents into the esophagus. Unfortunately, symptomatic relief is often only temporary for most patients and the procedure must often be repeated. Biodegradable injectable materials (such as collagen, hyaluronic acid and others described above) are absorbed by the body over time and lose their structural integrity—necessitating replacement of the material via repeat injection. Non degradable materials (such as acrylics, hydroxyapatite, polymeric beads, and others described above) do not regenerate the normal structural anatomy or biomechanics of the tissues surrounding the lower esophageal sphincter. The addition of a fibrosis-inducing agent to a bulking agent solves several of these problems. The fibrosis-inducing agent encourages the formation of the body's own fibrous tissue (including collagen) around the lower esophageal sphincter. This results in the formation of continuously sustainable connective tissue which supports the LES in a manner more closely approximating normal gastroesophageal anatomy and biomechanics. The result is a treatment that lasts longer, provides better symptomatic relief and requires fewer re-interventions.

In one aspect, the present invention provides injectable compositions (bulking agents) for use in treating GERD. Specifically, the fibrosis-inducing agent can be produced with or without a carrier (such as collagen, hyaluronic acid, and/or another biocompatible polymer) which is then injected in and around the anal sphincter to provide support and continence. In one embodiment, fibrosis-inducing agents can be incorporated directly into the formulation to produce a suspension or a solution (e.g., silk powder, bleomycin) or it can be incorporated into a secondary carrier (e.g., micelles, liposomes, microspheres, microparticles, nanospheres, microparticulates, emulsions and/or microemulsions) that is then incorporated into the bulking composition. In another embodiment, the fibrosis-inducing agent can be electrostatically or covalently bound to one or more of the polymeric components of the in situ forming composition. Injection of the bulking agent (many commercial examples of which were described above) containing the fibrosing agent into the perimuscular space (alone or in combination with a polymeric carrier) can enhance scarring and support to the lower esophageal sphincter and may result in endogenous collagen production.

In another embodiment, the fibrosis-inducing agent can be incorporated into the bulking agent during the manufacture of the agent. For example, silk powder can be added as a reagent during the manufacture of microspheres that are used as bulking agents.

It should be apparent to one of skill in the art that potentially any adhesion or fibrosis-inducing agents described above may be utilized alone, or in combination, in the practice of this embodiment. Exemplary fibrosing agents for use in GERD bulking agents include talc, silk, wool, chitosan, polylysine, fibronectin, bleomycin, and CTGF, as well as analogues and derivatives of the aforementioned.

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or an analogue or derivative thereof.

Furthermore, the device may additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

The appropriate agents and their dosages can be further described below in section (iii).

(ii) Devices Used in GERD

A variety of implantable devices and methods have been described for use in treating GERD. Representative treatment methods include, for example, suture-based treatments and the use of energy based devices. Suture based treatments for GERD are described in, e.g., U.S. Pat. No. 6,494,888, U.S. Patent Application Publication No. 2002/0138075A1 describes a sphincter electropotential mapping device. U.S. Pat. No. 6,321,121 describes a lower esophageal sphincter tightening device. Other devices for treating GERD are described in, e.g., U.S. Pat. Nos. 6,092,528, 6,159,146; 6,113,609; 5,571,116; 6,432,040; and 6,264,700; U.S. Patent Application Publication No. 2003/0199731A1, and PCT Publication Nos. WO 99/44520A1 and WO 01/24721A1.

Suture-based treatments for treating GERD may be combined with one or more fibrosis-inducing agents according to the present invention. Several commercially available products can be combined with fibrosis-inducing agents including: (a) the ENDOCINCH AND ENDOCINCH II Suturing System (C.R. Bard) which uses a procedure that creates plications, or pleats, at the lower esophageal sphincter; (b) the ENDOSCOPIC Suturing Device (ESD) (Wilson-Cook, Winston-Salem, N.C.) which is composed of the Flexible SEW-RIGHT device, the Flexible TI-KNOT device, and an external accessory channel; (c) the PLICATOR SYSTEM (NDO Surgical, Mansfield Mass.) which allows physicians to create a full-thickness plication at the gastroesophageal junction, permitting serosa-to-serosa healing and restructuring healing and restructuring of the LES; and (d) the HISWIZ (Olympus, Inc.) suture-based device.

Another approach to treating GERD is through the use of energy-based devices. Energy delivery devices for treating esophageal sphincters are described, e.g., in U.S. Pat. Nos. 6,613,047 and 6,009,877. Tissue ablation devices are described e.g., in U.S. Pat. Nos. 6,112,123 and 6,258,087. Energy-based devices for treating GERD which may be combined with one or more fibrosis-inducing agents according to the present invention include several commercially available products, such as the STRETTA system (Curon Medical) radio frequency (RF) ablation device.

In the present invention, fibrosis-inducing agents are combined with suture-based and energy-based treatments of GERD to enhance scarring around the device, re-enforce LES anatomy and prevent gastroesophageal reflux. Numerous polymeric and non-polymeric carrier systems described previously can be used to deliver one or more fibrosis-inducing agents and promote the formation of granulation tissue around the implanted device. The methods for incorporating fibrosis-inducing agents onto or into the implanted GERD devices include: (a) directly affixing to the implanted suture a fibrosing composition (e.g., by either a spraying process or dipping process as described previously, with or without a carrier); (b) directly incorporating into the polymers which compose the sutures themselves a fibrosing composition; (c) by coating the sutures with a substance such as a hydrogel which can in turn absorb the fibrosing composition, (d) by interweaving fibrosing composition coated thread (or the polymer itself formed into a thread) into the suturing material; (e) by constructing the suture itself or a portion of the suture with a fibrosing composition (particularly silk); or (f) by covalently binding the fibrosing agent directly to the surface of the suture or the surface of the gastric mucosa (or utilizing a linker small molecule or polymer to accomplish this); (g) by applying (e.g., infusing, spraying, injecting) the fibrosis-inducing agent into the LES or the gastric mucosal (or serosal) surface, either alone or in a polymeric carrier (e.g., collagen, COSTASIS, materials made from 4-armed thiol PEG (10K), a 4-armed NHS PEG(10K) and methylated collagen such as described above, fibrin, PMMA, CORTOSS, cyanoacrylate, hyaluronic acid, EVA, PLA and other polymers described previously), to induce scarring in the sphincter or across the plication created by the suture device; and/or (h) applying (e.g., infusing, spraying, injecting) a fibrosis-inducing agent, with or without a polymeric carrier, into the tissues into which energy is being applied (to enhance scarring).

It should be apparent to one of skill in the art that potentially any adhesion or fibrosis-inducing agents described above may be utilized alone, or in combination, in the practice of this embodiment. Exemplary fibrosing agents for use in the treatment of GERD include talc, silk, wool, chitosan, polylysine, fibronectin, bleomycin, and CTGF, as well as analogues and derivatives of the aforementioned.

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or an analogue or derivative thereof.

Furthermore, the device may additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

Preferred specific agents and dosages of use for coating implantable, prosthetic devices used in the management of GERD are described in section (iii) immediately below.

(iii) Fibrosis-Inducing Agents for GERD

As GERD devices are made in a variety of configurations and sizes (including injectables and implants), the exact dosage administered can vary with the amount injected or the size, surface area and design of the implant material. However, certain principles can be applied in the application of this art. Drug dose can be calculated as a function of dose per unit volume/area (of the total volume of bulking agent injected or of the surface area of the portion of the implant being coated), total drug dose administered can be measured and appropriate surface concentrations of active drug can be determined. Regardless of the method of application of the fibrosis-inducing agent in the management of GERD, the exemplary fibrosing agents, used alone or in combination, should be administered under the following dosing guidelines:

Utilizing talc as an exemplary fibrosis-inducing agent, whether it is applied using a polymer coating, incorporated into the polymers which make up the device or implant, or applied without a polymeric carrier, the total dose of talc delivered in bulking agent injection, or coated onto the surface of a GERD implant or device, should not exceed 100 mg (range of 1 µg to 100 mg). In one embodiment, the total amount of talc released should be in the range of 10 µg to 50 mg. The dose per unit volume of the injectable bulking agent (i.e., the dosage of talc as a function of the volume of bulking agent injected) should fall within the range of 0.05 µg–10 µg per $mm^3$. In another embodiment, talc should be applied to a GERD implant or device surface at a dose of 0.05 µg/$mm^2$–10 µg/$mm^2$ of surface area coated. In one embodiment, talc is released from a GERD bulking agent, device or implant such that fibrosis in the tissue is promoted for a period ranging from several hours to several months.

For example, in a preferred embodiment talc may be released in effective concentrations for a period ranging from 3–12 months. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymer coating, incorporated into the polymers which make up the device or implant, or applied without a polymeric carrier, the total dose of silk delivered in bulking agent injection, or coated onto the surface of a GERD implant or device, should not exceed 100 mg (range of 1 µg to 100 mg). In one embodiment, the total amount of silk released should be in the range of 10 µg to 50 mg. The dose per unit volume of the injectable bulking agent (i.e., the dosage of silk as a function of the volume of bulking agent injected) should fall within the range of 0.05 µg–10 µg per mm$^3$. In another embodiment, silk should be applied to a GERD implant or device surface at a dose of 0.05 µg/mm$^2$–10 µg/mm$^2$ of surface area coated. As specific (polymeric and non-polymeric) drug delivery vehicles and specific bulking agents, implants and devices can release silk at differing rates, the above dosing parameters should be utilized in combination with the release rate of the drug from the GERD bulking agent, implant or device such that a minimum concentration of 0.01 nM to 1000 µM of silk is delivered to the tissue. In one embodiment, silk is released from a GERD bulking injection, implant or device such that fibrosis in the tissue is promoted for a period ranging from several hours to several months. For example, in a preferred embodiment silk may be released in effective concentrations for a period ranging from 3–12 months. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymer coating, incorporated into the polymers which make up the device or implant, or applied without a polymeric carrier, the total dose of chitosan delivered in bulking agent injection, or coated onto the surface of a GERD implant or device, should not exceed 100 mg (range of 1 µg to 100 mg). In one embodiment, the total amount of chitosan released should be in the range of 10 µg to 50 mg. The dose per unit volume of the injectable bulking agent (i.e., the dosage of chitosan as a function of the volume of bulking agent injected) should fall within the range of 0.05 µg–10 µg per mm$^3$. In another embodiment, chitosan should be applied to a GERD implant or device surface at a dose of 0.05 µg/mm$^2$–10 µg/mm$^2$ of surface area coated. As specific (polymeric and non-polymeric) drug delivery vehicles and specific bulking agents, implants and devices can release chitosan at differing rates, the above dosing parameters should be utilized in combination with the release rate of the drug from the GERD bulking agent, implant or device such that a minimum concentration of 0.01 nM to 1000 µM of chitosan is delivered to the tissue. In one embodiment, chitosan is released from of a GERD bulking agent, implant or device such that fibrosis in the tissue is promoted for a period ranging from several hours to several months. For example, in a preferred embodiment chitosan may be released in effective concentrations for a period ranging from 3–12 months. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as a exemplary fibrosis-inducing agent, whether it is applied using a polymer coating, incorporated into the polymers which make up the device or implant, or applied without a polymeric carrier, the total dose of polylysine delivered in bulking agent injection, or coated onto the surface of a GERD implant or device, should not exceed 100 mg (range of 1 µg to 100 mg). In one embodiment, the total amount of polylysine released should be in the range of 10 µg to 50 mg. The dose per unit volume of the injectable bulking agent (i.e., the dosage of polylysine as a function of the volume of bulking agent injected) should fall within the range of 0.05 µg–10 µg per mm$^3$. In another embodiment, polylysine should be applied to a GERD implant or device surface at a dose of 0.05 µg/mm$^2$–10 µg/mm$^2$ of surface area coated. As specific (polymeric and non-polymeric) drug delivery vehicles and specific bulking agents, implants and devices can release polylysine at differing rates, the above dosing parameters should be utilized in combination with the release rate of the drug from the GERD bulking agent, device or implant such that a minimum concentration of 0.01 nM to 1000 µM of polylysine is delivered to the tissue. In one embodiment, polylysine is released from a GERD bulking agent, implant or device such that fibrosis in the tissue is promoted for a period ranging from several hours to several months. For example, in a preferred embodiment polylysine may be released in effective concentrations for a period ranging from 3–12 months. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymer coating, incorporated into the polymers which make up the device or implant, or applied without a polymeric carrier, the total dose of fibronectin delivered in bulking agent injection, or coated onto the surface of a GERD implant or device, should not exceed 100 mg (range of 1 µg to 100 mg). In one embodiment, the total amount of fibronectin released should be in the range of 10 µg to 50 mg. The dose per unit volume of the injectable bulking agent (i.e., the dosage of fibronectin as a function of the volume of bulking agent injected) should fall within the range of 0.05 µg–10 µg per mm$^3$. In another embodiment, fibronectin should be applied to a GERD implant or device surface at a dose of 0.05 µg/mm$^2$–10

µg/mm² of surface area coated. As specific (polymeric and non-polymeric) drug delivery vehicles and specific bulking agents, implants and devices can release fibronectin at differing rates, the above dosing parameters should be utilized in combination with the release rate of the drug from the GERD bulking agent, implant or device such that a minimum concentration of 0.01 nM to 1000 µM of fibronectin is delivered to the tissue. In one embodiment, fibronectin is released from a GERD bulking agent, implant or device such that fibrosis in the tissue is promoted for a period ranging from several hours to several months. For example, in a preferred embodiment fibronectin may be released in effective concentrations for a period ranging from 3–12 months. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, whether it is applied using a polymer coating, incorporated into the polymers which make up the device or implant, or applied without a polymeric carrier, the total dose of bleomycin delivered in bulking agent injection, or coated onto the surface of a GERD implant or device, should not exceed 100 mg (range of 0.01 µg to 100 mg). In one embodiment, the total amount of bleomycin released should be in the range of 0.10 µg to 50 mg. The dose per unit volume of the injectable bulking agent (i.e., the dosage of bleomycin as a function of the volume of bulking agent injected) should fall within the range of 0.005 µg–10 µg per mm³. In another embodiment, bleomycin should be applied to a GERD implant or device surface at a dose of 0.005 µg/mm²–10 µg/mm² of surface area coated. As specific (polymeric and non-polymeric) drug delivery vehicles and specific bulking agents, implants and devices can release bleomycin at differing rates, the above dosing parameters should be utilized in combination with the release rate of the drug from the GERD bulking agent, implant or device such that a minimum concentration of 0.001 nM to 1000 µM of bleomycin is delivered to the tissue. In one embodiment, bleomycin is released from a GERD bulking agent, implant or device such that fibrosis in the tissue is promoted for a period ranging from several hours to several months. For example, in a preferred embodiment bleomycin may be released in effective concentrations for a period ranging from 3–12 months. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as an exemplary fibrosis-inducing agent, whether it is applied using a polymer coating, incorporated into the polymers which make up the device or implant, or applied without a polymeric carrier, the total dose of CTGF delivered in bulking agent injection, or coated onto the surface of a GERD implant or device, should not exceed 100 mg (range of 0.01 µg to 100 mg). In one embodiment, the total amount of CTGF released should be in the range of 0.10 µg to 50 mg. The dose per unit volume of the injectable bulking agent (i.e., the dosage of CTGF as a function of the volume of bulking agent injected) should fall within the range of 0.005 µg–10 µg per mm³. In another embodiment, CTGF should be applied to a GERD implant or device surface at a dose of 0.005 µg/mm²–10 µg/mm² of surface area coated. As specific (polymeric and non-polymeric) drug delivery vehicles and specific bulking agents, implants and devices can release CTGF at differing rates, the above dosing parameters should be utilized in combination with the release rate of the drug from the GERD bulking agent, implant or device such that a minimum concentration of 0.001 nM to 1000 µM of CTGF is delivered to the tissue. In one embodiment, CTGF is released from a GERD bulking agent, implant or device such that fibrosis in the tissue is promoted for a period ranging from several hours to several months. For example, in a preferred embodiment CTGF may be released in effective concentrations for a period ranging from 3–12 months. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or an analogue or derivative thereof.

Inflammatory cytokines are to be used in formulations at concentrations that range from 0.0001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 µg to 100 mg); preferred 0.001 µg to 50 mg. When used as a device coating, the dose is per unit area of 0.0001 µg–500 µg per mm²; with a preferred dose of 0.001 µg/mm²–200 µg/mm². Minimum concentration of $10^{-10}$–$10^{-4}$ g/ml of inflammatory cytokine is to be maintained on the device surface.

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof. Doses used are those concentrations which are demonstrated to stimulate cell proliferation (see, e.g., Example 16). The proliferative agents are to be used in formulations at concentrations that range from 0.1 ng/ml to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 µg to 200 mg); preferred 0.001 µg to 100 mg. When used as a device coating, the dose is per unit area of 0.00001 µg–500 µg per mm$^2$; with a preferred dose of 0.0001 µg/mm$^2$–200 µg/mm$^2$. Minimum concentration of $10^{-11}$–$10^{-6}$ M of proliferative agent is to be maintained on the device surface.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

10. Morbid Obesity

The present invention provides fibrosis-inducing compositions and devices for use in the management of morbid obesity. Morbid obesity (people who are more than 50% above their ideal body weight) is a significant public health problem that affects a significant (and growing) percentage of the population in the Western world. Morbid obesity predisposes the patient to a variety of significant health problems including heart disease, diabetes, stroke, kidney disease, joint disease and a shortened lifespan. Numerous interventional procedures have been developed to address the problem including strategies designed to surgically decrease the size of the stomach. This physically limits the amount of food that can be consumed, provides a sense of satiety and ultimately leads to weight loss due to decreased food and caloric intake. The present invention describes the addition of fibrosis-inducing agents combined with gastric restriction devices to improve the efficacy of the procedure.

An example of a gastric restriction device is a laparoscopically installed inflatable cuff (referred to as a lap-band) that is placed around the top of the stomach just below the lower esophageal sphincter (LES). For a further description, see, for example, U.S. Pat. Nos. 5,601,604; 5,226,429; and 5,074,868. Additional examples of restriction devices used for the management of obesity are described in, e.g., U.S. Pat. Nos. 6,067,991; 6,454,699; 6,453,907; 6,450,946; 6,210,347; and 6,067,991. Other minimally invasive devices include, but are not limited to, space occupying devices, suture-based endoluminal devices for partitioning the stomach, electrostimulation devices (e.g., neural and non-neural), and radio frequency antralplasty devices. Space occupying devices (e.g., intragastric balloons) are described, for example, in U.S. Pat. Nos. 5,259,399; 4,485,805; 5,129,915; 5,259,399; and 6,454,785. Electrostimulation devices for the treatment of obesity are described in, e.g., U.S. Pat. Nos. 6,615,084; 6,129,685; 5,782,798, 6,535,764; and 6,606,523.

In one aspect, restriction devices can be combined with fibrosis-inducing agents for the treatment of obesity. Specifically, several commercially available restriction products are suitable for the practice of this invention including: the LAP-BAND Adjustable Gastric Banding System (made by Inamed) which involves a small ring of inflatable silicone that can be inflated or deflated from an attached tubing connected to a subcutaneous port), the SWEDISH ADJUSTABLE GASTRIC BAND (by Ethicon-Endosurgery) is a low pressure inflatable device reinforced with a DACRON net that is fitted around the uppermost part of the stomach laparoscopically and can be adjusted after placement by injecting or removing fluid).

Also in the present invention, numerous commercially available minimally invasive devices for treating obesity can be combined with one or more fibrosis-inducing agents. Specifically, space occupying minimally invasive devices suitable for use in the practice of this invention include: the BARIATRIC INTRAGASTRIC BALLOON (by Inamed) is a spherical silicon implant placed in the stomach and expanded with saline to 400–800 ml that can be left in place for 3–6 months), an intragastric balloon available from Satiety, Inc., the BOWTIE space occupying device made from a continuous ribbon of polyester (Wilson-Cook, Inc.), and a suture-based endoluminal device for partitioning the stomach, such as the EAGLE CLAW (Olympus America).

The addition of a fibrosis-inducing agent to a gastric band device or a space occupying device can enhance efficacy and longevity of the procedure in several ways. For example, inducing fibrous tissue around the implant can secure the implant in place allowing it to maintain the proper anatomical position in the stomach. Also, fibrous tissue can form a permanent "band" in the stomach that results in sustained, host tissue shrinkage of the stomach. As the scar matures it can also contract, further reducing the size of the stomach and improving the efficacy of the procedure.

Numerous polymeric and non-polymeric carrier systems described in detail previously can be used in the practice of this invention. These compositions can further comprise one or more fibrosis-inducing agents to promote the formation of granulation tissue. The methods for incorporating fibrosing compositions onto or into gastric restriction or space occupying obesity devices include: (a) directly affixing to the device a fibrosing composition (e.g., by either a spraying process or dipping process as described above, with or without a carrier); (b) directly incorporating into the device a fibrosing composition (e.g., by either a spraying process or dipping process as described above, with or without a carrier); (c) by coating the device with a substance such as a hydrogel which can in turn absorb the fibrosing composition; (d) by interweaving fibrosing composition coated thread (or the polymer itself formed into a thread) into the device structure; (e) by inserting the device into a sleeve or mesh which is comprised of or coated with a fibrosing composition; (f) constructing the device itself or a portion of the device with a fibrosing composition; and/or (g) by covalently binding the fibrosing agent directly to the device surface or to a linker (small molecule or polymer) that is coated or attached to the device surface. For these devices, the coating process can be performed in such a manner as to a) coat the exterior surfaces of the device, b) coat the interior surfaces of the device or c) coat all or parts of both external and internal surface of the device. In addition to coating the device with the fibrosing composition, the fibrosing agent can be mixed with the materials that are used to make the device such that the fibrosing agent is incorporated into the final device.

In one embodiment fibrosis-inducing agents can be incorporated directly into the formulation to produce a suspension or a solution (e.g., silk powder, bleomycin) or it can be incorporated into a secondary carrier (e.g., micelles, liposomes, microspheres, microparticles, nanospheres, microparticulates, emulsions and/or microemulsions) that is then incorporated into the gastric restriction device or space occupying device. In another embodiment, the fibrosis-inducing agent can be electrostatically or covalently bound to one or more of the polymeric components of the in situ forming composition.

It should be apparent to one of skill in the art that potentially any adhesion or fibrosis-inducing agents described above may be utilized alone, or in combination, in the practice of this embodiment. Exemplary fibrosing agents for use in obesity devices and compositions include talc, silk, wool, chitosan, polylysine, fibronectin, bleomycin, and CTGF, as well as analogues and derivatives of the aforementioned.

As obesity devices are made in a variety of configurations and sizes, the exact dose administered can vary with device size, surface area and design. However, certain principles can be applied in the application of this art. Drug dose can be calculated as a function of dose per unit area (of the portion of the device being coated), total drug dose administered can be measured and appropriate surface concentrations of active drug can be determined. Regardless of the method of application of the drug to the obesity device, the exemplary fibrosing agents, used alone or in combination, should be administered under the following dosing guidelines:

Utilizing talc as an exemplary fibrosis-inducing agent, whether it is applied using a polymer coating, incorporated into the polymers which make up the device or implant, or applied without a polymeric carrier, the total dose of talc delivered from a obesity device, or coated onto the surface of an obesity device, should not exceed 100 mg (range of 1 µg to 100 mg). In one embodiment, the total amount of talc released from the prosthesis should be in the range of 10 µg to 50 mg. The dose per unit area of the device (i.e., the dosage of talc as a function of the surface area of the portion of the device to which drug is applied and/or incorporated) should fall within the range of 0.05 µg–10 µg per mm$^2$ of surface area coated. In another embodiment, talc should be applied to an obesity device surface at a dose of 0.05 µg/mm$^2$–10 µg/mm$^2$ of surface area coated. In one embodiment, talc is released from the surface of an obesity device such that fibrosis in the tissue is promoted for a period ranging from several hours to several months. For example, talc may be released in effective concentrations for a period ranging from 1–9 months. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymer coating, incorporated into the polymers which make up the device or implant, or applied without a polymeric carrier, the total dose of silk delivered from a obesity device, or coated onto the surface of an obesity device, should not exceed 100 mg (range of 1 µg to 100 mg). In one embodiment, the total amount of silk released from the prosthesis should be in the range of 10 µg to 50 mg. The dose per unit area of the device (i.e., the dosage of silk as a function of the surface area of the portion of the device to which drug is applied and/or incorporated) should fall within the range of 0.05 µg–10 µg per mm$^2$ of surface area coated. In another embodiment, silk should be applied to an obesity device surface at a dose of 0.05 µg/mm$^2$–10 µg/mm$^2$ of surface area coated. As specific (polymeric and non-polymeric) drug delivery vehicles and specific medical devices can release silk at differing rates, the above dosing parameters should be utilized in combination with the release rate of the drug from the obesity device such that a minimum concentration of 0.01 nM to 1000 µM of silk is delivered to the tissue. In one embodiment, silk is released from the surface of an obesity device such that fibrosis in the tissue is promoted for a period ranging from several hours to several months. For example, silk may be released in effective concentrations for a period ranging from 1–9 months. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymer coating, incorporated into the polymers which make up the device or implant, or applied without a polymeric carrier, the total dose of chitosan delivered from an obesity device, or coated onto the surface of an obesity device, should not exceed 100 mg (range of 1 µg to 100 mg). In one embodiment, the total amount of chitosan released from the prosthesis should be in the range of 10 µg to 50 mg. The dose per unit area of the device (i.e., the dosage of chitosan as a function of the surface area of the portion of the device to which drug is applied and/or incorporated) should fall within the range of 0.05 µg–10 µg per mm$^2$ of surface area coated. In another embodiment, chitosan should be applied to an obesity device surface at a dose of 0.05 µg/mm$^2$–10 µg/mm$^2$ of surface area coated. As specific (polymeric and non-polymeric) drug delivery vehicles and specific medical devices can release chitosan at differing rates, the above dosing parameters should be utilized in combination with the release rate of the drug from the obesity device such that a minimum concentration of 0.01 nM to 1000 µM of chitosan is delivered to the tissue. In one embodiment, chitosan is released from the surface of an obesity device such that fibrosis in the tissue is promoted for a period ranging from several hours to several months. For example, chitosan may be released in effective concentrations for a period ranging from 1–9 months. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as an exemplary fibrosis-inducing agent, whether it is applied using a polymer coating, incorporated into the polymers which make up the device or implant, or applied without a polymeric carrier, the total dose of polylysine delivered from an obesity device, or coated onto the surface of an obesity device, should not exceed 100 mg (range of 1 µg to 100 mg). In one embodiment, the total amount of polylysine released from the prosthesis should be in the range of 10 µg to 50 mg. The dose per unit area of the device (i.e., the dosage of polylysine as a function of the surface area of the portion of the device to which drug is applied and/or incorporated) should fall within the range of 0.05 µg–10 µg per mm$^2$ of surface area coated. In another embodiment, polylysine should be applied to an obesity device surface at a dose of 0.05 µg/mm$^2$–10 µg/mm$^2$ of surface area coated. As specific (polymeric and non-polymeric) drug delivery vehicles and specific medical devices can release polylysine at differing rates, the above dosing parameters should be utilized in combination with the release rate of the drug from the obesity device such that a minimum concentration of 0.01 nM to 1000 µM of polylysine is delivered to the tissue. In one embodiment, polylysine is released from the surface of an obesity device such that fibrosis in the tissue is promoted for a period ranging from several hours to several months. For example, polylysine may be released in effective concentrations for a period ranging from 1–9 months. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymer coating, incorporated into the polymers which make up the device or implant, or applied without a polymeric carrier, the total dose of fibronectin delivered from an obesity device, or coated onto the surface of an obesity device, should not exceed 100 mg (range of 1 µg to 100 mg). In one embodiment, the total amount of fibronectin released from the prosthesis should be in the range of 10 µg to 50 mg. The dose per unit area of the device (i.e., the dosage of fibronectin as a function of the surface area of the portion of the device to which drug is applied and/or incorporated) should fall within the range of 0.05 µg–10 µg per $mm^2$ of surface area coated. In another embodiment, fibronectin should be applied to an obesity device surface at a dose of 0.05 µg/$mm^2$–10 µg/$mm^2$ of surface area coated. As specific (polymeric and non-polymeric) drug delivery vehicles and specific medical devices can release fibronectin at differing rates, the above dosing parameters should be utilized in combination with the release rate of the drug from the obesity device such that a minimum concentration of 0.01 nM to 1000 µM of fibronectin is delivered to the tissue. In one embodiment, fibronectin is released from the surface of an obesity device such that fibrosis in the tissue is promoted for a period ranging from several hours to several months. For example, fibronectin may be released in effective concentrations for a period ranging from 1–9 months. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, whether it is applied using a polymer coating, incorporated into the polymers which make up the device or implant, or applied without a polymeric carrier, the total dose of bleomycin delivered from an obesity device, or coated onto the surface of an obesity device, should not exceed 100 mg (range of 0.01 µg to 100 mg). In one embodiment, the total amount of bleomycin released from the prosthesis should be in the range of 0.10 µg to 50 mg. The dose per unit area of the device (i.e., the dosage of bleomycin as a function of the surface area of the portion of the device to which drug is applied and/or incorporated) should fall within the range of 0.005 µg–10 µg per $mm^2$ of surface area coated. In another embodiment, bleomycin should be applied to an obesity device surface at a dose of 0.005 µg/$mm^2$–10 µg/$mm^2$ of surface area coated. As specific (polymeric and non-polymeric) drug delivery vehicles and specific medical devices can release bleomycin at differing rates, the above dosing parameters should be utilized in combination with the release rate of the drug from the obesity device such that a minimum concentration of 0.001 nM to 1000 µM of bleomycin is delivered to the tissue. In one embodiment, bleomycin is released from the surface of an obesity device such that fibrosis in the tissue is promoted for a period ranging from several hours to several months. For example, bleomycin may be released in effective concentrations for a period ranging from 1–9 months. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as a exemplary fibrosis-inducing agent, whether it is applied using a polymer coating, incorporated into the polymers which make up the device or implant, or applied without a polymeric carrier, the total dose of CTGF delivered from an obesity device, or coated onto the surface of an obesity device, should not exceed 100 mg (range of 0.01 µg to 100 mg). In one embodiment, the total amount of CTGF released from the prosthesis should be in the range of 0.10 µg to 50 mg. The dose per unit area of the device (i.e., the dosage of CTGF as a function of the surface area of the portion of the device to which drug is applied and/or incorporated) should fall within the range of 0.005 µg–10 µg per $mm^2$ of surface area coated. In another embodiment, CTGF should be applied to an obesity device surface at a dose of 0.005 µg/$mm^2$–10 µg/$mm^2$ of surface area coated. As specific (polymeric and non-polymeric) drug delivery vehicles and specific medical devices can release CTGF at differing rates, the above dosing parameters should be utilized in combination with the release rate of the drug from the obesity device such that a minimum concentration of 0.001 nM to 1000 µM of CTGF is delivered to the tissue. In one embodiment, CTGF is released from the surface of an obesity device such that fibrosis in the tissue is promoted for a period ranging from several hours to several months. For example, CTGF may be released in effective concentrations for a period ranging from 1–9 months. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone or an analogue or derivative thereof). Inflammatory cytokines are to be used in formulations at concentrations that range from 0.0001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 μg to 100 mg); preferred 0.001 μg to 50 mg. When used as a device coating, the dose is per unit area of 0.0001 μg–500 μg per $mm^2$; with a preferred dose of 0.001 $μg/mm^2$–200 $μg/mm^2$. Minimum concentration of $10^{-11}$–$10^4$ g/ml of inflammatory cytokine is to be maintained on the device surface.

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof. Doses used are those concentrations which are demonstrated to stimulate cell proliferation (see, e.g., Example 16). The proliferative agents are to be used in formulations at concentrations that range from 0.1 ng/ml to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 μg to 200 mg); preferred 0.001 μg to 100 mg. When used as a device coating, the dose is per unit area of 0.00001 μg–500 μg per $mm^2$; with a preferred dose of 0.0001 $μg/mm^2$–200 $μg/mm^2$. Minimum concentration of $10^{-11}$–$10^{-6}$ M of proliferative agent is to be maintained on the device surface.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

11. Soft Palate Implants

The present invention provides for the combination of a fibrosis-inducing agent and soft palate implant devices for the treatment of snoring and sleep apnea (also referred to as obstructive sleep apnea (OSA)). Sleep apnea refers to the inability to maintain normal respiration and oxygenation while sleeping. Obstructive sleep apnea is characterized by frequent periods of airway occlusion during sleep, with concomitant obstruction of inspiratory airflow, drop in blood oxygen and interruption of sleep when the patient awakes to use voluntary muscle contraction to open the airway and take a few deep breaths. Also of consideration is the impact that loud snoring (often reaching decibel levels equated with the take-off of an airplane) has on the sleeping patterns and lifestyle of the partner of a patient with obstructive sleep apnea. Sleep apnea can arise from a mechanical obstruction of an airway and can involve painful and/or insufficient breathing, an abnormal heartbeat, and hypertension. The mechanical locations and structural causes of obstruction are multiple. The most frequent mechanisms include settling of the tongue, uvula, soft palate or other tissues against the airway during the negative pressure associated with inspiration. This may be related to adipose tissue accumulation, lack of muscle tone or inadequate central respiratory drive to the tongue and/or other accessory respiratory muscles around the oropharyngeal airway. Treatment of sleep apnea includes surgical procedures (such as uvulectomy or removal of the uvula, surgical removal of soft tissue in the airway, or stiffening the palate through the removal of tissue and the induction of scarring), behavioral control of sleep posture, positive airway pressure applied via a face mask, and the use of implantable sleep apnea devices (such as soft palate implants).

The present invention describes soft palate implants combined with a fibrosis-inducing agent to enhance scarring around the implant and improve efficacy of the device. Injectable compositions, with or without the addition of a fibrosis-inducing agent, described in section (i), may be injected into the submucosa of the palate to provide physical support of the tissue. The combination of a fibrosis-inducing agent with soft palate prosthesis (or solid implant) is described in section (ii).

Regardless of their design, soft palate injectables and implants are designed to provide physical support for the uvula and prevent the soft palate from obstructing the airway during sleep. Unfortunately, the symptomatic relief can be only temporary for many patients as support of the soft palate is incomplete or there is insufficient scarring around the implant to create a permanent result. The addition of a fibrosis-inducing agent to a palatal implant can increase the amount of scar tissue surrounding the implant and improve the long term outcome of the procedure. The fibrosis-inducing agent encourages the formation of the body's own fibrous tissue (including collagen) around the soft palate implant to provide support; the natural contracture of the scar with time further elevates the uvula and increases the size of the airway. This results in the formation of continuously sustainable connective tissue which supports the uvula in a manner more closely approximating nasopharyngeal anatomy and biomechanics. The result is a treatment that lasts longer, provides better symptomatic relief and requires fewer re-interventions.

(i) Injectable Fibrosis-Inducing Palatal Implants

The present invention describes degradable and non-degradable injectable biomaterials and implants, alone or combined with a fibrosis-inducing agent, growth factor or sclerosing agent, for injection into the soft palate for the treatment of sleep apnea. Typically, a needle or catheter is advanced into the submucosa of the soft palate and the injectable implant is deployed. The addition of a fibrosis-inducing agent, sclerosing agent and/or growth factor to the materials injected into the soft palate produces a permanent scar that supports the uvula and opens the airway.

A variety of injectable polymer-based products have been developed that are suitable for the practice of this invention and can be used alone or in combination with a fibrosis-inducing agent. Examples of products suitable for injection into the soft palate, alone or with a fibrosis-inducing agent, include: TRUFILL n-butyl cyanoacrylate (n-BCA) Liquid Embolic System (Cordis, a division of Johnson and Johnson, Miami, Fla.); EMBOSPHERE and EMBOGOLD Microspheres; ONYX Liquid Embolic System; BEAD BLOCK; PVA particles from Cook, Inc. and Angiodynamics, Inc.; and in situ forming materials from Biocure, Angiotech Pharmaceuticals, Inc., 3M Company and Neomend.

Several other injectable compositions are suitable for injection into the soft palate for the treatment of sleep apnea. All involve the deployment of a biomaterial into the tissues of the soft palate, with or without the addition of a fibrosis-inducing agent, sclerosing agent, and/or suitable growth factor(s). The following compositions can be delivered via specialized delivery catheters, a needle or other applicator, or a surgically placed access device under direct or endoscopic vision. Examples of appropriate injectable materials which may be injected into the soft palate include: (a) fluids, suspensions, emulsions, microemulsions, microspheres, pastes, gels, microparticulates, sprays, aerosols, solid implants and other formulations which release a biologically active agent(s); (b) microparticulate silk and/or silk strands (linear, branched, and/or coiled) either alone, or loaded with an additional fibrosis-inducing agent, sclerosing agent, and/or growth factor injected into the soft palate; (c) injectable collagen-containing formulations such as COSTASIS or materials prepared from a 4-armed thiol PEG (10K), a 4-armed NHS PEG(10K) and methylated collagen such as described above, either alone, or loaded with a fibrosis-inducing agent, sclerosing agent, and/or growth factor; (d) injectable PEG-containing formulations such as COSEAL, FOCALSEAL, SPRAYGEL or DURASEAL, either alone, or loaded with a fibrosis-inducing agent, sclerosing agent, and/or growth factor; (e) fibrinogen-containing formulations such as FLOSEAL or TISSEAL, either alone, or loaded with a fibrosis-inducing agent, sclerosing agent, and/or growth factor; (f) hyaluronic acid-containing formulations such as RESTYLANE, HYLAFORM, PERLANE, SYNVISC, SEPRAFILM, SEPRACOAT, either alone, or loaded with a fibrosis-inducing agent, sclerosing agent, and/or growth factor; (g) polymeric gels for surgical implantation such as REPEL or FLOWGEL either alone, or loaded with a fibrosis-inducing agent, sclerosing agent, and/or growth factor; (h) orthopedic "cements" such as OSTEOBOND, LVC, SIMPLEX P, PALACOS, CORTOSS, and ENDURANCE, either alone, or loaded with a fibrosis-inducing agent, sclerosing agent, and/or growth factor; (i) surgical adhesives containing cyanoacrylates such as DERMABOND, INDERMIL, GLUSTITCH, VETBOND, HISTOACRYL BLUE and ORABASE SOOTHE-N-SEAL LIQUID PROTECTANT, either alone, or loaded with a fibrosis-inducing agent, sclerosing agent, and/or growth factor, injected into the soft palate; (j) surgical implants containing hydroxyapatite, calcium phosphate (such as VITOSS), or calcium sulfate, alone or loaded with a fibrosis-inducing agent, sclerosing agent, and/or growth factor; (k) other biocompatible tissue fillers, such as those made by BioCure, 3M Company and Neomend, either alone, or loaded with a fibrosis-inducing agent, sclerosing agent, and/or growth factor; (l) polysaccharide gels such as the ADCON series of gels, either alone, or loaded with a fibrosis-inducing agent, sclerosing agent, and/or growth factor; (m) films, sponges or meshes such as INTERCEED, VICRYL mesh, and GELFOAM either alone, or loaded with a fibrosis-inducing agent, sclerosing agent, and/or growth factor and/or (n) a hydrogel that is formed from an amino-functionalized polyethylene glycol (e.g., 4-armed tetra-amino PEG [10k]) and a 4-armed NHS functionalized PEG (e.g., pentaerythritol poly(ethylene glycol)ether tetra-succinimidyl glutarate [10K]). This hydrogel may further contain collagen, methylated collagen and/or gelatin. This hydrogel can further comprise the fibrosis-inducing agents described above (e.g., silk powder or silk threads). Films, sponges, and meshes may be placed into the soft palate. Also of use for injection into the soft palate are non-degradable polymers such as polyesters (e.g., PET), polyurethanes, silicones, PE, PP, PS, PAA, PMA, silk, blends, copolymers thereof as well as other known non-degradable polymers that are known in the art.

Degradable polymers that can be injected into the soft palate to provide tissue support include polyesters, polyanhydrides, poly(anhydride esters), poly(ester-amides), poly(ester-ureas), polyorthoesters, polyphosphoesters, polyphosphazines, cyanoacrylate polymers, collagen, chitosan, hyaluronic acid, chromic cat gut, alginates, starch, cellulose, cellulose esters, blends and copolymers thereof, as well as other known degradable polymers.

In one embodiment, the injectable polymer system is prepared from a 4-armed thiol PEG (10K), a 4-armed NHS PEG(10K) and methylated collagen such as described above. The injectable polymer system may be combined with a biologically active agent (e.g., fibrosis-inducing agents such as talc, silk, wool, chitosan, polylysine, fibronectin, bleomycin, CTGF; sclerosing agents such as ethanol, DMSO, surfactants, sucrose, sodium morrhuate, ethanolamine oleate NaCl, dextrose, glycerin, minocycline, tetracycline, doxycycline, polidocanol, sodium tetradecyl sulfate, sodium morrhuate, sotradecol; growth factors such as transforming growth factor, platelet-derived growth factor, fibroblast growth factor, and bone morphogenic proteins; and/or analogues and derivatives of these compounds) and injected into the soft palate. The injectable polymer system can further comprise agents such as glycerol, glycerin, PEG 200, triethyl citrate, and triacetin as plasticizers.

In another embodiment, the injectable materials delivered to the soft palate can be formulated to be delivered from the catheter (or needle) as a particulate material that has the ability to induce fibrosis. The injectable particles can be loaded with, coated with, or comprised of a fibrosis-inducing agent. These particles can be either degradable or non-degradable and are similar in composition to those described above. In addition to the aforementioned polymers, particulate materials useful for the practice of this embodiment include talc, starch, glass, silicates, silica, calcium phosphate, calcium sulfate, calcium carbonate, hydroxyapatite, synthetic mineral (VITOSS and CORTOSS), PMMA, silver nitrate, ceramic particles and other inorganic particles known in the art to induce a fibroproliferative response. The particles used in this embodiment can be all of the same composition or a blend of differing compositions. These particles can also be used in combination with the injectable polymeric materials described above.

In many of the above embodiments, it may also be useful to add a radio-opaque material (such as tantalum, barium, other metal, or contrast material) such that the injected material can be visualized radiographically. Also, when performing direct injection into the soft palate, techniques can be used to enhance visualization of needle (or catheter) via ultrasound through the use of a needle coated with ECHO—COAT or the injection of air (microbubbles).

It should be apparent to one of skill in the art that potentially any adhesion or fibrosis-inducing agent, sclerosing agent, or growth factor may be utilized alone, or in combination, in the practice of this embodiment. Exemplary fibrosing agents for use in injectable soft palate implant procedures include talc, silk, wool, chitosan, polylysine, fibronectin, bleomycin, CTGF, sclerosing agents, and/or growth factors (such as transforming growth factor, platelet-derived growth factor, fibroblast growth factor, bone morphogenic proteins) as well as analogues and derivatives of the aforementioned.

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or a bone morphogenic protein (BMP)

(e.g., BMP-2, BMP-3, BMP-4, BMP-5, BMP-6, or BMP-7 or an analogue or derivative thereof).

Furthermore, the device may additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

In some clinical situations, repeated injections of the active agents may be required. Specific agents and dosages for use in injectable soft palate implants can be described in greater detail in section (iii) below.

(ii) Soft Palate Implants Combined with a Fibrosis-Inducing Agent

Soft palate implants are devices that are designed to be inserted under the mucosa in the soft palate in the roof of the mouth of a person with snoring or sleep apnea. Soft palate implants are described in, e.g., U.S. Pat. Nos. 6,626,181; 6,571,798 and 6,578,580. Other medical devices used for treating sleep apnea include soft palate implants that provide electrostimulation (see, e.g., 6,240,316; 6,574,507; 5,284,161 and 5,792,067).

Soft palate implants, which may be combined with one or more fibrosis-inducing agents, sclerosing agents and/or growth factors according to the present invention, include several commercially available products. For example, the PILLAR Palatal Implant System from Restore Medical Inc. (St. Paul, Minn.) for the treatment of snoring is a woven polyester material implanted into the soft palate that stiffens and supports the palate (thereby reducing vibration and the tendency for the soft palate to "flop down" and obstruct the airway) without heating or removing tissue.

Numerous polymeric and non-polymeric carrier systems described above may be used to deliver fibrosis-inducing agents, sclerosing agents and growth factors from soft palate implants. Methods for incorporating fibrosing, sclerosing and growth factor compositions onto or into soft palate implants include: (a) directly affixing to the palatal implant a fibrosing, sclerosing and/or growth factor composition (e.g., by either spraying the surface of the implant or dipping the implant into a solution containing the active agent; the agent can be applied alone or with a polymeric carrier); (b) directly incorporating into the components or the polymers that make up the palatal implant a fibrosing, sclerosing and/or growth factor composition (e.g., by either a spraying process or dipping process with or without a polymeric carrier; (c) by coating the palatal implant with a substance such as a hydrogel which can in turn absorb the fibrosing, sclerosing and/or growth factor composition; (d) by interweaving a thread coated with (or composed of) a fibrosing, sclerosing and/or growth factor into the structure of the palatal implant; (e) by inserting the palatal implant into a sleeve or mesh which is comprised of, or coated with, a fibrosing, sclerosing and/or growth factor composition; (f) constructing the palatal implant itself, or a portion of the implant, with a fibrosing, sclerosing and/or growth factor composition (particularly effective for silk); and/or (g) by covalently binding the fibrosing agent, sclerosing agent, and/or growth factor directly to the palatal implant surface or to a linker (small molecule or polymer) that is coated or attached to the implant surface. For palatal implants, the coating process can be performed in such a manner as to: a) coat the exterior surfaces of the implant, b) coat the interior surfaces of the implant or c) coat all or parts of both external and internal surface of the implant. In addition to coating the palatal implant with the fibrosing, sclerosing and/or growth factor composition, the active agent can be mixed with the materials that are used to make the implant such that the fibrosing, sclerosing and/or growth factor is incorporated into the final implant.

It should be apparent to one of skill in the art that potentially any fibrosis-inducing agent, sclerosing agent or growth factor may be utilized alone, or in combination, in the practice of this embodiment. Exemplary fibrosing agents for use in combination with soft palate implants include talc, silk, wool, chitosan, polylysine, fibronectin, bleomycin, CTGF; sclerosing agents such as sodium morrhuate, ethanolamine oleate, ethanol, DMSO, surfactants, sucrose, NaCl, dextrose, glycerin, minocycline, tetracycline, doxycycline, polidocanol, sodium tetradecyl sulfate, sodium morrhuate, sotradecol; and/or growth factors such as transforming growth factor, platelet-derived growth factor, fibroblast growth factor, and bone morphogenic proteins, as well as analogues and derivatives of the aforementioned.

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or a bone morphogenic protein (BMP) (e.g., BMP-2, BMP-3, BMP-4, BMP-5, BMP-6, or BMP-7 or an analogue or derivative thereof).

Furthermore, the device may additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

In some clinical situations, repeated injections of the active agents may be required. Specific agents and dosages for use in injectable soft palate implants can be described in greater detail in section (iii) below.

(iii) Agents for Use in the Management Sleep Apnea

There are several commercially available sclerosing agents which may be suitable for use according to the present invention. One example available from Wyeth Pharmaceuticals (Collegeville, Pa.), a division of Wyeth (Madison, N.J.), is SOTRADECOL, which is sodium tetradecyl sulfate. Other sclerosing agents include sodium morrhuate, ethanolamine oleate, compositions containing ethanol, DMSO, surfactants, sucrose, NaCl, dextrose, glycerin, minocycline, tetracycline, doxycycline, polidocanol, sodium morrhuate, sotradecol and others. Other examples of compositions suitable for injection into the soft palate or combining with a soft palate implant include silk (e.g., microparticulate silk) and polymeric gels (such as those available from Polymerix Corporation) composed of fibrosis-inducing agents, sclerosing agents, and growth factors.

Since palatal implants and devices are made in a variety of configurations and sizes (including injectables and implants), the exact dosage administered can vary with the amount injected, or the size, surface area and design of the implant. However, certain principles can be applied in the application of this art. Drug dose can be calculated as a function of dose per unit volume/area (of the total volume of material injected or of the surface area of the portion of the palatal implant being coated), total drug dose administered can be measured and appropriate surface concentrations of active drug can be determined. Regardless of the method of application of the fibrosis-inducing agent in the management of sleep apnea, the exemplary fibrosing agents, used alone or in combination, should be administered under the following dosing guidelines:

Utilizing talc as an exemplary fibrosis-inducing agent, whether it is applied using a polymer coating, incorporated into the polymers which make up the device or implant, or applied without a polymeric carrier, the total dose of talc delivered in a soft palate injection, or coated onto the surface of a palatal implant or device, should not exceed 100 mg (range of 1 µg to 100 mg). In one embodiment, the total amount of talc released should be in the range of 10 µg to 50 mg. The dose per unit volume of a soft palate injectable (i.e., the dosage of talc as a function of the volume of material injected) should fall within the range of 0.05 µg–10 µg per mm$^3$. In another embodiment, talc should be applied to a palatal implant or device surface at a dose of 0.05 µg/mm$^2$–10 µg/mm$^2$ of surface area coated. In one embodiment, talc is released from a soft palate injectable, device or implant such that fibrosis in the tissue is promoted for a period ranging from several hours to several months. For example, in a preferred embodiment talc may be released in effective concentrations for a period ranging from 3–12 months. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymer coating, incorporated into the polymers which make up the device or implant, or applied without a polymeric carrier, the total dose of silk delivered in soft palate injection, or coated onto the surface of a soft palate implant or device, should not exceed 100 mg (range of 1 µg to 100 mg). In one embodiment, the total amount of silk released should be in the range of 10 µg to 50 mg. The dose per unit volume of a soft palate injectable (i.e., the dosage of silk as a function of the volume of material injected) should fall within the range of 0.05 µg–10 µg per mm$^3$. In another embodiment, silk should be applied to a soft palate implant or device surface at a dose of 0.05 µg/mm$^2$–10 µg/mm$^2$ of surface area coated. As specific (polymeric and non-polymeric) drug delivery vehicles and specific soft palate injectables, implants and devices can release silk at differing rates, the above dosing parameters should be utilized in combination with the release rate of the drug from the soft palate injectable, implant or device such that a minimum concentration of 0.01 nM to 1000 µM of silk is delivered to the tissue. In one embodiment, silk is released from a soft palate injection, implant or device such that fibrosis in the tissue is promoted for a period ranging from several hours to several months. For example, in a preferred embodiment silk may be released in effective concentrations for a period ranging from 3–12 months. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymer coating, incorporated into the polymers which make up the device or implant, or applied without a polymeric carrier, the total dose of chitosan delivered in soft palate injection, or coated onto the surface of a soft palate implant or device, should not exceed 100 mg (range of 1 µg to 100 mg). In one embodiment, the total amount of chitosan released should be in the range of 10 µg to 50 mg. The dose per unit volume of the soft palate injectable (i.e., the dosage of chitosan as a function of the volume of material injected) should fall within the range of 0.05 µg–10 µg per mm$^3$. In another embodiment, chitosan should be applied to a soft palate implant or device surface at a dose of 0.05 µg/mm$^2$–10 µg/mm$^2$ of surface area coated. As specific (polymeric and non-polymeric) drug delivery vehicles and specific palatal injectables, implants and devices can release chitosan at differing rates, the above dosing parameters should be utilized in combination with the release rate of the drug from the soft palate injectable, implant or device such that a minimum concentration of 0.01 nM to 1000 µM of chitosan is delivered to the tissue. In one embodiment, chitosan is released from of a soft palate injectable, implant or device such that fibrosis in the tissue is promoted for a period ranging from several hours to several months. For example, in a preferred embodiment chitosan may be released in effective concentrations for a period ranging from 3–12 months. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as a exemplary fibrosis-inducing agent, whether it is applied using a polymer coating, incorporated into the polymers which make up the device or implant, or applied without a polymeric carrier, the total dose of polylysine delivered in soft palate injection, or coated onto the surface of a soft palate implant or device, should not exceed 100 mg (range of 1 µg to 100 mg). In one embodiment, the total amount of polylysine released should be in the range of 10 µg to 50 mg. The dose per unit volume of the soft palate injectable (i.e., the dosage of polylysine as a function of the volume of material injected) should fall within the range of 0.05 µg–10 µg per mm$^3$. In another embodiment, polylysine should be applied to a soft palate implant or device surface at a dose of 0.05 µg/mm$^2$–10 µg/mm$^2$ of surface area coated. As specific (polymeric and non-polymeric) drug delivery vehicles and specific palatal injectables, implants and devices can release polylysine at differing rates, the above dosing parameters should be utilized in combination with the release rate of the drug from the soft palate injectable, device or implant such that a minimum concentration of 0.01 nM to 1000 µM of polylysine is delivered to the tissue. In one embodiment, polylysine is released from a soft palate injectable, implant or device such that fibrosis in the tissue is promoted for a period ranging from several hours to several months. For example, in a preferred embodiment polylysine may be released in effective concentrations for a period ranging from 3–12 months. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymer coating, incorporated into the polymers which make up the device or implant, or applied without a polymeric carrier, the total dose of fibronectin delivered in soft palate injection, or coated onto the surface of a soft palate implant or device, should not exceed 100 mg (range of 1 µg to 100 mg). In one embodiment, the total amount of fibronectin released should be in the range of 10 µg to 50 mg. The dose per unit volume of the soft palate injectable (i.e., the dosage of fibronectin as a function of the volume of material injected) should fall within the range of 0.05 µg–10 µg per $mm^3$. In another embodiment, fibronectin should be applied to a soft palate implant or device surface at a dose of 0.05 µg/$mm^2$–10 µg/$mm^2$ of surface area coated. As specific (polymeric and non-polymeric) drug delivery vehicles and specific soft palate injectables, implants and devices can release fibronectin at differing rates, the above dosing parameters should be utilized in combination with the release rate of the drug from the soft palate injectable, implant or device such that a minimum concentration of 0.01 nM to 1000 µM of fibronectin is delivered to the tissue. In one embodiment, fibronectin is released from a soft palate injectable, implant or device such that fibrosis in the tissue is promoted for a period ranging from several hours to several months. For example, in a preferred embodiment fibronectin may be released in effective concentrations for a period ranging from 3–12 months. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibrohectin is administered at half the above parameters, a compound half as potent as fibronectin is administered at twice the above parameters, etc.).

Utilizing bleomycin as an exemplary fibrosis-inducing agent, whether it is applied using a polymer coating, incorporated into the polymers which make up the device or implant, or applied without a polymeric carrier, the total dose of bleomycin delivered in soft palate injection, or coated onto the surface of a soft palate implant or device, should not exceed 100 mg (range of 0.01 µg to 100 mg). In one embodiment, the total amount of bleomycin released should be in the range of 0.10 µg to 50 mg. The dose per unit volume of the soft palate injectable (i.e., the dosage of bleomycin as a function of the volume of material injected) should fall within the range of 0.005 µg–10 µg per $mm^3$. In another embodiment, bleomycin should be applied to a soft palate implant or device surface at a dose of 0.005 µg/$mm^2$–10 µg/$mm^2$ of surface area coated. As specific (polymeric and non-polymeric) drug delivery vehicles and specific soft palate injectables, implants and devices can release bleomycin at differing rates, the above dosing parameters should be utilized in combination with the release rate of the drug from the soft palate injectable, implant or device such that a minimum concentration of 0.001 nM to 1000 µM of bleomycin is delivered to the tissue. In one embodiment, bleomycin is released from a soft palate injectable, implant or device such that fibrosis in the tissue is promoted for a period ranging from several hours to several months. For example, in a preferred embodiment bleomycin may be released in effective concentrations for a period ranging from 3–12 months. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as an exemplary fibrosis-inducing agent, whether it is applied using a polymer coating, incorporated into the polymers which make up the device or implant, or applied without a polymeric carrier, the total dose of CTGF delivered in a soft palate injection, or coated onto the surface of a soft palate implant or device, should not exceed 100 mg (range of 0.01 µg to 100 mg). In one embodiment, the total amount of CTGF released should be in the range of 0.10 µg to 50 mg. The dose per unit volume of the soft palate injectable (i.e., the dosage of CTGF as a function of the volume of material injected) should fall within the range of 0.005 µg–10 µg per $mm^3$. In another embodiment, CTGF should be applied to a soft palate implant or device surface at a dose of 0.005 µg/$mm^2$–10 µg/$mm^2$ of surface area coated. As specific (polymeric and non-polymeric) drug delivery vehicles and specific soft palate injectables, implants and devices can release CTGF at differing rates, the above dosing parameters should be utilized in combination with the release rate of the drug from the soft palate injectable, implant or device such that a minimum concentration of 0.001 nM to 1000 µM of CTGF is delivered to the tissue. In one embodiment, CTGF is released from a soft palate injectable, implant or device such that fibrosis in the tissue is promoted for a period ranging from several hours to several months. For example, in a preferred embodiment CTGF may be released in effective concentrations for a period ranging from 3–12 months. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or a bone morphogenic protein (BMP) (e.g., BMP-2, BMP-3, BMP-4, BMP-5, BMP-6, or BMP-7 or an analogue or derivative thereof. Bone morphogenic protein(s) (e.g., BMP-2, BMP-3, BMP-4, BMP-5, BMP-6, or BMP-7 or an analogue or derivative thereof) are to be used in formulations at concentrations that range from 0.001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the bone morphogenic protein is released in effective concentrations for a period ranging from 1–180 days. The total dose for a single application is typically not to exceed 500 mg (range of 0.001 µg to 500 mg); preferred 1 µg to 250 mg. When used as a device coating, the dose is per unit area of 0.001 µg–1000 µg per $mm^2$; with a preferred dose of 0.01 µg/$mm^2$–200 µg/$mm^2$. Minimum concentration of $10^{-9}$–$10^{-4}$ M of bone morphogenic protein is to be maintained on the device surface.

Inflammatory cytokines are to be used in formulations at concentrations that range from 0.0001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 µg to 100 mg); preferred 0.001 µg to 50 mg. When used as a device coating, the dose is per unit area of 0.0001 µg–500 µg per $mm^2$; with a preferred dose of 0.001 $µg/mm^2$–200 $µg/mm^2$. Minimum concentration of $10^{-10}$–$10^{-4}$ g/ml of inflammatory cytokine is to be maintained on the device surface.

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof. Doses used are those concentrations which are demonstrated to stimulate cell proliferation (see, e.g., Example 16). The proliferative agents are to be used in formulations at concentrations that range from 0.1 ng/ml to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 μg to 200 mg); preferred 0.001 μg to 100 mg. When used as a device coating, the dose is per unit area of 0.00001 μg–500 μg per $mm^2$; with a preferred dose of 0.0001 μg/$mm^2$–200 μg/$mm^2$. Minimum concentration of $10^{-11}$–$10^{-6}$ M of proliferative agent is to be maintained on the device surface.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

12. Embolic Agents and Embolization Devices

In one aspect, the present invention provides for the combination of a fibrosing agent with embolization devices and aneurysm coils. Embolization devices are designed to slow or eliminate blood flow to a tissue and may be used to treat a variety of medical conditions which include, without limitation, uncontrolled vascular bleeding (such as menorrhagia), vascular aneurysms (such as thoracic aortic aneurysm, abdominal aortic aneurysms, cerebral aneurysms), benign tumor growth (such as uterine fibroids), malignant tumor growth (particularly hepatic, renal and other solid tumors) and vascular malformations (AV malformations, vascular tumors).

Embolization devices refer to devices that are designed to be placed within the vasculature (typically an artery) of the patient such that the flow of blood through a vessel (or portion of a vessel in the case of an aneurysm) is largely or completely obstructed. The embolic agent or device can be inserted such that it becomes physically lodged in the artery lumen causing interruption of blood flow to a tissue. The embolic agent or device can also induce clotting in the vessel (or portion of a vessel) such that blood flow becomes obstructed by clot (or a combination of the device and clot). In either case, blood supply to a particular anatomical region (e.g., a tumor, an aneurysm sac, a vascular malformation) is reduced, or eliminated, leading to ischemic damage or complete destruction of the unwanted tissue.

Examples of embolization devices include, without limitation, vascular coils, vaso-occlusion devices, vascular wires, intravascular embolization devices, vascular occlusion apparatus, microcoils, injectable embolic agents, polymeric embolic agents, embolizing agents, embolic vascular implants, embolic plugs, expandable implants, vascular plugs, vascular endoprostheses and embolic microspheres.

In one aspect, the embolization device is a vascular (vaso-)occlusive device. Vaso-occlusion devices can be inserted into the vasculature or some other region which is to be occluded, such as fallopian tubes and bile ducts. Vaso-occlusion devices may be take a variety of forms. For example, the primary shape of a vascular (vaso-)occlusive device may be a in the form of a coil (e.g., a helical coil or spiral), also referred to herein as a vaso-occlusive coil implant. Alternatively, the vaso-occlusive device may be in a non-coil (i.e., non-helical or non-spiral) form. Representative examples of non-coiled vaso-occlusive implants may be in the form of a braid, a random shaped implant, a spherically shaped, ovoid shaped, fibered (see, e.g., U.S. Pat. No. 5,226,911), strands, flower-shaped, a sphere, threads, and other non-helical forms. Helical and non-helical vaso-occlusive devices also may have a variety of secondary shapes. Specific examples of embolization coils and other types of embolization devices are described in further detail in the following sections.

In one aspect, the vaso-occlusive device may be an expandable vascular occlusion device. Expandable vaso-occlusive devices may include a resilient or shape memory material which will self-expand from its operative configuration by its own resilient force or by undergoing a phase transformation when exposed and warmed to body temperature. Alternatively, such devices may include plastically deformable material which may be deformed from its radially compact configuration to its operative configuration by application of pressure or force. Alternatively, some of these devices may be inflatable from their radially compact configuration to their operative configuration. An example of an expandable embolization device is a lumen blocking apparatus that includes a blood vessel engaging portion which is operative to anchor the apparatus to the surrounding wall of the blood vessel and a radially expandable lumen blocking portion which is operative to prevent the flow of blood in at least one direction, through the lumen of the blood vessel. (see, e.g., U.S. Pat. No. 6,638,293) Upon implantation of the device, the radially expandable portion can expand to an operative configuration wherein the blood vessel engaging portion of the apparatus will engage the blood vessel wall and the lumen blocking portion of the apparatus will block the lumen of the blood vessel to prevent blood flow in at least one direction.

Unfortunately, in a significant number of cases blood flow is re-established with time (a process called recanalization) leading to treatment failure. This puts the patient back at risk for the potentially life-threatening consequences of the condition that was treated with the initial intervention such as bleeding, aneurysm rupture, cerebral hemorrhage, or tumor growth. Treatment failure occurs in some clinical situations in part because currently available agents do not produce permanent fibrosis (true luminal scarring where the walls of the vessel adhere to each other and permanent fibrous tissue occludes the vessel) leading to the possibility of recanalization, re-establishment of blood flow, and ultimately disease recurrence. The present invention describes the addition of fibrosis-inducing agents to the materials injected (or devices implanted) into the vasculature for the purpose of producing a permanent, obstructive scar in the vascular lumen (or aneurysm sac) that results in regression and absorption of the unwanted vessel (or portion of the vessel). If blood flow is permanently prevented in the vessel due to obstructive fibrosis, the body can resorb the non-functioning vascular tissue and can eliminate the blood vessel, leaving little or no chance for recurrence.

(i) Aneurysm "Coils" Combined with a Fibrosis-Inducing Agent

Vascular aneurysms occur due to the focal weakening of a portion of the arterial wall that eventually leads to bulging of the vessel (called an aneurysm "sac"). The thin, weak wall of the aneurysm sac is at an increased risk for rupturing under the pressure of arterial blood flow; a risk that increases progressively as the sac increases in size. Aneurysm rupture can have catastrophic consequences including subarachnoid hemorrhage, stroke, permanent neurological deficits, and death for cerebral aneurysms and massive hemorrhage and death for aortic aneurysms. Surgical procedures to treat this condition, especially if located in the brain (known as aneurysm "clipping"), can be extremely risky or even impossible, depending upon the anatomical location of the aneurysm. As an alternative to surgery, minimally invasive interventions have been developed whereby both ruptured and unruptured aneurysms can be treated using embolization devices. Embolization devices may be delivered to the aneurysm using a catheter or guide-wire that is advanced from the groin to the area of the aneurysm. The embolization device is then inserted through the catheter and into the aneurysm. Once within the aneurysm, it physically occupies space within the aneurysm sac, induces the formation of clot, "fills" the aneurysm sac, and prevents arterial blood flow from entering the aneurysm and thus, prevents further damage. Numerous implants have been described for insertion into an aneurysm sac and are suitable for combining with a fibrosis-inducing agent. One of the most common treatments for cerebral aneurysms involves the implantation of vascular "coils" (i.e., aneurysm coil) into the aneurysm sac. The coil is advanced into the sac via a delivery catheter under radiologic guidance, detached (often by the induction of current in metal coils) from the delivery catheter and released into the sac; the procedure is then repeated until enough coils are "packed" into the aneurysm sac to fill it completely. Although a significant advancement in the treatment of aneurysms, detachable coils are not without their limitations. Complications associated with these procedures include inadvertent occlusion of the parent artery (occurs approximately 21% of the time), persistent filling of the aneurysm lumen (incomplete occlusion), and recanalization (i.e., return of blood flow into the aneurysm following initially successful occlusion) rate of 2–5% per year. The consequences of incomplete occlusion (occurring in 38% of cases for small necked aneurysms, 60–85% of cases for broad necked aneurysms) and recanalization are that there is an increased risk that the aneurysm can rebleed. Specifically, the coil-thrombus complex formed after initial successful deployment is thought to be unstable. Recanalization can be due to compression of the coil bundle and rearrangement of individual coil loops which have a tendency to revert back to their original helical form (especially when not densely packed). The clinical result of recanalization is that the patient is at risk for aneurysm rupture and bleeding (subarachnoid hemorrhage), which is associated with a high mortality rate (25–50%) and high morbidity rate (50% of survivors have a significant neurologic deficit). In contrast, completely occluded aneurysms are thought to have a low (or no) risk of rebleeding. The addition of a fibrosis-inducing agent to an aneurysm coil can help reduce the risk of failure by stabilizing the coil-thrombus complex with fibrous tissue (preventing incomplete occlusion) and filling the sac with permanent scar tissue (preventing recanalization).

A variety of aneurysm coils can be combined with a fibrosis-inducing agent for the purposes of this invention. It should be obvious to one of skill in the art that the exact physical shape of the coil is not critical to the practice of this invention, however, numerous coil designs are presented by way of illustration. In one aspect, the aneurysm coil may be composed of a biocompatible metal alloy (e.g., platinum or tungsten) and/or a biocompatible polymer, which may or may not be biodegradable. In one aspect, aneurysm coils and wires are provided that are made from a biodegradable material, such as a polymer, which is flexible (malleable) and strong. The polymer may be capable of expanding in size after deployment. Representative examples of expansible polymers for use in aneurysm coils and wires are crosslinked poly(vinyl alcohol), crosslinked poly(ethylene glycol), poly(acrylic acid), poly(hydroxethyl methacrylate), as well as copolymers and blends thereof. Degradation of the polymeric coil in the days to weeks following deployment has several advantages. For example, polymeric aneurysm coils, in contrast to metallic coils, may reduce the risk of aneurysm perforation during deployment. Since the coils do not persist, they also may be less likely to migrate into the parent vessel circulation. Further, degradable coils can become incorporated into the thrombus-coil complex, thus reducing the incidence of recanalization.

The vascular aneurysm coil may be coated or uncoated, and/or may include other elements (e.g., strands, filaments, meshes and/or other particles) along the coil. In one aspect, aneurysm coils can be coated with or contain a non-thrombogenic substance (e.g., heparin, antithrombin, antithrombin-heparin complex), which prevents thrombus from occurring prior to final placement of the device. This temporary coating can be designed to persist for minutes to hours depending upon the time required to deploy the device.

The aneurysm coil may be composed of a porous, flexible PTFE material, such as expanded PTFE (ePTFE). The PTFE material may take a variety of forms. For example, the material may take the form of a thin strand or ribbon and may be reinforced with a metallic strand or a biodegradable polymeric strand. The PTFE material can be coated with a water-soluble polymer that also may provide some rigidity to the material for delivery purposes, but, upon dissolution out of the material, the material becomes very flexible. The material can be impregnated or coated, with or without the use of a carrier, with one or a combination of fibrosing agents and other biologically active agents (e.g., agents to promote thrombosis or cellular growth). The material may be delivered into the aneurysm using a catheter-based delivery system as described above. With the appropriate design, the catheter could deliver fixed lengths of the material or could deliver a continuous strand of the material that could be cut to the desired length by a cutting device at the end of the catheter. The material is preferably thin enough so that it is very flexible and does not exert significant pressure on the aneurysm wall once deployed. For materials that do not have the structural strength to be delivered through a catheter, a thin metallic strand can be incorporated into the material to produce a more rigid material. The metallic strand may be made from, for example, stainless steel, titanium, platinum, gold, nickel, nitinol, or other alloy. A biodegradable polymeric strand may be used in place of the metallic strand. Once deployed, the polymeric strand can degrade, thereby eliminating the potential for late strage perforation of the aneurysm. Polymeric strands may be made from, e.g., a polyester (e.g., PLGA, PLA, PCL, PGA, and the like), polyanhydrides, polyorthoesters, tyrosine based polymers, polyphosphazines, polyamides (e.g., proteins such as gelatin), carbohydrates, polysaccharides and blends thereof. The strands can be incorporated into the material by threading them through the material or by laminating them between two layers of the material or by thermal fusion into the material. The strand may also be made of a non-degradable polymer such as, for example, a polyurethane, silicone, PE, PP, polyacrylate or poly(methacrylate) based polymer, polyamide polymer, or vinyl based polymer. The material may also be made more rigid by incorporating a polymer into the pores of the material. This polymer may be either water-soluble or water insoluble and may be biodegradable or non-degradable. An example of a water-soluble, non-degradable polymer is PEG. A tyrosine based polymer such as DTE is an example of a water-insoluble polymer that has a relatively short degradation time. Polymers may be used to supply some degree of structural rigidity for the deployment process by filling the pores of the porous PTFE but would degrade or dissolve rapidly after deployment, such that the material would revert to its flexible state and can be packed into the aneurysm sac more densely.

The vascular coil may be composed of a bioactive component or may be biologically inert. Since vascular coils may be delivered through a microcatheter to the vascular site, they may be designed to have both a primary phase and a secondary phase. The phases of the vascular coil may be characterized by a different shape or configuration, composition, physical state and/or level of bioactivity. Typically, these phases represent the state of the vascular coil prior to insertion (i.e., primary phase) and then the state of the vascular coil post-insertion (i.e., secondary phase). For example, the vascular coil may be designed as an outer helically wound device having a stretch-resistant polymeric filament in which a secondary shape is formed and heat-treated to preserve that form. See e.g., U.S. Pat. No. 6,193,728. The vascular coil may be designed to be a linear helical configuration when stretched, and a folded, convoluted configuration when relaxed. See e.g., U.S. Pat. No. 4,994,069. The vascular coil may be composed of a flexible, helically wound coil having two primary coil ends and a primary diameter which in a relaxed secondary configuration comprises at least two longitudinal focal axes. See e.g., U.S. Pat. No. 5,639,277. The vascular coil may have attached fibrous elements which extend in a sinusoidal fashion down the length of the coil and thus, produce a variety of secondary shapes. See e.g., U.S. Pat. No. 5,304,194. The vascular coil may be a metal coil that has one or more fiber bundles having a serpentine configuration in which the loops extend about the individual windings of the coil. See e.g., U.S. Pat. No. 5,226,911. The embolization device (e.g., vascular coil) may be composed of a helical coil having a multiplicity of windings that define a lumen and a plug of thermoplastic biocompatible polymer that is located at the ends of the coil into the lumen space. See e.g., U.S. Pat. No. 5,690,667. The vascular coil may be composed of an elongated helical coil of a biocompatible metal having a plurality of axial spaced windings and a plurality of strands of a polymeric, bioactive, occlusion-causing material extending axially through the coil. See e.g., U.S. Pat. No. 5,658,308. The embolization device may be an expandable support element having a relaxed expanded state and a stretched collapsed state, and an embolization element which is mounted on the support element which serves to substantially prevent the blood flow (e.g., polymer mesh). See e.g., U.S. Pat. No. 6,554,849. The embolization device may be composed of an elongated, flexible filamentous carrier and an embolizing element in the form of an expansile polymer (e.g., porous hydrogel) which is fixed to the carrier. See e.g., U.S. Pat. No. 6,602,261. The vascular coil may contain a positive charge, electric current, or magnetic field on the coil which promotes embolization. See e.g., U.S. Pat. Nos. 5,122,136, 6,066,133 and 6,603,994. Other vascular types of coils are described in, e.g., U.S. Pat. Nos. 5,133,731; 5,312,415; 5,354,294; 5,382,259; 5,382,260; 5,417,708; 5,423,849; 5,476,472; 5,578,074; 5,582,619; 5,624,461; 5,645,558 and 5,718,711.

Aneurysm coils, which may be combined with one or more fibrosis-inducing agents according to the present invention, include several commercially available products. For example, the GDC (GUGLIELMI DETACHABLE COIL) and the MATRIX detachable coils (from Boston Scientific Corporation) are particularly useful for the practice of this embodiment. The MICROPLEX and HYDROCOIL Coil System (from MicroVention, Inc., Aliso Viejo, Calif.), TORNADO Embolization Microcoils from Cook Diagnostic and Interventional Products (Bloomington, Ind.), HELIPAQ helical and MICRUSPHERE spherical coils from Micrus Corp. (Sunnyvale, Calif.), the GDC Coils 2D and 3D from Target Therapeutics, Inc. (Fremont, Calif.)/Boston Scientific Corporation, and the TRUFILL Pushable Coils from Cordis Corporation (Miami Lakes, Fla.)/Johnson & Johnson are also suitable.

Several injectable polymeric systems and embolization agents have been described for injection into the aneurysm sac for the treatment of cerebral and thoracic aneurysm. These vascular "fillers" are further described in section (ii) below. Vascular polymeric implants can be combined with a fibrosis-inducing agent for the purposes of this invention in the treatment of aneurysms. It should be obvious to one of skill in the art that the composition of the polymeric aneurysm implant is not critical to the practice of this invention.

Numerous polymeric and non-polymeric carrier systems described above may be used to deliver fibrosis-inducing agents from implantable aneurysm treatments such as coils and polymeric implants. Methods for incorporating fibrosis-inducing compositions onto or into aneurysm coils and implants include: (a) directly affixing to the aneurysm coil or implant a fibrosing composition (e.g., by either spraying the surface of the implant or dipping the implant into a solution containing the active agent; the agent can be applied alone or with a polymeric carrier); (b) directly incorporating a fibrosing composition into the components or the polymers that make up the aneurysm coil or implant (e.g., by either a spraying process or dipping process with or without a polymeric carrier—particularly effective for coils that have polymeric components such as coatings, meshes and hydrogels described above); (c) by coating the aneurysm coil or implant with a substance such as a hydrogel which can in turn absorb the fibrosing composition; the hydrogel can also swell to better fill the aneurysm sac; (d) by interweaving or attaching "threads" coated with (or composed of—particularly in the case of silk) a fibrosing agent into the structure of the aneurysm coil or implant; the threads in turn can be branched or "arborized" to increase the surface area; (e) by inserting the aneurysm coil or implant into a sleeve or mesh which is comprised of, or coated with, a fibrosing composition; (f) constructing the aneurysm coil or implant itself, or a portion of the coil or implant, with a fibrosing composition (particularly effective for polymeric drug compositions, silk and EVA—e.g., to create a silk and/or EVA aneurysm coil); this has the added benefit of creating a "floppy coil" that can not perforate through the weakened aneurysm wall (aneurysm perforation by metallic coils occurs in 5% of cases); the floppy coil can be further coated with hard polymer surface (to provide stiffness during deployment) that dissipates quickly after deployment to leave behind a floppy coil; in a particularly preferred embodiment, the aneurysm coil is composed of silk and/or EVA backbone with multiple "branches" of silk and/or EVA emanating from it to increase surface area (there can be branches upon branches; i.e., multiple generations of arborizations); or (g) by covalently binding the fibrosing agent directly to the aneurysm coil or implant surface or to a linker (small molecule or polymer) that is coated or attached to the surface. For aneurysm coils and implants, the coating process can be performed in such a manner as to: (a) coat the exterior surfaces of the device; (b) coat the interior surfaces of the device, (c) coat all or parts of both external and internal surface of the device, or (d) coat the coil with a non-thrombogenic substance (e.g., heparin, antithrombin, antithrombin-heparin complex) which prevents thrombosis from occurring prior to final placement of the device and then dissipates to allow thrombosis to occur. In addition to coating the aneurysm coil or implant with the fibrosing composition, the active agent can be mixed with the materials that are used to make the coil or implant such that the fibrosing agent is incorporated into the final implant.

In one embodiment, the aneurysm coil may include a starch (e.g., corn starch or maize starch). The starch material may be incorporated into the device as a coating and/or in combination with polymeric threads (e.g., silk) that are attached to the aneurysm coil. The starch or a starch-containing composition may be coated onto the device by applying starch powder directly to the device surface. Alternatively, the starch can be applied to the device using a solvent process or an extrusion process. The entire device or only a portion of the device may be coated with the starch. For example, starch can be made into a solution (e.g., by placing a 5% aqueous solution in an autoclave for 45 min.) which can be coated onto the outer surface of the device. The solvent then is removed to leave the starch coated on the device. In another approach, the starch can be incorporated into a secondary carrier (e.g., a degradable or non-degradable polymer, wax, lipid, oil, and the like), which may, optionally, be cross-linked. The secondary carrier (e.g., polymer) can be coated onto the device. In another aspect, the starch may be incorporated into or onto a non-degradable polymer (e.g., silk or DACRON) or biodegradable polymer (e.g., PLGA) which is then coated onto the device. As the polymer degrades, the starch is released to the surrounding tissue where it may cause the desired biological response. Alternatively, or in addition, the starch may be incorporated into the materials used to make the device.

The aneurysm coil may include polymeric threads, such that the presence of the polymeric threads results in an enhanced cellular and extracellular matrix response to the exterior of the device. The polymeric threads can be made from any polymer that results in an enhanced cellular and/or fibrotic response. For example, the threads may be a silk suture material or another type of biocompatible polymer (e.g., starch) which is coated with a polymer that results in an enhanced cellular response. The polymeric threads can be attached to the aneurysm coil in various configurations that may result in either partial or complete coverage of the exterior of the aneurysm coil. Any combination of the above methods may be used in the practice of this embodiment.

The fibrosing agent containing threads may be attached to the aneurysm coil using any appropriate method, e.g., an adhesive, thermal welding, stitching, wrapping, weaving, knotting, or a combination of any of these methods.

The threads can be coated with a material that delays the time it takes for the thread material to come into contact with the surrounding tissue. This allows for placement of the device without concern of thrombotic events as a result of the polymeric threads. Coatings may be from degradable materials that dissolve once implanted (e.g., gelatin, polyesters, such as PLGA, PLA, MePEG-PLGA, PLGA-PEG-PLGA, and copolymers and blends thereof, lipids, fatty acids, sugar esters, nucleic acid esters, polyanhydrides, polyorthoesters, PVA, and the like). These coatings may include a fibrosis-inducing agent and/or an agent that reduces the probability of an immediate thrombotic event (e.g., heparin and heparin derivatives, such as hydrophobic quaternary amine heparin complexes).

It should be apparent to one of skill in the art that potentially any fibrosis-inducing agent may be utilized alone, or in combination, in the practice of this embodiment. Exemplary fibrosing agents for use in combination with aneurysm coils and implants include talc, silk, wool, chitosan, polylysine, fibronectin, bleomycin, and CTGF as well as analogues and derivatives of the aforementioned. These can be further combined with other agents such as sclerosing agents (sodium morrhuate, ethanolamine oleate, ethanol, DMSO, surfactants, sucrose, NaCl, dextrose, glycerin, minocycline, tetracycline, doxycycline, polidocanol, sodium tetradecyl sulfate, sodium morrhuate, sotradecol) and/or growth factors (transforming growth factor, platelet-derived growth factor, fibroblast growth factor, and bone morphogenic proteins) to further enhance efficacy.

Optionally, the device may additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) and/or a bone morphogenic protein (BMP) (e.g., BMP-2, BMP-3, BMP-4, BMP-5, BMP-6, or BMP-7 or an analogue or derivative thereof).

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

(ii) Embolization Agents Containing a Fibrosis-Inducing Agent

Embolization products are used to reduce or eliminate blood flow to a particular organ or tissue. Typically they are used in the treatment of bleeding (e.g., embolization of the uterine artery for the management of severe menorrhagia), benign tumor growth (e.g., uterine fibroid embolization), malignant tumor growth (hepatic tumors, renal cell carcinoma, solid tumors), varicoseals, or to treat abnormal vascular structures (arterio-venous malformations, vascular tumors). Classically the procedure is performed by inserting a catheter into the vasculature (often the femoral artery), advancing it under radiologic guidance to the artery that supplies the tissue to be embolized, advancing a delivery catheter over the guidewire, and delivering particles/microspheres/gels into the lumen of the vessel that travel in the blood stream until they become lodged in a downstream vessel (whose caliber is smaller than that of the embolic particle). This obstructs the blood flow to the target tissue, starves it of oxygen and nutrients, leads to ischemia and, in some cases, tissue necrosis and death.

Numerous particles, microspheres and injectable polymer systems have been described for vascular injection as embolic agents and are suitable for combining with a fibrosis-inducing agent. Although initially successful in occluding blood flow, many embolic agents are able to sustain their efficacy due to recanalization of the treated vessel (i.e., return of blood flow through the artery following initially successful occlusion). As a consequence of recanalization, there is an increased risk that bleeding can recur or tumor growth can resume. In contrast, completely occluded blood vessels are thought to have a low (or no) risk of rebleeding and force tumor cells to recruit new vasculature to the tissue. The addition of a fibrosis-inducing agent to an embolization agent can help reduce the risk of failure by filling the arterial lumen with permanent scar tissue (preventing recanalization). If blood flow is obstructed for a prolonged period of time due to obstructive fibrosis, the vessel regresses, the body resorbs the nonfunctioning vascular tissue, the blood vessel is eliminated and the risk of recurrence is reduced.

Embolization agents, which may be combined with one or more fibrosis-inducing agents according to the present invention, include several commercially available products. For example, the TRUFILL n-Butyl Cyanoacrylate (n-BCA) Liquid Embolic System (Cordis, a division of Johnson and Johnson, Miami, Fla.); EMBOSPHERE Microspheres and EMBOGOLD Microspheres (Biosphere, Rockland, Mass.); and the ONYX Liquid Embolic System (Micro Therapeutics, Irvine, Calif.) are all polymeric embolization systems suitable for combining with a fibrosis-inducing agent. Other examples of suitable embolization devices include polymer/solvent systems containing a fibrosis-inducing agent in which the solvent diffuses from the polymer matrix once it has been injected at the treatment site (e.g., the degradable polymeric systems from Atrix, non-degradable polymeric compositions such as ONYX and EMBOLYX, and in situ forming materials such as those available from Biocure, Angiotech Pharmaceuticals, Inc., 3M Company and Neomend). Other types of commercially available embolic agents that can be loaded or made with a fibrosis-inducing agent include PVA particles (Cook, Inc. and Angiodynamics, Inc.) and microsphere formulations (e.g., EMBOSPHERE from Biosphere, Inc., Contour SE from Boston Scientific and BEAD BLOCK from Biocompatibles).

Numerous other vascular occlusion devices can be combined with a fibrosis-inducing agent. The embolization device may be composed of an expandable implant or plug that is guided into the vascular site and detached at the desired location. For example, the expandable implant may be a balloon delivered by an intravascular catheter which acts as an embolization element when it is inflated with solidifying fluid (e.g., polymerizing resin or gel). See e.g., U.S. Pat. No. 4,819,637. The expandable vascular implant can be composed of hydrogel stent that is guided to the vascular site using a microcatheter and then hydrated and expanded until it occludes the vessel. See e.g., U.S. Pat. No. 5,258,042. Polymeric foams (e.g., polyvinyl alcohol, polyurethane foam or polyethylene foam), pellets or particles that expand to induce vascular occlusion upon exposure to blood fluids (see e.g., U.S. Pat. No. 5,823,198) are also suitable for combining with fibrosis-inducing agents.

Another suitable expandable implant is composed of a plurality of expansible embolizing elements and an elongated filamentous carrier (formed from a flexible material with an elastic memory shaped into a looped structure whereby the elements are released from spaced intervals along the loop; see e.g., U.S. Pat. No. 6,238,403).

Injectable liquid embolic agents that change their physical properties (e.g., solidify and/or expand) in response to heating, enzymatic reactions and/or chemical polymerization can be combined with fibrosis-inducing agents. Injectable embolic agents that are an emulsion of particles or microspheres and coagulate with blood components and/or coalesce with each other at the vascular site can also be utilized. For example, the embolic agent may be composed of a cellulose diacetate polymer, a biocompatible solvent and a water insoluble contrasting agent which, when delivered, the solvent disperses into the bloodstream and leaves the remaining components behind to form into a gel that embolizes the vessel. See e.g., U.S. Pat. No. 5,580,568. Another suitable embolic agent is composed of a polymer and a solvent that is a liquid at body temperature and precipitates into a solid in situ in the presence of a non-particulate agent (e.g., vascular coil). See e.g., U.S. Pat. No. 6,017,977. Still another suitable embolic agent is composed of a thermosensitive polymer delivered as an aqueous solution at one temperature (i.e., above or below body temperature) that forms into a solid after warming up to (or cooling down to) body temperature. See e.g., U.S. Pat. No. 5,525,334. Still another suitable liquid embolic agent is an emulsion (composed of an aqueous matrix base and a liquid oil) which forms into an insoluble matrix by either heating, an enzymatic reaction, or chemical polymerization. See e.g., U.S. Pat. No. 5,894,022. The embolic agent may also be an injectable solution of microspheres composed of a copolymer coated with a cell adhesion promoter. See e.g., U.S. Pat. No. 5,648,100. Additional materials that are used as injectable liquid embolic agents are described in U.S. Pat. Nos. 4,551,132 and 4,795,741.

In one aspect, the present invention provides embolization agents combined with a fibrosis-inducing agent directly, or a composition (e.g., a polymeric or non-polymeric carrier) that includes a fibrosing agent, for the purpose of permanently occluding a blood vessel. The fibrosis-inducing agent can be delivered with the embolization agent in several ways, including: (a) fluids, suspensions, emulsions, microemulsions, microspheres, pastes, gels, microparticulates, sprays, aerosols, solid implants and other formulations (see those described above) which release a fibrosis-inducing agent(s); (b) microparticulate silk and/or silk strands (linear, branched, and/or coiled) either alone, or loaded with an additional fibrosis-inducing agent (or embolic material) and injected as an embolic agent; (c) gels, microspheres, or microparticles formed from polymeric formulations of fibrosing agents (e.g., polymeric drugs such as those described by Polymerix Corporation); (d) fibrosis-inducing agents coated on the surface of microspheres or microparticles, with or without a polymeric carrier; (e) fibrosis-inducing agents loaded into one or more phases of a liquid embolic system (see descriptions above); (f) fibrosis-inducing agents delivered in the aqueous phase (i.e., as an infusion into the treated tissue) in conjunction with (before, during or after) an embolization procedure; (g) for in situ forming embolic compositions, the fibrosis-inducing agents can be incorporated directly into the formulation as a suspension or a solution (e.g., silk powder, bleomycin), or loaded into a secondary carrier (e.g., micelles, liposomes, microspheres, microparticles, nanospheres, microparticulates, emulsions and/or micromulsions) that is then incorporated into the in situ forming compositions; (h) the fibrosis-inducing agent can be electrostatically or covalently bound to one or more of the polymeric components of the in situ forming embolization composition; and/or (i) the fibrosing agent can be mixed with the materials that are used to make the device such that the fibrosing agent is incorporated into the embolic agent during manufacturing (for example, silk powder can be added as a reagent during the manufacture of microspheres).

It should be apparent to one of skill in the art that potentially any fibrosis-inducing agents described above may be utilized alone, or in combination, in the practice of this embodiment. Exemplary fibrosing agents for use in embolization devices and compositions include talc, silk, wool, chitosan, polylysine, fibronectin, bleomycin, and CTGF, as well as analogues and derivatives of the aforementioned.

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or a bone morphogenic protein (BMP) (e.g., BMP-2, BMP-3, BMP-4, BMP-5, BMP-6, or BMP-7 or an analogue or derivative thereof).

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

In some clinical situations, repeated injections of the active agents may be required. Specific agents and dosages for use in aneurysm coils and implants can be described in greater detail in section (iii) below.

(iii) Agents for Use in Embolic Agents and Aneurysm Coils

As embolization agents and aneurysm treatment devices are made in a variety of configurations and sizes, the exact dose administered can vary with implant or device size, surface area and design. However, certain principles can be applied in the application of this art. Drug dose can be calculated as a function of dose per unit area (of the portion of the embolic material or aneurysm device being coated), total drug dose administered can be measured and appropriate surface concentrations of active drug can be determined. Regardless of the method of application of the drug to the embolization or aneurysm device, the exemplary fibrosing agents, used alone or in combination, should be administered under the following dosing guidelines:

Utilizing talc as an exemplary fibrosis-inducing agent, whether it is applied using a polymer coating, incorporated into the polymers which make up the device or implant, or applied without a polymeric carrier, the total dose of talc delivered from an embolization agent or aneurysm device, or coated onto the surface of an embolization or aneurysm device, should not exceed 100 mg (range of 1 μg to 100 mg). In one embodiment, the total amount of talc released from the embolization agent or aneurysm coil should be in the range of 10 μg to 50 mg. The dose per unit area of the embolic agent or aneurysm device (i.e., the dosage of talc as a function of the surface area of the portion of the implant or device to which drug is applied and/or incorporated) should fall within the range of 0.05 μg–10 μg per $mm^2$ of surface area coated. In another embodiment, talc should be applied to an embolization agent or aneurysm device surface at a dose of 0.05 μg/$mm^2$–10 μg/$mm^2$ of surface area coated.

In one embodiment, talc is released from the surface of an embolization or aneurysm device such that fibrosis in the tissue is promoted for a period ranging from several hours to several months. For example, talc may be released in effective concentrations for a period ranging from 1–9 months. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymer coating, incorporated into the polymers which make up the device or implant, or applied without a polymeric carrier, the total dose of silk delivered from an embolization agent or aneurysm device, or coated onto the surface of an embolization agent or aneurysm device, should not exceed 100 mg (range of 1 μg to 100 mg). In one embodiment, the total amount of silk released from the embolization agent or aneurysm coil should be in the range of 10 μg to 50 mg. The dose per unit area of the implant or device (i.e., the dosage of silk as a function of the surface area of the portion of the device to which drug is applied and/or incorporated) should fall within the range of 0.05 μL-10 μg per $mm^2$ of surface area coated. In another embodiment, silk should be applied to an embolization or aneurysm device surface at a dose of 0.05 μg/$mm^2$–10 μg/$mm^2$ of surface area coated. As specific (polymeric and non-polymeric) drug delivery vehicles and specific embolization agents and aneurysm devices can release silk at differing rates, the above dosing parameters should be utilized in combination with the release rate of the drug from the embolization or aneurysm device such that a minimum concentration of 0.01 nM to 1000 μM of silk is delivered to the tissue. In one embodiment, silk is released from the surface of an embolization or aneurysm device such that fibrosis in the tissue is promoted for a period ranging from several hours to several months. For example, silk may be released in effective concentrations for a period ranging from 1–9 months. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymer coating, incorporated into the polymers which make up the device or implant, or applied without a polymeric carrier, the total dose of chitosan delivered from an embolization agent or aneurysm device, or coated onto the surface of an embolization agent or aneurysm device, should not exceed 100 mg (range of 1 μg to 100 mg). In one embodiment, the total amount of chitosan released from the embolic agent or aneurysm coil should be in the range of 10 μg to 50 mg. The dose per unit area of the device (i.e., the dosage of chitosan as a function of the surface area of the portion of the implant or device to which drug is applied and/or incorporated) should fall within the range of 0.05 μg–10 μg per $mm^2$ of surface area coated. In another embodiment, chitosan should be applied to an embolization or aneurysm device surface at a dose of 0.05 µg/mm$^2$–10 µg/mm$^2$ of surface area coated. As specific (polymeric and non-polymeric) drug delivery vehicles and specific implants and devices can release chitosan at differing rates, the above dosing parameters should be utilized in combination with the release rate of the drug from the embolization or aneurysm device such that a minimum concentration of 0.01 nM to 1000 µM of chitosan is delivered to the tissue. In one embodiment, chitosan is released from the surface of an embolization or aneurysm device such that fibrosis in the tissue is promoted for a period ranging from several hours to several months. For example, chitosan may be released in effective concentrations for a period ranging from 1–9 months. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as an exemplary fibrosis-inducing agent, whether it is applied using a polymer coating, incorporated into the polymers which make up the device or implant, or applied without a polymeric carrier, the total dose of polylysine delivered from an embolization agent or aneurysm device, or coated onto the surface of an embolization agent or aneurysm device, should not exceed 100 mg (range of 1 µg to 100 mg). In one embodiment, the total amount of polylysine released from the embolization agent or aneurysm coil should be in the range of 10 µg to 50 mg. The dose per unit area of the device (i.e., the dosage of polylysine as a function of the surface area of the portion of the implant or device to which drug is applied and/or incorporated) should fall within the range of 0.05 µg–10 µg per mm$^2$ of surface area coated. In another embodiment, polylysine should be applied to an embolization or aneurysm device surface at a dose of 0.05 µg/mm$^2$–10 µg/mm$^2$ of surface area coated. As specific (polymeric and non-polymeric) drug delivery vehicles and specific embolization agents and aneurysm devices can release polylysine at differing rates, the above dosing parameters should be utilized in combination with the release rate of the drug from the embolization or aneurysm device such that a minimum concentration of 0.01 nM to 1000 µM of polylysine is delivered to the tissue. In one embodiment, polylysine is released from the surface of an embolization or aneurysm device such that fibrosis in the tissue is promoted for a period ranging from several hours to several months. For example, polylysine may be released in effective concentrations for a period ranging from 1–9 months. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymer coating, incorporated into the polymers which make up the device or implant, or applied without a polymeric carrier, the total dose of fibronectin delivered from an embolization agent or aneurysm device, or coated onto the surface of an embolization agent or aneurysm device, should not exceed 100 mg (range of 1 µg to 100 mg). In one embodiment, the total amount of fibronectin released from the embolization agent or aneurysm coil should be in the range of 10 µg to 50 mg. The dose per unit area of the device (i.e., the dosage of fibronectin as a function of the surface area of the portion of the implant or device to which drug is applied and/or incorporated) should fall within the range of 0.05 µg–10 µg per mm$^2$ of surface area coated. In another embodiment, talc should be applied to an embolization agent or aneurysm device surface at a dose of 0.05 µg/mm$^2$–10 µg/mm$^2$ of surface area coated. As specific (polymeric and non-polymeric) drug delivery vehicles and specific embolization agents and aneurysm devices can release fibronectin at differing rates, the above dosing parameters should be utilized in combination with the release rate of the drug from the embolization or aneurysm device such that a minimum concentration of 0.01 nM to 1000 µM of fibronectin is delivered to the tissue. In one embodiment, fibronectin is released from the surface of an embolization agent or aneurysm device such that fibrosis in the tissue is promoted for a period ranging from several hours to several months. For example, fibronectin may be released in effective concentrations for a period ranging from 1–9 months. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, whether it is applied using a polymer coating, incorporated into the polymers which make up the device or implant, or applied without a polymeric carrier, the total dose of bleomycin delivered from an embolization agent or aneurysm device, or coated onto the surface of an embolization agent or aneurysm device, should not exceed 100 mg (range of 0.01 µg to 100 mg). In one embodiment, the total amount of bleomycin released from the embolization agent or aneurysm coil should be in the range of 0.10 µg to 50 mg. The dose per unit area of the device (i.e., the dosage of bleomycin as a function of the surface area of the portion of the implant or device to which drug is applied and/or incorporated) should fall within the range of 0.005 µg–10 µg per mm$^2$ of surface area coated. In another embodiment, bleomycin should be applied to an embolization agent or aneurysm device surface at a dose of 0.005 µg/mm$^2$–10 µg/mm$^2$ of surface area coated. As specific (polymeric and non-polymeric) drug delivery vehicles and specific embolization agents and aneurysm devices can release bleomycin at differing rates, the above dosing parameters should be utilized in combination with the release rate of the drug from the an embolization or aneurysm device such that a minimum concentration of 0.001 nM to 1000 µM of bleomycin is delivered to the tissue. In one embodiment, bleomycin is released from the surface of an embolization or aneurysm device such that fibrosis in the tissue is promoted for a period ranging from several hours to several months. For example, bleomycin may be released in effective concentrations for a period ranging from 1–9 months. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as an exemplary fibrosis-inducing agent, whether it is applied using a polymer coating, incorporated into the polymers which make up the device or implant, or applied without a polymeric carrier, the total dose of CTGF delivered from an embolization agent or aneurysm device, or coated onto the surface of an embolization agent or aneurysm device, should not exceed 100 mg (range of 0.01 µg to 100 mg). In one embodiment, the total amount of CTGF released from the embolization agent or aneurysm coil should be in the range of 0.10 µg to 50 mg. The dose per unit area of the implant or device (i.e., the dosage of CTGF as a function of the surface area of the portion of the device to which drug is applied and/or incorporated) should fall within the range of 0.005 µg–10 µg per mm$^2$ of surface area coated. In another embodiment, CTGF should be applied to an embolization agent or aneurysm device surface at a dose of 0.005 µg/mm$^2$–10 µg/mm$^2$ of surface area coated. As specific (polymeric and non-polymeric) drug delivery vehicles and specific embolization agents and aneurysm devices can release CTGF at differing rates, the above dosing parameters should be utilized in combination with the release rate of the drug from the embolization agent or aneurysm device such that a minimum concentration of 0.001 nM to 1000 µM of CTGF is delivered to the tissue. In one embodiment, CTGF is released from the surface of an embolization agent or aneurysm device such that fibrosis in the tissue is promoted for a period ranging from several hours to several months. For example, CTGF may be released in effective concentrations for a period ranging from 1–9 months. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or a bone morphogenic protein (BMP) (e.g., BMP-2, BMP-3, BMP-4, BMP-5, BMP-6, or BMP-7 or an analogue or derivative thereof).

Bone morphogenic protein(s) (e.g., BMP-2, BMP-3, BMP-4, BMP-5, BMP-6, or BMP-7 or an analogue or derivative thereof) are to be used in formulations at concentrations that range from 0.001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the bone morphogenic protein is released in effective concentrations for a period ranging from 1–180 days. The total dose for a single application is typically not to exceed 500 mg (range of 0.001 µg to 500 mg); preferred 1 µg to 250 mg. When used as a device coating, the dose is per unit area of 0.001 µg–1000 µg per mm$^2$; with a preferred dose of 0.01 µg/mm$^2$–200 µg/mm$^2$. Minimum concentration of $10^{-9}$–$10^{-4}$ M of bone morphogenic protein is to be maintained on the device surface.

Inflammatory cytokines are to be used in formulations at concentrations that range from 0.0001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 µg to 100 mg); preferred 0.001 µg to 50 mg. When used as a device coating, the dose is per unit area of 0.0001 µg–500 µg per mm$^2$; with a preferred dose of 0.001 µg/mm$^2$–200 µg/mm$^2$. Minimum concentration of $10^{-10}$–$10^{-4}$ g/ml of inflammatory cytokine is to be maintained on the device surface.

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin D$_3$, diethylstibesterol, cyclosporine A, L-NAME, all-trans retinoic acid (ATRA), and analogues and derivatives thereof. Doses used are those concentrations which are demonstrated to stimulate cell proliferation (Example 16). The proliferative agents are to be used in formulations at concentrations that range from 0.01 ng/mL to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 µg to 200 mg); preferred 0.001 µg to 100 mg. When used as a device coating, the dose is per unit area of 0.00001 µg–500 µg per mm$^2$; with a preferred dose of 0.0001 µg/mm$^2$–200 µg/mm$^2$. Minimum concentration of $10^{-11}$–$10^{-6}$ M of proliferative agent is to be maintained on the device surface.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

13. Pulmonary Sealants

The present invention provides compositions and devices for use as pulmonary sealants during open or endoscopic lung reduction surgeries. The primary clinical application for pulmonary sealants is in the treatment of postoperative air leak in the lung. If air is able to leak from the lung into the plural space via small holes created during surgery, it can build up, exert pressure on the lung, and prevent the lung from fully expanding during inhalation. This prevents normal ventilation from occurring, and if severe, can create a medical emergency that requires urgent drainage of the air trapped in the plura via a chest tube inserted through the ribs and into the air pocket. For example, persistent air leakage is a frequent complication after open or endoscopic pulmonary resection for lung cancer or emphysema and can cause serious complications, such as empyema, chest tube insertion and prolonged hospitalization. Surgical sealants of different types have been developed for application to the lung surface to prevent or to reduce postoperative air leaks. The addition of a fibrosis-inducing agent to a pulmonary sealant can induce the formation of a stable, fibrous scar that permanently seals the parietal surface of the lung at the surgical location (or the alveolar surface of the lung if delivered endoscopically during lung reduction surgery), reduces hospitalization time and prevents recurrence of the air leak. Clinically a fibrosis-inducing pulmonary sealant can be useful to improve the outcomes in open lung surgery, endoscopic lung reduction surgery for emphysema (severe COPD), esophageal leaks after endoscopy or resection, complications of treatment of other intra-thoracic malignancies, pleural effusion, haemothorax, pneumothorax, chylothorax, complications of aspiration, and tuberculosis.

As used herein, the term "sealant" refers to a material which decreases or prevents the migration of fluid or air from one tissue cavity (e.g., the lung) to another tissue cavity (e.g., the plural space). Sealants are typically formed by the application of precursor molecules to a tissue followed by local in situ polymerization. The same sealant materials may also be used to "glue" tissues together, both when applied between them and then polymerized, or when used simultaneously and embedded between tissues. Generally, surgical sealants are absorbable materials used primarily to control internal bleeding and to seal tissue (to prevent leakage).

Sealant material and devices for delivering sealant materials for use in the present invention are described, e.g., in U.S. Pat. Nos. 6,624,245; 6,534,591; 6,495,127; 6,482,179; 6,458,889; 6,323,278; 6,312,725; 6,280,727; 6,277,394; 6,166,130; 6,110,484; 6,096,309; 6,051,648; and 5,874,500; 6,063,061; 5,895,412; 5,900,245 and 6,379,373. The performance of these materials may be enhanced through the addition of a fibrosis-inducing agent.

In one aspect, the present invention provides lung sealants that comprise a fibrosis-inducing agent. Numerous polymeric and non-polymeric carrier systems described above may be used in the practice of this embodiment. These compositions can further comprise one or more fibrosis-inducing agents to promote the formation of granulation tissue. One example of an appropriate sealant is prepared from a 4-armed thiol PEG (10K), a 4-armed NHS PEG(10K) and methylated collagen such as described above. Commercially available sealants suitable for combining with one or more fibrosis-inducing agents according to the present invention include: COSEAL; FLOSEAL; SPRAYGEL or a variation thereof; and FOCALSEAL.

In one aspect of the present invention, a fibrosing (i.e., scarring) agent can be included in a polymeric sealant spray which solidifies into a film or coating to promote fibrosis and seal air leaks. In another aspect, a sprayable fibrosis-inducing lung sealant may be used to seal off pulmonary bullae in open and endoscopic lung destruction procedures. In another embodiment, the spray includes a tissue adherent polymer containing a fibrosis-inducing agent and may be prepared from microspheres.

For sprayable in situ forming compositions, the fibrosis-inducing agent can be incorporated directly into the formulation to produce a suspension or a solution (e.g., silk powder, bleomycin), or they can be incorporated into a secondary carrier (e.g., micelles, liposomes, microspheres, microparticles, nanospheres, microparticulates, emulsions and/or microemulsions) that is then incorporated into the in situ forming compositions.

In another embodiment, the fibrosis-inducing agent can be electrostatically or covalently bound to one or more of the polymeric components of the in situ forming composition.

In another embodiment, the fibrosis-inducing agent can be incorporated directly, or via a secondary carrier, into a gel or thermogel (e.g., hyaluronic acid, PLURONIC F127, polyester-PEG-polyester (e.g., PLGA-PEG-PLGA)). These gels can then be applied to the treatment site prior to, or after, the application of a pulmonary sealant.

In another embodiment, the fibrosis-inducing agent can be incorporated into a biodegradable or dissolvable film (or mesh) that is then applied to the lung. An in situ forming composition can then be sprayed over the film, thereby sealing the lung and the film (or mesh) to the desired lung surface. In a variation of this embodiment, the in situ sealant can be applied to the lung prior to the application of a biodegradable film or mesh containing a fibrosis-inducing agent to the treatment area. Exemplary materials for the manufacture of these films or meshes are hyaluronic acid (crosslinked or non-crosslinked), cellulose derivatives (e.g., hydroxypropyl cellulose) and crosslinked poly(ethylene glycol).

It should be apparent to one of skill in the art that potentially any adhesion or fibrosis-inducing agents described above may be utilized alone, or in combination, in the practice of this embodiment. Exemplary fibrosing agents for use in pulmonary sealants include talc, silk, wool, chitosan, polylysine, fibronectin, bleomycin, and CTGF, as well as analogues and derivatives of the aforementioned.

As pulmonary sealants are made in a variety of forms, the exact dose administered can vary with the form. However, certain principles can be applied in the application of this art. Drug dose can be calculated as a function of dose per unit area (of the amount of the sealant being applied), total drug dose administered can be measured and appropriate surface concentrations of active drug can be determined. Regardless of the method of incorporation of the drug into the pulmonary sealants, the exemplary fibrosing agents, used alone or in combination, should be administered under the following dosing guidelines:

Utilizing talc as an exemplary fibrosis-inducing agent, the total dose of talc delivered from a pulmonary sealant, or coated onto the surface of a lung, should not exceed 100 mg (range of 1 µg to 100 mg). In one embodiment, the total amount of talc released from the sealant should be in the range of 10 µg to 50 mg. The dose per unit area (i.e., the dosage of talc as a function of the surface area of the lung to which drug is applied) should fall within the range of 0.05 µg–10 µg per $mm^2$ of surface area coated. In another embodiment, talc should be applied to a lung surface at a dose of 0.05 $µg/mm^2$–10 $µg/mm^2$ of surface area coated. In one embodiment, talc is released from the pulmonary sealant such that fibrosis in the tissue is promoted for a period ranging from several hours to several months. For example, talc may be released in effective concentrations for a period ranging from 1 hour–30 days. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, the total dose of silk delivered from a pulmonary sealant, or coated onto the surface of a lung, should not exceed 100 mg (range of 1 µg to 100 mg). In one embodiment, the total amount of silk released from the sealant should be in the range of 10 µg to 50 mg. The dose per unit area (i.e., the dosage of silk as a function of the surface area of the lung to which drug is applied) should fall within the range of 0.05 µg–10 µg per mm$^2$ of surface area coated. In another embodiment, silk should be applied to a lung surface at a dose of 0.05 µg/mm$^2$–10 µg/mm$^2$ of surface area coated. As specific (polymeric and non-polymeric) drug delivery vehicles and specific pulmonary sealants can release silk at differing rates, the above dosing parameters should be utilized in combination with the release rate of the drug from the sealant such that a minimum concentration of 0.01 nM to 1000 µM of silk is delivered to the tissue. In one embodiment, silk is released from the pulmonary sealant such that fibrosis in the tissue is promoted for a period ranging from several hours to several months. For example, silk may be released in effective concentrations for a period ranging from 1 hour–30 days. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, the total dose of chitosan delivered from a pulmonary sealant, or coated onto the surface of a lung, should not exceed 100 mg (range of 1 µg to 100 mg). In one embodiment, the total amount of chitosan released from the sealant should be in the range of 10 µg to 50 mg. The dose per unit area (i.e., the dosage of chitosan as a function of the surface area of the lung to which drug is applied) should fall within the range of 0.05 µg–10 µg per mm$^2$ of surface area coated. In another embodiment, chitosan should be applied to a lung surface at a dose of 0.05 µg/mm$^2$–10 µg/mm$^2$ of surface area coated. As specific (polymeric and non-polymeric) drug delivery vehicles and specific pulmonary sealants can release chitosan at differing rates, the above dosing parameters should be utilized in combination with the release rate of the drug from the sealant such that a minimum concentration of 0.01 nM to 1000 µM of chitosan is delivered to the tissue. In one embodiment, chitosan is released from the pulmonary sealant such that fibrosis in the tissue is promoted for a period ranging from several hours to several months. For example, chitosan may be released in effective concentrations for a period ranging from 1 hour–30 days. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as an exemplary fibrosis-inducing agent, the total dose of polylysine delivered from a pulmonary sealant, or coated onto the surface of a lung, should not exceed 100 mg (range of 1 µg to 100 mg). In one embodiment, the total amount of polylysine released from the sealant should be in the range of 10 µg to 50 mg. The dose per unit area (i.e., the dosage of polylysine as a function of the surface area of the lung to which drug is applied) should fall within the range of 0.05 µg–10 µg per mm$^2$ of surface area coated. In another embodiment, polylysine should be applied to a lung surface at a dose of 0.05 µg/mm$^2$–10 µg/mm$^2$ of surface area coated. As specific (polymeric and non-polymeric) drug delivery vehicles and specific pulmonary sealants can release polylysine at differing rates, the above dosing parameters should be utilized in combination with the release rate of the drug from the pulmonary sealant such that a minimum concentration of 0.01 nM to 1000 µM of polylysine is delivered to the tissue. In one embodiment, polylysine is released from the pulmonary sealant such that fibrosis in the tissue is promoted for a period ranging from several hours to several months. For example, polylysine may be released in effective concentrations for a period ranging from 1 hour–30 days. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, the total dose of fibronectin delivered from a pulmonary sealant, or coated onto the surface of a lung, should not exceed 100 mg (range of 1 µg to 100 mg). In one embodiment, the total amount of fibronectin released from the sealant should be in the range of 10 µg to 50 mg. The dose per unit area (i.e., the dosage of fibronectin as a function of the surface area of the lung to which drug is applied) should fall within the range of 0.05 µg–10 µg per mm$^2$ of surface area coated. In another embodiment, fibronectin should be applied to a lung surface at a dose of 0.05 µg/mm$^2$–10 µg/mm$^2$ of surface area coated. As specific (polymeric and non-polymeric) drug delivery vehicles and specific pulmonary sealants can release fibronectin at differing rates, the above dosing parameters should be utilized in combination with the release rate of the drug from the sealant such that a minimum concentration of 0.01 nM to 1000 µM of fibronectin is delivered to the tissue. In one embodiment, fibronectin is released from the pulmonary sealant such that fibrosis in the tissue is promoted for a period ranging from several hours to several months. For example, fibronectin may be released in effective concentrations for a period ranging from 1 hour–30 days. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, the total dose of bleomycin delivered from a pulmonary sealant, or coated onto the surface of a lung, should not exceed 100 mg (range of 0.01 µg to 100 mg). In one embodiment, the total amount of bleomycin released from the sealant should be in the range of 0.10 µg to 50 mg. The dose per unit area (i.e., the dosage of silk as a function of the surface area of the lung to which drug is applied) should fall within the range of 0.005 µg–10 µg per mm² of surface area coated. In another embodiment, bleomycin should be applied to a lung surface at a dose of 0.005 µg/mm²–10 µg/mm² of surface area coated. As specific (polymeric and non-polymeric) drug delivery vehicles and specific pulmonary sealants can release bleomycin at differing rates, the above dosing parameters should be utilized in combination with the release rate of the drug from the sealant such that a minimum concentration of 0.001 nM to 1000 μM of bleomycin is delivered to the tissue. In one embodiment, bleomycin is released from the pulmonary sealant such that fibrosis in the tissue is promoted for a period ranging from several hours to several months. For example, bleomycin may be released in effective concentrations for a period ranging from 1 hour–30 days. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as an exemplary fibrosis-inducing agent, the total dose of CTGF delivered from a pulmonary sealant, or coated onto the surface of a lung, should not exceed 100 mg (range of 0.01 μg to 100 mg). In one embodiment, the total amount of CTGF released from the sealant should be in the range of 0.10 μg to 50 mg. The dose per unit area (i.e., the dosage of CTGF as a function of the surface area of the lung to which drug is applied) should fall within the range of 0.005 μg–10 μg per $mm^2$ of surface area coated. In another embodiment, CTGF should be applied to a lung surface at a dose of 0.005 μg/$mm^2$–10 μg/$mm^2$ of surface area coated. As specific (polymeric and non-polymeric) drug delivery vehicles and specific pulmonary sealants can release CTGF at differing rates, the above dosing parameters should be utilized in combination with the release rate of the drug from the sealant such that a minimum concentration of 0.001 nM to 1000 μM of CTGF is delivered to the tissue. In one embodiment, CTGF is released from the pulmonary sealant such that fibrosis in the tissue is promoted for a period ranging from several hours to several months. For example, CTGF may be released in effective concentrations for a period ranging from 1 hour–30 days. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Optionally, the sealant may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or an analogue or derivative thereof. Inflammatory cytokines are to be used in formulations at concentrations that range from 0.0001 μg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 μg to 100 mg); preferred 0.001 μg to 50 mg. When used as a device coating, the dose is per unit area of 0.0001 μg–500 μg per $mm^2$; with a preferred dose of 0.001 μg/$mm^2$–200 μg/$mm^2$. Minimum concentration of $10^{-10}$–$10^{-4}$ g/ml of inflammatory cytokine is to be maintained on the device surface.

Furthermore, the sealant may alone or additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof. Doses used are those concentrations which are demonstrated to stimulate cell proliferation (see, e.g., Example 16). The proliferative agents are to be used in formulations at concentrations that range from 0.0000001 to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 μg to 200 mg); preferred 0.001 μg to 100 mg. When used as a device coating, the dose is per unit area of 0.00001 μg–500 μg per $mm^2$; with a preferred dose of 0.0001 μg/$mm^2$–200 μg/$mm^2$. Minimum concentration of $10^{-11}$–$10^{-6}$ M of proliferative agent is to be maintained on the device surface.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

14. Hernia Meshes

The present invention provides for the combination of a fibrosis-inducing agent and an implantable mesh used to reinforce tissue wall defects such as hernias. Hernias are abnormal protrusions (outpouchings) of an organ or other body structure through a defect or natural opening in a covering membrane, muscle or bone. Hernias are commonly caused by activities which result in overstraining (activities that typically increase intra-abdominal pressure), or they can occur as a result of childbirth. Conditions in which a hernia mesh may need to be used include, without limitation, the repair of inguinal (i.e., groin), umbilical, ventral, femoral, abdominal, diaphragmatic, epigastric, gastroesophageal, hiatal, intermuscular, mesenteric, paraperitoneal, rectovaginal, rectocecal, uterine, and vesical hernias.

Inguinal hernias are the most common type of hernias in adults and develop as the result of a weakness, tear, gap or opening in the muscle wall of the lower abdomen or groin (inguinal canal). As a result, the contents of the abdomen, such as intestine, may protrude through the opening creating, a bulge and/or pain. Inguinal hernias may be congenital and may become evident with pain or as a bulge at any time during life. They can also be acquired as a result of repetitive pressure, strain or injury to the muscles of the abdominal wall.

Umbilical hernias develop in and around the area of the belly button (i.e., navel) and gradually affects those people having a congenital weakness in the abdominal wall surrounding the umbilicus (the area at which the vessels of the fetal umbilical cord exited through the muscle of the abdominal wall). Hernias can occur in this area of weakness at any time from birth through late adulthood. The signs and symptoms include pain at or near the navel area as well as the development of an associated bulge or navel deformity. This bulge pushes out upon the skin beneath or around the navel, distorting the normal contour and architecture in or around the navel.

Incisional or ventral hernias may occur in the area of any prior surgical incision, and can vary in size from very small, to very large and complex. They develop as the result of disruption along or adjacent to the area of abdominal wall suturing, often subsequent tension placed on the tissue or other inhibition to adequate healing (infection, poor nutrition, obesity, or metabolic diseases). These hernias are present as a bulge or protrusion at or near the area of the prior incision scar. Numerous types of abdominal operations can subsequently develop an incisional hernia at the scar area (e.g., intestinal surgery, vascular surgery, appendectomy, or laparoscopy).

Femoral hernias, like inguinal hernias develop in the groin area. These hernias develop at or very near the leg crease. The defect itself occurs in between the inguinal ligament (a tendinous cord that creates the leg crease), the lower side of the pubic bone, and the femoral vein (the major vein of the leg). This gap is somewhat larger in females due to the shape and angle of the pelvis, therefore making femoral hernias more common in females.

Hernias themselves are not dangerous, but can become extremely problematic if they become incarcerated. In an incarcerated hernia, the protruding viscera are unable to retract back to their normal anatomical location and become "trapped" in the hernia sac. If the incarcerated viscera swell, the organ (typically the intestine) can become blocked (causing bowel obstruction) and/or the blood supply to the organ can become compromised, this can lead to necrosis and death of the incarcerated portion. As such hernias are often repaired surgically to prevent complications. In its simplest form, the viscera is returned to its normal location and the defect in the wall is primarily closed with sutures, but for bigger gaps, a mesh is placed over the defect to close the hernia opening. Surgical prostheses used in hernia repair (referred to herein as "hernia meshes") include prosthetic mesh- or gauze-like materials, which support the repaired hernia or other body structures during the healing process. The addition of a fibrosis-inducing agent to the implant can encourage the development and ingrowth of strong, fibrous tissue in and around the mesh. This can reinforce the tissue, form scar tissue over the abdominal wall defect and create a lasting repair that can reduce the incidence of recurrence. For smaller gaps, the fibrosis-inducing agent can be combined with the suture material to produce the same effect.

In one aspect, the hernia mesh may comprise a biodegradable or non-biodegradable material. In certain embodiments, the mesh fabric may be susceptible to the formation of adhesions with the surrounding tissue or organs and/or may promote enhanced tissue ingrowth.

Representative examples of non-biodegradable material for use in hernia repair meshes include the following: tantalum metallic meshes, stainless steel meshes, polyamides, polyolefins (e.g., polypropylene and polyethylene), polyurethanes, polyester/polyether block copolymers, polyesters (PET, polybutyleneterephthalate, and polyhexyleneterephthalate), polyester cloth (such as DACRON), polyester sheeting (such as MYLAR available from E.I. DuPont De Nemours and Company, Wilmington, Del.), nylon meshes, DACRON meshes (such as MERSILENE available from Ethicon, Inc., a Johnson & Johnson Company, Somerville, N.J.), acrylic cloth (ORLON available from E.I. DuPont De Nemours and Company), polyvinyl sponge (IVALON), polyvinyl cloth (VINYON-N), polypropylene mesh (MARLEX or BARD mesh available from CR Bard, Inc., Cranston, R.I.), and PROLENE available from Ethicon, Inc., a Johnson & Johnson Company, Somerville, N.J.), silicones, or fluoropolymers such as fluorinated ethylene propylene (FEP) or polytetrafluoroethylene (PTFE; such as TEFLON mesh and cloth available from E.I. DuPont De Nemours and Company (Wilmington, Del.) or expanded PTFE sold under the trade name GORE-TEX available from W.L. Gore & Associates, Inc.).

Hernia repair meshes may comprise a biodegradable or bioresorbable polymer such as polyglactin (VICRYL; Ethicon, Inc., a Johnson & Johnson Company (Somerville, N.J.)), polyglycolic acid (such as DEXON; United States Surgical/Syneture (Norwalk, Conn.)), carbon fiber mesh, autogenous, heterogenous, and xenogeneic tissue (e.g., pericardium or small intestine submucosa), or oxidized, regenerated cellulose.

The surgical mesh used in hernia repairs may be produced by knitting, weaving, braiding, or otherwise forming a plurality of yarns (e.g., monofilament or multifilament yarns made of polymeric materials such as polypropylene and polyester) into a support trellis. Mesh fabrics for use in connection with hernia repairs are disclosed in U.S. Pat. Nos. 6,638,284; 5,292,328; 4,769,038 and 2,671,444. Knitted and woven fabrics constructed from a variety of synthetic fibers and the use of the fabrics, in surgical repair are also discussed in U.S. Pat. Nos. 3,054,406; 3,124,136; 4,193,137; 4,347,847; 4,452,245; 4,520,821; 4,633,873; 4,652,264; 4,655,221; 4,838,884 and 5,002,551 and European Patent Application No. 334,046. Implantable hernia meshes are described in U.S. Pat. Nos. 6,610,006; 6,368,541 and 6,319,264. Hernia meshes for the repair of hiatal hernias are described in, e.g., U.S. Pat. No. 6,436,030. Hernia meshes for the repair of abdominal (e.g., ventral and umbilical) hernias are described in U.S. Pat. No. 6,383,201. Infection-resistant hernia meshes are described in, e.g., U.S. Pat. No. 6,375,662. Hernia meshes such as those described in the patents listed above are suitable for combining with a fibrosis-inducing agent to create a mesh which promotes the growth of fibrous tissue.

Commercially available hernia meshes can also be combined with one or more fibrosis-inducing drugs according to the present invention. Examples of commercially available meshes for use in hernia repair (e.g., inguinal hernias and other hernias of the abdominal wall) that can be combined with a fibrosis-inducing agent include: (a) MARLEX or BARD mesh (CR Bard, Inc., Cranston, R.I.)), which is a very dense knitted fabric structure with low porosity; (b) monofilament polypropylene mesh such as PROLENE available from Ethicon, Inc., a Johnson & Johnson Company, Somerville, N.J. (see, e.g., U.S. Pat. Nos. 5,634,931 and 5,824,082)); (c) SURGISIS GOLD and SURGISIS IHM soft tissue graft (both from Cook Surgical, Inc.) which are devices specifically configured for use to reinforce soft tissue in repair of inguinal hernias in open and laparoscopic procedures; (d) thin walled polypropylene surgical meshes such as are available from Atrium under the trade names PROLITE, PROLITE ULTRA, and LITEMESH; (e) COMPOSIX hernia mesh (C.R. Bard, Murray Hill, N.J.), which incorporates a mesh patch (the patch includes two layers of an inert synthetic mesh, generally made of polypropylene, and is described in U.S. Pat. No. 6,280,453) that includes a filament to stiffen and maintain the device in a flat configuration; (f) VISILEX mesh (from C.R. Bard), which is a polypropylene mesh that is constructed with monofilament polypropylene; (g) other hernia meshes available from C.R. Bard, Inc. which include PERFIX Plug, KUGEL Hernia Patch, 3D MAX mesh, LHI mesh, DULEX mesh, and the VENTRALEX Hernia Patch; and (h) other types of polypropylene monofilament hernia mesh and plug products include HERTRA mesh 1, 2, and 2A, HERMESH 3, 4 & 5 and 3-dimensional Plugs T1, T2, and T3 from Herniamesh USA, Inc (Great Neck, N.Y.). Another implant suitable for use in this embodiment is a prosthetic polypropylene mesh with a bioresorbable coating called SEPRAMESH Biosurgical Composite (Genzyme Corporation, Cambridge, Mass.). One side of the mesh is coated with a bioresorbable layer of sodium hyaluronate and carboxymethylcellulose, providing a temporary physical barrier that separates the underlying tissue and organ surfaces from the mesh. The other side of the mesh is uncoated, allowing for complete tissue ingrowth similar to bare polypropylene mesh. In one embodiment, the fibrosis-inducing agent may be applied only to the uncoated side of SEPRAMESH and not to the sodium hyaluronate/carboxymethylcellulose coated side.

Other commercially available materials may also be used as hernia meshes. Boston Scientific Corporation (Natick, Mass.) sells the TRELEX NATURAL Mesh which is composed of a unique knitted polypropylene material. Atrium Medical Corporation (Hudson, N.H.) sells the PROLITE Mesh and the PROLITE Ultra Mesh made of thin wall polypropylene and the 3-dimensional PROLOOP Plug composed of monofilament loops of polypropylene for the treatment of hernia repairs. Ethicon, Inc. makes the absorbable VICRYL (polyglactin 910) meshes (knitted and woven), PROLENE Polypropylene Hernia Meshes and MERSILENE Polyester Fiber Mesh. Dow Corning Corporation (Midland, Mich.) sells a mesh material formed from silicone elastomer known as SILASTIC Rx Medical Grade Sheeting (Platinum Cured). United States Surgical/Syneture (Norwalk, Conn.) sells a mesh made from absorbable polyglycolic acid under the trade name DEXON Mesh Products. Membrana Accurel Systems (Obernburg, Germany) sells the CELGARD microporous polypropylene fiber and membrane. Gynecare Worldwide, a division of Ethicon, Inc., a Johnson & Johnson Company (Somerville, N.J.) sells a mesh material made from oxidized, regenerated cellulose known as INTERCEED TC7.

In one aspect, the present invention provides a hernia repair mesh that includes a fibrosis-inducing agent to promote scarring and closure of an abdominal wall defect. The hernia mesh may be coated with the fibrosing agent (with or without a carrier). For example, a fibrosis-inducing drug may be applied to the surface of the mesh or woven into the fabric. Alternatively, or in addition, the hernia mesh may be composed either entirely or partially of fibers that are capable of inducing fibrosis. For example, silk strands or silk can be woven into the hernia mesh or the hernia mesh can be composed entirely of silk.

In another aspect, the present invention provides a sprayable composition that includes a fibrosis-inducing agent that can be used in endoscopic hernia repair procedures to promote scarring and closure of an abdominal wall defect.

Numerous polymeric and non-polymeric carrier systems described above may be used in the practice of this embodiment. These compositions can further comprise one or more fibrosis-inducing agents to promote the formation of fibrous scar tissue. Methods for incorporating fibrosing compositions onto or into hernia meshes include: (a) directly affixing to the implant a fibrosing composition (e.g., by either a spraying process or dipping process as described above, with or without a carrier); (b) directly incorporating into the device a fibrosing composition (e.g., by either a spraying process or dipping process as described above, with or without a carrier); (c) by coating the device with a substance such as a hydrogel which can in turn absorb the fibrosing composition; (d) by interweaving fibrosing composition coated thread (or the polymer itself formed into a thread) into the device structure; (e) by binding a film or mesh which is comprised of, or coated with, a fibrosing composition to the hernia mesh; (f) constructing the device itself or a portion of the device with a fibrosing composition; and/or (g) by covalently binding the fibrosing agent directly to the hernia mesh surface or to a linker (small molecule or polymer) that is coated or attached to the mesh surface. For hernia meshes, the coating process can be performed in such a manner as to (a) coat the exterior surfaces of the mesh, (b) coat the interior surfaces of the mesh, or (c) coat all or parts of both external and internal surface of the device.

In addition to coating the device with a fibrosis-inducing composition, the fibrosing agent can be mixed with the materials that are used to make the device such that the fibrosing agent is incorporated into the final device.

In addition to (or as an alternative to) applying the fibrosis agent to the hernia mesh, an in situ forming composition, gel or thermogel composition containing a fibrosis-inducing agent can be applied to (as a gel, solid implant, liquid or spray) the placement site of the hernia mesh, either: (a) prior to placement of the mesh; (b) after placement of the hernia mesh; (c) during the placement of the mesh; or (d) any combination of those three. For the in situ forming thermogel and gel compositions, the fibrosis-inducing agent(s) (e.g., silk powder, bleomycin) can be incorporated directly into the formulation to produce a suspension or a solution or it can be incorporated into a secondary carrier (e.g., micelles, liposomes, microspheres, microparticles, nanospheres, microparticulates, emulsions and/or microemulsions) that is then incorporated into the in situ forming compositions. In another embodiment, the fibrosis-inducing agent can be electrostatically or covalently bound to one or more of the polymeric components of the in-situ in situ forming composition.

In a particularly preferred embodiment, the composition may be prepared from a 4-armed thiol PEG (10K), a 4-armed NHS PEG(10K) and methylated collagen such as described above and contains a fibrosis-inducing agent that is sprayed onto the surgical site to affix the hernia mesh in place and induce fibrosis into the mesh.

In another embodiment, the fibrosis-inducing agent can be incorporated into a biodegradable or dissolvable film or mesh that is then applied to the treatment site prior to, or post, implantation of the hernia mesh. Exemplary materials for the manufacture of these films or meshes are hyaluronic acid (crosslinked or non-crosslinked), cellulose derivatives (e.g., hydroxypropyl cellulose), collagen and crosslinked poly(ethylene glycol).

It should be apparent to one of skill in the art that potentially any adhesion or fibrosis-inducing agents described above may be utilized alone, or in combination, in the practice of this embodiment. Exemplary fibrosing agents for use in hernia repair meshes include talc, silk, wool, chitosan, polylysine, fibronectin, bleomycin, and CTGF, as well as analogues and derivatives of the aforementioned.

As hernia meshes and compositions for use with hernia meshes are made in a variety of configurations and sizes, the exact dose administered can vary with mesh size, surface area and design. However, certain principles can be applied in the application of this art. Drug dose can be calculated as a function of dose per unit area (of the portion of the mesh being coated), total drug dose administered can be measured and appropriate surface concentrations of active drug can be determined. Regardless of the method of application of the drug to the hernia mesh, the exemplary fibrosing agents, used alone or in combination, should be administered under the following dosing guidelines:

Utilizing talc as an exemplary fibrosis-inducing agent, whether it is applied using a polymer coating, incorporated into the polymers which make up the hernia mesh, or applied without a polymeric carrier, the total dose of talc delivered from a hernia mesh, or coated onto the surface of a hernia mesh, should not exceed 100 mg (range of 1 µg to 100 mg). In one embodiment, the total amount of talc released from the prosthesis should be in the range of 10 µg to 50 mg. The dose per unit area of the implanted mesh (i.e., the dosage of talc as a function of the surface area of the portion of the mesh to which drug is applied and/or incorporated) should fall within the range of 0.05 µg–10 µg per mm$^2$ of surface area coated. In another embodiment, talc should be applied to a hernia mesh surface at a dose of 0.05 µg/mm$^2$–10 µg/mm$^2$ of surface area coated. In one embodiment, talc is released from the surface of a hernia mesh such that fibrosis in the tissue is promoted for a period ranging from several hours to several months. For example, talc may be released in effective concentrations for a period ranging from 1 week to 9 months. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymer coating, incorporated into the polymers which make up the hernia mesh, or applied without a polymeric carrier, the total dose of silk delivered from a hernia mesh, or coated onto the surface of a hernia mesh, should not exceed 100 mg (range of 1 µg to 100 mg). In one embodiment, the total amount of silk released from the hernia mesh should be in the range of 10 µg to 50 mg. The dose per unit area of the implanted mesh (i.e., the dosage of silk as a function of the surface area of the portion of the mesh to which drug is applied and/or incorporated) should fall within the range of 0.05 µg–10 µg per mm$^2$ of surface area coated. In another embodiment, silk should be applied to a hernia mesh surface at a dose of 0.05 µg/mm$^2$–10 µg/mm$^2$ of surface area coated. As specific (polymeric and non-polymeric) drug delivery vehicles and specific hernia meshes can release silk at differing rates, the above dosing parameters should be utilized in combination with the release rate of the drug from the hernia mesh such that a minimum concentration of 0.01 nM to 1000 µM of silk is delivered to the tissue. In one embodiment, silk is released from the surface of a hernia mesh such that fibrosis in the tissue is promoted for a period ranging from several hours to several months. For example, silk may be released in effective concentrations for a period ranging from 1 week–9 months. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymer coating, incorporated into the polymers which make up the hernia mesh, or applied without a polymeric carrier, the total dose of chitosan delivered from a hernia mesh, or coated onto the surface of a hernia mesh, should not exceed 100 mg (range of 1 µg to 100 mg). In one embodiment, the total amount of chitosan released from the hernia mesh should be in the range of 10 µg to 50 mg. The dose per unit area of the implanted mesh (i.e., the dosage of chitosan as a function of the surface area of the portion of the mesh to which drug is applied and/or incorporated) should fall within the range of 0.05 µg–10 µg per mm$^2$ of surface area coated. In another embodiment, chitosan should be applied to a hernia mesh surface at a dose of 0.05 µg/mm$^2$–10 µg/mm$^2$ of surface area coated. As specific (polymeric and non-polymeric) drug delivery vehicles and specific hernia meshes can release chitosan at differing rates, the above dosing parameters should be utilized in combination with the release rate of the drug from the hernia mesh such that a minimum concentration of 0.01 nM to 1000 µM of chitosan is delivered to the tissue. In one embodiment, chitosan is released from the surface of a hernia mesh such that fibrosis in the tissue is promoted for a period ranging from several hours to several months. For example, chitosan may be released in effective concentrations for a period ranging from 1 week to 9 months. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as an exemplary fibrosis-inducing agent, whether it is applied using a polymer coating, incorporated into the polymers which make up the hernia mesh, or applied without a polymeric carrier, the total dose of polylysine delivered from a hernia mesh, or coated onto the surface of a hernia mesh, should not exceed 100 mg (range of 1 µg to 100 mg). In one embodiment, the total amount of polylysine released from the hernia mesh should be in the range of 10 µg to 50 mg. The dose per unit area of the implanted mesh (i.e., the dosage of polylysine as a function of the surface area of the portion of the mesh to which drug is applied and/or incorporated) should fall within the range of 0.05 µg–10 µg per mm$^2$ of surface area coated. In another embodiment, polylysine should be applied to a hernia mesh surface at a dose of 0.05 µg/mm$^2$–10 µg/mm$^2$ of surface area coated. As specific (polymeric and non-polymeric) drug delivery vehicles and specific hernia meshes can release polylysine at differing rates, the above dosing parameters should be utilized in combination with the release rate of the drug from the hernia mesh such that a minimum concentration of 0.01 nM to 1000 μM of polylysine is delivered to the tissue. In one embodiment, polylysine is released from the surface of a hernia mesh such that fibrosis in the tissue is promoted for a period ranging from several hours to several months. For example, polylysine may be released in effective concentrations for a period ranging from 1 week to 9 months. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymer coating, incorporated into the polymers which make up the hernia mesh, or applied without a polymeric carrier, the total dose of fibronectin delivered from a hernia mesh, or coated onto the surface of a hernia mesh, should not exceed 100 mg (range of 1 μg to 100 mg). In one embodiment, the total amount of fibronectin released from the hernia mesh should be in the range of 10 μg to 50 mg. The dose per unit area of the implanted mesh (i.e., the dosage of fibronectin as a function of the surface area of the portion of the mesh to which drug is applied and/or incorporated) should fall within the range of 0.05 μg–10 μg per $mm^2$ of surface area coated. In another embodiment, fibronectin should be applied to a hernia mesh surface at a dose of 0.05 μg/$mm^2$–10 μg/$mm^2$ of surface area coated. As specific (polymeric and non-polymeric) drug delivery vehicles and specific hernia meshes can release fibronectin at differing rates, the above dosing parameters should be utilized in combination with the release rate of the drug from the hernia mesh such that a minimum concentration of 0.01 nM to 1000 μM of fibronectin is delivered to the tissue. In one embodiment, fibronectin is released from the surface of a hernia mesh such that fibrosis in the tissue is promoted for a period ranging from several hours to several months. For example, fibronectin may be released in effective concentrations for a period ranging from 1 week to 9 months. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, whether it is applied using a polymer coating, incorporated into the polymers which make up the hernia mesh, or applied without a polymeric carrier, the total dose of bleomycin delivered from a hernia mesh, or coated onto the surface of a hernia mesh, should not exceed 100 mg (range of 0.01 μg to 100 mg). In one embodiment, the total amount of bleomycin released from the hernia mesh should be in the range of 0.10 μg to 50 mg. The dose per unit area of the implanted mesh (i.e., the dosage of bleomycin as a function of the surface area of the portion of the mesh to which drug is applied and/or incorporated) should fall within the range of 0.005 μg–10 μg per $mm^2$ of surface area coated. In another embodiment, bleomycin should be applied to a hernia mesh surface at a dose of 0.005 μg/$mm^2$–10 μg/$mm^2$ of surface area coated. As specific (polymeric and non-polymeric) drug delivery vehicles and specific hernia meshes can release bleomycin at differing rates, the above dosing parameters should be utilized in combination with the release rate of the drug from the hernia mesh such that a minimum concentration of 0.001 nM to 1000 μM of bleomycin is delivered to the tissue. In one embodiment, bleomycin is released from the surface of a hernia mesh such that fibrosis in the tissue is promoted for a period ranging from several hours to several months. For example, bleomycin may be released in effective concentrations for a period ranging from 1 week to 9 months. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as an exemplary fibrosis-inducing agent, whether it is applied using a polymer coating, incorporated into the polymers which make up the hernia mesh, or applied without a polymeric carrier, the total dose of CTGF delivered from a hernia mesh, or coated onto the surface of a hernia mesh, should not exceed 100 mg (range of 0.01 μg to 100 mg). In one embodiment, the total amount of CTGF released from the hernia mesh should be in the range of 0.10 μg to 50 mg. The dose per unit area of the implanted mesh (i.e., the dosage of CTGF as a function of the surface area of the portion of the mesh to which drug is applied and/or incorporated) should fall within the range of 0.005 μg–10 μg per $mm^2$ of surface area coated. In another embodiment, CTGF should be applied to a hernia mesh surface at a dose of 0.005 μg/$mm^2$–10 μg/$mm^2$ of surface area coated. As specific (polymeric and non-polymeric) drug delivery vehicles and specific hernia meshes can release CTGF at differing rates, the above dosing parameters should be utilized in combination with the release rate of the drug from the hernia mesh such that a minimum concentration of 0.001 nM to 1000 μM of CTGF is delivered to the tissue. In one embodiment, CTGF is released from the surface of a hernia mesh such that fibrosis in the tissue is promoted for a period ranging from several hours to several months. For example, CTGF may be released in effective concentrations for a period ranging from 1 week to 9 months. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Optionally, the device or composition may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or an analogue or derivative thereof. Inflammatory cytokines are to be used in formulations at concentrations that range from 0.0001 μg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 µg to 100 mg); preferred 0.001 µg to 50 mg. When used as a device coating, the dose is per unit area of 0.0001 µg–500 µg per mm$^2$; with a preferred dose of 0.001 µg/mm$^2$–200 µg/mm$^2$. Minimum concentration of $10^{-10}$–$10^{-4}$ g/ml of inflammatory cytokine is to be maintained on the device surface.

Furthermore, the device or composition may alone or additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof. Doses used are those concentrations which are demonstrated to stimulate cell proliferation (see, e.g., Example 16). The proliferative agents are to be used in formulations at concentrations that range from 0.1 ng/ml to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 µg to 200 mg); preferred 0.001 µg to 100 mg. When used as a device coating, the dose is per unit area of 0.00001 µg–500 µg per mm$^2$; with a preferred dose of 0.0001 µg/mm$^2$–200 µg/mm$^2$. Minimum concentration of $10^{-11}$–$10^{-6}$ M of proliferative agent is to be maintained on the device surface.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

15. Shoulder Capsule, Ligament and Tendon Repairs

In one aspect, the present invention provides compositions and devices for use in shoulder capsule, ligament, and tendon repair surgeries. The term "ligament" refers to a band of fibrous connective tissue that connects bones to cartilage, which serves to support and strengthen a joint. The term "tendon" refers to a fibrous cord of connective tissue in which the fibers of a muscle end and by which the muscle is attached to a bone or other structure. Over 700,000 ligament and tendon repairs are performed annually in the United States including: repairs of the foot and ankle (11% of the total; particularly the Achilles tendon, but also the peroneal tendons, plantar fascia repair, extensor digitorum tendons, anterior tibial tendon, lateral stabilizing ligaments of the ankle, anterior inferior tibial fibular ligament, medial deltoid ligament), knee (38% of the total; particularly the medial collateral ligament, lateral collateral ligament, anterior cruciate ligament, posterior cruciate ligament, and meniscal repair, but also chondral surface repair, patellar tendon repair, bicep femoris tendon repair), hip (rectus femoris origin, gracilis tendon, avulsion of the hamstring muscle origins), pelvis (gracilis muscle origin, adductor muscle origins, rectus femoris insertion, pubic symphysis cartilage), shoulder (25% of the total; particularly the rotator cuff tendons; also acromioclavicular stabilizing ligaments, biceps tendons), back (sacroiliac stabilizing ligaments), elbow (biceps tendons, lateral epicondyle—extensor origins, medial epicondyle—flexor origins, triceps complex), and hand (26% of the total; flexor and extensor tendons of the wrist and hand). The addition of a fibrosis-inducing agent to a soft tissue repair procedure (such as those listed above) can increase scarring and lead to a more durable, sustainable and functional outcome for the patient.

Several collagen-based surgical meshes have been produced to function as tissue repair products for use during open surgery and are suitable for the delivery of a fibrosis-inducing agent. For example, collagen surgical patches, such as the FORTAFLEX Patch (Organogenesis Inc., Canton, Mass.), are used in tendon, ligament and cartilage repair surgeries to reinforce the tissue during surgical repair and healing. Tendon and ligament repair surgeries typically involve the use of suture anchors or suture-passing devices to secure the damaged tendons to the bone. Depending on the size of the tear, a collagen patch may be used to fill a defect in the tendon or ligament. The collagen implant serves as a resorbable scaffold that provides biomechanical strength, support and reinforcement of soft tissues that are surgically repaired. Eventually the collagen becomes infiltrated and replaced by host tissue cells (primarily fibroblasts) which are able to repair and regenerate the damaged tissue (primarily organized connective tissue).

Unfortunately, for many of these surgical interventions, durability of the collagen implant becomes an important clinical issue. In tendon and ligament repairs, it is desirable for the collagen implant to provide structural integrity until full healing and native tissue replacement can occur. In the case of large tissue defects, which can take several months to over a year to heal, limited durability of the collagen implant can become a clinical problem if it completely absorbs prior to the completion of healing. In an attempt to address this problem, manufacturers have sought to produce a collagen implant with improved durability through by increasing the amount crosslinking between the collagen fibers. However highly crosslinked collagen material has different scaffolding and degradation profiles than native collagen and does not function optimally in the healing process. The addition of one or more fibrosis-inducing agents to a collagen patch has several important clinical implications. First, since it does not require alteration of the collagen material itself, the collagen scaffold remains in its native state and is able to support the normal ingrowth of reparative fibrous connective tissue. Secondly, the fibrosis-inducing agent stimulates the ingrowth of the body's own fibrous connective tissue, speeding the healing process and allowing repair to occur prior to failure of the implant. The result is a more rapid, stronger, longer-lasting repair composed of the body's own connective tissue which leads to a better clinical outcome and a lower risk of failure.

In one aspect, the present invention provides compositions and devices that include a fibrosis-inducing agent, where the agent may encourage scar formation to strengthen the surgically repaired ligament (e.g., anterior or posterior cruciate ligament), tendon (e.g., Achilles tendon), or joint capsule (e.g., the anterior capsule to prevent recurrent shoulder dislocation). A variety of embodiments are suitable for the practice of this invention, including delivering to the soft tissue operative site: (1) a "thermopaste" containing a fibrosis-inducing agent that is applied to a desired site as a fluid, and hardens to a solid of the desired shape at a specified temperature (e.g., body temperature); (2) as a spray (i.e., "nanospray") containing a fibrosis-inducing agent that can be delivered to a desired site either directly in open surgery, or through a specialized surgical apparatus (e.g., an endoscope), and which subsequently hardens to a solid that adheres to the tissue it is applied to; (3) as an adherent, pliable, resilient, polymer film containing a fibrosis-inducing agent applied to a desired site either directly or through a specialized apparatus, and which preferably adheres to the site to which it is applied; and/or (4) as a fluid composed of a suspension of microspheres containing a fibrosis-inducing agent in an appropriate carrier medium, which is applied to a desired site either directly or via a specialized apparatus, and which leaves a layer of microspheres at the application site. Representative examples of each of the above embodiments are set forth in more detail below.

In another embodiment, tendons, ligaments or the shoulder capsule can be treated with a fibrosis-inducing agent combined with a composition that forms a gel in situ. These can be crosslinked gels, thermogels, or traditional gel compositions. For the in situ forming gels, thermogel and gel compositions, the fibrosis-inducing agent(s) can be incorporated directly into the formulation to produce a suspension or a solution (e.g., silk powder, bleomycin) or it can be incorporated into a secondary carrier (e.g., micelles, liposomes, microspheres, microparticles, nanospheres, microparticulates, emulsions and/or micromulsions) that is then incorporated into the in situ forming gel compositions. In certain embodiments, the fibrosis-inducing agent can be electrostatically or covalently bound to one or more of the polymeric components of the in situ forming gel composition.

In yet another embodiment, the fibrosis-inducing agent can be incorporated into a biodegradable or dissolvable film or mesh that is then applied to the treatment site prior to, during, or post treatment. The film or mesh can be applied to the entire treatment site, used to bridge or fill tissue defects, or they can be applied as a patch to a very specific location within the treatment site. Preferred materials for the manufacture of these films or meshes are hyaluronic acid (crosslinked or non-crosslinked), cellulose derivatives (e.g., hydroxypropyl cellulose), collagen and crosslinked poly (ethylene glycol).

In yet another embodiment, the fibrosis-inducing agent can be in an injectable or sprayable form (particularly useful for endoscopic delivery) that can be delivered directly into the treatment site, applied over the surgically repaired tendon, ligament or capsule, used to patch tissue defects, or applied to the tissue surrounding the treatment site. The compositions may be readily applied as a "spray", which subsequently solidifies into a film or coating. A sprayable formulation of a fibrosing agent may be used in, for example, knee surgery (e.g., MCL and ACL) repairs to reinforce the ligament or in ankle surgery to reinforce a tendon (e.g., Achilles' tendon). The compositions also may be used for cosmetic purposes, such as, reinforcement or augmentation of the Cooper's ligament (e.g., for support or lifting of the breast). For example, the ligament may be coated with a scarring fibrosing agent in order to cause the ligament to contract (i.e., shorten) and lift the breast tissue. The fibrosis-inducing agent(s) (e.g., silk powder, bleomycin) can be incorporated directly into the formulation to produce a suspension or a solution or incorporated into a secondary carrier (e.g., micelles, liposomes, microspheres, microparticles, nanospheres, microparticulates, emulsions and/or micromulsions) that is then incorporated into the injectable or sprayable composition. The spray, which includes a tissue adherent polymer containing a fibrosis-inducing agent, may be prepared from microspheres of a wide array of sizes. In another embodiment, the fibrosis-inducing agent can be electrostatically or covalently bound to one or more of the polymeric components of the injectable or sprayable composition.

The injectable and sprayable compositions can further comprise a polymer to enhance the viscosity of the solution. Polymers that can be used for this purpose include hyaluronic acid, CMC, PLURONICS, such as PLURONIC F127, and gels (including thermo gels) of the form X-Y, X-Y-X, or Y-X-Y (where X is a degradable polyester and Y is a polyalkylene oxide, preferably polyethylene glycol or the mono-methyl ether thereof). In another embodiment, the injectable or sprayable formulation can further comprise one or more biocompatible solvents. These can include ethanol, DMSO, NMP, poly(ethylene glycol)-200, and/or poly(ethylene glycol)-300.

One material that is of particular interest for the practice of this embodiment is prepared from a 4-armed thiol PEG (10K), a 4-armed NHS PEG(10K) and methylated collagen such as described above. In one embodiment, a material made from 4-armed thiol PEG (10K), a 4-armed NHS PEG(10K) and methylated collagen is loaded with a fibrosis-inducing agent and sprayed (directly or via endoscope) directly onto the treatment site, used to patch a tissue defect, applied to the tissue surrounding the treatment site, or applied over a damaged tendon, ligament or capsule to adhere the tissues together and induce fibrosis.

It should be apparent to one of skill in the art that potentially any fibrosis-inducing agents described above may be utilized alone, or in combination, in the practice of this embodiment. Exemplary fibrosing agents for use in capsule, ligament, and tendon repair devices and implants include talc, silk, wool, chitosan, polylysine, fibronectin, bleomycin, and CTGF, as well as analogues and derivatives of the aforementioned.

As shoulder capsule, ligament, and tendon repair devices and compositions are made in a variety of configurations and sizes depending upon the location and the degree of the injury, the exact dose administered can vary with implant size, surface area and design. However, certain principles can be applied in the application of this art. Drug dose can be calculated as a function of dose per unit area (or volume) of the implant, total drug dose administered can be measured and appropriate surface concentrations of active drug can be determined. Regardless of the method of application of the drug to the joint capsule, ligament, or tendon repair device or implant, the exemplary fibrosing agents, used alone or in combination, should be administered under the following dosing guidelines:

Utilizing talc as an exemplary fibrosis-inducing agent, whether it is applied using a polymer coating, incorporated into the polymers which make up the device or implant, or applied without a polymeric carrier, the total dose of talc delivered from a joint capsule, ligament, or tendon repair implant, or coated onto the surface of a joint capsule, ligament, or tendon repair implant, should not exceed 100 mg (range of 1 µg to 100 mg). In one embodiment, the total amount of talc released from the implant should be in the range of 10 µg to 50 mg. The dose per unit volume of the implant (i.e., the dosage of talc as a function of the volume of the portion of the implant to which drug is applied and/or incorporated) should fall within the range of 0.05 µg–10 µg per $mm^3$ of material implanted. In another embodiment, talc should be applied to a joint capsule, ligament, or tendon repair implant surface at a dose of 0.05 µg/mm²–10 µg/mm² of surface area coated. In one embodiment, talc is released from the surface of a joint capsule, ligament, or tendon repair implant such that fibrosis in the tissue is promoted for a period ranging from several hours to several months. For example, talc may be released in effective concentrations for a period ranging from 1 to 12 months. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymer coating, incorporated into the polymers which make up the device or implant, or applied without a polymeric carrier, the total dose of silk delivered from a joint capsule, ligament, or tendon repair implant, or coated onto the surface of a joint capsule, ligament, or tendon repair implant, should not exceed 100 mg (range of 1 µg to 100 mg). In one embodiment, the total amount of silk released from the implant should be in the range of 10 µg to 50 mg. The dose per unit volume of the implant (i.e., the dosage of silk as a function of the volume of the portion of the implant to which drug is applied and/or incorporated) should fall within the range of 0.05 µg–10 µg per mm³ of material implanted. In another embodiment, silk should be applied to a joint capsule, ligament, or tendon repair implant surface at a dose of 0.05 µg/mm²–10 µg/mm² of surface area coated. As specific (polymeric and non-polymeric) drug delivery vehicles and specific medical implants can release silk at differing rates, the above dosing parameters should be utilized in combination with the release rate of the drug from the joint capsule, ligament, or tendon repair implant such that a minimum concentration of 0.01 nM to 1000 µM of silk is delivered to the tissue. In one embodiment, silk is released from the surface of a joint capsule, ligament, or tendon repair implant such that fibrosis in the tissue is promoted for a period ranging from several hours to several months. For example, silk may be released in effective concentrations for a period ranging from 1 to 12 months. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymer coating, incorporated into the polymers which make up the device or implant, or applied without a polymeric carrier, the total dose of chitosan delivered from a joint capsule, ligament, or tendon repair implant, or coated onto the surface of a joint capsule, ligament, or tendon repair implant, should not exceed 100 mg (range of 1 µg to 100 mg). In one embodiment, the total amount of chitosan released from the implant should be in the range of 10 µg to 50 mg. The dose per unit volume of the implant (i.e., the dosage of chitosan as a function of the volume of the portion of the implant to which drug is applied and/or incorporated) should fall within the range of 0.05 µg–10 µg per mm³ of material implanted. In another embodiment, chitosan should be applied to a joint capsule, ligament, or tendon repair implant surface at a dose of 0.05 µg/mm²–10 µg/mm² of surface area coated. As specific (polymeric and non-polymeric) drug delivery vehicles and specific medical implants can release chitosan at differing rates, the above dosing parameters should be utilized in combination with the release rate of the drug from the joint capsule, ligament, or tendon repair implant such that a minimum concentration of 0.01 nM to 1000 µM of chitosan is delivered to the tissue. In one embodiment, chitosan is released from the surface of a joint capsule, ligament, or tendon repair implant such that fibrosis in the tissue is promoted for a period ranging from several hours to several months. For example, chitosan may be released in effective concentrations for a period ranging from 1 to 12 months. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as an exemplary fibrosis-inducing agent, whether it is applied using a polymer coating, incorporated into the polymers which make up the device or implant, or applied without a polymeric carrier, the total dose of polylysine delivered from a joint capsule, ligament, or tendon repair implant, or coated onto the surface of a joint capsule, ligament, or tendon repair implant, should not exceed 100 mg (range of 1 µg to 100 mg). In one embodiment, the total amount of polylysine released from the implant should be in the range of 10 µg to 50 mg. The dose per unit volume of the implant (i.e., the dosage of polylysine as a function of the volume of the portion of the implant to which drug is applied and/or incorporated) should fall within the range of 0.05 µg–10 µg per mm³ of material implanted. In another embodiment, polylysine should be applied to a joint capsule, ligament, or tendon repair implant surface at a dose of 0.05 µg/mm²–10 µg/mm² of surface area coated. As specific (polymeric and non-polymeric) drug delivery vehicles and specific medical implants can release polylysine at differing rates, the above dosing parameters should be utilized in combination with the release rate of the drug from the joint capsule, ligament, or tendon repair implant such that a minimum concentration of 0.01 nM to 1000 µM of polylysine is delivered to the tissue. In one embodiment, polylysine is released from the surface of a joint capsule, ligament, or tendon repair implant such that fibrosis in the tissue is promoted for a period ranging from several hours to several months. For example, polylysine may be released in effective concentrations for a period ranging from 1 to 12 months. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymer coating, incorporated into the polymers which make up the device or implant, or applied without a polymeric carrier, the total dose of fibronectin delivered from a joint capsule, ligament, or tendon repair implant, or coated onto the surface of a joint capsule, ligament, or tendon repair implant, should not exceed 100 mg (range of 1 µg to 100 mg). In one embodiment, the total amount of fibronectin released from the implant should be in the range of 10 µg to 50 mg. The dose per unit volume of the implant (i.e., the dosage of fibronectin as a function of the volume of the portion of the implant to which drug is applied and/or incorporated) should fall within the range of 0.05 µg–10 µg per $mm^3$ of material implanted. In another embodiment, fibronectin should be applied to a joint capsule, ligament, or tendon repair implant surface at a dose of 0.05 µg/$mm^2$–10 µg/$mm^2$ of surface area coated. As specific (polymeric and non-polymeric) drug delivery vehicles and specific medical implants can release fibronectin at differing rates, the above dosing parameters should be utilized in combination with the release rate of the drug from the joint capsule, ligament, or tendon repair implant such that a minimum concentration of 0.01 nM to 1000 µM of fibronectin is delivered to the tissue. In one embodiment, fibronectin is released from the surface of a joint capsule, ligament, or tendon repair implant such that fibrosis in the tissue is promoted for a period ranging from several hours to several months. For example, fibronectin may be released in effective concentrations for a period ranging from 1 to 12 months. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, whether it is applied using a polymer coating, incorporated into the polymers which make up the device or implant, or applied without a polymeric carrier, the total dose of bleomycin delivered from a joint capsule, ligament, or tendon repair implant, or coated onto the surface of a joint capsule, ligament, or tendon repair implant, should not exceed 100 mg (range of 0.01 µg to 100 mg). In one embodiment, the total amount of bleomycin released from the implant should be in the range of 0.10 µg to 50 mg. The dose per unit volume of the implant (i.e., the dosage of bleomycin as a function of the volume of the portion of the implant to which drug is applied and/or incorporated) should fall within the range of 0.005 µg–10 µg per $mm^3$ of material implanted. In another embodiment, bleomycin should be applied to a joint capsule, ligament, or tendon repair implant surface at a dose of 0.005 µg/$mm^2$–10 µg/$mm^2$ of surface area coated. As specific (polymeric and non-polymeric) drug delivery vehicles and specific medical implants can release bleomycin at differing rates, the above dosing parameters should be utilized in combination with the release rate of the drug from the joint capsule, ligament, or tendon repair implant such that a minimum concentration of 0.001 nM to 1000 µM of bleomycin is delivered to the tissue. In one embodiment, bleomycin is released from the surface of a joint capsule, ligament, or tendon repair implant such that fibrosis in the tissue is promoted for a period ranging from several hours to several months. For example, bleomycin may be released in effective concentrations for a period ranging from 1 to 12 months. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as an exemplary fibrosis-inducing agent, whether it is applied using a polymer coating, incorporated into the polymers which make up the device or implant, or applied without a polymeric carrier, the total dose of CTGF delivered from a joint capsule, ligament, or tendon repair implant, or coated onto the surface of a joint capsule, ligament, or tendon repair implant, should not exceed 100 mg (range of 0.01 µg to 100 mg). In one embodiment, the total amount of CTGF released from the implant should be in the range of 0.10 µg to 50 mg. The dose per unit volume of the implant (i.e., the dosage of CTGF as a function of the volume of the portion of the implant to which drug is applied and/or incorporated) should fall within the range of 0.005 µg–10 µg per $mm^3$ of material implanted. In another embodiment, CTGF should be applied to a joint capsule, ligament, or tendon repair implant surface at a dose of 0.005 µg/$mm^2$–10 µg/$mm^2$ of surface area coated. As specific (polymeric and non-polymeric) drug delivery vehicles and specific medical implants can release CTGF at differing rates, the above dosing parameters should be utilized in combination with the release rate of the drug from the joint capsule, ligament, or tendon repair implant such that a minimum concentration of 0.001 nM to 1000 µM of CTGF is delivered to the tissue. In one embodiment, CTGF is released from the surface of a joint capsule, ligament, or tendon repair implant such that fibrosis in the tissue is promoted for a period ranging from several hours to several months. For example, CTGF may be released in effective concentrations for a period ranging from 1 to 12 months. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Optionally, the device may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or a bone morphogenic protein (BMP) (e.g., BMP-2, BMP-3, BMP-4, BMP-5, BMP-6, or BMP-7 or an analogue or derivative thereof).

Bone morphogenic protein(s) (e.g., BMP-2, BMP-3, BMP-4, BMP-5, BMP-6, or BMP-7 or an analogue or derivative thereof) are to be used in formulations at concentrations that range from 0.001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the bone morphogenic protein is released in effective concentrations for a period ranging from 1–180 days. The total dose for a single application is typically not to exceed 500 mg (range of 0.001

µg to 500 mg); preferred 1 µg to 250 mg. When used as a device coating, the dose is per unit area of 0.001 µg–1000 µg per mm$^2$; with a preferred dose of 0.01 µg/mm$^2$–200 µg/mm$^2$. Minimum concentration of $10^{-9}$–$10^4$ M of bone morphogenic protein is to be maintained on the device surface.

Inflammatory cytokines are to be used in formulations at concentrations that range from 0.0001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 µg to 100 mg); preferred 0.001 µg to 50 mg. When used as a device coating, the dose is per unit area of 0.0001 µg–500 µg per mm$^2$; with a preferred dose of 0.001 µg/mm$^2$–200 µg/mm$^2$. Minimum concentration of $10^{-10}$–$10^{-4}$ g/ml of inflammatory cytokine is to be maintained on the device surface.

Furthermore, the device may alone or additionally comprise an agent that stimulates cellular proliferation. Examples include: dexamethasone, isotretinoin (13-cis retinoic acid), 17-β-estradiol, estradiol, 1-a-25 dihydroxyvitamin D$_3$, diethylstibesterol, cyclosporine A, L-NAME, all-trans retinoic acid (ATRA), and analogues and derivatives thereof. Doses used are those concentrations which are demonstrated to stimulate cell proliferation (see, e.g., Example 16). The proliferative agents are to be used in formulations at concentrations that range from 0.0000001 to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 µg to 200 mg); preferred 0.001 µg to 100 mg. When used as a device coating, the dose is per unit area of 0.00001 µg–500 µg per mm$^2$; with a preferred dose of 0.0001 µg/mm$^2$–200 µg/mm$^2$. Minimum concentration of $10^{-11}$–$10^{-6}$ M of proliferative agent is to be maintained on the device surface.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

16. Septal Occlusion Patches

The present invention provides for the combination of a fibrosis-inducing agent and a septal occlusion patch. Incorporation of a fibrosing agent into or onto a septal occlusion patch can promote tissue growth that will anchor the device to the septum and provide a better seal, thus reducing the incidence of leaks.

Approximately half of congenital cardiovascular defects let blood flow between the right and left chambers of the heart. The two most common types of defects are atrial septal defects involving an opening in the wall between the two atria and ventricular septal defects involving an opening in the wall between the ventricles. Other similar cardiac defects are patent foramen ovale and patent ductus arteriosus. In the United States alone, about 20,000 babies are born each year with one of these malformations. In addition approximately 1 million Americans with congenital cardiovascular defects are alive today and will develop complications, such as pulmonary hypertension, congestive heart failure, atrial arrhythmia, impaired aerobic capacity and stroke, which will require treatment.

Transcatheter closure of cardiac defects is becoming an attractive alternative to surgical closure because it reduces the risks and morbidity inherent to cardiac surgery. Several transcatheter techniques and septal occlusion devices have been developed and are used clinically. The latest generation of devices is composed of two disks joined by a center stalk. The stalk occludes the defect and the disks adhere to each side of the wall. The collapsed device is positioned via a catheter and released under fluoroscopy guidance. The size of these devices, however, limits the use of this technology in small patients. Further, patients with large defects and patients having an insufficient septal rim around the defect typically cannot be treated with septal occlusion devices. In addition, adverse complications associated with septal occlusion devices include incomplete closure (leaks), friction lesions and cardiac perforation.

The addition of a fibrosis-inducing agent to the implant can encourage the development and ingrowth of strong, fibrous tissue in and around the septal occlusion device. This can reinforce the tissue, form scar tissue over the implant and create a lasting repair. Tissue growth can anchor the device to the septum and provide an improved seal, thus minimizing the occurrence of leaks. Further, incorporation of the device by cardiac tissue can prevent friction fracture and cardiac perforation. Tissue growth in and/or on the device can strengthen the device and allow the use of thinner devices, thus reducing bulkiness and allowing inclusion of a wider patient population. Increased strength of the device can also allow for the treatment of larger defects. Finally, patients having a small septal rim that generally would be insufficient for transcatheter treatment will become eligible for this procedure because tissue growth will anchor the device in place.

The term septal occlusion patches refer to devices that are designed to be placed within or near the vasculature of the host to block the flow of blood through a vascular defect. Examples of septal occlusion patches include, without limitation, defect closure devices, shunt closure apparatus, intracardiac occluders, occluding disks, defect occluding systems, and intravascular shunt devices.

Septal occlusion patches may be composed of a variety of configurations. For example, the septal occlusion patch may center itself elastically against a margin of an opening by being shaped to form a closed loop with at least two spaced apart windings. See e.g., U.S. Pat. No. 6,355,052. The septal occlusion patch may be composed of a delivery shaft and a patch releasably held at the distal end whereby the patch has a collapsed configuration for positioning through the lumen of a sleeve and a deployment configuration for positioning across a septal defect. See e.g., U.S. Pat. No. 6,346,074. The septal occlusion patch may be composed of two flexible membranes having an elastically deformable frame extending along the periphery to allow the membranes to collapse for passage through a catheter while returning to their predetermined shape following implantation. See e.g., U.S. Pat. Nos. 6,077,291 and 5,334,217. The septal occlusion patch may be composed of an occlusion bag with two sacs connected to each other and an unattached super-elastic wire frame having two sets of multiple loops contained within the occlusion bag. See e.g., U.S. Pat. No. 5,861,003. The septal occlusion patch may be composed of at least two clips with fastening means that firmly grip the peripheral portions of the opening as well as a flat fabric occluder which is used to close the opening of the septum. See e.g., U.S. Pat. No. 5,507,811. The septal occlusion patch may be composed of two occluders connected by a fastener with a pivot for allowing rotation of the occluders when in an expanded configuration. See e.g., U.S. Pat. No. 5,451,235. The septal occlusion patch may be composed of two foldable foam resin or polyurethane discs with sutured wire skeletons whereby the discs are secured to each other using a buttoning technique through the heart defect. See e.g., U.S. Pat. Nos. 5,433,727; 5,284,488 and 4,917,089. The septal occlusion patch may be an umbrella-like expansive device composed of a plurality of struts movably mounted on a hub such that the patch has a first collapsed position and a second expanded position. See e.g., U.S. Pat. No. 4,007,743. The septal occlusion patch may be composed of a mechanical expansion means that has a dual set of umbrella-like structures with a central hub for placement on opposite sides of the shunt defect. See e.g., U.S. Pat. No. 3,874,388.

Commercially available septal occlusion patches can also be combined with one or more fibrosis-inducing drugs according to the present invention. For example, W.L. Gore and Associates, Inc. (Newark, Del.) sells its HELEX Septal Occluder which is used as a minimally invasive closure of atrial septal defects. NMT Medical, Inc. (Boston, Mass.) sells their CARDIOSEAL and STARFLEX which are designed for minimally invasive procedures. AGA Medical Corp. (Golden Valley, Minn.) sells their AMPLATZER Septal Occluder.

In one aspect, the present invention provides a septal occlusion patch that includes a fibrosis-inducing agent to promote scarring and closure of a cardiac defect. The septal occlusion patch may be coated with the fibrosing agent (with or without a carrier). For example, a fibrosis-inducing drug may be applied to the surface of the patch or woven into the fabric. Alternatively, or in addition, the septal occlusion patch may be composed either entirely or partially of fibers that are capable of inducing fibrosis. For example, silk strands or silk can be woven into the septal occlusion patch or the septal occlusion patch can be composed entirely of silk.

In another aspect, the present invention provides a sprayable composition that includes a fibrosis-inducing agent that can be used in transcatheter repair procedures to promote scarring and closure of a cardiac defect.

Numerous polymeric and non-polymeric carrier systems described above may be used in the practice of this embodiment. These compositions can further comprise one or more fibrosis-inducing agents to promote the formation of fibrous scar tissue. Methods for incorporating fibrosing compositions onto or into septal occlusion patch include: (a) directly affixing to the implant a fibrosing composition (e.g., by either a spraying process or dipping process as described above, with or without a carrier); (b) directly incorporating into the device a fibrosing composition (e.g., by either a spraying process or dipping process as described above, with or without a carrier); (c) by coating the device with a substance such as a hydrogel which can in turn absorb the fibrosing composition; (d) by interweaving fibrosing composition coated thread (or the polymer itself formed into a thread) into the device structure; (e) by binding a film or mesh which is comprised of, or coated with, a fibrosing composition to the septal occlusion patch; (f) constructing the device itself or a portion of the device with a fibrosing composition; and/or (g) by covalently binding the fibrosing agent directly to the septal occlusion patch surface or to a linker (small molecule or polymer) that is coated or attached to the patch surface. For septal occlusion patch, the coating process can be performed in such a manner as to (a) coat the exterior surfaces of the patch, (b) coat the interior surfaces of the patch, or (c) coat all or parts of both external and internal surface of the patch.

In addition to coating the device with a fibrosis-inducing composition, the fibrosing agent can be mixed with the materials that are used to make the device such that the fibrosing agent is incorporated into the final device.

In addition to (or as an alternative to) applying the fibrosis agent to the septal occlusion patch, an in situ forming composition, gel or thermogel composition containing a fibrosis-inducing agent can be applied to (as a gel, solid implant, liquid or spray) the placement site of the septal occlusion patch, either: (a) prior to placement of the patch; (b) after placement of the patch; (c) during the placement of the patch; or (d) any combination of those three. For the in situ forming thermogel and gel compositions, the fibrosis-inducing agent(s) (e.g., silk powder, bleomycin) can be incorporated directly into the formulation to produce a suspension or a solution or it can be incorporated into a secondary carrier (e.g., micelles, liposomes, microspheres, microparticles, nanospheres, microparticulates, emulsions and/or microemulsions) that is then incorporated into the in situ forming compositions. In another embodiment, the fibrosis-inducing agent can be electrostatically or covalently bound to one or more of the polymeric components of the in-situ in situ forming composition.

In a particularly preferred embodiment, the composition may be prepared from a 4-armed thiol PEG (10K), a 4-armed NHS PEG(10K) and methylated collagen such as described above and contains a fibrosis-inducing agent that is sprayed onto the surgical site to affix the septal occlusion patch in place and induce fibrosis into the patch.

In another embodiment, the fibrosis-inducing agent can be incorporated into a biodegradable or dissolvable film or mesh that is then applied to the treatment site prior to, or post, implantation of the septal occlusion patch. Exemplary materials for the manufacture of these films or meshes are hyaluronic acid (crosslinked or non-crosslinked), cellulose derivatives (e.g., hydroxypropyl cellulose), collagen and crosslinked poly(ethylene glycol).

It should be apparent to one of skill in the art that potentially any adhesion or fibrosis-inducing agents described above may be utilized alone, or in combination, in the practice of this embodiment. Exemplary fibrosing agents for use in septal occlusion patches include talc, silk, wool, chitosan, polylysine, fibronectin, bleomycin, and CTGF, as well as analogues and derivatives of the aforementioned.

As septal occlusion patches and compositions for use with septal occlusion patches are made in a variety of configurations and sizes, the exact dose administered can vary with patch size, surface area and design. However, certain principles can be applied in the application of this art. Drug dose can be calculated as a function of dose per unit area (of the portion of the patch being coated), total drug dose administered can be measured and appropriate surface concentrations of active drug can be determined. Regardless of the method of application of the drug to the septal occlusion patch, the exemplary fibrosing agents, used alone or in combination, should be administered under the following dosing guidelines:

Utilizing talc as an exemplary fibrosis-inducing agent, whether it is applied using a polymer coating, incorporated into the polymers which make up the septal occlusion patch, or applied without a polymeric carrier, the total dose of talc delivered from a septal occlusion patch, or coated onto the surface of a septal occlusion patch, should not exceed 100 mg (range of 1 μg to 100 mg). In one embodiment, the total amount of talc released from the prosthesis should be in the range of 10 μg to 50 mg. The dose per unit area of the implanted septal occlusion patch (i.e., the dosage of talc as a function of the surface area of the portion of the septal occlusion patch to which drug is applied and/or incorporated) should fall within the range of 0.05 μg–10 μg per $mm^2$ of surface area coated. In another embodiment, talc should be applied to a septal occlusion patch surface at a dose of 0.05 $μg/mm^2$–10 $μg/mm^2$ of surface area coated. In one embodiment, talc is released from the surface of a septal occlusion patch such that fibrosis in the tissue is promoted for a period ranging from several hours to several months. For example, talc may be released in effective concentrations for a period ranging from 1 week to 9 months. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymer coating, incorporated into the polymers which make up the septal occlusion patch, or applied without a polymeric carrier, the total dose of silk delivered from a septal occlusion patch, or coated onto the surface of a septal occlusion patch, should not exceed 100 mg (range of 1 μg to 100 mg). In one embodiment, the total amount of silk released from the septal occlusion patch should be in the range of 10 μg to 50 mg. The dose per unit area of the implanted septal occlusion patch (i.e., the dosage of silk as a function of the surface area of the portion of the septal occlusion patch to which drug is applied and/or incorporated) should fall within the range of 0.05 μg–10 μg per $mm^2$ of surface area coated. In another embodiment, silk should be applied to a septal occlusion patch surface at a dose of 0.05 $μg/mm^2$–10 $μg/mm^2$ of surface area coated. As specific (polymeric and non-polymeric) drug delivery vehicles and specific septal occlusion patch can release silk at differing rates, the above dosing parameters should be utilized in combination with the release rate of the drug from the septal occlusion patch such that a minimum concentration of 0.01 nM to 1000 μM of silk is delivered to the tissue. In one embodiment, silk is released from the surface of a septal occlusion patch such that fibrosis in the tissue is promoted for a period ranging from several hours to several months. For example, silk may be released in effective concentrations for a period ranging from 1 week–9 months. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymer coating, incorporated into the polymers which make up the septal occlusion patch, or applied without a polymeric carrier, the total dose of chitosan delivered from a septal occlusion patch, or coated onto the surface of a septal occlusion patch, should not exceed 100 mg (range of 1 μg to 100 mg). In one embodiment, the total amount of chitosan released from the septal occlusion patch should be in the range of 10 μg to 50 mg. The dose per unit area of the implanted septal occlusion patch (i.e., the dosage of chitosan as a function of the surface area of the portion of the septal occlusion patch to which drug is applied and/or incorporated) should fall within the range of 0.05 μg–10 μg per $mm^2$ of surface area coated. In another embodiment, chitosan should be applied to a septal occlusion patch surface at a dose of 0.05 $μg/mm^2$–10 $μg/mm^2$ of surface area coated. As specific (polymeric and non-polymeric) drug delivery vehicles and specific septal occlusion patches can release chitosan at differing rates, the above dosing parameters should be utilized in combination with the release rate of the drug from the septal occlusion patch such that a minimum concentration of 0.01 nM to 1000 μM of chitosan is delivered to the tissue. In one embodiment, chitosan is released from the surface of a septal occlusion patch such that fibrosis in the tissue is promoted for a period ranging from several hours to several months. For example, chitosan may be released in effective concentrations for a period ranging from 1 week to 9 months. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as an exemplary fibrosis-inducing agent, whether it is applied using a polymer coating, incorporated into the polymers which make up the septal occlusion patch, or applied without a polymeric carrier, the total dose of polylysine delivered from a septal occlusion patch, or coated onto the surface of a septal occlusion patch, should not exceed 100 mg (range of 1 μg to 100 mg). In one embodiment, the total amount of polylysine released from the septal occlusion patch should be in the range of 10 μg to 50 mg. The dose per unit area of the implanted septal occlusion patch (i.e., the dosage of polylysine as a function of the surface area of the portion of the septal occlusion patch to which drug is applied and/or incorporated) should fall within the range of 0.05 μg–10 μg per $mm^2$ of surface area coated. In another embodiment, polylysine should be applied to a septal occlusion patch surface at a dose of 0.05 $μg/mm^2$–10 $μg/mm^2$ of surface area coated. As specific (polymeric and non-polymeric) drug delivery vehicles and specific septal occlusion patches can release polylysine at differing rates, the above dosing parameters should be utilized in combination with the release rate of the drug from the septal occlusion patch such that a minimum concentration of 0.01 nM to 1000 μM of polylysine is delivered to the tissue. In one embodiment, polylysine is released from the surface of a septal occlusion patch such that fibrosis in the tissue is promoted for a period ranging from several hours to several months. For example, polylysine may be released in effective concentrations for a period ranging from 1 week to 9 months. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymer coating, incorporated into the polymers which make up the septal occlusion patch, or applied without a polymeric carrier, the total dose of fibronectin delivered from a septal occlusion patch, or coated onto the surface of a septal occlusion patch, should not exceed 100 mg (range of 1 µg to 100 mg). In one embodiment, the total amount of fibronectin released from the septal occlusion patch should be in the range of 10 µg to 50 mg. The dose per unit area of the implanted septal occlusion patch (i.e., the dosage of fibronectin as a function of the surface area of the portion of the septal occlusion patch to which drug is applied and/or incorporated) should fall within the range of 0.05 µg–10 µg per $mm^2$ of surface area coated. In another embodiment, fibronectin should be applied to a septal occlusion patch surface at a dose of 0.05 $µg/mm^2$–10 $µg/mm^2$ of surface area coated. As specific (polymeric and non-polymeric) drug delivery vehicles and specific septal occlusion patches can release fibronectin at differing rates, the above dosing parameters should be utilized in combination with the release rate of the drug from the septal occlusion patch such that a minimum concentration of 0.01 nM to 1000 µM of fibronectin is delivered to the tissue. In one embodiment, fibronectin is released from the surface of a septal occlusion patch such that fibrosis in the tissue is promoted for a period ranging from several hours to several months. For example, fibronectin may be released in effective concentrations for a period ranging from 1 week to 9 months. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, whether it is applied using a polymer coating, incorporated into the polymers which make up the septal occlusion patch, or applied without a polymeric carrier, the total dose of bleomycin delivered from a septal occlusion patch, or coated onto the surface of a septal occlusion patch, should not exceed 100 mg (range of 0.01 µg to 100 mg). In one embodiment, the total amount of bleomycin released from the septal occlusion patch should be in the range of 0.10 µg to 50 mg. The dose per unit area of the implanted septal occlusion patch (i.e., the dosage of bleomycin as a function of the surface area of the portion of the patch to which drug is applied and/or incorporated) should fall within the range of 0.005 µg–10 µg per $mm^2$ of surface area coated. In another embodiment, bleomycin should be applied to a septal occlusion patch surface at a dose of 0.005 $µg/mm^2$–10 $µg/mm^2$ of surface area coated. As specific (polymeric and non-polymeric) drug delivery vehicles and specific septal occlusion patches can release bleomycin at differing rates, the above dosing parameters should be utilized in combination with the release rate of the drug from the septal occlusion patch such that a minimum concentration of 0.001 nM to 1000 µM of bleomycin is delivered to the tissue. In one embodiment, bleomycin is released from the surface of a septal occlusion patch such that fibrosis in the tissue is promoted for a period ranging from several hours to several months. For example, bleomycin may be released in effective concentrations for a period ranging from 1 week to 9 months. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as an exemplary fibrosis-inducing agent, whether it is applied using a polymer coating, incorporated into the polymers which make up the septal occlusion patch, or applied without a polymeric carrier, the total dose of CTGF delivered from a septal occlusion patch, or coated onto the surface of a septal occlusion patch, should not exceed 100 mg (range of 0.01 µg to 100 mg). In one embodiment, the total amount of CTGF released from the septal occlusion patch should be in the range of 0.10 µg to 50 mg. The dose per unit area of the implanted septal occlusion patch (i.e., the dosage of CTGF as a function of the surface area of the portion of the septal occlusion patch to which drug is applied and/or incorporated) should fall within the range of 0.005 µg–10 µg per $mm^2$ of surface area coated. In another embodiment, CTGF should be applied to a septal occlusion patch surface at a dose of 0.005 $µg/mm^2$–10 $µg/mm^2$ of surface area coated. As specific (polymeric and non-polymeric) drug delivery vehicles and specific septal occlusion patches can release CTGF at differing rates, the above dosing parameters should be utilized in combination with the release rate of the drug from the septal occlusion patch such that a minimum concentration of 0.001 nM to 1000 µM of CTGF is delivered to the tissue. In one embodiment, CTGF is released from the surface of a septal occlusion patch such that fibrosis in the tissue is promoted for a period ranging from several hours to several months. For example, CTGF may be released in effective concentrations for a period ranging from 1 week to 9 months. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Optionally, the device or composition may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or an analogue or derivative thereof. Inflammatory cytokines are to be used in formulations at concentrations that range from 0.0001 µg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 µg to 100 mg); preferred 0.001 µg to 50 mg. When used as a device coating, the dose is per unit area of 0.0001 µg–500 µg per mm$^2$; with a preferred dose of 0.001 µg/mm$^2$–200 µg/mm$^2$. Minimum concentration of $10^{-10}$–$10^{-4}$ g/ml of inflammatory cytokine is to be maintained on the device surface.

Furthermore, the device or composition may alone or additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof. Doses used are those concentrations which are demonstrated to stimulate cell proliferation (see, e.g., Example 16). The proliferative agents are to be used in formulations at concentrations that range from 0.0000001 to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 µg to 200 mg); preferred 0.001 µg to 100 mg. When used as a device coating, the dose is per unit area of 0.00001 µg–500 µg per mm$^2$; with a preferred dose of 0.0001 µg/mm$^2$–200 µg/mm$^2$. Minimum concentration of $10^{-11}$–$10^{-6}$ M of proliferative agent is to be maintained on the device surface.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

17. Endoluminal Fasteners

The present invention provides for the combination of a fibrosis-inducing agent and an endoluminal fastener. Endoluminal fasteners may include, but are not limited to, staples (e.g., endostaples), sutures, wires, filaments, cords, pins, clips and other connector devices and materials.

Endoluminal fasteners are devices that act like ribets to increase the integrity of a damaged or perforated bodily tube or to secure an endoluminal graft to the wall of a bodily tube (e.g., blood vessel). Endoluminal fasteners may also be used in a variety of endoluminal surgeries, such as, but not limited to, transmural polypectomies, resections of submucosal lesions, bowel resections, resections of processes such as ulcers, controlling of bleeding, closing perforations, prophylactic or therapeutical appendectomies, resection of bleeding diverticuli or Meckel's diverticulum, anchoring tubes or grafts (e.g., anastomosis of a vascular artery to a graft), securing time-released medications, performing gastroplasty, fallopian tubal ligation, solid organ biopsies, bowel structuring or partial lung resectioning.

Endoluminal fasteners may be used by loading them into a delivery catheter and then introducing them percutaneously into a bodily lumen. The catheter is then guided through the bodily tube to the site to be repaired. The fastener is delivered from the tip of the delivery catheter so that it penetrates the desired site whereby the endoluminal fastener becomes secured to the wall of the bodily tube. The addition of a fibrosis-inducing agent to the endoluminal fastener may encourage the development and ingrowth of strong, fibrous tissue in and around the device. Incorporation of a fibrosing agent into or onto an endoluminal fastener can promote tissue growth that can help anchor the device to the wall of the lumen. Once the endoluminal fastener has been positioned across the wall, part of it remains in the lumen, exposed to the constituents of the bodily tube. For example, if the bodily tube was a blood vessel, the endoluminal fastener would be exposed to blood flow which can cause a thrombotic event. Thus, in another aspect of the invention, the endoluminal fastener may further comprise an antithrombotic agent to prevent thrombus formation.

Endoluminal fasteners may be composed of biocompatible metals, including, but not limited to, nitinol, tantalum, stainless steel or metallic alloys such as nickel, gold, silver, titanium nitride and chromium. Metallic fasteners have advantages when using them in a minimally invasive manner as the metal enables visualization during endoscopic delivery via catheter. However, endoluminal fasteners may also be composed of biocompatible polymers and other synthetic or natural materials either alone or in combination with metallic materials. These may include magnesium-based materials, plastics, ceramics, resin, protein-based materials, collagen and other similar materials. Non-metallic fasteners may be preferred in certain procedures, for example, if there is a need for a bioabsorbable fastener or to reduce the scattering of x-rays which occurs with metallic fasteners. Endoluminal fasteners may be made out of rigid, pliable, elastic, nonelastic, malleable, nonmalleable, retractable, or nonretractable material such that the fastener exerts the desired amount of pulling force required to attach to the luminal wall.

The endoluminal fasteners may be generally configured in a "T", "H" or "U" shape. Metallic endoluminal fasteners are often secured in place by crimping the fastener structure since they possess strength and ductility. Endoluminal fasteners made of polymers and/or other materials often do not possess the same physical characteristics of the metallic fasteners. Therefore, fasteners made of polymers, for example, are often made of two-parts, including a general U-shape fastener portion which engages and interlocks its legs with a retainer portion.

In one aspect, the endoluminal fastener may be of a variety of configurations and materials. For example, the endoluminal fastener may be a single-tipped device having a curved configuration with a sharpened end. See e.g., U.S. Pat. No. 6,491,707. The endoluminal fastener may have a stressed elongated shape and a second unstressed shape with a plurality of coils around a spring axis upon release from the delivery element. See e.g., U.S. Pat. No. 6,113,611. The endoluminal fastener may be a suturing staple for passing through and securing tissue together whereby the staple is positioned between lips of an endoluminal apparatus that aids in positioning, resecting and securing remaining tissue. See e.g., U.S. Pat. Nos. 6,264,086 and 5,868,760. The endoluminal fastener may be adapted to incorporate a radiation source such that it provides radiation to a wound repair site. See e.g., U.S. Pat. No. 5,906,573. The endoluminal fastener may be composed of a fastener and a retainer member made of resinous material which is absorbable and exhibits improved hemostasis. See e.g., U.S. Pat. No. 4,667, 674. The endoluminal fastener may be composed of a shape-memory surgical staple which may be formed as an open shape or closed shape based on a transition temperature, whereby the heating of the staple by an electric current elevates the temperature of the staple which causes it to close and thus, join abutting tissue. See e.g., U.S. Pat. No. 4,485,816. The endoluminal fastener may be a helical fastener having a penetrating end and a limiting end. See e.g., U.S. Pat. No. 6,592,593. The endoluminal fastener may be a pinned retainer surgical fastener that may be composed of a needle and a retainer that may be used to attach a graft to a vascular artery. See e.g., U.S. Pat. No. 6,074,401. The endoluminal fastener may be of a general U-shape having parallel prongs and a retainer portion with apertures to retain the tips of respective prongs. See e.g., U.S. Pat. No. 5,292,334.

Commercially available endoluminal fasteners may also be combined with one or more fibrosis-inducing drugs according to the present invention. Examples of commercially available endoluminal fasteners are often sold with an associated stapling device or endoscopic instrumentation. For example, Johnson & Johnson Gateway (Piscataway, N.J.) sells their PROXIMATE ILS and ENDOPATH STEALTH Intraluminal Staplers which are used for anastomotic repair. Angiolink Corporation (Taunton, Mass.) sells their EVS Vascular Closure System. U.S. Surgical (Norwalk, Conn.) also sells surgical stapling and endoscopic instrumentation.

In one aspect, the present invention provides an endoluminal fastener that includes a fibrosis-inducing agent to promote scarring between the endoluminal fastener and the blood vessel wall. The endoluminal fastener may be coated with the fibrosing agent (with or without a carrier). For example, a fibrosis-inducing drug may be applied to the surface of the endoluminal fastener. Alternatively, or in addition, the endoluminal fastener may be composed either entirely or partially of a material that is capable of inducing fibrosis. For example, silk strands or silk can be affixed to the endoluminal fastener or the endoluminal fastener can be composed partially or entirely of a fibrosing material (e.g., a fibrosing polymer).

In another aspect, the present invention provides a sprayable composition that includes a fibrosis-inducing agent that can be used in fastening procedures to promote scarring and attachment of an endoluminal fastener to a vessel wall.

Numerous polymeric and non-polymeric carrier systems described above may be used in the practice of this embodiment. These compositions can further comprise one or more fibrosis-inducing agents to promote the formation of fibrous scar tissue. Methods for incorporating fibrosing compositions onto or into endoluminal fasteners include: (a) directly affixing to the implant a fibrosing composition (e.g., by either a spraying process or dipping process as described above, with or without a carrier); (b) directly incorporating into the device a fibrosing composition (e.g., by either a spraying process or dipping process as described above, with or without a carrier); (c) by coating the device with a substance such as a hydrogel which can in turn absorb the fibrosing composition; (d) by interweaving fibrosing composition coated thread (or the polymer itself formed into a thread) into the device structure; (e) by binding a film or mesh which is comprised of, or coated with, a fibrosing composition to the endoluminal fastener; (f) constructing the device itself or a portion of the device with a fibrosing composition; and/or (g) by covalently binding the fibrosing agent directly to the endoluminal fastener surface or to a linker (small molecule or polymer) that is coated or attached to the endoluminal fastener surface.

In addition to coating the device with a fibrosis-inducing composition, the fibrosing agent can be mixed with the materials that are used to make the device such that the fibrosing agent is incorporated into the final device.

In addition to (or as an alternative to) applying the fibrosis agent to the endoluminal fastener, an in situ forming composition, gel or thermogel composition containing a fibrosis-inducing agent can be applied to (as a gel, solid implant, liquid or spray) the placement site of the endoluminal fastener, either: (a) prior to placement of the fastener; (b) after placement of the fastener; (c) during the placement of the fastener; or (d) any combination of these. For the in situ forming thermogel and gel compositions, the fibrosis-inducing agent(s) (e.g., silk powder, bleomycin) can be incorporated directly into the formulation to produce a suspension or a solution or it can be incorporated into a secondary carrier (e.g., micelles, liposomes, microspheres, microparticles, nanospheres, microparticulates, emulsions and/or microemulsions) that is then incorporated into the in situ forming compositions. In another embodiment, the fibrosis-inducing agent can be electrostatically or covalently bound to one or more of the polymeric components of the in-situ forming composition.

In a particularly preferred embodiment, the composition may be prepared from a 4-armed thiol PEG (10K), a 4-armed NHS PEG(10K) and methylated collagen such as described above and contains a fibrosis-inducing agent that is sprayed onto the surgical site to affix the endoluminal fastener in place and induce fibrosis between the fastener and the vessel wall.

In another embodiment, the fibrosis-inducing agent can be incorporated into a biodegradable or dissolvable film or mesh that is then applied to the treatment site prior to, or post, implantation of the endoluminal fastener. Exemplary materials for the manufacture of these films or meshes are hyaluronic acid (crosslinked or non-crosslinked), cellulose derivatives (e.g., hydroxypropyl cellulose), collagen and crosslinked poly(ethylene glycol).

It should be apparent to one of skill in the art that potentially any adhesion or fibrosis-inducing agents described above may be utilized alone, or in combination, in the practice of this embodiment. Exemplary fibrosing agents for use with endoluminal fasteners include talc, silk, wool, chitosan, polylysine, fibronectin, bleomycin, and CTGF, as well as analogues and derivatives of the aforementioned.

As endoluminal fasteners and compositions for use with endoluminal fasteners are made in a variety of configurations and sizes, the exact dose administered can vary with staple size, surface area and design. However, certain principles can be applied in the application of this art. Drug dose can be calculated as a function of dose per unit area (of the portion of the patch being coated), total drug dose administered can be measured and appropriate surface concentrations of active drug can be determined. Regardless of the method of application of the drug to the endoluminal fastener, the exemplary fibrosing agents, used alone or in combination, should be administered under the following dosing guidelines:

Utilizing talc as an exemplary fibrosis-inducing agent, whether it is applied using a polymer coating, incorporated into the polymers which make up the endostaples, or applied without a polymeric carrier, the total dose of talc delivered from an endostaple, or coated onto the surface of an endostaple, should not exceed 100 mg (range of 1 µg to 100 mg). In one embodiment, the total amount of talc released from the prosthesis should be in the range of 10 µg to 50 mg. The dose per unit area of the implanted endostaple (i.e., the dosage of talc as a function of the surface area of the portion of the endostaple to which drug is applied and/or incorporated) should fall within the range of 0.05 µg–10 µg per mm² of surface area coated. In another embodiment, talc should be applied to an endostaple surface at a dose of 0.05 µg/mm²–10 µg/mm² of surface area coated. In one embodiment, talc is released from the surface of an endostaple such that fibrosis in the tissue is promoted for a period ranging from several hours to several months. For example, talc may be released in effective concentrations for a period ranging from 1 week to 9 months. It should be readily evident given the discussions provided herein that analogues and derivatives of talc (as described previously) with similar functional activity can be utilized for the purposes of this invention; the above dosing parameters are then adjusted according to the relative potency of the analogue or derivative as compared to the parent compound (e.g., a compound twice as potent as talc is administered at half the above parameters, a compound half as potent as talc is administered at twice the above parameters, etc.).

Utilizing silk as an exemplary fibrosis-inducing agent, whether it is applied using a polymer coating, incorporated into the polymers which make up the endostaple, or applied without a polymeric carrier, the total dose of silk delivered from an endostaple, or coated onto the surface of an endostaple, should not exceed 100 mg (range of 1 µg to 100 mg). In one embodiment, the total amount of silk released from the endostaple should be in the range of 10 µg to 50 mg. The dose per unit area of the implanted endostaple (i.e., the dosage of silk as a function of the surface area of the portion of the endostaple to which drug is applied and/or incorporated) should fall within the range of 0.05 µg–10 µg per mm² of surface area coated. In another embodiment, silk should be applied to an endostaple surface at a dose of 0.05 µg/mm²–10 µg/mm² of surface area coated. As specific (polymeric and non-polymeric) drug delivery vehicles and specific endostaple can release silk at differing rates, the above dosing parameters should be utilized in combination with the release rate of the drug from the endostaple such that a minimum concentration of 0.01 nM to 1000 µM of silk is delivered to the tissue. In one embodiment, silk is released from the surface of an endostaple such that fibrosis in the tissue is promoted for a period ranging from several hours to several months. For example, silk may be released in effective concentrations for a period ranging from 1 week–9 months. It should be readily evident given the discussions provided herein that analogues and derivatives of silk (as described previously) with similar functional activity can be utilized for the purposes of this invention; the above dosing parameters are then adjusted according to the relative potency of the analogue or derivative as compared to the parent compound (e.g., a compound twice as potent as silk is administered at half the above parameters, a compound half as potent as silk is administered at twice the above parameters, etc.).

Utilizing chitosan as an exemplary fibrosis-inducing agent, whether it is applied using a polymer coating, incorporated into the polymers which make up the endostaple, or applied without a polymeric carrier, the total dose of chitosan delivered from an endostaple, or coated onto the surface of an endostaple, should not exceed 100 mg (range of 1 µg to 100 mg). In one embodiment, the total amount of chitosan released from the endostaple should be in the range of 10 µg to 50 mg. The dose per unit area of the implanted endostaple (i.e., the dosage of chitosan as a function of the surface area of the portion of the endostaple to which drug is applied and/or incorporated) should fall within the range of 0.05 µg–10 µg per mm² of surface area coated. In another embodiment, chitosan should be applied to an endostaple surface at a dose of 0.05 µg/mm²–10 µg/mm² of surface area coated. As specific (polymeric and non-polymeric) drug delivery vehicles and specific endostaples can release chitosan at differing rates, the above dosing parameters should be utilized in combination with the release rate of the drug from the endostaple such that a minimum concentration of 0.01 nM to 1000 µM of chitosan is delivered to the tissue. In one embodiment, chitosan is released from the surface of an endostaple such that fibrosis in the tissue is promoted for a period ranging from several hours to several months. For example, chitosan may be released in effective concentrations for a period ranging from 1 week to 9 months. It should be readily evident given the discussions provided herein that analogues and derivatives of chitosan (as described previously) with similar functional activity can be utilized for the purposes of this invention; the above dosing parameters are then adjusted according to the relative potency of the analogue or derivative as compared to the parent compound (e.g., a compound twice as potent as chitosan is administered at half the above parameters, a compound half as potent as chitosan is administered at twice the above parameters, etc.).

Utilizing polylysine as an exemplary fibrosis-inducing agent, whether it is applied using a polymer coating, incorporated into the polymers which make up the endostaple, or applied without a polymeric carrier, the total dose of polylysine delivered from an endostaple, or coated onto the surface of an endostaple, should not exceed 100 mg (range of 1 µg to 100 mg). In one embodiment, the total amount of polylysine released from the endostaple should be in the range of 10 µg to 50 mg. The dose per unit area of the implanted endostaple (i.e., the dosage of polylysine as a function of the surface area of the portion of the endostaple to which drug is applied and/or incorporated) should fall within the range of 0.05 µg–10 µg per mm² of surface area coated. In another embodiment, polylysine should be applied to an endostaple surface at a dose of 0.05 µg/mm²–10 µg/mm² of surface area coated. As specific (polymeric and non-polymeric) drug delivery vehicles and specific endostaples can release polylysine at differing rates, the above dosing parameters should be utilized in combination with the release rate of the drug from the endostaple such that a minimum concentration of 0.01 nM to 1000 µM of polylysine is delivered to the tissue. In one embodiment, polylysine is released from the surface of an endostaple such that fibrosis in the tissue is promoted for a period ranging from several hours to several months. For example, polylysine may be released in effective concentrations for a period ranging from 1 week to 9 months. It should be readily evident given the discussions provided herein that analogues and derivatives of polylysine (as described previously) with similar functional activity can be utilized for the purposes of this invention; the above dosing parameters are then adjusted according to the relative potency of the analogue or derivative as compared to the parent compound (e.g., a compound twice as potent as polylysine is administered at half the above parameters, a compound half as potent as polylysine is administered at twice the above parameters, etc.).

Utilizing fibronectin as an exemplary fibrosis-inducing agent, whether it is applied using a polymer coating, incorporated into the polymers which make up the endostaple, or applied without a polymeric carrier, the total dose of fibronectin delivered from an endostaple, or coated onto the surface of an endostaple, should not exceed 100 mg (range of 1 µg to 100 mg). In one embodiment, the total amount of fibronectin released from the endostaple should be in the range of 10 µg to 50 mg. The dose per unit area of the implanted endostaple (i.e., the dosage of fibronectin as a function of the surface area of the portion of the endostaple to which drug is applied and/or incorporated) should fall within the range of 0.05 μg–10 μg per mm² of surface area coated. In another embodiment, fibronectin should be applied to an endostaple surface at a dose of 0.05 μg/mm²–10 μg/mm² of surface area coated. As specific (polymeric and non-polymeric) drug delivery vehicles and specific endostaples can release fibronectin at differing rates, the above dosing parameters should be utilized in combination with the release rate of the drug from the endostaple such that a minimum concentration of 0.01 nM to 1000 μM of fibronectin is delivered to the tissue. In one embodiment, fibronectin is released from the surface of an endostaple such that fibrosis in the tissue is promoted for a period ranging from several hours to several months. For example, fibronectin may be released in effective concentrations for a period ranging from 1 week to 9 months. It should be readily evident given the discussions provided herein that analogues and derivatives of fibronectin (as described previously) with similar functional activity can be utilized for the purposes of this invention; the above dosing parameters are then adjusted according to the relative potency of the analogue or derivative as compared to the parent compound (e.g., a compound twice as potent as fibronectin is administered at half the above parameters, a compound half as potent as fibronectin is administered at twice the above parameters, etc.).

Utilizing bleomycin as an exemplary fibrosis-inducing agent, whether it is applied using a polymer coating, incorporated into the polymers which make up the endostaple, or applied without a polymeric carrier, the total dose of bleomycin delivered from an endostaple, or coated onto the surface of an endostaple, should not exceed 100 25 mg (range of 0.01 μg to 100 25 mg). In one embodiment, the total amount of bleomycin released from the endostaple should be in the range of 0.10 μg to 50 25 mg. The dose per unit area of the implanted endostaple (i.e., the dosage of bleomycin as a function of the surface area of the portion of the patch to which drug is applied and/or incorporated) should fall within the range of 0.005 μg–10 μg per mm² of surface area coated. In another embodiment, bleomycin should be applied to an endostaple surface at a dose of 0.005 μg/mm²–10 μg/mm² of surface area coated. As specific (polymeric and non-polymeric) drug delivery vehicles and specific endostaples can release bleomycin at differing rates, the above dosing parameters should be utilized in combination with the release rate of the drug from the endostaple such that a minimum concentration of 0.001 nM to 1000 μM of bleomycin is delivered to the tissue. In one embodiment, bleomycin is released from the surface of an endostaple such that fibrosis in the tissue is promoted for a period ranging from several hours to several months. For example, bleomycin may be released in effective concentrations for a period ranging from 1 week to 9 months. It should be readily evident given the discussions provided herein that analogues and derivatives of bleomycin (as described previously) with similar functional activity can be utilized for the purposes of this invention; the above dosing parameters are then adjusted according to the relative potency of the analogue or derivative as compared to the parent compound (e.g., a compound twice as potent as bleomycin is administered at half the above parameters, a compound half as potent as bleomycin is administered at twice the above parameters, etc.).

Utilizing CTGF as an exemplary fibrosis-inducing agent, whether it is applied using a polymer coating, incorporated into the polymers which make up the endostaple, or applied without a polymeric carrier, the total dose of CTGF delivered from an endostaple, or coated onto the surface of an endostaple, should not exceed 100 25 mg (range of 0.01 μg to 100 mg). In one embodiment, the total amount of CTGF released from the endostaple should be in the range of 0.10 μg to 50 25 mg. The dose per unit area of the implanted endostaple (i.e., the dosage of CTGF as a function of the surface area of the portion of the endostaple to which drug is applied and/or incorporated) should fall within the range of 0.005 μg–10 μg per mm² of surface area coated. In another embodiment, CTGF should be applied to an endostaple surface at a dose of 0.005 μg/mm²–10 μg/mm² of surface area coated. As specific (polymeric and non-polymeric) drug delivery vehicles and specific endostaples can release CTGF at differing rates, the above dosing parameters should be utilized in combination with the release rate of the drug from the endostaple such that a minimum concentration of 0.001 nM to 1000 μM of CTGF is delivered to the tissue. In one embodiment, CTGF is released from the surface of an endostaple such that fibrosis in the tissue is promoted for a period ranging from several hours to several months. For example, CTGF may be released in effective concentrations for a period ranging from 1 week to 9 months. It should be readily evident given the discussions provided herein that analogues and derivatives of CTGF (as described previously) with similar functional activity can be utilized for the purposes of this invention; the above dosing parameters are then adjusted according to the relative potency of the analogue or derivative as compared to the parent compound (e.g., a compound twice as potent as CTGF is administered at half the above parameters, a compound half as potent as CTGF is administered at twice the above parameters, etc.).

Optionally, the device or composition may alone or additionally comprise an inflammatory cytokine (e.g., TGFβ, PDGF, VEGF, bFGF, TNFα, NGF, GM-CSF, IGF-a, IL-1, IL-1-β, IL-8, IL-6, and growth hormone) or an analogue or derivative thereof. Inflammatory cytokines are to be used in formulations at concentrations that range from 0.0001 μg/ml to approximately 20 mg/ml depending on the specific clinical application, formulation type (e.g., gel, liquid, solid, semi-solid), formulation chemistry, duration of required application, type of medical device interface and formulation volume and or surface area coverage required. Preferably, the inflammatory cytokine is released in effective concentrations for a period ranging from 1–180 days. The total dose for a single application is typically not to exceed 500 mg (range of 0.0001 μg to 100 mg); preferred 0.001 μg to 50 mg. When used as a device coating, the dose is per unit area of 0.0001 μg–500 μg per mm²; with a preferred dose of 0.001 μg/mm²–200 μg/mm². Minimum concentration of $10^{-10}$–$10^{-4}$ g/ml of inflammatory cytokine is to be maintained on the device surface.

Furthermore, the device or composition may alone or additionally comprise an agent that stimulates cellular proliferation. Examples include: dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof. Doses used are those concentrations which are demonstrated to stimulate cell proliferation (see, e.g., Example 16). The proliferative agents are to be used in formulations at concentrations that range from 0.0000001 to 25 mg/ml depending on the specific clinical application, formulation type (e.g., gel, liquid, solid, semi-solid), formulation chemistry, duration of required application, type of medical device interface and formulation volume and or surface area coverage required. Preferably, the proliferative agent is released in effective concentrations for a period ranging from 1–180 days. The total dose for a single application is typically not to exceed 500 mg (range of 0.0001 µg to 200 mg); preferred 0.001 µg to 100 mg. When used as a device coating, the dose is per unit area of 0.00001 µg–500 µg per mm$^2$; with a preferred dose of 0.0001 µg/mm$^2$–200 µg/mm$^2$. Minimum concentration of $10^{-11}$–$10^{-6}$ M of proliferative agent is to be maintained on the device surface.

It should be readily evident to one of skill in the art that any of the previously described fibrosis inducing agents, or derivatives and analogues thereof, can be utilized to create variations of the above compositions without deviating from the spirit and scope of the invention. It should also be apparent that the agent can be utilized in a composition with or without polymer carrier and that altering the carrier does not deviate from the scope of this invention.

For all the previously described embodiments, suitable fibrosis-inducing agents include tissue irritants such tissue as silk, silica, bleomycin, neomycin, talcum powder, metallic beryllium, and copper are particularly suitable for the practice of this invention. Other agents which may be incorporated into or onto the implant or device or released from the implant or device include extracellular matrix components such as fibrous structural proteins (e.g., fibrillar collagens, nonfibrillar collagen and elastins), adhesive glycoproteins (e.g., laminin and fibronectin), proteoglycans (e.g., heparin sulfate, chondroitin sulfate, dermatan sulfate), hyaluronan (e.g., hyaluronic acid), secreted protein acidic and rich in cysteine (SPARC), thrombospondins, tenacin, inhibitors of matrix metalloproteinases (e.g., TIMPs and synthetic TIMPs such as marimistat, batimistat, doxycycline, tetracycline, minocycline, TROCADE, Ro-1130830, CGS 27023A, BMS-275291) and polylysine. Growth factors and inflammatory cytokines involved in angiogenesis, fibroblast migration, fibroblast proliferation, ECM synthesis and tissue remodeling such as epidermal growth factor (EGF) family, transforming growth factor-α (TGF-α), transforming growth factor-β (TGF-9-1, TGF-9-2, TGF-9-3), platelet-derived growth factor (PDGF), fibroblast growth factor (acidic—aFGF; and basic—bFGF), bone morphogenic proteins, activins, vascular endothelial growth factor (VEGF, VEGF-B, VEGF-C, placental growth factor—PlGF), angiopoietins, insulin-like growth factors (IGF), hepatocyte growth factor (HGF), connective tissue growth factor (CTGF), myeloid colony-stimulating factors (CSFs), granulocyte-macrophage colony-stimulating factors (GM-CSF), granulocyte colony-stimulating factor (G-CSF), macrophage colony-stimulating factor (M-CSF), erythropoietin, interleukins (particularly IL-1, IL-8, IL-6), tumor necrosis factor-α (TNF9), nerve growth factor (NGF), interferon-α, interferon-β, and growth hormone (GH) are also suitable for release from specific implants and devices. Other agents which may be coated onto or released by the implant or device include adhesives such as cyanoacrylate or materials made from 4-armed thiol PEG (10K), a 4-armed NHS PEG(10K) and methylated collagen such as described above.

Within related aspects of the present invention, orthopaedic implants (artificial joints, artificial ligaments and tendons, screws, plates, and the like), dental implants, intravascular implants (particularly arterial and venous occlusion, vascular destructive implants), male and female contraceptive or sterilization devices and implants, implantable tissue bulking agents for incontinence (esophageal, urethral, anal), soft palate implants, embolization agents, pulmonary sealants, surgical meshes (e.g., hernia repair meshes, tissue scaffolds), and spinal implants (e.g., artificial discs) are provided comprising an implant or device, wherein the implant or device releases an agent which induces fibrosis in vivo.

In one aspect, methods are provided for manufacturing a medical device or implant that release a fibrosis agent. Within yet other aspects of the present invention, methods are provided for manufacturing a medical device or implant, comprising the step of coating (e.g., spraying, dipping, wrapping, or administering drug through) a medical device or implant. Additionally, the implant or medical device can be constructed so that the device itself is comprised of materials, which induce fibrosis in or around the implant. A wide variety of medical devices and implants may be utilized within the context of the present invention, depending on the site and nature of treatment desired.

Within various embodiments of the invention, the implant or device is further coated with a composition or compound, which delays the onset of activity of the fibrosis-inducing agent for a period of time after implantation. Representative examples of such agents include heparin, PLGA/MePEG, PLA, and polyethylene glycol. Within further embodiments the fibrosis-inducing implant or device is activated before, during, or after deployment (e.g., an inactive agent on the device is first activated to one that induces or accelerates an in vivo fibrotic reaction).

Within various embodiments of the invention, a device or implant is coated one one aspect, portion or surface with a composition which promotes fibrosis, as well as being coated with a composition or compound which prevents scarring on another aspect, potion or surface of the device. Representative examples of agents that inhibit fibrosis and scarring include paclitaxel, sirolimus, everolimus, as well as analogues and derivatives thereof. Other examples are described in co-pending application entitled, "Medical Implants and Anti-Scarring Agents" (U.S. Ser. No. 60/523, 908), filed Nov. 20, 2003 and (U.S. Ser. No. 60/586,861), filed Jul. 9, 2004.

Also provided by the present invention are methods for treating patients undergoing surgical, endoscopic or minimally invasive therapies where a medical device or implant is placed as part of the procedure. As utilized herein, it should be understood that "induces fibrosis" refers to a statistically significant increase in the amount of scar tissue around the device or an improvement in the incorporation of the device/implant into the surrounding tissue and not to a permanent prohibition of any complications or failures of the device/implant.

The present invention also provides the following itemized embodiments.

1. A method comprising introducing into an intervertebral disc space of a patient in need thereof, a therapeutically effective amount of a fibrosing agent or a composition comprising a fibrosing agent, where the fibrosing agent induces a fibrotic response at the intervertebral disc space of the patient, thereby providing the patient with a beneficial result.

2. The method of item 1 wherein beneficial result is the repair of a spinal disc.

3. The method of item 1 wherein the beneficial result is fibrous ankylosis.

4. The method of item 1 wherein the beneficial result is bony ankylosis.

5. The method of item 1 wherein the fibrosing agent promotes regeneration.

6. The method of item 1 wherein the fibrosing agent promotes angiogenesis.

7. The method of item 1 wherein the fibrosing agent promotes fibroblast migration.

8. The method of item 1 wherein the fibrosing agent promotes fibroblast proliferation.

9. The method of item 1 wherein the fibrosing agent promotes deposition of extracellular matrix (ECM).

10. The method of item 1 wherein the fibrosing agent promotes tissue remodeling.

11. The method of item 1 wherein the fibrosing agent is an arterial vessel wall irritant.

12. The method of item 1 wherein the fibrosing agent is or comprises silk.

13. The method of item 1 wherein the fibrosing agent is or comprises silkworm silk.

14. The method of item 1 wherein the fibrosing agent is or comprises spider silk.

15. The method of item 1 wherein the fibrosing agent is or comprises recombinant silk.

16. The method of item 1 wherein the fibrosing agent is or comprises raw silk.

17. The method of item 1 wherein the fibrosing agent is or comprises hydrolyzed silk.

18. The method of item 1 wherein the fibrosing agent is or comprises acid-treated silk.

19. The method of item 1 wherein the fibrosing agent is or comprises acylated silk.

20. The method of item 1 wherein the fibrosing agent is in the form of strands.

21. The method of item 1 wherein the fibrosing agent is in the form of tufts.

22. The method of item 1 wherein the fibrosing agent is in the form of microparticulates.

23. The method of item 1 wherein the fibrosing agent is or comprises mineral particles.

24. The method of item 1 wherein the fibrosing agent is or comprises talc.

25. The method of item 1 wherein the fibrosing agent is or comprises chitosan.

26. The method of item 1 wherein the fibrosing agent is or comprises polylysine.

27. The method of item 1 wherein the fibrosing agent is or comprises fibronectin.

28. The method of item 1 wherein the fibrosing agent is or comprises bleomycin.

29. The method of item 1 wherein the fibrosing agent is or comprises CTGF.

30. The method of item 1 wherein the fibrosing agent is in the form of a thread, or is in contact with a thread.

31. The method of item 30 wherein the thread is biodegradable.

32. The method of item 31 wherein the biodegradable thread comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

33. The method of item 30 wherein the thread is non-biodegradable.

34. The method of item 33 wherein the non-biodegradable thread comprises a material selected from the group consisting of polyester, polyurethane, silicone, polyethylene, polypropylene, polystyrene, polyacrylate, polymethacrylate, and silk.

35. The method of item 30 wherein the thread is coated with a polymer.

36. The method of item 30 wherein the thread is coated with a pharmaceutical agent that induces a fibrotic response in the patient.

37. The method of item 30 wherein the thread is coated with a pharmaceutical agent that induces an osteogenic response in the patient.

38. The method of item 30 wherein the fibrosing agent is in the form of a particulate.

39. The method of item 38 wherein the particulate is a biodegradable particulate.

40. The method of item 39 wherein the biodegradable particulate comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

41. The method of item 38 wherein the particulate is non-biodegradable.

42. The method of item 41 wherein the non-biodegradable particulate comprises a material selected from the group consisting of polyester, polyurethane, silicone, polyethylene, polypropylene, polystyrene, polyacrylate, polymethacrylate, and silk.

43. The method of item 38 wherein the particulate is a particulate form of a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

44. The method of item 38 wherein the particulate is coated with a polymer.

45. The method of item 38 wherein the particulate is coated with a pharmaceutical agent that induces a fibrotic response in the patient.

46. The method of item 38 wherein the particulate is coated with a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

47. The method of item 38 wherein the particulate is coated with a pharmaceutical agent that induces an osteogenic response in the patient.

48. The method of item 1 wherein the composition further comprises an agent that promotes bone growth.

49. The method of item 48 wherein the fibrosing agent that promotes bone growth is a bone morphogenic protein.

50. The method of item 48 wherein the fibrosing agent that promotes bone growth is an osteogenic growth factor.

51. The method of item 50 wherein the osteogenic growth factor is selected from transforming growth factor, platelet-derived growth factor, and fibroblast growth factor.

52. The method of item 1 wherein the composition further comprises a pharmaceutical agent that induces sclerosis (a sclerosant).

53. The method of item 52 wherein the sclerosant is selected from the group consisting of ethanol, dimethyl sulfoxide, sucrose, sodium chloride, dextrose, glycerin, minocycline, tetracycline, doxycycline, polidocanol, sodium tetradecyl sulfate, sodium morrhuate, and sotradecol.

54. The method of item 52 wherein the sclerosant is a surfactant.

55. The method of item 1 wherein the composition further comprises an inflammatory cytokine.

56. The method of item 55 wherein the inflammatory cytokine is selected from the group consisting of TGFβ, PDGF, VEGF, bFGF, TNFα, NGF, GM-CSF, IGF-a, IL-1, IL-1-β, IL-8, IL-6, and growth hormone.

57. The method of item 1 wherein the composition further comprises an agent that stimulates cell proliferation.

58. The method of item 57 wherein the fibrosing agent that stimulates cell proliferation is selected from the group consisting of dexamethasone, isotretinoin (13-cis retinoic acid), 17-β-estradiol, estradiol, 1-a-25 dihydroxyvitamin $D_3$, diethylstibesterol, cyclosporine A, L-NAME, all-trans retinoic acid (ATRA), and analogues and derivatives thereof.

59. The method of item 1 wherein the composition further comprises a bulking agent.

60. The method of item 1 wherein the composition further comprises a sealant.

61. The method of item 1 wherein the composition further comprises a polymeric carrier.

62. The method of item 61 wherein the polymeric carrier provides sustained release for an active component of the composition.

63. The method of item 61 wherein the polymeric carrier is a non-biodegradable material.

64. The method of item 63 wherein the non-biodegradable material is crosslinked.

65. The method of item 64 wherein the crosslinked non-biodegradable material comprises a crosslinked form of polyvinylalcohol, polyvinylpyrrolidone, polyacrylamide, methyl methacrylate or methyl methacrylate-styrene copolymer.

66. The method of item 63 wherein the non-biodegradable material is a hydogel.

67. The method of item 61 wherein the polymeric carrier is a biodegradable material.

68. The method of item 67 wherein the biodegradable material is a crosslinked material prepared from, or incorporating units of, polyethyleneglycol, gelatin, collagen, bone allografts, mesenchymal stem cells, hyaluronic acid, hyaluronic acid derivatives, polysaccharides, carbohydrates, proteins, autologous bone, demineralized bone matrix, cellulose derivatives, chitosan, chitosan derivatives, and polyester-polyalkylene oxide block copolymers.

69. The method of item 61 wherein the polymeric carrier is prepared from a 4-armed thiol PEG, a 4-armed NHS PEG, and methylated collagen.

70. The method of item 1 wherein the composition further comprises a resorbable ceramic.

71. The method of item 70 wherein the resorbable ceramic comprises, or is prepared from, a material selected from the group consisting of □-tricalcium phosphate, hydroxyapatite, $Ca_{10}(PO_4)_6OH$, calcium carbonate, calcium sulfate and calcium phosphate.

72. The method of item 1 wherein the composition further comprises a contrast agent.

73. The method of item 72 wherein the contrast agent responds to x-ray.

74. The method of item 73 wherein the contrast agent is barium, tantalum, technetium, or gadolinium.

75. The method of item 1 wherein the composition further comprises a thread.

76. The method of item 75 wherein the thread is biodegradable.

77. The method of item 76 wherein the biodegradable thread comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

78. The method of item 75 wherein the thread is non-biodegradable.

79. The method of item 78 wherein the non-biodegradable thread comprises a material selected from the group consisting of polyester, polyurethane, silicone, polyethylene, polypropylene, polystyrene, polyacrylate, polymethacrylate, and silk.

80. The method of item 75 wherein the thread is coated with a polymer.

81. The method of item 75 wherein the thread is coated with a pharmaceutical agent that induces a fibrotic response in the patient.

82. The method of item 75 were in wherein the thread is coated with a pharmaceutical agent that induces a osteogenic response in the patient.

83. The method of item 1 wherein the composition is in the form of a gel.

84. The method of item 1 wherein the composition is in the form of a paste.

85. The method of item 1 wherein the composition is in the form of a spray.

86. The method of item 1 wherein the composition is in the form of an aerosol.

87. The method of item 1 wherein the composition is in the form of a suspension.

88. The method of item 1 wherein the composition is in the form of an emulsion or microemulsion.

89. The method of item 1 wherein the composition is in the form of a microsphere.

90. The method of item 1 wherein the composition is in the form of a microparticulate.

91. The method of item 1 wherein the composition is in the form of a solid implant.

92. An injectable composition comprising a fibrosing agent and a bulking agent.

93. The composition of item 92 wherein the fibrosing agent promotes fibrosis and promotes regeneration.

94. The composition of item 92 wherein the fibrosing agent promotes angiogenesis.

95. The composition of item 92 wherein the fibrosing agent promotes fibroblast migration.

96. The composition of item 92 wherein the fibrosing agent promotes fibroblast proliferation.

97. The composition of item 92 wherein the fibrosing agent promotes deposition of extracellular matrix (ECM).

98. The composition of item 92 wherein the fibrosing agent promotes tissue remodeling.

99. The composition of item 92 wherein the fibrosing agent is an arterial vessel wall irritant.

100. The composition of item 92 wherein the fibrosing agent is or comprises silk.

101. The composition of item 92 wherein the fibrosing agent is or comprises silkworm silk.

102. The composition of item 92 wherein the fibrosing agent is or comprises spider silk.

103. The composition of item 92 wherein the fibrosing agent is or comprises recombinant silk.

104. The composition of item 92 wherein the fibrosing agent is or comprises raw silk.

105. The composition of item 92 wherein the fibrosing agent is or comprises hydrolyzed silk.

106. The composition of item 92 wherein the fibrosing agent is or comprises acid-treated silk.

107. The composition of item 92 wherein the fibrosing agent is or comprises acylated silk.

108. The composition of item 92 wherein the fibrosing agent is in the form of strands.

109. The composition of item 92 wherein the fibrosing agent is in the form of tufts.

110. The composition of item 92 wherein the fibrosing agent is in the form of microparticulates.

111. The composition of item 92 wherein the fibrosing agent is or comprises mineral particles.

112. The composition of item 92 wherein the fibrosing agent is or comprises talc.

113. The composition of item 92 wherein the fibrosing agent is or comprises chitosan.

114. The composition of item 92 wherein the fibrosing agent is or comprises polylysine.

115. The composition of item 92 wherein the fibrosing agent is or comprises fibronectin.

116. The composition of item 92 wherein the fibrosing agent is or comprises bleomycin.

117. The composition of item 92 wherein the fibrosing agent is or comprises CTGF.

118. The composition of item 92 wherein the fibrosing agent is in the form of a thread, or is in contact with a thread.

119. The composition of item 118 wherein the thread is biodegradable.

120. The composition of item 119 wherein the biodegradable thread comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

121. The composition of item 118 wherein the thread is non-biodegradable.

122. The composition of item 121 wherein the non-bioderadable thread comprises a material selected from the group consisting of polyester, polyurethane, silicone, polyethylene, polypropylene, polystyrene, polyacrylate, polymethacrylate, and silk.

123. The composition of item 118 wherein the thread is coated with a polymer.

124. The composition of item 118 wherein the thread is coated with a pharmaceutical agent that induces a fibrotic response in the patient.

125. The composition of item 118 wherein the thread is coated with a pharmaceutical agent that induces an osteogenic response in the patient.

126. The composition of item 92 wherein the fibrosing agent is in the form of a particulate.

127. The composition of item 126 wherein the particulate is a biodegradable particulate.

128. The composition of item 127 wherein the biodegradable particulate comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

129. The composition of item 126 wherein the particulate is non-biodegradable.

130. The composition of item 129 wherein the non-biodegradable particulate comprises a material selected from the group consisting of polyester, polyurethane, silicone, polyethylene, polypropylene, polystyrene, polyacrylate, polymethacrylate, and silk.

131. The composition of item 126 wherein the particulate is a particulate form of a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

132. The composition of item 126 wherein the particulate is coated with a polymer.

133. The composition of item 126 wherein the particulate is coated with a pharmaceutical agent that induces a fibrotic response in the patient.

134. The composition of item 126 wherein the particulate is coated with a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

135. The composition of item 126 wherein the particulate is coated with a pharmaceutical agent that induces an osteogenic response in the patient.

136. The composition of item 92 wherein the composition further comprises an agent that promotes bone growth.

137. The composition of item 136 wherein the fibrosing agent that promotes bone growth is a bone morphogenic protein.

138. The composition of item 136 wherein the fibrosing agent that promotes bone growth is an osteogenic growth factor.

139. The composition of item 138 wherein the osteogenic growth factor is selected from transforming growth factor, platelet-derived growth factor, and fibroblast growth factor.

140. A method comprising introducing into a patient in need thereof, a therapeutically effective amount of a fibrosing agent or a composition comprising a fibrosing agent, where the fibrosing agent induces a fibrotic response at a specific site within the patient, thereby providing the patient with treatment of a shoulder capsule injury.

141. The method of item 140 wherein the agent promotes regeneration.

142. The method of item 140 wherein the agent promotes angiogenesis.

143. The method of item 140 wherein the agent promotes fibroblast migration.

144. The method of item 140 wherein the agent promotes fibroblast proliferation.

145. The method of item 140 wherein the agent promotes deposition of extracellular matrix (ECM).

146. The method of item 140 wherein the agent promotes tissue remodeling.

147. The method of item 140 wherein the agent is an arterial vessel wall irritant.

148. The method of item 140 wherein the fibrosing agent is or comprises silk.

149. The method of item 140 wherein the fibrosing agent is in the form of tufts.

150. The method of item 140 wherein the fibrosing agent is or comprises mineral particles.

151. The method of item 140 wherein the fibrosing agent is or comprises chitosan.

152. The method of item 140 wherein the fibrosing agent is or comprises polylysine.

153. The method of item 140 wherein the fibrosing agent is or comprises fibronectin.

154. The method of item 140 wherein the fibrosing agent is or comprises bleomycin.

155. The method of item 140 wherein the fibrosing agent is or comprises CTGF.

156. The method of item 140 wherein the fibrosing agent is in the form of a thread, or is in contact with a thread.

157. The method of item 140 wherein the fibrosing agent is in the form of a particulate.

158. The method of item 140, wherein the composition comprises a polymer.

159. The method of item 140, wherein the composition comprises a polymer, and the polymer is, or comprises, a copolymer.

160. The method of item 140, wherein the composition comprises a polymer, and the polymer is, or comprises, a block copolymer.

161. The method of item 140, wherein the composition comprises a polymer, and the polymer is, or comprises, a random copolymer.

162. The method of item 140, wherein the composition comprises a polymer, and the polymer is, or comprises, a biodegradable polymer.

163. The method of item 140, wherein the composition comprises a polymer, and the polymer is, or comprises, a non-biodegradable polymer.

164. The method of item 140, wherein the composition comprises a polymer, and the polymer is, or comprises, a hydrophilic polymer.

165. The method of item 140, wherein the composition comprises a polymer, and the polymer is, or comprises, a hydrophobic polymer.

166. The method of item 140, wherein the composition comprises a polymer, and the polymer is, or comprises, a polymer having hydrophilic domains.

167. The method of item 140, wherein the composition comprises a polymer, and the polymer is, or comprises, a polymer having hydrophobic domains.

168. The method of item 140, wherein the composition comprises a polymer, and the polymer is, or comprises, a non-conductive polymer.

169. The method of item 140, wherein the composition comprises a polymer, and the polymer is, or comprises, an elastomer.

170. The method of item 140, wherein the composition comprises a polymer, and the polymer is, or comprises, a hydrogel.

171. The method of item 140, wherein the composition comprises a polymer, and the polymer is, or comprises, a silicone polymer.

172. The method of item 140, wherein the composition comprises a polymer, and the polymer is, or comprises, a hydrocarbon polymer.

173. The method of item 140, wherein the composition comprises a polymer, and the polymer is, or comprises, a styrene-derived polymer.

174. The method of item 140, wherein the composition comprises a polymer, and the polymer is, or comprises, a butadiene-derived polymer.

175. The method of item 140, wherein the composition comprises a polymer, and the polymer is, or comprises, a macromer.

176. The method of item 140, wherein the composition comprises a polymer, and the polymer is, or comprises, a poly(ethylene glycol) polymer.

177. The method of item 140, wherein the composition comprises a polymer, and the polymer is, or comprises, an amorphous polymer.

178. The method of item 140, wherein the composition further comprises a second pharmaceutically active agent.

179. The method of item 140, wherein the composition further comprises an anti-inflammatory agent.

180. The method of item 140, wherein the composition further comprises an agent that inhibits infection.

181. The method of item 140, wherein the composition further comprises an anthracycline.

182. The method of item 140, wherein the composition further comprises doxorubicin.

183. The method of item 140 wherein the composition further comprises mitoxantrone.

184. The method of item 140 wherein the composition further comprises a fluoropyrimidine.

185. The method of item 140, wherein the composition further comprises 5-fluorouracil (5-FU).

186. The method of item 140, wherein the composition further comprises a folic acid antagonist.

187. The method of item 140, wherein the composition further comprises methotrexate.

188. The method of item 140, wherein the composition further comprises a podophylotoxin.

189. The method of item 140, wherein the composition further comprises etoposide.

190. The method of item 140, wherein the composition further comprises camptothecin.

191. The method of item 140, wherein the composition further comprises a hydroxyurea.

192. The method of item 140, wherein the composition further comprises a platinum complex.

193. The method of item 140, wherein the composition further comprises cisplatin.

194. The method of item 140 wherein the composition further comprises an anti-thrombotic agent.

195. The method of item 140, wherein the composition further comprises a visualization agent.

196. The method of item 140, wherein the composition further comprises a visualization agent, and the visualization agent is a radiopaque material, wherein the radiopaque material comprises a metal, a halogenated compound, or a barium containing compound.

197. The method of item 140, wherein the composition further comprises a visualization agent, and the visualization agent is, or comprises, barium, tantalum, or technetium.

198. The method of item 140, wherein the composition further comprises a visualization agent, and the visualization agent is, or comprises, an MRI responsive material.

199. The method of item 140, wherein the composition further comprises a visualization agent, and the visualization agent is, or comprises, a gadolinium chelate.

200. The method of item 140, wherein the composition further comprises a visualization agent, and the visualization agent is, or comprises, iron, magnesium, manganese, copper, or chromium.

201. The method of item 140, wherein the composition further comprises a visualization agent, and the visualization agent is, or comprises, iron oxide compound.

202. The method of item 140, wherein the composition further comprises a visualization agent, and the visualization agent is, or comprises, a dye, pigment, or colorant.

203. The method of item 140 wherein the fibrosing agent is released in effective concentrations from the composition comprising the fibrosing agent by diffusion over a period ranging from the time of administration to about 90 days.

204. The method of item 140 wherein the fibrosing agent is released in effective concentrations from the composition comprising the fibrosing agent by erosion of the composition over a period ranging from the time of administration to about 90 days.

205. The method of item 140 wherein the composition further comprises an inflammatory cytokine.

206. The method of item 140, wherein the composition further comprises an agent that stimulates cell proliferation.

207. The method of item 140 wherein the composition further comprises a polymeric carrier.

208. The method of item 140 wherein the composition is in the form of a gel, paste, or spray.

209. The method of item 140 wherein the agent is delivered from a device, and the device delivers the fibrosing agent locally to tissue proximate to the device.

210. The method of item 140 wherein the agent is delivered from a device, wherein the device further comprises a coating, and the coating comprises the fibrosing agent.

211. The method of item 140 wherein the agent is delivered from a device, wherein the device further comprises a coating, and the coating is disposed on a surface of the device.

212. The method of item 140, wherein the agent is delivered from a device, wherein the device further comprises a coating, and the coating directly contacts the device.

213. The method of item 140, wherein the agent is delivered from a device, wherein the device further comprises a coating, and the coating indirectly contacts the device.

214. The method of item 140 wherein the agent is delivered from a device, wherein the device further comprises a coating, wherein the coating partially covers the device.

215. The method of item 140, wherein the agent is delivered from a device, wherein the device further comprises a coating, and the coating completely covers the device.

216. The method of item 140 wherein the agent is delivered from a device, wherein the fibrosing agent is located within pores or holes of the device.

217. The method of item 140 wherein the agent is delivered from a device, wherein the fibrosing agent is located within a channel, lumen, or divet of the device.

218. The method of item 140 wherein the agent is delivered from a device, wherein the device further comprising an echogenic material.

219. The method of item 140 wherein the agent is delivered from a device, wherein the device further comprises an echogenic material, wherein the echogenic material is in the form of a coating.

220. The method of item 140 wherein the agent is delivered from a device, wherein the device is sterile.

221. The method of item 140 wherein the agent is delivered from a device, wherein the fibrosing agent is released into tissue in the vicinity of the device after deployment of the device.

222. The method of item 140 wherein the agent is delivered from a device, wherein the fibrosing agent is released into tissue in the vicinity of the device after deployment of the device, wherein the tissue is connective tissue.

223. The method of item 140 wherein the agent is delivered from a device, wherein the fibrosing agent is released into tissue in the vicinity of the device after deployment of the device, wherein the tissue is muscle tissue.

224. The method of item 140 wherein the agent is delivered from a device, wherein the fibrosing agent is released into tissue in the vicinity of the device after deployment of the device, wherein the tissue is nerve tissue.

225. The method of item 140 wherein the agent is delivered from a device, wherein the fibrosing agent is released into tissue in the vicinity of the device after deployment of the device, wherein the tissue is epithelium tissue.

226. The method of item 140 wherein the agent is delivered from a device, wherein the fibrosing agent is released in effective concentrations from the device over a period ranging from the time of deployment of the device to about 1 year.

227. The method of item 140 wherein the agent is delivered from a device, wherein the fibrosing agent is released in effective concentrations from the device over a period ranging from about 1 month to 6 months.

228. The method of item 140 wherein the agent is delivered from a device, wherein the fibrosing agent is released in effective concentrations from the device over a period ranging from about 1–90 days.

229. The method of item 140 wherein the agent is delivered from a device, wherein the fibrosing agent is released in effective concentrations from the device at a constant rate.

230. The method of item 140 wherein the fibrosing agent is released in effective concentrations from the device at an increasing rate.

231. The method of item 140 wherein the agent is delivered from a device, wherein the fibrosing agent is released in effective concentrations from the device at a decreasing rate.

232. The method of item 140 wherein the agent is delivered from a device, wherein the device comprises about 0.01 µg to about 10 µg of the fibrosing agent.

233. The method of item 140 wherein the agent is delivered from a device, wherein the device comprises about 10 µg to about 10 mg of the fibrosing agent.

234. The method of item 140 wherein the agent is delivered from a device, wherein the device comprises about 10 mg to about 250 mg of the fibrosing agent.

235. The method of item 140 wherein the agent is delivered from a device, wherein the device comprises about 250 mg to about 1000 mg of the fibrosing agent.

236. The method of item 140 wherein the agent is delivered from a device, wherein the device comprises about 1000 mg to about 2500 mg of the fibrosing agent.

237. The method of item 140 wherein the agent is delivered from a device, wherein a surface of the device comprises less than 0.01 µg of the fibrosing agent per mm$^2$ of device surface to which the fibrosing agent is applied.

238. The method of item 140 wherein the agent is delivered from a device, wherein a surface of the device comprises about 0.01 µg to about 1 µg of the fibrosing agent per mm$^2$ of device surface to which the fibrosing agent is applied.

239. The method of item 140 wherein the agent is delivered from a device, wherein a surface of the device comprises about 1 µg to about 10 µg of the fibrosing agent per mm$^2$ of device surface to which the fibrosing agent is applied.

240. The method of item 140 wherein the agent is delivered from a device, wherein a surface of the device comprises about 10 µg to about 250 µg of the fibrosing agent per mm$^2$ of device surface to which the fibrosing agent is applied.

241. The method of item 140 wherein the agent is delivered from a device, wherein a surface of the device comprises about 250 µg to about 1000 µg of the fibrosing agent of fibrosing agent per mm$^2$ of device surface to which the fibrosing agent is applied.

242. The method of item 140 wherein the agent is delivered from a device, wherein a surface of the device comprises about 1000 µg to about 2500 µg of the fibrosing agent per mm$^2$ of device surface to which the fibrosing agent is applied.

243. The method of item 140, wherein the agent is delivered from a device, wherein the device further comprises a coating, and the coating is a uniform coating.

244. The method of item 140, wherein the agent is delivered from a device, wherein the device further comprises a coating, and the coating is a non-uniform coating.

245. The method of item 140, wherein the agent is delivered from a device, wherein the device further comprises a coating, and the coating is a discontinuous coating.

246. The method of item 140, wherein the agent is delivered from a device, wherein the device further comprises a coating, and the coating is a patterned coating.

247. The method of item 140, wherein the agent is delivered from a device, wherein the device further comprises a coating, and the coating has a thickness of 100 µm or less.

248. The method of item 140, wherein the agent is delivered from a device, wherein the device further comprises a coating, and the coating has a thickness of 10 µm or less.

249. The method of item 140, wherein the agent is delivered from a device, wherein the device further comprises a coating, and the coating adheres to the surface of the device upon deployment of the device.

250. The method of item 140, wherein the agent is delivered from a device, wherein the device further comprises a coating, and the coating is stable at room temperature for a period of at least 1 year.

251. The method of item 140, wherein the agent is delivered from a device, wherein the device further comprises a coating, and the fibrosing agent is present in the coating in an amount ranging between about 0.0001% to about 1% by weight.

252. The method of item 140, wherein the agent is delivered from a device, wherein the device further comprises a coating, and the fibrosing agent is present in the coating in an amount ranging between about 1% to about 10% by weight.

253. The method of item 140, wherein the agent is delivered from a device, wherein the device further comprises a coating, and the fibrosing agent is present in the coating in an amount ranging between about 10% to about 25% by weight.

254. The method of item 140, wherein the agent is delivered from a device, wherein the device further comprises a coating, and the fibrosing agent is present in the coating in an amount ranging between about 25% to about 70% by weight.

255. The method of item 140, wherein the agent is delivered from a device, wherein the device further comprises a coating, and the coating comprises a polymer.

256. The method of item 140, wherein the agent is delivered from a device, wherein the device comprises a first coating having a first composition and a second coating having a second composition.

257. The method of item 140, wherein the agent is delivered from a device, wherein the device comprises a first coating having a first composition and a second coating having a second composition, wherein the first composition and the second composition are different.

258. A method comprising introducing into a patient in need thereof, a therapeutically effective amount of a fibrosing agent or a composition comprising a fibrosing agent, where the fibrosing agent induces a fibrotic response at a specific site within the patient, thereby providing the patient with ligament repair.

259. The method of item 258 wherein the agent promotes regeneration.

260. The method of item 258 wherein the agent promotes angiogenesis.

261. The method of item 258 wherein the agent promotes fibroblast migration.

262. The method of item 258 wherein the agent promotes fibroblast proliferation.

263. The method of item 258 wherein the agent promotes deposition of extracellular matrix (ECM).

264. The method of item 258 wherein the agent promotes tissue remodeling.

265. The method of item 258 wherein the agent is an arterial vessel wall irritant.

266. The method of item 258 wherein the fibrosing agent is or comprises silk.

267. The method of item 258 wherein the fibrosing agent is in the form of tufts.

268. The method of item 258 wherein the fibrosing agent is or comprises mineral particles.

269. The method of item 258 wherein the fibrosing agent is or comprises chitosan.

270. The method of item 258 wherein the fibrosing agent is or comprises polylysine.

271. The method of item 258 wherein the fibrosing agent is or comprises fibronectin.

272. The method of item 258 wherein the fibrosing agent is or comprises bleomycin.

273. The method of item 258 wherein the fibrosing agent is or comprises CTGF.

274. The method of item 258 wherein the fibrosing agent is in the form of a thread, or is in contact with a thread.

275. The method of item 258 wherein the fibrosing agent is in the form of a particulate.

276. The method of item 258, wherein the composition comprises a polymer.

277. The method of item 258, wherein the composition comprises a polymer, and the polymer is or comprises, a copolymer.

278. The method of item 258, wherein the composition comprises a polymer, and the polymer is, or comprises, a block copolymer.

279. The method of item 258, wherein the composition comprises a polymer, and the polymer is, or comprises, a random copolymer.

280. The method of item 258, wherein the composition comprises a polymer, and the polymer is, or comprises, a biodegradable polymer.

281. The method of item 258, wherein the composition comprises a polymer, and the polymer is, or comprises, a non-biodegradable polymer.

282. The method of item 258, wherein the composition comprises a polymer, and the polymer is, or comprises, a hydrophilic polymer.

283. The method of item 258, wherein the composition comprises a polymer, and the polymer is, or comprises, a hydrophobic polymer.

284. The method of item 258, wherein the composition comprises a polymer, and the polymer is, or comprises, a polymer having hydrophilic domains.

285. The method of item 258, wherein the composition comprises a polymer, and the polymer is, or comprises, a polymer having hydrophobic domains.

286. The method of item 258, wherein the composition comprises a polymer, and the polymer is, or comprises, a non-conductive polymer.

287. The method of item 258, wherein the composition comprises a polymer, and the polymer is, or comprises, an elastomer.

288. The method of item 258, wherein the composition comprises a polymer, and the polymer is, or comprises, a hydrogel.

289. The method of item 258, wherein the composition comprises a polymer, and the polymer is, or comprises, a silicone polymer.

290. The method of item 258, wherein the composition comprises a polymer, and the polymer is, or comprises, a hydrocarbon polymer.

291. The method of item 258, wherein the composition comprises a polymer, and the polymer is, or comprises, a styrene-derived polymer.

292. The method of item 258, wherein the composition comprises a polymer, and the polymer is, or comprises, a butadiene-derived polymer.

293. The method of item 258, wherein the composition comprises a polymer, and the polymer is, or comprises, a macromer.

294. The method of item 258, wherein the composition comprises a polymer, and the polymer is, or comprises, a poly(ethylene glycol) polymer.

295. The method of item 258, wherein the composition comprises a polymer, and the polymer is, or comprises, an amorphous polymer.

296. The method of item 258, wherein the composition further comprises a second pharmaceutically active agent.

297. The method of item 258, wherein the composition further comprises an anti-inflammatory agent.

298. The method of item 258, wherein the composition further comprises an agent that inhibits infection.

299. The method of item 258, wherein the composition further comprises an anthracycline.

300. The method of item 258, wherein the composition further comprises doxorubicin.

301. The method of item 258 wherein the composition further comprises mitoxantrone.

302. The method of item 258 wherein the composition further comprises a fluoropyrimidine.

303. The method of item 258, wherein the composition further comprises 5-fluorouracil (5-FU).

304. The method of item 258, wherein the composition further comprises a folic acid antagonist.

305. The method of item 258, wherein the composition further comprises methotrexate.

306. The method of item 258, wherein the composition further comprises a podophylotoxin.

307. The method of item 258, wherein the composition further comprises etoposide.

308. The method of item 258, wherein the composition further comprises camptothecin.

309. The method of item 258, wherein the composition further comprises a hydroxyurea.

310. The method of item 258, wherein the composition further comprises a platinum complex.

311. The method of item 258, wherein the composition further comprises cisplatin.

312. The method of item 258 wherein the composition further comprises an anti-thrombotic agent.

313. The method of item 258, wherein the composition further comprises a visualization agent.

314. The method of item 258, wherein the composition further comprises a visualization agent, and the visualization agent is a radiopaque material, wherein the radiopaque material comprises a metal, a halogenated compound, or a barium containing compound.

315. The method of item 258, wherein the composition further comprises a visualization agent, and the visualization agent is, or comprises, barium, tantalum, or technetium.

316. The method of item 258, wherein the composition further comprises a visualization agent, and the visualization agent is, or comprises, an MRI responsive material.

317. The method of item 258, wherein the composition further comprises a visualization agent, and the visualization agent is, or comprises, a gadolinium chelate.

318. The method of item 258, wherein the composition further comprises a visualization agent, and the visualization agent is, or comprises, iron, magnesium, manganese, copper, or chromium.

319. The method of item 258, wherein the composition further comprises a visualization agent, and the visualization agent is, or comprises, iron oxide compound.

320. The method of item 258, wherein the composition further comprises a visualization agent, and the visualization agent is, or comprises, a dye, pigment, or colorant.

321. The method of item 258 wherein the fibrosing agent is released in effective concentrations from the composition comprising the fibrosing agent by diffusion over a period ranging from the time of administration to about 90 days.

322. The method of item 258 wherein the fibrosing agent is released in effective concentrations from the composition comprising the fibrosing agent by erosion of the composition over a period ranging from the time of administration to about 90 days.

323. The method of item 258 wherein the composition further comprises an inflammatory cytokine.

324. The method of item 258 wherein the composition further comprises an agent that stimulates cell proliferation.

325. The method of item 258 wherein the composition further comprises a polymeric carrier.

326. The method of item 258 wherein the composition is in the form of a gel, paste, or spray.

327. The method of item 258 wherein the agent is delivered from a device, and the device delivers the fibrosing agent locally to tissue proximate to the device.

328. The method of item 258 wherein the agent is delivered from a device, wherein the device further comprises a coating, and the coating comprises the fibrosing agent.

329. The method of item 258 wherein the agent is delivered from a device, wherein the device further comprises a coating, and the coating is disposed on a surface of the device.

330. The method of item 258, wherein the agent is delivered from a device, wherein the device further comprises a coating, and the coating directly contacts the device.

331. The method of item 258, wherein the agent is delivered from a device, wherein the device further comprises a coating, and the coating indirectly contacts the device.

332. The method of item 258 wherein the agent is delivered from a device, wherein the device further comprises a coating, wherein the coating partially covers the device.

333. The method of item 258, wherein the agent is delivered from a device, wherein the device further comprises a coating, and the coating completely covers the device.

334. The method of item 258 wherein the agent is delivered from a device, wherein the fibrosing agent is located within pores or holes of the device.

335. The method of item 258 wherein the agent is delivered from a device, wherein the fibrosing agent is located within a channel, lumen, or divet of the device.

336. The method of item 258 wherein the agent is delivered from a device, wherein the device further comprising an echogenic material.

337. The method of item 258 wherein the agent is delivered from a device, wherein the device further comprises an echogenic material, wherein the echogenic material is in the form of a coating.

338. The method of item 258 wherein the agent is delivered from a device, wherein the device is sterile.

339. The method of item 258 wherein the agent is delivered from a device, wherein the fibrosing agent is released into tissue in the vicinity of the device after deployment of the device.

340. The method of item 258 wherein the agent is delivered from a device, wherein the fibrosing agent is released into tissue in the vicinity of the device after deployment of the device, wherein the tissue is connective tissue.

341. The method of item 258 wherein the agent is delivered from a device, wherein the fibrosing agent is released into tissue in the vicinity of the device after deployment of the device, wherein the tissue is muscle tissue.

342. The method of item 258 wherein the agent is delivered from a device, wherein the fibrosing agent is released into tissue in the vicinity of the device after deployment of the device, wherein the tissue is nerve tissue.

343. The method of item 258 wherein the agent is delivered from a device, wherein the fibrosing agent is released into tissue in the vicinity of the device after deployment of the device, wherein the tissue is epithelium tissue.

344. The method of item 258 wherein the agent is delivered from a device, wherein the fibrosing agent is released in effective concentrations from the device over a period ranging from the time of deployment of the device to about 1 year.

345. The method of item 258 wherein the agent is delivered from a device, wherein the fibrosing agent is released in effective concentrations from the device over a period ranging from about 1 month to 6 months.

346. The method of item 258 wherein the agent is delivered from a device, wherein the fibrosing agent is released in effective concentrations from the device over a period ranging from about 1–90 days.

347. The method of item 258 wherein the agent is delivered from a device, wherein the fibrosing agent is released in effective concentrations from the device at a constant rate.

348. The method of item 258 wherein the fibrosing agent is released in effective concentrations from the device at an increasing rate.

349. The method of item 258 wherein the agent is delivered from a device, wherein the fibrosing agent is released in effective concentrations from the device at a decreasing rate.

350. The method of item 258 wherein the agent is delivered from a device, wherein the device comprises about 0.01 µg to about 10 µg of the fibrosing agent.

351. The method of item 258 wherein the agent is delivered from a device, wherein the device comprises about 10 µg to about 10 mg of the fibrosing agent.

352. The method of item 258 wherein the agent is delivered from a device, wherein the device comprises about 10 mg to about 250 mg of the fibrosing agent.

353. The method of item 258 wherein the agent is delivered from a device, wherein the device comprises about 250 mg to about 1000 mg of the fibrosing agent.

354. The method of item 258 wherein the agent is delivered from a device, wherein the device comprises about 1000 mg to about 2500 mg of the fibrosing agent.

355. The method of item 258 wherein the agent is delivered from a device, wherein a surface of the device comprises less than 0.01 µg of the fibrosing agent per $mm^2$ of device surface to which the fibrosing agent is applied.

356. The method of item 258 wherein the agent is delivered from a device, wherein a surface of the device comprises about 0.01 µg to about 1 µg of the fibrosing agent per $mm^2$ of device surface to which the fibrosing agent is applied.

357. The method of item 258 wherein the agent is delivered from a device, wherein a surface of the device comprises about 1 µg to about 10 µg of the fibrosing agent per $mm^2$ of device surface to which the fibrosing agent is applied.

358. The method of item 258 wherein the agent is delivered from a device, wherein a surface of the device comprises about 10 µg to about 250 µg of the fibrosing agent per $mm^2$ of device surface to which the fibrosing agent is applied.

359. The method of item 258 wherein the agent is delivered from a device, wherein a surface of the device comprises about 250 µg to about 1000 µg of the fibrosing agent of fibrosing agent per $mm^2$ of device surface to which the fibrosing agent is applied.

360. The method of item 258 wherein the agent is delivered from a device, wherein a surface of the device comprises about 1000 µg to about 2500 µg of the fibrosing agent per $mm^2$ of device surface to which the fibrosing agent is applied.

361. The method of item 258, wherein the agent is delivered from a device, wherein the device further comprises a coating, and the coating is a uniform coating.

362. The method of item 258, wherein the agent is delivered from a device, wherein the device further comprises a coating, and the coating is a non-uniform coating.

363. The method of item 258, wherein the agent is delivered from a device, wherein the device further comprises a coating, and the coating is a discontinuous coating.

364. The method of item 258, wherein the agent is delivered from a device, wherein the device further comprises a coating, and the coating is a patterned coating.

365. The method of item 258, wherein the agent is delivered from a device, wherein the device further comprises a coating, and the coating has a thickness of 100 µm or less.

366. The method of item 258, wherein the agent is delivered from a device, wherein the device further comprises a coating, and the coating has a thickness of 10 µm or less.

367. The method of item 258, wherein the agent is delivered from a device, wherein the device further comprises a coating, and the coating adheres to the surface of the device upon deployment of the device.

368. The method of item 258, wherein the agent is delivered from a device, wherein the device further comprises a coating, and the coating is stable at room temperature for a period of at least 1 year.

369. The method of item 258, wherein the agent is delivered from a device, wherein the device further comprises a coating, and the fibrosing agent is present in the coating in an amount ranging between about 0.0001% to about 1% by weight.

370. The method of item 258, wherein the agent is delivered from a device, wherein the device further comprises a coating, and the fibrosing agent is present in the coating in an amount ranging between about 1% to about 10% by weight.

371. The method of item 258, wherein the agent is delivered from a device, wherein the device further comprises a coating, and the fibrosing agent is present in the coating in an amount ranging between about 10% to about 25% by weight.

372. The method of item 258, wherein the agent is delivered from a device, wherein the device further comprises a coating, and the fibrosing agent is present in the coating in an amount ranging between about 25% to about 70% by weight.

373. The method of item 258, wherein the agent is delivered from a device, wherein the device further comprises a coating, and the coating comprises a polymer.

374. The method of item 258, wherein the agent is delivered from a device, wherein the device comprises a first coating having a first composition and a second coating having a second composition.

375. The method of item 258, wherein the agent is delivered from a device, wherein the device comprises a first coating having a first composition and a second coating having a second composition, wherein the first composition and the second composition are different.

376. A method comprising introducing into a patient in need thereof, a therapeutically effective amount of a fibrosing agent or a composition comprising a fibrosing agent, where the fibrosing agent induces a fibrotic response at a specific site within the patient, thereby providing the patient with tendon repair.

377. The method of item 376 wherein the agent promotes regeneration.

378. The method of item 376 wherein the agent promotes angiogenesis.

379. The method of item 376 wherein the agent promotes fibroblast migration.

380. The method of item 376 wherein the agent promotes fibroblast proliferation.

381. The method of item 376 wherein the agent promotes deposition of extracellular matrix (ECM).

382. The method of item 376 wherein the agent promotes tissue remodeling.

383. The method of item 376 wherein the agent is an arterial vessel wall irritant.

384. The method of item 376 wherein the fibrosing agent is or comprises silk.

385. The method of item 376 wherein the fibrosing agent is in the form of tufts.

386. The method of item 376 wherein the fibrosing agent is or comprises mineral particles.

387. The method of item 376 wherein the fibrosing agent is or comprises chitosan.

388. The method of item 376 wherein the fibrosing agent is or comprises polylysine.

389. The method of item 376 wherein the fibrosing agent is or comprises fibronectin.

390. The method of item 376 wherein the fibrosing agent is or comprises bleomycin.

391. The method of item 376 wherein the fibrosing agent is or comprises CTGF.

392. The method of item 376 wherein the fibrosing agent is in the form of a thread, or is in contact with a thread.

393. The method of item 376 wherein the fibrosing agent is in the form of a particulate.

394. The method of item 376, wherein the composition comprises a polymer.

395. The method of item 376, wherein the composition comprises a polymer, and the polymer is, or comprises, a copolymer.

396. The method of item 376, wherein the composition comprises a polymer, and the polymer is, or comprises, a block copolymer.

397. The method of item 376, wherein the composition comprises a polymer, and the polymer is, or comprises, a random copolymer.

398. The method of item 376, wherein the composition comprises a polymer, and the polymer is, or comprises, a biodegradable polymer.

399. The method of item 376, wherein the composition comprises a polymer, and the polymer is, or comprises, a non-biodegradable polymer.

400. The method of item 376, wherein the composition comprises a polymer, and the polymer is, or comprises, a hydrophilic polymer.

401. The method of item 376, wherein the composition comprises a polymer, and the polymer is, or comprises, a hydrophobic polymer.

402. The method of item 376, wherein the composition comprises a polymer, and the polymer is, or comprises, a polymer having hydrophilic domains.

403. The method of item 376, wherein the composition comprises a polymer, and the polymer is, or comprises, a polymer having hydrophobic domains.

404. The method of item 376, wherein the composition comprises a polymer, and the polymer is, or comprises, a non-conductive polymer.

405. The method of item 376, wherein the composition comprises a polymer, and the polymer is, or comprises, an elastomer.

406. The method of item 376, wherein the composition comprises a polymer, and the polymer is, or comprises, a hydrogel.

407. The method of item 376, wherein the composition comprises a polymer, and the polymer is, or comprises, a silicone polymer.

408. The method of item 376, wherein the composition comprises a polymer, and the polymer is, or comprises, a hydrocarbon polymer.

409. The method of item 376, wherein the composition comprises a polymer, and the polymer is, or comprises, a styrene-derived polymer.

410. The method of item 376, wherein the composition comprises a polymer, and the polymer is, or comprises, a butadiene-derived polymer.

411. The method of item 376, wherein the composition comprises a polymer, and the polymer is, or comprises, a macromer.

412. The method of item 376, wherein the composition comprises a polymer, and the polymer is, or comprises, a poly(ethylene glycol) polymer.

413. The method of item 376, wherein the composition comprises a polymer, and the polymer is, or comprises, an amorphous polymer.

414. The method of item 376, wherein the composition further comprises a second pharmaceutically active agent.

415. The method of item 376, wherein the composition further comprises an anti-inflammatory agent.

416. The method of item 376, wherein the composition further comprises an agent that inhibits infection.

417. The method of item 376, wherein the composition further comprises an anthracycline.

418. The method of item 376, wherein the composition further comprises doxorubicin.

419. The method of item 376 wherein the composition further comprises mitoxantrone.

420. The method of item 376 wherein the composition further comprises a fluoropyrimidine.

421. The method of item 376, wherein the composition further comprises 5-fluorouracil (5-FU).

422. The method of item 376, wherein the composition further comprises a folic acid antagonist.

423. The method of item 376, wherein the composition further comprises methotrexate.

424. The method of item 376, wherein the composition further comprises a podophylotoxin.

425. The method of item 376, wherein the composition further comprises etoposide.

426. The method of item 376, wherein the composition further comprises camptothecin.

427. The method of item 376, wherein the composition further comprises a hydroxyurea.

428. The method of item 376, wherein the composition further comprises a platinum complex.

429. The method of item 376, wherein the composition further comprises cisplatin.

430. The method of item 376 wherein the composition further comprises an anti-thrombotic agent.

431. The method of item 376, wherein the composition further comprises a visualization agent.

432. The method of item 376, wherein the composition further comprises a visualization agent, and the visualization agent is a radiopaque material, wherein the radiopaque material comprises a metal, a halogenated compound, or a barium containing compound.

433. The method of item 376, wherein the composition further comprises a visualization agent, and the visualization agent is, or comprises, barium, tantalum, or technetium.

434. The method of item 376, wherein the composition further comprises a visualization agent, and the visualization agent is, or comprises, an MRI responsive material.

435. The method of item 376, wherein the composition further comprises a visualization agent, and the visualization agent is, or comprises, a gadolinium chelate.

436. The method of item 376, wherein the composition further comprises a visualization agent, and the visualization agent is, or comprises, iron, magnesium, manganese, copper, or chromium.

437. The method of item 376, wherein the composition further comprises a visualization agent, and the visualization agent is, or comprises, iron oxide compound.

438. The method of item 376, wherein the composition further comprises a visualization agent, and the visualization agent is, or comprises, a dye, pigment, or colorant.

439. The method of item 376 wherein the fibrosing agent is released in effective concentrations from the composition comprising the fibrosing agent by diffusion over a period ranging from the time of administration to about 90 days.

440. The method of item 376 wherein the fibrosing agent is released in effective concentrations from the composition comprising the fibrosing agent by erosion of the composition over a period ranging from the time of administration to about 90 days.

441. The method of item 376 wherein the composition further comprises an inflammatory cytokine.

442. The method of item 376 wherein the composition further comprises an agent that stimulates cell proliferation.

443. The method of item 376 wherein the composition further comprises a polymeric carrier.

444. The method of item 376 wherein the composition is in the form of a gel, paste, or spray.

445. The method of item 376 wherein the agent is delivered from a device, and the device delivers the fibrosing agent locally to tissue proximate to the device.

446. The method of item 376 wherein the agent is delivered from a device, wherein the device further comprises a coating, and the coating comprises the fibrosing agent.

447. The method of item 376 wherein the agent is delivered from a device, wherein the device further comprises a coating, and the coating is disposed on a surface of the device.

448. The method of item 376, wherein the agent is delivered from a device, wherein the device further comprises a coating, and the coating directly contacts the device.

449. The method of item 376, wherein the agent is delivered from a device, wherein the device further comprises a coating, and the coating indirectly contacts the device.

450. The method of item 376 wherein the agent is delivered from a device, wherein the device further comprises a coating, wherein the coating partially covers the device.

451. The method of item 376, wherein the agent is delivered from a device, wherein the device further comprises a coating, and the coating completely covers the device.

452. The method of item 376 wherein the agent is delivered from a device, wherein the fibrosing agent is located within pores or holes of the device.

453. The method of item 376 wherein the agent is delivered from a device, wherein the fibrosing agent is located within a channel, lumen, or divet of the device.

454. The method of item 376 wherein the agent is delivered from a device, wherein the device further comprising an echogenic material.

455. The method of item 376 wherein the agent is delivered from a device, wherein the device further comprises an echogenic material, wherein the echogenic material is in the form of a coating.

456. The method of item 376 wherein the agent is delivered from a device, wherein the device is sterile.

457. The method of item 376 wherein the agent is delivered from a device, wherein the fibrosing agent is released into tissue in the vicinity of the device after deployment of the device.

458. The method of item 376 wherein the agent is delivered from a device, wherein the fibrosing agent is released into tissue in the vicinity of the device after deployment of the device, wherein the tissue is connective tissue.

459. The method of item 376 wherein the agent is delivered from a device, wherein the fibrosing agent is released into tissue in the vicinity of the device after deployment of the device, wherein the tissue is muscle tissue.

460. The method of item 376 wherein the agent is delivered from a device, wherein the fibrosing agent is released into tissue in the vicinity of the device after deployment of the device, wherein the tissue is nerve tissue.

461. The method of item 376 wherein the agent is delivered from a device, wherein the fibrosing agent is released into tissue in the vicinity of the device after deployment of the device, wherein the tissue is epithelium tissue.

462. The method of item 376 wherein the agent is delivered from a device, wherein the fibrosing agent is released in effective concentrations from the device over a period ranging from the time of deployment of the device to about 1 year.

463. The method of item 376 wherein the agent is delivered from a device, wherein the fibrosing agent is released in effective concentrations from the device over a period ranging from about 1 month to 6 months.

464. The method of item 376 wherein the agent is delivered from a device, wherein the fibrosing agent is released in effective concentrations from the device over a period ranging from about 1–90 days.

465. The method of item 376 wherein the agent is delivered from a device, wherein the fibrosing agent is released in effective concentrations from the device at a constant rate.

466. The method of item 376 wherein the fibrosing agent is released in effective concentrations from the device at an increasing rate.

467. The method of item 376 wherein the agent is delivered from a device, wherein the fibrosing agent is released in effective concentrations from the device at a decreasing rate.

468. The method of item 376 wherein the agent is delivered from a device, wherein the device comprises about 0.01 µg to about 10 µg of the fibrosing agent.

469. The method of item 376 wherein the agent is delivered from a device, wherein the device comprises about 10 µg to about 10 mg of the fibrosing agent.

470. The method of item 376 wherein the agent is delivered from a device, wherein the device comprises about 10 mg to about 250 mg of the fibrosing agent.

471. The method of item 376 wherein the agent is delivered from a device, wherein the device comprises about 250 mg to about 1000 mg of the fibrosing agent.

472. The method of item 376 wherein the agent is delivered from a device, wherein the device comprises about 1000 mg to about 2500 mg of the fibrosing agent.

473. The method of item 376 wherein the agent is delivered from a device, wherein a surface of the device comprises less than 0.01 µg of the fibrosing agent per $mm^2$ of device surface to which the fibrosing agent is applied.

474. The method of item 376 wherein the agent is delivered from a device, wherein a surface of the device comprises about 0.01 µg to about 1 µg of the fibrosing agent per $mm^2$ of device surface to which the fibrosing agent is applied.

475. The method of item 376 wherein the agent is delivered from a device, wherein a surface of the device comprises about 1 µg to about 10 µg of the fibrosing agent per $mm^2$ of device surface to which the fibrosing agent is applied.

476. The method of item 376 wherein the agent is delivered from a device, wherein a surface of the device comprises about 10 µg to about 250 µg of the fibrosing agent per $mm^2$ of device surface to which the fibrosing agent is applied.

477. The method of item 376 wherein the agent is delivered from a device, wherein a surface of the device comprises about 250 µg to about 1000 µg of the fibrosing agent of fibrosing agent per $mm^2$ of device surface to which the fibrosing agent is applied.

478. The method of item 376 wherein the agent is delivered from a device, wherein a surface of the device comprises about 1000 µg to about 2500 µg of the fibrosing agent per $mm^2$ of device surface to which the fibrosing agent is applied.

479. The method of item 376, wherein the agent is delivered from a device, wherein the device further comprises a coating, and the coating is a uniform coating.

480. The method of item 376, wherein the agent is delivered from a device, wherein the device further comprises a coating, and the coating is a non-uniform coating.

481. The method of item 376, wherein the agent is delivered from a device, wherein the device further comprises a coating, and the coating is a discontinuous coating.

482. The method of item 376, wherein the agent is delivered from a device, wherein the device further comprises a coating, and the coating is a patterned coating.

483. The method of item 376, wherein the agent is delivered from a device, wherein the device further comprises a coating, and the coating has a thickness of 100 µm or less.

484. The method of item 376, wherein the agent is delivered from a device, wherein the device further comprises a coating, and the coating has a thickness of 10 µm or less.

485. The method of item 376, wherein the agent is delivered from a device, wherein the device further comprises a coating, and the coating adheres to the surface of the device upon deployment of the device.

486. The method of item 376, wherein the agent is delivered from a device, wherein the device further comprises a coating, and the coating is stable at room temperature for a period of at least 1 year.

487. The method of item 376, wherein the agent is delivered from a device, wherein the device further comprises a coating, and the fibrosing agent is present in the coating in an amount ranging between about 0.0001% to about 1% by weight.

488. The method of item 376, wherein the agent is delivered from a device, wherein the device further comprises a coating, and the fibrosing agent is present in the coating in an amount ranging between about 1% to about 10% by weight.

489. The method of item 376, wherein the agent is delivered from a device, wherein the device further comprises a coating, and the fibrosing agent is present in the coating in an amount ranging between about 10% to about 25% by weight.

490. The method of item 376, wherein the agent is delivered from a device, wherein the device further comprises a coating, and the fibrosing agent is present in the coating in an amount ranging between about 25% to about 70% by weight.

491. The method of item 376, wherein the agent is delivered from a device, wherein the device further comprises a coating, and the coating comprises a polymer.

492. The method of item 376, wherein the agent is delivered from a device, wherein the device comprises a first coating having a first composition and a second coating having a second composition.

493. The method of item 376, wherein the agent is delivered from a device, wherein the device comprises a first coating having a first composition and a second coating having a second composition, wherein the first composition and the second composition are different.

494. A method comprising introducing into a patient in need thereof, a therapeutically effective amount of a fibrosing agent or a composition comprising a fibrosing agent, where the fibrosing agent induces a fibrotic response at a specific site within the patient, thereby providing the patient with hernia repair.

495. The method of item 494 wherein the agent promotes regeneration.

496. The method of item 494 wherein the agent promotes angiogenesis.

497. The method of item 494 wherein the agent promotes fibroblast migration.

498. The method of item 494 wherein the agent promotes fibroblast proliferation.

499. The method of item 494 wherein the agent promotes deposition of extracellular matrix (ECM).

500. The method of item 494 wherein the agent promotes tissue remodeling.

501. The method of item 494 wherein the agent is an arterial vessel wall irritant.

502. The method of item 494 wherein the fibrosing agent is or comprises silk.

503. The method of item 494 wherein the fibrosing agent is in the form of tufts.

504. The method of item 494 wherein the fibrosing agent is or comprises mineral particles.

505. The method of item 494 wherein the fibrosing agent is or comprises chitosan.

506. The method of item 494 wherein the fibrosing agent is or comprises polylysine.

507. The method of item 494 wherein the fibrosing agent is or comprises fibronectin.

508. The method of item 494 wherein the fibrosing agent is or comprises bleomycin.

509. The method of item 494 wherein the fibrosing agent is or comprises CTGF.

510. The method of item 494 wherein the fibrosing agent is in the form of a thread, or is in contact with a thread.

511. The method of item 494 wherein the fibrosing agent is in the form of a particulate.

512. The method of item 494, wherein the composition comprises a polymer.

513. The method of item 494, wherein the composition comprises a polymer, and the polymer is, or comprises, a copolymer.

514. The method of item 494, wherein the composition comprises a polymer, and the polymer is, or comprises, a block copolymer.

515. The method of item 494, wherein the composition comprises a polymer, and the polymer is, or comprises, a random copolymer.

516. The method of item 494, wherein the composition comprises a polymer, and the polymer is, or comprises, a biodegradable polymer.

517. The method of item 494, wherein the composition comprises a polymer, and the polymer is, or comprises, a non-biodegradable polymer.

518. The method of item 494, wherein the composition comprises a polymer, and the polymer is, or comprises, a hydrophilic polymer.

519. The method of item 494, wherein the composition comprises a polymer, and the polymer is, or comprises, a hydrophobic polymer.

520. The method of item 494, wherein the composition comprises a polymer, and the polymer is, or comprises, a polymer having hydrophilic domains.

521. The method of item 494, wherein the composition comprises a polymer, and the polymer is, or comprises, a polymer having hydrophobic domains.

522. The method of item 494, wherein the composition comprises a polymer, and the polymer is, or comprises, a non-conductive polymer.

523. The method of item 494, wherein the composition comprises a polymer, and the polymer is, or comprises, an elastomer.

524. The method of item 494, wherein the composition comprises a polymer, and the polymer is, or comprises, a hydrogel.

525. The method of item 494, wherein the composition comprises a polymer, and the polymer is, or comprises, a silicone polymer.

526. The method of item 494, wherein the composition comprises a polymer, and the polymer is, or comprises, a hydrocarbon polymer.

527. The method of item 494, wherein the composition comprises a polymer, and the polymer is, or comprises, a styrene-derived polymer.

528. The method of item 494, wherein the composition comprises a polymer, and the polymer is, or comprises, a butadiene-derived polymer.

529. The method of item 494, wherein the composition comprises a polymer, and the polymer is, or comprises, a macromer.

530. The method of item 494, wherein the composition comprises a polymer, and the polymer is, or comprises, a poly(ethylene glycol) polymer.

531. The method of item 494, wherein the composition comprises a polymer, and the polymer is, or comprises, an amorphous polymer.

532. The method of item 494, wherein the composition further comprises a second pharmaceutically active agent.

533. The method of item 494, wherein the composition further comprises an anti-inflammatory agent.

534. The method of item 494, wherein the composition further comprises an agent that inhibits infection.

535. The method of item 494, wherein the composition further comprises an anthracycline.

536. The method of item 494, wherein the composition further comprises doxorubicin.

537. The method of item 494 wherein the composition further comprises mitoxantrone.

538. The method of item 494 wherein the composition further comprises a fluoropyrimidine.

539. The method of item 494, wherein the composition further comprises 5-fluorouracil (5-FU).

540. The method of item 494, wherein the composition further comprises a folic acid antagonist.

541. The method of item 494, wherein the composition further comprises methotrexate.

542. The method of item 494, wherein the composition further comprises a podophylotoxin.

543. The method of item 494, wherein the composition further comprises etoposide.

544. The method of item 494, wherein the composition further comprises camptothecin.

545. The method of item 494, wherein the composition further comprises a hydroxyurea.

546. The method of item 494, wherein the composition further comprises a platinum complex.

547. The method of item 494, wherein the composition further comprises cisplatin.

548. The method of item 494 wherein the composition further comprises an anti-thrombotic agent.

549. The method of item 494, wherein the composition further comprises a visualization agent.

550. The method of item 494, wherein the composition further comprises a visualization agent, and the visualization agent is a radiopaque material, wherein the radiopaque material comprises a metal, a halogenated compound, or a barium containing compound.

551. The method of item 494, wherein the composition further comprises a visualization agent, and the visualization agent is, or comprises, barium, tantalum, or technetium.

552. The method of item 494, wherein the composition further comprises a visualization agent, and the visualization agent is, or comprises, an MRI responsive material.

553. The method of item 494, wherein the composition further comprises a visualization agent, and the visualization agent is, or comprises, a gadolinium chelate.

554. The method of item 494, wherein the composition further comprises a visualization agent, and the visualization agent is, or comprises, iron, magnesium, manganese, copper, or chromium.

555. The method of item 494, wherein the composition further comprises a visualization agent, and the visualization agent is, or comprises, iron oxide compound.

556. The method of item 494, wherein the composition further comprises a visualization agent, and the visualization agent is, or comprises, a dye, pigment, or colorant.

557. The method of item 494 wherein the fibrosing agent is released in effective concentrations from the composition comprising the fibrosing agent by diffusion over a period ranging from the time of administration to about 90 days.

558. The method of item 494 wherein the fibrosing agent is released in effective concentrations from the composition comprising the fibrosing agent by erosion of the composition over a period ranging from the time of administration to about 90 days.

559. The method of item 494 wherein the composition further comprises an inflammatory cytokine.

560. The method of item 494 wherein the composition further comprises an agent that stimulates cell proliferation.

561. The method of item 494 wherein the composition further comprises a polymeric carrier.

562. The method of item 494 wherein the composition is in the form of a gel, paste, or spray.

563. The method of item 494 wherein the agent is delivered from a device, and the device delivers the fibrosing agent locally to tissue proximate to the device.

564. The method of item 494 wherein the agent is delivered from a device, wherein the device further comprises a coating, and the coating comprises the fibrosing agent.

565. The method of item 494 wherein the agent is delivered from a device, wherein the device further comprises a coating, and the coating is disposed on a surface of the device.

566. The method of item 494, wherein the agent is delivered from a device, wherein the device further comprises a coating, and the coating directly contacts the device.

567. The method of item 494, wherein the agent is delivered from a device, wherein the device further comprises a coating, and the coating indirectly contacts the device.

568. The method of item 494 wherein the agent is delivered from a device, wherein the device further comprises a coating, wherein the coating partially covers the device.

569. The method of item 494, wherein the agent is delivered from a device, wherein the device further comprises a coating, and the coating completely covers the device.

570. The method of item 494 wherein the agent is delivered from a device, wherein the fibrosing agent is located within pores or holes of the device.

571. The method of item 494 wherein the agent is delivered from a device, wherein the fibrosing agent is located within a channel, lumen, or divet of the device.

572. The method of item 494 wherein the agent is delivered from a device, wherein the device further comprising an echogenic material.

573. The method of item 494 wherein the agent is delivered from a device, wherein the device further comprises an echogenic material, wherein the echogenic material is in the form of a coating.

574. The method of item 494 wherein the agent is delivered from a device, wherein the device is sterile.

575. The method of item 494 wherein the agent is delivered from a device, wherein the fibrosing agent is released into tissue in the vicinity of the device after deployment of the device.

576. The method of item 494 wherein the agent is delivered from a device, wherein the fibrosing agent is released into tissue in the vicinity of the device after deployment of the device, wherein the tissue is connective tissue.

577. The method of item 494 wherein the agent is delivered from a device, wherein the fibrosing agent is released into tissue in the vicinity of the device after deployment of the device, wherein the tissue is muscle tissue.

578. The method of item 494 wherein the agent is delivered from a device, wherein the fibrosing agent is released into tissue in the vicinity of the device after deployment of the device, wherein the tissue is nerve tissue.

579. The method of item 494 wherein the agent is delivered from a device, wherein the fibrosing agent is released into tissue in the vicinity of the device after deployment of the device, wherein the tissue is epithelium tissue.

580. The method of item 494 wherein the agent is delivered from a device, wherein the fibrosing agent is released in effective concentrations from the device over a period ranging from the time of deployment of the device to about 1 year.

581. The method of item 494 wherein the agent is delivered from a device, wherein the fibrosing agent is released in effective concentrations from the device over a period ranging from about 1 month to 6 months.

582. The method of item 494 wherein the agent is delivered from a device, wherein the fibrosing agent is released in effective concentrations from the device over a period ranging from about 1–90 days.

583. The method of item 494 wherein the agent is delivered from a device, wherein the fibrosing agent is released in effective concentrations from the device at a constant rate.

584. The method of item 494 wherein the fibrosing agent is released in effective concentrations from the device at an increasing rate.

585. The method of item 494 wherein the agent is delivered from a device, wherein the fibrosing agent is released in effective concentrations from the device at a decreasing rate.

586. The method of item 494 wherein the agent is delivered from a device, wherein the device comprises about 0.01 μg to about 10 μg of the fibrosing agent.

587. The method of item 494 wherein the agent is delivered from a device, wherein the device comprises about 10 μg to about 10 mg of the fibrosing agent.

588. The method of item 494 wherein the agent is delivered from a device, wherein the device comprises about 10 mg to about 250 mg of the fibrosing agent.

589. The method of item 494 wherein the agent is delivered from a device, wherein the device comprises about 250 mg to about 1000 mg of the fibrosing agent.

590. The method of item 494 wherein the agent is delivered from a device, wherein the device comprises about 1000 mg to about 2500 mg of the fibrosing agent.

591. The method of item 494 wherein the agent is delivered from a device, wherein a surface of the device comprises less than 0.01 μg of the fibrosing agent per $mm^2$ of device surface to which the fibrosing agent is applied.

592. The method of item 494 wherein the agent is delivered from a device, wherein a surface of the device comprises about 0.01 μg to about 1 μg of the fibrosing agent per $mm^2$ of device surface to which the fibrosing agent is applied.

593. The method of item 494 wherein the agent is delivered from a device, wherein a surface of the device comprises about 1 μg to about 10 μg of the fibrosing agent per $mm^2$ of device surface to which the fibrosing agent is applied.

594. The method of item 494 wherein the agent is delivered from a device, wherein a surface of the device comprises about 10 μg to about 250 μg of the fibrosing agent per $mm^2$ of device surface to which the fibrosing agent is applied.

595. The method of item 494 wherein the agent is delivered from a device, wherein a surface of the device comprises about 250 μg to about 1000 μg of the fibrosing agent of fibrosing agent per $mm^2$ of device surface to which the fibrosing agent is applied.

596. The method of item 494 wherein the agent is delivered from a device, wherein a surface of the device comprises about 1000 μg to about 2500 μg of the fibrosing agent per $mm^2$ of device surface to which the fibrosing agent is applied.

597. The method of item 494, wherein the agent is delivered from a device, wherein the device further comprises a coating, and the coating is a uniform coating.

598. The method of item 494, wherein the agent is delivered from a device, wherein the device further comprises a coating, and the coating is a non-uniform coating.

599. The method of item 494, wherein the agent is delivered from a device, wherein the device further comprises a coating, and the coating is a discontinuous coating.

600. The method of item 494, wherein the agent is delivered from a device, wherein the device further comprises a coating, and the coating is a patterned coating.

601. The method of item 494, wherein the agent is delivered from a device, wherein the device further comprises a coating, and the coating has a thickness of 100 μm or less.

602. The method of item 494, wherein the agent is delivered from a device, wherein the device further comprises a coating, and the coating has a thickness of 10 μm or less.

603. The method of item 494, wherein the agent is delivered from a device, wherein the device further comprises a coating, and the coating adheres to the surface of the device upon deployment of the device.

604. The method of item 494, wherein the agent is delivered from a device, wherein the device further comprises a coating, and the coating is stable at room temperature for a period of at least 1 year.

605. The method of item 494, wherein the agent is delivered from a device, wherein the device further comprises a coating, and the fibrosing agent is present in the coating in an amount ranging between about 0.0001% to about 1% by weight.

606. The method of item 494, wherein the agent is delivered from a device, wherein the device further comprises a coating, and the fibrosing agent is present in the coating in an amount ranging between about 1% to about 10% by weight.

607. The method of item 494, wherein the agent is delivered from a device, wherein the device further comprises a coating, and the fibrosing agent is present in the coating in an amount ranging between about 10% to about 25% by weight.

608. The method of item 494, wherein the agent is delivered from a device, wherein the device further comprises a coating, and the fibrosing agent is present in the coating in an amount ranging between about 25% to about 70% by weight.

609. The method of item 494, wherein the agent is delivered from a device, wherein the device further comprises a coating, and the coating comprises a polymer.

610. The method of item 494, wherein the agent is delivered from a device, wherein the device comprises a first coating having a first composition and a second coating having a second composition.

611. The method of item 494, wherein the agent is delivered from a device, wherein the device comprises a first coating having a first composition and a second coating having a second composition, wherein the first composition and the second composition are different.

612. A method comprising introducing into a patient in need thereof, a therapeutically effective amount of a fibrosing agent or a composition comprising a fibrosing agent, where the fibrosing agent induces a fibrotic response at a specific site within the patient, thereby providing the patient with pulmonary sealing.

613. The method of item 612 wherein the agent promotes regeneration.

614. The method of item 612 wherein the agent promotes angiogenesis.

615. The method of item 612 wherein the agent promotes fibroblast migration.

616. The method of item 612 wherein the agent promotes fibroblast proliferation.

617. The method of item 612 wherein the agent promotes deposition of extracellular matrix (ECM).

618. The method of item 612 wherein the agent promotes tissue remodeling.

619. The method of item 612 wherein the agent is an arterial vessel wall irritant.

620. The method of item 612 wherein the fibrosing agent is or comprises silk.

621. The method of item 612 wherein the fibrosing agent is in the form of tufts.

622. The method of item 612 wherein the fibrosing agent is or comprises mineral particles.

623. The method of item 612 wherein the fibrosing agent is or comprises chitosan.

624. The method of item 612 wherein the fibrosing agent is or comprises polylysine.

625. The method of item 612 wherein the fibrosing agent is or comprises fibronectin.

626. The method of item 612 wherein the fibrosing agent is or comprises bleomycin.

627. The method of item 612 wherein the fibrosing agent is or comprises CTGF.

628. The method of item 612 wherein the fibrosing agent is in the form of a thread, or is in contact with a thread.

629. The method of item 612 wherein the fibrosing agent is in the form of a particulate.

630. The method of item 612, wherein the composition comprises a polymer.

631. The method of item 612, wherein the composition comprises a polymer, and the polymer is, or comprises, a copolymer.

632. The method of item 612, wherein the composition comprises a polymer, and the polymer is, or comprises, a block copolymer.

633. The method of item 612, wherein the composition comprises a polymer, and the polymer is, or comprises, a random copolymer.

634. The method of item 612, wherein the composition comprises a polymer, and the polymer is, or comprises, a biodegradable polymer.

635. The method of item 612, wherein the composition comprises a polymer, and the polymer is, or comprises, a non-biodegradable polymer.

636. The method of item 612, wherein the composition comprises a polymer, and the polymer is, or comprises, a hydrophilic polymer.

637. The method of item 612, wherein the composition comprises a polymer, and the polymer is, or comprises, a hydrophobic polymer.

638. The method of item 612, wherein the composition comprises a polymer, and the polymer is, or comprises, a polymer having hydrophilic domains.

639. The method of item 612, wherein the composition comprises a polymer, and the polymer is, or comprises, a polymer having hydrophobic domains.

640. The method of item 612, wherein the composition comprises a polymer, and the polymer is, or comprises, a non-conductive polymer.

641. The method of item 612, wherein the composition comprises a polymer, and the polymer is, or comprises, an elastomer.

642. The method of item 612, wherein the composition comprises a polymer, and the polymer is, or comprises, a hydrogel.

643. The method of item 612, wherein the composition comprises a polymer, and the polymer is, or comprises, a silicone polymer.

644. The method of item 612, wherein the composition comprises a polymer, and the polymer is, or comprises, a hydrocarbon polymer.

645. The method of item 612, wherein the composition comprises a polymer, and the polymer is, or comprises, a styrene-derived polymer.

646. The method of item 612, wherein the composition comprises a polymer, and the polymer is, or comprises, a butadiene-derived polymer.

647. The method of item 612, wherein the composition comprises a polymer, and the polymer is, or comprises, a macromer.

648. The method of item 612, wherein the composition comprises a polymer, and the polymer is, or comprises, a poly(ethylene glycol) polymer.

649. The method of item 612, wherein the composition comprises a polymer, and the polymer is, or comprises, an amorphous polymer.

650. The method of item 612, wherein the composition further comprises a second pharmaceutically active agent.

651. The method of item 612, wherein the composition further comprises an anti-inflammatory agent.

652. The method of item 612, wherein the composition further comprises an agent that inhibits infection.

653. The method of item 612, wherein the composition further comprises an anthracycline.

654. The method of item 612, wherein the composition further comprises doxorubicin.

655. The method of item 612 wherein the composition further comprises mitoxantrone.

656. The method of item 612 wherein the composition further comprises a fluoropyrimidine.

657. The method of item 612, wherein the composition further comprises 5-fluorouracil (5-FU).

658. The method of item 612, wherein the composition further comprises a folic acid antagonist.

659. The method of item 612, wherein the composition further comprises methotrexate.

660. The method of item 612, wherein the composition further comprises a podophylotoxin.

661. The method of item 612, wherein the composition further comprises etoposide.

662. The method of item 612, wherein the composition further comprises camptothecin.

663. The method of item 612, wherein the composition further comprises a hydroxyurea.

664. The method of item 612, wherein the composition further comprises a platinum complex.

665. The method of item 612, wherein the composition further comprises cisplatin.

666. The method of item 612 wherein the composition further comprises an anti-thrombotic agent.

667. The method of item 612, wherein the composition further comprises a visualization agent.

668. The method of item 612, wherein the composition further comprises a visualization agent, and the visualization agent is a radiopaque material, wherein the radiopaque material comprises a metal, a halogenated compound, or a barium containing compound.

669. The method of item 612, wherein the composition further comprises a visualization agent, and the visualization agent is, or comprises, barium, tantalum, or technetium.

670. The method of item 612, wherein the composition further comprises a visualization agent, and the visualization agent is, or comprises, an MRI responsive material.

671. The method of item 612, wherein the composition further comprises a visualization agent, and the visualization agent is, or comprises, a gadolinium chelate.

672. The method of item 612, wherein the composition further comprises a visualization agent, and the visualization agent is, or comprises, iron, magnesium, manganese, copper, or chromium.

673. The method of item 612, wherein the composition further comprises a visualization agent, and the visualization agent is, or comprises, iron oxide compound.

674. The method of item 612, wherein the composition further comprises a visualization agent, and the visualization agent is, or comprises, a dye, pigment, or colorant.

675. The method of item 612 wherein the fibrosing agent is released in effective concentrations from the composition comprising the fibrosing agent by diffusion over a period ranging from the time of administration to about 90 days.

676. The method of item 612 wherein the fibrosing agent is released in effective concentrations from the composition comprising the fibrosing agent by erosion of the composition over a period ranging from the time of administration to about 90 days.

677. The method of item 612 wherein the composition further comprises an inflammatory cytokine.

678. The method of item 612 wherein the composition further comprises an agent that stimulates cell proliferation.

679. The method of item 612 wherein the composition further comprises a polymeric carrier.

680. The method of item 612 wherein the composition is in the form of a gel, paste, or spray.

681. The method of item 612 wherein the agent is delivered from a device, and the device delivers the fibrosing agent locally to tissue proximate to the device.

682. The method of item 612 wherein the agent is delivered from a device, wherein the device further comprises a coating, and the coating comprises the fibrosing agent.

683. The method of item 612 wherein the agent is delivered from a device, wherein the device further comprises a coating, and the coating is disposed on a surface of the device.

684. The method of item 612, wherein the agent is delivered from a device, wherein the device further comprises a coating, and the coating directly contacts the device.

685. The method of item 612, wherein the agent is delivered from a device, wherein the device further comprises a coating, and the coating indirectly contacts the device.

686. The method of item 612 wherein the agent is delivered from a device, wherein the device further comprises a coating, wherein the coating partially covers the device.

687. The method of item 612, wherein the agent is delivered from a device, wherein the device further comprises a coating, and the coating completely covers the device.

688. The method of item 612 wherein the agent is delivered from a device, wherein the fibrosing agent is located within pores or holes of the device.

689. The method of item 612 wherein the agent is delivered from a device, wherein the fibrosing agent is located within a channel, lumen, or divet of the device.

690. The method of item 612 wherein the agent is delivered from a device, wherein the device further comprising an echogenic material.

691. The method of item 612 wherein the agent is delivered from a device, wherein the device further comprises an echogenic material, wherein the echogenic material is in the form of a coating.

692. The method of item 612 wherein the agent is delivered from a device, wherein the device is sterile.

693. The method of item 612 wherein the agent is delivered from a device, wherein the fibrosing agent is released into tissue in the vicinity of the device after deployment of the device.

694. The method of item 612 wherein the agent is delivered from a device, wherein the fibrosing agent is released into tissue in the vicinity of the device after deployment of the device, wherein the tissue is connective tissue.

695. The method of item 612 wherein the agent is delivered from a device, wherein the fibrosing agent is released into tissue in the vicinity of the device after deployment of the device, wherein the tissue is muscle tissue.

696. The method of item 612 wherein the agent is delivered from a device, wherein the fibrosing agent is released into tissue in the vicinity of the device after deployment of the device, wherein the tissue is nerve tissue.

697. The method of item 612 wherein the agent is delivered from a device, wherein the fibrosing agent is released into tissue in the vicinity of the device after deployment of the device, wherein the tissue is epithelium tissue.

698. The method of item 612 wherein the agent is delivered from a device, wherein the fibrosing agent is released in effective concentrations from the device over a period ranging from the time of deployment of the device to about 1 year.

699. The method of item 612 wherein the agent is delivered from a device, wherein the fibrosing agent is released in effective concentrations from the device over a period ranging from about 1 month to 6 months.

700. The method of item 612 wherein the agent is delivered from a device, wherein the fibrosing agent is released in effective concentrations from the device over a period ranging from about 1–90 days.

701. The method of item 612 wherein the agent is delivered from a device, wherein the fibrosing agent is released in effective concentrations from the device at a constant rate.

702. The method of item 612 wherein the fibrosing agent is released in effective concentrations from the device at an increasing rate.

703. The method of item 612 wherein the agent is delivered from a device, wherein the fibrosing agent is released in effective concentrations from the device at a decreasing rate.

704. The method of item 612 wherein the agent is delivered from a device, wherein the device comprises about 0.01 µg to about 10 µg of the fibrosing agent.

705. The method of item 612 wherein the agent is delivered from a device, wherein the device comprises about 10 µg to about 10 mg of the fibrosing agent.

706. The method of item 612 wherein the agent is delivered from a device, wherein the device comprises about 10 mg to about 250 mg of the fibrosing agent.

707. The method of item 612 wherein the agent is delivered from a device, wherein the device comprises about 250 mg to about 1000 mg of the fibrosing agent.

708. The method of item 612 wherein the agent is delivered from a device, wherein the device comprises about 1000 mg to about 2500 mg of the fibrosing agent.

709. The method of item 612 wherein the agent is delivered from a device, wherein a surface of the device comprises less than 0.01 µg of the fibrosing agent per mm$^2$ of device surface to which the fibrosing agent is applied.

710. The method of item 612 wherein the agent is delivered from a device, wherein a surface of the device comprises about 0.01 µg to about 1 µg of the fibrosing agent per mm² of device surface to which the fibrosing agent is applied.

711. The method of item 612 wherein the agent is delivered from a device, wherein a surface of the device comprises about 1 µg to about 10 µg of the fibrosing agent per mm² of device surface to which the fibrosing agent is applied.

712. The method of item 612 wherein the agent is delivered from a device, wherein a surface of the device comprises about 10 µg to about 250 µg of the fibrosing agent per mm² of device surface to which the fibrosing agent is applied.

713. The method of item 612 wherein the agent is delivered from a device, wherein a surface of the device comprises about 250 µg to about 1000 µg of the fibrosing agent of fibrosing agent per mm² of device surface to which the fibrosing agent is applied.

714. The method of item 612 wherein the agent is delivered from a device, wherein a surface of the device comprises about 1000 µg to about 2500 µg of the fibrosing agent per mm² of device surface to which the fibrosing agent is applied.

715. The method of item 612, wherein the agent is delivered from a device, wherein the device further comprises a coating, and the coating is a uniform coating.

716. The method of item 612, wherein the agent is delivered from a device, wherein the device further comprises a coating, and the coating is a non-uniform coating.

717. The method of item 612, wherein the agent is delivered from a device, wherein the device further comprises a coating, and the coating is a discontinuous coating.

718. The method of item 612, wherein the agent is delivered from a device, wherein the device further comprises a coating, and the coating is a patterned coating.

719. The method of item 612, wherein the agent is delivered from a device, wherein the device further comprises a coating, and the coating has a thickness of 100 µm or less.

720. The method of item 612, wherein the agent is delivered from a device, wherein the device further comprises a coating, and the coating has a thickness of 10 µm or less.

721. The method of item 612, wherein the agent is delivered from a device, wherein the device further comprises a coating, and the coating adheres to the surface of the device upon deployment of the device.

722. The method of item 612, wherein the agent is delivered from a device, wherein the device further comprises a coating, and the coating is stable at room temperature for a period of at least 1 year.

723. The method of item 612, wherein the agent is delivered from a device, wherein the device further comprises a coating, and the fibrosing agent is present in the coating in an amount ranging between about 0.0001% to about 1% by weight.

724. The method of item 612, wherein the agent is delivered from a device, wherein the device further comprises a coating, and the fibrosing agent is present in the coating in an amount ranging between about 1% to about 10% by weight.

725. The method of item 612, wherein the agent is delivered from a device, wherein the device further comprises a coating, and the fibrosing agent is present in the coating in an amount ranging between about 10% to about 25% by weight.

726. The method of item 612, wherein the agent is delivered from a device, wherein the device further comprises a coating, and the fibrosing agent is present in the coating in an amount ranging between about 25% to about 70% by weight.

727. The method of item 612, wherein the agent is delivered from a device, wherein the device further comprises a coating, and the coating comprises a polymer.

728. The method of item 612, wherein the agent is delivered from a device, wherein the device comprises a first coating having a first composition and a second coating having a second composition.

729. The method of item 612, wherein the agent is delivered from a device, wherein the device comprises a first coating having a first composition and a second coating having a second composition, wherein the first composition and the second composition are different.

730. A method comprising introducing into a patient in need thereof, a therapeutically effective amount of a fibrosing agent or a composition comprising a fibrosing agent, where the fibrosing agent induces a fibrotic response at a specific site within the patient, thereby providing the patient with treatment or prevention of an aneurysm.

731. The method of item 730 wherein the agent promotes regeneration.

732. The method of item 730 wherein the agent promotes angiogenesis.

733. The method of item 730 wherein the agent promotes fibroblast migration.

734. The method of item 730 wherein the agent promotes fibroblast proliferation.

735. The method of item 730 wherein the agent promotes deposition of extracellular matrix (ECM).

736. The method of item 730 wherein the agent promotes tissue remodeling.

737. The method of item 730 wherein the agent is an arterial vessel wall irritant.

738. The method of item 730 wherein the fibrosing agent is or comprises silk.

739. The method of item 730 wherein the fibrosing agent is in the form of tufts.

740. The method of item 730 wherein the fibrosing agent is or comprises mineral particles.

741. The method of item 730 wherein the fibrosing agent is or comprises chitosan.

742. The method of item 730 wherein the fibrosing agent is or comprises polylysine.

743. The method of item 730 wherein the fibrosing agent is or comprises fibronectin.

744. The method of item 730 wherein the fibrosing agent is or comprises bleomycin.

745. The method of item 730 wherein the fibrosing agent is or comprises CTGF.

746. The method of item 730 wherein the fibrosing agent is in the form of a thread, or is in contact with a thread.

747. The method of item 730 wherein the fibrosing agent is in the form of a particulate.

748. The method of item 730, wherein the composition comprises a polymer.

749. The method of item 730, wherein the composition comprises a polymer, and the polymer is, or comprises, a copolymer.

750. The method of item 730, wherein the composition comprises a polymer, and the polymer is, or comprises, a block copolymer.

751. The method of item 730, wherein the composition comprises a polymer, and the polymer is, or comprises, a random copolymer.

752. The method of item 730, wherein the composition comprises a polymer, and the polymer is, or comprises, a biodegradable polymer.

753. The method of item 730, wherein the composition comprises a polymer, and the polymer is, or comprises, a non-biodegradable polymer.

754. The method of item 730, wherein the composition comprises a polymer, and the polymer is, or comprises, a hydrophilic polymer.

755. The method of item 730, wherein the composition comprises a polymer, and the polymer is, or comprises, a hydrophobic polymer.

756. The method of item 730, wherein the composition comprises a polymer, and the polymer is, or comprises, a polymer having hydrophilic domains.

757. The method of item 730, wherein the composition comprises a polymer, and the polymer is, or comprises, a polymer having hydrophobic domains.

758. The method of item 730, wherein the composition comprises a polymer, and the polymer is, or comprises, a non-conductive polymer.

759. The method of item 730, wherein the composition comprises a polymer, and the polymer is, or comprises, an elastomer.

760. The method of item 730, wherein the composition comprises a polymer, and the polymer is, or comprises, a hydrogel.

761. The method of item 730, wherein the composition comprises a polymer, and the polymer is, or comprises, a silicone polymer.

762. The method of item 730, wherein the composition comprises a polymer, and the polymer is, or comprises, a hydrocarbon polymer.

763. The method of item 730, wherein the composition comprises a polymer, and the polymer is, or comprises, a styrene-derived polymer.

764. The method of item 730, wherein the composition comprises a polymer, and the polymer is, or comprises, a butadiene-derived polymer.

765. The method of item 730, wherein the composition comprises a polymer, and the polymer is, or comprises, a macromer.

766. The method of item 730, wherein the composition comprises a polymer, and the polymer is, or comprises, a poly(ethylene glycol) polymer.

767. The method of item 730, wherein the composition comprises a polymer, and the polymer is, or comprises, an amorphous polymer.

768. The method of item 730, wherein the composition further comprises a second pharmaceutically active agent.

769. The method of item 730, wherein the composition further comprises an anti-inflammatory agent.

770. The method of item 730, wherein the composition further comprises an agent that inhibits infection.

771. The method of item 730, wherein the composition further comprises an anthracycline.

772. The method of item 730, wherein the composition further comprises doxorubicin.

773. The method of item 730 wherein the composition further comprises mitoxantrone.

774. The method of item 730 wherein the composition further comprises a fluoropyrimidine.

775. The method of item 730, wherein the composition further comprises 5-fluorouracil (5-FU).

776. The method of item 730, wherein the composition further comprises a folic acid antagonist.

777. The method of item 730, wherein the composition further comprises methotrexate.

778. The method of item 730, wherein the composition further comprises a podophylotoxin.

779. The method of item 730, wherein the composition further comprises etoposide.

780. The method of item 730, wherein the composition further comprises camptothecin.

781. The method of item 730, wherein the composition further comprises a hydroxyurea.

782. The method of item 730, wherein the composition further comprises a platinum complex.

783. The method of item 730, wherein the composition further comprises cisplatin.

784. The method of item 730 wherein the composition further comprises an anti-thrombotic agent.

785. The method of item 730, wherein the composition further comprises a visualization agent.

786. The method of item 730, wherein the composition further comprises a visualization agent, and the visualization agent is a radiopaque material, wherein the radiopaque material comprises a metal, a halogenated compound, or a barium containing compound.

787. The method of item 730, wherein the composition further comprises a visualization agent, and the visualization agent is, or comprises, barium, tantalum, or technetium.

788. The method of item 730, wherein the composition further comprises a visualization agent, and the visualization agent is, or comprises, an MRI responsive material.

789. The method of item 730, wherein the composition further comprises a visualization agent, and the visualization agent is, or comprises, a gadolinium chelate.

790. The method of item 730, wherein the composition further comprises a visualization agent, and the visualization agent is, or comprises, iron, magnesium, manganese, copper, or chromium.

791. The method of item 730, wherein the composition further comprises a visualization agent, and the visualization agent is, or comprises, iron oxide compound.

792. The method of item 730, wherein the composition further comprises a visualization agent, and the visualization agent is, or comprises, a dye, pigment, or colorant.

793. The method of item 730 wherein the fibrosing agent is released in effective concentrations from the composition comprising the fibrosing agent by diffusion over a period ranging from the time of administration to about 90 days.

794. The method of item 730 wherein the fibrosing agent is released in effective concentrations from the composition comprising the fibrosing agent by erosion of the composition over a period ranging from the time of administration to about 90 days.

795. The method of item 730 wherein the composition further comprises an inflammatory cytokine.

796. The method of item 730 wherein the composition further comprises an agent that stimulates cell proliferation.

797. The method of item 730 wherein the composition further comprises a polymeric carrier.

798. The method of item 730 wherein the composition is in the form of a gel, paste, or spray.

799. The method of item 730 wherein the agent is delivered from a device, and the device delivers the fibrosing agent locally to tissue proximate to the device.

800. The method of item 730 wherein the agent is delivered from a device, wherein the device further comprises a coating, and the coating comprises the fibrosing agent.

801. The method of item 730 wherein the agent is delivered from a device, wherein the device further comprises a coating, and the coating is disposed on a surface of the device.

802. The method of item 730, wherein the agent is delivered from a device, wherein the device further comprises a coating, and the coating directly contacts the device.

803. The method of item 730, wherein the agent is delivered from a device, wherein the device further comprises a coating, and the coating indirectly contacts the device.

804. The method of item 730 wherein the agent is delivered from a device, wherein the device further comprises a coating, wherein the coating partially covers the device.

805. The method of item 730, wherein the agent is delivered from a device, wherein the device further comprises a coating, and the coating completely covers the device.

806. The method of item 730 wherein the agent is delivered from a device, wherein the fibrosing agent is located within pores or holes of the device.

807. The method of item 730 wherein the agent is delivered from a device, wherein the fibrosing agent is located within a channel, lumen, or divet of the device.

808. The method of item 730 wherein the agent is delivered from a device, wherein the device further comprising an echogenic material.

809. The method of item 730 wherein the agent is delivered from a device, wherein the device further comprises an echogenic material, wherein the echogenic material is in the form of a coating.

810. The method of item 730 wherein the agent is delivered from a device, wherein the device is sterile.

811. The method of item 730 wherein the agent is delivered from a device, wherein the fibrosing agent is released into tissue in the vicinity of the device after deployment of the device.

812. The method of item 730 wherein the agent is delivered from a device, wherein the fibrosing agent is released into tissue in the vicinity of the device after deployment of the device, wherein the tissue is connective tissue.

813. The method of item 730 wherein the agent is delivered from a device, wherein the fibrosing agent is released into tissue in the vicinity of the device after deployment of the device, wherein the tissue is muscle tissue.

814. The method of item 730 wherein the agent is delivered from a device, wherein the fibrosing agent is released into tissue in the vicinity of the device after deployment of the device, wherein the tissue is nerve tissue.

815. The method of item 730 wherein the agent is delivered from a device, wherein the fibrosing agent is released into tissue in the vicinity of the device after deployment of the device, wherein the tissue is epithelium tissue.

816. The method of item 730 wherein the agent is delivered from a device, wherein the fibrosing agent is released in effective concentrations from the device over a period ranging from the time of deployment of the device to about 1 year.

817. The method of item 730 wherein the agent is delivered from a device, wherein the fibrosing agent is released in effective concentrations from the device over a period ranging from about 1 month to 6 months.

818. The method of item 730 wherein the agent is delivered from a device, wherein the fibrosing agent is released in effective concentrations from the device over a period ranging from about 1–90 days.

819. The method of item 730 wherein the agent is delivered from a device, wherein the fibrosing agent is released in effective concentrations from the device at a constant rate.

820. The method of item 730 wherein the fibrosing agent is released in effective concentrations from the device at an increasing rate.

821. The method of item 730 wherein the agent is delivered from a device, wherein the fibrosing agent is released in effective concentrations from the device at a decreasing rate.

822. The method of item 730 wherein the agent is delivered from a device, wherein the device comprises about 0.01 µg to about 10 µg of the fibrosing agent.

823. The method of item 730 wherein the agent is delivered from a device, wherein the device comprises about 10 µg to about 10 mg of the fibrosing agent.

824. The method of item 730 wherein the agent is delivered from a device, wherein the device comprises about 10 mg to about 250 mg of the fibrosing agent.

825. The method of item 730 wherein the agent is delivered from a device, wherein the device comprises about 250 mg to about 1000 mg of the fibrosing agent.

826. The method of item 730 wherein the agent is delivered from a device, wherein the device comprises about 1000 mg to about 2500 mg of the fibrosing agent.

827. The method of item 730 wherein the agent is delivered from a device, wherein a surface of the device comprises less than 0.01 µg of the fibrosing agent per $mm^2$ of device surface to which the fibrosing agent is applied.

828. The method of item 730 wherein the agent is delivered from a device, wherein a surface of the device comprises about 0.01 µg to about 1 µg of the fibrosing agent per $mm^2$ of device surface to which the fibrosing agent is applied.

829. The method of item 730 wherein the agent is delivered from a device, wherein a surface of the device comprises about 1 µg to about 10 µg of the fibrosing agent per $mm^2$ of device surface to which the fibrosing agent is applied.

830. The method of item 730 wherein the agent is delivered from a device, wherein a surface of the device comprises about 10 µg to about 250 µg of the fibrosing agent per $mm^2$ of device surface to which the fibrosing agent is applied.

831. The method of item 730 wherein the agent is delivered from a device, wherein a surface of the device comprises about 250 µg to about 1000 µg of the fibrosing agent of fibrosing agent per $mm^2$ of device surface to which the fibrosing agent is applied.

832. The method of item 730 wherein the agent is delivered from a device, wherein a surface of the device comprises about 1000 µg to about 2500 µg of the fibrosing agent per $mm^2$ of device surface to which the fibrosing agent is applied.

833. The method of item 730, wherein the agent is delivered from a device, wherein the device further comprises a coating, and the coating is a uniform coating.

834. The method of item 730, wherein the agent is delivered from a device, wherein the device further comprises a coating, and the coating is a non-uniform coating.

835. The method of item 730, wherein the agent is delivered from a device, wherein the device further comprises a coating, and the coating is a discontinuous coating.

836. The method of item 730, wherein the agent is delivered from a device, wherein the device further comprises a coating, and the coating is a patterned coating.

837. The method of item 730, wherein the agent is delivered from a device, wherein the device further comprises a coating, and the coating has a thickness of 100 µm or less.

838. The method of item 730, wherein the agent is delivered from a device, wherein the device further comprises a coating, and the coating has a thickness of 10 µm or less.

839. The method of item 730, wherein the agent is delivered from a device, wherein the device further comprises a coating, and the coating adheres to the surface of the device upon deployment of the device.

840. The method of item 730, wherein the agent is delivered from a device, wherein the device further comprises a coating, and the coating is stable at room temperature for a period of at least 1 year.

841. The method of item 730, wherein the agent is delivered from a device, wherein the device further comprises a coating, and the fibrosing agent is present in the coating in an amount ranging between about 0.0001% to about 1% by weight.

842. The method of item 730, wherein the agent is delivered from a device, wherein the device further comprises a coating, and the fibrosing agent is present in the coating in an amount ranging between about 1% to about 10% by weight.

843. The method of item 730, wherein the agent is delivered from a device, wherein the device further comprises a coating, and the fibrosing agent is present in the coating in an amount ranging between about 10% to about 25% by weight.

844. The method of item 730, wherein the agent is delivered from a device, wherein the device further comprises a coating, and the fibrosing agent is present in the coating in an amount ranging between about 25% to about 70% by weight.

845. The method of item 730, wherein the agent is delivered from a device, wherein the device further comprises a coating, and the coating comprises a polymer.

846. The method of item 730, wherein the agent is delivered from a device, wherein the device comprises a first coating having a first composition and a second coating having a second composition.

847. The method of item 730, wherein the agent is delivered from a device, wherein the device comprises a first coating having a first composition and a second coating having a second composition, wherein the first composition and the second composition are different.

848. A method comprising introducing into a patient in need thereof, a therapeutically effective amount of a fibrosing agent or a composition comprising a fibrosing agent, where the fibrosing agent induces a fibrotic response at a specific site within the patient, thereby providing the patient with embolization.

849. The method of item 848 wherein the agent promotes regeneration.

850. The method of item 848 wherein the agent promotes angiogenesis.

851. The method of item 848 wherein the agent promotes fibroblast migration.

852. The method of item 848 wherein the agent promotes fibroblast proliferation.

853. The method of item 848 wherein the agent promotes deposition of extracellular matrix (ECM).

854. The method of item 848 wherein the agent promotes tissue remodeling.

855. The method of item 848 wherein the agent is an arterial vessel wall irritant.

856. The method of item 848 wherein the fibrosing agent is or comprises silk.

857. The method of item 848 wherein the fibrosing agent is in the form of tufts.

858. The method of item 848 wherein the fibrosing agent is or comprises mineral particles.

859. The method of item 848 wherein the fibrosing agent is or comprises chitosan.

860. The method of item 848 wherein the fibrosing agent is or comprises polylysine.

861. The method of item 848 wherein the fibrosing agent is or comprises fibronectin.

862. The method of item 848 wherein the fibrosing agent is or comprises bleomycin.

863. The method of item 848 wherein the fibrosing agent is or comprises CTGF.

864. The method of item 848 wherein the fibrosing agent is in the form of a thread, or is in contact with a thread.

865. The method of item 848 wherein the fibrosing agent is in the form of a particulate.

866. The method of item 848, wherein the composition comprises a polymer.

867. The method of item 848, wherein the composition comprises a polymer, and the polymer is, or comprises, a copolymer.

868. The method of item 848, wherein the composition comprises a polymer, and the polymer is, or comprises, a block copolymer.

869. The method of item 848, wherein the composition comprises a polymer, and the polymer is, or comprises, a random copolymer.

870. The method of item 848, wherein the composition comprises a polymer, and the polymer is, or comprises, a biodegradable polymer.

871. The method of item 848, wherein the composition comprises a polymer, and the polymer is, or comprises, a non-biodegradable polymer.

872. The method of item 848, wherein the composition comprises a polymer, and the polymer is, or comprises, a hydrophilic polymer.

873. The method of item 848, wherein the composition comprises a polymer, and the polymer is, or comprises, a hydrophobic polymer.

874. The method of item 848, wherein the composition comprises a polymer, and the polymer is, or comprises, a polymer having hydrophilic domains.

875. The method of item 848, wherein the composition comprises a polymer, and the polymer is, or comprises, a polymer having hydrophobic domains.

876. The method of item 848, wherein the composition comprises a polymer, and the polymer is, or comprises, a non-conductive polymer.

877. The method of item 848, wherein the composition comprises a polymer, and the polymer is, or comprises, an elastomer.

878. The method of item 848, wherein the composition comprises a polymer, and the polymer is, or comprises, a hydrogel.

879. The method of item 848, wherein the composition comprises a polymer, and the polymer is, or comprises, a silicone polymer.

880. The method of item 848, wherein the composition comprises a polymer, and the polymer is, or comprises, a hydrocarbon polymer.

881. The method of item 848, wherein the composition comprises a polymer, and the polymer is, or comprises, a styrene-derived polymer.

882. The method of item 848, wherein the composition comprises a polymer, and the polymer is, or comprises, a butadiene-derived polymer.

883. The method of item 848, wherein the composition comprises a polymer, and the polymer is, or comprises, a macromer.

884. The method of item 848, wherein the composition comprises a polymer, and the polymer is, or comprises, a poly(ethylene glycol) polymer.

885. The method of item 848, wherein the composition comprises a polymer, and the polymer is, or comprises, an amorphous polymer.

886. The method of item 848, wherein the composition further comprises a second pharmaceutically active agent.

887. The method of item 848, wherein the composition further comprises an anti-inflammatory agent.

888. The method of item 848, wherein the composition further comprises an agent that inhibits infection.

889. The method of item 848, wherein the composition further comprises an anthracycline.

890. The method of item 848, wherein the composition further comprises doxorubicin.

891. The method of item 848 wherein the composition further comprises mitoxantrone.

892. The method of item 848 wherein the composition further comprises a fluoropyrimidine.

893. The method of item 848, wherein the composition further comprises 5-fluorouracil (5-FU).

894. The method of item 848, wherein the composition further comprises a folic acid antagonist.

895. The method of item 848, wherein the composition further comprises methotrexate.

896. The method of item 848, wherein the composition further comprises a podophylotoxin.

897. The method of item 848, wherein the composition further comprises etoposide.

898. The method of item 848, wherein the composition further comprises camptothecin.

899. The method of item 848, wherein the composition further comprises a hydroxyurea.

900. The method of item 848, wherein the composition further comprises a platinum complex.

901. The method of item 848, wherein the composition further comprises cisplatin.

902. The method of item 848, wherein the composition further comprises an anti-thrombotic agent.

903. The method of item 848, wherein the composition further comprises a visualization agent.

904. The method of item 848, wherein the composition further comprises a visualization agent, and the visualization agent is a radiopaque material, wherein the radiopaque material comprises a metal, a halogenated compound, or a barium containing compound.

905. The method of item 848, wherein the composition further comprises a visualization agent, and the visualization agent is, or comprises, barium, tantalum, or technetium.

906. The method of item 848, wherein the composition further comprises a visualization agent, and the visualization agent is, or comprises, an MRI responsive material.

907. The method of item 848, wherein the composition further comprises a visualization agent, and the visualization agent is, or comprises, a gadolinium chelate.

908. The method of item 848, wherein the composition further comprises a visualization agent, and the visualization agent is, or comprises, iron, magnesium, manganese, copper, or chromium.

909. The method of item 848, wherein the composition further comprises a visualization agent, and the visualization agent is, or comprises, iron oxide compound.

910. The method of item 848, wherein the composition further comprises a visualization agent, and the visualization agent is, or comprises, a dye, pigment, or colorant.

911. The method of item 848 wherein the fibrosing agent is released in effective concentrations from the composition comprising the fibrosing agent by diffusion over a period ranging from the time of administration to about 90 days.

912. The method of item 848 wherein the fibrosing agent is released in effective concentrations from the composition comprising the fibrosing agent by erosion of the composition over a period ranging from the time of administration to about 90 days.

913. The method of item 848 wherein the composition further comprises an inflammatory cytokine.

914. The method of item 848 wherein the composition further comprises an agent that stimulates cell proliferation.

915. The method of item 848 wherein the composition further comprises a polymeric carrier.

916. The method of item 848 wherein the composition is in the form of a gel, paste, or spray.

917. The method of item 848 wherein the agent is delivered from a device, and the device delivers the fibrosing agent locally to tissue proximate to the device.

918. The method of item 848 wherein the agent is delivered from a device, wherein the device further comprises a coating, and the coating comprises the fibrosing agent.

919. The method of item 848 wherein the agent is delivered from a device, wherein the device further comprises a coating, and the coating is disposed on a surface of the device.

920. The method of item 848, wherein the agent is delivered from a device, wherein the device further comprises a coating, and the coating directly contacts the device.

921. The method of item 848, wherein the agent is delivered from a device, wherein the device further comprises a coating, and the coating indirectly contacts the device.

922. The method of item 848, wherein the agent is delivered from a device, wherein the device further comprises a coating, wherein the coating partially covers the device.

923. The method of item 848, wherein the agent is delivered from a device, wherein the device further comprises a coating, and the coating completely covers the device.

924. The method of item 848 wherein the agent is delivered from a device, wherein the fibrosing agent is located within pores or holes of the device.

925. The method of item 848 wherein the agent is delivered from a device, wherein the fibrosing agent is located within a channel, lumen, or divet of the device.

926. The method of item 848 wherein the agent is delivered from a device, wherein the device further comprising an echogenic material.

927. The method of item 848 wherein the agent is delivered from a device, wherein the device further comprises an echogenic material, wherein the echogenic material is in the form of a coating.

928. The method of item 848 wherein the agent is delivered from a device, wherein the device is sterile.

929. The method of item 848 wherein the agent is delivered from a device, wherein the fibrosing agent is released into tissue in the vicinity of the device after deployment of the device.

930. The method of item 848 wherein the agent is delivered from a device, wherein the fibrosing agent is released into tissue in the vicinity of the device after deployment of the device, wherein the tissue is connective tissue.

931. The method of item 848 wherein the agent is delivered from a device, wherein the fibrosing agent is released into tissue in the vicinity of the device after deployment of the device, wherein the tissue is muscle tissue.

932. The method of item 848 wherein the agent is delivered from a device, wherein the fibrosing agent is released into tissue in the vicinity of the device after deployment of the device, wherein the tissue is nerve tissue.

933. The method of item 848 wherein the agent is delivered from a device, wherein the fibrosing agent is released into tissue in the vicinity of the device after deployment of the device, wherein the tissue is epithelium tissue.

934. The method of item 848 wherein the agent is delivered from a device, wherein the fibrosing agent is released in effective concentrations from the device over a period ranging from the time of deployment of the device to about 1 year.

935. The method of item 848 wherein the agent is delivered from a device, wherein the fibrosing agent is released in effective concentrations from the device over a period ranging from about 1 month to 6 months.

936. The method of item 848 wherein the agent is delivered from a device, wherein the fibrosing agent is released in effective concentrations from the device over a period ranging from about 1–90 days.

937. The method of item 848 wherein the agent is delivered from a device, wherein the fibrosing agent is released in effective concentrations from the device at a constant rate.

938. The method of item 848 wherein the fibrosing agent is released in effective concentrations from the device at an increasing rate.

939. The method of item 848 wherein the agent is delivered from a device, wherein the fibrosing agent is released in effective concentrations from the device at a decreasing rate.

940. The method of item 848 wherein the agent is delivered from a device, wherein the device comprises about 0.01 µg to about 10 µg of the fibrosing agent.

941. The method of item 848 wherein the agent is delivered from a device, wherein the device comprises about 10 µg to about 10 mg of the fibrosing agent.

942. The method of item 848 wherein the agent is delivered from a device, wherein the device comprises about 10 mg to about 250 mg of the fibrosing agent.

943. The method of item 848 wherein the agent is delivered from a device, wherein the device comprises about 250 mg to about 1000 mg of the fibrosing agent.

944. The method of item 848 wherein the agent is delivered from a device, wherein the device comprises about 1000 mg to about 2500 mg of the fibrosing agent.

945. The method of item 848 wherein the agent is delivered from a device, wherein a surface of the device comprises less than 0.01 µg of the fibrosing agent per $mm^2$ of device surface to which the fibrosing agent is applied.

946. The method of item 848 wherein the agent is delivered from a device, wherein a surface of the device comprises about 0.01 µg to about 1 µg of the fibrosing agent per $mm^2$ of device surface to which the fibrosing agent is applied.

947. The method of item 848 wherein the agent is delivered from a device, wherein a surface of the device comprises about 1 µg to about 10 µg of the fibrosing agent per $mm^2$ of device surface to which the fibrosing agent is applied.

948. The method of item 848 wherein the agent is delivered from a device, wherein a surface of the device comprises about 10 µg to about 250 µg of the fibrosing agent per $mm^2$ of device surface to which the fibrosing agent is applied.

949. The method of item 848 wherein the agent is delivered from a device, wherein a surface of the device comprises about 250 µg to about 1000 µg of the fibrosing agent of fibrosing agent per $mm^2$ of device surface to which the fibrosing agent is applied.

950. The method of item 848 wherein the agent is delivered from a device, wherein a surface of the device comprises about 1000 µg to about 2500 µg of the fibrosing agent per $mm^2$ of device surface to which the fibrosing agent is applied.

951. The method of item 848, wherein the agent is delivered from a device, wherein the device further comprises a coating, and the coating is a uniform coating.

952. The method of item 848, wherein the agent is delivered from a device, wherein the device further comprises a coating, and the coating is a non-uniform coating.

953. The method of item 848, wherein the agent is delivered from a device, wherein the device further comprises a coating, and the coating is a discontinuous coating.

954. The method of item 848, wherein the agent is delivered from a device, wherein the device further comprises a coating, and the coating is a patterned coating.

955. The method of item 848, wherein the agent is delivered from a device, wherein the device further comprises a coating, and the coating has a thickness of 100 µm or less.

956. The method of item 848, wherein the agent is delivered from a device, wherein the device further comprises a coating, and the coating has a thickness of 10 µm or less.

957. The method of item 848, wherein the agent is delivered from a device, wherein the device further comprises a coating, and the coating adheres to the surface of the device upon deployment of the device.

958. The method of item 848, wherein the agent is delivered from a device, wherein the device further comprises a coating, and the coating is stable at room temperature for a period of at least 1 year.

959. The method of item 848, wherein the agent is delivered from a device, wherein the device further comprises a coating, and the fibrosing agent is present in the coating in an amount ranging between about 0.0001% to about 1% by weight.

960. The method of item 848, wherein the agent is delivered from a device, wherein the device further comprises a coating, and the fibrosing agent is present in the coating in an amount ranging between about 1% to about 10% by weight.

961. The method of item 848, wherein the agent is delivered from a device, wherein the device further comprises a coating, and the fibrosing agent is present in the coating in an amount ranging between about 10% to about 25% by weight.

962. The method of item 848, wherein the agent is delivered from a device, wherein the device further comprises a coating, and the fibrosing agent is present in the coating in an amount ranging between about 25% to about 70% by weight.

963. The method of item 848, wherein the agent is delivered from a device, wherein the device further comprises a coating, and the coating comprises a polymer.

964. The method of item 848, wherein the agent is delivered from a device, wherein the device comprises a first coating having a first composition and a second coating having a second composition.

965. The method of item 848, wherein the agent is delivered from a device, wherein the device comprises a first coating having a first composition and a second coating having a second composition, wherein the first composition and the second composition are different.

966. A method comprising introducing into a patient in need thereof, a therapeutically effective amount of a fibrosing agent or a composition comprising a fibrosing agent, where the fibrosing agent induces a fibrotic response at a specific site within the patient, thereby providing the patient with a fibrotic response between the patient and a soft palate implant.

967. The method of item 966 wherein the agent promotes regeneration.

968. The method of item 966 wherein the agent promotes angiogenesis.

969. The method of item 966 wherein the agent promotes fibroblast migration.

970. The method of item 966 wherein the agent promotes fibroblast proliferation.

971. The method of item 966 wherein the agent promotes deposition of extracellular matrix (ECM).

972. The method of item 966 wherein the agent promotes tissue remodeling.

973. The method of item 966 wherein the agent is an arterial vessel wall irritant.

974. The method of item 966 wherein the fibrosing agent is or comprises silk.

975. The method of item 966 wherein the fibrosing agent is in the form of tufts.

976. The method of item 966 wherein the fibrosing agent is or comprises mineral particles.

977. The method of item 966 wherein the fibrosing agent is or comprises chitosan.

978. The method of item 966 wherein the fibrosing agent is or comprises polylysine.

979. The method of item 966 wherein the fibrosing agent is or comprises fibronectin.

980. The method of item 966 wherein the fibrosing agent is or comprises bleomycin.

981. The method of item 966 wherein the fibrosing agent is or comprises CTGF.

982. The method of item 966 wherein the fibrosing agent is in the form of a thread, or is in contact with a thread.

983. The method of item 966 wherein the fibrosing agent is in the form of a particulate.

984. The method of item 966, wherein the composition comprises a polymer.

985. The method of item 966, wherein the composition comprises a polymer, and the polymer is, or comprises, a copolymer.

986. The method of item 966, wherein the composition comprises a polymer, and the polymer is, or comprises, a block copolymer.

987. The method of item 966, wherein the composition comprises a polymer, and the polymer is, or comprises, a random copolymer.

988. The method of item 966, wherein the composition comprises a polymer, and the polymer is, or comprises, a biodegradable polymer.

989. The method of item 966, wherein the composition comprises a polymer, and the polymer is, or comprises, a non-biodegradable polymer.

990. The method of item 966, wherein the composition comprises a polymer, and the polymer is, or comprises, a hydrophilic polymer.

991. The method of item 966, wherein the composition comprises a polymer, and the polymer is, or comprises, a hydrophobic polymer.

992. The method of item 966, wherein the composition comprises a polymer, and the polymer is, or comprises, a polymer having hydrophilic domains.

993. The method of item 966, wherein the composition comprises a polymer, and the polymer is, or comprises, a polymer having hydrophobic domains.

994. The method of item 966, wherein the composition comprises a polymer, and the polymer is, or comprises, a non-conductive polymer.

995. The method of item 966, wherein the composition comprises a polymer, and the polymer is, or comprises, an elastomer.

996. The method of item 966, wherein the composition comprises a polymer, and the polymer is, or comprises, a hydrogel.

997. The method of item 966, wherein the composition comprises a polymer, and the polymer is, or comprises, a silicone polymer.

998. The method of item 966, wherein the composition comprises a polymer, and the polymer is, or comprises, a hydrocarbon polymer.

999. The method of item 966, wherein the composition comprises a polymer, and the polymer is, or comprises, a styrene-derived polymer.

1000. The method of item 966, wherein the composition comprises a polymer, and the polymer is, or comprises, a butadiene-derived polymer.

1001. The method of item 966, wherein the composition comprises a polymer, and the polymer is, or comprises, a macromer.

1002. The method of item 966, wherein the composition comprises a polymer, and the polymer is, or comprises, a poly(ethylene glycol) polymer.

1003. The method of item 966, wherein the composition comprises a polymer, and the polymer is, or comprises, an amorphous polymer.

1004. The method of item 966, wherein the composition further comprises a second pharmaceutically active agent.

1005. The method of item 966, wherein the composition further comprises an anti-inflammatory agent.

1006. The method of item 966, wherein the composition further comprises an agent that inhibits infection.

1007. The method of item 966, wherein the composition further comprises an anthracycline.

1008. The method of item 966, wherein the composition further comprises doxorubicin.

1009. The method of item 966 wherein the composition further comprises mitoxantrone.

1010. The method of item 966 wherein the composition further comprises a fluoropyrimidine.

1011. The method of item 966, wherein the composition further comprises 5-fluorouracil (5-FU).

1012. The method of item 966, wherein the composition further comprises a folic acid antagonist.

1013. The method of item 966, wherein the composition further comprises methotrexate.

1014. The method of item 966, wherein the composition further comprises a podophylotoxin.

1015. The method of item 966, wherein the composition further comprises etoposide.

1016. The method of item 966, wherein the composition further comprises camptothecin.

1017. The method of item 966, wherein the composition further comprises a hydroxyurea.

1018. The method of item 966, wherein the composition further comprises a platinum complex.

1019. The method of item 966, wherein the composition further comprises cisplatin.

1020. The method of item 966 wherein the composition further comprises an anti-thrombotic agent.

1021. The method of item 966, wherein the composition further comprises a visualization agent.

1022. The method of item 966, wherein the composition further comprises a visualization agent, and the visualization agent is a radiopaque material, wherein the radiopaque material comprises a metal, a halogenated compound, or a barium containing compound.

1023. The method of item 966, wherein the composition further comprises a visualization agent, and the visualization agent is, or comprises, barium, tantalum, or technetium.

1024. The method of item 966, wherein the composition further comprises a visualization agent, and the visualization agent is, or comprises, an MRI responsive material.

1025. The method of item 966, wherein the composition further comprises a visualization agent, and the visualization agent is, or comprises, a gadolinium chelate.

1026. The method of item 966, wherein the composition further comprises a visualization agent, and the visualization agent is, or comprises, iron, magnesium, manganese, copper, or chromium.

1027. The method of item 966, wherein the composition further comprises a visualization agent, and the visualization agent is, or comprises, iron oxide compound.

1028. The method of item 966, wherein the composition further comprises a visualization agent, and the visualization agent is, or comprises, a dye, pigment, or colorant.

1029. The method of item 966 wherein the fibrosing agent is released in effective concentrations from the composition comprising the fibrosing agent by diffusion over a period ranging from the time of administration to about 90 days.

1030. The method of item 966 wherein the fibrosing agent is released in effective concentrations from the composition comprising the fibrosing agent by erosion of the composition over a period ranging from the time of administration to about 90 days.

1031. The method of item 966 wherein the composition further comprises an inflammatory cytokine.

1032. The method of item 966 wherein the composition further comprises an agent that stimulates cell proliferation.

1033. The method of item 966 wherein the composition further comprises a polymeric carrier.

1034. The method of item 966 wherein the composition is in the form of a gel, paste, or spray.

1035. The method of item 966 wherein the agent is delivered from a device, and the device delivers the fibrosing agent locally to tissue proximate to the device.

1036. The method of item 966 wherein the agent is delivered from a device, wherein the device further comprises a coating, and the coating comprises the fibrosing agent.

1037. The method of item 966 wherein the agent is delivered from a device, wherein the device further comprises a coating, and the coating is disposed on a surface of the device.

1038. The method of item 966, wherein the agent is delivered from a device, wherein the device further comprises a coating, and the coating directly contacts the device.

1039. The method of item 966, wherein the agent is delivered from a device, wherein the device further comprises a coating, and the coating indirectly contacts the device.

1040. The method of item 966 wherein the agent is delivered from a device, wherein the device further comprises a coating, wherein the coating partially covers the device.

1041. The method of item 966, wherein the agent is delivered from a device, wherein the device further comprises a coating, and the coating completely covers the device.

1042. The method of item 966 wherein the agent is delivered from a device, wherein the fibrosing agent is located within pores or holes of the device.

1043. The method of item 966 wherein the agent is delivered from a device, wherein the fibrosing agent is located within a channel, lumen, or divet of the device.

1044. The method of item 966 wherein the agent is delivered from a device, wherein the device further comprising an echogenic material.

1045. The method of item 966 wherein the agent is delivered from a device, wherein the device further comprises an echogenic material, wherein the echogenic material is in the form of a coating.

1046. The method of item 966 wherein the agent is delivered from a device, wherein the device is sterile.

1047. The method of item 966 wherein the agent is delivered from a device, wherein the fibrosing agent is released into tissue in the vicinity of the device after deployment of the device.

1048. The method of item 966 wherein the agent is delivered from a device, wherein the fibrosing agent is released into tissue in the vicinity of the device after deployment of the device, wherein the tissue is connective tissue.

1049. The method of item 966 wherein the agent is delivered from a device, wherein the fibrosing agent is released into tissue in the vicinity of the device after deployment of the device, wherein the tissue is muscle tissue.

1050. The method of item 966 wherein the agent is delivered from a device, wherein the fibrosing agent is released into tissue in the vicinity of the device after deployment of the device, wherein the tissue is nerve tissue.

1051. The method of item 966 wherein the agent is delivered from a device, wherein the fibrosing agent is released into tissue in the vicinity of the device after deployment of the device, wherein the tissue is epithelium tissue.

1052. The method of item 966 wherein the agent is delivered from a device, wherein the fibrosing agent is released in effective concentrations from the device over a period ranging from the time of deployment of the device to about 1 year.

1053. The method of item 966 wherein the agent is delivered from a device, wherein the fibrosing agent is released in effective concentrations from the device over a period ranging from about 1 month to 6 months.

1054. The method of item 966 wherein the agent is delivered from a device, wherein the fibrosing agent is released in effective concentrations from the device over a period ranging from about 1–90 days.

1055. The method of item 966 wherein the agent is delivered from a device, wherein the fibrosing agent is released in effective concentrations from the device at a constant rate.

1056. The method of item 966 wherein the fibrosing agent is released in effective concentrations from the device at an increasing rate.

1057. The method of item 966 wherein the agent is delivered from a device, wherein the fibrosing agent is released in effective concentrations from the device at a decreasing rate.

1058. The method of item 966 wherein the agent is delivered from a device, wherein the device comprises about 0.01 μg to about 10 μg of the fibrosing agent.

1059. The method of item 966 wherein the agent is delivered from a device, wherein the device comprises about 10 μg to about 10 mg of the fibrosing agent.

1060. The method of item 966 wherein the agent is delivered from a device, wherein the device comprises about 10 mg to about 250 mg of the fibrosing agent.

1061. The method of item 966 wherein the agent is delivered from a device, wherein the device comprises about 250 mg to about 1000 mg of the fibrosing agent.

1062. The method of item 966 wherein the agent is delivered from a device, wherein the device comprises about 1000 mg to about 2500 mg of the fibrosing agent.

1063. The method of item 966 wherein the agent is delivered from a device, wherein a surface of the device comprises less than 0.01 μg of the fibrosing agent per mm² of device surface to which the fibrosing agent is applied.

1064. The method of item 966 wherein the agent is delivered from a device, wherein a surface of the device comprises about 0.01 μg to about 1 μg of the fibrosing agent per mm² of device surface to which the fibrosing agent is applied.

1065. The method of item 966 wherein the agent is delivered from a device, wherein a surface of the device comprises about 1 μg to about 10 μg of the fibrosing agent per mm² of device surface to which the fibrosing agent is applied.

1066. The method of item 966 wherein the agent is delivered from a device, wherein a surface of the device comprises about 10 μg to about 250 μg of the fibrosing agent per mm² of device surface to which the fibrosing agent is applied.

1067. The method of item 966 wherein the agent is delivered from a device, wherein a surface of the device comprises about 250 μg to about 1000 μg of the fibrosing agent of fibrosing agent per mm² of device surface to which the fibrosing agent is applied.

1068. The method of item 966 wherein the agent is delivered from a device, wherein a surface of the device comprises about 1000 μg to about 2500 μg of the fibrosing agent per mm² of device surface to which the fibrosing agent is applied.

1069. The method of item 966, wherein the agent is delivered from a device, wherein the device further comprises a coating, and the coating is a uniform coating.

1070. The method of item 966, wherein the agent is delivered from a device, wherein the device further comprises a coating, and the coating is a non-uniform coating.

1071. The method of item 966, wherein the agent is delivered from a device, wherein the device further comprises a coating, and the coating is a discontinuous coating.

1072. The method of item 966, wherein the agent is delivered from a device, wherein the device further comprises a coating, and the coating is a patterned coating.

1073. The method of item 966, wherein the agent is delivered from a device, wherein the device further comprises a coating, and the coating has a thickness of 100 μm or less.

1074. The method of item 966, wherein the agent is delivered from a device, wherein the device further comprises a coating, and the coating has a thickness of 10 μm or less.

1075. The method of item 966, wherein the agent is delivered from a device, wherein the device further comprises a coating, and the coating adheres to the surface of the device upon deployment of the device.

1076. The method of item 966, wherein the agent is delivered from a device, wherein the device further comprises a coating, and the coating is stable at room temperature for a period of at least 1 year.

1077. The method of item 966, wherein the agent is delivered from a device, wherein the device further comprises a coating, and the fibrosing agent is present in the coating in an amount ranging between about 0.0001% to about 1% by weight.

1078. The method of item 966, wherein the agent is delivered from a device, wherein the device further comprises a coating, and the fibrosing agent is present in the coating in an amount ranging between about 1% to about 10% by weight.

1079. The method of item 966, wherein the agent is delivered from a device, wherein the device further comprises a coating, and the fibrosing agent is present in the coating in an amount ranging between about 10% to about 25% by weight.

1080. The method of item 966, wherein the agent is delivered from a device, wherein the device further comprises a coating, and the fibrosing agent is present in the coating in an amount ranging between about 25% to about 70% by weight.

1081. The method of item 966, wherein the agent is delivered from a device, wherein the device further comprises a coating, and the coating comprises a polymer.

1082. The method of item 966, wherein the agent is delivered from a device, wherein the device comprises a first coating having a first composition and a second coating having a second composition.

1083. The method of item 966, wherein the agent is delivered from a device, wherein the device comprises a first coating having a first composition and a second coating having a second composition, wherein the first composition and the second composition are different.

1084. A method comprising introducing into a patient in need thereof, a therapeutically effective amount of a fibrosing agent or a composition comprising a fibrosing agent, where the fibrosing agent induces a fibrotic response at a specific site within the patient, thereby providing the patient with treatment for obesity.

1085. The method of item 1084 wherein the agent promotes regeneration.

1086. The method of item 1084 wherein the agent promotes angiogenesis.

1087. The method of item 1084 wherein the agent promotes fibroblast migration.

1088. The method of item 1084 wherein the agent promotes fibroblast proliferation.

1089. The method of item 1084 wherein the agent promotes deposition of extracellular matrix (ECM).

1090. The method of item 1084 wherein the agent promotes tissue remodeling.

1091. The method of item 1084 wherein the agent is an arterial vessel wall irritant.

1092. The method of item 1084 wherein the fibrosing agent is or comprises silk.

1093. The method of item 1084 wherein the fibrosing agent is in the form of tufts.

1094. The method of item 1084 wherein the fibrosing agent is or comprises mineral particles.

1095. The method of item 1084 wherein the fibrosing agent is or comprises chitosan.

1096. The method of item 1084 wherein the fibrosing agent is or comprises polylysine.

1097. The method of item 1084 wherein the fibrosing agent is or comprises fibronectin.

1098. The method of item 1084 wherein the fibrosing agent is or comprises bleomycin.

1099. The method of item 1084 wherein the fibrosing agent is or comprises CTGF.

1100. The method of item 1084 wherein the fibrosing agent is in the form of a thread, or is in contact with a thread.

1101. The method of item 1084 wherein the fibrosing agent is in the form of a particulate.

1102. The method of item 1084, wherein the composition comprises a polymer.

1103. The method of item 1084, wherein the composition comprises a polymer, and the polymer is, or comprises, a copolymer.

1104. The method of item 1084, wherein the composition comprises a polymer, and the polymer is, or comprises, a block copolymer.

1105. The method of item 1084, wherein the composition comprises a polymer, and the polymer is, or comprises, a random copolymer.

1106. The method of item 1084, wherein the composition comprises a polymer, and the polymer is, or comprises, a biodegradable polymer.

1107. The method of item 1084, wherein the composition comprises a polymer, and the polymer is, or comprises, a non-biodegradable polymer.

1108. The method of item 1084, wherein the composition comprises a polymer, and the polymer is, or comprises, a hydrophilic polymer.

1109. The method of item 1084, wherein the composition comprises a polymer, and the polymer is, or comprises, a hydrophobic polymer.

1110. The method of item 1084, wherein the composition comprises a polymer, and the polymer is, or comprises, a polymer having hydrophilic domains.

1111. The method of item 1084, wherein the composition comprises a polymer, and the polymer is, or comprises, a polymer having hydrophobic domains.

1112. The method of item 1084, wherein the composition comprises a polymer, and the polymer is, or comprises, a non-conductive polymer.

1113. The method of item 1084, wherein the composition comprises a polymer, and the polymer is, or comprises, an elastomer.

1114. The method of item 1084, wherein the composition comprises a polymer, and the polymer is, or comprises, a hydrogel.

1115. The method of item 1084, wherein the composition comprises a polymer, and the polymer is, or comprises, a silicone polymer.

1116. The method of item 1084, wherein the composition comprises a polymer, and the polymer is, or comprises, a hydrocarbon polymer.

1117. The method of item 1084, wherein the composition comprises a polymer, and the polymer is, or comprises, a styrene-derived polymer.

1118. The method of item 1084, wherein the composition comprises a polymer, and the polymer is, or comprises, a butadiene-derived polymer.

1119. The method of item 1084, wherein the composition comprises a polymer, and the polymer is, or comprises, a macromer.

1120. The method of item 1084, wherein the composition comprises a polymer, and the polymer is, or comprises, a poly(ethylene glycol) polymer.

1121. The method of item 1084, wherein the composition comprises a polymer, and the polymer is, or comprises, an amorphous polymer.

1122. The method of item 1084, wherein the composition further comprises a second pharmaceutically active agent.

1123. The method of item 1084, wherein the composition further comprises an anti-inflammatory agent.

1124. The method of item 1084, wherein the composition further comprises an agent that inhibits infection.

1125. The method of item 1084, wherein the composition further comprises an anthracycline.

1126. The method of item 1084, wherein the composition further comprises doxorubicin.

1127. The method of item 1084 wherein the composition further comprises mitoxantrone.

1128. The method of item 1084 wherein the composition further comprises a fluoropyrimidine.

1129. The method of item 1084, wherein the composition further comprises 5-fluorouracil (5-FU).

1130. The method of item 1084, wherein the composition further comprises a folic acid antagonist.

1131. The method of item 1084, wherein the composition further comprises methotrexate.

1132. The method of item 1084, wherein the composition further comprises a podophylotoxin.

1133. The method of item 1084, wherein the composition further comprises etoposide.

1134. The method of item 1084, wherein the composition further comprises camptothecin.

1135. The method of item 1084, wherein the composition further comprises a hydroxyurea.

1136. The method of item 1084, wherein the composition further comprises a platinum complex.

1137. The method of item 1084, wherein the composition further comprises cisplatin.

1138. The method of item 1084 wherein the composition further comprises an anti-thrombotic agent.

1139. The method of item 1084, wherein the composition further comprises a visualization agent.

1140. The method of item 1084, wherein the composition further comprises a visualization agent, and the visualization agent is a radiopaque material, wherein the radiopaque material comprises a metal, a halogenated compound, or a barium containing compound.

1141. The method of item 1084, wherein the composition further comprises a visualization agent, and the visualization agent is, or comprises, barium, tantalum, or technetium.

1142. The method of item 1084, wherein the composition further comprises a visualization agent, and the visualization agent is, or comprises, an MRI responsive material.

1143. The method of item 1084, wherein the composition further comprises a visualization agent, and the visualization agent is, or comprises, a gadolinium chelate.

1144. The method of item 1084, wherein the composition further comprises a visualization agent, and the visualization agent is, or comprises, iron, magnesium, manganese, copper, or chromium.

1145. The method of item 1084, wherein the composition further comprises a visualization agent, and the visualization agent is, or comprises, iron oxide compound.

1146. The method of item 1084, wherein the composition further comprises a visualization agent, and the visualization agent is, or comprises, a dye, pigment, or colorant.

1147. The method of item 1084 wherein the fibrosing agent is released in effective concentrations from the composition comprising the fibrosing agent by diffusion over a period ranging from the time of administration to about 90 days.

1148. The method of item 1084 wherein the fibrosing agent is released in effective concentrations from the composition comprising the fibrosing agent by erosion of the composition over a period ranging from the time of administration to about 90 days.

1149. The method of item 1084 wherein the composition further comprises an inflammatory cytokine.

1150. The method of item 1084 wherein the composition further comprises an agent that stimulates cell proliferation.

1151. The method of item 1084 wherein the composition further comprises a polymeric carrier.

1152. The method of item 1084 wherein the composition is in the form of a gel, paste, or spray.

1153. The method of item 1084 wherein the agent is delivered from a device, and the device delivers the fibrosing agent locally to tissue proximate to the device.

1154. The method of item 1084 wherein the agent is delivered from a device, wherein the device further comprises a coating, and the coating comprises the fibrosing agent.

1155. The method of item 1084 wherein the agent is delivered from a device, wherein the device further comprises a coating, and the coating is disposed on a surface of the device.

1156. The method of item 1084, wherein the agent is delivered from a device, wherein the device further comprises a coating, and the coating directly contacts the device.

1157. The method of item 1084, wherein the agent is delivered from a device, wherein the device further comprises a coating, and the coating indirectly contacts the device.

1158. The method of item 1084 wherein the agent is delivered from a device, wherein the device further comprises a coating, wherein the coating partially covers the device.

1159. The method of item 1084, wherein the agent is delivered from a device, wherein the device further comprises a coating, and the coating completely covers the device.

1160. The method of item 1084 wherein the agent is delivered from a device, wherein the fibrosing agent is located within pores or holes of the device.

1161. The method of item 1084 wherein the agent is delivered from a device, wherein the fibrosing agent is located within a channel, lumen, or divet of the device.

1162. The method of item 1084 wherein the agent is delivered from a device, wherein the device further comprising an echogenic material.

1163. The method of item 1084 wherein the agent is delivered from a device, wherein the device further comprises an echogenic material, wherein the echogenic material is in the form of a coating.

1164. The method of item 1084 wherein the agent is delivered from a device, wherein the device is sterile.

1165. The method of item 1084 wherein the agent is delivered from a device, wherein the fibrosing agent is released into tissue in the vicinity of the device after deployment of the device.

1166. The method of item 1084 wherein the agent is delivered from a device, wherein the fibrosing agent is released into tissue in the vicinity of the device after deployment of the device, wherein the tissue is connective tissue.

1167. The method of item 1084 wherein the agent is delivered from a device, wherein the fibrosing agent is released into tissue in the vicinity of the device after deployment of the device, wherein the tissue is muscle tissue.

1168. The method of item 1084 wherein the agent is delivered from a device, wherein the fibrosing agent is released into tissue in the vicinity of the device after deployment of the device, wherein the tissue is nerve tissue.

1169. The method of item 1084 wherein the agent is delivered from a device, wherein the fibrosing agent is released into tissue in the vicinity of the device after deployment of the device, wherein the tissue is epithelium tissue.

1170. The method of item 1084 wherein the agent is delivered from a device, wherein the fibrosing agent is released in effective concentrations from the device over a period ranging from the time of deployment of the device to about 1 year.

1171. The method of item 1084 wherein the agent is delivered from a device, wherein the fibrosing agent is released in effective concentrations from the device over a period ranging from about 1 month to 6 months.

1172. The method of item 1084 wherein the agent is delivered from a device, wherein the fibrosing agent is released in effective concentrations from the device over a period ranging from about 1–90 days.

1173. The method of item 1084 wherein the agent is delivered from a device, wherein the fibrosing agent is released in effective concentrations from the device at a constant rate.

1174. The method of item 1084 wherein the fibrosing agent is released in effective concentrations from the device at an increasing rate.

1175. The method of item 1084 wherein the agent is delivered from a device, wherein the fibrosing agent is released in effective concentrations from the device at a decreasing rate.

1176. The method of item 1084 wherein the agent is delivered from a device, wherein the device comprises about 0.01 μg to about 10 μg of the fibrosing agent.

1177. The method of item 1084 wherein the agent is delivered from a device, wherein the device comprises about 10 μg to about 10 mg of the fibrosing agent.

1178. The method of item 1084 wherein the agent is delivered from a device, wherein the device comprises about 10 mg to about 250 mg of the fibrosing agent.

1179. The method of item 1084 wherein the agent is delivered from a device, wherein the device comprises about 250 mg to about 1000 mg of the fibrosing agent.

1180. The method of item 1084 wherein the agent is delivered from a device, wherein the device comprises about 1000 mg to about 2500 mg of the fibrosing agent.

1181. The method of item 1084 wherein the agent is delivered from a device, wherein a surface of the device comprises less than 0.01 μg of the fibrosing agent per mm$^2$ of device surface to which the fibrosing agent is applied.

1182. The method of item 1084 wherein the agent is delivered from a device, wherein a surface of the device comprises about 0.01 μg to about 1 μg of the fibrosing agent per mm$^2$ of device surface to which the fibrosing agent is applied.

1183. The method of item 1084 wherein the agent is delivered from a device, wherein a surface of the device comprises about 1 μg to about 10 μg of the fibrosing agent per mm$^2$ of device surface to which the fibrosing agent is applied.

1184. The method of item 1084 wherein the agent is delivered from a device, wherein a surface of the device comprises about 10 μg to about 250 μg of the fibrosing agent per mm$^2$ of device surface to which the fibrosing agent is applied.

1185. The method of item 1084 wherein the agent is delivered from a device, wherein a surface of the device comprises about 250 μg to about 1000 μg of the fibrosing agent of fibrosing agent per mm$^2$ of device surface to which the fibrosing agent is applied.

1186. The method of item 1084 wherein the agent is delivered from a device, wherein a surface of the device comprises about 1000 μg to about 2500 μg of the fibrosing agent per mm$^2$ of device surface to which the fibrosing agent is applied.

1187. The method of item 1084, wherein the agent is delivered from a device, wherein the device further comprises a coating, and the coating is a uniform coating.

1188. The method of item 1084, wherein the agent is delivered from a device, wherein the device further comprises a coating, and the coating is a non-uniform coating.

1189. The method of item 1084, wherein the agent is delivered from a device, wherein the device further comprises a coating, and the coating is a discontinuous coating.

1190. The method of item 1084, wherein the agent is delivered from a device, wherein the device further comprises a coating, and the coating is a patterned coating.

1191. The method of item 1084, wherein the agent is delivered from a device, wherein the device further comprises a coating, and the coating has a thickness of 100 μm or less.

1192. The method of item 1084, wherein the agent is delivered from a device, wherein the device further comprises a coating, and the coating has a thickness of 10 μm or less.

1193. The method of item 1084, wherein the agent is delivered from a device, wherein the device further comprises a coating, and the coating adheres to the surface of the device upon deployment of the device.

1194. The method of item 1084, wherein the agent is delivered from a device, wherein the device further comprises a coating, and the coating is stable at room temperature for a period of at least 1 year.

1195. The method of item 1084, wherein the agent is delivered from a device, wherein the device further comprises a coating, and the fibrosing agent is present in the coating in an amount ranging between about 0.0001% to about 1% by weight.

1196. The method of item 1084, wherein the agent is delivered from a device, wherein the device further comprises a coating, and the fibrosing agent is present in the coating in an amount ranging between about 1% to about 10% by weight.

1197. The method of item 1084, wherein the agent is delivered from a device, wherein the device further comprises a coating, and the fibrosing agent is present in the coating in an amount ranging between about 10% to about 25% by weight.

1198. The method of item 1084, wherein the agent is delivered from a device, wherein the device further comprises a coating, and the fibrosing agent is present in the coating in an amount ranging between about 25% to about 70% by weight.

1199. The method of item 1084, wherein the agent is delivered from a device, wherein the device further comprises a coating, and the coating comprises a polymer.

1200. The method of item 1084, wherein the agent is delivered from a device, wherein the device comprises a first coating having a first composition and a second coating having a second composition.

1201. The method of item 1084, wherein the agent is delivered from a device, wherein the device comprises a first coating having a first composition and a second coating having a second composition, wherein the first composition and the second composition are different.

1202. A method comprising introducing into a patient in need thereof, a therapeutically effective amount of a fibrosing agent or a composition comprising a fibrosing agent, where the fibrosing agent induces a fibrotic response at a specific site within the patient, thereby providing the patient with treatment for GERD.

1203. The method of item 1202 wherein the agent promotes regeneration.

1204. The method of item 1202 wherein the agent promotes angiogenesis.

1205. The method of item 1202 wherein the agent promotes fibroblast migration.

1206. The method of item 1202 wherein the agent promotes fibroblast proliferation.

1207. The method of item 1202 wherein the agent promotes deposition of extracellular matrix (ECM).

1208. The method of item 1202 wherein the agent promotes tissue remodeling.

1209. The method of item 1202 wherein the agent is an arterial vessel wall irritant.

1210. The method of item 1202 wherein the fibrosing agent is or comprises silk.

1211. The method of item 1202 wherein the fibrosing agent is in the form of tufts.

1212. The method of item 1202 wherein the fibrosing agent is or comprises mineral particles.

1213. The method of item 1202 wherein the fibrosing agent is or comprises chitosan.

1214. The method of item 1202 wherein the fibrosing agent is or comprises polylysine.

1215. The method of item 1202 wherein the fibrosing agent is or comprises fibronectin.

1216. The method of item 1202 wherein the fibrosing agent is or comprises bleomycin.

1217. The method of item 1202 wherein the fibrosing agent is or comprises CTGF.

1218. The method of item 1202 wherein the fibrosing agent is in the form of a thread, or is in contact with a thread.

1219. The method of item 1202 wherein the fibrosing agent is in the form of a particulate.

1220. The method of item 1202, wherein the composition comprises a polymer.

1221. The method of item 1202, wherein the composition comprises a polymer, and the polymer is, or comprises, a copolymer.

1222. The method of item 1202, wherein the composition comprises a polymer, and the polymer is, or comprises, a block copolymer.

1223. The method of item 1202, wherein the composition comprises a polymer, and the polymer is, or comprises, a random copolymer.

1224. The method of item 1202, wherein the composition comprises a polymer, and the polymer is, or comprises, a biodegradable polymer.

1225. The method of item 1202, wherein the composition comprises a polymer, and the polymer is, or comprises, a non-biodegradable polymer.

1226. The method of item 1202, wherein the composition comprises a polymer, and the polymer is, or comprises, a hydrophilic polymer.

1227. The method of item 1202, wherein the composition comprises a polymer, and the polymer is, or comprises, a hydrophobic polymer.

1228. The method of item 1202, wherein the composition comprises a polymer, and the polymer is, or comprises, a polymer having hydrophilic domains.

1229. The method of item 1202, wherein the composition comprises a polymer, and the polymer is, or comprises, a polymer having hydrophobic domains.

1230. The method of item 1202, wherein the composition comprises a polymer, and the polymer is, or comprises, a non-conductive polymer.

1231. The method of item 1202, wherein the composition comprises a polymer, and the polymer is, or comprises, an elastomer.

1232. The method of item 1202, wherein the composition comprises a polymer, and the polymer is, or comprises, a hydrogel.

1233. The method of item 1202, wherein the composition comprises a polymer, and the polymer is, or comprises, a silicone polymer.

1234. The method of item 1202, wherein the composition comprises a polymer, and the polymer is, or comprises, a hydrocarbon polymer.

1235. The method of item 1202, wherein the composition comprises a polymer, and the polymer is, or comprises, a styrene-derived polymer.

1236. The method of item 1202, wherein the composition comprises a polymer, and the polymer is, or comprises, a butadiene-derived polymer.

1237. The method of item 1202, wherein the composition comprises a polymer, and the polymer is, or comprises, a macromer.

1238. The method of item 1202, wherein the composition comprises a polymer, and the polymer is, or comprises, a poly(ethylene glycol) polymer.

1239. The method of item 1202, wherein the composition comprises a polymer, and the polymer is, or comprises, an amorphous polymer.

1240. The method of item 1202, wherein the composition further comprises a second pharmaceutically active agent.

1241. The method of item 1202, wherein the composition further comprises an anti-inflammatory agent.

1242. The method of item 1202, wherein the composition further comprises an agent that inhibits infection.

1243. The method of item 1202, wherein the composition further comprises an anthracycline.

1244. The method of item 1202, wherein the composition further comprises doxorubicin.

1245. The method of item 1202 wherein the composition further comprises mitoxantrone.

1246. The method of item 1202, wherein the composition further comprises a fluoropyrimidine.

1247. The method of item 1202, wherein the composition further comprises 5-fluorouracil (5-FU).

1248. The method of item 1202, wherein the composition further comprises a folic acid antagonist.

1249. The method of item 1202, wherein the composition further comprises methotrexate.

1250. The method of item 1202, wherein the composition further comprises a podophylotoxin.

1251. The method of item 1202, wherein the composition further comprises etoposide.

1252. The method of item 1202, wherein the composition further comprises camptothecin.

1253. The method of item 1202, wherein the composition further comprises a hydroxyurea.

1254. The method of item 1202, wherein the composition further comprises a platinum complex.

1255. The method of item 1202, wherein the composition further comprises cisplatin.

1256. The method of item 1202 wherein the composition further comprises an anti-thrombotic agent.

1257. The method of item 1202, wherein the composition further comprises a visualization agent.

1258. The method of item 1202, wherein the composition further comprises a visualization agent, and the visualization agent is a radiopaque material, wherein the radiopaque material comprises a metal, a halogenated compound, or a barium containing compound.

1259. The method of item 1202, wherein the composition further comprises a visualization agent, and the visualization agent is, or comprises, barium, tantalum, or technetium.

1260. The method of item 1202, wherein the composition further comprises a visualization agent, and the visualization agent is, or comprises, an MRI responsive material.

1261. The method of item 1202, wherein the composition further comprises a visualization agent, and the visualization agent is, or comprises, a gadolinium chelate.

1262. The method of item 1202, wherein the composition further comprises a visualization agent, and the visualization agent is, or comprises, iron, magnesium, manganese, copper, or chromium.

1263. The method of item 1202, wherein the composition further comprises a visualization agent, and the visualization agent is, or comprises, iron oxide compound.

1264. The method of item 1202, wherein the composition further comprises a visualization agent, and the visualization agent is, or comprises, a dye, pigment, or colorant.

1265. The method of item 1202 wherein the fibrosing agent is released in effective concentrations from the composition comprising the fibrosing agent by diffusion over a period ranging from the time of administration to about 90 days.

1266. The method of item 1202 wherein the fibrosing agent is released in effective concentrations from the composition comprising the fibrosing agent by erosion of the composition over a period ranging from the time of administration to about 90 days.

1267. The method of item 1202 wherein the composition further comprises an inflammatory cytokine.

1268. The method of item 1202 wherein the composition further comprises an agent that stimulates cell proliferation.

1269. The method of item 1202 wherein the composition further comprises a polymeric carrier.

1270. The method of item 1202 wherein the composition is in the form of a gel, paste, or spray.

1271. The method of item 1202 wherein the agent is delivered from a device, and the device delivers the fibrosing agent locally to tissue proximate to the device.

1272. The method of item 1202 wherein the agent is delivered from a device, wherein the device further comprises a coating, and the coating comprises the fibrosing agent.

1273. The method of item 1202 wherein the agent is delivered from a device, wherein the device further comprises a coating, and the coating is disposed on a surface of the device.

1274. The method of item 1202, wherein the agent is delivered from a device, wherein the device further comprises a coating, and the coating directly contacts the device.

1275. The method of item 1202, wherein the agent is delivered from a device, wherein the device further comprises a coating, and the coating indirectly contacts the device.

1276. The method of item 1202 wherein the agent is delivered from a device, wherein the device further comprises a coating, wherein the coating partially covers the device.

1277. The method of item 1202, wherein the agent is delivered from a device, wherein the device further comprises a coating, and the coating completely covers the device.

1278. The method of item 1202 wherein the agent is delivered from a device, wherein the fibrosing agent is located within pores or holes of the device.

1279. The method of item 1202 wherein the agent is delivered from a device, wherein the fibrosing agent is located within a channel, lumen, or divet of the device.

1280. The method of item 1202 wherein the agent is delivered from a device, wherein the device further comprising an echogenic material.

1281. The method of item 1202 wherein the agent is delivered from a device, wherein the device further comprises an echogenic material, wherein the echogenic material is in the form of a coating.

1282. The method of item 1202 wherein the agent is delivered from a device, wherein the device is sterile.

1283. The method of item 1202 wherein the agent is delivered from a device, wherein the fibrosing agent is released into tissue in the vicinity of the device after deployment of the device.

1284. The method of item 1202 wherein the agent is delivered from a device, wherein the fibrosing agent is released into tissue in the vicinity of the device after deployment of the device, wherein the tissue is connective tissue.

1285. The method of item 1202 wherein the agent is delivered from a device, wherein the fibrosing agent is released into tissue in the vicinity of the device after deployment of the device, wherein the tissue is muscle tissue.

1286. The method of item 1202 wherein the agent is delivered from a device, wherein the fibrosing agent is released into tissue in the vicinity of the device after deployment of the device, wherein the tissue is nerve tissue.

1287. The method of item 1202 wherein the agent is delivered from a device, wherein the fibrosing agent is released into tissue in the vicinity of the device after deployment of the device, wherein the tissue is epithelium tissue.

1288. The method of item 1202 wherein the agent is delivered from a device, wherein the fibrosing agent is released in effective concentrations from the device over a period ranging from the time of deployment of the device to about 1 year.

1289. The method of item 1202 wherein the agent is delivered from a device, wherein the fibrosing agent is released in effective concentrations from the device over a period ranging from about 1 month to 6 months.

1290. The method of item 1202 wherein the agent is delivered from a device, wherein the fibrosing agent is released in effective concentrations from the device over a period ranging from about 1–90 days.

1291. The method of item 1202 wherein the agent is delivered from a device, wherein the fibrosing agent is released in effective concentrations from the device at a constant rate.

1292. The method of item 1202 wherein the fibrosing agent is released in effective concentrations from the device at an increasing rate.

1293. The method of item 1202 wherein the agent is delivered from a device, wherein the fibrosing agent is released in effective concentrations from the device at a decreasing rate.

1294. The method of item 1202 wherein the agent is delivered from a device, wherein the device comprises about 0.01 µg to about 10 µg of the fibrosing agent.

1295. The method of item 1202 wherein the agent is delivered from a device, wherein the device comprises about 10 µg to about 10 mg of the fibrosing agent.

1296. The method of item 1202 wherein the agent is delivered from a device, wherein the device comprises about 10 mg to about 250 mg of the fibrosing agent.

1297. The method of item 1202 wherein the agent is delivered from a device, wherein the device comprises about 250 mg to about 1000 mg of the fibrosing agent.

1298. The method of item 1202 wherein the agent is delivered from a device, wherein the device comprises about 1000 mg to about 2500 mg of the fibrosing agent.

1299. The method of item 1202 wherein the agent is delivered from a device, wherein a surface of the device comprises less than 0.01 µg of the fibrosing agent per mm$^2$ of device surface to which the fibrosing agent is applied.

1300. The method of item 1202 wherein the agent is delivered from a device, wherein a surface of the device comprises about 0.01 µg to about 1 µg of the fibrosing agent per mm$^2$ of device surface to which the fibrosing agent is applied.

1301. The method of item 1202 wherein the agent is delivered from a device, wherein a surface of the device comprises about 1 µg to about 10 µg of the fibrosing agent per mm² of device surface to which the fibrosing agent is applied.

1302. The method of item 1202 wherein the agent is delivered from a device, wherein a surface of the device comprises about 10 µg to about 250 µg of the fibrosing agent per mm² of device surface to which the fibrosing agent is applied.

1303. The method of item 1202 wherein the agent is delivered from a device, wherein a surface of the device comprises about 250 µg to about 1000 µg of the fibrosing agent of fibrosing agent per mm² of device surface to which the fibrosing agent is applied.

1304. The method of item 1202 wherein the agent is delivered from a device, wherein a surface of the device comprises about 1000 µg to about 2500 µg of the fibrosing agent per mm² of device surface to which the fibrosing agent is applied.

1305. The method of item 1202, wherein the agent is delivered from a device, wherein the device further comprises a coating, and the coating is a uniform coating.

1306. The method of item 1202, wherein the agent is delivered from a device, wherein the device further comprises a coating, and the coating is a non-uniform coating.

1307. The method of item 1202, wherein the agent is delivered from a device, wherein the device further comprises a coating, and the coating is a discontinuous coating.

1308. The method of item 1202, wherein the agent is delivered from a device, wherein the device further comprises a coating, and the coating is a patterned coating.

1309. The method of item 1202, wherein the agent is delivered from a device, wherein the device further comprises a coating, and the coating has a thickness of 100 µm or less.

1310. The method of item 1202, wherein the agent is delivered from a device, wherein the device further comprises a coating, and the coating has a thickness of 10 µm or less.

1311. The method of item 1202, wherein the agent is delivered from a device, wherein the device further comprises a coating, and the coating adheres to the surface of the device upon deployment of the device.

1312. The method of item 1202, wherein the agent is delivered from a device, wherein the device further comprises a coating, and the coating is stable at room temperature for a period of at least 1 year.

1313. The method of item 1202, wherein the agent is delivered from a device, wherein the device further comprises a coating, and the fibrosing agent is present in the coating in an amount ranging between about 0.0001% to about 1% by weight.

1314. The method of item 1202, wherein the agent is delivered from a device, wherein the device further comprises a coating, and the fibrosing agent is present in the coating in an amount ranging between about 1% to about 10% by weight.

1315. The method of item 1202, wherein the agent is delivered from a device, wherein the device further comprises a coating, and the fibrosing agent is present in the coating in an amount ranging between about 10% to about 25% by weight.

1316. The method of item 1202, wherein the agent is delivered from a device, wherein the device further comprises a coating, and the fibrosing agent is present in the coating in an amount ranging between about 25% to about 70% by weight.

1317. The method of item 1202, wherein the agent is delivered from a device, wherein the device further comprises a coating, and the coating comprises a polymer.

1318. The method of item 1202, wherein the agent is delivered from a device, wherein the device comprises a first coating having a first composition and a second coating having a second composition.

1319. The method of item 1202, wherein the agent is delivered from a device, wherein the device comprises a first coating having a first composition and a second coating having a second composition, wherein the first composition and the second composition are different.

1320. A method comprising introducing into a patient in need thereof, a therapeutically effective amount of a fibrosing agent or a composition comprising a fibrosing agent, where the fibrosing agent induces a fibrotic response at a specific site within the patient, thereby providing the patient with treatment or prevention of fecal incontinence.

1321. The method of item 1320 wherein the agent promotes regeneration.

1322. The method of item 1320 wherein the agent promotes angiogenesis.

1323. The method of item 1320 wherein the agent promotes fibroblast migration.

1324. The method of item 1320 wherein the agent promotes fibroblast proliferation.

1325. The method of item 1320 wherein the agent promotes deposition of extracellular matrix (ECM).

1326. The method of item 1320 wherein the agent promotes tissue remodeling.

1327. The method of item 1320 wherein the agent is an arterial vessel wall irritant.

1328. The method of item 1320 wherein the fibrosing agent is or comprises silk.

1329. The method of item 1320 wherein the fibrosing agent is in the form of tufts.

1330. The method of item 1320 wherein the fibrosing agent is or comprises mineral particles.

1331. The method of item 1320 wherein the fibrosing agent is or comprises chitosan.

1332. The method of item 1320 wherein the fibrosing agent is or comprises polylysine.

1333. The method of item 1320 wherein the fibrosing agent is or comprises fibronectin.

1334. The method of item 1320 wherein the fibrosing agent is or comprises bleomycin.

1335. The method of item 1320 wherein the fibrosing agent is or comprises CTGF.

1336. The method of item 1320 wherein the fibrosing agent is in the form of a thread, or is in contact with a thread.

1337. The method of item 1320 wherein the fibrosing agent is in the form of a particulate.

1338. The method of item 1320, wherein the composition comprises a polymer.

1339. The method of item 1320, wherein the composition comprises a polymer, and the polymer is, or comprises, a copolymer.

1340. The method of item 1320, wherein the composition comprises a polymer, and the polymer is, or comprises, a block copolymer.

1341. The method of item 1320, wherein the composition comprises a polymer, and the polymer is, or comprises, a random copolymer.

1342. The method of item 1320, wherein the composition comprises a polymer, and the polymer is, or comprises, a biodegradable polymer.

1343. The method of item 1320, wherein the composition comprises a polymer, and the polymer is, or comprises, a non-biodegradable polymer.

1344. The method of item 1320, wherein the composition comprises a polymer, and the polymer is, or comprises, a hydrophilic polymer.

1345. The method of item 1320, wherein the composition comprises a polymer, and the polymer is, or comprises, a hydrophobic polymer.

1346. The method of item 1320, wherein the composition comprises a polymer, and the polymer is, or comprises, a polymer having hydrophilic domains.

1347. The method of item 1320, wherein the composition comprises a polymer, and the polymer is, or comprises, a polymer having hydrophobic domains.

1348. The method of item 1320, wherein the composition comprises a polymer, and the polymer is, or comprises, a non-conductive polymer.

1349. The method of item 1320, wherein the composition comprises a polymer, and the polymer is, or comprises, an elastomer.

1350. The method of item 1320, wherein the composition comprises a polymer, and the polymer is, or comprises, a hydrogel.

1351. The method of item 1320, wherein the composition comprises a polymer, and the polymer is, or comprises, a silicone polymer.

1352. The method of item 1320, wherein the composition comprises a polymer, and the polymer is, or comprises, a hydrocarbon polymer.

1353. The method of item 1320, wherein the composition comprises a polymer, and the polymer is, or comprises, a styrene-derived polymer.

1354. The method of item 1320, wherein the composition comprises a polymer, and the polymer is, or comprises, a butadiene-derived polymer.

1355. The method of item 1320, wherein the composition comprises a polymer, and the polymer is, or comprises, a macromer.

1356. The method of item 1320, wherein the composition comprises a polymer, and the polymer is, or comprises, a poly(ethylene glycol) polymer.

1357. The method of item 1320, wherein the composition comprises a polymer, and the polymer is, or comprises, an amorphous polymer.

1358. The method of item 1320, wherein the composition further comprises a second pharmaceutically active agent.

1359. The method of item 1320, wherein the composition further comprises an anti-inflammatory agent.

1360. The method of item 1320, wherein the composition further comprises an agent that inhibits infection.

1361. The method of item 1320, wherein the composition further comprises an anthracycline.

1362. The method of item 1320, wherein the composition further comprises doxorubicin.

1363. The method of item 1320 wherein the composition further comprises mitoxantrone.

1364. The method of item 1320, wherein the composition further comprises a fluoropyrimidine.

1365. The method of item 1320, wherein the composition further comprises 5-fluorouracil (5-FU).

1366. The method of item 1320, wherein the composition further comprises a folic acid antagonist.

1367. The method of item 1320, wherein the composition further comprises methotrexate.

1368. The method of item 1320, wherein the composition further comprises a podophylotoxin.

1369. The method of item 1320, wherein the composition further comprises etoposide.

1370. The method of item 1320, wherein the composition further comprises camptothecin.

1371. The method of item 1320, wherein the composition further comprises a hydroxyurea.

1372. The method of item 1320, wherein the composition further comprises a platinum complex.

1373. The method of item 1320, wherein the composition further comprises cisplatin.

1374. The method of item 1320 wherein the composition further comprises an anti-thrombotic agent.

1375. The method of item 1320, wherein the composition further comprises a visualization agent.

1376. The method of item 1320, wherein the composition further comprises a visualization agent, and the visualization agent is a radiopaque material, wherein the radiopaque material comprises a metal, a halogenated compound, or a barium containing compound.

1377. The method of item 1320, wherein the composition further comprises a visualization agent, and the visualization agent is, or comprises, barium, tantalum, or technetium.

1378. The method of item 1320, wherein the composition further comprises a visualization agent, and the visualization agent is, or comprises, an MRI responsive material.

1379. The method of item 1320, wherein the composition further comprises a visualization agent, and the visualization agent is, or comprises, a gadolinium chelate.

1380. The method of item 1320, wherein the composition further comprises a visualization agent, and the visualization agent is, or comprises, iron, magnesium, manganese, copper, or chromium.

1381. The method of item 1320, wherein the composition further comprises a visualization agent, and the visualization agent is, or comprises, iron oxide compound.

1382. The method of item 1320, wherein the composition further comprises a visualization agent, and the visualization agent is, or comprises, a dye, pigment, or colorant.

1383. The method of item 1320 wherein the fibrosing agent is released in effective concentrations from the composition comprising the fibrosing agent by diffusion over a period ranging from the time of administration to about 90 days.

1384. The method of item 1320 wherein the fibrosing agent is released in effective concentrations from the composition comprising the fibrosing agent by erosion of the composition over a period ranging from the time of administration to about 90 days.

1385. The method of item 1320 wherein the composition further comprises an inflammatory cytokine.

1386. The method of item 1320 wherein the composition further comprises an agent that stimulates cell proliferation.

1387. The method of item 1320 wherein the composition further comprises a polymeric carrier.

1388. The method of item 1320 wherein the composition is in the form of a gel, paste, or spray.

1389. The method of item 1320 wherein the agent is delivered from a device, and the device delivers the fibrosing agent locally to tissue proximate to the device.

1390. The method of item 1320 wherein the agent is delivered from a device, wherein the device further comprises a coating, and the coating comprises the fibrosing agent.

1391. The method of item 1320 wherein the agent is delivered from a device, wherein the device further comprises a coating, and the coating is disposed on a surface of the device.

1392. The method of item 1320, wherein the agent is delivered from a device, wherein the device further comprises a coating, and the coating directly contacts the device.

1393. The method of item 1320, wherein the agent is delivered from a device, wherein the device further comprises a coating, and the coating indirectly contacts the device.

1394. The method of item 1320 wherein the agent is delivered from a device, wherein the device further comprises a coating, wherein the coating partially covers the device.

1395. The method of item 1320, wherein the agent is delivered from a device, wherein the device further comprises a coating, and the coating completely covers the device.

1396. The method of item 1320 wherein the agent is delivered from a device, wherein the fibrosing agent is located within pores or holes of the device.

1397. The method of item 1320 wherein the agent is delivered from a device, wherein the fibrosing agent is located within a channel, lumen, or divet of the device.

1398. The method of item 1320 wherein the agent is delivered from a device, wherein the device further comprising an echogenic material.

1399. The method of item 1320 wherein the agent is delivered from a device, wherein the device further comprises an echogenic material, wherein the echogenic material is in the form of a coating.

1400. The method of item 1320 wherein the agent is delivered from a device, wherein the device is sterile.

1401. The method of item 1320 wherein the agent is delivered from a device, wherein the fibrosing agent is released into tissue in the vicinity of the device after deployment of the device.

1402. The method of item 1320 wherein the agent is delivered from a device, wherein the fibrosing agent is released into tissue in the vicinity of the device after deployment of the device, wherein the tissue is connective tissue.

1403. The method of item 1320 wherein the agent is delivered from a device, wherein the fibrosing agent is released into tissue in the vicinity of the device after deployment of the device, wherein the tissue is muscle tissue.

1404. The method of item 1320 wherein the agent is delivered from a device, wherein the fibrosing agent is released into tissue in the vicinity of the device after deployment of the device, wherein the tissue is nerve tissue.

1405. The method of item 1320 wherein the agent is delivered from a device, wherein the fibrosing agent is released into tissue in the vicinity of the device after deployment of the device, wherein the tissue is epithelium tissue.

1406. The method of item 1320 wherein the agent is delivered from a device, wherein the fibrosing agent is released in effective concentrations from the device over a period ranging from the time of deployment of the device to about 1 year.

1407. The method of item 1320 wherein the agent is delivered from a device, wherein the fibrosing agent is released in effective concentrations from the device over a period ranging from about 1 month to 6 months.

1408. The method of item 1320 wherein the agent is delivered from a device, wherein the fibrosing agent is released in effective concentrations from the device over a period ranging from about 1–90 days.

1409. The method of item 1320 wherein the agent is delivered from a device, wherein the fibrosing agent is released in effective concentrations from the device at a constant rate.

1410. The method of item 1320 wherein the fibrosing agent is released in effective concentrations from the device at an increasing rate.

1411. The method of item 1320 wherein the agent is delivered from a device, wherein the fibrosing agent is released in effective concentrations from the device at a decreasing rate.

1412. The method of item 1320 wherein the agent is delivered from a device, wherein the device comprises about 0.01 µg to about 10 µg of the fibrosing agent.

1413. The method of item 1320 wherein the agent is delivered from a device, wherein the device comprises about 10 µg to about 10 mg of the fibrosing agent.

1414. The method of item 1320 wherein the agent is delivered from a device, wherein the device comprises about 10 mg to about 250 mg of the fibrosing agent.

1415. The method of item 1320 wherein the agent is delivered from a device, wherein the device comprises about 250 mg to about 1000 mg of the fibrosing agent.

1416. The method of item 1320 wherein the agent is delivered from a device, wherein the device comprises about 1000 mg to about 2500 mg of the fibrosing agent.

1417. The method of item 1320 wherein the agent is delivered from a device, wherein a surface of the device comprises less than 0.01 µg of the fibrosing agent per $mm^2$ of device surface to which the fibrosing agent is applied.

1418. The method of item 1320 wherein the agent is delivered from a device, wherein a surface of the device comprises about 0.01 µg to about 1 µg of the fibrosing agent per $mm^2$ of device surface to which the fibrosing agent is applied.

1419. The method of item 1320 wherein the agent is delivered from a device, wherein a surface of the device comprises about 1 µg to about 10 µg of the fibrosing agent per $mm^2$ of device surface to which the fibrosing agent is applied.

1420. The method of item 1320 wherein the agent is delivered from a device, wherein a surface of the device comprises about 10 µg to about 250 µg of the fibrosing agent per $mm^2$ of device surface to which the fibrosing agent is applied.

1421. The method of item 1320 wherein the agent is delivered from a device, wherein a surface of the device comprises about 250 µg to about 1000 µg of the fibrosing agent of fibrosing agent per $mm^2$ of device surface to which the fibrosing agent is applied.

1422. The method of item 1320 wherein the agent is delivered from a device, wherein a surface of the device comprises about 1000 µg to about 2500 µg of the fibrosing agent per $mm^2$ of device surface to which the fibrosing agent is applied.

1423. The method of item 1320, wherein the agent is delivered from a device, wherein the device further comprises a coating, and the coating is a uniform coating.

1424. The method of item 1320, wherein the agent is delivered from a device, wherein the device further comprises a coating, and the coating is a non-uniform coating.

1425. The method of item 1320, wherein the agent is delivered from a device, wherein the device further comprises a coating, and the coating is a discontinuous coating.

1426. The method of item 1320, wherein the agent is delivered from a device, wherein the device further comprises a coating, and the coating is a patterned coating.

1427. The method of item 1320, wherein the agent is delivered from a device, wherein the device further comprises a coating, and the coating has a thickness of 100 μm or less.

1428. The method of item 1320, wherein the agent is delivered from a device, wherein the device further comprises a coating, and the coating has a thickness of 10 μm or less.

1429. The method of item 1320, wherein the agent is delivered from a device, wherein the device further comprises a coating, and the coating adheres to the surface of the device upon deployment of the device.

1430. The method of item 1320, wherein the agent is delivered from a device, wherein the device further comprises a coating, and the coating is stable at room temperature for a period of at least 1 year.

1431. The method of item 1320, wherein the agent is delivered from a device, wherein the device further comprises a coating, and the fibrosing agent is present in the coating in an amount ranging between about 0.0001% to about 1% by weight.

1432. The method of item 1320, wherein the agent is delivered from a device, wherein the device further comprises a coating, and the fibrosing agent is present in the coating in an amount ranging between about 1% to about 10% by weight.

1433. The method of item 1320, wherein the agent is delivered from a device, wherein the device further comprises a coating, and the fibrosing agent is present in the coating in an amount ranging between about 10% to about 25% by weight.

1434. The method of item 1320, wherein the agent is delivered from a device, wherein the device further comprises a coating, and the fibrosing agent is present in the coating in an amount ranging between about 25% to about 70% by weight.

1435. The method of item 1320, wherein the agent is delivered from a device, wherein the device further comprises a coating, and the coating comprises a polymer.

1436. The method of item 1320, wherein the agent is delivered from a device, wherein the device comprises a first coating having a first composition and a second coating having a second composition.

1437. The method of item 1320, wherein the agent is delivered from a device, wherein the device comprises a first coating having a first composition and a second coating having a second composition, wherein the first composition and the second composition are different.

1438. A method comprising introducing into a patient in need thereof, a therapeutically effective amount of a fibrosing agent or a composition comprising a fibrosing agent, where the fibrosing agent induces a fibrotic response at a specific site within the patient, thereby providing the patient with treatment or prevention of varicose veins.

1439. The method of item 1438 wherein the agent promotes regeneration.

1440. The method of item 1438 wherein the agent promotes angiogenesis.

1441. The method of item 1438 wherein the agent promotes fibroblast migration.

1442. The method of item 1438 wherein the agent promotes fibroblast proliferation.

1443. The method of item 1438 wherein the agent promotes deposition of extracellular matrix (ECM).

1444. The method of item 1438 wherein the agent promotes tissue remodeling.

1445. The method of item 1438 wherein the agent is an arterial vessel wall irritant.

1446. The method of item 1438 wherein the fibrosing agent is or comprises silk.

1447. The method of item 1438 wherein the fibrosing agent is in the form of tufts.

1448. The method of item 1438 wherein the fibrosing agent is or comprises mineral particles.

1449. The method of item 1438 wherein the fibrosing agent is or comprises chitosan.

1450. The method of item 1438 wherein the fibrosing agent is or comprises polylysine.

1451. The method of item 1438 wherein the fibrosing agent is or comprises fibronectin.

1452. The method of item 1438 wherein the fibrosing agent is or comprises bleomycin.

1453. The method of item 1438 wherein the fibrosing agent is or comprises CTGF.

1454. The method of item 1438 wherein the fibrosing agent is in the form of a thread, or is in contact with a thread.

1455. The method of item 1438 wherein the fibrosing agent is in the form of a particulate.

1456. The method of item 1438, wherein the composition comprises a polymer.

1457. The method of item 1438, wherein the composition comprises a polymer, and the polymer is, or comprises, a copolymer.

1458. The method of item 1438, wherein the composition comprises a polymer, and the polymer is, or comprises, a block copolymer.

1459. The method of item 1438, wherein the composition comprises a polymer, and the polymer is, or comprises, a random copolymer.

1460. The method of item 1438, wherein the composition comprises a polymer, and the polymer is, or comprises, a biodegradable polymer.

1461. The method of item 1438, wherein the composition comprises a polymer, and the polymer is, or comprises, a non-biodegradable polymer.

1462. The method of item 1438, wherein the composition comprises a polymer, and the polymer is, or comprises, a hydrophilic polymer.

1463. The method of item 1438, wherein the composition comprises a polymer, and the polymer is, or comprises, a hydrophobic polymer.

1464. The method of item 1438, wherein the composition comprises a polymer, and the polymer is, or comprises, a polymer having hydrophilic domains.

1465. The method of item 1438, wherein the composition comprises a polymer, and the polymer is, or comprises, a polymer having hydrophobic domains.

1466. The method of item 1438, wherein the composition comprises a polymer, and the polymer is, or comprises, a non-conductive polymer.

1467. The method of item 1438, wherein the composition comprises a polymer, and the polymer is, or comprises, an elastomer.

1468. The method of item 1438, wherein the composition comprises a polymer, and the polymer is, or comprises, a hydrogel.

1469. The method of item 1438, wherein the composition comprises a polymer, and the polymer is, or comprises, a silicone polymer.

1470. The method of item 1438, wherein the composition comprises a polymer, and the polymer is, or comprises, a hydrocarbon polymer.

1471. The method of item 1438, wherein the composition comprises a polymer, and the polymer is, or comprises, a styrene-derived polymer.

1472. The method of item 1438, wherein the composition comprises a polymer, and the polymer is, or comprises, a butadiene-derived polymer.

1473. The method of item 1438, wherein the composition comprises a polymer, and the polymer is, or comprises, a macromer.

1474. The method of item 1438, wherein the composition comprises a polymer, and the polymer is, or comprises, a poly(ethylene glycol) polymer.

1475. The method of item 1438, wherein the composition comprises a polymer, and the polymer is, or comprises, an amorphous polymer.

1476. The method of item 1438, wherein the composition further comprises a second pharmaceutically active agent.

1477. The method of item 1438, wherein the composition further comprises an anti-inflammatory agent.

1478. The method of item 1438, wherein the composition further comprises an agent that inhibits infection.

1479. The method of item 1438, wherein the composition further comprises an anthracycline.

1480. The method of item 1438, wherein the composition further comprises doxorubicin.

1481. The method of item 1438 wherein the composition further comprises mitoxantrone.

1482. The method of item 1438 wherein the composition further comprises a fluoropyrimidine.

1483. The method of item 1438, wherein the composition further comprises 5-fluorouracil (5-FU).

1484. The method of item 1438, wherein the composition further comprises a folic acid antagonist.

1485. The method of item 1438, wherein the composition further comprises methotrexate.

1486. The method of item 1438, wherein the composition further comprises a podophylotoxin.

1487. The method of item 1438, wherein the composition further comprises etoposide.

1488. The method of item 1438, wherein the composition further comprises camptothecin.

1489. The method of item 1438, wherein the composition further comprises a hydroxyurea.

1490. The method of item 1438, wherein the composition further comprises a platinum complex.

1491. The method of item 1438, wherein the composition further comprises cisplatin.

1492. The method of item 1438 wherein the composition further comprises an anti-thrombotic agent.

1493. The method of item 1438, wherein the composition further comprises a visualization agent.

1494. The method of item 1438, wherein the composition further comprises a visualization agent, and the visualization agent is a radiopaque material, wherein the radiopaque material comprises a metal, a halogenated compound, or a barium containing compound.

1495. The method of item 1438, wherein the composition further comprises a visualization agent, and the visualization agent is, or comprises, barium, tantalum, or technetium.

1496. The method of item 1438, wherein the composition further comprises a visualization agent, and the visualization agent is, or comprises, an MRI responsive material.

1497. The method of item 1438, wherein the composition further comprises a visualization agent, and the visualization agent is, or comprises, a gadolinium chelate.

1498. The method of item 1438, wherein the composition further comprises a visualization agent, and the visualization agent is, or comprises, iron, magnesium, manganese, copper, or chromium.

1499. The method of item 1438, wherein the composition further comprises a visualization agent, and the visualization agent is, or comprises, iron oxide compound.

1500. The method of item 1438, wherein the composition further comprises a visualization agent, and the visualization agent is, or comprises, a dye, pigment, or colorant.

1501. The method of item 1438 wherein the fibrosing agent is released in effective concentrations from the composition comprising the fibrosing agent by diffusion over a period ranging from the time of administration to about 90 days.

1502. The method of item 1438 wherein the fibrosing agent is released in effective concentrations from the composition comprising the fibrosing agent by erosion of the composition over a period ranging from the time of administration to about 90 days.

1503. The method of item 1438 wherein the composition further comprises an inflammatory cytokine.

1504. The method of item 1438 wherein the composition further comprises an agent that stimulates cell proliferation.

1505. The method of item 1438 wherein the composition further comprises a polymeric carrier.

1506. The method of item 1438 wherein the composition is in the form of a gel, paste, or spray.

1507. The method of item 1438 wherein the agent is delivered from a device, and the device delivers the fibrosing agent locally to tissue proximate to the device.

1508. The method of item 1438 wherein the agent is delivered from a device, wherein the device further comprises a coating, and the coating comprises the fibrosing agent.

1509. The method of item 1438 wherein the agent is delivered from a device, wherein the device further comprises a coating, and the coating is disposed on a surface of the device.

1510. The method of item 1438, wherein the agent is delivered from a device, wherein the device further comprises a coating, and the coating directly contacts the device.

1511. The method of item 1438, wherein the agent is delivered from a device, wherein the device further comprises a coating, and the coating indirectly contacts the device.

1512. The method of item 1438, wherein the agent is delivered from a device, wherein the device further comprises a coating, wherein the coating partially covers the device.

1513. The method of item 1438, wherein the agent is delivered from a device, wherein the device further comprises a coating, and the coating completely covers the device.

1514. The method of item 1438 wherein the agent is delivered from a device, wherein the fibrosing agent is located within pores or holes of the device.

1515. The method of item 1438 wherein the agent is delivered from a device, wherein the fibrosing agent is located within a channel, lumen, or divet of the device.

1516. The method of item 1438 wherein the agent is delivered from a device, wherein the device further comprising an echogenic material.

1517. The method of item 1438 wherein the agent is delivered from a device, wherein the device further comprises an echogenic material, wherein the echogenic material is in the form of a coating.

1518. The method of item 1438 wherein the agent is delivered from a device, wherein the device is sterile.

1519. The method of item 1438 wherein the agent is delivered from a device, wherein the fibrosing agent is released into tissue in the vicinity of the device after deployment of the device.

1520. The method of item 1438 wherein the agent is delivered from a device, wherein the fibrosing agent is released into tissue in the vicinity of the device after deployment of the device, wherein the tissue is connective tissue.

1521. The method of item 1438 wherein the agent is delivered from a device, wherein the fibrosing agent is released into tissue in the vicinity of the device after deployment of the device, wherein the tissue is muscle tissue.

1522. The method of item 1438 wherein the agent is delivered from a device, wherein the fibrosing agent is released into tissue in the vicinity of the device after deployment of the device, wherein the tissue is nerve tissue.

1523. The method of item 1438 wherein the agent is delivered from a device, wherein the fibrosing agent is released into tissue in the vicinity of the device after deployment of the device, wherein the tissue is epithelium tissue.

1524. The method of item 1438 wherein the agent is delivered from a device, wherein the fibrosing agent is released in effective concentrations from the device over a period ranging from the time of deployment of the device to about 1 year.

1525. The method of item 1438 wherein the agent is delivered from a device, wherein the fibrosing agent is released in effective concentrations from the device over a period ranging from about 1 month to 6 months.

1526. The method of item 1438 wherein the agent is delivered from a device, wherein the fibrosing agent is released in effective concentrations from the device over a period ranging from about 1–90 days.

1527. The method of item 1438 wherein the agent is delivered from a device, wherein the fibrosing agent is released in effective concentrations from the device at a constant rate.

1528. The method of item 1438 wherein the fibrosing agent is released in effective concentrations from the device at an increasing rate.

1529. The method of item 1438 wherein the agent is delivered from a device, wherein the fibrosing agent is released in effective concentrations from the device at a decreasing rate.

1530. The method of item 1438 wherein the agent is delivered from a device, wherein the device comprises about 0.01 µg to about 10 µg of the fibrosing agent.

1531. The method of item 1438 wherein the agent is delivered from a device, wherein the device comprises about 10 µg to about 10 mg of the fibrosing agent.

1532. The method of item 1438 wherein the agent is delivered from a device, wherein the device comprises about 10 mg to about 250 mg of the fibrosing agent.

1533. The method of item 1438 wherein the agent is delivered from a device, wherein the device comprises about 250 mg to about 1000 mg of the fibrosing agent.

1534. The method of item 1438 wherein the agent is delivered from a device, wherein the device comprises about 1000 mg to about 2500 mg of the fibrosing agent.

1535. The method of item 1438 wherein the agent is delivered from a device, wherein a surface of the device comprises less than 0.01 µg of the fibrosing agent per mm$^2$ of device surface to which the fibrosing agent is applied.

1536. The method of item 1438 wherein the agent is delivered from a device, wherein a surface of the device comprises about 0.01 µg to about 1 µg of the fibrosing agent per mm$^2$ of device surface to which the fibrosing agent is applied.

1537. The method of item 1438 wherein the agent is delivered from a device, wherein a surface of the device comprises about 1 µg to about 10 µg of the fibrosing agent per mm$^2$ of device surface to which the fibrosing agent is applied.

1538. The method of item 1438 wherein the agent is delivered from a device, wherein a surface of the device comprises about 10 µg to about 250 µg of the fibrosing agent per mm$^2$ of device surface to which the fibrosing agent is applied.

1539. The method of item 1438 wherein the agent is delivered from a device, wherein a surface of the device comprises about 250 µg to about 1000 µg of the fibrosing agent of fibrosing agent per mm$^2$ of device surface to which the fibrosing agent is applied.

1540. The method of item 1438 wherein the agent is delivered from a device, wherein a surface of the device comprises about 1000 µg to about 2500 µg of the fibrosing agent per mm$^2$ of device surface to which the fibrosing agent is applied.

1541. The method of item 1438, wherein the agent is delivered from a device, wherein the device further comprises a coating, and the coating is a uniform coating.

1542. The method of item 1438, wherein the agent is delivered from a device, wherein the device further comprises a coating, and the coating is a non-uniform coating.

1543. The method of item 1438, wherein the agent is delivered from a device, wherein the device further comprises a coating, and the coating is a discontinuous coating.

1544. The method of item 1438, wherein the agent is delivered from a device, wherein the device further comprises a coating, and the coating is a patterned coating.

1545. The method of item 1438, wherein the agent is delivered from a device, wherein the device further comprises a coating, and the coating has a thickness of 100 µm or less.

1546. The method of item 1438, wherein the agent is delivered from a device, wherein the device further comprises a coating, and the coating has a thickness of 10 µm or less.

1547. The method of item 1438, wherein the agent is delivered from a device, wherein the device further comprises a coating, and the coating adheres to the surface of the device upon deployment of the device.

1548. The method of item 1438, wherein the agent is delivered from a device, wherein the device further comprises a coating, and the coating is stable at room temperature for a period of at least 1 year.

1549. The method of item 1438, wherein the agent is delivered from a device, wherein the device further comprises a coating, and the fibrosing agent is present in the coating in an amount ranging between about 0.0001% to about 1% by weight.

1550. The method of item 1438, wherein the agent is delivered from a device, wherein the device further comprises a coating, and the fibrosing agent is present in the coating in an amount ranging between about 1% to about 10% by weight.

1551. The method of item 1438, wherein the agent is delivered from a device, wherein the device further comprises a coating, and the fibrosing agent is present in the coating in an amount ranging between about 10% to about 25% by weight.

1552. The method of item 1438, wherein the agent is delivered from a device, wherein the device further comprises a coating, and the fibrosing agent is present in the coating in an amount ranging between about 25% to about 70% by weight.

1553. The method of item 1438, wherein the agent is delivered from a device, wherein the device further comprises a coating, and the coating comprises a polymer.

1554. The method of item 1438, wherein the agent is delivered from a device, wherein the device comprises a first coating having a first composition and a second coating having a second composition.

1555. The method of item 1438, wherein the agent is delivered from a device, wherein the device comprises a first coating having a first composition and a second coating having a second composition, wherein the first composition and the second composition are different.

1556. A method comprising introducing into a patient in need thereof, a therapeutically effective amount of a fibrosing agent or a composition comprising a fibrosing agent, where the fibrosing agent induces a fibrotic response at a specific site within the patient, thereby providing the patient with treatment for urinary incontinence.

1557. The method of item 1556 wherein the agent promotes regeneration.

1558. The method of item 1556 wherein the agent promotes angiogenesis.

1559. The method of item 1556 wherein the agent promotes fibroblast migration.

1560. The method of item 1556 wherein the agent promotes fibroblast proliferation.

1561. The method of item 1556 wherein the agent promotes deposition of extracellular matrix (ECM).

1562. The method of item 1556 wherein the agent promotes tissue remodeling.

1563. The method of item 1556 wherein the agent is an arterial vessel wall irritant.

1564. The method of item 1556 wherein the fibrosing agent is or comprises silk.

1565. The method of item 1556 wherein the fibrosing agent is in the form of tufts.

1566. The method of item 1556 wherein the fibrosing agent is or comprises mineral particles.

1567. The method of item 1556 wherein the fibrosing agent is or comprises chitosan.

1568. The method of item 1556 wherein the fibrosing agent is or comprises polylysine.

1569. The method of item 1556 wherein the fibrosing agent is or comprises fibronectin.

1570. The method of item 1556 wherein the fibrosing agent is or comprises bleomycin.

1571. The method of item 1556 wherein the fibrosing agent is or comprises CTGF.

1572. The method of item 1556 wherein the fibrosing agent is in the form of a thread, or is in contact with a thread.

1573. The method of item 1556 wherein the fibrosing agent is in the form of a particulate.

1574. The method of item 1556, wherein the composition comprises a polymer.

1575. The method of item 1556, wherein the composition comprises a polymer, and the polymer is, or comprises, a copolymer.

1576. The method of item 1556, wherein the composition comprises a polymer, and the polymer is, or comprises, a block copolymer.

1577. The method of item 1556, wherein the composition comprises a polymer, and the polymer is, or comprises, a random copolymer.

1578. The method of item 1556, wherein the composition comprises a polymer, and the polymer is, or comprises, a biodegradable polymer.

1579. The method of item 1556, wherein the composition comprises a polymer, and the polymer is, or comprises, a non-biodegradable polymer.

1580. The method of item 1556, wherein the composition comprises a polymer, and the polymer is, or comprises, a hydrophilic polymer.

1581. The method of item 1556, wherein the composition comprises a polymer, and the polymer is, or comprises, a hydrophobic polymer.

1582. The method of item 1556, wherein the composition comprises a polymer, and the polymer is, or comprises, a polymer having hydrophilic domains.

1583. The method of item 1556, wherein the composition comprises a polymer, and the polymer is, or comprises, a polymer having hydrophobic domains.

1584. The method of item 1556, wherein the composition comprises a polymer, and the polymer is, or comprises, a non-conductive polymer.

1585. The method of item 1556, wherein the composition comprises a polymer, and the polymer is, or comprises, an elastomer.

1586. The method of item 1556, wherein the composition comprises a polymer, and the polymer is, or comprises, a hydrogel.

1587. The method of item 1556, wherein the composition comprises a polymer, and the polymer is, or comprises, a silicone polymer.

1588. The method of item 1556, wherein the composition comprises a polymer, and the polymer is, or comprises, a hydrocarbon polymer.

1589. The method of item 1556, wherein the composition comprises a polymer, and the polymer is, or comprises, a styrene-derived polymer.

1590. The method of item 1556, wherein the composition comprises a polymer, and the polymer is, or comprises, a butadiene-derived polymer.

1591. The method of item 1556, wherein the composition comprises a polymer, and the polymer is, or comprises, a macromer.

1592. The method of item 1556, wherein the composition comprises a polymer, and the polymer is, or comprises, a poly(ethylene glycol) polymer.

1593. The method of item 1556, wherein the composition comprises a polymer, and the polymer is, or comprises, an amorphous polymer.

1594. The method of item 1556, wherein the composition further comprises a second pharmaceutically active agent.

1595. The method of item 1556, wherein the composition further comprises an anti-inflammatory agent.

1596. The method of item 1556, wherein the composition further comprises an agent that inhibits infection.

1597. The method of item 1556, wherein the composition further comprises an anthracycline.

1598. The method of item 1556, wherein the composition further comprises doxorubicin.

1599. The method of item 1556 wherein the composition further comprises mitoxantrone.

1600. The method of item 1556 wherein the composition further comprises a fluoropyrimidine.

1601. The method of item 1556, wherein the composition further comprises 5-fluorouracil (5-FU).

1602. The method of item 1556, wherein the composition further comprises a folic acid antagonist.

1603. The method of item 1556, wherein the composition further comprises methotrexate.

1604. The method of item 1556, wherein the composition further comprises a podophylotoxin.

1605. The method of item 1556, wherein the composition further comprises etoposide.

1606. The method of item 1556, wherein the composition further comprises camptothecin.

1607. The method of item 1556, wherein the composition further comprises a hydroxyurea.

1608. The method of item 1556, wherein the composition further comprises a platinum complex.

1609. The method of item 1556, wherein the composition further comprises cisplatin.

1610. The method of item 1556 wherein the composition further comprises an anti-thrombotic agent.

1611. The method of item 1556, wherein the composition further comprises a visualization agent.

1612. The method of item 1556, wherein the composition further comprises a visualization agent, and the visualization agent is a radiopaque material, wherein the radiopaque material comprises a metal, a halogenated compound, or a barium containing compound.

1613. The method of item 1556, wherein the composition further comprises a visualization agent, and the visualization agent is, or comprises, barium, tantalum, or technetium.

1614. The method of item 1556, wherein the composition further comprises a visualization agent, and the visualization agent is, or comprises, an MRI responsive material.

1615. The method of item 1556, wherein the composition further comprises a visualization agent, and the visualization agent is, or comprises, a gadolinium chelate.

1616. The method of item 1556, wherein the composition further comprises a visualization agent, and the visualization agent is, or comprises, iron, magnesium, manganese, copper, or chromium.

1617. The method of item 1556, wherein the composition further comprises a visualization agent, and the visualization agent is, or comprises, iron oxide compound.

1618. The method of item 1556, wherein the composition further comprises a visualization agent, and the visualization agent is, or comprises, a dye, pigment, or colorant.

1619. The method of item 1556 wherein the fibrosing agent is released in effective concentrations from the composition comprising the fibrosing agent by diffusion over a period ranging from the time of administration to about 90 days.

1620. The method of item 1556 wherein the fibrosing agent is released in effective concentrations from the composition comprising the fibrosing agent by erosion of the composition over a period ranging from the time of administration to about 90 days.

1621. The method of item 1556 wherein the composition further comprises an inflammatory cytokine.

1622. The method of item 1556 wherein the composition further comprises an agent that stimulates cell proliferation.

1623. The method of item 1556 wherein the composition further comprises a polymeric carrier.

1624. The method of item 1556 wherein the composition is in the form of a gel, paste, or spray.

1625. The method of item 1556 wherein the agent is delivered from a device, and the device delivers the fibrosing agent locally to tissue proximate to the device.

1626. The method of item 1556 wherein the agent is delivered from a device, wherein the device further comprises a coating, and the coating comprises the fibrosing agent.

1627. The method of item 1556 wherein the agent is delivered from a device, wherein the device further comprises a coating, and the coating is disposed on a surface of the device.

1628. The method of item 1556, wherein the agent is delivered from a device, wherein the device further comprises a coating, and the coating directly contacts the device.

1629. The method of item 1556, wherein the agent is delivered from a device, wherein the device further comprises a coating, and the coating indirectly contacts the device.

1630. The method of item 1556 wherein the agent is delivered from a device, wherein the device further comprises a coating, wherein the coating partially covers the device.

1631. The method of item 1556, wherein the agent is delivered from a device, wherein the device further comprises a coating, and the coating completely covers the device.

1632. The method of item 1556 wherein the agent is delivered from a device, wherein the fibrosing agent is located within pores or holes of the device.

1633. The method of item 1556 wherein the agent is delivered from a device, wherein the fibrosing agent is located within a channel, lumen, or divet of the device.

1634. The method of item 1556 wherein the agent is delivered from a device, wherein the device further comprising an echogenic material.

1635. The method of item 1556 wherein the agent is delivered from a device, wherein the device further comprises an echogenic material, wherein the echogenic material is in the form of a coating.

1636. The method of item 1556 wherein the agent is delivered from a device, wherein the device is sterile.

1637. The method of item 1556 wherein the agent is delivered from a device, wherein the fibrosing agent is released into tissue in the vicinity of the device after deployment of the device.

1638. The method of item 1556 wherein the agent is delivered from a device, wherein the fibrosing agent is released into tissue in the vicinity of the device after deployment of the device, wherein the tissue is connective tissue.

1639. The method of item 1556 wherein the agent is delivered from a device, wherein the fibrosing agent is released into tissue in the vicinity of the device after deployment of the device, wherein the tissue is muscle tissue.

1640. The method of item 1556 wherein the agent is delivered from a device, wherein the fibrosing agent is released into tissue in the vicinity of the device after deployment of the device, wherein the tissue is nerve tissue.

1641. The method of item 1556 wherein the agent is delivered from a device, wherein the fibrosing agent is released into tissue in the vicinity of the device after deployment of the device, wherein the tissue is epithelium tissue.

1642. The method of item 1556 wherein the agent is delivered from a device, wherein the fibrosing agent is released in effective concentrations from the device over a period ranging from the time of deployment of the device to about 1 year.

1643. The method of item 1556 wherein the agent is delivered from a device, wherein the fibrosing agent is released in effective concentrations from the device over a period ranging from about 1 month to 6 months.

1644. The method of item 1556 wherein the agent is delivered from a device, wherein the fibrosing agent is released in effective concentrations from the device over a period ranging from about 1–90 days.

1645. The method of item 1556 wherein the agent is delivered from a device, wherein the fibrosing agent is released in effective concentrations from the device at a constant rate.

1646. The method of item 1556 wherein the fibrosing agent is released in effective concentrations from the device at an increasing rate.

1647. The method of item 1556 wherein the agent is delivered from a device, wherein the fibrosing agent is released in effective concentrations from the device at a decreasing rate.

1648. The method of item 1556 wherein the agent is delivered from a device, wherein the device comprises about 0.01 μg to about 10 μg of the fibrosing agent.

1649. The method of item 1556 wherein the agent is delivered from a device, wherein the device comprises about 10 μg to about 10 mg of the fibrosing agent.

1650. The method of item 1556 wherein the agent is delivered from a device, wherein the device comprises about 10 mg to about 250 mg of the fibrosing agent.

1651. The method of item 1556 wherein the agent is delivered from a device, wherein the device comprises about 250 mg to about 1000 mg of the fibrosing agent.

1652. The method of item 1556 wherein the agent is delivered from a device, wherein the device comprises about 1000 mg to about 2500 mg of the fibrosing agent.

1653. The method of item 1556 wherein the agent is delivered from a device, wherein a surface of the device comprises less than 0.01 μg of the fibrosing agent per $mm^2$ of device surface to which the fibrosing agent is applied.

1654. The method of item 1556 wherein the agent is delivered from a device, wherein a surface of the device comprises about 0.01 μg to about 1 μg of the fibrosing agent per $mm^2$ of device surface to which the fibrosing agent is applied.

1655. The method of item 1556 wherein the agent is delivered from a device, wherein a surface of the device comprises about 1 μg to about 10 μg of the fibrosing agent per $mm^2$ of device surface to which the fibrosing agent is applied.

1656. The method of item 1556 wherein the agent is delivered from a device, wherein a surface of the device comprises about 10 μg to about 250 μg of the fibrosing agent per $mm^2$ of device surface to which the fibrosing agent is applied.

1657. The method of item 1556 wherein the agent is delivered from a device, wherein a surface of the device comprises about 250 μg to about 1000 μg of the fibrosing agent of fibrosing agent per $mm^2$ of device surface to which the fibrosing agent is applied.

1658. The method of item 1556 wherein the agent is delivered from a device, wherein a surface of the device comprises about 1000 μg to about 2500 μg of the fibrosing agent per $mm^2$ of device surface to which the fibrosing agent is applied.

1659. The method of item 1556, wherein the agent is delivered from a device, wherein the device further comprises a coating, and the coating is a uniform coating.

1660. The method of item 1556, wherein the agent is delivered from a device, wherein the device further comprises a coating, and the coating is a non-uniform coating.

1661. The method of item 1556, wherein the agent is delivered from a device, wherein the device further comprises a coating, and the coating is a discontinuous coating.

1662. The method of item 1556, wherein the agent is delivered from a device, wherein the device further comprises a coating, and the coating is a patterned coating.

1663. The method of item 1556, wherein the agent is delivered from a device, wherein the device further comprises a coating, and the coating has a thickness of 100 μm or less.

1664. The method of item 1556, wherein the agent is delivered from a device, wherein the device further comprises a coating, and the coating has a thickness of 10 μm or less.

1665. The method of item 1556, wherein the agent is delivered from a device, wherein the device further comprises a coating, and the coating adheres to the surface of the device upon deployment of the device.

1666. The method of item 1556, wherein the agent is delivered from a device, wherein the device further comprises a coating, and the coating is stable at room temperature for a period of at least 1 year.

1667. The method of item 1556, wherein the agent is delivered from a device, wherein the device further comprises a coating, and the fibrosing agent is present in the coating in an amount ranging between about 0.0001% to about 1% by weight.

1668. The method of item 1556, wherein the agent is delivered from a device, wherein the device further comprises a coating, and the fibrosing agent is present in the coating in an amount ranging between about 1% to about 10% by weight.

1669. The method of item 1556, wherein the agent is delivered from a device, wherein the device further comprises a coating, and the fibrosing agent is present in the coating in an amount ranging between about 10% to about 25% by weight.

1670. The method of item 1556, wherein the agent is delivered from a device, wherein the device further comprises a coating, and the fibrosing agent is present in the coating in an amount ranging between about 25% to about 70% by weight.

1671. The method of item 1556, wherein the agent is delivered from a device, wherein the device further comprises a coating, and the coating comprises a polymer.

1672. The method of item 1556, wherein the agent is delivered from a device, wherein the device comprises a first coating having a first composition and a second coating having a second composition.

1673. The method of item 1556, wherein the agent is delivered from a device, wherein the device comprises a first coating having a first composition and a second coating having a second composition, wherein the first composition and the second composition are different.

1674. A method comprising introducing into a patient in need thereof, a therapeutically effective amount of a fibrosing agent or a composition comprising a fibrosing agent, where the fibrosing agent induces a fibrotic response at a specific site within the patient, thereby providing the patient with contraception.

1675. The method of item 1674 wherein the agent promotes regeneration.

1676. The method of item 1674 wherein the agent promotes angiogenesis.

1677. The method of item 1674 wherein the agent promotes fibroblast migration.

1678. The method of item 1674 wherein the agent promotes fibroblast proliferation.

1679. The method of item 1674 wherein the agent promotes deposition of extracellular matrix (ECM).

1680. The method of item 1674 wherein the agent promotes tissue remodeling.

1681. The method of item 1674 wherein the agent is an arterial vessel wall irritant.

1682. The method of item 1674 wherein the fibrosing agent is or comprises silk.

1683. The method of item 1674 wherein the fibrosing agent is in the form of tufts.

1684. The method of item 1674 wherein the fibrosing agent is or comprises mineral particles.

1685. The method of item 1674 wherein the fibrosing agent is or comprises chitosan.

1686. The method of item 1674 wherein the fibrosing agent is or comprises polylysine.

1687. The method of item 1674 wherein the fibrosing agent is or comprises fibronectin.

1688. The method of item 1674 wherein the fibrosing agent is or comprises bleomycin.

1689. The method of item 1674 wherein the fibrosing agent is or comprises CTGF.

1690. The method of item 1674 wherein the fibrosing agent is in the form of a thread, or is in contact with a thread.

1691. The method of item 1674 wherein the fibrosing agent is in the form of a particulate.

1692. The method of item 1674, wherein the composition comprises a polymer.

1693. The method of item 1674, wherein the composition comprises a polymer, and the polymer is, or comprises, a copolymer.

1694. The method of item 1674, wherein the composition comprises a polymer, and the polymer is, or comprises, a block copolymer.

1695. The method of item 1674, wherein the composition comprises a polymer, and the polymer is, or comprises, a random copolymer.

1696. The method of item 1674, wherein the composition comprises a polymer, and the polymer is, or comprises, a biodegradable polymer.

1697. The method of item 1674, wherein the composition comprises a polymer, and the polymer is, or comprises, a non-biodegradable polymer.

1698. The method of item 1674, wherein the composition comprises a polymer, and the polymer is, or comprises, a hydrophilic polymer.

1699. The method of item 1674, wherein the composition comprises a polymer, and the polymer is, or comprises, a hydrophobic polymer.

1700. The method of item 1674, wherein the composition comprises a polymer, and the polymer is, or comprises, a polymer having hydrophilic domains.

1701. The method of item 1674, wherein the composition comprises a polymer, and the polymer is, or comprises, a polymer having hydrophobic domains.

1702. The method of item 1674, wherein the composition comprises a polymer, and the polymer is, or comprises, a non-conductive polymer.

1703. The method of item 1674, wherein the composition comprises a polymer, and the polymer is, or comprises, an elastomer.

1704. The method of item 1674, wherein the composition comprises a polymer, and the polymer is, or comprises, a hydrogel.

1705. The method of item 1674, wherein the composition comprises a polymer, and the polymer is, or comprises, a silicone polymer.

1706. The method of item 1674, wherein the composition comprises a polymer, and the polymer is, or comprises, a hydrocarbon polymer.

1707. The method of item 1674, wherein the composition comprises a polymer, and the polymer is, or comprises, a styrene-derived polymer.

1708. The method of item 1674, wherein the composition comprises a polymer, and the polymer is, or comprises, a butadiene-derived polymer.

1709. The method of item 1674, wherein the composition comprises a polymer, and the polymer is, or comprises, a macromer.

1710. The method of item 1674, wherein the composition comprises a polymer, and the polymer is, or comprises, a poly(ethylene glycol) polymer.

1711. The method of item 1674, wherein the composition comprises a polymer, and the polymer is, or comprises, an amorphous polymer.

1712. The method of item 1674, wherein the composition further comprises a second pharmaceutically active agent.

1713. The method of item 1674, wherein the composition further comprises an anti-inflammatory agent.

1714. The method of item 1674, wherein the composition further comprises an agent that inhibits infection.

1715. The method of item 1674, wherein the composition further comprises an anthracycline.

1716. The method of item 1674, wherein the composition further comprises doxorubicin.

1717. The method of item 1674 wherein the composition further comprises mitoxantrone.

1718. The method of item 1674 wherein the composition further comprises a fluoropyrimidine.

1719. The method of item 1674, wherein the composition further comprises 5-fluorouracil (5-FU).

1720. The method of item 1674, wherein the composition further comprises a folic acid antagonist.

1721. The method of item 1674, wherein the composition further comprises methotrexate.

1722. The method of item 1674, wherein the composition further comprises a podophylotoxin.

1723. The method of item 1674, wherein the composition further comprises etoposide.

1724. The method of item 1674, wherein the composition further comprises camptothecin.

1725. The method of item 1674, wherein the composition further comprises a hydroxyurea.

1726. The method of item 1674, wherein the composition further comprises a platinum complex.

1727. The method of item 1674, wherein the composition further comprises cisplatin.

1728. The method of item 1674, wherein the composition further comprises an anti-thrombotic agent.

1729. The method of item 1674, wherein the composition further comprises a visualization agent.

1730. The method of item 1674, wherein the composition further comprises a visualization agent, and the visualization agent is a radiopaque material, wherein the radiopaque material comprises a metal, a halogenated compound, or a barium containing compound.

1731. The method of item 1674, wherein the composition further comprises a visualization agent, and the visualization agent is, or comprises, barium, tantalum, or technetium.

1732. The method of item 1674, wherein the composition further comprises a visualization agent, and the visualization agent is, or comprises, an MRI responsive material.

1733. The method of item 1674, wherein the composition further comprises a visualization agent, and the visualization agent is, or comprises, a gadolinium chelate.

1734. The method of item 1674, wherein the composition further comprises a visualization agent, and the visualization agent is, or comprises, iron, magnesium, manganese, copper, or chromium.

1735. The method of item 1674, wherein the composition further comprises a visualization agent, and the visualization agent is, or comprises, iron oxide compound.

1736. The method of item 1674, wherein the composition further comprises a visualization agent, and the visualization agent is, or comprises, a dye, pigment, or colorant.

1737. The method of item 1674 wherein the fibrosing agent is released in effective concentrations from the composition comprising the fibrosing agent by diffusion over a period ranging from the time of administration to about 90 days.

1738. The method of item 1674 wherein the fibrosing agent is released in effective concentrations from the composition comprising the fibrosing agent by erosion of the composition over a period ranging from the time of administration to about 90 days.

1739. The method of item 1674 wherein the composition further comprises an inflammatory cytokine.

1740. The method of item 1674 wherein the composition further comprises an agent that stimulates cell proliferation.

1741. The method of item 1674 wherein the composition further comprises a polymeric carrier.

1742. The method of item 1674 wherein the composition is in the form of a gel, paste, or spray.

1743. The method of item 1674 wherein the agent is delivered from a device, and the device delivers the fibrosing agent locally to tissue proximate to the device.

1744. The method of item 1674 wherein the agent is delivered from a device, wherein the device further comprises a coating, and the coating comprises the fibrosing agent.

1745. The method of item 1674 wherein the agent is delivered from a device, wherein the device further comprises a coating, and the coating is disposed on a surface of the device.

1746. The method of item 1674, wherein the agent is delivered from a device, wherein the device further comprises a coating, and the coating directly contacts the device.

1747. The method of item 1674, wherein the agent is delivered from a device, wherein the device further comprises a coating, and the coating indirectly contacts the device.

1748. The method of item 1674 wherein the agent is delivered from a device, wherein the device further comprises a coating, wherein the coating partially covers the device.

1749. The method of item 1674, wherein the agent is delivered from a device, wherein the device further comprises a coating, and the coating completely covers the device.

1750. The method of item 1674 wherein the agent is delivered from a device, wherein the fibrosing agent is located within pores or holes of the device.

1751. The method of item 1674 wherein the agent is delivered from a device, wherein the fibrosing agent is located within a channel, lumen, or divet of the device.

1752. The method of item 1674 wherein the agent is delivered from a device, wherein the device further comprising an echogenic material.

1753. The method of item 1674 wherein the agent is delivered from a device, wherein the device further comprises an echogenic material, wherein the echogenic material is in the form of a coating.

1754. The method of item 1674 wherein the agent is delivered from a device, wherein the device is sterile.

1755. The method of item 1674 wherein the agent is delivered from a device, wherein the fibrosing agent is released into tissue in the vicinity of the device after deployment of the device.

1756. The method of item 1674 wherein the agent is delivered from a device, wherein the fibrosing agent is released into tissue in the vicinity of the device after deployment of the device, wherein the tissue is connective tissue.

1757. The method of item 1674 wherein the agent is delivered from a device, wherein the fibrosing agent is released into tissue in the vicinity of the device after deployment of the device, wherein the tissue is muscle tissue.

1758. The method of item 1674 wherein the agent is delivered from a device, wherein the fibrosing agent is released into tissue in the vicinity of the device after deployment of the device, wherein the tissue is nerve tissue.

1759. The method of item 1674 wherein the agent is delivered from a device, wherein the fibrosing agent is released into tissue in the vicinity of the device after deployment of the device, wherein the tissue is epithelium tissue.

1760. The method of item 1674 wherein the agent is delivered from a device, wherein the fibrosing agent is released in effective concentrations from the device over a period ranging from the time of deployment of the device to about 1 year.

1761. The method of item 1674 wherein the agent is delivered from a device, wherein the fibrosing agent is released in effective concentrations from the device over a period ranging from about 1 month to 6 months.

1762. The method of item 1674 wherein the agent is delivered from a device, wherein the fibrosing agent is released in effective concentrations from the device over a period ranging from about 1–90 days.

1763. The method of item 1674 wherein the agent is delivered from a device, wherein the fibrosing agent is released in effective concentrations from the device at a constant rate.

1764. The method of item 1674 wherein the fibrosing agent is released in effective concentrations from the device at an increasing rate.

1765. The method of item 1674 wherein the agent is delivered from a device, wherein the fibrosing agent is released in effective concentrations from the device at a decreasing rate.

1766. The method of item 1674 wherein the agent is delivered from a device, wherein the device comprises about 0.01 µg to about 10 µg of the fibrosing agent.

1767. The method of item 1674 wherein the agent is delivered from a device, wherein the device comprises about 10 μg to about 10 mg of the fibrosing agent.

1768. The method of item 1674 wherein the agent is delivered from a device, wherein the device comprises about 10 mg to about 250 mg of the fibrosing agent.

1769. The method of item 1674 wherein the agent is delivered from a device, wherein the device comprises about 250 mg to about 1000 mg of the fibrosing agent.

1770. The method of item 1674 wherein the agent is delivered from a device, wherein the device comprises about 1000 mg to about 2500 mg of the fibrosing agent.

1771. The method of item 1674 wherein the agent is delivered from a device, wherein a surface of the device comprises less than 0.01 μg of the fibrosing agent per $mm^2$ of device surface to which the fibrosing agent is applied.

1772. The method of item 1674 wherein the agent is delivered from a device, wherein a surface of the device comprises about 0.01 μg to about 1 μg of the fibrosing agent per $mm^2$ of device surface to which the fibrosing agent is applied.

1773. The method of item 1674 wherein the agent is delivered from a device, wherein a surface of the device comprises about 1 μg to about 10 μg of the fibrosing agent per $mm^2$ of device surface to which the fibrosing agent is applied.

1774. The method of item 1674 wherein the agent is delivered from a device, wherein a surface of the device comprises about 10 μg to about 250 μg of the fibrosing agent per $mm^2$ of device surface to which the fibrosing agent is applied.

1775. The method of item 1674 wherein the agent is delivered from a device, wherein a surface of the device comprises about 250 μg to about 1000 μg of the fibrosing agent of fibrosing agent per $mm^2$ of device surface to which the fibrosing agent is applied.

1776. The method of item 1674 wherein the agent is delivered from a device, wherein a surface of the device comprises about 1000 μg to about 2500 μg of the fibrosing agent per $mm^2$ of device surface to which the fibrosing agent is applied.

1777. The method of item 1674, wherein the agent is delivered from a device, wherein the device further comprises a coating, and the coating is a uniform coating.

1778. The method of item 1674, wherein the agent is delivered from a device, wherein the device further comprises a coating, and the coating is a non-uniform coating.

1779. The method of item 1674, wherein the agent is delivered from a device, wherein the device further comprises a coating, and the coating is a discontinuous coating.

1780. The method of item 1674, wherein the agent is delivered from a device, wherein the device further comprises a coating, and the coating is a patterned coating.

1781. The method of item 1674, wherein the agent is delivered from a device, wherein the device further comprises a coating, and the coating has a thickness of 100 μm or less.

1782. The method of item 1674, wherein the agent is delivered from a device, wherein the device further comprises a coating, and the coating has a thickness of 10 μm or less.

1783. The method of item 1674, wherein the agent is delivered from a device, wherein the device further comprises a coating, and the coating adheres to the surface of the device upon deployment of the device.

1784. The method of item 1674, wherein the agent is delivered from a device, wherein the device further comprises a coating, and the coating is stable at room temperature for a period of at least 1 year.

1785. The method of item 1674, wherein the agent is delivered from a device, wherein the device further comprises a coating, and the fibrosing agent is present in the coating in an amount ranging between about 0.0001% to about 1% by weight.

1786. The method of item 1674, wherein the agent is delivered from a device, wherein the device further comprises a coating, and the fibrosing agent is present in the coating in an amount ranging between about 1% to about 10% by weight.

1787. The method of item 1674, wherein the agent is delivered from a device, wherein the device further comprises a coating, and the fibrosing agent is present in the coating in an amount ranging between about 10% to about 25% by weight.

1788. The method of item 1674, wherein the agent is delivered from a device, wherein the device further comprises a coating, and the fibrosing agent is present in the coating in an amount ranging between about 25% to about 70% by weight.

1789. The method of item 1674, wherein the agent is delivered from a device, wherein the device further comprises a coating, and the coating comprises a polymer.

1790. The method of item 1674, wherein the agent is delivered from a device, wherein the device comprises a first coating having a first composition and a second coating having a second composition.

1791. The method of item 1674, wherein the agent is delivered from a device, wherein the device comprises a first coating having a first composition and a second coating having a second composition, wherein the first composition and the second composition are different.

1792. A method comprising introducing into a patient in need thereof, a therapeutically effective amount of a fibrosing agent or a composition comprising a fibrosing agent, where the fibrosing agent induces a fibrotic response at a specific site within the patient, thereby providing the patient with treatment for an orthopedic condition.

1793. The method of item 1792 wherein the agent promotes regeneration.

1794. The method of item 1792 wherein the agent promotes angiogenesis.

1795. The method of item 1792 wherein the agent promotes fibroblast migration.

1796. The method of item 1792 wherein the agent promotes fibroblast proliferation.

1797. The method of item 1792 wherein the agent promotes deposition of extracellular matrix (ECM).

1798. The method of item 1792 wherein the agent promotes tissue remodeling.

1799. The method of item 1792 wherein the agent is an arterial vessel wall irritant.

1800. The method of item 1792 wherein the fibrosing agent is or comprises silk.

1801. The method of item 1792 wherein the fibrosing agent is in the form of tufts.

1802. The method of item 1792 wherein the fibrosing agent is or comprises mineral particles.

1803. The method of item 1792 wherein the fibrosing agent is or comprises chitosan.

1804. The method of item 1792 wherein the fibrosing agent is or comprises polylysine.

1805. The method of item 1792 wherein the fibrosing agent is or comprises fibronectin.

1806. The method of item 1792 wherein the fibrosing agent is or comprises bleomycin.

1807. The method of item 1792 wherein the fibrosing agent is or comprises CTGF.

1808. The method of item 1792 wherein the fibrosing agent is in the form of a thread, or is in contact with a thread.

1809. The method of item 1792 wherein the fibrosing agent is in the form of a particulate.

1810. The method of item 1792, wherein the composition comprises a polymer.

1811. The method of item 1792, wherein the composition comprises a polymer, and the polymer is, or comprises, a copolymer.

1812. The method of item 1792, wherein the composition comprises a polymer, and the polymer is, or comprises, a block copolymer.

1813. The method of item 1792, wherein the composition comprises a polymer, and the polymer is, or comprises, a random copolymer.

1814. The method of item 1792, wherein the composition comprises a polymer, and the polymer is, or comprises, a biodegradable polymer.

1815. The method of item 1792, wherein the composition comprises a polymer, and the polymer is, or comprises, a non-biodegradable polymer.

1816. The method of item 1792, wherein the composition comprises a polymer, and the polymer is, or comprises, a hydrophilic polymer.

1817. The method of item 1792, wherein the composition comprises a polymer, and the polymer is, or comprises, a hydrophobic polymer.

1818. The method of item 1792, wherein the composition comprises a polymer, and the polymer is, or comprises, a polymer having hydrophilic domains.

1819. The method of item 1792, wherein the composition comprises a polymer, and the polymer is, or comprises, a polymer having hydrophobic domains.

1820. The method of item 1792, wherein the composition comprises a polymer, and the polymer is, or comprises, a non-conductive polymer.

1821. The method of item 1792, wherein the composition comprises a polymer, and the polymer is, or comprises, an elastomer.

1822. The method of item 1792, wherein the composition comprises a polymer, and the polymer is, or comprises, a hydrogel.

1823. The method of item 1792, wherein the composition comprises a polymer, and the polymer is, or comprises, a silicone polymer.

1824. The method of item 1792, wherein the composition comprises a polymer, and the polymer is, or comprises, a hydrocarbon polymer.

1825. The method of item 1792, wherein the composition comprises a polymer, and the polymer is, or comprises, a styrene-derived polymer.

1826. The method of item 1792, wherein the composition comprises a polymer, and the polymer is, or comprises, a butadiene-derived polymer.

1827. The method of item 1792, wherein the composition comprises a polymer, and the polymer is, or comprises, a macromer.

1828. The method of item 1792, wherein the composition comprises a polymer, and the polymer is, or comprises, a poly(ethylene glycol) polymer.

1829. The method of item 1792, wherein the composition comprises a polymer, and the polymer is, or comprises, an amorphous polymer.

1830. The method of item 1792, wherein the composition further comprises a second pharmaceutically active agent.

1831. The method of item 1792, wherein the composition further comprises an anti-inflammatory agent.

1832. The method of item 1792, wherein the composition further comprises an agent that inhibits infection.

1833. The method of item 1792, wherein the composition further comprises an anthracycline.

1834. The method of item 1792, wherein the composition further comprises doxorubicin.

1835. The method of item 1792 wherein the composition further comprises mitoxantrone.

1836. The method of item 1792 wherein the composition further comprises a fluoropyrimidine.

1837. The method of item 1792, wherein the composition further comprises 5-fluorouracil (5-FU).

1838. The method of item 1792, wherein the composition further comprises a folic acid antagonist.

1839. The method of item 1792, wherein the composition further comprises methotrexate.

1840. The method of item 1792, wherein the composition further comprises a podophylotoxin.

1841. The method of item 1792, wherein the composition further comprises etoposide.

1842. The method of item 1792, wherein the composition further comprises camptothecin.

1843. The method of item 1792, wherein the composition further comprises a hydroxyurea.

1844. The method of item 1792, wherein the composition further comprises a platinum complex.

1845. The method of item 1792, wherein the composition further comprises cisplatin.

1846. The method of item 1792 wherein the composition further comprises an anti-thrombotic agent.

1847. The method of item 1792, wherein the composition further comprises a visualization agent.

1848. The method of item 1792, wherein the composition further comprises a visualization agent, and the visualization agent is a radiopaque material, wherein the radiopaque material comprises a metal, a halogenated compound, or a barium containing compound.

1849. The method of item 1792, wherein the composition further comprises a visualization agent, and the visualization agent is, or comprises, barium, tantalum, or technetium.

1850. The method of item 1792, wherein the composition further comprises a visualization agent, and the visualization agent is, or comprises, an MRI responsive material.

1851. The method of item 1792, wherein the composition further comprises a visualization agent, and the visualization agent is, or comprises, a gadolinium chelate.

1852. The method of item 1792, wherein the composition further comprises a visualization agent, and the visualization agent is, or comprises, iron, magnesium, manganese, copper, or chromium.

1853. The method of item 1792, wherein the composition further comprises a visualization agent, and the visualization agent is, or comprises, iron oxide compound.

1854. The method of item 1792, wherein the composition further comprises a visualization agent, and the visualization agent is, or comprises, a dye, pigment, or colorant.

1855. The method of item 1792 wherein the fibrosing agent is released in effective concentrations from the composition comprising the fibrosing agent by diffusion over a period ranging from the time of administration to about 90 days.

1856. The method of item 1792 wherein the fibrosing agent is released in effective concentrations from the composition comprising the fibrosing agent by erosion of the composition over a period ranging from the time of administration to about 90 days.

1857. The method of item 1792 wherein the composition further comprises an inflammatory cytokine.

1858. The method of item 1792 wherein the composition further comprises an agent that stimulates cell proliferation.

1859. The method of item 1792 wherein the composition further comprises a polymeric carrier.

1860. The method of item 1792 wherein the composition is in the form of a gel, paste, or spray.

1861. The method of item 1792 wherein the agent is delivered from a device, and the device delivers the fibrosing agent locally to tissue proximate to the device.

1862. The method of item 1792 wherein the agent is delivered from a device, wherein the device further comprises a coating, and the coating comprises the fibrosing agent.

1863. The method of item 1792 wherein the agent is delivered from a device, wherein the device further comprises a coating, and the coating is disposed on a surface of the device.

1864. The method of item 1792, wherein the agent is delivered from a device, wherein the device further comprises a coating, and the coating directly contacts the device.

1865. The method of item 1792, wherein the agent is delivered from a device, wherein the device further comprises a coating, and the coating indirectly contacts the device.

1866. The method of item 1792 wherein the agent is delivered from a device, wherein the device further comprises a coating, wherein the coating partially covers the device.

1867. The method of item 1792, wherein the agent is delivered from a device, wherein the device further comprises a coating, and the coating completely covers the device.

1868. The method of item 1792 wherein the agent is delivered from a device, wherein the fibrosing agent is located within pores or holes of the device.

1869. The method of item 1792 wherein the agent is delivered from a device, wherein the fibrosing agent is located within a channel, lumen, or divet of the device.

1870. The method of item 1792 wherein the agent is delivered from a device, wherein the device further comprising an echogenic material.

1871. The method of item 1792 wherein the agent is delivered from a device, wherein the device further comprises an echogenic material, wherein the echogenic material is in the form of a coating.

1872. The method of item 1792 wherein the agent is delivered from a device, wherein the device is sterile.

1873. The method of item 1792 wherein the agent is delivered from a device, wherein the fibrosing agent is released into tissue in the vicinity of the device after deployment of the device.

1874. The method of item 1792 wherein the agent is delivered from a device, wherein the fibrosing agent is released into tissue in the vicinity of the device after deployment of the device, wherein the tissue is connective tissue.

1875. The method of item 1792 wherein the agent is delivered from a device, wherein the fibrosing agent is released into tissue in the vicinity of the device after deployment of the device, wherein the tissue is muscle tissue.

1876. The method of item 1792 wherein the agent is delivered from a device, wherein the fibrosing agent is released into tissue in the vicinity of the device after deployment of the device, wherein the tissue is nerve tissue.

1877. The method of item 1792 wherein the agent is delivered from a device, wherein the fibrosing agent is released into tissue in the vicinity of the device after deployment of the device, wherein the tissue is epithelium tissue.

1878. The method of item 1792 wherein the agent is delivered from a device, wherein the fibrosing agent is released in effective concentrations from the device over a period ranging from the time of deployment of the device to about 1 year.

1879. The method of item 1792 wherein the agent is delivered from a device, wherein the fibrosing agent is released in effective concentrations from the device over a period ranging from about 1 month to 6 months.

1880. The method of item 1792 wherein the agent is delivered from a device, wherein the fibrosing agent is released in effective concentrations from the device over a period ranging from about 1–90 days.

1881. The method of item 1792 wherein the agent is delivered from a device, wherein the fibrosing agent is released in effective concentrations from the device at a constant rate.

1882. The method of item 1792 wherein the fibrosing agent is released in effective concentrations from the device at an increasing rate.

1883. The method of item 1792 wherein the agent is delivered from a device, wherein the fibrosing agent is released in effective concentrations from the device at a decreasing rate.

1884. The method of item 1792 wherein the agent is delivered from a device, wherein the device comprises about 0.01 µg to about 10 µg of the fibrosing agent.

1885. The method of item 1792 wherein the agent is delivered from a device, wherein the device comprises about 10 µg to about 10 mg of the fibrosing agent.

1886. The method of item 1792 wherein the agent is delivered from a device, wherein the device comprises about 10 mg to about 250 mg of the fibrosing agent.

1887. The method of item 1792 wherein the agent is delivered from a device, wherein the device comprises about 250 mg to about 1000 mg of the fibrosing agent.

1888. The method of item 1792 wherein the agent is delivered from a device, wherein the device comprises about 1000 mg to about 2500 mg of the fibrosing agent.

1889. The method of item 1792 wherein the agent is delivered from a device, wherein a surface of the device comprises less than 0.01 µg of the fibrosing agent per mm$^2$ of device surface to which the fibrosing agent is applied.

1890. The method of item 1792 wherein the agent is delivered from a device, wherein a surface of the device comprises about 0.01 µg to about 1 µg of the fibrosing agent per mm$^2$ of device surface to which the fibrosing agent is applied.

1891. The method of item 1792 wherein the agent is delivered from a device, wherein a surface of the device comprises about 1 µg to about 10 µg of the fibrosing agent per mm$^2$ of device surface to which the fibrosing agent is applied.

1892. The method of item 1792 wherein the agent is delivered from a device, wherein a surface of the device comprises about 10 µg to about 250 µg of the fibrosing agent per mm$^2$ of device surface to which the fibrosing agent is applied.

1893. The method of item 1792 wherein the agent is delivered from a device, wherein a surface of the device comprises about 250 μg to about 1000 μg of the fibrosing agent of fibrosing agent per mm² of device surface to which the fibrosing agent is applied.

1894. The method of item 1792 wherein the agent is delivered from a device, wherein a surface of the device comprises about 1000 μg to about 2500 μg of the fibrosing agent per mm² of device surface to which the fibrosing agent is applied.

1895. The method of item 1792, wherein the agent is delivered from a device, wherein the device further comprises a coating, and the coating is a uniform coating.

1896. The method of item 1792, wherein the agent is delivered from a device, wherein the device further comprises a coating, and the coating is a non-uniform coating.

1897. The method of item 1792, wherein the agent is delivered from a device, wherein the device further comprises a coating, and the coating is a discontinuous coating.

1898. The method of item 1792, wherein the agent is delivered from a device, wherein the device further comprises a coating, and the coating is a patterned coating.

1899. The method of item 1792, wherein the agent is delivered from a device, wherein the device further comprises a coating, and the coating has a thickness of 100 μm or less.

1900. The method of item 1792, wherein the agent is delivered from a device, wherein the device further comprises a coating, and the coating has a thickness of 10 μm or less.

1901. The method of item 1792, wherein the agent is delivered from a device, wherein the device further comprises a coating, and the coating adheres to the surface of the device upon deployment of the device.

1902. The method of item 1792, wherein the agent is delivered from a device, wherein the device further comprises a coating, and the coating is stable at room temperature for a period of at least 1 year.

1903. The method of item 1792, wherein the agent is delivered from a device, wherein the device further comprises a coating, and the fibrosing agent is present in the coating in an amount ranging between about 0.0001% to about 1% by weight.

1904. The method of item 1792, wherein the agent is delivered from a device, wherein the device further comprises a coating, and the fibrosing agent is present in the coating in an amount ranging between about 1% to about 10% by weight.

1905. The method of item 1792, wherein the agent is delivered from a device, wherein the device further comprises a coating, and the fibrosing agent is present in the coating in an amount ranging between about 10% to about 25% by weight.

1906. The method of item 1792, wherein the agent is delivered from a device, wherein the device further comprises a coating, and the fibrosing agent is present in the coating in an amount ranging between about 25% to about 70% by weight.

1907. The method of item 1792, wherein the agent is delivered from a device, wherein the device further comprises a coating, and the coating comprises a polymer.

1908. The method of item 1792, wherein the agent is delivered from a device, wherein the device comprises a first coating having a first composition and a second coating having a second composition.

1909. The method of item 1792, wherein the agent is delivered from a device, wherein the device comprises a first coating having a first composition and a second coating having a second composition, wherein the first composition and the second composition are different.

1910. A method comprising introducing into a patient in need thereof, a therapeutically effective amount of a fibrosing agent or a composition comprising a fibrosing agent, where the fibrosing agent induces a fibrotic response at a specific site within the patient, thereby providing the patient with treatment for a dental condition.

1911. The method of item 1910 wherein the agent promotes regeneration.

1912. The method of item 1910 wherein the agent promotes angiogenesis.

1913. The method of item 1910 wherein the agent promotes fibroblast migration.

1914. The method of item 1910 wherein the agent promotes fibroblast proliferation.

1915. The method of item 1910 wherein the agent promotes deposition of extracellular matrix (ECM).

1916. The method of item 1910 wherein the agent promotes tissue remodeling.

1917. The method of item 1910 wherein the agent is an arterial vessel wall irritant.

1918. The method of item 1910 wherein the fibrosing agent is or comprises silk.

1919. The method of item 1910 wherein the fibrosing agent is in the form of tufts.

1920. The method of item 1910 wherein the fibrosing agent is or comprises mineral particles.

1921. The method of item 1910 wherein the fibrosing agent is or comprises chitosan.

1922. The method of item 1910 wherein the fibrosing agent is or comprises polylysine.

1923. The method of item 1910 wherein the fibrosing agent is or comprises fibronectin.

1924. The method of item 1910 wherein the fibrosing agent is or comprises bleomycin.

1925. The method of item 1910 wherein the fibrosing agent is or comprises CTGF.

1926. The method of item 1910 wherein the fibrosing agent is in the form of a thread, or is in contact with a thread.

1927. The method of item 1910 wherein the fibrosing agent is in the form of a particulate.

1928. The method of item 1910, wherein the composition comprises a polymer.

1929. The method of item 1910, wherein the composition comprises a polymer, and the polymer is, or comprises, a copolymer.

1930. The method of item 1910, wherein the composition comprises a polymer, and the polymer is, or comprises, a block copolymer.

1931. The method of item 1910, wherein the composition comprises a polymer, and the polymer is, or comprises, a random copolymer.

1932. The method of item 1910, wherein the composition comprises a polymer, and the polymer is, or comprises, a biodegradable polymer.

1933. The method of item 1910, wherein the composition comprises a polymer, and the polymer is, or comprises, a non-biodegradable polymer.

1934. The method of item 1910, wherein the composition comprises a polymer, and the polymer is, or comprises, a hydrophilic polymer.

1935. The method of item 1910, wherein the composition comprises a polymer, and the polymer is, or comprises, a hydrophobic polymer.

1936. The method of item 1910, wherein the composition comprises a polymer, and the polymer is, or comprises, a polymer having hydrophilic domains.

1937. The method of item 1910, wherein the composition comprises a polymer, and the polymer is, or comprises, a polymer having hydrophobic domains.

1938. The method of item 1910, wherein the composition comprises a polymer, and the polymer is, or comprises, a non-conductive polymer.

1939. The method of item 1910, wherein the composition comprises a polymer, and the polymer is, or comprises, an elastomer.

1940. The method of item 1910, wherein the composition comprises a polymer, and the polymer is, or comprises, a hydrogel.

1941. The method of item 1910, wherein the composition comprises a polymer, and the polymer is, or comprises, a silicone polymer.

1942. The method of item 1910, wherein the composition comprises a polymer, and the polymer is, or comprises, a hydrocarbon polymer.

1943. The method of item 1910, wherein the composition comprises a polymer, and the polymer is, or comprises, a styrene-derived polymer.

1944. The method of item 1910, wherein the composition comprises a polymer, and the polymer is, or comprises, a butadiene-derived polymer.

1945. The method of item 1910, wherein the composition comprises a polymer, and the polymer is, or comprises, a macromer.

1946. The method of item 1910, wherein the composition comprises a polymer, and the polymer is, or comprises, a poly(ethylene glycol) polymer.

1947. The method of item 1910, wherein the composition comprises a polymer, and the polymer is, or comprises, an amorphous polymer.

1948. The method of item 1910, wherein the composition further comprises a second pharmaceutically active agent.

1949. The method of item 1910, wherein the composition further comprises an anti-inflammatory agent.

1950. The method of item 1910, wherein the composition further comprises an agent that inhibits infection.

1951. The method of item 1910, wherein the composition further comprises an anthracycline.

1952. The method of item 1910, wherein the composition further comprises doxorubicin.

1953. The method of item 1910 wherein the composition further comprises mitoxantrone.

1954. The method of item 1910 wherein the composition further comprises a fluoropyrimidine.

1955. The method of item 1910, wherein the composition further comprises 5-fluorouracil (5-FU).

1956. The method of item 1910, wherein the composition further comprises a folic acid antagonist.

1957. The method of item 1910, wherein the composition further comprises methotrexate.

1958. The method of item 1910, wherein the composition further comprises a podophylotoxin.

1959. The method of item 1910, wherein the composition further comprises etoposide.

1960. The method of item 1910, wherein the composition further comprises camptothecin.

1961. The method of item 1910, wherein the composition further comprises a hydroxyurea.

1962. The method of item 1910, wherein the composition further comprises a platinum complex.

1963. The method of item 1910, wherein the composition further comprises cisplatin.

1964. The method of item 1910 wherein the composition further comprises an anti-thrombotic agent.

1965. The method of item 1910, wherein the composition further comprises a visualization agent.

1966. The method of item 1910, wherein the composition further comprises a visualization agent, and the visualization agent is a radiopaque material, wherein the radiopaque material comprises a metal, a halogenated compound, or a barium containing compound.

1967. The method of item 1910, wherein the composition further comprises a visualization agent, and the visualization agent is, or comprises, barium, tantalum, or technetium.

1968. The method of item 1910, wherein the composition further comprises a visualization agent, and the visualization agent is, or comprises, an MRI responsive material.

1969. The method of item 1910, wherein the composition further comprises a visualization agent, and the visualization agent is, or comprises, a gadolinium chelate.

1970. The method of item 1910, wherein the composition further comprises a visualization agent, and the visualization agent is, or comprises, iron, magnesium, manganese, copper, or chromium.

1971. The method of item 1910, wherein the composition further comprises a visualization agent, and the visualization agent is, or comprises, iron oxide compound.

1972. The method of item 1910, wherein the composition further comprises a visualization agent, and the visualization agent is, or comprises, a dye, pigment, or colorant.

1973. The method of item 1910 wherein the fibrosing agent is released in effective concentrations from the composition comprising the fibrosing agent by diffusion over a period ranging from the time of administration to about 90 days.

1974. The method of item 1910 wherein the fibrosing agent is released in effective concentrations from the composition comprising the fibrosing agent by erosion of the composition over a period ranging from the time of administration to about 90 days.

1975. The method of item 1910 wherein the composition further comprises an inflammatory cytokine.

1976. The method of item 1910 wherein the composition further comprises an agent that stimulates cell proliferation.

1977. The method of item 1910 wherein the composition further comprises a polymeric carrier.

1978. The method of item 1910 wherein the composition is in the form of a gel, paste, or spray.

1979. The method of item 1910 wherein the agent is delivered from a device, and the device delivers the fibrosing agent locally to tissue proximate to the device.

1980. The method of item 1910 wherein the agent is delivered from a device, wherein the device further comprises a coating, and the coating comprises the fibrosing agent.

1981. The method of item 1910 wherein the agent is delivered from a device, wherein the device further comprises a coating, and the coating is disposed on a surface of the device.

1982. The method of item 1910, wherein the agent is delivered from a device, wherein the device further comprises a coating, and the coating directly contacts the device.

1983. The method of item 1910, wherein the agent is delivered from a device, wherein the device further comprises a coating, and the coating indirectly contacts the device.

1984. The method of item 1910 wherein the agent is delivered from a device, wherein the device further comprises a coating, wherein the coating partially covers the device.

1985. The method of item 1910, wherein the agent is delivered from a device, wherein the device further comprises a coating, and the coating completely covers the device.

1986. The method of item 1910 wherein the agent is delivered from a device, wherein the fibrosing agent is located within pores or holes of the device.

1987. The method of item 1910 wherein the agent is delivered from a device, wherein the fibrosing agent is located within a channel, lumen, or divet of the device.

1988. The method of item 1910 wherein the agent is delivered from a device, wherein the device further comprising an echogenic material.

1989. The method of item 1910 wherein the agent is delivered from a device, wherein the device further comprises an echogenic material, wherein the echogenic material is in the form of a coating.

1990. The method of item 1910 wherein the agent is delivered from a device, wherein the device is sterile.

1991. The method of item 1910 wherein the agent is delivered from a device, wherein the fibrosing agent is released into tissue in the vicinity of the device after deployment of the device.

1992. The method of item 1910 wherein the agent is delivered from a device, wherein the fibrosing agent is released into tissue in the vicinity of the device after deployment of the device, wherein the tissue is connective tissue.

1993. The method of item 1910 wherein the agent is delivered from a device, wherein the fibrosing agent is released into tissue in the vicinity of the device after deployment of the device, wherein the tissue is muscle tissue.

1994. The method of item 1910 wherein the agent is delivered from a device, wherein the fibrosing agent is released into tissue in the vicinity of the device after deployment of the device, wherein the tissue is nerve tissue.

1995. The method of item 1910 wherein the agent is delivered from a device, wherein the fibrosing agent is released into tissue in the vicinity of the device after deployment of the device, wherein the tissue is epithelium tissue.

1996. The method of item 1910 wherein the agent is delivered from a device, wherein the fibrosing agent is released in effective concentrations from the device over a period ranging from the time of deployment of the device to about 1 year.

1997. The method of item 1910 wherein the agent is delivered from a device, wherein the fibrosing agent is released in effective concentrations from the device over a period ranging from about 1 month to 6 months.

1998. The method of item 1910 wherein the agent is delivered from a device, wherein the fibrosing agent is released in effective concentrations from the device over a period ranging from about 1–90 days.

1999. The method of item 1910 wherein the agent is delivered from a device, wherein the fibrosing agent is released in effective concentrations from the device at a constant rate.

2000. The method of item 1910 wherein the fibrosing agent is released in effective concentrations from the device at an increasing rate.

2001. The method of item 1910 wherein the agent is delivered from a device, wherein the fibrosing agent is released in effective concentrations from the device at a decreasing rate.

2002. The method of item 1910 wherein the agent is delivered from a device, wherein the device comprises about 0.01 µg to about 10 µg of the fibrosing agent.

2003. The method of item 1910 wherein the agent is delivered from a device, wherein the device comprises about 10 µg to about 10 mg of the fibrosing agent.

2004. The method of item 1910 wherein the agent is delivered from a device, wherein the device comprises about 10 mg to about 250 mg of the fibrosing agent.

2005. The method of item 1910 wherein the agent is delivered from a device, wherein the device comprises about 250 mg to about 1000 mg of the fibrosing agent.

2006. The method of item 1910 wherein the agent is delivered from a device, wherein the device comprises about 1000 mg to about 2500 mg of the fibrosing agent.

2007. The method of item 1910 wherein the agent is delivered from a device, wherein a surface of the device comprises less than 0.01 µg of the fibrosing agent per $mm^2$ of device surface to which the fibrosing agent is applied.

2008. The method of item 1910 wherein the agent is delivered from a device, wherein a surface of the device comprises about 0.01 µg to about 1 µg of the fibrosing agent per $mm^2$ of device surface to which the fibrosing agent is applied.

2009. The method of item 1910 wherein the agent is delivered from a device, wherein a surface of the device comprises about 1 µg to about 10 µg of the fibrosing agent per $mm^2$ of device surface to which the fibrosing agent is applied.

2010. The method of item 1910 wherein the agent is delivered from a device, wherein a surface of the device comprises about 10 µg to about 250 µg of the fibrosing agent per $mm^2$ of device surface to which the fibrosing agent is applied.

2011. The method of item 1910 wherein the agent is delivered from a device, wherein a surface of the device comprises about 250 µg to about 1000 µg of the fibrosing agent of fibrosing agent per $mm^2$ of device surface to which the fibrosing agent is applied.

2012. The method of item 1910 wherein the agent is delivered from a device, wherein a surface of the device comprises about 1000 µg to about 2500 µg of the fibrosing agent per $mm^2$ of device surface to which the fibrosing agent is applied.

2013. The method of item 1910, wherein the agent is delivered from a device, wherein the device further comprises a coating, and the coating is a uniform coating.

2014. The method of item 1910, wherein the agent is delivered from a device, wherein the device further comprises a coating, and the coating is a non-uniform coating.

2015. The method of item 1910, wherein the agent is delivered from a device, wherein the device further comprises a coating, and the coating is a discontinuous coating.

2016. The method of item 1910, wherein the agent is delivered from a device, wherein the device further comprises a coating, and the coating is a patterned coating.

2017. The method of item 1910, wherein the agent is delivered from a device, wherein the device further comprises a coating, and the coating has a thickness of 100 µm or less.

2018. The method of item 1910, wherein the agent is delivered from a device, wherein the device further comprises a coating, and the coating has a thickness of 10 µm or less.

2019. The method of item 1910, wherein the agent is delivered from a device, wherein the device further comprises a coating, and the coating adheres to the surface of the device upon deployment of the device.

2020. The method of item 1910, wherein the agent is delivered from a device, wherein the device further comprises a coating, and the coating is stable at room temperature for a period of at least 1 year.

2021. The method of item 1910, wherein the agent is delivered from a device, wherein the device further comprises a coating, and the fibrosing agent is present in the coating in an amount ranging between about 0.0001% to about 1% by weight.

2022. The method of item 1910, wherein the agent is delivered from a device, wherein the device further comprises a coating, and the fibrosing agent is present in the coating in an amount ranging between about 1% to about 10% by weight.

2023. The method of item 1910, wherein the agent is delivered from a device, wherein the device further comprises a coating, and the fibrosing agent is present in the coating in an amount ranging between about 10% to about 25% by weight.

2024. The method of item 1910, wherein the agent is delivered from a device, wherein the device further comprises a coating, and the fibrosing agent is present in the coating in an amount ranging between about 25% to about 70% by weight.

2025. The method of item 1910, wherein the agent is delivered from a device, wherein the device further comprises a coating, and the coating comprises a polymer.

2026. The method of item 1910, wherein the agent is delivered from a device, wherein the device comprises a first coating having a first composition and a second coating having a second composition.

2027. The method of item 1910, wherein the agent is delivered from a device, wherein the device comprises a first coating having a first composition and a second coating having a second composition, wherein the first composition and the second composition are different.

2028. A medical device comprising an orthopedic implant and a fibrosing agent, where the fibrosing agent induces a fibrotic response between the device and a patient in which the device is implanted.

2029. The device of item 2028 wherein the fibrosing agent promotes regeneration.

2030. The device of item 2028 wherein the fibrosing agent promotes angiogenesis.

2031. The device of item 2028 wherein the fibrosing agent promotes fibroblast migration.

2032. The device of item 2028 wherein the fibrosing agent promotes fibroblast proliferation.

2033. The device of item 2028 wherein the fibrosing agent promotes deposition of extracellular matrix (ECM).

2034. The device of item 2028 wherein the fibrosing agent promotes tissue remodeling.

2035. The device of item 2028 wherein the fibrosing agent is an arterial vessel wall irritant.

2036. The device of item 2028 wherein the fibrosing agent promotes adhesion between the device and a host into which the device is implanted.

2037. The device of item 2028 wherein the device delivers the fibrosing agent locally to tissue proximate to the device.

2038. The device of item 2028 wherein the fibrosing agent is or comprises silk.

2039. The device of item 2028 wherein the fibrosing agent is or comprises mineral particles.

2040. The device of item 2028 wherein the fibrosing agent is or comprises chitosan.

2041. The device of item 2028 wherein the fibrosing agent is or comprises polylysine.

2042. The device of item 2028 wherein the fibrosing agent is or comprises fibronectin.

2043. The device of item 2028 wherein the fibrosing agent is or comprises bleomycin.

2044. The device of item 2028 wherein the fibrosing agent is or comprises CTGF.

2045. The device of item 2028 wherein the fibrosing agent is in the form of a thread, or is in contact with a thread.

2046. The device of item 2028 wherein the fibrosing agent is in the form of a particulate.

2047. The device of item 2028 wherein the composition further comprises an inflammatory cytokine.

2048. The device of item 2028 wherein the composition further comprises an agent that stimulates cell proliferation.

2049. The device of item 2028 wherein the composition is in the form of a gel, paste, or spray.

2050. The device of item 2028 wherein the fibrosing agent is in the form of tufts.

2051. The device of item 2028, further comprising a polymer.

2052. The device of item 2028, further comprising a polymeric carrier.

2053. The device of item 2028 wherein the fibrosing agent promotes adhesion between the device and a host into which the device is implanted.

2054. The device of item 2028 wherein the device delivers the fibrosing agent locally to tissue proximate to the device.

2055. The device of item 2028, further comprising a coating, wherein the coating comprises the fibrosing agent.

2056. The device of item 2028, further comprising a coating, wherein the coating is disposed on a surface of the device.

2057. The device of item 2028, further comprising a coating, wherein the coating directly contacts the device.

2058. The device of item 2028, further comprising a coating, wherein the coating indirectly contacts the device.

2059. The device of item 2028, further comprising a coating, wherein the coating partially covers the device.

2060. The device of item 2028, further comprising a coating, wherein the coating completely covers the device.

2061. The device of item 2028, further comprising a coating, wherein the coating is a uniform coating.

2062. The device of item 2028, further comprising a coating, wherein the coating is a non-uniform coating.

2063. The device of item 2028, further comprising a coating, wherein the coating is a discontinuous coating.

2064. The device of item 2028, further comprising a coating, wherein the coating is a patterned coating.

2065. The device of item 2028, further comprising a coating, wherein the coating has a thickness of 100 µm or less.

2066. The device of item 2028, further comprising a coating, wherein the coating has a thickness of 10 µm or less.

2067. The device of item 2028, further comprising a coating, wherein the coating adheres to the surface of the device upon deployment of the device.

2068. The device of item 2028, further comprising a coating, wherein the coating is stable at room temperature for a period of 1 year.

2069. The device of item 2028, further comprising a coating, wherein the fibrosing agent is present in the coating in an amount ranging between about 0.0001% to about 1% by weight.

2070. The device of item 2028, further comprising a coating, wherein the fibrosing agent is present in the coating in an amount ranging between about 1% to about 10% by weight.

2071. The device of item 2028, further comprising a coating, wherein the fibrosing agent is present in the coating in an amount ranging between about 10% to about 25% by weight.

2072. The device of item 2028, further comprising a coating, wherein the fibrosing agent is present in the coating in an amount ranging between about 25% to about 70% by weight.

2073. The device of item 2028, further comprising a coating, wherein the coating further comprises a polymer.

2074. The device of item 2028, further comprising a first coating having a first composition and the second coating having a second composition.

2075. The device of item 2028, further comprising a first coating having a first composition and the second coating having a second composition, wherein the first composition and the second composition are different.

2076. The device of item 2028, further comprising a polymer.

2077. The device of item 2028, further comprising a polymeric carrier.

2078. The device of item 2028, further comprising a polymeric carrier, wherein the polymeric carrier comprises a copolymer.

2079. The device of item 2028, further comprising a polymeric carrier, wherein the polymeric carrier comprises a block copolymer.

2080. The device of item 2028, further comprising a polymeric carrier, wherein the polymeric carrier comprises a random copolymer.

2081. The device of item 2028, further comprising a polymeric carrier, wherein the polymeric carrier comprises a biodegradable polymer.

2082. The device of item 2028, further comprising a polymeric carrier, wherein the polymeric carrier comprises a non-biodegradable polymer.

2083. The device of item 2028, further comprising a polymeric carrier, wherein the polymeric carrier comprises a hydrophilic polymer.

2084. The device of item 2028, further comprising a polymeric carrier, wherein the polymeric carrier comprises a hydrophobic polymer.

2085. The device of item 2028, further comprising a polymeric carrier, wherein the polymeric carrier comprises a polymer having hydrophilic domains.

2086. The device of item 2028, further comprising a polymeric carrier, wherein the polymeric carrier comprises a polymer having hydrophobic domains.

2087. The device of item 2028, further comprising a polymeric carrier, wherein the polymeric carrier comprises a non-conductive polymer.

2088. The device of item 2028, further comprising a polymeric carrier, wherein the polymeric carrier comprises an elastomer.

2089. The device of item 2028, further comprising a polymeric carrier, wherein the polymeric carrier comprises a hydrogel.

2090. The device of item 2028, further comprising a polymeric carrier, wherein the polymeric carrier comprises a silicone polymer.

2091. The device of item 2028, further comprising a polymeric carrier, wherein the polymeric carrier comprises a hydrocarbon polymer.

2092. The device of item 2028, further comprising a polymeric carrier, wherein the polymeric carrier comprises a styrene-derived polymer.

2093. The device of item 2028, further comprising a polymeric carrier, wherein the polymeric carrier comprises a butadiene polymer.

2094. The device of item 2028, further comprising a polymeric carrier, wherein the polymeric carrier comprises a macromer.

2095. The device of item 2028, further comprising a polymeric carrier, wherein the polymeric carrier comprises a poly(ethylene glycol) polymer.

2096. The device of item 2028, further comprising a polymeric carrier, wherein the polymeric carrier comprises an amorphous polymer.

2097. The device of item 2028, further comprising a lubricious coating.

2098. The device of item 2028 wherein the fibrosing agent is located within pores or holes of the device.

2099. The device of item 2028 wherein the fibrosing agent is located within a channel, lumen, or divet of the device.

2100. The device of item 2028, further comprising a second pharmaceutically active agent.

2101. The device of item 2028, further comprising an anti-inflammatory agent.

2102. The device of item 2028, further comprising an agent that inhibits infection.

2103. The device of item 2028, further comprising an agent that inhibits infection, wherein the agent is an anthracycline.

2104. The device of item 2028, further comprising an agent that inhibits infection, wherein the agent is doxorubicin.

2105. The device of item 2028, further comprising an agent that inhibits infection, wherein the agent is mitoxantrone.

2106. The device of item 2028, further comprising an agent that inhibits infection, wherein the agent is a fluoropyrimidine.

2107. The device of item 2028, further comprising an agent that inhibits infection, wherein the agent is 5-fluorouracil (5-FU).

2108. The device of item 2028, further comprising an agent that inhibits infection, wherein the agent is a folic acid antagonist.

2109. The device of item 2028, further comprising an agent that inhibits infection, wherein the agent is methotrexate.

2110. The device of item 2028, further comprising an agent that inhibits infection, wherein the agent is a podophylotoxin.

2111. The device of item 2028, further comprising an agent that inhibits infection, wherein the agent is etoposide.

2112. The device of item 2028, further comprising an agent that inhibits infection, wherein the agent is a camptothecin.

2113. The device of item 2028, further comprising an agent that inhibits infection, wherein the agent is a hydroxyurea.

2114. The device of item 2028, further comprising an agent that inhibits infection, wherein the agent is a platinum complex.

2115. The device of item 2028, further comprising an agent that inhibits infection, wherein the agent is cisplatin.

2116. The device of item 2028, further comprising an anti-thrombotic agent.

2117. The device of item 2028, further comprising a visualization agent.

2118. The device of item 2028, further comprising a visualization agent, wherein the visualization agent is a radiopaque material, wherein the radiopaque material comprises a metal, a halogenated compound, or a barium containing compound.

2119. The device of item 2028, further comprising a visualization agent, wherein the visualization agent is a radiopaque material, wherein the radiopaque material comprises barium, tantalum, or technetium.

2120. The device of item 2028, further comprising a visualization agent, wherein the visualization agent is a MRI responsive material.

2121. The device of item 2028, further comprising a visualization agent, wherein the visualization agent comprises a gadolinium chelate.

2122. The device of item 2028, further comprising a visualization agent, wherein the visualization agent comprises iron, magnesium, manganese, copper, or chromium.

2123. The device of item 2028, further comprising a visualization agent, wherein the visualization agent comprises an iron oxide compound.

2124. The device of item 2028, further comprising a visualization agent, wherein the visualization agent comprises a dye, pigment, or colorant.

2125. The device of item 2028, further comprising an echogenic material.

2126. The device of item 2028, further comprising an echogenic material, wherein the echogenic material is in the form of a coating.

2127. The device of item 2028 wherein the device is sterile.

2128. The device of item 2028 wherein the fibrosing agent is released into tissue in the vicinity of the device after deployment of the device.

2129. The device of item 2028 wherein the fibrosing agent is released into tissue in the vicinity of the device after deployment of the device, wherein the tissue is connective tissue.

2130. The device of item 2028 wherein the fibrosing agent is released into tissue in the vicinity of the device after deployment of the device, wherein the tissue is muscle tissue.

2131. The device of item 2028 wherein the fibrosing agent is released into tissue in the vicinity of the device after deployment of the device, wherein the tissue is nerve tissue.

2132. The device of item 2028 wherein the fibrosing agent is released into tissue in the vicinity of the device after deployment of the device, wherein the tissue is epithelium tissue.

2133. The device of item 2028 wherein the fibrosing agent is released in effective concentrations from the device over a period ranging from the time of deployment of the device to about 1 year.

2134. The device of item 2028 wherein the fibrosing agent is released in effective concentrations from the device over a period ranging from about 1 month to 6 months.

2135. The device of item 2028 wherein the fibrosing agent is released in effective concentrations from the device over a period ranging from about 1–90 days.

2136. The device of item 2028 wherein the fibrosing agent is released in effective concentrations from the device at a constant rate.

2137. The device of item 2028 wherein the fibrosing agent is released in effective concentrations from the device at an increasing rate.

2138. The device of item 2028 wherein the fibrosing agent is released in effective concentrations from the device at a decreasing rate.

2139. The device of item 2028 wherein the fibrosing agent is released in effective concentrations from the composition comprising the fibrosing agent by diffusion over a period ranging from the time of deployment of the device to about 90 days.

2140. The device of item 2028 wherein the fibrosing agent is released in effective concentrations from the composition comprising the fibrosing agent by erosion of the composition over a period ranging from the time of deployment of the device to about 90 days.

2141. The device of item 2028 wherein the device comprises about 0.01 µg to about 10 µg of the fibrosing agent.

2142. The device of item 2028 wherein the device comprises about 10 µg to about 10 mg of the fibrosing agent.

2143. The device of item 2028 wherein the device comprises about 10 mg to about 250 mg of the fibrosing agent.

2144. The device of item 2028 wherein the device comprises about 250 mg to about 1000 mg of the fibrosing agent.

2145. The device of item 2028 wherein the device comprises about 1000 mg to about 2500 mg of the fibrosing agent.

2146. The device of item 2028 wherein a surface of the device comprises less than 0.01 µg of the fibrosing agent per mm$^2$ of device surface to which the fibrosing agent is applied.

2147. The device of item 2028 wherein a surface of the device comprises about 0.01 µg to about 1 µg of the fibrosing agent per mm$^2$ of device surface to which the fibrosing agent is applied.

2148. The device of item 2028 wherein a surface of the device comprises about 1 µg to about 10 µg of the fibrosing agent per mm$^2$ of device surface to which the fibrosing agent is applied.

2149. The device of item 2028 wherein a surface of the device comprises about 10 µg to about 250 µg of the fibrosing agent per mm$^2$ of device surface to which the fibrosing agent is applied.

2150. The device of item 2028 wherein a surface of the device comprises about 250 µg to about 1000 µg of the fibrosing agent of fibrosing agent per mm$^2$ of device surface to which the fibrosing agent is applied.

2151. The device of item 2028 wherein a surface of the device comprises about 1000 µg to about 2500 µg of the fibrosing agent per mm$^2$ of device surface to which the fibrosing agent is applied.

2152. The device of item 2028 wherein the orthopedic implant is used as a substitute for a bone graft.

2153. The device of item 2028 wherein the orthopedic implant is an orthopedic pin implant.

2154. The device of item 2028 wherein the orthopedic implant is an orthopedic nail implant.

2155. A medical device comprising an orthopedic prosthesis and a fibrosing agent, where the fibrosing agent induces a fibrotic response between the device and a patient in which the device is implanted.

2156. The device of item 2155 wherein the fibrosing agent promotes regeneration.

2157. The device of item 2155 wherein the fibrosing agent promotes angiogenesis.

2158. The device of item 2155 wherein the fibrosing agent promotes fibroblast migration.

2159. The device of item 2155 wherein the fibrosing agent promotes fibroblast proliferation.

2160. The device of item 2155 wherein the fibrosing agent promotes deposition of extracellular matrix (ECM).

2161. The device of item 2155 wherein the fibrosing agent promotes tissue remodeling.

2162. The device of item 2155 wherein the fibrosing agent is an arterial vessel wall irritant.

2163. The device of item 2155 wherein the fibrosing agent promotes adhesion between the device and a host into which the device is implanted.

2164. The device of item 2155 wherein the device delivers the fibrosing agent locally to tissue proximate to the device.

2165. The device of item 2155 wherein the fibrosing agent is or comprises silk.

2166. The device of item 2155 wherein the fibrosing agent is or comprises mineral particles.

2167. The device of item 2155 wherein the fibrosing agent is or comprises chitosan.

2168. The device of item 2155 wherein the fibrosing agent is or comprises polylysine.

2169. The device of item 2155 wherein the fibrosing agent is or comprises fibronectin.

2170. The device of item 2155 wherein the fibrosing agent is or comprises bleomycin.

2171. The device of item 2155 wherein the fibrosing agent is or comprises CTGF.

2172. The device of item 2155 wherein the fibrosing agent is in the form of a thread, or is in contact with a thread.

2173. The device of item 2155 wherein the fibrosing agent is in the form of a particulate.

2174. The device of item 2155 wherein the composition further comprises an inflammatory cytokine.

2175. The device of item 2155 wherein the composition further comprises an agent that stimulates cell proliferation.

2176. The device of item 2155 wherein the composition is in the form of a gel, paste, or spray.

2177. The device of item 2155 wherein the fibrosing agent is in the form of tufts.

2178. The device of item 2155, further comprising a polymer.

2179. The device of item 2155, further comprising a polymeric carrier.

2180. The device of item 2155 wherein the fibrosing agent promotes adhesion between the device and a host into which the device is implanted.

2181. The device of item 2155 wherein the device delivers the fibrosing agent locally to tissue proximate to the device.

2182. The device of item 2155, further comprising a coating, wherein the coating comprises the fibrosing agent.

2183. The device of item 2155, further comprising a coating, wherein the coating is disposed on a surface of the device.

2184. The device of item 2155, further comprising a coating, wherein the coating directly contacts the device.

2185. The device of item 2155, further comprising a coating, wherein the coating indirectly contacts the device.

2186. The device of item 2155, further comprising a coating, wherein the coating partially covers the device.

2187. The device of item 2155, further comprising a coating, wherein the coating completely covers the device.

2188. The device of item 2155, further comprising a coating, wherein the coating is a uniform coating.

2189. The device of item 2155, further comprising a coating, wherein the coating is a non-uniform coating.

2190. The device of item 2155, further comprising a coating, wherein the coating is a discontinuous coating.

2191. The device of item 2155, further comprising a coating, wherein the coating is a patterned coating.

2192. The device of item 2155, further comprising a coating, wherein the coating has a thickness of 100 µm or less.

2193. The device of item 2155, further comprising a coating, wherein the coating has a thickness of 10 µm or less.

2194. The device of item 2155, further comprising a coating, wherein the coating adheres to the surface of the device upon deployment of the device.

2195. The device of item 2155, further comprising a coating, wherein the coating is stable at room temperature for a period of 1 year.

2196. The device of item 2155, further comprising a coating, wherein the fibrosing agent is present in the coating in an amount ranging between about 0.0001% to about 1% by weight.

2197. The device of item 2155, further comprising a coating, wherein the fibrosing agent is present in the coating in an amount ranging between about 1% to about 10% by weight.

2198. The device of item 2155, further comprising a coating, wherein the fibrosing agent is present in the coating in an amount ranging between about 10% to about 25% by weight.

2199. The device of item 2155, further comprising a coating, wherein the fibrosing agent is present in the coating in an amount ranging between about 25% to about 70% by weight.

2200. The device of item 2155, further comprising a coating, wherein the coating further comprises a polymer.

2201. The device of item 2155, further comprising a first coating having a first composition and the second coating having a second composition.

2202. The device of item 2155, further comprising a first coating having a first composition and the second coating having a second composition, wherein the first composition and the second composition are different.

2203. The device of item 2155, further comprising a polymer.

2204. The device of item 2155, further comprising a polymeric carrier.

2205. The device of item 2155, further comprising a polymeric carrier, wherein the polymeric carrier comprises a copolymer.

2206. The device of item 2155, further comprising a polymeric carrier, wherein the polymeric carrier comprises a block copolymer.

2207. The device of item 2155, further comprising a polymeric carrier, wherein the polymeric carrier comprises a random copolymer.

2208. The device of item 2155, further comprising a polymeric carrier, wherein the polymeric carrier comprises a biodegradable polymer.

2209. The device of item 2155, further comprising a polymeric carrier, wherein the polymeric carrier comprises a non-biodegradable polymer.

2210. The device of item 2155, further comprising a polymeric carrier, wherein the polymeric carrier comprises a hydrophilic polymer.

2211. The device of item 2155, further comprising a polymeric carrier, wherein the polymeric carrier comprises a hydrophobic polymer.

2212. The device of item 2155, further comprising a polymeric carrier, wherein the polymeric carrier comprises a polymer having hydrophilic domains.

2213. The device of item 2155, further comprising a polymeric carrier, wherein the polymeric carrier comprises a polymer having hydrophobic domains.

2214. The device of item 2155, further comprising a polymeric carrier, wherein the polymeric carrier comprises a non-conductive polymer.

2215. The device of item 2155, further comprising a polymeric carrier, wherein the polymeric carrier comprises an elastomer.

2216. The device of item 2155, further comprising a polymeric carrier, wherein the polymeric carrier comprises a hydrogel.

2217. The device of item 2155, further comprising a polymeric carrier, wherein the polymeric carrier comprises a silicone polymer.

2218. The device of item 2155, further comprising a polymeric carrier, wherein the polymeric carrier comprises a hydrocarbon polymer.

2219. The device of item 2155, further comprising a polymeric carrier, wherein the polymeric carrier comprises a styrene-derived polymer.

2220. The device of item 2155, further comprising a polymeric carrier, wherein the polymeric carrier comprises a butadiene polymer.

2221. The device of item 2155, further comprising a polymeric carrier, wherein the polymeric carrier comprises a macromer.

2222. The device of item 2155, further comprising a polymeric carrier, wherein the polymeric carrier comprises a poly(ethylene glycol) polymer.

2223. The device of item 2155, further comprising a polymeric carrier, wherein the polymeric carrier comprises an amorphous polymer.

2224. The device of item 2155, further comprising a lubricious coating.

2225. The device of item 2155 wherein the fibrosing agent is located within pores or holes of the device.

2226. The device of item 2155 wherein the fibrosing agent is located within a channel, lumen, or divet of the device.

2227. The device of item 2155, further comprising a second pharmaceutically active agent.

2228. The device of item 2155, further comprising an anti-inflammatory agent.

2229. The device of item 2155, further comprising an agent that inhibits infection.

2230. The device of item 2155, further comprising an agent that inhibits infection, wherein the agent is an anthracycline.

2231. The device of item 2155, further comprising an agent that inhibits infection, wherein the agent is doxorubicin.

2232. The device of item 2155, further comprising an agent that inhibits infection, wherein the agent is mitoxantrone.

2233. The device of item 2155, further comprising an agent that inhibits infection, wherein the agent is a fluoropyrimidine.

2234. The device of item 2155, further comprising an agent that inhibits infection, wherein the agent is 5-fluorouracil (5-FU).

2235. The device of item 2155, further comprising an agent that inhibits infection, wherein the agent is a folic acid antagonist.

2236. The device of item 2155, further comprising an agent that inhibits infection, wherein the agent is methotrexate.

2237. The device of item 2155, further comprising an agent that inhibits infection, wherein the agent is a podophylotoxin.

2238. The device of item 2155, further comprising an agent that inhibits infection, wherein the agent is etoposide.

2239. The device of item 2155, further comprising an agent that inhibits infection, wherein the agent is a camptothecin.

2240. The device of item 2155, further comprising an agent that inhibits infection, wherein the agent is a hydroxyurea.

2241. The device of item 2155, further comprising an agent that inhibits infection, wherein the agent is a platinum complex.

2242. The device of item 2155, further comprising an agent that inhibits infection, wherein the agent is cisplatin.

2243. The device of item 2155, further comprising an anti-thrombotic agent.

2244. The device of item 2155, further comprising a visualization agent.

2245. The device of item 2155, further comprising a visualization agent, wherein the visualization agent is a radiopaque material, wherein the radiopaque material comprises a metal, a halogenated compound, or a barium containing compound.

2246. The device of item 2155, further comprising a visualization agent, wherein the visualization agent is a radiopaque material, wherein the radiopaque material comprises barium, tantalum, or technetium.

2247. The device of item 2155, further comprising a visualization agent, wherein the visualization agent is a MRI responsive material.

2248. The device of item 2155, further comprising a visualization agent, wherein the visualization agent comprises a gadolinium chelate.

2249. The device of item 2155, further comprising a visualization agent, wherein the visualization agent comprises iron, magnesium, manganese, copper, or chromium.

2250. The device of item 2155, further comprising a visualization agent, wherein the visualization agent comprises an iron oxide compound.

2251. The device of item 2155, further comprising a visualization agent, wherein the visualization agent comprises a dye, pigment, or colorant.

2252. The device of item 2155, further comprising an echogenic material.

2253. The device of item 2155, further comprising an echogenic material, wherein the echogenic material is in the form of a coating.

2254. The device of item 2155 wherein the device is sterile.

2255. The device of item 2155 wherein the fibrosing agent is released into tissue in the vicinity of the device after deployment of the device.

2256. The device of item 2155 wherein the fibrosing agent is released into tissue in the vicinity of the device after deployment of the device, wherein the tissue is connective tissue.

2257. The device of item 2155 wherein the fibrosing agent is released into tissue in the vicinity of the device after deployment of the device, wherein the tissue is muscle tissue.

2258. The device of item 2155 wherein the fibrosing agent is released into tissue in the vicinity of the device after deployment of the device, wherein the tissue is nerve tissue.

2259. The device of item 2155 wherein the fibrosing agent is released into tissue in the vicinity of the device after deployment of the device, wherein the tissue is epithelium tissue.

2260. The device of item 2155 wherein the fibrosing agent is released in effective concentrations from the device over a period ranging from the time of deployment of the device to about 1 year.

2261. The device of item 2155 wherein the fibrosing agent is released in effective concentrations from the device over a period ranging from about 1 month to 6 months.

2262. The device of item 2155 wherein the fibrosing agent is released in effective concentrations from the device over a period ranging from about 1–90 days.

2263. The device of item 2155 wherein the fibrosing agent is released in effective concentrations from the device at a constant rate.

2264. The device of item 2155 wherein the fibrosing agent is released in effective concentrations from the device at an increasing rate.

2265. The device of item 2155 wherein the fibrosing agent is released in effective concentrations from the device at a decreasing rate.

2266. The device of item 2155 wherein the fibrosing agent is released in effective concentrations from the composition comprising the fibrosing agent by diffusion over a period ranging from the time of deployment of the device to about 90 days.

2267. The device of item 2155 wherein the fibrosing agent is released in effective concentrations from the composition comprising the fibrosing agent by erosion of the composition over a period ranging from the time of deployment of the device to about 90 days.

2268. The device of item 2155 wherein the device comprises about 0.01 µg to about 10 µg of the fibrosing agent.

2269. The device of item 2155 wherein the device comprises about 10 µg to about 10 mg of the fibrosing agent.

2270. The device of item 2155 wherein the device comprises about 10 mg to about 250 mg of the fibrosing agent.

2271. The device of item 2155 wherein the device comprises about 250 mg to about 1000 mg of the fibrosing agent.

2272. The device of item 2155 wherein the device comprises about 1000 mg to about 2500 mg of the fibrosing agent.

2273. The device of item 2155 wherein a surface of the device comprises less than 0.01 µg of the fibrosing agent per $mm^2$ of device surface to which the fibrosing agent is applied.

2274. The device of item 2155 wherein a surface of the device comprises about 0.01 µg to about 1 µg of the fibrosing agent per $mm^2$ of device surface to which the fibrosing agent is applied.

2275. The device of item 2155 wherein a surface of the device comprises about 1 µg to about 10 µg of the fibrosing agent per $mm^2$ of device surface to which the fibrosing agent is applied.

2276. The device of item 2155 wherein a surface of the device comprises about 10 µg to about 250 µg of the fibrosing agent per $mm^2$ of device surface to which the fibrosing agent is applied.

2277. The device of item 2155 wherein a surface of the device comprises about 250 µg to about 1000 µg of the fibrosing agent of fibrosing agent per $mm^2$ of device surface to which the fibrosing agent is applied.

2278. The device of item 2155 wherein a surface of the device comprises about 1000 µg to about 2500 µg of the fibrosing agent per $mm^2$ of device surface to which the fibrosing agent is applied.

2279. A medical device comprising a modular implant and a fibrosing agent, where the fibrosing agent induces a fibrotic response between the device and a patient in which the device is implanted.

2280. The device of item 2279 wherein the fibrosing agent promotes regeneration.

2281. The device of item 2279 wherein the fibrosing agent promotes angiogenesis.

2282. The device of item 2279 wherein the fibrosing agent promotes fibroblast migration.

2283. The device of item 2279 wherein the fibrosing agent promotes fibroblast proliferation.

2284. The device of item 2279 wherein the fibrosing agent promotes deposition of extracellular matrix (ECM).

2285. The device of item 2279 wherein the fibrosing agent promotes tissue remodeling.

2286. The device of item 2279 wherein the fibrosing agent is an arterial vessel wall irritant.

2287. The device of item 2279 wherein the fibrosing agent promotes adhesion between the device and a host into which the device is implanted.

2288. The device of item 2279 wherein the device delivers the fibrosing agent locally to tissue proximate to the device.

2289. The device of item 2279 wherein the fibrosing agent is or comprises silk.

2290. The device of item 2279 wherein the fibrosing agent is or comprises mineral particles.

2291. The device of item 2279 wherein the fibrosing agent is or comprises chitosan.

2292. The device of item 2279 wherein the fibrosing agent is or comprises polylysine.

2293. The device of item 2279 wherein the fibrosing agent is or comprises fibronectin.

2294. The device of item 2279 wherein the fibrosing agent is or comprises bleomycin.

2295. The device of item 2279 wherein the fibrosing agent is or comprises CTGF.

2296. The device of item 2279 wherein the fibrosing agent is in the form of a thread, or is in contact with a thread.

2297. The device of item 2279 wherein the fibrosing agent is in the form of a particulate.

2298. The device of item 2279 wherein the composition further comprises an inflammatory cytokine.

2299. The device of item 2279 wherein the composition further comprises an agent that stimulates cell proliferation.

2300. The device of item 2279 wherein the composition is in the form of a gel, paste, or spray.

2301. The device of item 2279 wherein the fibrosing agent is in the form of tufts.

2302. The device of item 2279, further comprising a polymer.

2303. The device of item 2279, further comprising a polymeric carrier.

2304. The device of item 2279 wherein the fibrosing agent promotes adhesion between the device and a host into which the device is implanted.

2305. The device of item 2279 wherein the device delivers the fibrosing agent locally to tissue proximate to the device.

2306. The device of item 2279, further comprising a coating, wherein the coating comprises the fibrosing agent.

2307. The device of item 2279, further comprising a coating, wherein the coating is disposed on a surface of the device.

2308. The device of item 2279, further comprising a coating, wherein the coating directly contacts the device.

2309. The device of item 2279, further comprising a coating, wherein the coating indirectly contacts the device.

2310. The device of item 2279, further comprising a coating, wherein the coating partially covers the device.

2311. The device of item 2279, further comprising a coating, wherein the coating completely covers the device.

2312. The device of item 2279, further comprising a coating, wherein the coating is a uniform coating.

2313. The device of item 2279, further comprising a coating, wherein the coating is a non-uniform coating.

2314. The device of item 2279, further comprising a coating, wherein the coating is a discontinuous coating.

2315. The device of item 2279, further comprising a coating, wherein the coating is a patterned coating.

2316. The device of item 2279, further comprising a coating, wherein the coating has a thickness of 100 μm or less.

2317. The device of item 2279, further comprising a coating, wherein the coating has a thickness of 10 μm or less.

2318. The device of item 2279, further comprising a coating, wherein the coating adheres to the surface of the device upon deployment of the device.

2319. The device of item 2279, further comprising a coating, wherein the coating is stable at room temperature for a period of 1 year.

2320. The device of item 2279, further comprising a coating, wherein the fibrosing agent is present in the coating in an amount ranging between about 0.0001% to about 1% by weight.

2321. The device of item 2279, further comprising a coating, wherein the fibrosing agent is present in the coating in an amount ranging between about 1% to about 10% by weight.

2322. The device of item 2279, further comprising a coating, wherein the fibrosing agent is present in the coating in an amount ranging between about 10% to about 25% by weight.

2323. The device of item 2279, further comprising a coating, wherein the fibrosing agent is present in the coating in an amount ranging between about 25% to about 70% by weight.

2324. The device of item 2279, further comprising a coating, wherein the coating further comprises a polymer.

2325. The device of item 2279, further comprising a first coating having a first composition and the second coating having a second composition.

2326. The device of item 2279, further comprising a first coating having a first composition and the second coating having a second composition, wherein the first composition and the second composition are different.

2327. The device of item 2279, further comprising a polymer.

2328. The device of item 2279, further comprising a polymeric carrier.

2329. The device of item 2279, further comprising a polymeric carrier, wherein the polymeric carrier comprises a copolymer.

2330. The device of item 2279, further comprising a polymeric carrier, wherein the polymeric carrier comprises a block copolymer.

2331. The device of item 2279, further comprising a polymeric carrier, wherein the polymeric carrier comprises a random copolymer.

2332. The device of item 2279, further comprising a polymeric carrier, wherein the polymeric carrier comprises a biodegradable polymer.

2333. The device of item 2279, further comprising a polymeric carrier, wherein the polymeric carrier comprises a non-biodegradable polymer.

2334. The device of item 2279, further comprising a polymeric carrier, wherein the polymeric carrier comprises a hydrophilic polymer.

2335. The device of item 2279, further comprising a polymeric carrier, wherein the polymeric carrier comprises a hydrophobic polymer.

2336. The device of item 2279, further comprising a polymeric carrier, wherein the polymeric carrier comprises a polymer having hydrophilic domains.

2337. The device of item 2279, further comprising a polymeric carrier, wherein the polymeric carrier comprises a polymer having hydrophobic domains.

2338. The device of item 2279, further comprising a polymeric carrier, wherein the polymeric carrier comprises a non-conductive polymer.

2339. The device of item 2279, further comprising a polymeric carrier, wherein the polymeric carrier comprises an elastomer.

2340. The device of item 2279, further comprising a polymeric carrier, wherein the polymeric carrier comprises a hydrogel.

2341. The device of item 2279, further comprising a polymeric carrier, wherein the polymeric carrier comprises a silicone polymer.

2342. The device of item 2279, further comprising a polymeric carrier, wherein the polymeric carrier comprises a hydrocarbon polymer.

2343. The device of item 2279, further comprising a polymeric carrier, wherein the polymeric carrier comprises a styrene-derived polymer.

2344. The device of item 2279, further comprising a polymeric carrier, wherein the polymeric carrier comprises a butadiene polymer.

2345. The device of item 2279, further comprising a polymeric carrier, wherein the polymeric carrier comprises a macromer.

2346. The device of item 2279, further comprising a polymeric carrier, wherein the polymeric carrier comprises a poly(ethylene glycol) polymer.

2347. The device of item 2279, further comprising a polymeric carrier, wherein the polymeric carrier comprises an amorphous polymer.

2348. The device of item 2279, further comprising a lubricious coating.

2349. The device of item 2279 wherein the fibrosing agent is located within pores or holes of the device.

2350. The device of item 2279 wherein the fibrosing agent is located within a channel, lumen, or divet of the device.

2351. The device of item 2279, further comprising a second pharmaceutically active agent.

2352. The device of item 2279, further comprising an anti-inflammatory agent.

2353. The device of item 2279, further comprising an agent that inhibits infection.

2354. The device of item 2279, further comprising an agent that inhibits infection, wherein the agent is an anthracycline.

2355. The device of item 2279, further comprising an agent that inhibits infection, wherein the agent is doxorubicin.

2356. The device of item 2279, further comprising an agent that inhibits infection, wherein the agent is mitoxantrone.

2357. The device of item 2279, further comprising an agent that inhibits infection, wherein the agent is a fluoropyrimidine.

2358. The device of item 2279, further comprising an agent that inhibits infection, wherein the agent is 5-fluorouracil (5-FU).

2359. The device of item 2279, further comprising an agent that inhibits infection, wherein the agent is a folic acid antagonist.

2360. The device of item 2279, further comprising an agent that inhibits infection, wherein the agent is methotrexate.

2361. The device of item 2279, further comprising an agent that inhibits infection, wherein the agent is a podophylotoxin.

2362. The device of item 2279, further comprising an agent that inhibits infection, wherein the agent is etoposide.

2363. The device of item 2279, further comprising an agent that inhibits infection, wherein the agent is a camptothecin.

2364. The device of item 2279, further comprising an agent that inhibits infection, wherein the agent is a hydroxyurea.

2365. The device of item 2279, further comprising an agent that inhibits infection, wherein the agent is a platinum complex.

2366. The device of item 2279, further comprising an agent that inhibits infection, wherein the agent is cisplatin.

2367. The device of item 2279, further comprising an anti-thrombotic agent.

2368. The device of item 2279, further comprising a visualization agent.

2369. The device of item 2279, further comprising a visualization agent, wherein the visualization agent is a radiopaque material, wherein the radiopaque material comprises a metal, a halogenated compound, or a barium containing compound.

2370. The device of item 2279, further comprising a visualization agent, wherein the visualization agent is a radiopaque material, wherein the radiopaque material comprises barium, tantalum, or technetium.

2371. The device of item 2279, further comprising a visualization agent, wherein the visualization agent is a MRI responsive material.

2372. The device of item 2279, further comprising a visualization agent, wherein the visualization agent comprises a gadolinium chelate.

2373. The device of item 2279, further comprising a visualization agent, wherein the visualization agent comprises iron, magnesium, manganese, copper, or chromium.

2374. The device of item 2279, further comprising a visualization agent, wherein the visualization agent comprises an iron oxide compound.

2375. The device of item 2279, further comprising a visualization agent, wherein the visualization agent comprises a dye, pigment, or colorant.

2376. The device of item 2279, further comprising an echogenic material.

2377. The device of item 2279, further comprising an echogenic material, wherein the echogenic material is in the form of a coating.

2378. The device of item 2279 wherein the device is sterile.

2379. The device of item 2279 wherein the fibrosing agent is released into tissue in the vicinity of the device after deployment of the device.

2380. The device of item 2279 wherein the fibrosing agent is released into tissue in the vicinity of the device after deployment of the device, wherein the tissue is connective tissue.

2381. The device of item 2279 wherein the fibrosing agent is released into tissue in the vicinity of the device after deployment of the device, wherein the tissue is muscle tissue.

2382. The device of item 2279 wherein the fibrosing agent is released into tissue in the vicinity of the device after deployment of the device, wherein the tissue is nerve tissue.

2383. The device of item 2279 wherein the fibrosing agent is released into tissue in the vicinity of the device after deployment of the device, wherein the tissue is epithelium tissue.

2384. The device of item 2279 wherein the fibrosing agent is released in effective concentrations from the device over a period ranging from the time of deployment of the device to about 1 year.

2385. The device of item 2279 wherein the fibrosing agent is released in effective concentrations from the device over a period ranging from about 1 month to 6 months.

2386. The device of item 2279 wherein the fibrosing agent is released in effective concentrations from the device over a period ranging from about 1–90 days.

2387. The device of item 2279 wherein the fibrosing agent is released in effective concentrations from the device at a constant rate.

2388. The device of item 2279 wherein the fibrosing agent is released in effective concentrations from the device at an increasing rate.

2389. The device of item 2279 wherein the fibrosing agent is released in effective concentrations from the device at a decreasing rate.

2390. The device of item 2279 wherein the fibrosing agent is released in effective concentrations from the composition comprising the fibrosing agent by diffusion over a period ranging from the time of deployment of the device to about 90 days.

2391. The device of item 2279 wherein the fibrosing agent is released in effective concentrations from the composition comprising the fibrosing agent by erosion of the composition over a period ranging from the time of deployment of the device to about 90 days.

2392. The device of item 2279 wherein the device comprises about 0.01 µg to about 10 µg of the fibrosing agent.

2393. The device of item 2279 wherein the device comprises about 10 µg to about 10 mg of the fibrosing agent.

2394. The device of item 2279 wherein the device comprises about 10 mg to about 250 mg of the fibrosing agent.

2395. The device of item 2279 wherein the device comprises about 250 mg to about 1000 mg of the fibrosing agent.

2396. The device of item 2279 wherein the device comprises about 1000 mg to about 2500 mg of the fibrosing agent.

2397. The device of item 2279 wherein a surface of the device comprises less than 0.01 μg of the fibrosing agent per mm² of device surface to which the fibrosing agent is applied.

2398. The device of item 2279 wherein a surface of the device comprises about 0.01 μg to about 1 μg of the fibrosing agent per mm² of device surface to which the fibrosing agent is applied.

2399. The device of item 2279 wherein a surface of the device comprises about 1 μg to about 10 μg of the fibrosing agent per mm² of device surface to which the fibrosing agent is applied.

2400. The device of item 2279 wherein a surface of the device comprises about 10 μg to about 250 μg of the fibrosing agent per mm² of device surface to which the fibrosing agent is applied.

2401. The device of item 2279 wherein a surface of the device comprises about 250 μg to about 1000 μg of the fibrosing agent of fibrosing agent per mm² of device surface to which the fibrosing agent is applied.

2402. The device of item 2279 wherein a surface of the device comprises about 1000 μg to about 2500 μg of the fibrosing agent per mm² of device surface to which the fibrosing agent is applied.

2403. A medical device comprising a urinary sling and a fibrosing agent, where the fibrosing agent induces a fibrotic response between the device and a patient in which the device is implanted.

2404. The device of item 2403 wherein the fibrosing agent promotes regeneration.

2405. The device of item 2403 wherein the fibrosing agent promotes angiogenesis.

2406. The device of item 2403 wherein the fibrosing agent promotes fibroblast migration.

2407. The device of item 2403 wherein the fibrosing agent promotes fibroblast proliferation.

2408. The device of item 2403 wherein the fibrosing agent promotes deposition of extracellular matrix (ECM).

2409. The device of item 2403 wherein the fibrosing agent promotes tissue remodeling.

2410. The device of item 2403 wherein the fibrosing agent is an arterial vessel wall irritant.

2411. The device of item 2403 wherein the fibrosing agent promotes adhesion between the device and a host into which the device is implanted.

2412. The device of item 2403 wherein the device delivers the fibrosing agent locally to tissue proximate to the device.

2413. The device of item 2403 wherein the fibrosing agent is or comprises silk.

2414. The device of item 2403 wherein the fibrosing agent is or comprises mineral particles.

2415. The device of item 2403 wherein the fibrosing agent is or comprises chitosan.

2416. The device of item 2403 wherein the fibrosing agent is or comprises polylysine.

2417. The device of item 2403 wherein the fibrosing agent is or comprises fibronectin.

2418. The device of item 2403 wherein the fibrosing agent is or comprises bleomycin.

2419. The device of item 2403 wherein the fibrosing agent is or comprises CTGF.

2420. The device of item 2403 wherein the fibrosing agent is in the form of a thread, or is in contact with a thread.

2421. The device of item 2403 wherein the fibrosing agent is in the form of a particulate.

2422. The device of item 2403 wherein the composition further comprises an inflammatory cytokine.

2423. The device of item 2403 wherein the composition further comprises an agent that stimulates cell proliferation.

2424. The device of item 2403 wherein the composition is in the form of a gel, paste, or spray.

2425. The device of item 2403 wherein the fibrosing agent is in the form of tufts.

2426. The device of item 2403, further comprising a polymer.

2427. The device of item 2403, further comprising a polymeric carrier.

2428. The device of item 2403 wherein the fibrosing agent promotes adhesion between the device and a host into which the device is implanted.

2429. The device of item 2403 wherein the device delivers the fibrosing agent locally to tissue proximate to the device.

2430. The device of item 2403, further comprising a coating, wherein the coating comprises the fibrosing agent.

2431. The device of item 2403, further comprising a coating, wherein the coating is disposed on a surface of the device.

2432. The device of item 2403, further comprising a coating, wherein the coating directly contacts the device.

2433. The device of item 2403, further comprising a coating, wherein the coating indirectly contacts the device.

2434. The device of item 2403, further comprising a coating, wherein the coating partially covers the device.

2435. The device of item 2403, further comprising a coating, wherein the coating completely covers the device.

2436. The device of item 2403, further comprising a coating, wherein the coating is a uniform coating.

2437. The device of item 2403, further comprising a coating, wherein the coating is a non-uniform coating.

2438. The device of item 2403, further comprising a coating, wherein the coating is a discontinuous coating.

2439. The device of item 2403, further comprising a coating, wherein the coating is a patterned coating.

2440. The device of item 2403, further comprising a coating, wherein the coating has a thickness of 100 μm or less.

2441. The device of item 2403, further comprising a coating, wherein the coating has a thickness of 10 μm or less.

2442. The device of item 2403, further comprising a coating, wherein the coating adheres to the surface of the device upon deployment of the device.

2443. The device of item 2403, further comprising a coating, wherein the coating is stable at room temperature for a period of 1 year.

2444. The device of item 2403, further comprising a coating, wherein the fibrosing agent is present in the coating in an amount ranging between about 0.0001% to about 1% by weight.

2445. The device of item 2403, further comprising a coating, wherein the fibrosing agent is present in the coating in an amount ranging between about 1% to about 10% by weight.

2446. The device of item 2403, further comprising a coating, wherein the fibrosing agent is present in the coating in an amount ranging between about 10% to about 25% by weight.

2447. The device of item 2403, further comprising a coating, wherein the fibrosing agent is present in the coating in an amount ranging between about 25% to about 70% by weight.

2448. The device of item 2403, further comprising a coating, wherein the coating further comprises a polymer.

2449. The device of item 2403, further comprising a first coating having a first composition and the second coating having a second composition.

2450. The device of item 2403, further comprising a first coating having a first composition and the second coating having a second composition, wherein the first composition and the second composition are different.

2451. The device of item 2403, further comprising a polymer.

2452. The device of item 2403, further comprising a polymeric carrier.

2453. The device of item 2403, further comprising a polymeric carrier, wherein the polymeric carrier comprises a copolymer.

2454. The device of item 2403, further comprising a polymeric carrier, wherein the polymeric carrier comprises a block copolymer.

2455. The device of item 2403, further comprising a polymeric carrier, wherein the polymeric carrier comprises a random copolymer.

2456. The device of item 2403, further comprising a polymeric carrier, wherein the polymeric carrier comprises a biodegradable polymer.

2457. The device of item 2403, further comprising a polymeric carrier, wherein the polymeric carrier comprises a non-biodegradable polymer.

2458. The device of item 2403, further comprising a polymeric carrier, wherein the polymeric carrier comprises a hydrophilic polymer.

2459. The device of item 2403, further comprising a polymeric carrier, wherein the polymeric carrier comprises a hydrophobic polymer.

2460. The device of item 2403, further comprising a polymeric carrier, wherein the polymeric carrier comprises a polymer having hydrophilic domains.

2461. The device of item 2403, further comprising a polymeric carrier, wherein the polymeric carrier comprises a polymer having hydrophobic domains.

2462. The device of item 2403, further comprising a polymeric carrier, wherein the polymeric carrier comprises a non-conductive polymer.

2463. The device of item 2403, further comprising a polymeric carrier, wherein the polymeric carrier comprises an elastomer.

2464. The device of item 2403, further comprising a polymeric carrier, wherein the polymeric carrier comprises a hydrogel.

2465. The device of item 2403, further comprising a polymeric carrier, wherein the polymeric carrier comprises a silicone polymer.

2466. The device of item 2403, further comprising a polymeric carrier, wherein the polymeric carrier comprises a hydrocarbon polymer.

2467. The device of item 2403, further comprising a polymeric carrier, wherein the polymeric carrier comprises a styrene-derived polymer.

2468. The device of item 2403, further comprising a polymeric carrier, wherein the polymeric carrier comprises a butadiene polymer.

2469. The device of item 2403, further comprising a polymeric carrier, wherein the polymeric carrier comprises a macromer.

2470. The device of item 2403, further comprising a polymeric carrier, wherein the polymeric carrier comprises a poly(ethylene glycol) polymer.

2471. The device of item 2403, further comprising a polymeric carrier, wherein the polymeric carrier comprises an amorphous polymer.

2472. The device of item 2403, further comprising a lubricious coating.

2473. The device of item 2403 wherein the fibrosing agent is located within pores or holes of the device.

2474. The device of item 2403 wherein the fibrosing agent is located within a channel, lumen, or divet of the device.

2475. The device of item 2403, further comprising a second pharmaceutically active agent.

2476. The device of item 2403, further comprising an anti-inflammatory agent.

2477. The device of item 2403, further comprising an agent that inhibits infection.

2478. The device of item 2403, further comprising an agent that inhibits infection, wherein the agent is an anthracycline.

2479. The device of item 2403, further comprising an agent that inhibits infection, wherein the agent is doxorubicin.

2480. The device of item 2403, further comprising an agent that inhibits infection, wherein the agent is mitoxantrone.

2481. The device of item 2403, further comprising an agent that inhibits infection, wherein the agent is a fluoropyrimidine.

2482. The device of item 2403, further comprising an agent that inhibits infection, wherein the agent is 5-fluorouracil (5-FU).

2483. The device of item 2403, further comprising an agent that inhibits infection, wherein the agent is a folic acid antagonist.

2484. The device of item 2403, further comprising an agent that inhibits infection, wherein the agent is methotrexate.

2485. The device of item 2403, further comprising an agent that inhibits infection, wherein the agent is a podophylotoxin.

2486. The device of item 2403, further comprising an agent that inhibits infection, wherein the agent is etoposide.

2487. The device of item 2403, further comprising an agent that inhibits infection, wherein the agent is a camptothecin.

2488. The device of item 2403, further comprising an agent that inhibits infection, wherein the agent is a hydroxyurea.

2489. The device of item 2403, further comprising an agent that inhibits infection, wherein the agent is a platinum complex.

2490. The device of item 2403, further comprising an agent that inhibits infection, wherein the agent is cisplatin.

2491. The device of item 2403, further comprising an anti-thrombotic agent.

2492. The device of item 2403, further comprising a visualization agent.

2493. The device of item 2403, further comprising a visualization agent, wherein the visualization agent is a radiopaque material, wherein the radiopaque material comprises a metal, a halogenated compound, or a barium containing compound.

2494. The device of item 2403, further comprising a visualization agent, wherein the visualization agent is a radiopaque material, wherein the radiopaque material comprises barium, tantalum, or technetium.

2495. The device of item 2403, further comprising a visualization agent, wherein the visualization agent is a MRI responsive material.

2496. The device of item 2403, further comprising a visualization agent, wherein the visualization agent comprises a gadolinium chelate.

2497. The device of item 2403, further comprising a visualization agent, wherein the visualization agent comprises iron, magnesium, manganese, copper, or chromium.

2498. The device of item 2403, further comprising a visualization agent, wherein the visualization agent comprises an iron oxide compound.

2499. The device of item 2403, further comprising a visualization agent, wherein the visualization agent comprises a dye, pigment, or colorant.

2500. The device of item 2403, further comprising an echogenic material.

2501. The device of item 2403, further comprising an echogenic material, wherein the echogenic material is in the form of a coating.

2502. The device of item 2403 wherein the device is sterile.

2503. The device of item 2403 wherein the fibrosing agent is released into tissue in the vicinity of the device after deployment of the device.

2504. The device of item 2403 wherein the fibrosing agent is released into tissue in the vicinity of the device after deployment of the device, wherein the tissue is connective tissue.

2505. The device of item 2403 wherein the fibrosing agent is released into tissue in the vicinity of the device after deployment of the device, wherein the tissue is muscle tissue.

2506. The device of item 2403 wherein the fibrosing agent is released into tissue in the vicinity of the device after deployment of the device, wherein the tissue is nerve tissue.

2507. The device of item 2403 wherein the fibrosing agent is released into tissue in the vicinity of the device after deployment of the device, wherein the tissue is epithelium tissue.

2508. The device of item 2403 wherein the fibrosing agent is released in effective concentrations from the device over a period ranging from the time of deployment of the device to about 1 year.

2509. The device of item 2403 wherein the fibrosing agent is released in effective concentrations from the device over a period ranging from about 1 month to 6 months.

2510. The device of item 2403 wherein the fibrosing agent is released in effective concentrations from the device over a period ranging from about 1–90 days.

2511. The device of item 2403 wherein the fibrosing agent is released in effective concentrations from the device at a constant rate.

2512. The device of item 2403 wherein the fibrosing agent is released in effective concentrations from the device at an increasing rate.

2513. The device of item 2403 wherein the fibrosing agent is released in effective concentrations from the device at a decreasing rate.

2514. The device of item 2403 wherein the fibrosing agent is released in effective concentrations from the composition comprising the fibrosing agent by diffusion over a period ranging from the time of deployment of the device to about 90 days.

2515. The device of item 2403 wherein the fibrosing agent is released in effective concentrations from the composition comprising the fibrosing agent by erosion of the composition over a period ranging from the time of deployment of the device to about 90 days.

2516. The device of item 2403 wherein the device comprises about 0.01 µg to about 10 µg of the fibrosing agent.

2517. The device of item 2403 wherein the device comprises about 10 µg to about 10 mg of the fibrosing agent.

2518. The device of item 2403 wherein the device comprises about 10 mg to about 250 mg of the fibrosing agent.

2519. The device of item 2403 wherein the device comprises about 250 mg to about 1000 mg of the fibrosing agent.

2520. The device of item 2403 wherein the device comprises about 1000 mg to about 2500 mg of the fibrosing agent.

2521. The device of item 2403 wherein a surface of the device comprises less than 0.01 µg of the fibrosing agent per mm$^2$ of device surface to which the fibrosing agent is applied.

2522. The device of item 2403 wherein a surface of the device comprises about 0.01 µg to about 1 µg of the fibrosing agent per mm$^2$ of device surface to which the fibrosing agent is applied.

2523. The device of item 2403 wherein a surface of the device comprises about 1 µg to about 10 µg of the fibrosing agent per mm$^2$ of device surface to which the fibrosing agent is applied.

2524. The device of item 2403 wherein a surface of the device comprises about 10 µg to about 250 µg of the fibrosing agent per mm$^2$ of device surface to which the fibrosing agent is applied.

2525. The device of item 2403 wherein a surface of the device comprises about 250 µg to about 1000 µg of the fibrosing agent of fibrosing agent per mm$^2$ of device surface to which the fibrosing agent is applied.

2526. The device of item 2403 wherein a surface of the device comprises about 1000 µg to about 2500 µg of the fibrosing agent per mm$^2$ of device surface to which the fibrosing agent is applied.

2527. A medical device comprising a prosthetic joint and a fibrosing agent, where the fibrosing agent induces a fibrotic response between the device and a patient in which the device is implanted.

2528. The device of item 2527 wherein the fibrosing agent promotes regeneration.

2529. The device of item 2527 wherein the fibrosing agent promotes angiogenesis.

2530. The device of item 2527 wherein the fibrosing agent promotes fibroblast migration.

2531. The device of item 2527 wherein the fibrosing agent promotes fibroblast proliferation.

2532. The device of item 2527 wherein the fibrosing agent promotes deposition of extracellular matrix (ECM).

2533. The device of item 2527 wherein the fibrosing agent promotes tissue remodeling.

2534. The device of item 2527 wherein the fibrosing agent is an arterial vessel wall irritant.

2535. The device of item 2527 wherein the fibrosing agent promotes adhesion between the device and a host into which the device is implanted.

2536. The device of item 2527 wherein the device delivers the fibrosing agent locally to tissue proximate to the device.

2537. The device of item 2527 wherein the fibrosing agent is or comprises silk.

2538. The device of item 2527 wherein the fibrosing agent is or comprises mineral particles.

2539. The device of item 2527 wherein the fibrosing agent is or comprises chitosan.

2540. The device of item 2527 wherein the fibrosing agent is or comprises polylysine.

2541. The device of item 2527 wherein the fibrosing agent is or comprises fibronectin.

2542. The device of item 2527 wherein the fibrosing agent is or comprises bleomycin.

2543. The device of item 2527 wherein the fibrosing agent is or comprises CTGF.

2544. The device of item 2527 wherein the fibrosing agent is in the form of a thread, or is in contact with a thread.

2545. The device of item 2527 wherein the fibrosing agent is in the form of a particulate.

2546. The device of item 2527 wherein the composition further comprises an inflammatory cytokine.

2547. The device of item 2527 wherein the composition further comprises an agent that stimulates cell proliferation.

2548. The device of item 2527 wherein the composition is in the form of a gel, paste, or spray.

2549. The device of item 2527 wherein the fibrosing agent is in the form of tufts.

2550. The device of item 2527, further comprising a polymer.

2551. The device of item 2527, further comprising a polymeric carrier.

2552. The device of item 2527 wherein the fibrosing agent promotes adhesion between the device and a host into which the device is implanted.

2553. The device of item 2527 wherein the device delivers the fibrosing agent locally to tissue proximate to the device.

2554. The device of item 2527, further comprising a coating, wherein the coating comprises the fibrosing agent.

2555. The device of item 2527, further comprising a coating, wherein the coating is disposed on a surface of the device.

2556. The device of item 2527, further comprising a coating, wherein the coating directly contacts the device.

2557. The device of item 2527, further comprising a coating, wherein the coating indirectly contacts the device.

2558. The device of item 2527, further comprising a coating, wherein the coating partially covers the device.

2559. The device of item 2527, further comprising a coating, wherein the coating completely covers the device.

2560. The device of item 2527, further comprising a coating, wherein the coating is a uniform coating.

2561. The device of item 2527, further comprising a coating, wherein the coating is a non-uniform coating.

2562. The device of item 2527, further comprising a coating, wherein the coating is a discontinuous coating.

2563. The device of item 2527, further comprising a coating, wherein the coating is a patterned coating.

2564. The device of item 2527, further comprising a coating, wherein the coating has a thickness of 100 μm or less.

2565. The device of item 2527, further comprising a coating, wherein the coating has a thickness of 10 μm or less.

2566. The device of item 2527, further comprising a coating, wherein the coating adheres to the surface of the device upon deployment of the device.

2567. The device of item 2527, further comprising a coating, wherein the coating is stable at room temperature for a period of 1 year.

2568. The device of item 2527, further comprising a coating, wherein the fibrosing agent is present in the coating in an amount ranging between about 0.0001% to about 1% by weight.

2569. The device of item 2527, further comprising a coating, wherein the fibrosing agent is present in the coating in an amount ranging between about 1% to about 10% by weight.

2570. The device of item 2527, further comprising a coating, wherein the fibrosing agent is present in the coating in an amount ranging between about 10% to about 25% by weight.

2571. The device of item 2527, further comprising a coating, wherein the fibrosing agent is present in the coating in an amount ranging between about 25% to about 70% by weight.

2572. The device of item 2527, further comprising a coating, wherein the coating further comprises a polymer.

2573. The device of item 2527, further comprising a first coating having a first composition and the second coating having a second composition.

2574. The device of item 2527, further comprising a first coating having a first composition and the second coating having a second composition, wherein the first composition and the second composition are different.

2575. The device of item 2527, further comprising a polymer.

2576. The device of item 2527, further comprising a polymeric carrier.

2577. The device of item 2527, further comprising a polymeric carrier, wherein the polymeric carrier comprises a copolymer.

2578. The device of item 2527, further comprising a polymeric carrier, wherein the polymeric carrier comprises a block copolymer.

2579. The device of item 2527, further comprising a polymeric carrier, wherein the polymeric carrier comprises a random copolymer.

2580. The device of item 2527, further comprising a polymeric carrier, wherein the polymeric carrier comprises a biodegradable polymer.

2581. The device of item 2527, further comprising a polymeric carrier, wherein the polymeric carrier comprises a non-biodegradable polymer.

2582. The device of item 2527, further comprising a polymeric carrier, wherein the polymeric carrier comprises a hydrophilic polymer.

2583. The device of item 2527, further comprising a polymeric carrier, wherein the polymeric carrier comprises a hydrophobic polymer.

2584. The device of item 2527, further comprising a polymeric carrier, wherein the polymeric carrier comprises a polymer having hydrophilic domains.

2585. The device of item 2527, further comprising a polymeric carrier, wherein the polymeric carrier comprises a polymer having hydrophobic domains.

2586. The device of item 2527, further comprising a polymeric carrier, wherein the polymeric carrier comprises a non-conductive polymer.

2587. The device of item 2527, further comprising a polymeric carrier, wherein the polymeric carrier comprises an elastomer.

2588. The device of item 2527, further comprising a polymeric carrier, wherein the polymeric carrier comprises a hydrogel.

2589. The device of item 2527, further comprising a polymeric carrier, wherein the polymeric carrier comprises a silicone polymer.

2590. The device of item 2527, further comprising a polymeric carrier, wherein the polymeric carrier comprises a hydrocarbon polymer.

2591. The device of item 2527, further comprising a polymeric carrier, wherein the polymeric carrier comprises a styrene-derived polymer.

2592. The device of item 2527, further comprising a polymeric carrier, wherein the polymeric carrier comprises a butadiene polymer.

2593. The device of item 2527, further comprising a polymeric carrier, wherein the polymeric carrier comprises a macromer.

2594. The device of item 2527, further comprising a polymeric carrier, wherein the polymeric carrier comprises a poly(ethylene glycol) polymer.

2595. The device of item 2527, further comprising a polymeric carrier, wherein the polymeric carrier comprises an amorphous polymer.

2596. The device of item 2527, further comprising a lubricious coating.

2597. The device of item 2527 wherein the fibrosing agent is located within pores or holes of the device.

2598. The device of item 2527 wherein the fibrosing agent is located within a channel, lumen, or divet of the device.

2599. The device of item 2527, further comprising a second pharmaceutically active agent.

2600. The device of item 2527, further comprising an anti-inflammatory agent.

2601. The device of item 2527, further comprising an agent that inhibits infection.

2602. The device of item 2527, further comprising an agent that inhibits infection, wherein the agent is an anthracycline.

2603. The device of item 2527, further comprising an agent that inhibits infection, wherein the agent is doxorubicin.

2604. The device of item 2527, further comprising an agent that inhibits infection, wherein the agent is mitoxantrone.

2605. The device of item 2527, further comprising an agent that inhibits infection, wherein the agent is a fluoropyrimidine.

2606. The device of item 2527, further comprising an agent that inhibits infection, wherein the agent is 5-fluorouracil (5-FU).

2607. The device of item 2527, further comprising an agent that inhibits infection, wherein the agent is a folic acid antagonist.

2608. The device of item 2527, further comprising an agent that inhibits infection, wherein the agent is methotrexate.

2609. The device of item 2527, further comprising an agent that inhibits infection, wherein the agent is a podophylotoxin.

2610. The device of item 2527, further comprising an agent that inhibits infection, wherein the agent is etoposide.

2611. The device of item 2527, further comprising an agent that inhibits infection, wherein the agent is a camptothecin.

2612. The device of item 2527, further comprising an agent that inhibits infection, wherein the agent is a hydroxyurea.

2613. The device of item 2527, further comprising an agent that inhibits infection, wherein the agent is a platinum complex.

2614. The device of item 2527, further comprising an agent that inhibits infection, wherein the agent is cisplatin.

2615. The device of item 2527, further comprising an anti-thrombotic agent.

2616. The device of item 2527, further comprising a visualization agent.

2617. The device of item 2527, further comprising a visualization agent, wherein the visualization agent is a radiopaque material, wherein the radiopaque material comprises a metal, a halogenated compound, or a barium containing compound.

2618. The device of item 2527, further comprising a visualization agent, wherein the visualization agent is a radiopaque material, wherein the radiopaque material comprises barium, tantalum, or technetium.

2619. The device of item 2527, further comprising a visualization agent, wherein the visualization agent is a MRI responsive material.

2620. The device of item 2527, further comprising a visualization agent, wherein the visualization agent comprises a gadolinium chelate.

2621. The device of item 2527, further comprising a visualization agent, wherein the visualization agent comprises iron, magnesium, manganese, copper, or chromium.

2622. The device of item 2527, further comprising a visualization agent, wherein the visualization agent comprises an iron oxide compound.

2623. The device of item 2527, further comprising a visualization agent, wherein the visualization agent comprises a dye, pigment, or colorant.

2624. The device of item 2527, further comprising an echogenic material.

2625. The device of item 2527, further comprising an echogenic material, wherein the echogenic material is in the form of a coating.

2626. The device of item 2527 wherein the device is sterile.

2627. The device of item 2527 wherein the fibrosing agent is released into tissue in the vicinity of the device after deployment of the device.

2628. The device of item 2527 wherein the fibrosing agent is released into tissue in the vicinity of the device after deployment of the device, wherein the tissue is connective tissue.

2629. The device of item 2527 wherein the fibrosing agent is released into tissue in the vicinity of the device after deployment of the device, wherein the tissue is muscle tissue.

2630. The device of item 2527 wherein the fibrosing agent is released into tissue in the vicinity of the device after deployment of the device, wherein the tissue is nerve tissue.

2631. The device of item 2527 wherein the fibrosing agent is released into tissue in the vicinity of the device after deployment of the device, wherein the tissue is epithelium tissue.

2632. The device of item 2527 wherein the fibrosing agent is released in effective concentrations from the device over a period ranging from the time of deployment of the device to about 1 year.

2633. The device of item 2527 wherein the fibrosing agent is released in effective concentrations from the device over a period ranging from about 1 month to 6 months.

2634. The device of item 2527 wherein the fibrosing agent is released in effective concentrations from the device over a period ranging from about 1–90 days.

2635. The device of item 2527 wherein the fibrosing agent is released in effective concentrations from the device at a constant rate.

2636. The device of item 2527 wherein the fibrosing agent is released in effective concentrations from the device at an increasing rate.

2637. The device of item 2527 wherein the fibrosing agent is released in effective concentrations from the device at a decreasing rate.

2638. The device of item 2527 wherein the fibrosing agent is released in effective concentrations from the composition comprising the fibrosing agent by diffusion over a period ranging from the time of deployment of the device to about 90 days.

2639. The device of item 2527 wherein the fibrosing agent is released in effective concentrations from the composition comprising the fibrosing agent by erosion of the composition over a period ranging from the time of deployment of the device to about 90 days.

2640. The device of item 2527 wherein the device comprises about 0.01 μg to about 10 μg of the fibrosing agent.

2641. The device of item 2527 wherein the device comprises about 10 μg to about 10 mg of the fibrosing agent.

2642. The device of item 2527 wherein the device comprises about 10 mg to about 250 mg of the fibrosing agent.

2643. The device of item 2527 wherein the device comprises about 250 mg to about 1000 mg of the fibrosing agent.

2644. The device of item 2527 wherein the device comprises about 1000 mg to about 2500 mg of the fibrosing agent.

2645. The device of item 2527 wherein a surface of the device comprises less than 0.01 μg of the fibrosing agent per mm$^2$ of device surface to which the fibrosing agent is applied.

2646. The device of item 2527 wherein a surface of the device comprises about 0.01 μg to about 1 μg of the fibrosing agent per mm$^2$ of device surface to which the fibrosing agent is applied.

2647. The device of item 2527 wherein a surface of the device comprises about 1 μg to about 10 μg of the fibrosing agent per mm$^2$ of device surface to which the fibrosing agent is applied.

2648. The device of item 2527 wherein a surface of the device comprises about 10 μg to about 250 μg of the fibrosing agent per mm$^2$ of device surface to which the fibrosing agent is applied.

2649. The device of item 2527 wherein a surface of the device comprises about 250 μg to about 1000 μg of the fibrosing agent of fibrosing agent per mm$^2$ of device surface to which the fibrosing agent is applied.

2650. The device of item 2527 wherein a surface of the device comprises about 1000 μg to about 2500 μg of the fibrosing agent per mm$^2$ of device surface to which the fibrosing agent is applied.

2651. A medical device comprising a modular prosthesis and a fibrosing agent, where the fibrosing agent induces a fibrotic response between the device and a patient in which the device is implanted.

2652. The device of item 2651 wherein the fibrosing agent promotes regeneration.

2653. The device of item 2651 wherein the fibrosing agent promotes angiogenesis.

2654. The device of item 2651 wherein the fibrosing agent promotes fibroblast migration.

2655. The device of item 2651 wherein the fibrosing agent promotes fibroblast proliferation.

2656. The device of item 2651 wherein the fibrosing agent promotes deposition of extracellular matrix (ECM).

2657. The device of item 2651 wherein the fibrosing agent promotes tissue remodeling.

2658. The device of item 2651 wherein the fibrosing agent is an arterial vessel wall irritant.

2659. The device of item 2651 wherein the fibrosing agent promotes adhesion between the device and a host into which the device is implanted.

2660. The device of item 2651 wherein the device delivers the fibrosing agent locally to tissue proximate to the device.

2661. The device of item 2651 wherein the fibrosing agent is or comprises silk.

2662. The device of item 2651 wherein the fibrosing agent is or comprises mineral particles.

2663. The device of item 2651 wherein the fibrosing agent is or comprises chitosan.

2664. The device of item 2651 wherein the fibrosing agent is or comprises polylysine.

2665. The device of item 2651 wherein the fibrosing agent is or comprises fibronectin.

2666. The device of item 2651 wherein the fibrosing agent is or comprises bleomycin.

2667. The device of item 2651 wherein the fibrosing agent is or comprises CTGF.

2668. The device of item 2651 wherein the fibrosing agent is in the form of a thread, or is in contact with a thread.

2669. The device of item 2651 wherein the fibrosing agent is in the form of a particulate.

2670. The device of item 2651 wherein the composition further comprises an inflammatory cytokine.

2671. The device of item 2651 wherein the composition further comprises an agent that stimulates cell proliferation.

2672. The device of item 2651 wherein the composition is in the form of a gel, paste, or spray.

2673. The device of item 2651 wherein the fibrosing agent is in the form of tufts.

2674. The device of item 2651, further comprising a polymer.

2675. The device of item 2651, further comprising a polymeric carrier.

2676. The device of item 2651 wherein the fibrosing agent promotes adhesion between the device and a host into which the device is implanted.

2677. The device of item 2651 wherein the device delivers the fibrosing agent locally to tissue proximate to the device.

2678. The device of item 2651, further comprising a coating, wherein the coating comprises the fibrosing agent.

2679. The device of item 2651, further comprising a coating, wherein the coating is disposed on a surface of the device.

2680. The device of item 2651, further comprising a coating, wherein the coating directly contacts the device.

2681. The device of item 2651, further comprising a coating, wherein the coating indirectly contacts the device.

2682. The device of item 2651, further comprising a coating, wherein the coating partially covers the device.

2683. The device of item 2651, further comprising a coating, wherein the coating completely covers the device.

2684. The device of item 2651, further comprising a coating, wherein the coating is a uniform coating.

2685. The device of item 2651, further comprising a coating, wherein the coating is a non-uniform coating.

2686. The device of item 2651, further comprising a coating, wherein the coating is a discontinuous coating.

2687. The device of item 2651, further comprising a coating, wherein the coating is a patterned coating.

2688. The device of item 2651, further comprising a coating, wherein the coating has a thickness of 100 µm or less.

2689. The device of item 2651, further comprising a coating, wherein the coating has a thickness of 10 µm or less.

2690. The device of item 2651, further comprising a coating, wherein the coating adheres to the surface of the device upon deployment of the device.

2691. The device of item 2651, further comprising a coating, wherein the coating is stable at room temperature for a period of 1 year.

2692. The device of item 2651, further comprising a coating, wherein the fibrosing agent is present in the coating in an amount ranging between about 0.0001% to about 1% by weight.

2693. The device of item 2651, further comprising a coating, wherein the fibrosing agent is present in the coating in an amount ranging between about 1% to about 10% by weight.

2694. The device of item 2651, further comprising a coating, wherein the fibrosing agent is present in the coating in an amount ranging between about 10% to about 25% by weight.

2695. The device of item 2651, further comprising a coating, wherein the fibrosing agent is present in the coating in an amount ranging between about 25% to about 70% by weight.

2696. The device of item 2651, further comprising a coating, wherein the coating further comprises a polymer.

2697. The device of item 2651, further comprising a first coating having a first composition and the second coating having a second composition.

2698. The device of item 2651, further comprising a first coating having a first composition and the second coating having a second composition, wherein the first composition and the second composition are different.

2699. The device of item 2651, further comprising a polymer.

2700. The device of item 2651, further comprising a polymeric carrier.

2701. The device of item 2651, further comprising a polymeric carrier, wherein the polymeric carrier comprises a copolymer.

2702. The device of item 2651, further comprising a polymeric carrier, wherein the polymeric carrier comprises a block copolymer.

2703. The device of item 2651, further comprising a polymeric carrier, wherein the polymeric carrier comprises a random copolymer.

2704. The device of item 2651, further comprising a polymeric carrier, wherein the polymeric carrier comprises a biodegradable polymer.

2705. The device of item 2651, further comprising a polymeric carrier, wherein the polymeric carrier comprises a non-biodegradable polymer.

2706. The device of item 2651, further comprising a polymeric carrier, wherein the polymeric carrier comprises a hydrophilic polymer.

2707. The device of item 2651, further comprising a polymeric carrier, wherein the polymeric carrier comprises a hydrophobic polymer.

2708. The device of item 2651, further comprising a polymeric carrier, wherein the polymeric carrier comprises a polymer having hydrophilic domains.

2709. The device of item 2651, further comprising a polymeric carrier, wherein the polymeric carrier comprises a polymer having hydrophobic domains.

2710. The device of item 2651, further comprising a polymeric carrier, wherein the polymeric carrier comprises a non-conductive polymer.

2711. The device of item 2651, further comprising a polymeric carrier, wherein the polymeric carrier comprises an elastomer.

2712. The device of item 2651, further comprising a polymeric carrier, wherein the polymeric carrier comprises a hydrogel.

2713. The device of item 2651, further comprising a polymeric carrier, wherein the polymeric carrier comprises a silicone polymer.

2714. The device of item 2651, further comprising a polymeric carrier, wherein the polymeric carrier comprises a hydrocarbon polymer.

2715. The device of item 2651, further comprising a polymeric carrier, wherein the polymeric carrier comprises a styrene-derived polymer.

2716. The device of item 2651, further comprising a polymeric carrier, wherein the polymeric carrier comprises a butadiene polymer.

2717. The device of item 2651, further comprising a polymeric carrier, wherein the polymeric carrier comprises a macromer.

2718. The device of item 2651, further comprising a polymeric carrier, wherein the polymeric carrier comprises a poly(ethylene glycol) polymer.

2719. The device of item 2651, further comprising a polymeric carrier, wherein the polymeric carrier comprises an amorphous polymer.

2720. The device of item 2651, further comprising a lubricious coating.

2721. The device of item 2651 wherein the fibrosing agent is located within pores or holes of the device.

2722. The device of item 2651 wherein the fibrosing agent is located within a channel, lumen, or divet of the device.

2723. The device of item 2651, further comprising a second pharmaceutically active agent.

2724. The device of item 2651, further comprising an anti-inflammatory agent.

2725. The device of item 2651, further comprising an agent that inhibits infection.

2726. The device of item 2651, further comprising an agent that inhibits infection, wherein the agent is an anthracycline.

2727. The device of item 2651, further comprising an agent that inhibits infection, wherein the agent is doxorubicin.

2728. The device of item 2651, further comprising an agent that inhibits infection, wherein the agent is mitoxantrone.

2729. The device of item 2651, further comprising an agent that inhibits infection, wherein the agent is a fluoropyrimidine.

2730. The device of item 2651, further comprising an agent that inhibits infection, wherein the agent is 5-fluorouracil (5-FU).

2731. The device of item 2651, further comprising an agent that inhibits infection, wherein the agent is a folic acid antagonist.

2732. The device of item 2651, further comprising an agent that inhibits infection, wherein the agent is methotrexate.

2733. The device of item 2651, further comprising an agent that inhibits infection, wherein the agent is a podophylotoxin.

2734. The device of item 2651, further comprising an agent that inhibits infection, wherein the agent is etoposide.

2735. The device of item 2651, further comprising an agent that inhibits infection, wherein the agent is a camptothecin.

2736. The device of item 2651, further comprising an agent that inhibits infection, wherein the agent is a hydroxyurea.

2737. The device of item 2651, further comprising an agent that inhibits infection, wherein the agent is a platinum complex.

2738. The device of item 2651, further comprising an agent that inhibits infection, wherein the agent is cisplatin.

2739. The device of item 2651, further comprising an anti-thrombotic agent.

2740. The device of item 2651, further comprising a visualization agent.

2741. The device of item 2651, further comprising a visualization agent, wherein the visualization agent is a radiopaque material, wherein the radiopaque material comprises a metal, a halogenated compound, or a barium containing compound.

2742. The device of item 2651, further comprising a visualization agent, wherein the visualization agent is a radiopaque material, wherein the radiopaque material comprises barium, tantalum, or technetium.

2743. The device of item 2651, further comprising a visualization agent, wherein the visualization agent is a MRI responsive material.

2744. The device of item 2651, further comprising a visualization agent, wherein the visualization agent comprises a gadolinium chelate.

2745. The device of item 2651, further comprising a visualization agent, wherein the visualization agent comprises iron, magnesium, manganese, copper, or chromium.

2746. The device of item 2651, further comprising a visualization agent, wherein the visualization agent comprises an iron oxide compound.

2747. The device of item 2651, further comprising a visualization agent, wherein the visualization agent comprises a dye, pigment, or colorant.

2748. The device of item 2651, further comprising an echogenic material.

2749. The device of item 2651, further comprising an echogenic material, wherein the echogenic material is in the form of a coating.

2750. The device of item 2651 wherein the device is sterile.

2751. The device of item 2651 wherein the fibrosing agent is released into tissue in the vicinity of the device after deployment of the device.

2752. The device of item 2651 wherein the fibrosing agent is released into tissue in the vicinity of the device after deployment of the device, wherein the tissue is connective tissue.

2753. The device of item 2651 wherein the fibrosing agent is released into tissue in the vicinity of the device after deployment of the device, wherein the tissue is muscle tissue.

2754. The device of item 2651 wherein the fibrosing agent is released into tissue in the vicinity of the device after deployment of the device, wherein the tissue is nerve tissue.

2755. The device of item 2651 wherein the fibrosing agent is released into tissue in the vicinity of the device after deployment of the device, wherein the tissue is epithelium tissue.

2756. The device of item 2651 wherein the fibrosing agent is released in effective concentrations from the device over a period ranging from the time of deployment of the device to about 1 year.

2757. The device of item 2651 wherein the fibrosing agent is released in effective concentrations from the device over a period ranging from about 1 month to 6 months.

2758. The device of item 2651 wherein the fibrosing agent is released in effective concentrations from the device over a period ranging from about 1–90 days.

2759. The device of item 2651 wherein the fibrosing agent is released in effective concentrations from the device at a constant rate.

2760. The device of item 2651 wherein the fibrosing agent is released in effective concentrations from the device at an increasing rate.

2761. The device of item 2651 wherein the fibrosing agent is released in effective concentrations from the device at a decreasing rate.

2762. The device of item 2651 wherein the fibrosing agent is released in effective concentrations from the composition comprising the fibrosing agent by diffusion over a period ranging from the time of deployment of the device to about 90 days.

2763. The device of item 2651 wherein the fibrosing agent is released in effective concentrations from the composition comprising the fibrosing agent by erosion of the composition over a period ranging from the time of deployment of the device to about 90 days.

2764. The device of item 2651 wherein the device comprises about 0.01 µg to about 10 µg of the fibrosing agent.

2765. The device of item 2651 wherein the device comprises about 10 µg to about 10 mg of the fibrosing agent.

2766. The device of item 2651 wherein the device comprises about 10 mg to about 250 mg of the fibrosing agent.

2767. The device of item 2651 wherein the device comprises about 250 mg to about 1000 mg of the fibrosing agent.

2768. The device of item 2651 wherein the device comprises about 1000 mg to about 2500 mg of the fibrosing agent.

2769. The device of item 2651 wherein a surface of the device comprises less than 0.01 µg of the fibrosing agent per $mm^2$ of device surface to which the fibrosing agent is applied.

2770. The device of item 2651 wherein a surface of the device comprises about 0.01 µg to about 1 µg of the fibrosing agent per $mm^2$ of device surface to which the fibrosing agent is applied.

2771. The device of item 2651 wherein a surface of the device comprises about 1 µg to about 10 µg of the fibrosing agent per $mm^2$ of device surface to which the fibrosing agent is applied.

2772. The device of item 2651 wherein a surface of the device comprises about 10 μg to about 250 μg of the fibrosing agent per mm² of device surface to which the fibrosing agent is applied.

2773. The device of item 2651 wherein a surface of the device comprises about 250 μg to about 1000 μg of the fibrosing agent of fibrosing agent per mm² of device surface to which the fibrosing agent is applied.

2774. The device of item 2651 wherein a surface of the device comprises about 1000 μg to about 2500 μg of the fibrosing agent per mm² of device surface to which the fibrosing agent is applied.

2775. A medical device comprising a joint prosthesis and a fibrosing agent, where the fibrosing agent induces a fibrotic response between the device and a patient in which the device is implanted.

2776. The device of item 2775 wherein the fibrosing agent promotes regeneration.

2777. The device of item 2775 wherein the fibrosing agent promotes angiogenesis.

2778. The device of item 2775 wherein the fibrosing agent promotes fibroblast migration.

2779. The device of item 2775 wherein the fibrosing agent promotes fibroblast proliferation.

2780. The device of item 2775 wherein the fibrosing agent promotes deposition of extracellular matrix (ECM).

2781. The device of item 2775 wherein the fibrosing agent promotes tissue remodeling.

2782. The device of item 2775 wherein the fibrosing agent is an arterial vessel wall irritant.

2783. The device of item 2775 wherein the fibrosing agent promotes adhesion between the device and a host into which the device is implanted.

2784. The device of item 2775 wherein the device delivers the fibrosing agent locally to tissue proximate to the device.

2785. The device of item 2775 wherein the fibrosing agent is or comprises silk.

2786. The device of item 2775 wherein the fibrosing agent is or comprises mineral particles.

2787. The device of item 2775 wherein the fibrosing agent is or comprises chitosan.

2788. The device of item 2775 wherein the fibrosing agent is or comprises polylysine.

2789. The device of item 2775 wherein the fibrosing agent is or comprises fibronectin.

2790. The device of item 2775 wherein the fibrosing agent is or comprises bleomycin.

2791. The device of item 2775 wherein the fibrosing agent is or comprises CTGF.

2792. The device of item 2775 wherein the fibrosing agent is in the form of a thread, or is in contact with a thread.

2793. The device of item 2775 wherein the fibrosing agent is in the form of a particulate.

2794. The device of item 2775 wherein the composition further comprises an inflammatory cytokine.

2795. The device of item 2775 wherein the composition further comprises an agent that stimulates cell proliferation.

2796. The device of item 2775 wherein the composition is in the form of a gel, paste, or spray.

2797. The device of item 2775 wherein the fibrosing agent is in the form of tufts.

2798. The device of item 2775, further comprising a polymer.

2799. The device of item 2775, further comprising a polymeric carrier.

2800. The device of item 2775 wherein the fibrosing agent promotes adhesion between the device and a host into which the device is implanted.

2801. The device of item 2775 wherein the device delivers the fibrosing agent locally to tissue proximate to the device.

2802. The device of item 2775, further comprising a coating, wherein the coating comprises the fibrosing agent.

2803. The device of item 2775, further comprising a coating, wherein the coating is disposed on a surface of the device.

2804. The device of item 2775, further comprising a coating, wherein the coating directly contacts the device.

2805. The device of item 2775, further comprising a coating, wherein the coating indirectly contacts the device.

2806. The device of item 2775, further comprising a coating, wherein the coating partially covers the device.

2807. The device of item 2775, further comprising a coating, wherein the coating completely covers the device.

2808. The device of item 2775, further comprising a coating, wherein the coating is a uniform coating.

2809. The device of item 2775, further comprising a coating, wherein the coating is a non-uniform coating.

2810. The device of item 2775, further comprising a coating, wherein the coating is a discontinuous coating.

2811. The device of item 2775, further comprising a coating, wherein the coating is a patterned coating.

2812. The device of item 2775, further comprising a coating, wherein the coating has a thickness of 100 μm or less.

2813. The device of item 2775, further comprising a coating, wherein the coating has a thickness of 10 μm or less.

2814. The device of item 2775, further comprising a coating, wherein the coating adheres to the surface of the device upon deployment of the device.

2815. The device of item 2775, further comprising a coating, wherein the coating is stable at room temperature for a period of 1 year.

2816. The device of item 2775, further comprising a coating, wherein the fibrosing agent is present in the coating in an amount ranging between about 0.0001% to about 1% by weight.

2817. The device of item 2775, further comprising a coating, wherein the fibrosing agent is present in the coating in an amount ranging between about 1% to about 10% by weight.

2818. The device of item 2775, further comprising a coating, wherein the fibrosing agent is present in the coating in an amount ranging between about 10% to about 25% by weight.

2819. The device of item 2775, further comprising a coating, wherein the fibrosing agent is present in the coating in an amount ranging between about 25% to about 70% by weight.

2820. The device of item 2775, further comprising a coating, wherein the coating further comprises a polymer.

2821. The device of item 2775, further comprising a first coating having a first composition and the second coating having a second composition.

2822. The device of item 2775, further comprising a first coating having a first composition and the second coating having a second composition, wherein the first composition and the second composition are different.

2823. The device of item 2775, further comprising a polymer.

2824. The device of item 2775, further comprising a polymeric carrier.

2825. The device of item 2775, further comprising a polymeric carrier, wherein the polymeric carrier comprises a copolymer.

2826. The device of item 2775, further comprising a polymeric carrier, wherein the polymeric carrier comprises a block copolymer.

2827. The device of item 2775, further comprising a polymeric carrier, wherein the polymeric carrier comprises a random copolymer.

2828. The device of item 2775, further comprising a polymeric carrier, wherein the polymeric carrier comprises a biodegradable polymer.

2829. The device of item 2775, further comprising a polymeric carrier, wherein the polymeric carrier comprises a non-biodegradable polymer.

2830. The device of item 2775, further comprising a polymeric carrier, wherein the polymeric carrier comprises a hydrophilic polymer.

2831. The device of item 2775, further comprising a polymeric carrier, wherein the polymeric carrier comprises a hydrophobic polymer.

2832. The device of item 2775, further comprising a polymeric carrier, wherein the polymeric carrier comprises a polymer having hydrophilic domains.

2833. The device of item 2775, further comprising a polymeric carrier, wherein the polymeric carrier comprises a polymer having hydrophobic domains.

2834. The device of item 2775, further comprising a polymeric carrier, wherein the polymeric carrier comprises a non-conductive polymer.

2835. The device of item 2775, further comprising a polymeric carrier, wherein the polymeric carrier comprises an elastomer.

2836. The device of item 2775, further comprising a polymeric carrier, wherein the polymeric carrier comprises a hydrogel.

2837. The device of item 2775, further comprising a polymeric carrier, wherein the polymeric carrier comprises a silicone polymer.

2838. The device of item 2775, further comprising a polymeric carrier, wherein the polymeric carrier comprises a hydrocarbon polymer.

2839. The device of item 2775, further comprising a polymeric carrier, wherein the polymeric carrier comprises a styrene-derived polymer.

2840. The device of item 2775, further comprising a polymeric carrier, wherein the polymeric carrier comprises a butadiene polymer.

2841. The device of item 2775, further comprising a polymeric carrier, wherein the polymeric carrier comprises a macromer.

2842. The device of item 2775, further comprising a polymeric carrier, wherein the polymeric carrier comprises a poly(ethylene glycol) polymer.

2843. The device of item 2775, further comprising a polymeric carrier, wherein the polymeric carrier comprises an amorphous polymer.

2844. The device of item 2775, further comprising a lubricious coating.

2845. The device of item 2775 wherein the fibrosing agent is located within pores or holes of the device.

2846. The device of item 2775 wherein the fibrosing agent is located within a channel, lumen, or divet of the device.

2847. The device of item 2775, further comprising a second pharmaceutically active agent.

2848. The device of item 2775, further comprising an anti-inflammatory agent.

2849. The device of item 2775, further comprising an agent that inhibits infection.

2850. The device of item 2775, further comprising an agent that inhibits infection, wherein the agent is an anthracycline.

2851. The device of item 2775, further comprising an agent that inhibits infection, wherein the agent is doxorubicin.

2852. The device of item 2775, further comprising an agent that inhibits infection, wherein the agent is mitoxantrone.

2853. The device of item 2775, further comprising an agent that inhibits infection, wherein the agent is a fluoropyrimidine.

2854. The device of item 2775, further comprising an agent that inhibits infection, wherein the agent is 5-fluorouracil (5-FU).

2855. The device of item 2775, further comprising an agent that inhibits infection, wherein the agent is a folic acid antagonist.

2856. The device of item 2775, further comprising an agent that inhibits infection, wherein the agent is methotrexate.

2857. The device of item 2775, further comprising an agent that inhibits infection, wherein the agent is a podophylotoxin.

2858. The device of item 2775, further comprising an agent that inhibits infection, wherein the agent is etoposide.

2859. The device of item 2775, further comprising an agent that inhibits infection, wherein the agent is a camptothecin.

2860. The device of item 2775, further comprising an agent that inhibits infection, wherein the agent is a hydroxyurea.

2861. The device of item 2775, further comprising an agent that inhibits infection, wherein the agent is a platinum complex.

2862. The device of item 2775, further comprising an agent that inhibits infection, wherein the agent is cisplatin.

2863. The device of item 2775, further comprising an anti-thrombotic agent.

2864. The device of item 2775, further comprising a visualization agent.

2865. The device of item 2775, further comprising a visualization agent, wherein the visualization agent is a radiopaque material, wherein the radiopaque material comprises a metal, a halogenated compound, or a barium containing compound.

2866. The device of item 2775, further comprising a visualization agent, wherein the visualization agent is a radiopaque material, wherein the radiopaque material comprises barium, tantalum, or technetium.

2867. The device of item 2775, further comprising a visualization agent, wherein the visualization agent is a MRI responsive material.

2868. The device of item 2775, further comprising a visualization agent, wherein the visualization agent comprises a gadolinium chelate.

2869. The device of item 2775, further comprising a visualization agent, wherein the visualization agent comprises iron, magnesium, manganese, copper, or chromium.

2870. The device of item 2775, further comprising a visualization agent, wherein the visualization agent comprises an iron oxide compound.

2871. The device of item 2775, further comprising a visualization agent, wherein the visualization agent comprises a dye, pigment, or colorant.

2872. The device of item 2775, further comprising an echogenic material.

2873. The device of item 2775, further comprising an echogenic material, wherein the echogenic material is in the form of a coating.

2874. The device of item 2775 wherein the device is sterile.

2875. The device of item 2775 wherein the fibrosing agent is released into tissue in the vicinity of the device after deployment of the device.

2876. The device of item 2775 wherein the fibrosing agent is released into tissue in the vicinity of the device after deployment of the device, wherein the tissue is connective tissue.

2877. The device of item 2775 wherein the fibrosing agent is released into tissue in the vicinity of the device after deployment of the device, wherein the tissue is muscle tissue.

2878. The device of item 2775 wherein the fibrosing agent is released into tissue in the vicinity of the device after deployment of the device, wherein the tissue is nerve tissue.

2879. The device of item 2775 wherein the fibrosing agent is released into tissue in the vicinity of the device after deployment of the device, wherein the tissue is epithelium tissue.

2880. The device of item 2775 wherein the fibrosing agent is released in effective concentrations from the device over a period ranging from the time of deployment of the device to about 1 year.

2881. The device of item 2775 wherein the fibrosing agent is released in effective concentrations from the device over a period ranging from about 1 month to 6 months.

2882. The device of item 2775 wherein the fibrosing agent is released in effective concentrations from the device over a period ranging from about 1–90 days.

2883. The device of item 2775 wherein the fibrosing agent is released in effective concentrations from the device at a constant rate.

2884. The device of item 2775 wherein the fibrosing agent is released in effective concentrations from the device at an increasing rate.

2885. The device of item 2775 wherein the fibrosing agent is released in effective concentrations from the device at a decreasing rate.

2886. The device of item 2775 wherein the fibrosing agent is released in effective concentrations from the composition comprising the fibrosing agent by diffusion over a period ranging from the time of deployment of the device to about 90 days.

2887. The device of item 2775 wherein the fibrosing agent is released in effective concentrations from the composition comprising the fibrosing agent by erosion of the composition over a period ranging from the time of deployment of the device to about 90 days.

2888. The device of item 2775 wherein the device comprises about 0.01 µg to about 10 µg of the fibrosing agent.

2889. The device of item 2775 wherein the device comprises about 10 µg to about 10 mg of the fibrosing agent.

2890. The device of item 2775 wherein the device comprises about 10 mg to about 250 mg of the fibrosing agent.

2891. The device of item 2775 wherein the device comprises about 250 mg to about 1000 mg of the fibrosing agent.

2892. The device of item 2775 wherein the device comprises about 1000 mg to about 2500 mg of the fibrosing agent.

2893. The device of item 2775 wherein a surface of the device comprises less than 0.01 µg of the fibrosing agent per $mm^2$ of device surface to which the fibrosing agent is applied.

2894. The device of item 2775 wherein a surface of the device comprises about 0.01 µg to about 1 µg of the fibrosing agent per $mm^2$ of device surface to which the fibrosing agent is applied.

2895. The device of item 2775 wherein a surface of the device comprises about 1 µg to about 10 µg of the fibrosing agent per $mm^2$ of device surface to which the fibrosing agent is applied.

2896. The device of item 2775 wherein a surface of the device comprises about 10 µg to about 250 µg of the fibrosing agent per $mm^2$ of device surface to which the fibrosing agent is applied.

2897. The device of item 2775 wherein a surface of the device comprises about 250 µg to about 1000 µg of the fibrosing agent of fibrosing agent per $mm^2$ of device surface to which the fibrosing agent is applied.

2898. The device of item 2775 wherein a surface of the device comprises about 1000 µg to about 2500 µg of the fibrosing agent per $mm^2$ of device surface to which the fibrosing agent is applied.

2899. A medical device comprising a partial prosthesis and a fibrosing agent, where the fibrosing agent induces a fibrotic response between the device and a patient in which the device is implanted.

2900. The device of item 2899 wherein the fibrosing agent promotes regeneration.

2901. The device of item 2899 wherein the fibrosing agent promotes angiogenesis.

2902. The device of item 2899 wherein the fibrosing agent promotes fibroblast migration.

2903. The device of item 2899 wherein the fibrosing agent promotes fibroblast proliferation.

2904. The device of item 2899 wherein the fibrosing agent promotes deposition of extracellular matrix (ECM).

2905. The device of item 2899 wherein the fibrosing agent promotes tissue remodeling.

2906. The device of item 2899 wherein the fibrosing agent is an arterial vessel wall irritant.

2907. The device of item 2899 wherein the fibrosing agent promotes adhesion between the device and a host into which the device is implanted.

2908. The device of item 2899 wherein the device delivers the fibrosing agent locally to tissue proximate to the device.

2909. The device of item 2899 wherein the fibrosing agent is or comprises silk.

2910. The device of item 2899 wherein the fibrosing agent is or comprises mineral particles.

2911. The device of item 2899 wherein the fibrosing agent is or comprises chitosan.

2912. The device of item 2899 wherein the fibrosing agent is or comprises polylysine.

2913. The device of item 2899 wherein the fibrosing agent is or comprises fibronectin.

2914. The device of item 2899 wherein the fibrosing agent is or comprises bleomycin.

2915. The device of item 2899 wherein the fibrosing agent is or comprises CTGF.

2916. The device of item 2899 wherein the fibrosing agent is in the form of a thread, or is in contact with a thread.

2917. The device of item 2899 wherein the fibrosing agent is in the form of a particulate.

2918. The device of item 2899 wherein the composition further comprises an inflammatory cytokine.

2919. The device of item 2899 wherein the composition further comprises an agent that stimulates cell proliferation.

2920. The device of item 2899 wherein the composition is in the form of a gel, paste, or spray.

2921. The device of item 2899 wherein the fibrosing agent is in the form of tufts.

2922. The device of item 2899, further comprising a polymer.

2923. The device of item 2899, further comprising a polymeric carrier.

2924. The device of item 2899 wherein the fibrosing agent promotes adhesion between the device and a host into which the device is implanted.

2925. The device of item 2899 wherein the device delivers the fibrosing agent locally to tissue proximate to the device.

2926. The device of item 2899, further comprising a coating, wherein the coating comprises the fibrosing agent.

2927. The device of item 2899, further comprising a coating, wherein the coating is disposed on a surface of the device.

2928. The device of item 2899, further comprising a coating, wherein the coating directly contacts the device.

2929. The device of item 2899, further comprising a coating, wherein the coating indirectly contacts the device.

2930. The device of item 2899, further comprising a coating, wherein the coating partially covers the device.

2931. The device of item 2899, further comprising a coating, wherein the coating completely covers the device.

2932. The device of item 2899, further comprising a coating, wherein the coating is a uniform coating.

2933. The device of item 2899, further comprising a coating, wherein the coating is a non-uniform coating.

2934. The device of item 2899, further comprising a coating, wherein the coating is a discontinuous coating.

2935. The device of item 2899, further comprising a coating, wherein the coating is a patterned coating.

2936. The device of item 2899, further comprising a coating, wherein the coating has a thickness of 100 µm or less.

2937. The device of item 2899, further comprising a coating, wherein the coating has a thickness of 10 µm or less.

2938. The device of item 2899, further comprising a coating, wherein the coating adheres to the surface of the device upon deployment of the device.

2939. The device of item 2899, further comprising a coating, wherein the coating is stable at room temperature for a period of 1 year.

2940. The device of item 2899, further comprising a coating, wherein the fibrosing agent is present in the coating in an amount ranging between about 0.0001% to about 1% by weight.

2941. The device of item 2899, further comprising a coating, wherein the fibrosing agent is present in the coating in an amount ranging between about 1% to about 10% by weight.

2942. The device of item 2899, further comprising a coating, wherein the fibrosing agent is present in the coating in an amount ranging between about 10% to about 25% by weight.

2943. The device of item 2899, further comprising a coating, wherein the fibrosing agent is present in the coating in an amount ranging between about 25% to about 70% by weight.

2944. The device of item 2899, further comprising a coating, wherein the coating further comprises a polymer.

2945. The device of item 2899, further comprising a first coating having a first composition and the second coating having a second composition.

2946. The device of item 2899, further comprising a first coating having a first composition and the second coating having a second composition, wherein the first composition and the second composition are different.

2947. The device of item 2899, further comprising a polymer.

2948. The device of item 2899, further comprising a polymeric carrier.

2949. The device of item 2899, further comprising a polymeric carrier, wherein the polymeric carrier comprises a copolymer.

2950. The device of item 2899, further comprising a polymeric carrier, wherein the polymeric carrier comprises a block copolymer.

2951. The device of item 2899, further comprising a polymeric carrier, wherein the polymeric carrier comprises a random copolymer.

2952. The device of item 2899, further comprising a polymeric carrier, wherein the polymeric carrier comprises a biodegradable polymer.

2953. The device of item 2899, further comprising a polymeric carrier, wherein the polymeric carrier comprises a non-biodegradable polymer.

2954. The device of item 2899, further comprising a polymeric carrier, wherein the polymeric carrier comprises a hydrophilic polymer.

2955. The device of item 2899, further comprising a polymeric carrier, wherein the polymeric carrier comprises a hydrophobic polymer.

2956. The device of item 2899, further comprising a polymeric carrier, wherein the polymeric carrier comprises a polymer having hydrophilic domains.

2957. The device of item 2899, further comprising a polymeric carrier, wherein the polymeric carrier comprises a polymer having hydrophobic domains.

2958. The device of item 2899, further comprising a polymeric carrier, wherein the polymeric carrier comprises a non-conductive polymer.

2959. The device of item 2899, further comprising a polymeric carrier, wherein the polymeric carrier comprises an elastomer.

2960. The device of item 2899, further comprising a polymeric carrier, wherein the polymeric carrier comprises a hydrogel.

2961. The device of item 2899, further comprising a polymeric carrier, wherein the polymeric carrier comprises a silicone polymer.

2962. The device of item 2899, further comprising a polymeric carrier, wherein the polymeric carrier comprises a hydrocarbon polymer.

2963. The device of item 2899, further comprising a polymeric carrier, wherein the polymeric carrier comprises a styrene-derived polymer.

2964. The device of item 2899, further comprising a polymeric carrier, wherein the polymeric carrier comprises a butadiene polymer.

2965. The device of item 2899, further comprising a polymeric carrier, wherein the polymeric carrier comprises a macromer.

2966. The device of item 2899, further comprising a polymeric carrier, wherein the polymeric carrier comprises a poly(ethylene glycol) polymer.

2967. The device of item 2899, further comprising a polymeric carrier, wherein the polymeric carrier comprises an amorphous polymer.

2968. The device of item 2899, further comprising a lubricious coating.

2969. The device of item 2899 wherein the fibrosing agent is located within pores or holes of the device.

2970. The device of item 2899 wherein the fibrosing agent is located within a channel, lumen, or divet of the device.

2971. The device of item 2899, further comprising a second pharmaceutically active agent.

2972. The device of item 2899, further comprising an anti-inflammatory agent.

2973. The device of item 2899, further comprising an agent that inhibits infection.

2974. The device of item 2899, further comprising an agent that inhibits infection, wherein the agent is an anthracycline.

2975. The device of item 2899, further comprising an agent that inhibits infection, wherein the agent is doxorubicin.

2976. The device of item 2899, further comprising an agent that inhibits infection, wherein the agent is mitoxantrone.

2977. The device of item 2899, further comprising an agent that inhibits infection, wherein the agent is a fluoropyrimidine.

2978. The device of item 2899, further comprising an agent that inhibits infection, wherein the agent is 5-fluorouracil (5-FU).

2979. The device of item 2899, further comprising an agent that inhibits infection, wherein the agent is a folic acid antagonist.

2980. The device of item 2899, further comprising an agent that inhibits infection, wherein the agent is methotrexate.

2981. The device of item 2899, further comprising an agent that inhibits infection, wherein the agent is a podophylotoxin.

2982. The device of item 2899, further comprising an agent that inhibits infection, wherein the agent is etoposide.

2983. The device of item 2899, further comprising an agent that inhibits infection, wherein the agent is a camptothecin.

2984. The device of item 2899, further comprising an agent that inhibits infection, wherein the agent is a hydroxyurea.

2985. The device of item 2899, further comprising an agent that inhibits infection, wherein the agent is a platinum complex.

2986. The device of item 2899, further comprising an agent that inhibits infection, wherein the agent is cisplatin.

2987. The device of item 2899, further comprising an anti-thrombotic agent.

2988. The device of item 2899, further comprising a visualization agent.

2989. The device of item 2899, further comprising a visualization agent, wherein the visualization agent is a radiopaque material, wherein the radiopaque material comprises a metal, a halogenated compound, or a barium containing compound.

2990. The device of item 2899, further comprising a visualization agent, wherein the visualization agent is a radiopaque material, wherein the radiopaque material comprises barium, tantalum, or technetium.

2991. The device of item 2899, further comprising a visualization agent, wherein the visualization agent is a MRI responsive material.

2992. The device of item 2899, further comprising a visualization agent, wherein the visualization agent comprises a gadolinium chelate.

2993. The device of item 2899, further comprising a visualization agent, wherein the visualization agent comprises iron, magnesium, manganese, copper, or chromium.

2994. The device of item 2899, further comprising a visualization agent, wherein the visualization agent comprises an iron oxide compound.

2995. The device of item 2899, further comprising a visualization agent, wherein the visualization agent comprises a dye, pigment, or colorant.

2996. The device of item 2899, further comprising an echogenic material.

2997. The device of item 2899, further comprising an echogenic material, wherein the echogenic material is in the form of a coating.

2998. The device of item 2899 wherein the device is sterile.

2999. The device of item 2899 wherein the fibrosing agent is released into tissue in the vicinity of the device after deployment of the device.

3000. The device of item 2899 wherein the fibrosing agent is released into tissue in the vicinity of the device after deployment of the device, wherein the tissue is connective tissue.

3001. The device of item 2899 wherein the fibrosing agent is released into tissue in the vicinity of the device after deployment of the device, wherein the tissue is muscle tissue.

3002. The device of item 2899 wherein the fibrosing agent is released into tissue in the vicinity of the device after deployment of the device, wherein the tissue is nerve tissue.

3003. The device of item 2899 wherein the fibrosing agent is released into tissue in the vicinity of the device after deployment of the device, wherein the tissue is epithelium tissue.

3004. The device of item 2899 wherein the fibrosing agent is released in effective concentrations from the device over a period ranging from the time of deployment of the device to about 1 year.

3005. The device of item 2899 wherein the fibrosing agent is released in effective concentrations from the device over a period ranging from about 1 month to 6 months.

3006. The device of item 2899 wherein the fibrosing agent is released in effective concentrations from the device over a period ranging from about 1–90 days.

3007. The device of item 2899 wherein the fibrosing agent is released in effective concentrations from the device at a constant rate.

3008. The device of item 2899 wherein the fibrosing agent is released in effective concentrations from the device at an increasing rate.

3009. The device of item 2899 wherein the fibrosing agent is released in effective concentrations from the device at a decreasing rate.

3010. The device of item 2899 wherein the fibrosing agent is released in effective concentrations from the composition comprising the fibrosing agent by diffusion over a period ranging from the time of deployment of the device to about 90 days.

3011. The device of item 2899 wherein the fibrosing agent is released in effective concentrations from the composition comprising the fibrosing agent by erosion of the composition over a period ranging from the time of deployment of the device to about 90 days.

3012. The device of item 2899 wherein the device comprises about 0.01 µg to about 10 µg of the fibrosing agent.

3013. The device of item 2899 wherein the device comprises about 10 µg to about 10 mg of the fibrosing agent.

3014. The device of item 2899 wherein the device comprises about 10 mg to about 250 mg of the fibrosing agent.

3015. The device of item 2899 wherein the device comprises about 250 mg to about 1000 mg of the fibrosing agent.

3016. The device of item 2899 wherein the device comprises about 1000 mg to about 2500 mg of the fibrosing agent.

3017. The device of item 2899 wherein a surface of the device comprises less than 0.01 µg of the fibrosing agent per $mm^2$ of device surface to which the fibrosing agent is applied.

3018. The device of item 2899 wherein a surface of the device comprises about 0.01 µg to about 1 µg of the fibrosing agent per $mm^2$ of device surface to which the fibrosing agent is applied.

3019. The device of item 2899 wherein a surface of the device comprises about 1 µg to about 10 µg of the fibrosing agent per $mm^2$ of device surface to which the fibrosing agent is applied.

3020. The device of item 2899 wherein a surface of the device comprises about 10 µg to about 250 µg of the fibrosing agent per $mm^2$ of device surface to which the fibrosing agent is applied.

3021. The device of item 2899 wherein a surface of the device comprises about 250 µg to about 1000 µg of the fibrosing agent of fibrosing agent per $mm^2$ of device surface to which the fibrosing agent is applied.

3022. The device of item 2899 wherein a surface of the device comprises about 1000 µg to about 2500 µg of the fibrosing agent per $mm^2$ of device surface to which the fibrosing agent is applied.

3023. A medical device comprising a hip implant and a fibrosing agent, where the fibrosing agent induces a fibrotic response between the device and a patient in which the device is implanted.

3024. The device of item 3023 wherein the fibrosing agent promotes regeneration.

3025. The device of item 3023 wherein the fibrosing agent promotes angiogenesis.

3026. The device of item 3023 wherein the fibrosing agent promotes fibroblast migration.

3027. The device of item 3023 wherein the fibrosing agent promotes fibroblast proliferation.

3028. The device of item 3023 wherein the fibrosing agent promotes deposition of extracellular matrix (ECM).

3029. The device of item 3023 wherein the fibrosing agent promotes tissue remodeling.

3030. The device of item 3023 wherein the fibrosing agent is an arterial vessel wall irritant.

3031. The device of item 3023 wherein the fibrosing agent promotes adhesion between the device and a host into which the device is implanted.

3032. The device of item 3023 wherein the device delivers the fibrosing agent locally to tissue proximate to the device.

3033. The device of item 3023 wherein the fibrosing agent is or comprises silk.

3034. The device of item 3023 wherein the fibrosing agent is or comprises mineral particles.

3035. The device of item 3023 wherein the fibrosing agent is or comprises chitosan.

3036. The device of item 3023 wherein the fibrosing agent is or comprises polylysine.

3037. The device of item 3023 wherein the fibrosing agent is or comprises fibronectin.

3038. The device of item 3023 wherein the fibrosing agent is or comprises bleomycin.

3039. The device of item 3023 wherein the fibrosing agent is or comprises CTGF.

3040. The device of item 3023 wherein the fibrosing agent is in the form of a thread, or is in contact with a thread.

3041. The device of item 3023 wherein the fibrosing agent is in the form of a particulate.

3042. The device of item 3023 wherein the composition further comprises an inflammatory cytokine.

3043. The device of item 3023 wherein the composition further comprises an agent that stimulates cell proliferation.

3044. The device of item 3023 wherein the composition is in the form of a gel, paste, or spray.

3045. The device of item 3023 wherein the fibrosing agent is in the form of tufts.

3046. The device of item 3023, further comprising a polymer.

3047. The device of item 3023, further comprising a polymeric carrier.

3048. The device of item 3023 wherein the fibrosing agent promotes adhesion between the device and a host into which the device is implanted.

3049. The device of item 3023 wherein the device delivers the fibrosing agent locally to tissue proximate to the device.

3050. The device of item 3023, further comprising a coating, wherein the coating comprises the fibrosing agent.

3051. The device of item 3023, further comprising a coating, wherein the coating is disposed on a surface of the device.

3052. The device of item 3023, further comprising a coating, wherein the coating directly contacts the device.

3053. The device of item 3023, further comprising a coating, wherein the coating indirectly contacts the device.

3054. The device of item 3023, further comprising a coating, wherein the coating partially covers the device.

3055. The device of item 3023, further comprising a coating, wherein the coating completely covers the device.

3056. The device of item 3023, further comprising a coating, wherein the coating is a uniform coating.

3057. The device of item 3023, further comprising a coating, wherein the coating is a non-uniform coating.

3058. The device of item 3023, further comprising a coating, wherein the coating is a discontinuous coating.

3059. The device of item 3023, further comprising a coating, wherein the coating is a patterned coating.

3060. The device of item 3023, further comprising a coating, wherein the coating has a thickness of 100 µm or less.

3061. The device of item 3023, further comprising a coating, wherein the coating has a thickness of 10 µm or less.

3062. The device of item 3023, further comprising a coating, wherein the coating adheres to the surface of the device upon deployment of the device.

3063. The device of item 3023, further comprising a coating, wherein the coating is stable at room temperature for a period of 1 year.

3064. The device of item 3023, further comprising a coating, wherein the fibrosing agent is present in the coating in an amount ranging between about 0.0001% to about 1% by weight.

3065. The device of item 3023, further comprising a coating, wherein the fibrosing agent is present in the coating in an amount ranging between about 1% to about 10% by weight.

3066. The device of item 3023, further comprising a coating, wherein the fibrosing agent is present in the coating in an amount ranging between about 10% to about 25% by weight.

3067. The device of item 3023, further comprising a coating, wherein the fibrosing agent is present in the coating in an amount ranging between about 25% to about 70% by weight.

3068. The device of item 3023, further comprising a coating, wherein the coating further comprises a polymer.

3069. The device of item 3023, further comprising a first coating having a first composition and the second coating having a second composition.

3070. The device of item 3023, further comprising a first coating having a first composition and the second coating having a second composition, wherein the first composition and the second composition are different.

3071. The device of item 3023, further comprising a polymer.

3072. The device of item 3023, further comprising a polymeric carrier.

3073. The device of item 3023, further comprising a polymeric carrier, wherein the polymeric carrier comprises a copolymer.

3074. The device of item 3023, further comprising a polymeric carrier, wherein the polymeric carrier comprises a block copolymer.

3075. The device of item 3023, further comprising a polymeric carrier, wherein the polymeric carrier comprises a random copolymer.

3076. The device of item 3023, further comprising a polymeric carrier, wherein the polymeric carrier comprises a biodegradable polymer.

3077. The device of item 3023, further comprising a polymeric carrier, wherein the polymeric carrier comprises a non-biodegradable polymer.

3078. The device of item 3023, further comprising a polymeric carrier, wherein the polymeric carrier comprises a hydrophilic polymer.

3079. The device of item 3023, further comprising a polymeric carrier, wherein the polymeric carrier comprises a hydrophobic polymer.

3080. The device of item 3023, further comprising a polymeric carrier, wherein the polymeric carrier comprises a polymer having hydrophilic domains.

3081. The device of item 3023, further comprising a polymeric carrier, wherein the polymeric carrier comprises a polymer having hydrophobic domains.

3082. The device of item 3023, further comprising a polymeric carrier, wherein the polymeric carrier comprises a non-conductive polymer.

3083. The device of item 3023, further comprising a polymeric carrier, wherein the polymeric carrier comprises an elastomer.

3084. The device of item 3023, further comprising a polymeric carrier, wherein the polymeric carrier comprises a hydrogel.

3085. The device of item 3023, further comprising a polymeric carrier, wherein the polymeric carrier comprises a silicone polymer.

3086. The device of item 3023, further comprising a polymeric carrier, wherein the polymeric carrier comprises a hydrocarbon polymer.

3087. The device of item 3023, further comprising a polymeric carrier, wherein the polymeric carrier comprises a styrene-derived polymer.

3088. The device of item 3023, further comprising a polymeric carrier, wherein the polymeric carrier comprises a butadiene polymer.

3089. The device of item 3023, further comprising a polymeric carrier, wherein the polymeric carrier comprises a macromer.

3090. The device of item 3023, further comprising a polymeric carrier, wherein the polymeric carrier comprises a poly(ethylene glycol) polymer.

3091. The device of item 3023, further comprising a polymeric carrier, wherein the polymeric carrier comprises an amorphous polymer.

3092. The device of item 3023, further comprising a lubricious coating.

3093. The device of item 3023 wherein the fibrosing agent is located within pores or holes of the device.

3094. The device of item 3023 wherein the fibrosing agent is located within a channel, lumen, or divet of the device.

3095. The device of item 3023, further comprising a second pharmaceutically active agent.

3096. The device of item 3023, further comprising an anti-inflammatory agent.

3097. The device of item 3023, further comprising an agent that inhibits infection.

3098. The device of item 3023, further comprising an agent that inhibits infection, wherein the agent is an anthracycline.

3099. The device of item 3023, further comprising an agent that inhibits infection, wherein the agent is doxorubicin.

3100. The device of item 3023, further comprising an agent that inhibits infection, wherein the agent is mitoxantrone.

3101. The device of item 3023, further comprising an agent that inhibits infection, wherein the agent is a fluoropyrimidine.

3102. The device of item 3023, further comprising an agent that inhibits infection, wherein the agent is 5-fluorouracil (5-FU).

3103. The device of item 3023, further comprising an agent that inhibits infection, wherein the agent is a folic acid antagonist.

3104. The device of item 3023, further comprising an agent that inhibits infection, wherein the agent is methotrexate.

3105. The device of item 3023, further comprising an agent that inhibits infection, wherein the agent is a podophylotoxin.

3106. The device of item 3023, further comprising an agent that inhibits infection, wherein the agent is etoposide.

3107. The device of item 3023, further comprising an agent that inhibits infection, wherein the agent is a camptothecin.

3108. The device of item 3023, further comprising an agent that inhibits infection, wherein the agent is a hydroxyurea.

3109. The device of item 3023, further comprising an agent that inhibits infection, wherein the agent is a platinum complex.

3110. The device of item 3023, further comprising an agent that inhibits infection, wherein the agent is cisplatin.

3111. The device of item 3023, further comprising an anti-thrombotic agent.

3112. The device of item 3023, further comprising a visualization agent.

3113. The device of item 3023, further comprising a visualization agent, wherein the visualization agent is a radiopaque material, wherein the radiopaque material comprises a metal, a halogenated compound, or a barium containing compound.

3114. The device of item 3023, further comprising a visualization agent, wherein the visualization agent is a radiopaque material, wherein the radiopaque material comprises barium, tantalum, or technetium.

3115. The device of item 3023, further comprising a visualization agent, wherein the visualization agent is a MRI responsive material.

3116. The device of item 3023, further comprising a visualization agent, wherein the visualization agent comprises a gadolinium chelate.

3117. The device of item 3023, further comprising a visualization agent, wherein the visualization agent comprises iron, magnesium, manganese, copper, or chromium.

3118. The device of item 3023, further comprising a visualization agent, wherein the visualization agent comprises an iron oxide compound.

3119. The device of item 3023, further comprising a visualization agent, wherein the visualization agent comprises a dye, pigment, or colorant.

3120. The device of item 3023, further comprising an echogenic material.

3121. The device of item 3023, further comprising an echogenic material, wherein the echogenic material is in the form of a coating.

3122. The device of item 3023 wherein the device is sterile.

3123. The device of item 3023 wherein the fibrosing agent is released into tissue in the vicinity of the device after deployment of the device.

3124. The device of item 3023 wherein the fibrosing agent is released into tissue in the vicinity of the device after deployment of the device, wherein the tissue is connective tissue.

3125. The device of item 3023 wherein the fibrosing agent is released into tissue in the vicinity of the device after deployment of the device, wherein the tissue is muscle tissue.

3126. The device of item 3023 wherein the fibrosing agent is released into tissue in the vicinity of the device after deployment of the device, wherein the tissue is nerve tissue.

3127. The device of item 3023 wherein the fibrosing agent is released into tissue in the vicinity of the device after deployment of the device, wherein the tissue is epithelium tissue.

3128. The device of item 3023 wherein the fibrosing agent is released in effective concentrations from the device over a period ranging from the time of deployment of the device to about 1 year.

3129. The device of item 3023 wherein the fibrosing agent is released in effective concentrations from the device over a period ranging from about 1 month to 6 months.

3130. The device of item 3023 wherein the fibrosing agent is released in effective concentrations from the device over a period ranging from about 1–90 days.

3131. The device of item 3023 wherein the fibrosing agent is released in effective concentrations from the device at a constant rate.

3132. The device of item 3023 wherein the fibrosing agent is released in effective concentrations from the device at an increasing rate.

3133. The device of item 3023 wherein the fibrosing agent is released in effective concentrations from the device at a decreasing rate.

3134. The device of item 3023 wherein the fibrosing agent is released in effective concentrations from the composition comprising the fibrosing agent by diffusion over a period ranging from the time of deployment of the device to about 90 days.

3135. The device of item 3023 wherein the fibrosing agent is released in effective concentrations from the composition comprising the fibrosing agent by erosion of the composition over a period ranging from the time of deployment of the device to about 90 days.

3136. The device of item 3023 wherein the device comprises about 0.01 µg to about 10 µg of the fibrosing agent.

3137. The device of item 3023 wherein the device comprises about 10 µg to about 10 mg of the fibrosing agent.

3138. The device of item 3023 wherein the device comprises about 10 mg to about 250 mg of the fibrosing agent.

3139. The device of item 3023 wherein the device comprises about 250 mg to about 1000 mg of the fibrosing agent.

3140. The device of item 3023 wherein the device comprises about 1000 mg to about 2500 mg of the fibrosing agent.

3141. The device of item 3023 wherein a surface of the device comprises less than 0.01 µg of the fibrosing agent per $mm^2$ of device surface to which the fibrosing agent is applied.

3142. The device of item 3023 wherein a surface of the device comprises about 0.01 µg to about 1 µg of the fibrosing agent per $mm^2$ of device surface to which the fibrosing agent is applied.

3143. The device of item 3023 wherein a surface of the device comprises about 1 µg to about 10 µg of the fibrosing agent per $mm^2$ of device surface to which the fibrosing agent is applied.

3144. The device of item 3023 wherein a surface of the device comprises about 10 µg to about 250 µg of the fibrosing agent per $mm^2$ of device surface to which the fibrosing agent is applied.

3145. The device of item 3023 wherein a surface of the device comprises about 250 µg to about 1000 µg of the fibrosing agent of fibrosing agent per $mm^2$ of device surface to which the fibrosing agent is applied.

3146. The device of item 3023 wherein a surface of the device comprises about 1000 µg to about 2500 µg of the fibrosing agent per $mm^2$ of device surface to which the fibrosing agent is applied.

3147. The device of item 3023 wherein the hip implant is a full hip replacement.

3148. The device of item 3023 wherein the hip implant is a partial hip replacement.

3149. The device of item 3023 wherein the hip implant is modular.

3150. A medical device comprising a knee implant and a fibrosing agent, where the fibrosing agent induces a fibrotic response between the device and a patient in which the device is implanted.

3151. The device of item 3150 wherein the fibrosing agent promotes regeneration.

3152. The device of item 3150 wherein the fibrosing agent promotes angiogenesis.

3153. The device of item 3150 wherein the fibrosing agent promotes fibroblast migration.

3154. The device of item 3150 wherein the fibrosing agent promotes fibroblast proliferation.

3155. The device of item 3150 wherein the fibrosing agent promotes deposition of extracellular matrix (ECM).

3156. The device of item 3150 wherein the fibrosing agent promotes tissue remodeling.

3157. The device of item 3150 wherein the fibrosing agent is an arterial vessel wall irritant.

3158. The device of item 3150 wherein the fibrosing agent promotes adhesion between the device and a host into which the device is implanted.

3159. The device of item 3150 wherein the device delivers the fibrosing agent locally to tissue proximate to the device.

3160. The device of item 3150 wherein the fibrosing agent is or comprises silk.

3161. The device of item 3150 wherein the fibrosing agent is or comprises mineral particles.

3162. The device of item 3150 wherein the fibrosing agent is or comprises chitosan.

3163. The device of item 3150 wherein the fibrosing agent is or comprises polylysine.

3164. The device of item 3150 wherein the fibrosing agent is or comprises fibronectin.

3165. The device of item 3150 wherein the fibrosing agent is or comprises bleomycin.

3166. The device of item 3150 wherein the fibrosing agent is or comprises CTGF.

3167. The device of item 3150 wherein the fibrosing agent is in the form of a thread, or is in contact with a thread.

3168. The device of item 3150 wherein the fibrosing agent is in the form of a particulate.

3169. The device of item 3150 wherein the composition further comprises an inflammatory cytokine.

3170. The device of item 3150 wherein the composition further comprises an agent that stimulates cell proliferation.

3171. The device of item 3150 wherein the composition is in the form of a gel, paste, or spray.

3172. The device of item 3150 wherein the fibrosing agent is in the form of tufts.

3173. The device of item 3150, further comprising a polymer.

3174. The device of item 3150, further comprising a polymeric carrier.

3175. The device of item 3150 wherein the fibrosing agent promotes adhesion between the device and a host into which the device is implanted.

3176. The device of item 3150 wherein the device delivers the fibrosing agent locally to tissue proximate to the device.

3177. The device of item 3150, further comprising a coating, wherein the coating comprises the fibrosing agent.

3178. The device of item 3150, further comprising a coating, wherein the coating is disposed on a surface of the device.

3179. The device of item 3150, further comprising a coating, wherein the coating directly contacts the device.

3180. The device of item 3150, further comprising a coating, wherein the coating indirectly contacts the device.

3181. The device of item 3150, further comprising a coating, wherein the coating partially covers the device.

3182. The device of item 3150, further comprising a coating, wherein the coating completely covers the device.

3183. The device of item 3150, further comprising a coating, wherein the coating is a uniform coating.

3184. The device of item 3150, further comprising a coating, wherein the coating is a non-uniform coating.

3185. The device of item 3150, further comprising a coating, wherein the coating is a discontinuous coating.

3186. The device of item 3150, further comprising a coating, wherein the coating is a patterned coating.

3187. The device of item 3150, further comprising a coating, wherein the coating has a thickness of 100 µm or less.

3188. The device of item 3150, further comprising a coating, wherein the coating has a thickness of 10 µm or less.

3189. The device of item 3150, further comprising a coating, wherein the coating adheres to the surface of the device upon deployment of the device.

3190. The device of item 3150, further comprising a coating, wherein the coating is stable at room temperature for a period of 1 year.

3191. The device of item 3150, further comprising a coating, wherein the fibrosing agent is present in the coating in an amount ranging between about 0.0001% to about 1% by weight.

3192. The device of item 3150, further comprising a coating, wherein the fibrosing agent is present in the coating in an amount ranging between about 1% to about 10% by weight.

3193. The device of item 3150, further comprising a coating, wherein the fibrosing agent is present in the coating in an amount ranging between about 10% to about 25% by weight.

3194. The device of item 3150, further comprising a coating, wherein the fibrosing agent is present in the coating in an amount ranging between about 25% to about 70% by weight.

3195. The device of item 3150, further comprising a coating, wherein the coating further comprises a polymer.

3196. The device of item 3150, further comprising a first coating having a first composition and the second coating having a second composition.

3197. The device of item 3150, further comprising a first coating having a first composition and the second coating having a second composition, wherein the first composition and the second composition are different.

3198. The device of item 3150, further comprising a polymer.

3199. The device of item 3150, further comprising a polymeric carrier.

3200. The device of item 3150, further comprising a polymeric carrier, wherein the polymeric carrier comprises a copolymer.

3201. The device of item 3150, further comprising a polymeric carrier, wherein the polymeric carrier comprises a block copolymer.

3202. The device of item 3150, further comprising a polymeric carrier, wherein the polymeric carrier comprises a random copolymer.

3203. The device of item 3150, further comprising a polymeric carrier, wherein the polymeric carrier comprises a biodegradable polymer.

3204. The device of item 3150, further comprising a polymeric carrier, wherein the polymeric carrier comprises a non-biodegradable polymer.

3205. The device of item 3150, further comprising a polymeric carrier, wherein the polymeric carrier comprises a hydrophilic polymer.

3206. The device of item 3150, further comprising a polymeric carrier, wherein the polymeric carrier comprises a hydrophobic polymer.

3207. The device of item 3150, further comprising a polymeric carrier, wherein the polymeric carrier comprises a polymer having hydrophilic domains.

3208. The device of item 3150, further comprising a polymeric carrier, wherein the polymeric carrier comprises a polymer having hydrophobic domains.

3209. The device of item 3150, further comprising a polymeric carrier, wherein the polymeric carrier comprises a non-conductive polymer.

3210. The device of item 3150, further comprising a polymeric carrier, wherein the polymeric carrier comprises an elastomer.

3211. The device of item 3150, further comprising a polymeric carrier, wherein the polymeric carrier comprises a hydrogel.

3212. The device of item 3150, further comprising a polymeric carrier, wherein the polymeric carrier comprises a silicone polymer.

3213. The device of item 3150, further comprising a polymeric carrier, wherein the polymeric carrier comprises a hydrocarbon polymer.

3214. The device of item 3150, further comprising a polymeric carrier, wherein the polymeric carrier comprises a styrene-derived polymer.

3215. The device of item 3150, further comprising a polymeric carrier, wherein the polymeric carrier comprises a butadiene polymer.

3216. The device of item 3150, further comprising a polymeric carrier, wherein the polymeric carrier comprises a macromer.

3217. The device of item 3150, further comprising a polymeric carrier, wherein the polymeric carrier comprises a poly(ethylene glycol) polymer.

3218. The device of item 3150, further comprising a polymeric carrier, wherein the polymeric carrier comprises an amorphous polymer.

3219. The device of item 3150, further comprising a lubricious coating.

3220. The device of item 3150 wherein the fibrosing agent is located within pores or holes of the device.

3221. The device of item 3150 wherein the fibrosing agent is located within a channel, lumen, or divet of the device.

3222. The device of item 3150, further comprising a second pharmaceutically active agent.

3223. The device of item 3150, further comprising an anti-inflammatory agent.

3224. The device of item 3150, further comprising an agent that inhibits infection.

3225. The device of item 3150, further comprising an agent that inhibits infection, wherein the agent is an anthracycline.

3226. The device of item 3150, further comprising an agent that inhibits infection, wherein the agent is doxorubicin.

3227. The device of item 3150, further comprising an agent that inhibits infection, wherein the agent is mitoxantrone.

3228. The device of item 3150, further comprising an agent that inhibits infection, wherein the agent is a fluoropyrimidine.

3229. The device of item 3150, further comprising an agent that inhibits infection, wherein the agent is 5-fluorouracil (5-FU).

3230. The device of item 3150, further comprising an agent that inhibits infection, wherein the agent is a folic acid antagonist.

3231. The device of item 3150, further comprising an agent that inhibits infection, wherein the agent is methotrexate.

3232. The device of item 3150, further comprising an agent that inhibits infection, wherein the agent is a podophylotoxin.

3233. The device of item 3150, further comprising an agent that inhibits infection, wherein the agent is etoposide.

3234. The device of item 3150, further comprising an agent that inhibits infection, wherein the agent is a camptothecin.

3235. The device of item 3150, further comprising an agent that inhibits infection, wherein the agent is a hydroxyurea.

3236. The device of item 3150, further comprising an agent that inhibits infection, wherein the agent is a platinum complex.

3237. The device of item 3150, further comprising an agent that inhibits infection, wherein the agent is cisplatin.

3238. The device of item 3150, further comprising an anti-thrombotic agent.

3239. The device of item 3150, further comprising a visualization agent.

3240. The device of item 3150, further comprising a visualization agent, wherein the visualization agent is a radiopaque material, wherein the radiopaque material comprises a metal, a halogenated compound, or a barium containing compound.

3241. The device of item 3150, further comprising a visualization agent, wherein the visualization agent is a radiopaque material, wherein the radiopaque material comprises barium, tantalum, or technetium.

3242. The device of item 3150, further comprising a visualization agent, wherein the visualization agent is a MRI responsive material.

3243. The device of item 3150, further comprising a visualization agent, wherein the visualization agent comprises a gadolinium chelate.

3244. The device of item 3150, further comprising a visualization agent, wherein the visualization agent comprises iron, magnesium, manganese, copper, or chromium.

3245. The device of item 3150, further comprising a visualization agent, wherein the visualization agent comprises an iron oxide compound.

3246. The device of item 3150, further comprising a visualization agent, wherein the visualization agent comprises a dye, pigment, or colorant.

3247. The device of item 3150, further comprising an echogenic material.

3248. The device of item 3150, further comprising an echogenic material, wherein the echogenic material is in the form of a coating.

3249. The device of item 3150 wherein the device is sterile.

3250. The device of item 3150 wherein the fibrosing agent is released into tissue in the vicinity of the device after deployment of the device.

3251. The device of item 3150 wherein the fibrosing agent is released into tissue in the vicinity of the device after deployment of the device, wherein the tissue is connective tissue.

3252. The device of item 3150 wherein the fibrosing agent is released into tissue in the vicinity of the device after deployment of the device, wherein the tissue is muscle tissue.

3253. The device of item 3150 wherein the fibrosing agent is released into tissue in the vicinity of the device after deployment of the device, wherein the tissue is nerve tissue.

3254. The device of item 3150 wherein the fibrosing agent is released into tissue in the vicinity of the device after deployment of the device, wherein the tissue is epithelium tissue.

3255. The device of item 3150 wherein the fibrosing agent is released in effective concentrations from the device over a period ranging from the time of deployment of the device to about 1 year.

3256. The device of item 3150 wherein the fibrosing agent is released in effective concentrations from the device over a period ranging from about 1 month to 6 months.

3257. The device of item 3150 wherein the fibrosing agent is released in effective concentrations from the device over a period ranging from about 1–90 days.

3258. The device of item 3150 wherein the fibrosing agent is released in effective concentrations from the device at a constant rate.

3259. The device of item 3150 wherein the fibrosing agent is released in effective concentrations from the device at an increasing rate.

3260. The device of item 3150 wherein the fibrosing agent is released in effective concentrations from the device at a decreasing rate.

3261. The device of item 3150 wherein the fibrosing agent is released in effective concentrations from the composition comprising the fibrosing agent by diffusion over a period ranging from the time of deployment of the device to about 90 days.

3262. The device of item 3150 wherein the fibrosing agent is released in effective concentrations from the composition comprising the fibrosing agent by erosion of the composition over a period ranging from the time of deployment of the device to about 90 days.

3263. The device of item 3150 wherein the device comprises about 0.01 µg to about 10 µg of the fibrosing agent.

3264. The device of item 3150 wherein the device comprises about 10 µg to about 10 mg of the fibrosing agent.

3265. The device of item 3150 wherein the device comprises about 10 mg to about 250 mg of the fibrosing agent.

3266. The device of item 3150 wherein the device comprises about 250 mg to about 1000 mg of the fibrosing agent.

3267. The device of item 3150 wherein the device comprises about 1000 mg to about 2500 mg of the fibrosing agent.

3268. The device of item 3150 wherein a surface of the device comprises less than 0.01 µg of the fibrosing agent per $mm^2$ of device surface to which the fibrosing agent is applied.

3269. The device of item 3150 wherein a surface of the device comprises about 0.01 µg to about 1 µg of the fibrosing agent per $mm^2$ of device surface to which the fibrosing agent is applied.

3270. The device of item 3150 wherein a surface of the device comprises about 1 µg to about 10 µg of the fibrosing agent per $mm^2$ of device surface to which the fibrosing agent is applied.

3271. The device of item 3150 wherein a surface of the device comprises about 10 µg to about 250 µg of the fibrosing agent per $mm^2$ of device surface to which the fibrosing agent is applied.

3272. The device of item 3150 wherein a surface of the device comprises about 250 µg to about 1000 µg of the fibrosing agent of fibrosing agent per $mm^2$ of device surface to which the fibrosing agent is applied.

3273. The device of item 3150 wherein a surface of the device comprises about 1000 µg to about 2500 µg of the fibrosing agent per $mm^2$ of device surface to which the fibrosing agent is applied.

3274. A medical device comprising a shoulder implant and a fibrosing agent, where the fibrosing agent induces a fibrotic response between the device and a patient in which the device is implanted.

3275. The device of item 3274 wherein the fibrosing agent promotes regeneration.

3276. The device of item 3274 wherein the fibrosing agent promotes angiogenesis.

3277. The device of item 3274 wherein the fibrosing agent promotes fibroblast migration.

3278. The device of item 3274 wherein the fibrosing agent promotes fibroblast proliferation.

3279. The device of item 3274 wherein the fibrosing agent promotes deposition of extracellular matrix (ECM).

3280. The device of item 3274 wherein the fibrosing agent promotes tissue remodeling.

3281. The device of item 3274 wherein the fibrosing agent is an arterial vessel wall irritant.

3282. The device of item 3274 wherein the fibrosing agent promotes adhesion between the device and a host into which the device is implanted.

3283. The device of item 3274 wherein the device delivers the fibrosing agent locally to tissue proximate to the device.

3284. The device of item 3274 wherein the fibrosing agent is or comprises silk.

3285. The device of item 3274 wherein the fibrosing agent is or comprises mineral particles.

3286. The device of item 3274 wherein the fibrosing agent is or comprises chitosan.

3287. The device of item 3274 wherein the fibrosing agent is or comprises polylysine.

3288. The device of item 3274 wherein the fibrosing agent is or comprises fibronectin.

3289. The device of item 3274 wherein the fibrosing agent is or comprises bleomycin.

3290. The device of item 3274 wherein the fibrosing agent is or comprises CTGF.

3291. The device of item 3274 wherein the fibrosing agent is in the form of a thread, or is in contact with a thread.

3292. The device of item 3274 wherein the fibrosing agent is in the form of a particulate.

3293. The device of item 3274 wherein the composition further comprises an inflammatory cytokine.

3294. The device of item 3274 wherein the composition further comprises an agent that stimulates cell proliferation.

3295. The device of item 3274 wherein the composition is in the form of a gel, paste, or spray.

3296. The device of item 3274 wherein the fibrosing agent is in the form of tufts.

3297. The device of item 3274, further comprising a polymer.

3298. The device of item 3274, further comprising a polymeric carrier.

3299. The device of item 3274 wherein the fibrosing agent promotes adhesion between the device and a host into which the device is implanted.

3300. The device of item 3274 wherein the device delivers the fibrosing agent locally to tissue proximate to the device.

3301. The device of item 3274, further comprising a coating, wherein the coating comprises the fibrosing agent.

3302. The device of item 3274, further comprising a coating, wherein the coating is disposed on a surface of the device.

3303. The device of item 3274, further comprising a coating, wherein the coating directly contacts the device.

3304. The device of item 3274, further comprising a coating, wherein the coating indirectly contacts the device.

3305. The device of item 3274, further comprising a coating, wherein the coating partially covers the device.

3306. The device of item 3274, further comprising a coating, wherein the coating completely covers the device.

3307. The device of item 3274, further comprising a coating, wherein the coating is a uniform coating.

3308. The device of item 3274, further comprising a coating, wherein the coating is a non-uniform coating.

3309. The device of item 3274, further comprising a coating, wherein the coating is a discontinuous coating.

3310. The device of item 3274, further comprising a coating, wherein the coating is a patterned coating.

3311. The device of item 3274, further comprising a coating, wherein the coating has a thickness of 100 µm or less.

3312. The device of item 3274, further comprising a coating, wherein the coating has a thickness of 10 µm or less.

3313. The device of item 3274, further comprising a coating, wherein the coating adheres to the surface of the device upon deployment of the device.

3314. The device of item 3274, further comprising a coating, wherein the coating is stable at room temperature for a period of 1 year.

3315. The device of item 3274, further comprising a coating, wherein the fibrosing agent is present in the coating in an amount ranging between about 0.0001% to about 1% by weight.

3316. The device of item 3274, further comprising a coating, wherein the fibrosing agent is present in the coating in an amount ranging between about 1% to about 10% by weight.

3317. The device of item 3274, further comprising a coating, wherein the fibrosing agent is present in the coating in an amount ranging between about 10% to about 25% by weight.

3318. The device of item 3274, further comprising a coating, wherein the fibrosing agent is present in the coating in an amount ranging between about 25% to about 70% by weight.

3319. The device of item 3274, further comprising a coating, wherein the coating further comprises a polymer.

3320. The device of item 3274, further comprising a first coating having a first composition and the second coating having a second composition.

3321. The device of item 3274, further comprising a first coating having a first composition and the second coating having a second composition, wherein the first composition and the second composition are different.

3322. The device of item 3274, further comprising a polymer.

3323. The device of item 3274, further comprising a polymeric carrier.

3324. The device of item 3274, further comprising a polymeric carrier, wherein the polymeric carrier comprises a copolymer.

3325. The device of item 3274, further comprising a polymeric carrier, wherein the polymeric carrier comprises a block copolymer.

3326. The device of item 3274, further comprising a polymeric carrier, wherein the polymeric carrier comprises a random copolymer.

3327. The device of item 3274, further comprising a polymeric carrier, wherein the polymeric carrier comprises a biodegradable polymer.

3328. The device of item 3274, further comprising a polymeric carrier, wherein the polymeric carrier comprises a non-biodegradable polymer.

3329. The device of item 3274, further comprising a polymeric carrier, wherein the polymeric carrier comprises a hydrophilic polymer.

3330. The device of item 3274, further comprising a polymeric carrier, wherein the polymeric carrier comprises a hydrophobic polymer.

3331. The device of item 3274, further comprising a polymeric carrier, wherein the polymeric carrier comprises a polymer having hydrophilic domains.

3332. The device of item 3274, further comprising a polymeric carrier, wherein the polymeric carrier comprises a polymer having hydrophobic domains.

3333. The device of item 3274, further comprising a polymeric carrier, wherein the polymeric carrier comprises a non-conductive polymer.

3334. The device of item 3274, further comprising a polymeric carrier, wherein the polymeric carrier comprises an elastomer.

3335. The device of item 3274, further comprising a polymeric carrier, wherein the polymeric carrier comprises a hydrogel.

3336. The device of item 3274, further comprising a polymeric carrier, wherein the polymeric carrier comprises a silicone polymer.

3337. The device of item 3274, further comprising a polymeric carrier, wherein the polymeric carrier comprises a hydrocarbon polymer.

3338. The device of item 3274, further comprising a polymeric carrier, wherein the polymeric carrier comprises a styrene-derived polymer.

3339. The device of item 3274, further comprising a polymeric carrier, wherein the polymeric carrier comprises a butadiene polymer.

3340. The device of item 3274, further comprising a polymeric carrier, wherein the polymeric carrier comprises a macromer.

3341. The device of item 3274, further comprising a polymeric carrier, wherein the polymeric carrier comprises a poly(ethylene glycol) polymer.

3342. The device of item 3274, further comprising a polymeric carrier, wherein the polymeric carrier comprises an amorphous polymer.

3343. The device of item 3274, further comprising a lubricious coating.

3344. The device of item 3274 wherein the fibrosing agent is located within pores or holes of the device.

3345. The device of item 3274 wherein the fibrosing agent is located within a channel, lumen, or divet of the device.

3346. The device of item 3274, further comprising a second pharmaceutically active agent.

3347. The device of item 3274, further comprising an anti-inflammatory agent.

3348. The device of item 3274, further comprising an agent that inhibits infection.

3349. The device of item 3274, further comprising an agent that inhibits infection, wherein the agent is an anthracycline.

3350. The device of item 3274, further comprising an agent that inhibits infection, wherein the agent is doxorubicin.

3351. The device of item 3274, further comprising an agent that inhibits infection, wherein the agent is mitoxantrone.

3352. The device of item 3274, further comprising an agent that inhibits infection, wherein the agent is a fluoropyrimidine.

3353. The device of item 3274, further comprising an agent that inhibits infection, wherein the agent is 5-fluorouracil (5-FU).

3354. The device of item 3274, further comprising an agent that inhibits infection, wherein the agent is a folic acid antagonist.

3355. The device of item 3274, further comprising an agent that inhibits infection, wherein the agent is methotrexate.

3356. The device of item 3274, further comprising an agent that inhibits infection, wherein the agent is a podophylotoxin.

3357. The device of item 3274, further comprising an agent that inhibits infection, wherein the agent is etoposide.

3358. The device of item 3274, further comprising an agent that inhibits infection, wherein the agent is a camptothecin.

3359. The device of item 3274, further comprising an agent that inhibits infection, wherein the agent is a hydroxyurea.

3360. The device of item 3274, further comprising an agent that inhibits infection, wherein the agent is a platinum complex.

3361. The device of item 3274, further comprising an agent that inhibits infection, wherein the agent is cisplatin.

3362. The device of item 3274, further comprising an anti-thrombotic agent.

3363. The device of item 3274, further comprising a visualization agent.

3364. The device of item 3274, further comprising a visualization agent, wherein the visualization agent is a radiopaque material, wherein the radiopaque material comprises a metal, a halogenated compound, or a barium containing compound.

3365. The device of item 3274, further comprising a visualization agent, wherein the visualization agent is a radiopaque material, wherein the radiopaque material comprises barium, tantalum, or technetium.

3366. The device of item 3274, further comprising a visualization agent, wherein the visualization agent is a MRI responsive material.

3367. The device of item 3274, further comprising a visualization agent, wherein the visualization agent comprises a gadolinium chelate.

3368. The device of item 3274, further comprising a visualization agent, wherein the visualization agent comprises iron, magnesium, manganese, copper, or chromium.

3369. The device of item 3274, further comprising a visualization agent, wherein the visualization agent comprises an iron oxide compound.

3370. The device of item 3274, further comprising a visualization agent, wherein the visualization agent comprises a dye, pigment, or colorant.

3371. The device of item 3274, further comprising an echogenic material.

3372. The device of item 3274, further comprising an echogenic material, wherein the echogenic material is in the form of a coating.

3373. The device of item 3274 wherein the device is sterile.

3374. The device of item 3274 wherein the fibrosing agent is released into tissue in the vicinity of the device after deployment of the device.

3375. The device of item 3274 wherein the fibrosing agent is released into tissue in the vicinity of the device after deployment of the device, wherein the tissue is connective tissue.

3376. The device of item 3274 wherein the fibrosing agent is released into tissue in the vicinity of the device after deployment of the device, wherein the tissue is muscle tissue.

3377. The device of item 3274 wherein the fibrosing agent is released into tissue in the vicinity of the device after deployment of the device, wherein the tissue is nerve tissue.

3378. The device of item 3274 wherein the fibrosing agent is released into tissue in the vicinity of the device after deployment of the device, wherein the tissue is epithelium tissue.

3379. The device of item 3274 wherein the fibrosing agent is released in effective concentrations from the device over a period ranging from the time of deployment of the device to about 1 year.

3380. The device of item 3274 wherein the fibrosing agent is released in effective concentrations from the device over a period ranging from about 1 month to 6 months.

3381. The device of item 3274 wherein the fibrosing agent is released in effective concentrations from the device over a period ranging from about 1–90 days.

3382. The device of item 3274 wherein the fibrosing agent is released in effective concentrations from the device at a constant rate.

3383. The device of item 3274 wherein the fibrosing agent is released in effective concentrations from the device at an increasing rate.

3384. The device of item 3274 wherein the fibrosing agent is released in effective concentrations from the device at a decreasing rate.

3385. The device of item 3274 wherein the fibrosing agent is released in effective concentrations from the composition comprising the fibrosing agent by diffusion over a period ranging from the time of deployment of the device to about 90 days.

3386. The device of item 3274 wherein the fibrosing agent is released in effective concentrations from the composition comprising the fibrosing agent by erosion of the composition over a period ranging from the time of deployment of the device to about 90 days.

3387. The device of item 3274 wherein the device comprises about 0.01 µg to about 10 µg of the fibrosing agent.

3388. The device of item 3274 wherein the device comprises about 10 µg to about 10 mg of the fibrosing agent.

3389. The device of item 3274 wherein the device comprises about 10 mg to about 250 mg of the fibrosing agent.

3390. The device of item 3274 wherein the device comprises about 250 mg to about 1000 mg of the fibrosing agent.

3391. The device of item 3274 wherein the device comprises about 1000 mg to about 2500 mg of the fibrosing agent.

3392. The device of item 3274 wherein a surface of the device comprises less than 0.01 µg of the fibrosing agent per $mm^2$ of device surface to which the fibrosing agent is applied.

3393. The device of item 3274 wherein a surface of the device comprises about 0.01 μg to about 1 μg of the fibrosing agent per mm² of device surface to which the fibrosing agent is applied.

3394. The device of item 3274 wherein a surface of the device comprises about 1 μg to about 10 μg of the fibrosing agent per mm² of device surface to which the fibrosing agent is applied.

3395. The device of item 3274 wherein a surface of the device comprises about 10 μg to about 250 μg of the fibrosing agent per mm² of device surface to which the fibrosing agent is applied.

3396. The device of item 3274 wherein a surface of the device comprises about 250 μg to about 1000 μg of the fibrosing agent of fibrosing agent per mm² of device surface to which the fibrosing agent is applied.

3397. The device of item 3274 wherein a surface of the device comprises about 1000 μg to about 2500 μg of the fibrosing agent per mm² of device surface to which the fibrosing agent is applied.

3398. The device of item 3274 wherein the shoulder implant is a hemiarthroplasty.

3399. The device of item 3274 wherein the shoulder implant is a total shoulder replacement.

3400. A medical device comprising a digit implant and a fibrosing agent, where the fibrosing agent induces a fibrotic response between the device and a patient in which the device is implanted.

3401. The device of item 3400 wherein the fibrosing agent promotes regeneration.

3402. The device of item 3400 wherein the fibrosing agent promotes angiogenesis.

3403. The device of item 3400 wherein the fibrosing agent promotes fibroblast migration.

3404. The device of item 3400 wherein the fibrosing agent promotes fibroblast proliferation.

3405. The device of item 3400 wherein the fibrosing agent promotes deposition of extracellular matrix (ECM).

3406. The device of item 3400 wherein the fibrosing agent promotes tissue remodeling.

3407. The device of item 3400 wherein the fibrosing agent is an arterial vessel wall irritant.

3408. The device of item 3400 wherein the fibrosing agent promotes adhesion between the device and a host into which the device is implanted.

3409. The device of item 3400 wherein the device delivers the fibrosing agent locally to tissue proximate to the device.

3410. The device of item 3400 wherein the fibrosing agent is or comprises silk.

3411. The device of item 3400 wherein the fibrosing agent is or comprises mineral particles.

3412. The device of item 3400 wherein the fibrosing agent is or comprises chitosan.

3413. The device of item 3400 wherein the fibrosing agent is or comprises polylysine.

3414. The device of item 3400 wherein the fibrosing agent is or comprises fibronectin.

3415. The device of item 3400 wherein the fibrosing agent is or comprises bleomycin.

3416. The device of item 3400 wherein the fibrosing agent is or comprises CTGF.

3417. The device of item 3400 wherein the fibrosing agent is in the form of a thread, or is in contact with a thread.

3418. The device of item 3400 wherein the fibrosing agent is in the form of a particulate.

3419. The device of item 3400 wherein the composition further comprises an inflammatory cytokine.

3420. The device of item 3400 wherein the composition further comprises an agent that stimulates cell proliferation.

3421. The device of item 3400 wherein the composition is in the form of a gel, paste, or spray.

3422. The device of item 3400 wherein the fibrosing agent is in the form of tufts.

3423. The device of item 3400, further comprising a polymer.

3424. The device of item 3400, further comprising a polymeric carrier.

3425. The device of item 3400 wherein the fibrosing agent promotes adhesion between the device and a host into which the device is implanted.

3426. The device of item 3400 wherein the device delivers the fibrosing agent locally to tissue proximate to the device.

3427. The device of item 3400, further comprising a coating, wherein the coating comprises the fibrosing agent.

3428. The device of item 3400, further comprising a coating, wherein the coating is disposed on a surface of the device.

3429. The device of item 3400, further comprising a coating, wherein the coating directly contacts the device.

3430. The device of item 3400, further comprising a coating, wherein the coating indirectly contacts the device.

3431. The device of item 3400, further comprising a coating, wherein the coating partially covers the device.

3432. The device of item 3400, further comprising a coating, wherein the coating completely covers the device.

3433. The device of item 3400, further comprising a coating, wherein the coating is a uniform coating.

3434. The device of item 3400, further comprising a coating, wherein the coating is a non-uniform coating.

3435. The device of item 3400, further comprising a coating, wherein the coating is a discontinuous coating.

3436. The device of item 3400, further comprising a coating, wherein the coating is a patterned coating.

3437. The device of item 3400, further comprising a coating, wherein the coating has a thickness of 100 μm or less.

3438. The device of item 3400, further comprising a coating, wherein the coating has a thickness of 10 μm or less.

3439. The device of item 3400, further comprising a coating, wherein the coating adheres to the surface of the device upon deployment of the device.

3440. The device of item 3400, further comprising a coating, wherein the coating is stable at room temperature for a period of 1 year.

3441. The device of item 3400, further comprising a coating, wherein the fibrosing agent is present in the coating in an amount ranging between about 0.0001% to about 1% by weight.

3442. The device of item 3400, further comprising a coating, wherein the fibrosing agent is present in the coating in an amount ranging between about 1% to about 10% by weight.

3443. The device of item 3400, further comprising a coating, wherein the fibrosing agent is present in the coating in an amount ranging between about 10% to about 25% by weight.

3444. The device of item 3400, further comprising a coating, wherein the fibrosing agent is present in the coating in an amount ranging between about 25% to about 70% by weight.

3445. The device of item 3400, further comprising a coating, wherein the coating further comprises a polymer.

3446. The device of item 3400, further comprising a first coating having a first composition and the second coating having a second composition.

3447. The device of item 3400, further comprising a first coating having a first composition and the second coating having a second composition, wherein the first composition and the second composition are different.

3448. The device of item 3400, further comprising a polymer.

3449. The device of item 3400, further comprising a polymeric carrier.

3450. The device of item 3400, further comprising a polymeric carrier, wherein the polymeric carrier comprises a copolymer.

3451. The device of item 3400, further comprising a polymeric carrier, wherein the polymeric carrier comprises a block copolymer.

3452. The device of item 3400, further comprising a polymeric carrier, wherein the polymeric carrier comprises a random copolymer.

3453. The device of item 3400, further comprising a polymeric carrier, wherein the polymeric carrier comprises a biodegradable polymer.

3454. The device of item 3400, further comprising a polymeric carrier, wherein the polymeric carrier comprises a non-biodegradable polymer.

3455. The device of item 3400, further comprising a polymeric carrier, wherein the polymeric carrier comprises a hydrophilic polymer.

3456. The device of item 3400, further comprising a polymeric carrier, wherein the polymeric carrier comprises a hydrophobic polymer.

3457. The device of item 3400, further comprising a polymeric carrier, wherein the polymeric carrier comprises a polymer having hydrophilic domains.

3458. The device of item 3400, further comprising a polymeric carrier, wherein the polymeric carrier comprises a polymer having hydrophobic domains.

3459. The device of item 3400, further comprising a polymeric carrier, wherein the polymeric carrier comprises a non-conductive polymer.

3460. The device of item 3400, further comprising a polymeric carrier, wherein the polymeric carrier comprises an elastomer.

3461. The device of item 3400, further comprising a polymeric carrier, wherein the polymeric carrier comprises a hydrogel.

3462. The device of item 3400, further comprising a polymeric carrier, wherein the polymeric carrier comprises a silicone polymer.

3463. The device of item 3400, further comprising a polymeric carrier, wherein the polymeric carrier comprises a hydrocarbon polymer.

3464. The device of item 3400, further comprising a polymeric carrier, wherein the polymeric carrier comprises a styrene-derived polymer.

3465. The device of item 3400, further comprising a polymeric carrier, wherein the polymeric carrier comprises a butadiene polymer.

3466. The device of item 3400, further comprising a polymeric carrier, wherein the polymeric carrier comprises a macromer.

3467. The device of item 3400, further comprising a polymeric carrier, wherein the polymeric carrier comprises a poly(ethylene glycol) polymer.

3468. The device of item 3400, further comprising a polymeric carrier, wherein the polymeric carrier comprises an amorphous polymer.

3469. The device of item 3400, further comprising a lubricious coating.

3470. The device of item 3400 wherein the fibrosing agent is located within pores or holes of the device.

3471. The device of item 3400 wherein the fibrosing agent is located within a channel, lumen, or divet of the device.

3472. The device of item 3400, further comprising a second pharmaceutically active agent.

3473. The device of item 3400, further comprising an anti-inflammatory agent.

3474. The device of item 3400, further comprising an agent that inhibits infection.

3475. The device of item 3400, further comprising an agent that inhibits infection, wherein the agent is an anthracycline.

3476. The device of item 3400, further comprising an agent that inhibits infection, wherein the agent is doxorubicin.

3477. The device of item 3400, further comprising an agent that inhibits infection, wherein the agent is mitoxantrone.

3478. The device of item 3400, further comprising an agent that inhibits infection, wherein the agent is a fluoropyrimidine.

3479. The device of item 3400, further comprising an agent that inhibits infection, wherein the agent is 5-fluorouracil (5-FU).

3480. The device of item 3400, further comprising an agent that inhibits infection, wherein the agent is a folic acid antagonist.

3481. The device of item 3400, further comprising an agent that inhibits infection, wherein the agent is methotrexate.

3482. The device of item 3400, further comprising an agent that inhibits infection, wherein the agent is a podophylotoxin.

3483. The device of item 3400, further comprising an agent that inhibits infection, wherein the agent is etoposide.

3484. The device of item 3400, further comprising an agent that inhibits infection, wherein the agent is a camptothecin.

3485. The device of item 3400, further comprising an agent that inhibits infection, wherein the agent is a hydroxyurea.

3486. The device of item 3400, further comprising an agent that inhibits infection, wherein the agent is a platinum complex.

3487. The device of item 3400, further comprising an agent that inhibits infection, wherein the agent is cisplatin.

3488. The device of item 3400, further comprising an anti-thrombotic agent.

3489. The device of item 3400, further comprising a visualization agent.

3490. The device of item 3400, further comprising a visualization agent, wherein the visualization agent is a radiopaque material, wherein the radiopaque material comprises a metal, a halogenated compound, or a barium containing compound.

3491. The device of item 3400, further comprising a visualization agent, wherein the visualization agent is a radiopaque material, wherein the radiopaque material comprises barium, tantalum, or technetium.

3492. The device of item 3400, further comprising a visualization agent, wherein the visualization agent is a MRI responsive material.

3493. The device of item 3400, further comprising a visualization agent, wherein the visualization agent comprises a gadolinium chelate.

3494. The device of item 3400, further comprising a visualization agent, wherein the visualization agent comprises iron, magnesium, manganese, copper, or chromium.

3495. The device of item 3400, further comprising a visualization agent, wherein the visualization agent comprises an iron oxide compound.

3496. The device of item 3400, further comprising a visualization agent, wherein the visualization agent comprises a dye, pigment, or colorant.

3497. The device of item 3400, further comprising an echogenic material.

3498. The device of item 3400, further comprising an echogenic material, wherein the echogenic material is in the form of a coating.

3499. The device of item 3400 wherein the device is sterile.

3500. The device of item 3400 wherein the fibrosing agent is released into tissue in the vicinity of the device after deployment of the device.

3501. The device of item 3400 wherein the fibrosing agent is released into tissue in the vicinity of the device after deployment of the device, wherein the tissue is connective tissue.

3502. The device of item 3400 wherein the fibrosing agent is released into tissue in the vicinity of the device after deployment of the device, wherein the tissue is muscle tissue.

3503. The device of item 3400 wherein the fibrosing agent is released into tissue in the vicinity of the device after deployment of the device, wherein the tissue is nerve tissue.

3504. The device of item 3400 wherein the fibrosing agent is released into tissue in the vicinity of the device after deployment of the device, wherein the tissue is epithelium tissue.

3505. The device of item 3400 wherein the fibrosing agent is released in effective concentrations from the device over a period ranging from the time of deployment of the device to about 1 year.

3506. The device of item 3400 wherein the fibrosing agent is released in effective concentrations from the device over a period ranging from about 1 month to 6 months.

3507. The device of item 3400 wherein the fibrosing agent is released in effective concentrations from the device over a period ranging from about 1–90 days.

3508. The device of item 3400 wherein the fibrosing agent is released in effective concentrations from the device at a constant rate.

3509. The device of item 3400 wherein the fibrosing agent is released in effective concentrations from the device at an increasing rate.

3510. The device of item 3400 wherein the fibrosing agent is released in effective concentrations from the device at a decreasing rate.

3511. The device of item 3400 wherein the fibrosing agent is released in effective concentrations from the composition comprising the fibrosing agent by diffusion over a period ranging from the time of deployment of the device to about 90 days.

3512. The device of item 3400 wherein the fibrosing agent is released in effective concentrations from the composition comprising the fibrosing agent by erosion of the composition over a period ranging from the time of deployment of the device to about 90 days.

3513. The device of item 3400 wherein the device comprises about 0.01 µg to about 10 µg of the fibrosing agent.

3514. The device of item 3400 wherein the device comprises about 10 µg to about 10 mg of the fibrosing agent.

3515. The device of item 3400 wherein the device comprises about 10 mg to about 250 mg of the fibrosing agent.

3516. The device of item 3400 wherein the device comprises about 250 mg to about 1000 mg of the fibrosing agent.

3517. The device of item 3400 wherein the device comprises about 1000 mg to about 2500 mg of the fibrosing agent.

3518. The device of item 3400 wherein a surface of the device comprises less than 0.01 µg of the fibrosing agent per $mm^2$ of device surface to which the fibrosing agent is applied.

3519. The device of item 3400 wherein a surface of the device comprises about 0.01 µg to about 1 µg of the fibrosing agent per $mm^2$ of device surface to which the fibrosing agent is applied.

3520. The device of item 3400 wherein a surface of the device comprises about 1 µg to about 10 µg of the fibrosing agent per $mm^2$ of device surface to which the fibrosing agent is applied.

3521. The device of item 3400 wherein a surface of the device comprises about 10 µg to about 250 µg of the fibrosing agent per $mm^2$ of device surface to which the fibrosing agent is applied.

3522. The device of item 3400 wherein a surface of the device comprises about 250 µg to about 1000 µg of the fibrosing agent of fibrosing agent per $mm^2$ of device surface to which the fibrosing agent is applied.

3523. The device of item 3400 wherein a surface of the device comprises about 1000 µg to about 2500 µg of the fibrosing agent per $mm^2$ of device surface to which the fibrosing agent is applied.

3524. A medical device comprising a titanium fixture for replacement of the root portion of a missing natural tooth and a fibrosing agent, where the fibrosing agent induces a fibrotic response between the device and a patient in which the device is implanted.

3525. The device of item 3524 wherein the fibrosing agent promotes regeneration.

3526. The device of item 3524 wherein the fibrosing agent promotes angiogenesis.

3527. The device of item 3524 wherein the fibrosing agent promotes fibroblast migration.

3528. The device of item 3524 wherein the fibrosing agent promotes fibroblast proliferation.

3529. The device of item 3524 wherein the fibrosing agent promotes deposition of extracellular matrix (ECM).

3530. The device of item 3524 wherein the fibrosing agent promotes tissue remodeling.

3531. The device of item 3524 wherein the fibrosing agent is an arterial vessel wall irritant.

3532. The device of item 3524 wherein the fibrosing agent promotes adhesion between the device and a host into which the device is implanted.

3533. The device of item 3524 wherein the device delivers the fibrosing agent locally to tissue proximate to the device.

3534. The device of item 3524 wherein the fibrosing agent is or comprises silk.

3535. The device of item 3524 wherein the fibrosing agent is or comprises mineral particles.

3536. The device of item 3524 wherein the fibrosing agent is or comprises chitosan.

3537. The device of item 3524 wherein the fibrosing agent is or comprises polylysine.

3538. The device of item 3524 wherein the fibrosing agent is or comprises fibronectin.

3539. The device of item 3524 wherein the fibrosing agent is or comprises bleomycin.

3540. The device of item 3524 wherein the fibrosing agent is or comprises CTGF.

3541. The device of item 3524 wherein the fibrosing agent is in the form of a thread, or is in contact with a thread.

3542. The device of item 3524 wherein the fibrosing agent is in the form of a particulate.

3543. The device of item 3524 wherein the composition further comprises an inflammatory cytokine.

3544. The device of item 3524 wherein the composition further comprises an agent that stimulates cell proliferation.

3545. The device of item 3524 wherein the composition is in the form of a gel, paste, or spray.

3546. The device of item 3524 wherein the fibrosing agent is in the form of tufts.

3547. The device of item 3524, further comprising a polymer.

3548. The device of item 3524, further comprising a polymeric carrier.

3549. The device of item 3524 wherein the fibrosing agent promotes adhesion between the device and a host into which the device is implanted.

3550. The device of item 3524 wherein the device delivers the fibrosing agent locally to tissue proximate to the device.

3551. The device of item 3524, further comprising a coating, wherein the coating comprises the fibrosing agent.

3552. The device of item 3524, further comprising a coating, wherein the coating is disposed on a surface of the device.

3553. The device of item 3524, further comprising a coating, wherein the coating directly contacts the device.

3554. The device of item 3524, further comprising a coating, wherein the coating indirectly contacts the device.

3555. The device of item 3524, further comprising a coating, wherein the coating partially covers the device.

3556. The device of item 3524, further comprising a coating, wherein the coating completely covers the device.

3557. The device of item 3524, further comprising a coating, wherein the coating is a uniform coating.

3558. The device of item 3524, further comprising a coating, wherein the coating is a non-uniform coating.

3559. The device of item 3524, further comprising a coating, wherein the coating is a discontinuous coating.

3560. The device of item 3524, further comprising a coating, wherein the coating is a patterned coating.

3561. The device of item 3524, further comprising a coating, wherein the coating has a thickness of 100 µm or less.

3562. The device of item 3524, further comprising a coating, wherein the coating has a thickness of 10 µm or less.

3563. The device of item 3524, further comprising a coating, wherein the coating adheres to the surface of the device upon deployment of the device.

3564. The device of item 3524, further comprising a coating, wherein the coating is stable at room temperature for a period of 1 year.

3565. The device of item 3524, further comprising a coating, wherein the fibrosing agent is present in the coating in an amount ranging between about 0.0001% to about 1% by weight.

3566. The device of item 3524, further comprising a coating, wherein the fibrosing agent is present in the coating in an amount ranging between about 1% to about 10% by weight.

3567. The device of item 3524, further comprising a coating, wherein the fibrosing agent is present in the coating in an amount ranging between about 10% to about 25% by weight.

3568. The device of item 3524, further comprising a coating, wherein the fibrosing agent is present in the coating in an amount ranging between about 25% to about 70% by weight.

3569. The device of item 3524, further comprising a coating, wherein the coating further comprises a polymer.

3570. The device of item 3524, further comprising a first coating having a first composition and the second coating having a second composition.

3571. The device of item 3524, further comprising a first coating having a first composition and the second coating having a second composition, wherein the first composition and the second composition are different.

3572. The device of item 3524, further comprising a polymer.

3573. The device of item 3524, further comprising a polymeric carrier.

3574. The device of item 3524, further comprising a polymeric carrier, wherein the polymeric carrier comprises a copolymer.

3575. The device of item 3524, further comprising a polymeric carrier, wherein the polymeric carrier comprises a block copolymer.

3576. The device of item 3524, further comprising a polymeric carrier, wherein the polymeric carrier comprises a random copolymer.

3577. The device of item 3524, further comprising a polymeric carrier, wherein the polymeric carrier comprises a biodegradable polymer.

3578. The device of item 3524, further comprising a polymeric carrier, wherein the polymeric carrier comprises a non-biodegradable polymer.

3579. The device of item 3524, further comprising a polymeric carrier, wherein the polymeric carrier comprises a hydrophilic polymer.

3580. The device of item 3524, further comprising a polymeric carrier, wherein the polymeric carrier comprises a hydrophobic polymer.

3581. The device of item 3524, further comprising a polymeric carrier, wherein the polymeric carrier comprises a polymer having hydrophilic domains.

3582. The device of item 3524, further comprising a polymeric carrier, wherein the polymeric carrier comprises a polymer having hydrophobic domains.

3583. The device of item 3524, further comprising a polymeric carrier, wherein the polymeric carrier comprises a non-conductive polymer.

3584. The device of item 3524, further comprising a polymeric carrier, wherein the polymeric carrier comprises an elastomer.

3585. The device of item 3524, further comprising a polymeric carrier, wherein the polymeric carrier comprises a hydrogel.

3586. The device of item 3524, further comprising a polymeric carrier, wherein the polymeric carrier comprises a silicone polymer.

3587. The device of item 3524, further comprising a polymeric carrier, wherein the polymeric carrier comprises a hydrocarbon polymer.

3588. The device of item 3524, further comprising a polymeric carrier, wherein the polymeric carrier comprises a styrene-derived polymer.

3589. The device of item 3524, further comprising a polymeric carrier, wherein the polymeric carrier comprises a butadiene polymer.

3590. The device of item 3524, further comprising a polymeric carrier, wherein the polymeric carrier comprises a macromer.

3591. The device of item 3524, further comprising a polymeric carrier, wherein the polymeric carrier comprises a poly(ethylene glycol) polymer.

3592. The device of item 3524, further comprising a polymeric carrier, wherein the polymeric carrier comprises an amorphous polymer.

3593. The device of item 3524, further comprising a lubricious coating.

3594. The device of item 3524 wherein the fibrosing agent is located within pores or holes of the device.

3595. The device of item 3524 wherein the fibrosing agent is located within a channel, lumen, or divet of the device.

3596. The device of item 3524, further comprising a second pharmaceutically active agent.

3597. The device of item 3524, further comprising an anti-inflammatory agent.

3598. The device of item 3524, further comprising an agent that inhibits infection.

3599. The device of item 3524, further comprising an agent that inhibits infection, wherein the agent is an anthracycline.

3600. The device of item 3524, further comprising an agent that inhibits infection, wherein the agent is doxorubicin.

3601. The device of item 3524, further comprising an agent that inhibits infection, wherein the agent is mitoxantrone.

3602. The device of item 3524, further comprising an agent that inhibits infection, wherein the agent is a fluoropyrimidine.

3603. The device of item 3524, further comprising an agent that inhibits infection, wherein the agent is 5-fluorouracil (5-FU).

3604. The device of item 3524, further comprising an agent that inhibits infection, wherein the agent is a folic acid antagonist.

3605. The device of item 3524, further comprising an agent that inhibits infection, wherein the agent is methotrexate.

3606. The device of item 3524, further comprising an agent that inhibits infection, wherein the agent is a podophylotoxin.

3607. The device of item 3524, further comprising an agent that inhibits infection, wherein the agent is etoposide.

3608. The device of item 3524, further comprising an agent that inhibits infection, wherein the agent is a camptothecin.

3609. The device of item 3524, further comprising an agent that inhibits infection, wherein the agent is a hydroxyurea.

3610. The device of item 3524, further comprising an agent that inhibits infection, wherein the agent is a platinum complex.

3611. The device of item 3524, further comprising an agent that inhibits infection, wherein the agent is cisplatin.

3612. The device of item 3524, further comprising an anti-thrombotic agent.

3613. The device of item 3524, further comprising a visualization agent.

3614. The device of item 3524, further comprising a visualization agent, wherein the visualization agent is a radiopaque material, wherein the radiopaque material comprises a metal, a halogenated compound, or a barium containing compound.

3615. The device of item 3524, further comprising a visualization agent, wherein the visualization agent is a radiopaque material, wherein the radiopaque material comprises barium, tantalum, or technetium.

3616. The device of item 3524, further comprising a visualization agent, wherein the visualization agent is a MRI responsive material.

3617. The device of item 3524, further comprising a visualization agent, wherein the visualization agent comprises a gadolinium chelate.

3618. The device of item 3524, further comprising a visualization agent, wherein the visualization agent comprises iron, magnesium, manganese, copper, or chromium.

3619. The device of item 3524, further comprising a visualization agent, wherein the visualization agent comprises an iron oxide compound.

3620. The device of item 3524, further comprising a visualization agent, wherein the visualization agent comprises a dye, pigment, or colorant.

3621. The device of item 3524, further comprising an echogenic material.

3622. The device of item 3524, further comprising an echogenic material, wherein the echogenic material is in the form of a coating.

3623. The device of item 3524 wherein the device is sterile.

3624. The device of item 3524 wherein the fibrosing agent is released into tissue in the vicinity of the device after deployment of the device.

3625. The device of item 3524 wherein the fibrosing agent is released into tissue in the vicinity of the device after deployment of the device, wherein the tissue is connective tissue.

3626. The device of item 3524 wherein the fibrosing agent is released into tissue in the vicinity of the device after deployment of the device, wherein the tissue is muscle tissue.

3627. The device of item 3524 wherein the fibrosing agent is released into tissue in the vicinity of the device after deployment of the device, wherein the tissue is nerve tissue.

3628. The device of item 3524 wherein the fibrosing agent is released into tissue in the vicinity of the device after deployment of the device, wherein the tissue is epithelium tissue.

3629. The device of item 3524 wherein the fibrosing agent is released in effective concentrations from the device over a period ranging from the time of deployment of the device to about 1 year.

3630. The device of item 3524 wherein the fibrosing agent is released in effective concentrations from the device over a period ranging from about 1 month to 6 months.

3631. The device of item 3524 wherein the fibrosing agent is released in effective concentrations from the device over a period ranging from about 1–90 days.

3632. The device of item 3524 wherein the fibrosing agent is released in effective concentrations from the device at a constant rate.

3633. The device of item 3524 wherein the fibrosing agent is released in effective concentrations from the device at an increasing rate.

3634. The device of item 3524 wherein the fibrosing agent is released in effective concentrations from the device at a decreasing rate.

3635. The device of item 3524 wherein the fibrosing agent is released in effective concentrations from the composition comprising the fibrosing agent by diffusion over a period ranging from the time of deployment of the device to about 90 days.

3636. The device of item 3524 wherein the fibrosing agent is released in effective concentrations from the composition comprising the fibrosing agent by erosion of the composition over a period ranging from the time of deployment of the device to about 90 days.

3637. The device of item 3524 wherein the device comprises about 0.01 µg to about 10 µg of the fibrosing agent.

3638. The device of item 3524 wherein the device comprises about 10 µg to about 10 mg of the fibrosing agent.

3639. The device of item 3524 wherein the device comprises about 10 mg to about 250 mg of the fibrosing agent.

3640. The device of item 3524 wherein the device comprises about 250 mg to about 1000 mg of the fibrosing agent.

3641. The device of item 3524 wherein the device comprises about 1000 mg to about 2500 mg of the fibrosing agent.

3642. The device of item 3524 wherein a surface of the device comprises less than 0.01 µg of the fibrosing agent per $mm^2$ of device surface to which the fibrosing agent is applied.

3643. The device of item 3524 wherein a surface of the device comprises about 0.01 µg to about 1 µg of the fibrosing agent per $mm^2$ of device surface to which the fibrosing agent is applied.

3644. The device of item 3524 wherein a surface of the device comprises about 1 µg to about 10 µg of the fibrosing agent per $mm^2$ of device surface to which the fibrosing agent is applied.

3645. The device of item 3524 wherein a surface of the device comprises about 10 µg to about 250 µg of the fibrosing agent per $mm^2$ of device surface to which the fibrosing agent is applied.

3646. The device of item 3524 wherein a surface of the device comprises about 250 µg to about 1000 µg of the fibrosing agent of fibrosing agent per $mm^2$ of device surface to which the fibrosing agent is applied.

3647. The device of item 3524 wherein a surface of the device comprises about 1000 µg to about 2500 µg of the fibrosing agent per $mm^2$ of device surface to which the fibrosing agent is applied.

3648. A medical device comprising an endosteal implant and a fibrosing agent, where the fibrosing agent induces a fibrotic response between the device and a patient in which the device is implanted.

3649. The device of item 3648 wherein the fibrosing agent promotes regeneration.

3650. The device of item 3648 wherein the fibrosing agent promotes angiogenesis.

3651. The device of item 3648 wherein the fibrosing agent promotes fibroblast migration.

3652. The device of item 3648 wherein the fibrosing agent promotes fibroblast proliferation.

3653. The device of item 3648 wherein the fibrosing agent promotes deposition of extracellular matrix (ECM).

3654. The device of item 3648 wherein the fibrosing agent promotes tissue remodeling.

3655. The device of item 3648 wherein the fibrosing agent is an arterial vessel wall irritant.

3656. The device of item 3648 wherein the fibrosing agent promotes adhesion between the device and a host into which the device is implanted.

3657. The device of item 3648 wherein the device delivers the fibrosing agent locally to tissue proximate to the device.

3658. The device of item 3648 wherein the fibrosing agent is or comprises silk.

3659. The device of item 3648 wherein the fibrosing agent is or comprises mineral particles.

3660. The device of item 3648 wherein the fibrosing agent is or comprises chitosan.

3661. The device of item 3648 wherein the fibrosing agent is or comprises polylysine.

3662. The device of item 3648 wherein the fibrosing agent is or comprises fibronectin.

3663. The device of item 3648 wherein the fibrosing agent is or comprises bleomycin.

3664. The device of item 3648 wherein the fibrosing agent is or comprises CTGF.

3665. The device of item 3648 wherein the fibrosing agent is in the form of a thread, or is in contact with a thread.

3666. The device of item 3648 wherein the fibrosing agent is in the form of a particulate.

3667. The device of item 3648 wherein the composition further comprises an inflammatory cytokine.

3668. The device of item 3648 wherein the composition further comprises an agent that stimulates cell proliferation.

3669. The device of item 3648 wherein the composition is in the form of a gel, paste, or spray.

3670. The device of item 3648 wherein the fibrosing agent is in the form of tufts.

3671. The device of item 3648, further comprising a polymer.

3672. The device of item 3648, further comprising a polymeric carrier.

3673. The device of item 3648 wherein the fibrosing agent promotes adhesion between the device and a host into which the device is implanted.

3674. The device of item 3648 wherein the device delivers the fibrosing agent locally to tissue proximate to the device.

3675. The device of item 3648, further comprising a coating, wherein the coating comprises the fibrosing agent.

3676. The device of item 3648, further comprising a coating, wherein the coating is disposed on a surface of the device.

3677. The device of item 3648, further comprising a coating, wherein the coating directly contacts the device.

3678. The device of item 3648, further comprising a coating, wherein the coating indirectly contacts the device.

3679. The device of item 3648, further comprising a coating, wherein the coating partially covers the device.

3680. The device of item 3648, further comprising a coating, wherein the coating completely covers the device.

3681. The device of item 3648, further comprising a coating, wherein the coating is a uniform coating.

3682. The device of item 3648, further comprising a coating, wherein the coating is a non-uniform coating.

3683. The device of item 3648, further comprising a coating, wherein the coating is a discontinuous coating.

3684. The device of item 3648, further comprising a coating, wherein the coating is a patterned coating.

3685. The device of item 3648, further comprising a coating, wherein the coating has a thickness of 100 μm or less.

3686. The device of item 3648, further comprising a coating, wherein the coating has a thickness of 10 μm or less.

3687. The device of item 3648, further comprising a coating, wherein the coating adheres to the surface of the device upon deployment of the device.

3688. The device of item 3648, further comprising a coating, wherein the coating is stable at room temperature for a period of 1 year.

3689. The device of item 3648, further comprising a coating, wherein the fibrosing agent is present in the coating in an amount ranging between about 0.0001% to about 1% by weight.

3690. The device of item 3648, further comprising a coating, wherein the fibrosing agent is present in the coating in an amount ranging between about 1% to about 10% by weight.

3691. The device of item 3648, further comprising a coating, wherein the fibrosing agent is present in the coating in an amount ranging between about 10% to about 25% by weight.

3692. The device of item 3648, further comprising a coating, wherein the fibrosing agent is present in the coating in an amount ranging between about 25% to about 70% by weight.

3693. The device of item 3648, further comprising a coating, wherein the coating further comprises a polymer.

3694. The device of item 3648, further comprising a first coating having a first composition and the second coating having a second composition.

3695. The device of item 3648, further comprising a first coating having a first composition and the second coating having a second composition, wherein the first composition and the second composition are different.

3696. The device of item 3648, further comprising a polymer.

3697. The device of item 3648, further comprising a polymeric carrier.

3698. The device of item 3648, further comprising a polymeric carrier, wherein the polymeric carrier comprises a copolymer.

3699. The device of item 3648, further comprising a polymeric carrier, wherein the polymeric carrier comprises a block copolymer.

3700. The device of item 3648, further comprising a polymeric carrier, wherein the polymeric carrier comprises a random copolymer.

3701. The device of item 3648, further comprising a polymeric carrier, wherein the polymeric carrier comprises a biodegradable polymer.

3702. The device of item 3648, further comprising a polymeric carrier, wherein the polymeric carrier comprises a non-biodegradable polymer.

3703. The device of item 3648, further comprising a polymeric carrier, wherein the polymeric carrier comprises a hydrophilic polymer.

3704. The device of item 3648, further comprising a polymeric carrier, wherein the polymeric carrier comprises a hydrophobic polymer.

3705. The device of item 3648, further comprising a polymeric carrier, wherein the polymeric carrier comprises a polymer having hydrophilic domains.

3706. The device of item 3648, further comprising a polymeric carrier, wherein the polymeric carrier comprises a polymer having hydrophobic domains.

3707. The device of item 3648, further comprising a polymeric carrier, wherein the polymeric carrier comprises a non-conductive polymer.

3708. The device of item 3648, further comprising a polymeric carrier, wherein the polymeric carrier comprises an elastomer.

3709. The device of item 3648, further comprising a polymeric carrier, wherein the polymeric carrier comprises a hydrogel.

3710. The device of item 3648, further comprising a polymeric carrier, wherein the polymeric carrier comprises a silicone polymer.

3711. The device of item 3648, further comprising a polymeric carrier, wherein the polymeric carrier comprises a hydrocarbon polymer.

3712. The device of item 3648, further comprising a polymeric carrier, wherein the polymeric carrier comprises a styrene-derived polymer.

3713. The device of item 3648, further comprising a polymeric carrier, wherein the polymeric carrier comprises a butadiene polymer.

3714. The device of item 3648, further comprising a polymeric carrier, wherein the polymeric carrier comprises a macromer.

3715. The device of item 3648, further comprising a polymeric carrier, wherein the polymeric carrier comprises a poly(ethylene glycol) polymer.

3716. The device of item 3648, further comprising a polymeric carrier, wherein the polymeric carrier comprises an amorphous polymer.

3717. The device of item 3648, further comprising a lubricious coating.

3718. The device of item 3648 wherein the fibrosing agent is located within pores or holes of the device.

3719. The device of item 3648 wherein the fibrosing agent is located within a channel, lumen, or divet of the device.

3720. The device of item 3648, further comprising a second pharmaceutically active agent.

3721. The device of item 3648, further comprising an anti-inflammatory agent.

3722. The device of item 3648, further comprising an agent that inhibits infection.

3723. The device of item 3648, further comprising an agent that inhibits infection, wherein the agent is an anthracycline.

3724. The device of item 3648, further comprising an agent that inhibits infection, wherein the agent is doxorubicin.

3725. The device of item 3648, further comprising an agent that inhibits infection, wherein the agent is mitoxantrone.

3726. The device of item 3648, further comprising an agent that inhibits infection, wherein the agent is a fluoropyrimidine.

3727. The device of item 3648, further comprising an agent that inhibits infection, wherein the agent is 5-fluorouracil (5-FU).

3728. The device of item 3648, further comprising an agent that inhibits infection, wherein the agent is a folic acid antagonist.

3729. The device of item 3648, further comprising an agent that inhibits infection, wherein the agent is methotrexate.

3730. The device of item 3648, further comprising an agent that inhibits infection, wherein the agent is a podophylotoxin.

3731. The device of item 3648, further comprising an agent that inhibits infection, wherein the agent is etoposide.

3732. The device of item 3648, further comprising an agent that inhibits infection, wherein the agent is a camptothecin.

3733. The device of item 3648, further comprising an agent that inhibits infection, wherein the agent is a hydroxyurea.

3734. The device of item 3648, further comprising an agent that inhibits infection, wherein the agent is a platinum complex.

3735. The device of item 3648, further comprising an agent that inhibits infection, wherein the agent is cisplatin.

3736. The device of item 3648, further comprising an anti-thrombotic agent.

3737. The device of item 3648, further comprising a visualization agent.

3738. The device of item 3648, further comprising a visualization agent, wherein the visualization agent is a radiopaque material, wherein the radiopaque material comprises a metal, a halogenated compound, or a barium containing compound.

3739. The device of item 3648, further comprising a visualization agent, wherein the visualization agent is a radiopaque material, wherein the radiopaque material comprises barium, tantalum, or technetium.

3740. The device of item 3648, further comprising a visualization agent, wherein the visualization agent is a MRI responsive material.

3741. The device of item 3648, further comprising a visualization agent, wherein the visualization agent comprises a gadolinium chelate.

3742. The device of item 3648, further comprising a visualization agent, wherein the visualization agent comprises iron, magnesium, manganese, copper, or chromium.

3743. The device of item 3648, further comprising a visualization agent, wherein the visualization agent comprises an iron oxide compound.

3744. The device of item 3648, further comprising a visualization agent, wherein the visualization agent comprises a dye, pigment, or colorant.

3745. The device of item 3648, further comprising an echogenic material.

3746. The device of item 3648, further comprising an echogenic material, wherein the echogenic material is in the form of a coating.

3747. The device of item 3648 wherein the device is sterile.

3748. The device of item 3648 wherein the fibrosing agent is released into tissue in the vicinity of the device after deployment of the device.

3749. The device of item 3648 wherein the fibrosing agent is released into tissue in the vicinity of the device after deployment of the device, wherein the tissue is connective tissue.

3750. The device of item 3648 wherein the fibrosing agent is released into tissue in the vicinity of the device after deployment of the device, wherein the tissue is muscle tissue.

3751. The device of item 3648 wherein the fibrosing agent is released into tissue in the vicinity of the device after deployment of the device, wherein the tissue is nerve tissue.

3752. The device of item 3648 wherein the fibrosing agent is released into tissue in the vicinity of the device after deployment of the device, wherein the tissue is epithelium tissue.

3753. The device of item 3648 wherein the fibrosing agent is released in effective concentrations from the device over a period ranging from the time of deployment of the device to about 1 year.

3754. The device of item 3648 wherein the fibrosing agent is released in effective concentrations from the device over a period ranging from about 1 month to 6 months.

3755. The device of item 3648 wherein the fibrosing agent is released in effective concentrations from the device over a period ranging from about 1–90 days.

3756. The device of item 3648 wherein the fibrosing agent is released in effective concentrations from the device at a constant rate.

3757. The device of item 3648 wherein the fibrosing agent is released in effective concentrations from the device at an increasing rate.

3758. The device of item 3648 wherein the fibrosing agent is released in effective concentrations from the device at a decreasing rate.

3759. The device of item 3648 wherein the fibrosing agent is released in effective concentrations from the composition comprising the fibrosing agent by diffusion over a period ranging from the time of deployment of the device to about 90 days.

3760. The device of item 3648 wherein the fibrosing agent is released in effective concentrations from the composition comprising the fibrosing agent by erosion of the composition over a period ranging from the time of deployment of the device to about 90 days.

3761. The device of item 3648 wherein the device comprises about 0.01 µg to about 10 µg of the fibrosing agent.

3762. The device of item 3648 wherein the device comprises about 10 µg to about 10 mg of the fibrosing agent.

3763. The device of item 3648 wherein the device comprises about 10 mg to about 250 mg of the fibrosing agent.

3764. The device of item 3648 wherein the device comprises about 250 mg to about 1000 mg of the fibrosing agent.

3765. The device of item 3648 wherein the device comprises about 1000 mg to about 2500 mg of the fibrosing agent.

3766. The device of item 3648 wherein a surface of the device comprises less than 0.01 µg of the fibrosing agent per $mm^2$ of device surface to which the fibrosing agent is applied.

3767. The device of item 3648 wherein a surface of the device comprises about 0.01 µg to about 1 µg of the fibrosing agent per $mm^2$ of device surface to which the fibrosing agent is applied.

3768. The device of item 3648 wherein a surface of the device comprises about 1 µg to about 10 µg of the fibrosing agent per $mm^2$ of device surface to which the fibrosing agent is applied.

3769. The device of item 3648 wherein a surface of the device comprises about 10 µg to about 250 µg of the fibrosing agent per $mm^2$ of device surface to which the fibrosing agent is applied.

3770. The device of item 3648 wherein a surface of the device comprises about 250 µg to about 1000 µg of the fibrosing agent of fibrosing agent per $mm^2$ of device surface to which the fibrosing agent is applied.

3771. The device of item 3648 wherein a surface of the device comprises about 1000 µg to about 2500 µg of the fibrosing agent per mm² of device surface to which the fibrosing agent is applied.

3772. A medical device comprising a subperiosteal implant and a fibrosing agent, where the fibrosing agent induces a fibrotic response between the device and a patient in which the device is implanted.

3773. The device of item 3772 wherein the fibrosing agent promotes regeneration.

3774. The device of item 3772 wherein the fibrosing agent promotes angiogenesis.

3775. The device of item 3772 wherein the fibrosing agent promotes fibroblast migration.

3776. The device of item 3772 wherein the fibrosing agent promotes fibroblast proliferation.

3777. The device of item 3772 wherein the fibrosing agent promotes deposition of extracellular matrix (ECM).

3778. The device of item 3772 wherein the fibrosing agent promotes tissue remodeling.

3779. The device of item 3772 wherein the fibrosing agent is an arterial vessel wall irritant.

3780. The device of item 3772 wherein the fibrosing agent promotes adhesion between the device and a host into which the device is implanted.

3781. The device of item 3772 wherein the device delivers the fibrosing agent locally to tissue proximate to the device.

3782. The device of item 3772 wherein the fibrosing agent is or comprises silk.

3783. The device of item 3772 wherein the fibrosing agent is or comprises mineral particles.

3784. The device of item 3772 wherein the fibrosing agent is or comprises chitosan.

3785. The device of item 3772 wherein the fibrosing agent is or comprises polylysine.

3786. The device of item 3772 wherein the fibrosing agent is or comprises fibronectin.

3787. The device of item 3772 wherein the fibrosing agent is or comprises bleomycin.

3788. The device of item 3772 wherein the fibrosing agent is or comprises CTGF.

3789. The device of item 3772 wherein the fibrosing agent is in the form of a thread, or is in contact with a thread.

3790. The device of item 3772 wherein the fibrosing agent is in the form of a particulate.

3791. The device of item 3772 wherein the composition further comprises an inflammatory cytokine.

3792. The device of item 3772 wherein the composition further comprises an agent that stimulates cell proliferation.

3793. The device of item 3772 wherein the composition is in the form of a gel, paste, or spray.

3794. The device of item 3772 wherein the fibrosing agent is in the form of tufts.

3795. The device of item 3772, further comprising a polymer.

3796. The device of item 3772, further comprising a polymeric carrier.

3797. The device of item 3772 wherein the fibrosing agent promotes adhesion between the device and a host into which the device is implanted.

3798. The device of item 3772 wherein the device delivers the fibrosing agent locally to tissue proximate to the device.

3799. The device of item 3772, further comprising a coating, wherein the coating comprises the fibrosing agent.

3800. The device of item 3772, further comprising a coating, wherein the coating is disposed on a surface of the device.

3801. The device of item 3772, further comprising a coating, wherein the coating directly contacts the device.

3802. The device of item 3772, further comprising a coating, wherein the coating indirectly contacts the device.

3803. The device of item 3772, further comprising a coating, wherein the coating partially covers the device.

3804. The device of item 3772, further comprising a coating, wherein the coating completely covers the device.

3805. The device of item 3772, further comprising a coating, wherein the coating is a uniform coating.

3806. The device of item 3772, further comprising a coating, wherein the coating is a non-uniform coating.

3807. The device of item 3772, further comprising a coating, wherein the coating is a discontinuous coating.

3808. The device of item 3772, further comprising a coating, wherein the coating is a patterned coating.

3809. The device of item 3772, further comprising a coating, wherein the coating has a thickness of 100 µm or less.

3810. The device of item 3772, further comprising a coating, wherein the coating has a thickness of 10 µm or less.

3811. The device of item 3772, further comprising a coating, wherein the coating adheres to the surface of the device upon deployment of the device.

3812. The device of item 3772, further comprising a coating, wherein the coating is stable at room temperature for a period of 1 year.

3813. The device of item 3772, further comprising a coating, wherein the fibrosing agent is present in the coating in an amount ranging between about 0.0001% to about 1% by weight.

3814. The device of item 3772, further comprising a coating, wherein the fibrosing agent is present in the coating in an amount ranging between about 1% to about 10% by weight.

3815. The device of item 3772, further comprising a coating, wherein the fibrosing agent is present in the coating in an amount ranging between about 10% to about 25% by weight.

3816. The device of item 3772, further comprising a coating, wherein the fibrosing agent is present in the coating in an amount ranging between about 25% to about 70% by weight.

3817. The device of item 3772, further comprising a coating, wherein the coating further comprises a polymer.

3818. The device of item 3772, further comprising a first coating having a first composition and the second coating having a second composition.

3819. The device of item 3772, further comprising a first coating having a first composition and the second coating having a second composition, wherein the first composition and the second composition are different.

3820. The device of item 3772, further comprising a polymer.

3821. The device of item 3772, further comprising a polymeric carrier.

3822. The device of item 3772, further comprising a polymeric carrier, wherein the polymeric carrier comprises a copolymer.

3823. The device of item 3772, further comprising a polymeric carrier, wherein the polymeric carrier comprises a block copolymer.

3824. The device of item 3772, further comprising a polymeric carrier, wherein the polymeric carrier comprises a random copolymer.

3825. The device of item 3772, further comprising a polymeric carrier, wherein the polymeric carrier comprises a biodegradable polymer.

3826. The device of item 3772, further comprising a polymeric carrier, wherein the polymeric carrier comprises a non-biodegradable polymer.

3827. The device of item 3772, further comprising a polymeric carrier, wherein the polymeric carrier comprises a hydrophilic polymer.

3828. The device of item 3772, further comprising a polymeric carrier, wherein the polymeric carrier comprises a hydrophobic polymer.

3829. The device of item 3772, further comprising a polymeric carrier, wherein the polymeric carrier comprises a polymer having hydrophilic domains.

3830. The device of item 3772, further comprising a polymeric carrier, wherein the polymeric carrier comprises a polymer having hydrophobic domains.

3831. The device of item 3772, further comprising a polymeric carrier, wherein the polymeric carrier comprises a non-conductive polymer.

3832. The device of item 3772, further comprising a polymeric carrier, wherein the polymeric carrier comprises an elastomer.

3833. The device of item 3772, further comprising a polymeric carrier, wherein the polymeric carrier comprises a hydrogel.

3834. The device of item 3772, further comprising a polymeric carrier, wherein the polymeric carrier comprises a silicone polymer.

3835. The device of item 3772, further comprising a polymeric carrier, wherein the polymeric carrier comprises a hydrocarbon polymer.

3836. The device of item 3772, further comprising a polymeric carrier, wherein the polymeric carrier comprises a styrene-derived polymer.

3837. The device of item 3772, further comprising a polymeric carrier, wherein the polymeric carrier comprises a butadiene polymer.

3838. The device of item 3772, further comprising a polymeric carrier, wherein the polymeric carrier comprises a macromer.

3839. The device of item 3772, further comprising a polymeric carrier, wherein the polymeric carrier comprises a poly(ethylene glycol) polymer.

3840. The device of item 3772, further comprising a polymeric carrier, wherein the polymeric carrier comprises an amorphous polymer.

3841. The device of item 3772, further comprising a lubricious coating.

3842. The device of item 3772 wherein the fibrosing agent is located within pores or holes of the device.

3843. The device of item 3772 wherein the fibrosing agent is located within a channel, lumen, or divet of the device.

3844. The device of item 3772, further comprising a second pharmaceutically active agent.

3845. The device of item 3772, further comprising an anti-inflammatory agent.

3846. The device of item 3772, further comprising an agent that inhibits infection.

3847. The device of item 3772, further comprising an agent that inhibits infection, wherein the agent is an anthracycline.

3848. The device of item 3772, further comprising an agent that inhibits infection, wherein the agent is doxorubicin.

3849. The device of item 3772, further comprising an agent that inhibits infection, wherein the agent is mitoxantrone.

3850. The device of item 3772, further comprising an agent that inhibits infection, wherein the agent is a fluoropyrimidine.

3851. The device of item 3772, further comprising an agent that inhibits infection, wherein the agent is 5-fluorouracil (5-FU).

3852. The device of item 3772, further comprising an agent that inhibits infection, wherein the agent is a folic acid antagonist.

3853. The device of item 3772, further comprising an agent that inhibits infection, wherein the agent is methotrexate.

3854. The device of item 3772, further comprising an agent that inhibits infection, wherein the agent is a podophylotoxin.

3855. The device of item 3772, further comprising an agent that inhibits infection, wherein the agent is etoposide.

3856. The device of item 3772, further comprising an agent that inhibits infection, wherein the agent is a camptothecin.

3857. The device of item 3772, further comprising an agent that inhibits infection, wherein the agent is a hydroxyurea.

3858. The device of item 3772, further comprising an agent that inhibits infection, wherein the agent is a platinum complex.

3859. The device of item 3772, further comprising an agent that inhibits infection, wherein the agent is cisplatin.

3860. The device of item 3772, further comprising an anti-thrombotic agent.

3861. The device of item 3772, further comprising a visualization agent.

3862. The device of item 3772, further comprising a visualization agent, wherein the visualization agent is a radiopaque material, wherein the radiopaque material comprises a metal, a halogenated compound, or a barium containing compound.

3863. The device of item 3772, further comprising a visualization agent, wherein the visualization agent is a radiopaque material, wherein the radiopaque material comprises barium, tantalum, or technetium.

3864. The device of item 3772, further comprising a visualization agent, wherein the visualization agent is a MRI responsive material.

3865. The device of item 3772, further comprising a visualization agent, wherein the visualization agent comprises a gadolinium chelate.

3866. The device of item 3772, further comprising a visualization agent, wherein the visualization agent comprises iron, magnesium, manganese, copper, or chromium.

3867. The device of item 3772, further comprising a visualization agent, wherein the visualization agent comprises an iron oxide compound.

3868. The device of item 3772, further comprising a visualization agent, wherein the visualization agent comprises a dye, pigment, or colorant.

3869. The device of item 3772, further comprising an echogenic material.

3870. The device of item 3772, further comprising an echogenic material, wherein the echogenic material is in the form of a coating.

3871. The device of item 3772 wherein the device is sterile.

3872. The device of item 3772 wherein the fibrosing agent is released into tissue in the vicinity of the device after deployment of the device.

3873. The device of item 3772 wherein the fibrosing agent is released into tissue in the vicinity of the device after deployment of the device, wherein the tissue is connective tissue.

3874. The device of item 3772 wherein the fibrosing agent is released into tissue in the vicinity of the device after deployment of the device, wherein the tissue is muscle tissue.

3875. The device of item 3772 wherein the fibrosing agent is released into tissue in the vicinity of the device after deployment of the device, wherein the tissue is nerve tissue.

3876. The device of item 3772 wherein the fibrosing agent is released into tissue in the vicinity of the device after deployment of the device, wherein the tissue is epithelium tissue.

3877. The device of item 3772 wherein the fibrosing agent is released in effective concentrations from the device over a period ranging from the time of deployment of the device to about 1 year.

3878. The device of item 3772 wherein the fibrosing agent is released in effective concentrations from the device over a period ranging from about 1 month to 6 months.

3879. The device of item 3772 wherein the fibrosing agent is released in effective concentrations from the device over a period ranging from about 1–90 days.

3880. The device of item 3772 wherein the fibrosing agent is released in effective concentrations from the device at a constant rate.

3881. The device of item 3772 wherein the fibrosing agent is released in effective concentrations from the device at an increasing rate.

3882. The device of item 3772 wherein the fibrosing agent is released in effective concentrations from the device at a decreasing rate.

3883. The device of item 3772 wherein the fibrosing agent is released in effective concentrations from the composition comprising the fibrosing agent by diffusion over a period ranging from the time of deployment of the device to about 90 days.

3884. The device of item 3772 wherein the fibrosing agent is released in effective concentrations from the composition comprising the fibrosing agent by erosion of the composition over a period ranging from the time of deployment of the device to about 90 days.

3885. The device of item 3772 wherein the device comprises about 0.01 µg to about 10 µg of the fibrosing agent.

3886. The device of item 3772 wherein the device comprises about 10 µg to about 10 mg of the fibrosing agent.

3887. The device of item 3772 wherein the device comprises about 10 mg to about 250 mg of the fibrosing agent.

3888. The device of item 3772 wherein the device comprises about 250 mg to about 1000 mg of the fibrosing agent.

3889. The device of item 3772 wherein the device comprises about 1000 mg to about 2500 mg of the fibrosing agent.

3890. The device of item 3772 wherein a surface of the device comprises less than 0.01 µg of the fibrosing agent per $mm^2$ of device surface to which the fibrosing agent is applied.

3891. The device of item 3772 wherein a surface of the device comprises about 0.01 µg to about 1 µg of the fibrosing agent per $mm^2$ of device surface to which the fibrosing agent is applied.

3892. The device of item 3772 wherein a surface of the device comprises about 1 µg to about 10 µg of the fibrosing agent per $mm^2$ of device surface to which the fibrosing agent is applied.

3893. The device of item 3772 wherein a surface of the device comprises about 10 µg to about 250 µg of the fibrosing agent per $mm^2$ of device surface to which the fibrosing agent is applied.

3894. The device of item 3772 wherein a surface of the device comprises about 250 µg to about 1000 µg of the fibrosing agent of fibrosing agent per $mm^2$ of device surface to which the fibrosing agent is applied.

3895. The device of item 3772 wherein a surface of the device comprises about 1000 µg to about 2500 µg of the fibrosing agent per $mm^2$ of device surface to which the fibrosing agent is applied.

3896. A medical device comprising a guided bone regeneration (GBR) implant and a fibrosing agent, where the fibrosing agent induces a fibrotic response between the device and a patient in which the device is implanted.

3897. The device of item 3896 wherein the fibrosing agent promotes regeneration.

3898. The device of item 3896 wherein the fibrosing agent promotes angiogenesis.

3899. The device of item 3896 wherein the fibrosing agent promotes fibroblast migration.

3900. The device of item 3896 wherein the fibrosing agent promotes fibroblast proliferation.

3901. The device of item 3896 wherein the fibrosing agent promotes deposition of extracellular matrix (ECM).

3902. The device of item 3896 wherein the fibrosing agent promotes tissue remodeling.

3903. The device of item 3896 wherein the fibrosing agent is an arterial vessel wall irritant.

3904. The device of item 3896 wherein the fibrosing agent promotes adhesion between the device and a host into which the device is implanted.

3905. The device of item 3896 wherein the device delivers the fibrosing agent locally to tissue proximate to the device.

3906. The device of item 3896 wherein the fibrosing agent is or comprises silk.

3907. The device of item 3896 wherein the fibrosing agent is or comprises mineral particles.

3908. The device of item 3896 wherein the fibrosing agent is or comprises chitosan.

3909. The device of item 3896 wherein the fibrosing agent is or comprises polylysine.

3910. The device of item 3896 wherein the fibrosing agent is or comprises fibronectin.

3911. The device of item 3896 wherein the fibrosing agent is or comprises bleomycin.

3912. The device of item 3896 wherein the fibrosing agent is or comprises CTGF.

3913. The device of item 3896 wherein the fibrosing agent is in the form of a thread, or is in contact with a thread.

3914. The device of item 3896 wherein the fibrosing agent is in the form of a particulate.

3915. The device of item 3896 wherein the composition further comprises an inflammatory cytokine.

3916. The device of item 3896 wherein the composition further comprises an agent that stimulates cell proliferation.

3917. The device of item 3896 wherein the composition is in the form of a gel, paste, or spray.

3918. The device of item 3896 wherein the fibrosing agent is in the form of tufts.

3919. The device of item 3896, further comprising a polymer.

3920. The device of item 3896, further comprising a polymeric carrier.

3921. The device of item 3896 wherein the fibrosing agent promotes adhesion between the device and a host into which the device is implanted.

3922. The device of item 3896 wherein the device delivers the fibrosing agent locally to tissue proximate to the device.

3923. The device of item 3896, further comprising a coating, wherein the coating comprises the fibrosing agent.

3924. The device of item 3896, further comprising a coating, wherein the coating is disposed on a surface of the device.

3925. The device of item 3896, further comprising a coating, wherein the coating directly contacts the device.

3926. The device of item 3896, further comprising a coating, wherein the coating indirectly contacts the device.

3927. The device of item 3896, further comprising a coating, wherein the coating partially covers the device.

3928. The device of item 3896, further comprising a coating, wherein the coating completely covers the device.

3929. The device of item 3896, further comprising a coating, wherein the coating is a uniform coating.

3930. The device of item 3896, further comprising a coating, wherein the coating is a non-uniform coating.

3931. The device of item 3896, further comprising a coating, wherein the coating is a discontinuous coating.

3932. The device of item 3896, further comprising a coating, wherein the coating is a patterned coating.

3933. The device of item 3896, further comprising a coating, wherein the coating has a thickness of 100 µm or less.

3934. The device of item 3896, further comprising a coating, wherein the coating has a thickness of 10 µm or less.

3935. The device of item 3896, further comprising a coating, wherein the coating adheres to the surface of the device upon deployment of the device.

3936. The device of item 3896, further comprising a coating, wherein the coating is stable at room temperature for a period of 1 year.

3937. The device of item 3896, further comprising a coating, wherein the fibrosing agent is present in the coating in an amount ranging between about 0.0001% to about 1% by weight.

3938. The device of item 3896, further comprising a coating, wherein the fibrosing agent is present in the coating in an amount ranging between about 1% to about 10% by weight.

3939. The device of item 3896, further comprising a coating, wherein the fibrosing agent is present in the coating in an amount ranging between about 10% to about 25% by weight.

3940. The device of item 3896, further comprising a coating, wherein the fibrosing agent is present in the coating in an amount ranging between about 25% to about 70% by weight.

3941. The device of item 3896, further comprising a coating, wherein the coating further comprises a polymer.

3942. The device of item 3896, further comprising a first coating having a first composition and the second coating having a second composition.

3943. The device of item 3896, further comprising a first coating having a first composition and the second coating having a second composition, wherein the first composition and the second composition are different.

3944. The device of item 3896, further comprising a polymer.

3945. The device of item 3896, further comprising a polymeric carrier.

3946. The device of item 3896, further comprising a polymeric carrier, wherein the polymeric carrier comprises a copolymer.

3947. The device of item 3896, further comprising a polymeric carrier, wherein the polymeric carrier comprises a block copolymer.

3948. The device of item 3896, further comprising a polymeric carrier, wherein the polymeric carrier comprises a random copolymer.

3949. The device of item 3896, further comprising a polymeric carrier, wherein the polymeric carrier comprises a biodegradable polymer.

3950. The device of item 3896, further comprising a polymeric carrier, wherein the polymeric carrier comprises a non-biodegradable polymer.

3951. The device of item 3896, further comprising a polymeric carrier, wherein the polymeric carrier comprises a hydrophilic polymer.

3952. The device of item 3896, further comprising a polymeric carrier, wherein the polymeric carrier comprises a hydrophobic polymer.

3953. The device of item 3896, further comprising a polymeric carrier, wherein the polymeric carrier comprises a polymer having hydrophilic domains.

3954. The device of item 3896, further comprising a polymeric carrier, wherein the polymeric carrier comprises a polymer having hydrophobic domains.

3955. The device of item 3896, further comprising a polymeric carrier, wherein the polymeric carrier comprises a non-conductive polymer.

3956. The device of item 3896, further comprising a polymeric carrier, wherein the polymeric carrier comprises an elastomer.

3957. The device of item 3896, further comprising a polymeric carrier, wherein the polymeric carrier comprises a hydrogel.

3958. The device of item 3896, further comprising a polymeric carrier, wherein the polymeric carrier comprises a silicone polymer.

3959. The device of item 3896, further comprising a polymeric carrier, wherein the polymeric carrier comprises a hydrocarbon polymer.

3960. The device of item 3896, further comprising a polymeric carrier, wherein the polymeric carrier comprises a styrene-derived polymer.

3961. The device of item 3896, further comprising a polymeric carrier, wherein the polymeric carrier comprises a butadiene polymer.

3962. The device of item 3896, further comprising a polymeric carrier, wherein the polymeric carrier comprises a macromer.

3963. The device of item 3896, further comprising a polymeric carrier, wherein the polymeric carrier comprises a poly(ethylene glycol) polymer.

3964. The device of item 3896, further comprising a polymeric carrier, wherein the polymeric carrier comprises an amorphous polymer.

3965. The device of item 3896, further comprising a lubricious coating.

3966. The device of item 3896 wherein the fibrosing agent is located within pores or holes of the device.

3967. The device of item 3896 wherein the fibrosing agent is located within a channel, lumen, or divet of the device.

3968. The device of item 3896, further comprising a second pharmaceutically active agent.

3969. The device of item 3896, further comprising an anti-inflammatory agent.

3970. The device of item 3896, further comprising an agent that inhibits infection.

3971. The device of item 3896, further comprising an agent that inhibits infection, wherein the agent is an anthracycline.

3972. The device of item 3896, further comprising an agent that inhibits infection, wherein the agent is doxorubicin.

3973. The device of item 3896, further comprising an agent that inhibits infection, wherein the agent is mitoxantrone.

3974. The device of item 3896, further comprising an agent that inhibits infection, wherein the agent is a fluoropyrimidine.

3975. The device of item 3896, further comprising an agent that inhibits infection, wherein the agent is 5-fluorouracil (5-FU).

3976. The device of item 3896, further comprising an agent that inhibits infection, wherein the agent is a folic acid antagonist.

3977. The device of item 3896, further comprising an agent that inhibits infection, wherein the agent is methotrexate.

3978. The device of item 3896, further comprising an agent that inhibits infection, wherein the agent is a podophylotoxin.

3979. The device of item 3896, further comprising an agent that inhibits infection, wherein the agent is etoposide.

3980. The device of item 3896, further comprising an agent that inhibits infection, wherein the agent is a camptothecin.

3981. The device of item 3896, further comprising an agent that inhibits infection, wherein the agent is a hydroxyurea.

3982. The device of item 3896, further comprising an agent that inhibits infection, wherein the agent is a platinum complex.

3983. The device of item 3896, further comprising an agent that inhibits infection, wherein the agent is cisplatin.

3984. The device of item 3896, further comprising an anti-thrombotic agent.

3985. The device of item 3896, further comprising a visualization agent.

3986. The device of item 3896, further comprising a visualization agent, wherein the visualization agent is a radiopaque material, wherein the radiopaque material comprises a metal, a halogenated compound, or a barium containing compound.

3987. The device of item 3896, further comprising a visualization agent, wherein the visualization agent is a radiopaque material, wherein the radiopaque material comprises barium, tantalum, or technetium.

3988. The device of item 3896, further comprising a visualization agent, wherein the visualization agent is a MRI responsive material.

3989. The device of item 3896, further comprising a visualization agent, wherein the visualization agent comprises a gadolinium chelate.

3990. The device of item 3896, further comprising a visualization agent, wherein the visualization agent comprises iron, magnesium, manganese, copper, or chromium.

3991. The device of item 3896, further comprising a visualization agent, wherein the visualization agent comprises an iron oxide compound.

3992. The device of item 3896, further comprising a visualization agent, wherein the visualization agent comprises a dye, pigment, or colorant.

3993. The device of item 3896, further comprising an echogenic material.

3994. The device of item 3896, further comprising an echogenic material, wherein the echogenic material is in the form of a coating.

3995. The device of item 3896 wherein the device is sterile.

3996. The device of item 3896 wherein the fibrosing agent is released into tissue in the vicinity of the device after deployment of the device.

3997. The device of item 3896 wherein the fibrosing agent is released into tissue in the vicinity of the device after deployment of the device, wherein the tissue is connective tissue.

3998. The device of item 3896 wherein the fibrosing agent is released into tissue in the vicinity of the device after deployment of the device, wherein the tissue is muscle tissue.

3999. The device of item 3896 wherein the fibrosing agent is released into tissue in the vicinity of the device after deployment of the device, wherein the tissue is nerve tissue.

4000. The device of item 3896 wherein the fibrosing agent is released into tissue in the vicinity of the device after deployment of the device, wherein the tissue is epithelium tissue.

4001. The device of item 3896 wherein the fibrosing agent is released in effective concentrations from the device over a period ranging from the time of deployment of the device to about 1 year.

4002. The device of item 3896 wherein the fibrosing agent is released in effective concentrations from the device over a period ranging from about 1 month to 6 months.

4003. The device of item 3896 wherein the fibrosing agent is released in effective concentrations from the device over a period ranging from about 1–90 days.

4004. The device of item 3896 wherein the fibrosing agent is released in effective concentrations from the device at a constant rate.

4005. The device of item 3896 wherein the fibrosing agent is released in effective concentrations from the device at an increasing rate.

4006. The device of item 3896 wherein the fibrosing agent is released in effective concentrations from the device at a decreasing rate.

4007. The device of item 3896 wherein the fibrosing agent is released in effective concentrations from the composition comprising the fibrosing agent by diffusion over a period ranging from the time of deployment of the device to about 90 days.

4008. The device of item 3896 wherein the fibrosing agent is released in effective concentrations from the composition comprising the fibrosing agent by erosion of the composition over a period ranging from the time of deployment of the device to about 90 days.

4009. The device of item 3896 wherein the device comprises about 0.01 µg to about 10 µg of the fibrosing agent.

4010. The device of item 3896 wherein the device comprises about 10 µg to about 10 mg of the fibrosing agent.

4011. The device of item 3896 wherein the device comprises about 10 mg to about 250 mg of the fibrosing agent.

4012. The device of item 3896 wherein the device comprises about 250 mg to about 1000 mg of the fibrosing agent.

4013. The device of item 3896 wherein the device comprises about 1000 mg to about 2500 mg of the fibrosing agent.

4014. The device of item 3896 wherein a surface of the device comprises less than 0.01 µg of the fibrosing agent per $mm^2$ of device surface to which the fibrosing agent is applied.

4015. The device of item 3896 wherein a surface of the device comprises about 0.01 µg to about 1 µg of the fibrosing agent per $mm^2$ of device surface to which the fibrosing agent is applied.

4016. The device of item 3896 wherein a surface of the device comprises about 1 µg to about 10 µg of the fibrosing agent per $mm^2$ of device surface to which the fibrosing agent is applied.

4017. The device of item 3896 wherein a surface of the device comprises about 10 µg to about 250 µg of the fibrosing agent per $mm^2$ of device surface to which the fibrosing agent is applied.

4018. The device of item 3896 wherein a surface of the device comprises about 250 µg to about 1000 µg of the fibrosing agent of fibrosing agent per $mm^2$ of device surface to which the fibrosing agent is applied.

4019. The device of item 3896 wherein a surface of the device comprises about 1000 µg to about 2500 µg of the fibrosing agent per $mm^2$ of device surface to which the fibrosing agent is applied.

4020. The medical device of claqim 3896 wherein the GBR is resorbable bone substitutes for filing bony defects.

4021. A medical device comprising a dental implant to control the healing process subsequent to periodontal disease and a fibrosing agent, where the fibrosing agent induces a fibrotic response between the device and a patient in which the device is implanted.

4022. The device of item 4021 wherein the fibrosing agent promotes regeneration.

4023. The device of item 4021 wherein the fibrosing agent promotes angiogenesis.

4024. The device of item 4021 wherein the fibrosing agent promotes fibroblast migration.

4025. The device of item 4021 wherein the fibrosing agent promotes fibroblast proliferation.

4026. The device of item 4021 wherein the fibrosing agent promotes deposition of extracellular matrix (ECM).

4027. The device of item 4021 wherein the fibrosing agent promotes tissue remodeling.

4028. The device of item 4021 wherein the fibrosing agent is an arterial vessel wall irritant.

4029. The device of item 4021 wherein the fibrosing agent promotes adhesion between the device and a host into which the device is implanted.

4030. The device of item 4021 wherein the device delivers the fibrosing agent locally to tissue proximate to the device.

4031. The device of item 4021 wherein the fibrosing agent is or comprises silk.

4032. The device of item 4021 wherein the fibrosing agent is or comprises mineral particles.

4033. The device of item 4021 wherein the fibrosing agent is or comprises chitosan.

4034. The device of item 4021 wherein the fibrosing agent is or comprises polylysine.

4035. The device of item 4021 wherein the fibrosing agent is or comprises fibronectin.

4036. The device of item 4021 wherein the fibrosing agent is or comprises bleomycin.

4037. The device of item 4021 wherein the fibrosing agent is or comprises CTGF.

4038. The device of item 4021 wherein the fibrosing agent is in the form of a thread, or is in contact with a thread.

4039. The device of item 4021 wherein the fibrosing agent is in the form of a particulate.

4040. The device of item 4021 wherein the composition further comprises an inflammatory cytokine.

4041. The device of item 4021 wherein the composition further comprises an agent that stimulates cell proliferation.

4042. The device of item 4021 wherein the composition is in the form of a gel, paste, or spray.

4043. The device of item 4021 wherein the fibrosing agent is in the form of tufts.

4044. The device of item 4021, further comprising a polymer.

4045. The device of item 4021, further comprising a polymeric carrier.

4046. The device of item 4021 wherein the fibrosing agent promotes adhesion between the device and a host into which the device is implanted.

4047. The device of item 4021 wherein the device delivers the fibrosing agent locally to tissue proximate to the device.

4048. The device of item 4021, further comprising a coating, wherein the coating comprises the fibrosing agent.

4049. The device of item 4021, further comprising a coating, wherein the coating is disposed on a surface of the device.

4050. The device of item 4021, further comprising a coating, wherein the coating directly contacts the device.

4051. The device of item 4021, further comprising a coating, wherein the coating indirectly contacts the device.

4052. The device of item 4021, further comprising a coating, wherein the coating partially covers the device.

4053. The device of item 4021, further comprising a coating, wherein the coating completely covers the device.

4054. The device of item 4021, further comprising a coating, wherein the coating is a uniform coating.

4055. The device of item 4021, further comprising a coating, wherein the coating is a non-uniform coating.

4056. The device of item 4021, further comprising a coating, wherein the coating is a discontinuous coating.

4057. The device of item 4021, further comprising a coating, wherein the coating is a patterned coating.

4058. The device of item 4021, further comprising a coating, wherein the coating has a thickness of 100 µm or less.

4059. The device of item 4021, further comprising a coating, wherein the coating has a thickness of 10 µm or less.

4060. The device of item 4021, further comprising a coating, wherein the coating adheres to the surface of the device upon deployment of the device.

4061. The device of item 4021, further comprising a coating, wherein the coating is stable at room temperature for a period of 1 year.

4062. The device of item 4021, further comprising a coating, wherein the fibrosing agent is present in the coating in an amount ranging between about 0.0001% to about 1% by weight.

4063. The device of item 4021, further comprising a coating, wherein the fibrosing agent is present in the coating in an amount ranging between about 1% to about 10% by weight.

4064. The device of item 4021, further comprising a coating, wherein the fibrosing agent is present in the coating in an amount ranging between about 10% to about 25% by weight.

4065. The device of item 4021, further comprising a coating, wherein the fibrosing agent is present in the coating in an amount ranging between about 25% to about 70% by weight.

4066. The device of item 4021, further comprising a coating, wherein the coating further comprises a polymer.

4067. The device of item 4021, further comprising a first coating having a first composition and the second coating having a second composition.

4068. The device of item 4021, further comprising a first coating having a first composition and the second coating having a second composition, wherein the first composition and the second composition are different.

4069. The device of item 4021, further comprising a polymer.

4070. The device of item 4021, further comprising a polymeric carrier.

4071. The device of item 4021, further comprising a polymeric carrier, wherein the polymeric carrier comprises a copolymer.

4072. The device of item 4021, further comprising a polymeric carrier, wherein the polymeric carrier comprises a block copolymer.

4073. The device of item 4021, further comprising a polymeric carrier, wherein the polymeric carrier comprises a random copolymer.

4074. The device of item 4021, further comprising a polymeric carrier, wherein the polymeric carrier comprises a biodegradable polymer.

4075. The device of item 4021, further comprising a polymeric carrier, wherein the polymeric carrier comprises a non-biodegradable polymer.

4076. The device of item 4021, further comprising a polymeric carrier, wherein the polymeric carrier comprises a hydrophilic polymer.

4077. The device of item 4021, further comprising a polymeric carrier, wherein the polymeric carrier comprises a hydrophobic polymer.

4078. The device of item 4021, further comprising a polymeric carrier, wherein the polymeric carrier comprises a polymer having hydrophilic domains.

4079. The device of item 4021, further comprising a polymeric carrier, wherein the polymeric carrier comprises a polymer having hydrophobic domains.

4080. The device of item 4021, further comprising a polymeric carrier, wherein the polymeric carrier comprises a non-conductive polymer.

4081. The device of item 4021, further comprising a polymeric carrier, wherein the polymeric carrier comprises an elastomer.

4082. The device of item 4021, further comprising a polymeric carrier, wherein the polymeric carrier comprises a hydrogel.

4083. The device of item 4021, further comprising a polymeric carrier, wherein the polymeric carrier comprises a silicone polymer.

4084. The device of item 4021, further comprising a polymeric carrier, wherein the polymeric carrier comprises a hydrocarbon polymer.

4085. The device of item 4021, further comprising a polymeric carrier, wherein the polymeric carrier comprises a styrene-derived polymer.

4086. The device of item 4021, further comprising a polymeric carrier, wherein the polymeric carrier comprises a butadiene polymer.

4087. The device of item 4021, further comprising a polymeric carrier, wherein the polymeric carrier comprises a macromer.

4088. The device of item 4021, further comprising a polymeric carrier, wherein the polymeric carrier comprises a poly(ethylene glycol) polymer.

4089. The device of item 4021, further comprising a polymeric carrier, wherein the polymeric carrier comprises an amorphous polymer.

4090. The device of item 4021, further comprising a lubricious coating.

4091. The device of item 4021 wherein the fibrosing agent is located within pores or holes of the device.

4092. The device of item 4021 wherein the fibrosing agent is located within a channel, lumen, or divet of the device.

4093. The device of item 4021, further comprising a second pharmaceutically active agent.

4094. The device of item 4021, further comprising an anti-inflammatory agent.

4095. The device of item 4021, further comprising an agent that inhibits infection.

4096. The device of item 4021, further comprising an agent that inhibits infection, wherein the agent is an anthracycline.

4097. The device of item 4021, further comprising an agent that inhibits infection, wherein the agent is doxorubicin.

4098. The device of item 4021, further comprising an agent that inhibits infection, wherein the agent is mitoxantrone.

4099. The device of item 4021, further comprising an agent that inhibits infection, wherein the agent is a fluoropyrimidine.

4100. The device of item 4021, further comprising an agent that inhibits infection, wherein the agent is 5-fluorouracil (5-FU).

4101. The device of item 4021, further comprising an agent that inhibits infection, wherein the agent is a folic acid antagonist.

4102. The device of item 4021, further comprising an agent that inhibits infection, wherein the agent is methotrexate.

4103. The device of item 4021, further comprising an agent that inhibits infection, wherein the agent is a podophylotoxin.

4104. The device of item 4021, further comprising an agent that inhibits infection, wherein the agent is etoposide.

4105. The device of item 4021, further comprising an agent that inhibits infection, wherein the agent is a camptothecin.

4106. The device of item 4021, further comprising an agent that inhibits infection, wherein the agent is a hydroxyurea.

4107. The device of item 4021, further comprising an agent that inhibits infection, wherein the agent is a platinum complex.

4108. The device of item 4021, further comprising an agent that inhibits infection, wherein the agent is cisplatin.

4109. The device of item 4021, further comprising an anti-thrombotic agent.

4110. The device of item 4021, further comprising a visualization agent.

4111. The device of item 4021, further comprising a visualization agent, wherein the visualization agent is a radiopaque material, wherein the radiopaque material comprises a metal, a halogenated compound, or a barium containing compound.

4112. The device of item 4021, further comprising a visualization agent, wherein the visualization agent is a radiopaque material, wherein the radiopaque material comprises barium, tantalum, or technetium.

4113. The device of item 4021, further comprising a visualization agent, wherein the visualization agent is a MRI responsive material.

4114. The device of item 4021, further comprising a visualization agent, wherein the visualization agent comprises a gadolinium chelate.

4115. The device of item 4021, further comprising a visualization agent, wherein the visualization agent comprises iron, magnesium, manganese, copper, or chromium.

4116. The device of item 4021, further comprising a visualization agent, wherein the visualization agent comprises an iron oxide compound.

4117. The device of item 4021, further comprising a visualization agent, wherein the visualization agent comprises a dye, pigment, or colorant.

4118. The device of item 4021, further comprising an echogenic material.

4119. The device of item 4021, further comprising an echogenic material, wherein the echogenic material is in the form of a coating.

4120. The device of item 4021 wherein the device is sterile.

4121. The device of item 4021 wherein the fibrosing agent is released into tissue in the vicinity of the device after deployment of the device.

4122. The device of item 4021 wherein the fibrosing agent is released into tissue in the vicinity of the device after deployment of the device, wherein the tissue is connective tissue.

4123. The device of item 4021 wherein the fibrosing agent is released into tissue in the vicinity of the device after deployment of the device, wherein the tissue is muscle tissue.

4124. The device of item 4021 wherein the fibrosing agent is released into tissue in the vicinity of the device after deployment of the device, wherein the tissue is nerve tissue.

4125. The device of item 4021 wherein the fibrosing agent is released into tissue in the vicinity of the device after deployment of the device, wherein the tissue is epithelium tissue.

4126. The device of item 4021 wherein the fibrosing agent is released in effective concentrations from the device over a period ranging from the time of deployment of the device to about 1 year.

4127. The device of item 4021 wherein the fibrosing agent is released in effective concentrations from the device over a period ranging from about 1 month to 6 months.

4128. The device of item 4021 wherein the fibrosing agent is released in effective concentrations from the device over a period ranging from about 1–90 days.

4129. The device of item 4021 wherein the fibrosing agent is released in effective concentrations from the device at a constant rate.

4130. The device of item 4021 wherein the fibrosing agent is released in effective concentrations from the device at an increasing rate.

4131. The device of item 4021 wherein the fibrosing agent is released in effective concentrations from the device at a decreasing rate.

4132. The device of item 4021 wherein the fibrosing agent is released in effective concentrations from the composition comprising the fibrosing agent by diffusion over a period ranging from the time of deployment of the device to about 90 days.

4133. The device of item 4021 wherein the fibrosing agent is released in effective concentrations from the composition comprising the fibrosing agent by erosion of the composition over a period ranging from the time of deployment of the device to about 90 days.

4134. The device of item 4021 wherein the device comprises about 0.01 µg to about 10 µg of the fibrosing agent.

4135. The device of item 4021 wherein the device comprises about 10 µg to about 10 mg of the fibrosing agent.

4136. The device of item 4021 wherein the device comprises about 10 mg to about 250 mg of the fibrosing agent.

4137. The device of item 4021 wherein the device comprises about 250 mg to about 1000 mg of the fibrosing agent.

4138. The device of item 4021 wherein the device comprises about 1000 mg to about 2500 mg of the fibrosing agent.

4139. The device of item 4021 wherein a surface of the device comprises less than 0.01 µg of the fibrosing agent per $mm^2$ of device surface to which the fibrosing agent is applied.

4140. The device of item 4021 wherein a surface of the device comprises about 0.01 µg to about 1 µg of the fibrosing agent per $mm^2$ of device surface to which the fibrosing agent is applied.

4141. The device of item 4021 wherein a surface of the device comprises about 1 µg to about 10 µg of the fibrosing agent per $mm^2$ of device surface to which the fibrosing agent is applied.

4142. The device of item 4021 wherein a surface of the device comprises about 10 µg to about 250 µg of the fibrosing agent per $mm^2$ of device surface to which the fibrosing agent is applied.

4143. The device of item 4021 wherein a surface of the device comprises about 250 µg to about 1000 µg of the fibrosing agent of fibrosing agent per $mm^2$ of device surface to which the fibrosing agent is applied.

4144. The device of item 4021 wherein a surface of the device comprises about 1000 µg to about 2500 µg of the fibrosing agent per $mm^2$ of device surface to which the fibrosing agent is applied.

4145. A medical device comprising an internal fixation implant and a fibrosing agent, where the fibrosing agent induces a fibrotic response between the device and a patient in which the device is implanted.

4146. The device of item 4145 wherein the fibrosing agent promotes regeneration.

4147. The device of item 4145 wherein the fibrosing agent promotes angiogenesis.

4148. The device of item 4145 wherein the fibrosing agent promotes fibroblast migration.

4149. The device of item 4145 wherein the fibrosing agent promotes fibroblast proliferation.

4150. The device of item 4145 wherein the fibrosing agent promotes deposition of extracellular matrix (ECM).

4151. The device of item 4145 wherein the fibrosing agent promotes tissue remodeling.

4152. The device of item 4145 wherein the fibrosing agent is an arterial vessel wall irritant.

4153. The device of item 4145 wherein the fibrosing agent promotes adhesion between the device and a host into which the device is implanted.

4154. The device of item 4145 wherein the device delivers the fibrosing agent locally to tissue proximate to the device.

4155. The device of item 4145 wherein the fibrosing agent is or comprises silk.

4156. The device of item 4145 wherein the fibrosing agent is or comprises mineral particles.

4157. The device of item 4145 wherein the fibrosing agent is or comprises chitosan.

4158. The device of item 4145 wherein the fibrosing agent is or comprises polylysine.

4159. The device of item 4145 wherein the fibrosing agent is or comprises fibronectin.

4160. The device of item 4145 wherein the fibrosing agent is or comprises bleomycin.

4161. The device of item 4145 wherein the fibrosing agent is or comprises CTGF.

4162. The device of item 4145 wherein the fibrosing agent is in the form of a thread, or is in contact with a thread.

4163. The device of item 4145 wherein the fibrosing agent is in the form of a particulate.

4164. The device of item 4145 wherein the composition further comprises an inflammatory cytokine.

4165. The device of item 4145 wherein the composition further comprises an agent that stimulates cell proliferation.

4166. The device of item 4145 wherein the composition is in the form of a gel, paste, or spray.

4167. The device of item 4145 wherein the fibrosing agent is in the form of tufts.

4168. The device of item 4145, further comprising a polymer.

4169. The device of item 4145, further comprising a polymeric carrier.

4170. The device of item 4145 wherein the fibrosing agent promotes adhesion between the device and a host into which the device is implanted.

4171. The device of item 4145 wherein the device delivers the fibrosing agent locally to tissue proximate to the device.

4172. The device of item 4145, further comprising a coating, wherein the coating comprises the fibrosing agent.

4173. The device of item 4145, further comprising a coating, wherein the coating is disposed on a surface of the device.

4174. The device of item 4145, further comprising a coating, wherein the coating directly contacts the device.

4175. The device of item 4145, further comprising a coating, wherein the coating indirectly contacts the device.

4176. The device of item 4145, further comprising a coating, wherein the coating partially covers the device.

4177. The device of item 4145, further comprising a coating, wherein the coating completely covers the device.

4178. The device of item 4145, further comprising a coating, wherein the coating is a uniform coating.

4179. The device of item 4145, further comprising a coating, wherein the coating is a non-uniform coating.

4180. The device of item 4145, further comprising a coating, wherein the coating is a discontinuous coating.

4181. The device of item 4145, further comprising a coating, wherein the coating is a patterned coating.

4182. The device of item 4145, further comprising a coating, wherein the coating has a thickness of 100 μm or less.

4183. The device of item 4145, further comprising a coating, wherein the coating has a thickness of 10 μm or less.

4184. The device of item 4145, further comprising a coating, wherein the coating adheres to the surface of the device upon deployment of the device.

4185. The device of item 4145, further comprising a coating, wherein the coating is stable at room temperature for a period of 1 year.

4186. The device of item 4145, further comprising a coating, wherein the fibrosing agent is present in the coating in an amount ranging between about 0.0001% to about 1% by weight.

4187. The device of item 4145, further comprising a coating, wherein the fibrosing agent is present in the coating in an amount ranging between about 1% to about 10% by weight.

4188. The device of item 4145, further comprising a coating, wherein the fibrosing agent is present in the coating in an amount ranging between about 10% to about 25% by weight.

4189. The device of item 4145, further comprising a coating, wherein the fibrosing agent is present in the coating in an amount ranging between about 25% to about 70% by weight.

4190. The device of item 4145, further comprising a coating, wherein the coating further comprises a polymer.

4191. The device of item 4145, further comprising a first coating having a first composition and the second coating having a second composition.

4192. The device of item 4145, further comprising a first coating having a first composition and the second coating having a second composition, wherein the first composition and the second composition are different.

4193. The device of item 4145, further comprising a polymer.

4194. The device of item 4145, further comprising a polymeric carrier.

4195. The device of item 4145, further comprising a polymeric carrier, wherein the polymeric carrier comprises a copolymer.

4196. The device of item 4145, further comprising a polymeric carrier, wherein the polymeric carrier comprises a block copolymer.

4197. The device of item 4145, further comprising a polymeric carrier, wherein the polymeric carrier comprises a random copolymer.

4198. The device of item 4145, further comprising a polymeric carrier, wherein the polymeric carrier comprises a biodegradable polymer.

4199. The device of item 4145, further comprising a polymeric carrier, wherein the polymeric carrier comprises a non-biodegradable polymer.

4200. The device of item 4145, further comprising a polymeric carrier, wherein the polymeric carrier comprises a hydrophilic polymer.

4201. The device of item 4145, further comprising a polymeric carrier, wherein the polymeric carrier comprises a hydrophobic polymer.

4202. The device of item 4145, further comprising a polymeric carrier, wherein the polymeric carrier comprises a polymer having hydrophilic domains.

4203. The device of item 4145, further comprising a polymeric carrier, wherein the polymeric carrier comprises a polymer having hydrophobic domains.

4204. The device of item 4145, further comprising a polymeric carrier, wherein the polymeric carrier comprises a non-conductive polymer.

4205. The device of item 4145, further comprising a polymeric carrier, wherein the polymeric carrier comprises an elastomer.

4206. The device of item 4145, further comprising a polymeric carrier, wherein the polymeric carrier comprises a hydrogel.

4207. The device of item 4145, further comprising a polymeric carrier, wherein the polymeric carrier comprises a silicone polymer.

4208. The device of item 4145, further comprising a polymeric carrier, wherein the polymeric carrier comprises a hydrocarbon polymer.

4209. The device of item 4145, further comprising a polymeric carrier, wherein the polymeric carrier comprises a styrene-derived polymer.

4210. The device of item 4145, further comprising a polymeric carrier, wherein the polymeric carrier comprises a butadiene polymer.

4211. The device of item 4145, further comprising a polymeric carrier, wherein the polymeric carrier comprises a macromer.

4212. The device of item 4145, further comprising a polymeric carrier, wherein the polymeric carrier comprises a poly(ethylene glycol) polymer.

4213. The device of item 4145, further comprising a polymeric carrier, wherein the polymeric carrier comprises an amorphous polymer.

4214. The device of item 4145, further comprising a lubricious coating.

4215. The device of item 4145 wherein the fibrosing agent is located within pores or holes of the device.

4216. The device of item 4145 wherein the fibrosing agent is located within a channel, lumen, or divet of the device.

4217. The device of item 4145, further comprising a second pharmaceutically active agent.

4218. The device of item 4145, further comprising an anti-inflammatory agent.

4219. The device of item 4145, further comprising an agent that inhibits infection.

4220. The device of item 4145, further comprising an agent that inhibits infection, wherein the agent is an anthracycline.

4221. The device of item 4145, further comprising an agent that inhibits infection, wherein the agent is doxorubicin.

4222. The device of item 4145, further comprising an agent that inhibits infection, wherein the agent is mitoxantrone.

4223. The device of item 4145, further comprising an agent that inhibits infection, wherein the agent is a fluoropyrimidine.

4224. The device of item 4145, further comprising an agent that inhibits infection, wherein the agent is 5-fluorouracil (5-FU).

4225. The device of item 4145, further comprising an agent that inhibits infection, wherein the agent is a folic acid antagonist.

4226. The device of item 4145, further comprising an agent that inhibits infection, wherein the agent is methotrexate.

4227. The device of item 4145, further comprising an agent that inhibits infection, wherein the agent is a podophylotoxin.

4228. The device of item 4145, further comprising an agent that inhibits infection, wherein the agent is etoposide.

4229. The device of item 4145, further comprising an agent that inhibits infection, wherein the agent is a camptothecin.

4230. The device of item 4145, further comprising an agent that inhibits infection, wherein the agent is a hydroxyurea.

4231. The device of item 4145, further comprising an agent that inhibits infection, wherein the agent is a platinum complex.

4232. The device of item 4145, further comprising an agent that inhibits infection, wherein the agent is cisplatin.

4233. The device of item 4145, further comprising an anti-thrombotic agent.

4234. The device of item 4145, further comprising a visualization agent.

4235. The device of item 4145, further comprising a visualization agent, wherein the visualization agent is a radiopaque material, wherein the radiopaque material comprises a metal, a halogenated compound, or a barium containing compound.

4236. The device of item 4145, further comprising a visualization agent, wherein the visualization agent is a radiopaque material, wherein the radiopaque material comprises barium, tantalum, or technetium.

4237. The device of item 4145, further comprising a visualization agent, wherein the visualization agent is a MRI responsive material.

4238. The device of item 4145, further comprising a visualization agent, wherein the visualization agent comprises a gadolinium chelate.

4239. The device of item 4145, further comprising a visualization agent, wherein the visualization agent comprises iron, magnesium, manganese, copper, or chromium.

4240. The device of item 4145, further comprising a visualization agent, wherein the visualization agent comprises an iron oxide compound.

4241. The device of item 4145, further comprising a visualization agent, wherein the visualization agent comprises a dye, pigment, or colorant.

4242. The device of item 4145, further comprising an echogenic material.

4243. The device of item 4145, further comprising an echogenic material, wherein the echogenic material is in the form of a coating.

4244. The device of item 4145 wherein the device is sterile.

4245. The device of item 4145 wherein the fibrosing agent is released into tissue in the vicinity of the device after deployment of the device.

4246. The device of item 4145 wherein the fibrosing agent is released into tissue in the vicinity of the device after deployment of the device, wherein the tissue is connective tissue.

4247. The device of item 4145 wherein the fibrosing agent is released into tissue in the vicinity of the device after deployment of the device, wherein the tissue is muscle tissue.

4248. The device of item 4145 wherein the fibrosing agent is released into tissue in the vicinity of the device after deployment of the device, wherein the tissue is nerve tissue.

4249. The device of item 4145 wherein the fibrosing agent is released into tissue in the vicinity of the device after deployment of the device, wherein the tissue is epithelium tissue.

4250. The device of item 4145 wherein the fibrosing agent is released in effective concentrations from the device over a period ranging from the time of deployment of the device to about 1 year.

4251. The device of item 4145 wherein the fibrosing agent is released in effective concentrations from the device over a period ranging from about 1 month to 6 months.

4252. The device of item 4145 wherein the fibrosing agent is released in effective concentrations from the device over a period ranging from about 1–90 days.

4253. The device of item 4145 wherein the fibrosing agent is released in effective concentrations from the device at a constant rate.

4254. The device of item 4145 wherein the fibrosing agent is released in effective concentrations from the device at an increasing rate.

4255. The device of item 4145 wherein the fibrosing agent is released in effective concentrations from the device at a decreasing rate.

4256. The device of item 4145 wherein the fibrosing agent is released in effective concentrations from the composition comprising the fibrosing agent by diffusion over a period ranging from the time of deployment of the device to about 90 days.

4257. The device of item 4145 wherein the fibrosing agent is released in effective concentrations from the composition comprising the fibrosing agent by erosion of the composition over a period ranging from the time of deployment of the device to about 90 days.

4258. The device of item 4145 wherein the device comprises about 0.01 µg to about 10 µg of the fibrosing agent.

4259. The device of item 4145 wherein the device comprises about 10 µg to about 10 mg of the fibrosing agent.

4260. The device of item 4145 wherein the device comprises about 10 mg to about 250 mg of the fibrosing agent.

4261. The device of item 4145 wherein the device comprises about 250 mg to about 1000 mg of the fibrosing agent.

4262. The device of item 4145 wherein the device comprises about 1000 mg to about 2500 mg of the fibrosing agent.

4263. The device of item 4145 wherein a surface of the device comprises less than 0.01 µg of the fibrosing agent per $mm^2$ of device surface to which the fibrosing agent is applied.

4264. The device of item 4145 wherein a surface of the device comprises about 0.01 µg to about 1 µg of the fibrosing agent per $mm^2$ of device surface to which the fibrosing agent is applied.

4265. The device of item 4145 wherein a surface of the device comprises about 1 µg to about 10 µg of the fibrosing agent per $mm^2$ of device surface to which the fibrosing agent is applied.

4266. The device of item 4145 wherein a surface of the device comprises about 10 µg to about 250 µg of the fibrosing agent per $mm^2$ of device surface to which the fibrosing agent is applied.

4267. The device of item 4145 wherein a surface of the device comprises about 250 µg to about 1000 µg of the fibrosing agent of fibrosing agent per $mm^2$ of device surface to which the fibrosing agent is applied.

4268. The device of item 4145 wherein a surface of the device comprises about 1000 µg to about 2500 µg of the fibrosing agent per $mm^2$ of device surface to which the fibrosing agent is applied.

4269. A medical device comprising an external fixation implant and a fibrosing agent, where the fibrosing agent induces a fibrotic response between the device and a patient in which the device is implanted.

4270. The device of item 4269 wherein the fibrosing agent promotes regeneration.

4271. The device of item 4269 wherein the fibrosing agent promotes angiogenesis.

4272. The device of item 4269 wherein the fibrosing agent promotes fibroblast migration.

4273. The device of item 4269 wherein the fibrosing agent promotes fibroblast proliferation.

4274. The device of item 4269 wherein the fibrosing agent promotes deposition of extracellular matrix (ECM).

4275. The device of item 4269 wherein the fibrosing agent promotes tissue remodeling.

4276. The device of item 4269 wherein the fibrosing agent is an arterial vessel wall irritant.

4277. The device of item 4269 wherein the fibrosing agent promotes adhesion between the device and a host into which the device is implanted.

4278. The device of item 4269 wherein the device delivers the fibrosing agent locally to tissue proximate to the device.

4279. The device of item 4269 wherein the fibrosing agent is or comprises silk.

4280. The device of item 4269 wherein the fibrosing agent is or comprises mineral particles.

4281. The device of item 4269 wherein the fibrosing agent is or comprises chitosan.

4282. The device of item 4269 wherein the fibrosing agent is or comprises polylysine.

4283. The device of item 4269 wherein the fibrosing agent is or comprises fibronectin.

4284. The device of item 4269 wherein the fibrosing agent is or comprises bleomycin.

4285. The device of item 4269 wherein the fibrosing agent is or comprises CTGF.

4286. The device of item 4269 wherein the fibrosing agent is in the form of a thread, or is in contact with a thread.

4287. The device of item 4269 wherein the fibrosing agent is in the form of a particulate.

4288. The device of item 4269 wherein the composition further comprises an inflammatory cytokine.

4289. The device of item 4269 wherein the composition further comprises an agent that stimulates cell proliferation.

4290. The device of item 4269 wherein the composition is in the form of a gel, paste, or spray.

4291. The device of item 4269 wherein the fibrosing agent is in the form of tufts.

4292. The device of item 4269, further comprising a polymer.

4293. The device of item 4269, further comprising a polymeric carrier.

4294. The device of item 4269 wherein the fibrosing agent promotes adhesion between the device and a host into which the device is implanted.

4295. The device of item 4269 wherein the device delivers the fibrosing agent locally to tissue proximate to the device.

4296. The device of item 4269, further comprising a coating, wherein the coating comprises the fibrosing agent.

4297. The device of item 4269, further comprising a coating, wherein the coating is disposed on a surface of the device.

4298. The device of item 4269, further comprising a coating, wherein the coating directly contacts the device.

4299. The device of item 4269, further comprising a coating, wherein the coating indirectly contacts the device.

4300. The device of item 4269, further comprising a coating, wherein the coating partially covers the device.

4301. The device of item 4269, further comprising a coating, wherein the coating completely covers the device.

4302. The device of item 4269, further comprising a coating, wherein the coating is a uniform coating.

4303. The device of item 4269, further comprising a coating, wherein the coating is a non-uniform coating.

4304. The device of item 4269, further comprising a coating, wherein the coating is a discontinuous coating.

4305. The device of item 4269, further comprising a coating, wherein the coating is a patterned coating.

4306. The device of item 4269, further comprising a coating, wherein the coating has a thickness of 100 µm or less.

4307. The device of item 4269, further comprising a coating, wherein the coating has a thickness of 10 µm or less.

4308. The device of item 4269, further comprising a coating, wherein the coating adheres to the surface of the device upon deployment of the device.

4309. The device of item 4269, further comprising a coating, wherein the coating is stable at room temperature for a period of 1 year.

4310. The device of item 4269, further comprising a coating, wherein the fibrosing agent is present in the coating in an amount ranging between about 0.0001% to about 1% by weight.

4311. The device of item 4269, further comprising a coating, wherein the fibrosing agent is present in the coating in an amount ranging between about 1% to about 10% by weight.

4312. The device of item 4269, further comprising a coating, wherein the fibrosing agent is present in the coating in an amount ranging between about 10% to about 25% by weight.

4313. The device of item 4269, further comprising a coating, wherein the fibrosing agent is present in the coating in an amount ranging between about 25% to about 70% by weight.

4314. The device of item 4269, further comprising a coating, wherein the coating further comprises a polymer.

4315. The device of item 4269, further comprising a first coating having a first composition and the second coating having a second composition.

4316. The device of item 4269, further comprising a first coating having a first composition and the second coating having a second composition, wherein the first composition and the second composition are different.

4317. The device of item 4269, further comprising a polymer.

4318. The device of item 4269, further comprising a polymeric carrier.

4319. The device of item 4269, further comprising a polymeric carrier, wherein the polymeric carrier comprises a copolymer.

4320. The device of item 4269, further comprising a polymeric carrier, wherein the polymeric carrier comprises a block copolymer.

4321. The device of item 4269, further comprising a polymeric carrier, wherein the polymeric carrier comprises a random copolymer.

4322. The device of item 4269, further comprising a polymeric carrier, wherein the polymeric carrier comprises a biodegradable polymer.

4323. The device of item 4269, further comprising a polymeric carrier, wherein the polymeric carrier comprises a non-biodegradable polymer.

4324. The device of item 4269, further comprising a polymeric carrier, wherein the polymeric carrier comprises a hydrophilic polymer.

4325. The device of item 4269, further comprising a polymeric carrier, wherein the polymeric carrier comprises a hydrophobic polymer.

4326. The device of item 4269, further comprising a polymeric carrier, wherein the polymeric carrier comprises a polymer having hydrophilic domains.

4327. The device of item 4269, further comprising a polymeric carrier, wherein the polymeric carrier comprises a polymer having hydrophobic domains.

4328. The device of item 4269, further comprising a polymeric carrier, wherein the polymeric carrier comprises a non-conductive polymer.

4329. The device of item 4269, further comprising a polymeric carrier, wherein the polymeric carrier comprises an elastomer.

4330. The device of item 4269, further comprising a polymeric carrier, wherein the polymeric carrier comprises a hydrogel.

4331. The device of item 4269, further comprising a polymeric carrier, wherein the polymeric carrier comprises a silicone polymer.

4332. The device of item 4269, further comprising a polymeric carrier, wherein the polymeric carrier comprises a hydrocarbon polymer.

4333. The device of item 4269, further comprising a polymeric carrier, wherein the polymeric carrier comprises a styrene-derived polymer.

4334. The device of item 4269, further comprising a polymeric carrier, wherein the polymeric carrier comprises a butadiene polymer.

4335. The device of item 4269, further comprising a polymeric carrier, wherein the polymeric carrier comprises a macromer.

4336. The device of item 4269, further comprising a polymeric carrier, wherein the polymeric carrier comprises a poly(ethylene glycol) polymer.

4337. The device of item 4269, further comprising a polymeric carrier, wherein the polymeric carrier comprises an amorphous polymer.

4338. The device of item 4269, further comprising a lubricious coating.

4339. The device of item 4269 wherein the fibrosing agent is located within pores or holes of the device.

4340. The device of item 4269 wherein the fibrosing agent is located within a channel, lumen, or divet of the device.

4341. The device of item 4269, further comprising a second pharmaceutically active agent.

4342. The device of item 4269, further comprising an anti-inflammatory agent.

4343. The device of item 4269, further comprising an agent that inhibits infection.

4344. The device of item 4269, further comprising an agent that inhibits infection, wherein the agent is an anthracycline.

4345. The device of item 4269, further comprising an agent that inhibits infection, wherein the agent is doxorubicin.

4346. The device of item 4269, further comprising an agent that inhibits infection, wherein the agent is mitoxantrone.

4347. The device of item 4269, further comprising an agent that inhibits infection, wherein the agent is a fluoropyrimidine.

4348. The device of item 4269, further comprising an agent that inhibits infection, wherein the agent is 5-fluorouracil (5-FU).

4349. The device of item 4269, further comprising an agent that inhibits infection, wherein the agent is a folic acid antagonist.

4350. The device of item 4269, further comprising an agent that inhibits infection, wherein the agent is methotrexate.

4351. The device of item 4269, further comprising an agent that inhibits infection, wherein the agent is a podophylotoxin.

4352. The device of item 4269, further comprising an agent that inhibits infection, wherein the agent is etoposide.

4353. The device of item 4269, further comprising an agent that inhibits infection, wherein the agent is a camptothecin.

4354. The device of item 4269, further comprising an agent that inhibits infection, wherein the agent is a hydroxyurea.

4355. The device of item 4269, further comprising an agent that inhibits infection, wherein the agent is a platinum complex.

4356. The device of item 4269, further comprising an agent that inhibits infection, wherein the agent is cisplatin.

4357. The device of item 4269, further comprising an anti-thrombotic agent.

4358. The device of item 4269, further comprising a visualization agent.

4359. The device of item 4269, further comprising a visualization agent, wherein the visualization agent is a radiopaque material, wherein the radiopaque material comprises a metal, a halogenated compound, or a barium containing compound.

4360. The device of item 4269, further comprising a visualization agent, wherein the visualization agent is a radiopaque material, wherein the radiopaque material comprises barium, tantalum, or technetium.

4361. The device of item 4269, further comprising a visualization agent, wherein the visualization agent is a MRI responsive material.

4362. The device of item 4269, further comprising a visualization agent, wherein the visualization agent comprises a gadolinium chelate.

4363. The device of item 4269, further comprising a visualization agent, wherein the visualization agent comprises iron, magnesium, manganese, copper, or chromium.

4364. The device of item 4269, further comprising a visualization agent, wherein the visualization agent comprises an iron oxide compound.

4365. The device of item 4269, further comprising a visualization agent, wherein the visualization agent comprises a dye, pigment, or colorant.

4366. The device of item 4269, further comprising an echogenic material.

4367. The device of item 4269, further comprising an echogenic material, wherein the echogenic material is in the form of a coating.

4368. The device of item 4269 wherein the device is sterile.

4369. The device of item 4269 wherein the fibrosing agent is released into tissue in the vicinity of the device after deployment of the device.

4370. The device of item 4269 wherein the fibrosing agent is released into tissue in the vicinity of the device after deployment of the device, wherein the tissue is connective tissue.

4371. The device of item 4269 wherein the fibrosing agent is released into tissue in the vicinity of the device after deployment of the device, wherein the tissue is muscle tissue.

4372. The device of item 4269 wherein the fibrosing agent is released into tissue in the vicinity of the device after deployment of the device, wherein the tissue is nerve tissue.

4373. The device of item 4269 wherein the fibrosing agent is released into tissue in the vicinity of the device after deployment of the device, wherein the tissue is epithelium tissue.

4374. The device of item 4269 wherein the fibrosing agent is released in effective concentrations from the device over a period ranging from the time of deployment of the device to about 1 year.

4375. The device of item 4269 wherein the fibrosing agent is released in effective concentrations from the device over a period ranging from about 1 month to 6 months.

4376. The device of item 4269 wherein the fibrosing agent is released in effective concentrations from the device over a period ranging from about 1–90 days.

4377. The device of item 4269 wherein the fibrosing agent is released in effective concentrations from the device at a constant rate.

4378. The device of item 4269 wherein the fibrosing agent is released in effective concentrations from the device at an increasing rate.

4379. The device of item 4269 wherein the fibrosing agent is released in effective concentrations from the device at a decreasing rate.

4380. The device of item 4269 wherein the fibrosing agent is released in effective concentrations from the composition comprising the fibrosing agent by diffusion over a period ranging from the time of deployment of the device to about 90 days.

4381. The device of item 4269 wherein the fibrosing agent is released in effective concentrations from the composition comprising the fibrosing agent by erosion of the composition over a period ranging from the time of deployment of the device to about 90 days.

4382. The device of item 4269 wherein the device comprises about 0.01 µg to about 10 µg of the fibrosing agent.

4383. The device of item 4269 wherein the device comprises about 10 µg to about 10 mg of the fibrosing agent.

4384. The device of item 4269 wherein the device comprises about 10 mg to about 250 mg of the fibrosing agent.

4385. The device of item 4269 wherein the device comprises about 250 mg to about 1000 mg of the fibrosing agent.

4386. The device of item 4269 wherein the device comprises about 1000 mg to about 2500 mg of the fibrosing agent.

4387. The device of item 4269 wherein a surface of the device comprises less than 0.01 µg of the fibrosing agent per $mm^2$ of device surface to which the fibrosing agent is applied.

4388. The device of item 4269 wherein a surface of the device comprises about 0.01 µg to about 1 µg of the fibrosing agent per $mm^2$ of device surface to which the fibrosing agent is applied.

4389. The device of item 4269 wherein a surface of the device comprises about 1 µg to about 10 µg of the fibrosing agent per $mm^2$ of device surface to which the fibrosing agent is applied.

4390. The device of item 4269 wherein a surface of the device comprises about 10 µg to about 250 µg of the fibrosing agent per $mm^2$ of device surface to which the fibrosing agent is applied.

4391. The device of item 4269 wherein a surface of the device comprises about 250 µg to about 1000 µg of the fibrosing agent of fibrosing agent per mm² of device surface to which the fibrosing agent is applied.

4392. The device of item 4269 wherein a surface of the device comprises about 1000 µg to about 2500 µg of the fibrosing agent per mm² of device surface to which the fibrosing agent is applied.

4393. A medical device comprising a fixation screw and a fibrosing agent, where the fibrosing agent induces a fibrotic response between the device and a patient in which the device is implanted.

4394. The device of item 4393 wherein the fibrosing agent promotes regeneration.

4395. The device of item 4393 wherein the fibrosing agent promotes angiogenesis.

4396. The device of item 4393 wherein the fibrosing agent promotes fibroblast migration.

4397. The device of item 4393 wherein the fibrosing agent promotes fibroblast proliferation.

4398. The device of item 4393 wherein the fibrosing agent promotes deposition of extracellular matrix (ECM).

4399. The device of item 4393 wherein the fibrosing agent promotes tissue remodeling.

4400. The device of item 4393 wherein the fibrosing agent is an arterial vessel wall irritant.

4401. The device of item 4393 wherein the fibrosing agent promotes adhesion between the device and a host into which the device is implanted.

4402. The device of item 4393 wherein the device delivers the fibrosing agent locally to tissue proximate to the device.

4403. The device of item 4393 wherein the fibrosing agent is or comprises silk.

4404. The device of item 4393 wherein the fibrosing agent is or comprises mineral particles.

4405. The device of item 4393 wherein the fibrosing agent is or comprises chitosan.

4406. The device of item 4393 wherein the fibrosing agent is or comprises polylysine.

4407. The device of item 4393 wherein the fibrosing agent is or comprises fibronectin.

4408. The device of item 4393 wherein the fibrosing agent is or comprises bleomycin.

4409. The device of item 4393 wherein the fibrosing agent is or comprises CTGF.

4410. The device of item 4393 wherein the fibrosing agent is in the form of a thread, or is in contact with a thread.

4411. The device of item 4393 wherein the fibrosing agent is in the form of a particulate.

4412. The device of item 4393 wherein the composition further comprises an inflammatory cytokine.

4413. The device of item 4393 wherein the composition further comprises an agent that stimulates cell proliferation.

4414. The device of item 4393 wherein the composition is in the form of a gel, paste, or spray.

4415. The device of item 4393 wherein the fibrosing agent is in the form of tufts.

4416. The device of item 4393, further comprising a polymer.

4417. The device of item 4393, further comprising a polymeric carrier.

4418. The device of item 4393 wherein the fibrosing agent promotes adhesion between the device and a host into which the device is implanted.

4419. The device of item 4393 wherein the device delivers the fibrosing agent locally to tissue proximate to the device.

4420. The device of item 4393, further comprising a coating, wherein the coating comprises the fibrosing agent.

4421. The device of item 4393, further comprising a coating, wherein the coating is disposed on a surface of the device.

4422. The device of item 4393, further comprising a coating, wherein the coating directly contacts the device.

4423. The device of item 4393, further comprising a coating, wherein the coating indirectly contacts the device.

4424. The device of item 4393, further comprising a coating, wherein the coating partially covers the device.

4425. The device of item 4393, further comprising a coating, wherein the coating completely covers the device.

4426. The device of item 4393, further comprising a coating, wherein the coating is a uniform coating.

4427. The device of item 4393, further comprising a coating, wherein the coating is a non-uniform coating.

4428. The device of item 4393, further comprising a coating, wherein the coating is a discontinuous coating.

4429. The device of item 4393, further comprising a coating, wherein the coating is a patterned coating.

4430. The device of item 4393, further comprising a coating, wherein the coating has a thickness of 100 µm or less.

4431. The device of item 4393, further comprising a coating, wherein the coating has a thickness of 10 µm or less.

4432. The device of item 4393, further comprising a coating, wherein the coating adheres to the surface of the device upon deployment of the device.

4433. The device of item 4393, further comprising a coating, wherein the coating is stable at room temperature for a period of 1 year.

4434. The device of item 4393, further comprising a coating, wherein the fibrosing agent is present in the coating in an amount ranging between about 0.0001% to about 1% by weight.

4435. The device of item 4393, further comprising a coating, wherein the fibrosing agent is present in the coating in an amount ranging between about 1% to about 10% by weight.

4436. The device of item 4393, further comprising a coating, wherein the fibrosing agent is present in the coating in an amount ranging between about 10% to about 25% by weight.

4437. The device of item 4393, further comprising a coating, wherein the fibrosing agent is present in the coating in an amount ranging between about 25% to about 70% by weight.

4438. The device of item 4393, further comprising a coating, wherein the coating further comprises a polymer.

4439. The device of item 4393, further comprising a first coating having a first composition and the second coating having a second composition.

4440. The device of item 4393, further comprising a first coating having a first composition and the second coating having a second composition, wherein the first composition and the second composition are different.

4441. The device of item 4393, further comprising a polymer.

4442. The device of item 4393, further comprising a polymeric carrier.

4443. The device of item 4393, further comprising a polymeric carrier, wherein the polymeric carrier comprises a copolymer.

4444. The device of item 4393, further comprising a polymeric carrier, wherein the polymeric carrier comprises a block copolymer.

4445. The device of item 4393, further comprising a polymeric carrier, wherein the polymeric carrier comprises a random copolymer.

4446. The device of item 4393, further comprising a polymeric carrier, wherein the polymeric carrier comprises a biodegradable polymer.

4447. The device of item 4393, further comprising a polymeric carrier, wherein the polymeric carrier comprises a non-biodegradable polymer.

4448. The device of item 4393, further comprising a polymeric carrier, wherein the polymeric carrier comprises a hydrophilic polymer.

4449. The device of item 4393, further comprising a polymeric carrier, wherein the polymeric carrier comprises a hydrophobic polymer.

4450. The device of item 4393, further comprising a polymeric carrier, wherein the polymeric carrier comprises a polymer having hydrophilic domains.

4451. The device of item 4393, further comprising a polymeric carrier, wherein the polymeric carrier comprises a polymer having hydrophobic domains.

4452. The device of item 4393, further comprising a polymeric carrier, wherein the polymeric carrier comprises a non-conductive polymer.

4453. The device of item 4393, further comprising a polymeric carrier, wherein the polymeric carrier comprises an elastomer.

4454. The device of item 4393, further comprising a polymeric carrier, wherein the polymeric carrier comprises a hydrogel.

4455. The device of item 4393, further comprising a polymeric carrier, wherein the polymeric carrier comprises a silicone polymer.

4456. The device of item 4393, further comprising a polymeric carrier, wherein the polymeric carrier comprises a hydrocarbon polymer.

4457. The device of item 4393, further comprising a polymeric carrier, wherein the polymeric carrier comprises a styrene-derived polymer.

4458. The device of item 4393, further comprising a polymeric carrier, wherein the polymeric carrier comprises a butadiene polymer.

4459. The device of item 4393, further comprising a polymeric carrier, wherein the polymeric carrier comprises a macromer.

4460. The device of item 4393, further comprising a polymeric carrier, wherein the polymeric carrier comprises a poly(ethylene glycol) polymer.

4461. The device of item 4393, further comprising a polymeric carrier, wherein the polymeric carrier comprises an amorphous polymer.

4462. The device of item 4393, further comprising a lubricious coating.

4463. The device of item 4393 wherein the fibrosing agent is located within pores or holes of the device.

4464. The device of item 4393 wherein the fibrosing agent is located within a channel, lumen, or divet of the device.

4465. The device of item 4393, further comprising a second pharmaceutically active agent.

4466. The device of item 4393, further comprising an anti-inflammatory agent.

4467. The device of item 4393, further comprising an agent that inhibits infection.

4468. The device of item 4393, further comprising an agent that inhibits infection, wherein the agent is an anthracycline.

4469. The device of item 4393, further comprising an agent that inhibits infection, wherein the agent is doxorubicin.

4470. The device of item 4393, further comprising an agent that inhibits infection, wherein the agent is mitoxantrone.

4471. The device of item 4393, further comprising an agent that inhibits infection, wherein the agent is a fluoropyrimidine.

4472. The device of item 4393, further comprising an agent that inhibits infection, wherein the agent is 5-fluorouracil (5-FU).

4473. The device of item 4393, further comprising an agent that inhibits infection, wherein the agent is a folic acid antagonist.

4474. The device of item 4393, further comprising an agent that inhibits infection, wherein the agent is methotrexate.

4475. The device of item 4393, further comprising an agent that inhibits infection, wherein the agent is a podophylotoxin.

4476. The device of item 4393, further comprising an agent that inhibits infection, wherein the agent is etoposide.

4477. The device of item 4393, further comprising an agent that inhibits infection, wherein the agent is a camptothecin.

4478. The device of item 4393, further comprising an agent that inhibits infection, wherein the agent is a hydroxyurea.

4479. The device of item 4393, further comprising an agent that inhibits infection, wherein the agent is a platinum complex.

4480. The device of item 4393, further comprising an agent that inhibits infection, wherein the agent is cisplatin.

4481. The device of item 4393, further comprising an anti-thrombotic agent.

4482. The device of item 4393, further comprising a visualization agent.

4483. The device of item 4393, further comprising a visualization agent, wherein the visualization agent is a radiopaque material, wherein the radiopaque material comprises a metal, a halogenated compound, or a barium containing compound.

4484. The device of item 4393, further comprising a visualization agent, wherein the visualization agent is a radiopaque material, wherein the radiopaque material comprises barium, tantalum, or technetium.

4485. The device of item 4393, further comprising a visualization agent, wherein the visualization agent is a MRI responsive material.

4486. The device of item 4393, further comprising a visualization agent, wherein the visualization agent comprises a gadolinium chelate.

4487. The device of item 4393, further comprising a visualization agent, wherein the visualization agent comprises iron, magnesium, manganese, copper, or chromium.

4488. The device of item 4393, further comprising a visualization agent, wherein the visualization agent comprises an iron oxide compound.

4489. The device of item 4393, further comprising a visualization agent, wherein the visualization agent comprises a dye, pigment, or colorant.

4490. The device of item 4393, further comprising an echogenic material.

4491. The device of item 4393, further comprising an echogenic material, wherein the echogenic material is in the form of a coating.

4492. The device of item 4393 wherein the device is sterile.

4493. The device of item 4393 wherein the fibrosing agent is released into tissue in the vicinity of the device after deployment of the device.

4494. The device of item 4393 wherein the fibrosing agent is released into tissue in the vicinity of the device after deployment of the device, wherein the tissue is connective tissue.

4495. The device of item 4393 wherein the fibrosing agent is released into tissue in the vicinity of the device after deployment of the device, wherein the tissue is muscle tissue.

4496. The device of item 4393 wherein the fibrosing agent is released into tissue in the vicinity of the device after deployment of the device, wherein the tissue is nerve tissue.

4497. The device of item 4393 wherein the fibrosing agent is released into tissue in the vicinity of the device after deployment of the device, wherein the tissue is epithelium tissue.

4498. The device of item 4393 wherein the fibrosing agent is released in effective concentrations from the device over a period ranging from the time of deployment of the device to about 1 year.

4499. The device of item 4393 wherein the fibrosing agent is released in effective concentrations from the device over a period ranging from about 1 month to 6 months.

4500. The device of item 4393 wherein the fibrosing agent is released in effective concentrations from the device over a period ranging from about 1–90 days.

4501. The device of item 4393 wherein the fibrosing agent is released in effective concentrations from the device at a constant rate.

4502. The device of item 4393 wherein the fibrosing agent is released in effective concentrations from the device at an increasing rate.

4503. The device of item 4393 wherein the fibrosing agent is released in effective concentrations from the device at a decreasing rate.

4504. The device of item 4393 wherein the fibrosing agent is released in effective concentrations from the composition comprising the fibrosing agent by diffusion over a period ranging from the time of deployment of the device to about 90 days.

4505. The device of item 4393 wherein the fibrosing agent is released in effective concentrations from the composition comprising the fibrosing agent by erosion of the composition over a period ranging from the time of deployment of the device to about 90 days.

4506. The device of item 4393 wherein the device comprises about 0.01 μg to about 10 μg of the fibrosing agent.

4507. The device of item 4393 wherein the device comprises about 10 μg to about 10 mg of the fibrosing agent.

4508. The device of item 4393 wherein the device comprises about 10 mg to about 250 mg of the fibrosing agent.

4509. The device of item 4393 wherein the device comprises about 250 mg to about 1000 mg of the fibrosing agent.

4510. The device of item 4393 wherein the device comprises about 1000 mg to about 2500 mg of the fibrosing agent.

4511. The device of item 4393 wherein a surface of the device comprises less than 0.01 μg of the fibrosing agent per $mm^2$ of device surface to which the fibrosing agent is applied.

4512. The device of item 4393 wherein a surface of the device comprises about 0.01 μg to about 1 μg of the fibrosing agent per $mm^2$ of device surface to which the fibrosing agent is applied.

4513. The device of item 4393 wherein a surface of the device comprises about 1 μg to about 10 μg of the fibrosing agent per $mm^2$ of device surface to which the fibrosing agent is applied.

4514. The device of item 4393 wherein a surface of the device comprises about 10 μg to about 250 μg of the fibrosing agent per $mm^2$ of device surface to which the fibrosing agent is applied.

4515. The device of item 4393 wherein a surface of the device comprises about 250 μg to about 1000 μg of the fibrosing agent of fibrosing agent per $mm^2$ of device surface to which the fibrosing agent is applied.

4516. The device of item 4393 wherein a surface of the device comprises about 1000 μg to about 2500 μg of the fibrosing agent per $mm^2$ of device surface to which the fibrosing agent is applied.

4517. The device of item 4393 wherein the fixation screw is biodegradable.

4518. The device of item 4393 wherein the fixation screw is non-biodegradable.

4519. A medical device comprising an interferential screw and a fibrosing agent, where the fibrosing agent induces a fibrotic response between the device and a patient in which the device is implanted.

4520. The device of item 4519 wherein the fibrosing agent promotes regeneration.

4521. The device of item 4519 wherein the fibrosing agent promotes angiogenesis.

4522. The device of item 4519 wherein the fibrosing agent promotes fibroblast migration.

4523. The device of item 4519 wherein the fibrosing agent promotes fibroblast proliferation.

4524. The device of item 4519 wherein the fibrosing agent promotes deposition of extracellular matrix (ECM).

4525. The device of item 4519 wherein the fibrosing agent promotes tissue remodeling.

4526. The device of item 4519 wherein the fibrosing agent is an arterial vessel wall irritant.

4527. The device of item 4519 wherein the fibrosing agent promotes adhesion between the device and a host into which the device is implanted.

4528. The device of item 4519 wherein the device delivers the fibrosing agent locally to tissue proximate to the device.

4529. The device of item 4519 wherein the fibrosing agent is or comprises silk.

4530. The device of item 4519 wherein the fibrosing agent is or comprises mineral particles.

4531. The device of item 4519 wherein the fibrosing agent is or comprises chitosan.

4532. The device of item 4519 wherein the fibrosing agent is or comprises polylysine.

4533. The device of item 4519 wherein the fibrosing agent is or comprises fibronectin.

4534. The device of item 4519 wherein the fibrosing agent is or comprises bleomycin.

4535. The device of item 4519 wherein the fibrosing agent is or comprises CTGF.

4536. The device of item 4519 wherein the fibrosing agent is in the form of a thread, or is in contact with a thread.

4537. The device of item 4519 wherein the fibrosing agent is in the form of a particulate.

4538. The device of item 4519 wherein the composition further comprises an inflammatory cytokine.

4539. The device of item 4519 wherein the composition further comprises an agent that stimulates cell proliferation.

4540. The device of item 4519 wherein the composition is in the form of a gel, paste, or spray.

4541. The device of item 4519 wherein the fibrosing agent is in the form of tufts.

4542. The device of item 4519, further comprising a polymer.

4543. The device of item 4519, further comprising a polymeric carrier.

4544. The device of item 4519 wherein the fibrosing agent promotes adhesion between the device and a host into which the device is implanted.

4545. The device of item 4519 wherein the device delivers the fibrosing agent locally to tissue proximate to the device.

4546. The device of item 4519, further comprising a coating, wherein the coating comprises the fibrosing agent.

4547. The device of item 4519, further comprising a coating, wherein the coating is disposed on a surface of the device.

4548. The device-of item 4519, further comprising a coating, wherein the coating directly contacts the device.

4549. The device of item 4519, further comprising a coating, wherein the coating indirectly contacts the device.

4550. The device of item 4519, further comprising a coating, wherein the coating partially covers the device.

4551. The device of item 4519, further comprising a coating, wherein the coating completely covers the device.

4552. The device of item 4519, further comprising a coating, wherein the coating is a uniform coating.

4553. The device of item 4519, further comprising a coating, wherein the coating is a non-uniform coating.

4554. The device of item 4519, further comprising a coating, wherein the coating is a discontinuous coating.

4555. The device of item 4519, further comprising a coating, wherein the coating is a patterned coating.

4556. The device of item 4519, further comprising a coating, wherein the coating has a thickness of 100 μm or less.

4557. The device of item 4519, further comprising a coating, wherein the coating has a thickness of 10 μm or less.

4558. The device of item 4519, further comprising a coating, wherein the coating adheres to the surface of the device upon deployment of the device.

4559. The device of item 4519, further comprising a coating, wherein the coating is stable at room temperature for a period of 1 year.

4560. The device of item 4519, further comprising a coating, wherein the fibrosing agent is present in the coating in an amount ranging between about 0.0001% to about 1% by weight.

4561. The device of item 4519, further comprising a coating, wherein the fibrosing agent is present in the coating in an amount ranging between about 1% to about 10% by weight.

4562. The device of item 4519, further comprising a coating, wherein the fibrosing agent is present in the coating in an amount ranging between about 10% to about 25% by weight.

4563. The device of item 4519, further comprising a coating, wherein the fibrosing agent is present in the coating in an amount ranging between about 25% to about 70% by weight.

4564. The device of item 4519, further comprising a coating, wherein the coating further comprises a polymer.

4565. The device of item 4519, further comprising a first coating having a first composition and the second coating having a second composition.

4566. The device of item 4519, further comprising a first coating having a first composition and the second coating having a second composition, wherein the first composition and the second composition are different.

4567. The device of item 4519, further comprising a polymer.

4568. The device of item 4519, further comprising a polymeric carrier.

4569. The device of item 4519, further comprising a polymeric carrier, wherein the polymeric carrier comprises a copolymer.

4570. The device of item 4519, further comprising a polymeric carrier, wherein the polymeric carrier comprises a block copolymer.

4571. The device of item 4519, further comprising a polymeric carrier, wherein the polymeric carrier comprises a random copolymer.

4572. The device of item 4519, further comprising a polymeric carrier, wherein the polymeric carrier comprises a biodegradable polymer.

4573. The device of item 4519, further comprising a polymeric carrier, wherein the polymeric carrier comprises a non-biodegradable polymer.

4574. The device of item 4519, further comprising a polymeric carrier, wherein the polymeric carrier comprises a hydrophilic polymer.

4575. The device of item 4519, further comprising a polymeric carrier, wherein the polymeric carrier comprises a hydrophobic polymer.

4576. The device of item 4519, further comprising a polymeric carrier, wherein the polymeric carrier comprises a polymer having hydrophilic domains.

4577. The device of item 4519, further comprising a polymeric carrier, wherein the polymeric carrier comprises a polymer having hydrophobic domains.

4578. The device of item 4519, further comprising a polymeric carrier, wherein the polymeric carrier comprises a non-conductive polymer.

4579. The device of item 4519, further comprising a polymeric carrier, wherein the polymeric carrier comprises an elastomer.

4580. The device of item 4519, further comprising a polymeric carrier, wherein the polymeric carrier comprises a hydrogel.

4581. The device of item 4519, further comprising a polymeric carrier, wherein the polymeric carrier comprises a silicone polymer.

4582. The device of item 4519, further comprising a polymeric carrier, wherein the polymeric carrier comprises a hydrocarbon polymer.

4583. The device of item 4519, further comprising a polymeric carrier, wherein the polymeric carrier comprises a styrene-derived polymer.

4584. The device of item 4519, further comprising a polymeric carrier, wherein the polymeric carrier comprises a butadiene polymer.

4585. The device of item 4519, further comprising a polymeric carrier, wherein the polymeric carrier comprises a macromer.

4586. The device of item 4519, further comprising a polymeric carrier, wherein the polymeric carrier comprises a poly(ethylene glycol) polymer.

4587. The device of item 4519, further comprising a polymeric carrier, wherein the polymeric carrier comprises an amorphous polymer.

4588. The device of item 4519, further comprising a lubricious coating.

4589. The device of item 4519 wherein the fibrosing agent is located within pores or holes of the device.

4590. The device of item 4519 wherein the fibrosing agent is located within a channel, lumen, or divet of the device.

4591. The device of item 4519, further comprising a second pharmaceutically active agent.

4592. The device of item 4519, further comprising an anti-inflammatory agent.

4593. The device of item 4519, further comprising an agent that inhibits infection.

4594. The device of item 4519, further comprising an agent that inhibits infection, wherein the agent is an anthracycline.

4595. The device of item 4519, further comprising an agent that inhibits infection, wherein the agent is doxorubicin.

4596. The device of item 4519, further comprising an agent that inhibits infection, wherein the agent is mitoxantrone.

4597. The device of item 4519, further comprising an agent that inhibits infection, wherein the agent is a fluoropyrimidine.

4598. The device of item 4519, further comprising an agent that inhibits infection, wherein the agent is 5-fluorouracil (5-FU).

4599. The device of item 4519, further comprising an agent that inhibits infection, wherein the agent is a folic acid antagonist.

4600. The device of item 4519, further comprising an agent that inhibits infection, wherein the agent is methotrexate.

4601. The device of item 4519, further comprising an agent that inhibits infection, wherein the agent is a podophylotoxin.

4602. The device of item 4519, further comprising an agent that inhibits infection, wherein the agent is etoposide.

4603. The device of item 4519, further comprising an agent that inhibits infection, wherein the agent is a camptothecin.

4604. The device of item 4519, further comprising an agent that inhibits infection, wherein the agent is a hydroxyurea.

4605. The device of item 4519, further comprising an agent that inhibits infection, wherein the agent is a platinum complex.

4606. The device of item 4519, further comprising an agent that inhibits infection, wherein the agent is cisplatin.

4607. The device of item 4519, further comprising an anti-thrombotic agent.

4608. The device of item 4519, further comprising a visualization agent.

4609. The device of item 4519, further comprising a visualization agent, wherein the visualization agent is a radiopaque material, wherein the radiopaque material comprises a metal, a halogenated compound, or a barium containing compound.

4610. The device of item 4519, further comprising a visualization agent, wherein the visualization agent is a radiopaque material, wherein the radiopaque material comprises barium, tantalum, or technetium.

4611. The device of item 4519, further comprising a visualization agent, wherein the visualization agent is a MRI responsive material.

4612. The device of item 4519, further comprising a visualization agent, wherein the visualization agent comprises a gadolinium chelate.

4613. The device of item 4519, further comprising a visualization agent, wherein the visualization agent comprises iron, magnesium, manganese, copper, or chromium.

4614. The device of item 4519, further comprising a visualization agent, wherein the visualization agent comprises an iron oxide compound.

4615. The device of item 4519, further comprising a visualization agent, wherein the visualization agent comprises a dye, pigment, or colorant.

4616. The device of item 4519, further comprising an echogenic material.

4617. The device of item 4519, further comprising an echogenic material, wherein the echogenic material is in the form of a coating.

4618. The device of item 4519 wherein the device is sterile.

4619. The device of item 4519 wherein the fibrosing agent is released into tissue in the vicinity of the device after deployment of the device.

4620. The device of item 4519 wherein the fibrosing agent is released into tissue in the vicinity of the device after deployment of the device, wherein the tissue is connective tissue.

4621. The device of item 4519 wherein the fibrosing agent is released into tissue in the vicinity of the device after deployment of the device, wherein the tissue is muscle tissue.

4622. The device of item 4519 wherein the fibrosing agent is released into tissue in the vicinity of the device after deployment of the device, wherein the tissue is nerve tissue.

4623. The device of item 4519 wherein the fibrosing agent is released into tissue in the vicinity of the device after deployment of the device, wherein the tissue is epithelium tissue.

4624. The device of item 4519 wherein the fibrosing agent is released in effective concentrations from the device over a period ranging from the time of deployment of the device to about 1 year.

4625. The device of item 4519 wherein the fibrosing agent is released in effective concentrations from the device over a period ranging from about 1 month to 6 months.

4626. The device of item 4519 wherein the fibrosing agent is released in effective concentrations from the device over a period ranging from about 1–90 days.

4627. The device of item 4519 wherein the fibrosing agent is released in effective concentrations from the device at a constant rate.

4628. The device of item 4519 wherein the fibrosing agent is released in effective concentrations from the device at an increasing rate.

4629. The device of item 4519 wherein the fibrosing agent is released in effective concentrations from the device at a decreasing rate.

4630. The device of item 4519 wherein the fibrosing agent is released in effective concentrations from the composition comprising the fibrosing agent by diffusion over a period ranging from the time of deployment of the device to about 90 days.

4631. The device of item 4519 wherein the fibrosing agent is released in effective concentrations from the composition comprising the fibrosing agent by erosion of the composition over a period ranging from the time of deployment of the device to about 90 days.

4632. The device of item 4519 wherein the device comprises about 0.01 µg to about 10 µg of the fibrosing agent.

4633. The device of item 4519 wherein the device comprises about 10 µg to about 10 mg of the fibrosing agent.

4634. The device of item 4519 wherein the device comprises about 10 mg to about 250 mg of the fibrosing agent.

4635. The device of item 4519 wherein the device comprises about 250 mg to about 1000 mg of the fibrosing agent.

4636. The device of item 4519 wherein the device comprises about 1000 mg to about 2500 mg of the fibrosing agent.

4637. The device of item 4519 wherein a surface of the device comprises less than 0.01 µg of the fibrosing agent per mm$^2$ of device surface to which the fibrosing agent is applied.

4638. The device of item 4519 wherein a surface of the device comprises about 0.01 µg to about 1 µg of the fibrosing agent per mm$^2$ of device surface to which the fibrosing agent is applied.

4639. The device of item 4519 wherein a surface of the device comprises about 1 µg to about 10 µg of the fibrosing agent per mm$^2$ of device surface to which the fibrosing agent is applied.

4640. The device of item 4519 wherein a surface of the device comprises about 10 µg to about 250 µg of the fibrosing agent per mm$^2$ of device surface to which the fibrosing agent is applied.

4641. The device of item 4519 wherein a surface of the device comprises about 250 µg to about 1000 µg of the fibrosing agent of fibrosing agent per mm$^2$ of device surface to which the fibrosing agent is applied.

4642. The device of item 4519 wherein a surface of the device comprises about 1000 µg to about 2500 µg of the fibrosing agent per mm$^2$ of device surface to which the fibrosing agent is applied.

4643. The device of item 4519 wherein the interferential screw is degradable.

4644. The device of item 4519 wherein the interferential screw is non-degradable.

4645. A medical device comprising a trochanteric screw and a fibrosing agent, where the fibrosing agent induces a fibrotic response between the device and a patient in which the device is implanted.

4646. The device of item 4645 wherein the fibrosing agent promotes regeneration.

4647. The device of item 4645 wherein the fibrosing agent promotes angiogenesis.

4648. The device of item 4645 wherein the fibrosing agent promotes fibroblast migration.

4649. The device of item 4645 wherein the fibrosing agent promotes fibroblast proliferation.

4650. The device of item 4645 wherein the fibrosing agent promotes deposition of extracellular matrix (ECM).

4651. The device of item 4645 wherein the fibrosing agent promotes tissue remodeling.

4652. The device of item 4645 wherein the fibrosing agent is an arterial vessel wall irritant.

4653. The device of item 4645 wherein the fibrosing agent promotes adhesion between the device and a host into which the device is implanted.

4654. The device of item 4645 wherein the device delivers the fibrosing agent locally to tissue proximate to the device.

4655. The device of item 4645 wherein the fibrosing agent is or comprises silk.

4656. The device of item 4645 wherein the fibrosing agent is or comprises mineral particles.

4657. The device of item 4645 wherein the fibrosing agent is or comprises chitosan.

4658. The device of item 4645 wherein the fibrosing agent is or comprises polylysine.

4659. The device of item 4645 wherein the fibrosing agent is or comprises fibronectin.

4660. The device of item 4645 wherein the fibrosing agent is or comprises bleomycin.

4661. The device of item 4645 wherein the fibrosing agent is or comprises CTGF.

4662. The device of item 4645 wherein the fibrosing agent is in the form of a thread, or is in contact with a thread.

4663. The device of item 4645 wherein the fibrosing agent is in the form of a particulate.

4664. The device of item 4645 wherein the composition further comprises an inflammatory cytokine.

4665. The device of item 4645 wherein the composition further comprises an agent that stimulates cell proliferation.

4666. The device of item 4645 wherein the composition is in the form of a gel, paste, or spray.

4667. The device of item 4645 wherein the fibrosing agent is in the form of tufts.

4668. The device of item 4645, further comprising a polymer.

4669. The device of item 4645, further comprising a polymeric carrier.

4670. The device of item 4645 wherein the fibrosing agent promotes adhesion between the device and a host into which the device is implanted.

4671. The device of item 4645 wherein the device delivers the fibrosing agent locally to tissue proximate to the device.

4672. The device of item 4645, further comprising a coating, wherein the coating comprises the fibrosing agent.

4673. The device of item 4645, further comprising a coating, wherein the coating is disposed on a surface of the device.

4674. The device of item 4645, further comprising a coating, wherein the coating directly contacts the device.

4675. The device of item 4645, further comprising a coating, wherein the coating indirectly contacts the device.

4676. The device of item 4645, further comprising a coating, wherein the coating partially covers the device.

4677. The device of item 4645, further comprising a coating, wherein the coating completely covers the device.

4678. The device of item 4645, further comprising a coating, wherein the coating is a uniform coating.

4679. The device of item 4645, further comprising a coating, wherein the coating is a non-uniform coating.

4680. The device of item 4645, further comprising a coating, wherein the coating is a discontinuous coating.

4681. The device of item 4645, further comprising a coating, wherein the coating is a patterned coating.

4682. The device of item 4645, further comprising a coating, wherein the coating has a thickness of 100 µm or less.

4683. The device of item 4645, further comprising a coating, wherein the coating has a thickness of 10 µm or less.

4684. The device of item 4645, further comprising a coating, wherein the coating adheres to the surface of the device upon deployment of the device.

4685. The device of item 4645, further comprising a coating, wherein the coating is stable at room temperature for a period of 1 year.

4686. The device of item 4645, further comprising a coating, wherein the fibrosing agent is present in the coating in an amount ranging between about 0.0001% to about 1% by weight.

4687. The device of item 4645, further comprising a coating, wherein the fibrosing agent is present in the coating in an amount ranging between about 1% to about 10% by weight.

4688. The device of item 4645, further comprising a coating, wherein the fibrosing agent is present in the coating in an amount ranging between about 10% to about 25% by weight.

4689. The device of item 4645, further comprising a coating, wherein the fibrosing agent is present in the coating in an amount ranging between about 25% to about 70% by weight.

4690. The device of item 4645, further comprising a coating, wherein the coating further comprises a polymer.

4691. The device of item 4645, further comprising a first coating having a first composition and the second coating having a second composition.

4692. The device of item 4645, further comprising a first coating having a first composition and the second coating having a second composition, wherein the first composition and the second composition are different.

4693. The device of item 4645, further comprising a polymer.

4694. The device of item 4645, further comprising a polymeric carrier.

4695. The device of item 4645, further comprising a polymeric carrier, wherein the polymeric carrier comprises a copolymer.

4696. The device of item 4645, further comprising a polymeric carrier, wherein the polymeric carrier comprises a block copolymer.

4697. The device of item 4645, further comprising a polymeric carrier, wherein the polymeric carrier comprises a random copolymer.

4698. The device of item 4645, further comprising a polymeric carrier, wherein the polymeric carrier comprises a biodegradable polymer.

4699. The device of item 4645, further comprising a polymeric carrier, wherein the polymeric carrier comprises a non-biodegradable polymer.

4700. The device of item 4645, further comprising a polymeric carrier, wherein the polymeric carrier comprises a hydrophilic polymer.

4701. The device of item 4645, further comprising a polymeric carrier, wherein the polymeric carrier comprises a hydrophobic polymer.

4702. The device of item 4645, further comprising a polymeric carrier, wherein the polymeric carrier comprises a polymer having hydrophilic domains.

4703. The device of item 4645, further comprising a polymeric carrier, wherein the polymeric carrier comprises a polymer having hydrophobic domains.

4704. The device of item 4645, further comprising a polymeric carrier, wherein the polymeric carrier comprises a non-conductive polymer.

4705. The device of item 4645, further comprising a polymeric carrier, wherein the polymeric carrier comprises an elastomer.

4706. The device of item 4645, further comprising a polymeric carrier, wherein the polymeric carrier comprises a hydrogel.

4707. The device of item 4645, further comprising a polymeric carrier, wherein the polymeric carrier comprises a silicone polymer.

4708. The device of item 4645, further comprising a polymeric carrier, wherein the polymeric carrier comprises a hydrocarbon polymer.

4709. The device of item 4645, further comprising a polymeric carrier, wherein the polymeric carrier comprises a styrene-derived polymer.

4710. The device of item 4645, further comprising a polymeric carrier, wherein the polymeric carrier comprises a butadiene polymer.

4711. The device of item 4645, further comprising a polymeric carrier, wherein the polymeric carrier comprises a macromer.

4712. The device of item 4645, further comprising a polymeric carrier, wherein the polymeric carrier comprises a poly(ethylene glycol) polymer.

4713. The device of item 4645, further comprising a polymeric carrier, wherein the polymeric carrier comprises an amorphous polymer.

4714. The device of item 4645, further comprising a lubricious coating.

4715. The device of item 4645 wherein the fibrosing agent is located within pores or holes of the device.

4716. The device of item 4645 wherein the fibrosing agent is located within a channel, lumen, or divet of the device.

4717. The device of item 4645, further comprising a second pharmaceutically active agent.

4718. The device of item 4645, further comprising an anti-inflammatory agent.

4719. The device of item 4645, further comprising an agent that inhibits infection.

4720. The device of item 4645, further comprising an agent that inhibits infection, wherein the agent is an anthracycline.

4721. The device of item 4645, further comprising an agent that inhibits infection, wherein the agent is doxorubicin.

4722. The device of item 4645, further comprising an agent that inhibits infection, wherein the agent is mitoxantrone.

4723. The device of item 4645, further comprising an agent that inhibits infection, wherein the agent is a fluoropyrimidine.

4724. The device of item 4645, further comprising an agent that inhibits infection, wherein the agent is 5-fluorouracil (5-FU).

4725. The device of item 4645, further comprising an agent that inhibits infection, wherein the agent is a folic acid antagonist.

4726. The device of item 4645, further comprising an agent that inhibits infection, wherein the agent is methotrexate.

4727. The device of item 4645, further comprising an agent that inhibits infection, wherein the agent is a podophylotoxin.

4728. The device of item 4645, further comprising an agent that inhibits infection, wherein the agent is etoposide.

4729. The device of item 4645, further comprising an agent that inhibits infection, wherein the agent is a camptothecin.

4730. The device of item 4645, further comprising an agent that inhibits infection, wherein the agent is a hydroxyurea.

4731. The device of item 4645, further comprising an agent that inhibits infection, wherein the agent is a platinum complex.

4732. The device of item 4645, further comprising an agent that inhibits infection, wherein the agent is cisplatin.

4733. The device of item 4645, further comprising an anti-thrombotic agent.

4734. The device of item 4645, further comprising a visualization agent.

4735. The device of item 4645, further comprising a visualization agent, wherein the visualization agent is a radiopaque material, wherein the radiopaque material comprises a metal, a halogenated compound, or a barium containing compound.

4736. The device of item 4645, further comprising a visualization agent, wherein the visualization agent is a radiopaque material, wherein the radiopaque material comprises barium, tantalum, or technetium.

4737. The device of item 4645, further comprising a visualization agent, wherein the visualization agent is a MRI responsive material.

4738. The device of item 4645, further comprising a visualization agent, wherein the visualization agent comprises a gadolinium chelate.

4739. The device of item 4645, further comprising a visualization agent, wherein the visualization agent comprises iron, magnesium, manganese, copper, or chromium.

4740. The device of item 4645, further comprising a visualization agent, wherein the visualization agent comprises an iron oxide compound.

4741. The device of item 4645, further comprising a visualization agent, wherein the visualization agent comprises a dye, pigment, or colorant.

4742. The device of item 4645, further comprising an echogenic material.

4743. The device of item 4645, further comprising an echogenic material, wherein the echogenic material is in the form of a coating.

4744. The device of item 4645 wherein the device is sterile.

4745. The device of item 4645 wherein the fibrosing agent is released into tissue in the vicinity of the device after deployment of the device.

4746. The device of item 4645 wherein the fibrosing agent is released into tissue in the vicinity of the device after deployment of the device, wherein the tissue is connective tissue.

4747. The device of item 4645 wherein the fibrosing agent is released into tissue in the vicinity of the device after deployment of the device, wherein the tissue is muscle tissue.

4748. The device of item 4645 wherein the fibrosing agent is released into tissue in the vicinity of the device after deployment of the device, wherein the tissue is nerve tissue.

4749. The device of item 4645 wherein the fibrosing agent is released into tissue in the vicinity of the device after deployment of the device, wherein the tissue is epithelium tissue.

4750. The device of item 4645 wherein the fibrosing agent is released in effective concentrations from the device over a period ranging from the time of deployment of the device to about 1 year.

4751. The device of item 4645 wherein the fibrosing agent is released in effective concentrations from the device over a period ranging from about 1 month to 6 months.

4752. The device of item 4645 wherein the fibrosing agent is released in effective concentrations from the device over a period ranging from about 1–90 days.

4753. The device of item 4645 wherein the fibrosing agent is released in effective concentrations from the device at a constant rate.

4754. The device of item 4645 wherein the fibrosing agent is released in effective concentrations from the device at an increasing rate.

4755. The device of item 4645 wherein the fibrosing agent is released in effective concentrations from the device at a decreasing rate.

4756. The device of item 4645 wherein the fibrosing agent is released in effective concentrations from the composition comprising the fibrosing agent by diffusion over a period ranging from the time of deployment of the device to about 90 days.

4757. The device of item 4645 wherein the fibrosing agent is released in effective concentrations from the composition comprising the fibrosing agent by erosion of the composition over a period ranging from the time of deployment of the device to about 90 days.

4758. The device of item 4645 wherein the device comprises about 0.01 µg to about 10 µg of the fibrosing agent.

4759. The device of item 4645 wherein the device comprises about 10 µg to about 10 mg of the fibrosing agent.

4760. The device of item 4645 wherein the device comprises about 10 mg to about 250 mg of the fibrosing agent.

4761. The device of item 4645 wherein the device comprises about 250 mg to about 1000 mg of the fibrosing agent.

4762. The device of item 4645 wherein the device comprises about 1000 mg to about 2500 mg of the fibrosing agent.

4763. The device of item 4645 wherein a surface of the device comprises less than 0.01 µg of the fibrosing agent per $mm^2$ of device surface to which the fibrosing agent is applied.

4764. The device of item 4645 wherein a surface of the device comprises about 0.01 µg to about 1 µg of the fibrosing agent per $mm^2$ of device surface to which the fibrosing agent is applied.

4765. The device of item 4645 wherein a surface of the device comprises about 1 µg to about 10 µg of the fibrosing agent per $mm^2$ of device surface to which the fibrosing agent is applied.

4766. The device of item 4645 wherein a surface of the device comprises about 10 µg to about 250 µg of the fibrosing agent per $mm^2$ of device surface to which the fibrosing agent is applied.

4767. The device of item 4645 wherein a surface of the device comprises about 250 µg to about 1000 µg of the fibrosing agent of fibrosing agent per $mm^2$ of device surface to which the fibrosing agent is applied.

4768. The device of item 4645 wherein a surface of the device comprises about 1000 µg to about 2500 µg of the fibrosing agent per $mm^2$ of device surface to which the fibrosing agent is applied.

4769. A medical device comprising a plate implant and a fibrosing agent, where the fibrosing agent induces a fibrotic response between the device and a patient in which the device is implanted.

4770. The device of item 4769 wherein the fibrosing agent promotes regeneration.

4771. The device of item 4769 wherein the fibrosing agent promotes angiogenesis.

4772. The device of item 4769 wherein the fibrosing agent promotes fibroblast migration.

4773. The device of item 4769 wherein the fibrosing agent promotes fibroblast proliferation.

4774. The device of item 4769 wherein the fibrosing agent promotes deposition of extracellular matrix (ECM).

4775. The device of item 4769 wherein the fibrosing agent promotes tissue remodeling.

4776. The device of item 4769 wherein the fibrosing agent is an arterial vessel wall irritant.

4777. The device of item 4769 wherein the fibrosing agent promotes adhesion between the device and a host into which the device is implanted.

4778. The device of item 4769 wherein the device delivers the fibrosing agent locally to tissue proximate to the device.

4779. The device of item 4769 wherein the fibrosing agent is or comprises silk.

4780. The device of item 4769 wherein the fibrosing agent is or comprises mineral particles.

4781. The device of item 4769 wherein the fibrosing agent is or comprises chitosan.

4782. The device of item 4769 wherein the fibrosing agent is or comprises polylysine.

4783. The device of item 4769 wherein the fibrosing agent is or comprises fibronectin.

4784. The device of item 4769 wherein the fibrosing agent is or comprises bleomycin.

4785. The device of item 4769 wherein the fibrosing agent is or comprises CTGF.

4786. The device of item 4769 wherein the fibrosing agent is in the form of a thread, or is in contact with a thread.

4787. The device of item 4769 wherein the fibrosing agent is in the form of a particulate.

4788. The device of item 4769 wherein the composition further comprises an inflammatory cytokine.

4789. The device of item 4769 wherein the composition further comprises an agent that stimulates cell proliferation.

4790. The device of item 4769 wherein the composition is in the form of a gel, paste, or spray.

4791. The device of item 4769 wherein the fibrosing agent is in the form of tufts.

4792. The device of item 4769, further comprising a polymer.

4793. The device of item 4769, further comprising a polymeric carrier.

4794. The device of item 4769 wherein the fibrosing agent promotes adhesion between the device and a host into which the device is implanted.

4795. The device of item 4769 wherein the device delivers the fibrosing agent locally to tissue proximate to the device.

4796. The device of item 4769, further comprising a coating, wherein the coating comprises the fibrosing agent.

4797. The device of item 4769, further comprising a coating, wherein the coating is disposed on a surface of the device.

4798. The device of item 4769, further comprising a coating, wherein the coating directly contacts the device.

4799. The device of item 4769, further comprising a coating, wherein the coating indirectly contacts the device.

4800. The device of item 4769, further comprising a coating, wherein the coating partially covers the device.

4801. The device of item 4769, further comprising a coating, wherein the coating completely covers the device.

4802. The device of item 4769, further comprising a coating, wherein the coating is a uniform coating.

4803. The device of item 4769, further comprising a coating, wherein the coating is a non-uniform coating.

4804. The device of item 4769, further comprising a coating, wherein the coating is a discontinuous coating.

4805. The device of item 4769, further comprising a coating, wherein the coating is a patterned coating.

4806. The device of item 4769, further comprising a coating, wherein the coating has a thickness of 100 µm or less.

4807. The device of item 4769, further comprising a coating, wherein the coating has a thickness of 10 µm or less.

4808. The device of item 4769, further comprising a coating, wherein the coating adheres to the surface of the device upon deployment of the device.

4809. The device of item 4769, further comprising a coating, wherein the coating is stable at room temperature for a period of 1 year.

4810. The device of item 4769, further comprising a coating, wherein the fibrosing agent is present in the coating in an amount ranging between about 0.0001% to about 1% by weight.

4811. The device of item 4769, further comprising a coating, wherein the fibrosing agent is present in the coating in an amount ranging between about 1% to about 10% by weight.

4812. The device of item 4769, further comprising a coating, wherein the fibrosing agent is present in the coating in an amount ranging between about 10% to about 25% by weight.

4813. The device of item 4769, further comprising a coating, wherein the fibrosing agent is present in the coating in an amount ranging between about 25% to about 70% by weight.

4814. The device of item 4769, further comprising a coating, wherein the coating further comprises a polymer.

4815. The device of item 4769, further comprising a first coating having a first composition and the second coating having a second composition.

4816. The device of item 4769, further comprising a first coating having a first composition and the second coating having a second composition, wherein the first composition and the second composition are different.

4817. The device of item 4769, further comprising a polymer.

4818. The device of item 4769, further comprising a polymeric carrier.

4819. The device of item 4769, further comprising a polymeric carrier, wherein the polymeric carrier comprises a copolymer.

4820. The device of item 4769, further comprising a polymeric carrier, wherein the polymeric carrier comprises a block copolymer.

4821. The device of item 4769, further comprising a polymeric carrier, wherein the polymeric carrier comprises a random copolymer.

4822. The device of item 4769, further comprising a polymeric carrier, wherein the polymeric carrier comprises a biodegradable polymer.

4823. The device of item 4769, further comprising a polymeric carrier, wherein the polymeric carrier comprises a non-biodegradable polymer.

4824. The device of item 4769, further comprising a polymeric carrier, wherein the polymeric carrier comprises a hydrophilic polymer.

4825. The device of item 4769, further comprising a polymeric carrier, wherein the polymeric carrier comprises a hydrophobic polymer.

4826. The device of item 4769, further comprising a polymeric carrier, wherein the polymeric carrier comprises a polymer having hydrophilic domains.

4827. The device of item 4769, further comprising a polymeric carrier, wherein the polymeric carrier comprises a polymer having hydrophobic domains.

4828. The device of item 4769, further comprising a polymeric carrier, wherein the polymeric carrier comprises a non-conductive polymer.

4829. The device of item 4769, further comprising a polymeric carrier, wherein the polymeric carrier comprises an elastomer.

4830. The device of item 4769, further comprising a polymeric carrier, wherein the polymeric carrier comprises a hydrogel.

4831. The device of item 4769, further comprising a polymeric carrier, wherein the polymeric carrier comprises a silicone polymer.

4832. The device of item 4769, further comprising a polymeric carrier, wherein the polymeric carrier comprises a hydrocarbon polymer.

4833. The device of item 4769, further comprising a polymeric carrier, wherein the polymeric carrier comprises a styrene-derived polymer.

4834. The device of item 4769, further comprising a polymeric carrier, wherein the polymeric carrier comprises a butadiene polymer.

4835. The device of item 4769, further comprising a polymeric carrier, wherein the polymeric carrier comprises a macromer.

4836. The device of item 4769, further comprising a polymeric carrier, wherein the polymeric carrier comprises a poly(ethylene glycol) polymer.

4837. The device of item 4769, further comprising a polymeric carrier, wherein the polymeric carrier comprises an amorphous polymer.

4838. The device of item 4769, further comprising a lubricious coating.

4839. The device of item 4769 wherein the fibrosing agent is located within pores or holes of the device.

4840. The device of item 4769 wherein the fibrosing agent is located within a channel, lumen, or divet of the device.

4841. The device of item 4769, further comprising a second pharmaceutically active agent.

4842. The device of item 4769, further comprising an anti-inflammatory agent.

4843. The device of item 4769, further comprising an agent that inhibits infection.

4844. The device of item 4769, further comprising an agent that inhibits infection, wherein the agent is an anthracycline.

4845. The device of item 4769, further comprising an agent that inhibits infection, wherein the agent is doxorubicin.

4846. The device of item 4769, further comprising an agent that inhibits infection, wherein the agent is mitoxantrone.

4847. The device of item 4769, further comprising an agent that inhibits infection, wherein the agent is a fluoropyrimidine.

4848. The device of item 4769, further comprising an agent that inhibits infection, wherein the agent is 5-fluorouracil (5-FU).

4849. The device of item 4769, further comprising an agent that inhibits infection, wherein the agent is a folic acid antagonist.

4850. The device of item 4769, further comprising an agent that inhibits infection, wherein the agent is methotrexate.

4851. The device of item 4769, further comprising an agent that inhibits infection, wherein the agent is a podophylotoxin.

4852. The device of item 4769, further comprising an agent that inhibits infection, wherein the agent is etoposide.

4853. The device of item 4769, further comprising an agent that inhibits infection, wherein the agent is a camptothecin.

4854. The device of item 4769, further comprising an agent that inhibits infection, wherein the agent is a hydroxyurea.

4855. The device of item 4769, further comprising an agent that inhibits infection, wherein the agent is a platinum complex.

4856. The device of item 4769, further comprising an agent that inhibits infection, wherein the agent is cisplatin.

4857. The device of item 4769, further comprising an anti-thrombotic agent.

4858. The device of item 4769, further comprising a visualization agent.

4859. The device of item 4769, further comprising a visualization agent, wherein the visualization agent is a radiopaque material, wherein the radiopaque material comprises a metal, a halogenated compound, or a barium containing compound.

4860. The device of item 4769, further comprising a visualization agent, wherein the visualization agent is a radiopaque material, wherein the radiopaque material comprises barium, tantalum, or technetium.

4861. The device of item 4769, further comprising a visualization agent, wherein the visualization agent is a MRI responsive material.

4862. The device of item 4769, further comprising a visualization agent, wherein the visualization agent comprises a gadolinium chelate.

4863. The device of item 4769, further comprising a visualization agent, wherein the visualization agent comprises iron, magnesium, manganese, copper, or chromium.

4864. The device of item 4769, further comprising a visualization agent, wherein the visualization agent comprises an iron oxide compound.

4865. The device of item 4769, further comprising a visualization agent, wherein the visualization agent comprises a dye, pigment, or colorant.

4866. The device of item 4769, further comprising an echogenic material.

4867. The device of item 4769, further comprising an echogenic material, wherein the echogenic material is in the form of a coating.

4868. The device of item 4769 wherein the device is sterile.

4869. The device of item 4769 wherein the fibrosing agent is released into tissue in the vicinity of the device after deployment of the device.

4870. The device of item 4769 wherein the fibrosing agent is released into tissue in the vicinity of the device after deployment of the device, wherein the tissue is connective tissue.

4871. The device of item 4769 wherein the fibrosing agent is released into tissue in the vicinity of the device after deployment of the device, wherein the tissue is muscle tissue.

4872. The device of item 4769 wherein the fibrosing agent is released into tissue in the vicinity of the device after deployment of the device, wherein the tissue is nerve tissue.

4873. The device of item 4769 wherein the fibrosing agent is released into tissue in the vicinity of the device after deployment of the device, wherein the tissue is epithelium tissue.

4874. The device of item 4769 wherein the fibrosing agent is released in effective concentrations from the device over a period ranging from the time of deployment of the device to about 1 year.

4875. The device of item 4769 wherein the fibrosing agent is released in effective concentrations from the device over a period ranging from about 1 month to 6 months.

4876. The device of item 4769 wherein the fibrosing agent is released in effective concentrations from the device over a period ranging from about 190 days.

4877. The device of item 4769 wherein the fibrosing agent is released in effective concentrations from the device at a constant rate.

4878. The device of item 4769 wherein the fibrosing agent is released in effective concentrations from the device at an increasing rate.

4879. The device of item 4769 wherein the fibrosing agent is released in effective concentrations from the device at a decreasing rate.

4880. The device of item 4769 wherein the fibrosing agent is released in effective concentrations from the composition comprising the fibrosing agent by diffusion over a period ranging from the time of deployment of the device to about 90 days.

4881. The device of item 4769 wherein the fibrosing agent is released in effective concentrations from the composition comprising the fibrosing agent by erosion of the composition over a period ranging from the time of deployment of the device to about 90 days.

4882. The device of item 4769 wherein the device comprises about 0.01 µg to about 10 µg of the fibrosing agent.

4883. The device of item 4769 wherein the device comprises about 10 µg to about 10 mg of the fibrosing agent.

4884. The device of item 4769 wherein the device comprises about 10 mg to about 250 mg of the fibrosing agent.

4885. The device of item 4769 wherein the device comprises about 250 mg to about 1000 mg of the fibrosing agent.

4886. The device of item 4769 wherein the device comprises about 1000 mg to about 2500 mg of the fibrosing agent.

4887. The device of item 4769 wherein a surface of the device comprises less than 0.01 µg of the fibrosing agent per $mm^2$ of device surface to which the fibrosing agent is applied.

4888. The device of item 4769 wherein a surface of the device comprises about 0.01 µg to about 1 µg of the fibrosing agent per $mm^2$ of device surface to which the fibrosing agent is applied.

4889. The device of item 4769 wherein a surface of the device comprises about 1 µg to about 10 µg of the fibrosing agent per $mm^2$ of device surface to which the fibrosing agent is applied.

4890. The device of item 4769 wherein a surface of the device comprises about 10 µg to about 250 µg of the fibrosing agent per $mm^2$ of device surface to which the fibrosing agent is applied.

4891. The device of item 4769 wherein a surface of the device comprises about 250 µg to about 1000 µg of the fibrosing agent of fibrosing agent per $mm^2$ of device surface to which the fibrosing agent is applied.

4892. The device of item 4769 wherein a surface of the device comprises about 1000 µg to about 2500 µg of the fibrosing agent per $mm^2$ of device surface to which the fibrosing agent is applied.

4893. A medical device comprising a wire implant and a fibrosing agent, where the fibrosing agent induces a fibrotic response between the device and a patient in which the device is implanted.

4894. The device of item 4893 wherein the fibrosing agent promotes regeneration.

4895. The device of item 4893 wherein the fibrosing agent promotes angiogenesis.

4896. The device of item 4893 wherein the fibrosing agent promotes fibroblast migration.

4897. The device of item 4893 wherein the fibrosing agent promotes fibroblast proliferation.

4898. The device of item 4893 wherein the fibrosing agent promotes deposition of extracellular matrix (ECM).

4899. The device of item 4893 wherein the fibrosing agent promotes tissue remodeling.

4900. The device of item 4893 wherein the fibrosing agent is an arterial vessel wall irritant.

4901. The device of item 4893 wherein the fibrosing agent promotes adhesion between the device and a host into which the device is implanted.

4902. The device of item 4893 wherein the device delivers the fibrosing agent locally to tissue proximate to the device.

4903. The device of item 4893 wherein the fibrosing agent is or comprises silk.

4904. The device of item 4893 wherein the fibrosing agent is or comprises mineral particles.

4905. The device of item 4893 wherein the fibrosing agent is or comprises chitosan.

4906. The device of item 4893 wherein the fibrosing agent is or comprises polylysine.

4907. The device of item 4893 wherein the fibrosing agent is or comprises fibronectin.

4908. The device of item 4893 wherein the fibrosing agent is or comprises bleomycin.

4909. The device of item 4893 wherein the fibrosing agent is or comprises CTGF.

4910. The device of item 4893 wherein the fibrosing agent is in the form of a thread, or is in contact with a thread.

4911. The device of item 4893 wherein the fibrosing agent is in the form of a particulate.

4912. The device of item 4893 wherein the composition further comprises an inflammatory cytokine.

4913. The device of item 4893 wherein the composition further comprises an agent that stimulates cell proliferation.

4914. The device of item 4893 wherein the composition is in the form of a gel, paste, or spray.

4915. The device of item 4893 wherein the fibrosing agent is in the form of tufts.

4916. The device of item 4893, further comprising a polymer.

4917. The device of item 4893, further comprising a polymeric carrier.

4918. The device of item 4893 wherein the fibrosing agent promotes adhesion between the device and a host into which the device is implanted.

4919. The device of item 4893 wherein the device delivers the fibrosing agent locally to tissue proximate to the device.

4920. The device of item 4893, further comprising a coating, wherein the coating comprises the fibrosing agent.

4921. The device of item 4893, further comprising a coating, wherein the coating is disposed on a surface of the device.

4922. The device of item 4893, further comprising a coating, wherein the coating directly contacts the device.

4923. The device of item 4893, further comprising a coating, wherein the coating indirectly contacts the device.

4924. The device of item 4893, further comprising a coating, wherein the coating partially covers the device.

4925. The device of item 4893, further comprising a coating, wherein the coating completely covers the device.

4926. The device of item 4893, further comprising a coating, wherein the coating is a uniform coating.

4927. The device of item 4893, further comprising a coating, wherein the coating is a non-uniform coating.

4928. The device of item 4893, further comprising a coating, wherein the coating is a discontinuous coating.

4929. The device of item 4893, further comprising a coating, wherein the coating is a patterned coating.

4930. The device of item 4893, further comprising a coating, wherein the coating has a thickness of 100 μm or less.

4931. The device of item 4893, further comprising a coating, wherein the coating has a thickness of 10 μm or less.

4932. The device of item 4893, further comprising a coating, wherein the coating adheres to the surface of the device upon deployment of the device.

4933. The device of item 4893, further comprising a coating, wherein the coating is stable at room temperature for a period of 1 year.

4934. The device of item 4893, further comprising a coating, wherein the fibrosing agent is present in the coating in an amount ranging between about 0.0001% to about 1% by weight.

4935. The device of item 4893, further comprising a coating, wherein the fibrosing agent is present in the coating in an amount ranging between about 1% to about 10% by weight.

4936. The device of item 4893, further comprising a coating, wherein the fibrosing agent is present in the coating in an amount ranging between about 10% to about 25% by weight.

4937. The device of item 4893, further comprising a coating, wherein the fibrosing agent is present in the coating in an amount ranging between about 25% to about 70% by weight.

4938. The device of item 4893, further comprising a coating, wherein the coating further comprises a polymer.

4939. The device of item 4893, further comprising a first coating having a first composition and the second coating having a second composition.

4940. The device of item 4893, further comprising a first coating having a first composition and the second coating having a second composition, wherein the first composition and the second composition are different.

4941. The device of item 4893, further comprising a polymer.

4942. The device of item 4893, further comprising a polymeric carrier.

4943. The device of item 4893, further comprising a polymeric carrier, wherein the polymeric carrier comprises a copolymer.

4944. The device of item 4893, further comprising a polymeric carrier, wherein the polymeric carrier comprises a block copolymer.

4945. The device of item 4893, further comprising a polymeric carrier, wherein the polymeric carrier comprises a random copolymer.

4946. The device of item 4893, further comprising a polymeric carrier, wherein the polymeric carrier comprises a biodegradable polymer.

4947. The device of item 4893, further comprising a polymeric carrier, wherein the polymeric carrier comprises a non-biodegradable polymer.

4948. The device of item 4893, further comprising a polymeric carrier, wherein the polymeric carrier comprises a hydrophilic polymer.

4949. The device of item 4893, further comprising a polymeric carrier, wherein the polymeric carrier comprises a hydrophobic polymer.

4950. The device of item 4893, further comprising a polymeric carrier, wherein the polymeric carrier comprises a polymer having hydrophilic domains.

4951. The device of item 4893, further comprising a polymeric carrier, wherein the polymeric carrier comprises a polymer having hydrophobic domains.

4952. The device of item 4893, further comprising a polymeric carrier, wherein the polymeric carrier comprises a non-conductive polymer.

4953. The device of item 4893, further comprising a polymeric carrier, wherein the polymeric carrier comprises an elastomer.

4954. The device of item 4893, further comprising a polymeric carrier, wherein the polymeric carrier comprises a hydrogel.

4955. The device of item 4893, further comprising a polymeric carrier, wherein the polymeric carrier comprises a silicone polymer.

4956. The device of item 4893, further comprising a polymeric carrier, wherein the polymeric carrier comprises a hydrocarbon polymer.

4957. The device of item 4893, further comprising a polymeric carrier, wherein the polymeric carrier comprises a styrene-derived polymer.

4958. The device of item 4893, further comprising a polymeric carrier, wherein the polymeric carrier comprises a butadiene polymer.

4959. The device of item 4893, further comprising a polymeric carrier, wherein the polymeric carrier comprises a macromer.

4960. The device of item 4893, further comprising a polymeric carrier, wherein the polymeric carrier comprises a poly(ethylene glycol) polymer.

4961. The device of item 4893, further comprising a polymeric carrier, wherein the polymeric carrier comprises an amorphous polymer.

4962. The device of item 4893, further comprising a lubricious coating.

4963. The device of item 4893 wherein the fibrosing agent is located within pores or holes of the device.

4964. The device of item 4893 wherein the fibrosing agent is located within a channel, lumen, or divet of the device.

4965. The device of item 4893, further comprising a second pharmaceutically active agent.

4966. The device of item 4893, further comprising an anti-inflammatory agent.

4967. The device of item 4893, further comprising an agent that inhibits infection.

4968. The device of item 4893, further comprising an agent that inhibits infection, wherein the agent is an anthracycline.

4969. The device of item 4893, further comprising an agent that inhibits infection, wherein the agent is doxorubicin.

4970. The device of item 4893, further comprising an agent that inhibits infection, wherein the agent is mitoxantrone.

4971. The device of item 4893, further comprising an agent that inhibits infection, wherein the agent is a fluoropyrimidine.

4972. The device of item 4893, further comprising an agent that inhibits infection, wherein the agent is 5-fluorouracil (5-FU).

4973. The device of item 4893, further comprising an agent that inhibits infection, wherein the agent is a folic acid antagonist.

4974. The device of item 4893, further comprising an agent that inhibits infection, wherein the agent is methotrexate.

4975. The device of item 4893, further comprising an agent that inhibits infection, wherein the agent is a podophylotoxin.

4976. The device of item 4893, further comprising an agent that inhibits infection, wherein the agent is etoposide.

4977. The device of item 4893, further comprising an agent that inhibits infection, wherein the agent is a camptothecin.

4978. The device of item 4893, further comprising an agent that inhibits infection, wherein the agent is a hydroxyurea.

4979. The device of item 4893, further comprising an agent that inhibits infection, wherein the agent is a platinum complex.

4980. The device of item 4893, further comprising an agent that inhibits infection, wherein the agent is cisplatin.

4981. The device of item 4893, further comprising an anti-thrombotic agent.

4982. The device of item 4893, further comprising a visualization agent.

4983. The device of item 4893, further comprising a visualization agent, wherein the visualization agent is a radiopaque material, wherein the radiopaque material comprises a metal, a halogenated compound, or a barium containing compound.

4984. The device of item 4893, further comprising a visualization agent, wherein the visualization agent is a radiopaque material, wherein the radiopaque material comprises barium, tantalum, or technetium.

4985. The device of item 4893, further comprising a visualization agent, wherein the visualization agent is a MRI responsive material.

4986. The device of item 4893, further comprising a visualization agent, wherein the visualization agent comprises a gadolinium chelate.

4987. The device of item 4893, further comprising a visualization agent, wherein the visualization agent comprises iron, magnesium, manganese, copper, or chromium.

4988. The device of item 4893, further comprising a visualization agent, wherein the visualization agent comprises an iron oxide compound.

4989. The device of item 4893, further comprising a visualization agent, wherein the visualization agent comprises a dye, pigment, or colorant.

4990. The device of item 4893, further comprising an echogenic material.

4991. The device of item 4893, further comprising an echogenic material, wherein the echogenic material is in the form of a coating.

4992. The device of item 4893 wherein the device is sterile.

4993. The device of item 4893 wherein the fibrosing agent is released into tissue in the vicinity of the device after deployment of the device.

4994. The device of item 4893 wherein the fibrosing agent is released into tissue in the vicinity of the device after deployment of the device, wherein the tissue is connective tissue.

4995. The device of item 4893 wherein the fibrosing agent is released into tissue in the vicinity of the device after deployment of the device, wherein the tissue is muscle tissue.

4996. The device of item 4893 wherein the fibrosing agent is released into tissue in the vicinity of the device after deployment of the device, wherein the tissue is nerve tissue.

4997. The device of item 4893 wherein the fibrosing agent is released into tissue in the vicinity of the device after deployment of the device, wherein the tissue is epithelium tissue.

4998. The device of item 4893 wherein the fibrosing agent is released in effective concentrations from the device over a period ranging from the time of deployment of the device to about 1 year.

4999. The device of item 4893 wherein the fibrosing agent is released in effective concentrations from the device over a period ranging from about 1 month to 6 months.

5000. The device of item 4893 wherein the fibrosing agent is released in effective concentrations from the device over a period ranging from about 1–90 days.

5001. The device of item 4893 wherein the fibrosing agent is released in effective concentrations from the device at a constant rate.

5002. The device of item 4893 wherein the fibrosing agent is released in effective concentrations from the device at an increasing rate.

5003. The device of item 4893 wherein the fibrosing agent is released in effective concentrations from the device at a decreasing rate.

5004. The device of item 4893 wherein the fibrosing agent is released in effective concentrations from the composition comprising the fibrosing agent by diffusion over a period ranging from the time of deployment of the device to about 90 days.

5005. The device of item 4893 wherein the fibrosing agent is released in effective concentrations from the composition comprising the fibrosing agent by erosion of the composition over a period ranging from the time of deployment of the device to about 90 days.

5006. The device of item 4893 wherein the device comprises about 0.01 μg to about 10 μg of the fibrosing agent.

5007. The device of item 4893 wherein the device comprises about 10 μg to about 10 mg of the fibrosing agent.

5008. The device of item 4893 wherein the device comprises about 10 mg to about 250 mg of the fibrosing agent.

5009. The device of item 4893 wherein the device comprises about 250 mg to about 1000 mg of the fibrosing agent.

5010. The device of item 4893 wherein the device comprises about 1000 mg to about 2500 mg of the fibrosing agent.

5011. The device of item 4893 wherein a surface of the device comprises less than 0.01 μg of the fibrosing agent per $mm^2$ of device surface to which the fibrosing agent is applied.

5012. The device of item 4893 wherein a surface of the device comprises about 0.01 µg to about 1 µg of the fibrosing agent per mm² of device surface to which the fibrosing agent is applied.

5013. The device of item 4893 wherein a surface of the device comprises about 1 µg to about 10 µg of the fibrosing agent per mm² of device surface to which the fibrosing agent is applied.

5014. The device of item 4893 wherein a surface of the device comprises about 10 µg to about 250 µg of the fibrosing agent per mm² of device surface to which the fibrosing agent is applied.

5015. The device of item 4893 wherein a surface of the device comprises about 250 µg to about 1000 µg of the fibrosing agent of fibrosing agent per mm² of device surface to which the fibrosing agent is applied.

5016. The device of item 4893 wherein a surface of the device comprises about 1000 µg to about 2500 µg of the fibrosing agent per mm² of device surface to which the fibrosing agent is applied.

5017. A medical device comprising a collagen implant and a fibrosing agent, where the fibrosing agent induces a fibrotic response between the device and a patient in which the device is implanted.

5018. The device of item 5017 wherein the fibrosing agent promotes regeneration.

5019. The device of item 5017 wherein the fibrosing agent promotes angiogenesis.

5020. The device of item 5017 wherein the fibrosing agent promotes fibroblast migration.

5021. The device of item 5017 wherein the fibrosing agent promotes fibroblast proliferation.

5022. The device of item 5017 wherein the fibrosing agent promotes deposition of extracellular matrix (ECM).

5023. The device of item 5017 wherein the fibrosing agent promotes tissue remodeling.

5024. The device of item 5017 wherein the fibrosing agent is an arterial vessel wall irritant.

5025. The device of item 5017 wherein the fibrosing agent promotes adhesion between the device and a host into which the device is implanted.

5026. The device of item 5017 wherein the device delivers the fibrosing agent locally to tissue proximate to the device.

5027. The device of item 5017 wherein the fibrosing agent is or comprises silk.

5028. The device of item 5017 wherein the fibrosing agent is or comprises mineral particles.

5029. The device of item 5017 wherein the fibrosing agent is or comprises chitosan.

5030. The device of item 5017 wherein the fibrosing agent is or comprises polylysine.

5031. The device of item 5017 wherein the fibrosing agent is or comprises fibronectin.

5032. The device of item 5017 wherein the fibrosing agent is or comprises bleomycin.

5033. The device of item 5017 wherein the fibrosing agent is or comprises CTGF.

5034. The device of item 5017 wherein the fibrosing agent is in the form of a thread, or is in contact with a thread.

5035. The device of item 5017 wherein the fibrosing agent is in the form of a particulate.

5036. The device of item 5017 wherein the composition further comprises an inflammatory cytokine.

5037. The device of item 5017 wherein the composition further comprises an agent that stimulates cell proliferation.

5038. The device of item 5017 wherein the composition is in the form of a gel, paste, or spray.

5039. The device of item 5017 wherein the fibrosing agent is in the form of tufts.

5040. The device of item 5017, further comprising a polymer.

5041. The device of item 5017, further comprising a polymeric carrier.

5042. The device of item 5017 wherein the fibrosing agent promotes adhesion between the device and a host into which the device is implanted.

5043. The device of item 5017 wherein the device delivers the fibrosing agent locally to tissue proximate to the device.

5044. The device of item 5017, further comprising a coating, wherein the coating comprises the fibrosing agent.

5045. The device of item 5017, further comprising a coating, wherein the coating is disposed on a surface of the device.

5046. The device of item 5017, further comprising a coating, wherein the coating directly contacts the device.

5047. The device of item 5017, further comprising a coating, wherein the coating indirectly contacts the device.

5048. The device of item 5017, further comprising a coating, wherein the coating partially covers the device.

5049. The device of item 5017, further comprising a coating, wherein the coating completely covers the device.

5050. The device of item 5017, further comprising a coating, wherein the coating is a uniform coating.

5051. The device of item 5017, further comprising a coating, wherein the coating is a non-uniform coating.

5052. The device of item 5017, further comprising a coating, wherein the coating is a discontinuous coating.

5053. The device of item 5017, further comprising a coating, wherein the coating is a patterned coating.

5054. The device of item 5017, further comprising a coating, wherein the coating has a thickness of 100 µm or less.

5055. The device of item 5017, further comprising a coating, wherein the coating has a thickness of 10 µm or less.

5056. The device of item 5017, further comprising a coating, wherein the coating adheres to the surface of the device upon deployment of the device.

5057. The device of item 5017, further comprising a coating, wherein the coating is stable at room temperature for a period of 1 year.

5058. The device of item 5017, further comprising a coating, wherein the fibrosing agent is present in the coating in an amount ranging between about 0.0001% to about 1% by weight.

5059. The device of item 5017, further comprising a coating, wherein the fibrosing agent is present in the coating in an amount ranging between about 1% to about 10% by weight.

5060. The device of item 5017, further comprising a coating, wherein the fibrosing agent is present in the coating in an amount ranging between about 10% to about 25% by weight.

5061. The device of item 5017, further comprising a coating, wherein the fibrosing agent is present in the coating in an amount ranging between about 25% to about 70% by weight.

5062. The device of item 5017, further comprising a coating, wherein the coating further comprises a polymer.

5063. The device of item 5017, further comprising a first coating having a first composition and the second coating having a second composition.

5064. The device of item 5017, further comprising a first coating having a first composition and the second coating having a second composition, wherein the first composition and the second composition are different.

5065. The device of item 5017, further comprising a polymer.

5066. The device of item 5017, further comprising a polymeric carrier.

5067. The device of item 5017, further comprising a polymeric carrier, wherein the polymeric carrier comprises a copolymer.

5068. The device of item 5017, further comprising a polymeric carrier, wherein the polymeric carrier comprises a block copolymer.

5069. The device of item 5017, further comprising a polymeric carrier, wherein the polymeric carrier comprises a random copolymer.

5070. The device of item 5017, further comprising a polymeric carrier, wherein the polymeric carrier comprises a biodegradable polymer.

5071. The device of item 5017, further comprising a polymeric carrier, wherein the polymeric carrier comprises a non-biodegradable polymer.

5072. The device of item 5017, further comprising a polymeric carrier, wherein the polymeric carrier comprises a hydrophilic polymer.

5073. The device of item 5017, further comprising a polymeric carrier, wherein the polymeric carrier comprises a hydrophobic polymer.

5074. The device of item 5017, further comprising a polymeric carrier, wherein the polymeric carrier comprises a polymer having hydrophilic domains.

5075. The device of item 5017, further comprising a polymeric carrier, wherein the polymeric carrier comprises a polymer having hydrophobic domains.

5076. The device of item 5017, further comprising a polymeric carrier, wherein the polymeric carrier comprises a non-conductive polymer.

5077. The device of item 5017, further comprising a polymeric carrier, wherein the polymeric carrier comprises an elastomer.

5078. The device of item 5017, further comprising a polymeric carrier, wherein the polymeric carrier comprises a hydrogel.

5079. The device of item 5017, further comprising a polymeric carrier, wherein the polymeric carrier comprises a silicone polymer.

5080. The device of item 5017, further comprising a polymeric carrier, wherein the polymeric carrier comprises a hydrocarbon polymer.

5081. The device of item 5017, further comprising a polymeric carrier, wherein the polymeric carrier comprises a styrene-derived polymer.

5082. The device of item 5017, further comprising a polymeric carrier, wherein the polymeric carrier comprises a butadiene polymer.

5083. The device of item 5017, further comprising a polymeric carrier, wherein the polymeric carrier comprises a macromer.

5084. The device of item 5017, further comprising a polymeric carrier, wherein the polymeric carrier comprises a poly(ethylene glycol) polymer.

5085. The device of item 5017, further comprising a polymeric carrier, wherein the polymeric carrier comprises an amorphous polymer.

5086. The device of item 5017, further comprising a lubricious coating.

5087. The device of item 5017 wherein the fibrosing agent is located within pores or holes of the device.

5088. The device of item 5017 wherein the fibrosing agent is located within a channel, lumen, or divet of the device.

5089. The device of item 5017, further comprising a second pharmaceutically active agent.

5090. The device of item 5017, further comprising an anti-inflammatory agent.

5091. The device of item 5017, further comprising an agent that inhibits infection.

5092. The device of item 5017, further comprising an agent that inhibits infection, wherein the agent is an anthracycline.

5093. The device of item 5017, further comprising an agent that inhibits infection, wherein the agent is doxorubicin.

5094. The device of item 5017, further comprising an agent that inhibits infection, wherein the agent is mitoxantrone.

5095. The device of item 5017, further comprising an agent that inhibits infection, wherein the agent is a fluoropyrimidine.

5096. The device of item 5017, further comprising an agent that inhibits infection, wherein the agent is 5-fluorouracil (5-FU).

5097. The device of item 5017, further comprising an agent that inhibits infection, wherein the agent is a folic acid antagonist.

5098. The device of item 5017, further comprising an agent that inhibits infection, wherein the agent is methotrexate.

5099. The device of item 5017, further comprising an agent that inhibits infection, wherein the agent is a podophylotoxin.

5100. The device of item 5017, further comprising an agent that inhibits infection, wherein the agent is etoposide.

5101. The device of item 5017, further comprising an agent that inhibits infection, wherein the agent is a camptothecin.

5102. The device of item 5017, further comprising an agent that inhibits infection, wherein the agent is a hydroxyurea.

5103. The device of item 5017, further comprising an agent that inhibits infection, wherein the agent is a platinum complex.

5104. The device of item 5017, further comprising an agent that inhibits infection, wherein the agent is cisplatin.

5105. The device of item 5017, further comprising an anti-thrombotic agent.

5106. The device of item 5017, further comprising a visualization agent.

5107. The device of item 5017, further comprising a visualization agent, wherein the visualization agent is a radiopaque material, wherein the radiopaque material comprises a metal, a halogenated compound, or a barium containing compound.

5108. The device of item 5017, further comprising a visualization agent, wherein the visualization agent is a radiopaque material, wherein the radiopaque material comprises barium, tantalum, or technetium.

5109. The device of item 5017, further comprising a visualization agent, wherein the visualization agent is a MRI responsive material.

5110. The device of item 5017, further comprising a visualization agent, wherein the visualization agent comprises a gadolinium chelate.

5111. The device of item 5017, further comprising a visualization agent, wherein the visualization agent comprises iron, magnesium, manganese, copper, or chromium.

5112. The device of item 5017, further comprising a visualization agent, wherein the visualization agent comprises an iron oxide compound.

5113. The device of item 5017, further comprising a visualization agent, wherein the visualization agent comprises a dye, pigment, or colorant.

5114. The device of item 5017, further comprising an echogenic material.

5115. The device of item 5017, further comprising an echogenic material, wherein the echogenic material is in the form of a coating.

5116. The device of item 5017 wherein the device is sterile.

5117. The device of item 5017 wherein the fibrosing agent is released into tissue in the vicinity of the device after deployment of the device.

5118. The device of item 5017 wherein the fibrosing agent is released into tissue in the vicinity of the device after deployment of the device, wherein the tissue is connective tissue.

5119. The device of item 5017 wherein the fibrosing agent is released into tissue in the vicinity of the device after deployment of the device, wherein the tissue is muscle tissue.

5120. The device of item 5017 wherein the fibrosing agent is released into tissue in the vicinity of the device after deployment of the device, wherein the tissue is nerve tissue.

5121. The device of item 5017 wherein the fibrosing agent is released into tissue in the vicinity of the device after deployment of the device, wherein the tissue is epithelium tissue.

5122. The device of item 5017 wherein the fibrosing agent is released in effective concentrations from the device over a period ranging from the time of deployment of the device to about 1 year.

5123. The device of item 5017 wherein the fibrosing agent is released in effective concentrations from the device over a period ranging from about 1 month to 6 months.

5124. The device of item 5017 wherein the fibrosing agent is released in effective concentrations from the device over a period ranging from about 1–90 days.

5125. The device of item 5017 wherein the fibrosing agent is released in effective concentrations from the device at a constant rate.

5126. The device of item 5017 wherein the fibrosing agent is released in effective concentrations from the device at an increasing rate.

5127. The device of item 5017 wherein the fibrosing agent is released in effective concentrations from the device at a decreasing rate.

5128. The device of item 5017 wherein the fibrosing agent is released in effective concentrations from the composition comprising the fibrosing agent by diffusion over a period ranging from the time of deployment of the device to about 90 days.

5129. The device of item 5017 wherein the fibrosing agent is released in effective concentrations from the composition comprising the fibrosing agent by erosion of the composition over a period ranging from the time of deployment of the device to about 90 days.

5130. The device of item 5017 wherein the device comprises about 0.01 µg to about 10 µg of the fibrosing agent.

5131. The device of item 5017 wherein the device comprises about 10 µg to about 10 mg of the fibrosing agent.

5132. The device of item 5017 wherein the device comprises about 10 mg to about 250 mg of the fibrosing agent.

5133. The device of item 5017 wherein the device comprises about 250 mg to about 1000 mg of the fibrosing agent.

5134. The device of item 5017 wherein the device comprises about 1000 mg to about 2500 mg of the fibrosing agent.

5135. The device of item 5017 wherein a surface of the device comprises less than 0.01 µg of the fibrosing agent per $mm^2$ of device surface to which the fibrosing agent is applied.

5136. The device of item 5017 wherein a surface of the device comprises about 0.01 µg to about 1 µg of the fibrosing agent per $mm^2$ of device surface to which the fibrosing agent is applied.

5137. The device of item 5017 wherein a surface of the device comprises about 1 µg to about 10 µg of the fibrosing agent per $mm^2$ of device surface to which the fibrosing agent is applied.

5138. The device of item 5017 wherein a surface of the device comprises about 10 µg to about 250 µg of the fibrosing agent per $mm^2$ of device surface to which the fibrosing agent is applied.

5139. The device of item 5017 wherein a surface of the device comprises about 250 µg to about 1000 µg of the fibrosing agent of fibrosing agent per $mm^2$ of device surface to which the fibrosing agent is applied.

5140. The device of item 5017 wherein a surface of the device comprises about 1000 µg to about 2500 µg of the fibrosing agent per $mm^2$ of device surface to which the fibrosing agent is applied.

5141. A medical device comprising a Fallopian tube implant and a fibrosing agent, where the fibrosing agent induces a fibrotic response between the device and a patient in which the device is implanted.

5142. The device of item 5141 wherein the fibrosing agent promotes regeneration.

5143. The device of item 5141 wherein the fibrosing agent promotes angiogenesis.

5144. The device of item 5141 wherein the fibrosing agent promotes fibroblast migration.

5145. The device of item 5141 wherein the fibrosing agent promotes fibroblast proliferation.

5146. The device of item 5141 wherein the fibrosing agent promotes deposition of extracellular matrix (ECM).

5147. The device of item 5141 wherein the fibrosing agent promotes tissue remodeling.

5148. The device of item 5141 wherein the fibrosing agent is an arterial vessel wall irritant.

5149. The device of item 5141 wherein the fibrosing agent promotes adhesion between the device and a host into which the device is implanted.

5150. The device of item 5141 wherein the device delivers the fibrosing agent locally to tissue proximate to the device.

5151. The device of item 5141 wherein the fibrosing agent is or comprises silk.

5152. The device of item 5141 wherein the fibrosing agent is or comprises mineral particles.

5153. The device of item 5141 wherein the fibrosing agent is or comprises chitosan.

5154. The device of item 5141 wherein the fibrosing agent is or comprises polylysine.

5155. The device of item 5141 wherein the fibrosing agent is or comprises fibronectin.

5156. The device of item 5141 wherein the fibrosing agent is or comprises bleomycin.

5157. The device of item 5141 wherein the fibrosing agent is or comprises CTGF.

5158. The device of item 5141 wherein the fibrosing agent is in the form of a thread, or is in contact with a thread.

5159. The device of item 5141 wherein the fibrosing agent is in the form of a particulate.

5160. The device of item 5141 wherein the composition further comprises an inflammatory cytokine.

5161. The device of item 5141 wherein the composition further comprises an agent that stimulates cell proliferation.

5162. The device of item 5141 wherein the composition is in the form of a gel, paste, or spray.

5163. The device of item 5141 wherein the fibrosing agent is in the form of tufts.

5164. The device of item 5141, further comprising a polymer.

5165. The device of item 5141, further comprising a polymeric carrier.

5166. The device of item 5141 wherein the fibrosing agent promotes adhesion between the device and a host into which the device is implanted.

5167. The device of item 5141 wherein the device delivers the fibrosing agent locally to tissue proximate to the device.

5168. The device of item 5141, further comprising a coating, wherein the coating comprises the fibrosing agent.

5169. The device of item 5141, further comprising a coating, wherein the coating is disposed on a surface of the device.

5170. The device of item 5141, further comprising a coating, wherein the coating directly contacts the device.

5171. The device of item 5141, further comprising a coating, wherein the coating indirectly contacts the device.

5172. The device of item 5141, further comprising a coating, wherein the coating partially covers the device.

5173. The device of item 5141, further comprising a coating, wherein the coating completely covers the device.

5174. The device of item 5141, further comprising a coating, wherein the coating is a uniform coating.

5175. The device of item 5141, further comprising a coating, wherein the coating is a non-uniform coating.

5176. The device of item 5141, further comprising a coating, wherein the coating is a discontinuous coating.

5177. The device of item 5141, further comprising a coating, wherein the coating is a patterned coating.

5178. The device of item 5141, further comprising a coating, wherein the coating has a thickness of 100 μm or less.

5179. The device of item 5141, further comprising a coating, wherein the coating has a thickness of 10 μm or less.

5180. The device of item 5141, further comprising a coating, wherein the coating adheres to the surface of the device upon deployment of the device.

5181. The device of item 5141, further comprising a coating, wherein the coating is stable at room temperature for a period of 1 year.

5182. The device of item 5141, further comprising a coating, wherein the fibrosing agent is present in the coating in an amount ranging between about 0.0001% to about 1% by weight.

5183. The device of item 5141, further comprising a coating, wherein the fibrosing agent is present in the coating in an amount ranging between about 1% to about 10% by weight.

5184. The device of item 5141, further comprising a coating, wherein the fibrosing agent is present in the coating in an amount ranging between about 10% to about 25% by weight.

5185. The device of item 5141, further comprising a coating, wherein the fibrosing agent is present in the coating in an amount ranging between about 25% to about 70% by weight.

5186. The device of item 5141, further comprising a coating, wherein the coating further comprises a polymer.

5187. The device of item 5141, further comprising a first coating having a first composition and the second coating having a second composition.

5188. The device of item 5141, further comprising a first coating having a first composition and the second coating having a second composition, wherein the first composition and the second composition are different.

5189. The device of item 5141, further comprising a polymer.

5190. The device of item 5141, further comprising a polymeric carrier.

5191. The device of item 5141, further comprising a polymeric carrier, wherein the polymeric carrier comprises a copolymer.

5192. The device of item 5141, further comprising a polymeric carrier, wherein the polymeric carrier comprises a block copolymer.

5193. The device of item 5141, further comprising a polymeric carrier, wherein the polymeric carrier comprises a random copolymer.

5194. The device of item 5141, further comprising a polymeric carrier, wherein the polymeric carrier comprises a biodegradable polymer.

5195. The device of item 5141, further comprising a polymeric carrier, wherein the polymeric carrier comprises a non-biodegradable polymer.

5196. The device of item 5141, further comprising a polymeric carrier, wherein the polymeric carrier comprises a hydrophilic polymer.

5197. The device of item 5141, further comprising a polymeric carrier, wherein the polymeric carrier comprises a hydrophobic polymer.

5198. The device of item 5141, further comprising a polymeric carrier, wherein the polymeric carrier comprises a polymer having hydrophilic domains.

5199. The device of item 5141, further comprising a polymeric carrier, wherein the polymeric carrier comprises a polymer having hydrophobic domains.

5200. The device of item 5141, further comprising a polymeric carrier, wherein the polymeric carrier comprises a non-conductive polymer.

5201. The device of item 5141, further comprising a polymeric carrier, wherein the polymeric carrier comprises an elastomer.

5202. The device of item 5141, further comprising a polymeric carrier, wherein the polymeric carrier comprises a hydrogel.

5203. The device of item 5141, further comprising a polymeric carrier, wherein the polymeric carrier comprises a silicone polymer.

5204. The device of item 5141, further comprising a polymeric carrier, wherein the polymeric carrier comprises a hydrocarbon polymer.

5205. The device of item 5141, further comprising a polymeric carrier, wherein the polymeric carrier comprises a styrene-derived polymer.

5206. The device of item 5141, further comprising a polymeric carrier, wherein the polymeric carrier comprises a butadiene polymer.

5207. The device of item 5141, further comprising a polymeric carrier, wherein the polymeric carrier comprises a macromer.

5208. The device of item 5141, further comprising a polymeric carrier, wherein the polymeric carrier comprises a poly(ethylene glycol) polymer.

5209. The device of item 5141, further comprising a polymeric carrier, wherein the polymeric carrier comprises an amorphous polymer.

5210. The device of item 5141, further comprising a lubricious coating.

5211. The device of item 5141 wherein the fibrosing agent is located within pores or holes of the device.

5212. The device of item 5141 wherein the fibrosing agent is located within a channel, lumen, or divet of the device.

5213. The device of item 5141, further comprising a second pharmaceutically active agent.

5214. The device of item 5141, further comprising an anti-inflammatory agent.

5215. The device of item 5141, further comprising an agent that inhibits infection.

5216. The device of item 5141, further comprising an agent that inhibits infection, wherein the agent is an anthracycline.

5217. The device of item 5141, further comprising an agent that inhibits infection, wherein the agent is doxorubicin.

5218. The device of item 5141, further comprising an agent that inhibits infection, wherein the agent is mitoxantrone.

5219. The device of item 5141, further comprising an agent that inhibits infection, wherein the agent is a fluoropyrimidine.

5220. The device of item 5141, further comprising an agent that inhibits infection, wherein the agent is 5-fluorouracil (5-FU).

5221. The device of item 5141, further comprising an agent that inhibits infection, wherein the agent is a folic acid antagonist.

5222. The device of item 5141, further comprising an agent that inhibits infection, wherein the agent is methotrexate.

5223. The device of item 5141, further comprising an agent that inhibits infection, wherein the agent is a podophylotoxin.

5224. The device of item 5141, further comprising an agent that inhibits infection, wherein the agent is etoposide.

5225. The device of item 5141, further comprising an agent that inhibits infection, wherein the agent is a camptothecin.

5226. The device of item 5141, further comprising an agent that inhibits infection, wherein the agent is a hydroxyurea.

5227. The device of item 5141, further comprising an agent that inhibits infection, wherein the agent is a platinum complex.

5228. The device of item 5141, further comprising an agent that inhibits infection, wherein the agent is cisplatin.

5229. The device of item 5141, further comprising an anti-thrombotic agent.

5230. The device of item 5141, further comprising a visualization agent.

5231. The device of item 5141, further comprising a visualization agent, wherein the visualization agent is a radiopaque material, wherein the radiopaque material comprises a metal, a halogenated compound, or a barium containing compound.

5232. The device of item 5141, further comprising a visualization agent, wherein the visualization agent is a radiopaque material, wherein the radiopaque material comprises barium, tantalum, or technetium.

5233. The device of item 5141, further comprising a visualization agent, wherein the visualization agent is a MRI responsive material.

5234. The device of item 5141, further comprising a visualization agent, wherein the visualization agent comprises a gadolinium chelate.

5235. The device of item 5141, further comprising a visualization agent, wherein the visualization agent comprises iron, magnesium, manganese, copper, or chromium.

5236. The device of item 5141, further comprising a visualization agent, wherein the visualization agent comprises an iron oxide compound.

5237. The device of item 5141, further comprising a visualization agent, wherein the visualization agent comprises a dye, pigment, or colorant.

5238. The device of item 5141, further comprising an echogenic material.

5239. The device of item 5141, further comprising an echogenic material, wherein the echogenic material is in the form of a coating.

5240. The device of item 5141 wherein the device is sterile.

5241. The device of item 5141 wherein the fibrosing agent is released into tissue in the vicinity of the device after deployment of the device.

5242. The device of item 5141 wherein the fibrosing agent is released into tissue in the vicinity of the device after deployment of the device, wherein the tissue is connective tissue.

5243. The device of item 5141 wherein the fibrosing agent is released into tissue in the vicinity of the device after deployment of the device, wherein the tissue is muscle tissue.

5244. The device of item 5141 wherein the fibrosing agent is released into tissue in the vicinity of the device after deployment of the device, wherein the tissue is nerve tissue.

5245. The device of item 5141 wherein the fibrosing agent is released into tissue in the vicinity of the device after deployment of the device, wherein the tissue is epithelium tissue.

5246. The device of item 5141 wherein the fibrosing agent is released in effective concentrations from the device over a period ranging from the time of deployment of the device to about 1 year.

5247. The device of item 5141 wherein the fibrosing agent is released in effective concentrations from the device over a period ranging from about 1 month to 6 months.

5248. The device of item 5141 wherein the fibrosing agent is released in effective concentrations from the device over a period ranging from about 1–90 days.

5249. The device of item 5141 wherein the fibrosing agent is released in effective concentrations from the device at a constant rate.

5250. The device of item 5141 wherein the fibrosing agent is released in effective concentrations from the device at an increasing rate.

5251. The device of item 5141 wherein the fibrosing agent is released in effective concentrations from the device at a decreasing rate.

5252. The device of item 5141 wherein the fibrosing agent is released in effective concentrations from the composition comprising the fibrosing agent by diffusion over a period ranging from the time of deployment of the device to about 90 days.

5253. The device of item 5141 wherein the fibrosing agent is released in effective concentrations from the composition comprising the fibrosing agent by erosion of the composition over a period ranging from the time of deployment of the device to about 90 days.

5254. The device of item 5141 wherein the device comprises about 0.01 µg to about 10 µg of the fibrosing agent.

5255. The device of item 5141 wherein the device comprises about 10 µg to about 10 mg of the fibrosing agent.

5256. The device of item 5141 wherein the device comprises about 10 mg to about 250 mg of the fibrosing agent.

5257. The device of item 5141 wherein the device comprises about 250 mg to about 1000 mg of the fibrosing agent.

5258. The device of item 5141 wherein the device comprises about 1000 mg to about 2500 mg of the fibrosing agent.

5259. The device of item 5141 wherein a surface of the device comprises less than 0.01 µg of the fibrosing agent per $mm^2$ of device surface to which the fibrosing agent is applied.

5260. The device of item 5141 wherein a surface of the device comprises about 0.01 µg to about 1 µg of the fibrosing agent per $mm^2$ of device surface to which the fibrosing agent is applied.

5261. The device of item 5141 wherein a surface of the device comprises about 1 µg to about 10 µg of the fibrosing agent per $mm^2$ of device surface to which the fibrosing agent is applied.

5262. The device of item 5141 wherein a surface of the device comprises about 10 µg to about 250 µg of the fibrosing agent per $mm^2$ of device surface to which the fibrosing agent is applied.

5263. The device of item 5141 wherein a surface of the device comprises about 250 µg to about 1000 µg of the fibrosing agent of fibrosing agent per $mm^2$ of device surface to which the fibrosing agent is applied.

5264. The device of item 5141 wherein a surface of the device comprises about 1000 µg to about 2500 µg of the fibrosing agent per $mm^2$ of device surface to which the fibrosing agent is applied.

5265. The device of item 5141 wherein the fallopian tube implant is injectable.

5266. The device of item 5141 wherein the fallopian tube implant is an fallopian tumbe occlusive wire.

5267. The device of item 5141 wherein the fallopian tube implant is a coil fallopian tube implants.

5268. The device of item 5141 wherein the fallopian tube implant is a contraceptive uterine implant.

5269. A medical device comprising a transcatheter occluding implant and a fibrosing agent, where the fibrosing agent induces a fibrotic response between the device and a patient in which the device is implanted.

5270. The device of item 5269 wherein the fibrosing agent promotes regeneration.

5271. The device of item 5269 wherein the fibrosing agent promotes angiogenesis.

5272. The device of item 5269 wherein the fibrosing agent promotes fibroblast migration.

5273. The device of item 5269 wherein the fibrosing agent promotes fibroblast proliferation.

5274. The device of item 5269 wherein the fibrosing agent promotes deposition of extracellular matrix (ECM).

5275. The device of item 5269 wherein the fibrosing agent promotes tissue remodeling.

5276. The device of item 5269 wherein the fibrosing agent is an arterial vessel wall irritant.

5277. The device of item 5269 wherein the fibrosing agent promotes adhesion between the device and a host into which the device is implanted.

5278. The device of item 5269 wherein the device delivers the fibrosing agent locally to tissue proximate to the device.

5279. The device of item 5269 wherein the fibrosing agent is or comprises silk.

5280. The device of item 5269 wherein the fibrosing agent is or comprises mineral particles.

5281. The device of item 5269 wherein the fibrosing agent is or comprises chitosan.

5282. The device of item 5269 wherein the fibrosing agent is or comprises polylysine.

5283. The device of item 5269 wherein the fibrosing agent is or comprises fibronectin.

5284. The device of item 5269 wherein the fibrosing agent is or comprises bleomycin.

5285. The device of item 5269 wherein the fibrosing agent is or comprises CTGF.

5286. The device of item 5269 wherein the fibrosing agent is in the form of a thread, or is in contact with a thread.

5287. The device of item 5269 wherein the fibrosing agent is in the form of a particulate.

5288. The device of item 5269 wherein the composition further comprises an inflammatory cytokine.

5289. The device of item 5269 wherein the composition further comprises an agent that stimulates cell proliferation.

5290. The device of item 5269 wherein the composition is in the form of a gel, paste, or spray.

5291. The device of item 5269 wherein the fibrosing agent is in the form of tufts.

5292. The device of item 5269, further comprising a polymer.

5293. The device of item 5269, further comprising a polymeric carrier.

5294. The device of item 5269 wherein the fibrosing agent promotes adhesion between the device and a host into which the device is implanted.

5295. The device of item 5269 wherein the device delivers the fibrosing agent locally to tissue proximate to the device.

5296. The device of item 5269, further comprising a coating, wherein the coating comprises the fibrosing agent.

5297. The device of item 5269, further comprising a coating, wherein the coating is disposed on a surface of the device.

5298. The device of item 5269, further comprising a coating, wherein the coating directly contacts the device.

5299. The device of item 5269, further comprising a coating, wherein the coating indirectly contacts the device.

5300. The device of item 5269, further comprising a coating, wherein the coating partially covers the device.

5301. The device of item 5269, further comprising a coating, wherein the coating completely covers the device.

5302. The device of item 5269, further comprising a coating, wherein the coating is a uniform coating.

5303. The device of item 5269, further comprising a coating, wherein the coating is a non-uniform coating.

5304. The device of item 5269, further comprising a coating, wherein the coating is a discontinuous coating.

5305. The device of item 5269, further comprising a coating, wherein the coating is a patterned coating.

5306. The device of item 5269, further comprising a coating, wherein the coating has a thickness of 100 μm or less.

5307. The device of item 5269, further comprising a coating, wherein the coating has a thickness of 10 μm or less.

5308. The device of item 5269, further comprising a coating, wherein the coating adheres to the surface of the device upon deployment of the device.

5309. The device of item 5269, further comprising a coating, wherein the coating is stable at room temperature for a period of 1 year.

5310. The device of item 5269, further comprising a coating, wherein the fibrosing agent is present in the coating in an amount ranging between about 0.0001% to about 1% by weight.

5311. The device of item 5269, further comprising a coating, wherein the fibrosing agent is present in the coating in an amount ranging between about 1% to about 10% by weight.

5312. The device of item 5269, further comprising a coating, wherein the fibrosing agent is present in the coating in an amount ranging between about 10% to about 25% by weight.

5313. The device of item 5269, further comprising a coating, wherein the fibrosing agent is present in the coating in an amount ranging between about 25% to about 70% by weight.

5314. The device of item 5269, further comprising a coating, wherein the coating further comprises a polymer.

5315. The device of item 5269, further comprising a first coating having a first composition and the second coating having a second composition.

5316. The device of item 5269, further comprising a first coating having a first composition and the second coating having a second composition, wherein the first composition and the second composition are different.

5317. The device of item 5269, further comprising a polymer.

5318. The device of item 5269, further comprising a polymeric carrier.

5319. The device of item 5269, further comprising a polymeric carrier, wherein the polymeric carrier comprises a copolymer.

5320. The device of item 5269, further comprising a polymeric carrier, wherein the polymeric carrier comprises a block copolymer.

5321. The device of item 5269, further comprising a polymeric carrier, wherein the polymeric carrier comprises a random copolymer.

5322. The device of item 5269, further comprising a polymeric carrier, wherein the polymeric carrier comprises a biodegradable polymer.

5323. The device of item 5269, further comprising a polymeric carrier, wherein the polymeric carrier comprises a non-biodegradable polymer.

5324. The device of item 5269, further comprising a polymeric carrier, wherein the polymeric carrier comprises a hydrophilic polymer.

5325. The device of item 5269, further comprising a polymeric carrier, wherein the polymeric carrier comprises a hydrophobic polymer.

5326. The device of item 5269, further comprising a polymeric carrier, wherein the polymeric carrier comprises a polymer having hydrophilic domains.

5327. The device of item 5269, further comprising a polymeric carrier, wherein the polymeric carrier comprises a polymer having hydrophobic domains.

5328. The device of item 5269, further comprising a polymeric carrier, wherein the polymeric carrier comprises a non-conductive polymer.

5329. The device of item 5269, further comprising a polymeric carrier, wherein the polymeric carrier comprises an elastomer.

5330. The device of item 5269, further comprising a polymeric carrier, wherein the polymeric carrier comprises a hydrogel.

5331. The device of item 5269, further comprising a polymeric carrier, wherein the polymeric carrier comprises a silicone polymer.

5332. The device of item 5269, further comprising a polymeric carrier, wherein the polymeric carrier comprises a hydrocarbon polymer.

5333. The device of item 5269, further comprising a polymeric carrier, wherein the polymeric carrier comprises a styrene-derived polymer.

5334. The device of item 5269, further comprising a polymeric carrier, wherein the polymeric carrier comprises a butadiene polymer.

5335. The device of item 5269, further comprising a polymeric carrier, wherein the polymeric carrier comprises a macromer.

5336. The device of item 5269, further comprising a polymeric carrier, wherein the polymeric carrier comprises a poly(ethylene glycol) polymer.

5337. The device of item 5269, further comprising a polymeric carrier, wherein the polymeric carrier comprises an amorphous polymer.

5338. The device of item 5269, further comprising a lubricious coating.

5339. The device of item 5269 wherein the fibrosing agent is located within pores or holes of the device.

5340. The device of item 5269 wherein the fibrosing agent is located within a channel, lumen, or divet of the device.

5341. The device of item 5269, further comprising a second pharmaceutically active agent.

5342. The device of item 5269, further comprising an anti-inflammatory agent.

5343. The device of item 5269, further comprising an agent that inhibits infection.

5344. The device of item 5269, further comprising an agent that inhibits infection, wherein the agent is an anthracycline.

5345. The device of item 5269, further comprising an agent that inhibits infection, wherein the agent is doxorubicin.

5346. The device of item 5269, further comprising an agent that inhibits infection, wherein the agent is mitoxantrone.

5347. The device of item 5269, further comprising an agent that inhibits infection, wherein the agent is a fluoropyrimidine.

5348. The device of item 5269, further comprising an agent that inhibits infection, wherein the agent is 5-fluorouracil (5-FU).

5349. The device of item 5269, further comprising an agent that inhibits infection, wherein the agent is a folic acid antagonist.

5350. The device of item 5269, further comprising an agent that inhibits infection, wherein the agent is methotrexate.

5351. The device of item 5269, further comprising an agent that inhibits infection, wherein the agent is a podophylotoxin.

5352. The device of item 5269, further comprising an agent that inhibits infection, wherein the agent is etoposide.

5353. The device of item 5269, further comprising an agent that inhibits infection, wherein the agent is a camptothecin.

5354. The device of item 5269, further comprising an agent that inhibits infection, wherein the agent is a hydroxyurea.

5355. The device of item 5269, further comprising an agent that inhibits infection, wherein the agent is a platinum complex.

5356. The device of item 5269, further comprising an agent that inhibits infection, wherein the agent is cisplatin.

5357. The device of item 5269, further comprising an anti-thrombotic agent.

5358. The device of item 5269, further comprising a visualization agent.

5359. The device of item 5269, further comprising a visualization agent, wherein the visualization agent is a radiopaque material, wherein the radiopaque material comprises a metal, a halogenated compound, or a barium containing compound.

5360. The device of item 5269, further comprising a visualization agent, wherein the visualization agent is a radiopaque material, wherein the radiopaque material comprises barium, tantalum, or technetium.

5361. The device of item 5269, further comprising a visualization agent, wherein the visualization agent is a MRI responsive material.

5362. The device of item 5269, further comprising a visualization agent, wherein the visualization agent comprises a gadolinium chelate.

5363. The device of item 5269, further comprising a visualization agent, wherein the visualization agent comprises iron, magnesium, manganese, copper, or chromium.

5364. The device of item 5269, further comprising a visualization agent, wherein the visualization agent comprises an iron oxide compound.

5365. The device of item 5269, further comprising a visualization agent, wherein the visualization agent comprises a dye, pigment, or colorant.

5366. The device of item 5269, further comprising an echogenic material.

5367. The device of item 5269, further comprising an echogenic material, wherein the echogenic material is in the form of a coating.

5368. The device of item 5269 wherein the device is sterile.

5369. The device of item 5269 wherein the fibrosing agent is released into tissue in the vicinity of the device after deployment of the device.

5370. The device of item 5269 wherein the fibrosing agent is released into tissue in the vicinity of the device after deployment of the device, wherein the tissue is connective tissue.

5371. The device of item 5269 wherein the fibrosing agent is released into tissue in the vicinity of the device after deployment of the device, wherein the tissue is muscle tissue.

5372. The device of item 5269 wherein the fibrosing agent is released into tissue in the vicinity of the device after deployment of the device, wherein the tissue is nerve tissue.

5373. The device of item 5269 wherein the fibrosing agent is released into tissue in the vicinity of the device after deployment of the device, wherein the tissue is epithelium tissue.

5374. The device of item 5269 wherein the fibrosing agent is released in effective concentrations from the device over a period ranging from the time of deployment of the device to about 1 year.

5375. The device of item 5269 wherein the fibrosing agent is released in effective concentrations from the device over a period ranging from about 1 month to 6 months.

5376. The device of item 5269 wherein the fibrosing agent is released in effective concentrations from the device over a period ranging from about 1–90 days.

5377. The device of item 5269 wherein the fibrosing agent is released in effective concentrations from the device at a constant rate.

5378. The device of item 5269 wherein the fibrosing agent is released in effective concentrations from the device at an increasing rate.

5379. The device of item 5269 wherein the fibrosing agent is released in effective concentrations from the device at a decreasing rate.

5380. The device of item 5269 wherein the fibrosing agent is released in effective concentrations from the composition comprising the fibrosing agent by diffusion over a period ranging from the time of deployment of the device to about 90 days.

5381. The device of item 5269 wherein the fibrosing agent is released in effective concentrations from the composition comprising the fibrosing agent by erosion of the composition over a period ranging from the time of deployment of the device to about 90 days.

5382. The device of item 5269 wherein the device comprises about 0.01 μg to about 10 μg of the fibrosing agent.

5383. The device of item 5269 wherein the device comprises about 10 μg to about 10 mg of the fibrosing agent.

5384. The device of item 5269 wherein the device comprises about 10 mg to about 0.250 mg of the fibrosing agent.

5385. The device of item 5269 wherein the device comprises about 250 mg to about 1000 mg of the fibrosing agent.

5386. The device of item 5269 wherein the device comprises about 1000 mg to about 2500 mg of the fibrosing agent.

5387. The device of item 5269 wherein a surface of the device comprises less than 0.01 μg of the fibrosing agent per mm$^2$ of device surface to which the fibrosing agent is applied.

5388. The device of item 5269 wherein a surface of the device comprises about 0.01 μg to about 1 μg of the fibrosing agent per mm$^2$ of device surface to which the fibrosing agent is applied.

5389. The device of item 5269 wherein a surface of the device comprises about 1 μg to about 10 μg of the fibrosing agent per mm$^2$ of device surface to which the fibrosing agent is applied.

5390. The device of item 5269 wherein a surface of the device comprises about 10 μg to about 250 μg of the fibrosing agent per mm$^2$ of device surface to which the fibrosing agent is applied.

5391. The device of item 5269 wherein a surface of the device comprises about 250 μg to about 1000 μg of the fibrosing agent of fibrosing agent per mm$^2$ of device surface to which the fibrosing agent is applied.

5392. The device of item 5269 wherein a surface of the device comprises about 1000 μg to about 2500 μg of the fibrosing agent per mm$^2$ of device surface to which the fibrosing agent is applied.

5393. A medical device comprising a prosthetic anal sphincter and a fibrosing agent, where the fibrosing agent induces a fibrotic response between the device and a patient in which the device is implanted.

5394. The device of item 5393 wherein the fibrosing agent promotes regeneration.

5395. The device of item 5393 wherein the fibrosing agent promotes angiogenesis.

5396. The device of item 5393 wherein the fibrosing agent promotes fibroblast migration.

5397. The device of item 5393 wherein the fibrosing agent promotes fibroblast proliferation.

5398. The device of item 5393 wherein the fibrosing agent promotes deposition of extracellular matrix (ECM).

5399. The device of item 5393 wherein the fibrosing agent promotes tissue remodeling.

5400. The device of item 5393 wherein the fibrosing agent is an arterial vessel wall irritant.

5401. The device of item 5393 wherein the fibrosing agent promotes adhesion between the device and a host into which the device is implanted.

5402. The device of item 5393 wherein the device delivers the fibrosing agent locally to tissue proximate to the device.

5403. The device of item 5393 wherein the fibrosing agent is or comprises silk.

5404. The device of item 5393 wherein the fibrosing agent is or comprises mineral particles.

5405. The device of item 5393 wherein the fibrosing agent is or comprises chitosan.

5406. The device of item 5393 wherein the fibrosing agent is or comprises polylysine.

5407. The device of item 5393 wherein the fibrosing agent is or comprises fibronectin.

5408. The device of item 5393 wherein the fibrosing agent is or comprises bleomycin.

5409. The device of item 5393 wherein the fibrosing agent is or comprises CTGF.

5410. The device of item 5393 wherein the fibrosing agent is in the form of a thread, or is in contact with a thread.

5411. The device of item 5393 wherein the fibrosing agent is in the form of a particulate.

5412. The device of item 5393 wherein the composition further comprises an inflammatory cytokine.

5413. The device of item 5393 wherein the composition further comprises an agent that stimulates cell proliferation.

5414. The device of item 5393 wherein the composition is in the form of a gel, paste, or spray.

5415. The device of item 5393 wherein the fibrosing agent is in the form of tufts.

5416. The device of item 5393, further comprising a polymer.

5417. The device of item 5393, further comprising a polymeric carrier.

5418. The device of item 5393 wherein the fibrosing agent promotes adhesion between the device and a host into which the device is implanted.

5419. The device of item 5393 wherein the device delivers the fibrosing agent locally to tissue proximate to the device.

5420. The device of item 5393, further comprising a coating, wherein the coating comprises the fibrosing agent.

5421. The device of item 5393, further comprising a coating, wherein the coating is disposed on a surface of the device.

5422. The device of item 5393, further comprising a coating, wherein the coating directly contacts the device.

5423. The device of item 5393, further comprising a coating, wherein the coating indirectly contacts the device.

5424. The device of item 5393, further comprising a coating, wherein the coating partially covers the device.

5425. The device of item 5393, further comprising a coating, wherein the coating completely covers the device.

5426. The device of item 5393, further comprising a coating, wherein the coating is a uniform coating.

5427. The device of item 5393, further comprising a coating, wherein the coating is a non-uniform coating.

5428. The device of item 5393, further comprising a coating, wherein the coating is a discontinuous coating.

5429. The device of item 5393, further comprising a coating, wherein the coating is a patterned coating.

5430. The device of item 5393, further comprising a coating, wherein the coating has a thickness of 100 µm or less.

5431. The device of item 5393, further comprising a coating, wherein the coating has a thickness of 10 µm or less.

5432. The device of item 5393, further comprising a coating, wherein the coating adheres to the surface of the device upon deployment of the device.

5433. The device of item 5393, further comprising a coating, wherein the coating is stable at room temperature for a period of 1 year.

5434. The device of item 5393, further comprising a coating, wherein the fibrosing agent is present in the coating in an amount ranging between about 0.0001% to about 1% by weight.

5435. The device of item 5393, further comprising a coating, wherein the fibrosing agent is present in the coating in an amount ranging between about 1% to about 10% by weight.

5436. The device of item 5393, further comprising a coating, wherein the fibrosing agent is present in the coating in an amount ranging between about 10% to about 25% by weight.

5437. The device of item 5393, further comprising a coating, wherein the fibrosing agent is present in the coating in an amount ranging between about 25% to about 70% by weight.

5438. The device of item 5393, further comprising a coating, wherein the coating further comprises a polymer.

5439. The device of item 5393, further comprising a first coating having a first composition and the second coating having a second composition.

5440. The device of item 5393, further comprising a first coating having a first composition and the second coating having a second composition, wherein the first composition and the second composition are different.

5441. The device of item 5393, further comprising a polymer.

5442. The device of item 5393, further comprising a polymeric carrier.

5443. The device of item 5393, further comprising a polymeric carrier, wherein the polymeric carrier comprises a copolymer.

5444. The device of item 5393, further comprising a polymeric carrier, wherein the polymeric carrier comprises a block copolymer.

5445. The device of item 5393, further comprising a polymeric carrier, wherein the polymeric carrier comprises a random copolymer.

5446. The device of item 5393, further comprising a polymeric carrier, wherein the polymeric carrier comprises a biodegradable polymer.

5447. The device of item 5393, further comprising a polymeric carrier, wherein the polymeric carrier comprises a non-biodegradable polymer.

5448. The device of item 5393, further comprising a polymeric carrier, wherein the polymeric carrier comprises a hydrophilic polymer.

5449. The device of item 5393, further comprising a polymeric carrier, wherein the polymeric carrier comprises a hydrophobic polymer.

5450. The device of item 5393, further comprising a polymeric carrier, wherein the polymeric carrier comprises a polymer having hydrophilic domains.

5451. The device of item 5393, further comprising a polymeric carrier, wherein the polymeric carrier comprises a polymer having hydrophobic domains.

5452. The device of item 5393, further comprising a polymeric carrier, wherein the polymeric carrier comprises a non-conductive polymer.

5453. The device of item 5393, further comprising a polymeric carrier, wherein the polymeric carrier comprises an elastomer.

5454. The device of item 5393, further comprising a polymeric carrier, wherein the polymeric carrier comprises a hydrogel.

5455. The device of item 5393, further comprising a polymeric carrier, wherein the polymeric carrier comprises a silicone polymer.

5456. The device of item 5393, further comprising a polymeric carrier, wherein the polymeric carrier comprises a hydrocarbon polymer.

5457. The device of item 5393, further comprising a polymeric carrier, wherein the polymeric carrier comprises a styrene-derived polymer.

5458. The device of item 5393, further comprising a polymeric carrier, wherein the polymeric carrier comprises a butadiene polymer.

5459. The device of item 5393, further comprising a polymeric carrier, wherein the polymeric carrier comprises a macromer.

5460. The device of item 5393, further comprising a polymeric carrier, wherein the polymeric carrier comprises a poly(ethylene glycol) polymer.

5461. The device of item 5393, further comprising a polymeric carrier, wherein the polymeric carrier comprises an amorphous polymer.

5462. The device of item 5393, further comprising a lubricious coating.

5463. The device of item 5393 wherein the fibrosing agent is located within pores or holes of the device.

5464. The device of item 5393 wherein the fibrosing agent is located within a channel, lumen, or divet of the device.

5465. The device of item 5393, further comprising a second pharmaceutically active agent.

5466. The device of item 5393, further comprising an anti-inflammatory agent.

5467. The device of item 5393, further comprising an agent that inhibits infection.

5468. The device of item 5393, further comprising an agent that inhibits infection, wherein the agent is an anthracycline.

5469. The device of item 5393, further comprising an agent that inhibits infection, wherein the agent is doxorubicin.

5470. The device of item 5393, further comprising an agent that inhibits infection, wherein the agent is mitoxantrone.

5471. The device of item 5393, further comprising an agent that inhibits infection, wherein the agent is a fluoropyrimidine.

5472. The device of item 5393, further comprising an agent that inhibits infection, wherein the agent is 5-fluorouracil (5-FU).

5473. The device of item 5393, further comprising an agent that inhibits infection, wherein the agent is a folic acid antagonist.

5474. The device of item 5393, further comprising an agent that inhibits infection, wherein the agent is methotrexate.

5475. The device of item 5393, further comprising an agent that inhibits infection, wherein the agent is a podophylotoxin.

5476. The device of item 5393, further comprising an agent that inhibits infection, wherein the agent is etoposide.

5477. The device of item 5393, further comprising an agent that inhibits infection, wherein the agent is a camptothecin.

5478. The device of item 5393, further comprising an agent that inhibits infection, wherein the agent is a hydroxyurea.

5479. The device of item 5393, further comprising an agent that inhibits infection, wherein the agent is a platinum complex.

5480. The device of item 5393, further comprising an agent that inhibits infection, wherein the agent is cisplatin.

5481. The device of item 5393, further comprising an anti-thrombotic agent.

5482. The device of item 5393, further comprising a visualization agent.

5483. The device of item 5393, further comprising a visualization agent, wherein the visualization agent is a radiopaque material, wherein the radiopaque material comprises a metal, a halogenated compound, or a barium containing compound.

5484. The device of item 5393, further comprising a visualization agent, wherein the visualization agent is a radiopaque material, wherein the radiopaque material comprises barium, tantalum, or technetium.

5485. The device of item 5393, further comprising a visualization agent, wherein the visualization agent is a MRI responsive material.

5486. The device of item 5393, further comprising a visualization agent, wherein the visualization agent comprises a gadolinium chelate.

5487. The device of item 5393, further comprising a visualization agent, wherein the visualization agent comprises iron, magnesium, manganese, copper, or chromium.

5488. The device of item 5393, further comprising a visualization agent, wherein the visualization agent comprises an iron oxide compound.

5489. The device of item 5393, further comprising a visualization agent, wherein the visualization agent comprises a dye, pigment, or colorant.

5490. The device of item 5393, further comprising an echogenic material.

5491. The device of item 5393, further comprising an echogenic material, wherein the echogenic material is in the form of a coating.

5492. The device of item 5393 wherein the device is sterile.

5493. The device of item 5393 wherein the fibrosing agent is released into tissue in the vicinity of the device after deployment of the device.

5494. The device of item 5393 wherein the fibrosing agent is released into tissue in the vicinity of the device after deployment of the device, wherein the tissue is connective tissue.

5495. The device of item 5393 wherein the fibrosing agent is released into tissue in the vicinity of the device after deployment of the device, wherein the tissue is muscle tissue.

5496. The device of item 5393 wherein the fibrosing agent is released into tissue in the vicinity of the device after deployment of the device, wherein the tissue is nerve tissue.

5497. The device of item 5393 wherein the fibrosing agent is released into tissue in the vicinity of the device after deployment of the device, wherein the tissue is epithelium tissue.

5498. The device of item 5393 wherein the fibrosing agent is released in effective concentrations from the device over a period ranging from the time of deployment of the device to about 1 year.

5499. The device of item 5393 wherein the fibrosing agent is released in effective concentrations from the device over a period ranging from about 1 month to 6 months.

5500. The device of item 5393 wherein the fibrosing agent is released in effective concentrations from the device over a period ranging from about 1–90 days.

5501. The device of item 5393 wherein the fibrosing agent is released in effective concentrations from the device at a constant rate.

5502. The device of item 5393 wherein the fibrosing agent is released in effective concentrations from the device at an increasing rate.

5503. The device of item 5393 wherein the fibrosing agent is released in effective concentrations from the device at a decreasing rate.

5504. The device of item 5393 wherein the fibrosing agent is released in effective concentrations from the composition comprising the fibrosing agent by diffusion over a period ranging from the time of deployment of the device to about 90 days.

5505. The device of item 5393 wherein the fibrosing agent is released in effective concentrations from the composition comprising the fibrosing agent by erosion of the composition over a period ranging from the time of deployment of the device to about 90 days.

5506. The device of item 5393 wherein the device comprises about 0.01 μg to about 10 μg of the fibrosing agent.

5507. The device of item 5393 wherein the device comprises about 10 μg to about 10 mg of the fibrosing agent.

5508. The device of item 5393 wherein the device comprises about 10 mg to about 250 mg of the fibrosing agent.

5509. The device of item 5393 wherein the device comprises about 250 mg to about 1000 mg of the fibrosing agent.

5510. The device of item 5393 wherein the device comprises about 1000 mg to about 2500 mg of the fibrosing agent.

5511. The device of item 5393 wherein a surface of the device comprises less than 0.01 μg of the fibrosing agent per $mm^2$ of device surface to which the fibrosing agent is applied.

5512. The device of item 5393 wherein a surface of the device comprises about 0.01 μg to about 1 μg of the fibrosing agent per $mm^2$ of device surface to which the fibrosing agent is applied.

5513. The device of item 5393 wherein a surface of the device comprises about 1 μg to about 10 μg of the fibrosing agent per $mm^2$ of device surface to which the fibrosing agent is applied.

5514. The device of item 5393 wherein a surface of the device comprises about 10 μg to about 250 μg of the fibrosing agent per $mm^2$ of device surface to which the fibrosing agent is applied.

5515. The device of item 5393 wherein a surface of the device comprises about 250 μg to about 1000 μg of the fibrosing agent of fibrosing agent per $mm^2$ of device surface to which the fibrosing agent is applied.

5516. The device of item 5393 wherein a surface of the device comprises about 1000 μg to about 2500 μg of the fibrosing agent per $mm^2$ of device surface to which the fibrosing agent is applied.

5517. A medical device comprising a Fallopian tube stent and a fibrosing agent, where the fibrosing agent induces a fibrotic response between the device and a patient in which the device is implanted.

5518. The device of item 5517 wherein the fibrosing agent promotes regeneration.

5519. The device of item 5517 wherein the fibrosing agent promotes angiogenesis.

5520. The device of item 5517 wherein the fibrosing agent promotes fibroblast migration.

5521. The device of item 5517 wherein the fibrosing agent promotes fibroblast proliferation.

5522. The device of item 5517 wherein the fibrosing agent promotes deposition of extracellular matrix (ECM).

5523. The device of item 5517 wherein the fibrosing agent promotes tissue remodeling.

5524. The device of item 5517 wherein the fibrosing agent is an arterial vessel wall irritant.

5525. The device of item 5517 wherein the fibrosing agent promotes adhesion between the device and a host into which the device is implanted.

5526. The device of item 5517 wherein the device delivers the fibrosing agent locally to tissue proximate to the device.

5527. The device of item 5517 wherein the fibrosing agent is or comprises silk.

5528. The device of item 5517 wherein the fibrosing agent is or comprises mineral particles.

5529. The device of item 5517 wherein the fibrosing agent is or comprises chitosan.

5530. The device of item 5517 wherein the fibrosing agent is or comprises polylysine.

5531. The device of item 5517 wherein the fibrosing agent is or comprises fibronectin.

5532. The device of item 5517 wherein the fibrosing agent is or comprises bleomycin.

5533. The device of item 5517 wherein the fibrosing agent is or comprises CTGF.

5534. The device of item 5517 wherein the fibrosing agent is in the form of a thread, or is in contact with a thread.

5535. The device of item 5517 wherein the fibrosing agent is in the form of a particulate.

5536. The device of item 5517 wherein the composition further comprises an inflammatory cytokine.

5537. The device of item 5517 wherein the composition further comprises an agent that stimulates cell proliferation.

5538. The device of item 5517 wherein the composition is in the form of a gel, paste, or spray.

5539. The device of item 5517 wherein the fibrosing agent is in the form of tufts.

5540. The device of item 5517, further comprising a polymer.

5541. The device of item 5517, further comprising a polymeric carrier.

5542. The device of item 5517 wherein the fibrosing agent promotes adhesion between the device and a host into which the device is implanted.

5543. The device of item 5517 wherein the device delivers the fibrosing agent locally to tissue proximate to the device.

5544. The device of item 5517, further comprising a coating, wherein the coating comprises the fibrosing agent.

5545. The device of item 5517, further comprising a coating, wherein the coating is disposed on a surface of the device.

5546. The device of item 5517, further comprising a coating, wherein the coating directly contacts the device.

5547. The device of item 5517, further comprising a coating, wherein the coating indirectly contacts the device.

5548. The device of item 5517, further comprising a coating, wherein the coating partially covers the device.

5549. The device of item 5517, further comprising a coating, wherein the coating completely covers the device.

5550. The device of item 5517, further comprising a coating, wherein the coating is a uniform coating.

5551. The device of item 5517, further comprising a coating, wherein the coating is a non-uniform coating.

5552. The device of item 5517, further comprising a coating, wherein the coating is a discontinuous coating.

5553. The device of item 5517, further comprising a coating, wherein the coating is a patterned coating.

5554. The device of item 5517, further comprising a coating, wherein the coating has a thickness of 100 µm or less.

5555. The device of item 5517, further comprising a coating, wherein the coating has a thickness of 10 µm or less.

5556. The device of item 5517, further comprising a coating, wherein the coating adheres to the surface of the device upon deployment of the device.

5557. The device of item 5517, further comprising a coating, wherein the coating is stable at room temperature for a period of 1 year.

5558. The device of item 5517, further comprising a coating, wherein the fibrosing agent is present in the coating in an amount ranging between about 0.0001% to about 1% by weight.

5559. The device of item 5517, further comprising a coating, wherein the fibrosing agent is present in the coating in an amount ranging between about 1% to about 10% by weight.

5560. The device of item 5517, further comprising a coating, wherein the fibrosing agent is present in the coating in an amount ranging between about 10% to about 25% by weight.

5561. The device of item 5517, further comprising a coating, wherein the fibrosing agent is present in the coating in an amount ranging between about 25% to about 70% by weight.

5562. The device of item 5517, further comprising a coating, wherein the coating further comprises a polymer.

5563. The device of item 5517, further comprising a first coating having a first composition and the second coating having a second composition.

5564. The device of item 5517, further comprising a first coating having a first composition and the second coating having a second composition, wherein the first composition and the second composition are different.

5565. The device of item 5517, further comprising a polymer.

5566. The device of item 5517, further comprising a polymeric carrier.

5567. The device of item 5517, further comprising a polymeric carrier, wherein the polymeric carrier comprises a copolymer.

5568. The device of item 5517, further comprising a polymeric carrier, wherein the polymeric carrier comprises a block copolymer.

5569. The device of item 5517, further comprising a polymeric carrier, wherein the polymeric carrier comprises a random copolymer.

5570. The device of item 5517, further comprising a polymeric carrier, wherein the polymeric carrier comprises a biodegradable polymer.

5571. The device of item 5517, further comprising a polymeric carrier, wherein the polymeric carrier comprises a non-biodegradable polymer.

5572. The device of item 5517, further comprising a polymeric carrier, wherein the polymeric carrier comprises a hydrophilic polymer.

5573. The device of item 5517, further comprising a polymeric carrier, wherein the polymeric carrier comprises a hydrophobic polymer.

5574. The device of item 5517, further comprising a polymeric carrier, wherein the polymeric carrier comprises a polymer having hydrophilic domains.

5575. The device of item 5517, further comprising a polymeric carrier, wherein the polymeric carrier comprises a polymer having hydrophobic domains.

5576. The device of item 5517, further comprising a polymeric carrier, wherein the polymeric carrier comprises a non-conductive polymer.

5577. The device of item 5517, further comprising a polymeric carrier, wherein the polymeric carrier comprises an elastomer.

5578. The device of item 5517, further comprising a polymeric carrier, wherein the polymeric carrier comprises a hydrogel.

5579. The device of item 5517, further comprising a polymeric carrier, wherein the polymeric carrier comprises a silicone polymer.

5580. The device of item 5517, further comprising a polymeric carrier, wherein the polymeric carrier comprises a hydrocarbon polymer.

5581. The device of item 5517, further comprising a polymeric carrier, wherein the polymeric carrier comprises a styrene-derived polymer.

5582. The device of item 5517, further comprising a polymeric carrier, wherein the polymeric carrier comprises a butadiene polymer.

5583. The device of item 5517, further comprising a polymeric carrier, wherein the polymeric carrier comprises a macromer.

5584. The device of item 5517, further comprising a polymeric carrier, wherein the polymeric carrier comprises a poly(ethylene glycol) polymer.

5585. The device of item 5517, further comprising a polymeric carrier, wherein the polymeric carrier comprises an amorphous polymer.

5586. The device of item 5517, further comprising a lubricious coating.

5587. The device of item 5517 wherein the fibrosing agent is located within pores or holes of the device.

5588. The device of item 5517 wherein the fibrosing agent is located within a channel, lumen, or divet of the device.

5589. The device of item 5517, further comprising a second pharmaceutically active agent.

5590. The device of item 5517, further comprising an anti-inflammatory agent.

5591. The device of item 5517, further comprising an agent that inhibits infection.

5592. The device of item 5517, further comprising an agent that inhibits infection, wherein the agent is an anthracycline.

5593. The device of item 5517, further comprising an agent that inhibits infection, wherein the agent is doxorubicin.

5594. The device of item 5517, further comprising an agent that inhibits infection, wherein the agent is mitoxantrone.

5595. The device of item 5517, further comprising an agent that inhibits infection, wherein the agent is a fluoropyrimidine.

5596. The device of item 5517, further comprising an agent that inhibits infection, wherein the agent is 5-fluorouracil (5-FU).

5597. The device of item 5517, further comprising an agent that inhibits infection, wherein the agent is a folic acid antagonist.

5598. The device of item 5517, further comprising an agent that inhibits infection, wherein the agent is methotrexate.

5599. The device of item 5517, further comprising an agent that inhibits infection, wherein the agent is a podophylotoxin.

5600. The device of item 5517, further comprising an agent that inhibits infection, wherein the agent is etoposide.

5601. The device of item 5517, further comprising an agent that inhibits infection, wherein the agent is a camptothecin.

5602. The device of item 5517, further comprising an agent that inhibits infection, wherein the agent is a hydroxyurea.

5603. The device of item 5517, further comprising an agent that inhibits infection, wherein the agent is a platinum complex.

5604. The device of item 5517, further comprising an agent that inhibits infection, wherein the agent is cisplatin.

5605. The device of item 5517, further comprising an anti-thrombotic agent.

5606. The device of item 5517, further comprising a visualization agent.

5607. The device of item 5517, further comprising a visualization agent, wherein the visualization agent is a radiopaque material, wherein the radiopaque material comprises a metal, a halogenated compound, or a barium containing compound.

5608. The device of item 5517, further comprising a visualization agent, wherein the visualization agent is a radiopaque material, wherein the radiopaque material comprises barium, tantalum, or technetium.

5609. The device of item 5517, further comprising a visualization agent, wherein the visualization agent is a MRI responsive material.

5610. The device of item 5517, further comprising a visualization agent, wherein the visualization agent comprises a gadolinium chelate.

5611. The device of item 5517, further comprising a visualization agent, wherein the visualization agent comprises iron, magnesium, manganese, copper, or chromium.

5612. The device of item 5517, further comprising a visualization agent, wherein the visualization agent comprises an iron oxide compound.

5613. The device of item 5517, further comprising a visualization agent, wherein the visualization agent comprises a dye, pigment, or colorant.

5614. The device of item 5517, further comprising an echogenic material.

5615. The device of item 5517, further comprising an echogenic material, wherein the echogenic material is in the form of a coating.

5616. The device of item 5517 wherein the device is sterile.

5617. The device of item 5517 wherein the fibrosing agent is released into tissue in the vicinity of the device after deployment of the device.

5618. The device of item 5517 wherein the fibrosing agent is released into tissue in the vicinity of the device after deployment of the device, wherein the tissue is connective tissue.

5619. The device of item 5517 wherein the fibrosing agent is released into tissue in the vicinity of the device after deployment of the device, wherein the tissue is muscle tissue.

5620. The device of item 5517 wherein the fibrosing agent is released into tissue in the vicinity of the device after deployment of the device, wherein the tissue is nerve tissue.

5621. The device of item 5517 wherein the fibrosing agent is released into tissue in the vicinity of the device after deployment of the device, wherein the tissue is epithelium tissue.

5622. The device of item 5517 wherein the fibrosing agent is released in effective concentrations from the device over a period ranging from the time of deployment of the device to about 1 year.

5623. The device of item 5517 wherein the fibrosing agent is released in effective concentrations from the device over a period ranging from about 1 month to 6 months.

5624. The device of item 5517 wherein the fibrosing agent is released in effective concentrations from the device over a period ranging from about 1–90 days.

5625. The device of item 5517 wherein the fibrosing agent is released in effective concentrations from the device at a constant rate.

5626. The device of item 5517 wherein the fibrosing agent is released in effective concentrations from the device at an increasing rate.

5627. The device of item 5517 wherein the fibrosing agent is released in effective concentrations from the device at a decreasing rate.

5628. The device of item 5517 wherein the fibrosing agent is released in effective concentrations from the composition comprising the fibrosing agent by diffusion over a period ranging from the time of deployment of the device to about 90 days.

5629. The device of item 5517 wherein the fibrosing agent is released in effective concentrations from the composition comprising the fibrosing agent by erosion of the composition over a period ranging from the time of deployment of the device to about 90 days.

5630. The device of item 5517 wherein the device comprises about 0.01 μg to about 10 μg of the fibrosing agent.

5631. The device of item 5517 wherein the device comprises about 10 μg to about 10 mg of the fibrosing agent.

5632. The device of item 5517 wherein the device comprises about 10 mg to about 250 mg of the fibrosing agent.

5633. The device of item 5517 wherein the device comprises about 250 mg to about 1000 mg of the fibrosing agent.

5634. The device of item 5517 wherein the device comprises about 1000 mg to about 2500 mg of the fibrosing agent.

5635. The device of item 5517 wherein a surface of the device comprises less than 0.01 μg of the fibrosing agent per mm$^2$ of device surface to which the fibrosing agent is applied.

5636. The device of item 5517 wherein a surface of the device comprises about 0.01 μg to about 1 μg of the fibrosing agent per mm² of device surface to which the fibrosing agent is applied.

5637. The device of item 5517 wherein a surface of the device comprises about 1 μg to about 10 μg of the fibrosing agent per mm² of device surface to which the fibrosing agent is applied.

5638. The device of item 5517 wherein a surface of the device comprises about 10 μg to about 250 μg of the fibrosing agent per mm² of device surface to which the fibrosing agent is applied.

5639. The device of item 5517 wherein a surface of the device comprises about 250 μg to about 1000 μg of the fibrosing agent of fibrosing agent per mm² of device surface to which the fibrosing agent is applied.

5640. The device of item 5517 wherein a surface of the device comprises about 1000 μg to about 2500 μg of the fibrosing agent per mm² of device surface to which the fibrosing agent is applied.

5641. A medical device comprising a Vas Deferens implant and a fibrosing agent, where the fibrosing agent induces a fibrotic response between the device and a patient in which the device is implanted.

5642. The device of item 5641 wherein the fibrosing agent promotes regeneration.

5643. The device of item 5641 wherein the fibrosing agent promotes angiogenesis.

5644. The device of item 5641 wherein the fibrosing agent promotes fibroblast migration.

5645. The device of item 5641 wherein the fibrosing agent promotes fibroblast proliferation.

5646. The device of item 5641 wherein the fibrosing agent promotes deposition of extracellular matrix (ECM).

5647. The device of item 5641 wherein the fibrosing agent promotes tissue remodeling.

5648. The device of item 5641 wherein the fibrosing agent is an arterial vessel wall irritant.

5649. The device of item 5641 wherein the fibrosing agent promotes adhesion between the device and a host into which the device is implanted.

5650. The device of item 5641 wherein the device delivers the fibrosing agent locally to tissue proximate to the device.

5651. The device of item 5641 wherein the fibrosing agent is or comprises silk.

5652. The device of item 5641 wherein the fibrosing agent is or comprises mineral particles.

5653. The device of item 5641 wherein the fibrosing agent is or comprises chitosan.

5654. The device of item 5641 wherein the fibrosing agent is or comprises polylysine.

5655. The device of item 5641 wherein the fibrosing agent is or comprises fibronectin.

5656. The device of item 5641 wherein the fibrosing agent is or comprises bleomycin.

5657. The device of item 5641 wherein the fibrosing agent is or comprises CTGF.

5658. The device of item 5641 wherein the fibrosing agent is in the form of a thread, or is in contact with a thread.

5659. The device of item 5641 wherein the fibrosing agent is in the form of a particulate.

5660. The device of item 5641 wherein the composition further comprises an inflammatory cytokine.

5661. The device of item 5641 wherein the composition further comprises an agent that stimulates cell proliferation.

5662. The device of item 5641 wherein the composition is in the form of a gel, paste, or spray.

5663. The device of item 5641 wherein the fibrosing agent is in the form of tufts.

5664. The device of item 5641, further comprising a polymer.

5665. The device of item 5641, further comprising a polymeric carrier.

5666. The device of item 5641 wherein the fibrosing agent promotes adhesion between the device and a host into which the device is implanted.

5667. The device of item 5641 wherein the device delivers the fibrosing agent locally to tissue proximate to the device.

5668. The device of item 5641, further comprising a coating, wherein the coating comprises the fibrosing agent.

5669. The device of item 5641, further comprising a coating, wherein the coating is disposed on a surface of the device.

5670. The device of item 5641, further comprising a coating, wherein the coating directly contacts the device.

5671. The device of item 5641, further comprising a coating, wherein the coating indirectly contacts the device.

5672. The device of item 5641, further comprising a coating, wherein the coating partially covers the device.

5673. The device of item 5641, further comprising a coating, wherein the coating completely covers the device.

5674. The device of item 5641, further comprising a coating, wherein the coating is a uniform coating.

5675. The device of item 5641, further comprising a coating, wherein the coating is a non-uniform coating.

5676. The device of item 5641, further comprising a coating, wherein the coating is a discontinuous coating.

5677. The device of item 5641, further comprising a coating, wherein the coating is a patterned coating.

5678. The device of item 5641, further comprising a coating, wherein the coating has a thickness of 100 μm or less.

5679. The device of item 5641, further comprising a coating, wherein the coating has a thickness of 10 μm or less.

5680. The device of item 5641, further comprising a coating, wherein the coating adheres to the surface of the device upon deployment of the device.

5681. The device of item 5641, further comprising a coating, wherein the coating is stable at room temperature for a period of 1 year.

5682. The device of item 5641, further comprising a coating, wherein the fibrosing agent is present in the coating in an amount ranging between about 0.0001% to about 1% by weight.

5683. The device of item 5641, further comprising a coating, wherein the fibrosing agent is present in the coating in an amount ranging between about 1% to about 10% by weight., 5684. The device of item 5641, further comprising a coating, wherein the fibrosing agent is present in the coating in an amount ranging between about 10% to about 25% by weight.

5685. The device of item 5641, further comprising a coating, wherein the fibrosing agent is present in the coating in an amount ranging between about 25% to about 70% by weight.

5686. The device of item 5641, further comprising a coating, wherein the coating further comprises a polymer.

5687. The device of item 5641, further comprising a first coating having a first composition and the second coating having a second composition.

5688. The device of item 5641, further comprising a first coating having a first composition and the second coating having a second composition, wherein the first composition and the second composition are different.

5689. The device of item 5641, further comprising a polymer.

5690. The device of item 5641, further comprising a polymeric carrier.

5691. The device of item 5641, further comprising a polymeric carrier, wherein the polymeric carrier comprises a copolymer.

5692. The device of item 5641, further comprising a polymeric carrier, wherein the polymeric carrier comprises a block copolymer.

5693. The device of item 5641, further comprising a polymeric carrier, wherein the polymeric carrier comprises a random copolymer.

5694. The device of item 5641, further comprising a polymeric carrier, wherein the polymeric carrier comprises a biodegradable polymer.

5695. The device of item 5641, further comprising a polymeric carrier, wherein the polymeric carrier comprises a non-biodegradable polymer.

5696. The device of item 5641, further comprising a polymeric carrier, wherein the polymeric carrier comprises a hydrophilic polymer.

5697. The device of item 5641, further comprising a polymeric carrier, wherein the polymeric carrier comprises a hydrophobic polymer.

5698. The device of item 5641, further comprising a polymeric carrier, wherein the polymeric carrier comprises a polymer having hydrophilic domains.

5699. The device of item 5641, further comprising a polymeric carrier, wherein the polymeric carrier comprises a polymer having hydrophobic domains.

5700. The device of item 5641, further comprising a polymeric carrier, wherein the polymeric carrier comprises a non-conductive polymer.

5701. The device of item 5641, further comprising a polymeric carrier, wherein the polymeric carrier comprises an elastomer.

5702. The device of item 5641, further comprising a polymeric carrier, wherein the polymeric carrier comprises a hydrogel.

5703. The device of item 5641, further comprising a polymeric carrier, wherein the polymeric carrier comprises a silicone polymer.

5704. The device of item 5641, further comprising a polymeric carrier, wherein the polymeric carrier comprises a hydrocarbon polymer.

5705. The device of item 5641, further comprising a polymeric carrier, wherein the polymeric carrier comprises a styrene-derived polymer.

5706. The device of item 5641, further comprising a polymeric carrier, wherein the polymeric carrier comprises a butadiene polymer.

5707. The device of item 5641, further comprising a polymeric carrier, wherein the polymeric carrier comprises a macromer.

5708. The device of item 5641, further comprising a polymeric carrier, wherein the polymeric carrier comprises a poly(ethylene glycol) polymer.

5709. The device of item 5641, further comprising a polymeric carrier, wherein the polymeric carrier comprises an amorphous polymer.

5710. The device of item 5641, further comprising a lubricious coating.

5711. The device of item 5641 wherein the fibrosing agent is located within pores or holes of the device.

5712. The device of item 5641 wherein the fibrosing agent is located within a channel, lumen, or divet of the device.

5713. The device of item 5641, further comprising a second pharmaceutically active agent.

5714. The device of item 5641, further comprising an anti-inflammatory agent.

5715. The device of item 5641, further comprising an agent that inhibits infection.

5716. The device of item 5641, further comprising an agent that inhibits infection, wherein the agent is an anthracycline.

5717. The device of item 5641, further comprising an agent that inhibits infection, wherein the agent is doxorubicin.

5718. The device of item 5641, further comprising an agent that inhibits infection, wherein the agent is mitoxantrone.

5719. The device of item 5641, further comprising an agent that inhibits infection, wherein the agent is a fluoropyrimidine.

5720. The device of item 5641, further comprising an agent that inhibits infection, wherein the agent is 5-fluorouracil (5-FU).

5721. The device of item 5641, further comprising an agent that inhibits infection, wherein the agent is a folic acid antagonist.

5722. The device of item 5641, further comprising an agent that inhibits infection, wherein the agent is methotrexate.

5723. The device of item 5641, further comprising an agent that inhibits infection, wherein the agent is a podophylotoxin.

5724. The device of item 5641, further comprising an agent that inhibits infection, wherein the agent is etoposide.

5725. The device of item 5641, further comprising an agent that inhibits infection, wherein the agent is a camptothecin.

5726. The device of item 5641, further comprising an agent that inhibits infection, wherein the agent is a hydroxyurea.

5727. The device of item 5641, further comprising an agent that inhibits infection, wherein the agent is a platinum complex.

5728. The device of item 5641, further comprising an agent that inhibits infection, wherein the agent is cisplatin.

5729. The device of item 5641, further comprising an anti-thrombotic agent.

5730. The device of item 5641, further comprising a visualization agent.

5731. The device of item 5641, further comprising a visualization agent, wherein the visualization agent is a radiopaque material, wherein the radiopaque material comprises a metal, a halogenated compound, or a barium containing compound.

5732. The device of item 5641, further comprising a visualization agent, wherein the visualization agent is a radiopaque material, wherein the radiopaque material comprises barium, tantalum, or technetium.

5733. The device of item 5641, further comprising a visualization agent, wherein the visualization agent is a MRI responsive material.

5734. The device of item 5641, further comprising a visualization agent, wherein the visualization agent comprises a gadolinium chelate.

5735. The device of item 5641, further comprising a visualization agent, wherein the visualization agent comprises iron, magnesium, manganese, copper, or chromium.

5736. The device of item 5641, further comprising a visualization agent, wherein the visualization agent comprises an iron oxide compound.

5737. The device of item 5641, further comprising a visualization agent, wherein the visualization agent comprises a dye, pigment, or colorant.

5738. The device of item 5641, further comprising an echogenic material.

5739. The device of item 5641, further comprising an echogenic material, wherein the echogenic material is in the form of a coating.

5740. The device of item 5641 wherein the device is sterile.

5741. The device of item 5641 wherein the fibrosing agent is released into tissue in the vicinity of the device after deployment of the device.

5742. The device of item 5641 wherein the fibrosing agent is released into tissue in the vicinity of the device after deployment of the device, wherein the tissue is connective tissue.

5743. The device of item 5641 wherein the fibrosing agent is released into tissue in the vicinity of the device after deployment of the device, wherein the tissue is muscle tissue.

5744. The device of item 5641 wherein the fibrosing agent is released into tissue in the vicinity of the device after deployment of the device, wherein the tissue is nerve tissue.

5745. The device of item 5641 wherein the fibrosing agent is released into tissue in the vicinity of the device after deployment of the device, wherein the tissue is epithelium tissue.

5746. The device of item 5641 wherein the fibrosing agent is released in effective concentrations from the device over a period ranging from the time of deployment of the device to about 1 year.

5747. The device of item 5641 wherein the fibrosing agent is released in effective concentrations from the device over a period ranging from about 1 month to 6 months.

5748. The device of item 5641 wherein the fibrosing agent is released in effective concentrations from the device over a period ranging from about 1–90 days.

5749. The device of item 5641 wherein the fibrosing agent is released in effective concentrations from the device at a constant rate.

5750. The device of item 5641 wherein the fibrosing agent is released in effective concentrations from the device at an increasing rate.

5751. The device of item 5641 wherein the fibrosing agent is released in effective concentrations from the device at a decreasing rate.

5752. The device of item 5641 wherein the fibrosing agent is released in effective concentrations from the composition comprising the fibrosing agent by diffusion over a period ranging from the time of deployment of the device to about 90 days.

5753. The device of item 5641 wherein the fibrosing agent is released in effective concentrations from the composition comprising the fibrosing agent by erosion of the composition over a period ranging from the time of deployment of the device to about 90 days.

5754. The device of item 5641 wherein the device comprises about 0.01 µg to about 10 µg of the fibrosing agent.

5755. The device of item 5641 wherein the device comprises about 10 µg to about 10 mg of the fibrosing agent.

5756. The device of item 5641 wherein the device comprises about 10 mg to about 250 mg of the fibrosing agent.

5757. The device of item 5641 wherein the device comprises about 250 mg to about 1000 mg of the fibrosing agent.

5758. The device of item 5641 wherein the device comprises about 1000 mg to about 2500 mg of the fibrosing agent.

5759. The device of item 5641 wherein a surface of the device comprises less than 0.01 µg of the fibrosing agent per $mm^2$ of device surface to which the fibrosing agent is applied.

5760. The device of item 5641 wherein a surface of the device comprises about 0.01 µg to about 1 µg of the fibrosing agent per $mm^2$ of device surface to which the fibrosing agent is applied.

5761. The device of item 5641 wherein a surface of the device comprises about 1 µg to about 10 µg of the fibrosing agent per $mm^2$ of device surface to which the fibrosing agent is applied.

5762. The device of item 5641 wherein a surface of the device comprises about 10 µg to about 250 µg of the fibrosing agent per $mm^2$ of device surface to which the fibrosing agent is applied.

5763. The device of item 5641 wherein a surface of the device comprises about 250 µg to about 1000 µg of the fibrosing agent of fibrosing agent per $mm^2$ of device surface to which the fibrosing agent is applied.

5764. The device of item 5641 wherein a surface of the device comprises about 1000 µg to about 2500 µg of the fibrosing agent per $mm^2$ of device surface to which the fibrosing agent is applied.

5765. The device of item 5641 wherein the Vas Deferens implant is injectable.

5766. The device of item 5641 wherein the Vas Deferens implant is a vasectomy suture.

5767. The device of item 5641 wherein the Vas Deferens implant is a vasectomy clip.

5768. A medical device comprising a gastric restriction implant and a fibrosing agent, where the fibrosing agent induces a fibrotic response between the device and a patient in which the device is implanted.

5769. The device of item 5768 wherein the fibrosing agent promotes regeneration.

5770. The device of item 5768 wherein the fibrosing agent promotes angiogenesis.

5771. The device of item 5768 wherein the fibrosing agent promotes fibroblast migration.

5772. The device of item 5768 wherein the fibrosing agent promotes fibroblast proliferation.

5773. The device of item 5768 wherein the fibrosing agent promotes deposition of extracellular matrix (ECM).

5774. The device of item 5768 wherein the fibrosing agent promotes tissue remodeling.

5775. The device of item 5768 wherein the fibrosing agent is an arterial vessel wall irritant.

5776. The device of item 5768 wherein the fibrosing agent promotes adhesion between the device and a host into which the device is implanted.

5777. The device of item 5768 wherein the device delivers the fibrosing agent locally to tissue proximate to the device.

5778. The device of item 5768 wherein the fibrosing agent is or comprises silk.

5779. The device of item 5768 wherein the fibrosing agent is or comprises mineral particles.

5780. The device of item 5768 wherein the fibrosing agent is or comprises chitosan.

5781. The device of item 5768 wherein the fibrosing agent is or comprises polylysine.

5782. The device of item 5768 wherein the fibrosing agent is or comprises fibronectin.

5783. The device of item 5768 wherein the fibrosing agent is or comprises bleomycin.

5784. The device of item 5768 wherein the fibrosing agent is or comprises CTGF.

5785. The device of item 5768 wherein the fibrosing agent is in the form of a thread, or is in contact with a thread.

5786. The device of item 5768 wherein the fibrosing agent is in the form of a particulate.

5787. The device of item 5768 wherein the composition further comprises an inflammatory cytokine.

5788. The device of item 5768 wherein the composition further comprises an agent that stimulates cell proliferation.

5789. The device of item 5768 wherein the composition is in the form of a gel, paste, or spray.

5790. The device of item 5768 wherein the fibrosing agent is in the form of tufts.

5791. The device of item 5768, further comprising a polymer.

5792. The device of item 5768, further comprising a polymeric carrier.

5793. The device of item 5768 wherein the fibrosing agent promotes adhesion between the device and a host into which the device is implanted.

5794. The device of item 5768 wherein the device delivers the fibrosing agent locally to tissue proximate to the device.

5795. The device of item 5768, further comprising a coating, wherein the coating comprises the fibrosing agent.

5796. The device of item 5768, further comprising a coating, wherein the coating is disposed on a surface of the device.

5797. The device of item 5768, further comprising a coating, wherein the coating directly contacts the device.

5798. The device of item 5768, further comprising a coating, wherein the coating indirectly contacts the device.

5799. The device of item 5768, further comprising a coating, wherein the coating partially covers the device.

5800. The device of item 5768, further comprising a coating, wherein the coating completely covers the device.

5801. The device of item 5768, further comprising a coating, wherein the coating is a uniform coating.

5802. The device of item 5768, further comprising a coating, wherein the coating is a non-uniform coating.

5803. The device of item 5768, further comprising a coating, wherein the coating is a discontinuous coating.

5804. The device of item 5768, further comprising a coating, wherein the coating is a patterned coating.

5805. The device of item 5768, further comprising a coating, wherein the coating has a thickness of 100 μm or less.

5806. The device of item 5768, further comprising a coating, wherein the coating has a thickness of 10 μm or less.

5807. The device of item 5768, further comprising a coating, wherein the coating adheres to the surface of the device upon deployment of the device.

5808. The device of item 5768, further comprising a coating, wherein the coating is stable at room temperature for a period of 1 year.

5809. The device of item 5768, further comprising a coating, wherein the fibrosing agent is present in the coating in an amount ranging between about 0.0001% to about 1% by weight.

5810. The device of item 5768, further comprising a coating, wherein the fibrosing agent is present in the coating in an amount ranging between about 1% to about 10% by weight.

5811. The device of item 5768, further comprising a coating, wherein the fibrosing agent is present in the coating in an amount ranging between about 10% to about 25% by weight.

5812. The device of item 5768, further comprising a coating, wherein the fibrosing agent is present in the coating in an amount ranging between about 25% to about 70% by weight.

5813. The device of item 5768, further comprising a coating, wherein the coating further comprises a polymer.

5814. The device of item 5768, further comprising a first coating having a first composition and the second coating having a second composition.

5815. The device of item 5768, further comprising a first coating having a first composition and the second coating having a second composition, wherein the first composition and the second composition are different.

5816. The device of item 5768, further comprising a polymer.

5817. The device of item 5768, further comprising a polymeric carrier.

5818. The device of item 5768, further comprising a polymeric carrier, wherein the polymeric carrier comprises a copolymer.

5819. The device of item 5768, further comprising a polymeric carrier, wherein the polymeric carrier comprises a block copolymer.

5820. The device of item 5768, further comprising a polymeric carrier, wherein the polymeric carrier comprises a random copolymer.

5821. The device of item 5768, further comprising a polymeric carrier, wherein the polymeric carrier comprises a biodegradable polymer.

5822. The device of item 5768, further comprising a polymeric carrier, wherein the polymeric carrier comprises a non-biodegradable polymer.

5823. The device of item 5768, further comprising a polymeric carrier, wherein the polymeric carrier comprises a hydrophilic polymer.

5824. The device of item 5768, further comprising a polymeric carrier, wherein the polymeric carrier comprises a hydrophobic polymer.

5825. The device of item 5768, further comprising a polymeric carrier, wherein the polymeric carrier comprises a polymer having hydrophilic domains.

5826. The device of item 5768, further comprising a polymeric carrier, wherein the polymeric carrier comprises a polymer having hydrophobic domains.

5827. The device of item 5768, further comprising a polymeric carrier, wherein the polymeric carrier comprises a non-conductive polymer.

5828. The device of item 5768, further comprising a polymeric carrier, wherein the polymeric carrier comprises an elastomer.

5829. The device of item 5768, further comprising a polymeric carrier, wherein the polymeric carrier comprises a hydrogel.

5830. The device of item 5768, further comprising a polymeric carrier, wherein the polymeric carrier comprises a silicone polymer.

5831. The device of item 5768, further comprising a polymeric carrier, wherein the polymeric carrier comprises a hydrocarbon polymer.

5832. The device of item 5768, further comprising a polymeric carrier, wherein the polymeric carrier comprises a styrene-derived polymer.

5833. The device of item 5768, further comprising a polymeric carrier, wherein the polymeric carrier comprises a butadiene polymer.

5834. The device of item 5768, further comprising a polymeric carrier, wherein the polymeric carrier comprises a macromer.

5835. The device of item 5768, further comprising a polymeric carrier, wherein the polymeric carrier comprises a poly(ethylene glycol) polymer.

5836. The device of item 5768, further comprising a polymeric carrier, wherein the polymeric carrier comprises an amorphous polymer.

5837. The device of item 5768, further comprising a lubricious coating.

5838. The device of item 5768 wherein the fibrosing agent is located within pores or holes of the device.

5839. The device of item 5768 wherein the fibrosing agent is located within a channel, lumen, or divet of the device.

5840. The device of item 5768, further comprising a second pharmaceutically active agent.

5841. The device of item 5768, further comprising an anti-inflammatory agent.

5842. The device of item 5768, further comprising an agent that inhibits infection.

5843. The device of item 5768, further comprising an agent that inhibits infection, wherein the agent is an anthracycline.

5844. The device of item 5768, further comprising an agent that inhibits infection, wherein the agent is doxorubicin.

5845. The device of item 5768, further comprising an agent that inhibits infection, wherein the agent is mitoxantrone.

5846. The device of item 5768, further comprising an agent that inhibits infection, wherein the agent is a fluoropyrimidine.

5847. The device of item 5768, further comprising an agent that inhibits infection, wherein the agent is 5-fluorouracil (5-FU).

5848. The device of item 5768, further comprising an agent that inhibits infection, wherein the agent is a folic acid antagonist.

5849. The device of item 5768, further comprising an agent that inhibits infection, wherein the agent is methotrexate.

5850. The device of item 5768, further comprising an agent that inhibits infection, wherein the agent is a podophylotoxin.

5851. The device of item 5768, further comprising an agent that inhibits infection, wherein the agent is etoposide.

5852. The device of item 5768, further comprising an agent that inhibits infection, wherein the agent is a camptothecin.

5853. The device of item 5768, further comprising an agent that inhibits infection, wherein the agent is a hydroxyurea.

5854. The device of item 5768, further comprising an agent that inhibits infection, wherein the agent is a platinum complex.

5855. The device of item 5768, further comprising an agent that inhibits infection, wherein the agent is cisplatin.

5856. The device of item 5768, further comprising an anti-thrombotic agent.

5857. The device of item 5768, further comprising a visualization agent.

5858. The device of item 5768, further comprising a visualization agent, wherein the visualization agent is a radiopaque material, wherein the radiopaque material comprises a metal, a halogenated compound, or a barium containing compound.

5859. The device of item 5768, further comprising a visualization agent, wherein the visualization agent is a radiopaque material, wherein the radiopaque material comprises barium, tantalum, or technetium.

5860. The device of item 5768, further comprising a visualization agent, wherein the visualization agent is a MRI responsive material.

5861. The device of item 5768, further comprising a visualization agent, wherein the visualization agent comprises a gadolinium chelate.

5862. The device of item 5768, further comprising a visualization agent, wherein the visualization agent comprises iron, magnesium, manganese, copper, or chromium.

5863. The device of item 5768, further comprising a visualization agent, wherein the visualization agent comprises an iron oxide compound.

5864. The device of item 5768, further comprising a visualization agent, wherein the visualization agent comprises a dye, pigment, or colorant.

5865. The device of item 5768, further comprising an echogenic material.

5866. The device of item 5768, further comprising an echogenic material, wherein the echogenic material is in the form of a coating.

5867. The device of item 5768 wherein the device is sterile.

5868. The device of item 5768 wherein the fibrosing agent is released into tissue in the vicinity of the device after deployment of the device.

5869. The device of item 5768 wherein the fibrosing agent is released into tissue in the vicinity of the device after deployment of the device, wherein the tissue is connective tissue.

5870. The device of item 5768 wherein the fibrosing agent is released into tissue in the vicinity of the device after deployment of the device, wherein the tissue is muscle tissue.

5871. The device of item 5768 wherein the fibrosing agent is released into tissue in the vicinity of the device after deployment of the device, wherein the tissue is nerve tissue.

5872. The device of item 5768 wherein the fibrosing agent is released into tissue in the vicinity of the device after deployment of the device, wherein the tissue is epithelium tissue.

5873. The device of item 5768 wherein the fibrosing agent is released in effective concentrations from the device over a period ranging from the time of deployment of the device to about 1 year.

5874. The device of item 5768 wherein the fibrosing agent is released in effective concentrations from the device over a period ranging from about 1 month to 6 months.

5875. The device of item 5768 wherein the fibrosing agent is released in effective concentrations from the device over a period ranging from about 1–90 days.

5876. The device of item 5768 wherein the fibrosing agent is released in effective concentrations from the device at a constant rate.

5877. The device of item 5768 wherein the fibrosing agent is released in effective concentrations from the device at an increasing rate.

5878. The device of item 5768 wherein the fibrosing agent is released in effective concentrations from the device at a decreasing rate.

5879. The device of item 5768 wherein the fibrosing agent is released in effective concentrations from the composition comprising the fibrosing agent by diffusion over a period ranging from the time of deployment of the device to about 90 days.

5880. The device of item 5768 wherein the fibrosing agent is released in effective concentrations from the composition comprising the fibrosing agent by erosion of the composition over a period ranging from the time of deployment of the device to about 90 days.

5881. The device of item 5768 wherein the device comprises about 0.01 µg to about 10 µg of the fibrosing agent.

5882. The device of item 5768 wherein the device comprises about 10 µg to about 10 mg of the fibrosing agent.

5883. The device of item 5768 wherein the device comprises about 10 mg to about 250 mg of the fibrosing agent.

5884. The device of item 5768 wherein the device comprises about 250 mg to about 1000 mg of the fibrosing agent.

5885. The device of item 5768 wherein the device comprises about 1000 mg to about 2500 mg of the fibrosing agent.

5886. The device of item 5768 wherein a surface of the device comprises less than 0.01 µg of the fibrosing agent per mm$^2$ of device surface to which the fibrosing agent is applied.

5887. The device of item 5768 wherein a surface of the device comprises about 0.01 µg to about 1 µg of the fibrosing agent per mm$^2$ of device surface to which the fibrosing agent is applied.

5888. The device of item 5768 wherein a surface of the device comprises about 1 µg to about 10 µg of the fibrosing agent per mm$^2$ of device surface to which the fibrosing agent is applied.

5889. The device of item 5768 wherein a surface of the device comprises about 10 µg to about 250 µg of the fibrosing agent per mm$^2$ of device surface to which the fibrosing agent is applied.

5890. The device of item 5768 wherein a surface of the device comprises about 250 µg to about 1000 µg of the fibrosing agent of fibrosing agent per mm$^2$ of device surface to which the fibrosing agent is applied.

5891. The device of item 5768 wherein a surface of the device comprises about 1000 µg to about 2500 µg of the fibrosing agent per mm$^2$ of device surface to which the fibrosing agent is applied.

5892. The device of item 5768 wherein the gastric restriction implant is an inflatable cuff.

5893. The device of item 5768 wherein the gastric restriction implant is a space occuping device.

5894. A medical device comprising a suture-based endoluminal implant for partitioning the stomach, and a fibrosing agent, where the fibrosing agent induces a fibrotic response between the device and a patient in which the device is implanted.

5895. The device of item 5894 wherein the fibrosing agent promotes regeneration.

5896. The device of item 5894 wherein the fibrosing agent promotes angiogenesis.

5897. The device of item 5894 wherein the fibrosing agent promotes fibroblast migration.

5898. The device of item 5894 wherein the fibrosing agent promotes fibroblast proliferation.

5899. The device of item 5894 wherein the fibrosing agent promotes deposition of extracellular matrix (ECM).

5900. The device of item 5894 wherein the fibrosing agent promotes tissue remodeling.

5901. The device of item 5894 wherein the fibrosing agent is an arterial vessel wall irritant.

5902. The device of item 5894 wherein the fibrosing agent promotes adhesion between the device and a host into which the device is implanted.

5903. The device of item 5894 wherein the device delivers the fibrosing agent locally to tissue proximate to the device.

5904. The device of item 5894 wherein the fibrosing agent is or comprises silk.

5905. The device of item 5894 wherein the fibrosing agent is or comprises mineral particles.

5906. The device of item 5894 wherein the fibrosing agent is or comprises chitosan.

5907. The device of item 5894 wherein the fibrosing agent is or comprises polylysine.

5908. The device of item 5894 wherein the fibrosing agent is or comprises fibronectin.

5909. The device of item 5894 wherein the fibrosing agent is or comprises bleomycin.

5910. The device of item 5894 wherein the fibrosing agent is or comprises CTGF.

5911. The device of item 5894 wherein the fibrosing agent is in the form of a thread, or is in contact with a thread.

5912. The device of item 5894 wherein the fibrosing agent is in the form of a particulate.

5913. The device of item 5894 wherein the composition further comprises an inflammatory cytokine.

5914. The device of item 5894 wherein the composition further comprises an agent that stimulates cell proliferation.

5915. The device of item 5894 wherein the composition is in the form of a gel, paste, or spray.

5916. The device of item 5894 wherein the fibrosing agent is in the form of tufts.

5917. The device of item 5894, further comprising a polymer.

5918. The device of item 5894, further comprising a polymeric carrier.

5919. The device of item 5894 wherein the fibrosing agent promotes adhesion between the device and a host into which the device is implanted.

5920. The device of item 5894 wherein the device delivers the fibrosing agent locally to tissue proximate to the device.

5921. The device of item 5894, further comprising a coating, wherein the coating comprises the fibrosing agent.

5922. The device of item 5894, further comprising a coating, wherein the coating is disposed on a surface of the device.

5923. The device of item 5894, further comprising a coating, wherein the coating directly contacts the device.

5924. The device of item 5894, further comprising a coating, wherein the coating indirectly contacts the device.

5925. The device of item 5894, further comprising a coating, wherein the coating partially covers the device.

5926. The device of item 5894, further comprising a coating, wherein the coating completely covers the device.

5927. The device of item 5894, further comprising a coating, wherein the coating is a uniform coating.

5928. The device of item 5894, further comprising a coating, wherein the coating is a non-uniform coating.

5929. The device of item 5894, further comprising a coating, wherein the coating is a discontinuous coating.

5930. The device of item 5894, further comprising a coating, wherein the coating is a patterned coating.

5931. The device of item 5894, further comprising a coating, wherein the coating has a thickness of 100 μm or less.

5932. The device of item 5894, further comprising a coating, wherein the coating has a thickness of 10 μm or less.

5933. The device of item 5894, further comprising a coating, wherein the coating adheres to the surface of the device upon deployment of the device.

5934. The device of item 5894, further comprising a coating, wherein the coating is stable at room temperature for a period of 1 year.

5935. The device of item 5894, further comprising a coating, wherein the fibrosing agent is present in the coating in an amount ranging between about 0.0001% to about 1% by weight.

5936. The device of item 5894, further comprising a coating, wherein the fibrosing agent is present in the coating in an amount ranging between about 1% to about 10% by weight.

5937. The device of item 5894, further comprising a coating, wherein the fibrosing agent is present in the coating in an amount ranging between about 10% to about 25% by weight.

5938. The device of item 5894, further comprising a coating, wherein the fibrosing agent is present in the coating in an amount ranging between about 25% to about 70% by weight.

5939. The device of item 5894, further comprising a coating, wherein the coating further comprises a polymer.

5940. The device of item 5894, further comprising a first coating having a first composition and the second coating having a second composition.

5941. The device of item 5894, further comprising a first coating having a first composition and the second coating having a second composition, wherein the first composition and the second composition are different.

5942. The device of item 5894, further comprising a polymer.

5943. The device of item 5894, further comprising a polymeric carrier.

5944. The device of item 5894, further comprising a polymeric carrier, wherein the polymeric carrier comprises a copolymer.

5945. The device of item 5894, further comprising a polymeric carrier, wherein the polymeric carrier comprises a block copolymer.

5946. The device of item 5894, further comprising a polymeric carrier, wherein the polymeric carrier comprises a random copolymer.

5947. The device of item 5894, further comprising a polymeric carrier, wherein the polymeric carrier comprises a biodegradable polymer.

5948. The device of item 5894, further comprising a polymeric carrier, wherein the polymeric carrier comprises a non-biodegradable polymer.

5949. The device of item 5894, further comprising a polymeric carrier, wherein the polymeric carrier comprises a hydrophilic polymer.

5950. The device of item 5894, further comprising a polymeric carrier, wherein the polymeric carrier comprises a hydrophobic polymer.

5951. The device of item 5894, further comprising a polymeric carrier, wherein the polymeric carrier comprises a polymer having hydrophilic domains.

5952. The device of item 5894, further comprising a polymeric carrier, wherein the polymeric carrier comprises a polymer having hydrophobic domains.

5953. The device of item 5894, further comprising a polymeric carrier, wherein the polymeric carrier comprises a non-conductive polymer.

5954. The device of item 5894, further comprising a polymeric carrier, wherein the polymeric carrier comprises an elastomer.

5955. The device of item 5894, further comprising a polymeric carrier, wherein the polymeric carrier comprises a hydrogel.

5956. The device of item 5894, further comprising a polymeric carrier, wherein the polymeric carrier comprises a silicone polymer.

5957. The device of item 5894, further comprising a polymeric carrier, wherein the polymeric carrier comprises a hydrocarbon polymer.

5958. The device of item 5894, further comprising a polymeric carrier, wherein the polymeric carrier comprises a styrene-derived polymer.

5959. The device of item 5894, further comprising a polymeric carrier, wherein the polymeric carrier comprises a butadiene polymer.

5960. The device of item 5894, further comprising a polymeric carrier, wherein the polymeric carrier comprises a macromer.

5961. The device of item 5894, further comprising a polymeric carrier, wherein the polymeric carrier comprises a poly(ethylene glycol) polymer.

5962. The device of item 5894, further comprising a polymeric carrier, wherein the polymeric carrier comprises an amorphous polymer.

5963. The device of item 5894, further comprising a lubricious coating.

5964. The device of item 5894 wherein the fibrosing agent is located within pores or holes of the device.

5965. The device of item 5894 wherein the fibrosing agent is located within a channel, lumen, or divet of the device.

5966. The device of item 5894, further comprising a second pharmaceutically active agent.

5967. The device of item 5894, further comprising an anti-inflammatory agent.

5968. The device of item 5894, further comprising an agent that inhibits infection.

5969. The device of item 5894, further comprising an agent that inhibits infection, wherein the agent is an anthracycline.

5970. The device of item 5894, further comprising an agent that inhibits infection, wherein the agent is doxorubicin.

5971. The device of item 5894, further comprising an agent that inhibits infection, wherein the agent is mitoxantrone.

5972. The device of item 5894, further comprising an agent that inhibits infection, wherein the agent is a fluoropyrimidine.

5973. The device of item 5894, further comprising an agent that inhibits infection, wherein the agent is 5-fluorouracil (5-FU).

5974. The device of item 5894, further comprising an agent that inhibits infection, wherein the agent is a folic acid antagonist.

5975. The device of item 5894, further comprising an agent that inhibits infection, wherein the agent is methotrexate.

5976. The device of item 5894, further comprising an agent that inhibits infection, wherein the agent is a podophylotoxin.

5977. The device of item 5894, further comprising an agent that inhibits infection, wherein the agent is etoposide.

5978. The device of item 5894, further comprising an agent that inhibits infection, wherein the agent is a camptothecin.

5979. The device of item 5894, further comprising an agent that inhibits infection, wherein the agent is a hydroxyurea.

5980. The device of item 5894, further comprising an agent that inhibits infection, wherein the agent is a platinum complex.

5981. The device of item 5894, further comprising an agent that inhibits infection, wherein the agent is cisplatin.

5982. The device of item 5894, further comprising an anti-thrombotic agent.

5983. The device of item 5894, further comprising a visualization agent.

5984. The device of item 5894, further comprising a visualization agent, wherein the visualization agent is a radiopaque material, wherein the radiopaque material comprises a metal, a halogenated compound, or a barium containing compound.

5985. The device of item 5894, further comprising a visualization agent, wherein the visualization agent is a radiopaque material, wherein the radiopaque material comprises barium, tantalum, or technetium.

5986. The device of item 5894, further comprising a visualization agent, wherein the visualization agent is a MRI responsive material.

5987. The device of item 5894, further comprising a visualization agent, wherein the visualization agent comprises a gadolinium chelate.

5988. The device of item 5894, further comprising a visualization agent, wherein the visualization agent comprises iron, magnesium, manganese, copper, or chromium.

5989. The device of item 5894, further comprising a visualization agent, wherein the visualization agent comprises an iron oxide compound.

5990. The device of item 5894, further comprising a visualization agent, wherein the visualization agent comprises a dye, pigment, or colorant.

5991. The device of item 5894, further comprising an echogenic material.

5992. The device of item 5894, further comprising an echogenic material, wherein the echogenic material is in the form of a coating.

5993. The device of item 5894 wherein the device is sterile.

5994. The device of item 5894 wherein the fibrosing agent is released into tissue in the vicinity of the device after deployment of the device.

5995. The device of item 5894 wherein the fibrosing agent is released into tissue in the vicinity of the device after deployment of the device, wherein the tissue is connective tissue.

5996. The device of item 5894 wherein the fibrosing agent is released into tissue in the vicinity of the device after deployment of the device, wherein the tissue is muscle tissue.

5997. The device of item 5894 wherein the fibrosing agent is released into tissue in the vicinity of the device after deployment of the device, wherein the tissue is nerve tissue.

5998. The device of item 5894 wherein the fibrosing agent is released into tissue in the vicinity of the device after deployment of the device, wherein the tissue is epithelium tissue.

5999. The device of item 5894 wherein the fibrosing agent is released in effective concentrations from the device over a period ranging from the time of deployment of the device to about 1 year.

6000. The device of item 5894 wherein the fibrosing agent is released in effective concentrations from the device over a period ranging from about 1 month to 6 months.

6001. The device of item 5894 wherein the fibrosing agent is released in effective concentrations from the device over a period ranging from about 1–90 days.

6002. The device of item 5894 wherein the fibrosing agent is released in effective concentrations from the device at a constant rate.

6003. The device of item 5894 wherein the fibrosing agent is released in effective concentrations from the device at an increasing rate.

6004. The device of item 5894 wherein the fibrosing agent is released in effective concentrations from the device at a decreasing rate.

6005. The device of item 5894 wherein the fibrosing agent is released in effective concentrations from the composition comprising the fibrosing agent by diffusion over a period ranging from the time of deployment of the device to about 90 days.

6006. The device of item 5894 wherein the fibrosing agent is released in effective concentrations from the composition comprising the fibrosing agent by erosion of the composition over a period ranging from the time of deployment of the device to about 90 days.

6007. The device of item 5894 wherein the device comprises about 0.01 g to about 10 μg of the fibrosing agent.

6008. The device of item 5894 wherein the device comprises about 10 μg to about 10 mg of the fibrosing agent.

6009. The device of item 5894 wherein the device comprises about 10 mg to about 250 mg of the fibrosing agent.

6010. The device of item 5894 wherein the device comprises about 250 mg to about 1000 mg of the fibrosing agent.

6011. The device of item 5894 wherein the device comprises about 1000 mg to about 2500 mg of the fibrosing agent.

6012. The device of item 5894 wherein a surface of the device comprises less than 0.01 μg of the fibrosing agent per $mm^2$ of device surface to which the fibrosing agent is applied.

6013. The device of item 5894 wherein a surface of the device comprises about 0.01 μg to about 1 μg of the fibrosing agent per $mm^2$ of device surface to which the fibrosing agent is applied.

6014. The device of item 5894 wherein a surface of the device comprises about 1 μg to about 10 μg of the fibrosing agent per $mm^2$ of device surface to which the fibrosing agent is applied.

6015. The device of item 5894 wherein a surface of the device comprises about 10 μg to about 250 μg of the fibrosing agent per $mm^2$ of device surface to which the fibrosing agent is applied.

6016. The device of item 5894 wherein a surface of the device comprises about 250 μg to about 1000 μg of the fibrosing agent of fibrosing agent per $mm^2$ of device surface to which the fibrosing agent is applied.

6017. The device of item 5894 wherein a surface of the device comprises about 1000 μg to about 2500 μg of the fibrosing agent per $mm^2$ of device surface to which the fibrosing agent is applied.

6018. A medical device comprising an electrostimulation implant and a fibrosing agent, where the fibrosing agent induces a fibrotic response between the device and a patient in which the device is implanted.

6019. The device of item 6018 wherein the fibrosing agent promotes regeneration.

6020. The device of item 6018 wherein the fibrosing agent promotes angiogenesis.

6021. The device of item 6018 wherein the fibrosing agent promotes fibroblast migration.

6022. The device of item 6018 wherein the fibrosing agent promotes fibroblast proliferation.

6023. The device of item 6018 wherein the fibrosing agent promotes deposition of extracellular matrix (ECM).

6024. The device of item 6018 wherein the fibrosing agent promotes tissue remodeling.

6025. The device of item 6018 wherein the fibrosing agent is an arterial vessel wall irritant.

6026. The device of item 6018 wherein the fibrosing agent promotes adhesion between the device and a host into which the device is implanted.

6027. The device of item 6018 wherein the device delivers the fibrosing agent locally to tissue proximate to the device.

6028. The device of item 6018 wherein the fibrosing agent is or comprises silk.

6029. The device of item 6018 wherein the fibrosing agent is or comprises mineral particles.

6030. The device of item 6018 wherein the fibrosing agent is or comprises chitosan.

6031. The device of item 6018 wherein the fibrosing agent is or comprises polylysine.

6032. The device of item 6018 wherein the fibrosing agent is or comprises fibronectin.

6033. The device of item 6018 wherein the fibrosing agent is or comprises bleomycin.

6034. The device of item 6018 wherein the fibrosing agent is or comprises CTGF.

6035. The device of item 6018 wherein the fibrosing agent is in the form of a thread, or is in contact with a thread.

6036. The device of item 6018 wherein the fibrosing agent is in the form of a particulate.

6037. The device of item 6018 wherein the composition further comprises an inflammatory cytokine.

6038. The device of item 6018 wherein the composition further comprises an agent that stimulates cell proliferation.

6039. The device of item 6018 wherein the composition is in the form of a gel, paste, or spray.

6040. The device of item 6018 wherein the fibrosing agent is in the form of tufts.

6041. The device of item 6018, further comprising a polymer.

6042. The device of item 6018, further comprising a polymeric carrier.

6043. The device of item 6018 wherein the fibrosing agent promotes adhesion between the device and a host into which the device is implanted.

6044. The device of item 6018 wherein the device delivers the fibrosing agent locally to tissue proximate to the device.

6045. The device of item 6018, further comprising a coating, wherein the coating comprises the fibrosing agent.

6046. The device of item 6018, further comprising a coating, wherein the coating is disposed on a surface of the device.

6047. The device of item 6018, further comprising a coating, wherein the coating directly contacts the device.

6048. The device of item 6018, further comprising a coating, wherein the coating indirectly contacts the device.

6049. The device of item 6018, further comprising a coating, wherein the coating partially covers the device.

6050. The device of item 6018, further comprising a coating, wherein the coating completely covers the device.

6051. The device of item 6018, further comprising a coating, wherein the coating is a uniform coating.

6052. The device of item 6018, further comprising a coating, wherein the coating is a non-uniform coating.

6053. The device of item 6018, further comprising a coating, wherein the coating is a discontinuous coating.

6054. The device of item 6018, further comprising a coating, wherein the coating is a patterned coating.

6055. The device of item 6018, further comprising a coating, wherein the coating has a thickness of 100 μm or less.

6056. The device of item 6018, further comprising a coating, wherein the coating has a thickness of 10 μm or less.

6057. The device of item 6018, further comprising a coating, wherein the coating adheres to the surface of the device upon deployment of the device.

6058. The device of item 6018, further comprising a coating, wherein the coating is stable at room temperature for a period of 1 year.

6059. The device of item 6018, further comprising a coating, wherein the fibrosing agent is present in the coating in an amount ranging between about 0.0001% to about 1% by weight.

6060. The device of item 6018, further comprising a coating, wherein the fibrosing agent is present in the coating in an amount ranging between about 1% to about 10% by weight.

6061. The device of item 6018, further comprising a coating, wherein the fibrosing agent is present in the coating in an amount ranging between about 10% to about 25% by weight.

6062. The device of item 6018, further comprising a coating, wherein the fibrosing agent is present in the coating in an amount ranging between about 25% to about 70% by weight.

6063. The device of item 6018, further comprising a coating, wherein the coating further comprises a polymer.

6064. The device of item 6018, further comprising a first coating having a first composition and the second coating having a second composition.

6065. The device of item 6018, further comprising a first coating having a first composition and the second coating having a second composition, wherein the first composition and the second composition are different.

6066. The device of item 6018, further comprising a polymer.

6067. The device of item 6018, further comprising a polymeric carrier.

6068. The device of item 6018, further comprising a polymeric carrier, wherein the polymeric carrier comprises a copolymer.

6069. The device of item 6018, further comprising a polymeric carrier, wherein the polymeric carrier comprises a block copolymer.

6070. The device of item 6018, further comprising a polymeric carrier, wherein the polymeric carrier comprises a random copolymer.

6071. The device of item 6018, further comprising a polymeric carrier, wherein the polymeric carrier comprises a biodegradable polymer.

6072. The device of item 6018, further comprising a polymeric carrier, wherein the polymeric carrier comprises a non-biodegradable polymer.

6073. The device of item 6018, further comprising a polymeric carrier, wherein the polymeric carrier comprises a hydrophilic polymer.

6074. The device of item 6018, further comprising a polymeric carrier, wherein the polymeric carrier comprises a hydrophobic polymer.

6075. The device of item 6018, further comprising a polymeric carrier, wherein the polymeric carrier comprises a polymer having hydrophilic domains.

6076. The device of item 6018, further comprising a polymeric carrier, wherein the polymeric carrier comprises a polymer having hydrophobic domains.

6077. The device of item 6018, further comprising a polymeric carrier, wherein the polymeric carrier comprises a non-conductive polymer.

6078. The device of item 6018, further comprising a polymeric carrier, wherein the polymeric carrier comprises an elastomer.

6079. The device of item 6018, further comprising a polymeric carrier, wherein the polymeric carrier comprises a hydrogel.

6080. The device of item 6018, further comprising a polymeric carrier, wherein the polymeric carrier comprises a silicone polymer.

6081. The device of item 6018, further comprising a polymeric carrier, wherein the polymeric carrier comprises a hydrocarbon polymer.

6082. The device of item 6018, further comprising a polymeric carrier, wherein the polymeric carrier comprises a styrene-derived polymer.

6083. The device of item 6018, further comprising a polymeric carrier, wherein the polymeric carrier comprises a butadiene polymer.

6084. The device of item 6018, further comprising a polymeric carrier, wherein the polymeric carrier comprises a macromer.

6085. The device of item 6018, further comprising a polymeric carrier, wherein the polymeric carrier comprises a poly(ethylene glycol) polymer.

6086. The device of item 6018, further comprising a polymeric carrier, wherein the polymeric carrier comprises an amorphous polymer.

6087. The device of item 6018, further comprising a lubricious coating.

6088. The device of item 6018 wherein the fibrosing agent is located within pores or holes of the device.

6089. The device of item 6018 wherein the fibrosing agent is located within a channel, lumen, or divet of the device.

6090. The device of item 6018, further comprising a second pharmaceutically active agent.

6091. The device of item 6018, further comprising an anti-inflammatory agent.

6092. The device of item 6018, further comprising an agent that inhibits infection.

6093. The device of item 6018, further comprising an agent that inhibits infection, wherein the agent is an anthracycline.

6094. The device of item 6018, further comprising an agent that inhibits infection, wherein the agent is doxorubicin.

6095. The device of item 6018, further comprising an agent that inhibits infection, wherein the agent is mitoxantrone.

6096. The device of item 6018, further comprising an agent that inhibits infection, wherein the agent is a fluoropyrimidine.

6097. The device of item 6018, further comprising an agent that inhibits infection, wherein the agent is 5-fluorouracil (5-FU).

6098. The device of item 6018, further comprising an agent that inhibits infection, wherein the agent is a folic acid antagonist.

6099. The device of item 6018, further comprising an agent that inhibits infection, wherein the agent is methotrexate.

6100. The device of item 6018, further comprising an agent that inhibits infection, wherein the agent is a podophylotoxin.

6101. The device of item 6018, further comprising an agent that inhibits infection, wherein the agent is etoposide.

6102. The device of item 6018, further comprising an agent that inhibits infection, wherein the agent is a camptothecin.

6103. The device of item 6018, further comprising an agent that inhibits infection, wherein the agent is a hydroxyurea.

6104. The device of item 6018, further comprising an agent that inhibits infection, wherein the agent is a platinum complex.

6105. The device of item 6018, further comprising an agent that inhibits infection, wherein the agent is cisplatin.

6106. The device of item 6018, further comprising an anti-thrombotic agent.

6107. The device of item 6018, further comprising a visualization agent.

6108. The device of item 6018, further comprising a visualization agent, wherein the visualization agent is a radiopaque material, wherein the radiopaque material comprises a metal, a halogenated compound, or a barium containing compound.

6109. The device of item 6018, further comprising a visualization agent, wherein the visualization agent is a radiopaque material, wherein the radiopaque material comprises barium, tantalum, or technetium.

6110. The device of item 6018, further comprising a visualization agent, wherein the visualization agent is a MRI responsive material.

6111. The device of item 6018, further comprising a visualization agent, wherein the visualization agent comprises a gadolinium chelate.

6112. The device of item 6018, further comprising a visualization agent, wherein the visualization agent comprises iron, magnesium, manganese, copper, or chromium.

6113. The device of item 6018, further comprising a visualization agent, wherein the visualization agent comprises an iron oxide compound.

6114. The device of item 6018, further comprising a visualization agent, wherein the visualization agent comprises a dye, pigment, or colorant.

6115. The device of item 6018, further comprising an echogenic material.

6116. The device of item 6018, further comprising an echogenic material, wherein the echogenic material is in the form of a coating.

6117. The device of item 6018 wherein the device is sterile.

6118. The device of item 6018 wherein the fibrosing agent is released into tissue in the vicinity of the device after deployment of the device.

6119. The device of item 6018 wherein the fibrosing agent is released into tissue in the vicinity of the device after deployment of the device, wherein the tissue is connective tissue.

6120. The device of item 6018 wherein the fibrosing agent is released into tissue in the vicinity of the device after deployment of the device, wherein the tissue is muscle tissue.

6121. The device of item 6018 wherein the fibrosing agent is released into tissue in the vicinity of the device after deployment of the device, wherein the tissue is nerve tissue.

6122. The device of item 6018 wherein the fibrosing agent is released into tissue in the vicinity of the device after deployment of the device, wherein the tissue is epithelium tissue.

6123. The device of item 6018 wherein the fibrosing agent is released in effective concentrations from the device over a period ranging from the time of deployment of the device to about 1 year.

6124. The device of item 6018 wherein the fibrosing agent is released in effective concentrations from the device over a period ranging from about 1 month to 6 months.

6125. The device of item 6018 wherein the fibrosing agent is released in effective concentrations from the device over a period ranging from about 1–90 days.

6126. The device of item 6018 wherein the fibrosing agent is released in effective concentrations from the device at a constant rate.

6127. The device of item 6018 wherein the fibrosing agent is released in effective concentrations from the device at an increasing rate.

6128. The device of item 6018 wherein the fibrosing agent is released in effective concentrations from the device at a decreasing rate.

6129. The device of item 6018 wherein the fibrosing agent is released in effective concentrations from the composition comprising the fibrosing agent by diffusion over a period ranging from the time of deployment of the device to about 90 days.

6130. The device of item 6018 wherein the fibrosing agent is released in effective concentrations from the composition comprising the fibrosing agent by erosion of the composition over a period ranging from the time of deployment of the device to about 90 days.

6131. The device of item 6018 wherein the device comprises about 0.01 μg to about 10 μg of the fibrosing agent.

6132. The device of item 6018 wherein the device comprises about 10 μg to about 10 mg of the fibrosing agent.

6133. The device of item 6018 wherein the device comprises about 10 mg to about 250 mg of the fibrosing agent.

6134. The device of item 6018 wherein the device comprises about 250 mg to about 1000 mg of the fibrosing agent.

6135. The device of item 6018 wherein the device comprises about 1000 mg to about 2500 mg of the fibrosing agent.

6136. The device of item 6018 wherein a surface of the device comprises less than 0.01 μg of the fibrosing agent per $mm^2$ of device surface to which the fibrosing agent is applied.

6137. The device of item 6018 wherein a surface of the device comprises about 0.01 μg to about 1 μg of the fibrosing agent per $mm^2$ of device surface to which the fibrosing agent is applied.

6138. The device of item 6018 wherein a surface of the device comprises about 1 μg to about 10 μg of the fibrosing agent per $mm^2$ of device surface to which the fibrosing agent is applied.

6139. The device of item 6018 wherein a surface of the device comprises about 10 μg to about 250 μg of the fibrosing agent per $mm^2$ of device surface to which the fibrosing agent is applied.

6140. The device of item 6018 wherein a surface of the device comprises about 250 μg to about 1000 μg of the fibrosing agent of fibrosing agent per $mm^2$ of device surface to which the fibrosing agent is applied.

6141. The device of item 6018 wherein a surface of the device comprises about 1000 μg to about 2500 μg of the fibrosing agent per $mm^2$ of device surface to which the fibrosing agent is applied.

6142. The device of item 6018 wherein the electostimulation implant is a neural electostimulation implant.

6143. The device of item 6018 wherein the electostimulation implant is a non-neural electostimulation implant.

6144. A medical device comprising a soft palate implant and a fibrosing agent, where the fibrosing agent induces a fibrotic response between the device and a patient in which the device is implanted.

6145. The device of item 6144 wherein the fibrosing agent promotes regeneration.

6146. The device of item 6144 wherein the fibrosing agent promotes angiogenesis.

6147. The device of item 6144 wherein the fibrosing agent promotes fibroblast migration.

6148. The device of item 6144 wherein the fibrosing agent promotes fibroblast proliferation.

6149. The device of item 6144 wherein the fibrosing agent promotes deposition of extracellular matrix (ECM).

6150. The device of item 6144 wherein the fibrosing agent promotes tissue remodeling.

6151. The device of item 6144 wherein the fibrosing agent is an arterial vessel wall irritant.

6152. The device of item 6144 wherein the fibrosing agent promotes adhesion between the device and a host into which the device is implanted.

6153. The device of item 6144 wherein the device delivers the fibrosing agent locally to tissue proximate to the device.

6154. The device of item 6144 wherein the fibrosing agent is or comprises silk.

6155. The device of item 6144 wherein the fibrosing agent is or comprises mineral particles.

6156. The device of item 6144 wherein the fibrosing agent is or comprises chitosan.

6157. The device of item 6144 wherein the fibrosing agent is or comprises polylysine.

6158. The device of item 6144 wherein the fibrosing agent is or comprises fibronectin.

6159. The device of item 6144 wherein the fibrosing agent is or comprises bleomycin.

6160. The device of item 6144 wherein the fibrosing agent is or comprises CTGF.

6161. The device of item 6144 wherein the fibrosing agent is in the form of a thread, or is in contact with a thread.

6162. The device of item 6144 wherein the fibrosing agent is in the form of a particulate.

6163. The device of item 6144 wherein the composition further comprises an inflammatory cytokine.

6164. The device of item 6144 wherein the composition further comprises an agent that stimulates cell proliferation.

6165. The device of item 6144 wherein the composition is in the form of a gel, paste, or spray.

6166. The device of item 6144 wherein the fibrosing agent is in the form of tufts.

6167. The device of item 6144, further comprising a polymer.

6168. The device of item 6144, further comprising a polymeric carrier.

6169. The device of item 6144 wherein the fibrosing agent promotes adhesion between the device and a host into which the device is implanted.

6170. The device of item 6144 wherein the device delivers the fibrosing agent locally to tissue proximate to the device.

6171. The device of item 6144, further comprising a coating, wherein the coating comprises the fibrosing agent.

6172. The device of item 6144, further comprising a coating, wherein the coating is disposed on a surface of the device.

6173. The device of item 6144, further comprising a coating, wherein the coating directly contacts the device.

6174. The device of item 6144, further comprising a coating, wherein the coating indirectly contacts the device.

6175. The device of item 6144, further comprising a coating, wherein the coating partially covers the device.

6176. The device of item 6144, further comprising a coating, wherein the coating completely covers the device.

6177. The device of item 6144, further comprising a coating, wherein the coating is a uniform coating.

6178. The device of item 6144, further comprising a coating, wherein the coating is a non-uniform coating.

6179. The device of item 6144, further comprising a coating, wherein the coating is a discontinuous coating.

6180. The device of item 6144, further comprising a coating, wherein the coating is a patterned coating.

6181. The device of item 6144, further comprising a coating, wherein the coating has a thickness of 100 µm or less.

6182. The device of item 6144, further comprising a coating, wherein the coating has a thickness of 10 µm or less.

6183. The device of item 6144, further comprising a coating, wherein the coating adheres to the surface of the device upon deployment of the device.

6184. The device of item 6144, further comprising a coating, wherein the coating is stable at room temperature for a period of 1 year.

6185. The device of item 6144, further comprising a coating, wherein the fibrosing agent is present in the coating in an amount ranging between about 0.0001% to about 1% by weight.

6186. The device of item 6144, further comprising a coating, wherein the fibrosing agent is present in the coating in an amount ranging between about 1% to about 10% by weight.

6187. The device of item 6144, further comprising a coating, wherein the fibrosing agent is present in the coating in an amount ranging between about 10% to about 25% by weight.

6188. The device of item 6144, further comprising a coating, wherein the fibrosing agent is present in the coating in an amount ranging between about 25% to about 70% by weight.

6189. The device of item 6144, further comprising a coating, wherein the coating further comprises a polymer.

6190. The device of item 6144, further comprising a first coating having a first composition and the second coating having a second composition.

6191. The device of item 6144, further comprising a first coating having a first composition and the second coating having a second composition, wherein the first composition and the second composition are different.

6192. The device of item 6144, further comprising a polymer.

6193. The device of item 6144, further comprising a polymeric carrier.

6194. The device of item 6144, further comprising a polymeric carrier, wherein the polymeric carrier comprises a copolymer.

6195. The device of item 6144, further comprising a polymeric carrier, wherein the polymeric carrier comprises a block copolymer.

6196. The device of item 6144, further comprising a polymeric carrier, wherein the polymeric carrier comprises a random copolymer.

6197. The device of item 6144, further comprising a polymeric carrier, wherein the polymeric carrier comprises a biodegradable polymer.

6198. The device of item 6144, further comprising a polymeric carrier, wherein the polymeric carrier comprises a non-biodegradable polymer.

6199. The device of item 6144, further comprising a polymeric carrier, wherein the polymeric carrier comprises a hydrophilic polymer.

6200. The device of item 6144, further comprising a polymeric carrier, wherein the polymeric carrier comprises a hydrophobic polymer.

6201. The device of item 6144, further comprising a polymeric carrier, wherein the polymeric carrier comprises a polymer having hydrophilic domains.

6202. The device of item 6144, further comprising a polymeric carrier, wherein the polymeric carrier comprises a polymer having hydrophobic domains.

6203. The device of item 6144, further comprising a polymeric carrier, wherein the polymeric carrier comprises a non-conductive polymer.

6204. The device of item 6144, further comprising a polymeric carrier, wherein the polymeric carrier comprises an elastomer.

6205. The device of item 6144, further comprising a polymeric carrier, wherein the polymeric carrier comprises a hydrogel.

6206. The device of item 6144, further comprising a polymeric carrier, wherein the polymeric carrier comprises a silicone polymer.

6207. The device of item 6144, further comprising a polymeric carrier, wherein the polymeric carrier comprises a hydrocarbon polymer.

6208. The device of item 6144, further comprising a polymeric carrier, wherein the polymeric carrier comprises a styrene-derived polymer.

6209. The device of item 6144, further comprising a polymeric carrier, wherein the polymeric carrier comprises a butadiene polymer.

6210. The device of item 6144, further comprising a polymeric carrier, wherein the polymeric carrier comprises a macromer.

6211. The device of item 6144, further comprising a polymeric carrier, wherein the polymeric carrier comprises a poly(ethylene glycol) polymer.

6212. The device of item 6144, further comprising a polymeric carrier, wherein the polymeric carrier comprises an amorphous polymer.

6213. The device of item 6144, further comprising a lubricious coating.

6214. The device of item 6144 wherein the fibrosing agent is located within pores or holes of the device.

6215. The device of item 6144 wherein the fibrosing agent is located within a channel, lumen, or divet of the device.

6216. The device of item 6144, further comprising a second pharmaceutically active agent.

6217. The device of item 6144, further comprising an anti-inflammatory agent.

6218. The device of item 6144, further comprising an agent that inhibits infection.

6219. The device of item 6144, further comprising an agent that inhibits infection, wherein the agent is an anthracycline.

6220. The device of item 6144, further comprising an agent that inhibits infection, wherein the agent is doxorubicin.

6221. The device of item 6144, further comprising an agent that inhibits infection, wherein the agent is mitoxantrone.

6222. The device of item 6144, further comprising an agent that inhibits infection, wherein the agent is a fluoropyrimidine.

6223. The device of item 6144, further comprising an agent that inhibits infection, wherein the agent is 5-fluorouracil (5-FU).

6224. The device of item 6144, further comprising an agent that inhibits infection, wherein the agent is a folic acid antagonist.

6225. The device of item 6144, further comprising an agent that inhibits infection, wherein the agent is methotrexate.

6226. The device of item 6144, further comprising an agent that inhibits infection, wherein the agent is a podophylotoxin.

6227. The device of item 6144, further comprising an agent that inhibits infection, wherein the agent is etoposide.

6228. The device of item 6144, further comprising an agent that inhibits infection, wherein the agent is a camptothecin.

6229. The device of item 6144, further comprising an agent that inhibits infection, wherein the agent is a hydroxyurea.

6230. The device of item 6144, further comprising an agent that inhibits infection, wherein the agent is a platinum complex.

6231. The device of item 6144, further comprising an agent that inhibits infection, wherein the agent is cisplatin.

6232. The device of item 6144, further comprising an anti-thrombotic agent.

6233. The device of item 6144, further comprising a visualization agent.

6234. The device of item 6144, further comprising a visualization agent, wherein the visualization agent is a radiopaque material, wherein the radiopaque material comprises a metal, a halogenated compound, or a barium containing compound.

6235. The device of item 6144, further comprising a visualization agent, wherein the visualization agent is a radiopaque material, wherein the radiopaque material comprises barium, tantalum, or technetium.

6236. The device of item 6144, further comprising a visualization agent, wherein the visualization agent is a MRI responsive material.

6237. The device of item 6144, further comprising a visualization agent, wherein the visualization agent comprises a gadolinium chelate.

6238. The device of item 6144, further comprising a visualization agent, wherein the visualization agent comprises iron, magnesium, manganese, copper, or chromium.

6239. The device of item 6144, further comprising a visualization agent, wherein the visualization agent comprises an iron oxide compound.

6240. The device of item 6144, further comprising a visualization agent, wherein the visualization agent comprises a dye, pigment, or colorant.

6241. The device of item 6144, further comprising an echogenic material.

6242. The device of item 6144, further comprising an echogenic material, wherein the echogenic material is in the form of a coating.

6243. The device of item 6144 wherein the device is sterile.

6244. The device of item 6144 wherein the fibrosing agent is released into tissue in the vicinity of the device after deployment of the device.

6245. The device of item 6144 wherein the fibrosing agent is released into tissue in the vicinity of the device after deployment of the device, wherein the tissue is connective tissue.

6246. The device of item 6144 wherein the fibrosing agent is released into tissue in the vicinity of the device after deployment of the device, wherein the tissue is muscle tissue.

6247. The device of item 6144 wherein the fibrosing agent is released into tissue in the vicinity of the device after deployment of the device, wherein the tissue is nerve tissue.

6248. The device of item 6144 wherein the fibrosing agent is released into tissue in the vicinity of the device after deployment of the device, wherein the tissue is epithelium tissue.

6249. The device of item 6144 wherein the fibrosing agent is released in effective concentrations from the device over a period ranging from the time of deployment of the device to about 1 year.

6250. The device of item 6144 wherein the fibrosing agent is released in effective concentrations from the device over a period ranging from about 1 month to 6 months.

6251. The device of item 6144 wherein the fibrosing agent is released in effective concentrations from the device over a period ranging from about 1–90 days.

6252. The device of item 6144 wherein the fibrosing agent is released in effective concentrations from the device at a constant rate.

6253. The device of item 6144 wherein the fibrosing agent is released in effective concentrations from the device at an increasing rate.

6254. The device of item 6144 wherein the fibrosing agent is released in effective concentrations from the device at a decreasing rate.

6255. The device of item 6144 wherein the fibrosing agent is released in effective concentrations from the composition comprising the fibrosing agent by diffusion over a period ranging from the time of deployment of the device to about 90 days.

6256. The device of item 6144 wherein the fibrosing agent is released in effective concentrations from the composition comprising the fibrosing agent by erosion of the composition over a period ranging from the time of deployment of the device to about 90 days.

6257. The device of item 6144 wherein the device comprises about 0.01 µg to about 10 µg of the fibrosing agent.

6258. The device of item 6144 wherein the device comprises about 10 µg to about 10 mg of the fibrosing agent.

6259. The device of item 6144 wherein the device comprises about 10 mg to about 250 mg of the fibrosing agent.

6260. The device of item 6144 wherein the device comprises about 250 mg to about 1000 mg of the fibrosing agent.

6261. The device of item 6144 wherein the device comprises about 1000 mg to about 2500 mg of the fibrosing agent.

6262. The device of item 6144 wherein a surface of the device comprises less than 0.01 μg of the fibrosing agent per mm² of device surface to which the fibrosing agent is applied.

6263. The device of item 6144 wherein a surface of the device comprises about 0.01 μg to about 1 μg of the fibrosing agent per mm² of device surface to which the fibrosing agent is applied.

6264. The device of item 6144 wherein a surface of the device comprises about 1 μg to about 10 μg of the fibrosing agent per mm² of device surface to which the fibrosing agent is applied.

6265. The device of item 6144 wherein a surface of the device comprises about 10 μg to about 250 μg of the fibrosing agent per mm² of device surface to which the fibrosing agent is applied.

6266. The device of item 6144 wherein a surface of the device comprises about 250 μg to about 1000 μg of the fibrosing agent of fibrosing agent per mm² of device surface to which the fibrosing agent is applied.

6267. The device of item 6144 wherein a surface of the device comprises about 1000 μg to about 2500 μg of the fibrosing agent per mm² of device surface to which the fibrosing agent is applied.

6268. The device of item 6144 wherein the soft palate implant is injectable.

6269. A medical device comprising a vascular coil implant and a fibrosing agent, where the fibrosing agent induces a fibrotic response between the device and a patient in which the device is implanted.

6270. The device of item 6269 wherein the fibrosing agent promotes regeneration.

6271. The device of item 6269 wherein the fibrosing agent promotes angiogenesis.

6272. The device of item 6269 wherein the fibrosing agent promotes fibroblast migration.

6273. The device of item 6269 wherein the fibrosing agent promotes fibroblast proliferation.

6274. The device of item 6269 wherein the fibrosing agent promotes deposition of extracellular matrix (ECM).

6275. The device of item 6269 wherein the fibrosing agent promotes tissue remodeling.

6276. The device of item 6269 wherein the fibrosing agent is an arterial vessel wall irritant.

6277. The device of item 6269 wherein the fibrosing agent promotes adhesion between the device and a host into which the device is implanted.

6278. The device of item 6269 wherein the device delivers the fibrosing agent locally to tissue proximate to the device.

6279. The device of item 6269 wherein the fibrosing agent is or comprises silk.

6280. The device of item 6269 wherein the fibrosing agent is or comprises mineral particles.

6281. The device of item 6269 wherein the fibrosing agent is or comprises chitosan.

6282. The device of item 6269 wherein the fibrosing agent is or comprises polylysine.

6283. The device of item 6269 wherein the fibrosing agent is or comprises fibronectin.

6284. The device of item 6269 wherein the fibrosing agent is or comprises bleomycin.

6285. The device of item 6269 wherein the fibrosing agent is or comprises CTGF.

6286. The device of item 6269 wherein the fibrosing agent is in the form of a thread, or is in contact with a thread.

6287. The device of item 6269 wherein the fibrosing agent is in the form of a particulate.

6288. The device of item 6269 wherein the composition further comprises an inflammatory cytokine.

6289. The device of item 6269 wherein the composition further comprises an agent that stimulates cell proliferation.

6290. The device of item 6269 wherein the composition is in the form of a gel, paste, or spray.

6291. The device of item 6269 wherein the fibrosing agent is in the form of tufts.

6292. The device of item 6269, further comprising a polymer.

6293. The device of item 6269, further comprising a polymeric carrier.

6294. The device of item 6269 wherein the fibrosing agent promotes adhesion between the device and a host into which the device is implanted.

6295. The device of item 6269 wherein the device delivers the fibrosing agent locally to tissue proximate to the device.

6296. The device of item 6269, further comprising a coating, wherein the coating comprises the fibrosing agent.

6297. The device of item 6269, further comprising a coating, wherein the coating is disposed on a surface of the device.

6298. The device of item 6269, further comprising a coating, wherein the coating directly contacts the device.

6299. The device of item 6269, further comprising a coating, wherein the coating indirectly contacts the device.

6300. The device of item 6269, further comprising a coating, wherein the coating partially covers the device.

6301. The device of item 6269, further comprising a coating, wherein the coating completely covers the device.

6302. The device of item 6269, further comprising a coating, wherein the coating is a uniform coating.

6303. The device of item 6269, further comprising a coating, wherein the coating is a non-uniform coating.

6304. The device of item 6269, further comprising a coating, wherein the coating is a discontinuous coating.

6305. The device of item 6269, further comprising a coating, wherein the coating is a patterned coating.

6306. The device of item 6269, further comprising a coating, wherein the coating has a thickness of 100 μm or less.

6307. The device of item 6269, further comprising a coating, wherein the coating has a thickness of 10 μm or less.

6308. The device of item 6269, further comprising a coating, wherein the coating adheres to the surface of the device upon deployment of the device.

6309. The device of item 6269, further comprising a coating, wherein the coating is stable at room temperature for a period of 1 year.

6310. The device of item 6269, further comprising a coating, wherein the fibrosing agent is present in the coating in an amount ranging between about 0.0001% to about 1% by weight.

6311. The device of item 6269, further comprising a coating, wherein the fibrosing agent is present in the coating in an amount ranging between about 1% to about 10% by weight.

6312. The device of item 6269, further comprising a coating, wherein the fibrosing agent is present in the coating in an amount ranging between about 10% to about 25% by weight.

6313. The device of item 6269, further comprising a coating, wherein the fibrosing agent is present in the coating in an amount ranging between about 25% to about 70% by weight.

6314. The device of item 6269, further comprising a coating, wherein the coating further comprises a polymer.

6315. The device of item 6269, further comprising a first coating having a first composition and the second coating having a second composition.

6316. The device of item 6269, further comprising a first coating having a first composition and the second coating having a second composition, wherein the first composition and the second composition are different.

6317. The device of item 6269, further comprising a polymer.

6318. The device of item 6269, further comprising a polymeric carrier.

6319. The device of item 6269, further comprising a polymeric carrier, wherein the polymeric carrier comprises a copolymer.

6320. The device of item 6269, further comprising a polymeric carrier, wherein the polymeric carrier comprises a block copolymer.

6321. The device of item 6269, further comprising a polymeric carrier, wherein the polymeric carrier comprises a random copolymer.

6322. The device of item 6269, further comprising a polymeric carrier, wherein the polymeric carrier comprises a biodegradable polymer.

6323. The device of item 6269, further comprising a polymeric carrier, wherein the polymeric carrier comprises a non-biodegradable polymer.

6324. The device of item 6269, further comprising a polymeric carrier, wherein the polymeric carrier comprises a hydrophilic polymer.

6325. The device of item 6269, further comprising a polymeric carrier, wherein the polymeric carrier comprises a hydrophobic polymer.

6326. The device of item 6269, further comprising a polymeric carrier, wherein the polymeric carrier comprises a polymer having hydrophilic domains.

6327. The device of item 6269, further comprising a polymeric carrier, wherein the polymeric carrier comprises a polymer having hydrophobic domains.

6328. The device of item 6269, further comprising a polymeric carrier, wherein the polymeric carrier comprises a non-conductive polymer.

6329. The device of item 6269, further comprising a polymeric carrier, wherein the polymeric carrier comprises an elastomer.

6330. The device of item 6269, further comprising a polymeric carrier, wherein the polymeric carrier comprises a hydrogel.

6331. The device of item 6269, further comprising a polymeric carrier, wherein the polymeric carrier comprises a silicone polymer.

6332. The device of item 6269, further comprising a polymeric carrier, wherein the polymeric carrier comprises a hydrocarbon polymer.

6333. The device of item 6269, further comprising a polymeric carrier, wherein the polymeric carrier comprises a styrene-derived polymer.

6334. The device of item 6269, further comprising a polymeric carrier, wherein the polymeric carrier comprises a butadiene polymer.

6335. The device of item 6269, further comprising a polymeric carrier, wherein the polymeric carrier comprises a macromer.

6336. The device of item 6269, further comprising a polymeric carrier, wherein the polymeric carrier comprises a poly(ethylene glycol) polymer.

6337. The device of item 6269, further comprising a polymeric carrier, wherein the polymeric carrier comprises an amorphous polymer.

6338. The device of item 6269, further comprising a lubricious coating.

6339. The device of item 6269 wherein the fibrosing agent is located within pores or holes of the device.

6340. The device of item 6269 wherein the fibrosing agent is located within a channel, lumen, or divet of the device.

6341. The device of item 6269, further comprising a second pharmaceutically active agent.

6342. The device of item 6269, further comprising an anti-inflammatory agent.

6343. The device of item 6269, further comprising an agent that inhibits infection.

6344. The device of item 6269, further comprising an agent that inhibits infection, wherein the agent is an anthracycline.

6345. The device of item 6269, further comprising an agent that inhibits infection, wherein the agent is doxorubicin.

6346. The device of item 6269, further comprising an agent that inhibits infection, wherein the agent is mitoxantrone.

6347. The device of item 6269, further comprising an agent that inhibits infection, wherein the agent is a fluoropyrimidine.

6348. The device of item 6269, further comprising an agent that inhibits infection, wherein the agent is 5-fluorouracil (5-FU).

6349. The device of item 6269, further comprising an agent that inhibits infection, wherein the agent is a folic acid antagonist.

6350. The device of item 6269, further comprising an agent that inhibits infection, wherein the agent is methotrexate.

6351. The device of item 6269, further comprising an agent that inhibits infection, wherein the agent is a podophylotoxin.

6352. The device of item 6269, further comprising an agent that inhibits infection, wherein the agent is etoposide.

6353. The device of item 6269, further comprising an agent that inhibits infection, wherein the agent is a camptothecin.

6354. The device of item 6269, further comprising an agent that inhibits infection, wherein the agent is a hydroxyurea.

6355. The device of item 6269, further comprising an agent that inhibits infection, wherein the agent is a platinum complex.

6356. The device of item 6269, further comprising an agent that inhibits infection, wherein the agent is cisplatin.

6357. The device of item 6269, further comprising an anti-thrombotic agent.

6358. The device of item 6269, further comprising a visualization agent.

6359. The device of item 6269, further comprising a visualization agent, wherein the visualization agent is a radiopaque material, wherein the radiopaque material comprises a metal, a halogenated compound, or a barium containing compound.

6360. The device of item 6269, further comprising a visualization agent, wherein the visualization agent is a radiopaque material, wherein the radiopaque material comprises barium, tantalum, or technetium.

6361. The device of item 6269, further comprising a visualization agent, wherein the visualization agent is a MRI responsive material.

6362. The device of item 6269, further comprising a visualization agent, wherein the visualization agent comprises a gadolinium chelate.

6363. The device of item 6269, further comprising a visualization agent, wherein the visualization agent comprises iron, magnesium, manganese, copper, or chromium.

6364. The device of item 6269, further comprising a visualization agent, wherein the visualization agent comprises an iron oxide compound.

6365. The device of item 6269, further comprising a visualization agent, wherein the visualization agent comprises a dye, pigment, or colorant.

6366. The device of item 6269, further comprising an echogenic material.

6367. The device of item 6269, further comprising an echogenic material, wherein the echogenic material is in the form of a coating.

6368. The device of item 6269 wherein the device is sterile.

6369. The device of item 6269 wherein the fibrosing agent is released into tissue in the vicinity of the device after deployment of the device.

6370. The device of item 6269 wherein the fibrosing agent is released into tissue in the vicinity of the device after deployment of the device, wherein the tissue is connective tissue.

6371. The device of item 6269 wherein the fibrosing agent is released into tissue in the vicinity of the device after deployment of the device, wherein the tissue is muscle tissue.

6372. The device of item 6269 wherein the fibrosing agent is released into tissue in the vicinity of the device after deployment of the device, wherein the tissue is nerve tissue.

6373. The device of item 6269 wherein the fibrosing agent is released into tissue in the vicinity of the device after deployment of the device, wherein the tissue is epithelium tissue.

6374. The device of item 6269 wherein the fibrosing agent is released in effective concentrations from the device over a period ranging from the time of deployment of the device to about 1 year.

6375. The device of item 6269 wherein the fibrosing agent is released in effective concentrations from the device over a period ranging from about 1 month to 6 months.

6376. The device of item 6269 wherein the fibrosing agent is released in effective concentrations from the device over a period ranging from about 1–90 days.

6377. The device of item 6269 wherein the fibrosing agent is released in effective concentrations from the device at a constant rate.

6378. The device of item 6269 wherein the fibrosing agent is released in effective concentrations from the device at an increasing rate.

6379. The device of item 6269 wherein the fibrosing agent is released in effective concentrations from the device at a decreasing rate.

6380. The device of item 6269 wherein the fibrosing agent is released in effective concentrations from the composition comprising the fibrosing agent by diffusion over a period ranging from the time of deployment of the device to about 90 days.

6381. The device of item 6269 wherein the fibrosing agent is released in effective concentrations from the composition comprising the fibrosing agent by erosion of the composition over a period ranging from the time of deployment of the device to about 90 days.

6382. The device of item 6269 wherein the device comprises about 0.01 μg to about 10 μg of the fibrosing agent.

6383. The device of item 6269 wherein the device comprises about 10 μg to about 10 mg of the fibrosing agent.

6384. The device of item 6269 wherein the device comprises about 10 mg to about 250 mg of the fibrosing agent.

6385. The device of item 6269 wherein the device comprises about 250 mg to about 1000 mg of the fibrosing agent.

6386. The device of item 6269 wherein the device comprises about 1000 mg to about 2500 mg of the fibrosing agent.

6387. The device of item 6269 wherein a surface of the device comprises less than 0.01 μg of the fibrosing agent per $mm^2$ of device surface to which the fibrosing agent is applied.

6388. The device of item 6269 wherein a surface of the device comprises about 0.01 μg to about 1 μg of the fibrosing agent per $mm^2$ of device surface to which the fibrosing agent is applied.

6389. The device of item 6269 wherein a surface of the device comprises about 1 μg to about 10 μg of the fibrosing agent per $mm^2$ of device surface to which the fibrosing agent is applied.

6390. The device of item 6269 wherein a surface of the device comprises about 10 μg to about 250 μg of the fibrosing agent per $mm^2$ of device surface to which the fibrosing agent is applied.

6391. The device of item 6269 wherein a surface of the device comprises about 250 μg to about 1000 μg of the fibrosing agent of fibrosing agent per $mm^2$ of device surface to which the fibrosing agent is applied.

6392. The device of item 6269 wherein a surface of the device comprises about 1000 μg to about 2500 μg of the fibrosing agent per $mm^2$ of device surface to which the fibrosing agent is applied.

6393. The device of item 6269 wherein the vascular coil implant is composed of a porous, flexible PTFE material.

6394. The device of item 6269 wherein the vascular coil implant is composed of a bioactive component.

6395. The device of item 6269 wherein the vascular coil implant is biologically inert.

6396. The device of item 6269 wherein the vascular coil implant have a first state prior to insertion (primary phase) and a second state post insertion (secondary phase).

6397. A medical device comprising a vaso-occlusive coil implant and a fibrosing agent, where the fibrosing agent induces a fibrotic response between the device and a patient in which the device is implanted.

6398. The device of item 6397 wherein the fibrosing agent promotes regeneration.

6399. The device of item 6397 wherein the fibrosing agent promotes angiogenesis.

6400. The device of item 6397 wherein the fibrosing agent promotes fibroblast migration.

6401. The device of item 6397 wherein the fibrosing agent promotes fibroblast proliferation.

6402. The device of item 6397 wherein the fibrosing agent promotes deposition of extracellular matrix (ECM).

6403. The device of item 6397 wherein the fibrosing agent promotes tissue remodeling.

6404. The device of item 6397 wherein the fibrosing agent is an arterial vessel wall irritant.

6405. The device of item 6397 wherein the fibrosing agent promotes adhesion between the device and a host into which the device is implanted.

6406. The device of item 6397 wherein the device delivers the fibrosing agent locally to tissue proximate to the device.

6407. The device of item 6397 wherein the fibrosing agent is or comprises silk.

6408. The device of item 6397 wherein the fibrosing agent is or comprises mineral particles.

6409. The device of item 6397 wherein the fibrosing agent is or comprises chitosan.

6410. The device of item 6397 wherein the fibrosing agent is or comprises polylysine.

6411. The device of item 6397 wherein the fibrosing agent is or comprises fibronectin.

6412. The device of item 6397 wherein the fibrosing agent is or comprises bleomycin.

6413. The device of item 6397 wherein the fibrosing agent is or comprises CTGF.

6414. The device of item 6397 wherein the fibrosing agent is in the form of a thread, or is in contact with a thread.

6415. The device of item 6397 wherein the fibrosing agent is in the form of a particulate.

6416. The device of item 6397 wherein the composition further comprises an inflammatory cytokine.

6417. The device of item 6397 wherein the composition further comprises an agent that stimulates cell proliferation.

6418. The device of item 6397 wherein the composition is in the form of a gel, paste, or spray.

6419. The device of item 6397 wherein the fibrosing agent is in the form of tufts.

6420. The device of item 6397, further comprising a polymer.

6421. The device of item 6397, further comprising a polymeric carrier.

6422. The device of item 6397 wherein the fibrosing agent promotes adhesion between the device and a host into which the device is implanted.

6423. The device of item 6397 wherein the device delivers the fibrosing agent locally to tissue proximate to the device.

6424. The device of item 6397, further comprising a coating, wherein the coating comprises the fibrosing agent.

6425. The device of item 6397, further comprising a coating, wherein the coating is disposed on a surface of the device.

6426. The device of item 6397, further comprising a coating, wherein the coating directly contacts the device.

6427. The device of item 6397, further comprising a coating, wherein the coating indirectly contacts the device.

6428. The device of item 6397, further comprising a coating, wherein the coating partially covers the device.

6429. The device of item 6397, further comprising a coating, wherein the coating completely covers the device.

6430. The device of item 6397, further comprising a coating, wherein the coating is a uniform coating.

6431. The device of item 6397, further comprising a coating, wherein the coating is a non-uniform coating.

6432. The device of item 6397, further comprising a coating, wherein the coating is a discontinuous coating.

6433. The device of item 6397, further comprising a coating, wherein the coating is a patterned coating.

6434. The device of item 6397, further comprising a coating, wherein the coating has a thickness of 100 µm or less.

6435. The device of item 6397, further comprising a coating, wherein the coating has a thickness of 10 µm or less.

6436. The device of item 6397, further comprising a coating, wherein the coating adheres to the surface of the device upon deployment of the device.

6437. The device of item 6397, further comprising a coating, wherein the coating is stable at room temperature for a period of 1 year.

6438. The device of item 6397, further comprising a coating, wherein the fibrosing agent is present in the coating in an amount ranging between about 0.0001% to about 1% by weight.

6439. The device of item 6397, further comprising a coating, wherein the fibrosing agent is present in the coating in an amount ranging between about 1% to about 10% by weight.

6440. The device of item 6397, further comprising a coating, wherein the fibrosing agent is present in the coating in an amount ranging between about 10% to about 25% by weight.

6441. The device of item 6397, further comprising a coating, wherein the fibrosing agent is present in the coating in an amount ranging between about 25% to about 70% by weight.

6442. The device of item 6397, further comprising a coating, wherein the coating further comprises a polymer.

6443. The device of item 6397, further comprising a first coating having a first composition and the second coating having a second composition.

6444. The device of item 6397, further comprising a first coating having a first composition and the second coating having a second composition, wherein the first composition and the second composition are different.

6445. The device of item 6397, further comprising a polymer.

6446. The device of item 6397, further comprising a polymeric carrier.

6447. The device of item 6397, further comprising a polymeric carrier, wherein the polymeric carrier comprises a copolymer.

6448. The device of item 6397, further comprising a polymeric carrier, wherein the polymeric carrier comprises a block copolymer.

6449. The device of item 6397, further comprising a polymeric carrier, wherein the polymeric carrier comprises a random copolymer.

6450. The device of item 6397, further comprising a polymeric carrier, wherein the polymeric carrier comprises a biodegradable polymer.

6451. The device of item 6397, further comprising a polymeric carrier, wherein the polymeric carrier comprises a non-biodegradable polymer.

6452. The device of item 6397, further comprising a polymeric carrier, wherein the polymeric carrier comprises a hydrophilic polymer.

6453. The device of item 6397, further comprising a polymeric carrier, wherein the polymeric carrier comprises a hydrophobic polymer.

6454. The device of item 6397, further comprising a polymeric carrier, wherein the polymeric carrier comprises a polymer having hydrophilic domains.

6455. The device of item 6397, further comprising a polymeric carrier, wherein the polymeric carrier comprises a polymer having hydrophobic domains.

6456. The device of item 6397, further comprising a polymeric carrier, wherein the polymeric carrier comprises a non-conductive polymer.

6457. The device of item 6397, further comprising a polymeric carrier, wherein the polymeric carrier comprises an elastomer.

6458. The device of item 6397, further comprising a polymeric carrier, wherein the polymeric carrier comprises a hydrogel.

6459. The device of item 6397, further comprising a polymeric carrier, wherein the polymeric carrier comprises a silicone polymer.

6460. The device of item 6397, further comprising a polymeric carrier, wherein the polymeric carrier comprises a hydrocarbon polymer.

6461. The device of item 6397, further comprising a polymeric carrier, wherein the polymeric carrier comprises a styrene-derived polymer.

6462. The device of item 6397, further comprising a polymeric carrier, wherein the polymeric carrier comprises a butadiene polymer.

6463. The device of item 6397, further comprising a polymeric carrier, wherein the polymeric carrier comprises a macromer.

6464. The device of item 6397, further comprising a polymeric carrier, wherein the polymeric carrier comprises a poly(ethylene glycol) polymer.

6465. The device of item 6397, further comprising a polymeric carrier, wherein the polymeric carrier comprises an amorphous polymer.

6466. The device of item 6397, further comprising a lubricious coating.

6467. The device of item 6397 wherein the fibrosing agent is located within pores or holes of the device.

6468. The device of item 6397 wherein the fibrosing agent is located within a channel, lumen, or divet of the device.

6469. The device of item 6397, further comprising a second pharmaceutically active agent.

6470. The device of item 6397, further comprising an anti-inflammatory agent.

6471. The device of item 6397, further comprising an agent that inhibits infection.

6472. The device of item 6397, further comprising an agent that inhibits infection, wherein the agent is an anthracycline.

6473. The device of item 6397, further comprising an agent that inhibits infection, wherein the agent is doxorubicin.

6474. The device of item 6397, further comprising an agent that inhibits infection, wherein the agent is mitoxantrone.

6475. The device of item 6397, further comprising an agent that inhibits infection, wherein the agent is a fluoropyrimidine.

6476. The device of item 6397, further comprising an agent that inhibits infection, wherein the agent is 5-fluorouracil (5-FU).

6477. The device of item 6397, further comprising an agent that inhibits infection, wherein the agent is a folic acid antagonist.

6478. The device of item 6397, further comprising an agent that inhibits infection, wherein the agent is methotrexate.

6479. The device of item 6397, further comprising an agent that inhibits infection, wherein the agent is a podophylotoxin.

6480. The device of item 6397, further comprising an agent that inhibits infection, wherein the agent is etoposide.

6481. The device of item 6397, further comprising an agent that inhibits infection, wherein the agent is a camptothecin.

6482. The device of item 6397, further comprising an agent that inhibits infection, wherein the agent is a hydroxyurea.

6483. The device of item 6397, further comprising an agent that inhibits infection, wherein the agent is a platinum complex.

6484. The device of item 6397, further comprising an agent that inhibits infection, wherein the agent is cisplatin.

6485. The device of item 6397, further comprising an anti-thrombotic agent.

6486. The device of item 6397, further comprising a visualization agent.

6487. The device of item 6397, further comprising a visualization agent, wherein the visualization agent is a radiopaque material, wherein the radiopaque material comprises a metal, a halogenated compound, or a barium containing compound.

6488. The device of item 6397, further comprising a visualization agent, wherein the visualization agent is a radiopaque material, wherein the radiopaque material comprises barium, tantalum, or technetium.

6489. The device of item 6397, further comprising a visualization agent, wherein the visualization agent is a MRI responsive material.

6490. The device of item 6397, further comprising a visualization agent, wherein the visualization agent comprises a gadolinium chelate.

6491. The device of item 6397, further comprising a visualization agent, wherein the visualization agent comprises iron, magnesium, manganese, copper, or chromium.

6492. The device of item 6397, further comprising a visualization agent, wherein the visualization agent comprises an iron oxide compound.

6493. The device of item 6397, further comprising a visualization agent, wherein the visualization agent comprises a dye, pigment, or colorant.

6494. The device of item 6397, further comprising an echogenic material.

6495. The device of item 6397, further comprising an echogenic material, wherein the echogenic material is in the form of a coating.

6496. The device of item 6397 wherein the device is sterile.

6497. The device of item 6397 wherein the fibrosing agent is released into tissue in the vicinity of the device after deployment of the device.

6498. The device of item 6397 wherein the fibrosing agent is released into tissue in the vicinity of the device after deployment of the device, wherein the tissue is connective tissue.

6499. The device of item 6397 wherein the fibrosing agent is released into tissue in the vicinity of the device after deployment of the device, wherein the tissue is muscle tissue.

6500. The device of item 6397 wherein the fibrosing agent is released into tissue in the vicinity of the device after deployment of the device, wherein the tissue is nerve tissue.

6501. The device of item 6397 wherein the fibrosing agent is released into tissue in the vicinity of the device after deployment of the device, wherein the tissue is epithelium tissue.

6502. The device of item 6397 wherein the fibrosing agent is released in effective concentrations from the device over a period ranging from the time of deployment of the device to about 1 year.

6503. The device of item 6397 wherein the fibrosing agent is released in effective concentrations from the device over a period ranging from about 1 month to 6 months.

6504. The device of item 6397 wherein the fibrosing agent is released in effective concentrations from the device over a period ranging from about 1–90 days.

6505. The device of item 6397 wherein the fibrosing agent is released in effective concentrations from the device at a constant rate.

6506. The device of item 6397 wherein the fibrosing agent is released in effective concentrations from the device at an increasing rate.

6507. The device of item 6397 wherein the fibrosing agent is released in effective concentrations from the device at a decreasing rate.

6508. The device of item 6397 wherein the fibrosing agent is released in effective concentrations from the composition comprising the fibrosing agent by diffusion over a period ranging from the time of deployment of the device to about 90 days.

6509. The device of item 6397 wherein the fibrosing agent is released in effective concentrations from the composition comprising the fibrosing agent by erosion of the composition over a period ranging from the time of deployment of the device to about 90 days.

6510. The device of item 6397 wherein the device comprises about 0.01 µg to about 10 µg of the fibrosing agent.

6511. The device of item 6397 wherein the device comprises about 10 µg to about 10 mg of the fibrosing agent.

6512. The device of item 6397 wherein the device comprises about 10 mg to about 250 mg of the fibrosing agent.

6513. The device of item 6397 wherein the device comprises about 250 mg to about 1000 mg of the fibrosing agent.

6514. The device of item 6397 wherein the device comprises about 1000 mg to about 2500 mg of the fibrosing agent.

6515. The device of item 6397 wherein a surface of the device comprises less than 0.01 µg of the fibrosing agent per mm$^2$ of device surface to which the fibrosing agent is applied.

6516. The device of item 6397 wherein a surface of the device comprises about 0.01 µg to about 1 µg of the fibrosing agent per mm$^2$ of device surface to which the fibrosing agent is applied.

6517. The device of item 6397 wherein a surface of the device comprises about 1 µg to about 10 µg of the fibrosing agent per mm$^2$ of device surface to which the fibrosing agent is applied.

6518. The device of item 6397 wherein a surface of the device comprises about 10 µg to about 250 µg of the fibrosing agent per mm$^2$ of device surface to which the fibrosing agent is applied.

6519. The device of item 6397 wherein a surface of the device comprises about 250 µg to about 1000 µg of the fibrosing agent of fibrosing agent per mm$^2$ of device surface to which the fibrosing agent is applied.

6520. The device of item 6397 wherein a surface of the device comprises about 1000 µg to about 2500 µg of the fibrosing agent per mm$^2$ of device surface to which the fibrosing agent is applied.

6521. A medical device comprising a vaso-occlusion implant and a fibrosing agent, where the fibrosing agent induces a fibrotic response between the device and a patient in which the device is implanted.

6522. The device of item 6521 wherein the fibrosing agent promotes regeneration.

6523. The device of item 6521 wherein the fibrosing agent promotes angiogenesis.

6524. The device of item 6521 wherein the fibrosing agent promotes fibroblast migration.

6525. The device of item 6521 wherein the fibrosing agent promotes fibroblast proliferation.

6526. The device of item 6521 wherein the fibrosing agent promotes deposition of extracellular matrix (ECM).

6527. The device of item 6521 wherein the fibrosing agent promotes tissue remodeling.

6528. The device of item 6521 wherein the fibrosing agent is an arterial vessel wall irritant.

6529. The device of item 6521 wherein the fibrosing agent promotes adhesion between the device and a host into which the device is implanted.

6530. The device of item 6521 wherein the device delivers the fibrosing agent locally to tissue proximate to the device.

6531. The device of item 6521 wherein the fibrosing agent is or comprises silk.

6532. The device of item 6521 wherein the fibrosing agent is or comprises mineral particles.

6533. The device of item 6521 wherein the fibrosing agent is or comprises chitosan.

6534. The device of item 6521 wherein the fibrosing agent is or comprises polylysine.

6535. The device of item 6521 wherein the fibrosing agent is or comprises fibronectin.

6536. The device of item 6521 wherein the fibrosing agent is or comprises bleomycin.

6537. The device of item 6521 wherein the fibrosing agent is or comprises CTGF.

6538. The device of item 6521 wherein the fibrosing agent is in the form of a thread, or is in contact with a thread.

6539. The device of item 6521 wherein the fibrosing agent is in the form of a particulate.

6540. The device of item 6521 wherein the composition further comprises an inflammatory cytokine.

6541. The device of item 6521 wherein the composition further comprises an agent that stimulates cell proliferation.

6542. The device of item 6521 wherein the composition is in the form of a gel, paste, or spray.

6543. The device of item 6521 wherein the fibrosing agent is in the form of tufts.

6544. The device of item 6521, further comprising a polymer.

6545. The device of item 6521, further comprising a polymeric carrier.

6546. The device of item 6521 wherein the fibrosing agent promotes adhesion between the device and a host into which the device is implanted.

6547. The device of item 6521 wherein the device delivers the fibrosing agent locally to tissue proximate to the device.

6548. The device of item 6521, further comprising a coating, wherein the coating comprises the fibrosing agent.

6549. The device of item 6521, further comprising a coating, wherein the coating is disposed on a surface of the device.

6550. The device of item 6521, further comprising a coating, wherein the coating directly contacts the device.

6551. The device of item 6521, further comprising a coating, wherein the coating indirectly contacts the device.

6552. The device of item 6521, further comprising a coating, wherein the coating partially covers the device.

6553. The device of item 6521, further comprising a coating, wherein the coating completely covers the device.

6554. The device of item 6521, further comprising a coating, wherein the coating is a uniform coating.

6555. The device of item 6521, further comprising a coating, wherein the coating is a non-uniform coating.

6556. The device of item 6521, further comprising a coating, wherein the coating is a discontinuous coating.

6557. The device of item 6521, further comprising a coating, wherein the coating is a patterned coating.

6558. The device of item 6521, further comprising a coating, wherein the coating has a thickness of 100 µm or less.

6559. The device of item 6521, further comprising a coating, wherein the coating has a thickness of 10 µm or less.

6560. The device of item 6521, further comprising a coating, wherein the coating adheres to the surface of the device upon deployment of the device.

6561. The device of item 6521, further comprising a coating, wherein the coating is stable at room temperature for a period of 1 year.

6562. The device of item 6521, further comprising a coating, wherein the fibrosing agent is present in the coating in an amount ranging between about 0.0001% to about 1% by weight.

6563. The device of item 6521, further comprising a coating, wherein the fibrosing agent is present in the coating in an amount ranging between about 1% to about 10% by weight.

6564. The device of item 6521, further comprising a coating, wherein the fibrosing agent is present in the coating in an amount ranging between about 10% to about 25% by weight.

6565. The device of item 6521, further comprising a coating, wherein the fibrosing agent is present in the coating in an amount ranging between about 25% to about 70% by weight.

6566. The device of item 6521, further comprising a coating, wherein the coating further comprises a polymer.

6567. The device of item 6521, further comprising a first coating having a first composition and the second coating having a second composition.

6568. The device of item 6521, further comprising a first coating having a first composition and the second coating having a second composition, wherein the first composition and the second composition are different.

6569. The device of item 6521, further comprising a polymer.

6570. The device of item 6521, further comprising a polymeric carrier.

6571. The device of item 6521, further comprising a polymeric carrier, wherein the polymeric carrier comprises a copolymer.

6572. The device of item 6521, further comprising a polymeric carrier, wherein the polymeric carrier comprises a block copolymer.

6573. The device of item 6521, further comprising a polymeric carrier, wherein the polymeric carrier comprises a random copolymer.

6574. The device of item 6521, further comprising a polymeric carrier, wherein the polymeric carrier comprises a biodegradable polymer.

6575. The device of item 6521, further comprising a polymeric carrier, wherein the polymeric carrier comprises a non-biodegradable polymer.

6576. The device of item 6521, further comprising a polymeric carrier, wherein the polymeric carrier comprises a hydrophilic polymer.

6577. The device of item 6521, further comprising a polymeric carrier, wherein the polymeric carrier comprises a hydrophobic polymer.

6578. The device of item 6521, further comprising a polymeric carrier, wherein the polymeric carrier comprises a polymer having hydrophilic domains.

6579. The device of item 6521, further comprising a polymeric carrier, wherein the polymeric carrier comprises a polymer having hydrophobic domains.

6580. The device of item 6521, further comprising a polymeric carrier, wherein the polymeric carrier comprises a non-conductive polymer.

6581. The device of item 6521, further comprising a polymeric carrier, wherein the polymeric carrier comprises an elastomer.

6582. The device of item 6521, further comprising a polymeric carrier, wherein the polymeric carrier comprises a hydrogel.

6583. The device of item 6521, further comprising a polymeric carrier, wherein the polymeric carrier comprises a silicone polymer.

6584. The device of item 6521, further comprising a polymeric carrier, wherein the polymeric carrier comprises a hydrocarbon polymer.

6585. The device of item 6521, further comprising a polymeric carrier, wherein the polymeric carrier comprises a styrene-derived polymer.

6586. The device of item 6521, further comprising a polymeric carrier, wherein the polymeric carrier comprises a butadiene polymer.

6587. The device of item 6521, further comprising a polymeric carrier, wherein the polymeric carrier comprises a macromer.

6588. The device of item 6521, further comprising a polymeric carrier, wherein the polymeric carrier comprises a poly(ethylene glycol) polymer.

6589. The device of item 6521, further comprising a polymeric carrier, wherein the polymeric carrier comprises an amorphous polymer.

6590. The device of item 6521, further comprising a lubricious coating.

6591. The device of item 6521 wherein the fibrosing agent is located within pores or holes of the device.

6592. The device of item 6521 wherein the fibrosing agent is located within a channel, lumen, or divet of the device.

6593. The device of item 6521, further comprising a second pharmaceutically active agent.

6594. The device of item 6521, further comprising an anti-inflammatory agent.

6595. The device of item 6521, further comprising an agent that inhibits infection.

6596. The device of item 6521, further comprising an agent that inhibits infection, wherein the agent is an anthracycline.

6597. The device of item 6521, further comprising an agent that inhibits infection, wherein the agent is doxorubicin.

6598. The device of item 6521, further comprising an agent that inhibits infection, wherein the agent is mitoxantrone.

6599. The device of item 6521, further comprising an agent that inhibits infection, wherein the agent is a fluoropyrimidine.

6600. The device of item 6521, further comprising an agent that inhibits infection, wherein the agent is 5-fluorouracil (5-FU).

6601. The device of item 6521, further comprising an agent that inhibits infection, wherein the agent is a folic acid antagonist.

6602. The device of item 6521, further comprising an agent that inhibits infection, wherein the agent is methotrexate.

6603. The device of item 6521, further comprising an agent that inhibits infection, wherein the agent is a podophylotoxin.

6604. The device of item 6521, further comprising an agent that inhibits infection, wherein the agent is etoposide.

6605. The device of item 6521, further comprising an agent that inhibits infection, wherein the agent is a camptothecin.

6606. The device of item 6521, further comprising an agent that inhibits infection, wherein the agent is a hydroxyurea.

6607. The device of item 6521, further comprising an agent that inhibits infection, wherein the agent is a platinum complex.

6608. The device of item 6521, further comprising an agent that inhibits infection, wherein the agent is cisplatin.

6609. The device of item 6521, further comprising an anti-thrombotic agent.

6610. The device of item 6521, further comprising a visualization agent.

6611. The device of item 6521, further comprising a visualization agent, wherein the visualization agent is a radiopaque material, wherein the radiopaque material comprises a metal, a halogenated compound, or a barium containing compound.

6612. The device of item 6521, further comprising a visualization agent, wherein the visualization agent is a radiopaque material, wherein the radiopaque material comprises barium, tantalum, or technetium.

6613. The device of item 6521, further comprising a visualization agent, wherein the visualization agent is a MRI responsive material.

6614. The device of item 6521, further comprising a visualization agent, wherein the visualization agent comprises a gadolinium chelate.

6615. The device of item 6521, further comprising a visualization agent, wherein the visualization agent comprises iron, magnesium, manganese, copper, or chromium.

6616. The device of item 6521, further comprising a visualization agent, wherein the visualization agent comprises an iron oxide compound.

6617. The device of item 6521, further comprising a visualization agent, wherein the visualization agent comprises a dye, pigment, or colorant.

6618. The device of item 6521, further comprising an echogenic material.

6619. The device of item 6521, further comprising an echogenic material, wherein the echogenic material is in the form of a coating.

6620. The device of item 6521 wherein the device is sterile.

6621. The device of item 6521 wherein the fibrosing agent is released into tissue in the vicinity of the device after deployment of the device.

6622. The device of item 6521 wherein the fibrosing agent is released into tissue in the vicinity of the device after deployment of the device, wherein the tissue is connective tissue.

6623. The device of item 6521 wherein the fibrosing agent is released into tissue in the vicinity of the device after deployment of the device, wherein the tissue is muscle tissue.

6624. The device of item 6521 wherein the fibrosing agent is released into tissue in the vicinity of the device after deployment of the device, wherein the tissue is nerve tissue.

6625. The device of item 6521 wherein the fibrosing agent is released into tissue in the vicinity of the device after deployment of the device, wherein the tissue is epithelium tissue.

6626. The device of item 6521 wherein the fibrosing agent is released in effective concentrations from the device over a period ranging from the time of deployment of the device to about 1 year.

6627. The device of item 6521 wherein the fibrosing agent is released in effective concentrations from the device over a period ranging from about 1 month to 6 months.

6628. The device of item 6521 wherein the fibrosing agent is released in effective concentrations from the device over a period ranging from about 1–90 days.

6629. The device of item 6521 wherein the fibrosing agent is released in effective concentrations from the device at a constant rate.

6630. The device of item 6521 wherein the fibrosing agent is released in effective concentrations from the device at an increasing rate.

6631. The device of item 6521 wherein the fibrosing agent is released in effective concentrations from the device at a decreasing rate.

6632. The device of item 6521 wherein the fibrosing agent is released in effective concentrations from the composition comprising the fibrosing agent by diffusion over a period ranging from the time of deployment of the device to about 90 days.

6633. The device of item 6521 wherein the fibrosing agent is released in effective concentrations from the composition comprising the fibrosing agent by erosion of the composition over a period ranging from the time of deployment of the device to about 90 days.

6634. The device of item 6521 wherein the device comprises about 0.01 µg to about 10 µg of the fibrosing agent.

6635. The device of item 6521 wherein the device comprises about 10 µg to about 10 mg of the fibrosing agent.

6636. The device of item 6521 wherein the device comprises about 10 mg to about 250 mg of the fibrosing agent.

6637. The device of item 6521 wherein the device comprises about 250 mg to about 1000 mg of the fibrosing agent.

6638. The device of item 6521 wherein the device comprises about 1000 mg to about 2500 mg of the fibrosing agent.

6639. The device of item 6521 wherein a surface of the device comprises less than 0.01 µg of the fibrosing agent per $mm^2$ of device surface to which the fibrosing agent is applied.

6640. The device of item 6521 wherein a surface of the device comprises about 0.01 µg to about 1 µg of the fibrosing agent per $mm^2$ of device surface to which the fibrosing agent is applied.

6641. The device of item 6521 wherein a surface of the device comprises about 1 µg to about 10 µg of the fibrosing agent per $mm^2$ of device surface to which the fibrosing agent is applied.

6642. The device of item 6521 wherein a surface of the device comprises about 10 µg to about 250 µg of the fibrosing agent per $mm^2$ of device surface to which the fibrosing agent is applied.

6643. The device of item 6521 wherein a surface of the device comprises about 250 µg to about 1000 µg of the fibrosing agent of fibrosing agent per mm² of device surface to which the fibrosing agent is applied.

6644. The device of item 6521 wherein a surface of the device comprises about 1000 µg to about 2500 µg of the fibrosing agent per mm² of device surface to which the fibrosing agent is applied.

6645. A medical device comprising a non-coiled vaso-occlusive implant and a fibrosing agent, where the fibrosing agent induces a fibrotic response between the device and a patient in which the device is implanted.

6646. The device of item 6645 wherein the fibrosing agent promotes regeneration.

6647. The device of item 6645 wherein the fibrosing agent promotes angiogenesis.

6648. The device of item 6645 wherein the fibrosing agent promotes fibroblast migration.

6649. The device of item 6645 wherein the fibrosing agent promotes fibroblast proliferation.

6650. The device of item 6645 wherein the fibrosing agent promotes deposition of extracellular matrix (ECM).

6651. The device of item 6645 wherein the fibrosing agent promotes tissue remodeling.

6652. The device of item 6645 wherein the fibrosing agent is an arterial vessel wall irritant.

6653. The device of item 6645 wherein the fibrosing agent promotes adhesion between the device and a host into which the device is implanted.

6654. The device of item 6645 wherein the device delivers the fibrosing agent locally to tissue proximate to the device.

6655. The device of item 6645 wherein the fibrosing agent is or comprises silk.

6656. The device of item 6645 wherein the fibrosing agent is or comprises mineral particles.

6657. The device of item 6645 wherein the fibrosing agent is or comprises chitosan.

6658. The device of item 6645 wherein the fibrosing agent is or comprises polylysine.

6659. The device of item 6645 wherein the fibrosing agent is or comprises fibronectin.

6660. The device of item 6645 wherein the fibrosing agent is or comprises bleomycin.

6661. The device of item 6645 wherein the fibrosing agent is or comprises CTGF.

6662. The device of item 6645 wherein the fibrosing agent is in the form of a thread, or is in contact with a thread.

6663. The device of item 6645 wherein the fibrosing agent is in the form of a particulate.

6664. The device of item 6645 wherein the composition further comprises an inflammatory cytokine.

6665. The device of item 6645 wherein the composition further comprises an agent that stimulates cell proliferation.

6666. The device of item 6645 wherein the composition is in the form of a gel, paste, or spray.

6667. The device of item 6645 wherein the fibrosing agent is in the form of tufts.

6668. The device of item 6645, further comprising a polymer.

6669. The device of item 6645, further comprising a polymeric carrier.

6670. The device of item 6645 wherein the fibrosing agent promotes adhesion between the device and a host into which the device is implanted.

6671. The device of item 6645 wherein the device delivers the fibrosing agent locally to tissue proximate to the device.

6672. The device of item 6645, further comprising a coating, wherein the coating comprises the fibrosing agent.

6673. The device of item 6645, further comprising a coating, wherein the coating is disposed on a surface of the device.

6674. The device of item 6645, further comprising a coating, wherein the coating directly contacts the device.

6675. The device of item 6645, further comprising a coating, wherein the coating indirectly contacts the device.

6676. The device of item 6645, further comprising a coating, wherein the coating partially covers the device.

6677. The device of item 6645, further comprising a coating, wherein the coating completely covers the device.

6678. The device of item 6645, further comprising a coating, wherein the coating is a uniform coating.

6679. The device of item 6645, further comprising a coating, wherein the coating is a non-uniform coating.

6680. The device of item 6645, further comprising a coating, wherein the coating is a discontinuous coating.

6681. The device of item 6645, further comprising a coating, wherein the coating is a patterned coating.

6682. The device of item 6645, further comprising a coating, wherein the coating has a thickness of 100 µm or less.

6683. The device of item 6645, further comprising a coating, wherein the coating has a thickness of 10 µm or less.

6684. The device of item 6645, further comprising a coating, wherein the coating adheres to the surface of the device upon deployment of the device.

6685. The device of item 6645, further comprising a coating, wherein the coating is stable at room temperature for a period of 1 year.

6686. The device of item 6645, further comprising a coating, wherein the fibrosing agent is present in the coating in an amount ranging between about 0.0001% to about 1% by weight.

6687. The device of item 6645, further comprising a coating, wherein the fibrosing agent is present in the coating in an amount ranging between about 1% to about 10% by weight.

6688. The device of item 6645, further comprising a coating, wherein the fibrosing agent is present in the coating in an amount ranging between about 10% to about 25% by weight.

6689. The device of item 6645, further comprising a coating, wherein the fibrosing agent is present in the coating in an amount ranging between about 25% to about 70% by weight.

6690. The device of item 6645, further comprising a coating, wherein the coating further comprises a polymer.

6691. The device of item 6645, further comprising a first coating having a first composition and the second coating having a second composition.

6692. The device of item 6645, further comprising a first coating having a first composition and the second coating having a second composition, wherein the first composition and the second composition are different.

6693. The device of item 6645, further comprising a polymer.

6694. The device of item 6645, further comprising a polymeric carrier.

6695. The device of item 6645, further comprising a polymeric carrier, wherein the polymeric carrier comprises a copolymer.

6696. The device of item 6645, further comprising a polymeric carrier, wherein the polymeric carrier comprises a block copolymer.

6697. The device of item 6645, further comprising a polymeric carrier, wherein the polymeric carrier comprises a random copolymer.

6698. The device of item 6645, further comprising a polymeric carrier, wherein the polymeric carrier comprises a biodegradable polymer.

6699. The device of item 6645, further comprising a polymeric carrier, wherein the polymeric carrier comprises a non-biodegradable polymer.

6700. The device of item 6645, further comprising a polymeric carrier, wherein the polymeric carrier comprises a hydrophilic polymer.

6701. The device of item 6645, further comprising a polymeric carrier, wherein the polymeric carrier comprises a hydrophobic polymer.

6702. The device of item 6645, further comprising a polymeric carrier, wherein the polymeric carrier comprises a polymer having hydrophilic domains.

6703. The device of item 6645, further comprising a polymeric carrier, wherein the polymeric carrier comprises a polymer having hydrophobic domains.

6704. The device of item 6645, further comprising a polymeric carrier, wherein the polymeric carrier comprises a non-conductive polymer.

6705. The device of item 6645, further comprising a polymeric carrier, wherein the polymeric carrier comprises an elastomer.

6706. The device of item 6645, further comprising a polymeric carrier, wherein the polymeric carrier comprises a hydrogel.

6707. The device of item 6645, further comprising a polymeric carrier, wherein the polymeric carrier comprises a silicone polymer.

6708. The device of item 6645, further comprising a polymeric carrier, wherein the polymeric carrier comprises a hydrocarbon polymer.

6709. The device of item 6645, further comprising a polymeric carrier, wherein the polymeric carrier comprises a styrene-derived polymer.

6710. The device of item 6645, further comprising a polymeric carrier, wherein the polymeric carrier comprises a butadiene polymer.

6711. The device of item 6645, further comprising a polymeric carrier, wherein the polymeric carrier comprises a macromer.

6712. The device of item 6645, further comprising a polymeric carrier, wherein the polymeric carrier comprises a poly(ethylene glycol) polymer.

6713. The device of item 6645, further comprising a polymeric carrier, wherein the polymeric carrier comprises an amorphous polymer.

6714. The device of item 6645, further comprising a lubricious coating.

6715. The device of item 6645 wherein the fibrosing agent is located within pores or holes of the device.

6716. The device of item 6645 wherein the fibrosing agent is located within a channel, lumen, or divet of the device.

6717. The device of item 6645, further comprising a second pharmaceutically active agent.

6718. The device of item 6645, further comprising an anti-inflammatory agent.

6719. The device of item 6645, further comprising an agent that inhibits infection.

6720. The device of item 6645, further comprising an agent that inhibits infection, wherein the agent is an anthracycline.

6721. The device of item 6645, further comprising an agent that inhibits infection, wherein the agent is doxorubicin.

6722. The device of item 6645, further comprising an agent that inhibits infection, wherein the agent is mitoxantrone.

6723. The device of item 6645, further comprising an agent that inhibits infection, wherein the agent is a fluoropyrimidine.

6724. The device of item 6645, further comprising an agent that inhibits infection, wherein the agent is 5-fluorouracil (5-FU).

6725. The device of item 6645, further comprising an agent that inhibits infection, wherein the agent is a folic acid antagonist.

6726. The device of item 6645, further comprising an agent that inhibits infection, wherein the agent is methotrexate.

6727. The device of item 6645, further comprising an agent that inhibits infection, wherein the agent is a podophylotoxin.

6728. The device of item 6645, further comprising an agent that inhibits infection, wherein the agent is etoposide.

6729. The device of item 6645, further comprising an agent that inhibits infection, wherein the agent is a camptothecin.

6730. The device of item 6645, further comprising an agent that inhibits infection, wherein the agent is a hydroxyurea.

6731. The device of item 6645, further comprising an agent that inhibits infection, wherein the agent is a platinum complex.

6732. The device of item 6645, further comprising an agent that inhibits infection, wherein the agent is cisplatin.

6733. The device of item 6645, further comprising an anti-thrombotic agent.

6734. The device of item 6645, further comprising a visualization agent.

6735. The device of item 6645, further comprising a visualization agent, wherein the visualization agent is a radiopaque material, wherein the radiopaque material comprises a metal, a halogenated compound, or a barium containing compound.

6736. The device of item 6645, further comprising a visualization agent, wherein the visualization agent is a radiopaque material, wherein the radiopaque material comprises barium, tantalum, or technetium.

6737. The device of item 6645, further comprising a visualization agent, wherein the visualization agent is a MRI responsive material.

6738. The device of item 6645, further comprising a visualization agent, wherein the visualization agent comprises a gadolinium chelate.

6739. The device of item 6645, further comprising a visualization agent, wherein the visualization agent comprises iron, magnesium, manganese, copper, or chromium.

6740. The device of item 6645, further comprising a visualization agent, wherein the visualization agent comprises an iron oxide compound.

6741. The device of item 6645, further comprising a visualization agent, wherein the visualization agent comprises a dye, pigment, or colorant.

6742. The device of item 6645, further comprising an echogenic material.

6743. The device of item 6645, further comprising an echogenic material, wherein the echogenic material is in the form of a coating.

6744. The device of item 6645 wherein the device is sterile.

6745. The device of item 6645 wherein the fibrosing agent is released into tissue in the vicinity of the device after deployment of the device.

6746. The device of item 6645 wherein the fibrosing agent is released into tissue in the vicinity of the device after deployment of the device, wherein the tissue is connective tissue.

6747. The device of item 6645 wherein the fibrosing agent is released into tissue in the vicinity of the device after deployment of the device, wherein the tissue is muscle tissue.

6748. The device of item 6645 wherein the fibrosing agent is released into tissue in the vicinity of the device after deployment of the device, wherein the tissue is nerve tissue.

6749. The device of item 6645 wherein the fibrosing agent is released into tissue in the vicinity of the device after deployment of the device, wherein the tissue is epithelium tissue.

6750. The device of item 6645 wherein the fibrosing agent is released in effective concentrations from the device over a period ranging from the time of deployment of the device to about 1 year.

6751. The device of item 6645 wherein the fibrosing agent is released in effective concentrations from the device over a period ranging from about 1 month to 6 months.

6752. The device of item 6645 wherein the fibrosing agent is released in effective concentrations from the device over a period ranging from about 1–90 days.

6753. The device of item 6645 wherein the fibrosing agent is released in effective concentrations from the device at a constant rate.

6754. The device of item 6645 wherein the fibrosing agent is released in effective concentrations from the device at an increasing rate.

6755. The device of item 6645 wherein the fibrosing agent is released in effective concentrations from the device at a decreasing rate.

6756. The device of item 6645 wherein the fibrosing agent is released in effective concentrations from the composition comprising the fibrosing agent by diffusion over a period ranging from the time of deployment of the device to about 90 days.

6757. The device of item 6645 wherein the fibrosing agent is released in effective concentrations from the composition comprising the fibrosing agent by erosion of the composition over a period ranging from the time of deployment of the device to about 90 days.

6758. The device of item 6645 wherein the device comprises about 0.01 μg to about 10 μg of the fibrosing agent.

6759. The device of item 6645 wherein the device comprises about 10 μg to about 10 mg of the fibrosing agent.

6760. The device of item 6645 wherein the device comprises about 10 mg to about 250 mg of the fibrosing agent.

6761. The device of item 6645 wherein the device comprises about 250 mg to about 1000 mg of the fibrosing agent.

6762. The device of item 6645 wherein the device comprises about 1000 mg to about 2500 mg of the fibrosing agent.

6763. The device of item 6645 wherein a surface of the device comprises less than 0.01 μg of the fibrosing agent per mm$^2$ of device surface to which the fibrosing agent is applied.

6764. The device of item 6645 wherein a surface of the device comprises about 0.01 μg to about 1 μg of the fibrosing agent per mm$^2$ of device surface to which the fibrosing agent is applied.

6765. The device of item 6645 wherein a surface of the device comprises about 1 μg to about 10 μg of the fibrosing agent per mm$^2$ of device surface to which the fibrosing agent is applied.

6766. The device of item 6645 wherein a surface of the device comprises about 10 μg to about 250 μg of the fibrosing agent per mm$^2$ of device surface to which the fibrosing agent is applied.

6767. The device of item 6645 wherein a surface of the device comprises about 250 μg to about 1000 μg of the fibrosing agent of fibrosing agent per mm$^2$ of device surface to which the fibrosing agent is applied.

6768. The device of item 6645 wherein a surface of the device comprises about 1000 μg to about 2500 μg of the fibrosing agent per mm$^2$ of device surface to which the fibrosing agent is applied.

6769. The device of item 6645 wherein the vascular occlusion implant is expandable.

6770. A medical device comprising a hernia mesh implant and a fibrosing agent, where the fibrosing agent induces a fibrotic response between the device and a patient in which the device is implanted.

6771. The device of item 6770 wherein the fibrosing agent promotes regeneration.

6772. The device of item 6770 wherein the fibrosing agent promotes angiogenesis.

6773. The device of item 6770 wherein the fibrosing agent promotes fibroblast migration.

6774. The device of item 6770 wherein the fibrosing agent promotes fibroblast proliferation.

6775. The device of item 6770 wherein the fibrosing agent promotes deposition of extracellular matrix (ECM).

6776. The device of item 6770 wherein the fibrosing agent promotes tissue remodeling.

6777. The device of item 6770 wherein the fibrosing agent is an arterial vessel wall irritant.

6778. The device of item 6770 wherein the fibrosing agent promotes adhesion between the device and a host into which the device is implanted.

6779. The device of item 6770 wherein the device delivers the fibrosing agent locally to tissue proximate to the device.

6780. The device of item 6770 wherein the fibrosing agent is or comprises silk.

6781. The device of item 6770 wherein the fibrosing agent is or comprises mineral particles.

6782. The device of item 6770 wherein the fibrosing agent is or comprises chitosan.

6783. The device of item 6770 wherein the fibrosing agent is or comprises polylysine.

6784. The device of item 6770 wherein the fibrosing agent is or comprises fibronectin.

6785. The device of item 6770 wherein the fibrosing agent is or comprises bleomycin.

6786. The device of item 6770 wherein the fibrosing agent is or comprises CTGF.

6787. The device of item 6770 wherein the fibrosing agent is in the form of a thread, or is in contact with a thread.

6788. The device of item 6770 wherein the fibrosing agent is in the form of a particulate.

6789. The device of item 6770 wherein the composition further comprises an inflammatory cytokine.

6790. The device of item 6770 wherein the composition further comprises an agent that stimulates cell proliferation.

6791. The device of item 6770 wherein the composition is in the form of a gel, paste, or spray.

6792. The device of item 6770 wherein the fibrosing agent is in the form of tufts.

6793. The device of item 6770, further comprising a polymer.

6794. The device of item 6770, further comprising a polymeric carrier.

6795. The device of item 6770 wherein the fibrosing agent promotes adhesion between the device and a host into which the device is implanted.

6796. The device of item 6770 wherein the device delivers the fibrosing agent locally to tissue proximate to the device.

6797. The device of item 6770, further comprising a coating, wherein the coating comprises the fibrosing agent.

6798. The device of item 6770, further comprising a coating, wherein the coating is disposed on a surface of the device.

6799. The device of item 6770, further comprising a coating, wherein the coating directly contacts the device.

6800. The device of item 6770, further comprising a coating, wherein the coating indirectly contacts the device.

6801. The device of item 6770, further comprising a coating, wherein the coating partially covers the device.

6802. The device of item 6770, further comprising a coating, wherein the coating completely covers the device.

6803. The device of item 6770, further comprising a coating, wherein the coating is a uniform coating.

6804. The device of item 6770, further comprising a coating, wherein the coating is a non-uniform coating.

6805. The device of item 6770, further comprising a coating, wherein the coating is a discontinuous coating.

6806. The device of item 6770, further comprising a coating, wherein the coating is a patterned coating.

6807. The device of item 6770, further comprising a coating, wherein the coating has a thickness of 100 µm or less.

6808. The device of item 6770, further comprising a coating, wherein the coating has a thickness of 10 µm or less.

6809. The device of item 6770, further comprising a coating, wherein the coating adheres to the surface of the device upon deployment of the device.

6810. The device of item 6770, further comprising a coating, wherein the coating is stable at room temperature for a period of 1 year.

6811. The device of item 6770, further comprising a coating, wherein the fibrosing agent is present in the coating in an amount ranging between about 0.0001% to about 1% by weight.

6812. The device of item 6770, further comprising a coating, wherein the fibrosing agent is present in the coating in an amount ranging between about 1% to about 10% by weight.

6813. The device of item 6770, further comprising a coating, wherein the fibrosing agent is present in the coating in an amount ranging between about 10% to about 25% by weight.

6814. The device of item 6770, further comprising a coating, wherein the fibrosing agent is present in the coating in an amount ranging between about 25% to about 70% by weight.

6815. The device of item 6770, further comprising a coating, wherein the coating further comprises a polymer.

6816. The device of item 6770, further comprising a first coating having a first composition and the second coating having a second composition.

6817. The device of item 6770, further comprising a first coating having a first composition and the second coating having a second composition, wherein the first composition and the second composition are different.

6818. The device of item 6770, further comprising a polymer.

6819. The device of item 6770, further comprising a polymeric carrier.

6820. The device of item 6770, further comprising a polymeric carrier, wherein the polymeric carrier comprises a copolymer.

6821. The device of item 6770, further comprising a polymeric carrier, wherein the polymeric carrier comprises a block copolymer.

6822. The device of item 6770, further comprising a polymeric carrier, wherein the polymeric carrier comprises a random copolymer.

6823. The device of item 6770, further comprising a polymeric carrier, wherein the polymeric carrier comprises a biodegradable polymer.

6824. The device of item 6770, further comprising a polymeric carrier, wherein the polymeric carrier comprises a non-biodegradable polymer.

6825. The device of item 6770, further comprising a polymeric carrier, wherein the polymeric carrier comprises a hydrophilic polymer.

6826. The device of item 6770, further comprising a polymeric carrier, wherein the polymeric carrier comprises a hydrophobic polymer.

6827. The device of item 6770, further comprising a polymeric carrier, wherein the polymeric carrier comprises a polymer having hydrophilic domains.

6828. The device of item 6770, further comprising a polymeric carrier, wherein the polymeric carrier comprises a polymer having hydrophobic domains.

6829. The device of item 6770, further comprising a polymeric carrier, wherein the polymeric carrier comprises a non-conductive polymer.

6830. The device of item 6770, further comprising a polymeric carrier, wherein the polymeric carrier comprises an elastomer.

6831. The device of item 6770, further comprising a polymeric carrier, wherein the polymeric carrier comprises a hydrogel.

6832. The device of item 6770, further comprising a polymeric carrier, wherein the polymeric carrier comprises a silicone polymer.

6833. The device of item 6770, further comprising a polymeric carrier, wherein the polymeric carrier comprises a hydrocarbon polymer.

6834. The device of item 6770, further comprising a polymeric carrier, wherein the polymeric carrier comprises a styrene-derived polymer.

6835. The device of item 6770, further comprising a polymeric carrier, wherein the polymeric carrier comprises a butadiene polymer.

6836. The device of item 6770, further comprising a polymeric carrier, wherein the polymeric carrier comprises a macromer.

6837. The device of item 6770, further comprising a polymeric carrier, wherein the polymeric carrier comprises a poly(ethylene glycol) polymer.

6838. The device of item 6770, further comprising a polymeric carrier, wherein the polymeric carrier comprises an amorphous polymer.

6839. The device of item 6770, further comprising a lubricious coating.

6840. The device of item 6770 wherein the fibrosing agent is located within pores or holes of the device.

6841. The device of item 6770 wherein the fibrosing agent is located within a channel, lumen, or divet of the device.

6842. The device of item 6770, further comprising a second pharmaceutically active agent.

6843. The device of item 6770, further comprising an anti-inflammatory agent.

6844. The device of item 6770, further comprising an agent that inhibits infection.

6845. The device of item 6770, further comprising an agent that inhibits infection, wherein the agent is an anthracycline.

6846. The device of item 6770, further comprising an agent that inhibits infection, wherein the agent is doxorubicin.

6847. The device of item 6770, further comprising an agent that inhibits infection, wherein the agent is mitoxantrone.

6848. The device of item 6770, further comprising an agent that inhibits infection, wherein the agent is a fluoropyrimidine.

6849. The device of item 6770, further comprising an agent that inhibits infection, wherein the agent is 5-fluorouracil (5-FU).

6850. The device of item 6770, further comprising an agent that inhibits infection, wherein the agent is a folic acid antagonist.

6851. The device of item 6770, further comprising an agent that inhibits infection, wherein the agent is methotrexate.

6852. The device of item 6770, further comprising an agent that inhibits infection, wherein the agent is a podophylotoxin.

6853. The device of item 6770, further comprising an agent that inhibits infection, wherein the agent is etoposide.

6854. The device of item 6770, further comprising an agent that inhibits infection, wherein the agent is a camptothecin.

6855. The device of item 6770, further comprising an agent that inhibits infection, wherein the agent is a hydroxyurea.

6856. The device of item 6770, further comprising an agent that inhibits infection, wherein the agent is a platinum complex.

6857. The device of item 6770, further comprising an agent that inhibits infection, wherein the agent is cisplatin.

6858. The device of item 6770, further comprising an anti-thrombotic agent.

6859. The device of item 6770, further comprising a visualization agent.

6860. The device of item 6770, further comprising a visualization agent, wherein the visualization agent is a radiopaque material, wherein the radiopaque material comprises a metal, a halogenated compound, or a barium containing compound.

6861. The device of item 6770, further comprising a visualization agent, wherein the visualization agent is a radiopaque material, wherein the radiopaque material comprises barium, tantalum, or technetium.

6862. The device of item 6770, further comprising a visualization agent, wherein the visualization agent is a MRI responsive material.

6863. The device of item 6770, further comprising a visualization agent, wherein the visualization agent comprises a gadolinium chelate.

6864. The device of item 6770, further comprising a visualization agent, wherein the visualization agent comprises iron, magnesium, manganese, copper, or chromium.

6865. The device of item 6770, further comprising a visualization agent, wherein the visualization agent comprises an iron oxide compound.

6866. The device of item 6770, further comprising a visualization agent, wherein the visualization agent comprises a dye, pigment, or colorant.

6867. The device of item 6770, further comprising an echogenic material.

6868. The device of item 6770, further comprising an echogenic material, wherein the echogenic material is in the form of a coating.

6869. The device of item 6770 wherein the device is sterile.

6870. The device of item 6770 wherein the fibrosing agent is released into tissue in the vicinity of the device after deployment of the device.

6871. The device of item 6770 wherein the fibrosing agent is released into tissue in the vicinity of the device after deployment of the device, wherein the tissue is connective tissue.

6872. The device of item 6770 wherein the fibrosing agent is released into tissue in the vicinity of the device after deployment of the device, wherein the tissue is muscle tissue.

6873. The device of item 6770 wherein the fibrosing agent is released into tissue in the vicinity of the device after deployment of the device, wherein the tissue is nerve tissue.

6874. The device of item 6770 wherein the fibrosing agent is released into tissue in the vicinity of the device after deployment of the device, wherein the tissue is epithelium tissue.

6875. The device of item 6770 wherein the fibrosing agent is released in effective concentrations from the device over a period ranging from the time of deployment of the device to about 1 year.

6876. The device of item 6770 wherein the fibrosing agent is released in effective concentrations from the device over a period ranging from about 1 month to 6 months.

6877. The device of item 6770 wherein the fibrosing agent is released in effective concentrations from the device over a period ranging from about 1–90 days.

6878. The device of item 6770 wherein the fibrosing agent is released in effective concentrations from the device at a constant rate.

6879. The device of item 6770 wherein the fibrosing agent is released in effective concentrations from the device at an increasing rate.

6880. The device of item 6770 wherein the fibrosing agent is released in effective concentrations from the device at a decreasing rate.

6881. The device of item 6770 wherein the fibrosing agent is released in effective concentrations from the composition comprising the fibrosing agent by diffusion over a period ranging from the time of deployment of the device to about 90 days.

6882. The device of item 6770 wherein the fibrosing agent is released in effective concentrations from the composition comprising the fibrosing agent by erosion of the composition over a period ranging from the time of deployment of the device to about 90 days.

6883. The device of item 6770 wherein the device comprises about 0.01 µg to about 10 µg of the fibrosing agent.

6884. The device of item 6770 wherein the device comprises about 10 µg to about 10 mg of the fibrosing agent.

6885. The device of item 6770 wherein the device comprises about 10 mg to about 250 mg of the fibrosing agent.

6886. The device of item 6770 wherein the device comprises about 250 mg to about 1000 mg of the fibrosing agent.

6887. The device of item 6770 wherein the device comprises about 1000 mg to about 2500 mg of the fibrosing agent.

6888. The device of item 6770 wherein a surface of the device comprises less than 0.01 µg of the fibrosing agent per $mm^2$ of device surface to which the fibrosing agent is applied.

6889. The device of item 6770 wherein a surface of the device comprises about 0.01 µg to about 1 µg of the fibrosing agent per $mm^2$ of device surface to which the fibrosing agent is applied.

6890. The device of item 6770 wherein a surface of the device comprises about 1 µg to about 10 µg of the fibrosing agent per $mm^2$ of device surface to which the fibrosing agent is applied.

6891. The device of item 6770 wherein a surface of the device comprises about 10 µg to about 250 µg of the fibrosing agent per $mm^2$ of device surface to which the fibrosing agent is applied.

6892. The device of item 6770 wherein a surface of the device comprises about 250 µg to about 1000 µg of the fibrosing agent of fibrosing agent per $mm^2$ of device surface to which the fibrosing agent is applied.

6893. The device of item 6770 wherein a surface of the device comprises about 1000 µg to about 2500 µg of the fibrosing agent per $mm^2$ of device surface to which the fibrosing agent is applied.

6894. The device of item 6770 wherein the hernia mesh implant is expandable.

6895. A medical device comprising a surgical film implant and a fibrosing agent, where the fibrosing agent induces a fibrotic response between the device and a patient in which the device is implanted.

6896. The device of item 6895 wherein the fibrosing agent promotes regeneration.

6897. The device of item 6895 wherein the fibrosing agent promotes angiogenesis.

6898. The device of item 6895 wherein the fibrosing agent promotes fibroblast migration.

6899. The device of item 6895 wherein the fibrosing agent promotes fibroblast proliferation.

6900. The device of item 6895 wherein the fibrosing agent promotes deposition of extracellular matrix (ECM).

6901. The device of item 6895 wherein the fibrosing agent promotes tissue remodeling.

6902. The device of item 6895 wherein the fibrosing agent is an arterial vessel wall irritant.

6903. The device of item 6895 wherein the fibrosing agent promotes adhesion between the device and a host into which the device is implanted.

6904. The device of item 6895 wherein the device delivers the fibrosing agent locally to tissue proximate to the device.

6905. The device of item 6895 wherein the fibrosing agent is or comprises silk.

6906. The device of item 6895 wherein the fibrosing agent is or comprises mineral particles.

6907. The device of item 6895 wherein the fibrosing agent is or comprises chitosan.

6908. The device of item 6895 wherein the fibrosing agent is or comprises polylysine.

6909. The device of item 6895 wherein the fibrosing agent is or comprises fibronectin.

6910. The device of item 6895 wherein the fibrosing agent is or comprises bleomycin.

6911. The device of item 6895 wherein the fibrosing agent is or comprises CTGF.

6912. The device of item 6895 wherein the fibrosing agent is in the form of a thread, or is in contact with a thread.

6913. The device of item 6895 wherein the fibrosing agent is in the form of a particulate.

6914. The device of item 6895 wherein the composition further comprises an inflammatory cytokine.

6915. The device of item 6895 wherein the composition further comprises an agent that stimulates cell proliferation.

6916. The device of item 6895 wherein the composition is in the form of a gel, paste, or spray.

6917. The device of item 6895 wherein the fibrosing agent is in the form of tufts.

6918. The device of item 6895, further comprising a polymer.

6919. The device of item 6895, further comprising a polymeric carrier.

6920. The device of item 6895 wherein the fibrosing agent promotes adhesion between the device and a host into which the device is implanted.

6921. The device of item 6895 wherein the device delivers the fibrosing agent locally to tissue proximate to the device.

6922. The device of item 6895, further comprising a coating, wherein the coating comprises the fibrosing agent.

6923. The device of item 6895, further comprising a coating, wherein the coating is disposed on a surface of the device.

6924. The device of item 6895, further comprising a coating, wherein the coating directly contacts the device.

6925. The device of item 6895, further comprising a coating, wherein the coating indirectly contacts the device.

6926. The device of item 6895, further comprising a coating, wherein the coating partially covers the device.

6927. The device of item 6895, further comprising a coating, wherein the coating completely covers the device.

6928. The device of item 6895, further comprising a coating, wherein the coating is a uniform coating.

6929. The device of item 6895, further comprising a coating, wherein the coating is a non-uniform coating.

6930. The device of item 6895, further comprising a coating, wherein the coating is a discontinuous coating.

6931. The device of item 6895, further comprising a coating, wherein the coating is a patterned coating.

6932. The device of item 6895, further comprising a coating, wherein the coating has a thickness of 100 µm or less.

6933. The device of item 6895, further comprising a coating, wherein the coating has a thickness of 10 µm or less.

6934. The device of item 6895, further comprising a coating, wherein the coating adheres to the surface of the device upon deployment of the device.

6935. The device of item 6895, further comprising a coating, wherein the coating is stable at room temperature for a period of 1 year.

6936. The device of item 6895, further comprising a coating, wherein the fibrosing agent is present in the coating in an amount ranging between about 0.0001% to about 1% by weight.

6937. The device of item 6895, further comprising a coating, wherein the fibrosing agent is present in the coating in an amount ranging between about 1% to about 10% by weight.

6938. The device of item 6895, further comprising a coating, wherein the fibrosing agent is present in the coating in an amount ranging between about 10% to about 25% by weight.

6939. The device of item 6895, further comprising a coating, wherein the fibrosing agent is present in the coating in an amount ranging between about 25% to about 70% by weight.

6940. The device of item 6895, further comprising a coating, wherein the coating further comprises a polymer.

6941. The device of item 6895, further comprising a first coating having a first composition and the second coating having a second composition.

6942. The device of item 6895, further comprising a first coating having a first composition and the second coating having a second composition, wherein the first composition and the second composition are different.

6943. The device of item 6895, further comprising a polymer.

6944. The device of item 6895, further comprising a polymeric carrier.

6945. The device of item 6895, further comprising a polymeric carrier, wherein the polymeric carrier comprises a copolymer.

6946. The device of item 6895, further comprising a polymeric carrier, wherein the polymeric carrier comprises a block copolymer.

6947. The device of item 6895, further comprising a polymeric carrier, wherein the polymeric carrier comprises a random copolymer.

6948. The device of item 6895, further comprising a polymeric carrier, wherein the polymeric carrier comprises a biodegradable polymer.

6949. The device of item 6895, further comprising a polymeric carrier, wherein the polymeric carrier comprises a non-biodegradable polymer.

6950. The device of item 6895, further comprising a polymeric carrier, wherein the polymeric carrier comprises a hydrophilic polymer.

6951. The device of item 6895, further comprising a polymeric carrier, wherein the polymeric carrier comprises a hydrophobic polymer.

6952. The device of item 6895, further comprising a polymeric carrier, wherein the polymeric carrier comprises a polymer having hydrophilic domains.

6953. The device of item 6895, further comprising a polymeric carrier, wherein the polymeric carrier comprises a polymer having hydrophobic domains.

6954. The device of item 6895, further comprising a polymeric carrier, wherein the polymeric carrier comprises a non-conductive polymer.

6955. The device of item 6895, further comprising a polymeric carrier, wherein the polymeric carrier comprises an elastomer.

6956. The device of item 6895, further comprising a polymeric carrier, wherein the polymeric carrier comprises a hydrogel.

6957. The device of item 6895, further comprising a polymeric carrier, wherein the polymeric carrier comprises a silicone polymer.

6958. The device of item 6895, further comprising a polymeric carrier, wherein the polymeric carrier comprises a hydrocarbon polymer.

6959. The device of item 6895, further comprising a polymeric carrier, wherein the polymeric carrier comprises a styrene-derived polymer.

6960. The device of item 6895, further comprising a polymeric carrier, wherein the polymeric carrier comprises a butadiene polymer.

6961. The device of item 6895, further comprising a polymeric carrier, wherein the polymeric carrier comprises a macromer.

6962. The device of item 6895, further comprising a polymeric carrier, wherein the polymeric carrier comprises a poly(ethylene glycol) polymer.

6963. The device of item 6895, further comprising a polymeric carrier, wherein the polymeric carrier comprises an amorphous polymer.

6964. The device of item 6895, further comprising a lubricious coating.

6965. The device of item 6895 wherein the fibrosing agent is located within pores or holes of the device.

6966. The device of item 6895 wherein the fibrosing agent is located within a channel, lumen, or divet of the device.

6967. The device of item 6895, further comprising a second pharmaceutically active agent.

6968. The device of item 6895, further comprising an anti-inflammatory agent.

6969. The device of item 6895, further comprising an agent that inhibits infection.

6970. The device of item 6895, further comprising an agent that inhibits infection, wherein the agent is an anthracycline.

6971. The device of item 6895, further comprising an agent that inhibits infection, wherein the agent is doxorubicin.

6972. The device of item 6895, further comprising an agent that inhibits infection, wherein the agent is mitoxantrone.

6973. The device of item 6895, further comprising an agent that inhibits infection, wherein the agent is a fluoropyrimidine.

6974. The device of item 6895, further comprising an agent that inhibits infection, wherein the agent is 5-fluorouracil (5-FU).

6975. The device of item 6895, further comprising an agent that inhibits infection, wherein the agent is a folic acid antagonist.

6976. The device of item 6895, further comprising an agent that inhibits infection, wherein the agent is methotrexate.

6977. The device of item 6895, further comprising an agent that inhibits infection, wherein the agent is a podophylotoxin.

6978. The device of item 6895, further comprising an agent that inhibits infection, wherein the agent is etoposide.

6979. The device of item 6895, further comprising an agent that inhibits infection, wherein the agent is a camptothecin.

6980. The device of item 6895, further comprising an agent that inhibits infection, wherein the agent is a hydroxyurea.

6981. The device of item 6895, further comprising an agent that inhibits infection, wherein the agent is a platinum complex.

6982. The device of item 6895, further comprising an agent that inhibits infection, wherein the agent is cisplatin.

6983. The device of item 6895, further comprising an anti-thrombotic agent.

6984. The device of item 6895, further comprising a visualization agent.

6985. The device of item 6895, further comprising a visualization agent, wherein the visualization agent is a radiopaque material, wherein the radiopaque material comprises a metal, a halogenated compound, or a barium containing compound.

6986. The device of item 6895, further comprising a visualization agent, wherein the visualization agent is a radiopaque material, wherein the radiopaque material comprises barium, tantalum, or technetium.

6987. The device of item 6895, further comprising a visualization agent, wherein the visualization agent is a MRI responsive material.

6988. The device of item 6895, further comprising a visualization agent, wherein the visualization agent comprises a gadolinium chelate.

6989. The device of item 6895, further comprising a visualization agent, wherein the visualization agent comprises iron, magnesium, manganese, copper, or chromium.

6990. The device of item 6895, further comprising a visualization agent, wherein the visualization agent comprises an iron oxide compound.

6991. The device of item 6895, further comprising a visualization agent, wherein the visualization agent comprises a dye, pigment, or colorant.

6992. The device of item 6895, further comprising an echogenic material.

6993. The device of item 6895, further comprising an echogenic material, wherein the echogenic material is in the form of a coating.

6994. The device of item 6895 wherein the device is sterile.

6995. The device of item 6895 wherein the fibrosing agent is released into tissue in the vicinity of the device after deployment of the device.

6996. The device of item 6895 wherein the fibrosing agent is released into tissue in the vicinity of the device after deployment of the device, wherein the tissue is connective tissue.

6997. The device of item 6895 wherein the fibrosing agent is released into tissue in the vicinity of the device after deployment of the device, wherein the tissue is muscle tissue.

6998. The device of item 6895 wherein the fibrosing agent is released into tissue in the vicinity of the device after deployment of the device, wherein the tissue is nerve tissue.

6999. The device of item 6895 wherein the fibrosing agent is released into tissue in the vicinity of the device after deployment of the device, wherein the tissue is epithelium tissue.

7000. The device of item 6895 wherein the fibrosing agent is released in effective concentrations from the device over a period ranging from the time of deployment of the device to about 1 year.

7001. The device of item 6895 wherein the fibrosing agent is released in effective concentrations from the device over a period ranging from about 1 month to 6 months.

7002. The device of item 6895 wherein the fibrosing agent is released in effective concentrations from the device over a period ranging from about 1–90 days.

7003. The device of item 6895 wherein the fibrosing agent is released in effective concentrations from the device at a constant rate.

7004. The device of item 6895 wherein the fibrosing agent is released in effective concentrations from the device at an increasing rate.

7005. The device of item 6895 wherein the fibrosing agent is released in effective concentrations from the device at a decreasing rate.

7006. The device of item 6895 wherein the fibrosing agent is released in effective concentrations from the composition comprising the fibrosing agent by diffusion over a period ranging from the time of deployment of the device to about 90 days.

7007. The device of item 6895 wherein the fibrosing agent is released in effective concentrations from the composition comprising the fibrosing agent by erosion of the composition over a period ranging from the time of deployment of the device to about 90 days.

7008. The device of item 6895 wherein the device comprises about 0.01 µg to about 10 µg of the fibrosing agent.

7009. The device of item 6895 wherein the device comprises about 10 µg to about 10 mg of the fibrosing agent.

7010. The device of item 6895 wherein the device comprises about 10 mg to about 250 mg of the fibrosing agent.

7011. The device of item 6895 wherein the device comprises about 250 mg to about 1000 mg of the fibrosing agent.

7012. The device of item 6895 wherein the device comprises about 1000 mg to about 2500 mg of the fibrosing agent.

7013. The device of item 6895 wherein a surface of the device comprises less than 0.01 µg of the fibrosing agent per $mm^2$ of device surface to which the fibrosing agent is applied.

7014. The device of item 6895 wherein a surface of the device comprises about 0.01 µg to about 1 µg of the fibrosing agent per $mm^2$ of device surface to which the fibrosing agent is applied.

7015. The device of item 6895 wherein a surface of the device comprises about 1 µg to about 10 µg of the fibrosing agent per $mm^2$ of device surface to which the fibrosing agent is applied.

7016. The device of item 6895 wherein a surface of the device comprises about 10 µg to about 250 µg of the fibrosing agent per $mm^2$ of device surface to which the fibrosing agent is applied.

7017. The device of item 6895 wherein a surface of the device comprises about 250 µg to about 1000 µg of the fibrosing agent of fibrosing agent per $mm^2$ of device surface to which the fibrosing agent is applied.

7018. The device of item 6895 wherein a surface of the device comprises about 1000 µg to about 2500 µg of the fibrosing agent per $mm^2$ of device surface to which the fibrosing agent is applied.

7019. A medical device comprising a spinal fusion device and a fibrosing agent, where the fibrosing agent induces a fibrotic response between the device and a patient in which the device is implanted.

7020. The device of item 7019 wherein the fibrosing agent promotes regeneration.

7021. The device of item 7019 wherein the fibrosing agent promotes angiogenesis.

7022. The device of item 7019 wherein the fibrosing agent promotes fibroblast migration.

7023. The device of item 7019 wherein the fibrosing agent promotes fibroblast proliferation.

7024. The device of item 7019 wherein the fibrosing agent promotes deposition of extracellular matrix (ECM).

7025. The device of item 7019 wherein the fibrosing agent promotes tissue remodeling.

7026. The device of item 7019 wherein the fibrosing agent is an arterial vessel wall irritant.

7027. The device of item 7019 wherein the fibrosing agent promotes adhesion between the device and a host into which the device is implanted.

7028. The device of item 7019 wherein the device delivers the fibrosing agent locally to tissue proximate to the device.

7029. The device of item 7019 wherein the fibrosing agent is or comprises silk.

7030. The device of item 7019 wherein the fibrosing agent is or comprises mineral particles.

7031. The device of item 7019 wherein the fibrosing agent is or comprises chitosan.

7032. The device of item 7019 wherein the fibrosing agent is or comprises polylysine.

7033. The device of item 7019 wherein the fibrosing agent is or comprises fibronectin.

7034. The device of item 7019 wherein the fibrosing agent is or comprises bleomycin.

7035. The device of item 7019 wherein the fibrosing agent is or comprises CTGF.

7036. The device of item 7019 wherein the fibrosing agent is in the form of a thread, or is in contact with a thread.

7037. The device of item 7019 wherein the fibrosing agent is in the form of a particulate.

7038. The device of item 7019 wherein the composition further comprises an inflammatory cytokine.

7039. The device of item 7019 wherein the composition further comprises an agent that stimulates cell proliferation.

7040. The device of item 7019 wherein the composition is in the form of a gel, paste, or spray.

7041. The device of item 7019 wherein the fibrosing agent is in the form of tufts.

7042. The device of item 7019, further comprising a polymer.

7043. The device of item 7019, further comprising a polymeric carrier.

7044. The device of item 7019 wherein the fibrosing agent promotes adhesion between the device and a host into which the device is implanted.

7045. The device of item 7019 wherein the device delivers the fibrosing agent locally to tissue proximate to the device.

7046. The device of item 7019, further comprising a coating, wherein the coating comprises the fibrosing agent.

7047. The device of item 7019, further comprising a coating, wherein the coating is disposed on a surface of the device.

7048. The device of item 7019, further comprising a coating, wherein the coating directly contacts the device.

7049. The device of item 7019, further comprising a coating, wherein the coating indirectly contacts the device.

7050. The device of item 7019, further comprising a coating, wherein the coating partially covers the device.

7051. The device of item 7019, further comprising a coating, wherein the coating completely covers the device.

7052. The device of item 7019, further comprising a coating, wherein the coating is a uniform coating.

7053. The device of item 7019, further comprising a coating, wherein the coating is a non-uniform coating.

7054. The device of item 7019, further comprising a coating, wherein the coating is a discontinuous coating.

7055. The device of item 7019, further comprising a coating, wherein the coating is a patterned coating.

7056. The device of item 7019, further comprising a coating, wherein the coating has a thickness of 100 µm or less.

7057. The device of item 7019, further comprising a coating, wherein the coating has a thickness of 10 µm or less.

7058. The device of item 7019, further comprising a coating, wherein the coating adheres to the surface of the device upon deployment of the device.

7059. The device of item 7019, further comprising a coating, wherein the coating is stable at room temperature for a period of 1 year.

7060. The device of item 7019, further comprising a coating, wherein the fibrosing agent is present in the coating in an amount ranging between about 0.0001% to about 1% by weight.

7061. The device of item 7019, further comprising a coating, wherein the fibrosing agent is present in the coating in an amount ranging between about 1% to about 10% by weight.

7062. The device of item 7019, further comprising a coating, wherein the fibrosing agent is present in the coating in an amount ranging between about 10% to about 25% by weight.

7063. The device of item 7019, further comprising a coating, wherein the fibrosing agent is present in the coating in an amount ranging between about 25% to about 70% by weight.

7064. The device of item 7019, further comprising a coating, wherein the coating further comprises a polymer.

7065. The device of item 7019, further comprising a first coating having a first composition and the second coating having a second composition.

7066. The device of item 7019, further comprising a first coating having a first composition and the second coating having a second composition, wherein the first composition and the second composition are different.

7067. The device of item 7019, further comprising a polymer.

7068. The device of item 7019, further comprising a polymeric carrier.

7069. The device of item 7019, further comprising a polymeric carrier, wherein the polymeric carrier comprises a copolymer.

7070. The device of item 7019, further comprising a polymeric carrier, wherein the polymeric carrier comprises a block copolymer.

7071. The device of item 7019, further comprising a polymeric carrier, wherein the polymeric carrier comprises a random copolymer.

7072. The device of item 7019, further comprising a polymeric carrier, wherein the polymeric carrier comprises a biodegradable polymer.

7073. The device of item 7019, further comprising a polymeric carrier, wherein the polymeric carrier comprises a non-biodegradable polymer.

7074. The device of item 7019, further comprising a polymeric carrier, wherein the polymeric carrier comprises a hydrophilic polymer.

7075. The device of item 7019, further comprising a polymeric carrier, wherein the polymeric carrier comprises a hydrophobic polymer.

7076. The device of item 7019, further comprising a polymeric carrier, wherein the polymeric carrier comprises a polymer having hydrophilic domains.

7077. The device of item 7019, further comprising a polymeric carrier, wherein the polymeric carrier comprises a polymer having hydrophobic domains.

7078. The device of item 7019, further comprising a polymeric carrier, wherein the polymeric carrier comprises a non-conductive polymer.

7079. The device of item 7019, further comprising a polymeric carrier, wherein the polymeric carrier comprises an elastomer.

7080. The device of item 7019, further comprising a polymeric carrier, wherein the polymeric carrier comprises a hydrogel.

7081. The device of item 7019, further comprising a polymeric carrier, wherein the polymeric carrier comprises a silicone polymer.

7082. The device of item 7019, further comprising a polymeric carrier, wherein the polymeric carrier comprises a hydrocarbon polymer.

7083. The device of item 7019, further comprising a polymeric carrier, wherein the polymeric carrier comprises a styrene-derived polymer.

7084. The device of item 7019, further comprising a polymeric carrier, wherein the polymeric carrier comprises a butadiene polymer.

7085. The device of item 7019, further comprising a polymeric carrier, wherein the polymeric carrier comprises a macromer.

7086. The device of item 7019, further comprising a polymeric carrier, wherein the polymeric carrier comprises a poly(ethylene glycol) polymer.

7087. The device of item 7019, further comprising a polymeric carrier, wherein the polymeric carrier comprises an amorphous polymer.

7088. The device of item 7019, further comprising a lubricious coating.

7089. The device of item 7019 wherein the fibrosing agent is located within pores or holes of the device.

7090. The device of item 7019 wherein the fibrosing agent is located within a channel, lumen, or divet of the device.

7091. The device of item 7019, further comprising a second pharmaceutically active agent.

7092. The device of item 7019, further comprising an anti-inflammatory agent.

7093. The device of item 7019, further comprising an agent that inhibits infection.

7094. The device of item 7019, further comprising an agent that inhibits infection, wherein the agent is an anthracycline.

7095. The device of item 7019, further comprising an agent that inhibits infection, wherein the agent is doxorubicin.

7096. The device of item 7019, further comprising an agent that inhibits infection, wherein the agent is mitoxantrone.

7097. The device of item 7019, further comprising an agent that inhibits infection, wherein the agent is a fluoropyrimidine.

7098. The device of item 7019, further comprising an agent that inhibits infection, wherein the agent is 5-fluorouracil (5-FU).

7099. The device of item 7019, further comprising an agent that inhibits infection, wherein the agent is a folic acid antagonist.

7100. The device of item 7019, further comprising an agent that inhibits infection, wherein the agent is methotrexate.

7101. The device of item 7019, further comprising an agent that inhibits infection, wherein the agent is a podophylotoxin.

7102. The device of item 7019, further comprising an agent that inhibits infection, wherein the agent is etoposide.

7103. The device of item 7019, further comprising an agent that inhibits infection, wherein the agent is a camptothecin.

7104. The device of item 7019, further comprising an agent that inhibits infection, wherein the agent is a hydroxyurea.

7105. The device of item 7019, further comprising an agent that inhibits infection, wherein the agent is a platinum complex.

7106. The device of item 7019, further comprising an agent that inhibits infection, wherein the agent is cisplatin.

7107. The device of item 7019, further comprising an anti-thrombotic agent.

7108. The device of item 7019, further comprising a visualization agent.

7109. The device of item 7019, further comprising a visualization agent, wherein the visualization agent is a radiopaque material, wherein the radiopaque material comprises a metal, a halogenated compound, or a barium containing compound.

7110. The device of item 7019, further comprising a visualization agent, wherein the visualization agent is a radiopaque material, wherein the radiopaque material comprises barium, tantalum, or technetium.

7111. The device of item 7019, further comprising a visualization agent, wherein the visualization agent is a MRI responsive material.

7112. The device of item 7019, further comprising a visualization agent, wherein the visualization agent comprises a gadolinium chelate.

7113. The device of item 7019, further comprising a visualization agent, wherein the visualization agent comprises iron, magnesium, manganese, copper, or chromium.

7114. The device of item 7019, further comprising a visualization agent, wherein the visualization agent comprises an iron oxide compound.

7115. The device of item 7019, further comprising a visualization agent, wherein the visualization agent comprises a dye, pigment, or colorant.

7116. The device of item 7019, further comprising an echogenic material.

7117. The device of item 7019, further comprising an echogenic material, wherein the echogenic material is in the form of a coating.

7118. The device of item 7019 wherein the device is sterile.

7119. The device of item 7019 wherein the fibrosing agent is released into tissue in the vicinity of the device after deployment of the device.

7120. The device of item 7019 wherein the fibrosing agent is released into tissue in the vicinity of the device after deployment of the device, wherein the tissue is connective tissue.

7121. The device of item 7019 wherein the fibrosing agent is released into tissue in the vicinity of the device after deployment of the device, wherein the tissue is muscle tissue.

7122. The device of item 7019 wherein the fibrosing agent is released into tissue in the vicinity of the device after deployment of the device, wherein the tissue is nerve tissue.

7123. The device of item 7019 wherein the fibrosing agent is released into tissue in the vicinity of the device after deployment of the device, wherein the tissue is epithelium tissue.

7124. The device of item 7019 wherein the fibrosing agent is released in effective concentrations from the device over a period ranging from the time of deployment of the device to about 1 year.

7125. The device of item 7019 wherein the fibrosing agent is released in effective concentrations from the device over a period ranging from about 1 month to 6 months.

7126. The device of item 7019 wherein the fibrosing agent is released in effective concentrations from the device over a period ranging from about 1–90 days.

7127. The device of item 7019 wherein the fibrosing agent is released in effective concentrations from the device at a constant rate.

7128. The device of item 7019 wherein the fibrosing agent is released in effective concentrations from the device at an increasing rate.

7129. The device of item 7019 wherein the fibrosing agent is released in effective concentrations from the device at a decreasing rate.

7130. The device of item 7019 wherein the fibrosing agent is released in effective concentrations from the composition comprising the fibrosing agent by diffusion over a period ranging from the time of deployment of the device to about 90 days.

7131. The device of item 7019 wherein the fibrosing agent is released in effective concentrations from the composition comprising the fibrosing agent by erosion of the composition over a period ranging from the time of deployment of the device to about 90 days.

7132. The device of item 7019 wherein the device comprises about 0.01 µg to about 10 µg of the fibrosing agent.

7133. The device of item 7019 wherein the device comprises about 10 µg to about 10 mg of the fibrosing agent.

7134. The device of item 7019 wherein the device comprises about 10 mg to about 250 mg of the fibrosing agent.

7135. The device of item 7019 wherein the device comprises about 250 mg to about 1000 mg of the fibrosing agent.

7136. The device of item 7019 wherein the device comprises about 1000 mg to about 2500 mg of the fibrosing agent.

7137. The device of item 7019 wherein a surface of the device comprises less than 0.01 µg of the fibrosing agent per $mm^2$ of device surface to which the fibrosing agent is applied.

7138. The device of item 7019 wherein a surface of the device comprises about 0.01 µg to about 1 µg of the fibrosing agent per $mm^2$ of device surface to which the fibrosing agent is applied.

7139. The device of item 7019 wherein a surface of the device comprises about 1 µg to about 10 µg of the fibrosing agent per $mm^2$ of device surface to which the fibrosing agent is applied.

7140. The device of item 7019 wherein a surface of the device comprises about 10 µg to about 250 µg of the fibrosing agent per $mm^2$ of device surface to which the fibrosing agent is applied.

7141. The device of item 7019 wherein a surface of the device comprises about 250 µg to about 1000 µg of the fibrosing agent of fibrosing agent per $mm^2$ of device surface to which the fibrosing agent is applied.

7142. The device of item 7019 wherein a surface of the device comprises about 1000 µg to about 2500 µg of the fibrosing agent per $mm^2$ of device surface to which the fibrosing agent is applied.

7143. The device of item 7019 wherein the spinal fusion device is a fusion basket.

7144. The device of item 7019 wherein the spinal fusion device is a fusion casge apparatus.

7145. The device of item 7019 wherein the spinal fusion device is an interbody case.

7146. The device of item 7019 wherein the spinal fusion device is an interbody implant.

7147. The device of item 7019 wherein the spinal fusion device is a fusion cage anchoring device.

7148. The device of item 7019 wherein the spinal fusion device is a fusion stabilization chamber.

7149. The device of item 7019 wherein the spinal fusion device is a fusion cage anchoring plate.

7150. The device of item 7019 wherein the spinal fusion device is a bone fixation device.

7151. The device of item 7019 wherein the spinal fusion device is an anchoring bone plate.

7152. The device of item 7019 wherein the spinal fusion device is an anchoring bone screw.

7153. The device of item 7019 wherein the spinal fusion device is a tissue filler.

7154. The device of item 7019 wherein the spinal fusion device is a bone cement.

7155. The device of item 7019 wherein the spinal fusion device is an allograft material.

7156. The device of item 7019 wherein the spinal fusion device is an autograft material.

7157. The device of item 7019 wherein the spinal fusion device is a collagen implant.

7158. The device of item 7019 wherein the spinal fusion device is injectable.

7159. A medical device comprising a septal occlusion patch and a fibrosing agent, where the fibrosing agent induces a fibrotic response between the device and a patient in which the device is implanted.

7160. The device of item 7159 wherein the fibrosing agent promotes regeneration.

7161. The device of item 7159 wherein the fibrosing agent promotes angiogenesis.

7162. The device of item 7159 wherein the fibrosing agent promotes fibroblast migration.

7163. The device of item 7159 wherein the fibrosing agent promotes fibroblast proliferation.

7164. The device of item 7159 wherein the fibrosing agent promotes deposition of extracellular matrix (ECM).

7165. The device of item 7159 wherein the fibrosing agent promotes tissue remodeling.

7166. The device of item 7159 wherein the fibrosing agent is an arterial vessel wall irritant.

7167. The device of item 7159 wherein the fibrosing agent promotes adhesion between the device and a host into which the device is implanted.

7168. The device of item 7159 wherein the device delivers the fibrosing agent locally to tissue proximate to the device.

7169. The device of item 7159 wherein the fibrosing agent is or comprises silk.

7170. The device of item 7159 wherein the fibrosing agent is or comprises mineral particles.

7171. The device of item 7159 wherein the fibrosing agent is or comprises chitosan.

7172. The device of item 7159 wherein the fibrosing agent is or comprises polylysine.

7173. The device of item 7159 wherein the fibrosing agent is or comprises fibronectin.

7174. The device of item 7159 wherein the fibrosing agent is or comprises bleomycin.

7175. The device of item 7159 wherein the fibrosing agent is or comprises CTGF.

7176. The device of item 7159 wherein the fibrosing agent is in the form of a thread, or is in contact with a thread.

7177. The device of item 7159 wherein the fibrosing agent is in the form of a particulate.

7178. The device of item 7159 wherein the composition further comprises an inflammatory cytokine.

7179. The device of item 7159 wherein the composition further comprises an agent that stimulates cell proliferation.

7180. The device of item 7159 wherein the composition is in the form of a gel, paste, or spray.

7181. The device of item 7159 wherein the fibrosing agent is in the form of tufts.

7182. The device of item 7159, further comprising a polymer.

7183. The device of item 7159, further comprising a polymeric carrier.

7184. The device of item 7159 wherein the fibrosing agent promotes adhesion between the device and a host into which the device is implanted.

7185. The device of item 7159 wherein the device delivers the fibrosing agent locally to tissue proximate to the device.

7186. The device of item 7159, further comprising a coating, wherein the coating comprises the fibrosing agent.

7187. The device of item 7159, further comprising a coating, wherein the coating is disposed on a surface of the device.

7188. The device of item 7159, further comprising a coating, wherein the coating directly contacts the device.

7189. The device of item 7159, further comprising a coating, wherein the coating indirectly contacts the device.

7190. The device of item 7159, further comprising a coating, wherein the coating partially covers the device.

7191. The device of item 7159, further comprising a coating, wherein the coating completely covers the device.

7192. The device of item 7159, further comprising a coating, wherein the coating is a uniform coating.

7193. The device of item 7159, further comprising a coating, wherein the coating is a non-uniform coating.

7194. The device of item 7159, further comprising a coating, wherein the coating is a discontinuous coating.

7195. The device of item 7159, further comprising a coating, wherein the coating is a patterned coating.

7196. The device of item 7159, further comprising a coating, wherein the coating has a thickness of 100 μm or less.

7197. The device of item 7159, further comprising a coating, wherein the coating has a thickness of 10 μm or less.

7198. The device of item 7159, further comprising a coating, wherein the coating adheres to the surface of the device upon deployment of the device.

7199. The device of item 7159, further comprising a coating, wherein the coating is stable at room temperature for a period of 1 year.

7200. The device of item 7159, further comprising a coating, wherein the fibrosing agent is present in the coating in an amount ranging between about 0.0001% to about 1% by weight.

7201. The device of item 7159, further comprising a coating, wherein the fibrosing agent is present in the coating in an amount ranging between about 1% to about 10% by weight.

7202. The device of item 7159, further comprising a coating, wherein the fibrosing agent is present in the coating in an amount ranging between about 10% to about 25% by weight.

7203. The device of item 7159, further comprising a coating, wherein the fibrosing agent is present in the coating in an amount ranging between about 25% to about 70% by weight.

7204. The device of item 7159, further comprising a coating, wherein the coating further comprises a polymer.

7205. The device of item 7159, further comprising a first coating having a first composition and the second coating having a second composition.

7206. The device of item 7159, further comprising a first coating having a first composition and the second coating having a second composition, wherein the first composition and the second composition are different.

7207. The device of item 7159, further comprising a polymer.

7208. The device of item 7159, further comprising a polymeric carrier.

7209. The device of item 7159, further comprising a polymeric carrier, wherein the polymeric carrier comprises a copolymer.

7210. The device of item 7159, further comprising a polymeric carrier, wherein the polymeric carrier comprises a block copolymer.

7211. The device of item 7159, further comprising a polymeric carrier, wherein the polymeric carrier comprises a random copolymer.

7212. The device of item 7159, further comprising a polymeric carrier, wherein the polymeric carrier comprises a biodegradable polymer.

7213. The device of item 7159, further comprising a polymeric carrier, wherein the polymeric carrier comprises a non-biodegradable polymer.

7214. The device of item 7159, further comprising a polymeric carrier, wherein the polymeric carrier comprises a hydrophilic polymer.

7215. The device of item 7159, further comprising a polymeric carrier, wherein the polymeric carrier comprises a hydrophobic polymer.

7216. The device of item 7159, further comprising a polymeric carrier, wherein the polymeric carrier comprises a polymer having hydrophilic domains.

7217. The device of item 7159, further comprising a polymeric carrier, wherein the polymeric carrier comprises a polymer having hydrophobic domains.

7218. The device of item 7159, further comprising a polymeric carrier, wherein the polymeric carrier comprises a non-conductive polymer.

7219. The device of item 7159, further comprising a polymeric carrier, wherein the polymeric carrier comprises an elastomer.

7220. The device of item 7159, further comprising a polymeric carrier, wherein the polymeric carrier comprises a hydrogel.

7221. The device of item 7159, further comprising a polymeric carrier, wherein the polymeric carrier comprises a silicone polymer.

7222. The device of item 7159, further comprising a polymeric carrier, wherein the polymeric carrier comprises a hydrocarbon polymer.

7223. The device of item 7159, further comprising a polymeric carrier, wherein the polymeric carrier comprises a styrene-derived polymer.

7224. The device of item 7159, further comprising a polymeric carrier, wherein the polymeric carrier comprises a butadiene polymer.

7225. The device of item 7159, further comprising a polymeric carrier, wherein the polymeric carrier comprises a macromer.

7226. The device of item 7159, further comprising a polymeric carrier, wherein the polymeric carrier comprises a poly(ethylene glycol) polymer.

7227. The device of item 7159, further comprising a polymeric carrier, wherein the polymeric carrier comprises an amorphous polymer.

7228. The device of item 7159, further comprising a lubricious coating.

7229. The device of item 7159 wherein the fibrosing agent is located within pores or holes of the device.

7230. The device of item 7159 wherein the fibrosing agent is located within a channel, lumen, or divet of the device.

7231. The device of item 7159, further comprising a second pharmaceutically active agent.

7232. The device of item 7159, further comprising an anti-inflammatory agent.

7233. The device of item 7159, further comprising an agent that inhibits infection.

7234. The device of item 7159, further comprising an agent that inhibits infection, wherein the agent is an anthracycline.

7235. The device of item 7159, further comprising an agent that inhibits infection, wherein the agent is doxorubicin.

7236. The device of item 7159, further comprising an agent that inhibits infection, wherein the agent is mitoxantrone.

7237. The device of item 7159, further comprising an agent that inhibits infection, wherein the agent is a fluoropyrimidine.

7238. The device of item 7159, further comprising an agent that inhibits infection, wherein the agent is 5-fluorouracil (5-FU).

7239. The device of item 7159, further comprising an agent that inhibits infection, wherein the agent is a folic acid antagonist.

7240. The device of item 7159, further comprising an agent that inhibits infection, wherein the agent is methotrexate.

7241. The device of item 7159, further comprising an agent that inhibits infection, wherein the agent is a podophylotoxin.

7242. The device of item 7159, further comprising an agent that inhibits infection, wherein the agent is etoposide.

7243. The device of item 7159, further comprising an agent that inhibits infection, wherein the agent is a camptothecin.

7244. The device of item 7159, further comprising an agent that inhibits infection, wherein the agent is a hydroxyurea.

7245. The device of item 7159, further comprising an agent that inhibits infection, wherein the agent is a platinum complex.

7246. The device of item 7159, further comprising an agent that inhibits infection, wherein the agent is cisplatin.

7247. The device of item 7159, further comprising an anti-thrombotic agent.

7248. The device of item 7159, further comprising a visualization agent.

7249. The device of item 7159, further comprising a visualization agent, wherein the visualization agent is a radiopaque material, wherein the radiopaque material comprises a metal, a halogenated compound, or a barium containing compound.

7250. The device of item 7159, further comprising a visualization agent, wherein the visualization agent is a radiopaque material, wherein the radiopaque material comprises barium, tantalum, or technetium.

7251. The device of item 7159, further comprising a visualization agent, wherein the visualization agent is a MRI responsive material.

7252. The device of item 7159, further comprising a visualization agent, wherein the visualization agent comprises a gadolinium chelate.

7253. The device of item 7159, further comprising a visualization agent, wherein the visualization agent comprises iron, magnesium, manganese, copper, or chromium.

7254. The device of item 7159, further comprising a visualization agent, wherein the visualization agent comprises an iron oxide compound.

7255. The device of item 7159, further comprising a visualization agent, wherein the visualization agent comprises a dye, pigment, or colorant.

7256. The device of item 7159, further comprising an echogenic material.

7257. The device of item 7159, further comprising an echogenic material, wherein the echogenic material is in the form of a coating.

7258. The device of item 7159 wherein the device is sterile.

7259. The device of item 7159 wherein the fibrosing agent is released into tissue in the vicinity of the device after deployment of the device.

7260. The device of item 7159 wherein the fibrosing agent is released into tissue in the vicinity of the device after deployment of the device, wherein the tissue is connective tissue.

7261. The device of item 7159 wherein the fibrosing agent is released into tissue in the vicinity of the device after deployment of the device, wherein the tissue is muscle tissue.

7262. The device of item 7159 wherein the fibrosing agent is released into tissue in the vicinity of the device after deployment of the device, wherein the tissue is nerve tissue.

7263. The device of item 7159 wherein the fibrosing agent is released into tissue in the vicinity of the device after deployment of the device, wherein the tissue is epithelium tissue.

7264. The device of item 7159 wherein the fibrosing agent is released in effective concentrations from the device over a period ranging from the time of deployment of the device to about 1 year.

7265. The device of item 7159 wherein the fibrosing agent is released in effective concentrations from the device over a period ranging from about 1 month to 6 months.

7266. The device of item 7159 wherein the fibrosing agent is released in effective concentrations from the device over a period ranging from about 1–90 days.

7267. The device of item 7159 wherein the fibrosing agent is released in effective concentrations from the device at a constant rate.

7268. The device of item 7159 wherein the fibrosing agent is released in effective concentrations from the device at an increasing rate.

7269. The device of item 7159 wherein the fibrosing agent is released in effective concentrations from the device at a decreasing rate.

7270. The device of item 7159 wherein the fibrosing agent is released in effective concentrations from the composition comprising the fibrosing agent by diffusion over a period ranging from the time of deployment of the device to about 90 days.

7271. The device of item 7159 wherein the fibrosing agent is released in effective concentrations from the composition comprising the fibrosing agent by erosion of the composition over a period ranging from the time of deployment of the device to about 90 days.

7272. The device of item 7159 wherein the device comprises about 0.01 µg to about 10 µg of the fibrosing agent.

7273. The device of item 7159 wherein the device comprises about 10 µg to about 10 mg of the fibrosing agent.

7274. The device of item 7159 wherein the device comprises about 10 mg to about 250 mg of the fibrosing agent.

7275. The device of item 7159 wherein the device comprises about 250 mg to about 1000 mg of the fibrosing agent.

7276. The device of item 7159 wherein the device comprises about 1000 mg to about 2500 mg of the fibrosing agent.

7277. The device of item 7159 wherein a surface of the device comprises less than 0.01 µg of the fibrosing agent per $mm^2$ of device surface to which the fibrosing agent is applied.

7278. The device of item 7159 wherein a surface of the device comprises about 0.01 µg to about 1 µg of the fibrosing agent per $mm^2$ of device surface to which the fibrosing agent is applied.

7279. The device of item 7159 wherein a surface of the device comprises about 1 µg to about 10 µg of the fibrosing agent per $mm^2$ of device surface to which the fibrosing agent is applied.

7280. The device of item 7159 wherein a surface of the device comprises about 10 µg to about 250 µg of the fibrosing agent per $mm^2$ of device surface to which the fibrosing agent is applied.

7281. The device of item 7159 wherein a surface of the device comprises about 250 µg to about 1000 µg of the fibrosing agent of fibrosing agent per $mm^2$ of device surface to which the fibrosing agent is applied.

7282. The device of item 7159 wherein a surface of the device comprises about 1000 µg to about 2500 µg of the fibrosing agent per $mm^2$ of device surface to which the fibrosing agent is applied.

7283. The device of item 7159 wherein the septal occlusion patch is a septal closure device.

7284. The device of item 7159 wherein the septal occlusion patch is a shunt closure device.

7285. The device of item 7159 wherein the septal occlusion patch is an intracardic occluder.

7286. The device of item 7159 wherein the septal occlusion patch is an occluding disk.

7287. The device of item 7159 wherein the septal occlusion patch is a defect occluding system.

7288. The device of item 7159 wherein the septal occlusion patch is an intravascular shunt device.

7289. A medical device comprising an endoluminal fastener and a fibrosing agent, where the fibrosing agent induces a fibrotic response between the device and a patient in which the device is implanted.

7290. The device of item 7289 wherein the fibrosing agent promotes regeneration.

7291. The device of item 7289 wherein the fibrosing agent promotes angiogenesis.

7292. The device of item 7289 wherein the fibrosing agent promotes fibroblast migration.

7293. The device of item 7289 wherein the fibrosing agent promotes fibroblast proliferation.

7294. The device of item 7289 wherein the fibrosing agent promotes deposition of extracellular matrix (ECM).

7295. The device of item 7289 wherein the fibrosing agent promotes tissue remodeling.

7296. The device of item 7289 wherein the fibrosing agent is an arterial vessel wall irritant.

7297. The device of item 7289 wherein the fibrosing agent promotes adhesion between the device and a host into which the device is implanted.

7298. The device of item 7289 wherein the device delivers the fibrosing agent locally to tissue proximate to the device.

7299. The device of item 7289 wherein the fibrosing agent is or comprises silk.

7300. The device of item 7289 wherein the fibrosing agent is or comprises mineral particles.

7301. The device of item 7289 wherein the fibrosing agent is or comprises chitosan.

7302. The device of item 7289 wherein the fibrosing agent is or comprises polylysine.

7303. The device of item 7289 wherein the fibrosing agent is or comprises fibronectin.

7304. The device of item 7289 wherein the fibrosing agent is or comprises bleomycin.

7305. The device of item 7289 wherein the fibrosing agent is or comprises CTGF.

7306. The device of item 7289 wherein the fibrosing agent is in the form of a thread, or is in contact with a thread.

7307. The device of item 7289 wherein the fibrosing agent is in the form of a particulate.

7308. The device of item 7289 wherein the composition further comprises an inflammatory cytokine.

7309. The device of item 7289 wherein the composition further comprises an agent that stimulates cell proliferation.

7310. The device of item 7289 wherein the composition is in the form of a gel, paste, or spray.

7311. The device of item 7289 wherein the fibrosing agent is in the form of tufts.

7312. The device of item 7289, further comprising a polymer.

7313. The device of item 7289, further comprising a polymeric carrier.

7314. The device of item 7289 wherein the fibrosing agent promotes adhesion between the device and a host into which the device is implanted.

7315. The device of item 7289 wherein the device delivers the fibrosing agent locally to tissue proximate to the device.

7316. The device of item 7289, further comprising a coating, wherein the coating comprises the fibrosing agent.

7317. The device of item 7289, further comprising a coating, wherein the coating is disposed on a surface of the device.

7318. The device of item 7289, further comprising a coating, wherein the coating directly contacts the device.

7319. The device of item 7289, further comprising a coating, wherein the coating indirectly contacts the device.

7320. The device of item 7289, further comprising a coating, wherein the coating partially covers the device.

7321. The device of item 7289, further comprising a coating, wherein the coating completely covers the device.

7322. The device of item 7289, further comprising a coating, wherein the coating is a uniform coating.

7323. The device of item 7289, further comprising a coating, wherein the coating is a non-uniform coating.

7324. The device of item 7289, further comprising a coating, wherein the coating is a discontinuous coating.

7325. The device of item 7289, further comprising a coating, wherein the coating is a patterned coating.

7326. The device of item 7289, further comprising a coating, wherein the coating has a thickness of 100 µm or less.

7327. The device of item 7289, further comprising a coating, wherein the coating has a thickness of 10 µm or less.

7328. The device of item 7289, further comprising a coating, wherein the coating adheres to the surface of the device upon deployment of the device.

7329. The device of item 7289, further comprising a coating, wherein the coating is stable at room temperature for a period of 1 year.

7330. The device of item 7289, further comprising a coating, wherein the fibrosing agent is present in the coating in an amount ranging between about 0.0001% to about 1% by weight.

7331. The device of item 7289, further comprising a coating, wherein the fibrosing agent is present in the coating in an amount ranging between about 1% to about 10% by weight.

7332. The device of item 7289, further comprising a coating, wherein the fibrosing agent is present in the coating in an amount ranging between about 10% to about 25% by weight.

7333. The device of item 7289, further comprising a coating, wherein the fibrosing agent is present in the coating in an amount ranging between about 25% to about 70% by weight.

7334. The device of item 7289, further comprising a coating, wherein the coating further comprises a polymer.

7335. The device of item 7289, further comprising a first coating having a first composition and the second coating having a second composition.

7336. The device of item 7289, further comprising a first coating having a first composition and the second coating having a second composition, wherein the first composition and the second composition are different.

7337. The device of item 7289, further comprising a polymer.

7338. The device of item 7289, further comprising a polymeric carrier.

7339. The device of item 7289, further comprising a polymeric carrier, wherein the polymeric carrier comprises a copolymer.

7340. The device of item 7289, further comprising a polymeric carrier, wherein the polymeric carrier comprises a block copolymer.

7341. The device of item 7289, further comprising a polymeric carrier, wherein the polymeric carrier comprises a random copolymer.

7342. The device of item 7289, further comprising a polymeric carrier, wherein the polymeric carrier comprises a biodegradable polymer.

7343. The device of item 7289, further comprising a polymeric carrier, wherein the polymeric carrier comprises a non-biodegradable polymer.

7344. The device of item 7289, further comprising a polymeric carrier, wherein the polymeric carrier comprises a hydrophilic polymer.

7345. The device of item 7289, further comprising a polymeric carrier, wherein the polymeric carrier comprises a hydrophobic polymer.

7346. The device of item 7289, further comprising a polymeric carrier, wherein the polymeric carrier comprises a polymer having hydrophilic domains.

7347. The device of item 7289, further comprising a polymeric carrier, wherein the polymeric carrier comprises a polymer having hydrophobic domains.

7348. The device of item 7289, further comprising a polymeric carrier, wherein the polymeric carrier comprises a non-conductive polymer.

7349. The device of item 7289, further comprising a polymeric carrier, wherein the polymeric carrier comprises an elastomer.

7350. The device of item 7289, further comprising a polymeric carrier, wherein the polymeric carrier comprises a hydrogel.

7351. The device of item 7289, further comprising a polymeric carrier, wherein the polymeric carrier comprises a silicone polymer.

7352. The device of item 7289, further comprising a polymeric carrier, wherein the polymeric carrier comprises a hydrocarbon polymer.

7353. The device of item 7289, further comprising a polymeric carrier, wherein the polymeric carrier comprises a styrene-derived polymer.

7354. The device of item 7289, further comprising a polymeric carrier, wherein the polymeric carrier comprises a butadiene polymer.

7355. The device of item 7289, further comprising a polymeric carrier, wherein the polymeric carrier comprises a macromer.

7356. The device of item 7289, further comprising a polymeric carrier, wherein the polymeric carrier comprises a poly(ethylene glycol) polymer.

7357. The device of item 7289, further comprising a polymeric carrier, wherein the polymeric carrier comprises an amorphous polymer.

7358. The device of item 7289, further comprising a lubricious coating.

7359. The device of item 7289 wherein the fibrosing agent is located within pores or holes of the device.

7360. The device of item 7289 wherein the fibrosing agent is located within a channel, lumen, or divet of the device.

7361. The device of item 7289, further comprising a second pharmaceutically active agent.

7362. The device of item 7289, further comprising an anti-inflammatory agent.

7363. The device of item 7289, further comprising an agent that inhibits infection.

7364. The device of item 7289, further comprising an agent that inhibits infection, wherein the agent is an anthracycline.

7365. The device of item 7289, further comprising an agent that inhibits infection, wherein the agent is doxorubicin.

7366. The device of item 7289, further comprising an agent that inhibits infection, wherein the agent is mitoxantrone.

7367. The device of item 7289, further comprising an agent that inhibits infection, wherein the agent is a fluoropyrimidine.

7368. The device of item 7289, further comprising an agent that inhibits infection, wherein the agent is 5-fluorouracil (5-FU).

7369. The device of item 7289, further comprising an agent that inhibits infection, wherein the agent is a folic acid antagonist.

7370. The device of item 7289, further comprising an agent that inhibits infection, wherein the agent is methotrexate.

7371. The device of item 7289, further comprising an agent that inhibits infection, wherein the agent is a podophylotoxin.

7372. The device of item 7289, further comprising an agent that inhibits infection, wherein the agent is etoposide.

7373. The device of item 7289, further comprising an agent that inhibits infection, wherein the agent is a camptothecin.

7374. The device of item 7289, further comprising an agent that inhibits infection, wherein the agent is a hydroxyurea.

7375. The device of item 7289, further comprising an agent that inhibits infection, wherein the agent is a platinum complex.

7376. The device of item 7289, further comprising an agent that inhibits infection, wherein the agent is cisplatin.

7377. The device of item 7289, further comprising an anti-thrombotic agent.

7378. The device of item 7289, further comprising a visualization agent.

7379. The device of item 7289, further comprising a visualization agent, wherein the visualization agent is a radiopaque material, wherein the radiopaque material comprises a metal, a halogenated compound, or a barium containing compound.

7380. The device of item 7289, further comprising a visualization agent, wherein the visualization agent is a radiopaque material, wherein the radiopaque material comprises barium, tantalum, or technetium.

7381. The device of item 7289, further comprising a visualization agent, wherein the visualization agent is a MRI responsive material.

7382. The device of item 7289, further comprising a visualization agent, wherein the visualization agent comprises a gadolinium chelate.

7383. The device of item 7289, further comprising a visualization agent, wherein the visualization agent comprises iron, magnesium, manganese, copper, or chromium.

7384. The device of item 7289, further comprising a visualization agent, wherein the visualization agent comprises an iron oxide compound.

7385. The device of item 7289, further comprising a visualization agent, wherein the visualization agent comprises a dye, pigment, or colorant.

7386. The device of item 7289, further comprising an echogenic material.

7387. The device of item 7289, further comprising an echogenic material, wherein the echogenic material is in the form of a coating.

7388. The device of item 7289 wherein the device is sterile.

7389. The device of item 7289 wherein the fibrosing agent is released into tissue in the vicinity of the device after deployment of the device.

7390. The device of item 7289 wherein the fibrosing agent is released into tissue in the vicinity of the device after deployment of the device, wherein the tissue is connective tissue.

7391. The device of item 7289 wherein the fibrosing agent is released into tissue in the vicinity of the device after deployment of the device, wherein the tissue is muscle tissue.

7392. The device of item 7289 wherein the fibrosing agent is released into tissue in the vicinity of the device after deployment of the device, wherein the tissue is nerve tissue.

7393. The device of item 7289 wherein the fibrosing agent is released into tissue in the vicinity of the device after deployment of the device, wherein the tissue is epithelium tissue.

7394. The device of item 7289 wherein the fibrosing agent is released in effective concentrations from the device over a period ranging from the time of deployment of the device to about 1 year.

7395. The device of item 7289 wherein the fibrosing agent is released in effective concentrations from the device over a period ranging from about 1 month to 6 months.

7396. The device of item 7289 wherein the fibrosing agent is released in effective concentrations from the device over a period ranging from about 1–90 days.

7397. The device of item 7289 wherein the fibrosing agent is released in effective concentrations from the device at a constant rate.

7398. The device of item 7289 wherein the fibrosing agent is released in effective concentrations from the device at an increasing rate.

7399. The device of item 7289 wherein the fibrosing agent is released in effective concentrations from the device at a decreasing rate.

7400. The device of item 7289 wherein the fibrosing agent is released in effective concentrations from the composition comprising the fibrosing agent by diffusion over a period ranging from the time of deployment of the device to about 90 days.

7401. The device of item 7289 wherein the fibrosing agent is released in effective concentrations from the composition comprising the fibrosing agent by erosion of the composition over a period ranging from the time of deployment of the device to about 90 days.

7402. The device of item 7289 wherein the device comprises about 0.01 µg to about 10 µg of the fibrosing agent.

7403. The device of item 7289 wherein the device comprises about 10 µg to about 10 mg of the fibrosing agent.

7404. The device of item 7289 wherein the device comprises about 10 mg to about 250 mg of the fibrosing agent.

7405. The device of item 7289 wherein the device comprises about 250 mg to about 1000 mg of the fibrosing agent.

7406. The device of item 7289 wherein the device comprises about 1000 mg to about 2500 mg of the fibrosing agent.

7407. The device of item 7289 wherein a surface of the device comprises less than 0.01 µg of the fibrosing agent per $mm^2$ of device surface to which the fibrosing agent is applied.

7408. The device of item 7289 wherein a surface of the device comprises about 0.01 µg to about 1 µg of the fibrosing agent per $mm^2$ of device surface to which the fibrosing agent is applied.

7409. The device of item 7289 wherein a surface of the device comprises about 1 µg to about 10 µg of the fibrosing agent per $mm^2$ of device surface to which the fibrosing agent is applied.

7410. The device of item 7289 wherein a surface of the device comprises about 10 µg to about 250 µg of the fibrosing agent per $mm^2$ of device surface to which the fibrosing agent is applied.

7411. The device of item 7289 wherein a surface of the device comprises about 250 μg to about 1000 μg of the fibrosing agent of fibrosing agent per mm² of device surface to which the fibrosing agent is applied.

7412. The device of item 7289 wherein a surface of the device comprises about 1000 μg to about 2500 μg of the fibrosing agent per mm² of device surface to which the fibrosing agent is applied.

7413. A method of making an injectable composition comprising combining a fibrosing agent and a bulking agent.

7414. The method of item 7413 wherein the fibrosing agent promotes fibrosis and promotes regeneration.

7415. The method of item 7413 wherein the fibrosing agent promotes angiogenesis.

7416. The method of item 7413 wherein the fibrosing agent promotes fibroblast migration.

7417. The method of item 7413 wherein the fibrosing agent promotes fibroblast proliferation.

7418. The method of item 7413 wherein the fibrosing agent promotes deposition of extracellular matrix (ECM).

7419. The method of item 7413 wherein the fibrosing agent promotes tissue remodeling.

7420. The method of item 7413 wherein the fibrosing agent is or comprises an arterial vessel wall irritant.

7421. The method of item 7413 wherein the fibrosing agent is or comprises silk.

7422. The method of item 7413 wherein the fibrosing agent is or comprises silkworm silk.

7423. The method of item 7413 wherein the fibrosing agent is or comprises spider silk.

7424. The method of item 7413 wherein the fibrosing agent is or comprises recombinant silk.

7425. The method of item 7413 wherein the fibrosing agent is or comprises raw silk.

7426. The method of item 7413 wherein the fibrosing agent is or comprises hydrolyzed silk.

7427. The method of item 7413 wherein the fibrosing agent is or comprises acid-treated silk.

7428. The method of item 7413 wherein the fibrosing agent is or comprises acylated silk.

7429. The method of item 7413 wherein the fibrosing agent is in the form of strands.

7430. The method of item 7413 wherein the fibrosing agent is in the form of tufts.

7431. The method of item 7413 wherein the fibrosing agent is in the form of microparticulates.

7432. The method of item 7413 wherein the fibrosing agent is or comprises mineral particles.

7433. The method of item 7413 wherein the fibrosing agent is or comprises talc.

7434. The method of item 7413 wherein the fibrosing agent is or comprises chitosan.

7435. The method of item 7413 wherein the fibrosing agent is or comprises polylysine.

7436. The method of item 7413 wherein the fibrosing agent is or comprises fibronectin.

7437. The method of item 7413 wherein the fibrosing agent is or comprises bleomycin.

7438. The method of item 7413 wherein the fibrosing agent is or comprises CTGF.

7439. The method of item 7413 wherein the fibrosing agent is in the form of a thread, or is in contact with a thread.

7440. The method of item 7439 wherein the thread is biodegradable.

7441. The method of item 7440 wherein the biodegradable thread comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

7442. The method of item 7439 wherein the thread is non-biodegradable.

7443. The method of item 7442 wherein the non-nonbioderadable thread comprises a material selected from the group consisting of polyester, polyurethane, silicone, polyethylene, polypropylene, polystyrene, polyacrylate, polymethacrylate, and silk.

7444. The method of item 7439 wherein the thread is coated with a polymer.

7445. The method of item 7439 wherein the thread is coated with a pharmaceutical agent that induces a fibrotic response in the patient.

7446. The method of item 7439 wherein the thread is coated with a pharmaceutical agent that induces an osteogenic response in the patient.

7447. The method of item 7413 wherein the fibrosing agent is in the form of a particulate.

7448. The method of item 7447 wherein the particulate is a biodegradable particulate.

7449. The method of item 7448 wherein the biodegradable particulate comprises a material selected from the group consisting of polyester, polyanhydride, poly(anhydride ester), poly(ester-amide), poly(ester-urea), polyorthoester, polyphosphoester, polyphosphazine, polycyanoacrylate, collagen, chitosan, hyaluronic acid, chromic cat gut, alginate, starch, cellulose and cellulose ester.

7450. The method of item 7447 wherein the particulate is non-biodegradable.

7451. The method of item 7450 wherein the non-biodegradable particulate comprises a material selected from the group consisting of polyester, polyurethane, silicone, polyethylene, polypropylene, polystyrene, polyacrylate, polymethacrylate, and silk.

7452. The method of item 7447 wherein the particulate is a particulate form of a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

7453. The method of item 7447 wherein the particulate is coated with a polymer.

7454. The method of item 7447 wherein the particulate is coated with a pharmaceutical agent that induces a fibrotic response in the patient.

7455. The method of item 7447 wherein the particulate is coated with a member selected from the group consisting of silk, talc, starch, glass, silicate, silica, calcium phosphate, calcium sulfate, calcium carbonate, hydroxyapatite, synthetic mineral, polymethylmethacrylate, silver nitrate, ceramic and other inorganic particles.

7456. The method of item 7447 wherein the particulate is coated with a pharmaceutical agent that induces an osteogenic response in the patient.

7457. The method of item 7413 wherein the composition further comprises an agent that promotes bone growth.

7458. The method of item 7457 wherein the agent that promotes bone growth is a bone morphogenic protein.

7459. The method of item 7457 wherein the agent that promotes bone growth is an osteogenic growth factor.

7460. The method of item 7459 wherein the osteogenic growth factor is selected from transforming growth factor, platelet-derived growth factor, and fibroblast growth factor.

7461. The method of item 7413 wherein the bulking agent comprises collagen or crosslinked collagen.

7462. The method of item 7413 wherein the bulking agent comprises hydroxya patite.

7463. The method of item 7413 wherein the bulking agent comprises micronized alloderm acellular matrix.

7464. The method of item 7413 wherein the bulking agent comprises hyaluronic acid.

7465. The method of item 7413 wherein the bulking agent is a hydrogel.

7466. The method of item 7413 wherein the bulking agent comprises beta-glucan.

7467. The method of item 7413 wherein the bulking agent comprises collagen fibrils.

7468. The method of item 7413 wherein the bulking agent comprises hylan polymer.

7469. The method of item 7413 wherein the bulking agent comprises microspheres.

7470. The method of item 7413 wherein the bulking agent comprises polyacrylic acid or polyacrylate.

7471. The method of item 7413 wherein the bulking agent comprises silicon or crosslinked silicon.

7472. The method of item 7413 wherein a visualization agent is combined with the fibrosing agent and/or the bulking agent.

7473. The method of item 7413 wherein a coloring agent is combined with the fibrosing agent and/or the bulking agent.

7474. The method of item 7413 wherein the composition is treated to provide a sterile composition.

7475. The method of item 7413 wherein the composition is formulated to be an urethral bulking agent.

7476. The method of item 7413 wherein the composition is formulated to be an esophageal bulking agent.

7477. The method of item 7413 wherein the composition is formulated to be an anal bulking agent.

7478. The method of item 7413 wherein the fibrosing agent is present in the composition at a concentration within the range of about 0.005 µg–10 µg per mm$^3$.

7479. A method of making a medical device comprising combining i) an orthopedic implant and ii) a fibrosing agent or a composition comprising a fibrosing agent, where the fibrosing agent induces a fibrotic response between the device and a patient in which the device is implanted.

7480. The method of item 7479 wherein the fibrosing agent promotes regeneration.

7481. The method of item 7479 wherein the fibrosing agent promotes angiogenesis.

7482. The method of item 7479 wherein the fibrosing agent promotes fibroblast migration.

7483. The method of item 7479 wherein the fibrosing agent promotes fibroblast proliferation.

7484. The method of item 7479 wherein the fibrosing agent promotes deposition of extracellular matrix (ECM).

7485. The method of item 7479 wherein the fibrosing agent promotes tissue remodeling.

7486. The method of item 7479 wherein the fibrosing agent is an arterial vessel wall irritant.

7487. The method of item 7479 wherein the fibrosing agent promotes adhesion between the device and a host into which the device is implanted.

7488. The method of item 7479 wherein the device delivers the fibrosing agent locally to tissue proximate to the device.

7489. The method of item 7479 wherein the fibrosing agent is or comprises silk.

7490. The method of item 7479 wherein the fibrosing agent is or comprises mineral particles.

7491. The method of item 7479 wherein the fibrosing agent is or comprises chitosan.

7492. The method of item 7479 wherein the fibrosing agent is or comprises polylysine.

7493. The method of item 7479 wherein the fibrosing agent is or comprises fibronectin.

7494. The method of item 7479 wherein the fibrosing agent is or comprises bleomycin.

7495. The method of item 7479 wherein the fibrosing agent is or comprises CTGF.

7496. The method of item 7479 wherein the fibrosing agent is in the form of a thread, or is in contact with a thread.

7497. The method of item 7479 wherein the fibrosing agent is in the form of a particulate.

7498. The method of item 7479 wherein the composition further comprises an inflammatory cytokine.

7499. The method of item 7479 wherein the composition further comprises an agent that stimulates cell proliferation.

7500. The method of item 7479 wherein the composition is in the form of a gel or paste.

7501. The method of item 7479 wherein the fibrosing agent is in the form of tufts.

7502. The method of item 7479 wherein the fibrosing agent promotes adhesion between the device and a host into which the device is implanted.

7503. The method of item 7479 wherein the device delivers the fibrosing agent locally to tissue proximate to the device.

7504. The method of item 7479, wherein the implant is combined with a coating, and the coating comprises the fibrosing agent.

7505. The method of item 7479, wherein the implant is combined with a coating, and the coating is disposed on a surface of the device.

7506. The method of item 7479, wherein the implant is combined with a coating, and the coating directly contacts the device.

7507. The method of item 7479, wherein the implant is combined with a coating, and the coating indirectly contacts the device.

7508. The method of item 7479, wherein the implant is combined with a coating, and the coating partially covers the device.

7509. The method of item 7479, wherein the implant is combined with a coating, and the coating completely covers the device.

7510. The method of item 7479, wherein the implant is combined with a coating, and the coating is a uniform coating.

7511. The method of item 7479, wherein the implant is combined with a coating, and the coating is a non-uniform coating.

7512. The method of item 7479, wherein the implant is combined with a coating, and the coating is a discontinuous coating.

7513. The method of item 7479 wherein the implant is combined with a coating, and the coating is a patterned coating.

7514. The method of item 7479, wherein the implant is combined with a coating, and the coating has a thickness of 100 µm or less.

7515. The method of item 7479, wherein the implant is combined with a coating, and the coating has a thickness of 10 µm or less.

7516. The method of item 7479, wherein the implant is combined with a coating, and the coating adheres to the surface of the device upon deployment of the device.

7517. The method of item 7479, wherein the implant is combined with a coating, and the coating is stable at room temperature for a period of at least 1 year.

7518. The method of item 7479, wherein the implant is combined with a coating, and the fibrosing agent is present in the coating in an amount ranging between about 0.0001% to about 1% by weight.

7519. The method of item 7479, wherein the implant is combined with a coating, and the fibrosing agent is present in the coating in an amount ranging between about 1% to about 10% by weight.

7520. The method of item 7479, wherein the implant is combined with a coating, and the fibrosing agent is present in the coating in an amount ranging between about 10% to about 25% by weight.

7521. The method of item 7479, wherein the implant is combined with a coating, and the fibrosing agent is present in the coating in an amount ranging between about 25% to about 70% by weight.

7522. The method of item 7479, wherein the implant is combined with a coating, and the coating further comprises a polymer.

7523. The method of item 7479, wherein the device comprises a first coating having a first composition and a second coating having a second composition.

7524. The method of item 7479, wherein the device comprises a first coating having a first composition and a second coating having a second composition, where the first composition and the second composition are different.

7525. The method of item 7479, wherein the device comprises a polymer.

7526. The method of item 7479, wherein the device comprises a polymer, and the polymer is a component of the composition.

7527. The method of item 7479, wherein the implant is combined with a polymer, and the polymer is a copolymer.

7528. The method of item 7479, wherein the implant is combined with a polymer, and the polymer is a block copolymer.

7529. The method of item 7479, wherein the implant is combined with a polymer, and the polymer is a random copolymer.

7530. The method of item 7479, wherein the implant is combined with a polymer, and the polymer is a biodegradable polymer.

7531. The method of item 7479, wherein the implant is combined with a polymer, and the polymer is a non-biodegradable polymer.

7532. The method of item 7479, wherein the implant is combined with a polymer, and the polymer is a hydrophilic polymer.

7533. The method of item 7479, wherein the implant is combined with a polymer, and the polymer is a hydrophobic polymer.

7534. The method of item 7479, wherein the implant is combined with a polymer, and the polymer has hydrophilic domains.

7535. The method of item 7479, wherein the implant is combined with a polymer, and the polymer has hydrophobic domains.

7536. The method of item 7479, wherein the implant is combined with a polymer, and the polymer is a non-conductive polymer.

7537. The method of item 7479, wherein the implant is combined with a polymer, and the polymer is an elastomer.

7538. The method of item 7479, wherein the implant is combined with a polymer, and the polymer is a hydrogel.

7539. The method of item 7479, wherein the implant is combined with a polymer, and the polymer is a silicone polymer.

7540. The method of item 7479, wherein the implant is combined with a polymer, and the polymer is a hydrocarbon polymer.

7541. The method of item 7479, wherein the implant is combined with a polymer, and the polymer is a styrene-derived polymer.

7542. The method of item 7479, wherein the implant is combined with a polymer, and the polymer is a butadiene polymer.

7543. The method of item 7479, wherein the implant is combined with a polymer, and the polymer is a macromer.

7544. The method of item 7479, wherein the implant is combined with a polymer, and the polymer is a poly(ethylene glycol) polymer.

7545. The method of item 7479, wherein the implant is combined with a polymer, and the polymer is an amorphous polymer.

7546. The method of item 7479, wherein the implant is combined with a polymer, and the polymer is a lubricious coating.

7547. The method of item 7479 wherein the fibrosing agent is located within pores or holes of the device.

7548. The method of item 7479 wherein the fibrosing agent is located within a channel, lumen, or divet of the device.

7549. The method of item 7479, wherein the implant is further combined with a second pharmaceutically active agent.

7550. The method of item 7479, wherein the implant is further combined with an anti-inflammatory agent.

7551. The method of item 7479 wherein the implant is further combined with an agent that inhibits infection.

7552. The method of item 7479, wherein the implant is further combined with an anthracycline.

7553. The method of item 7479, wherein the implant is further combined with doxorubicin.

7554. The method of item 7479, wherein the implant is further combined with mitoxantrone.

7555. The method of item 7479, wherein the implant is further combined with a fluoropyrimidine.

7556. The method of item 7479, wherein the implant is further combined with 5-fluorouracil (5-FU).

7557. The method of item 7479, wherein the implant is further combined with a folic acid antagonist.

7558. The method of item 7479, wherein the implant is further combined with methotrexate.

7559. The method of item 7479, wherein the implant is further combined with a podophylotoxin.

7560. The method of item 7479, wherein the implant is further combined with etoposide.

7561. The method of item 7479 wherein the implant is further combined with a camptothecin.

7562. The method of item 7479, wherein the implant is further combined with a hydroxyurea.

7563. The method of item 7479, wherein the implant is further combined with a platinum complex.

7564. The method of item 7479, wherein the implant is further combined with cisplatin.

7565. The method of item 7479, wherein the implant is further combined with an anti-thrombotic agent.

7566. The method of item 7479, wherein the implant is further combined with a visualization agent.

7567. The method of item 7479, wherein the implant is further combined with a visualization agent, wherein the visualization agent is a radiopaque material, wherein the radiopaque material comprises a metal, a halogenated compound, or a barium containing compound.

7568. The method of item 7479, wherein the implant is further combined with a visualization agent, wherein the visualization agent is a radiopaque material, wherein the radiopaque material comprises barium, tantalum, or technetium.

7569. The method of item 7479, wherein the implant is further combined with a visualization agent, wherein the visualization agent is a MRI responsive material.

7570. The method of item 7479, wherein the implant is further combined with a visualization agent, wherein the visualization agent comprises a gadolinium chelate.

7571. The method of item 7479, wherein the implant is further combined with a visualization agent, wherein the visualization agent comprises iron, magnesium, manganese, copper, or chromium.

7572. The method of item 7479, wherein the implant is further combined with a visualization agent, wherein the visualization agent comprises an iron oxide compound.

7573. The method of item 7479, wherein the implant is further combined with a visualization agent, wherein the visualization agent comprises a dye, pigment, or colorant.

7574. The method of item 7479, wherein the implant is further combined with an echogenic material.

7575. The method of item 7479, wherein the implant is further combined with an echogenic material, and the echogenic material is in the form of a coating.

7576. The method of item 7479 wherein the device is sterilized.

7577. The method of item 7479 wherein the fibrosing agent is released into tissue in the vicinity of the device after deployment of the device.

7578. The method of item 7479 wherein the fibrosing agent is released into tissue in the vicinity of the device after deployment of the device, wherein the tissue is connective tissue.

7579. The method of item 7479 wherein the fibrosing agent is released into tissue in the vicinity of the device after deployment of the device, wherein the tissue is muscle tissue.

7580. The method of item 7479 wherein the fibrosing agent is released into tissue in the vicinity of the device after deployment of the device, wherein the tissue is nerve tissue.

7581. The method of item 7479 wherein the fibrosing agent is released into tissue in the vicinity of the device after deployment of the device, wherein the tissue is epithelium tissue.

7582. The method of item 7479 wherein the fibrosing agent is released in effective concentrations from the device over a period ranging from the time of deployment of the device to about 1 year.

7583. The method of item 7479 wherein the fibrosing agent is released in effective concentrations from the device over a period ranging from about 1 month to 6 months.

7584. The method of item 7479 wherein the fibrosing agent is released in effective concentrations from the device over a period ranging from about 1–90 days.

7585. The method of item 7479 wherein the fibrosing agent is released in effective concentrations from the device at a constant rate.

7586. The method of item 7479 wherein the fibrosing agent is released in effective concentrations from the device at an increasing rate.

7587. The method of item 7479 wherein the fibrosing agent is released in effective concentrations from the device at a decreasing rate.

7588. The method of item 7479 wherein the fibrosing agent is released in effective concentrations from the composition comprising the fibrosing agent by diffusion over a period ranging from the time of deployment of the device to about 90 days.

7589. The method of item 7479 wherein the fibrosing agent is released in effective concentrations from the composition comprising the fibrosing agent by erosion of the composition over a period ranging from the time of deployment of the device to about 90 days.

7590. The method of item 7479 wherein the device comprises about 0.01 µg to about 10 µg of the fibrosing agent.

7591. The method of item 7479 wherein the device comprises about 10 µg to about 10 mg of the fibrosing agent.

7592. The method of item 7479 wherein the device comprises about 10 mg to about 250 mg of the fibrosing agent.

7593. The method of item 7479 wherein the device comprises about 250 mg to about 1000 mg of the fibrosing agent.

7594. The method of item 7479 wherein the device comprises about 1000 mg to about 2500 mg of the fibrosing agent.

7595. The method of item 7479 wherein a surface of the device comprises less than 0.01 µg of the fibrosing agent per $mm^2$ of device surface to which the fibrosing agent is applied.

7596. The method of item 7479 wherein a surface of the device comprises about 0.01 µg to about 1 µg of the fibrosing agent per $mm^2$ of device surface to which the fibrosing agent is applied.

7597. The method of item 7479 wherein a surface of the device comprises about 1 µg to about 10 µg of the fibrosing agent per $mm^2$ of device surface to which the fibrosing agent is applied.

7598. The method of item 7479 wherein a surface of the device comprises about 10 µg to about 250 µg of the fibrosing agent per $mm^2$ of device surface to which the fibrosing agent is applied.

7599. The method of item 7479 wherein a surface of the device comprises about 250 µg to about 1000 µg of the fibrosing agent of fibrosing agent per $mm^2$ of device surface to which the fibrosing agent is applied.

7600. The method of item 7479 wherein a surface of the device comprises about 1000 µg to about 2500 µg of the fibrosing agent per $mm^2$ of device surface to which the fibrosing agent is applied.

7601. The method of item 7479 wherein the orthopedic implant is used as a substitute for a bone graft.

7602. The method of item 7479 wherein the orthopedic implant is an orthopedic pin implant.

7603. The method of item 7479 wherein the orthopedic implant is an orthopedic nail implant.

7604. A method of making a medical device comprising combining i) an orthopedic prosthesis and ii) a fibrosing agent or a composition comprising a fibrosing agent, where the fibrosing agent induces a fibrotic response between the device and a patient in which the device is implanted.

7605. The method of item 7604 wherein the fibrosing agent promotes regeneration.

7606. The method of item 7604 wherein the fibrosing agent promotes angiogenesis.

7607. The method of item 7604 wherein the fibrosing agent promotes fibroblast migration.

7608. The method of item 7604 wherein the fibrosing agent promotes fibroblast proliferation.

7609. The method of item 7604 wherein the fibrosing agent promotes deposition of extracellular matrix (ECM).

7610. The method of item 7604 wherein the fibrosing agent promotes tissue remodeling.

7611. The method of item 7604 wherein the fibrosing agent is an arterial vessel wall irritant.

7612. The method of item 7604 wherein the fibrosing agent promotes adhesion between the device and a host into which the device is implanted.

7613. The method of item 7604 wherein the device delivers the fibrosing agent locally to tissue proximate to the device.

7614. The method of item 7604 wherein the fibrosing agent is or comprises silk.

7615. The method of item 7604 wherein the fibrosing agent is or comprises mineral particles.

7616. The method of item 7604 wherein the fibrosing agent is or comprises chitosan.

7617. The method of item 7604 wherein the fibrosing agent is or comprises polylysine.

7618. The method of item 7604 wherein the fibrosing agent is or comprises fibronectin.

7619. The method of item 7604 wherein the fibrosing agent is or comprises bleomycin.

7620. The method of item 7604 wherein the fibrosing agent is or comprises CTGF.

7621. The method of item 7604 wherein the fibrosing agent is in the form of a thread, or is in contact with a thread.

7622. The method of item 7604 wherein the fibrosing agent is in the form of a particulate.

7623. The method of item 7604 wherein the composition further comprises an inflammatory cytokine.

7624. The method of item 7604 wherein the composition further comprises an agent that stimulates cell proliferation.

7625. The method of item 7604 wherein the composition is in the form of a gel or paste.

7626. The method of item 7604 wherein the fibrosing agent is in the form of tufts.

7627. The method of item 7604 wherein the fibrosing agent promotes adhesion between the device and a host into which the device is implanted.

7628. The method of item 7604 wherein the device delivers the fibrosing agent locally to tissue proximate to the device.

7629. The method of item 7604, wherein the prosthesis is combined with a coating, and the coating comprises the fibrosing agent.

7630. The method of item 7604, wherein the prosthesis is combined with a coating, and the coating is disposed on a surface of the device.

7631. The method of item 7604, wherein the prosthesis is combined with a coating, and the coating directly contacts the device.

7632. The method of item 7604, wherein the prosthesis is combined with a coating, and the coating indirectly contacts the device.

7633. The method of item 7604, wherein the prosthesis is combined with a coating, and the coating partially covers the device.

7634. The method of item 7604, wherein the prosthesis is combined with a coating, and the coating completely covers the device.

7635. The method of item 7604, wherein the prosthesis is combined with a coating, and the coating is a uniform coating.

7636. The method of item 7604, wherein the prosthesis is combined with a coating, and the coating is a non-uniform coating.

7637. The method of item 7604, wherein the prosthesis is combined with a coating, and the coating is a discontinuous coating.

7638. The method of item 7604 wherein the prosthesis is combined with a coating, and the coating is a patterned coating.

7639. The method of item 7604, wherein the prosthesis is combined with a coating, and the coating has a thickness of 100 µm or less.

7640. The method of item 7604, wherein the prosthesis is combined with a coating, and the coating has a thickness of 10 µm or less.

7641. The method of item 7604, wherein the prosthesis is combined with a coating, and the coating adheres to the surface of the device upon deployment of the device.

7642. The method of item 7604, wherein the prosthesis is combined with a coating, and the coating is stable at room temperature for a period of at least 1 year.

7643. The method of item 7604, wherein the prosthesis is combined with a coating, and the fibrosing agent is present in the coating in an amount ranging between about 0.0001% to about 1% by weight.

7644. The method of item 7604, wherein the prosthesis is combined with a coating, and the fibrosing agent is present in the coating in an amount ranging between about 1% to about 10% by weight.

7645. The method of item 7604, wherein the prosthesis is combined with a coating, and the fibrosing agent is present in the coating in an amount ranging between about 10% to about 25% by weight.

7646. The method of item 7604, wherein the prosthesis is combined with a coating, and the fibrosing agent is present in the coating in an amount ranging between about 25% to about 70% by weight.

7647. The method of item 7604, wherein the prosthesis is combined with a coating, and the coating further comprises a polymer.

7648. The method of item 7604, wherein the device comprises a first coating having a first composition and a second coating having a second composition.

7649. The method of item 7604, wherein the device comprises a first coating having a first composition and a second coating having a second composition, where the first composition and the second composition are different.

7650. The method of item 7604, wherein the device comprises a polymer.

7651. The method of item 7604, wherein the device comprises a polymer, and the polymer is a component of the composition.

7652. The method of item 7604, wherein the prosthesis is combined with a polymer, and the polymer is a copolymer.

7653. The method of item 7604, wherein the prosthesis is combined with a polymer, and the polymer is a block copolymer.

7654. The method of item 7604, wherein the prosthesis is combined with a polymer, and the polymer is a random copolymer.

7655. The method of item 7604, wherein the prosthesis is combined with a polymer, and the polymer is a biodegradable polymer.

7656. The method of item 7604, wherein the prosthesis is combined with a polymer, and the polymer is a non-biodegradable polymer.

7657. The method of item 7604, wherein the prosthesis is combined with a polymer, and the polymer is a hydrophilic polymer.

7658. The method of item 7604, wherein the prosthesis is combined with a polymer, and the polymer is a hydrophobic polymer.

7659. The method of item 7604, wherein the prosthesis is combined with a polymer, and the polymer has hydrophilic domains.

7660. The method of item 7604, wherein the prosthesis is combined with a polymer, and the polymer has hydrophobic domains.

7661. The method of item 7604, wherein the prosthesis is combined with a polymer, and the polymer is a non-conductive polymer.

7662. The method of item 7604, wherein the prosthesis is combined with a polymer, and the polymer is an elastomer.

7663. The method of item 7604, wherein the prosthesis is combined with a polymer, and the polymer is a hydrogel.

7664. The method of item 7604, wherein the prosthesis is combined with a polymer, and the polymer is a silicone polymer.

7665. The method of item 7604, wherein the prosthesis is combined with a polymer, and the polymer is a hydrocarbon polymer.

7666. The method of item 7604, wherein the prosthesis is combined with a polymer, and the polymer is a styrene-derived polymer.

7667. The method of item 7604, wherein the prosthesis is combined with a polymer, and the polymer is a butadiene polymer.

7668. The method of item 7604, wherein the prosthesis is combined with a polymer, and the polymer is a macromer.

7669. The method of item 7604, wherein the prosthesis is combined with a polymer, and the polymer is a poly(ethylene glycol) polymer.

7670. The method of item 7604, wherein the prosthesis is combined with a polymer, and the polymer is an amorphous polymer.

7671. The method of item 7604, wherein the prosthesis is combined with a polymer, and the polymer is a lubricious coating.

7672. The method of item 7604 wherein the fibrosing agent is located within pores or holes of the device.

7673. The method of item 7604 wherein the fibrosing agent is located within a channel, lumen, or divet of the device.

7674. The method of item 7604, wherein the prosthesis is further combined with a second pharmaceutically active agent.

7675. The method of item 7604, wherein the prosthesis is further combined with an anti-inflammatory agent.

7676. The method of item 7604 wherein the prosthesis is further combined with an agent that inhibits infection.

7677. The method of item 7604, wherein the prosthesis is further combined with an anthracycline.

7678. The method of item 7604, wherein the prosthesis is further combined with doxorubicin.

7679. The method of item 7604, wherein the prosthesis is further combined with mitoxantrone.

7680. The method of item 7604, wherein the prosthesis is further combined with a fluoropyrimidine.

7681. The method of item 7604, wherein the prosthesis is further combined with 5-fluorouracil (5-FU).

7682. The method of item 7604, wherein the prosthesis is further combined with a folic acid antagonist.

7683. The method of item 7604, wherein the prosthesis is further combined with methotrexate.

7684. The method of item 7604, wherein the prosthesis is further combined with a podophylotoxin.

7685. The method of item 7604, wherein the prosthesis is further combined with etoposide.

7686. The method of item 7604 wherein the prosthesis is further combined with a camptothecin.

7687. The method of item 7604, wherein the prosthesis is further combined with a hydroxyurea.

7688. The method of item 7604, wherein the prosthesis is further combined with a platinum complex.

7689. The method of item 7604, wherein the prosthesis is further combined with cisplatin.

7690. The method of item 7604, wherein the prosthesis is further combined with an anti-thrombotic agent.

7691. The method of item 7604, wherein the prosthesis is further combined with a visualization agent.

7692. The method of item 7604, wherein the prosthesis is further combined with a visualization agent, wherein the visualization agent is a radiopaque material, wherein the radiopaque material comprises a metal, a halogenated compound, or a barium containing compound.

7693. The method of item 7604, wherein the prosthesis is further combined with a visualization agent, wherein the visualization agent is a radiopaque material, wherein the radiopaque material comprises barium, tantalum, or technetium.

7694. The method of item 7604, wherein the prosthesis is further combined with a visualization agent, wherein the visualization agent is a MRI responsive material.

7695. The method of item 7604, wherein the prosthesis is further combined with a visualization agent, wherein the visualization agent comprises a gadolinium chelate.

7696. The method of item 7604, wherein the prosthesis is further combined with a visualization agent, wherein the visualization agent comprises iron, magnesium, manganese, copper, or chromium.

7697. The method of item 7604, wherein the prosthesis is further combined with a visualization agent, wherein the visualization agent comprises an iron oxide compound.

7698. The method of item 7604, wherein the prosthesis is further combined with a visualization agent, wherein the visualization agent comprises a dye, pigment, or colorant.

7699. The method of item 7604, wherein the prosthesis is further combined with an echogenic material.

7700. The method of item 7604, wherein the prosthesis is further combined with an echogenic material, and the echogenic material is in the form of a coating.

7701. The method of item 7604 wherein the device is sterilized.

7702. The method of item 7604 wherein the fibrosing agent is released into tissue in the vicinity of the device after deployment of the device.

7703. The method of item 7604 wherein the fibrosing agent is released into tissue in the vicinity of the device after deployment of the device, wherein the tissue is connective tissue.

7704. The method of item 7604 wherein the fibrosing agent is released into tissue in the vicinity of the device after deployment of the device, wherein the tissue is muscle tissue.

7705. The method of item 7604 wherein the fibrosing agent is released into tissue in the vicinity of the device after deployment of the device, wherein the tissue is nerve tissue.

7706. The method of item 7604 wherein the fibrosing agent is released into tissue in the vicinity of the device after deployment of the device, wherein the tissue is epithelium tissue.

7707. The method of item 7604 wherein the fibrosing agent is released in effective concentrations from the device over a period ranging from the time of deployment of the device to about 1 year.

7708. The method of item 7604 wherein the fibrosing agent is released in effective concentrations from the device over a period ranging from about 1 month to 6 months.

7709. The method of item 7604 wherein the fibrosing agent is released in effective concentrations from the device over a period ranging from about 1–90 days.

7710. The method of item 7604 wherein the fibrosing agent is released in effective concentrations from the device at a constant rate.

7711. The method of item 7604 wherein the fibrosing agent is released in effective concentrations from the device at an increasing rate.

7712. The method of item 7604 wherein the fibrosing agent is released in effective concentrations from the device at a decreasing rate.

7713. The method of item 7604 wherein the fibrosing agent is released in effective concentrations from the composition comprising the fibrosing agent by diffusion over a period ranging from the time of deployment of the device to about 90 days.

7714. The method of item 7604 wherein the fibrosing agent is released in effective concentrations from the composition comprising the fibrosing agent by erosion of the composition over a period ranging from the time of deployment of the device to about 90 days.

7715. The method of item 7604 wherein the device comprises about 0.01 µg to about 10 µg of the fibrosing agent.

7716. The method of item 7604 wherein the device comprises about 10 µg to about 10 mg of the fibrosing agent.

7717. The method of item 7604 wherein the device comprises about 10 mg to about 250 mg of the fibrosing agent.

7718. The method of item 7604 wherein the device comprises about 250 mg to about 1000 mg of the fibrosing agent.

7719. The method of item 7604 wherein the device comprises about 1000 mg to about 2500 mg of the fibrosing agent.

7720. The method of item 7604 wherein a surface of the device comprises less than 0.01 µg of the fibrosing agent per $mm^2$ of device surface to which the fibrosing agent is applied.

7721. The method of item 7604 wherein a surface of the device comprises about 0.01 µg to about 1 µg of the fibrosing agent per $mm^2$ of device surface to which the fibrosing agent is applied.

7722. The method of item 7604 wherein a surface of the device comprises about 1 µg to about 10 µg of the fibrosing agent per $mm^2$ of device surface to which the fibrosing agent is applied.

7723. The method of item 7604 wherein a surface of the device comprises about 10 µg to about 250 µg of the fibrosing agent per $mm^2$ of device surface to which the fibrosing agent is applied.

7724. The method of item 7604 wherein a surface of the device comprises about 250 µg to about 1000 µg of the fibrosing agent of fibrosing agent per $mm^2$ of device surface to which the fibrosing agent is applied.

7725. The method of item 7604 wherein a surface of the device comprises about 1000 µg to about 2500 µg of the fibrosing agent per $mm^2$ of device surface to which the fibrosing agent is applied.

7726. The method of item 7604 wherein the orthopedic implant is a knee implant.

7727. The method of item 7604 wherein the orthopedic implant is hip implant.

7728. The method of item 7604 wherein the orthopedic implant is a shoulder implant.

7729. The method of item 7604 wherein the orthopedic implant is a digit implant.

7730. A method of making a medical device comprising combining i) a dental implant and ii) a fibrosing agent or a composition comprising a fibrosing agent, where the fibrosing agent induces a fibrotic response between the device and a patient in which the device is implanted.

7731. The method of item 7730 wherein the fibrosing agent promotes regeneration.

7732. The method of item 7730 wherein the fibrosing agent promotes angiogenesis.

7733. The method of item 7730 wherein the fibrosing agent promotes fibroblast migration.

7734. The method of item 7730 wherein the fibrosing agent promotes fibroblast proliferation.

7735. The method of item 7730 wherein the fibrosing agent promotes deposition of extracellular matrix (ECM).

7736. The method of item 7730 wherein the fibrosing agent promotes tissue remodeling.

7737. The method of item 7730 wherein the fibrosing agent is an arterial vessel wall irritant.

7738. The method of item 7730 wherein the fibrosing agent promotes adhesion between the device and a host into which the device is implanted.

7739. The method of item 7730 wherein the device delivers the fibrosing agent locally to tissue proximate to the device.

7740. The method of item 7730 wherein the fibrosing agent is or comprises silk.

7741. The method of item 7730 wherein the fibrosing agent is or comprises mineral particles.

7742. The method of item 7730 wherein the fibrosing agent is or comprises chitosan.

7743. The method of item 7730 wherein the fibrosing agent is or comprises polylysine.

7744. The method of item 7730 wherein the fibrosing agent is or comprises fibronectin.

7745. The method of item 7730 wherein the fibrosing agent is or comprises bleomycin.

7746. The method of item 7730 wherein the fibrosing agent is or comprises CTGF.

7747. The method of item 7730 wherein the fibrosing agent is in the form of a thread, or is in contact with a thread.

7748. The method of item 7730 wherein the fibrosing agent is in the form of a particulate.

7749. The method of item 7730 wherein the composition further comprises an inflammatory cytokine.

7750. The method of item 7730 wherein the composition further comprises an agent that stimulates cell proliferation.

7751. The method of item 7730 wherein the composition is in the form of a gel or paste.

7752. The method of item 7730 wherein the fibrosing agent is in the form of tufts.

7753. The method of item 7730 wherein the fibrosing agent promotes adhesion between the device and a host into which the device is implanted.

7754. The method of item 7730 wherein the device delivers the fibrosing agent locally to tissue proximate to the device.

7755. The method of item 7730, wherein the implant is combined with a coating, and the coating comprises the fibrosing agent.

7756. The method of item 7730, wherein the implant is combined with a coating, and the coating is disposed on a surface of the device.

7757. The method of item 7730, wherein the implant is combined with a coating, and the coating directly contacts the device.

7758. The method of item 7730, wherein the implant is combined with a coating, and the coating indirectly contacts the device.

7759. The method of item 7730, wherein the implant is combined with a coating, and the coating partially covers the device.

7760. The method of item 7730, wherein the implant is combined with a coating, and the coating completely covers the device.

7761. The method of item 7730, wherein the implant is combined with a coating, and the coating is a uniform coating.

7762. The method of item 7730, wherein the implant is combined with a coating, and the coating is a non-uniform coating.

7763. The method of item 7730, wherein the implant is combined with a coating, and the coating is a discontinuous coating.

7764. The method of item 7730 wherein the implant is combined with a coating, and the coating is a patterned coating.

7765. The method of item 7730, wherein the implant is combined with a coating, and the coating has a thickness of 100 µm or less.

7766. The method of item 7730, wherein the implant is combined with a coating, and the coating has a thickness of 10 µm or less.

7767. The method of item 7730, wherein the implant is combined with a coating, and the coating adheres to the surface of the device upon deployment of the device.

7768. The method of item 7730, wherein the implant is combined with a coating, and the coating is stable at room temperature for a period of at least 1 year.

7769. The method of item 7730, wherein the implant is combined with a coating, and the fibrosing agent is present in the coating in an amount ranging between about 0.0001% to about 1% by weight.

7770. The method of item 7730, wherein the implant is combined with a coating, and the fibrosing agent is present in the coating in an amount ranging between about 1% to about 10% by weight.

7771. The method of item 7730, wherein the implant is combined with a coating, and the fibrosing agent is present in the coating in an amount ranging between about 10% to about 25% by weight.

7772. The method of item 7730, wherein the implant is combined with a coating, and the fibrosing agent is present in the coating in an amount ranging between about 25% to about 70% by weight.

7773. The method of item 7730, wherein the implant is combined with a coating, and the coating further comprises a polymer.

7774. The method of item 7730, wherein the device comprises a first coating having a first composition and a second coating having a second composition.

7775. The method of item 7730, wherein the device comprises a first coating having a first composition and a second coating having a second composition, where the first composition and the second composition are different.

7776. The method of item 7730, wherein the device comprises a polymer.

7777. The method of item 7730, wherein the device comprises a polymer, and the polymer is a component of the composition.

7778. The method of item 7730, wherein the implant is combined with a polymer, and the polymer is a copolymer.

7779. The method of item 7730, wherein the implant is combined with a polymer, and the polymer is a block copolymer.

7780. The method of item 7730, wherein the implant is combined with a polymer, and the polymer is a random copolymer.

7781. The method of item 7730, wherein the implant is combined with a polymer, and the polymer is a biodegradable polymer.

7782. The method of item 7730, wherein the implant is combined with a polymer, and the polymer is a non-biodegradable polymer.

7783. The method of item 7730, wherein the implant is combined with a polymer, and the polymer is a hydrophilic polymer.

7784. The method of item 7730, wherein the implant is combined with a polymer, and the polymer is a hydrophobic polymer.

7785. The method of item 7730, wherein the implant is combined with a polymer, and the polymer has hydrophilic domains.

7786. The method of item 7730, wherein the implant is combined with a polymer, and the polymer has hydrophobic domains.

7787. The method of item 7730, wherein the implant is combined with a polymer, and the polymer is a non-conductive polymer.

7788. The method of item 7730, wherein the implant is combined with a polymer, and the polymer is an elastomer.

7789. The method of item 7730, wherein the implant is combined with a polymer, and the polymer is a hydrogel.

7790. The method of item 7730, wherein the implant is combined with a polymer, and the polymer is a silicone polymer.

7791. The method of item 7730, wherein the implant is combined with a polymer, and the polymer is a hydrocarbon polymer.

7792. The method of item 7730, wherein the implant is combined with a polymer, and the polymer is a styrene-derived polymer.

7793. The method of item 7730, wherein the implant is combined with a polymer, and the polymer is a butadiene polymer.

7794. The method of item 7730, wherein the implant is combined with a polymer, and the polymer is a macromer.

7795. The method of item 7730, wherein the implant is combined with a polymer, and the polymer is a poly(ethylene glycol) polymer.

7796. The method of item 7730, wherein the implant is combined with a polymer, and the polymer is an amorphous polymer.

7797. The method of item 7730, wherein the implant is combined with a polymer, and the polymer is a lubricious coating.

7798. The method of item 7730 wherein the fibrosing agent is located within pores or holes of the device.

7799. The method of item 7730 wherein the fibrosing agent is located within a channel, lumen, or divet of the device.

7800. The method of item 7730, wherein the implant is further combined with a second pharmaceutically active agent.

7801. The method of item 7730, wherein the implant is further combined with an anti-inflammatory agent.

7802. The method of item 7730 wherein the implant is further combined with an agent that inhibits infection.

7803. The method of item 7730, wherein the implant is further combined with an anthracycline.

7804. The method of item 7730, wherein the implant is further combined with doxorubicin.

7805. The method of item 7730, wherein the implant is further combined with mitoxantrone.

7806. The method of item 7730, wherein the implant is further combined with a fluoropyrimidine.

7807. The method of item 7730, wherein the implant is further combined with 5-fluorouracil (5-FU).

7808. The method of item 7730, wherein the implant is further combined with a folic acid antagonist.

7809. The method of item 7730, wherein the implant is further combined with methotrexate.

7810. The method of item 7730, wherein the implant is further combined with a podophylotoxin.

7811. The method of item 7730, wherein the implant is further combined with etoposide.

7812. The method of item 7730 wherein the implant is further combined with a camptothecin.

7813. The method of item 7730, wherein the implant is further combined with a hydroxyurea.

7814. The method of item 7730, wherein the implant is further combined with a platinum complex.

7815. The method of item 7730, wherein the implant is further combined with cisplatin.

7816. The method of item 7730, wherein the implant is further combined with an anti-thrombotic agent.

7817. The method of item 7730, wherein the implant is further combined with a visualization agent.

7818. The method of item 7730, wherein the implant is further combined with a visualization agent, wherein the visualization agent is a radiopaque material, wherein the radiopaque material comprises a metal, a halogenated compound, or a barium containing compound.

7819. The method of item 7730, wherein the implant is further combined with a visualization agent, wherein the visualization agent is a radiopaque material, wherein the radiopaque material comprises barium, tantalum, or technetium.

7820. The method of item 7730, wherein the implant is further combined with a visualization agent, wherein the visualization agent is a MRI responsive material.

7821. The method of item 7730, wherein the implant is further combined with a visualization agent, wherein the visualization agent comprises a gadolinium chelate.

7822. The method of item 7730, wherein the implant is further combined with a visualization agent, wherein the visualization agent comprises iron, magnesium, manganese, copper, or chromium.

7823. The method of item 7730, wherein the implant is further combined with a visualization agent, wherein the visualization agent comprises an iron oxide compound.

7824. The method of item 7730, wherein the implant is further combined with a visualization agent, wherein the visualization agent comprises a dye, pigment, or colorant.

7825. The method of item 7730, wherein the implant is further combined with an echogenic material.

7826. The method of item 7730, wherein the implant is further combined with an echogenic material, and the echogenic material is in the form of a coating.

7827. The method of item 7730 wherein the device is sterilized.

7828. The method of item 7730 wherein the fibrosing agent is released into tissue in the vicinity of the device after deployment of the device.

7829. The method of item 7730 wherein the fibrosing agent is released into tissue in the vicinity of the device after deployment of the device, wherein the tissue is connective tissue.

7830. The method of item 7730 wherein the fibrosing agent is released into tissue in the vicinity of the device after deployment of the device, wherein the tissue is muscle tissue.

7831. The method of item 7730 wherein the fibrosing agent is released into tissue in the vicinity of the device after deployment of the device, wherein the tissue is nerve tissue.

7832. The method of item 7730 wherein the fibrosing agent is released into tissue in the vicinity of the device after deployment of the device, wherein the tissue is epithelium tissue.

7833. The method of item 7730 wherein the fibrosing agent is released in effective concentrations from the device over a period ranging from the time of deployment of the device to about 1 year.

7834. The method of item 7730 wherein the fibrosing agent is released in effective concentrations from the device over a period ranging from about 1 month to 6 months.

7835. The method of item 7730 wherein the fibrosing agent is released in effective concentrations from the device over a period ranging from about 1–90 days.

7836. The method of item 7730 wherein the fibrosing agent is released in effective concentrations from the device at a constant rate.

7837. The method of item 7730 wherein the fibrosing agent is released in effective concentrations from the device at an increasing rate.

7838. The method of item 7730 wherein the fibrosing agent is released in effective concentrations from the device at a decreasing rate.

7839. The method of item 7730 wherein the fibrosing agent is released in effective concentrations from the composition comprising the fibrosing agent by diffusion over a period ranging from the time of deployment of the device to about 90 days.

7840. The method of item 7730 wherein the fibrosing agent is released in effective concentrations from the composition comprising the fibrosing agent by erosion of the composition over a period ranging from the time of deployment of the device to about 90 days.

7841. The method of item 7730 wherein the device comprises about 0.01 µg to about 10 µg of the fibrosing agent.

7842. The method of item 7730 wherein the device comprises about 10 µg to about 10 mg of the fibrosing agent.

7843. The method of item 7730 wherein the device comprises about 10 mg to about 250 mg of the fibrosing agent.

7844. The method of item 7730 wherein the device comprises about 250 mg to about 1000 mg of the fibrosing agent.

7845. The method of item 7730 wherein the device comprises about 1000 mg to about 2500 mg of the fibrosing agent.

7846. The method of item 7730 wherein a surface of the device comprises less than 0.01 µg of the fibrosing agent per $mm^2$ of device surface to which the fibrosing agent is applied.

7847. The method of item 7730 wherein a surface of the device comprises about 0.01 µg to about 1 µg of the fibrosing agent per $mm^2$ of device surface to which the fibrosing agent is applied.

7848. The method of item 7730 wherein a surface of the device comprises about 1 µg to about 10 µg of the fibrosing agent per $mm^2$ of device surface to which the fibrosing agent is applied.

7849. The method of item 7730 wherein a surface of the device comprises about 10 µg to about 250 µg of the fibrosing agent per $mm^2$ of device surface to which the fibrosing agent is applied.

7850. The method of item 7730 wherein a surface of the device comprises about 250 µg to about 1000 µg of the fibrosing agent of fibrosing agent per $mm^2$ of device surface to which the fibrosing agent is applied.

7851. The method of item 7730 wherein a surface of the device comprises about 1000 µg to about 2500 µg of the fibrosing agent per $mm^2$ of device surface to which the fibrosing agent is applied.

7852. The method of item 7730 wherein the implant is a titanium fixture for replacement of the root portion of a missing natural tooth.

7853. The method of item 7730 wherein the implant is an endosteal implant.

7854. The method of item 7730 wherein the implant is an subperiosteal implant.

7855. The method of item 7730 wherein the implant is a guided bone regeneration (GBR) implant.

7856. The method of item 7730 wherein the implant is a dental implant that controls the healing process subsequent to periodontal disease.

7857. A method of making a medical device comprising combining i) an internal fixation implant and ii) a fibrosing agent or a composition comprising a fibrosing agent, where the fibrosing agent induces a fibrotic response between the device and a patient in which the device is implanted.

7858. The method of item 7857 wherein the fibrosing agent promotes regeneration.

7859. The method of item 7857 wherein the fibrosing agent promotes angiogenesis.

7860. The method of item 7857 wherein the fibrosing agent promotes fibroblast migration.

7861. The method of item 7857 wherein the fibrosing agent promotes fibroblast proliferation.

7862. The method of item 7857 wherein the fibrosing agent promotes deposition of extracellular matrix (ECM).

7863. The method of item 7857 wherein the fibrosing agent promotes tissue remodeling.

7864. The method of item 7857 wherein the fibrosing agent is an arterial vessel wall irritant.

7865. The method of item 7857 wherein the fibrosing agent promotes adhesion between the device and a host into which the device is implanted.

7866. The method of item 7857 wherein the device delivers the fibrosing agent locally to tissue proximate to the device.

7867. The method of item 7857 wherein the fibrosing agent is or comprises silk.

7868. The method of item 7857 wherein the fibrosing agent is or comprises mineral particles.

7869. The method of item 7857 wherein the fibrosing agent is or comprises chitosan.

7870. The method of item 7857 wherein the fibrosing agent is or comprises polylysine.

7871. The method of item 7857 wherein the fibrosing agent is or comprises fibronectin.

7872. The method of item 7857 wherein the fibrosing agent is or comprises bleomycin.

7873. The method of item 7857 wherein the fibrosing agent is or comprises CTGF.

7874. The method of item 7857 wherein the fibrosing agent is in the form of a thread, or is in contact with a thread.

7875. The method of item 7857 wherein the fibrosing agent is in the form of a particulate.

7876. The method of item 7857 wherein the composition further comprises an inflammatory cytokine.

7877. The method of item 7857 wherein the composition further comprises an agent that stimulates cell proliferation.

7878. The method of item 7857 wherein the composition is in the form of a gel or paste.

7879. The method of item 7857 wherein the fibrosing agent is in the form of tufts.

7880. The method of item 7857 wherein the fibrosing agent promotes adhesion between the device and a host into which the device is implanted.

7881. The method of item 7857 wherein the device delivers the fibrosing agent locally to tissue proximate to the device.

7882. The method of item 7857, wherein the implant is combined with a coating, and the coating comprises the fibrosing agent.

7883. The method of item 7857, wherein the implant is combined with a coating, and the coating is disposed on a surface of the device.

7884. The method of item 7857, wherein the implant is combined with a coating, and the coating directly contacts the device.

7885. The method of item 7857, wherein the implant is combined with a coating, and the coating indirectly contacts the device.

7886. The method of item 7857, wherein the implant is combined with a coating, and the coating partially covers the device.

7887. The method of item 7857, wherein the implant is combined with a coating, and the coating completely covers the device.

7888. The method of item 7857, wherein the implant is combined with a coating, and the coating is a uniform coating.

7889. The method of item 7857, wherein the implant is combined with a coating, and the coating is a non-uniform coating.

7890. The method of item 7857, wherein the implant is combined with a coating, and the coating is a discontinuous coating.

7891. The method of item 7857 wherein the implant is combined with a coating, and the coating is a patterned coating.

7892. The method of item 7857, wherein the implant is combined with a coating, and the coating has a thickness of 100 μm or less.

7893. The method of item 7857, wherein the implant is combined with a coating, and the coating has a thickness of 10 μm or less.

7894. The method of item 7857, wherein the implant is combined with a coating, and the coating adheres to the surface of the device upon deployment of the device.

7895. The method of item 7857, wherein the implant is combined with a coating, and the coating is stable at room temperature for a period of at least 1 year.

7896. The method of item 7857, wherein the implant is combined with a coating, and the fibrosing agent is present in the coating in an amount ranging between about 0.0001% to about 1% by weight.

7897. The method of item 7857, wherein the implant is combined with a coating, and the fibrosing agent is present in the coating in an amount ranging between about 1% to about 10% by weight.

7898. The method of item 7857, wherein the implant is combined with a coating, and the fibrosing agent is present in the coating in an amount ranging between about 10% to about 25% by weight.

7899. The method of item 7857, wherein the implant is combined with a coating, and the fibrosing agent is present in the coating in an amount ranging between about 25% to about 70% by weight.

7900. The method of item 7857, wherein the implant is combined with a coating, and the coating further comprises a polymer.

7901. The method of item 7857, wherein the device comprises a first coating having a first composition and a second coating having a second composition.

7902. The method of item 7857, wherein the device comprises a first coating having a first composition and a second coating having a second composition, where the first composition and the second composition are different.

7903. The method of item 7857, wherein the device comprises a polymer.

7904. The method of item 7857, wherein the device comprises a polymer, and the polymer is a component of the composition.

7905. The method of item 7857, wherein the implant is combined with a polymer, and the polymer is a copolymer.

7906. The method of item 7857, wherein the implant is combined with a polymer, and the polymer is a block copolymer.

7907. The method of item 7857, wherein the implant is combined with a polymer, and the polymer is a random copolymer.

7908. The method of item 7857, wherein the implant is combined with a polymer, and the polymer is a biodegradable polymer.

7909. The method of item 7857, wherein the implant is combined with a polymer, and the polymer is a non-biodegradable polymer.

7910. The method of item 7857, wherein the implant is combined with a polymer, and the polymer is a hydrophilic polymer.

7911. The method of item 7857, wherein the implant is combined with a polymer, and the polymer is a hydrophobic polymer.

7912. The method of item 7857, wherein the implant is combined with a polymer, and the polymer has hydrophilic domains.

7913. The method of item 7857, wherein the implant is combined with a polymer, and the polymer has hydrophobic domains.

7914. The method of item 7857, wherein the implant is combined with a polymer, and the polymer is a non-conductive polymer.

7915. The method of item 7857, wherein the implant is combined with a polymer, and the polymer is an elastomer.

7916. The method of item 7857, wherein the implant is combined with a polymer, and the polymer is a hydrogel.

7917. The method of item 7857, wherein the implant is combined with a polymer, and the polymer is a silicone polymer.

7918. The method of item 7857, wherein the implant is combined with a polymer, and the polymer is a hydrocarbon polymer.

7919. The method of item 7857, wherein the implant is combined with a polymer, and the polymer is a styrene-derived polymer.

7920. The method of item 7857, wherein the implant is combined with a polymer, and the polymer is a butadiene polymer.

7921. The method of item 7857, wherein the implant is combined with a polymer, and the polymer is a macromer.

7922. The method of item 7857, wherein the implant is combined with a polymer, and the polymer is a poly(ethylene glycol) polymer.

7923. The method of item 7857, wherein the implant is combined with a polymer, and the polymer is an amorphous polymer.

7924. The method of item 7857, wherein the implant is combined with a polymer, and the polymer is a lubricious coating.

7925. The method of item 7857 wherein the fibrosing agent is located within pores or holes of the device.

7926. The method of item 7857 wherein the fibrosing agent is located within a channel, lumen, or divet of the device.

7927. The method of item 7857, wherein the implant is further combined with a second pharmaceutically active agent.

7928. The method of item 7857, wherein the implant is further combined with an anti-inflammatory agent.

7929. The method of item 7857 wherein the implant is further combined with an agent that inhibits infection.

7930. The method of item 7857, wherein the implant is further combined with an anthracycline.

7931. The method of item 7857, wherein the implant is further combined with doxorubicin.

7932. The method of item 7857, wherein the implant is further combined with mitoxantrone.

7933. The method of item 7857, wherein the implant is further combined with a fluoropyrimidine.

7934. The method of item 7857, wherein the implant is further combined with 5-fluorouracil (5-FU).

7935. The method of item 7857, wherein the implant is further combined with a folic acid antagonist.

7936. The method of item 7857, wherein the implant is further combined with methotrexate.

7937. The method of item 7857, wherein the implant is further combined with a podophylotoxin.

7938. The method of item 7857, wherein the implant is further combined with etoposide.

7939. The method of item 7857 wherein the implant is further combined with a camptothecin.

7940. The method of item 7857, wherein the implant is further combined with a hydroxyurea.

7941. The method of item 7857, wherein the implant is further combined with a platinum complex.

7942. The method of item 7857, wherein the implant is further combined with cisplatin.

7943. The method of item 7857, wherein the implant is further combined with an anti-thrombotic agent.

7944. The method of item 7857, wherein the implant is further combined with a visualization agent.

7945. The method of item 7857, wherein the implant is further combined with a visualization agent, wherein the visualization agent is a radiopaque material, wherein the radiopaque material comprises a metal, a halogenated compound, or a barium containing compound.

7946. The method of item 7857, wherein the implant is further combined with a visualization agent, wherein the visualization agent is a radiopaque material, wherein the radiopaque material comprises barium, tantalum, or technetium.

7947. The method of item 7857, wherein the implant is further combined with a visualization agent, wherein the visualization agent is a MRI responsive material.

7948. The method of item 7857, wherein the implant is further combined with a visualization agent, wherein the visualization agent comprises a gadolinium chelate.

7949. The method of item 7857, wherein the implant is further combined with a visualization agent, wherein the visualization agent comprises iron, magnesium, manganese, copper, or chromium.

7950. The method of item 7857, wherein the implant is further combined with a visualization agent, wherein the visualization agent comprises an iron oxide compound.

7951. The method of item 7857, wherein the implant is further combined with a visualization agent, wherein the visualization agent comprises a dye, pigment, or colorant.

7952. The method of item 7857, wherein the implant is further combined with an echogenic material.

7953. The method of item 7857, wherein the implant is further combined with an echogenic material, and the echogenic material is in the form of a coating.

7954. The method of item 7857 wherein the device is sterilized.

7955. The method of item 7857 wherein the fibrosing agent is released into tissue in the vicinity of the device after deployment of the device.

7956. The method of item 7857 wherein the fibrosing agent is released into tissue in the vicinity of the device after deployment of the device, wherein the tissue is connective tissue.

7957. The method of item 7857 wherein the fibrosing agent is released into tissue in the vicinity of the device after deployment of the device, wherein the tissue is muscle tissue.

7958. The method of item 7857 wherein the fibrosing agent is released into tissue in the vicinity of the device after deployment of the device, wherein the tissue is nerve tissue.

7959. The method of item 7857 wherein the fibrosing agent is released into tissue in the vicinity of the device after deployment of the device, wherein the tissue is epithelium tissue.

7960. The method of item 7857 wherein the fibrosing agent is released in effective concentrations from the device over a period ranging from the time of deployment of the device to about 1 year.

7961. The method of item 7857 wherein the fibrosing agent is released in effective concentrations from the device over a period ranging from about 1 month to 6 months.

7962. The method of item 7857 wherein the fibrosing agent is released in effective concentrations from the device over a period ranging from about 1–90 days.

7963. The method of item 7857 wherein the fibrosing agent is released in effective concentrations from the device at a constant rate.

7964. The method of item 7857 wherein the fibrosing agent is released in effective concentrations from the device at an increasing rate.

7965. The method of item 7857 wherein the fibrosing agent is released in effective concentrations from the device at a decreasing rate.

7966. The method of item 7857 wherein the fibrosing agent is released in effective concentrations from the composition comprising the fibrosing agent by diffusion over a period ranging from the time of deployment of the device to about 90 days.

7967. The method of item 7857 wherein the fibrosing agent is released in effective concentrations from the composition comprising the fibrosing agent by erosion of the composition over a period ranging from the time of deployment of the device to about 90 days.

7968. The method of item 7857 wherein the device comprises about 0.01 µg to about 10 µg of the fibrosing agent.

7969. The method of item 7857 wherein the device comprises about 10 µg to about 10 mg of the fibrosing agent.

7970. The method of item 7857 wherein the device comprises about 10 mg to about 250 mg of the fibrosing agent.

7971. The method of item 7857 wherein the device comprises about 250 mg to about 1000 mg of the fibrosing agent.

7972. The method of item 7857 wherein the device comprises about 1000 mg to about 2500 mg of the fibrosing agent.

7973. The method of item 7857 wherein a surface of the device comprises less than 0.01 µg of the fibrosing agent per mm$^2$ of device surface to which the fibrosing agent is applied.

7974. The method of item 7857 wherein a surface of the device comprises about 0.01 µg to about 1 µg of the fibrosing agent per mm$^2$ of device surface to which the fibrosing agent is applied.

7975. The method of item 7857 wherein a surface of the device comprises about 1 µg to about 10 µg of the fibrosing agent per mm$^2$ of device surface to which the fibrosing agent is applied.

7976. The method of item 7857 wherein a surface of the device comprises about 10 µg to about 250 µg of the fibrosing agent per mm$^2$ of device surface to which the fibrosing agent is applied.

7977. The method of item 7857 wherein a surface of the device comprises about 250 µg to about 1000 µg of the fibrosing agent of fibrosing agent per mm$^2$ of device surface to which the fibrosing agent is applied.

7978. The method of item 7857 wherein a surface of the device comprises about 1000 µg to about 2500 µg of the fibrosing agent per mm$^2$ of device surface to which the fibrosing agent is applied.

7979. The method of item 7857 wherein the implant comprises a screw.

7980. The method of item 7857 wherein the implant is, or comprises, a fixation screw.

7981. The method of item 7857 wherein the implant is, or comprises, an interferential screw.

7982. The method of item 7857 wherein the implant is, or comprises, a trochanteric screw.

7983. The method of item 7857 wherein the implant comprises a pin.

7984. The method of item 7857 wherein the implant comprises a side plate.

7985. The method of item 7857 wherein the implant is an intramedullary nail.

7986. The method of item 7857 wherein the implant is an intramedullary pin.

7987. The method of item 7857 wherein the implant is a bone plate.

7988. The method of item 7857 wherein the implant is bone screw.

7989. The method of item 7857 wherein the implant is a smooth pin.

7990. The method of item 7857 wherein the implant is a threaded pin.

7991. The method of item 7857 wherein the implant is a wire.

7992. The method of item 7857 wherein the implant is a plate.

7993. A method of making a medical device comprising combining i) an external fixation implant and ii) a fibrosing agent or a composition comprising a fibrosing agent, where the fibrosing agent induces a fibrotic response between the device and a patient in which the device is implanted.

7994. The method of item 7993 wherein the fibrosing agent promotes regeneration.

7995. The method of item 7993 wherein the fibrosing agent promotes angiogenesis.

7996. The method of item 7993 wherein the fibrosing agent promotes fibroblast migration.

7997. The method of item 7993 wherein the fibrosing agent promotes fibroblast proliferation.

7998. The method of item 7993 wherein the fibrosing agent promotes deposition of extracellular matrix (ECM).

7999. The method of item 7993 wherein the fibrosing agent promotes tissue remodeling.

8000. The method of item 7993 wherein the fibrosing agent is an arterial vessel wall irritant.

8001. The method of item 7993 wherein the fibrosing agent promotes adhesion between the device and a host into which the device is implanted.

8002. The method of item 7993 wherein the device delivers the fibrosing agent locally to tissue proximate to the device.

8003. The method of item 7993 wherein the fibrosing agent is or comprises silk.

8004. The method of item 7993 wherein the fibrosing agent is or comprises mineral particles.

8005. The method of item 7993 wherein the fibrosing agent is or comprises chitosan.

8006. The method of item 7993 wherein the fibrosing agent is or comprises polylysine.

8007. The method of item 7993 wherein the fibrosing agent is or comprises fibronectin.

8008. The method of item 7993 wherein the fibrosing agent is or comprises bleomycin.

8009. The method of item 7993 wherein the fibrosing agent is or comprises CTGF.

8010. The method of item 7993 wherein the fibrosing agent is in the form of a thread, or is in contact with a thread.

8011. The method of item 7993 wherein the fibrosing agent is in the form of a particulate.

8012. The method of item 7993 wherein the composition further comprises an inflammatory cytokine.

8013. The method of item 7993 wherein the composition further comprises an agent that stimulates cell proliferation.

8014. The method of item 7993 wherein the composition is in the form of a gel or paste.

8015. The method of item 7993 wherein the fibrosing agent is in the form of tufts.

8016. The method of item 7993 wherein the fibrosing agent promotes adhesion between the device and a host into which the device is implanted.

8017. The method of item 7993 wherein the device delivers the fibrosing agent locally to tissue proximate to the device.

8018. The method of item 7993, wherein the implant is combined with a coating, and the coating comprises the fibrosing agent.

8019. The method of item 7993, wherein the implant is combined with a coating, and the coating is disposed on a surface of the device.

8020. The method of item 7993, wherein the implant is combined with a coating, and the coating directly contacts the device.

8021. The method of item 7993, wherein the implant is combined with a coating, and the coating indirectly contacts the device.

8022. The method of item 7993, wherein the implant is combined with a coating, and the coating partially covers the device.

8023. The method of item 7993, wherein the implant is combined with a coating, and the coating completely covers the device.

8024. The method of item 7993, wherein the implant is combined with a coating, and the coating is a uniform coating.

8025. The method of item 7993, wherein the implant is combined with a coating, and the coating is a non-uniform coating.

8026. The method of item 7993, wherein the implant is combined with a coating, and the coating is a discontinuous coating.

8027. The method of item 7993, wherein the implant is combined with a coating, and the coating is a patterned coating.

8028. The method of item 7993, wherein the implant is combined with a coating, and the coating has a thickness of 100 μm or less.

8029. The method of item 7993, wherein the implant is combined with a coating, and the coating has a thickness of 10 μm or less.

8030. The method of item 7993, wherein the implant is combined with a coating, and the coating adheres to the surface of the device upon deployment of the device.

8031. The method of item 7993, wherein the implant is combined with a coating, and the coating is stable at room temperature for a period of at least 1 year.

8032. The method of item 7993, wherein the implant is combined with a coating, and the fibrosing agent is present in the coating in an amount ranging between about 0.0001% to about 1% by weight.

8033. The method of item 7993, wherein the implant is combined with a coating, and the fibrosing agent is present in the coating in an amount ranging between about 1% to about 10% by weight.

8034. The method of item 7993, wherein the implant is combined with a coating, and the fibrosing agent is present in the coating in an amount ranging between about 10% to about 25% by weight.

8035. The method of item 7993, wherein the implant is combined with a coating, and the fibrosing agent is present in the coating in an amount ranging between about 25% to about 70% by weight.

8036. The method of item 7993, wherein the implant is combined with a coating, and the coating further comprises a polymer.

8037. The method of item 7993, wherein the device comprises a first coating having a first composition and a second coating having a second composition.

8038. The method of item 7993, wherein the device comprises a first coating having a first composition and a second coating having a second composition, where the first composition and the second composition are different.

8039. The method of item 7993, wherein the device comprises a polymer.

8040. The method of item 7993, wherein the device comprises a polymer, and the polymer is a component of the composition.

8041. The method of item 7993, wherein the implant is combined with a polymer, and the polymer is a copolymer.

8042. The method of item 7993, wherein the implant is combined with a polymer, and the polymer is a block copolymer.

8043. The method of item 7993, wherein the implant is combined with a polymer, and the polymer is a random copolymer.

8044. The method of item 7993, wherein the implant is combined with a polymer, and the polymer is a biodegradable polymer.

8045. The method of item 7993, wherein the implant is combined with a polymer, and the polymer is a non-biodegradable polymer.

8046. The method of item 7993, wherein the implant is combined with a polymer, and the polymer is a hydrophilic polymer.

8047. The method of item 7993, wherein the implant is combined with a polymer, and the polymer is a hydrophobic polymer.

8048. The method of item 7993, wherein the implant is combined with a polymer, and the polymer has hydrophilic domains.

8049. The method of item 7993, wherein the implant is combined with a polymer, and the polymer has hydrophobic domains.

8050. The method of item 7993, wherein the implant is combined with a polymer, and the polymer is a non-conductive polymer.

8051. The method of item 7993, wherein the implant is combined with a polymer, and the polymer is an elastomer.

8052. The method of item 7993, wherein the implant is combined with a polymer, and the polymer is a hydrogel.

8053. The method of item 7993, wherein the implant is combined with a polymer, and the polymer is a silicone polymer.

8054. The method of item 7993, wherein the implant is combined with a polymer, and the polymer is a hydrocarbon polymer.

8055. The method of item 7993, wherein the implant is combined with a polymer, and the polymer is a styrene-derived polymer.

8056. The method of item 7993, wherein the implant is combined with a polymer, and the polymer is a butadiene polymer.

8057. The method of item 7993, wherein the implant is combined with a polymer, and the polymer is a macromer.

8058. The method of item 7993, wherein the implant is combined with a polymer, and the polymer is a poly(ethylene glycol) polymer.

8059. The method of item 7993, wherein the implant is combined with a polymer, and the polymer is an amorphous polymer.

8060. The method of item 7993, wherein the implant is combined with a polymer, and the polymer is a lubricious coating.

8061. The method of item 7993 wherein the fibrosing agent is located within pores or holes of the device.

8062. The method of item 7993 wherein the fibrosing agent is located within a channel, lumen, or divet of the device.

8063. The method of item 7993, wherein the implant is further combined with a second pharmaceutically active agent.

8064. The method of item 7993, wherein the implant is further combined with an anti-inflammatory agent.

8065. The method of item 7993 wherein the implant is further combined with an agent that inhibits infection.

8066. The method of item 7993, wherein the implant is further combined with an anthracycline.

8067. The method of item 7993, wherein the implant is further combined with doxorubicin.

8068. The method of item 7993, wherein the implant is further combined with mitoxantrone.

8069. The method of item 7993, wherein the implant is further combined with a fluoropyrimidine.

8070. The method of item 7993, wherein the implant is further combined with 5-fluorouracil (5-FU).

8071. The method of item 7993, wherein the implant is further combined with a folic acid antagonist.

8072. The method of item 7993, wherein the implant is further combined with methotrexate.

8073. The method of item 7993, wherein the implant is further combined with a podophylotoxin.

8074. The method of item 7993, wherein the implant is further combined with etoposide.

8075. The method of item 7993 wherein the implant is further combined with a camptothecin.

8076. The method of item 7993, wherein the implant is further combined with a hydroxyurea.

8077. The method of item 7993, wherein the implant is further combined with a platinum complex.

8078. The method of item 7993, wherein the implant is further combined with cisplatin.

8079. The method of item 7993, wherein the implant is further combined with an anti-thrombotic agent.

8080. The method of item 7993, wherein the implant is further combined with a visualization agent.

8081. The method of item 7993, wherein the implant is further combined with a visualization agent, wherein the visualization agent is a radiopaque material, wherein the radiopaque material comprises a metal, a halogenated compound, or a barium containing compound.

8082. The method of item 7993, wherein the implant is further combined with a visualization agent, wherein the visualization agent is a radiopaque material, wherein the radiopaque material comprises barium, tantalum, or technetium.

8083. The method of item 7993, wherein the implant is further combined with a visualization agent, wherein the visualization agent is a MRI responsive material.

8084. The method of item 7993, wherein the implant is further combined with a visualization agent, wherein the visualization agent comprises a gadolinium chelate.

8085. The method of item 7993, wherein the implant is further combined with a visualization agent, wherein the visualization agent comprises iron, magnesium, manganese, copper, or chromium.

8086. The method of item 7993, wherein the implant is further combined with a visualization agent, wherein the visualization agent comprises an iron oxide compound.

8087. The method of item 7993, wherein the implant is further combined with a visualization agent, wherein the visualization agent comprises a dye, pigment, or colorant.

8088. The method of item 7993, wherein the implant is further combined with an echogenic material.

8089. The method of item 7993, wherein the implant is further combined with an echogenic material, and the echogenic material is in the form of a coating.

8090. The method of item 7993 wherein the device is sterilized.

8091. The method of item 7993 wherein the fibrosing agent is released into tissue in the vicinity of the device after deployment of the device.

8092. The method of item 7993 wherein the fibrosing agent is released into tissue in the vicinity of the device after deployment of the device, wherein the tissue is connective tissue.

8093. The method of item 7993 wherein the fibrosing agent is released into tissue in the vicinity of the device after deployment of the device, wherein the tissue is muscle tissue.

8094. The method of item 7993 wherein the fibrosing agent is released into tissue in the vicinity of the device after deployment of the device, wherein the tissue is nerve tissue.

8095. The method of item 7993 wherein the fibrosing agent is released into tissue in the vicinity of the device after deployment of the device, wherein the tissue is epithelium tissue.

8096. The method of item 7993 wherein the fibrosing agent is released in effective concentrations from the device over a period ranging from the time of deployment of the device to about 1 year.

8097. The method of item 7993 wherein the fibrosing agent is released in effective concentrations from the device over a period ranging from about 1 month to 6 months.

8098. The method of item 7993 wherein the fibrosing agent is released in effective concentrations from the device over a period ranging from about 1–90 days.

8099. The method of item 7993 wherein the fibrosing agent is released in effective concentrations from the device at a constant rate.

8100. The method of item 7993 wherein the fibrosing agent is released in effective concentrations from the device at an increasing rate.

8101. The method of item 7993 wherein the fibrosing agent is released in effective concentrations from the device at a decreasing rate.

8102. The method of item 7993 wherein the fibrosing agent is released in effective concentrations from the composition comprising the fibrosing agent by diffusion over a period ranging from the time of deployment of the device to about 90 days.

8103. The method of item 7993 wherein the fibrosing agent is released in effective concentrations from the composition comprising the fibrosing agent by erosion of the composition over a period ranging from the time of deployment of the device to about 90 days.

8104. The method of item 7993 wherein the device comprises about 0.01 µg to about 10 µg of the fibrosing agent.

8105. The method of item 7993 wherein the device comprises about 10 µg to about 10 mg of the fibrosing agent.

8106. The method of item 7993 wherein the device comprises about 10 mg to about 250 mg of the fibrosing agent.

8107. The method of item 7993 wherein the device comprises about 250 mg to about 1000 mg of the fibrosing agent.

8108. The method of item 7993 wherein the device comprises about 1000 mg to about 2500 mg of the fibrosing agent.

8109. The method of item 7993 wherein a surface of the device comprises less than 0.01 µg of the fibrosing agent per $mm^2$ of device surface to which the fibrosing agent is applied.

8110. The method of item 7993 wherein a surface of the device comprises about 0.01 µg to about 1 µg of the fibrosing agent per $mm^2$ of device surface to which the fibrosing agent is applied.

8111. The method of item 7993 wherein a surface of the device comprises about 1 µg to about 10 µg of the fibrosing agent per $mm^2$ of device surface to which the fibrosing agent is applied.

8112. The method of item 7993 wherein a surface of the device comprises about 10 µg to about 250 µg of the fibrosing agent per $mm^2$ of device surface to which the fibrosing agent is applied.

8113. The method of item 7993 wherein a surface of the device comprises about 250 µg to about 1000 µg of the fibrosing agent of fibrosing agent per $mm^2$ of device surface to which the fibrosing agent is applied.

8114. The method of item 7993 wherein a surface of the device comprises about 1000 µg to about 2500 µg of the fibrosing agent per $mm^2$ of device surface to which the fibrosing agent is applied.

8115. The method of item 7993 wherein the implant is in the form of a pin.

8116. The method of item 7993 wherein the implant is used to stabilize transverse fractures.

8117. The method of item 7993 wherein the implant comprises steel.

8118. A method of making a medical device comprising combining i) a collagen implant and ii) a fibrosing agent or a composition comprising a fibrosing agent, where the fibrosing agent induces a fibrotic response between the device and a patient in which the device is implanted.

8119. The method of item 8118 wherein the fibrosing agent promotes regeneration.

8120. The method of item 8118 wherein the fibrosing agent promotes angiogenesis.

8121. The method of item 8118 wherein the fibrosing agent promotes fibroblast migration.

8122. The method of item 8118 wherein the fibrosing agent promotes fibroblast proliferation.

8123. The method of item 8118 wherein the fibrosing agent promotes deposition of extracellular matrix (ECM).

8124. The method of item 8118 wherein the fibrosing agent promotes tissue remodeling.

8125. The method of item 8118 wherein the fibrosing agent is an arterial vessel wall irritant.

8126. The method of item 8118 wherein the fibrosing agent promotes adhesion between the device and a host into which the device is implanted.

8127. The method of item 8118 wherein the device delivers the fibrosing agent locally to tissue proximate to the device.

8128. The method of item 8118 wherein the fibrosing agent is or comprises silk.

8129. The method of item 8118 wherein the fibrosing agent is or comprises mineral particles.

8130. The method of item 8118 wherein the fibrosing agent is or comprises chitosan.

8131. The method of item 8118 wherein the fibrosing agent is or comprises polylysine.

8132. The method of item 8118 wherein the fibrosing agent is or comprises fibronectin.

8133. The method of item 8118 wherein the fibrosing agent is or comprises bleomycin.

8134. The method of item 8118 wherein the fibrosing agent is or comprises CTGF.

8135. The method of item 8118 wherein the fibrosing agent is in the form of a thread, or is in contact with a thread.

8136. The method of item 8118 wherein the fibrosing agent is in the form of a particulate.

8137. The method of item 8118 wherein the composition further comprises an inflammatory cytokine.

8138. The method of item 8118 wherein the composition further comprises an agent that stimulates cell proliferation.

8139. The method of item 8118 wherein the composition is in the form of a gel or paste.

8140. The method of item 8118 wherein the fibrosing agent is in the form of tufts.

8141. The method of item 8118 wherein the fibrosing agent promotes adhesion between the device and a host into which the device is implanted.

8142. The method of item 8118 wherein the device delivers the fibrosing agent locally to tissue proximate to the device.

8143. The method of item 8118, wherein the implant is combined with a coating, and the coating comprises the fibrosing agent.

8144. The method of item 8118, wherein the implant is combined with a coating, and the coating is disposed on a surface of the device.

8145. The method of item 8118, wherein the implant is combined with a coating, and the coating directly contacts the device.

8146. The method of item 8118, wherein the implant is combined with a coating, and the coating indirectly contacts the device.

8147. The method of item 8118, wherein the implant is combined with a coating, and the coating partially covers the device.

8148. The method of item 8118, wherein the implant is combined with a coating, and the coating completely covers the device.

8149. The method of item 8118, wherein the implant is combined with a coating, and the coating is a uniform coating.

8150. The method of item 8118, wherein the implant is combined with a coating, and the coating is a non-uniform coating.

8151. The method of item 8118, wherein the implant is combined with a coating, and the coating is a discontinuous coating.

8152. The method of item 8118 wherein the implant is combined with a coating, and the coating is a patterned coating.

8153. The method of item 8118, wherein the implant is combined with a coating, and the coating has a thickness of 100 µm or less.

8154. The method of item 8118, wherein the implant is combined with a coating, and the coating has a thickness of 10 µm or less.

8155. The method of item 8118, wherein the implant is combined with a coating, and the coating adheres to the surface of the device upon deployment of the device.

8156. The method of item 8118, wherein the implant is combined with a coating, and the coating is stable at room temperature for a period of at least 1 year.

8157. The method of item 8118, wherein the implant is combined with a coating, and the fibrosing agent is present in the coating in an amount ranging between about 0.0001% to about 1% by weight.

8158. The method of item 8118, wherein the implant is combined with a coating, and the fibrosing agent is present in the coating in an amount ranging between about 1% to about 10% by weight.

8159. The method of item 8118, wherein the implant is combined with a coating, and the fibrosing agent is present in the coating in an amount ranging between about 10% to about 25% by weight.

8160. The method of item 8118, wherein the implant is combined with a coating, and the fibrosing agent is present in the coating in an amount ranging between about 25% to about 70% by weight.

8161. The method of item 8118, wherein the implant is combined with a coating, and the coating further comprises a polymer.

8162. The method of item 8118, wherein the device comprises a first coating having a first composition and a second coating having a second composition.

8163. The method of item 8118, wherein the device comprises a first coating having a first composition and a second coating having a second composition, where the first composition and the second composition are different.

8164. The method of item 8118, wherein the device comprises a polymer.

8165. The method of item 8118, wherein the device comprises a polymer, and the polymer is a component of the composition.

8166. The method of item 8118, wherein the implant is combined with a polymer, and the polymer is a copolymer.

8167. The method of item 8118, wherein the implant is combined with a polymer, and the polymer is a block copolymer.

8168. The method of item 8118, wherein the implant is combined with a polymer, and the polymer is a random copolymer.

8169. The method of item 8118, wherein the implant is combined with a polymer, and the polymer is a biodegradable polymer.

8170. The method of item 8118, wherein the implant is combined with a polymer, and the polymer is a non-biodegradable polymer.

8171. The method of item 8118, wherein the implant is combined with a polymer, and the polymer is a hydrophilic polymer.

8172. The method of item 8118, wherein the implant is combined with a polymer, and the polymer is a hydrophobic polymer.

8173. The method of item 8118, wherein the implant is combined with a polymer, and the polymer has hydrophilic domains.

8174. The method of item 8118, wherein the implant is combined with a polymer, and the polymer has hydrophobic domains.

8175. The method of item 8118, wherein the implant is combined with a polymer, and the polymer is a non-conductive polymer.

8176. The method of item 8118, wherein the implant is combined with a polymer, and the polymer is an elastomer.

8177. The method of item 8118, wherein the implant is combined with a polymer, and the polymer is a hydrogel.

8178. The method of item 8118, wherein the implant is combined with a polymer, and the polymer is a silicone polymer.

8179. The method of item 8118, wherein the implant is combined with a polymer, and the polymer is a hydrocarbon polymer.

8180. The method of item 8118, wherein the implant is combined with a polymer, and the polymer is a styrene-derived polymer.

8181. The method of item 8118, wherein the implant is combined with a polymer, and the polymer is a butadiene polymer.

8182. The method of item 8118, wherein the implant is combined with a polymer, and the polymer is a macromer.

8183. The method of item 8118, wherein the implant is combined with a polymer, and the polymer is a poly(ethylene glycol) polymer.

8184. The method of item 8118, wherein the implant is combined with a polymer, and the polymer is an amorphous polymer.

8185. The method of item 8118, wherein the implant is combined with a polymer, and the polymer is a lubricious coating.

8186. The method of item 8118 wherein the fibrosing agent is located within pores or holes of the device.

8187. The method of item 8118 wherein the fibrosing agent is located within a channel, lumen, or divet of the device.

8188. The method of item 8118, wherein the implant is further combined with a second pharmaceutically active agent.

8189. The method of item 8118, wherein the implant is further combined with an anti-inflammatory agent.

8190. The method of item 8118 wherein the implant is further combined with an agent that inhibits infection.

8191. The method of item 8118, wherein the implant is further combined with an anthracycline.

8192. The method of item 8118, wherein the implant is further combined with doxorubicin.

8193. The method of item 8118, wherein the implant is further combined with mitoxantrone.

8194. The method of item 8118, wherein the implant is further combined with a fluoropyrimidine.

8195. The method of item 8118, wherein the implant is further combined with 5-fluorouracil (5-FU).

8196. The method of item 8118, wherein the implant is further combined with a folic acid antagonist.

8197. The method of item 8118, wherein the implant is further combined with methotrexate.

8198. The method of item 8118, wherein the implant is further combined with a podophylotoxin.

8199. The method of item 8118, wherein the implant is further combined with etoposide.

8200. The method of item 8118 wherein the implant is further combined with a camptothecin.

8201. The method of item 8118, wherein the implant is further combined with a hydroxyurea.

8202. The method of item 8118, wherein the implant is further combined with a platinum complex.

8203. The method of item 8118, wherein the implant is further combined with cisplatin.

8204. The method of item 8118, wherein the implant is further combined with an anti-thrombotic agent.

8205. The method of item 8118, wherein the implant is further combined with a visualization agent.

8206. The method of item 8118, wherein the implant is further combined with a visualization agent, wherein the visualization agent is a radiopaque material, wherein the radiopaque material comprises a metal, a halogenated compound, or a barium containing compound.

8207. The method of item 8118, wherein the implant is further combined with a visualization agent, wherein the visualization agent is a radiopaque material, wherein the radiopaque material comprises barium, tantalum, or technetium.

8208. The method of item 8118, wherein the implant is further combined with a visualization agent, wherein the visualization agent is a MRI responsive material.

8209. The method of item 8118, wherein the implant is further combined with a visualization agent, wherein the visualization agent comprises a gadolinium chelate.

8210. The method of item 8118, wherein the implant is further combined with a visualization agent, wherein the visualization agent comprises iron, magnesium, manganese, copper, or chromium.

8211. The method of item 8118, wherein the implant is further combined with a visualization agent, wherein the visualization agent comprises an iron oxide compound.

8212. The method of item 8118, wherein the implant is further combined with a visualization agent, wherein the visualization agent comprises a dye, pigment, or colorant.

8213. The method of item 8118, wherein the implant is further combined with an echogenic material.

8214. The method of item 8118, wherein the implant is further combined with an echogenic material, and the echogenic material is in the form of a coating.

8215. The method of item 8118 wherein the device is sterilized.

8216. The method of item 8118 wherein the fibrosing agent is released into tissue in the vicinity of the device after deployment of the device.

8217. The method of item 8118 wherein the fibrosing agent is released into tissue in the vicinity of the device after deployment of the device, wherein the tissue is connective tissue.

8218. The method of item 8118 wherein the fibrosing agent is released into tissue in the vicinity of the device after deployment of the device, wherein the tissue is muscle tissue.

8219. The method of item 8118 wherein the fibrosing agent is released into tissue in the vicinity of the device after deployment of the device, wherein the tissue is nerve tissue.

8220. The method of item 8118 wherein the fibrosing agent is released into tissue in the vicinity of the device after deployment of the device, wherein the tissue is epithelium tissue.

8221. The method of item 8118 wherein the fibrosing agent is released in effective concentrations from the device over a period ranging from the time of deployment of the device to about 1 year.

8222. The method of item 8118 wherein the fibrosing agent is released in effective concentrations from the device over a period ranging from about 1 month to 6 months.

8223. The method of item 8118 wherein the fibrosing agent is released in effective concentrations from the device over a period ranging from about 1–90 days.

8224. The method of item 8118 wherein the fibrosing agent is released in effective concentrations from the device at a constant rate.

8225. The method of item 8118 wherein the fibrosing agent is released in effective concentrations from the device at an increasing rate.

8226. The method of item 8118 wherein the fibrosing agent is released in effective concentrations from the device at a decreasing rate.

8227. The method of item 8118 wherein the fibrosing agent is released in effective concentrations from the composition comprising the fibrosing agent by diffusion over a period ranging from the time of deployment of the device to about 90 days.

8228. The method of item 8118 wherein the fibrosing agent is released in effective concentrations from the composition comprising the fibrosing agent by erosion of the composition over a period ranging from the time of deployment of the device to about 90 days.

8229. The method of item 8118 wherein the device comprises about 0.01 µg to about 10 µg of the fibrosing agent.

8230. The method of item 8118 wherein the device comprises about 10 µg to about 10 mg of the fibrosing agent.

8231. The method of item 8118 wherein the device comprises about 10 mg to about 250 mg of the fibrosing agent.

8232. The method of item 8118 wherein the device comprises about 250 mg to about 1000 mg of the fibrosing agent.

8233. The method of item 8118 wherein the device comprises about 1000 mg to about 2500 mg of the fibrosing agent.

8234. The method of item 8118 wherein a surface of the device comprises less than 0.01 µg of the fibrosing agent per mm$^2$ of device surface to which the fibrosing agent is applied.

8235. The method of item 8118 wherein a surface of the device comprises about 0.01 µg to about 1 µg of the fibrosing agent per mm$^2$ of device surface to which the fibrosing agent is applied.

8236. The method of item 8118 wherein a surface of the device comprises about 1 µg to about 10 µg of the fibrosing agent per mm$^2$ of device surface to which the fibrosing agent is applied.

8237. The method of item 8118 wherein a surface of the device comprises about 10 µg to about 250 µg of the fibrosing agent per mm$^2$ of device surface to which the fibrosing agent is applied.

8238. The method of item 8118 wherein a surface of the device comprises about 250 µg to about 1000 µg of the fibrosing agent of fibrosing agent per mm$^2$ of device surface to which the fibrosing agent is applied.

8239. The method of item 8118 wherein a surface of the device comprises about 1000 µg to about 2500 µg of the fibrosing agent per mm$^2$ of device surface to which the fibrosing agent is applied.

8240. The method of item 8118 wherein the implant is a dental implant.

8241. The method of item 8118 wherein the implant is an orthopedic implant.

8242. The method of item 8118 wherein the implant is a surgical mesh.

8243. The method of item 8118 wherein the implant is made, in whole or part, from crosslinked collagen.

8244. A method of making a medical device comprising combining i) a Fallopian tube implant and ii) a fibrosing agent or a composition comprising a fibrosing agent, where the fibrosing agent induces a fibrotic response between the device and a patient in which the device is implanted.

8245. The method of item 8244 wherein the fibrosing agent promotes regeneration.

8246. The method of item 8244 wherein the fibrosing agent promotes angiogenesis.

8247. The method of item 8244 wherein the fibrosing agent promotes fibroblast migration.

8248. The method of item 8244 wherein the fibrosing agent promotes fibroblast proliferation.

8249. The method of item 8244 wherein the fibrosing agent promotes deposition of extracellular matrix (ECM).

8250. The method of item 8244 wherein the fibrosing agent promotes tissue remodeling.

8251. The method of item 8244 wherein the fibrosing agent is an arterial vessel wall irritant.

8252. The method of item 8244 wherein the fibrosing agent promotes adhesion between the device and a host into which the device is implanted.

8253. The method of item 8244 wherein the device delivers the fibrosing agent locally to tissue proximate to the device.

8254. The method of item 8244 wherein the fibrosing agent is or comprises silk.

8255. The method of item 8244 wherein the fibrosing agent is or comprises mineral particles.

8256. The method of item 8244 wherein the fibrosing agent is or comprises chitosan.

8257. The method of item 8244 wherein the fibrosing agent is or comprises polylysine.

8258. The method of item 8244 wherein the fibrosing agent is or comprises fibronectin.

8259. The method of item 8244 wherein the fibrosing agent is or comprises bleomycin.

8260. The method of item 8244 wherein the fibrosing agent is or comprises CTGF.

8261. The method of item 8244 wherein the fibrosing agent is in the form of a thread, or is in contact with a thread.

8262. The method of item 8244 wherein the fibrosing agent is in the form of a particulate.

8263. The method of item 8244 wherein the composition further comprises an inflammatory cytokine.

8264. The method of item 8244 wherein the composition further comprises an agent that stimulates cell proliferation.

8265. The method of item 8244 wherein the composition is in the form of a gel or paste.

8266. The method of item 8244 wherein the fibrosing agent is in the form of tufts.

8267. The method of item 8244 wherein the fibrosing agent promotes adhesion between the device and a host into which the device is implanted.

8268. The method of item 8244 wherein the device delivers the fibrosing agent locally to tissue proximate to the device.

8269. The method of item 8244, wherein the implant is combined with a coating, and the coating comprises the fibrosing agent.

8270. The method of item 8244, wherein the implant is combined with a coating, and the coating is disposed on a surface of the device.

8271. The method of item 8244, wherein the implant is combined with a coating, and the coating directly contacts the device.

8272. The method of item 8244, wherein the implant is combined with a coating, and the coating indirectly contacts the device.

8273. The method of item 8244, wherein the implant is combined with a coating, and the coating partially covers the device.

8274. The method of item 8244, wherein the implant is combined with a coating, and the coating completely covers the device.

8275. The method of item 8244, wherein the implant is combined with a coating, and the coating is a uniform coating.

8276. The method of item 8244, wherein the implant is combined with a coating, and the coating is a non-uniform coating.

8277. The method of item 8244, wherein the implant is combined with a coating, and the coating is a discontinuous coating.

8278. The method of item 8244 wherein the implant is combined with a coating, and the coating is a patterned coating.

8279. The method of item 8244, wherein the implant is combined with a coating, and the coating has a thickness of 100 µm or less.

8280. The method of item 8244, wherein the implant is combined with a coating, and the coating has a thickness of 10 µm or less.

8281. The method of item 8244, wherein the implant is combined with a coating, and the coating adheres to the surface of the device upon deployment of the device.

8282. The method of item 8244, wherein the implant is combined with a coating, and the coating is stable at room temperature for a period of at least 1 year.

8283. The method of item 8244, wherein the implant is combined with a coating, and the fibrosing agent is present in the coating in an amount ranging between about 0.0001% to about 1% by weight.

8284. The method of item 8244, wherein the implant is combined with a coating, and the fibrosing agent is present in the coating in an amount ranging between about 1% to about 10% by weight.

8285. The method of item 8244, wherein the implant is combined with a coating, and the fibrosing agent is present in the coating in an amount ranging between about 10% to about 25% by weight.

8286. The method of item 8244, wherein the implant is combined with a coating, and the fibrosing agent is present in the coating in an amount ranging between about 25% to about 70% by weight.

8287. The method of item 8244, wherein the implant is combined with a coating, and the coating further comprises a polymer.

8288. The method of item 8244, wherein the device comprises a first coating having a first composition and a second coating having a second composition.

8289. The method of item 8244, wherein the device comprises a first coating having a first composition and a second coating having a second composition, where the first composition and the second composition are different.

8290. The method of item 8244, wherein the device comprises a polymer.

8291. The method of item 8244, wherein the device comprises a polymer, and the polymer is a component of the composition.

8292. The method of item 8244, wherein the implant is combined with a polymer, and the polymer is a copolymer.

8293. The method of item 8244, wherein the implant is combined with a polymer, and the polymer is a block copolymer.

8294. The method of item 8244, wherein the implant is combined with a polymer, and the polymer is a random copolymer.

8295. The method of item 8244, wherein the implant is combined with a polymer, and the polymer is a biodegradable polymer.

8296. The method of item 8244, wherein the implant is combined with a polymer, and the polymer is a non-biodegradable polymer.

8297. The method of item 8244, wherein the implant is combined with a polymer, and the polymer is a hydrophilic polymer.

8298. The method of item 8244, wherein the implant is combined with a polymer, and the polymer is a hydrophobic polymer.

8299. The method of item 8244, wherein the implant is combined with a polymer, and the polymer has hydrophilic domains.

8300. The method of item 8244, wherein the implant is combined with a polymer, and the polymer has hydrophobic domains.

8301. The method of item 8244, wherein the implant is combined with a polymer, and the polymer is a non-conductive polymer.

8302. The method of item 8244, wherein the implant is combined with a polymer, and the polymer is an elastomer.

8303. The method of item 8244, wherein the implant is combined with a polymer, and the polymer is a hydrogel.

8304. The method of item 8244, wherein the implant is combined with a polymer, and the polymer is a silicone polymer.

8305. The method of item 8244, wherein the implant is combined with a polymer, and the polymer is a hydrocarbon polymer.

8306. The method of item 8244, wherein the implant is combined with a polymer, and the polymer is a styrene-derived polymer.

8307. The method of item 8244, wherein the implant is combined with a polymer, and the polymer is a butadiene polymer.

8308. The method of item 8244, wherein the implant is combined with a polymer, and the polymer is a macromer.

8309. The method of item 8244, wherein the implant is combined with a polymer, and the polymer is a poly(ethylene glycol) polymer.

8310. The method of item 8244, wherein the implant is combined with a polymer, and the polymer is an amorphous polymer.

8311. The method of item 8244, wherein the implant is combined with a polymer, and the polymer is a lubricious coating.

8312. The method of item 8244 wherein the fibrosing agent is located within pores or holes of the device.

8313. The method of item 8244 wherein the fibrosing agent is located within a channel, lumen, or divet of the device.

8314. The method of item 8244, wherein the implant is further combined with a second pharmaceutically active agent.

8315. The method of item 8244, wherein the implant is further combined with an anti-inflammatory agent.

8316. The method of item 8244 wherein the implant is further combined with an agent that inhibits infection.

8317. The method of item 8244, wherein the implant is further combined with an anthracycline.

8318. The method of item 8244, wherein the implant is further combined with doxorubicin.

8319. The method of item 8244, wherein the implant is further combined with mitoxantrone.

8320. The method of item 8244, wherein the implant is further combined with a fluoropyrimidine.

8321. The method of item 8244, wherein the implant is further combined with 5-fluorouracil (5-FU).

8322. The method of item 8244, wherein the implant is further combined with a folic acid antagonist.

8323. The method of item 8244, wherein the implant is further combined with methotrexate.

8324. The method of item 8244, wherein the implant is further combined with a podophylotoxin.

8325. The method of item 8244, wherein the implant is further combined with etoposide.

8326. The method of item 8244, wherein the implant is further combined with a camptothecin.

8327. The method of item 8244, wherein the implant is further combined with a hydroxyurea.

8328. The method of item 8244, wherein the implant is further combined with a platinum complex.

8329. The method of item 8244, wherein the implant is further combined with cisplatin.

8330. The method of item 8244, wherein the implant is further combined with an anti-thrombotic agent.

8331. The method of item 8244, wherein the implant is further combined with a visualization agent.

8332. The method of item 8244, wherein the implant is further combined with a visualization agent, wherein the visualization agent is a radiopaque material, wherein the radiopaque material comprises a metal, a halogenated compound, or a barium containing compound.

8333. The method of item 8244, wherein the implant is further combined with a visualization agent, wherein the visualization agent is a radiopaque material, wherein the radiopaque material comprises barium, tantalum, or technetium.

8334. The method of item 8244, wherein the implant is further combined with a visualization agent, wherein the visualization agent is a MRI responsive material.

8335. The method of item 8244, wherein the implant is further combined with a visualization agent, wherein the visualization agent comprises a gadolinium chelate.

8336. The method of item 8244, wherein the implant is further combined with a visualization agent, wherein the visualization agent comprises iron, magnesium, manganese, copper, or chromium.

8337. The method of item 8244, wherein the implant is further combined with a visualization agent, wherein the visualization agent comprises an iron oxide compound.

8338. The method of item 8244, wherein the implant is further combined with a visualization agent, wherein the visualization agent comprises a dye, pigment, or colorant.

8339. The method of item 8244, wherein the implant is further combined with an echogenic material.

8340. The method of item 8244, wherein the implant is further combined with an echogenic material, and the echogenic material is in the form of a coating.

8341. The method of item 8244 wherein the device is sterilized.

8342. The method of item 8244 wherein the fibrosing agent is released into tissue in the vicinity of the device after deployment of the device.

8343. The method of item 8244 wherein the fibrosing agent is released into tissue in the vicinity of the device after deployment of the device, wherein the tissue is connective tissue.

8344. The method of item 8244 wherein the fibrosing agent is released into tissue in the vicinity of the device after deployment of the device, wherein the tissue is muscle tissue.

8345. The method of item 8244 wherein the fibrosing agent is released into tissue in the vicinity of the device after deployment of the device, wherein the tissue is nerve tissue.

8346. The method of item 8244 wherein the fibrosing agent is released into tissue in the vicinity of the device after deployment of the device, wherein the tissue is epithelium tissue.

8347. The method of item 8244 wherein the fibrosing agent is released in effective concentrations from the device over a period ranging from the time of deployment of the device to about 1 year.

8348. The method of item 8244 wherein the fibrosing agent is released in effective concentrations from the device over a period ranging from about 1 month to 6 months.

8349. The method of item 8244 wherein the fibrosing agent is released in effective concentrations from the device over a period ranging from about 1–90 days.

8350. The method of item 8244 wherein the fibrosing agent is released in effective concentrations from the device at a constant rate.

8351. The method of item 8244 wherein the fibrosing agent is released in effective concentrations from the device at an increasing rate.

8352. The method of item 8244 wherein the fibrosing agent is released in effective concentrations from the device at a decreasing rate.

8353. The method of item 8244 wherein the fibrosing agent is released in effective concentrations from the composition comprising the fibrosing agent by diffusion over a period ranging from the time of deployment of the device to about 90 days.

8354. The method of item 8244 wherein the fibrosing agent is released in effective concentrations from the composition comprising the fibrosing agent by erosion of the composition over a period ranging from the time of deployment of the device to about 90 days.

8355. The method of item 8244 wherein the device comprises about 0.01 µg to about 10 µg of the fibrosing agent.

8356. The method of item 8244 wherein the device comprises about 10 µg to about 10 mg of the fibrosing agent.

8357. The method of item 8244 wherein the device comprises about 10 mg to about 250 mg of the fibrosing agent.

8358. The method of item 8244 wherein the device comprises about 250 mg to about 1000 mg of the fibrosing agent.

8359. The method of item 8244 wherein the device comprises about 1000 mg to about 2500 mg of the fibrosing agent.

8360. The method of item 8244 wherein a surface of the device comprises less than 0.01 µg of the fibrosing agent per mm$^2$ of device surface to which the fibrosing agent is applied.

8361. The method of item 8244 wherein a surface of the device comprises about 0.01 µg to about 1 µg of the fibrosing agent per mm² of device surface to which the fibrosing agent is applied.

8362. The method of item 8244 wherein a surface of the device comprises about 1 µg to about 10 µg of the fibrosing agent per mm² of device surface to which the fibrosing agent is applied.

8363. The method of item 8244 wherein a surface of the device comprises about 10 µg to about 250 µg of the fibrosing agent per mm² of device surface to which the fibrosing agent is applied.

8364. The method of item 8244 wherein a surface of the device comprises about 250 µg to about 1000 µg of the fibrosing agent of fibrosing agent per mm² of device surface to which the fibrosing agent is applied.

8365. The method of item 8244 wherein a surface of the device comprises about 1000 µg to about 2500 µg of the fibrosing agent per mm² of device surface to which the fibrosing agent is applied.

8366. The method of item 8244 wherein the implant is a duct clamp.

8367. The method of item 8244 wherein the implant is a valved sterilization device.

8368. The method of item 8244 wherein the implant is an implantable, intrafallopian, female sterilization device.

8369. The method of item 8244 wherein the implant is an occlusive wire or coil fallopian tube implant.

8370. The method of item 8244 wherein the implant is a transcatheter occluding implant.

8371. The method of item 8244 wherein the implant is a fallopian tube stent.

8372. The method of item 8244 wherein the implant is a contraceptive uterine implant.

8373. A method of making a medical device comprising combining i) a prosthetic anal sphincter and ii) a fibrosing agent or a composition comprising a fibrosing agent, where the fibrosing agent induces a fibrotic response between the device and a patient in which the device is implanted.

8374. The method of item 8373 wherein the fibrosing agent promotes regeneration.

8375. The method of item 8373 wherein the fibrosing agent promotes angiogenesis.

8376. The method of item 8373 wherein the fibrosing agent promotes fibroblast migration.

8377. The method of item 8373 wherein the fibrosing agent promotes fibroblast proliferation.

8378. The method of item 8373 wherein the fibrosing agent promotes deposition of extracellular matrix (ECM).

8379. The method of item 8373 wherein the fibrosing agent promotes tissue remodeling.

8380. The method of item 8373 wherein the fibrosing agent is an arterial vessel wall irritant.

8381. The method of item 8373 wherein the fibrosing agent promotes adhesion between the device and a host into which the device is implanted.

8382. The method of item 8373 wherein the device delivers the fibrosing agent locally to tissue proximate to the device.

8383. The method of item 8373 wherein the fibrosing agent is or comprises silk.

8384. The method of item 8373 wherein the fibrosing agent is or comprises mineral particles.

8385. The method of item 8373 wherein the fibrosing agent is or comprises chitosan.

8386. The method of item 8373 wherein the fibrosing agent is or comprises polylysine.

8387. The method of item 8373 wherein the fibrosing agent is or comprises fibronectin.

8388. The method of item 8373 wherein the fibrosing agent is or comprises bleomycin.

8389. The method of item 8373 wherein the fibrosing agent is or comprises CTGF.

8390. The method of item 8373 wherein the fibrosing agent is in the form of a thread, or is in contact with a thread.

8391. The method of item 8373 wherein the fibrosing agent is in the form of a particulate.

8392. The method of item 8373 wherein the composition further comprises an inflammatory cytokine.

8393. The method of item 8373 wherein the composition further comprises an agent that stimulates cell proliferation.

8394. The method of item 8373 wherein the composition is in the form of a gel or paste.

8395. The method of item 8373 wherein the fibrosing agent is in the form of tufts.

8396. The method of item 8373 wherein the fibrosing agent promotes adhesion between the device and a host into which the device is implanted.

8397. The method of item 8373 wherein the device delivers the fibrosing agent locally to tissue proximate to the device.

8398. The method of item 8373, wherein the implant is combined with a coating, and the coating comprises the fibrosing agent.

8399. The method of item 8373, wherein the implant is combined with a coating, and the coating is disposed on a surface of the device.

8400. The method of item 8373, wherein the implant is combined with a coating, and the coating directly contacts the device.

8401. The method of item 8373, wherein the implant is combined with a coating, and the coating indirectly contacts the device.

8402. The method of item 8373, wherein the implant is combined with a coating, and the coating partially covers the device.

8403. The method of item 8373, wherein the implant is combined with a coating, and the coating completely covers the device.

8404. The method of item 8373, wherein the implant is combined with a coating, and the coating is a uniform coating.

8405. The method of item 8373, wherein the implant is combined with a coating, and the coating is a non-uniform coating.

8406. The method of item 8373, wherein the implant is combined with a coating, and the coating is a discontinuous coating.

8407. The method of item 8373 wherein the implant is combined with a coating, and the coating is a patterned coating.

8408. The method of item 8373, wherein the implant is combined with a coating, and the coating has a thickness of 100 µm or less.

8409. The method of item 8373, wherein the implant is combined with a coating, and the coating has a thickness of 10 µm or less.

8410. The method of item 8373, wherein the implant is combined with a coating, and the coating adheres to the surface of the device upon deployment of the device.

8411. The method of item 8373, wherein the implant is combined with a coating, and the coating is stable at room temperature for a period of at least 1 year.

8412. The method of item 8373, wherein the implant is combined with a coating, and the fibrosing agent is present in the coating in an amount ranging between about 0.0001% to about 1% by weight.

8413. The method of item 8373, wherein the implant is combined with a coating, and the fibrosing agent is present in the coating in an amount ranging between about 1% to about 10% by weight.

8414. The method of item 8373, wherein the implant is combined with a coating, and the fibrosing agent is present in the coating in an amount ranging between about 10% to about 25% by weight.

8415. The method of item 8373, wherein the implant is combined with a coating, and the fibrosing agent is present in the coating in an amount ranging between about 25% to about 70% by weight.

8416. The method of item 8373, wherein the implant is combined with a coating, and the coating further comprises a polymer.

8417. The method of item 8373, wherein the device comprises a first coating having a first composition and a second coating having a second composition.

8418. The method of item 8373, wherein the device comprises a first coating having a first composition and a second coating having a second composition, where the first composition and the second composition are different.

8419. The method of item 8373, wherein the device comprises a polymer.

8420. The method of item 8373, wherein the device comprises a polymer, and the polymer is a component of the composition.

8421. The method of item 8373, wherein the implant is combined with a polymer, and the polymer is a copolymer.

8422. The method of item 8373, wherein the implant is combined with a polymer, and the polymer is a block copolymer.

8423. The method of item 8373, wherein the implant is combined with a polymer, and the polymer is a random copolymer.

8424. The method of item 8373, wherein the implant is combined with a polymer, and the polymer is a biodegradable polymer.

8425. The method of item 8373, wherein the implant is combined with a polymer, and the polymer is a non-biodegradable polymer.

8426. The method of item 8373, wherein the implant is combined with a polymer, and the polymer is a hydrophilic polymer.

8427. The method of item 8373, wherein the implant is combined with a polymer, and the polymer is a hydrophobic polymer.

8428. The method of item 8373, wherein the implant is combined with a polymer, and the polymer has hydrophilic domains.

8429. The method of item 8373, wherein the implant is combined with a polymer, and the polymer has hydrophobic domains.

8430. The method of item 8373, wherein the implant is combined with a polymer, and the polymer is a non-conductive polymer.

8431. The method of item 8373, wherein the implant is combined with a polymer, and the polymer is an elastomer.

8432. The method of item 8373, wherein the implant is combined with a polymer, and the polymer is a hydrogel.

8433. The method of item 8373, wherein the implant is combined with a polymer, and the polymer is a silicone polymer.

8434. The method of item 8373, wherein the implant is combined with a polymer, and the polymer is a hydrocarbon polymer.

8435. The method of item 8373, wherein the implant is combined with a polymer, and the polymer is a styrene-derived polymer.

8436. The method of item 8373, wherein the implant is combined with a polymer, and the polymer is a butadiene polymer.

8437. The method of item 8373, wherein the implant is combined with a polymer, and the polymer is a macromer.

8438. The method of item 8373, wherein the implant is combined with a polymer, and the polymer is a poly(ethylene glycol) polymer.

8439. The method of item 8373, wherein the implant is combined with a polymer, and the polymer is an amorphous polymer.

8440. The method of item 8373, wherein the implant is combined with a polymer, and the polymer is a lubricious coating.

8441. The method of item 8373 wherein the fibrosing agent is located within pores or holes of the device.

8442. The method of item 8373 wherein the fibrosing agent is located within a channel, lumen, or divet of the device.

8443. The method of item 8373, wherein the implant is further combined with a second pharmaceutically active agent.

8444. The method of item 8373, wherein the implant is further combined with an anti-inflammatory agent.

8445. The method of item 8373 wherein the implant is further combined with an agent that inhibits infection.

8446. The method of item 8373, wherein the implant is further combined with an anthracycline.

8447. The method of item 8373, wherein the implant is further combined with doxorubicin.

8448. The method of item 8373, wherein the implant is further combined with mitoxantrone.

8449. The method of item 8373, wherein the implant is further combined with a fluoropyrimidine.

8450. The method of item 8373, wherein the implant is further combined with 5-fluorouracil (5-FU).

8451. The method of item 8373, wherein the implant is further combined with a folic acid antagonist.

8452. The method of item 8373, wherein the implant is further combined with methotrexate.

8453. The method of item 8373, wherein the implant is further combined with a podophylotoxin.

8454. The method of item 8373, wherein the implant is further combined with etoposide.

8455. The method of item 8373 wherein the implant is further combined with a camptothecin.

8456. The method of item 8373, wherein the implant is further combined with a hydroxyurea.

8457. The method of item 8373, wherein the implant is further combined with a platinum complex.

8458. The method of item 8373, wherein the implant is further combined with cisplatin.

8459. The method of item 8373, wherein the implant is further combined with an anti-thrombotic agent.

8460. The method of item 8373, wherein the implant is further combined with a visualization agent.

8461. The method of item 8373, wherein the implant is further combined with a visualization agent, wherein the visualization agent is a radiopaque material, wherein the radiopaque material comprises a metal, a halogenated compound, or a barium containing compound.

8462. The method of item 8373, wherein the implant is further combined with a visualization agent, wherein the visualization agent is a radiopaque material, wherein the radiopaque material comprises barium, tantalum, or technetium.

8463. The method of item 8373, wherein the implant is further combined with a visualization agent, wherein the visualization agent is a MRI responsive material.

8464. The method of item 8373, wherein the implant is further combined with a visualization agent, wherein the visualization agent comprises a gadolinium chelate.

8465. The method of item 8373, wherein the implant is further combined with a visualization agent, wherein the visualization agent comprises iron, magnesium, manganese, copper, or chromium.

8466. The method of item 8373, wherein the implant is further combined with a visualization agent, wherein the visualization agent comprises an iron oxide compound.

8467. The method of item 8373, wherein the implant is further combined with a visualization agent, wherein the visualization agent comprises a dye, pigment, or colorant.

8468. The method of item 8373, wherein the implant is further combined with an echogenic material.

8469. The method of item 8373, wherein the implant is further combined with an echogenic material, and the echogenic material is in the form of a coating.

8470. The method of item 8373 wherein the device is sterilized.

8471. The method of item 8373 wherein the fibrosing agent is released into tissue in the vicinity of the device after deployment of the device.

8472. The method of item 8373 wherein the fibrosing agent is released into tissue in the vicinity of the device after deployment of the device, wherein the tissue is connective tissue.

8473. The method of item 8373 wherein the fibrosing agent is released into tissue in the vicinity of the device after deployment of the device, wherein the tissue is muscle tissue.

8474. The method of item 8373 wherein the fibrosing agent is released into tissue in the vicinity of the device after deployment of the device, wherein the tissue is nerve tissue.

8475. The method of item 8373 wherein the fibrosing agent is released into tissue in the vicinity of the device after deployment of the device, wherein the tissue is epithelium tissue.

8476. The method of item 8373 wherein the fibrosing agent is released in effective concentrations from the device over a period ranging from the time of deployment of the device to about 1 year.

8477. The method of item 8373 wherein the fibrosing agent is released in effective concentrations from the device over a period ranging from about 1 month to 6 months.

8478. The method of item 8373 wherein the fibrosing agent is released in effective concentrations from the device over a period ranging from about 1–90 days.

8479. The method of item 8373 wherein the fibrosing agent is released in effective concentrations from the device at a constant rate.

8480. The method of item 8373 wherein the fibrosing agent is released in effective concentrations from the device at an increasing rate.

8481. The method of item 8373 wherein the fibrosing agent is released in effective concentrations from the device at a decreasing rate.

8482. The method of item 8373 wherein the fibrosing agent is released in effective concentrations from the composition comprising the fibrosing agent by diffusion over a period ranging from the time of deployment of the device to about 90 days.

8483. The method of item 8373 wherein the fibrosing agent is released in effective concentrations from the composition comprising the fibrosing agent by erosion of the composition over a period ranging from the time of deployment of the device to about 90 days.

8484. The method of item 8373 wherein the device comprises about 0.01 µg to about 10 µg of the fibrosing agent.

8485. The method of item 8373 wherein the device comprises about 10 µg to about 10 mg of the fibrosing agent.

8486. The method of item 8373 wherein the device comprises about 10 mg to about 250 mg of the fibrosing agent.

8487. The method of item 8373 wherein the device comprises about 250 mg to about 1000 mg of the fibrosing agent.

8488. The method of item 8373 wherein the device comprises about 1000 mg to about 2500 mg of the fibrosing agent.

8489. The method of item 8373 wherein a surface of the device comprises less than 0.01 µg of the fibrosing agent per $mm^2$ of device surface to which the fibrosing agent is applied.

8490. The method of item 8373 wherein a surface of the device comprises about 0.01 µg to about 1 µg of the fibrosing agent per $mm^2$ of device surface to which the fibrosing agent is applied.

8491. The method of item 8373 wherein a surface of the device comprises about 1 µg to about 10 µg of the fibrosing agent per $mm^2$ of device surface to which the fibrosing agent is applied.

8492. The method of item 8373 wherein a surface of the device comprises about 10 µg to about 250 µg of the fibrosing agent per $mm^2$ of device surface to which the fibrosing agent is applied.

8493. The method of item 8373 wherein a surface of the device comprises about 250 µg to about 1000 µg of the fibrosing agent of fibrosing agent per $mm^2$ of device surface to which the fibrosing agent is applied.

8494. The method of item 8373 wherein a surface of the device comprises about 1000 µg to about 2500 µg of the fibrosing agent per $mm^2$ of device surface to which the fibrosing agent is applied.

8495. The method of item 8373 wherein the implant is, or comprises, an ablation device.

8496. The method of item 8373 wherein the implant is, or comprises, a nerve stimulator.

8497. The method of item 8373 wherein the implant is, or comprises, a pump.

8498. The method of item 8373 wherein the implant is, or comprises, a stapling device.

8499. A method of making a medical device comprising combining i) an implantable male contraceptive device and ii) a fibrosing agent or a composition comprising a fibrosing agent, where the fibrosing agent induces a fibrotic response between the device and a patient in which the device is implanted.

8500. The method of item 8499 wherein the fibrosing agent promotes regeneration.

8501. The method of item 8499 wherein the fibrosing agent promotes angiogenesis.

8502. The method of item 8499 wherein the fibrosing agent promotes fibroblast migration.

8503. The method of item 8499 wherein the fibrosing agent promotes fibroblast proliferation.

8504. The method of item 8499 wherein the fibrosing agent promotes deposition of extracellular matrix (ECM).

8505. The method of item 8499 wherein the fibrosing agent promotes tissue remodeling.

8506. The method of item 8499 wherein the fibrosing agent is an arterial vessel wall irritant.

8507. The method of item 8499 wherein the fibrosing agent promotes adhesion between the device and a host into which the device is implanted.

8508. The method of item 8499 wherein the device delivers the fibrosing agent locally to tissue proximate to the device.

8509. The method of item 8499 wherein the fibrosing agent is or comprises silk.

8510. The method of item 8499 wherein the fibrosing agent is or comprises mineral particles.

8511. The method of item 8499 wherein the fibrosing agent is or comprises chitosan.

8512. The method of item 8499 wherein the fibrosing agent is or comprises polylysine.

8513. The method of item 8499 wherein the fibrosing agent is or comprises fibronectin.

8514. The method of item 8499 wherein the fibrosing agent is or comprises bleomycin.

8515. The method of item 8499 wherein the fibrosing agent is or comprises CTGF.

8516. The method of item 8499 wherein the fibrosing agent is in the form of a thread, or is in contact with a thread.

8517. The method of item 8499 wherein the fibrosing agent is in the form of a particulate.

8518. The method of item 8499 wherein the composition further comprises an inflammatory cytokine.

8519. The method of item 8499 wherein the composition further comprises an agent that stimulates cell proliferation.

8520. The method of item 8499 wherein the composition is in the form of a gel or paste.

8521. The method of item 8499 wherein the fibrosing agent is in the form of tufts.

8522. The method of item 8499 wherein the fibrosing agent promotes adhesion between the device and a host into which the device is implanted.

8523. The method of item 8499 wherein the device delivers the fibrosing agent locally to tissue proximate to the device.

8524. The method of item 8499, wherein the implant is combined with a coating, and the coating comprises the fibrosing agent.

8525. The method of item 8499, wherein the implant is combined with a coating, and the coating is disposed on a surface of the device.

8526. The method of item 8499, wherein the implant is combined with a coating, and the coating directly contacts the device.

8527. The method of item 8499, wherein the implant is combined with a coating, and the coating indirectly contacts the device.

8528. The method of item 8499, wherein the implant is combined with a coating, and the coating partially covers the device.

8529. The method of item 8499, wherein the implant is combined with a coating, and the coating completely covers the device.

8530. The method of item 8499, wherein the implant is combined with a coating, and the coating is a uniform coating.

8531. The method of item 8499, wherein the implant is combined with a coating, and the coating is a non-uniform coating.

8532. The method of item 8499, wherein the implant is combined with a coating, and the coating is a discontinuous coating.

8533. The method of item 8499 wherein the implant is combined with a coating, and the coating is a patterned coating.

8534. The method of item 8499, wherein the implant is combined with a coating, and the coating has a thickness of 100 µm or less.

8535. The method of item 8499, wherein the implant is combined with a coating, and the coating has a thickness of 10 µm or less.

8536. The method of item 8499, wherein the implant is combined with a coating, and the coating adheres to the surface of the device upon deployment of the device.

8537. The method of item 8499, wherein the implant is combined with a coating, and the coating is stable at room temperature for a period of at least 1 year.

8538. The method of item 8499, wherein the implant is combined with a coating, and the fibrosing agent is present in the coating in an amount ranging between about 0.0001% to about 1% by weight.

8539. The method of item 8499, wherein the implant is combined with a coating, and the fibrosing agent is present in the coating in an amount ranging between about 1% to about 10% by weight.

8540. The method of item 8499, wherein the implant is combined with a coating, and the fibrosing agent is present in the coating in an amount ranging between about 10% to about 25% by weight.

8541. The method of item 8499, wherein the implant is combined with a coating, and the fibrosing agent is present in the coating in an amount ranging between about 25% to about 70% by weight.

8542. The method of item 8499, wherein the implant is combined with a coating, and the coating further comprises a polymer.

8543. The method of item 8499, wherein the device comprises a first coating having a first composition and a second coating having a second composition.

8544. The method of item 8499, wherein the device comprises a first coating having a first composition and a second coating having a second composition, where the first composition and the second composition are different.

8545. The method of item 8499, wherein the device comprises a polymer.

8546. The method of item 8499, wherein the device comprises a polymer, and the polymer is a component of the composition.

8547. The method of item 8499, wherein the implant is combined with a polymer, and the polymer is a copolymer.

8548. The method of item 8499, wherein the implant is combined with a polymer, and the polymer is a block copolymer.

8549. The method of item 8499, wherein the implant is combined with a polymer, and the polymer is a random copolymer.

8550. The method of item 8499, wherein the implant is combined with a polymer, and the polymer is a biodegradable polymer.

8551. The method of item 8499, wherein the implant is combined with a polymer, and the polymer is a non-biodegradable polymer.

8552. The method of item 8499, wherein the implant is combined with a polymer, and the polymer is a hydrophilic polymer.

8553. The method of item 8499, wherein the implant is combined with a polymer, and the polymer is a hydrophobic polymer.

8554. The method of item 8499, wherein the implant is combined with a polymer, and the polymer has hydrophilic domains.

8555. The method of item 8499, wherein the implant is combined with a polymer, and the polymer has hydrophobic domains.

8556. The method of item 8499, wherein the implant is combined with a polymer, and the polymer is a non-conductive polymer.

8557. The method of item 8499, wherein the implant is combined with a polymer, and the polymer is an elastomer.

8558. The method of item 8499, wherein the implant is combined with a polymer, and the polymer is a hydrogel.

8559. The method of item 8499, wherein the implant is combined with a polymer, and the polymer is a silicone polymer.

8560. The method of item 8499, wherein the implant is combined with a polymer, and the polymer is a hydrocarbon polymer.

8561. The method of item 8499, wherein the implant is combined with a polymer, and the polymer is a styrene-derived polymer.

8562. The method of item 8499, wherein the implant is combined with a polymer, and the polymer is a butadiene polymer.

8563. The method of item 8499, wherein the implant is combined with a polymer, and the polymer is a macromer.

8564. The method of item 8499, wherein the implant is combined with a polymer, and the polymer is a poly(ethylene glycol) polymer.

8565. The method of item 8499, wherein the implant is combined with a polymer, and the polymer is an amorphous polymer.

8566. The method of item 8499, wherein the implant is combined with a polymer, and the polymer is a lubricious coating.

8567. The method of item 8499 wherein the fibrosing agent is located within pores or holes of the device.

8568. The method of item 8499 wherein the fibrosing agent is located within a channel, lumen, or divet of the device.

8569. The method of item 8499, wherein the implant is further combined with a second pharmaceutically active agent.

8570. The method of item 8499, wherein the implant is further combined with an anti-inflammatory agent.

8571. The method of item 8499 wherein the implant is further combined with an agent that inhibits infection.

8572. The method of item 8499, wherein the implant is further combined with an anthracycline.

8573. The method of item 8499, wherein the implant is further combined with doxorubicin.

8574. The method of item 8499, wherein the implant is further combined with mitoxantrone.

8575. The method of item 8499, wherein the implant is further combined with a fluoropyrimidine.

8576. The method of item 8499, wherein the implant is further combined with 5-fluorouracil (5-FU).

8577. The method of item 8499, wherein the implant is further combined with a folic acid antagonist.

8578. The method of item 8499, wherein the implant is further combined with methotrexate.

8579. The method of item 8499, wherein the implant is further combined with a podophylotoxin.

8580. The method of item 8499, wherein the implant is further combined with etoposide.

8581. The method of item 8499 wherein the implant is further combined with a camptothecin.

8582. The method of item 8499, wherein the implant is further combined with a hydroxyurea.

8583. The method of item 8499, wherein the implant is further combined with a platinum complex.

8584. The method of item 8499, wherein the implant is further combined with cisplatin.

8585. The method of item 8499, wherein the implant is further combined with an anti-thrombotic agent.

8586. The method of item 8499, wherein the implant is further combined with a visualization agent.

8587. The method of item 8499, wherein the implant is further combined with a visualization agent, wherein the visualization agent is a radiopaque material, wherein the radiopaque material comprises a metal, a halogenated compound, or a barium containing compound.

8588. The method of item 8499, wherein the implant is further combined with a visualization agent, wherein the visualization agent is a radiopaque material, wherein the radiopaque material comprises barium, tantalum, or technetium.

8589. The method of item 8499, wherein the implant is further combined with a visualization agent, wherein the visualization agent is a MRI responsive material.

8590. The method of item 8499, wherein the implant is further combined with a visualization agent, wherein the visualization agent comprises a gadolinium chelate.

8591. The method of item 8499, wherein the implant is further combined with a visualization agent, wherein the visualization agent comprises iron, magnesium, manganese, copper, or chromium.

8592. The method of item 8499, wherein the implant is further combined with a visualization agent, wherein the visualization agent comprises an iron oxide compound.

8593. The method of item 8499, wherein the implant is further combined with a visualization agent, wherein the visualization agent comprises a dye, pigment, or colorant.

8594. The method of item 8499, wherein the implant is further combined with an echogenic material.

8595. The method of item 8499, wherein the implant is further combined with an echogenic material, and the echogenic material is in the form of a coating.

8596. The method of item 8499 wherein the device is sterilized.

8597. The method of item 8499 wherein the fibrosing agent is released into tissue in the vicinity of the device after deployment of the device.

8598. The method of item 8499 wherein the fibrosing agent is released into tissue in the vicinity of the device after deployment of the device, wherein the tissue is connective tissue.

8599. The method of item 8499 wherein the fibrosing agent is released into tissue in the vicinity of the device after deployment of the device, wherein the tissue is muscle tissue.

8600. The method of item 8499 wherein the fibrosing agent is released into tissue in the vicinity of the device after deployment of the device, wherein the tissue is nerve tissue.

8601. The method of item 8499 wherein the fibrosing agent is released into tissue in the vicinity of the device after deployment of the device, wherein the tissue is epithelium tissue.

8602. The method of item 8499 wherein the fibrosing agent is released in effective concentrations from the device over a period ranging from the time of deployment of the device to about 1 year.

8603. The method of item 8499 wherein the fibrosing agent is released in effective concentrations from the device over a period ranging from about 1 month to 6 months.

8604. The method of item 8499 wherein the fibrosing agent is released in effective concentrations from the device over a period ranging from about 1–90 days.

8605. The method of item 8499 wherein the fibrosing agent is released in effective concentrations from the device at a constant rate.

8606. The method of item 8499 wherein the fibrosing agent is released in effective concentrations from the device at an increasing rate.

8607. The method of item 8499 wherein the fibrosing agent is released in effective concentrations from the device at a decreasing rate.

8608. The method of item 8499 wherein the fibrosing agent is released in effective concentrations from the composition comprising the fibrosing agent by diffusion over a period ranging from the time of deployment of the device to about 90 days.

8609. The method of item 8499 wherein the fibrosing agent is released in effective concentrations from the composition comprising the fibrosing agent by erosion of the composition over a period ranging from the time of deployment of the device to about 90 days.

8610. The method of item 8499 wherein the device comprises about 0.01 µg to about 10 µg of the fibrosing agent.

8611. The method of item 8499 wherein the device comprises about 10 µg to about 10 mg of the fibrosing agent.

8612. The method of item 8499 wherein the device comprises about 10 mg to about 250 mg of the fibrosing agent.

8613. The method of item 8499 wherein the device comprises about 250 mg to about 1000 mg of the fibrosing agent.

8614. The method of item 8499 wherein the device comprises about 1000 mg to about 2500 mg of the fibrosing agent.

8615. The method of item 8499 wherein a surface of the device comprises less than 0.01 µg of the fibrosing agent per mm$^2$ of device surface to which the fibrosing agent is applied.

8616. The method of item 8499 wherein a surface of the device comprises about 0.01 µg to about 1 µg of the fibrosing agent per mm$^2$ of device surface to which the fibrosing agent is applied.

8617. The method of item 8499 wherein a surface of the device comprises about 1 µg to about 10 µg of the fibrosing agent per mm$^2$ of device surface to which the fibrosing agent is applied.

8618. The method of item 8499 wherein a surface of the device comprises about 10 µg to about 250 µg of the fibrosing agent per mm$^2$ of device surface to which the fibrosing agent is applied.

8619. The method of item 8499 wherein a surface of the device comprises about 250 µg to about 1000 µg of the fibrosing agent of fibrosing agent per mm$^2$ of device surface to which the fibrosing agent is applied.

8620. The method of item 8499 wherein a surface of the device comprises about 1000 µg to about 2500 µg of the fibrosing agent per mm$^2$ of device surface to which the fibrosing agent is applied.

8621. The method of item 8499 wherein the implant is, or comprises, a valved sterilization device for surgical insertion into the Vas Deferens.

8622. The method of item 8499 wherein the implant is, or comprises, a reversible male sterilization device.

8623. The method of item 8499 wherein the implant is, or comprises, a vasectomy clip.

8624. The method of item 8499 wherein the implant is, or comprises, a vasectomy suture.

8625. The method of item 8499 wherein the implant is implanted in the Vas Deferens.

8626. A method of making a medical device comprising combining i) gastric restriction implant and ii) a fibrosing agent or a composition comprising a fibrosing agent, where the fibrosing agent induces a fibrotic response between the device and a patient in which the device is implanted.

8627. The method of item 8626 wherein the fibrosing agent promotes regeneration.

8628. The method of item 8626 wherein the fibrosing agent promotes angiogenesis.

8629. The method of item 8626 wherein the fibrosing agent promotes fibroblast migration.

8630. The method of item 8626 wherein the fibrosing agent promotes fibroblast proliferation.

8631. The method of item 8626 wherein the fibrosing agent promotes deposition of extracellular matrix (ECM).

8632. The method of item 8626 wherein the fibrosing agent promotes tissue remodeling.

8633. The method of item 8626 wherein the fibrosing agent is an arterial vessel wall irritant.

8634. The method of item 8626 wherein the fibrosing agent promotes adhesion between the device and a host into which the device is implanted.

8635. The method of item 8626 wherein the device delivers the fibrosing agent locally to tissue proximate to the device.

8636. The method of item 8626 wherein the fibrosing agent is or comprises silk.

8637. The method of item 8626 wherein the fibrosing agent is or comprises mineral particles.

8638. The method of item 8626 wherein the fibrosing agent is or comprises chitosan.

8639. The method of item 8626 wherein the fibrosing agent is or comprises polylysine.

8640. The method of item 8626 wherein the fibrosing agent is or comprises fibronectin.

8641. The method of item 8626 wherein the fibrosing agent is or comprises bleomycin.

8642. The method of item 8626 wherein the fibrosing agent is or comprises CTGF.

8643. The method of item 8626 wherein the fibrosing agent is in the form of a thread, or is in contact with a thread.

8644. The method of item 8626 wherein the fibrosing agent is in the form of a particulate.

8645. The method of item 8626 wherein the composition further comprises an inflammatory cytokine.

8646. The method of item 8626 wherein the composition further comprises an agent that stimulates cell proliferation.

8647. The method of item 8626 wherein the composition is in the form of a gel or paste.

8648. The method of item 8626 wherein the fibrosing agent is in the form of tufts.

8649. The method of item 8626 wherein the fibrosing agent promotes adhesion between the device and a host into which the device is implanted.

8650. The method of item 8626 wherein the device delivers the fibrosing agent locally to tissue proximate to the device.

8651. The method of item 8626, wherein the implant is combined with a coating, and the coating comprises the fibrosing agent.

8652. The method of item 8626, wherein the implant is combined with a coating, and the coating is disposed on a surface of the device.

8653. The method of item 8626, wherein the implant is combined with a coating, and the coating directly contacts the device.

8654. The method of item 8626, wherein the implant is combined with a coating, and the coating indirectly contacts the device.

8655. The method of item 8626, wherein the implant is combined with a coating, and the coating partially covers the device.

8656. The method of item 8626, wherein the implant is combined with a coating, and the coating completely covers the device.

8657. The method of item 8626, wherein the implant is combined with a coating, and the coating is a uniform coating.

8658. The method of item 8626, wherein the implant is combined with a coating, and the coating is a non-uniform coating.

8659. The method of item 8626, wherein the implant is combined with a coating, and the coating is a discontinuous coating.

8660. The method of item 8626 wherein the implant is combined with a coating, and the coating is a patterned coating.

8661. The method of item 8626, wherein the implant is combined with a coating, and the coating has a thickness of 100 µm or less.

8662. The method of item 8626, wherein the implant is combined with a coating, and the coating has a thickness of 10 µm or less.

8663. The method of item 8626, wherein the implant is combined with a coating, and the coating adheres to the surface of the device upon deployment of the device.

8664. The method of item 8626, wherein the implant is combined with a coating, and the coating is stable at room temperature for a period of at least 1 year.

8665. The method of item 8626, wherein the implant is combined with a coating, and the fibrosing agent is present in the coating in an amount ranging between about 0.0001% to about 1% by weight.

8666. The method of item 8626, wherein the implant is combined with a coating, and the fibrosing agent is present in the coating in an amount ranging between about 1% to about 10% by weight.

8667. The method of item 8626, wherein the implant is combined with a coating, and the fibrosing agent is present in the coating in an amount ranging between about 10% to about 25% by weight.

8668. The method of item 8626, wherein the implant is combined with a coating, and the fibrosing agent is present in the coating in an amount ranging between about 25% to about 70% by weight.

8669. The method of item 8626, wherein the implant is combined with a coating, and the coating further comprises a polymer.

8670. The method of item 8626, wherein the device comprises a first coating having a first composition and a second coating having a second composition.

8671. The method of item 8626, wherein the device comprises a first coating having a first composition and a second coating having a second composition, where the first composition and the second composition are different.

8672. The method of item 8626, wherein the device comprises a polymer.

8673. The method of item 8626, wherein the device comprises a polymer, and the polymer is a component of the composition.

8674. The method of item 8626, wherein the implant is combined with a polymer, and the polymer is a copolymer.

8675. The method of item 8626, wherein the implant is combined with a polymer, and the polymer is a block copolymer.

8676. The method of item 8626, wherein the implant is combined with a polymer, and the polymer is a random copolymer.

8677. The method of item 8626, wherein the implant is combined with a polymer, and the polymer is a biodegradable polymer.

8678. The method of item 8626, wherein the implant is combined with a polymer, and the polymer is a non-biodegradable polymer.

8679. The method of item 8626, wherein the implant is combined with a polymer, and the polymer is a hydrophilic polymer.

8680. The method of item 8626, wherein the implant is combined with a polymer, and the polymer is a hydrophobic polymer.

8681. The method of item 8626, wherein the implant is combined with a polymer, and the polymer has hydrophilic domains.

8682. The method of item 8626, wherein the implant is combined with a polymer, and the polymer has hydrophobic domains.

8683. The method of item 8626, wherein the implant is combined with a polymer, and the polymer is a non-conductive polymer.

8684. The method of item 8626, wherein the implant is combined with a polymer, and the polymer is an elastomer.

8685. The method of item 8626, wherein the implant is combined with a polymer, and the polymer is a hydrogel.

8686. The method of item 8626, wherein the implant is combined with a polymer, and the polymer is a silicone polymer.

8687. The method of item 8626, wherein the implant is combined with a polymer, and the polymer is a hydrocarbon polymer.

8688. The method of item 8626, wherein the implant is combined with a polymer, and the polymer is a styrene-derived polymer.

8689. The method of item 8626, wherein the implant is combined with a polymer, and the polymer is a butadiene polymer.

8690. The method of item 8626, wherein the implant is combined with a polymer, and the polymer is a macromer.

8691. The method of item 8626, wherein the implant is combined with a polymer, and the polymer is a poly(ethylene glycol) polymer.

8692. The method of item 8626, wherein the implant is combined with a polymer, and the polymer is an amorphous polymer.

8693. The method of item 8626, wherein the implant is combined with a polymer, and the polymer is a lubricious coating.

8694. The method of item 8626 wherein the fibrosing agent is located within pores or holes of the device.

8695. The method of item 8626 wherein the fibrosing agent is located within a channel, lumen, or divet of the device.

8696. The method of item 8626, wherein the implant is further combined with a second pharmaceutically active agent.

8697. The method of item 8626, wherein the implant is further combined with an anti-inflammatory agent.

8698. The method of item 8626 wherein the implant is further combined with an agent that inhibits infection.

8699. The method of item 8626, wherein the implant is further combined with an anthracycline.

8700. The method of item 8626, wherein the implant is further combined with doxorubicin.

8701. The method of item 8626, wherein the implant is further combined with mitoxantrone.

8702. The method of item 8626, wherein the implant is further combined with a fluoropyrimidine.

8703. The method of item 8626, wherein the implant is further combined with 5-fluorouracil (5-FU).

8704. The method of item 8626, wherein the implant is further combined with a folic acid antagonist.

8705. The method of item 8626, wherein the implant is further combined with methotrexate.

8706. The method of item 8626, wherein the implant is further combined with a podophylotoxin.

8707. The method of item 8626, wherein the implant is further combined with etoposide.

8708. The method of item 8626 wherein the implant is further combined with a camptothecin.

8709. The method of item 8626, wherein the implant is further combined with a hydroxyurea.

8710. The method of item 8626, wherein the implant is further combined with a platinum complex.

8711. The method of item 8626, wherein the implant is further combined with cisplatin.

8712. The method of item 8626, wherein the implant is further combined with an anti-thrombotic agent.

8713. The method of item 8626, wherein the implant is further combined with a visualization agent.

8714. The method of item 8626, wherein the implant is further combined with a visualization agent, wherein the visualization agent is a radiopaque material, wherein the radiopaque material comprises a metal, a halogenated compound, or a barium containing compound.

8715. The method of item 8626, wherein the implant is further combined with a visualization agent, wherein the visualization agent is a radiopaque material, wherein the radiopaque material comprises barium, tantalum, or technetium.

8716. The method of item 8626, wherein the implant is further combined with a visualization agent, wherein the visualization agent is a MRI responsive material.

8717. The method of item 8626, wherein the implant is further combined with a visualization agent, wherein the visualization agent comprises a gadolinium chelate.

8718. The method of item 8626, wherein the implant is further combined with a visualization agent, wherein the visualization agent comprises iron, magnesium, manganese, copper, or chromium.

8719. The method of item 8626, wherein the implant is further combined with a visualization agent, wherein the visualization agent comprises an iron oxide compound.

8720. The method of item 8626, wherein the implant is further combined with a visualization agent, wherein the visualization agent comprises a dye, pigment, or colorant.

8721. The method of item 8626, wherein the implant is further combined with an echogenic material.

8722. The method of item 8626, wherein the implant is further combined with an echogenic material, and the echogenic material is in the form of a coating.

8723. The method of item 8626 wherein the device is sterilized.

8724. The method of item 8626 wherein the fibrosing agent is released into tissue in the vicinity of the device after deployment of the device.

8725. The method of item 8626 wherein the fibrosing agent is released into tissue in the vicinity of the device after deployment of the device, wherein the tissue is connective tissue.

8726. The method of item 8626 wherein the fibrosing agent is released into tissue in the vicinity of the device after deployment of the device, wherein the tissue is muscle tissue.

8727. The method of item 8626 wherein the fibrosing agent is released into tissue in the vicinity of the device after deployment of the device, wherein the tissue is nerve tissue.

8728. The method of item 8626 wherein the fibrosing agent is released into tissue in the vicinity of the device after deployment of the device, wherein the tissue is epithelium tissue.

8729. The method of item 8626 wherein the fibrosing agent is released in effective concentrations from the device over a period ranging from the time of deployment of the device to about 1 year.

8730. The method of item 8626 wherein the fibrosing agent is released in effective concentrations from the device over a period ranging from about 1 month to 6 months.

8731. The method of item 8626 wherein the fibrosing agent is released in effective concentrations from the device over a period ranging from about 1–90 days.

8732. The method of item 8626 wherein the fibrosing agent is released in effective concentrations from the device at a constant rate.

8733. The method of item 8626 wherein the fibrosing agent is released in effective concentrations from the device at an increasing rate.

8734. The method of item 8626 wherein the fibrosing agent is released in effective concentrations from the device at a decreasing rate.

8735. The method of item 8626 wherein the fibrosing agent is released in effective concentrations from the composition comprising the fibrosing agent by diffusion over a period ranging from the time of deployment of the device to about 90 days.

8736. The method of item 8626 wherein the fibrosing agent is released in effective concentrations from the composition comprising the fibrosing agent by erosion of the composition over a period ranging from the time of deployment of the device to about 90 days.

8737. The method of item 8626 wherein the device comprises about 0.01 µg to about 10 µg of the fibrosing agent.

8738. The method of item 8626 wherein the device comprises about 10 µg to about 10 mg of the fibrosing agent.

8739. The method of item 8626 wherein the device comprises about 10 mg to about 250 mg of the fibrosing agent.

8740. The method of item 8626 wherein the device comprises about 250 mg to about 1000 mg of the fibrosing agent.

8741. The method of item 8626 wherein the device comprises about 1000 mg to about 2500 mg of the fibrosing agent.

8742. The method of item 8626 wherein a surface of the device comprises less than 0.01 µg of the fibrosing agent per mm² of device surface to which the fibrosing agent is applied.

8743. The method of item 8626 wherein a surface of the device comprises about 0.01 µg to about 1 µg of the fibrosing agent per mm² of device surface to which the fibrosing agent is applied.

8744. The method of item 8626 wherein a surface of the device comprises about 1 µg to about 10 µg of the fibrosing agent per mm² of device surface to which the fibrosing agent is applied.

8745. The method of item 8626 wherein a surface of the device comprises about 10 µg to about 250 µg of the fibrosing agent per mm² of device surface to which the fibrosing agent is applied.

8746. The method of item 8626 wherein a surface of the device comprises about 250 µg to about 1000 µg of the fibrosing agent of fibrosing agent per mm² of device surface to which the fibrosing agent is applied.

8747. The method of item 8626 wherein a surface of the device comprises about 1000 µg to about 2500 µg of the fibrosing agent per mm² of device surface to which the fibrosing agent is applied.

8748. The method of item 8626 wherein the implant is, or comprises, an inflatable cuff.

8749. The method of item 8626 wherein the implant is, or comprises, a space-occupying device.

8750. A method of making a medical device comprising combining i) a suture-based endoluminal implant for partitioning a stomach, with ii) a fibrosing agent or a composition comprising a fibrosing agent, where the fibrosing agent induces a fibrotic response between the device and a patient in which the device is implanted.

8751. The method of item 8750 wherein the fibrosing agent promotes regeneration.

8752. The method of item 8750 wherein the fibrosing agent promotes angiogenesis.

8753. The method of item 8750 wherein the fibrosing agent promotes fibroblast migration.

8754. The method of item 8750 wherein the fibrosing agent promotes fibroblast proliferation.

8755. The method of item 8750 wherein the fibrosing agent promotes deposition of extracellular matrix (ECM).

8756. The method of item 8750 wherein the fibrosing agent promotes tissue remodeling.

8757. The method of item 8750 wherein the fibrosing agent is an arterial vessel wall irritant.

8758. The method of item 8750 wherein the fibrosing agent promotes adhesion between the device and a host into which the device is implanted.

8759. The method of item 8750 wherein the device delivers the fibrosing agent locally to tissue proximate to the device.

8760. The method of item 8750 wherein the fibrosing agent is or comprises silk.

8761. The method of item 8750 wherein the fibrosing agent is or comprises mineral particles.

8762. The method of item 8750 wherein the fibrosing agent is or comprises chitosan.

8763. The method of item 8750 wherein the fibrosing agent is or comprises polylysine.

8764. The method of item 8750 wherein the fibrosing agent is or comprises fibronectin.

8765. The method of item 8750 wherein the fibrosing agent is or comprises bleomycin.

8766. The method of item 8750 wherein the fibrosing agent is or comprises CTGF.

8767. The method of item 8750 wherein the fibrosing agent is in the form of a thread, or is in contact with a thread.

8768. The method of item 8750 wherein the fibrosing agent is in the form of a particulate.

8769. The method of item 8750 wherein the composition further comprises an inflammatory cytokine.

8770. The method of item 8750 wherein the composition further comprises an agent that stimulates cell proliferation.

8771. The method of item 8750 wherein the composition is in the form of a gel or paste.

8772. The method of item 8750 wherein the fibrosing agent is in the form of tufts.

8773. The method of item 8750 wherein the fibrosing agent promotes adhesion between the device and a host into which the device is implanted.

8774. The method of item 8750 wherein the device delivers the fibrosing agent locally to tissue proximate to the device.

8775. The method of item 8750, wherein the implant is combined with a coating, and the coating comprises the fibrosing agent.

8776. The method of item 8750, wherein the implant is combined with a coating, and the coating is disposed on a surface of the device.

8777. The method of item 8750, wherein the implant is combined with a coating, and the coating directly contacts the device.

8778. The method of item 8750, wherein the implant is combined with a coating, and the coating indirectly contacts the device.

8779. The method of item 8750, wherein the implant is combined with a coating, and the coating partially covers the device.

8780. The method of item 8750, wherein the implant is combined with a coating, and the coating completely covers the device.

8781. The method of item 8750, wherein the implant is combined with a coating, and the coating is a uniform coating.

8782. The method of item 8750, wherein the implant is combined with a coating, and the coating is a non-uniform coating.

8783. The method of item 8750, wherein the implant is combined with a coating, and the coating is a discontinuous coating.

8784. The method of item 8750 wherein the implant is combined with a coating, and the coating is a patterned coating.

8785. The method of item 8750, wherein the implant is combined with a coating, and the coating has a thickness of 100 µm or less.

8786. The method of item 8750, wherein the implant is combined with a coating, and the coating has a thickness of 10 µm or less.

8787. The method of item 8750, wherein the implant is combined with a coating, and the coating adheres to the surface of the device upon deployment of the device.

8788. The method of item 8750, wherein the implant is combined with a coating, and the coating is stable at room temperature for a period of at least 1 year.

8789. The method of item 8750, wherein the implant is combined with a coating, and the fibrosing agent is present in the coating in an amount ranging between about 0.0001% to about 1% by weight.

8790. The method of item 8750, wherein the implant is combined with a coating, and the fibrosing agent is present in the coating in an amount ranging between about 1% to about 10% by weight.

8791. The method of item 8750, wherein the implant is combined with a coating, and the fibrosing agent is present in the coating in an amount ranging between about 10% to about 25% by weight.

8792. The method of item 8750, wherein the implant is combined with a coating, and the fibrosing agent is present in the coating in an amount ranging between about 25% to about 70% by weight.

8793. The method of item 8750, wherein the implant is combined with a coating, and the coating further comprises a polymer.

8794. The method of item 8750, wherein the device comprises a first coating having a first composition and a second coating having a second composition.

8795. The method of item 8750, wherein the device comprises a first coating having a first composition and a second coating having a second composition, where the first composition and the second composition are different.

8796. The method of item 8750, wherein the device comprises a polymer.

8797. The method of item 8750, wherein the device comprises a polymer, and the polymer is a component of the composition.

8798. The method of item 8750, wherein the implant is combined with a polymer, and the polymer is a copolymer.

8799. The method of item 8750, wherein the implant is combined with a polymer, and the polymer is a block copolymer.

8800. The method of item 8750, wherein the implant is combined with a polymer, and the polymer is a random copolymer.

8801. The method of item 8750, wherein the implant is combined with a polymer, and the polymer is a biodegradable polymer.

8802. The method of item 8750, wherein the implant is combined with a polymer, and the polymer is a non-biodegradable polymer.

8803. The method of item 8750, wherein the implant is combined with a polymer, and the polymer is a hydrophilic polymer.

8804. The method of item 8750, wherein the implant is combined with a polymer, and the polymer is a hydrophobic polymer.

8805. The method of item 8750, wherein the implant is combined with a polymer, and the polymer has hydrophilic domains.

8806. The method of item 8750, wherein the implant is combined with a polymer, and the polymer has hydrophobic domains.

8807. The method of item 8750, wherein the implant is combined with a polymer, and the polymer is a non-conductive polymer.

8808. The method of item 8750, wherein the implant is combined with a polymer, and the polymer is an elastomer.

8809. The method of item 8750, wherein the implant is combined with a polymer, and the polymer is a hydrogel.

8810. The method of item 8750, wherein the implant is combined with a polymer, and the polymer is a silicone polymer.

8811. The method of item 8750, wherein the implant is combined with a polymer, and the polymer is a hydrocarbon polymer.

8812. The method of item 8750, wherein the implant is combined with a polymer, and the polymer is a styrene-derived polymer.

8813. The method of item 8750, wherein the implant is combined with a polymer, and the polymer is a butadiene polymer.

8814. The method of item 8750, wherein the implant is combined with a polymer, and the polymer is a macromer.

8815. The method of item 8750, wherein the implant is combined with a polymer, and the polymer is a poly(ethylene glycol) polymer.

8816. The method of item 8750, wherein the implant is combined with a polymer, and the polymer is an amorphous polymer.

8817. The method of item 8750, wherein the implant is combined with a polymer, and the polymer is a lubricious coating.

8818. The method of item 8750 wherein the fibrosing agent is located within pores or holes of the device.

8819. The method of item 8750 wherein the fibrosing agent is located within a channel, lumen, or divet of the device.

8820. The method of item 8750, wherein the implant is further combined with a second pharmaceutically active agent.

8821. The method of item 8750, wherein the implant is further combined with an anti-inflammatory agent.

8822. The method of item 8750 wherein the implant is further combined with an agent that inhibits infection.

8823. The method of item 8750, wherein the implant is further combined with an anthracycline.

8824. The method of item 8750, wherein the implant is further combined with doxorubicin.

8825. The method of item 8750, wherein the implant is further combined with mitoxantrone.

8826. The method of item 8750, wherein the implant is further combined with a fluoropyrimidine.

8827. The method of item 8750, wherein the implant is further combined with 5-fluorouracil (5-FU).

8828. The method of item 8750, wherein the implant is further combined with a folic acid antagonist.

8829. The method of item 8750, wherein the implant is further combined with methotrexate.

8830. The method of item 8750, wherein the implant is further combined with a podophylotoxin.

8831. The method of item 8750, wherein the implant is further combined with etoposide.

8832. The method of item 8750 wherein the implant is further combined with a camptothecin.

8833. The method of item 8750, wherein the implant is further combined with a hydroxyurea.

8834. The method of item 8750 wherein the implant is further combined with a platinum complex.

8835. The method of item 8750, wherein the implant is further combined with cisplatin.

8836. The method of item 8750, wherein the implant is further combined with an anti-thrombotic agent.

8837. The method of item 8750, wherein the implant is further combined with a visualization agent.

8838. The method of item 8750, wherein the implant is further combined with a visualization agent, wherein the visualization agent is a radiopaque material, wherein the radiopaque material comprises a metal, a halogenated compound, or a barium containing compound.

8839. The method of item 8750, wherein the implant is further combined with a visualization agent, wherein the visualization agent is a radiopaque material, wherein the radiopaque material comprises barium, tantalum, or technetium.

8840. The method of item 8750, wherein the implant is further combined with a visualization agent, wherein the visualization agent is a MRI responsive material.

8841. The method of item 8750, wherein the implant is further combined with a visualization agent, wherein the visualization agent comprises a gadolinium chelate.

8842. The method of item 8750, wherein the implant is further combined with a visualization agent, wherein the visualization agent comprises iron, magnesium, manganese, copper, or chromium.

8843. The method of item 8750, wherein the implant is further combined with a visualization agent, wherein the visualization agent comprises an iron oxide compound.

8844. The method of item 8750, wherein the implant is further combined with a visualization agent, wherein the visualization agent comprises a dye, pigment, or colorant.

8845. The method of item 8750, wherein the implant is further combined with an echogenic material.

8846. The method of item 8750, wherein the implant is further combined with an echogenic material, and the echogenic material is in the form of a coating.

8847. The method of item 8750 wherein the device is sterilized.

8848. The method of item 8750 wherein the fibrosing agent is released into tissue in the vicinity of the device after deployment of the device.

8849. The method of item 8750 wherein the fibrosing agent is released into tissue in the vicinity of the device after deployment of the device, wherein the tissue is connective tissue.

8850. The method of item 8750 wherein the fibrosing agent is released into tissue in the vicinity of the device after deployment of the device, wherein the tissue is muscle tissue.

8851. The method of item 8750 wherein the fibrosing agent is released into tissue in the vicinity of the device after deployment of the device, wherein the tissue is nerve tissue.

8852. The method of item 8750 wherein the fibrosing agent is released into tissue in the vicinity of the device after deployment of the device, wherein the tissue is epithelium tissue.

8853. The method of item 8750 wherein the fibrosing agent is released in effective concentrations from the device over a period ranging from the time of deployment of the device to about 1 year.

8854. The method of item 8750 wherein the fibrosing agent is released in effective concentrations from the device over a period ranging from about 1 month to 6 months.

8855. The method of item 8750 wherein the fibrosing agent is released in effective concentrations from the device over a period ranging from about 1–90 days.

8856. The method of item 8750 wherein the fibrosing agent is released in effective concentrations from the device at a constant rate.

8857. The method of item 8750 wherein the fibrosing agent is released in effective concentrations from the device at an increasing rate.

8858. The method of item 8750 wherein the fibrosing agent is released in effective concentrations from the device at a decreasing rate.

8859. The method of item 8750 wherein the fibrosing agent is released in effective concentrations from the composition comprising the fibrosing agent by diffusion over a period ranging from the time of deployment of the device to about 90 days.

8860. The method of item 8750 wherein the fibrosing agent is released in effective concentrations from the composition comprising the fibrosing agent by erosion of the composition over a period ranging from the time of deployment of the device to about 90 days.

8861. The method of item 8750 wherein the device comprises about 0.01 µg to about 10 µg of the fibrosing agent.

8862. The method of item 8750 wherein the device comprises about 10 µg to about 10 mg of the fibrosing agent.

8863. The method of item 8750 wherein the device comprises about 10 mg to about 250 mg of the fibrosing agent.

8864. The method of item 8750 wherein the device comprises about 250 mg to about 1000 mg of the fibrosing agent.

8865. The method of item 8750 wherein the device comprises about 1000 mg to about 2500 mg of the fibrosing agent.

8866. The method of item 8750 wherein a surface of the device comprises less than 0.01 µg of the fibrosing agent per $mm^2$ of device surface to which the fibrosing agent is applied.

8867. The method of item 8750 wherein a surface of the device comprises about 0.01 µg to about 1 µg of the fibrosing agent per $mm^2$ of device surface to which the fibrosing agent is applied.

8868. The method of item 8750 wherein a surface of the device comprises about 1 µg to about 10 µg of the fibrosing agent per $mm^2$ of device surface to which the fibrosing agent is applied.

8869. The method of item 8750 wherein a surface of the device comprises about 10 µg to about 250 µg of the fibrosing agent per $mm^2$ of device surface to which the fibrosing agent is applied.

8870. The method of item 8750 wherein a surface of the device comprises about 250 µg to about 1000 µg of the fibrosing agent of fibrosing agent per $mm^2$ of device surface to which the fibrosing agent is applied.

8871. The method of item 8750 wherein a surface of the device comprises about 1000 µg to about 2500 µg of the fibrosing agent per $mm^2$ of device surface to which the fibrosing agent is applied.

8872. A method of making a medical device comprising combining i) an electrostimulation implant for partitioning a stomach, with ii) a fibrosing agent or a composition comprising a fibrosing agent, where the fibrosing agent induces a fibrotic response between the device and a patient in which the device is implanted.

8873. The method of item 8872 wherein the fibrosing agent promotes regeneration.

8874. The method of item 8872 wherein the fibrosing agent promotes angiogenesis.

8875. The method of item 8872 wherein the fibrosing agent promotes fibroblast migration.

8876. The method of item 8872 wherein the fibrosing agent promotes fibroblast proliferation.

8877. The method of item 8872 wherein the fibrosing agent promotes deposition of extracellular matrix (ECM).

8878. The method of item 8872 wherein the fibrosing agent promotes tissue remodeling.

8879. The method of item 8872 wherein the fibrosing agent is an arterial vessel wall irritant.

8880. The method of item 8872 wherein the fibrosing agent promotes adhesion between the device and a host into which the device is implanted.

8881. The method of item 8872 wherein the device delivers the fibrosing agent locally to tissue proximate to the device.

8882. The method of item 8872 wherein the fibrosing agent is or comprises silk.

8883. The method of item 8872 wherein the fibrosing agent is or comprises mineral particles.

8884. The method of item 8872 wherein the fibrosing agent is or comprises chitosan.

8885. The method of item 8872 wherein the fibrosing agent is or comprises polylysine.

8886. The method of item 8872 wherein the fibrosing agent is or comprises fibronectin.

8887. The method of item 8872 wherein the fibrosing agent is or comprises bleomycin.

8888. The method of item 8872 wherein the fibrosing agent is or comprises CTGF.

8889. The method of item 8872 wherein the fibrosing agent is in the form of a thread, or is in contact with a thread.

8890. The method of item 8872 wherein the fibrosing agent is in the form of a particulate.

8891. The method of item 8872 wherein the composition further comprises an inflammatory cytokine.

8892. The method of item 8872 wherein the composition further comprises an agent that stimulates cell proliferation.

8893. The method of item 8872 wherein the composition is in the form of a gel or paste.

8894. The method of item 8872 wherein the fibrosing agent is in the form of tufts.

8895. The method of item 8872 wherein the fibrosing agent promotes adhesion between the device and a host into which the device is implanted.

8896. The method of item 8872 wherein the device delivers the fibrosing agent locally to tissue proximate to the device.

8897. The method of item 8872, wherein the implant is combined with a coating, and the coating comprises the fibrosing agent.

8898. The method of item 8872, wherein the implant is combined with a coating, and the coating is disposed on a surface of the device.

8899. The method of item 8872, wherein the implant is combined with a coating, and the coating directly contacts the device.

8900. The method of item 8872, wherein the implant is combined with a coating, and the coating indirectly contacts the device.

8901. The method of item 8872, wherein the implant is combined with a coating, and the coating partially covers the device.

8902. The method of item 8872, wherein the implant is combined with a coating, and the coating completely covers the device.

8903. The method of item 8872, wherein the implant is combined with a coating, and the coating is a uniform coating.

8904. The method of item 8872, wherein the implant is combined with a coating, and the coating is a non-uniform coating.

8905. The method of item 8872, wherein the implant is combined with a coating, and the coating is a discontinuous coating.

8906. The method of item 8872 wherein the implant is combined with a coating, and the coating is a patterned coating.

8907. The method of item 8872, wherein the implant is combined with a coating, and the coating has a thickness of 100 μm or less.

8908. The method of item 8872, wherein the implant is combined with a coating, and the coating has a thickness of 10 μm or less.

8909. The method of item 8872, wherein the implant is combined with a coating, and the coating adheres to the surface of the device upon deployment of the device.

8910. The method of item 8872, wherein the implant is combined with a coating, and the coating is stable at room temperature for a period of at least 1 year.

8911. The method of item 8872, wherein the implant is combined with a coating, and the fibrosing agent is present in the coating in an amount ranging between about 0.0001% to about 1% by weight.

8912. The method of item 8872, wherein the implant is combined with a coating, and the fibrosing agent is present in the coating in an amount ranging between about 1% to about 10% by weight.

8913. The method of item 8872, wherein the implant is combined with a coating, and the fibrosing agent is present in the coating in an amount ranging between about 10% to about 25% by weight.

8914. The method of item 8872, wherein the implant is combined with a coating, and the fibrosing agent is present in the coating in an amount ranging between about 25% to about 70% by weight.

8915. The method of item 8872, wherein the implant is combined with a coating, and the coating further comprises a polymer.

8916. The method of item 8872, wherein the device comprises a first coating having a first composition and a second coating having a second composition.

8917. The method of item 8872, wherein the device comprises a first coating having a first composition and a second coating having a second composition, where the first composition and the second composition are different.

8918. The method of item 8872, wherein the device comprises a polymer.

8919. The method of item 8872, wherein the device comprises a polymer, and the polymer is a component of the composition.

8920. The method of item 8872, wherein the implant is combined with a polymer, and the polymer is a copolymer.

8921. The method of item 8872, wherein the implant is combined with a polymer, and the polymer is a block copolymer.

8922. The method of item 8872, wherein the implant is combined with a polymer, and the polymer is a random copolymer.

8923. The method of item 8872, wherein the implant is combined with a polymer, and the polymer is a biodegradable polymer.

8924. The method of item 8872, wherein the implant is combined with a polymer, and the polymer is a non-biodegradable polymer.

8925. The method of item 8872, wherein the implant is combined with a polymer, and the polymer is a hydrophilic polymer.

8926. The method of item 8872, wherein the implant is combined with a polymer, and the polymer is a hydrophobic polymer.

8927. The method of item 8872, wherein the implant is combined with a polymer, and the polymer has hydrophilic domains.

8928. The method of item 8872, wherein the implant is combined with a polymer, and the polymer has hydrophobic domains.

8929. The method of item 8872, wherein the implant is combined with a polymer, and the polymer is a non-conductive polymer.

8930. The method of item 8872, wherein the implant is combined with a polymer, and the polymer is an elastomer.

8931. The method of item 8872, wherein the implant is combined with a polymer, and the polymer is a hydrogel.

8932. The method of item 8872, wherein the implant is combined with a polymer, and the polymer is a silicone polymer.

8933. The method of item 8872, wherein the implant is combined with a polymer, and the polymer is a hydrocarbon polymer.

8934. The method of item 8872, wherein the implant is combined with a polymer, and the polymer is a styrene-derived polymer.

8935. The method of item 8872, wherein the implant is combined with a polymer, and the polymer is a butadiene polymer.

8936. The method of item 8872, wherein the implant is combined with a polymer, and the polymer is a macromer.

8937. The method of item 8872, wherein the implant is combined with a polymer, and the polymer is a poly(ethylene glycol) polymer.

8938. The method of item 8872, wherein the implant is combined with a polymer, and the polymer is an amorphous polymer.

8939. The method of item 8872, wherein the implant is combined with a polymer, and the polymer is a lubricious coating.

8940. The method of item 8872 wherein the fibrosing agent is located within pores or holes of the device.

8941. The method of item 8872 wherein the fibrosing agent is located within a channel, lumen, or divet of the device.

8942. The method of item 8872, wherein the implant is further combined with a second pharmaceutically active agent.

8943. The method of item 8872, wherein the implant is further combined with an anti-inflammatory agent.

8944. The method of item 8872 wherein the implant is further combined with an agent that inhibits infection.

8945. The method of item 8872, wherein the implant is further combined with an anthracycline.

8946. The method of item 8872, wherein the implant is further combined with doxorubicin.

8947. The method of item 8872, wherein the implant is further combined with mitoxantrone.

8948. The method of item 8872, wherein the implant is further combined with a fluoropyrimidine.

8949. The method of item 8872, wherein the implant is further combined with 5-fluorouracil (5-FU).

8950. The method of item 8872, wherein the implant is further combined with a folic acid antagonist.

8951. The method of item 8872, wherein the implant is further combined with methotrexate.

8952. The method of item 8872, wherein the implant is further combined with a podophylotoxin.

8953. The method of item 8872, wherein the implant is further combined with etoposide.

8954. The method of item 8872 wherein the implant is further combined with a camptothecin.

8955. The method of item 8872, wherein the implant is further combined with a hydroxyurea.

8956. The method of item 8872, wherein the implant is further combined with a platinum complex.

8957. The method of item 8872, wherein the implant is further combined with cisplatin.

8958. The method of item 8872, wherein the implant is further combined with an anti-thrombotic agent.

8959. The method of item 8872, wherein the implant is further combined with a visualization agent.

8960. The method of item 8872, wherein the implant is further combined with a visualization agent, wherein the visualization agent is a radiopaque material, wherein the radiopaque material comprises a metal, a halogenated compound, or a barium containing compound.

8961. The method of item 8872, wherein the implant is further combined with a visualization agent, wherein the visualization agent is a radiopaque material, wherein the radiopaque material comprises barium, tantalum, or technetium.

8962. The method of item 8872, wherein the implant is further combined with a visualization agent, wherein the visualization agent is a MRI responsive material.

8963. The method of item 8872, wherein the implant is further combined with a visualization agent, wherein the visualization agent comprises a gadolinium chelate.

8964. The method of item 8872, wherein the implant is further combined with a visualization agent, wherein the visualization agent comprises iron, magnesium, manganese, copper, or chromium.

8965. The method of item 8872, wherein the implant is further combined with a visualization agent, wherein the visualization agent comprises an iron oxide compound.

8966. The method of item 8872, wherein the implant is further combined with a visualization agent, wherein the visualization agent comprises a dye, pigment, or colorant.

8967. The method of item 8872, wherein the implant is further combined with an echogenic material.

8968. The method of item 8872, wherein the implant is further combined with an echogenic material, and the echogenic material is in the form of a coating.

8969. The method of item 8872 wherein the device is sterilized.

8970. The method of item 8872 wherein the fibrosing agent is released into tissue in the vicinity of the device after deployment of the device.

8971. The method of item 8872 wherein the fibrosing agent is released into tissue in the vicinity of the device after deployment of the device, wherein the tissue is connective tissue.

8972. The method of item 8872 wherein the fibrosing agent is released into tissue in the vicinity of the device after deployment of the device, wherein the tissue is muscle tissue.

8973. The method of item 8872 wherein the fibrosing agent is released into tissue in the vicinity of the device after deployment of the device, wherein the tissue is nerve tissue.

8974. The method of item 8872 wherein the fibrosing agent is released into tissue in the vicinity of the device after deployment of the device, wherein the tissue is epithelium tissue.

8975. The method of item 8872 wherein the fibrosing agent is released in effective concentrations from the device over a period ranging from the time of deployment of the device to about 1 year.

8976. The method of item 8872 wherein the fibrosing agent is released in effective concentrations from the device over a period ranging from about 1 month to 6 months.

8977. The method of item 8872 wherein the fibrosing agent is released in effective concentrations from the device over a period ranging from about 1–90 days.

8978. The method of item 8872 wherein the fibrosing agent is released in effective concentrations from the device at a constant rate.

8979. The method of item 8872 wherein the fibrosing agent is released in effective concentrations from the device at an increasing rate.

8980. The method of item 8872 wherein the fibrosing agent is released in effective concentrations from the device at a decreasing rate.

8981. The method of item 8872 wherein the fibrosing agent is released in effective concentrations from the composition comprising the fibrosing agent by diffusion over a period ranging from the time of deployment of the device to about 90 days.

8982. The method of item 8872 wherein the fibrosing agent is released in effective concentrations from the composition comprising the fibrosing agent by erosion of the composition over a period ranging from the time of deployment of the device to about 90 days.

8983. The method of item 8872 wherein the device comprises about 0.01 µg to about 10 µg of the fibrosing agent.

8984. The method of item 8872 wherein the device comprises about 10 µg to about 10 mg of the fibrosing agent.

8985. The method of item 8872 wherein the device comprises about 10 mg to about 250 mg of the fibrosing agent.

8986. The method of item 8872 wherein the device comprises about 250 mg to about 1000 mg of the fibrosing agent.

8987. The method of item 8872 wherein the device comprises about 1000 mg to about 2500 mg of the fibrosing agent.

8988. The method of item 8872 wherein a surface of the device comprises less than 0.01 µg of the fibrosing agent per $mm^2$ of device surface to which the fibrosing agent is applied.

8989. The method of item 8872 wherein a surface of the device comprises about 0.01 µg to about 1 µg of the fibrosing agent per $mm^2$ of device surface to which the fibrosing agent is applied.

8990. The method of item 8872 wherein a surface of the device comprises about 1 µg to about 10 µg of the fibrosing agent per $mm^2$ of device surface to which the fibrosing agent is applied.

8991. The method of item 8872 wherein a surface of the device comprises about 10 µg to about 250 µg of the fibrosing agent per $mm^2$ of device surface to which the fibrosing agent is applied.

8992. The method of item 8872 wherein a surface of the device comprises about 250 µg to about 1000 µg of the fibrosing agent of fibrosing agent per $mm^2$ of device surface to which the fibrosing agent is applied.

8993. The method of item 8872 wherein a surface of the device comprises about 1000 µg to about 2500 µg of the fibrosing agent per $mm^2$ of device surface to which the fibrosing agent is applied.

8994. The method of item 8872 wherein the implant is a neural electrostimulation implant.

8995. The method of item 8872 wherein the implant is a non-neural electrostimulation implant.

8996. A method of making a medical device comprising combining i) a soft palate implant, with ii) a fibrosing agent or a composition comprising a fibrosing agent, where the fibrosing agent induces a fibrotic response between the device and a patient in which the device is implanted.

8997. The method of item 8996 wherein the fibrosing agent promotes regeneration.

8998. The method of item 8996 wherein the fibrosing agent promotes angiogenesis.

8999. The method of item 8996 wherein the fibrosing agent promotes fibroblast migration.

9000. The method of item 8996 wherein the fibrosing agent promotes fibroblast proliferation.

9001. The method of item 8996 wherein the fibrosing agent promotes deposition of extracellular matrix (ECM).

9002. The method of item 8996 wherein the fibrosing agent promotes tissue remodeling.

9003. The method of item 8996 wherein the fibrosing agent is an arterial vessel wall irritant.

9004. The method of item 8996 wherein the fibrosing agent promotes adhesion between the device and a host into which the device is implanted.

9005. The method of item 8996 wherein the device delivers the fibrosing agent locally to tissue proximate to the device.

9006. The method of item 8996 wherein the fibrosing agent is or comprises silk.

9007. The method of item 8996 wherein the fibrosing agent is or comprises mineral particles.

9008. The method of item 8996 wherein the fibrosing agent is or comprises chitosan.

9009. The method of item 8996 wherein the fibrosing agent is or comprises polylysine.

9010. The method of item 8996 wherein the fibrosing agent is or comprises fibronectin.

9011. The method of item 8996 wherein the fibrosing agent is or comprises bleomycin.

9012. The method of item 8996 wherein the fibrosing agent is or comprises CTGF.

9013. The method of item 8996 wherein the fibrosing agent is in the form of a thread, or is in contact with a thread.

9014. The method of item 8996 wherein the fibrosing agent is in the form of a particulate.

9015. The method of item 8996 wherein the composition further comprises an inflammatory cytokine.

9016. The method of item 8996 wherein the composition further comprises an agent that stimulates cell proliferation.

9017. The method of item 8996 wherein the composition is in the form of a gel or paste.

9018. The method of item 8996 wherein the fibrosing agent is in the form of tufts.

9019. The method of item 8996 wherein the fibrosing agent promotes adhesion between the device and a host into which the device is implanted.

9020. The method of item 8996 wherein the device delivers the fibrosing agent locally to tissue proximate to the device.

9021. The method of item 8996, wherein the implant is combined with a coating, and the coating comprises the fibrosing agent.

9022. The method of item 8996, wherein the implant is combined with a coating, and the coating is disposed on a surface of the device.

9023. The method of item 8996, wherein the implant is combined with a coating, and the coating directly contacts the device.

9024. The method of item 8996, wherein the implant is combined with a coating, and the coating indirectly contacts the device.

9025. The method of item 8996, wherein the implant is combined with a coating, and the coating partially covers the device.

9026. The method of item 8996, wherein the implant is combined with a coating, and the coating completely covers the device.

9027. The method of item 8996, wherein the implant is combined with a coating, and the coating is a uniform coating.

9028. The method of item 8996, wherein the implant is combined with a coating, and the coating is a non-uniform coating.

9029. The method of item 8996, wherein the implant is combined with a coating, and the coating is a discontinuous coating.

9030. The method of item 8996 wherein the implant is combined with a coating, and the coating is a patterned coating.

9031. The method of item 8996, wherein the implant is combined with a coating, and the coating has a thickness of 100 µm or less.

9032. The method of item 8996, wherein the implant is combined with a coating, and the coating has a thickness of 10 µm or less.

9033. The method of item 8996, wherein the implant is combined with a coating, and the coating adheres to the surface of the device upon deployment of the device.

9034. The method of item 8996, wherein the implant is combined with a coating, and the coating is stable at room temperature for a period of at least 1 year.

9035. The method of item 8996, wherein the implant is combined with a coating, and the fibrosing agent is present in the coating in an amount ranging between about 0.0001% to about 1% by weight.

9036. The method of item 8996, wherein the implant is combined with a coating, and the fibrosing agent is present in the coating in an amount ranging between about 1% to about 10% by weight.

9037. The method of item 8996, wherein the implant is combined with a coating, and the fibrosing agent is present in the coating in an amount ranging between about 10% to about 25% by weight.

9038. The method of item 8996, wherein the implant is combined with a coating, and the fibrosing agent is present in the coating in an amount ranging between about 25% to about 70% by weight.

9039. The method of item 8996, wherein the implant is combined with a coating, and the coating further comprises a polymer.

9040. The method of item 8996, wherein the device comprises a first coating having a first composition and a second coating having a second composition.

9041. The method of item 8996, wherein the device comprises a first coating having a first composition and a second coating having a second composition, where the first composition and the second composition are different.

9042. The method of item 8996, wherein the device comprises a polymer.

9043. The method of item 8996, wherein the device comprises a polymer, and the polymer is a component of the composition.

9044. The method of item 8996, wherein the implant is combined with a polymer, and the polymer is a copolymer.

9045. The method of item 8996, wherein the implant is combined with a polymer, and the polymer is a block copolymer.

9046. The method of item 8996, wherein the implant is combined with a polymer, and the polymer is a random copolymer.

9047. The method of item 8996, wherein the implant is combined with a polymer, and the polymer is a biodegradable polymer.

9048. The method of item 8996, wherein the implant is combined with a polymer, and the polymer is a non-biodegradable polymer.

9049. The method of item 8996, wherein the implant is combined with a polymer, and the polymer is a hydrophilic polymer.

9050. The method of item 8996, wherein the implant is combined with a polymer, and the polymer is a hydrophobic polymer.

9051. The method of item 8996, wherein the implant is combined with a polymer, and the polymer has hydrophilic domains.

9052. The method of item 8996, wherein the implant is combined with a polymer, and the polymer has hydrophobic domains.

9053. The method of item 8996, wherein the implant is combined with a polymer, and the polymer is a non-conductive polymer.

9054. The method of item 8996, wherein the implant is combined with a polymer, and the polymer is an elastomer.

9055. The method of item 8996, wherein the implant is combined with a polymer, and the polymer is a hydrogel.

9056. The method of item 8996, wherein the implant is combined with a polymer, and the polymer is a silicone polymer.

9057. The method of item 8996, wherein the implant is combined with a polymer, and the polymer is a hydrocarbon polymer.

9058. The method of item 8996, wherein the implant is combined with a polymer, and the polymer is a styrene-derived polymer.

9059. The method of item 8996, wherein the implant is combined with a polymer, and the polymer is a butadiene polymer.

9060. The method of item 8996, wherein the implant is combined with a polymer, and the polymer is a macromer.

9061. The method of item 8996, wherein the implant is combined with a polymer, and the polymer is a poly(ethylene glycol) polymer.

9062. The method of item 8996, wherein the implant is combined with a polymer, and the polymer is an amorphous polymer.

9063. The method of item 8996, wherein the implant is combined with a polymer, and the polymer is a lubricious coating.

9064. The method of item 8996 wherein the fibrosing agent is located within pores or holes of the device.

9065. The method of item 8996 wherein the fibrosing agent is located within a channel, lumen, or divet of the device.

9066. The method of item 8996, wherein the implant is further combined with a second pharmaceutically active agent.

9067. The method of item 8996, wherein the implant is further combined with an anti-inflammatory agent.

9068. The method of item 8996 wherein the implant is further combined with an agent that inhibits infection.

9069. The method of item 8996, wherein the implant is further combined with an anthracycline.

9070. The method of item 8996, wherein the implant is further combined with doxorubicin.

9071. The method of item 8996, wherein the implant is further combined with mitoxantrone.

9072. The method of item 8996, wherein the implant is further combined with a fluoropyrimidine.

9073. The method of item 8996, wherein the implant is further combined with 5-fluorouracil (5-FU).

9074. The method of item 8996, wherein the implant is further combined with a folic acid antagonist.

9075. The method of item 8996, wherein the implant is further combined with methotrexate.

9076. The method of item 8996, wherein the implant is further combined with a podophylotoxin.

9077. The method of item 8996, wherein the implant is further combined with etoposide.

9078. The method of item 8996 wherein the implant is further combined with a camptothecin.

9079. The method of item 8996, wherein the implant is further combined with a hydroxyurea.

9080. The method of item 8996, wherein the implant is further combined with a platinum complex.

9081. The method of item 8996, wherein the implant is further combined with cisplatin.

9082. The method of item 8996, wherein the implant is further combined with an anti-thrombotic agent.

9083. The method of item 8996, wherein the implant is further combined with a visualization agent.

9084. The method of item 8996, wherein the implant is further combined with a visualization agent, wherein the visualization agent is a radiopaque material, wherein the radiopaque material comprises a metal, a halogenated compound, or a barium containing compound.

9085. The method of item 8996, wherein the implant is further combined with a visualization agent, wherein the visualization agent is a radiopaque material, wherein the radiopaque material comprises barium, tantalum, or technetium.

9086. The method of item 8996, wherein the implant is further combined with a visualization agent, wherein the visualization agent is a MRI responsive material.

9087. The method of item 8996, wherein the implant is further combined with a visualization agent, wherein the visualization agent comprises a gadolinium chelate.

9088. The method of item 8996, wherein the implant is further combined with a visualization agent, wherein the visualization agent comprises iron, magnesium, manganese, copper, or chromium.

9089. The method of item 8996, wherein the implant is further combined with a visualization agent, wherein the visualization agent comprises an iron oxide compound.

9090. The method of item 8996, wherein the implant is further combined with a visualization agent, wherein the visualization agent comprises a dye, pigment, or colorant.

9091. The method of item 8996, wherein the implant is further combined with an echogenic material.

9092. The method of item 8996, wherein the implant is further combined with an echogenic material, and the echogenic material is in the form of a coating.

9093. The method of item 8996 wherein the device is sterilized.

9094. The method of item 8996 wherein the fibrosing agent is released into tissue in the vicinity of the device after deployment of the device.

9095. The method of item 8996 wherein the fibrosing agent is released into tissue in the vicinity of the device after deployment of the device, wherein the tissue is connective tissue.

9096. The method of item 8996 wherein the fibrosing agent is released into tissue in the vicinity of the device after deployment of the device, wherein the tissue is muscle tissue.

9097. The method of item 8996 wherein the fibrosing agent is released into tissue in the vicinity of the device after deployment of the device, wherein the tissue is nerve tissue.

9098. The method of item 8996 wherein the fibrosing agent is released into tissue in the vicinity of the device after deployment of the device, wherein the tissue is epithelium tissue.

9099. The method of item 8996 wherein the fibrosing agent is released in effective concentrations from the device over a period ranging from the time of deployment of the device to about 1 year.

9100. The method of item 8996 wherein the fibrosing agent is released in effective concentrations from the device over a period ranging from about 1 month to 6 months.

9101. The method of item 8996 wherein the fibrosing agent is released in effective concentrations from the device over a period ranging from about 1–90 days.

9102. The method of item 8996 wherein the fibrosing agent is released in effective concentrations from the device at a constant rate.

9103. The method of item 8996 wherein the fibrosing agent is released in effective concentrations from the device at an increasing rate.

9104. The method of item 8996 wherein the fibrosing agent is released in effective concentrations from the device at a decreasing rate.

9105. The method of item 8996 wherein the fibrosing agent is released in effective concentrations from the composition comprising the fibrosing agent by diffusion over a period ranging from the time of deployment of the device to about 90 days.

9106. The method of item 8996 wherein the fibrosing agent is released in effective concentrations from the composition comprising the fibrosing agent by erosion of the composition over a period ranging from the time of deployment of the device to about 90 days.

9107. The method of item 8996 wherein the device comprises about 0.01 μg to about 10 μg of the fibrosing agent.

9108. The method of item 8996 wherein the device comprises about 10 μg to about 10 mg of the fibrosing agent.

9109. The method of item 8996 wherein the device comprises about 10 mg to about 250 mg of the fibrosing agent.

9110. The method of item 8996 wherein the device comprises about 250 mg to about 1000 mg of the fibrosing agent.

9111. The method of item 8996 wherein the device comprises about 1000 mg to about 2500 mg of the fibrosing agent.

9112. The method of item 8996 wherein a surface of the device comprises less than 0.01 μg of the fibrosing agent per $mm^2$ of device surface to which the fibrosing agent is applied.

9113. The method of item 8996 wherein a surface of the device comprises about 0.01 μg to about 1 μg of the fibrosing agent per mm$^2$ of device surface to which the fibrosing agent is applied.

9114. The method of item 8996 wherein a surface of the device comprises about 1 μg to about 10 μg of the fibrosing agent per mm$^2$ of device surface to which the fibrosing agent is applied.

9115. The method of item 8996 wherein a surface of the device comprises about 10 μg to about 250 μg of the fibrosing agent per mm$^2$ of device surface to which the fibrosing agent is applied.

9116. The method of item 8996 wherein a surface of the device comprises about 250 μg to about 1000 μg of the fibrosing agent of fibrosing agent per mm$^2$ of device surface to which the fibrosing agent is applied.

9117. The method of item 8996 wherein a surface of the device comprises about 1000 μg to about 2500 μg of the fibrosing agent per mm$^2$ of device surface to which the fibrosing agent is applied.

9118. A method of making a medical device comprising combining i) a vascular coil implant, with ii) a fibrosing agent or a composition comprising a fibrosing agent, where the fibrosing agent induces a fibrotic response between the device and a patient in which the device is implanted.

9119. The method of item 9118 wherein the fibrosing agent promotes regeneration.

9120. The method of item 9118 wherein the fibrosing agent promotes angiogenesis.

9121. The method of item 9118 wherein the fibrosing agent promotes fibroblast migration.

9122. The method of item 9118 wherein the fibrosing agent promotes fibroblast proliferation.

9123. The method of item 9118 wherein the fibrosing agent promotes deposition of extracellular matrix (ECM).

9124. The method of item 9118 wherein the fibrosing agent promotes tissue remodeling.

9125. The method of item 9118 wherein the fibrosing agent is an arterial vessel wall irritant.

9126. The method of item 9118 wherein the fibrosing agent promotes adhesion between the device and a host into which the device is implanted.

9127. The method of item 9118 wherein the device delivers the fibrosing agent locally to tissue proximate to the device.

9128. The method of item 9118 wherein the fibrosing agent is or comprises silk.

9129. The method of item 9118 wherein the fibrosing agent is or comprises mineral particles.

9130. The method of item 9118 wherein the fibrosing agent is or comprises chitosan.

9131. The method of item 9118 wherein the fibrosing agent is or comprises polylysine.

9132. The method of item 9118 wherein the fibrosing agent is or comprises fibronectin.

9133. The method of item 9118 wherein the fibrosing agent is or comprises bleomycin.

9134. The method of item 9118 wherein the fibrosing agent is or comprises CTGF.

9135. The method of item 9118 wherein the fibrosing agent is in the form of a thread, or is in contact with a thread.

9136. The method of item 9118 wherein the fibrosing agent is in the form of a particulate.

9137. The method of item 9118 wherein the composition further comprises an inflammatory cytokine.

9138. The method of item 9118 wherein the composition further comprises an agent that stimulates cell proliferation.

9139. The method of item 9118 wherein the composition is in the form of a gel or paste.

9140. The method of item 9118 wherein the fibrosing agent is in the form of tufts.

9141. The method of item 9118 wherein the fibrosing agent promotes adhesion between the device and a host into which the device is implanted.

9142. The method of item 9118 wherein the device delivers the fibrosing agent locally to tissue proximate to the device.

9143. The method of item 9118, wherein the implant is combined with a coating, and the coating comprises the fibrosing agent.

9144. The method of item 9118, wherein the implant is combined with a coating, and the coating is disposed on a surface of the device.

9145. The method of item 9118, wherein the implant is combined with a coating, and the coating directly contacts the device.

9146. The method of item 9118, wherein the implant is combined with a coating, and the coating indirectly contacts the device.

9147. The method of item 9118, wherein the implant is combined with a coating, and the coating partially covers the device.

9148. The method of item 9118, wherein the implant is combined with a coating, and the coating completely covers the device.

9149. The method of item 9118, wherein the implant is combined with a coating, and the coating is a uniform coating.

9150. The method of item 9118, wherein the implant is combined with a coating, and the coating is a non-uniform coating.

9151. The method of item 9118, wherein the implant is combined with a coating, and the coating is a discontinuous coating.

9152. The method of item 9118 wherein the implant is combined with a coating, and the coating is a patterned coating.

9153. The method of item 9118, wherein the implant is combined with a coating, and the coating has a thickness of 100 μm or less.

9154. The method of item 9118, wherein the implant is combined with a coating, and the coating has a thickness of 10 μm or less.

9155. The method of item 9118, wherein the implant is combined with a coating, and the coating adheres to the surface of the device upon deployment of the device.

9156. The method of item 9118, wherein the implant is combined with a coating, and the coating is stable at room temperature for a period of at least 1 year.

9157. The method of item 9118, wherein the implant is combined with a coating, and the fibrosing agent is present in the coating in an amount ranging between about 0.0001% to about 1% by weight.

9158. The method of item 9118, wherein the implant is combined with a coating, and the fibrosing agent is present in the coating in an amount ranging between about 1% to about 10% by weight.

9159. The method of item 9118, wherein the implant is combined with a coating, and the fibrosing agent is present in the coating in an amount ranging between about 10% to about 25% by weight.

9160. The method of item 9118, wherein the implant is combined with a coating, and the fibrosing agent is present in the coating in an amount ranging between about 25% to about 70% by weight.

9161. The method of item 9118, wherein the implant is combined with a coating, and the coating further comprises a polymer.

9162. The method of item 9118, wherein the device comprises a first coating having a first composition and a second coating having a second composition.

9163. The method of item 9118, wherein the device comprises a first coating having a first composition and a second coating having a second composition, where the first composition and the second composition are different.

9164. The method of item 9118, wherein the device comprises a polymer.

9165. The method of item 9118, wherein the device comprises a polymer, and the polymer is a component of the composition.

9166. The method of item 9118, wherein the implant is combined with a polymer, and the polymer is a copolymer.

9167. The method of item 9118, wherein the implant is combined with a polymer, and the polymer is a block copolymer.

9168. The method of item 9118, wherein the implant is combined with a polymer, and the polymer is a random copolymer.

9169. The method of item 9118, wherein the implant is combined with a polymer, and the polymer is a biodegradable polymer.

9170. The method of item 9118, wherein the implant is combined with a polymer, and the polymer is a non-biodegradable polymer.

9171. The method of item 9118, wherein the implant is combined with a polymer, and the polymer is a hydrophilic polymer.

9172. The method of item 9118, wherein the implant is combined with a polymer, and the polymer is a hydrophobic polymer.

9173. The method of item 9118, wherein the implant is combined with a polymer, and the polymer has hydrophilic domains.

9174. The method of item 9118, wherein the implant is combined with a polymer, and the polymer has hydrophobic domains.

9175. The method of item 9118, wherein the implant is combined with a polymer, and the polymer is a non-conductive polymer.

9176. The method of item 9118, wherein the implant is combined with a polymer, and the polymer is an elastomer.

9177. The method of item 9118, wherein the implant is combined with a polymer, and the polymer is a hydrogel.

9178. The method of item 9118, wherein the implant is combined with a polymer, and the polymer is a silicone polymer.

9179. The method of item 9118, wherein the implant is combined with a polymer, and the polymer is a hydrocarbon polymer.

9180. The method of item 9118, wherein the implant is combined with a polymer, and the polymer is a styrene-derived polymer.

9181. The method of item 9118, wherein the implant is combined with a polymer, and the polymer is a butadiene polymer.

9182. The method of item 9118, wherein the implant is combined with a polymer, and the polymer is a macromer.

9183. The method of item 9118, wherein the implant is combined with a polymer, and the polymer is a poly(ethylene glycol) polymer.

9184. The method of item 9118, wherein the implant is combined with a polymer, and the polymer is an amorphous polymer.

9185. The method of item 9118, wherein the implant is combined with a polymer, and the polymer is a lubricious coating.

9186. The method of item 9118 wherein the fibrosing agent is located within pores or holes of the device.

9187. The method of item 9118 wherein the fibrosing agent is located within a channel, lumen, or divet of the device.

9188. The method of item 9118, wherein the implant is further combined with a second pharmaceutically active agent.

9189. The method of item 9118, wherein the implant is further combined with an anti-inflammatory agent.

9190. The method of item 9118 wherein the implant is further combined with an agent that inhibits infection.

9191. The method of item 9118, wherein the implant is further combined with an anthracycline.

9192. The method of item 9118, wherein the implant is further combined with doxorubicin.

9193. The method of item 9118, wherein the implant is further combined with mitoxantrone.

9194. The method of item 9118, wherein the implant is further combined with a fluoropyrimidine.

9195. The method of item 9118, wherein the implant is further combined with 5-fluorouracil (5-FU).

9196. The method of item 9118, wherein the implant is further combined with a folic acid antagonist.

9197. The method of item 9118, wherein the implant is further combined with methotrexate.

9198. The method of item 9118, wherein the implant is further combined with a podophylotoxin.

9199. The method of item 9118, wherein the implant is further combined with etoposide.

9200. The method of item 9118 wherein the implant is further combined with a camptothecin.

9201. The method of item 9118, wherein the implant is further combined with a hydroxyurea.

9202. The method of item 9118, wherein the implant is further combined with a platinum complex.

9203. The method of item 9118, wherein the implant is further combined with cisplatin.

9204. The method of item 9118, wherein the implant is further combined with an anti-thrombotic agent.

9205. The method of item 9118, wherein the implant is further combined with a visualization agent.

9206. The method of item 9118, wherein the implant is further combined with a visualization agent, wherein the visualization agent is a radiopaque material, wherein the radiopaque material comprises a metal, a halogenated compound, or a barium containing compound.

9207. The method of item 9118, wherein the implant is further combined with a visualization agent, wherein the visualization agent is a radiopaque material, wherein the radiopaque material comprises barium, tantalum, or technetium.

9208. The method of item 9118, wherein the implant is further combined with a visualization agent, wherein the visualization agent is a MRI responsive material.

9209. The method of item 9118, wherein the implant is further combined with a visualization agent, wherein the visualization agent comprises a gadolinium chelate.

9210. The method of item 9118, wherein the implant is further combined with a visualization agent, wherein the visualization agent comprises iron, magnesium, manganese, copper, or chromium.

9211. The method of item 9118, wherein the implant is further combined with a visualization agent, wherein the visualization agent comprises an iron oxide compound.

9212. The method of item 9118, wherein the implant is further combined with a visualization agent, wherein the visualization agent comprises a dye, pigment, or colorant.

9213. The method of item 9118, wherein the implant is further combined with an echogenic material.

9214. The method of item 9118, wherein the implant is further combined with an echogenic material, and the echogenic material is in the form of a coating.

9215. The method of item 9118 wherein the device is sterilized.

9216. The method of item 9118 wherein the fibrosing agent is released into tissue in the vicinity of the device after deployment of the device.

9217. The method of item 9118 wherein the fibrosing agent is released into tissue in the vicinity of the device after deployment of the device, wherein the tissue is connective tissue.

9218. The method of item 9118 wherein the fibrosing agent is released into tissue in the vicinity of the device after deployment of the device, wherein the tissue is muscle tissue.

9219. The method of item 9118 wherein the fibrosing agent is released into tissue in the vicinity of the device after deployment of the device, wherein the tissue is nerve tissue.

9220. The method of item 9118 wherein the fibrosing agent is released into tissue in the vicinity of the device after deployment of the device, wherein the tissue is epithelium tissue.

9221. The method of item 9118 wherein the fibrosing agent is released in effective concentrations from the device over a period ranging from the time of deployment of the device to about 1 year.

9222. The method of item 9118 wherein the fibrosing agent is released in effective concentrations from the device over a period ranging from about 1 month to 6 months.

9223. The method of item 9118 wherein the fibrosing agent is released in effective concentrations from the device over a period ranging from about 1–90 days.

9224. The method of item 9118 wherein the fibrosing agent is released in effective concentrations from the device at a constant rate.

9225. The method of item 9118 wherein the fibrosing agent is released in effective concentrations from the device at an increasing rate.

9226. The method of item 9118 wherein the fibrosing agent is released in effective concentrations from the device at a decreasing rate.

9227. The method of item 9118 wherein the fibrosing agent is released in effective concentrations from the composition comprising the fibrosing agent by diffusion over a period ranging from the time of deployment of the device to about 90 days.

9228. The method of item 9118 wherein the fibrosing agent is released in effective concentrations from the composition comprising the fibrosing agent by erosion of the composition over a period ranging from the time of deployment of the device to about 90 days.

9229. The method of item 9118 wherein the device comprises about 0.01 µg to about 10 µg of the fibrosing agent.

9230. The method of item 9118 wherein the device comprises about 10 µg to about 10 mg of the fibrosing agent.

9231. The method of item 9118 wherein the device comprises about 10 mg to about 250 mg of the fibrosing agent.

9232. The method of item 9118 wherein the device comprises about 250 mg to about 1000 mg of the fibrosing agent.

9233. The method of item 9118 wherein the device comprises about 1000 mg to about 2500 mg of the fibrosing agent.

9234. The method of item 9118 wherein a surface of the device comprises less than 0.01 µg of the fibrosing agent per $mm^2$ of device surface to which the fibrosing agent is applied.

9235. The method of item 9118 wherein a surface of the device comprises about 0.01 µg to about 1 µg of the fibrosing agent per $mm^2$ of device surface to which the fibrosing agent is applied.

9236. The method of item 9118 wherein a surface of the device comprises about 1 µg to about 10 µg of the fibrosing agent per $mm^2$ of device surface to which the fibrosing agent is applied.

9237. The method of item 9118 wherein a surface of the device comprises about 10 µg to about 250 µg of the fibrosing agent per $mm^2$ of device surface to which the fibrosing agent is applied.

9238. The method of item 9118 wherein a surface of the device comprises about 250 µg to about 1000 µg of the fibrosing agent of fibrosing agent per $mm^2$ of device surface to which the fibrosing agent is applied.

9239. The method of item 9118 wherein a surface of the device comprises about 1000 µg to about 2500 µg of the fibrosing agent per $mm^2$ of device surface to which the fibrosing agent is applied.

9240. The method of item 9118 wherein the vascular coil implant comprises fluorinated polymer.

9241. The method of item 9118 wherein the vascular coil implant is porous.

9242. The method of item 9118 wherein the vascular coil implant comprises a bioactive material.

9243. The method of item 9118 wherein the vascular coil implant is biologically inert.

9244. The method of item 9118 wherein the vascular coil implant has a first state prior to insertion and a second state post insertion.

9245. A method of making a medical device comprising combining i) a vaso-occlusive coil implant, with ii) a fibrosing agent or a composition comprising a fibrosing agent, where the fibrosing agent induces a fibrotic response between the device and a patient in which the device is implanted.

9246. The method of item 9245 wherein the fibrosing agent promotes regeneration.

9247. The method of item 9245 wherein the fibrosing agent promotes angiogenesis.

9248. The method of item 9245 wherein the fibrosing agent promotes fibroblast migration.

9249. The method of item 9245 wherein the fibrosing agent promotes fibroblast proliferation.

9250. The method of item 9245 wherein the fibrosing agent promotes deposition of extracellular matrix (ECM).

9251. The method of item 9245 wherein the fibrosing agent promotes tissue remodeling.

9252. The method of item 9245 wherein the fibrosing agent is an arterial vessel wall irritant.

9253. The method of item 9245 wherein the fibrosing agent promotes adhesion between the device and a host into which the device is implanted.

9254. The method of item 9245 wherein the device delivers the fibrosing agent locally to tissue proximate to the device.

9255. The method of item 9245 wherein the fibrosing agent is or comprises silk.

9256. The method of item 9245 wherein the fibrosing agent is or comprises mineral particles.

9257. The method of item 9245 wherein the fibrosing agent is or comprises chitosan.

9258. The method of item 9245 wherein the fibrosing agent is or comprises polylysine.

9259. The method of item 9245 wherein the fibrosing agent is or comprises fibronectin.

9260. The method of item 9245 wherein the fibrosing agent is or comprises bleomycin.

9261. The method of item 9245 wherein the fibrosing agent is or comprises CTGF.

9262. The method of item 9245 wherein the fibrosing agent is in the form of a thread, or is in contact with a thread.

9263. The method of item 9245 wherein the fibrosing agent is in the form of a particulate.

9264. The method of item 9245 wherein the composition further comprises an inflammatory cytokine.

9265. The method of item 9245 wherein the composition further comprises an agent that stimulates cell proliferation.

9266. The method of item 9245 wherein the composition is in the form of a gel or paste.

9267. The method of item 9245 wherein the fibrosing agent is in the form of tufts.

9268. The method of item 9245 wherein the fibrosing agent promotes adhesion between the device and a host into which the device is implanted.

9269. The method of item 9245 wherein the device delivers the fibrosing agent locally to tissue proximate to the device.

9270. The method of item 9245, wherein the implant is combined with a coating, and the coating comprises the fibrosing agent.

9271. The method of item 9245, wherein the implant is combined with a coating, and the coating is disposed on a surface of the device.

9272. The method of item 9245, wherein the implant is combined with a coating, and the coating directly contacts the device.

9273. The method of item 9245, wherein the implant is combined with a coating, and the coating indirectly contacts the device.

9274. The method of item 9245, wherein the implant is combined with a coating, and the coating partially covers the device.

9275. The method of item 9245, wherein the implant is combined with a coating, and the coating completely covers the device.

9276. The method of item 9245, wherein the implant is combined with a coating, and the coating is a uniform coating.

9277. The method of item 9245, wherein the implant is combined with a coating, and the coating is a non-uniform coating.

9278. The method of item 9245, wherein the implant is combined with a coating, and the coating is a discontinuous coating.

9279. The method of item 9245 wherein the implant is combined with a coating, and the coating is a patterned coating.

9280. The method of item 9245, wherein the implant is combined with a coating, and the coating has a thickness of 100 µm or less.

9281. The method of item 9245, wherein the implant is combined with a coating, and the coating has a thickness of 10 µm or less.

9282. The method of item 9245, wherein the implant is combined with a coating, and the coating adheres to the surface of the device upon deployment of the device.

9283. The method of item 9245, wherein the implant is combined with a coating, and the coating is stable at room temperature for a period of at least 1 year.

9284. The method of item 9245, wherein the implant is combined with a coating, and the fibrosing agent is present in the coating in an amount ranging between about 0.0001% to about 1% by weight.

9285. The method of item 9245, wherein the implant is combined with a coating, and the fibrosing agent is present in the coating in an amount ranging between about 1% to about 10% by weight.

9286. The method of item 9245, wherein the implant is combined with a coating, and the fibrosing agent is present in the coating in an amount ranging between about 10% to about 25% by weight.

9287. The method of item 9245, wherein the implant is combined with a coating, and the fibrosing agent is present in the coating in an amount ranging between about 25% to about 70% by weight.

9288. The method of item 9245, wherein the implant is combined with a coating, and the coating further comprises a polymer.

9289. The method of item 9245, wherein the device comprises a first coating having a first composition and a second coating having a second composition.

9290. The method of item 9245, wherein the device comprises a first coating having a first composition and a second coating having a second composition, where the first composition and the second composition are different.

9291. The method of item 9245, wherein the device comprises a polymer.

9292. The method of item 9245, wherein the device comprises a polymer, and the polymer is a component of the composition.

9293. The method of item 9245, wherein the implant is combined with a polymer, and the polymer is a copolymer.

9294. The method of item 9245, wherein the implant is combined with a polymer, and the polymer is a block copolymer.

9295. The method of item 9245, wherein the implant is combined with a polymer, and the polymer is a random copolymer.

9296. The method of item 9245, wherein the implant is combined with a polymer, and the polymer is a biodegradable polymer.

9297. The method of item 9245, wherein the implant is combined with a polymer, and the polymer is a non-biodegradable polymer.

9298. The method of item 9245, wherein the implant is combined with a polymer, and the polymer is a hydrophilic polymer.

9299. The method of item 9245, wherein the implant is combined with a polymer, and the polymer is a hydrophobic polymer.

9300. The method of item 9245, wherein the implant is combined with a polymer, and the polymer has hydrophilic domains.

9301. The method of item 9245, wherein the implant is combined with a polymer, and the polymer has hydrophobic domains.

9302. The method of item 9245, wherein the implant is combined with a polymer, and the polymer is a non-conductive polymer.

9303. The method of item 9245, wherein the implant is combined with a polymer, and the polymer is an elastomer.

9304. The method of item 9245, wherein the implant is combined with a polymer, and the polymer is a hydrogel.

9305. The method of item 9245, wherein the implant is combined with a polymer, and the polymer is a silicone polymer.

9306. The method of item 9245, wherein the implant is combined with a polymer, and the polymer is a hydrocarbon polymer.

9307. The method of item 9245, wherein the implant is combined with a polymer, and the polymer is a styrene-derived polymer.

9308. The method of item 9245, wherein the implant is combined with a polymer, and the polymer is a butadiene polymer.

9309. The method of item 9245, wherein the implant is combined with a polymer, and the polymer is a macromer.

9310. The method of item 9245, wherein the implant is combined with a polymer, and the polymer is a poly(ethylene glycol) polymer.

9311. The method of item 9245, wherein the implant is combined with a polymer, and the polymer is an amorphous polymer.

9312. The method of item 9245, wherein the implant is combined with a polymer, and the polymer is a lubricious coating.

9313. The method of item 9245 wherein the fibrosing agent is located within pores or holes of the device.

9314. The method of item 9245 wherein the fibrosing agent is located within a channel, lumen, or divet of the device.

9315. The method of item 9245, wherein the implant is further combined with a second pharmaceutically active agent.

9316. The method of item 9245, wherein the implant is further combined with an anti-inflammatory agent.

9317. The method of item 9245 wherein the implant is further combined with an agent that inhibits infection.

9318. The method of item 9245, wherein the implant is further combined with an anthracycline.

9319. The method of item 9245, wherein the implant is further combined with doxorubicin.

9320. The method of item 9245, wherein the implant is further combined with mitoxantrone.

9321. The method of item 9245, wherein the implant is further combined with a fluoropyrimidine.

9322. The method of item 9245, wherein the implant is further combined with 5-fluorouracil (5-FU).

9323. The method of item 9245, wherein the implant is further combined with a folic acid antagonist.

9324. The method of item 9245, wherein the implant is further combined with methotrexate.

9325. The method of item 9245, wherein the implant is further combined with a podophylotoxin.

9326. The method of item 9245, wherein the implant is further combined with etoposide.

9327. The method of item 9245 wherein the implant is further combined with a camptothecin.

9328. The method of item 9245, wherein the implant is further combined with a hydroxyurea.

9329. The method of item 9245, wherein the implant is further combined with a platinum complex.

9330. The method of item 9245, wherein the implant is further combined with cisplatin.

9331. The method of item 9245, wherein the implant is further combined with an anti-thrombotic agent.

9332. The method of item 9245, wherein the implant is further combined with a visualization agent.

9333. The method of item 9245, wherein the implant is further combined with a visualization agent, wherein the visualization agent is a radiopaque material, wherein the radiopaque material comprises a metal, a halogenated compound, or a barium containing compound.

9334. The method of item 9245, wherein the implant is further combined with a visualization agent, wherein the visualization agent is a radiopaque material, wherein the radiopaque material comprises barium, tantalum, or technetium.

9335. The method of item 9245, wherein the implant is further combined with a visualization agent, wherein the visualization agent is a MRI responsive material.

9336. The method of item 9245, wherein the implant is further combined with a visualization agent, wherein the visualization agent comprises a gadolinium chelate.

9337. The method of item 9245, wherein the implant is further combined with a visualization agent, wherein the visualization agent comprises iron, magnesium, manganese, copper, or chromium.

9338. The method of item 9245, wherein the implant is further combined with a visualization agent, wherein the visualization agent comprises an iron oxide compound.

9339. The method of item 9245, wherein the implant is further combined with a visualization agent, wherein the visualization agent comprises a dye, pigment, or colorant.

9340. The method of item 9245, wherein the implant is further combined with an echogenic material.

9341. The method of item 9245, wherein the implant is further combined with an echogenic material, and the echogenic material is in the form of a coating.

9342. The method of item 9245 wherein the device is sterilized.

9343. The method of item 9245 wherein the fibrosing agent is released into tissue in the vicinity of the device after deployment of the device.

9344. The method of item 9245 wherein the fibrosing agent is released into tissue in the vicinity of the device after deployment of the device, wherein the tissue is connective tissue.

9345. The method of item 9245 wherein the fibrosing agent is released into tissue in the vicinity of the device after deployment of the device, wherein the tissue is muscle tissue.

9346. The method of item 9245 wherein the fibrosing agent is released into tissue in the vicinity of the device after deployment of the device, wherein the tissue is nerve tissue.

9347. The method of item 9245 wherein the fibrosing agent is released into tissue in the vicinity of the device after deployment of the device, wherein the tissue is epithelium tissue.

9348. The method of item 9245 wherein the fibrosing agent is released in effective concentrations from the device over a period ranging from the time of deployment of the device to about 1 year.

9349. The method of item 9245 wherein the fibrosing agent is released in effective concentrations from the device over a period ranging from about 1 month to 6 months.

9350. The method of item 9245 wherein the fibrosing agent is released in effective concentrations from the device over a period ranging from about 1–90 days.

9351. The method of item 9245 wherein the fibrosing agent is released in effective concentrations from the device at a constant rate.

9352. The method of item 9245 wherein the fibrosing agent is released in effective concentrations from the device at an increasing rate.

9353. The method of item 9245 wherein the fibrosing agent is released in effective concentrations from the device at a decreasing rate.

9354. The method of item 9245 wherein the fibrosing agent is released in effective concentrations from the composition comprising the fibrosing agent by diffusion over a period ranging from the time of deployment of the device to about 90 days.

9355. The method of item 9245 wherein the fibrosing agent is released in effective concentrations from the composition comprising the fibrosing agent by erosion of the composition over a period ranging from the time of deployment of the device to about 90 days.

9356. The method of item 9245 wherein the device comprises about 0.01 µg to about 10 µg of the fibrosing agent.

9357. The method of item 9245 wherein the device comprises about 10 µg to about 10 mg of the fibrosing agent.

9358. The method of item 9245 wherein the device comprises about 10 mg to about 250 mg of the fibrosing agent.

9359. The method of item 9245 wherein the device comprises about 250 mg to about 1000 mg of the fibrosing agent.

9360. The method of item 9245 wherein the device comprises about 1000 mg to about 2500 mg of the fibrosing agent.

9361. The method of item 9245 wherein a surface of the device comprises less than 0.01 µg of the fibrosing agent per $mm^2$ of device surface to which the fibrosing agent is applied.

9362. The method of item 9245 wherein a surface of the device comprises about 0.01 µg to about 1 µg of the fibrosing agent per $mm^2$ of device surface to which the fibrosing agent is applied.

9363. The method of item 9245 wherein a surface of the device comprises about 1 µg to about 10 µg of the fibrosing agent per $mm^2$ of device surface to which the fibrosing agent is applied.

9364. The method of item 9245 wherein a surface of the device comprises about 10 µg to about 250 µg of the fibrosing agent per $mm^2$ of device surface to which the fibrosing agent is applied.

9365. The method of item 9245 wherein a surface of the device comprises about 250 µg to about 1000 µg of the fibrosing agent of fibrosing agent per $mm^2$ of device surface to which the fibrosing agent is applied.

9366. The method of item 9245 wherein a surface of the device comprises about 1000 µg to about 2500 µg of the fibrosing agent per $mm^2$ of device surface to which the fibrosing agent is applied.

9367. A method of making a medical device comprising combining i) a vaso-occlusion implant, with ii) a fibrosing agent or a composition comprising a fibrosing agent, where the fibrosing agent induces a fibrotic response between the device and a patient in which the device is implanted.

9368. The method of item 9367 wherein the fibrosing agent promotes regeneration.

9369. The method of item 9367 wherein the fibrosing agent promotes angiogenesis.

9370. The method of item 9367 wherein the fibrosing agent promotes fibroblast migration.

9371. The method of item 9367 wherein the fibrosing agent promotes fibroblast proliferation.

9372. The method of item 9367 wherein the fibrosing agent promotes deposition of extracellular matrix (ECM).

9373. The method of item 9367 wherein the fibrosing agent promotes tissue remodeling.

9374. The method of item 9367 wherein the fibrosing agent is an arterial vessel wall irritant.

9375. The method of item 9367 wherein the fibrosing agent promotes adhesion between the device and a host into which the device is implanted.

9376. The method of item 9367 wherein the device delivers the fibrosing agent locally to tissue proximate to the device.

9377. The method of item 9367 wherein the fibrosing agent is or comprises silk.

9378. The method of item 9367 wherein the fibrosing agent is or comprises mineral particles.

9379. The method of item 9367 wherein the fibrosing agent is or comprises chitosan.

9380. The method of item 9367 wherein the fibrosing agent is or comprises polylysine.

9381. The method of item 9367 wherein the fibrosing agent is or comprises fibronectin.

9382. The method of item 9367 wherein the fibrosing agent is or comprises bleomycin.

9383. The method of item 9367 wherein the fibrosing agent is or comprises CTGF.

9384. The method of item 9367 wherein the fibrosing agent is in the form of a thread, or is in contact with a thread.

9385. The method of item 9367 wherein the fibrosing agent is in the form of a particulate.

9386. The method of item 9367 wherein the composition further comprises an inflammatory cytokine.

9387. The method of item 9367 wherein the composition further comprises an agent that stimulates cell proliferation.

9388. The method of item 9367 wherein the composition is in the form of a gel or paste.

9389. The method of item 9367 wherein the fibrosing agent is in the form of tufts.

9390. The method of item 9367 wherein the fibrosing agent promotes adhesion between the device and a host into which the device is implanted.

9391. The method of item 9367 wherein the device delivers the fibrosing agent locally to tissue proximate to the device.

9392. The method of item 9367, wherein the implant is combined with a coating, and the coating comprises the fibrosing agent.

9393. The method of item 9367, wherein the implant is combined with a coating, and the coating is disposed on a surface of the device.

9394. The method of item 9367, wherein the implant is combined with a coating, and the coating directly contacts the device.

9395. The method of item 9367, wherein the implant is combined with a coating, and the coating indirectly contacts the device.

9396. The method of item 9367, wherein the implant is combined with a coating, and the coating partially covers the device.

9397. The method of item 9367, wherein the implant is combined with a coating, and the coating completely covers the device.

9398. The method of item 9367, wherein the implant is combined with a coating, and the coating is a uniform coating.

9399. The method of item 9367, wherein the implant is combined with a coating, and the coating is a non-uniform coating.

9400. The method of item 9367, wherein the implant is combined with a coating, and the coating is a discontinuous coating.

9401. The method of item 9367 wherein the implant is combined with a coating, and the coating is a patterned coating.

9402. The method of item 9367, wherein the implant is combined with a coating, and the coating has a thickness of 100 μm or less.

9403. The method of item 9367, wherein the implant is combined with a coating, and the coating has a thickness of 10 μm or less.

9404. The method of item 9367, wherein the implant is combined with a coating, and the coating adheres to the surface of the device upon deployment of the device.

9405. The method of item 9367, wherein the implant is combined with a coating, and the coating is stable at room temperature for a period of at least 1 year.

9406. The method of item 9367, wherein the implant is combined with a coating, and the fibrosing agent is present in the coating in an amount ranging between about 0.0001% to about 1% by weight.

9407. The method of item 9367, wherein the implant is combined with a coating, and the fibrosing agent is present in the coating in an amount ranging between about 1% to about 10% by weight.

9408. The method of item 9367, wherein the implant is combined with a coating, and the fibrosing agent is present in the coating in an amount ranging between about 10% to about 25% by weight.

9409. The method of item 9367, wherein the implant is combined with a coating, and the fibrosing agent is present in the coating in an amount ranging between about 25% to about 70% by weight.

9410. The method of item 9367, wherein the implant is combined with a coating, and the coating further comprises a polymer.

9411. The method of item 9367, wherein the device comprises a first coating having a first composition and a second coating having a second composition.

9412. The method of item 9367, wherein the device comprises a first coating having a first composition and a second coating having a second composition, where the first composition and the second composition are different.

9413. The method of item 9367, wherein the device comprises a polymer.

9414. The method of item 9367, wherein the device comprises a polymer, and the polymer is a component of the composition.

9415. The method of item 9367, wherein the implant is combined with a polymer, and the polymer is a copolymer.

9416. The method of item 9367, wherein the implant is combined with a polymer, and the polymer is a block copolymer.

9417. The method of item 9367, wherein the implant is combined with a polymer, and the polymer is a random copolymer.

9418. The method of item 9367, wherein the implant is combined with a polymer, and the polymer is a biodegradable polymer.

9419. The method of item 9367, wherein the implant is combined with a polymer, and the polymer is a non-biodegradable polymer.

9420. The method of item 9367, wherein the implant is combined with a polymer, and the polymer is a hydrophilic polymer.

9421. The method of item 9367, wherein the implant is combined with a polymer, and the polymer is a hydrophobic polymer.

9422. The method of item 9367, wherein the implant is combined with a polymer, and the polymer has hydrophilic domains.

9423. The method of item 9367, wherein the implant is combined with a polymer, and the polymer has hydrophobic domains.

9424. The method of item 9367, wherein the implant is combined with a polymer, and the polymer is a non-conductive polymer.

9425. The method of item 9367, wherein the implant is combined with a polymer, and the polymer is an elastomer.

9426. The method of item 9367, wherein the implant is combined with a polymer, and the polymer is a hydrogel.

9427. The method of item 9367, wherein the implant is combined with a polymer, and the polymer is a silicone polymer.

9428. The method of item 9367, wherein the implant is combined with a polymer, and the polymer is a hydrocarbon polymer.

9429. The method of item 9367, wherein the implant is combined with a polymer, and the polymer is a styrene-derived polymer.

9430. The method of item 9367, wherein the implant is combined with a polymer, and the polymer is a butadiene polymer.

9431. The method of item 9367, wherein the implant is combined with a polymer, and the polymer is a macromer.

9432. The method of item 9367, wherein the implant is combined with a polymer, and the polymer is a poly(ethylene glycol) polymer.

9433. The method of item 9367, wherein the implant is combined with a polymer, and the polymer is an amorphous polymer.

9434. The method of item 9367, wherein the implant is combined with a polymer, and the polymer is a lubricious coating.

9435. The method of item 9367 wherein the fibrosing agent is located within pores or holes of the device.

9436. The method of item 9367 wherein the fibrosing agent is located within a channel, lumen, or divet of the device.

9437. The method of item 9367, wherein the implant is further combined with a second pharmaceutically active agent.

9438. The method of item 9367, wherein the implant is further combined with an anti-inflammatory agent.

9439. The method of item 9367 wherein the implant is further combined with an agent that inhibits infection.

9440. The method of item 9367, wherein the implant is further combined with an anthracycline.

9441. The method of item 9367, wherein the implant is further combined with doxorubicin.

9442. The method of item 9367, wherein the implant is further combined with mitoxantrone.

9443. The method of item 9367, wherein the implant is further combined with a fluoropyrimidine.

9444. The method of item 9367, wherein the implant is further combined with 5-fluorouracil (5-FU).

9445. The method of item 9367, wherein the implant is further combined with a folic acid antagonist.

9446. The method of item 9367, wherein the implant is further combined with methotrexate.

9447. The method of item 9367, wherein the implant is further combined with a podophylotoxin.

9448. The method of item 9367, wherein the implant is further combined with etoposide.

9449. The method of item 9367 wherein the implant is further combined with a camptothecin.

9450. The method of item 9367, wherein the implant is further combined with a hydroxyurea.

9451. The method of item 9367, wherein the implant is further combined with a platinum complex.

9452. The method of item 9367, wherein the implant is further combined with cisplatin.

9453. The method of item 9367, wherein the implant is further combined with an anti-thrombotic agent.

9454. The method of item 9367, wherein the implant is further combined with a visualization agent.

9455. The method of item 9367, wherein the implant is further combined with a visualization agent, wherein the visualization agent is a radiopaque material, wherein the radiopaque material comprises a metal, a halogenated compound, or a barium containing compound.

9456. The method of item 9367, wherein the implant is further combined with a visualization agent, wherein the visualization agent is a radiopaque material, wherein the radiopaque material comprises barium, tantalum, or technetium.

9457. The method of item 9367, wherein the implant is further combined with a visualization agent, wherein the visualization agent is a MRI responsive material.

9458. The method of item 9367, wherein the implant is further combined with a visualization agent, wherein the visualization agent comprises a gadolinium chelate.

9459. The method of item 9367, wherein the implant is further combined with a visualization agent, wherein the visualization agent comprises iron, magnesium, manganese, copper, or chromium.

9460. The method of item 9367, wherein the implant is further combined with a visualization agent, wherein the visualization agent comprises an iron oxide compound.

9461. The method of item 9367, wherein the implant is further combined with a visualization agent, wherein the visualization agent comprises a dye, pigment, or colorant.

9462. The method of item 9367, wherein the implant is further combined with an echogenic material.

9463. The method of item 9367, wherein the implant is further combined with an echogenic material, and the echogenic material is in the form of a coating.

9464. The method of item 9367 wherein the device is sterilized.

9465. The method of item 9367 wherein the fibrosing agent is released into tissue in the vicinity of the device after deployment of the device.

9466. The method of item 9367 wherein the fibrosing agent is released into tissue in the vicinity of the device after deployment of the device, wherein the tissue is connective tissue.

9467. The method of item 9367 wherein the fibrosing agent is released into tissue in the vicinity of the device after deployment of the device, wherein the tissue is muscle tissue.

9468. The method of item 9367 wherein the fibrosing agent is released into tissue in the vicinity of the device after deployment of the device, wherein the tissue is nerve tissue.

9469. The method of item 9367 wherein the fibrosing agent is released into tissue in the vicinity of the device after deployment of the device, wherein the tissue is epithelium tissue.

9470. The method of item 9367 wherein the fibrosing agent is released in effective concentrations from the device over a period ranging from the time of deployment of the device to about 1 year.

9471. The method of item 9367 wherein the fibrosing agent is released in effective concentrations from the device over a period ranging from about 1 month to 6 months.

9472. The method of item 9367 wherein the fibrosing agent is released in effective concentrations from the device over a period ranging from about 1–90 days.

9473. The method of item 9367 wherein the fibrosing agent is released in effective concentrations from the device at a constant rate.

9474. The method of item 9367 wherein the fibrosing agent is released in effective concentrations from the device at an increasing rate.

9475. The method of item 9367 wherein the fibrosing agent is released in effective concentrations from the device at a decreasing rate.

9476. The method of item 9367 wherein the fibrosing agent is released in effective concentrations from the composition comprising the fibrosing agent by diffusion over a period ranging from the time of deployment of the device to about 90 days.

9477. The method of item 9367 wherein the fibrosing agent is released in effective concentrations from the composition comprising the fibrosing agent by erosion of the composition over a period ranging from the time of deployment of the device to about 90 days.

9478. The method of item 9367 wherein the device comprises about 0.01 µg to about 10 µg of the fibrosing agent.

9479. The method of item 9367 wherein the device comprises about 10 µg to about 10 mg of the fibrosing agent.

9480. The method of item 9367 wherein the device comprises about 10 mg to about 250 mg of the fibrosing agent.

9481. The method of item 9367 wherein the device comprises about 250 mg to about 1000 mg of the fibrosing agent.

9482. The method of item 9367 wherein the device comprises about 1000 mg to about 2500 mg of the fibrosing agent.

9483. The method of item 9367 wherein a surface of the device comprises less than 0.01 µg of the fibrosing agent per $mm^2$ of device surface to which the fibrosing agent is applied.

9484. The method of item 9367 wherein a surface of the device comprises about 0.01 µg to about 1 µg of the fibrosing agent per $mm^2$ of device surface to which the fibrosing agent is applied.

9485. The method of item 9367 wherein a surface of the device comprises about 1 µg to about 10 µg of the fibrosing agent per $mm^2$ of device surface to which the fibrosing agent is applied.

9486. The method of item 9367 wherein a surface of the device comprises about 10 μg to about 250 μg of the fibrosing agent per mm² of device surface to which the fibrosing agent is applied.

9487. The method of item 9367 wherein a surface of the device comprises about 250 μg to about 1000 μg of the fibrosing agent of fibrosing agent per mm² of device surface to which the fibrosing agent is applied.

9488. The method of item 9367 wherein a surface of the device comprises about 1000 μg to about 2500 μg of the fibrosing agent per mm² of device surface to which the fibrosing agent is applied.

9489. A method of making a medical device comprising combining i) a non-coiled vaso-occlusive implant, with ii) a fibrosing agent or a composition comprising a fibrosing agent, where the fibrosing agent induces a fibrotic response between the device and a patient in which the device is implanted.

9490. The method of item 9489 wherein the fibrosing agent promotes regeneration.

9491. The method of item 9489 wherein the fibrosing agent promotes angiogenesis.

9492. The method of item 9489 wherein the fibrosing agent promotes fibroblast migration.

9493. The method of item 9489 wherein the fibrosing agent promotes fibroblast proliferation.

9494. The method of item 9489 wherein the fibrosing agent promotes deposition of extracellular matrix (ECM).

9495. The method of item 9489 wherein the fibrosing agent promotes tissue remodeling.

9496. The method of item 9489 wherein the fibrosing agent is an arterial vessel wall irritant.

9497. The method of item 9489 wherein the fibrosing agent promotes adhesion between the device and a host into which the device is implanted.

9498. The method of item 9489 wherein the device delivers the fibrosing agent locally to tissue proximate to the device.

9499. The method of item 9489 wherein the fibrosing agent is or comprises silk.

9500. The method of item 9489 wherein the fibrosing agent is or comprises mineral particles.

9501. The method of item 9489 wherein the fibrosing agent is or comprises chitosan.

9502. The method of item 9489 wherein the fibrosing agent is or comprises polylysine.

9503. The method of item 9489 wherein the fibrosing agent is or comprises fibronectin.

9504. The method of item 9489 wherein the fibrosing agent is or comprises bleomycin.

9505. The method of item 9489 wherein the fibrosing agent is or comprises CTGF.

9506. The method of item 9489 wherein the fibrosing agent is in the form of a thread, or is in contact with a thread.

9507. The method of item 9489 wherein the fibrosing agent is in the form of a particulate.

9508. The method of item 9489 wherein the composition further comprises an inflammatory cytokine.

9509. The method of item 9489 wherein the composition further comprises an agent that stimulates cell proliferation.

9510. The method of item 9489 wherein the composition is in the form of a gel or paste.

9511. The method of item 9489 wherein the fibrosing agent is in the form of tufts.

9512. The method of item 9489 wherein the fibrosing agent promotes adhesion between the device and a host into which the device is implanted.

9513. The method of item 9489 wherein the device delivers the fibrosing agent locally to tissue proximate to the device.

9514. The method of item 9489, wherein the implant is combined with a coating, and the coating comprises the fibrosing agent.

9515. The method of item 9489, wherein the implant is combined with a coating, and the coating is disposed on a surface of the device.

9516. The method of item 9489, wherein the implant is combined with a coating, and the coating directly contacts the device.

9517. The method of item 9489, wherein the implant is combined with a coating, and the coating indirectly contacts the device.

9518. The method of item 9489, wherein the implant is combined with a coating, and the coating partially covers the device.

9519. The method of item 9489, wherein the implant is combined with a coating, and the coating completely covers the device.

9520. The method of item 9489, wherein the implant is combined with a coating, and the coating is a uniform coating.

9521. The method of item 9489, wherein the implant is combined with a coating, and the coating is a non-uniform coating.

9522. The method of item 9489, wherein the implant is combined with a coating, and the coating is a discontinuous coating.

9523. The method of item 9489, wherein the implant is combined with a coating, and the coating is a patterned coating.

9524. The method of item 9489, wherein the implant is combined with a coating, and the coating has a thickness of 100 μm or less.

9525. The method of item 9489, wherein the implant is combined with a coating, and the coating has a thickness of 10 μm or less.

9526. The method of item 9489, wherein the implant is combined with a coating, and the coating adheres to the surface of the device upon deployment of the device.

9527. The method of item 9489, wherein the implant is combined with a coating, and the coating is stable at room temperature for a period of at least 1 year.

9528. The method of item 9489, wherein the implant is combined with a coating, and the fibrosing agent is present in the coating in an amount ranging between about 0.0001% to about 1% by weight.

9529. The method of item 9489, wherein the implant is combined with a coating, and the fibrosing agent is present in the coating in an amount ranging between about 1% to about 10% by weight.

9530. The method of item 9489, wherein the implant is combined with a coating, and the fibrosing agent is present in the coating in an amount ranging between about 10% to about 25% by weight.

9531. The method of item 9489, wherein the implant is combined with a coating, and the fibrosing agent is present in the coating in an amount ranging between about 25% to about 70% by weight.

9532. The method of item 9489, wherein the implant is combined with a coating, and the coating further comprises a polymer.

9533. The method of item 9489, wherein the device comprises a first coating having a first composition and a second coating having a second composition.

9534. The method of item 9489, wherein the device comprises a first coating having a first composition and a second coating having a second composition, where the first composition and the second composition are different.

9535. The method of item 9489, wherein the device comprises a polymer.

9536. The method of item 9489, wherein the device comprises a polymer, and the polymer is a component of the composition.

9537. The method of item 9489, wherein the implant is combined with a polymer, and the polymer is a copolymer.

9538. The method of item 9489, wherein the implant is combined with a polymer, and the polymer is a block copolymer.

9539. The method of item 9489, wherein the implant is combined with a polymer, and the polymer is a random copolymer.

9540. The method of item 9489, wherein the implant is combined with a polymer, and the polymer is a biodegradable polymer.

9541. The method of item 9489, wherein the implant is combined with a polymer, and the polymer is a non-biodegradable polymer.

9542. The method of item 9489, wherein the implant is combined with a polymer, and the polymer is a hydrophilic polymer.

9543. The method of item 9489, wherein the implant is combined with a polymer, and the polymer is a hydrophobic polymer.

9544. The method of item 9489, wherein the implant is combined with a polymer, and the polymer has hydrophilic domains.

9545. The method of item 9489, wherein the implant is combined with a polymer, and the polymer has hydrophobic domains.

9546. The method of item 9489, wherein the implant is combined with a polymer, and the polymer is a non-conductive polymer.

9547. The method of item 9489, wherein the implant is combined with a polymer, and the polymer is an elastomer.

9548. The method of item 9489, wherein the implant is combined with a polymer, and the polymer is a hydrogel.

9549. The method of item 9489, wherein the implant is combined with a polymer, and the polymer is a silicone polymer.

9550. The method of item 9489, wherein the implant is combined with a polymer, and the polymer is a hydrocarbon polymer.

9551. The method of item 9489, wherein the implant is combined with a polymer, and the polymer is a styrene-derived polymer.

9552. The method of item 9489, wherein the implant is combined with a polymer, and the polymer is a butadiene polymer.

9553. The method of item 9489, wherein the implant is combined with a polymer, and the polymer is a macromer.

9554. The method of item 9489, wherein the implant is combined with a polymer, and the polymer is a poly(ethylene glycol) polymer.

9555. The method of item 9489, wherein the implant is combined with a polymer, and the polymer is an amorphous polymer.

9556. The method of item 9489, wherein the implant is combined with a polymer, and the polymer is a lubricious coating.

9557. The method of item 9489 wherein the fibrosing agent is located within pores or holes of the device.

9558. The method of item 9489 wherein the fibrosing agent is located within a channel, lumen, or divet of the device.

9559. The method of item 9489, wherein the implant is further combined with a second pharmaceutically active agent.

9560. The method of item 9489, wherein the implant is further combined with an anti-inflammatory agent.

9561. The method of item 9489 wherein the implant is further combined with an agent that inhibits infection.

9562. The method of item 9489, wherein the implant is further combined with an anthracycline.

9563. The method of item 9489, wherein the implant is further combined with doxorubicin.

9564. The method of item 9489, wherein the implant is further combined with mitoxantrone.

9565. The method of item 9489, wherein the implant is further combined with a fluoropyrimidine.

9566. The method of item 9489, wherein the implant is further combined with 5-fluorouracil (5-FU).

9567. The method of item 9489, wherein the implant is further combined with a folic acid antagonist.

9568. The method of item 9489, wherein the implant is further combined with methotrexate.

9569. The method of item 9489, wherein the implant is further combined with a podophylotoxin.

9570. The method of item 9489, wherein the implant is further combined with etoposide.

9571. The method of item 9489 wherein the implant is further combined with a camptothecin.

9572. The method of item 9489, wherein the implant is further combined with a hydroxyurea.

9573. The method of item 9489, wherein the implant is further combined with a platinum complex.

9574. The method of item 9489, wherein the implant is further combined with cisplatin.

9575. The method of item 9489, wherein the implant is further combined with an anti-thrombotic agent.

9576. The method of item 9489, wherein the implant is further combined with a visualization agent.

9577. The method of item 9489, wherein the implant is further combined with a visualization agent, wherein the visualization agent is a radiopaque material, wherein the radiopaque material comprises a metal, a halogenated compound, or a barium containing compound.

9578. The method of item 9489, wherein the implant is further combined with a visualization agent, wherein the visualization agent is a radiopaque material, wherein the radiopaque material comprises barium, tantalum, or technetium.

9579. The method of item 9489, wherein the implant is further combined with a visualization agent, wherein the visualization agent is a MRI responsive material.

9580. The method of item 9489, wherein the implant is further combined with a visualization agent, wherein the visualization agent comprises a gadolinium chelate.

9581. The method of item 9489, wherein the implant is further combined with a visualization agent, wherein the visualization agent comprises iron, magnesium, manganese, copper, or chromium.

9582. The method of item 9489, wherein the implant is further combined with a visualization agent, wherein the visualization agent comprises an iron oxide compound.

9583. The method of item 9489, wherein the implant is further combined with a visualization agent, wherein the visualization agent comprises a dye, pigment, or colorant.

9584. The method of item 9489, wherein the implant is further combined with an echogenic material.

9585. The method of item 9489, wherein the implant is further combined with an echogenic material, and the echogenic material is in the form of a coating.

9586. The method of item 9489 wherein the device is sterilized.

9587. The method of item 9489 wherein the fibrosing agent is released into tissue in the vicinity of the device after deployment of the device.

9588. The method of item 9489 wherein the fibrosing agent is released into tissue in the vicinity of the device after deployment of the device, wherein the tissue is connective tissue.

9589. The method of item 9489 wherein the fibrosing agent is released into tissue in the vicinity of the device after deployment of the device, wherein the tissue is muscle tissue.

9590. The method of item 9489 wherein the fibrosing agent is released into tissue in the vicinity of the device after deployment of the device, wherein the tissue is nerve tissue.

9591. The method of item 9489 wherein the fibrosing agent is released into tissue in the vicinity of the device after deployment of the device, wherein the tissue is epithelium tissue.

9592. The method of item 9489 wherein the fibrosing agent is released in effective concentrations from the device over a period ranging from the time of deployment of the device to about 1 year.

9593. The method of item 9489 wherein the fibrosing agent is released in effective concentrations from the device over a period ranging from about 1 month to 6 months.

9594. The method of item 9489 wherein the fibrosing agent is released in effective concentrations from the device over a period ranging from about 1–90 days.

9595. The method of item 9489 wherein the fibrosing agent is released in effective concentrations from the device at a constant rate.

9596. The method of item 9489 wherein the fibrosing agent is released in effective concentrations from the device at an increasing rate.

9597. The method of item 9489 wherein the fibrosing agent is released in effective concentrations from the device at a decreasing rate.

9598. The method of item 9489 wherein the fibrosing agent is released in effective concentrations from the composition comprising the fibrosing agent by diffusion over a period ranging from the time of deployment of the device to about 90 days.

9599. The method of item 9489 wherein the fibrosing agent is released in effective concentrations from the composition comprising the fibrosing agent by erosion of the composition over a period ranging from the time of deployment of the device to about 90 days.

9600. The method of item 9489 wherein the device comprises about 0.01 µg to about 10 µg of the fibrosing agent.

9601. The method of item 9489 wherein the device comprises about 10 µg to about 10 mg of the fibrosing agent.

9602. The method of item 9489 wherein the device comprises about 10 mg to about 250 mg of the fibrosing agent.

9603. The method of item 9489 wherein the device comprises about 250 mg to about 1000 mg of the fibrosing agent.

9604. The method of item 9489 wherein the device comprises about 1000 mg to about 2500 mg of the fibrosing agent.

9605. The method of item 9489 wherein a surface of the device comprises less than 0.01 µg of the fibrosing agent per $mm^2$ of device surface to which the fibrosing agent is applied.

9606. The method of item 9489 wherein a surface of the device comprises about 0.01 µg to about 1 µg of the fibrosing agent per $mm^2$ of device surface to which the fibrosing agent is applied.

9607. The method of item 9489 wherein a surface of the device comprises about 1 µg to about 10 µg of the fibrosing agent per $mm^2$ of device surface to which the fibrosing agent is applied.

9608. The method of item 9489 wherein a surface of the device comprises about 10 µg to about 250 µg of the fibrosing agent per $mm^2$ of device surface to which the fibrosing agent is applied.

9609. The method of item 9489 wherein a surface of the device comprises about 250 µg to about 1000 µg of the fibrosing agent of fibrosing agent per $mm^2$ of device surface to which the fibrosing agent is applied.

9610. The method of item 9489 wherein a surface of the device comprises about 1000 µg to about 2500 µg of the fibrosing agent per $mm^2$ of device surface to which the fibrosing agent is applied.

9611. The method of item 9489 wherein the implant is expandable.

9612. A method of making a medical device comprising combining i) a hernia mesh implant, with ii) a fibrosing agent or a composition comprising a fibrosing agent, where the fibrosing agent induces a fibrotic response between the device and a patient in which the device is implanted.

9613. The method of item 9612 wherein the fibrosing agent promotes regeneration.

9614. The method of item 9612 wherein the fibrosing agent promotes angiogenesis.

9615. The method of item 9612 wherein the fibrosing agent promotes fibroblast migration.

9616. The method of item 9612 wherein the fibrosing agent promotes fibroblast proliferation.

9617. The method of item 9612 wherein the fibrosing agent promotes deposition of extracellular matrix (ECM).

9618. The method of item 9612 wherein the fibrosing agent promotes tissue remodeling.

9619. The method of item 9612 wherein the fibrosing agent is an arterial vessel wall irritant.

9620. The method of item 9612 wherein the fibrosing agent promotes adhesion between the device and a host into which the device is implanted.

9621. The method of item 9612 wherein the device delivers the fibrosing agent locally to tissue proximate to the device.

9622. The method of item 9612 wherein the fibrosing agent is or comprises silk.

9623. The method of item 9612 wherein the fibrosing agent is or comprises mineral particles.

9624. The method of item 9612 wherein the fibrosing agent is or comprises chitosan.

9625. The method of item 9612 wherein the fibrosing agent is or comprises polylysine.

9626. The method of item 9612 wherein the fibrosing agent is or comprises fibronectin.

9627. The method of item 9612 wherein the fibrosing agent is or comprises bleomycin.

9628. The method of item 9612 wherein the fibrosing agent is or comprises CTGF.

9629. The method of item 9612 wherein the fibrosing agent is in the form of a thread, or is in contact with a thread.

9630. The method of item 9612 wherein the fibrosing agent is in the form of a particulate.

9631. The method of item 9612 wherein the composition further comprises an inflammatory cytokine.

9632. The method of item 9612 wherein the composition further comprises an agent that stimulates cell proliferation.

9633. The method of item 9612 wherein the composition is in the form of a gel or paste.

9634. The method of item 9612 wherein the fibrosing agent is in the form of tufts.

9635. The method of item 9612 wherein the fibrosing agent promotes adhesion between the device and a host into which the device is implanted.

9636. The method of item 9612 wherein the device delivers the fibrosing agent locally to tissue proximate to the device.

9637. The method of item 9612, wherein the implant is combined with a coating, and the coating comprises the fibrosing agent.

9638. The method of item 9612, wherein the implant is combined with a coating, and the coating is disposed on a surface of the device.

9639. The method of item 9612, wherein the implant is combined with a coating, and the coating directly contacts the device.

9640. The method of item 9612, wherein the implant is combined with a coating, and the coating indirectly contacts the device.

9641. The method of item 9612, wherein the implant is combined with a coating, and the coating partially covers the device.

9642. The method of item 9612, wherein the implant is combined with a coating, and the coating completely covers the device.

9643. The method of item 9612, wherein the implant is combined with a coating, and the coating is a uniform coating.

9644. The method of item 9612, wherein the implant is combined with a coating, and the coating is a non-uniform coating.

9645. The method of item 9612, wherein the implant is combined with a coating, and the coating is a discontinuous coating.

9646. The method of item 9612 wherein the implant is combined with a coating, and the coating is a patterned coating.

9647. The method of item 9612, wherein the implant is combined with a coating, and the coating has a thickness of 100 μm or less.

9648. The method of item 9612, wherein the implant is combined with a coating, and the coating has a thickness of 10 μm or less.

9649. The method of item 9612, wherein the implant is combined with a coating, and the coating adheres to the surface of the device upon deployment of the device.

9650. The method of item 9612, wherein the implant is combined with a coating, and the coating is stable at room temperature for a period of at least 1 year.

9651. The method of item 9612, wherein the implant is combined with a coating, and the fibrosing agent is present in the coating in an amount ranging between about 0.0001% to about 1% by weight.

9652. The method of item 9612, wherein the implant is combined with a coating, and the fibrosing agent is present in the coating in an amount ranging between about 1% to about 10% by weight.

9653. The method of item 9612, wherein the implant is combined with a coating, and the fibrosing agent is present in the coating in an amount ranging between about 10% to about 25% by weight.

9654. The method of item 9612, wherein the implant is combined with a coating, and the fibrosing agent is present in the coating in an amount ranging between about 25% to about 70% by weight.

9655. The method of item 9612, wherein the implant is combined with a coating, and the coating further comprises a polymer.

9656. The method of item 9612, wherein the device comprises a first coating having a first composition and a second coating having a second composition.

9657. The method of item 9612, wherein the device comprises a first coating having a first composition and a second coating having a second composition, where the first composition and the second composition are different.

9658. The method of item 9612, wherein the device comprises a polymer.

9659. The method of item 9612, wherein the device comprises a polymer, and the polymer is a component of the composition.

9660. The method of item 9612, wherein the implant is combined with a polymer, and the polymer is a copolymer.

9661. The method of item 9612, wherein the implant is combined with a polymer, and the polymer is a block copolymer.

9662. The method of item 9612, wherein the implant is combined with a polymer, and the polymer is a random copolymer.

9663. The method of item 9612, wherein the implant is combined with a polymer, and the polymer is a biodegradable polymer.

9664. The method of item 9612, wherein the implant is combined with a polymer, and the polymer is a non-biodegradable polymer.

9665. The method of item 9612, wherein the implant is combined with a polymer, and the polymer is a hydrophilic polymer.

9666. The method of item 9612, wherein the implant is combined with a polymer, and the polymer is a hydrophobic polymer.

9667. The method of item 9612, wherein the implant is combined with a polymer, and the polymer has hydrophilic domains.

9668. The method of item 9612, wherein the implant is combined with a polymer, and the polymer has hydrophobic domains.

9669. The method of item 9612, wherein the implant is combined with a polymer, and the polymer is a non-conductive polymer.

9670. The method of item 9612, wherein the implant is combined with a polymer, and the polymer is an elastomer.

9671. The method of item 9612, wherein the implant is combined with a polymer, and the polymer is a hydrogel.

9672. The method of item 9612, wherein the implant is combined with a polymer, and the polymer is a silicone polymer.

9673. The method of item 9612, wherein the implant is combined with a polymer, and the polymer is a hydrocarbon polymer.

9674. The method of item 9612, wherein the implant is combined with a polymer, and the polymer is a styrene-derived polymer.

9675. The method of item 9612, wherein the implant is combined with a polymer, and the polymer is a butadiene polymer.

9676. The method of item 9612, wherein the implant is combined with a polymer, and the polymer is a macromer.

9677. The method of item 9612, wherein the implant is combined with a polymer, and the polymer is a poly(ethylene glycol) polymer.

9678. The method of item 9612, wherein the implant is combined with a polymer, and the polymer is an amorphous polymer.

9679. The method of item 9612, wherein the implant is combined with a polymer, and the polymer is a lubricious coating.

9680. The method of item 9612 wherein the fibrosing agent is located within pores or holes of the device.

9681. The method of item 9612 wherein the fibrosing agent is located within a channel, lumen, or divet of the device.

9682. The method of item 9612, wherein the implant is further combined with a second pharmaceutically active agent.

9683. The method of item 9612, wherein the implant is further combined with an anti-inflammatory agent.

9684. The method of item 9612 wherein the implant is further combined with an agent that inhibits infection.

9685. The method of item 9612, wherein the implant is further combined with an anthracycline.

9686. The method of item 9612, wherein the implant is further combined with doxorubicin.

9687. The method of item 9612, wherein the implant is further combined with mitoxantrone.

9688. The method of item 9612, wherein the implant is further combined with a fluoropyrimidine.

9689. The method of item 9612, wherein the implant is further combined with 5-fluorouracil (5-FU).

9690. The method of item 9612, wherein the implant is further combined with a folic acid antagonist.

9691. The method of item 9612, wherein the implant is further combined with methotrexate.

9692. The method of item 9612, wherein the implant is further combined with a podophylotoxin.

9693. The method of item 9612, wherein the implant is further combined with etoposide.

9694. The method of item 9612 wherein the implant is further combined with a camptothecin.

9695. The method of item 9612, wherein the implant is further combined with a hydroxyurea.

9696. The method of item 9612, wherein the implant is further combined with a platinum complex.

9697. The method of item 9612, wherein the implant is further combined with cisplatin.

9698. The method of item 9612, wherein the implant is further combined with an anti-thrombotic agent.

9699. The method of item 9612, wherein the implant is further combined with a visualization agent.

9700. The method of item 9612, wherein the implant is further combined with a visualization agent, wherein the visualization agent is a radiopaque material, wherein the radiopaque material comprises a metal, a halogenated compound, or a barium containing compound.

9701. The method of item 9612, wherein the implant is further combined with a visualization agent, wherein the visualization agent is a radiopaque material, wherein the radiopaque material comprises barium, tantalum, or technetium.

9702. The method of item 9612, wherein the implant is further combined with a visualization agent, wherein the visualization agent is a MRI responsive material.

9703. The method of item 9612, wherein the implant is further combined with a visualization agent, wherein the visualization agent comprises a gadolinium chelate.

9704. The method of item 9612, wherein the implant is further combined with a visualization agent, wherein the visualization agent comprises iron, magnesium, manganese, copper, or chromium.

9705. The method of item 9612, wherein the implant is further combined with a visualization agent, wherein the visualization agent comprises an iron oxide compound.

9706. The method of item 9612, wherein the implant is further combined with a visualization agent, wherein the visualization agent comprises a dye, pigment, or colorant.

9707. The method of item 9612, wherein the implant is further combined with an echogenic material.

9708. The method of item 9612, wherein the implant is further combined with an echogenic material, and the echogenic material is in the form of a coating.

9709. The method of item 9612 wherein the device is sterilized.

9710. The method of item 9612 wherein the fibrosing agent is released into tissue in the vicinity of the device after deployment of the device.

9711. The method of item 9612 wherein the fibrosing agent is released into tissue in the vicinity of the device after deployment of the device, wherein the tissue is connective tissue.

9712. The method of item 9612 wherein the fibrosing agent is released into tissue in the vicinity of the device after deployment of the device, wherein the tissue is muscle tissue.

9713. The method of item 9612 wherein the fibrosing agent is released into tissue in the vicinity of the device after deployment of the device, wherein the tissue is nerve tissue.

9714. The method of item 9612 wherein the fibrosing agent is released into tissue in the vicinity of the device after deployment of the device, wherein the tissue is epithelium tissue.

9715. The method of item 9612 wherein the fibrosing agent is released in effective concentrations from the device over a period ranging from the time of deployment of the device to about 1 year.

9716. The method of item 9612 wherein the fibrosing agent is released in effective concentrations from the device over a period ranging from about 1 month to 6 months.

9717. The method of item 9612 wherein the fibrosing agent is released in effective concentrations from the device over a period ranging from about 1–90 days.

9718. The method of item 9612 wherein the fibrosing agent is released in effective concentrations from the device at a constant rate.

9719. The method of item 9612 wherein the fibrosing agent is released in effective concentrations from the device at an increasing rate.

9720. The method of item 9612 wherein the fibrosing agent is released in effective concentrations from the device at a decreasing rate.

9721. The method of item 9612 wherein the fibrosing agent is released in effective concentrations from the composition comprising the fibrosing agent by diffusion over a period ranging from the time of deployment of the device to about 90 days.

9722. The method of item 9612 wherein the fibrosing agent is released in effective concentrations from the composition comprising the fibrosing agent by erosion of the composition over a period ranging from the time of deployment of the device to about 90 days.

9723. The method of item 9612 wherein the device comprises about 0.01 µg to about 10 µg of the fibrosing agent.

9724. The method of item 9612 wherein the device comprises about 10 µg to about 10 mg of the fibrosing agent.

9725. The method of item 9612 wherein the device comprises about 10 mg to about 250 mg of the fibrosing agent.

9726. The method of item 9612 wherein the device comprises about 250 mg to about 1000 mg of the fibrosing agent.

9727. The method of item 9612 wherein the device comprises about 1000 mg to about 2500 mg of the fibrosing agent.

9728. The method of item 9612 wherein a surface of the device comprises less than 0.01 µg of the fibrosing agent per mm$^2$ of device surface to which the fibrosing agent is applied.

9729. The method of item 9612 wherein a surface of the device comprises about 0.01 µg to about 1 µg of the fibrosing agent per mm$^2$ of device surface to which the fibrosing agent is applied.

9730. The method of item 9612 wherein a surface of the device comprises about 1 µg to about 10 µg of the fibrosing agent per mm$^2$ of device surface to which the fibrosing agent is applied.

9731. The method of item 9612 wherein a surface of the device comprises about 10 µg to about 250 µg of the fibrosing agent per mm$^2$ of device surface to which the fibrosing agent is applied.

9732. The method of item 9612 wherein a surface of the device comprises about 250 µg to about 1000 µg of the fibrosing agent of fibrosing agent per mm$^2$ of device surface to which the fibrosing agent is applied.

9733. The method of item 9612 wherein a surface of the device comprises about 1000 µg to about 2500 µg of the fibrosing agent per mm$^2$ of device surface to which the fibrosing agent is applied.

9734. The method of item 9612 wherein the hernia mesh is made, in whole or part, from synthetic fiber.

9735. The method of item 9612 wherein the hernia mesh comprises polypropylene.

9736. A method of making a medical device comprising combining i) a surgical film implant, with ii) a fibrosing agent or a composition comprising a fibrosing agent, where the fibrosing agent induces a fibrotic response between the device and a patient in which the device is implanted.

9737. The method of item 9736 wherein the fibrosing agent promotes regeneration.

9738. The method of item 9736 wherein the fibrosing agent promotes angiogenesis.

9739. The method of item 9736 wherein the fibrosing agent promotes fibroblast migration.

9740. The method of item 9736 wherein the fibrosing agent promotes fibroblast proliferation.

9741. The method of item 9736 wherein the fibrosing agent promotes deposition of extracellular matrix (ECM).

9742. The method of item 9736 wherein the fibrosing agent promotes tissue remodeling.

9743. The method of item 9736 wherein the fibrosing agent is an arterial vessel wall irritant.

9744. The method of item 9736 wherein the fibrosing agent promotes adhesion between the device and a host into which the device is implanted.

9745. The method of item 9736 wherein the device delivers the fibrosing agent locally to tissue proximate to the device.

9746. The method of item 9736 wherein the fibrosing agent is or comprises silk.

9747. The method of item 9736 wherein the fibrosing agent is or comprises mineral particles.

9748. The method of item 9736 wherein the fibrosing agent is or comprises chitosan.

9749. The method of item 9736 wherein the fibrosing agent is or comprises polylysine.

9750. The method of item 9736 wherein the fibrosing agent is or comprises fibronectin.

9751. The method of item 9736 wherein the fibrosing agent is or comprises bleomycin.

9752. The method of item 9736 wherein the fibrosing agent is or comprises CTGF.

9753. The method of item 9736 wherein the fibrosing agent is in the form of a thread, or is in contact with a thread.

9754. The method of item 9736 wherein the fibrosing agent is in the form of a particulate.

9755. The method of item 9736 wherein the composition further comprises an inflammatory cytokine.

9756. The method of item 9736 wherein the composition further comprises an agent that stimulates cell proliferation.

9757. The method of item 9736 wherein the composition is in the form of a gel or paste.

9758. The method of item 9736 wherein the fibrosing agent is in the form of tufts.

9759. The method of item 9736 wherein the fibrosing agent promotes adhesion between the device and a host into which the device is implanted.

9760. The method of item 9736 wherein the device delivers the fibrosing agent locally to tissue proximate to the device.

9761. The method of item 9736, wherein the implant is combined with a coating, and the coating comprises the fibrosing agent.

9762. The method of item 9736, wherein the implant is combined with a coating, and the coating is disposed on a surface of the device.

9763. The method of item 9736, wherein the implant is combined with a coating, and the coating directly contacts the device.

9764. The method of item 9736, wherein the implant is combined with a coating, and the coating indirectly contacts the device.

9765. The method of item 9736, wherein the implant is combined with a coating, and the coating partially covers the device.

9766. The method of item 9736, wherein the implant is combined with a coating, and the coating completely covers the device.

9767. The method of item 9736, wherein the implant is combined with a coating, and the coating is a uniform coating.

9768. The method of item 9736, wherein the implant is combined with a coating, and the coating is a non-uniform coating.

9769. The method of item 9736, wherein the implant is combined with a coating, and the coating is a discontinuous coating.

9770. The method of item 9736 wherein the implant is combined with a coating, and the coating is a patterned coating.

9771. The method of item 9736, wherein the implant is combined with a coating, and the coating has a thickness of 100 μm or less.

9772. The method of item 9736, wherein the implant is combined with a coating, and the coating has a thickness of 10 μm or less.

9773. The method of item 9736, wherein the implant is combined with a coating, and the coating adheres to the surface of the device upon deployment of the device.

9774. The method of item 9736, wherein the implant is combined with a coating, and the coating is stable at room temperature for a period of at least 1 year.

9775. The method of item 9736, wherein the implant is combined with a coating, and the fibrosing agent is present in the coating in an amount ranging between about 0.0001% to about 1% by weight.

9776. The method of item 9736, wherein the implant is combined with a coating, and the fibrosing agent is present in the coating in an amount ranging between about 1% to about 10% by weight.

9777. The method of item 9736, wherein the implant is combined with a coating, and the fibrosing agent is present in the coating in an amount ranging between about 10% to about 25% by weight.

9778. The method of item 9736, wherein the implant is combined with a coating, and the fibrosing agent is present in the coating in an amount ranging between about 25% to about 70% by weight.

9779. The method of item 9736, wherein the implant is combined with a coating, and the coating further comprises a polymer.

9780. The method of item 9736, wherein the device comprises a first coating having a first composition and a second coating having a second composition.

9781. The method of item 9736, wherein the device comprises a first coating having a first composition and a second coating having a second composition, where the first composition and the second composition are different.

9782. The method of item 9736, wherein the device comprises a polymer.

9783. The method of item 9736, wherein the device comprises a polymer, and the polymer is a component of the composition.

9784. The method of item 9736, wherein the implant is combined with a polymer, and the polymer is a copolymer.

9785. The method of item 9736, wherein the implant is combined with a polymer, and the polymer is a block copolymer.

9786. The method of item 9736, wherein the implant is combined with a polymer, and the polymer is a random copolymer.

9787. The method of item 9736, wherein the implant is combined with a polymer, and the polymer is a biodegradable polymer.

9788. The method of item 9736, wherein the implant is combined with a polymer, and the polymer is a non-biodegradable polymer.

9789. The method of item 9736, wherein the implant is combined with a polymer, and the polymer is a hydrophilic polymer.

9790. The method of item 9736, wherein the implant is combined with a polymer, and the polymer is a hydrophobic polymer.

9791. The method of item 9736, wherein the implant is combined with a polymer, and the polymer has hydrophilic domains.

9792. The method of item 9736, wherein the implant is combined with a polymer, and the polymer has hydrophobic domains.

9793. The method of item 9736, wherein the implant is combined with a polymer, and the polymer is a non-conductive polymer.

9794. The method of item 9736, wherein the implant is combined with a polymer, and the polymer is an elastomer.

9795. The method of item 9736, wherein the implant is combined with a polymer, and the polymer is a hydrogel.

9796. The method of item 9736, wherein the implant is combined with a polymer, and the polymer is a silicone polymer.

9797. The method of item 9736, wherein the implant is combined with a polymer, and the polymer is a hydrocarbon polymer.

9798. The method of item 9736, wherein the implant is combined with a polymer, and the polymer is a styrene-derived polymer.

9799. The method of item 9736, wherein the implant is combined with a polymer, and the polymer is a butadiene polymer.

9800. The method of item 9736, wherein the implant is combined with a polymer, and the polymer is a macromer.

9801. The method of item 9736, wherein the implant is combined with a polymer, and the polymer is a poly(ethylene glycol) polymer.

9802. The method of item 9736, wherein the implant is combined with a polymer, and the polymer is an amorphous polymer.

9803. The method of item 9736, wherein the implant is combined with a polymer, and the polymer is a lubricious coating.

9804. The method of item 9736 wherein the fibrosing agent is located within pores or holes of the device.

9805. The method of item 9736 wherein the fibrosing agent is located within a channel, lumen, or divet of the device.

9806. The method of item 9736, wherein the implant is further combined with a second pharmaceutically active agent.

9807. The method of item 9736, wherein the implant is further combined with an anti-inflammatory agent.

9808. The method of item 9736 wherein the implant is further combined with an agent that inhibits infection.

9809. The method of item 9736, wherein the implant is further combined with an anthracycline.

9810. The method of item 9736, wherein the implant is further combined with doxorubicin.

9811. The method of item 9736, wherein the implant is further combined with mitoxantrone.

9812. The method of item 9736, wherein the implant is further combined with a fluoropyrimidine.

9813. The method of item 9736, wherein the implant is further combined with 5-fluorouracil (5-FU).

9814. The method of item 9736, wherein the implant is further combined with a folic acid antagonist.

9815. The method of item 9736, wherein the implant is further combined with methotrexate.

9816. The method of item 9736, wherein the implant is further combined with a podophylotoxin.

9817. The method of item 9736, wherein the implant is further combined with etoposide.

9818. The method of item 9736 wherein the implant is further combined with a camptothecin.

9819. The method of item 9736, wherein the implant is further combined with a hydroxyurea.

9820. The method of item 9736, wherein the implant is further combined with a platinum complex.

9821. The method of item 9736, wherein the implant is further combined with cisplatin.

9822. The method of item 9736, wherein the implant is further combined with an anti-thrombotic agent.

9823. The method of item 9736, wherein the implant is further combined with a visualization agent.

9824. The method of item 9736, wherein the implant is further combined with a visualization agent, wherein the visualization agent is a radiopaque material, wherein the radiopaque material comprises a metal, a halogenated compound, or a barium containing compound.

9825. The method of item 9736, wherein the implant is further combined with a visualization agent, wherein the visualization agent is a radiopaque material, wherein the radiopaque material comprises barium, tantalum, or technetium.

9826. The method of item 9736, wherein the implant is further combined with a visualization agent, wherein the visualization agent is a MRI responsive material.

9827. The method of item 9736, wherein the implant is further combined with a visualization agent, wherein the visualization agent comprises a gadolinium chelate.

9828. The method of item 9736, wherein the implant is further combined with a visualization agent, wherein the visualization agent comprises iron, magnesium, manganese, copper, or chromium.

9829. The method of item 9736, wherein the implant is further combined with a visualization agent, wherein the visualization agent comprises an iron oxide compound.

9830. The method of item 9736, wherein the implant is further combined with a visualization agent, wherein the visualization agent comprises a dye, pigment, or colorant.

9831. The method of item 9736, wherein the implant is further combined with an echogenic material.

9832. The method of item 9736, wherein the implant is further combined with an echogenic material, and the echogenic material is in the form of a coating.

9833. The method of item 9736 wherein the device is sterilized.

9834. The method of item 9736 wherein the fibrosing agent is released into tissue in the vicinity of the device after deployment of the device.

9835. The method of item 9736 wherein the fibrosing agent is released into tissue in the vicinity of the device after deployment of the device, wherein the tissue is connective tissue.

9836. The method of item 9736 wherein the fibrosing agent is released into tissue in the vicinity of the device after deployment of the device, wherein the tissue is muscle tissue.

9837. The method of item 9736 wherein the fibrosing agent is released into tissue in the vicinity of the device after deployment of the device, wherein the tissue is nerve tissue.

9838. The method of item 9736 wherein the fibrosing agent is released into tissue in the vicinity of the device after deployment of the device, wherein the tissue is epithelium tissue.

9839. The method of item 9736 wherein the fibrosing agent is released in effective concentrations from the device over a period ranging from the time of deployment of the device to about 1 year.

9840. The method of item 9736 wherein the fibrosing agent is released in effective concentrations from the device over a period ranging from about 1 month to 6 months.

9841. The method of item 9736 wherein the fibrosing agent is released in effective concentrations from the device over a period ranging from about 1–90 days.

9842. The method of item 9736 wherein the fibrosing agent is released in effective concentrations from the device at a constant rate.

9843. The method of item 9736 wherein the fibrosing agent is released in effective concentrations from the device at an increasing rate.

9844. The method of item 9736 wherein the fibrosing agent is released in effective concentrations from the device at a decreasing rate.

9845. The method of item 9736 wherein the fibrosing agent is released in effective concentrations from the composition comprising the fibrosing agent by diffusion over a period ranging from the time of deployment of the device to about 90 days.

9846. The method of item 9736 wherein the fibrosing agent is released in effective concentrations from the composition comprising the fibrosing agent by erosion of the composition over a period ranging from the time of deployment of the device to about 90 days.

9847. The method of item 9736 wherein the device comprises about 0.01 µg to about 10 µg of the fibrosing agent.

9848. The method of item 9736 wherein the device comprises about 10 µg to about 10 mg of the fibrosing agent.

9849. The method of item 9736 wherein the device comprises about 10 mg to about 250 mg of the fibrosing agent.

9850. The method of item 9736 wherein the device comprises about 250 mg to about 1000 mg of the fibrosing agent.

9851. The method of item 9736 wherein the device comprises about 1000 mg to about 2500 mg of the fibrosing agent.

9852. The method of item 9736 wherein a surface of the device comprises less than 0.01 µg of the fibrosing agent per $mm^2$ of device surface to which the fibrosing agent is applied.

9853. The method of item 9736 wherein a surface of the device comprises about 0.01 µg to about 1 µg of the fibrosing agent per $mm^2$ of device surface to which the fibrosing agent is applied.

9854. The method of item 9736 wherein a surface of the device comprises about 1 µg to about 10 µg of the fibrosing agent per $mm^2$ of device surface to which the fibrosing agent is applied.

9855. The method of item 9736 wherein a surface of the device comprises about 10 µg to about 250 µg of the fibrosing agent per $mm^2$ of device surface to which the fibrosing agent is applied.

9856. The method of item 9736 wherein a surface of the device comprises about 250 µg to about 1000 µg of the fibrosing agent of fibrosing agent per $mm^2$ of device surface to which the fibrosing agent is applied.

9857. The method of item 9736 wherein a surface of the device comprises about 1000 µg to about 2500 µg of the fibrosing agent per $mm^2$ of device surface to which the fibrosing agent is applied.

9858. The method of item 9736 wherein the surgical film implant comprises cellulose or a cellulose derivative.

9859. The method of item 9736 wherein the surgical film implant is porous.

9860. The method of item 9736 wherein the surgical film implant is biodegradable.

9861. A method of making a medical device comprising combining i) a spinal fusion implant, with ii) a fibrosing agent or a composition comprising a fibrosing agent, where the fibrosing agent induces a fibrotic response between the device and a patient in which the device is implanted.

9862. The method of item 9861 wherein the fibrosing agent promotes regeneration.

9863. The method of item 9861 wherein the fibrosing agent promotes angiogenesis.

9864. The method of item 9861 wherein the fibrosing agent promotes fibroblast migration.

9865. The method of item 9861 wherein the fibrosing agent promotes fibroblast proliferation.

9866. The method of item 9861 wherein the fibrosing agent promotes deposition of extracellular matrix (ECM).

9867. The method of item 9861 wherein the fibrosing agent promotes tissue remodeling.

9868. The method of item 9861 wherein the fibrosing agent is an arterial vessel wall irritant.

9869. The method of item 9861 wherein the fibrosing agent promotes adhesion between the device and a host into which the device is implanted.

9870. The method of item 9861 wherein the device delivers the fibrosing agent locally to tissue proximate to the device.

9871. The method of item 9861 wherein the fibrosing agent is or comprises silk.

9872. The method of item 9861 wherein the fibrosing agent is or comprises mineral particles.

9873. The method of item 9861 wherein the fibrosing agent is or comprises chitosan.

9874. The method of item 9861 wherein the fibrosing agent is or comprises polylysine.

9875. The method of item 9861 wherein the fibrosing agent is or comprises fibronectin.

9876. The method of item 9861 wherein the fibrosing agent is or comprises bleomycin.

9877. The method of item 9861 wherein the fibrosing agent is or comprises CTGF.

9878. The method of item 9861 wherein the fibrosing agent is in the form of a thread, or is in contact with a thread.

9879. The method of item 9861 wherein the fibrosing agent is in the form of a particulate.

9880. The method of item 9861 wherein the composition further comprises an inflammatory cytokine.

9881. The method of item 9861 wherein the composition further comprises an agent that stimulates cell proliferation.

9882. The method of item 9861 wherein the composition is in the form of a gel or paste.

9883. The method of item 9861 wherein the fibrosing agent is in the form of tufts.

9884. The method of item 9861 wherein the fibrosing agent promotes adhesion between the device and a host into which the device is implanted.

9885. The method of item 9861 wherein the device delivers the fibrosing agent locally to tissue proximate to the device.

9886. The method of item 9861, wherein the implant is combined with a coating, and the coating comprises the fibrosing agent.

9887. The method of item 9861, wherein the implant is combined with a coating, and the coating is disposed on a surface of the device.

9888. The method of item 9861, wherein the implant is combined with a coating, and the coating directly contacts the device.

9889. The method of item 9861, wherein the implant is combined with a coating, and the coating indirectly contacts the device.

9890. The method of item 9861, wherein the implant is combined with a coating, and the coating partially covers the device.

9891. The method of item 9861, wherein the implant is combined with a coating, and the coating completely covers the device.

9892. The method of item 9861, wherein the implant is combined with a coating, and the coating is a uniform coating.

9893. The method of item 9861, wherein the implant is combined with a coating, and the coating is a non-uniform coating.

9894. The method of item 9861, wherein the implant is combined with a coating, and the coating is a discontinuous coating.

9895. The method of item 9861 wherein the implant is combined with a coating, and the coating is a patterned coating.

9896. The method of item 9861, wherein the implant is combined with a coating, and the coating has a thickness of 100 μm or less.

9897. The method of item 9861, wherein the implant is combined with a coating, and the coating has a thickness of 10 μm or less.

9898. The method of item 9861, wherein the implant is combined with a coating, and the coating adheres to the surface of the device upon deployment of the device.

9899. The method of item 9861, wherein the implant is combined with a coating, and the coating is stable at room temperature for a period of at least 1 year.

9900. The method of item 9861, wherein the implant is combined with a coating, and the fibrosing agent is present in the coating in an amount ranging between about 0.0001% to about 1% by weight.

9901. The method of item 9861, wherein the implant is combined with a coating, and the fibrosing agent is present in the coating in an amount ranging between about 1% to about 10% by weight.

9902. The method of item 9861, wherein the implant is combined with a coating, and the fibrosing agent is present in the coating in an amount ranging between about 10% to about 25% by weight.

9903. The method of item 9861, wherein the implant is combined with a coating, and the fibrosing agent is present in the coating in an amount ranging between about 25% to about 70% by weight.

9904. The method of item 9861, wherein the implant is combined with a coating, and the coating further comprises a polymer.

9905. The method of item 9861, wherein the device comprises a first coating having a first composition and a second coating having a second composition.

9906. The method of item 9861, wherein the device comprises a first coating having a first composition and a second coating having a second composition, where the first composition and the second composition are different.

9907. The method of item 9861, wherein the device comprises a polymer.

9908. The method of item 9861, wherein the device comprises a polymer, and the polymer is a component of the composition.

9909. The method of item 9861, wherein the implant is combined with a polymer, and the polymer is a copolymer.

9910. The method of item 9861, wherein the implant is combined with a polymer, and the polymer is a block copolymer.

9911. The method of item 9861, wherein the implant is combined with a polymer, and the polymer is a random copolymer.

9912. The method of item 9861, wherein the implant is combined with a polymer, and the polymer is a biodegradable polymer.

9913. The method of item 9861, wherein the implant is combined with a polymer, and the polymer is a non-biodegradable polymer.

9914. The method of item 9861, wherein the implant is combined with a polymer, and the polymer is a hydrophilic polymer.

9915. The method of item 9861, wherein the implant is combined with a polymer, and the polymer is a hydrophobic polymer.

9916. The method of item 9861, wherein the implant is combined with a polymer, and the polymer has hydrophilic domains.

9917. The method of item 9861, wherein the implant is combined with a polymer, and the polymer has hydrophobic domains.

9918. The method of item 9861, wherein the implant is combined with a polymer, and the polymer is a non-conductive polymer.

9919. The method of item 9861, wherein the implant is combined with a polymer, and the polymer is an elastomer.

9920. The method of item 9861, wherein the implant is combined with a polymer, and the polymer is a hydrogel.

9921. The method of item 9861, wherein the implant is combined with a polymer, and the polymer is a silicone polymer.

9922. The method of item 9861, wherein the implant is combined with a polymer, and the polymer is a hydrocarbon polymer.

9923. The method of item 9861, wherein the implant is combined with a polymer, and the polymer is a styrene-derived polymer.

9924. The method of item 9861, wherein the implant is combined with a polymer, and the polymer is a butadiene polymer.

9925. The method of item 9861, wherein the implant is combined with a polymer, and the polymer is a macromer.

9926. The method of item 9861, wherein the implant is combined with a polymer, and the polymer is a poly(ethylene glycol) polymer.

9927. The method of item 9861, wherein the implant is combined with a polymer, and the polymer is an amorphous polymer.

9928. The method of item 9861, wherein the implant is combined with a polymer, and the polymer is a lubricious coating.

9929. The method of item 9861 wherein the fibrosing agent is located within pores or holes of the device.

9930. The method of item 9861 wherein the fibrosing agent is located within a channel, lumen, or divet of the device.

9931. The method of item 9861, wherein the implant is further combined with a second pharmaceutically active agent.

9932. The method of item 9861, wherein the implant is further combined with an anti-inflammatory agent.

9933. The method of item 9861 wherein the implant is further combined with an agent that inhibits infection.

9934. The method of item 9861, wherein the implant is further combined with an anthracycline.

9935. The method of item 9861, wherein the implant is further combined with doxorubicin.

9936. The method of item 9861, wherein the implant is further combined with mitoxantrone.

9937. The method of item 9861, wherein the implant is further combined with a fluoropyrimidine.

9938. The method of item 9861, wherein the implant is further combined with 5-fluorouracil (5-FU).

9939. The method of item 9861, wherein the implant is further combined with a folic acid antagonist.

9940. The method of item 9861, wherein the implant is further combined with methotrexate.

9941. The method of item 9861, wherein the implant is further combined with a podophylotoxin.

9942. The method of item 9861, wherein the implant is further combined with etoposide.

9943. The method of item 9861 wherein the implant is further combined with a camptothecin.

9944. The method of item 9861, wherein the implant is further combined with a hydroxyurea.

9945. The method of item 9861, wherein the implant is further combined with a platinum complex.

9946. The method of item 9861, wherein the implant is further combined with cisplatin.

9947. The method of item 9861, wherein the implant is further combined with an anti-thrombotic agent.

9948. The method of item 9861, wherein the implant is further combined with a visualization agent.

9949. The method of item 9861, wherein the implant is further combined with a visualization agent, wherein the visualization agent is a radiopaque material, wherein the radiopaque material comprises a metal, a halogenated compound, or a barium containing compound.

9950. The method of item 9861, wherein the implant is further combined with a visualization agent, wherein the visualization agent is a radiopaque material, wherein the radiopaque material comprises barium, tantalum, or technetium.

9951. The method of item 9861, wherein the implant is further combined with a visualization agent, wherein the visualization agent is a MRI responsive material.

9952. The method of item 9861, wherein the implant is further combined with a visualization agent, wherein the visualization agent comprises a gadolinium chelate.

9953. The method of item 9861, wherein the implant is further combined with a visualization agent, wherein the visualization agent comprises iron, magnesium, manganese, copper, or chromium.

9954. The method of item 9861, wherein the implant is further combined with a visualization agent, wherein the visualization agent comprises an iron oxide compound.

9955. The method of item 9861, wherein the implant is further combined with a visualization agent, wherein the visualization agent comprises a dye, pigment, or colorant.

9956. The method of item 9861, wherein the implant is further combined with an echogenic material.

9957. The method of item 986.1, wherein the implant is further combined with an echogenic material, and the echogenic material is in the form of a coating.

9958. The method of item 9861 wherein the device is sterilized.

9959. The method of item 9861 wherein the fibrosing agent is released into tissue in the vicinity of the device after deployment of the device.

9960. The method of item 9861 wherein the fibrosing agent is released into tissue in the vicinity of the device after deployment of the device, wherein the tissue is connective tissue.

9961. The method of item 9861 wherein the fibrosing agent is released into tissue in the vicinity of the device after deployment of the device, wherein the tissue is muscle tissue.

9962. The method of item 9861 wherein the fibrosing agent is released into tissue in the vicinity of the device after deployment of the device, wherein the tissue is nerve tissue.

9963. The method of item 9861 wherein the fibrosing agent is released into tissue in the vicinity of the device after deployment of the device, wherein the tissue is epithelium tissue.

9964. The method of item 9861 wherein the fibrosing agent is released in effective concentrations from the device over a period ranging from the time of deployment of the device to about 1 year.

9965. The method of item 9861 wherein the fibrosing agent is released in effective concentrations from the device over a period ranging from about 1 month to 6 months.

9966. The method of item 9861 wherein the fibrosing agent is released in effective concentrations from the device over a period ranging from about 1–90 days.

9967. The method of item 9861 wherein the fibrosing agent is released in effective concentrations from the device at a constant rate.

9968. The method of item 9861 wherein the fibrosing agent is released in effective concentrations from the device at an increasing rate.

9969. The method of item 9861 wherein the fibrosing agent is released in effective concentrations from the device at a decreasing rate.

9970. The method of item 9861 wherein the fibrosing agent is released in effective concentrations from the composition comprising the fibrosing agent by diffusion over a period ranging from the time of deployment of the device to about 90 days.

9971. The method of item 9861 wherein the fibrosing agent is released in effective concentrations from the composition comprising the fibrosing agent by erosion of the composition over a period ranging from the time of deployment of the device to about 90 days.

9972. The method of item 9861 wherein the device comprises about 0.01 µg to about 10 µg of the fibrosing agent.

9973. The method of item 9861 wherein the device comprises about 10 µg to about 10 mg of the fibrosing agent.

9974. The method of item 9861 wherein the device comprises about 10 mg to about 250 mg of the fibrosing agent.

9975. The method of item 9861 wherein the device comprises about 250 mg to about 1000 mg of the fibrosing agent.

9976. The method of item 9861 wherein the device comprises about 1000 mg to about 2500 mg of the fibrosing agent.

9977. The method of item 9861 wherein a surface of the device comprises less than 0.01 µg of the fibrosing agent per mm² of device surface to which the fibrosing agent is applied.

9978. The method of item 9861 wherein a surface of the device comprises about 0.01 µg to about 1 µg of the fibrosing agent per mm² of device surface to which the fibrosing agent is applied.

9979. The method of item 9861 wherein a surface of the device comprises about 1 µg to about 10 µg of the fibrosing agent per mm² of device surface to which the fibrosing agent is applied.

9980. The method of item 9861 wherein a surface of the device comprises about 10 µg to about 250 µg of the fibrosing agent per mm² of device surface to which the fibrosing agent is applied.

9981. The method of item 9861 wherein a surface of the device comprises about 250 µg to about 1000 µg of the fibrosing agent of fibrosing agent per mm² of device surface to which the fibrosing agent is applied.

9982. The method of item 9861 wherein a surface of the device comprises about 1000 µg to about 2500 µg of the fibrosing agent per mm² of device surface to which the fibrosing agent is applied.

9983. The method of item 9861 wherein the spinal fusion device is a fusion basket.

9984. The method of item 9861 wherein the spinal fusion device is a fusion cage apparatus.

9985. The method of item 9861 wherein the spinal fusion device is an interbody case.

9986. The method of item 9861 wherein the spinal fusion device is an interbody implant.

9987. The method of item 9861 wherein the spinal fusion device is a fusion cage anchoring device.

9988. The method of item 9861 wherein the spinal fusion device is a fusion stabilization chamber.

9989. The method of item 9861 wherein the spinal fusion device is a fusion cage anchoring plate.

9990. The method of item 9861 wherein the spinal fusion device is a bone fixation device.

9991. The method of item 9861 wherein the spinal fusion device is an anchoring bone plate.

9992. The method of item 9861 wherein the spinal fusion device is an anchoring bone screw.

9993. The method of item 9861 wherein the spinal fusion device is a tissue filler.

9994. The method of item 9861 wherein the spinal fusion device is a bone cement.

9995. The method of item 9861 wherein the spinal fusion device is an allograft material.

9996. The method of item 9861 wherein the spinal fusion device is an autograft material.

9997. The method of item 9861 wherein the spinal fusion device is a collagen implant.

9998. The method of item 9861 wherein the spinal fusion device is injectable.

9999. A method of making a medical device comprising combining i) a septal occlusion patch implant, with ii) a fibrosing agent or a composition comprising a fibrosing agent, where the fibrosing agent induces a fibrotic response between the device and a patient in which the device is implanted.

10000. The method of item 9999 wherein the fibrosing agent promotes regeneration.

10001. The method of item 9999 wherein the fibrosing agent promotes angiogenesis.

10002. The method of item 9999 wherein the fibrosing agent promotes fibroblast migration.

10003. The method of item 9999 wherein the fibrosing agent promotes fibroblast proliferation.

10004. The method of item 9999 wherein the fibrosing agent promotes deposition of extracellular matrix (ECM).

10005. The method of item 9999 wherein the fibrosing agent promotes tissue remodeling.

10006. The method of item 9999 wherein the fibrosing agent is an arterial vessel wall irritant.

10007. The method of item 9999 wherein the fibrosing agent promotes adhesion between the device and a host into which the device is implanted.

10008. The method of item 9999 wherein the device delivers the fibrosing agent locally to tissue proximate to the device.

10009. The method of item 9999 wherein the fibrosing agent is or comprises silk.

10010. The method of item 9999 wherein the fibrosing agent is or comprises mineral particles.

10011. The method of item 9999 wherein the fibrosing agent is or comprises chitosan.

10012. The method of item 9999 wherein the fibrosing agent is or comprises polylysine.

10013. The method of item 9999 wherein the fibrosing agent is or comprises fibronectin.

10014. The method of item 9999 wherein the fibrosing agent is or comprises bleomycin.

10015. The method of item 9999 wherein the fibrosing agent is or comprises CTGF.

10016. The method of item 9999 wherein the fibrosing agent is in the form of a thread, or is in contact with a thread.

10017. The method of item 9999 wherein the fibrosing agent is in the form of a particulate.

10018. The method of item 9999 wherein the composition further comprises an inflammatory cytokine.

10019. The method of item 9999 wherein the composition further comprises an agent that stimulates cell proliferation.

10020. The method of item 9999 wherein the composition is in the form of a gel or paste.

10021. The method of item 9999 wherein the fibrosing agent is in the form of tufts.

10022. The method of item 9999 wherein the fibrosing agent promotes adhesion between the device and a host into which the device is implanted.

10023. The method of item 9999 wherein the device delivers the fibrosing agent locally to tissue proximate to the device.

10024. The method of item 9999, wherein the implant is combined with a coating, and the coating comprises the fibrosing agent.

10025. The method of item 9999, wherein the implant is combined with a coating, and the coating is disposed on a surface of the device.

10026. The method of item 9999, wherein the implant is combined with a coating, and the coating directly contacts the device.

10027. The method of item 9999, wherein the implant is combined with a coating, and the coating indirectly contacts the device.

10028. The method of item 9999, wherein the implant is combined with a coating, and the coating partially covers the device.

10029. The method of item 9999, wherein the implant is combined with a coating, and the coating completely covers the device.

10030. The method of item 9999, wherein the implant is combined with a coating, and the coating is a uniform coating.

10031. The method of item 9999, wherein the implant is combined with a coating, and the coating is a non-uniform coating.

10032. The method of item 9999, wherein the implant is combined with a coating, and the coating is a discontinuous coating.

10033. The method of item 9999 wherein the implant is combined with a coating, and the coating is a patterned coating.

10034. The method of item 9999, wherein the implant is combined with a coating, and the coating has a thickness of 100 μm or less.

10035. The method of item 9999, wherein the implant is combined with a coating, and the coating has a thickness of 10 μm or less.

10036. The method of item 9999, wherein the implant is combined with a coating, and the coating adheres to the surface of the device upon deployment of the device.

10037. The method of item 9999, wherein the implant is combined with a coating, and the coating is stable at room temperature for a period of at least 1 year.

10038. The method of item 9999, wherein the implant is combined with a coating, and the fibrosing agent is present in the coating in an amount ranging between about 0.0001% to about 1% by weight.

10039. The method of item 9999, wherein the implant is combined with a coating, and the fibrosing agent is present in the coating in an amount ranging between about 1% to about 10% by weight.

10040. The method of item 9999, wherein the implant is combined with a coating, and the fibrosing agent is present in the coating in an amount ranging between about 10% to about 25% by weight.

10041. The method of item 9999, wherein the implant is combined with a coating, and the fibrosing agent is present in the coating in an amount ranging between about 25% to about 70% by weight.

10042. The method of item 9999, wherein the implant is combined with a coating, and the coating further comprises a polymer.

10043. The method of item 9999, wherein the device comprises a first coating having a first composition and a second coating having a second composition.

10044. The method of item 9999, wherein the device comprises a first coating having a first composition and a second coating having a second composition, where the first composition and the second composition are different.

10045. The method of item 9999, wherein the device comprises a polymer.

10046. The method of item 9999, wherein the device comprises a polymer, and the polymer is a component of the composition.

10047. The method of item 9999, wherein the implant is combined with a polymer, and the polymer is a copolymer.

10048. The method of item 9999, wherein the implant is combined with a polymer, and the polymer is a block copolymer.

10049. The method of item 9999, wherein the implant is combined with a polymer, and the polymer is a random copolymer.

10050. The method of item 9999, wherein the implant is combined with a polymer, and the polymer is a biodegradable polymer.

10051. The method of item 9999, wherein the implant is combined with a polymer, and the polymer is a non-biodegradable polymer.

10052. The method of item 9999, wherein the implant is combined with a polymer, and the polymer is a hydrophilic polymer.

10053. The method of item 9999, wherein the implant is combined with a polymer, and the polymer is a hydrophobic polymer.

10054. The method of item 9999, wherein the implant is combined with a polymer, and the polymer has hydrophilic domains.

10055. The method of item 9999, wherein the implant is combined with a polymer, and the polymer has hydrophobic domains.

10056. The method of item 9999, wherein the implant is combined with a polymer, and the polymer is a non-conductive polymer.

10057. The method of item 9999, wherein the implant is combined with a polymer, and the polymer is an elastomer.

10058. The method of item 9999, wherein the implant is combined with a polymer, and the polymer is a hydrogel.

10059. The method of item 9999, wherein the implant is combined with a polymer, and the polymer is a silicone polymer.

10060. The method of item 9999, wherein the implant is combined with a polymer, and the polymer is a hydrocarbon polymer.

10061. The method of item 9999, wherein the implant is combined with a polymer, and the polymer is a styrene-derived polymer.

10062. The method of item 9999, wherein the implant is combined with a polymer, and the polymer is a butadiene polymer.

10063. The method of item 9999, wherein the implant is combined with a polymer, and the polymer is a macromer.

10064. The method of item 9999, wherein the implant is combined with a polymer, and the polymer is a poly(ethylene glycol) polymer.

10065. The method of item 9999, wherein the implant is combined with a polymer, and the polymer is an amorphous polymer.

10066. The method of item 9999, wherein the implant is combined with a polymer, and the polymer is a lubricious coating.

10067. The method of item 9999 wherein the fibrosing agent is located within pores or holes of the device.

10068. The method of item 9999 wherein the fibrosing agent is located within a channel, lumen, or divet of the device.

10069. The method of item 9999, wherein the implant is further combined with a second pharmaceutically active agent.

10070. The method of item 9999, wherein the implant is further combined with an anti-inflammatory agent.

10071. The method of item 9999 wherein the implant is further combined with an agent that inhibits infection.

10072. The method of item 9999, wherein the implant is further combined with an anthracycline.

10073. The method of item 9999, wherein the implant is further combined with doxorubicin.

10074. The method of item 9999, wherein the implant is further combined with mitoxantrone.

10075. The method of item 9999, wherein the implant is further combined with a fluoropyrimidine.

10076. The method of item 9999, wherein the implant is further combined with 5-fluorouracil (5-FU).

10077. The method of item 9999, wherein the implant is further combined with a folic acid antagonist.

10078. The method of item 9999, wherein the implant is further combined with methotrexate.

10079. The method of item 9999, wherein the implant is further combined with a podophylotoxin.

10080. The method of item 9999, wherein the implant is further combined with etoposide.

10081. The method of item 9999 wherein the implant is further combined with a camptothecin.

10082. The method of item 9999, wherein the implant is further combined with a hydroxyurea.

10083. The method of item 9999, wherein the implant is further combined with a platinum complex.

10084. The method of item 9999, wherein the implant is further combined with cisplatin.

10085. The method of item 9999, wherein the implant is further combined with an anti-thrombotic agent.

10086. The method of item 9999, wherein the implant is further combined with a visualization agent.

10087. The method of item 9999, wherein the implant is further combined with a visualization agent, wherein the visualization agent is a radiopaque material, wherein the radiopaque material comprises a metal, a halogenated compound, or a barium containing compound.

10088. The method of item 9999, wherein the implant is further combined with a visualization agent, wherein the visualization agent is a radiopaque material, wherein the radiopaque material comprises barium, tantalum, or technetium.

10089. The method of item 9999, wherein the implant is further combined with a visualization agent, wherein the visualization agent is a MRI responsive material.

10090. The method of item 9999, wherein the implant is further combined with a visualization agent, wherein the visualization agent comprises a gadolinium chelate.

10091. The method of item 9999, wherein the implant is further combined with a visualization agent, wherein the visualization agent comprises iron, magnesium, manganese, copper, or chromium.

10092. The method of item 9999, wherein the implant is further combined with a visualization agent, wherein the visualization agent comprises an iron oxide compound.

10093. The method of item 9999, wherein the implant is further combined with a visualization agent, wherein the visualization agent comprises a dye, pigment, or colorant.

10094. The method of item 9999, wherein the implant is further combined with an echogenic material.

10095. The method of item 9999, wherein the implant is further combined with an echogenic material, and the echogenic material is in the form of a coating.

10096. The method of item 9999 wherein the device is sterilized.

10097. The method of item 9999 wherein the fibrosing agent is released into tissue in the vicinity of the device after deployment of the device.

10098. The method of item 9999 wherein the fibrosing agent is released into tissue in the vicinity of the device after deployment of the device, wherein the tissue is connective tissue.

10099. The method of item 9999 wherein the fibrosing agent is released into tissue in the vicinity of the device after deployment of the device, wherein the tissue is muscle tissue.

10100. The method of item 9999 wherein the fibrosing agent is released into tissue in the vicinity of the device after deployment of the device, wherein the tissue is nerve tissue.

10101. The method of item 9999 wherein the fibrosing agent is released into tissue in the vicinity of the device after deployment of the device, wherein the tissue is epithelium tissue.

10102. The method of item 9999 wherein the fibrosing agent is released in effective concentrations from the device over a period ranging from the time of deployment of the device to about 1 year.

10103. The method of item 9999 wherein the fibrosing agent is released in effective concentrations from the device over a period ranging from about 1 month to 6 months.

10104. The method of item 9999 wherein the fibrosing agent is released in effective concentrations from the device over a period ranging from about 1–90 days.

10105. The method of item 9999 wherein the fibrosing agent is released in effective concentrations from the device at a constant rate.

10106. The method of item 9999 wherein the fibrosing agent is released in effective concentrations from the device at an increasing rate.

10107. The method of item 9999 wherein the fibrosing agent is released in effective concentrations from the device at a decreasing rate.

10108. The method of item 9999 wherein the fibrosing agent is released in effective concentrations from the composition comprising the fibrosing agent by diffusion over a period ranging from the time of deployment of the device to about 90 days.

10109. The method of item 9999 wherein the fibrosing agent is released in effective concentrations from the composition comprising the fibrosing agent by erosion of the composition over a period ranging from the time of deployment of the device to about 90 days.

10110. The method of item 9999 wherein the device comprises about 0.01 µg to about 10 µg of the fibrosing agent.

10111. The method of item 9999 wherein the device comprises about 10 µg to about 10 mg of the fibrosing agent.

10112. The method of item 9999 wherein the device comprises about 10 mg to about 250 mg of the fibrosing agent.

10113. The method of item 9999 wherein the device comprises about 250 mg to about 1000 mg of the fibrosing agent.

10114. The method of item 9999 wherein the device comprises about 1000 mg to about 2500 mg of the fibrosing agent.

10115. The method of item 9999 wherein a surface of the device comprises less than 0.01 µg of the fibrosing agent per mm² of device surface to which the fibrosing agent is applied.

10116. The method of item 9999 wherein a surface of the device comprises about 0.01 µg to about 1 µg of the fibrosing agent per mm² of device surface to which the fibrosing agent is applied.

10117. The method of item 9999 wherein a surface of the device comprises about 1 µg to about 10 µg of the fibrosing agent per mm² of device surface to which the fibrosing agent is applied.

10118. The method of item 9999 wherein a surface of the device comprises about 10 µg to about 250 µg of the fibrosing agent per mm² of device surface to which the fibrosing agent is applied.

10119. The method of item 9999 wherein a surface of the device comprises about 250 µg to about 1000 µg of the fibrosing agent of fibrosing agent per mm² of device surface to which the fibrosing agent is applied.

10120. The method of item 9999 wherein a surface of the device comprises about 1000 µg to about 2500 µg of the fibrosing agent per mm² of device surface to which the fibrosing agent is applied.

10121. The method of item 9999 wherein the septal occlusion patch is a septal closure device.

10122. The method of item 9999 wherein the septal occlusion patch is a shunt closure device.

10123. The method of item 9999 wherein the septal occlusion patch is an intracardiac occluder.

10124. The method of item 9999 wherein the septal occlusion patch is a defect occluding system.

10125. The method of item 9999 wherein the septal occlusion patch is an intravascular shunt device.

10126. A method of making a medical device comprising combining i) an endoluminal fastener implant with ii) a fibrosing agent or a composition comprising a fibrosing agent, where the fibrosing agent induces a fibrotic response between the device and a patient in which the device is implanted.

10127. The method of item 10126 wherein the fibrosing agent promotes regeneration.

10128. The method of item 10126 wherein the fibrosing agent promotes angiogenesis.

10129. The method of item 10126 wherein the fibrosing agent promotes fibroblast migration.

10130. The method of item 10126 wherein the fibrosing agent promotes fibroblast proliferation.

10131. The method of item 10126 wherein the fibrosing agent promotes deposition of extracellular matrix (ECM).

10132. The method of item 10126 wherein the fibrosing agent promotes tissue remodeling.

10133. The method of item 10126 wherein the fibrosing agent is an arterial vessel wall irritant.

10134. The method of item 10126 wherein the fibrosing agent promotes adhesion between the device and a host into which the device is implanted.

10135. The method of item 10126 wherein the device delivers the fibrosing agent locally to tissue proximate to the device.

10136. The method of item 10126 wherein the fibrosing agent is or comprises silk.

10137. The method of item 10126 wherein the fibrosing agent is or comprises mineral particles.

10138. The method of item 10126 wherein the fibrosing agent is or comprises chitosan.

10139. The method of item 10126 wherein the fibrosing agent is or comprises polylysine.

10140. The method of item 10126 wherein the fibrosing agent is or comprises fibronectin.

10141. The method of item 10126 wherein the fibrosing agent is or comprises bleomycin.

10142. The method of item 10126 wherein the fibrosing agent is or comprises CTGF.

10143. The method of item 10126 wherein the fibrosing agent is in the form of a thread, or is in contact with a thread.

10144. The method of item 10126 wherein the fibrosing agent is in the form of a particulate.

10145. The method of item 10126 wherein the composition further comprises an inflammatory cytokine.

10146. The method of item 10126 wherein the composition further comprises an agent that stimulates cell proliferation.

10147. The method of item 10126 wherein the composition is in the form of a gel or paste.

10148. The method of item 10126 wherein the fibrosing agent is in the form of tufts.

10149. The method of item 10126 wherein the fibrosing agent promotes adhesion between the device and a host into which the device is implanted.

10150. The method of item 10126 wherein the device delivers the fibrosing agent locally to tissue proximate to the device.

10151. The method of item 10126, wherein the implant is combined with a coating, and the coating comprises the fibrosing agent.

10152. The method of item 10126, wherein the implant is combined with a coating, and the coating is disposed on a surface of the device.

10153. The method of item 10126, wherein the implant is combined with a coating, and the coating directly contacts the device.

10154. The method of item 10126, wherein the implant is combined with a coating, and the coating indirectly contacts the device.

10155. The method of item 10126, wherein the implant is combined with a coating, and the coating partially covers the device.

10156. The method of item 10126, wherein the implant is combined with a coating, and the coating completely covers the device.

10157. The method of item 10126, wherein the implant is combined with a coating, and the coating is a uniform coating.

10158. The method of item 10126, wherein the implant is combined with a coating, and the coating is a non-uniform coating.

10159. The method of item 10126, wherein the implant is combined with a coating, and the coating is a discontinuous coating.

10160. The method of item 10126 wherein the implant is combined with a coating, and the coating is a patterned coating.

10161. The method of item 10126, wherein the implant is combined with a coating, and the coating has a thickness of 100 μm or less.

10162. The method of item 10126, wherein the implant is combined with a coating, and the coating has a thickness of 10 μm or less.

10163. The method of item 10126, wherein the implant is combined with a coating, and the coating adheres to the surface of the device upon deployment of the device.

10164. The method of item 10126, wherein the implant is combined with a coating, and the coating is stable at room temperature for a period of at least 1 year.

10165. The method of item 10126, wherein the implant is combined with a coating, and the fibrosing agent is present in the coating in an amount ranging between about 0.0001% to about 1% by weight.

10166. The method of item 10126, wherein the implant is combined with a coating, and the fibrosing agent is present in the coating in an amount ranging between about 1% to about 10% by weight.

10167. The method of item 10126, wherein the implant is combined with a coating, and the fibrosing agent is present in the coating in an amount ranging between about 10% to about 25% by weight.

10168. The method of item 10126, wherein the implant is combined with a coating, and the fibrosing agent is present in the coating in an amount ranging between about 25% to about 70% by weight.

10169. The method of item 10126, wherein the implant is combined with a coating, and the coating further comprises a polymer.

10170. The method of item 10126, wherein the device comprises a first coating having a first composition and a second coating having a second composition.

10171. The method of item 10126, wherein the device comprises a first coating having a first composition and a second coating having a second composition, where the first composition and the second composition are different.

10172. The method of item 10126, wherein the device comprises a polymer.

10173. The method of item 10126, wherein the device comprises a polymer, and the polymer is a component of the composition.

10174. The method of item 10126, wherein the implant is combined with a polymer, and the polymer is a copolymer.

10175. The method of item 10126, wherein the implant is combined with a polymer, and the polymer is a block copolymer.

10176. The method of item 10126, wherein the implant is combined with a polymer, and the polymer is a random copolymer.

10177. The method of item 10126, wherein the implant is combined with a polymer, and the polymer is a biodegradable polymer.

10178. The method of item 10126, wherein the implant is combined with a polymer, and the polymer is a non-biodegradable polymer.

10179. The method of item 10126, wherein the implant is combined with a polymer, and the polymer is a hydrophilic polymer.

10180. The method of item 10126, wherein the implant is combined with a polymer, and the polymer is a hydrophobic polymer.

10181. The method of item 10126, wherein the implant is combined with a polymer, and the polymer has hydrophilic domains.

10182. The method of item 10126, wherein the implant is combined with a polymer, and the polymer has hydrophobic domains.

10183. The method of item 10126, wherein the implant is combined with a polymer, and the polymer is a non-conductive polymer.

10184. The method of item 10126, wherein the implant is combined with a polymer, and the polymer is an elastomer.

10185. The method of item 10126, wherein the implant is combined with a polymer, and the polymer is a hydrogel.

10186. The method of item 10126, wherein the implant is combined with a polymer, and the polymer is a silicone polymer.

10187. The method of item 10126, wherein the implant is combined with a polymer, and the polymer is a hydrocarbon polymer.

10188. The method of item 10126, wherein the implant is combined with a polymer, and the polymer is a styrene-derived polymer.

10189. The method of item 10126, wherein the implant is combined with a polymer, and the polymer is a butadiene polymer.

10190. The method of item 10126, wherein the implant is combined with a polymer, and the polymer is a macromer.

10191. The method of item 10126, wherein the implant is combined with a polymer, and the polymer is a poly(ethylene glycol) polymer.

10192. The method of item 10126, wherein the implant is combined with a polymer, and the polymer is an amorphous polymer.

10193. The method of item 10126, wherein the implant is combined with a polymer, and the polymer is a lubricious coating.

10194. The method of item 10126 wherein the fibrosing agent is located within pores or holes of the device.

10195. The method of item 10126 wherein the fibrosing agent is located within a channel, lumen, or divet of the device.

10196. The method of item 10126, wherein the implant is further combined with a second pharmaceutically active agent.

10197. The method of item 10126, wherein the implant is further combined with an anti-inflammatory agent.

10198. The method of item 10126 wherein the implant is further combined with an agent that inhibits infection.

10199. The method of item 10126, wherein the implant is further combined with an anthracycline.

10200. The method of item 10126, wherein the implant is further combined with doxorubicin.

10201. The method of item 10126, wherein the implant is further combined with mitoxantrone.

10202. The method of item 10126, wherein the implant is further combined with a fluoropyrimidine.

10203. The method of item 10126, wherein the implant is further combined with 5-fluorouracil (5-FU).

10204. The method of item 10126, wherein the implant is further combined with a folic acid antagonist.

10205. The method of item 10126, wherein the implant is further combined with methotrexate.

10206. The method of item 10126, wherein the implant is further combined with a podophylotoxin.

10207. The method of item 10126, wherein the implant is further combined with etoposide.

10208. The method of item 10126 wherein the implant is further combined with a camptothecin.

10209. The method of item 10126, wherein the implant is further combined with a hydroxyurea.

10210. The method of item 10126, wherein the implant is further combined with a platinum complex.

10211. The method of item 10126, wherein the implant is further combined with cisplatin.

10212. The method of item 10126, wherein the implant is further combined with an anti-thrombotic agent.

10213. The method of item 10126, wherein the implant is further combined with a visualization agent.

10214. The method of item 10126, wherein the implant is further combined with a visualization agent, wherein the visualization agent is a radiopaque material, wherein the radiopaque material comprises a metal, a halogenated compound, or a barium containing compound.

10215. The method of item 10126, wherein the implant is further combined with a visualization agent, wherein the visualization agent is a radiopaque material, wherein the radiopaque material comprises barium, tantalum, or technetium.

10216. The method of item 10126, wherein the implant is further combined with a visualization agent, wherein the visualization agent is a MRI responsive material.

10217. The method of item 10126, wherein the implant is further combined with a visualization agent, wherein the visualization agent comprises a gadolinium chelate.

10218. The method of item 10126, wherein the implant is further combined with a visualization agent, wherein the visualization agent comprises iron, magnesium, manganese, copper, or chromium.

10219. The method of item 10126, wherein the implant is further combined with a visualization agent, wherein the visualization agent comprises an iron oxide compound.

10220. The method of item 10126, wherein the implant is further combined with a visualization agent, wherein the visualization agent comprises a dye, pigment, or colorant.

10221. The method of item 10126, wherein the implant is further combined with an echogenic material.

10222. The method of item 10126, wherein the implant is further combined with an echogenic material, and the echogenic material is in the form of a coating.

10223. The method of item 10126 wherein the device is sterilized.

10224. The method of item 10126 wherein the fibrosing agent is released into tissue in the vicinity of the device after deployment of the device.

10225. The method of item 10126 wherein the fibrosing agent is released into tissue in the vicinity of the device after deployment of the device, wherein the tissue is connective tissue.

10226. The method of item 10126 wherein the fibrosing agent is released into tissue in the vicinity of the device after deployment of the device, wherein the tissue is muscle tissue.

10227. The method of item 10126 wherein the fibrosing agent is released into tissue in the vicinity of the device after deployment of the device, wherein the tissue is nerve tissue.

10228. The method of item 10126 wherein the fibrosing agent is released into tissue in the vicinity of the device after deployment of the device, wherein the tissue is epithelium tissue.

10229. The method of item 10126 wherein the fibrosing agent is released in effective concentrations from the device over a period ranging from the time of deployment of the device to about 1 year.

10230. The method of item 10126 wherein the fibrosing agent is released in effective concentrations from the device over a period ranging from about 1 month to 6 months.

10231. The method of item 10126 wherein the fibrosing agent is released in effective concentrations from the device over a period ranging from about 1–90 days.

10232. The method of item 10126 wherein the fibrosing agent is released in effective concentrations from the device at a constant rate.

10233. The method of item 10126 wherein the fibrosing agent is released in effective concentrations from the device at an increasing rate.

10234. The method of item 10126 wherein the fibrosing agent is released in effective concentrations from the device at a decreasing rate.

10235. The method of item 10126 wherein the fibrosing agent is released in effective concentrations from the composition comprising the fibrosing agent by diffusion over a period ranging from the time of deployment of the device to about 90 days.

10236. The method of item 10126 wherein the fibrosing agent is released in effective concentrations from the composition comprising the fibrosing agent by erosion of the composition over a period ranging from the time of deployment of the device to about 90 days.

10237. The method of item 10126 wherein the device comprises about 0.01 µg to about 10 µg of the fibrosing agent.

10238. The method of item 10126 wherein the device comprises about 10 µg to about 10 mg of the fibrosing agent.

10239. The method of item 10126 wherein the device comprises about 10 mg to about 250 mg of the fibrosing agent.

10240. The method of item 10126 wherein the device comprises about 250 mg to about 1000 mg of the fibrosing agent.

10241. The method of item 10126 wherein the device comprises about 1000 mg to about 2500 mg of the fibrosing agent.

10242. The method of item 10126 wherein a surface of the device comprises less than 0.01 µg of the fibrosing agent per mm$^2$ of device surface to which the fibrosing agent is applied.

10243. The method of item 10126 wherein a surface of the device comprises about 0.01 µg to about 1 µg of the fibrosing agent per mm$^2$ of device surface to which the fibrosing agent is applied.

10244. The method of item 10126 wherein a surface of the device comprises about 1 µg to about 10 µg of the fibrosing agent per mm$^2$ of device surface to which the fibrosing agent is applied.

10245. The method of item 10126 wherein a surface of the device comprises about 10 µg to about 250 µg of the fibrosing agent per mm$^2$ of device surface to which the fibrosing agent is applied.

10246. The method of item 10126 wherein a surface of the device comprises about 250 µg to about 1000 µg of the fibrosing agent of fibrosing agent per mm$^2$ of device surface to which the fibrosing agent is applied.

10247. The method of item 10126 wherein a surface of the device comprises about 1000 µg to about 2500 µg of the fibrosing agent per mm$^2$ of device surface to which the fibrosing agent is applied.

The following examples are offered by way of illustration, and not by way of limitation.

EXAMPLES

Example 1

Coating of Medical Implants with Fibronectin

The coating apparatus consisted of an overhead stirrer (Fisher Scientific) orientated horizontally. A conical stainless steel head is attached to the revolving chuck of the stirrer. One end of an aneurysm coil is pulled up onto the conical head until held firmly. The other end is attached to a clip-swivel device that holds the medical implant in a horizontal position, but allowed the medical implant to rotate along its axis. The stirrer is then set to rotate at 30 rpm so that the whole medical implant rotates along the horizontal axis at this speed. A 1% (w/w) fibronectin (Calbiochem, San Diego, Calif.) solution in sterile water is prepared. Two hundred microliters of this solution is slowly pipetted as a 3 mm wide ring located 5 mm from the end of the medical implant fixed in the conical steel head over a period of 2 minutes as the medical implant rotates. The fibronectin is then dried under a stream of nitrogen as the medical implant continues to rotate. When dry, the medical implant is removed, turned around and the other end of the medical implant coated in the same manner. Using this method a flexible ring of fibronectin is deposited on both ends of the medical implant without compromise of the physical characteristics of the medical implant. Other examples of medical implants that may be coated in a similar fashion include vascular (vaso-) occlusive coils and vascular (vaso-) occlusion implants.

Example 2

Coating of Medical Implants with Poly-L-Lysine

A medical implant is coated using the procedure described in Example 1. A 1% (w/w) poly-L-lysine (Sigma, St. Louis, Mo.) solution in sterile water is prepared. Two hundred microliters of this solution is slowly pipetted as a 3 mm wide ring located 5 mm from the end of the medical implant fixed in the conical steel head over a period of 2 minutes as the medical implant rotates. The poly-L-lysine is then dried under a stream of nitrogen as the medical implant continues to rotate. When dry, the medical implant is removed, turned around and the other end of the medical implant coated in the same manner. Using this method a flexible ring of poly-L-Lysine is deposited on both ends of the medical implant without compromise of the physical characteristics of the medical implant.

Example 3

Coating of Medical Implants with N-Carboxybutyl Chitosan

A medical implant is coated using the procedure described in Example 1. A 1% (w/w) n-carboxybutyl chitosan (Carbomer, Westborough, Mass.) solution in sterile water is prepared. Two hundred microliters of this solution is slowly pipetted as a 3 mm wide ring located 5 mm from the end of the medical implant fixed in the conical steel head over a period of 2 minutes as the medical implant rotates. The n-carboxybutyl chitosan is dried under a stream of nitrogen as the medical implant continues to rotate. When dry, the medical implant is removed, turned around and the other end coated in the same manner. Using this method a flexible ring of n-carboxybutyl chitosan is deposited on both ends of the medical implant without compromise of the physical characteristics of the medical implant.

Example 4

Coating of Medical Implants with Bromocriptine In Poly(Ethylene Vinyl Acetate)

A medical implant is coated using the procedure described in Example 1. A 4.5% w/w solution of EVA (60/40 ratio ethylene to vinyl acetate) (Polysciences USA) is prepared in dichloromethane. Bromocriptine mesylate (Sigma, St. Louis, Mo.) is dissolved/suspended in this solution at 5 mg/ml. Two hundred microliters of this solution is slowly pipetted as a 3 mm wide ring located 5 mm from the end of the medical implant fixed in the conical steel head over a period of 2 minutes as the medical implant rotates. The EVA/bromocriptine is dried under a stream of nitrogen as the medical implant continues to rotate. When dry, the medical implant is removed, turned around and the other end of the medical implant coated in the same manner. Using this method a flexible ring of EVA/bromocriptine is deposited on both ends of the medical implant without compromise of the physical characteristics of the medical implant.

Example 5

Preparation of Inflammatory Microcrystals

Monosodium urate monohydrate (MSUM) microcrystals were grown. A solution of uric acid and sodium hydroxide at 55° C. and pH 8.9 was left to stand overnight at room temperature. The crystals were rinsed several times with cold (4° C.) distilled water and dried at 60° C. for 12 hours in a circulating hot-air oven (Fisher, Isotemp).

Triclinic calcium pyrophosphate dihydrate (CPPD) crystals were prepared as follows. A 250 ml beaker containing 103 ml distilled water was heated in a water bath to 60° C., and stirred constantly with a TEFLON-coated stir bar. The stirring was slowed and 0.71 ml of concentrated hydrochloric acid and 0.32 ml of glacial acetic acid were added, followed by 0.6 g of calcium acetate. A 150 ml beaker containing 20 ml distilled water was heated to 60° C. in the water bath, and 0.6 g calcium acetate added. The rate of stir was increased in the 250 ml beaker, and 2 g of calcium acid pyrophosphate added rapidly. When the $CaH_2P_2O_7$ had nearly all dissolved, the rate of stirring was reduced for 5 minutes, then over a period of 15 seconds, the contents of the small beaker were poured into the large beaker with vigorous stirring. In the preparation of subsequent batches, a minute amount of triclinic CPPD crystals was added to the large beaker as seed material. Stirring was discontinued, leaving a white gel. This was allowed to remain undisturbed in the cooling water bath. The pH of the supernatant was always less than 3.0. The gel collapsed as CPPD crystals formed in 24 hours. The crystals were washed in distilled water 3 times, washed in ethanol then acetone, and air dried.

Example 6

Coating of Medical Implants with Inflammatory Microcrystals (Monosodium Urate Monohydrate or Calcium Pyrophosphate Dihydrate)

A medical implant is coated according to the procedure described in Example 1. A 4.5% w/w solution of EVA (60/40 ratio ethylene to vinyl acetate) (Polysciences) is prepared in dichloromethane. Inflammatory microcrystals (MSUM or CPPD) are ground in a pestle and mortar to a particle size of 10 to 50 micrometers and suspended in the solution at 5 mg/ml. Two hundred microliters of this suspension is slowly pipetted as a 3 mm wide ring located 5 mm from the end of the medical implant fixed in the conical steel head over a period of 2 minutes as the medical implant rotates. The EVA/microcrystal coating is then dried under a stream of nitrogen as the medical implant continues to rotate. When dry, the medical implant is removed, turned around and the other end of the medical implant coated in the same manner. Using this method a flexible ring of EVA/microcrystals is deposited on both ends of the medical implant without compromise of the physical characteristics of the medical implant.

Example 7

Coating of Medical Implants with Inflammatory Microcrystals (Monosodium Urate Monohydrate or Calcium Pyrophosphate Dihydrate)

A 1% w/w solution of medical grade polyurethane (PU) (Thermomedics, Woburn, Mass.) is prepared in dichloromethane. Inflammatory microcrystals (CPPD or MSUM) are ground in a pestle and mortar to a particle size of 10 to 50 micrometers and suspended in the solution at 2 mg/ml. Immediately prior to surgical insertion each end of a medical implant (e.g., aneurysm coil or hernia mesh) is inserted into the shaken suspension to a depth of approximately 5 mm for 2 seconds. The medical implant is air-dried (gently rotated by hand for 3 minutes). Using this method a flexible ring of coating of EVA/microcrystals is deposited on both ends of the medical implant without compromise of the physical characteristics of the medical implant.

Example 8

Coating of Medical Implants with Bromocriptine in Polyurethane

A 1% w/w solution of medical grade polyurethane (PU) (Thermomedics) is prepared in dichloromethane. Bromocriptine mesylate (Sigma) at 5% w/w to PU is dissolved/suspended in this solution. The solution is placed in a 5 ml Fisher TLC atomizer (Fisher Scientific). Prior to surgery the medical implant is suspended vertically in a fume hood and 1 ml of the solution sprayed (using nitrogen propellant) onto the bottom 1 cm of the medical implant by revolving the medical implant through 360 degrees. The medical implant is dried for 2 minutes and then the other end of the medical implant is sprayed in a similar manner. The medical implant is then further air dried (gently rotated by hand for 3 minutes). Using this method a flexible ring of bromocriptine/PU is deposited on both ends of the medical implant without compromise of the physical characteristics of the medical implant. It is envisaged that ultimately a bromocriptine/PU solution in DCM may be available to the surgeon in the form of a small aerosol can for the above procedure.

Example 9

Coating of Medical Implants with Inflammatory Microcrystals (Monosodium Urate Monohydrate or Calcium Pyrophosphate Dihydrate)

A medical implant is coated according to the procedure described in Example 1. A 4.5% w/w solution of poly(lactide co-glycolide) (85:15) (IV 0.61) (Birmingham Polymers, Birmingham, Ala.) blended with methoxypolyethylene glycol 350 (MePEG 350) (Union Carbide, Danbury, Conn.) in a ratio of 80:20 w/w (PLGA:MePEG) is prepared in dichloromethane. Inflammatory microcrystals are suspended in the solution at 5 mg/ml. Two hundred microliters of this suspension is slowly pipetted as a 3 mm wide ring located 5 mm from the end of the medical implant fixed in the conical steel head over a period of 2 minutes as the medical implant rotates. The PLGA/MePEG/inflammatory crystals are then dried under a stream of nitrogen as the medical implant continues to rotate. When dry, the medical implant is removed, turned around and the other end of the medical implant coated in the same manner. Using this method a flexible ring of PLGA/MePEG/microcrystals is deposited on both ends of the medical implant without compromise of the physical characteristics of the medical implant.

Example 10

Coating of Medical Implants with Angiotensin 2 Encapsulated in Polyethylene Glycol (PEG)

1.8 grams of polyethylene glycol (PEG 1475) (Union Carbide) is placed in a flat-bottomed 20 ml glass scintillation vial and warmed to 50° C. to melt the PEG in a water bath, 200 mg of glycerol (Fisher Scientific) is added. 2 mg of angiotensin 2 (Sigma) is weighed into the vial and blended/ dissolved into the melted PEG at 50° C. The vial is angled at 10 degrees in a water bath by use of a clamp. Each end of a medical implant (e.g., aneurysm coil or hernia mesh) is dipped rotated into the molten formulation, so that a ring of that a coating of the material is deposited on the bottom 5 mm of the exterior surface of the medical implant. The medical implant is then cooled and stored at 4° C. until use. Alternatively, to enable dipping immediately prior to surgery the PEG/angiotensin mixture is stored at 4° C. until use. Immediately prior to surgery, the vial of PEG/angiotensin is warmed to 50° C. for 2 minutes to melt and the medical implant is coated as described above.

Example 11

Coating of Medical Implants with Transforming Growth Factor-9 (TGF-9) in Crosslinked Hyaluronic Acid A medical implant is coated according to the procedure described in Example 1. A 1% solution of hyaluronic acid (HA) (Sodium salt, Sigma) in water, containing 30% glycerol (w/w to HA) (Fisher Scientific) and 8 mM 1-ethyl-3-(−3 dimethylaminopropyl)carbodiimide (EDAC) is prepared by dissolution overnight. TGF-9 (Calbiochem, San Diego, Calif.) is dissolved at 0.01 mg/ml in this solution. Two hundred microliters of this solution is slowly pipetted as a 3 mm wide ring located 5 mm from the end of the medical implant fixed in the conical steel head over a period of 2 minutes as the medical implant rotates. The HA/glycerol/TGF-9 solution is dried under a stream of nitrogen as the medical implant continues to rotate. When dry, the medical implant is removed, turned around and the other end coated in the same manner. Using this method a flexible ring of HA/glycerol/TGF-9 is deposited on both ends of the medical implant without compromise of the physical characteristics of the medical implant.

Example 12

Coating of Medical Implants with Fibroblast Growth Factor (FGF) in Crosslinked Chitosan A medical implant is coated according to the procedure described in Example 1. A 1% solution of chitosan (Medical grade, Carbomer, Westborough, Mass.) in dilute acetic acid (pH 5), containing 30% glycerol (w/w to chitosan) (Fisher Scientific) and 0.5% glutaraldehyde (Sigma, St. Louis, Mo.) is prepared by dissolution overnight. FGF (Calbiochem, San Diego, Calif.) is dissolved at 0.01 mg/ml in this solution. Two hundred microliters of this solution is slowly pipetted as a 3 mm wide ring located 5 mm from the end of the medical implant fixed in the conical steel head over a period of 2 minutes as the medical implant rotates. The chitosan/glycerol/FGF solution is dried under a stream of nitrogen as the medical implant continues to rotate. When dry, the medical implant is removed, turned around and the other end coated in the same manner. Using this method a flexible ring of chitosan/glycerol/FGF is deposited on both ends of the medical implant without compromise of the physical characteristics of the medical implant.

Example 13

Screening Procedure for Assessment of Perigraft Reaction

A rabbit perivascular model is described for identifying arterial vessel wall irritants. Large domestic rabbits are placed under general anesthetic. Using aseptic precautions, the infrarenal abdominal aorta is exposed and clamped at its superior and inferior aspects. A longitudinal arterial wall arteriotomy is performed and a 2 millimeter diameter, 1 centimeter long segment of PTFE graft is inserted within the aorta and the proximal and distal aspect of the graft is sewn so that the entire aortic blood flow is through the graft which is contained in the abdominal aorta in the manner of open surgical abdominal aortic repair in humans (except that no aneurysm is present in this model). The aortotomy is then surgically closed and the abdominal wound closed and the animal recovered.

The animals are randomized to receive standard PTFE grafts or grafts of which the middle 1 cm is coated alone circumferentially with nothing (control), or with an agent that induces a vessel wall reaction or adhesion between a stent graft and vessel wall alone or contained in a slow release, polymer such as polycaprolactone or polylactic acid.

The animals are sacrificed between 1 and 6 weeks post surgery, the aorta is removed en bloc and the area in relation to the graft is grossly examined for adhesive reaction. Any difference in morphology or histology of the vessel wall from portions of the artery which contain no graft, portion which contain graft without coating, and portion which contained graft with coating is noted.

Example 14

Animal Abdominal Aortic Aneurysm Model

An animal model is described for determining whether a stent graft containing a biologically active or irritative substance stimulates fibrosis. Pigs or sheep are placed under general anesthetic. Using aseptic precautions the abdominal aorta is exposed. The animal is heparinized and the aorta is cross clamped below the renal arteries and above the bifurcation. Collaterals are temporarily controlled with vessel loops or clips that are removed upon completion of the procedure. A longitudinal aortotomy is created in the arterial aspect of the aorta, and an elliptical shaped patch of rectus sheath from the same animal is sutured into the aortotomy to create an aneurysm. The aortic clamps from the lumbar arteries and collaterals are removed and the abdomen closed. After 30 days, the animal is reanesthesized and the abdominal wall again opened. A cutdown is performed on the iliac artery and through this, a stent graft is positioned across the infrarenal abdominal aorta aneurysm extending from normal infrarenal abdominal aorta above to normal infrarenal abdominal aorta below the surgically created aneurysm and the device is released in a conventional way.

Animals are randomized into groups of 5 receiving uncoated stent grafts, stent graft containing slow release polymer alone, and stent graft containing a biologically active or irritative substance as determined by the previously mentioned screening exam. After closure of the arteriotomy and of the abdominal wound, the animal is allowed to recover. At 6 weeks and 3 months post stent graft insertion, the animal is sacrificed and the aorta removed en bloc. The infrarenal abdominal aorta is examined for evidence of histologic reaction and perigraft leaking.

Example 15

Screening Assay for Assessing the Effect of Cyclosporine a on Cell Proliferation An in vitro assay is described for determining whether a substance stimulates cell (fibroblast) proliferation (see, In Vitro Toxicol. (1990) 3: 219; Biotech. Histochem. (1993) 68: 29; Anal. Biochem. (1993) 213: 426). Smooth muscle cells at 70–90% confluency are trypsinized, replated at 600 cells/well in media in 96-well plates and allowed to attachment overnight. Cyclosporine A is prepared in DMSO at a concentration of $10^{-2}$ M and diluted 10-fold to give a range of stock concentrations ($10^{-8}$ M to $10^{-2}$ M). Drug dilutions are diluted 1/1000 in media and added to cells to give a total volume of 200 µL/well. Each drug concentration is tested in triplicate wells. Plates containing smooth muscle cells and cyclosporine A are incubated at 37° C. for 72 hours.

To terminate the assay, the media is removed by gentle aspiration. A 1/400 dilution of CYQUANT 400×GR dye indicator (Molecular Probes; Eugene, Oreg.) is added to 1× cell lysis buffer, and 200 µL of the mixture is added to the wells of the plate. Plates are incubated at room temperature, protected from light for 3–5 minutes. Fluorescence is read in a fluorescence microplate reader at ~480 nm excitation wavelength and ~520 nm emission maxima. Activation of proliferation is determined by taking the average of triplicate wells and comparing average relative fluorescence units to the DMSO control (see FIG. 1).

Figure 2:
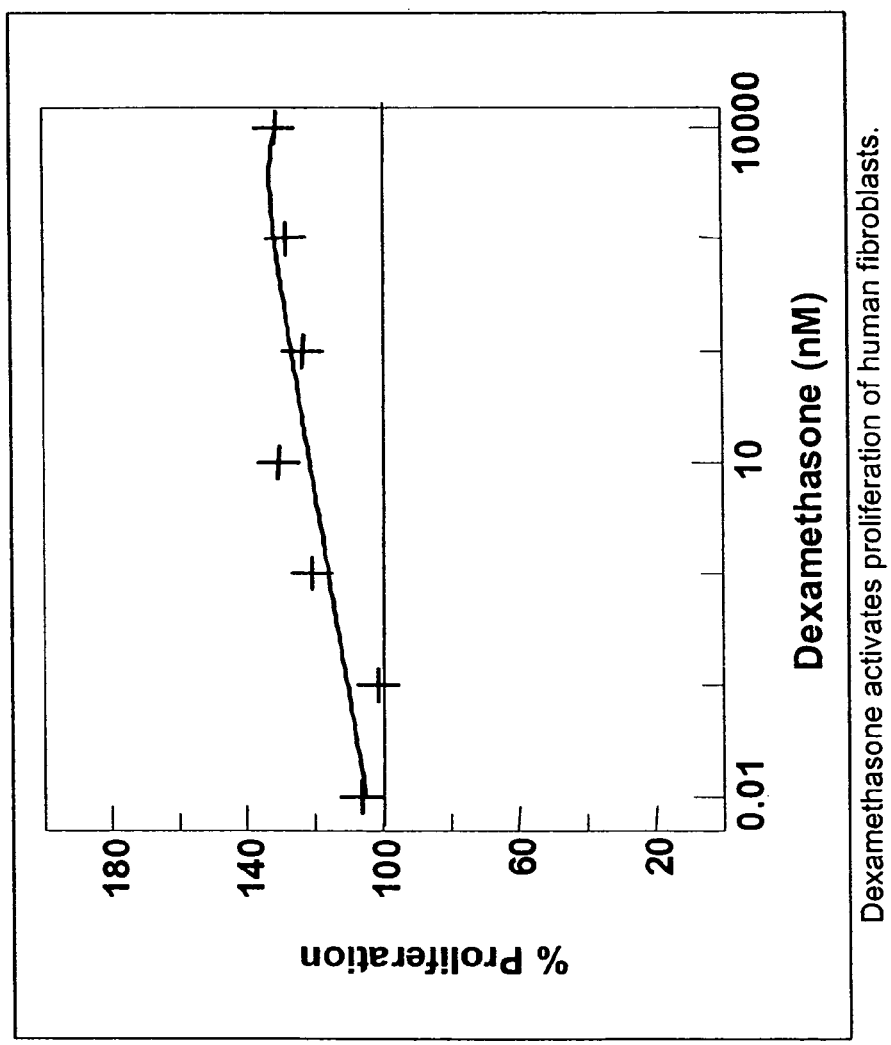
FIG. 2 is a graph showing the effect of dexamethasone on proliferation of human fibroblasts.
Figure 3:
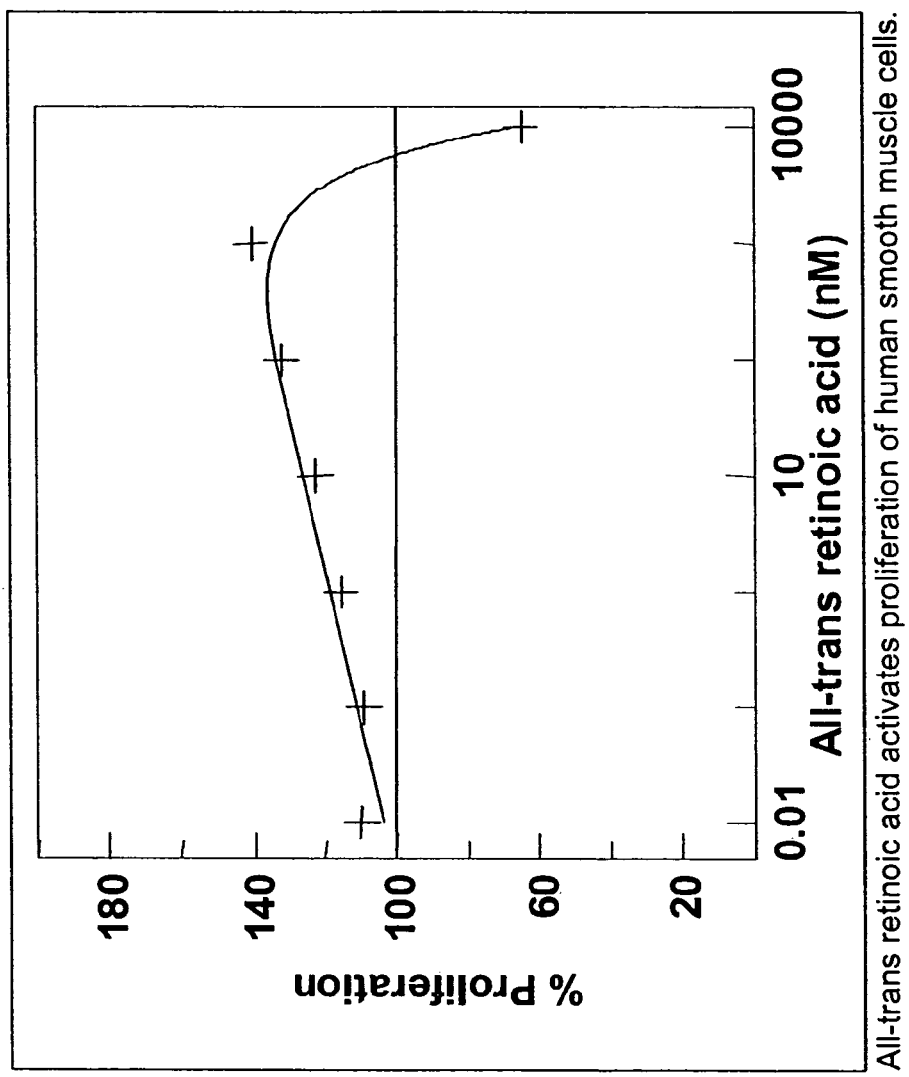
FIG. 3 is a graph showing the effect of all-trans retinoic acid (ATRA) on proliferation of human smooth muscle cells.
Figure 4:
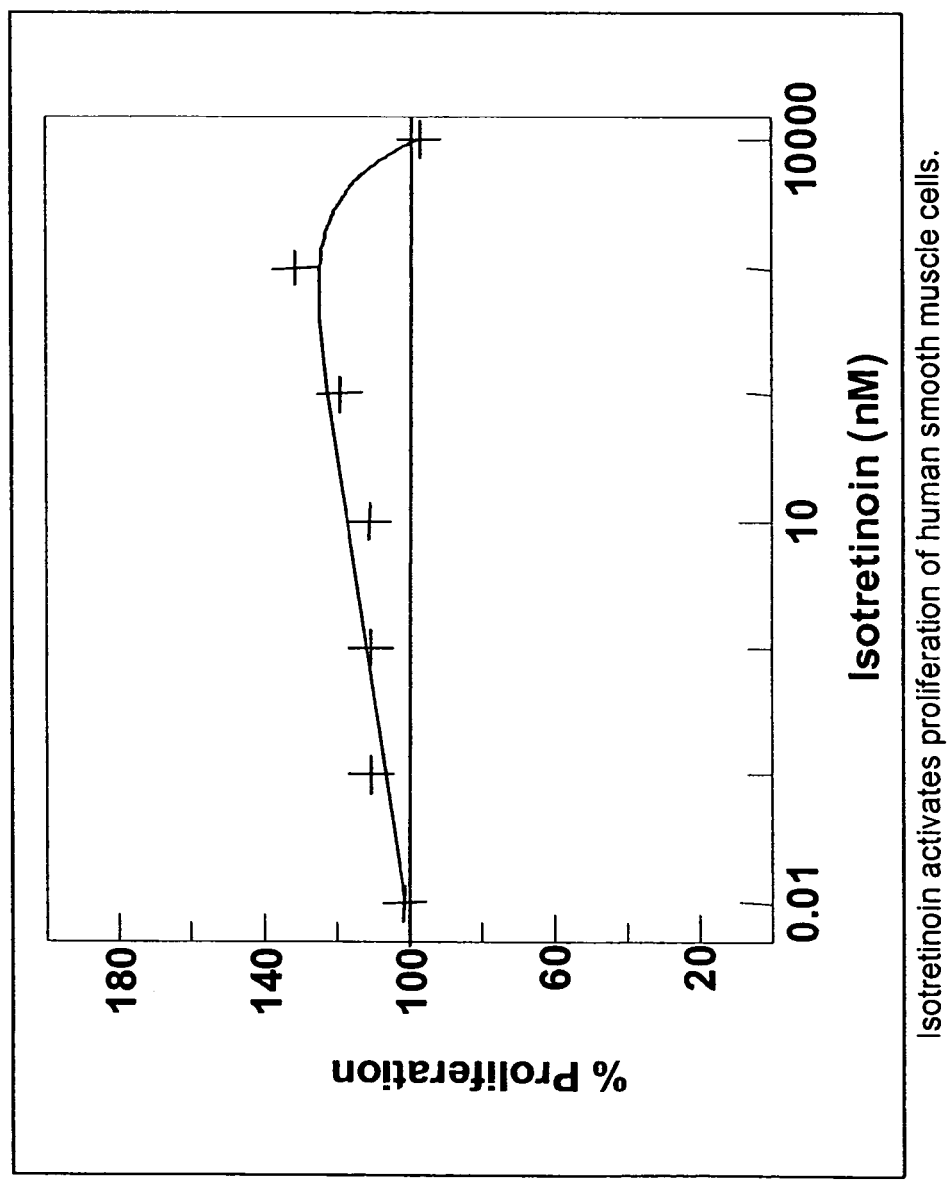
FIG. 4 is a graph showing the effect of isotretinoin on proliferation of human smooth muscle cells.
Figure 5:
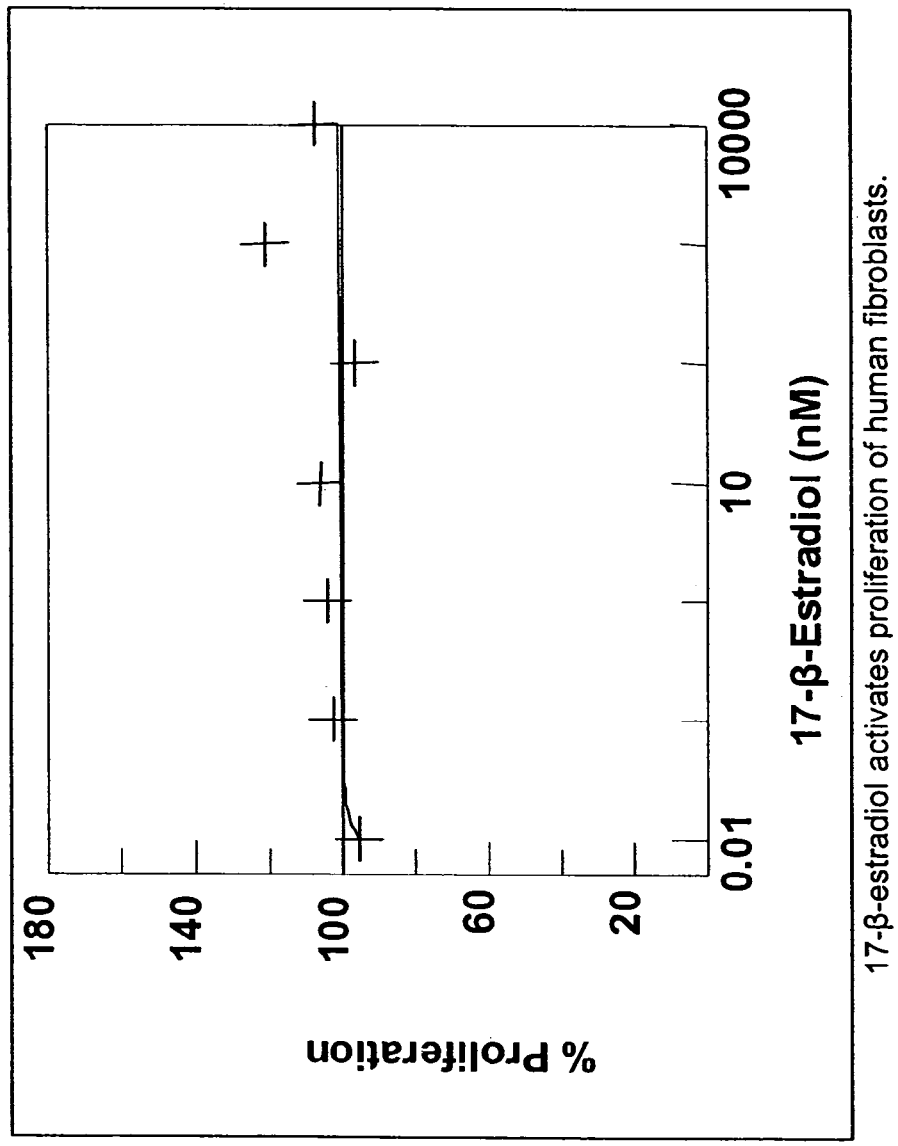
FIG. 5 is a graph showing the effect of 17-β-estradiol on proliferation of human fibroblasts.
Figure 6:
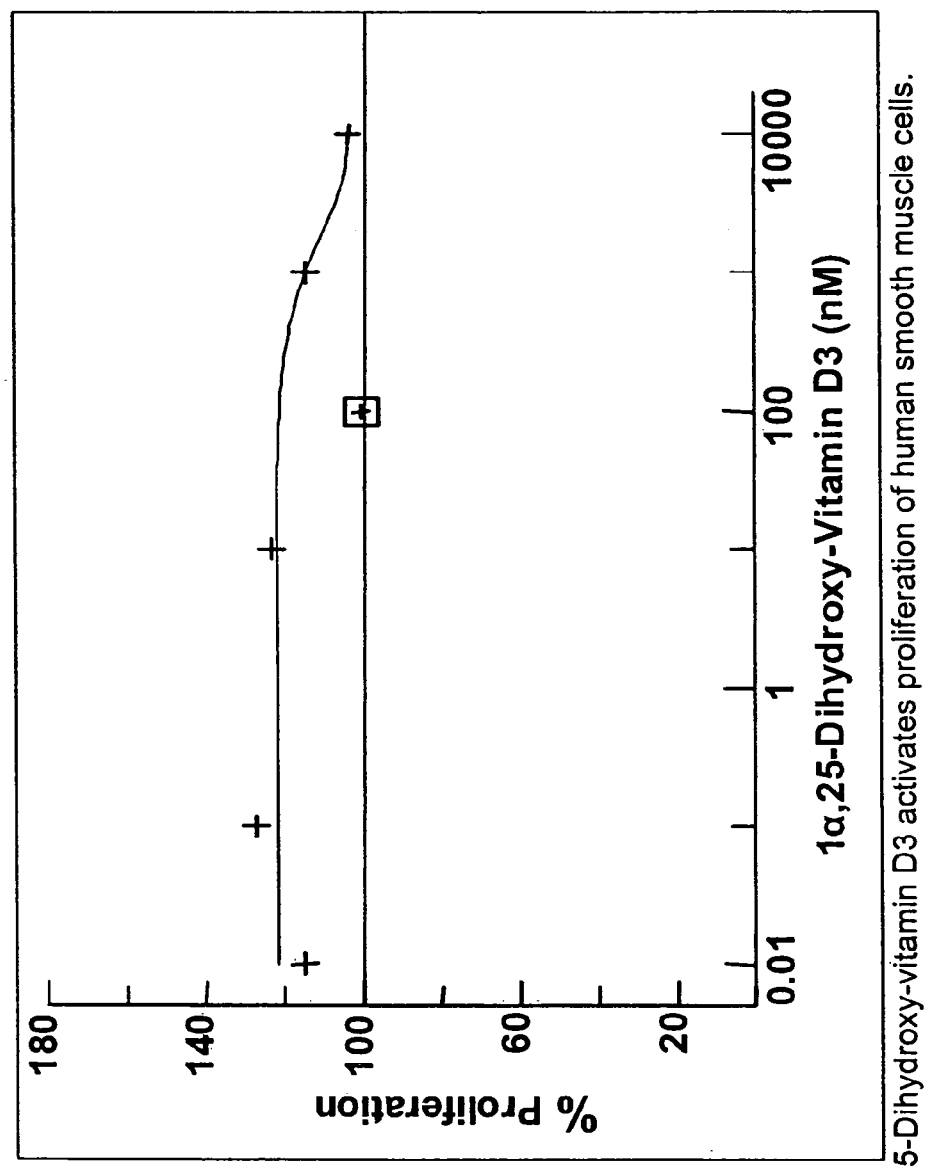
FIG. 6 is a graph showing the effect of 1a,25-dihydroxy-vitamin $D_3$ on proliferation of human smooth muscle cells.

The assay was repeated for the following proliferative therapeutic agents: dexamethasone (FIG. 2), all-trans retinoic acid (FIG. 3), isotretinoin (FIG. 4), 17-β-estradiol (FIG. 5), and 1a,25-dihydroxy-vitamin $D_3$ (FIG. 6).

Example 16

Screening Assay for Assessing the Effect of PDGF on Smooth Muscle Cell Migration An in vitro assay is described for determining whether a substance stimulates cell (fibroblast) migration. Primary human smooth muscle cells are starved of serum in smooth muscle cell basal media containing insulin and human basic fibroblast growth factor (bFGF) for 16 hours prior to the assay. For the migration assay, cells are trypsinized to remove cells from flasks, washed with migration media and diluted to a concentration of $2-2.5\times10^5$ cells/ml in migration media. Migration media consists of phenol red free Dulbecco's Modified Eagle Medium (DMEM) containing 0.35% human serum albumin. A 100 µL volume of smooth muscle cells (approximately 20,000–25,000 cells) is added to the top of a Boyden chamber assembly (Chemicon QCM CHEMOTAXIS 96-well migration plate). To the bottom wells, the chemotactic agent, recombinant human platelet derived growth factor (rhPDGF-BB) is added at a concentration of 10 ng/ml in a total volume of 150 µL. Paclitaxel is prepared in DMSO at a concentration of $10^{-2}$ M and serially diluted 10-fold to give a range of stock concentrations ($10^{-8}$ M to $10^{-2}$ M). Paclitaxel is added to cells by directly adding paclitaxel DMSO stock solutions, prepared earlier, at a 1/1000 dilution, to the cells in the top chamber. Plates are incubated for 4 hours to allow cell migration.

Figure 7:
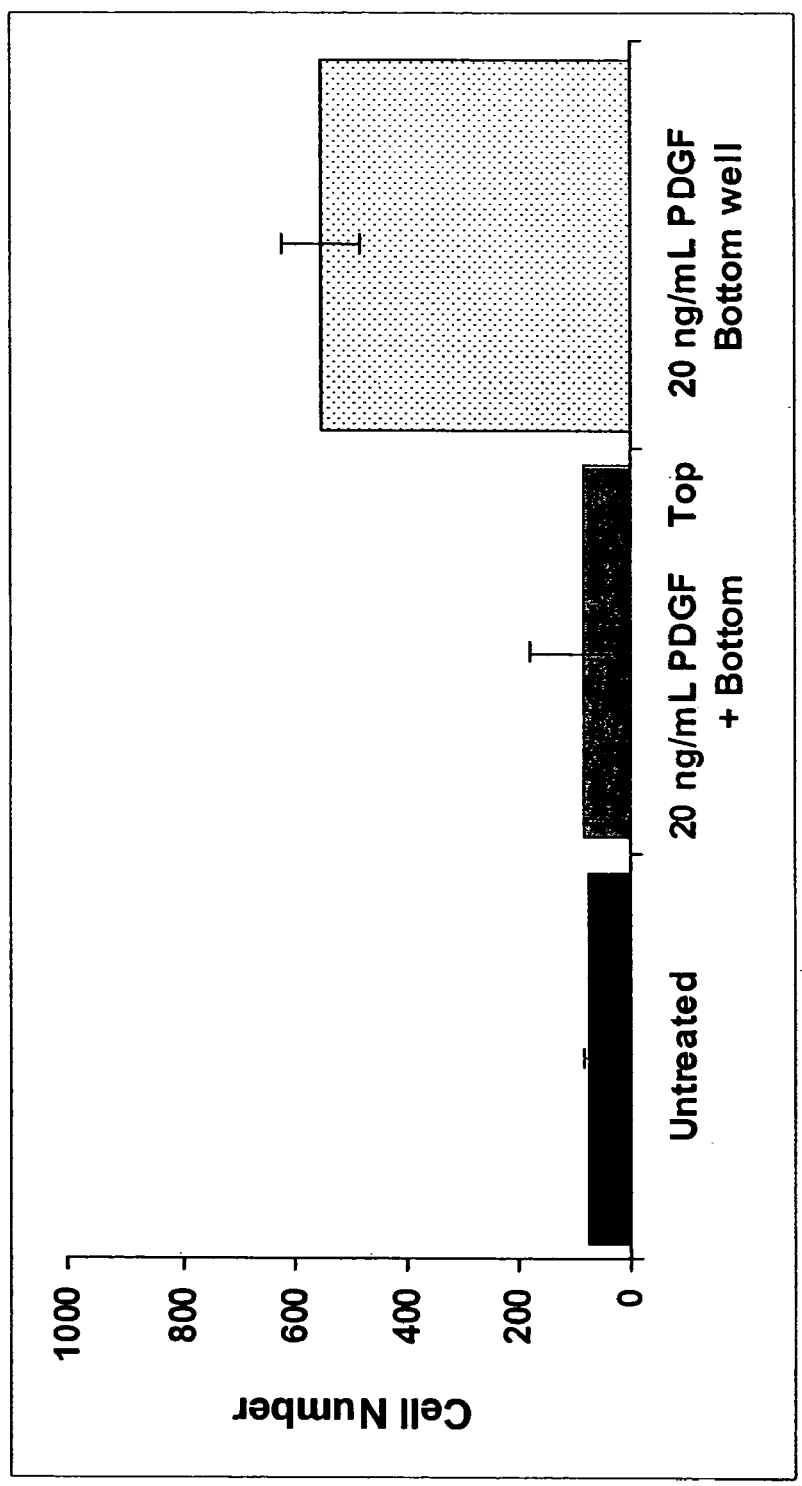
FIG. 7 is a graph showing the effect of PDGF-BB on smooth muscle cell migration.

At the end of the 4 hour period, cells in the top chamber are discarded and the smooth muscle cells attached to the underside of the filter are detached for 30 minutes at 37° C. in Cell Detachment Solution (Chemicon). Dislodged cells are lysed in lysis buffer containing the DNA binding CYQUANT GR dye and incubated at room temperature for 15 minutes. Fluorescence is read in a fluorescence microplate reader at ~480 nm excitation wavelength and ~520 nm emission maxima. Relative fluorescence units from triplicate wells are averaged after subtracting background fluorescence (control chamber without chemoattractant) and average number of cells migrating is obtained from a standard curve of smooth muscle cells serially diluted from 25,000 cells/well down to 98 cells/well. Inhibitory concentration of 50% ($IC_{50}$) is determined by comparing the average number of cells migrating in the presence of paclitaxel to the positive control (smooth muscle cell chemotaxis in response to rhPDGF-BB). See FIG. 7. References: Biotechniques (2000) 29: 81; J. Immunol Methods (2001) 254: 85.

Example 17

In Vivo Evaluation of Silk Coated Perivascular Pu Films to Assess Scarring

Figure 8:
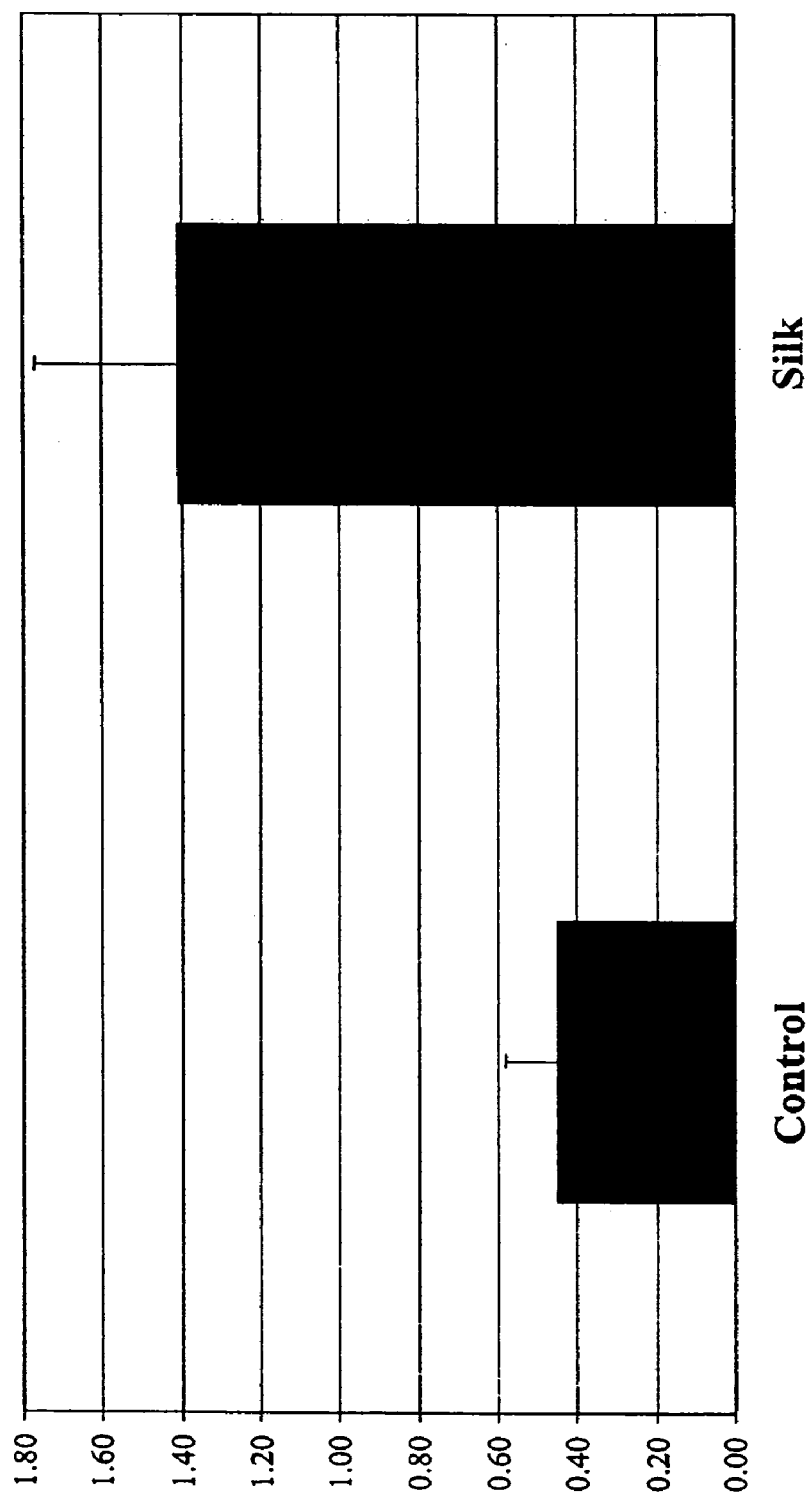
FIG. 8 is a bar graph showing the area of granulation tissue in carotid arteries exposed to silk coated perivascular polyurethane (PU) films relative to arteries exposed to uncoated PU films.

A rat carotid artery model is described for determining whether a substance stimulates fibrosis. Wistar rats weighing 300 g to 400 g are anesthetized with halothane. The skin over the neck region is shaved and the skin is sterilized. A vertical incision is made over the trachea and the left carotid artery is exposed. A polyurethane film covered with silk strands or a control uncoated PU film is wrapped around a distal segment of the common carotid artery. The wound is closed and the animal is recovered. After 28 days, the rats are sacrificed with carbon dioxide and pressure-perfused at 100 mmHg with 10% buffered formaldehyde. Both carotid arteries are harvested and processed for histology. Serial cross-sections can be cut every 2 mm in the treated left carotid artery and at corresponding levels in the untreated right carotid artery. Sections are stained with H&E and Movat's stains to evaluate tissue growth around the carotid artery. Area of perivascular granulation tissue is quantified by computer-assisted morphometric analysis. Area of the granulation tissue is significantly higher in the silk coated group than in the control uncoated group. See FIG. 8.

Example 18

In Vivo Evaluation of Perivascular PU Films Coated with Different Silk Suture Material to Assess Scarring A rat carotid artery model is described for determining whether a substance stimulates fibrosis. Wistar rats weighing 300 g to 400 g are anesthetized with halothane. The skin over the neck region is shaved and the skin is sterilized. A vertical incision is made over the trachea and the left carotid artery is exposed. A polyurethane film covered with silk sutures from one of three different manufacturers (3-0 Silk-Black Braided (Davis & Geck), 3-0 SOFSILK (U.S. Surgical/Davis & Geck), and 3-0 Silk-Black Braided (LIGAPAK) (Ethicon, Inc.) is wrapped around a distal segment of the common carotid artery. (The polyurethane film can also be coated with other agents to induce fibrosis.) The wound is closed and the animal is allowed to recover.

Figure 9:
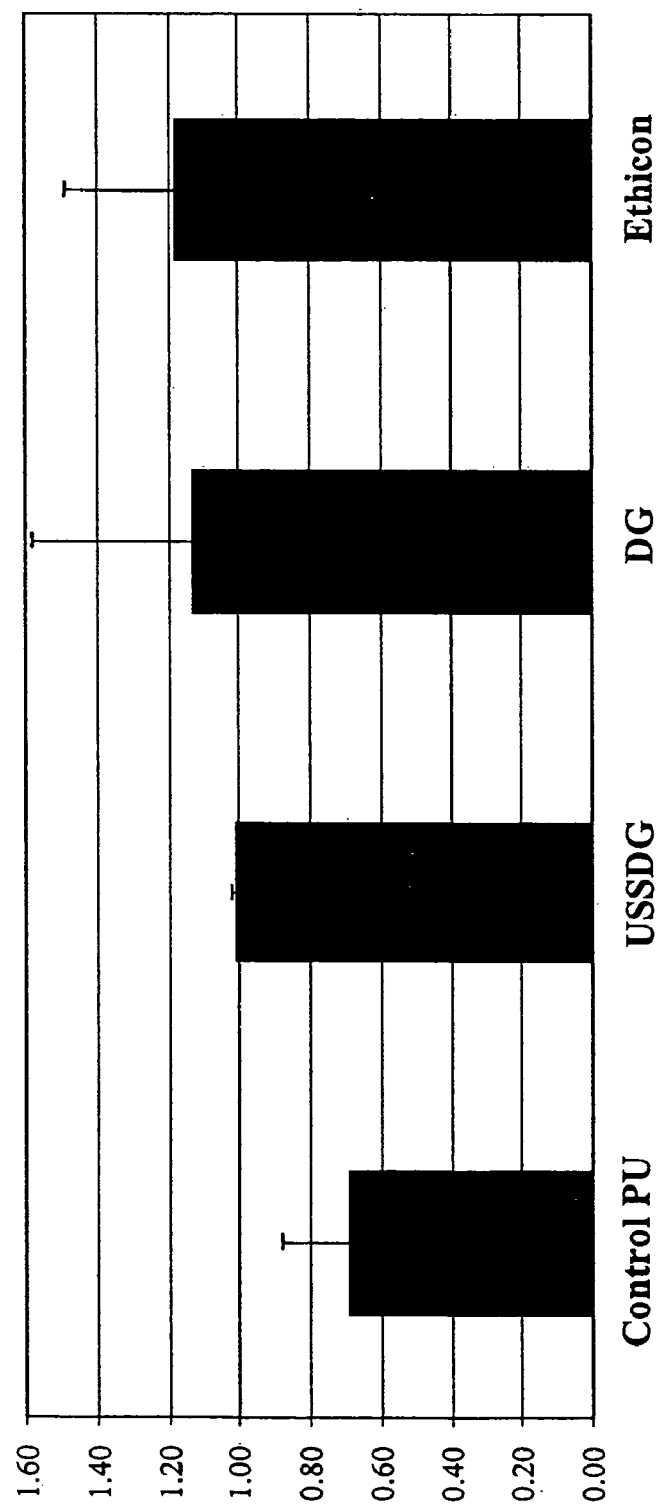
FIG. 9 is a bar graph showing the area of granulation tissue in carotid arteries exposed to silk suture coated perivascular PU films relative to arteries exposed to uncoated PU films.

After 28 days, the rats are sacrificed with carbon dioxide and pressure-perfused at 100 mmHg with 10% buffered formaldehyde. Both carotid arteries are harvested and processed for histology. Serial cross-sections are be cut every 2 mm in the treated left carotid artery and at corresponding levels in the untreated right carotid artery. Sections are stained with H&E and Movat's stains to evaluate tissue growth around the carotid artery. Area of perivascular granulation tissue is quantified by computer-assisted morphometric analysis. Thickness of the granulation tissue is the same in the three groups showing that tissue proliferation around silk suture is independent of manufacturing processes. See FIG. 9.

Example 19

In Vivo Evaluation of Perivascular Silk Powder to Assess Scarring

A rat carotid artery model is described for determining whether a substance stimulates fibrosis. Wistar rats weighing 300 g to 400 g are anesthetized with halothane. The skin over the neck region is shaved and the skin is sterilized. A vertical incision is made over the trachea and the left carotid artery is exposed. Silk powder is sprinkled on the exposed artery that is then wrapped with a PU film. Natural silk powder or purified silk powder (without contaminant proteins) is used in different groups of animals. Carotids wrapped with PU films only are used as a control group. The wound is closed and the animal is allowed to recover. After 28 days, the rats are sacrificed with carbon dioxide and pressure-perfused at 100 mmHg with 10% buffered formaldehyde. Both carotid arteries are harvested and processed for histology. Serial cross-sections can be cut every 2 mm in the treated left carotid artery and at corresponding levels in the untreated right carotid artery. Sections are stained with H&E and Movat's stains to evaluate tissue growth around the carotid artery. Area of tunica intima, tunica media and perivascular granulation tissue is quantified by computer-assisted morphometric analysis.

Figure 10:
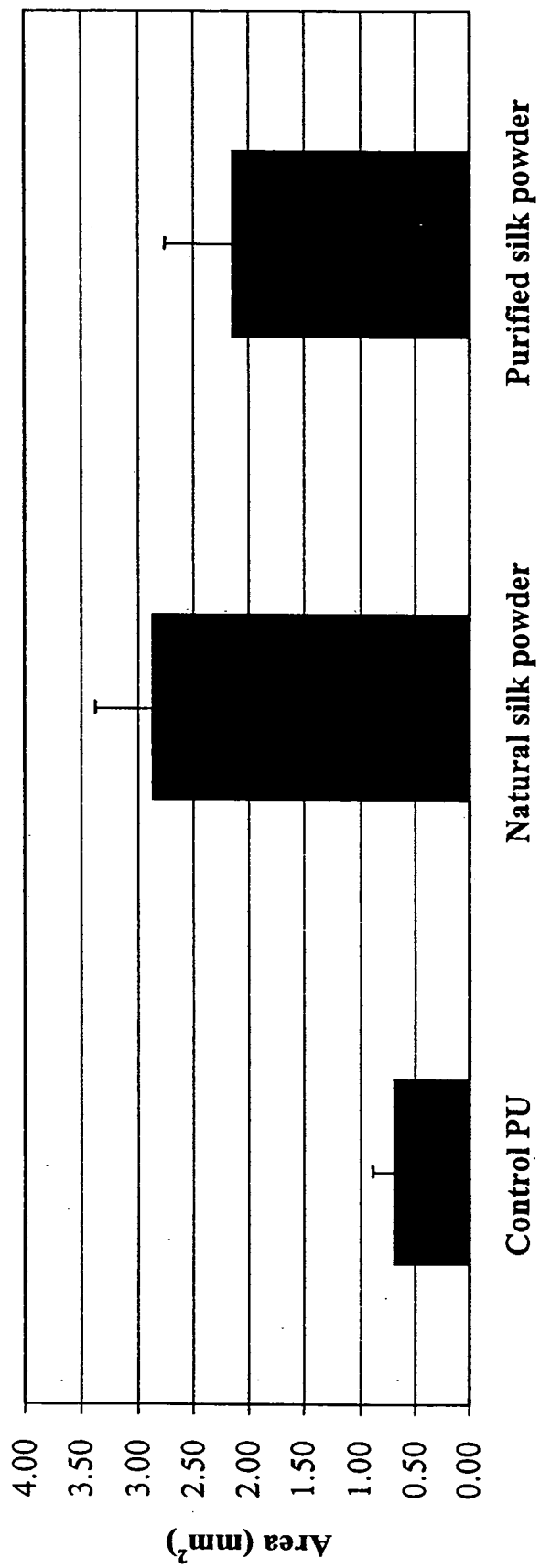
FIG. 10 is a bar graph showing the area of granulation tissue in carotid arteries exposed to natural and purified silk powder and wrapped with perivascular PU film relative to a control group in which arteries are wrapped with perivascular PU film only.

The natural silk caused a severe cellular inflammation consisting mainly of a neutrophil and lymphocyte infiltrate in a fibrin network without any extracellular matrix or blood vessels. In addition, the treated arteries were seriously damaged with hypocellular media, fragmented elastic laminae and thick intimal hyperplasia. Intimal hyperplasia contained many inflammatory cells and was occlusive in 2/6 cases. This severe immune response was likely triggered by antigenic proteins coating the silk protein in this formulation. On the other end, the regenerated silk powder triggered only a mild foreign body response surrounding the treated artery. This tissue response was characterized by inflammatory cells in extracellular matrix, giant cells and blood vessels. The treated artery was intact. These results show that removing the coating proteins from natural silk prevents the immune response and promotes benign tissue growth. Degradation of the regenerated silk powder was underway in some histology sections indicating that the tissue response can likely mature and heal over time. See FIG. 10.

Example 20

In Vivo Evaluation of Perivascular Talcum Powder to Assess Scarring

Figure 11:
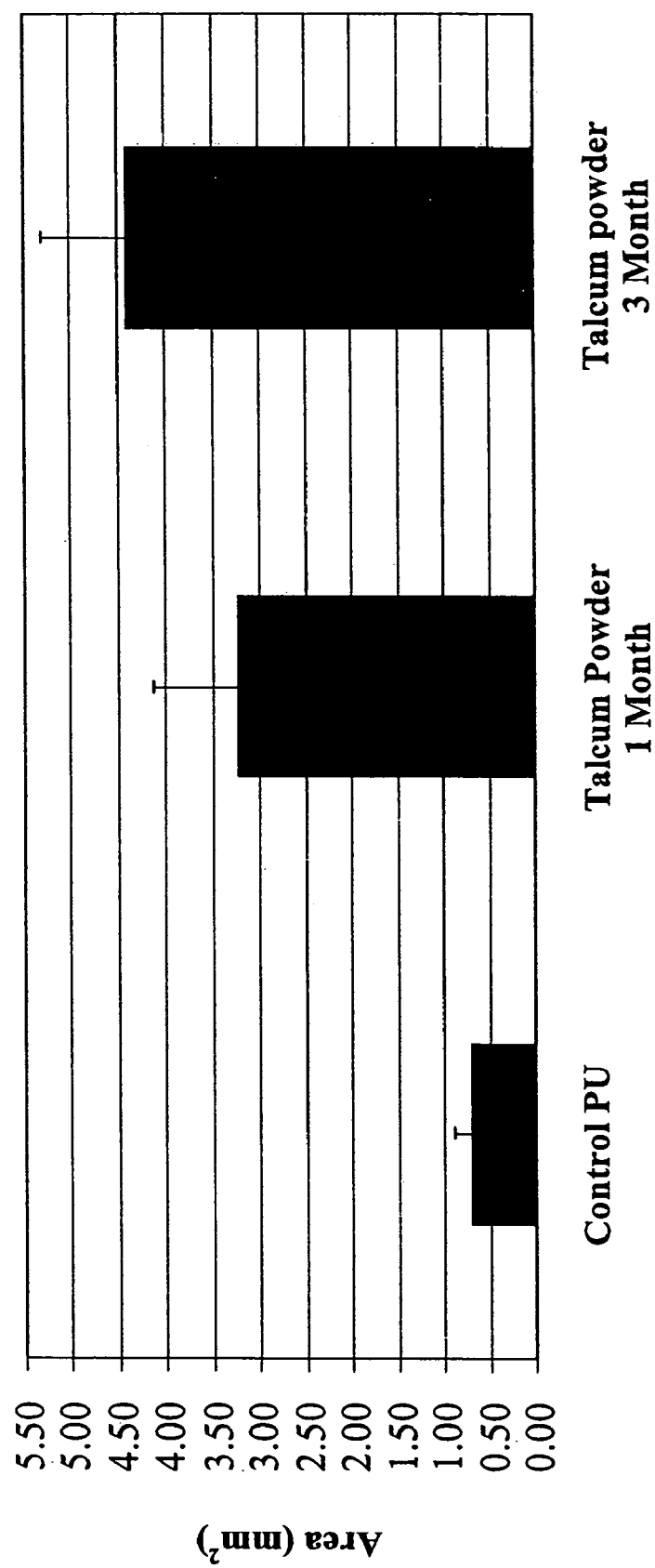
FIG. 11 is a bar graph showing the area of granulation tissue (at 1 month and 3 months) in carotid arteries sprinkled with talcum powder and wrapped with perivascular PU film relative to a control group in which arteries are wrapped with perivascular PU film only.

A rat carotid artery model is described for determining whether a substance stimulates fibrosis. Wistar rats weighing 300 g to 400 g are anesthetized with halothane. The skin over the neck region is shaved and the skin is sterilized. A vertical incision is made over the trachea and the left carotid artery is exposed. Talcum powder is sprinkled on the exposed artery that is then wrapped with a PU film. Carotids wrapped with PU films only are used as a control group. The wound is closed and the animal is recovered. After 1 or 3 months, the rats are sacrificed with carbon dioxide and pressure-perfused at 100 mmHg with 10% buffered formaldehyde. Both carotid arteries are harvested and processed for histology. Serial cross-sections are cut every 2 mm in the treated left carotid artery and at corresponding levels in the untreated right carotid artery. Sections are stained with H&E and Movat's stains to evaluate tissue growth around the carotid artery. Thickness of tunica intima, tunica media and perivascular granulation tissue is quantified by computer-assisted morphometric analysis. Histopathology results and morphometric analysis showed the same local response to talcum powder at 1 month and 3 months. A large tissue reaction trapped the talcum powder at the site of application around the blood vessel. This tissue was characterized by a large number of macrophages within a dense extracellular matrix with few neutrophiles, lymphocytes and blood vessels. The treated blood vessel appeared intact and unaffected by the treatment. Overall, this result showed that talcum powder induced a mild long-lasting fibrotic reaction that was subclinical in nature and did not harm any adjacent tissue. See FIG. 11.

Example 21

Preparation of Silk Powder

Several pieces of silk braid (Ethicon, 4-0, 638) are cut into lengths of approx 0.4 cm. These cut pieces are placed in a 100 ml round bottom flask that contains 50 ml 2M NaOH. The sample is stirred using a magnetic stirrer at room temperature for 24 h. The sample is neutralized using concentrated HCl. The neutralized contents are then dialyzed against deionized water using cellulose-based dialysis tubing (WMCO approx 3000; Spectrum). The sample is dialyzed for 48 hours with 5 water changes. The dialyzed sample is then poured into a 100 ml round bottom flask. The sample is frozen and freeze-dried to yield a fluffy powdered material.

Example 22

Coating of Medical Implants with a Powdered Silk/PLGA Coating

A medical device (e.g., aneurysm coil) attached to a stainless steel rod (with the aid of a bulldog clip) that is attached to a Fisher overhead stirrer that is orientated vertically. The stirrer is set to rotate at 30 rpm. A 2% PLGA (9K, 50:50, Birmingham Polymers) solution (ethyl acetate) that contains the powdered silk is sprayed onto the rotating implant using an airbrush spray device. The concentration of the powdered silk in the PLGA solution is altered from 0.1% to 50%. After the spraying process, the device is allowed to air dry for 30 minutes while still rotating. The device is then removed from the pipette tip and is further dried under vacuum for 24 h.

Example 23

Coating of Tube with a Powdered Silk/Polyurethane Coating

A polyurethane tube is pushed onto a 1 ml plastic pipette tip. The open end of the pipette tip is attached to a stainless steel rod that is attached to a Fisher overhead stirrer that is orientated horizontally. The stirrer is set to rotate at 30 rpm. A 2% CHRONOFLEX AL 85A (CT Biomaterials) solution (THF) that contains powdered silk (prepared using a cryomill) is sprayed onto the rotating tube using a TLC spray device. The concentration of the powdered silk in the polyurethane solution is altered from 0.1% to 50%. After the spraying process, the tube is allowed to air dry for 30 minutes while still rotating. The tube is then removed from the pipette tip and is further dried under vacuum for 24 h.

Example 24

Top-Coating of a Coated Tube with a Degradable Coating

The coated tube from Example 24 is reattached to the overhead stirrer and is rotated at 30 rpm. A 10% 20:80 MePEG(750)-PLA block copolymer solution (acetone) is sprayed onto the rotating tube using an TLC spray device. After the spraying process, the tube is allowed to air dry for 30 minutes while still rotating. The spray coating process can be repeated until the desired thickness or uniformity of coating is obtained. The tube is then removed from the pipette tip and is further dried under vacuum for 24 h.

Example 25

Top-Coating of a Coated Tube with a Heparin-Containing Degradable Coating

The coated tube from Example 24 is reattached to the overhead stirrer and is rotated at 30 rpm. A 10% 20:80 MePEG(750)-PLA block copolymer solution (acetone) that contains various amounts of a heparin benzalkonium chloride complex (PolySciences) is sprayed onto the rotating tube using an TLC spray device. After the spraying process, the tube is allowed to air dry for 30 minutes while still rotating. The spray coating process can be repeated until the desired thickness or uniformity of coating is obtained. The tube is then removed from the pipette tip and is further dried under vacuum for 24 h.

Example 26

Coating of a Coated Tube with a Heparin Coating

The coated tube from Example 24 is reattached to the overhead stirrer and is rotated at 30 rpm. A solution that contains various amounts of a Heparin benzalkonium chloride complex (PolySciences) in IPA is sprayed onto the rotating tube using a TLC spray device. After the spraying process, the tube is allowed to air dry for 30 minutes while still rotating. The spray coating process can be repeated until the desired thickness or uniformity of coating is obtained. The tube is then removed from the pipette tip and is further dried under vacuum for 24 h.

Example 27

Coating of Tube with a Powdered Silk/Cyclosporine a/Polyurethane Coating

A polyurethane tube is pushed onto a 1 ml plastic pipette tip. The open end of the pipette tip is attached to a stainless steel rod that is attached to a Fisher overhead stirrer that is orientated horizontally. The stirrer is set to rotate at 30 rpm. A 2% CHRONOFLEX AL 85A solution (THF) that contains the powdered silk and cyclosporine A is sprayed onto the rotating tube using an TLC spray device. The concentration of the powdered silk in the polyurethane solution is altered from 0.1% to 50% (w/w relative to the polymer) and the concentration of the Cyclosporine A is altered from 0.1% to 10% (w/w relative to the polymer). Afterthe spraying process, the tube is allowed to air dry for 30 minutes while still rotating. The tube is then removed from the pipette tip and is further dried under vacuum for 24 h.

Example 28

Film Impregnated with Silk Fibers

A 20% CHRONOFLEX AL 85A solution (THF) was cast onto a silicone-coated release liner. The solvent allowed to dry. Pieces of 3-0 Silk-Black Braided (LIGAPAK) (Ethicon, Inc.) were placed on the surface of the polyurethane film. Drops of THF were then added to the surface of the polyurethane film. Using a glass scintillation vial as a roller, the silk strands were embedded into the surface of the polyurethane film.

Example 29

In Situ Forming Silk—Containing Gel

Methylated collagen is prepared by the following process: bovine corium collagen is solubilized using pepsin and purified as described in U.S. Pat. No. 4,233,360. This purified, solubilized collagen is precipitated by neutralization into 0.2 M sodium phosphate, pH 7.2. The precipitate is isolated by centrifugation to a final concentration of 70 mg/ml. The material is dried for two days, and then pulverized. Dry methanol containing HCl (to 0.1 N) is added (40 ml) and stirred for four days. Collagen is separated from the acidic methanol, vacuum dried and sterilized by irradiation. The final product is dissolved in water at a pH of 3–4.

For delivery as a gel, 10 mg of the methylated collagen, 100 mg of a tetra-functional sulfhydryl-PEG (pentaerythritol poly(ethylene glycol)ether tetra-sulfhydryl), 10,000 MW, and 100 mg of a tetra-functional succinimidyl PEG (pentaerythritol poly(ethylene glycol)ether tetra-succinimidyl glutarate), 10,000 MW, are dissolved in water at pH 3–4 to a final volume of 1 ml (first component). The second component is 1 ml of phosphate/carbonate buffer (300 mM sodium monobasic phosphate is mixed with 300 mM sodium carbonate. If required, the pH is adjusted with NaOH or HCl to achieve pH 9.6. The final molarity is approximately 117 mM phosphate and 183 mM carbonate). Various amounts (1 mg to 100 mg) of silk powder (prepared using a cryomill) is added to the phosphate/carbonate buffer. Each component is placed in a syringe and mixed and sprayed on the desired test site using a manual dual-syringe delivery system or a air-assisted dual syringe delivery system (FibriJet, Micromedics).

Example 30

Coating of the Silk Braid with a Polymer/Biologically Agent—Direct Dipping

Silk braid (Ethicon, 4-0, 638) is cut into approximately 10 cm lengths. The silk braid is dipped into a chloroform solution of poly(lactide-co-glycolide) (PLGA) (9K, 50:50, Birmingham Polymers) and cyclosporine A. The concentration of the PLGA is altered from 0.1% to 20% (w/v) and concentration of the cyclosporine A in the solution is altered from 0.1% to a saturated solution. The silk braid is immersed in the PLGA/cyclosporine A solution for 5 minutes. The silk braid is then removed and air-dried. The cyclosporine A loaded silk braid is then further dried under vacuum. The silk braid is then attached to a polyurethane film by placing the coated-braids on the polyurethane film and then pressing the film/braids in a heat press for about 10 seconds such that the coated braid is embedded in the polyurethane film.

Example 31

In Situ Forming Silk—Containing Gel

For delivery as a gel, 200 mg of a tetra-functional succinimidyl PEG (pentaerythritol poly(ethylene glycol) ether tetra-succinimidyl glutarate) 10,000 MW s dissolved in water at pH 2.5 (adjusted with HCl) to a final volume of 1 ml (first component). The second component is 1 ml of phosphate/carbonate Buffer (300 mM sodium monobasic phosphate is mixed with 300 mM sodium carbonate. If required, the pH is adjusted with NaOH or HCl to achieve pH 9.6. The final molarity is approximately 117 mM phosphate and 183 mM carbonate) that contains 200 mg of a tetra-functional amino-PEG (pentaerythritol poly(ethylene glycol)ethertetra-amino), 10,000 MW. Various amounts (1 mg to 200 mg) of the silk powder are added to the acidic buffer. Each component is placed in a syringe and is sprayed on the desired test site using a manual dual-syringe delivery system or a air-assisted dual syringe delivery system (Fibri-Jet, Micromedics).

Example 32

Cyclosporine A—Containing Coating

A 5% CHRONOFLEX AL 85A solution (chloroform) containing from 0.1% to 10% cyclosporine A is prepared. A piece of polyurethane tubing is immersed in and then withdrawn from the coating solution. The coated sample is air-dried in the fume-hood. Samples of different coating thicknesses are prepared by repeating the dip-coating process. The coated sample is then dried under vacuum for 24 hours.

Example 33

Collagen Synthesis Assay

An in vitro assay is described for determining whether a substance promotes deposition of extracellular matrix (ECM). Normal human dermal fibroblasts were trypzanized, then re-plated in medium containing ascorbic acid-2-phosphate at 150,000 cells per well in a 12-well plate. The cells were cultured at 37° C. and 5% $CO_2$ for 2–3 weeks with media changes every three days so that they formed a 3-D matrix of cells and collagen. After 14–21 days of culture, the medium was replaced with serum free medium and the cells allowed to rest for 24 hours.

Drug was diluted in DMSO at $10^{-2}$M, then diluted 10 fold to give a range of stock concentrations from $10^{-2}$M to $10^{-8}$M. Drug was then diluted 1000 times in fresh serum free medium and added to the wells in a total volume of 3 ml per well. The plate(s) were then incubated for 72 hrs at 37° C. After 72 hrs the media was removed from the wells and put into microcentrifuge tubes and frozen at −20° C. until assayed.

The amount of collagen synthesized was measured using a Procollagen Type 1 C-Peptide (PIP) EIA kit (Takara), where the amount of collagen produced is stoichiometrically represented by the amount of pro-peptide cleaved from the collagen when it is secreted. Anti-PIP monoclonal antibodies are immobilized on an ELISA plate, the samples added, then a second PIP monoclonal antibody conjugated to horseradish peroxidase is added to the wells and incubated. Following incubation, the wells are washed, a substrate solution is added, and the absorbance measured in a plate reader at 450 nm and compared to a standard curve of PIP (ng/ml).

Example 34

Chick Chorioallantoic Membrane ("CAM") Assay

This example describes an in vitro assay for determining whether a substance promotes angiogenesis. Fertilized, domestic chick embryos are incubated for 3 days prior to shell-less culturing. In this procedure, the egg contents are emptied by removing the shell located around the air space. The interior shell membrane is then severed and the opposite end of the shell is perforated to allow the contents of the egg to gently slide out from the blunted end. The egg contents are emptied into round-bottom sterilized glass bowls and covered with petri dish covers. These are then placed into an incubator at 90% relative humidity and 3% $CO_2$ and incubated for 3 days. (Alternatively, egg contents can remain in the shell with the opening covered with parafilm.)

The agent (e.g., paclitaxel) (Sigma) can be mixed at concentrations of 0.25, 0.5, 1, 5, 10, 30 μg per 10 ul aliquot of 0.5% aqueous methylcellulose. Concentrations can be altered depending on the agent. Agents can be mixed with other compatible materials as appropriate depending on the solubility of the agent. Ten microliter aliquots of this solution are dried on parafilm for 1 hour forming disks 2 mm in diameter. The dried disks containing agent are then carefully placed at the growing edge of each CAM at day 6 of incubation. The day of disc placement can be altered depending on the amount of angiogenesis stimulation by the agent beyond control. Controls are obtained by placing agent-free methylcellulose disks on the CAMs over the same time course. After a 2 day exposure (day 8 of incubation) the vasculature is examined with the aid of a stereomicroscope. Liposyn II, a white opaque solution, is injected into the CAM to increase the visibility of the vascular details. The vasculature of unstained, living embryos were imaged using a Zeiss stereomicroscope which is interfaced with a video camera (Dage-MTI Inc., Michigan City, Ind.). These video signals are then displayed at 160× magnification and captured using an image analysis system (Vidas, Kontron; Etching, Germany). Image negatives are then made on a graphics recorder (Model 3000; Matrix Instruments, Orangeburg, N.Y.).

The membranes of the 8 day-old shell-less embryo are flooded with 2% glutaraldehyde in 0.1M sodium cacodylate buffer; additional fixative is injected under the CAM. After 10 minutes in situ, the CAM is removed and placed into fresh fixative for 2 hours at room temperature. The tissue is then washed overnight in cacodylate buffer containing 6% sucrose. The areas of interest are postfixed in 1% osmium tetroxide for 1.5 hours at 4° C. The tissues are then dehydrated in a graded series of ethanols, solvent exchanged with propylene oxide, and embedded in Spurr resin. Thin sections are cut with a diamond knife, placed on copper grids, stained, and examined in a Joel 1200EX electron microscope. Similarly, 0.5 mm sections are cut and stained with toluene blue for light microscopy.

At day 11 of development, chick embryos are used for the corrosion casting technique. Mercox resin (Ted Pella, Inc., Redding, Calif.) is injected into the CAM vasculature using a 30-gauge hypodermic needle. The casting material consists of 2.5 grams of Mercox CL-2B polymer and 0.05 grams of catalyst (55% benzoyl peroxide) having a 5 minute polymerization time. After injection, the plastic is allowed to sit in situ for an hour at room temperature and then overnight in an oven at 65° C. The CAM is then placed in 50% aqueous solution of sodium hydroxide to digest all organic components. The plastic casts are washed extensively in distilled water, air-dried, coated with gold/palladium, and viewed with the Philips 501B scanning electron microscope.

At day 6 of incubation, the embryo is centrally positioned to a radially expanding network of blood vessels; the CAM develops adjacent to the embryo. These growing vessels lie close to the surface and are readily visible making this system an idealized model for the study of angiogenesis. Living, unstained capillary networks of the CAM can be imaged non-invasively with a stereomicroscope.

Transverse sections through the CAM show an outer ectoderm consisting of a double cell layer, a broader mesodermal layer containing capillaries which lie subjacent to the ectoderm, adventitial cells, and an inner, single endodermal cell layer. At the electron microscopic level, the typical structural details of the CAM capillaries are demonstrated. Typically, these vessels lie in close association with the inner cell layer of ectoderm.

After 48 hours exposure to an agent at concentrations of 0.25, 0.5, 1, 5, 10, or 30 µg, each CAM is examined under living conditions with a stereomicroscope equipped with a video/computer interface to evaluate the effects on angiogenesis. This imaging setup is used at a magnification of 160× which permits the direct visualization of blood cells within the capillaries; thereby blood flow in areas of interest can be easily assessed and recorded. The change in the amount of angiogenesis is defined as an area of the CAM (measuring 2–6 mm in diameter) with increased capillary network and vascular blood flow. Throughout the experiments, zones are assessed on a 4 point gradient (Table 1). This scale represents the degree of increase in angiogenesis with maximal increase represented as a 3 on the vascular gradient scale. Scores of agents are compared with scores of controls.

TABLE 1

VASCULAR GRADIENT

0 -- no vascularity
1 -- some microvascular movement
2*-- richly vascularized zone approximately 2 mm in diameter
3*-- richly vascularized zone extending beyond the disk (6 mm in diameter)

*indicates a positive angiogenesis response

Example 35

Silk Suture Coated with Magnetically Active Particles

The end of a piece of silk 5-0 suture was immersed in a THF solution of CHRONOFLEX AL 85A polyurethane solution (about 10% w/v). The silk was removed, and the coated end was dipped into a vial containing magnetically active microparticles. The coated silk end was removed, and the particles were further embedded into the polyurethane coating by rolling the end between two fingertips. The solvent was removed by air-drying.

Example 36

Silk Suture Coated with Magnetically Active Beads

The end of a piece of silk 5-0 suture was immersed in a THF solution of CHRONOFLEX AL 85A polyurethane solution (about 10% w/v) that contained approximately 5% w/w (beads to polymer) magnetic beads. The silk was removed, and the coated end was dipped into a vial containing magnetically active microparticies. The coated silk end was removed, and the particles were further embedded into the polyurethane coating by rolling the end between two fingertips. The solvent was removed by air-drying.

Example 37

In-Vivo Evaluation of Perivascular Pu Films Coated with Degummed or Virgin Silk Strands Wistar rats weighing 300 g to 400 g are anesthetized with halothane. The skin over the neck region is shaved and the skin is sterilized. A vertical incision is made over the trachea and the left carotid artery is exposed. A polyurethane film covered with degummed silk strands, virgin silk strands or a control uncoated PU film is wrapped around a distal segment of the common carotid artery. The wound is closed and the animal is recovered.

Figure 12:
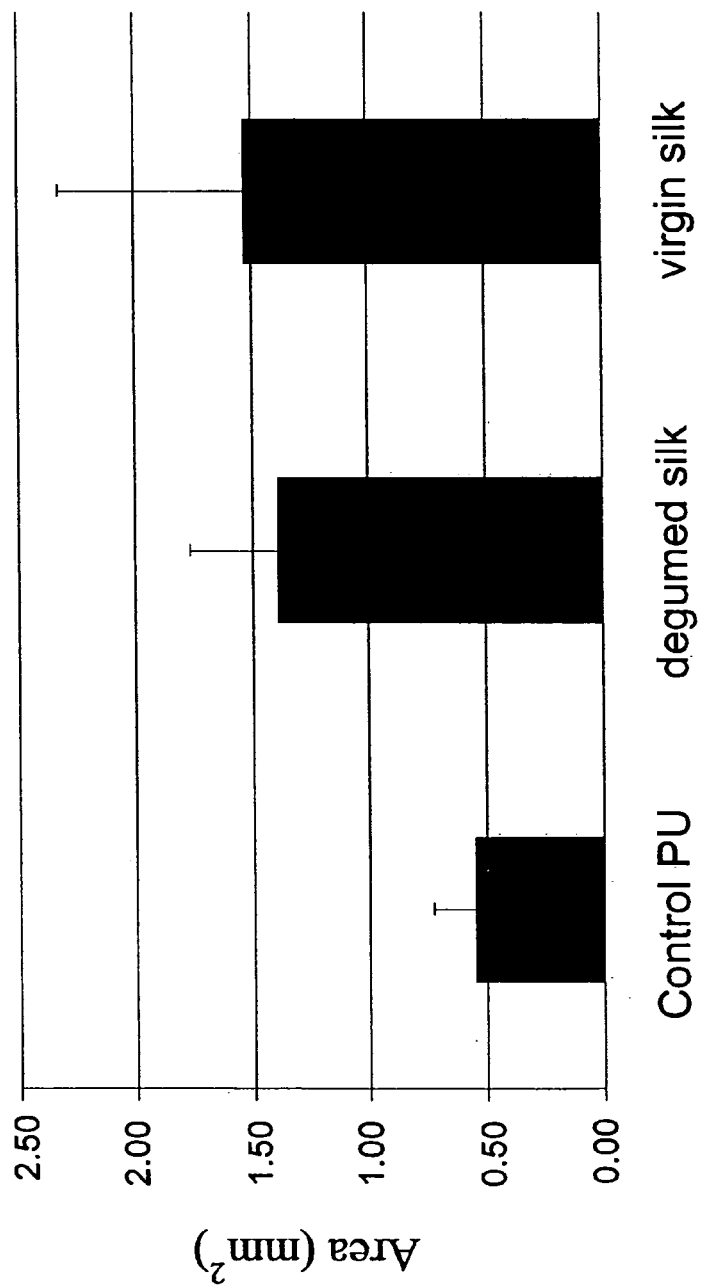
FIG. 12 is a bar graph showing indicating the area of perivascular granulation tissue quantified by computer-assisted morphometric analysis in rat carotid arteries treated with control uncoated PU films and with PU films treated with degummed and virgin silk strands. As shown in the figure, both types of silk markedly increased granulation tissue growth around the blood vessel to the same extent.
Figure 13:
FIG. 13 shows representative histology sections of rat carotid arteries treated with PU films coated with degummed and virgin silk strands. As shown in the figure, both types of silk induced a marked tissue reaction around the treated blood vessel. Movat stain, 100X.
Figure 14:
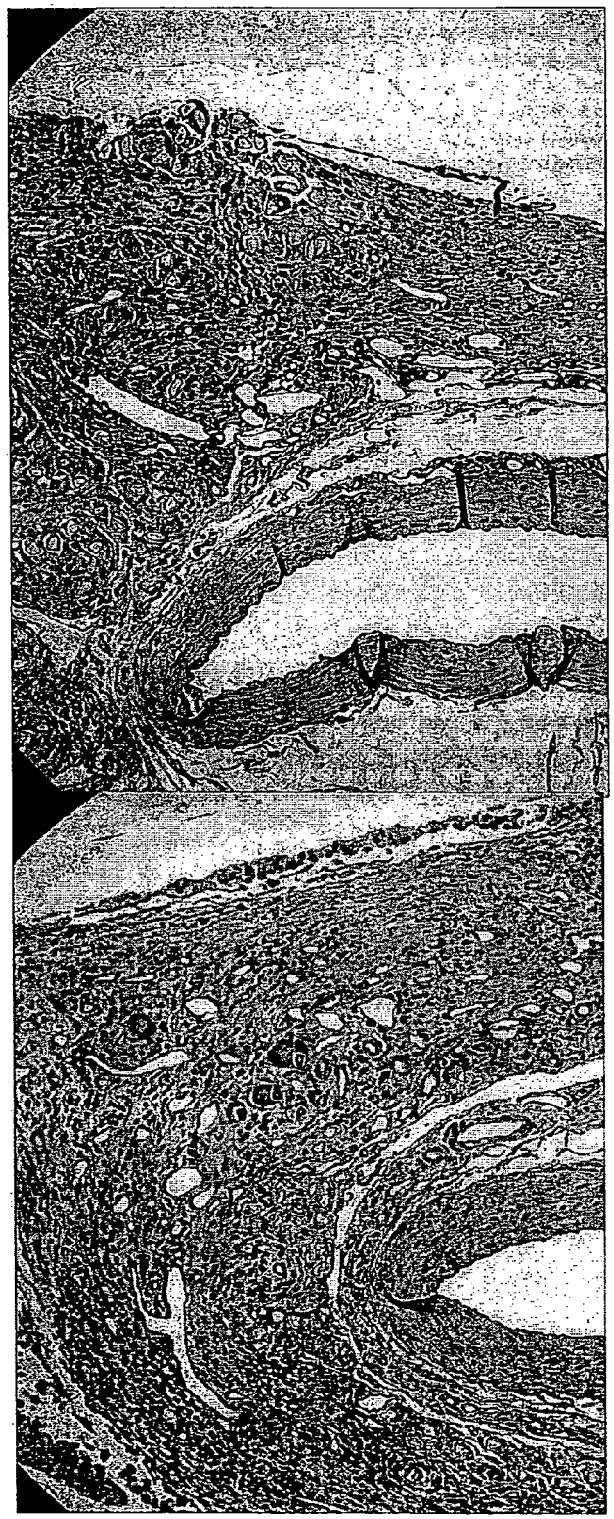
FIG. 14 shows representative histology sections of rat carotid arteries treated with PU films coated with degummed and virgin silk strands showing the granulation tissue that has grown around the treated vessels. The silk strands have broken down into small particles surrounded by giant cells and macrophages. The granulation tissue is highly vascularized and contains numerous inflammatory cells and fibroblasts. Extracellular matrix deposition is also extensive. H&E stain 200X.

After 28 days, the rats are sacrificed with carbon dioxide and pressure-perfused at 100 mmHg with 10% buffered formaldehyde. Both carotid arteries are harvested and processed for histology. Serial cross-sections will be cut every 2 mm in the treated left carotid artery and at corresponding levels in the untreated right carotid artery. Sections are stained with H&E and Movat's stains to evaluate tissue growth around the carotid artery. Thickness of perivascular granulation tissue is quantified by computer-assisted morphometric analysis. Both types of silk markedly increased granulation tissue growth around the blood vessel to the same extent. The silk strands in both groups has broken down into small particles (approximately 30 um in diameter) scattered around the blood vessel and surrounded by giant cells, macrophages, proteoglycan matrix and blood vessels. These features are typical of a foreign body response. The area covered by the foreign body response was more variable in the virgin silk group than in the degummed silk group. See FIGS. 12, 13 and 14.

Example 38

Preparation of Silk Powder Using a Cryomill

Fibers of degummed silk were cut into pieces approximately 1–2 cm in length. The material was then milled to a powder using a cryomill (Spex Certiprep Freezer/Mill—Model 6850). A portion of the milled powder was then sieved through a series of different sized metal sieves to obtain silk powder of different size ranges.

Example 39

Electrospinning of Silk-Loaded Material

20% solutions of PLGA (50:50, $Mw^-$ 54,000) are prepared by dissolving 2 g PLGA into 10 mL DCM. Various amounts of silk powder (25–53 um) are added to each solution such that the silk percentage of the polymers ranges from 2% to 50%. Each solution is then loaded into a 10 ml syringe fitted with a 18 gauge needle. The syringe is then loaded into a syringe pump and 20 kV positive high voltage (by Glassman High Voltage, Inc.) is applied on the syringe needle. The grounded target drum is a rotating drum that has a diameter of about 12 cm. The syringe pump is set to pump at 25 uL per minute and the drum is rotated at approximately 250 rpm. The distance from the tip of the needle to the outside of the drum surface is about 14 cm. The rotating drum is moved from side to side during the spinning process such that the drum is virtually completely covered in the spun material. After the spinning process is completed, a razor blade is used to make a cut through the entire length of the spun material. The material is removed from the drum and is further dried in a vacuum oven for 24 hours.

Example 40

MIC (Minimum Inhibitory Concentration) Determination by Microtitre Broth Dilution Method A. MIC Assay of Various Gram Negative and Positive Bacteria MIC assays were conducted essentially as described by Amsterdam, D. 1996, "Susceptibility testing of antimicrobials in liquid media," p. 52–111. In Loman, V., ed. Antibiotics in laboratory medicine, 4th ed. Williams and Wilkins, Baltimore, Md. Briefly, a variety of compounds were tested for antibacterial activity against isolates of *P. aeruginosa, K. pneumoniae, E. coli, S. epidermidis* and *S. aureus* in the MIC (minimum inhibitory concentration assay under aerobic conditions using 96 well polystyrene microtitre plates (Falcon 1177), and Mueller Hinton broth at 37° C. incubated for 24 h. (MHB was used for most testing except C721 (*S. pyogenes*), which used Todd Hewitt broth, and *Haemophilus influenzae*, which used *Haemophilus* test medium (HTM)) Tests were conducted in triplicate. The results are provided below in Table 2.

Example 41

Coating of a Hip Implant with Silk/PLGA

A solution of 5 g PLGA (50:50, IV=0.15, Birmingham Polymers, Inc.) is dissolved in 100 mL dichloromethane. 1 g of powdered silk (25–53 um, prepared using the cryomill as sieving as described above) is mixed into the solution. The hip implant (SECUR-FIT HA, Stryker Orthopaedics) is placed in a clamp system such that the ball segment of the hip implant is secured in the clamp. The clamp is then secured to an overhead stirrer (Fisher Scientific). The stirrer is set to a speed of about 30 rpm. The silk/PLGA solution is placed in a glass TLC spray device (Sigma-Aldrich Corp). Approx. ⅓ of the implant below the polished section of the implant is coated with the silk/PLGA using the TLC spray device (connected to a nitrogen tank). The spray device is swirled during the spraying process to ensure that the silk is evenly dispersed in the PLGA solution. The rate of spray application is controlled such that the solution does not drip off the device. Once an initial coating is accomplished, the spraying process is stopped and the device is air dried. If required the spray coating/drying process can be repeated until the desired thickness is accomplished. After the final air drying step, the device is removed from the clamp and is placed in a vacuum oven. The implant is dried for 6 hours under vacuum. Other examples of fibrosing agents that may be similarly coated onto a hip implant device include:

TABLE 2

MINIMUM INHIBITORY CONCENTRATIONS OF THERAPEUTIC AGENTS AGAINST VARIOUS GRAM NEGATIVE AND POSITIVE BACTERIA

| Drug | Bacterial Strain | | | | | |
|---|---|---|---|---|---|---|
| | *P. aeruginosa* PAE/K799 H187 Wt Gram– | *K. pneumoniae* ATCC13883 C238 wt Gram– | *E. coli* UB1005 C498 wt Gram– | *S. aureus* ATCC25923 C622 wt Gram+ | *S. epidermidis* C621 wt Gram+ | *S. pyogenes* C721 wt Gram+ |
| doxorubicin | $10^{-5}$ | $10^{-6}$ | $10^{-4}$ | $10^{-5}$ | $10^{-6}$ | $10^{-7}$ |
| mitoxantrone | $10^{-5}$ | $10^{-6}$ | $10^{-5}$ | $10^{-5}$ | $10^{-5}$ | $10^{-6}$ |
| 5-fluorouracil | $10^{-5}$ | $10^{-6}$ | $10^{-6}$ | $10^{-7}$ | $10^{-7}$ | $10^{-4}$ |
| methotrexate | N | $10^{-6}$ | N | $10^{-5}$ | N | $10^{-6}$ |
| etoposide | N | $10^{-5}$ | N | $10^{-5}$ | $10^{-6}$ | $10^{-5}$ |
| camptothecin | N | N | N | N | $10^{-4}$ | N |
| hydroxyurea | $10^{-4}$ | N | N | N | N | $10^{-4}$ |
| cisplatin | $10^{-4}$ | N | N | N | N | N |
| tubercidin | N | N | N | N | N | N |
| 2-mercaptopurine | N | N | N | N | N | N |
| 6-mercaptopurine | N | N | N | N | N | N |
| Cytarabine | N | N | N | N | N | N |

Activities are in Molar concentrations
Wt = wild type
N = No activity

B. MIC of Antibiotic-resistant Bacteria

Various concentrations of the following compounds, mitoxantrone, cisplatin, tubercidin, methotrexate, 5-fluorouracil, etoposide, 2-mercaptopurine, doxorubicin, 6-mercaptopurine, camptothecin, hydroxyurea and cytarabine were tested for antibacterial activity against clinical isolates of a methicillin resistant *S. aureus* and a vancomycin resistant pediocoocus clinical isolate in an MIC assay as described above. Compounds which showed inhibition of growth (MIC value of $<1.0\times10-3$) included: mitoxantrone (both strains), methotrexate (vancomycin resistant *pediococcus*), 5-fluorouracil (both strains), etoposide (both strains), and 2-mercaptopurine (vancomycin resistant *pediococcus*).

fibronectin, talc, silica, starch, poly(ethyl cyanoacrylate), polylysine, bleomycin, and CTGF. Other implant devices such as a knee implant, shoulder implant and a digit implant can be coated in a manner similar to that described above.

Example 42

Coating of a Hip Implant with Silk/Cyclosporine A/PLGA

A solution of 5 g PLGA (50:50, IV=0.15, Birmingham Polymers, Inc.) is dissolved in 100 mL chloroform. 1 g of powdered silk (25–53 um, prepared using the cryomill as sieving as described above) is mixed into the solution. 0.5 mg cyclosporine A is added to the solution. The hip implant (SECUR-FIT HA, Stryker Orthopaedics) is placed in a clamp system such that the ball segment of the hip implant is secured in the clamp. The clamp is then secured to an overhead stirrer (Fisher Scientific). The stirrer is set to a speed of about 30 rpm. The silk/PLGA solution is placed in a glass TLC spray device (Sigma-Aldrich Corp). Approx. ⅓ of the implant below the polished section of the implant is coated with the silk/PLGA using the TLC spray device (connected to a nitrogen tank). The spray device is swirled during the spraying process to ensure that the silk is evenly dispersed in the PLGA solution. The rate of spray application is controlled such that the solution does not drip off the device. Once an initial coating is accomplished, the spraying process is stopped and the device is air dried. If required the spray coating/drying process can be repeated until the desired thickness is accomplished. After the final air drying step, the device is removed from the clamp and is placed in a vacuum oven. The implant is dried for 6 hours under vacuum. Other examples of fibrosing agents that may be similarly coated onto a hip implant device include: talc, silica, starch, fibronectin, poly(ethyl cyanoacrylate), polylysine, bleomycin, and CTGF. Other implant devices such as a knee implant, shoulder implant and a digit implant can be coated in a manner similar to that described above.

Example 43

Coating of a Hip Implant with Silk

A silk solution is prepared by adding 10 g virgin silk fibers to 100 mL hexafluoroisopropanol (HFIP). The solution is allowed to stir for 48 hours at room temperature. The hip implant (SECUR-FIT HA, Stryker Orthopaedics) is placed in a clamp system such that the ball segment of the hip implant is secured in the clamp. The clamp is then secured to an overhead stirrer (Fisher Scientific). The stirrer is set to a speed of about 30 rpm. A Pasteur pipette is used to drip the silk/HFIP solution onto the hydroxyapatite (HA) coated portion of the hip implant. The volume added with each drop is such that the solution does not drip from the implant. Once the HA coating is wetted with the silk/HFIP solution, the material application is stopped and the implant is allowed to air dry. The process is repeated again and after the drying step, the device is removed from the clamp and is placed in a vacuum oven. The implant is dried for 6 hours under vacuum. Other examples of fibrosing agents that may be similarly coated onto a hip implant device include: talc, silica, starch, fibronectin, poly(ethyl cyanoacrylate), polylysine, bleomycin, and CTGF. Other implant devices such as a knee implant, shoulder implant and a digit implant can be coated in a manner similar to that described above.

Example 44

Coating of an Endosteal Implant with Silk/Plga

A solution of 5 g PLGA (50:50, IV=0.15, Birmingham Polymers, Inc.) is dissolved in 100 mL dichloromethane. 1 g of powdered silk (25–53 um, prepared using the cryomill as sieving as described above) is mixed into the solution. The endosteal implant is placed in a clamp system such that the threaded section is readily accessible. The clamp is then secured to an overhead stirrer (Fisher Scientific). The stirrer is set to a speed of about 30 rpm. The silk/PLGA solution is placed in a glass TLC spray device (Sigma-Aldrich Corp). The threaded section of the implant is coated with the silk/PLGA using the TLC spray device (connected to a nitrogen tank). The spray device is swirled during the spraying process to ensure that the silk is evenly dispersed in the PLGA solution. The rate of spray application is controlled such that the solution does not drip off the device. Once an initial coating is accomplished, the spraying process is stopped and the device is air dried. If required the spray coating/drying process can be repeated until the desired thickness is accomplished. After the final air drying step, the device is removed from the clamp and is placed in a vacuum oven. The implant is dried for 6 hours under vacuum. Other examples of fibrosing agents that may be similarly coated onto the implant device include: talc, silica, starch, fibronectin, poly(ethyl cyanoacrylate), polylysine, bleomycin, and CTGF.

Example 45

Coating of an Endosteal Implant with Silk/PLGA

A solution of 10 g PLGA (50:50, IV=0.15, Birmingham Polymers, Inc.) is dissolved in 100 mL dichloromethane. The threaded portion of the endosteal implant is dipped into the PLGA solution. The coated device is partially dried and then the silk powder is sprinkled onto the coated section of the coated implant. The implant is then rolled on a TEFLON sheet such that the silk particles are embedded into the PLGA coating. The implant is then air dried for 3 hours. After the air drying step, the device is placed in a vacuum oven. The implant is dried for 6 hours under vacuum. Other examples of fibrosing agents that may be similarly coated onto the implant device include: talc, silica, starch, fibronectin, poly(ethyl cyanoacrylate), polylysine, bleomycin, and CTGF.

Example 46

Coating of an Intramedullary Pin with Silk/PLGA

A solution of 10 g PLGA (50:50, IV=0.25, Birmingham Polymers, Inc.) is dissolved in 100 mL dichloromethane. The lower half of a intramedullary pin (cat #: 167430000, Sanatmetal) implant is dipped into the PLGA solution. The coated device is partially dried and then the silk powder is sprinkled onto the coated section of the coated implant. The implant is then rolled on a Teflon sheet such that the silk particles are embedded into the PLGA coating. The implant is then air dried for 3 hours. After the air drying step, the device is placed in a vacuum oven. The implant is dried for 6 hours under vacuum. Other examples of fibrosing agents that may be similarly coated onto the implant device include: talc, silica, starch, fibronectin, poly(ethyl cyanoacrylate), polylysine, bleomycin, and CTGF.

Example 47

Coating of an Intramedullary Pin with Silk/POLYURETHANE

A solution of 10 g CHRONOFLEX AL 85A (CT Biomaterials) is dissolved in 100 mL THF. The lower half of a intramedullary pin (cat #: 167430000, Sanatmetal) implant is dipped into the polyurethane solution. The coated device is partially dried and then the silk powder is sprinkled onto the coated section of the coated implant. The implant is then rolled on a TEFLON sheet such that the silk particles are embedded into the polyurethane coating. The implant is then air dried for 3 hours. After the air drying step, the device is placed in a vacuum oven. The implant is dried for 6 hours under vacuum. Other examples of fibrosing agents that may be similarly coated onto the implant device include: talc, silica, starch, fibronectin, poly(ethyl cyanoacrylate), polylysine, bleomycin, and CTGF.

Example 48

Coating of an Intramedullary Pin with Silk/PLGA

A solution of 10 g PLGA (50:50, IV=0.25, Birmingham Polymers, Inc.) is dissolved in 100 mL dichloromethane. A stainless steel wire is looped through the top hole of a broad bone plate (cat #: 934016005, Sanatmetal). The implant is dipped into the PLGA solution. The coated device is partially dried and then the silk powder is sprinkled onto the coated section of the coated implant. The implant is then air dried for 3 hours. After the air drying step, the device is placed in a vacuum oven. The implant is dried for 6 hours under vacuum. Other examples of fibrosing agents that may be similarly coated onto the implant device include: talc, silica, starch, fibronectin, poly(ethyl cyanoacrylate), polylysine, bleomycin, and CTGF.

Example 49

Coating of a Gastric Restriction Device with TALC/Polyurethane

A solution of 10 g CHRONOFLEX AL 85A (CT Biomaterials) is dissolved in 100 mL THF. The outer surface of the ring portion of a BIOENTERICS LAP-BAND System (Inamed Health) is dipped into the polyurethane solution. The coating is air dried until it is tacky at which point talc (hydrous magnesium silicate, powder particle size 10 µm, Aldrich Corp.) is sprinkled over the tacky coating. The device is gently shaken to remove the excess material. A TEFLON rod is then gently rolled over the surface to further embed the talc into the coating. The implant is then air dried for 2 hours. After the air drying step, the device is placed in a vacuum oven. The implant is dried for 24 hours under vacuum. Other examples of fibrosing agents that may be similarly coated onto the implant device include: silica, fibronectin, starch, silk, poly(ethyl cyanoacrylate), polylysine, bleomycin, and CTGF.

Example 50

Coating of a Gastric Restriction Device with Silk/PLGA

A solution of 10 g PLGA (50:50, IV=0.25, Birmingham Polymers, Inc.) is dissolved in 100 mL ethyl acetate. The outer surface of the ring portion of the BioEnterics LAP-BAND System (Inamed Health) is dipped into the polyurethane solution. The coating is air dried until it is tacky at which point silk powder (25–53 um, Prepared using a cryomill and sieves) is sprinkled over the tacky coating. The device is gently shaken to remove the excess material. A TEFLON rod is then gently rolled over the surface to further embed the silk into the coating. The implant is then air dried for 2 hours. After the air drying step, the device is placed in a vacuum oven. The implant is dried for 24 hours under vacuum. Other examples of fibrosing agents that may be similarly coated onto the implant device include: talc, silica, fibronectin, starch, poly(ethyl cyanoacrylate), polylysine, bleomycin, and CTGF.

Example 51

Coating of a Soft Palate Implant Device with Silk/PLGA

A solution of 2 g PLGA (50:50, IV=0.15, Birmingham Polymers, Inc.) is dissolved in 100 mL ethyl acetate. The end of a PILLAR palatal implant (Restore Medical, Inc) is held using clamp. The clamp is then secured to an overhead stirrer (Fisher Scientific). The stirrer is set to a speed of about 30 rpm. The PLGA solution is placed in a glass TLC spray device (Sigma-Aldrich Corp) and the device is sprayed with the PLGA solution until a thin coating of PLGA covered the device. The coating is air dried until it is tacky. Using a pair of tweezers, the device is removed from the clamp and silk powder (25–53 um, prepared using a cryomill and sieves) is sprinkled over the tacky coating. The device is gently shaken to remove the excess material. The implant is then air dried for 2 hours. After the air drying step, the device is placed in a vacuum oven. The implant is dried for 24 hours under vacuum. Other examples of fibrosing agents that may be similarly coated onto the implant device include: talc, silica, starch, poly(ethyl cyanoacrylate), polylysine, bleomycin, and CTGF.

Example 52

Coating of a Surgical Mesh with Talc/Polyurethane

A solution of 10 g CHRONOFLEX AL 85A (CT Biomaterials) is dissolved in 100 mL THF. 1 g talc (hydrous magnesium silicate, powder particle size 10 µm, Aldrich Corp.) is then added to the solution. A PROCEED Surgical Mesh (Ethicon) layed flat onto a piece of silicone coated release liner. The silk/PLGA solution is placed in a glass TLC spray device (Sigma-Aldrich Corp). The surface of the mesh is then coated with the polyurethane/talc solution using the TLC spray device (connected to a nitrogen tank). The spray device is swirled during the spraying process to ensure that the talc is evenly dispersed in the polyurethane solution. The rate of spray application is controlled such that the solution does not drip off the device. Once an initial coating is accomplished, the spraying process is stopped and the device is air dried. If required the spray coating/drying process can be repeated until the desired thickness is accomplished. After the final air drying step, the device is removed from the clamp and is placed in a vacuum oven. The implant is dried for 6 hours under vacuum. Other examples of fibrosing agents that may be similarly coated onto a hip implant device include: talc, silica, starch, silk, poly(ethyl cyanoacrylate), polylysine, bleomycin, and CTGF.

Example 53

Coating of a Surgical Mesh with Silk/PLGA

A solution of 2 g PLGA (50:50, IV=0.15, Birmingham Polymers, Inc.) is dissolved in 100 mL ethyl acetate. 1 g of powdered silk (25–53 um, prepared using the cryomill as sieving as described above) is mixed into the solution. A Bard Mesh (Flat Sheets, Cat # 0112680 3"×6" (7.5 cm×15 cm), DAVOL) laid flat onto a piece of silicone coated release liner. The silk/PLGA solution is placed in a glass TLC spray device (Sigma-Aldrich Corp). The surface of the mesh is then coated with the PLGA/silk solution using the TLC spray device (connected to a nitrogen tank). The spray device is swirled during the spraying process to ensure that the silk is evenly dispersed in the PLGA solution. Once an initial coating is accomplished, the spraying process is stopped and the device is air dried. If required the spray coating/drying process can be repeated. After the final air drying step, the mesh is placed in a vacuum oven and is dried for 6 hours under vacuum. Other examples of fibrosing agents that may be similarly coated onto the mesh include: talc, fibronectin, silica, starch, poly(ethyl cyanoacrylate), polylysine, bleomycin, and CTGF.

Example 54

Incorporation of Silk into a Surgical Mesh

A Bard Hernia Mesh (Flat Sheets, Cat # 0112680 3"×6" (7.5 cm×15 cm), DAVOL) is laid flat in a sheet of glass. Several silk sutures (PERMA-HAND Silk Suture—Taper Point, Cat: 7730G, Ethicon) are then sewn onto the mesh by inserting the needle through the mesh from one side if the mesh to the other side of the mesh. The silk is traversed through the mesh at least 4 times for each suture. The excess suture material is the cut away.

Example 55

Incorporating Silk onto an Embolization Coil

A 2 ply silk thread is looped around the platinum wire of a detachable TORNADO embolization coil (Cook, Inc) and then a knot is tied to secure the silk to the platinum coil. This process is repeated several times until the amount of silk present accounts for about 5% of the fibers present.

Example 56

Coating of a Septal Occlusion Device with Silk

A 5% silk solution in HFIP is prepared by adding 1 g virgin silk yard to 20 mL HFIP. The solution is stirred for 48 hours. The resultant solution is then dripped onto the PTFE portion of a HELEX septal occluder device (W.L. Gore). Once most of the PTFE protion of the device had been in contact with the HFIP/Silk solution, the device is air dried and is then vacuum dried for 24 hours.

Example 57

Coating of a Septal Occlusion Device with Polylysine

A 2% solution of poly(Lysine) [poly-D-lysine hydrobromide, mol wt 150,000–300,000 Sigma-Aldrich] is prepared by dissolving 0.1 g in 2 mL deionized water. The solution is poured into a small metal tray. An AMPLATZER septal occluder (AGA Medical Corporation, USA) is then dipped into the solution and is covered in the solution by using a Pasteur pipetted squirt the solution over the device. The device is then removed from the tray and is placed on a TEFLON sheet and is allowed to air dry. The device is then dried under vacuum for 24 hours.

Example 58

Coating of a Fallopian Tube Implant with Silk/PLGA

A solution of 2 g PLGA (50:50, IV=0.15, Birmingham Polymers, Inc.) is dissolved in 100 mL ethyl acetate. 1 g of powdered silk (25–53 um, prepared using the cryomill as sieving as described above) is mixed into the solution. The "stent" portion of the ECLIPSE permanent contraceptive device (Ovion, Redwood City, Calif.) is clamped using a pair of tweezers and a wire strand. The tweezers are then secured to an overhead stirrer (Fisher Scientific). The stirrer is set to a speed of about 45 rpm. The silk/PLGA solution is placed in a glass TLC spray device (Sigma-Aldrich Corp). Approximately ⅓ of the implant below the polished section of the implant is coated with the silk/PLGA using the TLC spray device (connected to a nitrogen tank). The spray device is swirled during the spraying process to ensure that the silk is evenly dispersed in the PLGA solution. The rate of spray application is controlled such that the solution does not drip off the device. Once an initial coating is accomplished, the spraying process is stopped and the device is air dried. If required the spray coating/drying process can be repeated until the desired thickness is accomplished. After the final air drying step, the device is removed from the clamp and is placed in a vacuum oven. The implant is dried for 6 hours under vacuum. Other examples of fibrosing agents that may be similarly coated onto a device include: talc, silica, starch, fibronectin, poly(ethyl cyanoacrylate), polylysine, bleomycin, and CTGF.

Example 59

Coating of a Vas Deferens Clip with Silk/PLGA

A solution of 2 g PLGA (50:50, IV=0.15, Birmingham Polymers, Inc.) is dissolved in 100 mL ethyl acetate. A vas deferens clip (VASCLIP, VMBC, LLC, Roseville, Minn.) is dipped into the PLGA solution and is air dried until it is tacky. The clip is then added to powdered silk (25–53 um, prepared using the cryomill as sieving) that is in a beaker. The clip is shaken in the beaker with the powdered silk. The clip is removed from the beaker of silk and gently shaken to remove excess silk. A TELFON rod is rolled over the surface of the coated clip to embed the silk powder further into the coating. The clip is then air dried for 6 hours after which it is vacuum dried for 24 hours.

Other examples of fibrosing agents that may be similarly coated onto a device include: talc, silica, starch, fibronectin, poly(ethyl cyanoacrylate), polylysine, bleomycin, and CTGF.

Example 60

Incorporation of Silk into a Bulking Agent 50 mg powdered silk (25–53 um, prepared using the cryomill as sieving) is added to 2.5 mL of a glutaradehyde crosslinked bovine collagens solution (35 mg/mL) [CONTIGEN, CR Bard]. The solution is vortexed to produce the final suspension. Other examples of fibrosing agents that may be similarly coated onto a device include: talc, silica, fibronectin, starch, poly(ethyl cyanoacrylate), polylysine, bleomycin, and CTGF.

Example 61

Coating of Silk onto a Prosthetic Anal Sphincter Device

A solution of 10 g CHRONOFLEX AL 85A (CT Biomaterials) is dissolved in 100 mL THF. The cuff portion of an ACTICON NEOSPHINCTER is placed on a TELFON sheet. The silk/polyurethane solution is placed in a glass TLC spray device (Sigma-Aldrich Corp). The cuff portion of the implant is coated with a thin coating of the silk/polyurethane using the TLC spray device (connected to a nitrogen tank). Once an initial coating is accomplished, the spraying process is stopped and the device is air dried to produce a tacky coating. Powdered silk (25–53 um, prepared using the cryomill as sieving) is then sprinkled over the tacky coating. A TELFON rod is then rolled over the surface of the device to aid in the embedding of the silk into the coating. The excess silk powder is then shaken off the device. The device is air dried for 24 hours after which it is dried under vacuum for 24 hours. Other examples of fibrosing agents that may be similarly coated onto a device include: talc, silica, fibronectin, starch, poly(ethyl cyanoacrylate), polylysine, bleomycin, and CTGF.

Example 62

Incorporation of Silk onto an External Fixation Device

A solution of 10 g PLGA (50:50, IV=0.15, Birmingham Polymers, Inc.) is dissolved in 100 mL dichloromethane. 1 g of powdered silk (25–53 um, prepared using the cryomill as sieving as described above) is mixed into the solution. The through skin components (The HOFFMANN II HYBRID EXTERNAL FIXATION System, Stryker) that screw into the bone are dipped into the PLGA/Silk solution. The lower ⅓ of these pins are coated. The coated pins are air dried and then vacuum dried.

Example 63

Incorporation of Silk into Surgical Film Implant

A 10% solution of a 70:30 PLLA:PDLLA polymer (RESOMER LR 708, Boehringer Ingelheim, KG, Germany) is prepared by dissolving 1 g of the polymer in 10 mL DCM. 1 g powdered silk (25–53 um, prepared using the cryomill and sieving) is added to the solution. The solution is stirred for 1 hour. The solution is cast into a film on a release liner using a 40 mil casting knife. The film is dried in forced-air oven (50° C., 3 hours) and then in a vacuum oven for 24 hours.

Example 64

Dripped-on Cyclosporine a Samples

A polyurethane (PU) (CHRONOFLEX AL 85A) is dissolved in tetrahydrofuran (THF) to form a 20% solution (20 mL). The PU film is prepared by casting the PU solution on release liner (using 40MIL opening knife). The film is dried in forced-air oven (50° C.) and then in a vacuum oven. The final film thickness is about 100–120 μm). Cyclosporin-A is dissolved in ethanol (500 ug/mL) to form a cyclosporin-A ethanol solution. A 50 μl aliquot of cyclosporin-A solution is dripped onto the 8×8 mm2 (precut) PU film. The ethanol is evaporated in fume hood and the PU samples are further dried in vacuum oven.

Example 65

Encapsulated Cyclosporine A Samples

A 20% polyurethane (CHRONOFLEX AL 85A) solution in THF (2 g PU in 10 mL THF, 20 mL glass scintillation vial) is prepared. 230 uL of a 100 ug/mL cyclosporine A/chloroform solution is added to the PU solution. The solution is stirred using a magnetic stirrer for 2 hours. The PU/cyclosporine A solution is cast into a film on a release liner using a 40 mil casting knife. The film is dried in forced-air oven (50° C.) and then in a vacuum oven. The final film thickness is about 100–120 μm).

Example 66

Release Study and Total Concent Analysis for Cyclosporin from Polyurethane Film

The release of cyclosporine A from a polyurethane film is analyzed by HPLC using the following parameters.

| Mobile Phase | 35:65:5:0.1 (water/acetonitrile, tert-butylmethylether, phosphoric acid) |
| Wavelength | 210 nm |
| Column | ACE C18 150 × 4.6 mm 5 μm |
| Flow rate | 1.2 mL/min |
| Diluent for samples | 1:1 (acetonitrile/water) |

Standards are prepared as follows: Approximately 25 mg of cyclosporine is weighted into a 25 mL volumetric flask. A diluent (1:1 acetonitrile/water) is added to dissolve the cyclosporine and diluent is added to achieve the correct volume. The following dilustions (shown in the table below) are made to obtain standards of 0.2, 0.5, 2, 5, 10 and 20 μg/mL.

| Stock solution concentration (μg/mL) | Dilution volume (mL) | Final volume (mL) | Final concentration (μg/mL) |
| --- | --- | --- | --- |
| 1000 | 8 | 10 | 800 |
| 1000 | 5 | 10 | 500 |
| 1000 | 3 | 10 | 300 |
| 1000 | 2 | 10 | 200 |
| 1000 | 1 | 10 | 100 |
| 100 | 1 | 10 | 10 |
| 500 | 1 | 10 | 50 |
| 50 | 1 | 10 | 0.5 |
| 800 | 1 | 10 | 80 |
| 80 | 1 | 10 | 0.8 |
| 200 | 1 | 10 | 20 |
| 20 | 1 | 10 | 2 |

Release Studies:

Release studies are performed as follows. A PU film is cut into 1 cm×1 cm piece, if not already this size, and weighed accurately into a 15 cm test tube. 14 mL of release media are dispensed into each test tube containing the sample, capped, and placed on a rotator at 37° C. until next time point. The time points are 5 hours, 1 day, 2 days, 3 days, 4 days, 5 days and then every other day after the first week until drug is not detected or until otherwise decided. At each time point, the sample is transferred into a new test tube and 14 mL of release media are added. The sample is placed back into the 37° C. oven until the next time point. The release media solution is injected at various time points directly onto the HPLC column for analysis.

Figure 15:
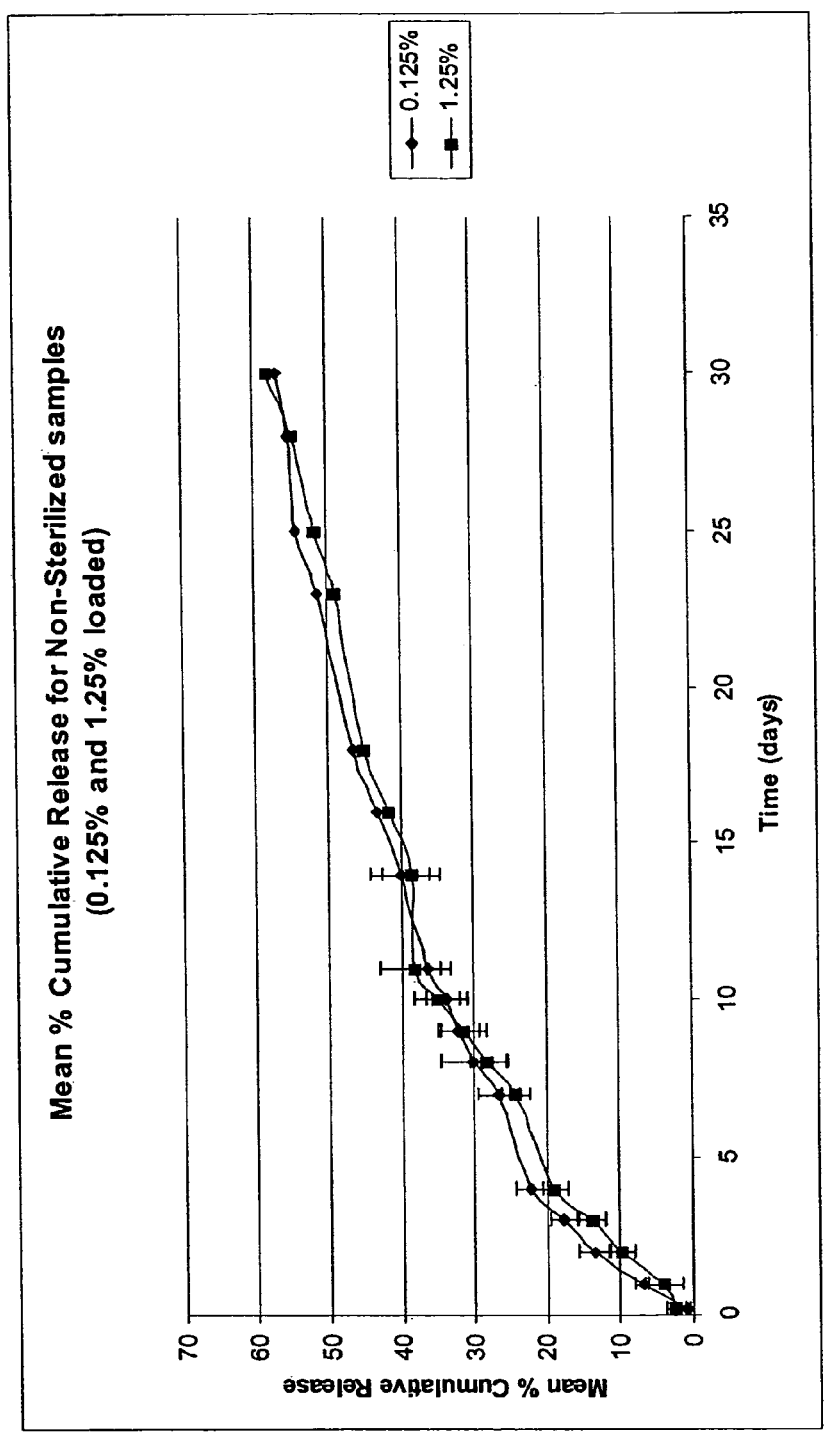
FIG. 15 shows the release profile for cyclosporine A from a polyurethane film as analyzed by HPLC.

Total Content Analysis:

A PU film is cut into 1 cm×1 cm piece, if not already this size, and weigh accurately into a 15 cm test tube. 0.5 mL of choloform is added to each test tube and completely dissolve the sample. Once the sample is dissolved, 6.0 mL of acetonitrile is added to each sample. The sample is capped and shaken vigorously to precipitate the polyurethane. The sample is centrifuged at 2500 rpm for 10 minutes. 5.0 mL of the supernatant is transferred into a clean test tube and dried under nitrogen at 35° C. The dried samples are reconstituted in 1.0 mL of acetonitrile and injected into the HPLC. The results of the release study for polyurethane films loaded with 1.25% and 0.125% cyclosporine are shown in FIG. 15.

From the foregoing, it is appreciated that, although specific embodiments of the invention have been described herein for purposes of illustration, various modifications may be made without deviating from the spirit and scope of the invention. Accordingly, the invention is not limited except as by the appended claims.

All of the above U.S. patents, U.S. patent application publications, U.S. patent applications, foreign patents, foreign patent applications and non-patent publications referred to in this specification and/or listed in the Application Data Sheet are incorporated herein by reference, in their entirety.

The invention claimed is:

1. A method for treating varicose or spider veins comprising injecting a therapeutically effective amount of a composition comprising silk into the lumen of a varicose or spider vein wherein the silk induces a fibrotic response.

2. The method of claim 1 wherein the silk is in the form of a thread, or is in contact with a thread.

3. The method of claim 1 wherein the silk is in the form of a particulate.

4. The method of claim 3 wherein the silk is in the form of a powder.

5. The method of claim 1 wherein the composition comprises a polyalkylene oxide-polyester block copolymer.

6. The method of claim 5 wherein the polyester is poly(glycolic acid) (PLGA), poly(lactic acid) (PLA), poly(caprolactone) (PCL), or polydioxanone.

7. The method of claim 5 wherein the polyester is poly(D,L-lactide), poly(D,L-lactide-co-glycolide), or poly(glycolide).

8. The method of claim 1 wherein the composition comprises a polyester-polyethylene glycol block copolymer.

9. The method of claim 8 wherein the polyester is D,L-lactide-co-glycolide and the polyethylene glycol is polyethylene glycol 400.

* * * * *

UNITED STATES PATENT AND TRADEMARK OFFICE
CERTIFICATE OF CORRECTION

PATENT NO. : 7,166,570 B2
APPLICATION NO. : 11/006893
DATED : January 23, 2007
INVENTOR(S) : William L. Hunter et al.

It is certified that error appears in the above-identified patent and that said Letters Patent is hereby corrected as shown below:

Title Page
Item [75], Inventors should be listed as:
-- William L. Hunter, Vancouver (CA); David M. Gravett, Vancouver (CA); Philip M. Toleikis, Vancouver (CA); Pierre E. Signore, Vancouver (CA); Richard T. Liggins, Coquitlam (CA); Dechi Guan, Vancouver (CA) --.

Signed and Sealed this

Fifth Day of June, 2007

JON W. DUDAS
*Director of the United States Patent and Trademark Office*